US008785171B2

(12) United States Patent
Souter et al.

(10) Patent No.: US 8,785,171 B2
(45) **Date of Patent: *Jul. 22, 2014**

(54) FABRIC AND HOME CARE PRODUCTS COMPRISING COLD WATER PROTEASES

(75) Inventors: Philip Frank Souter, Northumberland (GB); Glenn Steven Ward, Newcastle (GB); Viktor Yuryevich Alekseyev, Palo Alto, CA (US); Joshua Roy Basler, Palo Alto, CA (US); Luis Gustavo Cascão-Pereira, Redwood City, CA (US); David A. Estell, San Francisco, CA (US); Ayrookaran J. Poulose, Belmont, CA (US); James T. Kellis, Jr., Woodside, CA (US); Alexander Pisarchik, Belmont, CA (US); Daniel Esteban Torres-Pazmino, KA Leiden (NL)

(73) Assignee: The Procter & Gamble Company, Cincinnati, OH (US)

( * ) Notice: Subject to any disclaimer, the term of this patent is extended or adjusted under 35 U.S.C. 154(b) by 23 days.

This patent is subject to a terminal disclaimer.

(21) Appl. No.: 12/963,681

(22) Filed: Dec. 9, 2010

(65) Prior Publication Data

US 2011/0237487 A1 Sep. 29, 2011

Related U.S. Application Data

(60) Provisional application No. 61/267,878, filed on Dec. 9, 2009, provisional application No. 61/392,175, filed on Oct. 12, 2010.

(51) Int. Cl.
*C12N 9/48* (2006.01)

(52) U.S. Cl.
USPC .......... 435/212

(58) Field of Classification Search
None
See application file for complete search history.

(56) References Cited

U.S. PATENT DOCUMENTS

| | | | |
|---|---|---|---|
| 7,306,937 | B2 | 12/2007 | Poulose et al. |
| 2008/0004186 | A1 | 1/2008 | Estell et al. |
| 2008/0063774 | A1 | 3/2008 | Aehle et al. |
| 2009/0233831 | A1 | 9/2009 | Souter |
| 2009/0233832 | A1 | 9/2009 | Souter et al. |
| 2009/0263882 | A1 | 10/2009 | Shaw et al. |
| 2011/0082048 | A1 | 4/2011 | Estell et al. |

FOREIGN PATENT DOCUMENTS

| | | | |
|---|---|---|---|
| WO | WO 2008/002472 | A2 | 1/2008 |
| WO | WO 2009/149144 | A2 | 12/2009 |
| WO | WO 2009/149145 | A2 | 12/2009 |
| WO | WO 2010/056640 | A2 | 5/2010 |
| WO | WO 2011/072117 | | 6/2011 |

OTHER PUBLICATIONS

International Search Report dated Dec. 9, 2010 containing 22 pages.

*Primary Examiner* — Sheridan Swope
(74) *Attorney, Agent, or Firm* — Melissa G Krasovec

(57) ABSTRACT

This invention relates to fabric and home care products comprising one or more cold water proteases and processes for making and using such products. Such compositions provide improved cleaning and freshness. Such cold water proteases may be derived from parent enzymes, including BPN' subtilisin and subtilisin derived from *Bacillus lentus*, by substitution, insertion and/or deletion of one or more of the parent enzymes' amino acids.

6 Claims, 13 Drawing Sheets

```
BPN'    1 AQSVPYGVSQ IKAPALHSQG YTGSNVKVAV IDSGIDSSHP DLKVAGGASM VPSETNPFQD
GG36    1 AQSVPWGISR VQAPAAHNRG LTGSGVKVAV LDTGIS-THP DLNIRGGASF VPGEPST-QD

BPN'   61 NNSHGTHVAG TVAALNNSIG VLGVAPSASL YAVKVLGADG SGQYSWIING IEWAIANNMD
GG36   59 GNGHGTHVAG TIAALNNSIG VLGVAPSAEL YAVKVLGASG SGSVSSIAQG LEWAGNNGMH

BPN'  121 VINMSLGPS GSAALKAAVD KAVASGVVVV AAAGNEGTSG SSSTVGYPGK YPSVIAVGAV
GG36  119 VANLSLGSPS PSATLEQAVN SATSRGVLVV AASGNSGAGS ----ISYPAR YANAMAVGAT

BPN'  181 DSSNQRASFS QYGPELDVMA PGVSIQSTLP GNKYGAYNGT SMASPHVAGA YPSVIAVGAV
GG36  175 DQNNNRASFS QYGAGLDIVA PGVNVQSTYP GSTYASLNGT SMATPHVAGA AALVKQKNPS

BPN'  241 WTNTQVRSSL ENTTTKLGDS FYYGKGLINV QAAAQ
GG36  235 WSNVQIRNHL KNTATSLGST NLYGSGLVNA EAATR
```

Fig. 5

SEQUENCE LISTING

<160> NUMBER OF SEQ ID NOS: 765

<210> SEQ ID NO 1
<211> LENGTH: 1146
<212> TYPE: DNA
<213> ORGANISM: Bacillus Amyloliquefaciens

<400> SEQUENCE: 1

```
gtgagaagca aaaaattgtg gatcagtttg ctgtttgctt tagcgttaat ctttacgatg     60

gcgttcggca gcacatcctc tgcccaggcg gcagggaaat caaacgggga aaagaaatat    120

attgtcgggt ttaaacagac aatgagcacg atgagcgccg ctaagaagaa agatgtcatt    180

tctgaaaaag gcgggaaagt gcaaaagcaa ttcaaatatg tagacgcagc ttcagctaca    240

ttaaacgaaa aagctgtaaa agaattgaaa aaagacccga gcgtcgctta cgttgaagaa    300

gatcacgtag cacatgcgta cgcgcagtcc gtgccttacg gcgtatcaca aattaaagcc    360

cctgctctgc actctcaagg ctacactgga tcaaatgtta aagtagcggt tatcgacagc    420

ggtatcgact cgagccatcc agatcttaaa gtcgctggag gggcttctat ggtgccgtcc    480

gaaacaaacc cgtttcaaga taacaattct catggcacac acgtcgcagg aacggttgcg    540

gcgttaaaca attctattgg cgtgcttggt gtagccccgt ctgcttcgct ctacgccgtt    600

aaagttcttg gcgcagacgg atcaggccaa tactcatgga ttatcaacgg catcgaatgg    660

gccatcgcga ataacatgga tgtaatcaac atgagcctgg gaggaccaag cggcagtgcg    720

gcacttaaag cagcagttga taaagctgtt gcatctggtg tcgtcgtagt agcggcagct    780

gggaatgagg gaacatccgg atcatcgagt accgtcggtt atccaggcaa gtacccttca    840

gtgattgcag tgggcgctgt agactcttca aatcaacgtg cctctttttc ctccgtggga    900

ccggagctgg atgtcatggc ccctggcgtt tctattcaat cgacgcttcc agggaacaag    960

tatggtgcgt ataacgggac ttccatggcc tcgccgcatg tagctggggc ggccgcattg   1020

attctttcta agcacccgaa ctggacaaac actcaagtcc gcagcagttt agaaaacacc   1080

actacaaaac ttggtgattc tttctactat ggaaaagggc tgatcaacgt acaggcggca   1140

gctcag                                                              1146
```

<210> SEQ ID NO 2
<211> LENGTH: 275
<212> TYPE: PRT
<213> ORGANISM: Bacillus Amyloliquefaciens

<400> SEQUENCE: 2

```
Ala Gln Ser Val Pro Tyr Gly Val Ser Gln Ile Lys Ala Pro Ala Leu
1               5                   10                  15

His Ser Gln Gly Tyr Thr Gly Ser Asn Val Lys Val Ala Val Ile Asp
            20                  25                  30

Ser Gly Ile Asp Ser Ser His Pro Asp Leu Lys Val Ala Gly Gly Ala
        35                  40                  45

Ser Met Val Pro Ser Glu Thr Asn Pro Phe Gln Asp Asn Asn Ser His
    50                  55                  60
```

```
Gly Thr His Val Ala Gly Thr Val Ala Ala Leu Asn Asn Ser Ile Gly
65                  70                  75                  80

Val Leu Gly Val Ala Pro Ser Ala Ser Leu Tyr Ala Val Lys Val Leu
                85                  90                  95

Gly Ala Asp Gly Ser Gly Gln Tyr Ser Trp Ile Ile Asn Gly Ile Glu
            100                 105                 110

Trp Ala Ile Ala Asn Asn Met Asp Val Ile Asn Met Ser Leu Gly Gly
        115                 120                 125

Pro Ser Gly Ser Ala Ala Leu Lys Ala Ala Val Asp Lys Ala Val Ala
    130                 135                 140

Ser Gly Val Val Val Val Ala Ala Ala Gly Asn Glu Gly Thr Ser Gly
145                 150                 155                 160

Ser Ser Ser Thr Val Gly Tyr Pro Gly Lys Tyr Pro Ser Val Ile Ala
                165                 170                 175

Val Gly Ala Val Asp Ser Ser Asn Gln Arg Ala Ser Phe Ser Ser Val
            180                 185                 190

Gly Pro Glu Leu Asp Val Met Ala Pro Gly Val Ser Ile Gln Ser Thr
        195                 200                 205

Leu Pro Gly Asn Lys Tyr Gly Ala Tyr Asn Gly Thr Ser Met Ala Ser
    210                 215                 220

Pro His Val Ala Gly Ala Ala Ala Leu Ile Leu Ser Lys His Pro Asn
225                 230                 235                 240

Trp Thr Asn Thr Gln Val Arg Ser Ser Leu Glu Asn Thr Thr Thr Lys
                245                 250                 255

Leu Gly Asp Ser Phe Tyr Tyr Gly Lys Gly Leu Ile Asn Val Gln Ala
            260                 265                 270

Ala Ala Gln
        275
```

<210> SEQ ID NO 3
<211> LENGTH: 825
<212> TYPE: DNA
<213> ORGANISM: Artificial sequence
<220> FEATURE:
<223> OTHER INFORMATION: Mutant of BPN'

<400> SEQUENCE: 3

```
gcgcagtccg tgccttacgg cgtatcacaa attaaagccc ctgctctgca ctctcaaggc      60

tacactggat caaatgttaa agtagcggtt atcgacagcg gtatcgactc gagccatcca     120

gatcttaaag tcgctggagg ggcttctatg gtgccgtccg aaacaaaccc gtttcaagat     180

aacaattctc atggcacaca cgtcgcagga acggttgcgg cgttaaacaa ttctattggc     240

gtgcttggtg tagccccgtc tgcttcgctc tacgccgtta aagttcttgc agcagacgga     300

tcaggccaat actcatggat tatcaacggc atcgaatggg ccatcgcgaa taacatggat     360

gtaatcaaca tgagcctggg agcaccaagc ggcagtgcgg cacttaaagc agcagttgat     420

aaagctgttg catctggtgt cgtcgtagta gcggcagctg ggaatgaggg aacatccgga     480

tcatcgagta ccgtcggtta tccaggcaag tacccttcag tgattgcagt gggcgctgta     540

gactcttcaa atcaacgtgc ctctttttcc tccgtgggac cggagctgga tgtcatggcc     600

cctggcgttt ctattcaatc gacgcttcca gggaacaagt atggtgcgca aaacgggact     660

tccatggcct cgccgcatgt agctggggcg gccgcattga ttctttctaa gcacccgaac     720

tggacaaaca ctcaagtccg cagcagttta gaaaacacca ctacaaaact tggtgattct     780
```

```
ttctactatg gaaaagggct gatcaacgta caggcggcag ctcag                825


<210> SEQ ID NO 4
<211> LENGTH: 275
<212> TYPE: PRT
<213> ORGANISM: Artificial Sequence
<220> FEATURE:
<223> OTHER INFORMATION: Mutant of subtilisin BPN'

<400> SEQUENCE: 4

Ala Gln Ser Val Pro Tyr Gly Val Ser Gln Ile Lys Ala Pro Ala Leu
1               5                   10                  15

His Ser Gln Gly Tyr Thr Gly Ser Asn Val Lys Val Ala Val Ile Asp
            20                  25                  30

Ser Gly Ile Asp Ser Ser His Pro Asp Leu Lys Val Ala Gly Gly Ala
        35                  40                  45

Ser Met Val Pro Ser Glu Thr Asn Pro Phe Gln Asp Asn Asn Ser His
    50                  55                  60

Gly Thr His Val Ala Gly Thr Val Ala Ala Leu Asn Asn Ser Ile Gly
65                  70                  75                  80

Val Leu Gly Val Ala Pro Ser Ala Ser Leu Tyr Ala Val Lys Val Leu
                85                  90                  95

Ala Ala Asp Gly Ser Gly Gln Tyr Ser Trp Ile Ile Asn Gly Ile Glu
            100                 105                 110

Trp Ala Ile Ala Asn Asn Met Asp Val Ile Asn Met Ser Leu Gly Ala
        115                 120                 125

Pro Ser Gly Ser Ala Ala Leu Lys Ala Ala Val Asp Lys Ala Val Ala
    130                 135                 140

Ser Gly Val Val Val Val Ala Ala Ala Gly Asn Glu Gly Thr Ser Gly
145                 150                 155                 160

Ser Ser Ser Thr Val Gly Tyr Pro Gly Lys Tyr Pro Ser Val Ile Ala
                165                 170                 175

Val Gly Ala Val Asp Ser Ser Asn Gln Arg Ala Ser Phe Ser Ser Val
            180                 185                 190

Gly Pro Glu Leu Asp Val Met Ala Pro Gly Val Ser Ile Gln Ser Thr
        195                 200                 205

Leu Pro Gly Asn Lys Tyr Gly Ala Gln Asn Gly Thr Ser Met Ala Ser
    210                 215                 220

Pro His Val Ala Gly Ala Ala Ala Leu Ile Leu Ser Lys His Pro Asn
225                 230                 235                 240

Trp Thr Asn Thr Gln Val Arg Ser Ser Leu Glu Asn Thr Thr Thr Lys
                245                 250                 255

Leu Gly Asp Ser Phe Tyr Tyr Gly Lys Gly Leu Ile Asn Val Gln Ala
            260                 265                 270

Ala Ala Gln
        275


<210> SEQ ID NO 5
<211> LENGTH: 825
<212> TYPE: DNA
<213> ORGANISM: Artificial Sequence
<220> FEATURE:
<223> OTHER INFORMATION: Mutant of subtilisisn BPN'

<400> SEQUENCE: 5

gcgcagtccg tgccttacgg cgtatcacaa attaaagccc ctgctctgca ctctcaaggc     60

tacactggag gcaatgttaa agtagcggtt atcgacagcg gtatcgactc gagccatcca    120
```

```
gatcttaaag tcgctggagg ggcttctatg gtgccgggcg aaacaaaccc gtttcaagat    180

aacaattctc atggcacaca cgtcgcagga acggttgcgg cgttaaacaa taatattggc    240

gtgcttggtg tagccccgtc tgcttcgctc tacgccgtta aagttcttgg cgcagacgga    300

aatggccaat actcatggat tatcaacggc atcgaatggg ccatcgcgaa taacatggat    360

gtaatcaaca tgagcctggg agcaccaagc ggcagtgcgg cacttaaagc agcagttgat    420

aaagctgttg catctggtgt cgtcgtagta gcggcagctg ggaatgaggg aacatccgga    480

tcatcgagta ccgtcggtta tccaggcaag tacccttcag tgattgcagt gggcgctgta    540

gactcttcaa atcaacgtgc ctctttttcc tccgtgggac cggagctgga tgtcatggcc    600

cctggcgttt ctattcaatc gacgcttcca gggaacaagt atggtgcgca aaacgggact    660

tccatggcct cgccgcatgt agctggggcg gccgcattga ttctttctaa gcacccgaac    720

tggacaaaca ctcaagtccg cagcagttta gaaaacacca ctacaaaact tggtgattct    780

ttctactatg gaaaagggct gatcaacgta caggcggcag ctcag                    825


<210> SEQ ID NO 6
<211> LENGTH: 275
<212> TYPE: PRT
<213> ORGANISM: Artificial Sequence
<220> FEATURE:
<223> OTHER INFORMATION: Mutant of subtilisin BPN'

<400> SEQUENCE: 6

Ala Gln Ser Val Pro Tyr Gly Val Ser Gln Ile Lys Ala Pro Ala Leu
1               5                   10                  15

His Ser Gln Gly Tyr Thr Gly Gly Asn Val Lys Val Ala Val Ile Asp
            20                  25                  30

Ser Gly Ile Asp Ser Ser His Pro Asp Leu Lys Val Ala Gly Gly Ala
        35                  40                  45

Ser Met Val Pro Gly Glu Thr Asn Pro Phe Gln Asp Asn Asn Ser His
    50                  55                  60

Gly Thr His Val Ala Gly Thr Val Ala Ala Leu Asn Asn Asn Ile Gly
65                  70                  75                  80

Val Leu Gly Val Ala Pro Ser Ala Ser Leu Tyr Ala Val Lys Val Leu
                85                  90                  95

Gly Ala Asp Gly Asn Gly Gln Tyr Ser Trp Ile Ile Asn Gly Ile Glu
            100                 105                 110

Trp Ala Ile Ala Asn Asn Met Asp Val Ile Asn Met Ser Leu Gly Ala
        115                 120                 125

Pro Ser Gly Ser Ala Ala Leu Lys Ala Ala Val Asp Lys Ala Val Ala
    130                 135                 140

Ser Gly Val Val Val Val Ala Ala Ala Gly Asn Glu Gly Thr Ser Gly
145                 150                 155                 160

Ser Ser Ser Thr Val Gly Tyr Pro Gly Lys Tyr Pro Ser Val Ile Ala
                165                 170                 175

Val Gly Ala Val Asp Ser Ser Asn Gln Arg Ala Ser Phe Ser Ser Val
            180                 185                 190

Gly Pro Glu Leu Asp Val Met Ala Pro Gly Val Ser Ile Gln Ser Thr
        195                 200                 205

Leu Pro Gly Asn Lys Tyr Gly Ala Gln Asn Gly Thr Ser Met Ala Ser
    210                 215                 220

Pro His Val Ala Gly Ala Ala Ala Leu Ile Leu Ser Lys His Pro Asn
225                 230                 235                 240
```

```
Trp Thr Asn Thr Gln Val Arg Ser Ser Leu Glu Asn Thr Thr Thr Lys
                245                 250                 255

Leu Gly Asp Ser Phe Tyr Tyr Gly Lys Gly Leu Ile Asn Val Gln Ala
            260                 265                 270

Ala Ala Gln
        275


<210> SEQ ID NO 7
<211> LENGTH: 825
<212> TYPE: DNA
<213> ORGANISM: Artificial Sequence
<220> FEATURE:
<223> OTHER INFORMATION: Mutant of subtilisin BPN'

<400> SEQUENCE: 7

gcgcagtccg tgccttacgg cgtatcacaa attaaagccc ctgctctgca ctctcaaggc      60

tacactggat caaatgttaa agtagcggtt atcgacagcg gtattgattc gagccatcca     120

gatcttaaag tcgctggagg ggcttctatg gtgccgtccg aaacaaaccc gtttcaagat     180

aacaattctc atggcacaca cgtcgcagga acggttgcgg cgttaaacaa taatattggc     240

gtgcttggtg tagccccgtc tgcttcgctc tacgccgtta aagttcttgc agcagacgga     300

tcaggccaat actcatggat tatcaacggc atcgaatggg ccatcgcgaa taacatggat     360

gtaatcaaca tgagcctggg agcaccaagc ggcagtgcgg cacttaaagc agcagttgat     420

aaagctgttg catctggtgt cgtcgtagta gcggcagctg ggaatgaggg aacatccgga     480

tcatcgagta ccgtcggtta tccaggcaag taccettcag tgattgcagt gggcgctgta     540

gactcttcaa atcaacgtgc ctctttttcc tccgtgggac cggagctgga tgtcatggcc     600

cctggcgttt ctattcaatc gacgcttcca gggaacaagt atggtgcgca aaacgggact     660

tccatggcct cgccgcatgt agctggggcg gccgcattga ttctttctaa gcacccgaac     720

tggacaaaca ctcaagtccg cagcagttta gaaaacacca ctacaaaact tggtgattct     780

ttctactatg gaaaagggct gatcaacgta caggcggcag ctcag                     825


<210> SEQ ID NO 8
<211> LENGTH: 275
<212> TYPE: PRT
<213> ORGANISM: Artificial Sequence
<220> FEATURE:
<223> OTHER INFORMATION: Mutant of subtilisin BPN'

<400> SEQUENCE: 8

Ala Gln Ser Val Pro Tyr Gly Val Ser Gln Ile Lys Ala Pro Ala Leu
1               5                   10                  15

His Ser Gln Gly Tyr Thr Gly Ser Asn Val Lys Val Ala Val Ile Asp
            20                  25                  30

Ser Gly Ile Asp Ser Ser His Pro Asp Leu Lys Val Ala Gly Gly Ala
        35                  40                  45

Ser Met Val Pro Ser Glu Thr Asn Pro Phe Gln Asp Asn Asn Ser His
    50                  55                  60

Gly Thr His Val Ala Gly Thr Val Ala Ala Leu Asn Asn Asn Ile Gly
65                  70                  75                  80

Val Leu Gly Val Ala Pro Ser Ala Ser Leu Tyr Ala Val Lys Val Leu
                85                  90                  95

Ala Ala Asp Gly Ser Gly Gln Tyr Ser Trp Ile Ile Asn Gly Ile Glu
            100                 105                 110
```

```
Trp Ala Ile Ala Asn Asn Met Asp Val Ile Asn Met Ser Leu Gly Ala
        115                 120                 125

Pro Ser Gly Ser Ala Ala Leu Lys Ala Ala Val Asp Lys Ala Val Ala
    130                 135                 140

Ser Gly Val Val Val Val Ala Ala Ala Gly Asn Glu Gly Thr Ser Gly
145                 150                 155                 160

Ser Ser Ser Thr Val Gly Tyr Pro Gly Lys Tyr Pro Ser Val Ile Ala
                165                 170                 175

Val Gly Ala Val Asp Ser Ser Asn Gln Arg Ala Ser Phe Ser Ser Val
            180                 185                 190

Gly Pro Glu Leu Asp Val Met Ala Pro Gly Val Ser Ile Gln Ser Thr
        195                 200                 205

Leu Pro Gly Asn Lys Tyr Gly Ala Gln Asn Gly Thr Ser Met Ala Ser
    210                 215                 220

Pro His Val Ala Gly Ala Ala Ala Leu Ile Leu Ser Lys His Pro Asn
225                 230                 235                 240

Trp Thr Asn Thr Gln Val Arg Ser Ser Leu Glu Asn Thr Thr Thr Lys
                245                 250                 255

Leu Gly Asp Ser Phe Tyr Tyr Gly Lys Gly Leu Ile Asn Val Gln Ala
            260                 265                 270

Ala Ala Gln
        275
```

<210> SEQ ID NO 9
<211> LENGTH: 828
<212> TYPE: DNA
<213> ORGANISM: Artificial Sequence
<220> FEATURE:
<223> OTHER INFORMATION: Mutant of subtilisin BPN'

<400> SEQUENCE: 9

```
gcgcagtccg tgccttacgg cgtatcacaa attaaagccc ctgctctgca ctctcaaggc      60

tacactggat caaatgttaa agtagcggtt atcgacagcg gtatcgactc gagccatcca     120

gatcttaaag tcgctggagg ggcttctatg gtgccgggag aaacaaaccc gtttcaagat     180

aacaattctc atggcacaca cgcagcagga acggttgcgg cgttaaacaa taatattggc     240

gtgcttggtg tagccccgtc tgcttcgctc tacgccgtta aagttcttgc agcagacgga     300

tcagcacaat actcatggat tatcaacggc atcgaatggg ccatcgcgaa taacatggat     360

gtaatcaaca tgagcctggg agcaacaagc ggcagtgcgg cacttaaagc agcagttgat     420

aaagctgttg catctggtgt cgtcgtagta gcggcagctg ggaatgaggg aacatccgga     480

tcatcgagta ccgtcggtta tccaggcaag tacccttcag tgattgcagt gggcgctgta     540

gactcttcaa atacacgtgc ctctttttcc tccgtgggac cggagctgga tgtcatggcc     600

cctggcgttt ctattcaatc gacgcttcca gggaacaagt atggtgcgca aaacgggact     660

tccatggcct cgccgcatgt agctggggcg gccgcattga ttctttctaa gcacccgaac     720

tggacaaaca ctcaagtccg cagcagttta gaaaacacca ctacaaaact tggtgattct     780

ttctactatg gaaaagggct gatcaacgta caggcggcag ctcagtaa                  828
```

<210> SEQ ID NO 10
<211> LENGTH: 275
<212> TYPE: PRT
<213> ORGANISM: Artificial Sequence
<220> FEATURE:
<223> OTHER INFORMATION: Mutant of subtilisin BPN'

<400> SEQUENCE: 10

Ala Gln Ser Val Pro Tyr Gly Val Ser Gln Ile Lys Ala Pro Ala Leu
1 5 10 15

His Ser Gln Gly Tyr Thr Gly Ser Asn Val Lys Val Ala Val Ile Asp
20 25 30

Ser Gly Ile Asp Ser Ser His Pro Asp Leu Lys Val Ala Gly Gly Ala
35 40 45

Ser Met Val Pro Gly Glu Thr Asn Pro Phe Gln Asp Asn Asn Ser His
50 55 60

Gly Thr His Ala Ala Gly Thr Val Ala Ala Leu Asn Asn Asn Ile Gly
65 70 75 80

Val Leu Gly Val Ala Pro Ser Ala Ser Leu Tyr Ala Val Lys Val Leu
85 90 95

Ala Ala Asp Gly Ser Ala Gln Tyr Ser Trp Ile Ile Asn Gly Ile Glu
100 105 110

Trp Ala Ile Ala Asn Asn Met Asp Val Ile Asn Met Ser Leu Gly Ala
115 120 125

Thr Ser Gly Ser Ala Ala Leu Lys Ala Ala Val Asp Lys Ala Val Ala
130 135 140

Ser Gly Val Val Val Val Ala Ala Ala Gly Asn Glu Gly Thr Ser Gly
145 150 155 160

Ser Ser Ser Thr Val Gly Tyr Pro Gly Lys Tyr Pro Ser Val Ile Ala
165 170 175

Val Gly Ala Val Asp Ser Ser Asn Thr Arg Ala Ser Phe Ser Ser Val
180 185 190

Gly Pro Glu Leu Asp Val Met Ala Pro Gly Val Ser Ile Gln Ser Thr
195 200 205

Leu Pro Gly Asn Lys Tyr Gly Ala Gln Asn Gly Thr Ser Met Ala Ser
210 215 220

Pro His Val Ala Gly Ala Ala Ala Leu Ile Leu Ser Lys His Pro Asn
225 230 235 240

Trp Thr Asn Thr Gln Val Arg Ser Ser Leu Glu Asn Thr Thr Thr Lys
245 250 255

Leu Gly Asp Ser Phe Tyr Tyr Gly Lys Gly Leu Ile Asn Val Gln Ala
260 265 270

Ala Ala Gln
275

<210> SEQ ID NO 11
<211> LENGTH: 828
<212> TYPE: DNA
<213> ORGANISM: Artificial Sequence
<220> FEATURE:
<223> OTHER INFORMATION: Mutant of subtilisin BPN'

<400> SEQUENCE: 11
gcgcagtccg tgccttacgg cgtatcacaa attaaagccc ctgctctgca ctctcaaggc 60
tacactggat caaatgttaa agtagcggtt atcgacagcg gtatcgactc gagccatcca 120
gatcttaaag tcgctggagg ggcttctatg gtgccgtccg aaacaaaccc gtttgtcgat 180
aacaattctc atggcacaca cgtcgcagga acggttgcgg cgttaaacaa taatattggc 240
gtgcttggtg tagccccgtc tgcttcgctc tacgccgtta aagttcttgc agcagacgga 300
tcaggccaat actcatggat tgtcaacggc atcgaatggg ccatcgcgaa taacatggat 360
gtaatcaaca tgagcctggg agcaccaagc ggcagtgcgg cacttaaagc agcagttgat 420

```
aaagctgttg catctggtca agtcgtagta gcggcagctg ggaatgaggg aacatccgga    480

tcatcgagta ccgtcggtta tccaggcaag taccettcag tgattgcagt gggcgctgta    540

gactcttcaa atcaacgtgc ctctttttcc tccgtgggac cggagctgga tgtcatggcc    600

cctggcgttt ctattcaatc gacgcttcca gcaaacaagt atggtgcgca aaacgggact    660

tccatggcct cgccgcatgt agctggggcg gccgcattga ttctttctaa gcacccgaac    720

tggacaaaca ctcaagtccg cagcagttta gaacaaacca ctacaaaact tggtgattct    780

ttctactatg gaaaagggct gatcaacgta caggcggcag ctcagtaa                828


<210> SEQ ID NO 12
<211> LENGTH: 275
<212> TYPE: PRT
<213> ORGANISM: Artificial Sequence
<220> FEATURE:
<223> OTHER INFORMATION: Mutant of subtilisin BPN'

<400> SEQUENCE: 12

Ala Gln Ser Val Pro Tyr Gly Val Ser Gln Ile Lys Ala Pro Ala Leu
1               5                   10                  15

His Ser Gln Gly Tyr Thr Gly Ser Asn Val Lys Val Ala Val Ile Asp
            20                  25                  30

Ser Gly Ile Asp Ser Ser His Pro Asp Leu Lys Val Ala Gly Gly Ala
        35                  40                  45

Ser Met Val Pro Ser Glu Thr Asn Pro Phe Val Asp Asn Asn Ser His
    50                  55                  60

Gly Thr His Val Ala Gly Thr Val Ala Ala Leu Asn Asn Asn Ile Gly
65                  70                  75                  80

Val Leu Gly Val Ala Pro Ser Ala Ser Leu Tyr Ala Val Lys Val Leu
                85                  90                  95

Ala Ala Asp Gly Ser Gly Gln Tyr Ser Trp Ile Val Asn Gly Ile Glu
            100                 105                 110

Trp Ala Ile Ala Asn Asn Met Asp Val Ile Asn Met Ser Leu Gly Ala
        115                 120                 125

Pro Ser Gly Ser Ala Ala Leu Lys Ala Ala Val Asp Lys Ala Val Ala
    130                 135                 140

Ser Gly Gln Val Val Val Ala Ala Ala Gly Asn Glu Gly Thr Ser Gly
145                 150                 155                 160

Ser Ser Ser Thr Val Gly Tyr Pro Gly Lys Tyr Pro Ser Val Ile Ala
                165                 170                 175

Val Gly Ala Val Asp Ser Ser Asn Gln Arg Ala Ser Phe Ser Ser Val
            180                 185                 190

Gly Pro Glu Leu Asp Val Met Ala Pro Gly Val Ser Ile Gln Ser Thr
        195                 200                 205

Leu Pro Ala Asn Lys Tyr Gly Ala Gln Asn Gly Thr Ser Met Ala Ser
    210                 215                 220

Pro His Val Ala Gly Ala Ala Ala Leu Ile Leu Ser Lys His Pro Asn
225                 230                 235                 240

Trp Thr Asn Thr Gln Val Arg Ser Ser Leu Glu Gln Thr Thr Thr Lys
                245                 250                 255

Leu Gly Asp Ser Phe Tyr Tyr Gly Lys Gly Leu Ile Asn Val Gln Ala
            260                 265                 270

Ala Ala Gln
        275
```

<210> SEQ ID NO 13
<211> LENGTH: 828
<212> TYPE: DNA
<213> ORGANISM: Artificial Sequence
<220> FEATURE:
<223> OTHER INFORMATION: Mutant of subtilisin BPN'

<400> SEQUENCE: 13
gcgcagtccg tgccttacgg cgtatcacaa attaaagccc ctgctctgca ctctcaaggc 60
tacactggat caaatgttaa agtagcggtt atcgacagcg gtatcgactc gagccatcca 120
gatcttaaag tcgctggagg ggcttctatg gtgccgtccg aaacaaaccc gtttcaagat 180
gcaaattctc atggcacaca cgtcgcagga acggttgcgg cgttaaacaa taatattggc 240
gtgcttggtg tagccccgga agcttcgctc tacgccgtta aagttcttgc agcagacgga 300
tcaggccaat actcatggat tatcaacggc atcgaatggg ccatcgcgaa taacatggat 360
gtaatcaaca tcagcctggg agcaccaagc ggcagtgcgg cacttaaagc agcagttgat 420
aaagctgttg catctggtgt cgtcgtagta gcggcagctg ggaatgaggg aacatccgga 480
ccttcgagta ccgtcggtta tccaggcaag tacccttcag tgattgcagt gggcgctgta 540
gactcttcaa atcaacgtgc ctctttttcc tccgtgggac cggagctgga tgtcatggcc 600
cctggcgttt ctattcaatc gacgcttcca gggaacaagt atggtgcgca aaacgggact 660
tccatggccg caccgcatgt agctggggcg gccgcattga ttctttctaa gcacccgaac 720
tggacaaaca ctcaagtccg cagcagttta gaaaacacca ctacaaaact tggtgattct 780
ttctactatg gaaaagggct gatcaacgta caggcggcag ctcagtaa 828

<210> SEQ ID NO 14
<211> LENGTH: 275
<212> TYPE: PRT
<213> ORGANISM: Artificial Sequence
<220> FEATURE:
<223> OTHER INFORMATION: Mutant of subtilisn BPN'

<400> SEQUENCE: 14

Ala Gln Ser Val Pro Tyr Gly Val Ser Gln Ile Lys Ala Pro Ala Leu
1 5 10 15

His Ser Gln Gly Tyr Thr Gly Ser Asn Val Lys Val Ala Val Ile Asp
20 25 30

Ser Gly Ile Asp Ser Ser His Pro Asp Leu Lys Val Ala Gly Gly Ala
35 40 45

Ser Met Val Pro Ser Glu Thr Asn Pro Phe Gln Asp Ala Asn Ser His
50 55 60

Gly Thr His Val Ala Gly Thr Val Ala Ala Leu Asn Asn Asn Ile Gly
65 70 75 80

Val Leu Gly Val Ala Pro Glu Ala Ser Leu Tyr Ala Val Lys Val Leu
85 90 95

Ala Ala Asp Gly Ser Gly Gln Tyr Ser Trp Ile Ile Asn Gly Ile Glu
100 105 110

Trp Ala Ile Ala Asn Asn Met Asp Val Ile Asn Ile Ser Leu Gly Ala
115 120 125

Pro Ser Gly Ser Ala Ala Leu Lys Ala Ala Val Asp Lys Ala Val Ala
130 135 140

Ser Gly Val Val Val Val Ala Ala Ala Gly Asn Glu Gly Thr Ser Gly
145 150 155 160

Pro Ser Ser Thr Val Gly Tyr Pro Gly Lys Tyr Pro Ser Val Ile Ala

```
                165                 170                 175

Val Gly Ala Val Asp Ser Ser Asn Gln Arg Ala Ser Phe Ser Ser Val
            180                 185                 190

Gly Pro Glu Leu Asp Val Met Ala Pro Gly Val Ser Ile Gln Ser Thr
        195                 200                 205

Leu Pro Gly Asn Lys Tyr Gly Ala Gln Asn Gly Thr Ser Met Ala Ala
    210                 215                 220

Pro His Val Ala Gly Ala Ala Ala Leu Ile Leu Ser Lys His Pro Asn
225                 230                 235                 240

Trp Thr Asn Thr Gln Val Arg Ser Ser Leu Glu Asn Thr Thr Thr Lys
                245                 250                 255

Leu Gly Asp Ser Phe Tyr Tyr Gly Lys Gly Leu Ile Asn Val Gln Ala
            260                 265                 270

Ala Ala Gln
        275
```

<210> SEQ ID NO 15
<211> LENGTH: 828
<212> TYPE: DNA
<213> ORGANISM: Artificial Sequence
<220> FEATURE:
<223> OTHER INFORMATION: Mutant of subtilisin BPN'

<400> SEQUENCE: 15

```
gcgcagtccg tgccttacgg cgtatcacaa attaaagccc ctgctctgca ctctcaaggc      60

tacactggat caaatgttaa agtagcggtt atcgacagcg gtatcgactc gagccatcca     120

gatcttaaag tcgctggagg ggcttctatg gtgccgtccg aaacaaaccc gtttcaagat     180

aaccaatctc atggcacaca cgtcgcagga acggttgcgg cgttaaacaa taatattggc     240

gtgcttggtg tagccccgtc tgcttcgctc tacgccgtta aagttcttgc agcagacaac     300

tcaggccaat actcatggat tatcaacggc atcgaatggg ccatcgcgaa taacatggat     360

gtaatcaaca tggcactggg agcaccaagc ggcagtgcgg cacttaaagc agcagttgat     420

aaagctgttg catctggtgt cgtcgtagta gcggcagctg ggaatgaggg aacagatgga     480

tcatcgagta ccgtcggtta tccaggcaag tacccttcag tgattgcagt gggcgctgta     540

gactcttcaa atcaacgtgc ctctttttcc tccgtgggac cggagctgga tgtcatggcc     600

cctggcgttt ctattcaatc gacgcttcca gggaacaagt atggtgcgca aaacgggact     660

tccatggcct cgccgcatgt agctggggcg gccgcattga ttctttctaa gcacccgtca     720

tggacaaaca ctcaagtccg cagcagttta gaaaacacca ctacaaaact tggtgattct     780

ttctactatg gaaaagggct gatcaacgta caggcggcag ctcagtaa                  828
```

<210> SEQ ID NO 16
<211> LENGTH: 275
<212> TYPE: PRT
<213> ORGANISM: Artificial Sequence
<220> FEATURE:
<223> OTHER INFORMATION: Mutant of subtilisin BPN'

<400> SEQUENCE: 16

```
Ala Gln Ser Val Pro Tyr Gly Val Ser Gln Ile Lys Ala Pro Ala Leu
1               5                   10                  15

His Ser Gln Gly Tyr Thr Gly Ser Asn Val Lys Val Ala Val Ile Asp
            20                  25                  30

Ser Gly Ile Asp Ser Ser His Pro Asp Leu Lys Val Ala Gly Gly Ala
        35                  40                  45
```

Ser Met Val Pro Ser Glu Thr Asn Pro Phe Gln Asp Asn Gln Ser His
    50                  55                  60

Gly Thr His Val Ala Gly Thr Val Ala Ala Leu Asn Asn Asn Ile Gly
65                  70                  75                  80

Val Leu Gly Val Ala Pro Ser Ala Ser Leu Tyr Ala Val Lys Val Leu
                85                  90                  95

Ala Ala Asp Asn Ser Gly Gln Tyr Ser Trp Ile Ile Asn Gly Ile Glu
            100                 105                 110

Trp Ala Ile Ala Asn Asn Met Asp Val Ile Asn Met Ala Leu Gly Ala
        115                 120                 125

Pro Ser Gly Ser Ala Ala Leu Lys Ala Ala Val Asp Lys Ala Val Ala
    130                 135                 140

Ser Gly Val Val Val Val Ala Ala Ala Gly Asn Glu Gly Thr Asp Gly
145                 150                 155                 160

Ser Ser Ser Thr Val Gly Tyr Pro Gly Lys Tyr Pro Ser Val Ile Ala
                165                 170                 175

Val Gly Ala Val Asp Ser Ser Asn Gln Arg Ala Ser Phe Ser Ser Val
            180                 185                 190

Gly Pro Glu Leu Asp Val Met Ala Pro Gly Val Ser Ile Gln Ser Thr
        195                 200                 205

Leu Pro Gly Asn Lys Tyr Gly Ala Gln Asn Gly Thr Ser Met Ala Ser
    210                 215                 220

Pro His Val Ala Gly Ala Ala Ala Leu Ile Leu Ser Lys His Pro Ser
225                 230                 235                 240

Trp Thr Asn Thr Gln Val Arg Ser Ser Leu Glu Asn Thr Thr Thr Lys
                245                 250                 255

Leu Gly Asp Ser Phe Tyr Tyr Gly Lys Gly Leu Ile Asn Val Gln Ala
            260                 265                 270

Ala Ala Gln
        275

<210> SEQ ID NO 17
<211> LENGTH: 828
<212> TYPE: DNA
<213> ORGANISM: Artificial Sequence
<220> FEATURE:
<223> OTHER INFORMATION: Mutant of subtilisin BPN'

<400> SEQUENCE: 17
gcgcagtccg tgccttacgg cgtatcacaa attaaagccc ctgctctgca ctctcaaggc 60
tacactggat caaatgttaa agtagcggtt atcgacagcg gtatcgactc gagccatcca 120
gatcttaaag tcgctggagg ggcttctatg gtgccgtccg aaacaaaccc gtttcaagat 180
aacaatacac atggcacaca cgtcgcagga acggttgcgg cgttaaacaa taatattggc 240
gtgcttggtg tagccccgtc tgcttcgctc tacgccgtta aagttcttgc agcagacgga 300
gcaggccaat actcatggat tatcaacggc atcgaatggg ccatcgcgaa taacatggat 360
gtaatcaaca tgagcgtcgg agcaccaagc ggcagtgcgg cacttaaagc agcagttgat 420
aaagctgttg catctggtgt cgtcgtagta gcggcagctg ggaatgaggg aacatccgga 480
tcatcgagta ccgtcggtta tccaggcaag tacccttcag tgattgcagt gggcgctgta 540
gactctacaa atcaacgtgc ctctttttcc tccgtgggac cggagctgga tgtcatggcc 600
cctggcgttt ctattcaatc gacgcttcca gggaacaagt atggtgcgca aaacgggact 660
tccatggcct cgccgcatgt agctggggcg gccgcattga ttctttctaa gcacccgaac 720

-continued tggacaaaca accaagtccg cagcagttta gaaaacacca ctacaaaact tggtgattct 780
ttctactatg gaaaagggct gatcaacgta caggcggcag ctcagtaa 828

<210> SEQ ID NO 18
<211> LENGTH: 275
<212> TYPE: PRT
<213> ORGANISM: Artificial Sequence
<220> FEATURE:
<223> OTHER INFORMATION: Mutant of subtilisin BPN'

<400> SEQUENCE: 18

```
Ala Gln Ser Val Pro Tyr Gly Val Ser Gln Ile Lys Ala Pro Ala Leu
1               5                   10                  15

His Ser Gln Gly Tyr Thr Gly Ser Asn Val Lys Val Ala Val Ile Asp
            20                  25                  30

Ser Gly Ile Asp Ser Ser His Pro Asp Leu Lys Val Ala Gly Gly Ala
        35                  40                  45

Ser Met Val Pro Ser Glu Thr Asn Pro Phe Gln Asp Asn Asn Thr His
    50                  55                  60

Gly Thr His Val Ala Gly Thr Val Ala Ala Leu Asn Asn Asn Ile Gly
65                  70                  75                  80

Val Leu Gly Val Ala Pro Ser Ala Ser Leu Tyr Ala Val Lys Val Leu
                85                  90                  95

Ala Ala Asp Gly Ala Gly Gln Tyr Ser Trp Ile Ile Asn Gly Ile Glu
            100                 105                 110

Trp Ala Ile Ala Asn Asn Met Asp Val Ile Asn Met Ser Val Gly Ala
        115                 120                 125

Pro Ser Gly Ser Ala Ala Leu Lys Ala Ala Val Asp Lys Ala Val Ala
    130                 135                 140

Ser Gly Val Val Val Val Ala Ala Ala Gly Asn Glu Gly Thr Ser Gly
145                 150                 155                 160

Ser Ser Ser Thr Val Gly Tyr Pro Gly Lys Tyr Pro Ser Val Ile Ala
                165                 170                 175

Val Gly Ala Val Asp Ser Thr Asn Gln Arg Ala Ser Phe Ser Ser Val
            180                 185                 190

Gly Pro Glu Leu Asp Val Met Ala Pro Gly Val Ser Ile Gln Ser Thr
        195                 200                 205

Leu Pro Gly Asn Lys Tyr Gly Ala Gln Asn Gly Thr Ser Met Ala Ser
    210                 215                 220

Pro His Val Ala Gly Ala Ala Ala Leu Ile Leu Ser Lys His Pro Asn
225                 230                 235                 240

Trp Thr Asn Asn Gln Val Arg Ser Ser Leu Glu Asn Thr Thr Thr Lys
                245                 250                 255

Leu Gly Asp Ser Phe Tyr Tyr Gly Lys Gly Leu Ile Asn Val Gln Ala
            260                 265                 270

Ala Ala Gln
        275
```

<210> SEQ ID NO 19
<211> LENGTH: 828
<212> TYPE: DNA
<213> ORGANISM: Artificial Sequence
<220> FEATURE:
<223> OTHER INFORMATION: Mutant of subtilisin BPN'

<400> SEQUENCE: 19

```
gcgcagtccg tgccttacgg cgtatcacaa attaaagccc ctgctctgca ctctcaaggc     60

tacactggat caaatgttaa agtagcggtt atcgacagcg gtatcgactc gagccatctg    120

gatcttaaag tcgctggagg ggcttctatg gtgccgggag aaacaaaccc gtttgtcgat    180

gcacaaacac atggcacaca cgtcgcagga acggttgcgg cgttaaacaa taatattggc    240

gtgcttggtg tagccccgga agcttcgctc tacgccgtta aagttcttgc agcagacaac    300

gcagcacaat actcatggat tgtcaacggc atcgaatggg ccatcgcgaa taacatggat    360

gtaatcaaca tgagcctggg agcaccaagc ggcagtgcgg cacttaaagc agcagttgat    420

aaagctgttg catctggtgt cgtcgtagta gcggcagctg ggaatgaggg aacatccgga    480

tcatcgagta ccgtcggtta tccaggcaag tacccttcag tgattgcagt gggcgctgta    540

gactcttcaa atcaacgtgc ctctttttcc tccgtgggac cggagctgga tgtcatggcc    600

cctggcgttt ctattcaatc gacgcttcca gggaacaagt atggtgcgca aaacgggact    660

tccatggcct cgccgcatgt agctggggcg gccgcattga ttctttctaa gcacccgaac    720

tggacaaaca ctcaagtccg cagcagttta gaaaacacca ctacaaaact tggtgattct    780

ttctactatg gaaaagggct gatcaacgta caggcggcag ctcagtaa                 828
```

```
<210> SEQ ID NO 20
<211> LENGTH: 275
<212> TYPE: PRT
<213> ORGANISM: Artificial Sequence
<220> FEATURE:
<223> OTHER INFORMATION: Mutant of subtilisin BPN'

<400> SEQUENCE: 20

Ala Gln Ser Val Pro Tyr Gly Val Ser Gln Ile Lys Ala Pro Ala Leu
1               5                   10                  15

His Ser Gln Gly Tyr Thr Gly Ser Asn Val Lys Val Ala Val Ile Asp
            20                  25                  30

Ser Gly Ile Asp Ser Ser His Leu Asp Leu Lys Val Ala Gly Gly Ala
        35                  40                  45

Ser Met Val Pro Gly Glu Thr Asn Pro Phe Val Asp Ala Gln Thr His
    50                  55                  60

Gly Thr His Val Ala Gly Thr Val Ala Ala Leu Asn Asn Asn Ile Gly
65                  70                  75                  80

Val Leu Gly Val Ala Pro Glu Ala Ser Leu Tyr Ala Val Lys Val Leu
                85                  90                  95

Ala Ala Asp Asn Ala Ala Gln Tyr Ser Trp Ile Val Asn Gly Ile Glu
            100                 105                 110

Trp Ala Ile Ala Asn Asn Met Asp Val Ile Asn Met Ser Leu Gly Ala
        115                 120                 125

Pro Ser Gly Ser Ala Ala Leu Lys Ala Ala Val Asp Lys Ala Val Ala
    130                 135                 140

Ser Gly Val Val Val Val Ala Ala Ala Gly Asn Glu Gly Thr Ser Gly
145                 150                 155                 160

Ser Ser Ser Thr Val Gly Tyr Pro Gly Lys Tyr Pro Ser Val Ile Ala
                165                 170                 175

Val Gly Ala Val Asp Ser Ser Asn Gln Arg Ala Ser Phe Ser Ser Val
            180                 185                 190

Gly Pro Glu Leu Asp Val Met Ala Pro Gly Val Ser Ile Gln Ser Thr
        195                 200                 205

Leu Pro Gly Asn Lys Tyr Gly Ala Gln Asn Gly Thr Ser Met Ala Ser
    210                 215                 220
```

Pro His Val Ala Gly Ala Ala Ala Leu Ile Leu Ser Lys His Pro Asn
225 230 235 240

Trp Thr Asn Thr Gln Val Arg Ser Ser Leu Glu Asn Thr Thr Thr Lys
245 250 255

Leu Gly Asp Ser Phe Tyr Tyr Gly Lys Gly Leu Ile Asn Val Gln Ala
260 265 270

Ala Ala Gln
275

<210> SEQ ID NO 21
<211> LENGTH: 828
<212> TYPE: DNA
<213> ORGANISM: Artificial Sequence
<220> FEATURE:
<223> OTHER INFORMATION: Mutant of subtilisin BPN'

<400> SEQUENCE: 21
gcgcagtccg tgccttacgg cgtatcacaa attaaagccc ctgctctgca ctctcaaggc 60
tacactggat caaatgttaa agtagcggtt atcgacagcg gtatcgactc gagccatcca 120
gatcttaaag tcgctggagg ggcttctatg gtgccgtccg aaacaaaccc gtttcaagat 180
aacaattctc atggcacaca cgtcgcagga acggttgcgg cgttaaacaa taatattggc 240
gtgcttggtg tagccccgtc tgcttcgctc tacgccgtta aagttcttgc agcagacgga 300
tcaggccaat actcatggat tatcaacggc atcgaatggg ccatcgcgaa taacatggat 360
gtaatcaaca tgagcctggg agcaacaagc ggcagtgcgg cacttaaagc agcagttgat 420
aaagctgttg catctggtca agtcgtagta gcggcagctg ggaatgaggg aacagatgga 480
ccttcgagta ccgtcggtta tccaggcaag tacccttcag tgattgcagt gggcgctgta 540
gactctacaa atacacgtgc ctctttttcc tccgtgggac cggagctgga tgtcatggcc 600
cctggcgttt ctattcaatc gacgcttcca gcaaacaagt atggtgcgca aaacgggact 660
tccatggccg caccgcatgt agctggggcg gccgcattga ttctttctaa gcacccgtca 720
tggacaaaca accaagtccg cagcagttta gaacaaacca ctacaaaact tggtgattct 780
ttctactatg gaaaagggct gatcaacgta caggcggcag ctcagtaa 828

<210> SEQ ID NO 22
<211> LENGTH: 275
<212> TYPE: PRT
<213> ORGANISM: Artificial Sequence
<220> FEATURE:
<223> OTHER INFORMATION: Mutant of subtilisin BPN'

<400> SEQUENCE: 22

Ala Gln Ser Val Pro Tyr Gly Val Ser Gln Ile Lys Ala Pro Ala Leu
1 5 10 15

His Ser Gln Gly Tyr Thr Gly Ser Asn Val Lys Val Ala Val Ile Asp
20 25 30

Ser Gly Ile Asp Ser Ser His Pro Asp Leu Lys Val Ala Gly Gly Ala
35 40 45

Ser Met Val Pro Ser Glu Thr Asn Pro Phe Gln Asp Asn Asn Ser His
50 55 60

Gly Thr His Val Ala Gly Thr Val Ala Ala Leu Asn Asn Asn Ile Gly
65 70 75 80

Val Leu Gly Val Ala Pro Ser Ala Ser Leu Tyr Ala Val Lys Val Leu
85 90 95

```
Ala Ala Asp Gly Ser Gly Gln Tyr Ser Trp Ile Ile Asn Gly Ile Glu
            100                 105                 110

Trp Ala Ile Ala Asn Asn Met Asp Val Ile Asn Met Ser Leu Gly Ala
        115                 120                 125

Thr Ser Gly Ser Ala Ala Leu Lys Ala Ala Val Asp Lys Ala Val Ala
    130                 135                 140

Ser Gly Gln Val Val Val Ala Ala Ala Gly Asn Glu Gly Thr Asp Gly
145                 150                 155                 160

Pro Ser Ser Thr Val Gly Tyr Pro Gly Lys Tyr Pro Ser Val Ile Ala
                165                 170                 175

Val Gly Ala Val Asp Ser Thr Asn Thr Arg Ala Ser Phe Ser Ser Val
            180                 185                 190

Gly Pro Glu Leu Asp Val Met Ala Pro Gly Val Ser Ile Gln Ser Thr
        195                 200                 205

Leu Pro Ala Asn Lys Tyr Gly Ala Gln Asn Gly Thr Ser Met Ala Ala
    210                 215                 220

Pro His Val Ala Gly Ala Ala Ala Leu Ile Leu Ser Lys His Pro Ser
225                 230                 235                 240

Trp Thr Asn Asn Gln Val Arg Ser Ser Leu Glu Gln Thr Thr Thr Lys
                245                 250                 255

Leu Gly Asp Ser Phe Tyr Tyr Gly Lys Gly Leu Ile Asn Val Gln Ala
            260                 265                 270

Ala Ala Gln
        275
```

<210> SEQ ID NO 23
<211> LENGTH: 828
<212> TYPE: DNA
<213> ORGANISM: Artificial Sequence
<220> FEATURE:
<223> OTHER INFORMATION: Mutant of subtilisin BPN'

<400> SEQUENCE: 23

```
gcgcagtccg tgccttacgg cgtatcacaa attaaagccc ctgctctgca ctctcaaggc      60

tacactggat caaatgttaa agtagcggtt atcgacagcg gtatcgactc gagccatcca     120

gatcttaaag tcgctggagg ggcttctatg gtgccgtccg aaacaaaccc gtttcaagat     180

aacaattctc atggcacaca cgcagcagga acggttgcgg cgttaaacaa taatattggc     240

gtgcttggtg tagccccgtc tgcttcgctc tacgccgtta aagttcttgc agcagacgga     300

tcagcacaat actcatggat tatcaacggc atcgaatggg ccatcgcgaa taacatggat     360

gtaatcaaca tggcactggg agcaccaagc ggcagtgcgg cacttaaagc agcagttgat     420

aaagctgttg catctggtgt cgtcgtagta gcggcagctg ggaatgaggg aacatccgga     480

tcatcgagta ccgtcggtta tccaggcaag tacccttcag tgattgcagt gggcgctgta     540

gactcttcaa atcaacgtgc ctctttttcc tccgtgggac cggagctgga tgtcatggcc     600

cctggcgttt ctattcaatc gacgcttcca gcaaacaagt atggtgcgca aaacgggact     660

tccatggcct cgccgcatgt agctggggcg gccgcattga ttctttctaa gcacccgaac     720

tggacaaaca ctcaagtccg cagcagttta gaaaacacca ctacaaaact tggtgattct     780

ttctactatg gaaaagggct gatcaacgta caggcggcag ctcagtaa                  828
```

<210> SEQ ID NO 24
<211> LENGTH: 275
<212> TYPE: PRT
<213> ORGANISM: Artificial Sequence
<220> FEATURE:
<223> OTHER INFORMATION: Mutant of subtilisin BPN'

<400> SEQUENCE: 24

```
Ala Gln Ser Val Pro Tyr Gly Val Ser Gln Ile Lys Ala Pro Ala Leu
1               5                   10                  15

His Ser Gln Gly Tyr Thr Gly Ser Asn Val Lys Val Ala Val Ile Asp
            20                  25                  30

Ser Gly Ile Asp Ser Ser His Pro Asp Leu Lys Val Ala Gly Gly Ala
        35                  40                  45

Ser Met Val Pro Ser Glu Thr Asn Pro Phe Gln Asp Asn Asn Ser His
    50                  55                  60

Gly Thr His Ala Ala Gly Thr Val Ala Ala Leu Asn Asn Asn Ile Gly
65                  70                  75                  80

Val Leu Gly Val Ala Pro Ser Ala Ser Leu Tyr Ala Val Lys Val Leu
                85                  90                  95

Ala Ala Asp Gly Ser Ala Gln Tyr Ser Trp Ile Ile Asn Gly Ile Glu
            100                 105                 110

Trp Ala Ile Ala Asn Asn Met Asp Val Ile Asn Met Ala Leu Gly Ala
        115                 120                 125

Pro Ser Gly Ser Ala Ala Leu Lys Ala Ala Val Asp Lys Ala Val Ala
    130                 135                 140

Ser Gly Val Val Val Val Ala Ala Ala Gly Asn Glu Gly Thr Ser Gly
145                 150                 155                 160

Ser Ser Ser Thr Val Gly Tyr Pro Gly Lys Tyr Pro Ser Val Ile Ala
                165                 170                 175

Val Gly Ala Val Asp Ser Ser Asn Gln Arg Ala Ser Phe Ser Ser Val
            180                 185                 190

Gly Pro Glu Leu Asp Val Met Ala Pro Gly Val Ser Ile Gln Ser Thr
        195                 200                 205

Leu Pro Ala Asn Lys Tyr Gly Ala Gln Asn Gly Thr Ser Met Ala Ser
    210                 215                 220

Pro His Val Ala Gly Ala Ala Ala Leu Ile Leu Ser Lys His Pro Asn
225                 230                 235                 240

Trp Thr Asn Thr Gln Val Arg Ser Ser Leu Glu Asn Thr Thr Thr Lys
                245                 250                 255

Leu Gly Asp Ser Phe Tyr Tyr Gly Lys Gly Leu Ile Asn Val Gln Ala
            260                 265                 270

Ala Ala Gln
        275
```

<210> SEQ ID NO 25
<211> LENGTH: 36
<212> TYPE: DNA
<213> ORGANISM: Artificial Sequence
<220> FEATURE:
<223> OTHER INFORMATION: Primer

<400> SEQUENCE: 25
cttctatggt gccgtccgaa acaaacccgt ttcaag 36

<210> SEQ ID NO 26
<211> LENGTH: 34
<212> TYPE: DNA
<213> ORGANISM: Artificial Sequence
<220> FEATURE:
<223> OTHER INFORMATION: Primer

<400> SEQUENCE: 26
tcatggcaca cacgtcgcag gaacggttgc ggcg 34

<210> SEQ ID NO 27
<211> LENGTH: 37
<212> TYPE: DNA
<213> ORGANISM: Artificial Sequence
<220> FEATURE:
<223> OTHER INFORMATION: Primer

<400> SEQUENCE: 27
agcagacgga tcaggccaat actcatggat tatcaac 37

<210> SEQ ID NO 28
<211> LENGTH: 39
<212> TYPE: DNA
<213> ORGANISM: Artificial Sequence
<220> FEATURE:
<223> OTHER INFORMATION: Primer

<400> SEQUENCE: 28
tgagcctggg agcaccaagc ggcagtgcgg cacttaaag 39

<210> SEQ ID NO 29
<211> LENGTH: 38
<212> TYPE: DNA
<213> ORGANISM: Artificial Sequence
<220> FEATURE:
<223> OTHER INFORMATION: Primer

<400> SEQUENCE: 29
tagactcttc aaatcaacgt gcctcttttt cctccgtg 38

<210> SEQ ID NO 30
<211> LENGTH: 34
<212> TYPE: DNA
<213> ORGANISM: Artificial Sequence
<220> FEATURE:
<223> OTHER INFORMATION: Primer

<400> SEQUENCE: 30
gaaacaaacc cgtttcaaga taacaattct catg 34

<210> SEQ ID NO 31
<211> LENGTH: 37
<212> TYPE: DNA
<213> ORGANISM: Artificial Sequence
<220> FEATURE:
<223> OTHER INFORMATION: Primer

<400> SEQUENCE: 31
atactcatgg attatcaacg gcatcgaatg ggccatc 37

<210> SEQ ID NO 32
<211> LENGTH: 36
<212> TYPE: DNA
<213> ORGANISM: Artificial Sequence
<220> FEATURE:
<223> OTHER INFORMATION: Primer

<400> SEQUENCE: 32
tgttgcatct ggtgtcgtcg tagtagcggc agctgg 36

<210> SEQ ID NO 33
<211> LENGTH: 37

<212> TYPE: DNA
<213> ORGANISM: Artificial Sequence
<220> FEATURE:
<223> OTHER INFORMATION: Primer

<400> SEQUENCE: 33
atcgacgctt ccagggaaca agtatggtgc gcaaaac 37

<210> SEQ ID NO 34
<211> LENGTH: 35
<212> TYPE: DNA
<213> ORGANISM: Artificial Sequence
<220> FEATURE:
<223> OTHER INFORMATION: Primer

<400> SEQUENCE: 34
cagcagttta gaaaacacca ctacaaaact tggtg 35

<210> SEQ ID NO 35
<211> LENGTH: 38
<212> TYPE: DNA
<213> ORGANISM: Artificial Sequence
<220> FEATURE:
<223> OTHER INFORMATION: Primer

<400> SEQUENCE: 35
caaacccgtt tcaagataac aattctcatg gcacacac 38

<210> SEQ ID NO 36
<211> LENGTH: 39
<212> TYPE: DNA
<213> ORGANISM: Artificial Sequence
<220> FEATURE:
<223> OTHER INFORMATION: Primer

<400> SEQUENCE: 36
ttggtgtagc cccgtctgct tcgctctacg ccgttaaag 39

<210> SEQ ID NO 37
<211> LENGTH: 36
<212> TYPE: DNA
<213> ORGANISM: Artificial Sequence
<220> FEATURE:
<223> OTHER INFORMATION: Primer

<400> SEQUENCE: 37
tggatgtaat caacatgagc ctgggagcac caagcg 36

<210> SEQ ID NO 38
<211> LENGTH: 39
<212> TYPE: DNA
<213> ORGANISM: Artificial Sequence
<220> FEATURE:
<223> OTHER INFORMATION: Primer

<400> SEQUENCE: 38
agggaacatc cggatcatcg agtaccgtcg gttatccag 39

<210> SEQ ID NO 39
<211> LENGTH: 36
<212> TYPE: DNA
<213> ORGANISM: Artificial Sequence
<220> FEATURE:
<223> OTHER INFORMATION: Primer

<400> SEQUENCE: 39

-continued gacttccatg gcctcgccgc atgtagctgg ggcggc 36

<210> SEQ ID NO 40
<211> LENGTH: 36
<212> TYPE: DNA
<213> ORGANISM: Artificial Sequence
<220> FEATURE:
<223> OTHER INFORMATION: Primer

<400> SEQUENCE: 40
gtttcaagat aacaattctc atggcacaca cgtcgc 36

<210> SEQ ID NO 41
<211> LENGTH: 35
<212> TYPE: DNA
<213> ORGANISM: Artificial Sequence
<220> FEATURE:
<223> OTHER INFORMATION: Primer

<400> SEQUENCE: 41
gttcttgcag cagacggatc aggccaatac tcatg 35

<210> SEQ ID NO 42
<211> LENGTH: 37
<212> TYPE: DNA
<213> ORGANISM: Artificial Sequence
<220> FEATURE:
<223> OTHER INFORMATION: Primer

<400> SEQUENCE: 42
atgtaatcaa catgagcctg ggagcaccaa gcggcag 37

<210> SEQ ID NO 43
<211> LENGTH: 37
<212> TYPE: DNA
<213> ORGANISM: Artificial Sequence
<220> FEATURE:
<223> OTHER INFORMATION: Primer

<400> SEQUENCE: 43
ggaatgaggg aacatccgga tcatcgagta ccgtcgg 37

<210> SEQ ID NO 44
<211> LENGTH: 38
<212> TYPE: DNA
<213> ORGANISM: Artificial Sequence
<220> FEATURE:
<223> OTHER INFORMATION: Primer

<400> SEQUENCE: 44
ctttctaagc acccgaactg gacaaacact caagtccg 38

<210> SEQ ID NO 45
<211> LENGTH: 36
<212> TYPE: DNA
<213> ORGANISM: Artificial Sequence
<220> FEATURE:
<223> OTHER INFORMATION: Primer

<400> SEQUENCE: 45
tcaagataac aattctcatg gcacacacgt cgcagg 36

<210> SEQ ID NO 46
<211> LENGTH: 37
<212> TYPE: DNA
<213> ORGANISM: Artificial Sequence
<220> FEATURE:
<223> OTHER INFORMATION: Primer

<400> SEQUENCE: 46
tgcagcagac ggatcaggcc aatactcatg gattatc 37

<210> SEQ ID NO 47
<211> LENGTH: 35
<212> TYPE: DNA
<213> ORGANISM: Artificial Sequence
<220> FEATURE:
<223> OTHER INFORMATION: Primer

<400> SEQUENCE: 47
aatcaacatg agcctgggag caccaagcgg cagtg 35

<210> SEQ ID NO 48
<211> LENGTH: 37
<212> TYPE: DNA
<213> ORGANISM: Artificial Sequence
<220> FEATURE:
<223> OTHER INFORMATION: Primer

<400> SEQUENCE: 48
cgctgtagac tcttcaaatc aacgtgcctc tttttcc 37

<210> SEQ ID NO 49
<211> LENGTH: 35
<212> TYPE: DNA
<213> ORGANISM: Artificial Sequence
<220> FEATURE:
<223> OTHER INFORMATION: Primer

<400> SEQUENCE: 49
gaactggaca aacactcaag tccgcagcag tttag 35

<210> SEQ ID NO 50
<211> LENGTH: 34
<212> TYPE: DNA
<213> ORGANISM: Artificial Sequence
<220> FEATURE:
<223> OTHER INFORMATION: Primer

<400> SEQUENCE: 50
tcatggcaca cacgtcgcag gaacggttgc ggcg 34

<210> SEQ ID NO 51
<211> LENGTH: 37
<212> TYPE: DNA
<213> ORGANISM: Artificial Sequence
<220> FEATURE:
<223> OTHER INFORMATION: Primer

<400> SEQUENCE: 51
agcagacgga tcaggccaat actcatggat tatcaac 37

<210> SEQ ID NO 52
<211> LENGTH: 37
<212> TYPE: DNA
<213> ORGANISM: Artificial Sequence
<220> FEATURE:
<223> OTHER INFORMATION: Primer

<400> SEQUENCE: 52
atcgacgctt ccagggaaca agtatggtgc gcaaaac 37

<210> SEQ ID NO 53
<211> LENGTH: 37
<212> TYPE: DNA
<213> ORGANISM: Artificial Sequence
<220> FEATURE:
<223> OTHER INFORMATION: Primer

<400> SEQUENCE: 53
atgtaatcaa catgagcctg ggagcaccaa gcggcag 37

<210> SEQ ID NO 54
<211> LENGTH: 22
<212> TYPE: DNA
<213> ORGANISM: Artificial Sequence
<220> FEATURE:
<223> OTHER INFORMATION: Primer

<400> SEQUENCE: 54
tacatatgag ttatgcagtt tg 22

<210> SEQ ID NO 55
<211> LENGTH: 19
<212> TYPE: DNA
<213> ORGANISM: Artificial Sequence
<220> FEATURE:
<223> OTHER INFORMATION: Primer

<400> SEQUENCE: 55
ttatccttta ccttgtctc 19

<210> SEQ ID NO 56
<211> LENGTH: 35
<212> TYPE: DNA
<213> ORGANISM: Artificial Sequence
<220> FEATURE:
<223> OTHER INFORMATION: Primer

<400> SEQUENCE: 56
caacatgagc ctgggatcac caagcggcag tgcgg 35

<210> SEQ ID NO 57
<211> LENGTH: 35
<212> TYPE: DNA
<213> ORGANISM: Artificial Sequence
<220> FEATURE:
<223> OTHER INFORMATION: Primer

<400> SEQUENCE: 57
ccgcactgcc gcttggtgat cccaggctca tgttg 35

<210> SEQ ID NO 58
<211> LENGTH: 38
<212> TYPE: DNA
<213> ORGANISM: Artificial Sequence
<220> FEATURE:
<223> OTHER INFORMATION: Primer

<400> SEQUENCE: 58
ctatggtgcc gggcgaaaca aacccgtttc aagatccg 38

<210> SEQ ID NO 59
<211> LENGTH: 38
<212> TYPE: DNA
<213> ORGANISM: Artificial Sequence
<220> FEATURE:
<223> OTHER INFORMATION: Primer

<400> SEQUENCE: 59
cggatcttga aacgggtttg tttcgcccgg caccatag 38

<210> SEQ ID NO 60
<211> LENGTH: 21
<212> TYPE: DNA
<213> ORGANISM: Artificial Sequence
<220> FEATURE:
<223> OTHER INFORMATION: Primer

<400> SEQUENCE: 60
gcctcacatt tgtgccacct a 21

<210> SEQ ID NO 61
<211> LENGTH: 22
<212> TYPE: DNA
<213> ORGANISM: Artificial Sequence
<220> FEATURE:
<223> OTHER INFORMATION: Primer

<400> SEQUENCE: 61
cctctcggtt atgagttagt tc 22

<210> SEQ ID NO 62
<211> LENGTH: 24
<212> TYPE: DNA
<213> ORGANISM: Artificial Sequence
<220> FEATURE:
<223> OTHER INFORMATION: Primer

<400> SEQUENCE: 62
aaaggatcct aatcggcgct tttc 24

<210> SEQ ID NO 63
<211> LENGTH: 24
<212> TYPE: DNA
<213> ORGANISM: Artificial Sequence
<220> FEATURE:
<223> OTHER INFORMATION: Primer

<400> SEQUENCE: 63
cttgtctcca agcttaaaat aaaa 24

<210> SEQ ID NO 64
<211> LENGTH: 36
<212> TYPE: DNA
<213> ORGANISM: Artificial Sequence
<220> FEATURE:
<223> OTHER INFORMATION: Primer

<400> SEQUENCE: 64
cagatcttaa agtctctgga ggggcttcta tggtgc 36

<210> SEQ ID NO 65
<211> LENGTH: 40
<212> TYPE: DNA
<213> ORGANISM: Artificial Sequence
<220> FEATURE:
<223> OTHER INFORMATION: Primer

<400> SEQUENCE: 65
catagaagcc cctccagaga ctttaagatc tggatggctc 40

<210> SEQ ID NO 66

<211> LENGTH: 36
<212> TYPE: DNA
<213> ORGANISM: Artificial Sequence
<220> FEATURE:
<223> OTHER INFORMATION: Primer

<400> SEQUENCE: 66
gcattgattc tttacaagca cccgaactgg acaaac 36

<210> SEQ ID NO 67
<211> LENGTH: 39
<212> TYPE: DNA
<213> ORGANISM: Artificial Sequence
<220> FEATURE:
<223> OTHER INFORMATION: Primer

<400> SEQUENCE: 67
cagttcgggt gcttgtaaag aatcaatgcg gccgcccca 39

<210> SEQ ID NO 68
<211> LENGTH: 36
<212> TYPE: DNA
<213> ORGANISM: Artificial Sequence
<220> FEATURE:
<223> OTHER INFORMATION: Primer

<400> SEQUENCE: 68
gcattgattc ttggtaagca cccgaactgg acaaac 36

<210> SEQ ID NO 69
<211> LENGTH: 40
<212> TYPE: DNA
<213> ORGANISM: Artificial Sequence
<220> FEATURE:
<223> OTHER INFORMATION: Primer

<400> SEQUENCE: 69
ccagttcggg tgcttaccaa gaatcaatgc ggccgcccca 40

<210> SEQ ID NO 70
<211> LENGTH: 40
<212> TYPE: DNA
<213> ORGANISM: Artificial Sequence
<220> FEATURE:
<223> OTHER INFORMATION: Primer

<400> SEQUENCE: 70
catcgaatgg gccacagcga ataacatgga tgtaatcaac 40

<210> SEQ ID NO 71
<211> LENGTH: 40
<212> TYPE: DNA
<213> ORGANISM: Artificial Sequence
<220> FEATURE:
<223> OTHER INFORMATION: Primer

<400> SEQUENCE: 71
catccatgtt attcgctgtg gcccattcga tgccgttgat 40

<210> SEQ ID NO 72
<211> LENGTH: 40
<212> TYPE: DNA
<213> ORGANISM: Artificial Sequence
<220> FEATURE:
<223> OTHER INFORMATION: Primer

<400> SEQUENCE: 72
catcgaatgg gccgtagcga ataacatgga tgtaatcaac 40

<210> SEQ ID NO 73
<211> LENGTH: 40
<212> TYPE: DNA
<213> ORGANISM: Artificial Sequence
<220> FEATURE:
<223> OTHER INFORMATION: Primer

<400> SEQUENCE: 73
catccatgtt attcgctacg gcccattcga tgccgttgat 40

<210> SEQ ID NO 74
<211> LENGTH: 36
<212> TYPE: DNA
<213> ORGANISM: Artificial Sequence
<220> FEATURE:
<223> OTHER INFORMATION: Primer

<400> SEQUENCE: 74
ctgtagactc tacaaatcaa cgtgcctctt tttcct 36

<210> SEQ ID NO 75
<211> LENGTH: 40
<212> TYPE: DNA
<213> ORGANISM: Artificial Sequence
<220> FEATURE:
<223> OTHER INFORMATION: Primer

<400> SEQUENCE: 75
aaagaggcac gttgatttgt agagtctaca gcgcccactg 40

<210> SEQ ID NO 76
<211> LENGTH: 38
<212> TYPE: DNA
<213> ORGANISM: Artificial Sequence
<220> FEATURE:
<223> OTHER INFORMATION: Primer

<400> SEQUENCE: 76
ctgtagactc ttcataccaa cgtgcctctt tttcctcc 38

<210> SEQ ID NO 77
<211> LENGTH: 40
<212> TYPE: DNA
<213> ORGANISM: Artificial Sequence
<220> FEATURE:
<223> OTHER INFORMATION: Primer

<400> SEQUENCE: 77
gaaaaagagg cacgttggta tgaagagtct acagcgccca 40

<210> SEQ ID NO 78
<211> LENGTH: 51
<212> TYPE: DNA
<213> ORGANISM: Artificial Sequence
<220> FEATURE:
<223> OTHER INFORMATION: Primer

<400> SEQUENCE: 78
tagcggttac agacagcggt atcgacccaa gccatccaga tcttaaagtc g 51

<210> SEQ ID NO 79
<211> LENGTH: 50
<212> TYPE: DNA

<213> ORGANISM: Artificial Sequence
<220> FEATURE:
<223> OTHER INFORMATION: Primer

<400> SEQUENCE: 79
atggcttggg tcgataccgc tgtctgtaac cgctacttta acattgcctc 50

<210> SEQ ID NO 80
<211> LENGTH: 49
<212> TYPE: DNA
<213> ORGANISM: Artificial Sequence
<220> FEATURE:
<223> OTHER INFORMATION: Primer

<400> SEQUENCE: 80
taaagtagcg gttacagaca gcggtttaga ctcgagccat ccagatctt 49

<210> SEQ ID NO 81
<211> LENGTH: 50
<212> TYPE: DNA
<213> ORGANISM: Artificial Sequence
<220> FEATURE:
<223> OTHER INFORMATION: Primer

<400> SEQUENCE: 81
atggctcgag tctaaaccgc tgtctgtaac cgctacttta acattgcctc 50

<210> SEQ ID NO 82
<211> LENGTH: 50
<212> TYPE: DNA
<213> ORGANISM: Artificial Sequence
<220> FEATURE:
<223> OTHER INFORMATION: Primer

<400> SEQUENCE: 82
ggttgtagac agcggtatcg actcgtggca tccagatctt aaagtcgctg 50

<210> SEQ ID NO 83
<211> LENGTH: 50
<212> TYPE: DNA
<213> ORGANISM: Artificial Sequence
<220> FEATURE:
<223> OTHER INFORMATION: Primer

<400> SEQUENCE: 83
atgccacgag tcgataccgc tgtctacaac cgctacttta acattgcctc 50

<210> SEQ ID NO 84
<211> LENGTH: 38
<212> TYPE: DNA
<213> ORGANISM: Artificial Sequence
<220> FEATURE:
<223> OTHER INFORMATION: Primer

<400> SEQUENCE: 84
ctacactgga ggcaaagtta aagtagcggt tatcgaca 38

<210> SEQ ID NO 85
<211> LENGTH: 40
<212> TYPE: DNA
<213> ORGANISM: Artificial Sequence
<220> FEATURE:
<223> OTHER INFORMATION: Primer

<400> SEQUENCE: 85
ataaccgcta ctttaacttt gcctccagtg tagccttgag 40

<210> SEQ ID NO 86
<211> LENGTH: 37
<212> TYPE: DNA
<213> ORGANISM: Artificial Sequence
<220> FEATURE:
<223> OTHER INFORMATION: Primer

<400> SEQUENCE: 86
gagcctggga gcacgtagcg gcagtgcggc acttaaa 37

<210> SEQ ID NO 87
<211> LENGTH: 40
<212> TYPE: DNA
<213> ORGANISM: Artificial Sequence
<220> FEATURE:
<223> OTHER INFORMATION: Primer

<400> SEQUENCE: 87
gtgccgcact gccgctacgt gctcccaggc tcatgttgat 40

<210> SEQ ID NO 88
<211> LENGTH: 38
<212> TYPE: DNA
<213> ORGANISM: Artificial Sequence
<220> FEATURE:
<223> OTHER INFORMATION: Primer

<400> SEQUENCE: 88
tgagcctggg agcaaagagc ggcagtgcgg cacttaaa 38

<210> SEQ ID NO 89
<211> LENGTH: 38
<212> TYPE: DNA
<213> ORGANISM: Artificial Sequence
<220> FEATURE:
<223> OTHER INFORMATION: Primer

<400> SEQUENCE: 89
tgagcctggg agcaaagagc ggcagtgcgg cacttaaa 38

<210> SEQ ID NO 90
<211> LENGTH: 40
<212> TYPE: DNA
<213> ORGANISM: Artificial Sequence
<220> FEATURE:
<223> OTHER INFORMATION: Primer

<400> SEQUENCE: 90
atcacaaatt aaagccacag ctctgcactc tcaaggctac 40

<210> SEQ ID NO 91
<211> LENGTH: 40
<212> TYPE: DNA
<213> ORGANISM: Artificial Sequence
<220> FEATURE:
<223> OTHER INFORMATION: Primer

<400> SEQUENCE: 91
agagtgcaga gctgtggctt taatttgtga tacgccgtaa 40

<210> SEQ ID NO 92
<211> LENGTH: 40
<212> TYPE: DNA
<213> ORGANISM: Artificial Sequence
<220> FEATURE:

-continued

<223> OTHER INFORMATION: Primer

<400> SEQUENCE: 92
agagtgcaga gctgtggctt taatttgtga tacgccgtaa 40

<210> SEQ ID NO 93
<211> LENGTH: 40
<212> TYPE: DNA
<213> ORGANISM: Artificial Sequence
<220> FEATURE:
<223> OTHER INFORMATION: Primer

<400> SEQUENCE: 93
taagatctgg atggcttgtg tcgataccgc tgtcgataac 40

<210> SEQ ID NO 94
<211> LENGTH: 40
<212> TYPE: DNA
<213> ORGANISM: Artificial Sequence
<220> FEATURE:
<223> OTHER INFORMATION: Primer

<400> SEQUENCE: 94
gacagcggta tcgacccaag ccatccagat cttaaagtcg 40

<210> SEQ ID NO 95
<211> LENGTH: 40
<212> TYPE: DNA
<213> ORGANISM: Artificial Sequence
<220> FEATURE:
<223> OTHER INFORMATION: Primer

<400> SEQUENCE: 95
taagatctgg atggcttggg tcgataccgc tgtcgataac 40

<210> SEQ ID NO 96
<211> LENGTH: 40
<212> TYPE: DNA
<213> ORGANISM: Artificial Sequence
<220> FEATURE:
<223> OTHER INFORMATION: Primer

<400> SEQUENCE: 96
gacagcggta tcgactggag ccatccagat cttaaagtcg 40

<210> SEQ ID NO 97
<211> LENGTH: 40
<212> TYPE: DNA
<213> ORGANISM: Artificial Sequence
<220> FEATURE:
<223> OTHER INFORMATION: Primer

<400> SEQUENCE: 97
taagatctgg atggctccag tcgataccgc tgtcgataac 40

<210> SEQ ID NO 98
<211> LENGTH: 40
<212> TYPE: DNA
<213> ORGANISM: Artificial Sequence
<220> FEATURE:
<223> OTHER INFORMATION: Primer

<400> SEQUENCE: 98
acgcgcagtc cgtgttatac ggcgtatcac aaattaaagc 40

<210> SEQ ID NO 99
<211> LENGTH: 40
<212> TYPE: DNA
<213> ORGANISM: Artificial Sequence
<220> FEATURE:
<223> OTHER INFORMATION: Primer

<400> SEQUENCE: 99
atttgtgata cgccgtataa cacggactgc gcgtacgcat 40

<210> SEQ ID NO 100
<211> LENGTH: 37
<212> TYPE: DNA
<213> ORGANISM: Artificial Sequence
<220> FEATURE:
<223> OTHER INFORMATION: Primer

<400> SEQUENCE: 100
acaagtatgg tgcgaaaaac gggacttcca tggcctc 37

<210> SEQ ID NO 101
<211> LENGTH: 38
<212> TYPE: DNA
<213> ORGANISM: Artificial Sequence
<220> FEATURE:
<223> OTHER INFORMATION: Primer

<400> SEQUENCE: 101
catggaagtc ccgtttttcg caccatactt gttccctg 38

<210> SEQ ID NO 102
<211> LENGTH: 37
<212> TYPE: DNA
<213> ORGANISM: Artificial Sequence
<220> FEATURE:
<223> OTHER INFORMATION: Primer

<400> SEQUENCE: 102
acaagtatgg tgcgggaaac gggacttcca tggcctc 37

<210> SEQ ID NO 103
<211> LENGTH: 39
<212> TYPE: DNA
<213> ORGANISM: Artificial Sequence
<220> FEATURE:
<223> OTHER INFORMATION: Primer

<400> SEQUENCE: 103
ccatggaagt cccgtttccc gcaccatact tgttccctg 39

<210> SEQ ID NO 104
<211> LENGTH: 38
<212> TYPE: DNA
<213> ORGANISM: Artificial Sequence
<220> FEATURE:
<223> OTHER INFORMATION: Primer

<400> SEQUENCE: 104
cttacggcgt atcattaatt aaagccccctg ctctgcac 38

<210> SEQ ID NO 105
<211> LENGTH: 40
<212> TYPE: DNA
<213> ORGANISM: Artificial Sequence
<220> FEATURE:
<223> OTHER INFORMATION: Primer

<400> SEQUENCE: 105
gagcaggggc tttaattaat gatacgccgt aaggcacgga 40

<210> SEQ ID NO 106
<211> LENGTH: 38
<212> TYPE: DNA
<213> ORGANISM: Artificial Sequence
<220> FEATURE:
<223> OTHER INFORMATION: Primer

<400> SEQUENCE: 106
cttacggcgt atcacgtatt aaagcccctg ctctgcac 38

<210> SEQ ID NO 107
<211> LENGTH: 40
<212> TYPE: DNA
<213> ORGANISM: Artificial Sequence
<220> FEATURE:
<223> OTHER INFORMATION: Primer

<400> SEQUENCE: 107
gagcaggggc tttaatacgt gatacgccgt aaggcacgga 40

<210> SEQ ID NO 108
<211> LENGTH: 40
<212> TYPE: DNA
<213> ORGANISM: Artificial Sequence
<220> FEATURE:
<223> OTHER INFORMATION: Primer

<400> SEQUENCE: 108
tttagaaaac acctctacaa aacttggtga ttctttctac 40

<210> SEQ ID NO 109
<211> LENGTH: 40
<212> TYPE: DNA
<213> ORGANISM: Artificial Sequence
<220> FEATURE:
<223> OTHER INFORMATION: Primer

<400> SEQUENCE: 109
tcaccaagtt ttgtagaggt gttttctaaa ctgctgcgga 40

<210> SEQ ID NO 110
<211> LENGTH: 40
<212> TYPE: DNA
<213> ORGANISM: Artificial Sequence
<220> FEATURE:
<223> OTHER INFORMATION: Primer

<400> SEQUENCE: 110
aggctacact ggagcaaatg ttaaagtagc ggttatcgac 40

<210> SEQ ID NO 111
<211> LENGTH: 38
<212> TYPE: DNA
<213> ORGANISM: Artificial Sequence
<220> FEATURE:
<223> OTHER INFORMATION: Primer

<400> SEQUENCE: 111
gctactttaa catttgctcc agtgtagcct tgagagtg 38

<210> SEQ ID NO 112
<211> LENGTH: 39

<212> TYPE: DNA
<213> ORGANISM: Artificial Sequence
<220> FEATURE:
<223> OTHER INFORMATION: Primer

<400> SEQUENCE: 112
gagggaacat ccggaccatc gagtaccgtc ggttatcca 39

<210> SEQ ID NO 113
<211> LENGTH: 40
<212> TYPE: DNA
<213> ORGANISM: Artificial Sequence
<220> FEATURE:
<223> OTHER INFORMATION: Primer

<400> SEQUENCE: 113
accgacggta ctcgatggtc cggatgttcc ctcattccca 40

<210> SEQ ID NO 114
<211> LENGTH: 40
<212> TYPE: DNA
<213> ORGANISM: Artificial Sequence
<220> FEATURE:
<223> OTHER INFORMATION: Primer

<400> SEQUENCE: 114
agggaacatc cggaccatta agtaccgtcg gttatccagg 40

<210> SEQ ID NO 115
<211> LENGTH: 40
<212> TYPE: DNA
<213> ORGANISM: Artificial Sequence
<220> FEATURE:
<223> OTHER INFORMATION: Primer

<400> SEQUENCE: 115
accgacggta cttaatggtc cggatgttcc ctcattccca 40

<210> SEQ ID NO 116
<211> LENGTH: 39
<212> TYPE: DNA
<213> ORGANISM: Artificial Sequence
<220> FEATURE:
<223> OTHER INFORMATION: Primer

<400> SEQUENCE: 116
gaacatccgg atcattaagt accgtcggtt atccaggca 39

<210> SEQ ID NO 117
<211> LENGTH: 40
<212> TYPE: DNA
<213> ORGANISM: Artificial Sequence
<220> FEATURE:
<223> OTHER INFORMATION: Primer

<400> SEQUENCE: 117
ataaccgacg gtacttaatg atccggatgt tccctcattc 40

<210> SEQ ID NO 118
<211> LENGTH: 39
<212> TYPE: DNA
<213> ORGANISM: Artificial Sequence
<220> FEATURE:
<223> OTHER INFORMATION: Primer

<400> SEQUENCE: 118

-continued gaacatccgg atcaccaagt accgtcggtt atccaggca 39

<210> SEQ ID NO 119
<211> LENGTH: 40
<212> TYPE: DNA
<213> ORGANISM: Artificial Sequence
<220> FEATURE:
<223> OTHER INFORMATION: Primer

<400> SEQUENCE: 119
ataaccgacg gtacttggtg atccggatgt tccctcattc 40

<210> SEQ ID NO 120
<211> LENGTH: 38
<212> TYPE: DNA
<213> ORGANISM: Artificial Sequence
<220> FEATURE:
<223> OTHER INFORMATION: Primer

<400> SEQUENCE: 120
gtttagaaaa cgcaactaca aaacttggtg attctttc 38

<210> SEQ ID NO 121
<211> LENGTH: 40
<212> TYPE: DNA
<213> ORGANISM: Artificial Sequence
<220> FEATURE:
<223> OTHER INFORMATION: Primer

<400> SEQUENCE: 121
caccaagttt tgtagttgcg ttttctaaac tgctgcggac 40

<210> SEQ ID NO 122
<211> LENGTH: 40
<212> TYPE: DNA
<213> ORGANISM: Artificial Sequence
<220> FEATURE:
<223> OTHER INFORMATION: Primer

<400> SEQUENCE: 122
caaaacttgg tgatccattc tactatggaa aagggctgat 40

<210> SEQ ID NO 123
<211> LENGTH: 40
<212> TYPE: DNA
<213> ORGANISM: Artificial Sequence
<220> FEATURE:
<223> OTHER INFORMATION: Primer

<400> SEQUENCE: 123
tttccatagt agaatggatc accaagtttt gtagtggtgt 40

<210> SEQ ID NO 124
<211> LENGTH: 40
<212> TYPE: DNA
<213> ORGANISM: Artificial Sequence
<220> FEATURE:
<223> OTHER INFORMATION: Primer

<400> SEQUENCE: 124
caaaacttgg tgataacttc tactatggaa aagggctgat 40

<210> SEQ ID NO 125
<211> LENGTH: 40
<212> TYPE: DNA
<213> ORGANISM: Artificial Sequence
<220> FEATURE:
<223> OTHER INFORMATION: Primer

<400> SEQUENCE: 125
tttccatagt agaagttatc accaagtttt gtagtggtgt 40

<210> SEQ ID NO 126
<211> LENGTH: 40
<212> TYPE: DNA
<213> ORGANISM: Artificial Sequence
<220> FEATURE:
<223> OTHER INFORMATION: Primer

<400> SEQUENCE: 126
caaaacttgg tgatatcttc tactatggaa aagggctgat 40

<210> SEQ ID NO 127
<211> LENGTH: 40
<212> TYPE: DNA
<213> ORGANISM: Artificial Sequence
<220> FEATURE:
<223> OTHER INFORMATION: Primer

<400> SEQUENCE: 127
tttccatagt agaagatatc accaagtttt gtagtggtgt 40

<210> SEQ ID NO 128
<211> LENGTH: 40
<212> TYPE: DNA
<213> ORGANISM: Artificial Sequence
<220> FEATURE:
<223> OTHER INFORMATION: Primer

<400> SEQUENCE: 128
caaaacttgg tgatggattc tactatggaa aagggctgat 40

<210> SEQ ID NO 129
<211> LENGTH: 40
<212> TYPE: DNA
<213> ORGANISM: Artificial Sequence
<220> FEATURE:
<223> OTHER INFORMATION: Primer

<400> SEQUENCE: 129
tttccatagt agaatccatc accaagtttt gtagtggtgt 40

<210> SEQ ID NO 130
<211> LENGTH: 37
<212> TYPE: DNA
<213> ORGANISM: Artificial Sequence
<220> FEATURE:
<223> OTHER INFORMATION: Primer

<400> SEQUENCE: 130
gtgggcgctg tacactcttc aaatcaacgt gcctctt 37

<210> SEQ ID NO 131
<211> LENGTH: 40
<212> TYPE: DNA
<213> ORGANISM: Artificial Sequence
<220> FEATURE:
<223> OTHER INFORMATION: Primer

<400> SEQUENCE: 131
cacgttgatt tgaagagtgt acagcgccca ctgcaatcac 40

<210> SEQ ID NO 132
<211> LENGTH: 37
<212> TYPE: DNA
<213> ORGANISM: Artificial Sequence
<220> FEATURE:
<223> OTHER INFORMATION: Primer

<400> SEQUENCE: 132
gtgggcgctg taggatcttc aaatcaacgt gcctctt                              37

<210> SEQ ID NO 133
<211> LENGTH: 40
<212> TYPE: DNA
<213> ORGANISM: Artificial Sequence
<220> FEATURE:
<223> OTHER INFORMATION: Primer

<400> SEQUENCE: 133
cacgttgatt tgaagatcct acagcgccca ctgcaatcac                           40

<210> SEQ ID NO 134
<211> LENGTH: 37
<212> TYPE: DNA
<213> ORGANISM: Artificial Sequence
<220> FEATURE:
<223> OTHER INFORMATION: Primer

<400> SEQUENCE: 134
cctgctctgc acttccaagg ctacactgga ggcaatg                              37

<210> SEQ ID NO 135
<211> LENGTH: 40
<212> TYPE: DNA
<213> ORGANISM: Artificial Sequence
<220> FEATURE:
<223> OTHER INFORMATION: Primer

<400> SEQUENCE: 135
ctccagtgta gccttggaag tgcagagcag gggctttaat                           40

<210> SEQ ID NO 136
<211> LENGTH: 37
<212> TYPE: DNA
<213> ORGANISM: Artificial Sequence
<220> FEATURE:
<223> OTHER INFORMATION: Primer

<400> SEQUENCE: 136
cctgctctgc acacacaagg ctacactgga ggcaatg                              37

<210> SEQ ID NO 137
<211> LENGTH: 40
<212> TYPE: DNA
<213> ORGANISM: Artificial Sequence
<220> FEATURE:
<223> OTHER INFORMATION: Primer

<400> SEQUENCE: 137
ctccagtgta gccttgtgtg tgcagagcag gggctttaat                           40

<210> SEQ ID NO 138
<211> LENGTH: 37
<212> TYPE: DNA
<213> ORGANISM: Artificial Sequence
<220> FEATURE:
<223> OTHER INFORMATION: Primer

<400> SEQUENCE: 138
cctgctctgc acccacaagg ctacactgga ggcaatg 37

<210> SEQ ID NO 139
<211> LENGTH: 40
<212> TYPE: DNA
<213> ORGANISM: Artificial Sequence
<220> FEATURE:
<223> OTHER INFORMATION: Primer

<400> SEQUENCE: 139
ctccagtgta gccttgtggg tgcagagcag gggctttaat 40

<210> SEQ ID NO 140
<211> LENGTH: 37
<212> TYPE: DNA
<213> ORGANISM: Artificial Sequence
<220> FEATURE:
<223> OTHER INFORMATION: Primer

<400> SEQUENCE: 140
cctgctctgc actaccaagg ctacactgga ggcaatg 37

<210> SEQ ID NO 141
<211> LENGTH: 40
<212> TYPE: DNA
<213> ORGANISM: Artificial Sequence
<220> FEATURE:
<223> OTHER INFORMATION: Primer

<400> SEQUENCE: 141
ctccagtgta gccttggtag tgcagagcag gggctttaat 40

<210> SEQ ID NO 142
<211> LENGTH: 37
<212> TYPE: DNA
<213> ORGANISM: Artificial Sequence
<220> FEATURE:
<223> OTHER INFORMATION: Primer

<400> SEQUENCE: 142
cctgctctgc acttacaagg ctacactgga ggcaatg 37

<210> SEQ ID NO 143
<211> LENGTH: 40
<212> TYPE: DNA
<213> ORGANISM: Artificial Sequence
<220> FEATURE:
<223> OTHER INFORMATION: Primer

<400> SEQUENCE: 143
ctccagtgta gccttgtaag tgcagagcag gggctttaat 40

<210> SEQ ID NO 144
<211> LENGTH: 38
<212> TYPE: DNA
<213> ORGANISM: Artificial Sequence
<220> FEATURE:
<223> OTHER INFORMATION: Primer

<400> SEQUENCE: 144
tgctctgcac tctttaggct acactggagg caatgtta 38

<210> SEQ ID NO 145

<211> LENGTH: 40
<212> TYPE: DNA
<213> ORGANISM: Artificial Sequence
<220> FEATURE:
<223> OTHER INFORMATION: Primer

<400> SEQUENCE: 145
ttgcctccag tgtagcctaa agagtgcaga gcaggggctt 40

<210> SEQ ID NO 146
<211> LENGTH: 39
<212> TYPE: DNA
<213> ORGANISM: Artificial Sequence
<220> FEATURE:
<223> OTHER INFORMATION: Primer

<400> SEQUENCE: 146
atcgcgaata acatgaacgt aatcaacatg agcctggga 39

<210> SEQ ID NO 147
<211> LENGTH: 39
<212> TYPE: DNA
<213> ORGANISM: Artificial Sequence
<220> FEATURE:
<223> OTHER INFORMATION: Primer

<400> SEQUENCE: 147
ctcatgttga ttacgttcat gttattcgcg atggcccat 39

<210> SEQ ID NO 148
<211> LENGTH: 37
<212> TYPE: DNA
<213> ORGANISM: Artificial Sequence
<220> FEATURE:
<223> OTHER INFORMATION: Primer

<400> SEQUENCE: 148
cttccaggga accgttatgg tgcgcaaaac gggactt 37

<210> SEQ ID NO 149
<211> LENGTH: 39
<212> TYPE: DNA
<213> ORGANISM: Artificial Sequence
<220> FEATURE:
<223> OTHER INFORMATION: Primer

<400> SEQUENCE: 149
gttttgcgca ccataacggt tccctggaag cgtcgattg 39

<210> SEQ ID NO 150
<211> LENGTH: 40
<212> TYPE: DNA
<213> ORGANISM: Artificial Sequence
<220> FEATURE:
<223> OTHER INFORMATION: Primer

<400> SEQUENCE: 150
ctgcacttac aaggctctac tggaggcaat gttaaagtag 40

<210> SEQ ID NO 151
<211> LENGTH: 49
<212> TYPE: DNA
<213> ORGANISM: Artificial Sequence
<220> FEATURE:
<223> OTHER INFORMATION: Primer

<400> SEQUENCE: 151
taacattgcc tccagtagag ccttgtaagt gcagagcagg ggctttaat 49

<210> SEQ ID NO 152
<211> LENGTH: 43
<212> TYPE: DNA
<213> ORGANISM: Artificial Sequence
<220> FEATURE:
<223> OTHER INFORMATION: Primer

<400> SEQUENCE: 152
gctctgcact tacaaggcaa cactggaggc aatgttaaag tag 43

<210> SEQ ID NO 153
<211> LENGTH: 48
<212> TYPE: DNA
<213> ORGANISM: Artificial Sequence
<220> FEATURE:
<223> OTHER INFORMATION: Primer

<400> SEQUENCE: 153
aacattgcct ccagtgttgc cttgtaagtg cagagcaggg gctttaat 48

<210> SEQ ID NO 154
<211> LENGTH: 35
<212> TYPE: DNA
<213> ORGANISM: Artificial Sequence
<220> FEATURE:
<223> OTHER INFORMATION: Primer

<400> SEQUENCE: 154
cttacggcgt aacacaaatt aaagcccctg ctctg 35

<210> SEQ ID NO 155
<211> LENGTH: 38
<212> TYPE: DNA
<213> ORGANISM: Artificial Sequence
<220> FEATURE:
<223> OTHER INFORMATION: Primer

<400> SEQUENCE: 155
aggggcttta atttgtgtta cgccgtaagg cacggact 38

<210> SEQ ID NO 156
<211> LENGTH: 40
<212> TYPE: DNA
<213> ORGANISM: Artificial Sequence
<220> FEATURE:
<223> OTHER INFORMATION: Primer

<400> SEQUENCE: 156
ttaaagcagc agttgatttc gctgttgcat ctggtgtcgt 40

<210> SEQ ID NO 157
<211> LENGTH: 40
<212> TYPE: DNA
<213> ORGANISM: Artificial Sequence
<220> FEATURE:
<223> OTHER INFORMATION: Primer

<400> SEQUENCE: 157
agatgcaaca gcgaaatcaa ctgctgcttt aagtgccgca 40

<210> SEQ ID NO 158
<211> LENGTH: 40
<212> TYPE: DNA

<213> ORGANISM: Artificial Sequence
<220> FEATURE:
<223> OTHER INFORMATION: Primer

<400> SEQUENCE: 158
ttaaagcagc agttgatcgt gctgttgcat ctggtgtcgt 40

<210> SEQ ID NO 159
<211> LENGTH: 40
<212> TYPE: DNA
<213> ORGANISM: Artificial Sequence
<220> FEATURE:
<223> OTHER INFORMATION: Primer

<400> SEQUENCE: 159
agatgcaaca gcacgatcaa ctgctgcttt aagtgccgca 40

<210> SEQ ID NO 160
<211> LENGTH: 40
<212> TYPE: DNA
<213> ORGANISM: Artificial Sequence
<220> FEATURE:
<223> OTHER INFORMATION: Primer

<400> SEQUENCE: 160
aaacccgttt caagattcta attctcatgg cacacacgtc 40

<210> SEQ ID NO 161
<211> LENGTH: 40
<212> TYPE: DNA
<213> ORGANISM: Artificial Sequence
<220> FEATURE:
<223> OTHER INFORMATION: Primer

<400> SEQUENCE: 161
tgtgccatga gaattagaat cttgaaacgg gtttgtttcg 40

<210> SEQ ID NO 162
<211> LENGTH: 40
<212> TYPE: DNA
<213> ORGANISM: Artificial Sequence
<220> FEATURE:
<223> OTHER INFORMATION: Primer

<400> SEQUENCE: 162
aaacccgttt caagatgata attctcatgg cacacacgtc 40

<210> SEQ ID NO 163
<211> LENGTH: 40
<212> TYPE: DNA
<213> ORGANISM: Artificial Sequence
<220> FEATURE:
<223> OTHER INFORMATION: Primer

<400> SEQUENCE: 163
tgtgccatga gaattatcat cttgaaacgg gtttgtttcg 40

<210> SEQ ID NO 164
<211> LENGTH: 39
<212> TYPE: DNA
<213> ORGANISM: Artificial Sequence
<220> FEATURE:
<223> OTHER INFORMATION: Primer

<400> SEQUENCE: 164
aagcggcagt gcgacactta aagcagcagt tgataaagc 39

<210> SEQ ID NO 165
<211> LENGTH: 40
<212> TYPE: DNA
<213> ORGANISM: Artificial Sequence
<220> FEATURE:
<223> OTHER INFORMATION: Primer

<400> SEQUENCE: 165
tcaactgctg ctttaagtgt cgcactgccg cttggtgctc 40

<210> SEQ ID NO 166
<211> LENGTH: 37
<212> TYPE: DNA
<213> ORGANISM: Artificial Sequence
<220> FEATURE:
<223> OTHER INFORMATION: Primer

<400> SEQUENCE: 166
caagcggcag tgttgcactt aaagcagcag ttgataa 37

<210> SEQ ID NO 167
<211> LENGTH: 40
<212> TYPE: DNA
<213> ORGANISM: Artificial Sequence
<220> FEATURE:
<223> OTHER INFORMATION: Primer

<400> SEQUENCE: 167
actgctgctt taagtgcaac actgccgctt ggtgctccca 40

<210> SEQ ID NO 168
<211> LENGTH: 382
<212> TYPE: PRT
<213> ORGANISM: Bacillus Amyloliquefaciens

<400> SEQUENCE: 168

Val Arg Ser Lys Lys Leu Trp Ile Ser Leu Leu Phe Ala Leu Ala Leu
1 5 10 15

Ile Phe Thr Met Ala Phe Gly Ser Thr Ser Ser Ala Gln Ala Ala Gly
20 25 30

Lys Ser Asn Gly Glu Lys Lys Tyr Ile Val Gly Phe Lys Gln Thr Met
35 40 45

Ser Thr Met Ser Ala Ala Lys Lys Lys Asp Val Ile Ser Glu Lys Gly
50 55 60

Gly Lys Val Gln Lys Gln Phe Lys Tyr Val Asp Ala Ala Ser Ala Thr
65 70 75 80

Leu Asn Glu Lys Ala Val Lys Glu Leu Lys Lys Asp Pro Ser Val Ala
85 90 95

Tyr Val Glu Glu Asp His Val Ala His Ala Tyr Ala Gln Ser Val Pro
100 105 110

Tyr Gly Val Ser Gln Ile Lys Ala Pro Ala Leu His Ser Gln Gly Tyr
115 120 125

Thr Gly Ser Asn Val Lys Val Ala Val Ile Asp Ser Gly Ile Asp Ser
130 135 140

Ser His Pro Asp Leu Lys Val Ala Gly Gly Ala Ser Met Val Pro Ser
145 150 155 160

Glu Thr Asn Pro Phe Gln Asp Asn Asn Ser His Gly Thr His Val Ala
165 170 175

Gly Thr Val Ala Ala Leu Asn Asn Ser Ile Gly Val Leu Gly Val Ala

```
            180                 185                 190

Pro Ser Ala Ser Leu Tyr Ala Val Lys Val Leu Gly Ala Asp Gly Ser
        195                 200                 205

Gly Gln Tyr Ser Trp Ile Ile Asn Gly Ile Glu Trp Ala Ile Ala Asn
    210                 215                 220

Asn Met Asp Val Ile Asn Met Ser Leu Gly Gly Pro Ser Gly Ser Ala
225                 230                 235                 240

Ala Leu Lys Ala Ala Val Asp Lys Ala Val Ala Ser Gly Val Val Val
                245                 250                 255

Val Ala Ala Ala Gly Asn Glu Gly Thr Ser Gly Ser Ser Ser Thr Val
            260                 265                 270

Gly Tyr Pro Gly Lys Tyr Pro Ser Val Ile Ala Val Gly Ala Val Asp
        275                 280                 285

Ser Ser Asn Gln Arg Ala Ser Phe Ser Ser Val Gly Pro Glu Leu Asp
    290                 295                 300

Val Met Ala Pro Gly Val Ser Ile Gln Ser Thr Leu Pro Gly Asn Lys
305                 310                 315                 320

Tyr Gly Ala Tyr Asn Gly Thr Ser Met Ala Ser Pro His Val Ala Gly
                325                 330                 335

Ala Ala Ala Leu Ile Leu Ser Lys His Pro Asn Trp Thr Asn Thr Gln
            340                 345                 350

Val Arg Ser Ser Leu Glu Asn Thr Thr Thr Lys Leu Gly Asp Ser Phe
        355                 360                 365

Tyr Tyr Gly Lys Gly Leu Ile Asn Val Gln Ala Ala Ala Gln
    370                 375                 380
```

<210> SEQ ID NO 169
<211> LENGTH: 36
<212> TYPE: DNA
<213> ORGANISM: Artificial Sequence
<220> FEATURE:
<223> OTHER INFORMATION: Primer

<400> SEQUENCE: 169
cggcgttaaa caataacatt ggcgtgcttg gtgtag 36

<210> SEQ ID NO 170
<211> LENGTH: 37
<212> TYPE: DNA
<213> ORGANISM: Artificial Sequence
<220> FEATURE:
<223> OTHER INFORMATION: Primer

<400> SEQUENCE: 170
accaagcacg ccaatgttat tgtttaacgc cgcaacc 37

<210> SEQ ID NO 171
<211> LENGTH: 39
<212> TYPE: DNA
<213> ORGANISM: Artificial Sequence
<220> FEATURE:
<223> OTHER INFORMATION: Primer

<400> SEQUENCE: 171
gtatcgactc gagccatgaa gatcttaaag tcgctggag 39

<210> SEQ ID NO 172
<211> LENGTH: 38
<212> TYPE: DNA
<213> ORGANISM: Artificial Sequence
<220> FEATURE:
<223> OTHER INFORMATION: Primer

<400> SEQUENCE: 172
cagcgacttt aagatcttca tggctcgagt cgataccg 38

<210> SEQ ID NO 173
<211> LENGTH: 39
<212> TYPE: DNA
<213> ORGANISM: Artificial Sequence
<220> FEATURE:
<223> OTHER INFORMATION: Primer

<400> SEQUENCE: 173
ttggtgtagc cccggatgct tcgctctacg ccgttaaag 39

<210> SEQ ID NO 174
<211> LENGTH: 35
<212> TYPE: DNA
<213> ORGANISM: Artificial Sequence
<220> FEATURE:
<223> OTHER INFORMATION: Primer

<400> SEQUENCE: 174
cgtagagcga agcatccggg gctacaccaa gcacg 35

<210> SEQ ID NO 175
<211> LENGTH: 39
<212> TYPE: DNA
<213> ORGANISM: Artificial Sequence
<220> FEATURE:
<223> OTHER INFORMATION: Primer

<400> SEQUENCE: 175
gaacggttgc ggcgttagat aattctattg gcgtgcttg 39

<210> SEQ ID NO 176
<211> LENGTH: 37
<212> TYPE: DNA
<213> ORGANISM: Artificial Sequence
<220> FEATURE:
<223> OTHER INFORMATION: Primer

<400> SEQUENCE: 176
agcacgccaa tagaattatc taacgccgca accgttc 37

<210> SEQ ID NO 177
<211> LENGTH: 44
<212> TYPE: DNA
<213> ORGANISM: Artificial Sequence
<220> FEATURE:
<223> OTHER INFORMATION: Primer

<400> SEQUENCE: 177
aacggttgcg gcgttagata ataacattgg cgtgcttggt gtag 44

<210> SEQ ID NO 178
<211> LENGTH: 46
<212> TYPE: DNA
<213> ORGANISM: Artificial Sequence
<220> FEATURE:
<223> OTHER INFORMATION: Primer

<400> SEQUENCE: 178
acaccaagca cgccaatgtt attatctaac gccgcaaccg ttcctg 46

<210> SEQ ID NO 179
<211> LENGTH: 31
<212> TYPE: DNA
<213> ORGANISM: Artificial Sequence
<220> FEATURE:
<223> OTHER INFORMATION: Primer

<400> SEQUENCE: 179
cggcgttaaa caataatatt ggcgtgcttg g 31

<210> SEQ ID NO 180
<211> LENGTH: 31
<212> TYPE: DNA
<213> ORGANISM: Artificial Sequence
<220> FEATURE:
<223> OTHER INFORMATION: Primer

<400> SEQUENCE: 180
ccaagcacgc caatattatt gtttaacgcc g 31

<210> SEQ ID NO 181
<211> LENGTH: 28
<212> TYPE: DNA
<213> ORGANISM: Artificial Sequence
<220> FEATURE:
<223> OTHER INFORMATION: Primer

<400> SEQUENCE: 181
ggtgtagccc cggatgcttc gctctacg 28

<210> SEQ ID NO 182
<211> LENGTH: 28
<212> TYPE: DNA
<213> ORGANISM: Artificial Sequence
<220> FEATURE:
<223> OTHER INFORMATION: Primer

<400> SEQUENCE: 182
cgtagagcga agcatccggg gctacacc 28

<210> SEQ ID NO 183
<211> LENGTH: 30
<212> TYPE: DNA
<213> ORGANISM: Artificial Sequence
<220> FEATURE:
<223> OTHER INFORMATION: Primer

<400> SEQUENCE: 183
gtatcgactc gagccatgaa gatcttaaag 30

<210> SEQ ID NO 184
<211> LENGTH: 30
<212> TYPE: DNA
<213> ORGANISM: Artificial Sequence
<220> FEATURE:
<223> OTHER INFORMATION: Primer

<400> SEQUENCE: 184
ctttaagatc ttcatggctc gagtcgatac 30

<210> SEQ ID NO 185
<211> LENGTH: 28
<212> TYPE: DNA
<213> ORGANISM: Artificial Sequence
<220> FEATURE:
<223> OTHER INFORMATION: Primer -continued

<400> SEQUENCE: 185
cgcttccagg gaacaactat ggtgcgta 28

<210> SEQ ID NO 186
<211> LENGTH: 28
<212> TYPE: DNA
<213> ORGANISM: Artificial Sequence
<220> FEATURE:
<223> OTHER INFORMATION: Primer

<400> SEQUENCE: 186
tacgcaccat agttgttccc tggaagcg 28

<210> SEQ ID NO 187
<211> LENGTH: 31
<212> TYPE: DNA
<213> ORGANISM: Artificial Sequence
<220> FEATURE:
<223> OTHER INFORMATION: Primer

<400> SEQUENCE: 187
cactctcaag gctacgttgg atcaaatgtt a 31

<210> SEQ ID NO 188
<211> LENGTH: 31
<212> TYPE: DNA
<213> ORGANISM: Artificial Sequence
<220> FEATURE:
<223> OTHER INFORMATION: Primer

<400> SEQUENCE: 188
taacatttga tccaacgtag ccttgagagt g 31

<210> SEQ ID NO 189
<211> LENGTH: 29
<212> TYPE: DNA
<213> ORGANISM: Artificial Sequence
<220> FEATURE:
<223> OTHER INFORMATION: Primer

<400> SEQUENCE: 189
tggcgtttct attgaatcga cgcttccag 29

<210> SEQ ID NO 190
<211> LENGTH: 29
<212> TYPE: DNA
<213> ORGANISM: Artificial Sequence
<220> FEATURE:
<223> OTHER INFORMATION: Primer

<400> SEQUENCE: 190
ctggaagcgt cgattcaata gaaacgcca 29

<210> SEQ ID NO 191
<211> LENGTH: 39
<212> TYPE: DNA
<213> ORGANISM: Artificial Sequence
<220> FEATURE:
<223> OTHER INFORMATION: Primer

<400> SEQUENCE: 191
gaacggttgc ggcgttagat aattctattg gcgtgcttg 39

<210> SEQ ID NO 192

<211> LENGTH: 37
<212> TYPE: DNA
<213> ORGANISM: Artificial Sequence
<220> FEATURE:
<223> OTHER INFORMATION: Primer

<400> SEQUENCE: 192
agcacgccaa tagaattatc taacgccgca accgttc 37

<210> SEQ ID NO 193
<211> LENGTH: 39
<212> TYPE: DNA
<213> ORGANISM: Artificial Sequence
<220> FEATURE:
<223> OTHER INFORMATION: Primer

<400> SEQUENCE: 193
ttggtgtagc cccggatgct tcgctctacg ccgttaaag 39

<210> SEQ ID NO 194
<211> LENGTH: 35
<212> TYPE: DNA
<213> ORGANISM: Artificial Sequence
<220> FEATURE:
<223> OTHER INFORMATION: Primer

<400> SEQUENCE: 194
cgtagagcga agcatccggg gctacaccaa gcacg 35

<210> SEQ ID NO 195
<211> LENGTH: 35
<212> TYPE: DNA
<213> ORGANISM: Artificial Sequence
<220> FEATURE:
<223> OTHER INFORMATION: Primer

<400> SEQUENCE: 195
gcagcagacg gatcagcaca atactcatgg attat 35

<210> SEQ ID NO 196
<211> LENGTH: 35
<212> TYPE: DNA
<213> ORGANISM: Artificial Sequence
<220> FEATURE:
<223> OTHER INFORMATION: Primer

<400> SEQUENCE: 196
ataatccatg agtattgtgc tgatccgtct gctgc 35

<210> SEQ ID NO 197
<211> LENGTH: 45
<212> TYPE: DNA
<213> ORGANISM: Artificial Sequence
<220> FEATURE:
<223> OTHER INFORMATION: Primer

<400> SEQUENCE: 197
caacatgagc ctgggagcac caccgggcag tgcggcactt aaagc 45

<210> SEQ ID NO 198
<211> LENGTH: 45
<212> TYPE: DNA
<213> ORGANISM: Artificial Sequence
<220> FEATURE:
<223> OTHER INFORMATION: Primer

<400> SEQUENCE: 198
gctttaagtg ccgcactgcc cggtggtgct cccaggctca tgttg 45

<210> SEQ ID NO 199
<211> LENGTH: 39
<212> TYPE: DNA
<213> ORGANISM: Artificial Sequence
<220> FEATURE:
<223> OTHER INFORMATION: Primer

<400> SEQUENCE: 199
gttcttgcag cagacggaaa tggccaatac tcatggatt 39

<210> SEQ ID NO 200
<211> LENGTH: 39
<212> TYPE: DNA
<213> ORGANISM: Artificial Sequence
<220> FEATURE:
<223> OTHER INFORMATION: Primer

<400> SEQUENCE: 200
aatccatgag tattggccat ttccgtctgc tgcaagaac 39

<210> SEQ ID NO 201
<211> LENGTH: 42
<212> TYPE: DNA
<213> ORGANISM: Artificial Sequence
<220> FEATURE:
<223> OTHER INFORMATION: Primer

<400> SEQUENCE: 201
ttaaagttct tgcagcagac aattcaggcc aatactcatg ga 42

<210> SEQ ID NO 202
<211> LENGTH: 42
<212> TYPE: DNA
<213> ORGANISM: Artificial Sequence
<220> FEATURE:
<223> OTHER INFORMATION: Primer

<400> SEQUENCE: 202
tccatgagta ttggcctgaa ttgtctgctg caagaacttt aa 42

<210> SEQ ID NO 203
<211> LENGTH: 36
<212> TYPE: DNA
<213> ORGANISM: Artificial Sequence
<220> FEATURE:
<223> OTHER INFORMATION: Primer

<400> SEQUENCE: 203
ccgtttcaag atccgaattc tcatggcaca cacgtc 36

<210> SEQ ID NO 204
<211> LENGTH: 38
<212> TYPE: DNA
<213> ORGANISM: Artificial Sequence
<220> FEATURE:
<223> OTHER INFORMATION: Primer

<400> SEQUENCE: 204
tgccatgaga attcggatct tgaaacgggt ttgtttcg 38

<210> SEQ ID NO 205
<211> LENGTH: 40
<212> TYPE: DNA

<213> ORGANISM: Artificial Sequence
<220> FEATURE:
<223> OTHER INFORMATION: Primer

<400> SEQUENCE: 205
ttcaaatcaa cgtgattctt tttcctccgt gggaccggag 40

<210> SEQ ID NO 206
<211> LENGTH: 40
<212> TYPE: DNA
<213> ORGANISM: Artificial Sequence
<220> FEATURE:
<223> OTHER INFORMATION: Primer

<400> SEQUENCE: 206
acggaggaaa aagaatcacg ttgatttgaa gagtctacag 40

<210> SEQ ID NO 207
<211> LENGTH: 38
<212> TYPE: DNA
<213> ORGANISM: Artificial Sequence
<220> FEATURE:
<223> OTHER INFORMATION: Primer

<400> SEQUENCE: 207
caaatcaacg tgcctctgat tcctccgtgg gaccggag 38

<210> SEQ ID NO 208
<211> LENGTH: 38
<212> TYPE: DNA
<213> ORGANISM: Artificial Sequence
<220> FEATURE:
<223> OTHER INFORMATION: Primer

<400> SEQUENCE: 208
ctccggtccc acggaggaat cagaggcacg ttgatttg 38

<210> SEQ ID NO 209
<211> LENGTH: 44
<212> TYPE: DNA
<213> ORGANISM: Artificial Sequence
<220> FEATURE:
<223> OTHER INFORMATION: Primer

<400> SEQUENCE: 209
agcggcagtg cggcacttaa agttgcagtt gataaagctg ttgc 44

<210> SEQ ID NO 210
<211> LENGTH: 44
<212> TYPE: DNA
<213> ORGANISM: Artificial Sequence
<220> FEATURE:
<223> OTHER INFORMATION: Primer

<400> SEQUENCE: 210
gcaacagctt tatcaactgc aactttaagt gccgcactgc cgct 44

<210> SEQ ID NO 211
<211> LENGTH: 39
<212> TYPE: DNA
<213> ORGANISM: Artificial Sequence
<220> FEATURE:
<223> OTHER INFORMATION: Primer

<400> SEQUENCE: 211
tcaagataac aatacacatg gcacacacgt cgcaggaac 39

<210> SEQ ID NO 212
<211> LENGTH: 40
<212> TYPE: DNA
<213> ORGANISM: Artificial Sequence
<220> FEATURE:
<223> OTHER INFORMATION: Primer

<400> SEQUENCE: 212
acgtgtgtgc catgtgtatt gttatcttga aacgggtttg 40

<210> SEQ ID NO 213
<211> LENGTH: 40
<212> TYPE: DNA
<213> ORGANISM: Artificial Sequence
<220> FEATURE:
<223> OTHER INFORMATION: Primer

<400> SEQUENCE: 213
agacggatca ggcaattact catggattat caacggcatc 40

<210> SEQ ID NO 214
<211> LENGTH: 37
<212> TYPE: DNA
<213> ORGANISM: Artificial Sequence
<220> FEATURE:
<223> OTHER INFORMATION: Primer

<400> SEQUENCE: 214
taatccatga gtaattgcct gatccgtctg ctgcaag 37

<210> SEQ ID NO 215
<211> LENGTH: 38
<212> TYPE: DNA
<213> ORGANISM: Artificial Sequence
<220> FEATURE:
<223> OTHER INFORMATION: Primer

<400> SEQUENCE: 215
acccgtttca agataacgat tctcatggca cacacgtc 38

<210> SEQ ID NO 216
<211> LENGTH: 38
<212> TYPE: DNA
<213> ORGANISM: Artificial Sequence
<220> FEATURE:
<223> OTHER INFORMATION: Primer

<400> SEQUENCE: 216
gacgtgtgtg ccatgagaat cgttatcttg aaacgggt 38

<210> SEQ ID NO 217
<211> LENGTH: 37
<212> TYPE: DNA
<213> ORGANISM: Artificial Sequence
<220> FEATURE:
<223> OTHER INFORMATION: Primer

<400> SEQUENCE: 217
caatactcat ggattatcga tggcatcgaa tgggcca 37

<210> SEQ ID NO 218
<211> LENGTH: 37
<212> TYPE: DNA
<213> ORGANISM: Artificial Sequence
<220> FEATURE:

<223> OTHER INFORMATION: Primer

<400> SEQUENCE: 218
tggcccattc gatgccatcg ataatccatg agtattg 37

<210> SEQ ID NO 219
<211> LENGTH: 39
<212> TYPE: DNA
<213> ORGANISM: Artificial Sequence
<220> FEATURE:
<223> OTHER INFORMATION: Primer

<400> SEQUENCE: 219
ctcttcaaat caacgtgccg atttttcctc cgtgggacc 39

<210> SEQ ID NO 220
<211> LENGTH: 39
<212> TYPE: DNA
<213> ORGANISM: Artificial Sequence
<220> FEATURE:
<223> OTHER INFORMATION: Primer

<400> SEQUENCE: 220
ggtcccacgg aggaaaaatc ggcacgttga tttgaagag 39

<210> SEQ ID NO 221
<211> LENGTH: 37
<212> TYPE: DNA
<213> ORGANISM: Artificial Sequence
<220> FEATURE:
<223> OTHER INFORMATION: Primer

<400> SEQUENCE: 221
caaacactca agtccgcaga agtttagaaa acaccac 37

<210> SEQ ID NO 222
<211> LENGTH: 38
<212> TYPE: DNA
<213> ORGANISM: Artificial Sequence
<220> FEATURE:
<223> OTHER INFORMATION: Primer

<400> SEQUENCE: 222
gtgcttggtg tagccccgag agcttcgctc tacgccgt 38

<210> SEQ ID NO 223
<211> LENGTH: 38
<212> TYPE: DNA
<213> ORGANISM: Artificial Sequence
<220> FEATURE:
<223> OTHER INFORMATION: Primer

<400> SEQUENCE: 223
acggcgtaga gcgaagctct cggggctaca ccaagcac 38

<210> SEQ ID NO 224
<211> LENGTH: 37
<212> TYPE: DNA
<213> ORGANISM: Artificial Sequence
<220> FEATURE:
<223> OTHER INFORMATION: Primer

<400> SEQUENCE: 224
caaacactca agtccgcgat agtttagaaa acaccac 37

-continued

<210> SEQ ID NO 225
<211> LENGTH: 37
<212> TYPE: DNA
<213> ORGANISM: Artificial Sequence
<220> FEATURE:
<223> OTHER INFORMATION: Primer

<400> SEQUENCE: 225
gtggtgtttt ctaaactatc gcggacttga gtgtttg 37

<210> SEQ ID NO 226
<211> LENGTH: 38
<212> TYPE: DNA
<213> ORGANISM: Artificial Sequence
<220> FEATURE:
<223> OTHER INFORMATION: Primer

<400> SEQUENCE: 226
gtgcttggtg tagccccgtc tgcttcgctc tacgccgt 38

<210> SEQ ID NO 227
<211> LENGTH: 38
<212> TYPE: DNA
<213> ORGANISM: Artificial Sequence
<220> FEATURE:
<223> OTHER INFORMATION: Primer

<400> SEQUENCE: 227
acggcgtaga gcgaagcaga cggggctaca ccaagcac 38

<210> SEQ ID NO 228
<211> LENGTH: 37
<212> TYPE: DNA
<213> ORGANISM: Artificial Sequence
<220> FEATURE:
<223> OTHER INFORMATION: Primer

<400> SEQUENCE: 228
caatactcat ggattatcaa cggcatcgaa tgggcca 37

<210> SEQ ID NO 229
<211> LENGTH: 37
<212> TYPE: DNA
<213> ORGANISM: Artificial Sequence
<220> FEATURE:
<223> OTHER INFORMATION: Primer

<400> SEQUENCE: 229
tggcccattc gatgccgttg ataatccatg agtattg 37

<210> SEQ ID NO 230
<211> LENGTH: 37
<212> TYPE: DNA
<213> ORGANISM: Artificial Sequence
<220> FEATURE:
<223> OTHER INFORMATION: Primer

<400> SEQUENCE: 230
actcatggat tatcgatggc atcgaatggg ccatcgc 37

<210> SEQ ID NO 231
<211> LENGTH: 36
<212> TYPE: DNA
<213> ORGANISM: Artificial Sequence
<220> FEATURE:
<223> OTHER INFORMATION: Primer

<400> SEQUENCE: 231
cactcaagtc cgcagaagtt tagaaaacac cactac 36

<210> SEQ ID NO 232
<211> LENGTH: 36
<212> TYPE: DNA
<213> ORGANISM: Artificial Sequence
<220> FEATURE:
<223> OTHER INFORMATION: Primer

<400> SEQUENCE: 232
cactcaagtc cgcgatagtt tagaaaacac cactac 36

<210> SEQ ID NO 233
<211> LENGTH: 38
<212> TYPE: DNA
<213> ORGANISM: Artificial Sequence
<220> FEATURE:
<223> OTHER INFORMATION: Primer

<400> SEQUENCE: 233
caaatcaacg tgccagattt tcctccgtgg gaccggag 38

<210> SEQ ID NO 234
<211> LENGTH: 24
<212> TYPE: DNA
<213> ORGANISM: Artificial Sequence
<220> FEATURE:
<223> OTHER INFORMATION: Primer

<400> SEQUENCE: 234
aaaggggagg aaaatcgtga aaca 24

<210> SEQ ID NO 235
<211> LENGTH: 22
<212> TYPE: DNA
<213> ORGANISM: Artificial Sequence
<220> FEATURE:
<223> OTHER INFORMATION: Primer

<400> SEQUENCE: 235
gttctaaatc gtgtttttct tg 22

<210> SEQ ID NO 236
<211> LENGTH: 48
<212> TYPE: DNA
<213> ORGANISM: Artificial Sequence
<220> FEATURE:
<223> OTHER INFORMATION: Primer

<400> SEQUENCE: 236
gaactggaca aacactcaag tccgcgatag tttagaaaac accactac 48

<210> SEQ ID NO 237
<211> LENGTH: 36
<212> TYPE: DNA
<213> ORGANISM: Artificial Sequence
<220> FEATURE:
<223> OTHER INFORMATION: Primer

<400> SEQUENCE: 237
gacttgagtg tttgtccagt tcgggtgctt agaaag 36

<210> SEQ ID NO 238
<211> LENGTH: 37

<212> TYPE: DNA
<213> ORGANISM: Artificial Sequence
<220> FEATURE:
<223> OTHER INFORMATION: Primer

<400> SEQUENCE: 238
caaacactca agtccgcagc agtttagaaa acaccac 37

<210> SEQ ID NO 239
<211> LENGTH: 37
<212> TYPE: DNA
<213> ORGANISM: Artificial Sequence
<220> FEATURE:
<223> OTHER INFORMATION: Primer

<400> SEQUENCE: 239
gtggtgtttt ctaaactgct gcggacttga gtgtttg 37

<210> SEQ ID NO 240
<211> LENGTH: 49
<212> TYPE: DNA
<213> ORGANISM: Artificial Sequence
<220> FEATURE:
<223> OTHER INFORMATION: Primer

<400> SEQUENCE: 240
acgccgttaa agttcttgca gcagacgaat caggccaata ctcatggat 49

<210> SEQ ID NO 241
<211> LENGTH: 36
<212> TYPE: DNA
<213> ORGANISM: Artificial Sequence
<220> FEATURE:
<223> OTHER INFORMATION: Primer

<400> SEQUENCE: 241
tgctgcaaga actttaacgg cgtagagcga agcaga 36

<210> SEQ ID NO 242
<211> LENGTH: 37
<212> TYPE: DNA
<213> ORGANISM: Artificial Sequence
<220> FEATURE:
<223> OTHER INFORMATION: Primer

<400> SEQUENCE: 242
acatggatgt aatctgcatg agcctgggag gaccaag 37

<210> SEQ ID NO 243
<211> LENGTH: 38
<212> TYPE: DNA
<213> ORGANISM: Artificial Sequence
<220> FEATURE:
<223> OTHER INFORMATION: Primer

<400> SEQUENCE: 243
tcctcccagg ctcatgcaga ttacatccat gttattcg 38

<210> SEQ ID NO 244
<211> LENGTH: 22
<212> TYPE: DNA
<213> ORGANISM: Artificial Sequence
<220> FEATURE:
<223> OTHER INFORMATION: Primer

<400> SEQUENCE: 244
gttatgagtt agttcaaatt cg                                              22

<210> SEQ ID NO 245
<211> LENGTH: 46
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (16)..(17)
<223> OTHER INFORMATION: n is a, c, g, or t
<220> FEATURE:
<221> NAME/KEY: misc_feature
<222> LOCATION: (19)..(20)
<223> OTHER INFORMATION: n is a, c, g, or t
<220> FEATURE:
<221> NAME/KEY: misc_feature
<222> LOCATION: (22)..(23)
<223> OTHER INFORMATION: n is a, c, g, or t

<400> SEQUENCE: 245
tacgcgcagt ccgtgnntnn cnncgtatca caaattaaag cccctg                    46

<210> SEQ ID NO 246
<211> LENGTH: 44
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (17)..(18)
<223> OTHER INFORMATION: n is a, c, g, or t
<220> FEATURE:
<221> NAME/KEY: misc_feature
<222> LOCATION: (20)..(21)
<223> OTHER INFORMATION: n is a, c, g, or t
<220> FEATURE:
<221> NAME/KEY: misc_feature
<222> LOCATION: (23)..(24)
<223> OTHER INFORMATION: n is a, c, g, or t

<400> SEQUENCE: 246
tttaatttgt gatacgnngn nanncacgga ctgcgcgtac gcat                      44

<210> SEQ ID NO 247
<211> LENGTH: 43
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (16)..(17)
<223> OTHER INFORMATION: n is a, c, g, or t
<220> FEATURE:
<221> NAME/KEY: misc_feature
<222> LOCATION: (19)..(20)
<223> OTHER INFORMATION: n is a, c, g, or t
<220> FEATURE:
<221> NAME/KEY: misc_feature
<222> LOCATION: (22)..(23)
<223> OTHER INFORMATION: n is a, c, g, or t

<400> SEQUENCE: 247
tacggcgtat cacaanntnn annccctgct ctgcactctc aag                       43

<210> SEQ ID NO 248
<211> LENGTH: 45
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (17)..(18)
<223> OTHER INFORMATION: n is a, c, g, or t
<220> FEATURE:
<221> NAME/KEY: misc_feature
<222> LOCATION: (20)..(21)
<223> OTHER INFORMATION: n is a, c, g, or t
<220> FEATURE:
<221> NAME/KEY: misc_feature
<222> LOCATION: (23)..(24)
<223> OTHER INFORMATION: n is a, c, g, or t

<400> SEQUENCE: 248
agagtgcaga gcagggnntn nannttgtga tacgccgtaa ggcac 45

<210> SEQ ID NO 249
<211> LENGTH: 47
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (16)..(17)
<223> OTHER INFORMATION: n is a, c, g, or t
<220> FEATURE:
<221> NAME/KEY: misc_feature
<222> LOCATION: (19)..(20)
<223> OTHER INFORMATION: n is a, c, g, or t
<220> FEATURE:
<221> NAME/KEY: misc_feature
<222> LOCATION: (22)..(23)
<223> OTHER INFORMATION: n is a, c, g, or t

<400> SEQUENCE: 249
gctctgcact ctcaanncnn cnntggatca aatgttaaag tagcggt 47

<210> SEQ ID NO 250
<211> LENGTH: 47
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (17)..(18)
<223> OTHER INFORMATION: n is a, c, g, or t
<220> FEATURE:
<221> NAME/KEY: misc_feature
<222> LOCATION: (20)..(21)
<223> OTHER INFORMATION: n is a, c, g, or t
<220> FEATURE:
<221> NAME/KEY: misc_feature
<222> LOCATION: (23)..(24)
<223> OTHER INFORMATION: n is a, c, g, or t

<400> SEQUENCE: 250
tttaacattt gatccanngn ngnnttgaga gtgcagagca ggggctt 47

<210> SEQ ID NO 251
<211> LENGTH: 48
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (16)..(17)
<223> OTHER INFORMATION: n is a, c, g, or t
<220> FEATURE:

<221> NAME/KEY: misc_feature
<222> LOCATION: (19)..(20)
<223> OTHER INFORMATION: n is a, c, g, or t
<220> FEATURE:
<221> NAME/KEY: misc_feature
<222> LOCATION: (22)..(23)
<223> OTHER INFORMATION: n is a, c, g, or t

<400> SEQUENCE: 251
ctgcactctc aaggcnncnn tnnatcaaat gttaaagtag cggttatc 48

<210> SEQ ID NO 252
<211> LENGTH: 44
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (17)..(18)
<223> OTHER INFORMATION: n is a, c, g, or t
<220> FEATURE:
<221> NAME/KEY: misc_feature
<222> LOCATION: (20)..(21)
<223> OTHER INFORMATION: n is a, c, g, or t
<220> FEATURE:
<221> NAME/KEY: misc_feature
<222> LOCATION: (23)..(24)
<223> OTHER INFORMATION: n is a, c, g, or t

<400> SEQUENCE: 252
tactttaaca tttgatnnan ngnngccttg agagtgcaga gcag 44

<210> SEQ ID NO 253
<211> LENGTH: 47
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (16)..(17)
<223> OTHER INFORMATION: n is a, c, g, or t
<220> FEATURE:
<221> NAME/KEY: misc_feature
<222> LOCATION: (19)..(20)
<223> OTHER INFORMATION: n is a, c, g, or t
<220> FEATURE:
<221> NAME/KEY: misc_feature
<222> LOCATION: (22)..(23)
<223> OTHER INFORMATION: n is a, c, g, or t

<400> SEQUENCE: 253
cactctcaag gctacnntnn annaaatgtt aaagtagcgg ttatcga 47

<210> SEQ ID NO 254
<211> LENGTH: 44
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (17)..(18)
<223> OTHER INFORMATION: n is a, c, g, or t
<220> FEATURE:
<221> NAME/KEY: misc_feature
<222> LOCATION: (20)..(21)
<223> OTHER INFORMATION: n is a, c, g, or t
<220> FEATURE:
<221> NAME/KEY: misc_feature
<222> LOCATION: (23)..(24)
<223> OTHER INFORMATION: n is a, c, g, or t

<400> SEQUENCE: 254
cgctacttta acatttnntn nanngtagcc ttgagagtgc agag 44

<210> SEQ ID NO 255
<211> LENGTH: 46
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (16)..(17)
<223> OTHER INFORMATION: n is a, c, g, or t
<220> FEATURE:
<221> NAME/KEY: misc_feature
<222> LOCATION: (19)..(20)
<223> OTHER INFORMATION: n is a, c, g, or t
<220> FEATURE:
<221> NAME/KEY: misc_feature
<222> LOCATION: (22)..(23)
<223> OTHER INFORMATION: n is a, c, g, or t

<400> SEQUENCE: 255
tctcaaggct acactnnann anntgttaaa gtagcggtta tcgaca 46

<210> SEQ ID NO 256
<211> LENGTH: 45
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (17)..(18)
<223> OTHER INFORMATION: n is a, c, g, or t
<220> FEATURE:
<221> NAME/KEY: misc_feature
<222> LOCATION: (20)..(21)
<223> OTHER INFORMATION: n is a, c, g, or t
<220> FEATURE:
<221> NAME/KEY: misc_feature
<222> LOCATION: (23)..(24)
<223> OTHER INFORMATION: n is a, c, g, or t

<400> SEQUENCE: 256
aaccgctact ttaacanntn ntnnagtgta gccttgagag tgcag 45

<210> SEQ ID NO 257
<211> LENGTH: 45
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (16)..(17)
<223> OTHER INFORMATION: n is a, c, g, or t
<220> FEATURE:
<221> NAME/KEY: misc_feature
<222> LOCATION: (19)..(20)
<223> OTHER INFORMATION: n is a, c, g, or t
<220> FEATURE:
<221> NAME/KEY: misc_feature
<222> LOCATION: (22)..(23)
<223> OTHER INFORMATION: n is a, c, g, or t

<400> SEQUENCE: 257
caaggctaca ctggannann tnntaaagta gcggttatcg acagc 45

<210> SEQ ID NO 258

<211> LENGTH: 45
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (17)..(18)
<223> OTHER INFORMATION: n is a, c, g, or t
<220> FEATURE:
<221> NAME/KEY: misc_feature
<222> LOCATION: (20)..(21)
<223> OTHER INFORMATION: n is a, c, g, or t
<220> FEATURE:
<221> NAME/KEY: misc_feature
<222> LOCATION: (23)..(24)
<223> OTHER INFORMATION: n is a, c, g, or t

<400> SEQUENCE: 258
gataaccgct actttannan ntnntccagt gtagccttga gagtg 45

<210> SEQ ID NO 259
<211> LENGTH: 45
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (16)..(17)
<223> OTHER INFORMATION: n is a, c, g, or t
<220> FEATURE:
<221> NAME/KEY: misc_feature
<222> LOCATION: (19)..(20)
<223> OTHER INFORMATION: n is a, c, g, or t
<220> FEATURE:
<221> NAME/KEY: misc_feature
<222> LOCATION: (22)..(23)
<223> OTHER INFORMATION: n is a, c, g, or t

<400> SEQUENCE: 259
ggctacactg gatcanntnn tnnagtagcg gttatcgaca gcggt 45

<210> SEQ ID NO 260
<211> LENGTH: 45
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (17)..(18)
<223> OTHER INFORMATION: n is a, c, g, or t
<220> FEATURE:
<221> NAME/KEY: misc_feature
<222> LOCATION: (20)..(21)
<223> OTHER INFORMATION: n is a, c, g, or t
<220> FEATURE:
<221> NAME/KEY: misc_feature
<222> LOCATION: (23)..(24)
<223> OTHER INFORMATION: n is a, c, g, or t

<400> SEQUENCE: 260
gtcgataacc gctactnnan nanntgatcc agtgtagcct tgaga 45

<210> SEQ ID NO 261
<211> LENGTH: 44
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (16)..(17)
<223> OTHER INFORMATION: n is a, c, g, or t
<220> FEATURE:
<221> NAME/KEY: misc_feature
<222> LOCATION: (19)..(20)
<223> OTHER INFORMATION: n is a, c, g, or t
<220> FEATURE:
<221> NAME/KEY: misc_feature
<222> LOCATION: (22)..(23)
<223> OTHER INFORMATION: n is a, c, g, or t

<400> SEQUENCE: 261
tacactggat caaatnntnn annagcggtt atcgacagcg gtat 44

<210> SEQ ID NO 262
<211> LENGTH: 46
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (17)..(18)
<223> OTHER INFORMATION: n is a, c, g, or t
<220> FEATURE:
<221> NAME/KEY: misc_feature
<222> LOCATION: (20)..(21)
<223> OTHER INFORMATION: n is a, c, g, or t
<220> FEATURE:
<221> NAME/KEY: misc_feature
<222> LOCATION: (23)..(24)
<223> OTHER INFORMATION: n is a, c, g, or t

<400> SEQUENCE: 262
gctgtcgata accgctnntn nannatttga tccagtgtag ccttga 46

<210> SEQ ID NO 263
<211> LENGTH: 45
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (16)..(17)
<223> OTHER INFORMATION: n is a, c, g, or t
<220> FEATURE:
<221> NAME/KEY: misc_feature
<222> LOCATION: (19)..(20)
<223> OTHER INFORMATION: n is a, c, g, or t
<220> FEATURE:
<221> NAME/KEY: misc_feature
<222> LOCATION: (22)..(23)
<223> OTHER INFORMATION: n is a, c, g, or t

<400> SEQUENCE: 263
actggatcaa atgttnnann annggttatc gacagcggta tcgac 45

<210> SEQ ID NO 264
<211> LENGTH: 46
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (17)..(18)
<223> OTHER INFORMATION: n is a, c, g, or t
<220> FEATURE:
<221> NAME/KEY: misc_feature
<222> LOCATION: (20)..(21)
<223> OTHER INFORMATION: n is a, c, g, or t
<220> FEATURE:

<221> NAME/KEY: misc_feature
<222> LOCATION: (23)..(24)
<223> OTHER INFORMATION: n is a, c, g, or t

<400> SEQUENCE: 264
accgctgtcg ataaccnntn ntnnaacatt tgatccagtg tagcct 46

<210> SEQ ID NO 265
<211> LENGTH: 44
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (16)..(17)
<223> OTHER INFORMATION: n is a, c, g, or t
<220> FEATURE:
<221> NAME/KEY: misc_feature
<222> LOCATION: (19)..(20)
<223> OTHER INFORMATION: n is a, c, g, or t
<220> FEATURE:
<221> NAME/KEY: misc_feature
<222> LOCATION: (22)..(23)
<223> OTHER INFORMATION: n is a, c, g, or t

<400> SEQUENCE: 265
ggatcaaatg ttaaannann gnntatcgac agcggtatcg actc 44

<210> SEQ ID NO 266
<211> LENGTH: 47
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (17)..(18)
<223> OTHER INFORMATION: n is a, c, g, or t
<220> FEATURE:
<221> NAME/KEY: misc_feature
<222> LOCATION: (20)..(21)
<223> OTHER INFORMATION: n is a, c, g, or t
<220> FEATURE:
<221> NAME/KEY: misc_feature
<222> LOCATION: (23)..(24)
<223> OTHER INFORMATION: n is a, c, g, or t

<400> SEQUENCE: 266
gataccgctg tcgatanncn ntnntttaac atttgatcca gtgtagc 47

<210> SEQ ID NO 267
<211> LENGTH: 48
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (16)..(17)
<223> OTHER INFORMATION: n is a, c, g, or t
<220> FEATURE:
<221> NAME/KEY: misc_feature
<222> LOCATION: (19)..(20)
<223> OTHER INFORMATION: n is a, c, g, or t
<220> FEATURE:
<221> NAME/KEY: misc_feature
<222> LOCATION: (22)..(23)
<223> OTHER INFORMATION: n is a, c, g, or t

<400> SEQUENCE: 267
tcaaatgtta aagtanngnn tnncgacagc ggtatcgact cgagccat 48

<210> SEQ ID NO 268
<211> LENGTH: 48
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (17)..(18)
<223> OTHER INFORMATION: n is a, c, g, or t
<220> FEATURE:
<221> NAME/KEY: misc_feature
<222> LOCATION: (20)..(21)
<223> OTHER INFORMATION: n is a, c, g, or t
<220> FEATURE:
<221> NAME/KEY: misc_feature
<222> LOCATION: (23)..(24)
<223> OTHER INFORMATION: n is a, c, g, or t

<400> SEQUENCE: 268
gtcgataccg ctgtcgnnan ncnntacttt aacatttgat ccagtgta 48

<210> SEQ ID NO 269
<211> LENGTH: 45
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (16)..(17)
<223> OTHER INFORMATION: n is a, c, g, or t
<220> FEATURE:
<221> NAME/KEY: misc_feature
<222> LOCATION: (19)..(20)
<223> OTHER INFORMATION: n is a, c, g, or t
<220> FEATURE:
<221> NAME/KEY: misc_feature
<222> LOCATION: (22)..(23)
<223> OTHER INFORMATION: n is a, c, g, or t

<400> SEQUENCE: 269
aatgttaaag tagcgnntnn cnncagcggt atcgactcga gccat 45

<210> SEQ ID NO 270
<211> LENGTH: 47
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (17)..(18)
<223> OTHER INFORMATION: n is a, c, g, or t
<220> FEATURE:
<221> NAME/KEY: misc_feature
<222> LOCATION: (20)..(21)
<223> OTHER INFORMATION: n is a, c, g, or t
<220> FEATURE:
<221> NAME/KEY: misc_feature
<222> LOCATION: (23)..(24)
<223> OTHER INFORMATION: n is a, c, g, or t

<400> SEQUENCE: 270
cgagtcgata ccgctgnngn nanncgctac tttaacattt gatccag 47

<210> SEQ ID NO 271
<211> LENGTH: 45
<212> TYPE: DNA
<213> ORGANISM: Artificial Sequence
<220> FEATURE:

<223> OTHER INFORMATION: Primer
<220> FEATURE:
<221> NAME/KEY: misc_feature
<222> LOCATION: (16)..(17)
<223> OTHER INFORMATION: n is a, c, g, or t
<220> FEATURE:
<221> NAME/KEY: misc_feature
<222> LOCATION: (19)..(20)
<223> OTHER INFORMATION: n is a, c, g, or t
<220> FEATURE:
<221> NAME/KEY: misc_feature
<222> LOCATION: (22)..(23)
<223> OTHER INFORMATION: n is a, c, g, or t

<400> SEQUENCE: 271
gttaaagtag cggttnncnn cnncggtatc gactcgagcc atcca 45

<210> SEQ ID NO 272
<211> LENGTH: 47
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (17)..(18)
<223> OTHER INFORMATION: n is a, c, g, or t
<220> FEATURE:
<221> NAME/KEY: misc_feature
<222> LOCATION: (20)..(21)
<223> OTHER INFORMATION: n is a, c, g, or t
<220> FEATURE:
<221> NAME/KEY: misc_feature
<222> LOCATION: (23)..(24)
<223> OTHER INFORMATION: n is a, c, g, or t

<400> SEQUENCE: 272
gctcgagtcg ataccgnngn ngnnaaccgc tactttaaca tttgatc 47

<210> SEQ ID NO 273
<211> LENGTH: 45
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (16)..(17)
<223> OTHER INFORMATION: n is a, c, g, or t
<220> FEATURE:
<221> NAME/KEY: misc_feature
<222> LOCATION: (19)..(20)
<223> OTHER INFORMATION: n is a, c, g, or t
<220> FEATURE:
<221> NAME/KEY: misc_feature
<222> LOCATION: (22)..(23)
<223> OTHER INFORMATION: n is a, c, g, or t

<400> SEQUENCE: 273
aaagtagcgg ttatcnncnn cnntatcgac tcgagccatc cagat 45

<210> SEQ ID NO 274
<211> LENGTH: 47
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (17)..(18)
<223> OTHER INFORMATION: n is a, c, g, or t
<220> FEATURE:
<221> NAME/KEY: misc_feature
<222> LOCATION: (20)..(21)
<223> OTHER INFORMATION: n is a, c, g, or t
<220> FEATURE:
<221> NAME/KEY: misc_feature
<222> LOCATION: (23)..(24)
<223> OTHER INFORMATION: n is a, c, g, or t

<400> SEQUENCE: 274
atggctcgag tcgatanngn ngnngataac cgctacttta acatttg 47

<210> SEQ ID NO 275
<211> LENGTH: 44
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (16)..(17)
<223> OTHER INFORMATION: n is a, c, g, or t
<220> FEATURE:
<221> NAME/KEY: misc_feature
<222> LOCATION: (19)..(20)
<223> OTHER INFORMATION: n is a, c, g, or t
<220> FEATURE:
<221> NAME/KEY: misc_feature
<222> LOCATION: (22)..(23)
<223> OTHER INFORMATION: n is a, c, g, or t

<400> SEQUENCE: 275
gtagcggtta tcgacnncnn tnncgactcg agccatccag atct 44

<210> SEQ ID NO 276
<211> LENGTH: 46
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (17)..(18)
<223> OTHER INFORMATION: n is a, c, g, or t
<220> FEATURE:
<221> NAME/KEY: misc_feature
<222> LOCATION: (20)..(21)
<223> OTHER INFORMATION: n is a, c, g, or t
<220> FEATURE:
<221> NAME/KEY: misc_feature
<222> LOCATION: (23)..(24)
<223> OTHER INFORMATION: n is a, c, g, or t

<400> SEQUENCE: 276
tggatggctc gagtcgnnan ngnngtcgat aaccgctact ttaaca 46

<210> SEQ ID NO 277
<211> LENGTH: 46
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (16)..(17)
<223> OTHER INFORMATION: n is a, c, g, or t
<220> FEATURE:
<221> NAME/KEY: misc_feature
<222> LOCATION: (19)..(20)
<223> OTHER INFORMATION: n is a, c, g, or t
<220> FEATURE:
<221> NAME/KEY: misc_feature
<222> LOCATION: (22)..(23)
<223> OTHER INFORMATION: n is a, c, g, or t

<400> SEQUENCE: 277
gcggttatcg acagcnntnn cnnctcgagc catccagatc ttaaag 46

<210> SEQ ID NO 278
<211> LENGTH: 45
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (17)..(18)
<223> OTHER INFORMATION: n is a, c, g, or t
<220> FEATURE:
<221> NAME/KEY: misc_feature
<222> LOCATION: (20)..(21)
<223> OTHER INFORMATION: n is a, c, g, or t
<220> FEATURE:
<221> NAME/KEY: misc_feature
<222> LOCATION: (23)..(24)
<223> OTHER INFORMATION: n is a, c, g, or t

<400> SEQUENCE: 278
atctggatgg ctcgagnngn nanngctgtc gataaccgct acttt 45

<210> SEQ ID NO 279
<211> LENGTH: 45
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (16)..(17)
<223> OTHER INFORMATION: n is a, c, g, or t
<220> FEATURE:
<221> NAME/KEY: misc_feature
<222> LOCATION: (19)..(20)
<223> OTHER INFORMATION: n is a, c, g, or t
<220> FEATURE:
<221> NAME/KEY: misc_feature
<222> LOCATION: (22)..(23)
<223> OTHER INFORMATION: n is a, c, g, or t

<400> SEQUENCE: 279
gttatcgaca gcggtnncnn cnngagccat ccagatctta aagtc 45

<210> SEQ ID NO 280
<211> LENGTH: 44
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (17)..(18)
<223> OTHER INFORMATION: n is a, c, g, or t
<220> FEATURE:
<221> NAME/KEY: misc_feature
<222> LOCATION: (20)..(21)
<223> OTHER INFORMATION: n is a, c, g, or t
<220> FEATURE:
<221> NAME/KEY: misc_feature
<222> LOCATION: (23)..(24)
<223> OTHER INFORMATION: n is a, c, g, or t

<400> SEQUENCE: 280
aagatctgga tggctcnngn ngnnaccgct gtcgataacc gcta 44

<210> SEQ ID NO 281
<211> LENGTH: 46

<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (16)..(17)
<223> OTHER INFORMATION: n is a, c, g, or t
<220> FEATURE:
<221> NAME/KEY: misc_feature
<222> LOCATION: (19)..(20)
<223> OTHER INFORMATION: n is a, c, g, or t
<220> FEATURE:
<221> NAME/KEY: misc_feature
<222> LOCATION: (22)..(23)
<223> OTHER INFORMATION: n is a, c, g, or t

<400> SEQUENCE: 281
atcgacagcg gtatcnncnn gnnccatcca gatcttaaag tcgctg 46

<210> SEQ ID NO 282
<211> LENGTH: 47
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (17)..(18)
<223> OTHER INFORMATION: n is a, c, g, or t
<220> FEATURE:
<221> NAME/KEY: misc_feature
<222> LOCATION: (20)..(21)
<223> OTHER INFORMATION: n is a, c, g, or t
<220> FEATURE:
<221> NAME/KEY: misc_feature
<222> LOCATION: (23)..(24)
<223> OTHER INFORMATION: n is a, c, g, or t

<400> SEQUENCE: 282
tttaagatct ggatggnncn ngnngatacc gctgtcgata accgcta 47

<210> SEQ ID NO 283
<211> LENGTH: 45
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (16)..(17)
<223> OTHER INFORMATION: n is a, c, g, or t
<220> FEATURE:
<221> NAME/KEY: misc_feature
<222> LOCATION: (19)..(20)
<223> OTHER INFORMATION: n is a, c, g, or t
<220> FEATURE:
<221> NAME/KEY: misc_feature
<222> LOCATION: (22)..(23)
<223> OTHER INFORMATION: n is a, c, g, or t

<400> SEQUENCE: 283
gacagcggta tcgacnngnn cnntccagat cttaaagtcg ctgga 45

<210> SEQ ID NO 284
<211> LENGTH: 45
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (17)..(18)

<223> OTHER INFORMATION: n is a, c, g, or t
<220> FEATURE:
<221> NAME/KEY: misc_feature
<222> LOCATION: (20)..(21)
<223> OTHER INFORMATION: n is a, c, g, or t
<220> FEATURE:
<221> NAME/KEY: misc_feature
<222> LOCATION: (23)..(24)
<223> OTHER INFORMATION: n is a, c, g, or t

<400> SEQUENCE: 284
gactttaaga tctgganngn ncnngtcgat accgctgtcg ataac 45

<210> SEQ ID NO 285
<211> LENGTH: 44
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (16)..(17)
<223> OTHER INFORMATION: n is a, c, g, or t
<220> FEATURE:
<221> NAME/KEY: misc_feature
<222> LOCATION: (19)..(20)
<223> OTHER INFORMATION: n is a, c, g, or t
<220> FEATURE:
<221> NAME/KEY: misc_feature
<222> LOCATION: (22)..(23)
<223> OTHER INFORMATION: n is a, c, g, or t

<400> SEQUENCE: 285
agcggtatcg actcgnncnn tnnagatctt aaagtcgctg gagg 44

<210> SEQ ID NO 286
<211> LENGTH: 44
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (17)..(18)
<223> OTHER INFORMATION: n is a, c, g, or t
<220> FEATURE:
<221> NAME/KEY: misc_feature
<222> LOCATION: (20)..(21)
<223> OTHER INFORMATION: n is a, c, g, or t
<220> FEATURE:
<221> NAME/KEY: misc_feature
<222> LOCATION: (23)..(24)
<223> OTHER INFORMATION: n is a, c, g, or t

<400> SEQUENCE: 286
agcgacttta agatctnnan ngnncgagtc gataccgctg tcga 44

<210> SEQ ID NO 287
<211> LENGTH: 44
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (16)..(17)
<223> OTHER INFORMATION: n is a, c, g, or t
<220> FEATURE:
<221> NAME/KEY: misc_feature
<222> LOCATION: (19)..(20)
<223> OTHER INFORMATION: n is a, c, g, or t
<220> FEATURE:
<221> NAME/KEY: misc_feature
<222> LOCATION: (22)..(23)
<223> OTHER INFORMATION: n is a, c, g, or t

<400> SEQUENCE: 287
gactcgagcc atccanntnn tnnagtcgct ggaggggctt ctat 44

<210> SEQ ID NO 288
<211> LENGTH: 44
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (17)..(18)
<223> OTHER INFORMATION: n is a, c, g, or t
<220> FEATURE:
<221> NAME/KEY: misc_feature
<222> LOCATION: (20)..(21)
<223> OTHER INFORMATION: n is a, c, g, or t
<220> FEATURE:
<221> NAME/KEY: misc_feature
<222> LOCATION: (23)..(24)
<223> OTHER INFORMATION: n is a, c, g, or t

<400> SEQUENCE: 288
agcccctcca gcgactnnan nanntggatg gctcgagtcg atac 44

<210> SEQ ID NO 289
<211> LENGTH: 46
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (16)..(17)
<223> OTHER INFORMATION: n is a, c, g, or t
<220> FEATURE:
<221> NAME/KEY: misc_feature
<222> LOCATION: (19)..(20)
<223> OTHER INFORMATION: n is a, c, g, or t
<220> FEATURE:
<221> NAME/KEY: misc_feature
<222> LOCATION: (22)..(23)
<223> OTHER INFORMATION: n is a, c, g, or t

<400> SEQUENCE: 289
agccatccag atcttnnann cnntggaggg gcttctatgg tgccgt 46

<210> SEQ ID NO 290
<211> LENGTH: 47
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (16)..(16)
<223> OTHER INFORMATION: n is a, c, g, or t
<220> FEATURE:
<221> NAME/KEY: misc_feature
<222> LOCATION: (26)..(26)
<223> OTHER INFORMATION: n is a, c, g, or t

<400> SEQUENCE: 290
catagaagcc cctccnagcg actttnaaga tctggatggc tcgagtc 47

<210> SEQ ID NO 291
<211> LENGTH: 43
<212> TYPE: DNA

<213> ORGANISM: Artificial Sequence
<220> FEATURE:
<223> OTHER INFORMATION: Primer
<220> FEATURE:
<221> NAME/KEY: misc_feature
<222> LOCATION: (16)..(17)
<223> OTHER INFORMATION: n is a, c, g, or t
<220> FEATURE:
<221> NAME/KEY: misc_feature
<222> LOCATION: (19)..(20)
<223> OTHER INFORMATION: n is a, c, g, or t
<220> FEATURE:
<221> NAME/KEY: misc_feature
<222> LOCATION: (22)..(23)
<223> OTHER INFORMATION: n is a, c, g, or t

<400> SEQUENCE: 291
catccagatc ttaaanncnn tnnaggggct tctatggtgc cgt 43

<210> SEQ ID NO 292
<211> LENGTH: 46
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (17)..(18)
<223> OTHER INFORMATION: n is a, c, g, or t
<220> FEATURE:
<221> NAME/KEY: misc_feature
<222> LOCATION: (20)..(21)
<223> OTHER INFORMATION: n is a, c, g, or t
<220> FEATURE:
<221> NAME/KEY: misc_feature
<222> LOCATION: (23)..(24)
<223> OTHER INFORMATION: n is a, c, g, or t

<400> SEQUENCE: 292
caccatagaa gcccctnnan ngnntttaag atctggatgg ctcgag 46

<210> SEQ ID NO 293
<211> LENGTH: 47
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (16)..(17)
<223> OTHER INFORMATION: n is a, c, g, or t
<220> FEATURE:
<221> NAME/KEY: misc_feature
<222> LOCATION: (19)..(20)
<223> OTHER INFORMATION: n is a, c, g, or t
<220> FEATURE:
<221> NAME/KEY: misc_feature
<222> LOCATION: (22)..(23)
<223> OTHER INFORMATION: n is a, c, g, or t

<400> SEQUENCE: 293
ggaggggctt ctatgnngnn gnncgaaaca aacccgtttc aagataa 47

<210> SEQ ID NO 294
<211> LENGTH: 44
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (17)..(18)
<223> OTHER INFORMATION: n is a, c, g, or t
<220> FEATURE:
<221> NAME/KEY: misc_feature
<222> LOCATION: (20)..(21)
<223> OTHER INFORMATION: n is a, c, g, or t
<220> FEATURE:
<221> NAME/KEY: misc_feature
<222> LOCATION: (23)..(24)
<223> OTHER INFORMATION: n is a, c, g, or t

<400> SEQUENCE: 294
aaacgggttt gtttcgnncn ncnncataga agcccctcca gcga 44

<210> SEQ ID NO 295
<211> LENGTH: 47
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (16)..(17)
<223> OTHER INFORMATION: n is a, c, g, or t
<220> FEATURE:
<221> NAME/KEY: misc_feature
<222> LOCATION: (19)..(20)
<223> OTHER INFORMATION: n is a, c, g, or t
<220> FEATURE:
<221> NAME/KEY: misc_feature
<222> LOCATION: (22)..(23)
<223> OTHER INFORMATION: n is a, c, g, or t

<400> SEQUENCE: 295
ggggcttcta tggtgnngnn cnnaacaaac ccgtttcaag ataacaa 47

<210> SEQ ID NO 296
<211> LENGTH: 44
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (17)..(18)
<223> OTHER INFORMATION: n is a, c, g, or t
<220> FEATURE:
<221> NAME/KEY: misc_feature
<222> LOCATION: (20)..(21)
<223> OTHER INFORMATION: n is a, c, g, or t
<220> FEATURE:
<221> NAME/KEY: misc_feature
<222> LOCATION: (23)..(24)
<223> OTHER INFORMATION: n is a, c, g, or t

<400> SEQUENCE: 296
ttgaaacggg tttgttnngn ncnncaccat agaagcccct ccag 44

<210> SEQ ID NO 297
<211> LENGTH: 47
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (16)..(17)
<223> OTHER INFORMATION: n is a, c, g, or t
<220> FEATURE:
<221> NAME/KEY: misc_feature
<222> LOCATION: (19)..(20)
<223> OTHER INFORMATION: n is a, c, g, or t
<220> FEATURE:
<221> NAME/KEY: misc_feature
<222> LOCATION: (22)..(23)

<223> OTHER INFORMATION: n is a, c, g, or t

<400> SEQUENCE: 297
gcttctatgg tgccgnncnn annaaacccg tttcaagata acaattc 47

<210> SEQ ID NO 298
<211> LENGTH: 44
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (17)..(18)
<223> OTHER INFORMATION: n is a, c, g, or t
<220> FEATURE:
<221> NAME/KEY: misc_feature
<222> LOCATION: (20)..(21)
<223> OTHER INFORMATION: n is a, c, g, or t
<220> FEATURE:
<221> NAME/KEY: misc_feature
<222> LOCATION: (23)..(24)
<223> OTHER INFORMATION: n is a, c, g, or t

<400> SEQUENCE: 298
atcttgaaac gggtttnntn ngnncggcac catagaagcc cctc 44

<210> SEQ ID NO 299
<211> LENGTH: 47
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (16)..(17)
<223> OTHER INFORMATION: n is a, c, g, or t
<220> FEATURE:
<221> NAME/KEY: misc_feature
<222> LOCATION: (19)..(20)
<223> OTHER INFORMATION: n is a, c, g, or t
<220> FEATURE:
<221> NAME/KEY: misc_feature
<222> LOCATION: (22)..(23)
<223> OTHER INFORMATION: n is a, c, g, or t

<400> SEQUENCE: 299
tctatggtgc cgtccnnann anncccgttt caagataaca attctca 47

<210> SEQ ID NO 300
<211> LENGTH: 46
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (17)..(18)
<223> OTHER INFORMATION: n is a, c, g, or t
<220> FEATURE:
<221> NAME/KEY: misc_feature
<222> LOCATION: (20)..(21)
<223> OTHER INFORMATION: n is a, c, g, or t
<220> FEATURE:
<221> NAME/KEY: misc_feature
<222> LOCATION: (23)..(24)
<223> OTHER INFORMATION: n is a, c, g, or t

<400> SEQUENCE: 300
gttatcttga aacgggnntn ntnnggacgg caccatagaa gcccct 46

<210> SEQ ID NO 301
<211> LENGTH: 47
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (16)..(17)
<223> OTHER INFORMATION: n is a, c, g, or t
<220> FEATURE:
<221> NAME/KEY: misc_feature
<222> LOCATION: (19)..(20)
<223> OTHER INFORMATION: n is a, c, g, or t
<220> FEATURE:
<221> NAME/KEY: misc_feature
<222> LOCATION: (22)..(23)
<223> OTHER INFORMATION: n is a, c, g, or t

<400> SEQUENCE: 301
atggtgccgt ccgaannann cnngtttcaa gataacaatt ctcatgg 47

<210> SEQ ID NO 302
<211> LENGTH: 44
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (17)..(18)
<223> OTHER INFORMATION: n is a, c, g, or t
<220> FEATURE:
<221> NAME/KEY: misc_feature
<222> LOCATION: (20)..(21)
<223> OTHER INFORMATION: n is a, c, g, or t
<220> FEATURE:
<221> NAME/KEY: misc_feature
<222> LOCATION: (23)..(24)
<223> OTHER INFORMATION: n is a, c, g, or t

<400> SEQUENCE: 302
attgttatct tgaaacnngn ntnnttcgga cggcaccata gaag 44

<210> SEQ ID NO 303
<211> LENGTH: 47
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (16)..(17)
<223> OTHER INFORMATION: n is a, c, g, or t
<220> FEATURE:
<221> NAME/KEY: misc_feature
<222> LOCATION: (19)..(20)
<223> OTHER INFORMATION: n is a, c, g, or t
<220> FEATURE:
<221> NAME/KEY: misc_feature
<222> LOCATION: (22)..(23)
<223> OTHER INFORMATION: n is a, c, g, or t

<400> SEQUENCE: 303
gtgccgtccg aaacanncnn gnntcaagat aacaattctc atggcac 47

<210> SEQ ID NO 304
<211> LENGTH: 45
<212> TYPE: DNA
<213> ORGANISM: Artificial Sequence
<220> FEATURE:
<223> OTHER INFORMATION: Primer
<220> FEATURE:

<221> NAME/KEY: misc_feature
<222> LOCATION: (17)..(18)
<223> OTHER INFORMATION: n is a, c, g, or t
<220> FEATURE:
<221> NAME/KEY: misc_feature
<222> LOCATION: (20)..(21)
<223> OTHER INFORMATION: n is a, c, g, or t
<220> FEATURE:
<221> NAME/KEY: misc_feature
<222> LOCATION: (23)..(24)
<223> OTHER INFORMATION: n is a, c, g, or t

<400> SEQUENCE: 304
agaattgtta tcttganncn ngnntgtttc ggacggcacc ataga 45

<210> SEQ ID NO 305
<211> LENGTH: 46
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (16)..(17)
<223> OTHER INFORMATION: n is a, c, g, or t
<220> FEATURE:
<221> NAME/KEY: misc_feature
<222> LOCATION: (19)..(20)
<223> OTHER INFORMATION: n is a, c, g, or t
<220> FEATURE:
<221> NAME/KEY: misc_feature
<222> LOCATION: (22)..(23)
<223> OTHER INFORMATION: n is a, c, g, or t

<400> SEQUENCE: 305
ccgtccgaaa caaacnngnn tnnagataac aattctcatg gcacac 46

<210> SEQ ID NO 306
<211> LENGTH: 44
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (17)..(18)
<223> OTHER INFORMATION: n is a, c, g, or t
<220> FEATURE:
<221> NAME/KEY: misc_feature
<222> LOCATION: (20)..(21)
<223> OTHER INFORMATION: n is a, c, g, or t
<220> FEATURE:
<221> NAME/KEY: misc_feature
<222> LOCATION: (23)..(24)
<223> OTHER INFORMATION: n is a, c, g, or t

<400> SEQUENCE: 306
atgagaattg ttatctnnan ncnngtttgt ttcggacggc acca 44

<210> SEQ ID NO 307
<211> LENGTH: 45
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (16)..(17)
<223> OTHER INFORMATION: n is a, c, g, or t
<220> FEATURE:
<221> NAME/KEY: misc_feature
<222> LOCATION: (19)..(20)
<223> OTHER INFORMATION: n is a, c, g, or t
<220> FEATURE:
<221> NAME/KEY: misc_feature
<222> LOCATION: (22)..(23)
<223> OTHER INFORMATION: n is a, c, g, or t

<400> SEQUENCE: 307
tccgaaacaa acccgnntnn anntaacaat tctcatggca cacac 45

<210> SEQ ID NO 308
<211> LENGTH: 44
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (17)..(18)
<223> OTHER INFORMATION: n is a, c, g, or t
<220> FEATURE:
<221> NAME/KEY: misc_feature
<222> LOCATION: (20)..(21)
<223> OTHER INFORMATION: n is a, c, g, or t
<220> FEATURE:
<221> NAME/KEY: misc_feature
<222> LOCATION: (23)..(24)
<223> OTHER INFORMATION: n is a, c, g, or t

<400> SEQUENCE: 308
gccatgagaa ttgttanntn nanncgggtt tgtttcggac ggca 44

<210> SEQ ID NO 309
<211> LENGTH: 45
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (16)..(17)
<223> OTHER INFORMATION: n is a, c, g, or t
<220> FEATURE:
<221> NAME/KEY: misc_feature
<222> LOCATION: (19)..(20)
<223> OTHER INFORMATION: n is a, c, g, or t
<220> FEATURE:
<221> NAME/KEY: misc_feature
<222> LOCATION: (22)..(23)
<223> OTHER INFORMATION: n is a, c, g, or t

<400> SEQUENCE: 309
gaaacaaacc cgtttnnann tnncaattct catggcacac acgtc 45

<210> SEQ ID NO 310
<211> LENGTH: 44
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (17)..(18)
<223> OTHER INFORMATION: n is a, c, g, or t
<220> FEATURE:
<221> NAME/KEY: misc_feature
<222> LOCATION: (20)..(21)
<223> OTHER INFORMATION: n is a, c, g, or t
<220> FEATURE:
<221> NAME/KEY: misc_feature
<222> LOCATION: (23)..(24)
<223> OTHER INFORMATION: n is a, c, g, or t

<400> SEQUENCE: 310
tgtgccatga gaattgnnan ntnnaaacgg gtttgtttcg gacg 44

<210> SEQ ID NO 311
<211> LENGTH: 43
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (16)..(17)
<223> OTHER INFORMATION: n is a, c, g, or t
<220> FEATURE:
<221> NAME/KEY: misc_feature
<222> LOCATION: (19)..(20)
<223> OTHER INFORMATION: n is a, c, g, or t
<220> FEATURE:
<221> NAME/KEY: misc_feature
<222> LOCATION: (22)..(23)
<223> OTHER INFORMATION: n is a, c, g, or t

<400> SEQUENCE: 311
acaaacccgt ttcaanntnn cnnttctcat ggcacacacg tcg 43

<210> SEQ ID NO 312
<211> LENGTH: 46
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (17)..(18)
<223> OTHER INFORMATION: n is a, c, g, or t
<220> FEATURE:
<221> NAME/KEY: misc_feature
<222> LOCATION: (20)..(21)
<223> OTHER INFORMATION: n is a, c, g, or t
<220> FEATURE:
<221> NAME/KEY: misc_feature
<222> LOCATION: (23)..(24)
<223> OTHER INFORMATION: n is a, c, g, or t

<400> SEQUENCE: 312
gtgtgtgcca tgagaanngn nannttgaaa cgggtttgtt tcggac 46

<210> SEQ ID NO 313
<211> LENGTH: 43
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (16)..(17)
<223> OTHER INFORMATION: n is a, c, g, or t
<220> FEATURE:
<221> NAME/KEY: misc_feature
<222> LOCATION: (19)..(20)
<223> OTHER INFORMATION: n is a, c, g, or t
<220> FEATURE:
<221> NAME/KEY: misc_feature
<222> LOCATION: (22)..(23)
<223> OTHER INFORMATION: n is a, c, g, or t

<400> SEQUENCE: 313
aacccgtttc aagatnncnn tnntcatggc acacacgtcg cag 43

<210> SEQ ID NO 314
<211> LENGTH: 46
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (17)..(18)
<223> OTHER INFORMATION: n is a, c, g, or t
<220> FEATURE:
<221> NAME/KEY: misc_feature
<222> LOCATION: (20)..(21)
<223> OTHER INFORMATION: n is a, c, g, or t
<220> FEATURE:
<221> NAME/KEY: misc_feature
<222> LOCATION: (23)..(24)
<223> OTHER INFORMATION: n is a, c, g, or t

<400> SEQUENCE: 314
gacgtgtgtg ccatgannan ngnnatcttg aaacgggttt gtttcg 46

<210> SEQ ID NO 315
<211> LENGTH: 43
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (16)..(17)
<223> OTHER INFORMATION: n is a, c, g, or t
<220> FEATURE:
<221> NAME/KEY: misc_feature
<222> LOCATION: (19)..(20)
<223> OTHER INFORMATION: n is a, c, g, or t
<220> FEATURE:
<221> NAME/KEY: misc_feature
<222> LOCATION: (22)..(23)
<223> OTHER INFORMATION: n is a, c, g, or t

<400> SEQUENCE: 315
ccgtttcaag ataacnntnn tnntggcaca cacgtcgcag gaa 43

<210> SEQ ID NO 316
<211> LENGTH: 47
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (17)..(18)
<223> OTHER INFORMATION: n is a, c, g, or t
<220> FEATURE:
<221> NAME/KEY: misc_feature
<222> LOCATION: (20)..(21)
<223> OTHER INFORMATION: n is a, c, g, or t
<220> FEATURE:
<221> NAME/KEY: misc_feature
<222> LOCATION: (23)..(24)
<223> OTHER INFORMATION: n is a, c, g, or t

<400> SEQUENCE: 316
tgcgacgtgt gtgccannan nanngttatc ttgaaacggg tttgttt 47

<210> SEQ ID NO 317
<211> LENGTH: 44
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (16)..(17)
<223> OTHER INFORMATION: n is a, c, g, or t
<220> FEATURE:

<221> NAME/KEY: misc_feature
<222> LOCATION: (19)..(20)
<223> OTHER INFORMATION: n is a, c, g, or t
<220> FEATURE:
<221> NAME/KEY: misc_feature
<222> LOCATION: (22)..(23)
<223> OTHER INFORMATION: n is a, c, g, or t

<400> SEQUENCE: 317
aattctcatg gcacanncnn cnnaggaacg gttgcggcgt taaa 44

<210> SEQ ID NO 318
<211> LENGTH: 47
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (17)..(18)
<223> OTHER INFORMATION: n is a, c, g, or t
<220> FEATURE:
<221> NAME/KEY: misc_feature
<222> LOCATION: (20)..(21)
<223> OTHER INFORMATION: n is a, c, g, or t
<220> FEATURE:
<221> NAME/KEY: misc_feature
<222> LOCATION: (23)..(24)
<223> OTHER INFORMATION: n is a, c, g, or t

<400> SEQUENCE: 318
cgccgcaacc gttcctnngn ngnntgtgcc atgagaattg ttatctt 47

<210> SEQ ID NO 319
<211> LENGTH: 45
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (16)..(17)
<223> OTHER INFORMATION: n is a, c, g, or t
<220> FEATURE:
<221> NAME/KEY: misc_feature
<222> LOCATION: (19)..(20)
<223> OTHER INFORMATION: n is a, c, g, or t
<220> FEATURE:
<221> NAME/KEY: misc_feature
<222> LOCATION: (22)..(23)
<223> OTHER INFORMATION: n is a, c, g, or t

<400> SEQUENCE: 319
tctcatggca cacacnncnn annaacggtt gcggcgttaa acaat 45

<210> SEQ ID NO 320
<211> LENGTH: 46
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (17)..(18)
<223> OTHER INFORMATION: n is a, c, g, or t
<220> FEATURE:
<221> NAME/KEY: misc_feature
<222> LOCATION: (20)..(21)
<223> OTHER INFORMATION: n is a, c, g, or t
<220> FEATURE:
<221> NAME/KEY: misc_feature
<222> LOCATION: (23)..(24)
<223> OTHER INFORMATION: n is a, c, g, or t

<400> SEQUENCE: 320
taacgccgca accgttnntn ngnngtgtgt gccatgagaa ttgtta 46

<210> SEQ ID NO 321
<211> LENGTH: 47
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (16)..(17)
<223> OTHER INFORMATION: n is a, c, g, or t
<220> FEATURE:
<221> NAME/KEY: misc_feature
<222> LOCATION: (19)..(20)
<223> OTHER INFORMATION: n is a, c, g, or t
<220> FEATURE:
<221> NAME/KEY: misc_feature
<222> LOCATION: (22)..(23)
<223> OTHER INFORMATION: n is a, c, g, or t

<400> SEQUENCE: 321
acacacgtcg cagganngnn tnnggcgtta aacaattcta ttggcgt 47

<210> SEQ ID NO 322
<211> LENGTH: 44
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (17)..(18)
<223> OTHER INFORMATION: n is a, c, g, or t
<220> FEATURE:
<221> NAME/KEY: misc_feature
<222> LOCATION: (20)..(21)
<223> OTHER INFORMATION: n is a, c, g, or t
<220> FEATURE:
<221> NAME/KEY: misc_feature
<222> LOCATION: (23)..(24)
<223> OTHER INFORMATION: n is a, c, g, or t

<400> SEQUENCE: 322
agaattgttt aacgccnnan ncnntcctgc gacgtgtgtg ccat 44

<210> SEQ ID NO 323
<211> LENGTH: 46
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (16)..(17)
<223> OTHER INFORMATION: n is a, c, g, or t
<220> FEATURE:
<221> NAME/KEY: misc_feature
<222> LOCATION: (19)..(20)
<223> OTHER INFORMATION: n is a, c, g, or t
<220> FEATURE:
<221> NAME/KEY: misc_feature
<222> LOCATION: (22)..(23)
<223> OTHER INFORMATION: n is a, c, g, or t

<400> SEQUENCE: 323
gcaggaacgg ttgcgnngnn anncaattct attggcgtgc ttggtg 46

<210> SEQ ID NO 324

<211> LENGTH: 44
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (17)..(18)
<223> OTHER INFORMATION: n is a, c, g, or t
<220> FEATURE:
<221> NAME/KEY: misc_feature
<222> LOCATION: (20)..(21)
<223> OTHER INFORMATION: n is a, c, g, or t
<220> FEATURE:
<221> NAME/KEY: misc_feature
<222> LOCATION: (23)..(24)
<223> OTHER INFORMATION: n is a, c, g, or t

<400> SEQUENCE: 324
cacgccaata gaattgnntn ncnncgcaac cgttcctgcg acgt 44

<210> SEQ ID NO 325
<211> LENGTH: 44
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (16)..(17)
<223> OTHER INFORMATION: n is a, c, g, or t
<220> FEATURE:
<221> NAME/KEY: misc_feature
<222> LOCATION: (19)..(20)
<223> OTHER INFORMATION: n is a, c, g, or t
<220> FEATURE:
<221> NAME/KEY: misc_feature
<222> LOCATION: (22)..(23)
<223> OTHER INFORMATION: n is a, c, g, or t

<400> SEQUENCE: 325
acggttgcgg cgttanncnn tnntattggc gtgcttggtg tagc 44

<210> SEQ ID NO 326
<211> LENGTH: 44
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (17)..(18)
<223> OTHER INFORMATION: n is a, c, g, or t
<220> FEATURE:
<221> NAME/KEY: misc_feature
<222> LOCATION: (20)..(21)
<223> OTHER INFORMATION: n is a, c, g, or t
<220> FEATURE:
<221> NAME/KEY: misc_feature
<222> LOCATION: (23)..(24)
<223> OTHER INFORMATION: n is a, c, g, or t

<400> SEQUENCE: 326
accaagcacg ccaatannan ngnntaacgc cgcaaccgtt cctg 44

<210> SEQ ID NO 327
<211> LENGTH: 44
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (16)..(17)
<223> OTHER INFORMATION: n is a, c, g, or t
<220> FEATURE:
<221> NAME/KEY: misc_feature
<222> LOCATION: (19)..(20)
<223> OTHER INFORMATION: n is a, c, g, or t
<220> FEATURE:
<221> NAME/KEY: misc_feature
<222> LOCATION: (22)..(23)
<223> OTHER INFORMATION: n is a, c, g, or t

<400> SEQUENCE: 327
aacaattcta ttggcnngnn tnntgtagcc ccgtctgctt cgct 44

<210> SEQ ID NO 328
<211> LENGTH: 50
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (17)..(18)
<223> OTHER INFORMATION: n is a, c, g, or t
<220> FEATURE:
<221> NAME/KEY: misc_feature
<222> LOCATION: (20)..(21)
<223> OTHER INFORMATION: n is a, c, g, or t
<220> FEATURE:
<221> NAME/KEY: misc_feature
<222> LOCATION: (23)..(24)
<223> OTHER INFORMATION: n is a, c, g, or t

<400> SEQUENCE: 328
agcagacggg gctacannan ncnngccaat agaattgttt aacgccgcaa 50

<210> SEQ ID NO 329
<211> LENGTH: 43
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (16)..(17)
<223> OTHER INFORMATION: n is a, c, g, or t
<220> FEATURE:
<221> NAME/KEY: misc_feature
<222> LOCATION: (19)..(20)
<223> OTHER INFORMATION: n is a, c, g, or t
<220> FEATURE:
<221> NAME/KEY: misc_feature
<222> LOCATION: (22)..(23)
<223> OTHER INFORMATION: n is a, c, g, or t

<400> SEQUENCE: 329
tctattggcg tgcttnntnn anncccgtct gcttcgctct acg 43

<210> SEQ ID NO 330
<211> LENGTH: 47
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (17)..(18)
<223> OTHER INFORMATION: n is a, c, g, or t
<220> FEATURE:
<221> NAME/KEY: misc_feature
<222> LOCATION: (20)..(21)
<223> OTHER INFORMATION: n is a, c, g, or t
<220> FEATURE:

<221> NAME/KEY: misc_feature
<222> LOCATION: (23)..(24)
<223> OTHER INFORMATION: n is a, c, g, or t

<400> SEQUENCE: 330
gagcgaagca gacgggnntn nannaagcac gccaatagaa ttgttta 47

<210> SEQ ID NO 331
<211> LENGTH: 44
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (16)..(17)
<223> OTHER INFORMATION: n is a, c, g, or t
<220> FEATURE:
<221> NAME/KEY: misc_feature
<222> LOCATION: (19)..(20)
<223> OTHER INFORMATION: n is a, c, g, or t
<220> FEATURE:
<221> NAME/KEY: misc_feature
<222> LOCATION: (22)..(23)
<223> OTHER INFORMATION: n is a, c, g, or t

<400> SEQUENCE: 331
attggcgtgc ttggtnnann cnngtctgct tcgctctacg ccgt 44

<210> SEQ ID NO 332
<211> LENGTH: 46
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (17)..(18)
<223> OTHER INFORMATION: n is a, c, g, or t
<220> FEATURE:
<221> NAME/KEY: misc_feature
<222> LOCATION: (20)..(21)
<223> OTHER INFORMATION: n is a, c, g, or t
<220> FEATURE:
<221> NAME/KEY: misc_feature
<222> LOCATION: (23)..(24)
<223> OTHER INFORMATION: n is a, c, g, or t

<400> SEQUENCE: 332
gtagagcgaa gcagacnngn ntnnaccaag cacgccaata gaattg 46

<210> SEQ ID NO 333
<211> LENGTH: 45
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (17)..(18)
<223> OTHER INFORMATION: n is a, c, g, or t
<220> FEATURE:
<221> NAME/KEY: misc_feature
<222> LOCATION: (20)..(21)
<223> OTHER INFORMATION: n is a, c, g, or t
<220> FEATURE:
<221> NAME/KEY: misc_feature
<222> LOCATION: (23)..(24)
<223> OTHER INFORMATION: n is a, c, g, or t

<400> SEQUENCE: 333
tggcgtgctt ggtgtanncn ngnntgcttc gctctacgcc gttaa 45

<210> SEQ ID NO 334
<211> LENGTH: 45
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (17)..(18)
<223> OTHER INFORMATION: n is a, c, g, or t
<220> FEATURE:
<221> NAME/KEY: misc_feature
<222> LOCATION: (20)..(21)
<223> OTHER INFORMATION: n is a, c, g, or t
<220> FEATURE:
<221> NAME/KEY: misc_feature
<222> LOCATION: (23)..(24)
<223> OTHER INFORMATION: n is a, c, g, or t

<400> SEQUENCE: 334
ggcgtagagc gaagcanncn ngnntacacc aagcacgcca ataga 45

<210> SEQ ID NO 335
<211> LENGTH: 45
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (16)..(17)
<223> OTHER INFORMATION: n is a, c, g, or t
<220> FEATURE:
<221> NAME/KEY: misc_feature
<222> LOCATION: (19)..(20)
<223> OTHER INFORMATION: n is a, c, g, or t
<220> FEATURE:
<221> NAME/KEY: misc_feature
<222> LOCATION: (22)..(23)
<223> OTHER INFORMATION: n is a, c, g, or t

<400> SEQUENCE: 335
gtgcttggtg tagccnngnn tnnttcgctc tacgccgtta aagtt 45

<210> SEQ ID NO 336
<211> LENGTH: 44
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (17)..(18)
<223> OTHER INFORMATION: n is a, c, g, or t
<220> FEATURE:
<221> NAME/KEY: misc_feature
<222> LOCATION: (20)..(21)
<223> OTHER INFORMATION: n is a, c, g, or t
<220> FEATURE:
<221> NAME/KEY: misc_feature
<222> LOCATION: (23)..(24)
<223> OTHER INFORMATION: n is a, c, g, or t

<400> SEQUENCE: 336
aacggcgtag agcgaannan ncnnggctac accaagcacg ccaa 44

<210> SEQ ID NO 337
<211> LENGTH: 45
<212> TYPE: DNA
<213> ORGANISM: Artificial Sequence
<220> FEATURE:

<223> OTHER INFORMATION: Primer
<220> FEATURE:
<221> NAME/KEY: misc_feature
<222> LOCATION: (16)..(17)
<223> OTHER INFORMATION: n is a, c, g, or t
<220> FEATURE:
<221> NAME/KEY: misc_feature
<222> LOCATION: (19)..(20)
<223> OTHER INFORMATION: n is a, c, g, or t
<220> FEATURE:
<221> NAME/KEY: misc_feature
<222> LOCATION: (22)..(23)
<223> OTHER INFORMATION: n is a, c, g, or t

<400> SEQUENCE: 337
cttggtgtag ccccgnntnn tnngctctac gccgttaaag ttctt 45

<210> SEQ ID NO 338
<211> LENGTH: 48
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (17)..(18)
<223> OTHER INFORMATION: n is a, c, g, or t
<220> FEATURE:
<221> NAME/KEY: misc_feature
<222> LOCATION: (20)..(21)
<223> OTHER INFORMATION: n is a, c, g, or t
<220> FEATURE:
<221> NAME/KEY: misc_feature
<222> LOCATION: (23)..(24)
<223> OTHER INFORMATION: n is a, c, g, or t

<400> SEQUENCE: 338
tttaacggcg tagagcnnan nanncggggc tacaccaagc acgccaat 48

<210> SEQ ID NO 339
<211> LENGTH: 46
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (16)..(17)
<223> OTHER INFORMATION: n is a, c, g, or t
<220> FEATURE:
<221> NAME/KEY: misc_feature
<222> LOCATION: (19)..(20)
<223> OTHER INFORMATION: n is a, c, g, or t
<220> FEATURE:
<221> NAME/KEY: misc_feature
<222> LOCATION: (22)..(23)
<223> OTHER INFORMATION: n is a, c, g, or t

<400> SEQUENCE: 339
ggtgtagccc cgtctnntnn gnnctacgcc gttaaagttc ttgcag 46

<210> SEQ ID NO 340
<211> LENGTH: 44
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (17)..(18)
<223> OTHER INFORMATION: n is a, c, g, or t
<220> FEATURE:
<221> NAME/KEY: misc_feature
<222> LOCATION: (20)..(21)
<223> OTHER INFORMATION: n is a, c, g, or t
<220> FEATURE:
<221> NAME/KEY: misc_feature
<222> LOCATION: (23)..(24)
<223> OTHER INFORMATION: n is a, c, g, or t

<400> SEQUENCE: 340
aactttaacg gcgtagnncn nannagacgg ggctacacca agca 44

<210> SEQ ID NO 341
<211> LENGTH: 45
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (16)..(17)
<223> OTHER INFORMATION: n is a, c, g, or t
<220> FEATURE:
<221> NAME/KEY: misc_feature
<222> LOCATION: (19)..(20)
<223> OTHER INFORMATION: n is a, c, g, or t
<220> FEATURE:
<221> NAME/KEY: misc_feature
<222> LOCATION: (22)..(23)
<223> OTHER INFORMATION: n is a, c, g, or t

<400> SEQUENCE: 341
gtagccccgt ctgctnngnn cnncgccgtt aaagttcttg cagca 45

<210> SEQ ID NO 342
<211> LENGTH: 44
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (17)..(18)
<223> OTHER INFORMATION: n is a, c, g, or t
<220> FEATURE:
<221> NAME/KEY: misc_feature
<222> LOCATION: (20)..(21)
<223> OTHER INFORMATION: n is a, c, g, or t
<220> FEATURE:
<221> NAME/KEY: misc_feature
<222> LOCATION: (23)..(24)
<223> OTHER INFORMATION: n is a, c, g, or t

<400> SEQUENCE: 342
aagaacttta acggcgnngn ncnnagcaga cggggctaca ccaa 44

<210> SEQ ID NO 343
<211> LENGTH: 45
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (16)..(17)
<223> OTHER INFORMATION: n is a, c, g, or t
<220> FEATURE:
<221> NAME/KEY: misc_feature
<222> LOCATION: (19)..(20)
<223> OTHER INFORMATION: n is a, c, g, or t
<220> FEATURE:
<221> NAME/KEY: misc_feature
<222> LOCATION: (22)..(23)
<223> OTHER INFORMATION: n is a, c, g, or t

<400> SEQUENCE: 343
gccccgtctg cttcgnncnn cnncgttaaa gttcttgcag cagac 45

<210> SEQ ID NO 344
<211> LENGTH: 44
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (17)..(18)
<223> OTHER INFORMATION: n is a, c, g, or t
<220> FEATURE:
<221> NAME/KEY: misc_feature
<222> LOCATION: (20)..(21)
<223> OTHER INFORMATION: n is a, c, g, or t
<220> FEATURE:
<221> NAME/KEY: misc_feature
<222> LOCATION: (23)..(24)
<223> OTHER INFORMATION: n is a, c, g, or t

<400> SEQUENCE: 344
tgcaagaact ttaacgnngn ngnncgaagc agacggggct acac 44

<210> SEQ ID NO 345
<211> LENGTH: 45
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (16)..(17)
<223> OTHER INFORMATION: n is a, c, g, or t
<220> FEATURE:
<221> NAME/KEY: misc_feature
<222> LOCATION: (19)..(20)
<223> OTHER INFORMATION: n is a, c, g, or t
<220> FEATURE:
<221> NAME/KEY: misc_feature
<222> LOCATION: (22)..(23)
<223> OTHER INFORMATION: n is a, c, g, or t

<400> SEQUENCE: 345
ccgtctgctt cgctcnncnn cnntaaagtt cttgcagcag acgga 45

<210> SEQ ID NO 346
<211> LENGTH: 43
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (17)..(18)
<223> OTHER INFORMATION: n is a, c, g, or t
<220> FEATURE:
<221> NAME/KEY: misc_feature
<222> LOCATION: (20)..(21)
<223> OTHER INFORMATION: n is a, c, g, or t
<220> FEATURE:
<221> NAME/KEY: misc_feature
<222> LOCATION: (23)..(24)
<223> OTHER INFORMATION: n is a, c, g, or t

<400> SEQUENCE: 346
tgctgcaaga actttanngn ngnngagcga agcagacggg gct 43

<210> SEQ ID NO 347
<211> LENGTH: 44

<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (16)..(17)
<223> OTHER INFORMATION: n is a, c, g, or t
<220> FEATURE:
<221> NAME/KEY: misc_feature
<222> LOCATION: (19)..(20)
<223> OTHER INFORMATION: n is a, c, g, or t
<220> FEATURE:
<221> NAME/KEY: misc_feature
<222> LOCATION: (22)..(23)
<223> OTHER INFORMATION: n is a, c, g, or t

<400> SEQUENCE: 347
tctgcttcgc tctacnncnn tnnagttctt gcagcagacg gatc 44

<210> SEQ ID NO 348
<211> LENGTH: 47
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (17)..(18)
<223> OTHER INFORMATION: n is a, c, g, or t
<220> FEATURE:
<221> NAME/KEY: misc_feature
<222> LOCATION: (20)..(21)
<223> OTHER INFORMATION: n is a, c, g, or t
<220> FEATURE:
<221> NAME/KEY: misc_feature
<222> LOCATION: (23)..(24)
<223> OTHER INFORMATION: n is a, c, g, or t

<400> SEQUENCE: 348
gtctgctgca agaactnnan ngnngtagag cgaagcagac ggggcta 47

<210> SEQ ID NO 349
<211> LENGTH: 43
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (16)..(17)
<223> OTHER INFORMATION: n is a, c, g, or t
<220> FEATURE:
<221> NAME/KEY: misc_feature
<222> LOCATION: (19)..(20)
<223> OTHER INFORMATION: n is a, c, g, or t
<220> FEATURE:
<221> NAME/KEY: misc_feature
<222> LOCATION: (22)..(23)
<223> OTHER INFORMATION: n is a, c, g, or t

<400> SEQUENCE: 349
gcttcgctct acgccnntnn anntcttgca gcagacggat cag 43

<210> SEQ ID NO 350
<211> LENGTH: 44
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (17)..(18)

<223> OTHER INFORMATION: n is a, c, g, or t
<220> FEATURE:
<221> NAME/KEY: misc_feature
<222> LOCATION: (20)..(21)
<223> OTHER INFORMATION: n is a, c, g, or t
<220> FEATURE:
<221> NAME/KEY: misc_feature
<222> LOCATION: (23)..(24)
<223> OTHER INFORMATION: n is a, c, g, or t

<400> SEQUENCE: 350
tccgtctgct gcaaganntn nanggcgta gagcgaagca gacg            44

<210> SEQ ID NO 351
<211> LENGTH: 44
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (16)..(17)
<223> OTHER INFORMATION: n is a, c, g, or t
<220> FEATURE:
<221> NAME/KEY: misc_feature
<222> LOCATION: (19)..(20)
<223> OTHER INFORMATION: n is a, c, g, or t
<220> FEATURE:
<221> NAME/KEY: misc_feature
<222> LOCATION: (22)..(23)
<223> OTHER INFORMATION: n is a, c, g, or t

<400> SEQUENCE: 351
tcgctctacg ccgttnnann tnntgcagca gacggatcag gcca            44

<210> SEQ ID NO 352
<211> LENGTH: 44
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (17)..(18)
<223> OTHER INFORMATION: n is a, c, g, or t
<220> FEATURE:
<221> NAME/KEY: misc_feature
<222> LOCATION: (20)..(21)
<223> OTHER INFORMATION: n is a, c, g, or t
<220> FEATURE:
<221> NAME/KEY: misc_feature
<222> LOCATION: (23)..(24)
<223> OTHER INFORMATION: n is a, c, g, or t

<400> SEQUENCE: 352
tgatccgtct gctgcannan ntnnaacggc gtagagcgaa gcag            44

<210> SEQ ID NO 353
<211> LENGTH: 44
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (16)..(17)
<223> OTHER INFORMATION: n is a, c, g, or t
<220> FEATURE:
<221> NAME/KEY: misc_feature
<222> LOCATION: (19)..(20)
<223> OTHER INFORMATION: n is a, c, g, or t
<220> FEATURE:
<221> NAME/KEY: misc_feature
<222> LOCATION: (22)..(23)
<223> OTHER INFORMATION: n is a, c, g, or t

<400> SEQUENCE: 353
ctctacgccg ttaaanntnn tnnagcagac ggatcaggcc aata 44

<210> SEQ ID NO 354
<211> LENGTH: 44
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (17)..(18)
<223> OTHER INFORMATION: n is a, c, g, or t
<220> FEATURE:
<221> NAME/KEY: misc_feature
<222> LOCATION: (20)..(21)
<223> OTHER INFORMATION: n is a, c, g, or t
<220> FEATURE:
<221> NAME/KEY: misc_feature
<222> LOCATION: (23)..(24)
<223> OTHER INFORMATION: n is a, c, g, or t

<400> SEQUENCE: 354
gcctgatccg tctgctnnan nanntttaac ggcgtagagc gaag 44

<210> SEQ ID NO 355
<211> LENGTH: 44
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (16)..(17)
<223> OTHER INFORMATION: n is a, c, g, or t
<220> FEATURE:
<221> NAME/KEY: misc_feature
<222> LOCATION: (19)..(20)
<223> OTHER INFORMATION: n is a, c, g, or t
<220> FEATURE:
<221> NAME/KEY: misc_feature
<222> LOCATION: (22)..(23)
<223> OTHER INFORMATION: n is a, c, g, or t

<400> SEQUENCE: 355
tacgccgtta aagttnntnn annagacgga tcaggccaat actc 44

<210> SEQ ID NO 356
<211> LENGTH: 45
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (17)..(18)
<223> OTHER INFORMATION: n is a, c, g, or t
<220> FEATURE:
<221> NAME/KEY: misc_feature
<222> LOCATION: (20)..(21)
<223> OTHER INFORMATION: n is a, c, g, or t
<220> FEATURE:
<221> NAME/KEY: misc_feature
<222> LOCATION: (23)..(24)
<223> OTHER INFORMATION: n is a, c, g, or t

<400> SEQUENCE: 356
ttggcctgat ccgtctnntn nannaacttt aacggcgtag agcga 45

<210> SEQ ID NO 357
<211> LENGTH: 44
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (16)..(17)
<223> OTHER INFORMATION: n is a, c, g, or t
<220> FEATURE:
<221> NAME/KEY: misc_feature
<222> LOCATION: (19)..(20)
<223> OTHER INFORMATION: n is a, c, g, or t
<220> FEATURE:
<221> NAME/KEY: misc_feature
<222> LOCATION: (22)..(23)
<223> OTHER INFORMATION: n is a, c, g, or t

<400> SEQUENCE: 357
gccgttaaag ttcttnnann anncggatca ggccaatact catg 44

<210> SEQ ID NO 358
<211> LENGTH: 45
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (17)..(18)
<223> OTHER INFORMATION: n is a, c, g, or t
<220> FEATURE:
<221> NAME/KEY: misc_feature
<222> LOCATION: (20)..(21)
<223> OTHER INFORMATION: n is a, c, g, or t
<220> FEATURE:
<221> NAME/KEY: misc_feature
<222> LOCATION: (23)..(24)
<223> OTHER INFORMATION: n is a, c, g, or t

<400> SEQUENCE: 358
gtattggcct gatccgnntn ntnnaagaac tttaacggcg tagag 45

<210> SEQ ID NO 359
<211> LENGTH: 46
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (16)..(17)
<223> OTHER INFORMATION: n is a, c, g, or t
<220> FEATURE:
<221> NAME/KEY: misc_feature
<222> LOCATION: (19)..(20)
<223> OTHER INFORMATION: n is a, c, g, or t
<220> FEATURE:
<221> NAME/KEY: misc_feature
<222> LOCATION: (22)..(23)
<223> OTHER INFORMATION: n is a, c, g, or t

<400> SEQUENCE: 359
gttaaagttc ttgcannann cnnatcaggc caatactcat ggatta 46

<210> SEQ ID NO 360
<211> LENGTH: 46
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (17)..(18)
<223> OTHER INFORMATION: n is a, c, g, or t
<220> FEATURE:
<221> NAME/KEY: misc_feature
<222> LOCATION: (20)..(21)
<223> OTHER INFORMATION: n is a, c, g, or t
<220> FEATURE:
<221> NAME/KEY: misc_feature
<222> LOCATION: (23)..(24)
<223> OTHER INFORMATION: n is a, c, g, or t

<400> SEQUENCE: 360
tgagtattgg cctgatnngn ntnntgcaag aactttaacg gcgtag 46

<210> SEQ ID NO 361
<211> LENGTH: 45
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (16)..(17)
<223> OTHER INFORMATION: n is a, c, g, or t
<220> FEATURE:
<221> NAME/KEY: misc_feature
<222> LOCATION: (19)..(20)
<223> OTHER INFORMATION: n is a, c, g, or t
<220> FEATURE:
<221> NAME/KEY: misc_feature
<222> LOCATION: (22)..(23)
<223> OTHER INFORMATION: n is a, c, g, or t

<400> SEQUENCE: 361
aaagttcttg cagcanncnn annaggccaa tactcatgga ttatc 45

<210> SEQ ID NO 362
<211> LENGTH: 48
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (17)..(18)
<223> OTHER INFORMATION: n is a, c, g, or t
<220> FEATURE:
<221> NAME/KEY: misc_feature
<222> LOCATION: (20)..(21)
<223> OTHER INFORMATION: n is a, c, g, or t
<220> FEATURE:
<221> NAME/KEY: misc_feature
<222> LOCATION: (23)..(24)
<223> OTHER INFORMATION: n is a, c, g, or t

<400> SEQUENCE: 362
ccatgagtat tggcctnntn ngnntgctgc aagaacttta acggcgta 48

<210> SEQ ID NO 363
<211> LENGTH: 45
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (16)..(17)
<223> OTHER INFORMATION: n is a, c, g, or t
<220> FEATURE:
<221> NAME/KEY: misc_feature
<222> LOCATION: (19)..(20)

<223> OTHER INFORMATION: n is a, c, g, or t
<220> FEATURE:
<221> NAME/KEY: misc_feature
<222> LOCATION: (22)..(23)
<223> OTHER INFORMATION: n is a, c, g, or t

<400> SEQUENCE: 363
gttcttgcag cagacnnann annccaatac tcatggatta tcaac 45

<210> SEQ ID NO 364
<211> LENGTH: 46
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (17)..(18)
<223> OTHER INFORMATION: n is a, c, g, or t
<220> FEATURE:
<221> NAME/KEY: misc_feature
<222> LOCATION: (20)..(21)
<223> OTHER INFORMATION: n is a, c, g, or t
<220> FEATURE:
<221> NAME/KEY: misc_feature
<222> LOCATION: (23)..(24)
<223> OTHER INFORMATION: n is a, c, g, or t

<400> SEQUENCE: 364
aatccatgag tattggnntn ntnngtctgc tgcaagaact ttaacg 46

<210> SEQ ID NO 365
<211> LENGTH: 46
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (16)..(17)
<223> OTHER INFORMATION: n is a, c, g, or t
<220> FEATURE:
<221> NAME/KEY: misc_feature
<222> LOCATION: (19)..(20)
<223> OTHER INFORMATION: n is a, c, g, or t
<220> FEATURE:
<221> NAME/KEY: misc_feature
<222> LOCATION: (22)..(23)
<223> OTHER INFORMATION: n is a, c, g, or t

<400> SEQUENCE: 365
cttgcagcag acggannann cnnatactca tggattatca acggca 46

<210> SEQ ID NO 366
<211> LENGTH: 45
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (17)..(18)
<223> OTHER INFORMATION: n is a, c, g, or t
<220> FEATURE:
<221> NAME/KEY: misc_feature
<222> LOCATION: (20)..(21)
<223> OTHER INFORMATION: n is a, c, g, or t
<220> FEATURE:
<221> NAME/KEY: misc_feature
<222> LOCATION: (23)..(24)
<223> OTHER INFORMATION: n is a, c, g, or t

<400> SEQUENCE: 366
gataatccat gagtatnngn ntnntccgtc tgctgcaaga acttt 45

<210> SEQ ID NO 367
<211> LENGTH: 45
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (16)..(17)
<223> OTHER INFORMATION: n is a, c, g, or t
<220> FEATURE:
<221> NAME/KEY: misc_feature
<222> LOCATION: (19)..(20)
<223> OTHER INFORMATION: n is a, c, g, or t
<220> FEATURE:
<221> NAME/KEY: misc_feature
<222> LOCATION: (22)..(23)
<223> OTHER INFORMATION: n is a, c, g, or t

<400> SEQUENCE: 367
gcagcagacg gatcanncnn annctcatgg attatcaacg gcatc 45

<210> SEQ ID NO 368
<211> LENGTH: 44
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (16)..(17)
<223> OTHER INFORMATION: n is a, c, g, or t
<220> FEATURE:
<221> NAME/KEY: misc_feature
<222> LOCATION: (19)..(20)
<223> OTHER INFORMATION: n is a, c, g, or t
<220> FEATURE:
<221> NAME/KEY: misc_feature
<222> LOCATION: (22)..(23)
<223> OTHER INFORMATION: n is a, c, g, or t

<400> SEQUENCE: 368
ttgataatcc atgagnntnn gnntgatccg tctgctgcaa gaac 44

<210> SEQ ID NO 369
<211> LENGTH: 46
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (16)..(17)
<223> OTHER INFORMATION: n is a, c, g, or t
<220> FEATURE:
<221> NAME/KEY: misc_feature
<222> LOCATION: (19)..(20)
<223> OTHER INFORMATION: n is a, c, g, or t
<220> FEATURE:
<221> NAME/KEY: misc_feature
<222> LOCATION: (22)..(23)
<223> OTHER INFORMATION: n is a, c, g, or t

<400> SEQUENCE: 369
gcagacggat caggcnnann cnnatggatt atcaacggca tcgaat 46

<210> SEQ ID NO 370
<211> LENGTH: 44
<212> TYPE: DNA

<213> ORGANISM: Artificial Sequence
<220> FEATURE:
<223> OTHER INFORMATION: Primer
<220> FEATURE:
<221> NAME/KEY: misc_feature
<222> LOCATION: (17)..(18)
<223> OTHER INFORMATION: n is a, c, g, or t
<220> FEATURE:
<221> NAME/KEY: misc_feature
<222> LOCATION: (20)..(21)
<223> OTHER INFORMATION: n is a, c, g, or t
<220> FEATURE:
<221> NAME/KEY: misc_feature
<222> LOCATION: (23)..(24)
<223> OTHER INFORMATION: n is a, c, g, or t

<400> SEQUENCE: 370
gccgttgata atccatnngn ntnngcctga tccgtctgct gcaa 44

<210> SEQ ID NO 371
<211> LENGTH: 45
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (16)..(17)
<223> OTHER INFORMATION: n is a, c, g, or t
<220> FEATURE:
<221> NAME/KEY: misc_feature
<222> LOCATION: (19)..(20)
<223> OTHER INFORMATION: n is a, c, g, or t
<220> FEATURE:
<221> NAME/KEY: misc_feature
<222> LOCATION: (22)..(23)
<223> OTHER INFORMATION: n is a, c, g, or t

<400> SEQUENCE: 371
gacggatcag gccaanncnn anngattatc aacggcatcg aatgg 45

<210> SEQ ID NO 372
<211> LENGTH: 44
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (17)..(18)
<223> OTHER INFORMATION: n is a, c, g, or t
<220> FEATURE:
<221> NAME/KEY: misc_feature
<222> LOCATION: (20)..(21)
<223> OTHER INFORMATION: n is a, c, g, or t
<220> FEATURE:
<221> NAME/KEY: misc_feature
<222> LOCATION: (23)..(24)
<223> OTHER INFORMATION: n is a, c, g, or t

<400> SEQUENCE: 372
gatgccgttg ataatcnntn ngnnttggcc tgatccgtct gctg 44

<210> SEQ ID NO 373
<211> LENGTH: 47
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (16)..(17)
<223> OTHER INFORMATION: n is a, c, g, or t
<220> FEATURE:
<221> NAME/KEY: misc_feature
<222> LOCATION: (19)..(20)
<223> OTHER INFORMATION: n is a, c, g, or t
<220> FEATURE:
<221> NAME/KEY: misc_feature
<222> LOCATION: (22)..(23)
<223> OTHER INFORMATION: n is a, c, g, or t

<400> SEQUENCE: 373
ggatcaggcc aatacnnann gnntatcaac ggcatcgaat gggccat 47

<210> SEQ ID NO 374
<211> LENGTH: 44
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (17)..(18)
<223> OTHER INFORMATION: n is a, c, g, or t
<220> FEATURE:
<221> NAME/KEY: misc_feature
<222> LOCATION: (20)..(21)
<223> OTHER INFORMATION: n is a, c, g, or t
<220> FEATURE:
<221> NAME/KEY: misc_feature
<222> LOCATION: (23)..(24)
<223> OTHER INFORMATION: n is a, c, g, or t

<400> SEQUENCE: 374
ttcgatgccg ttgatanncn ntnngtattg gcctgatccg tctg 44

<210> SEQ ID NO 375
<211> LENGTH: 44
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (16)..(17)
<223> OTHER INFORMATION: n is a, c, g, or t
<220> FEATURE:
<221> NAME/KEY: misc_feature
<222> LOCATION: (19)..(20)
<223> OTHER INFORMATION: n is a, c, g, or t
<220> FEATURE:
<221> NAME/KEY: misc_feature
<222> LOCATION: (22)..(23)
<223> OTHER INFORMATION: n is a, c, g, or t

<400> SEQUENCE: 375
tcaggccaat actcanngnn tnncaacggc atcgaatggg ccat 44

<210> SEQ ID NO 376
<211> LENGTH: 45
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (17)..(18)
<223> OTHER INFORMATION: n is a, c, g, or t
<220> FEATURE:
<221> NAME/KEY: misc_feature
<222> LOCATION: (20)..(21)
<223> OTHER INFORMATION: n is a, c, g, or t
<220> FEATURE:
<221> NAME/KEY: misc_feature
<222> LOCATION: (23)..(24)

<223> OTHER INFORMATION: n is a, c, g, or t

<400> SEQUENCE: 376
ccattcgatg ccgttgnnan ncnntgagta ttggcctgat ccgtc 45

<210> SEQ ID NO 377
<211> LENGTH: 48
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (16)..(17)
<223> OTHER INFORMATION: n is a, c, g, or t
<220> FEATURE:
<221> NAME/KEY: misc_feature
<222> LOCATION: (19)..(20)
<223> OTHER INFORMATION: n is a, c, g, or t
<220> FEATURE:
<221> NAME/KEY: misc_feature
<222> LOCATION: (22)..(23)
<223> OTHER INFORMATION: n is a, c, g, or t

<400> SEQUENCE: 377
ggccaatact catggnntnn cnncggcatc gaatgggcca tcgcgaat 48

<210> SEQ ID NO 378
<211> LENGTH: 45
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (17)..(18)
<223> OTHER INFORMATION: n is a, c, g, or t
<220> FEATURE:
<221> NAME/KEY: misc_feature
<222> LOCATION: (20)..(21)
<223> OTHER INFORMATION: n is a, c, g, or t
<220> FEATURE:
<221> NAME/KEY: misc_feature
<222> LOCATION: (23)..(24)
<223> OTHER INFORMATION: n is a, c, g, or t

<400> SEQUENCE: 378
ggcccattcg atgccgnngn nannccatga gtattggcct gatcc 45

<210> SEQ ID NO 379
<211> LENGTH: 44
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (16)..(17)
<223> OTHER INFORMATION: n is a, c, g, or t
<220> FEATURE:
<221> NAME/KEY: misc_feature
<222> LOCATION: (19)..(20)
<223> OTHER INFORMATION: n is a, c, g, or t
<220> FEATURE:
<221> NAME/KEY: misc_feature
<222> LOCATION: (22)..(23)
<223> OTHER INFORMATION: n is a, c, g, or t

<400> SEQUENCE: 379
caatactcat ggattnncnn cnncatcgaa tgggccatcg cgaa 44

<210> SEQ ID NO 380
<211> LENGTH: 46
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (17)..(18)
<223> OTHER INFORMATION: n is a, c, g, or t
<220> FEATURE:
<221> NAME/KEY: misc_feature
<222> LOCATION: (20)..(21)
<223> OTHER INFORMATION: n is a, c, g, or t
<220> FEATURE:
<221> NAME/KEY: misc_feature
<222> LOCATION: (23)..(24)
<223> OTHER INFORMATION: n is a, c, g, or t

<400> SEQUENCE: 380
gatggcccat tcgatgnngn ngnnaatcca tgagtattgg cctgat 46

<210> SEQ ID NO 381
<211> LENGTH: 44
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (16)..(17)
<223> OTHER INFORMATION: n is a, c, g, or t
<220> FEATURE:
<221> NAME/KEY: misc_feature
<222> LOCATION: (19)..(20)
<223> OTHER INFORMATION: n is a, c, g, or t
<220> FEATURE:
<221> NAME/KEY: misc_feature
<222> LOCATION: (22)..(23)
<223> OTHER INFORMATION: n is a, c, g, or t

<400> SEQUENCE: 381
tactcatgga ttatcnncnn cnncgaatgg gccatcgcga ataa 44

<210> SEQ ID NO 382
<211> LENGTH: 46
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (17)..(18)
<223> OTHER INFORMATION: n is a, c, g, or t
<220> FEATURE:
<221> NAME/KEY: misc_feature
<222> LOCATION: (20)..(21)
<223> OTHER INFORMATION: n is a, c, g, or t
<220> FEATURE:
<221> NAME/KEY: misc_feature
<222> LOCATION: (23)..(24)
<223> OTHER INFORMATION: n is a, c, g, or t

<400> SEQUENCE: 382
cgcgatggcc cattcgnngn ngnngataat ccatgagtat tggcct 46

<210> SEQ ID NO 383
<211> LENGTH: 45
<212> TYPE: DNA
<213> ORGANISM: Artificial Sequence
<220> FEATURE:
<223> OTHER INFORMATION: Primer
<220> FEATURE:

<221> NAME/KEY: misc_feature
<222> LOCATION: (16)..(17)
<223> OTHER INFORMATION: n is a, c, g, or t
<220> FEATURE:
<221> NAME/KEY: misc_feature
<222> LOCATION: (19)..(20)
<223> OTHER INFORMATION: n is a, c, g, or t
<220> FEATURE:
<221> NAME/KEY: misc_feature
<222> LOCATION: (22)..(23)
<223> OTHER INFORMATION: n is a, c, g, or t

<400> SEQUENCE: 383
tcatggatta tcaacnncnn cnnatgggcc atcgcgaata acatg 45

<210> SEQ ID NO 384
<211> LENGTH: 46
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (17)..(18)
<223> OTHER INFORMATION: n is a, c, g, or t
<220> FEATURE:
<221> NAME/KEY: misc_feature
<222> LOCATION: (20)..(21)
<223> OTHER INFORMATION: n is a, c, g, or t
<220> FEATURE:
<221> NAME/KEY: misc_feature
<222> LOCATION: (23)..(24)
<223> OTHER INFORMATION: n is a, c, g, or t

<400> SEQUENCE: 384
attcgcgatg gcccatnngn ngnngttgat aatccatgag tattgg 46

<210> SEQ ID NO 385
<211> LENGTH: 44
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (16)..(17)
<223> OTHER INFORMATION: n is a, c, g, or t
<220> FEATURE:
<221> NAME/KEY: misc_feature
<222> LOCATION: (19)..(20)
<223> OTHER INFORMATION: n is a, c, g, or t
<220> FEATURE:
<221> NAME/KEY: misc_feature
<222> LOCATION: (22)..(23)
<223> OTHER INFORMATION: n is a, c, g, or t

<400> SEQUENCE: 385
tggattatca acggcnncnn annggccatc gcgaataaca tgga 44

<210> SEQ ID NO 386
<211> LENGTH: 46
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (17)..(18)
<223> OTHER INFORMATION: n is a, c, g, or t
<220> FEATURE:
<221> NAME/KEY: misc_feature
<222> LOCATION: (20)..(21)
<223> OTHER INFORMATION: n is a, c, g, or t
<220> FEATURE:
<221> NAME/KEY: misc_feature
<222> LOCATION: (23)..(24)
<223> OTHER INFORMATION: n is a, c, g, or t

<400> SEQUENCE: 386
gttattcgcg atggccnntn ngnngccgtt gataatccat gagtat 46

<210> SEQ ID NO 387
<211> LENGTH: 46
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (16)..(17)
<223> OTHER INFORMATION: n is a, c, g, or t
<220> FEATURE:
<221> NAME/KEY: misc_feature
<222> LOCATION: (19)..(20)
<223> OTHER INFORMATION: n is a, c, g, or t
<220> FEATURE:
<221> NAME/KEY: misc_feature
<222> LOCATION: (22)..(23)
<223> OTHER INFORMATION: n is a, c, g, or t

<400> SEQUENCE: 387
attatcaacg gcatcnnann gnncatcgcg aataacatgg atgtaa 46

<210> SEQ ID NO 388
<211> LENGTH: 46
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (17)..(18)
<223> OTHER INFORMATION: n is a, c, g, or t
<220> FEATURE:
<221> NAME/KEY: misc_feature
<222> LOCATION: (20)..(21)
<223> OTHER INFORMATION: n is a, c, g, or t
<220> FEATURE:
<221> NAME/KEY: misc_feature
<222> LOCATION: (23)..(24)
<223> OTHER INFORMATION: n is a, c, g, or t

<400> SEQUENCE: 388
catgttattc gcgatgnncn ntnngatgcc gttgataatc catgag 46

<210> SEQ ID NO 389
<211> LENGTH: 47
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (16)..(17)
<223> OTHER INFORMATION: n is a, c, g, or t
<220> FEATURE:
<221> NAME/KEY: misc_feature
<222> LOCATION: (19)..(20)
<223> OTHER INFORMATION: n is a, c, g, or t
<220> FEATURE:
<221> NAME/KEY: misc_feature
<222> LOCATION: (22)..(23)
<223> OTHER INFORMATION: n is a, c, g, or t

<400> SEQUENCE: 389
atcaacggca tcgaanngnn cnncgcgaat aacatggatg taatcaa 47

<210> SEQ ID NO 390
<211> LENGTH: 46
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (17)..(18)
<223> OTHER INFORMATION: n is a, c, g, or t
<220> FEATURE:
<221> NAME/KEY: misc_feature
<222> LOCATION: (20)..(21)
<223> OTHER INFORMATION: n is a, c, g, or t
<220> FEATURE:
<221> NAME/KEY: misc_feature
<222> LOCATION: (23)..(24)
<223> OTHER INFORMATION: n is a, c, g, or t

<400> SEQUENCE: 390
atccatgtta ttcgcgnngn ncnnttcgat gccgttgata atccat 46

<210> SEQ ID NO 391
<211> LENGTH: 47
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (16)..(17)
<223> OTHER INFORMATION: n is a, c, g, or t
<220> FEATURE:
<221> NAME/KEY: misc_feature
<222> LOCATION: (19)..(20)
<223> OTHER INFORMATION: n is a, c, g, or t
<220> FEATURE:
<221> NAME/KEY: misc_feature
<222> LOCATION: (22)..(23)
<223> OTHER INFORMATION: n is a, c, g, or t

<400> SEQUENCE: 391
aacggcatcg aatggnncnn cnngaataac atggatgtaa tcaacat 47

<210> SEQ ID NO 392
<211> LENGTH: 47
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (16)..(17)
<223> OTHER INFORMATION: n is a, c, g, or t
<220> FEATURE:
<221> NAME/KEY: misc_feature
<222> LOCATION: (19)..(20)
<223> OTHER INFORMATION: n is a, c, g, or t
<220> FEATURE:
<221> NAME/KEY: misc_feature
<222> LOCATION: (22)..(23)
<223> OTHER INFORMATION: n is a, c, g, or t

<400> SEQUENCE: 392
aacggcatcg aatggnncnn cnngaataac atggatgtaa tcaacat 47

<210> SEQ ID NO 393
<211> LENGTH: 47
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (16)..(17)
<223> OTHER INFORMATION: n is a, c, g, or t
<220> FEATURE:
<221> NAME/KEY: misc_feature
<222> LOCATION: (19)..(20)
<223> OTHER INFORMATION: n is a, c, g, or t
<220> FEATURE:
<221> NAME/KEY: misc_feature
<222> LOCATION: (22)..(23)
<223> OTHER INFORMATION: n is a, c, g, or t

<400> SEQUENCE: 393
ggcatcgaat gggccnncnn gnntaacatg gatgtaatca acatgag 47

<210> SEQ ID NO 394
<211> LENGTH: 44
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (17)..(18)
<223> OTHER INFORMATION: n is a, c, g, or t
<220> FEATURE:
<221> NAME/KEY: misc_feature
<222> LOCATION: (20)..(21)
<223> OTHER INFORMATION: n is a, c, g, or t
<220> FEATURE:
<221> NAME/KEY: misc_feature
<222> LOCATION: (23)..(24)
<223> OTHER INFORMATION: n is a, c, g, or t

<400> SEQUENCE: 394
gattacatcc atgttanncn ngnnggccca ttcgatgccg ttga 44

<210> SEQ ID NO 395
<211> LENGTH: 47
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (16)..(17)
<223> OTHER INFORMATION: n is a, c, g, or t
<220> FEATURE:
<221> NAME/KEY: misc_feature
<222> LOCATION: (19)..(20)
<223> OTHER INFORMATION: n is a, c, g, or t
<220> FEATURE:
<221> NAME/KEY: misc_feature
<222> LOCATION: (22)..(23)
<223> OTHER INFORMATION: n is a, c, g, or t

<400> SEQUENCE: 395
atcgaatggg ccatcnngnn tnncatggat gtaatcaaca tgagcct 47

<210> SEQ ID NO 396
<211> LENGTH: 44
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (17)..(18)
<223> OTHER INFORMATION: n is a, c, g, or t
<220> FEATURE:

<221> NAME/KEY: misc_feature
<222> LOCATION: (20)..(21)
<223> OTHER INFORMATION: n is a, c, g, or t
<220> FEATURE:
<221> NAME/KEY: misc_feature
<222> LOCATION: (23)..(24)
<223> OTHER INFORMATION: n is a, c, g, or t

<400> SEQUENCE: 396
gttgattaca tccatgnnan ncnngatggc ccattcgatg ccgt 44

<210> SEQ ID NO 397
<211> LENGTH: 45
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (16)..(17)
<223> OTHER INFORMATION: n is a, c, g, or t
<220> FEATURE:
<221> NAME/KEY: misc_feature
<222> LOCATION: (19)..(20)
<223> OTHER INFORMATION: n is a, c, g, or t
<220> FEATURE:
<221> NAME/KEY: misc_feature
<222> LOCATION: (22)..(23)
<223> OTHER INFORMATION: n is a, c, g, or t

<400> SEQUENCE: 397
gaatgggcca tcgcgnntnn cnnggatgta atcaacatga gcctg 45

<210> SEQ ID NO 398
<211> LENGTH: 44
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (17)..(18)
<223> OTHER INFORMATION: n is a, c, g, or t
<220> FEATURE:
<221> NAME/KEY: misc_feature
<222> LOCATION: (20)..(21)
<223> OTHER INFORMATION: n is a, c, g, or t
<220> FEATURE:
<221> NAME/KEY: misc_feature
<222> LOCATION: (23)..(24)
<223> OTHER INFORMATION: n is a, c, g, or t

<400> SEQUENCE: 398
catgttgatt acatccnngn nanncgcgat ggcccattcg atgc 44

<210> SEQ ID NO 399
<211> LENGTH: 45
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (16)..(17)
<223> OTHER INFORMATION: n is a, c, g, or t
<220> FEATURE:
<221> NAME/KEY: misc_feature
<222> LOCATION: (19)..(20)
<223> OTHER INFORMATION: n is a, c, g, or t
<220> FEATURE:
<221> NAME/KEY: misc_feature
<222> LOCATION: (22)..(23)
<223> OTHER INFORMATION: n is a, c, g, or t

<400> SEQUENCE: 399
tgggccatcg cgaatnncnn gnntgtaatc aacatgagcc tggga 45

<210> SEQ ID NO 400
<211> LENGTH: 44
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (17)..(18)
<223> OTHER INFORMATION: n is a, c, g, or t
<220> FEATURE:
<221> NAME/KEY: misc_feature
<222> LOCATION: (20)..(21)
<223> OTHER INFORMATION: n is a, c, g, or t
<220> FEATURE:
<221> NAME/KEY: misc_feature
<222> LOCATION: (23)..(24)
<223> OTHER INFORMATION: n is a, c, g, or t

<400> SEQUENCE: 400
gctcatgttg attacanncn ngnnattcgc gatggcccat tcga 44

<210> SEQ ID NO 401
<211> LENGTH: 45
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (16)..(17)
<223> OTHER INFORMATION: n is a, c, g, or t
<220> FEATURE:
<221> NAME/KEY: misc_feature
<222> LOCATION: (19)..(20)
<223> OTHER INFORMATION: n is a, c, g, or t
<220> FEATURE:
<221> NAME/KEY: misc_feature
<222> LOCATION: (22)..(23)
<223> OTHER INFORMATION: n is a, c, g, or t

<400> SEQUENCE: 401
gccatcgcga ataacnngnn tnnaatcaac atgagcctgg gagca 45

<210> SEQ ID NO 402
<211> LENGTH: 45
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (17)..(18)
<223> OTHER INFORMATION: n is a, c, g, or t
<220> FEATURE:
<221> NAME/KEY: misc_feature
<222> LOCATION: (20)..(21)
<223> OTHER INFORMATION: n is a, c, g, or t
<220> FEATURE:
<221> NAME/KEY: misc_feature
<222> LOCATION: (23)..(24)
<223> OTHER INFORMATION: n is a, c, g, or t

<400> SEQUENCE: 402
caggctcatg ttgattnnan ncnngttatt cgcgatggcc cattc 45

<210> SEQ ID NO 403

<211> LENGTH: 43
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (16)..(17)
<223> OTHER INFORMATION: n is a, c, g, or t
<220> FEATURE:
<221> NAME/KEY: misc_feature
<222> LOCATION: (19)..(20)
<223> OTHER INFORMATION: n is a, c, g, or t
<220> FEATURE:
<221> NAME/KEY: misc_feature
<222> LOCATION: (22)..(23)
<223> OTHER INFORMATION: n is a, c, g, or t

<400> SEQUENCE: 403
atcgcgaata acatgnntnn anncaacatg agcctgggag cac 43

<210> SEQ ID NO 404
<211> LENGTH: 46
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (17)..(18)
<223> OTHER INFORMATION: n is a, c, g, or t
<220> FEATURE:
<221> NAME/KEY: misc_feature
<222> LOCATION: (20)..(21)
<223> OTHER INFORMATION: n is a, c, g, or t
<220> FEATURE:
<221> NAME/KEY: misc_feature
<222> LOCATION: (23)..(24)
<223> OTHER INFORMATION: n is a, c, g, or t

<400> SEQUENCE: 404
tcccaggctc atgttgnntn nanncatgtt attcgcgatg gcccat 46

<210> SEQ ID NO 405
<211> LENGTH: 44
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (16)..(17)
<223> OTHER INFORMATION: n is a, c, g, or t
<220> FEATURE:
<221> NAME/KEY: misc_feature
<222> LOCATION: (19)..(20)
<223> OTHER INFORMATION: n is a, c, g, or t
<220> FEATURE:
<221> NAME/KEY: misc_feature
<222> LOCATION: (22)..(23)
<223> OTHER INFORMATION: n is a, c, g, or t

<400> SEQUENCE: 405
gcgaataaca tggatnnann cnncatgagc ctgggagcac caag 44

<210> SEQ ID NO 406
<211> LENGTH: 50
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (17)..(18)
<223> OTHER INFORMATION: n is a, c, g, or t
<220> FEATURE:
<221> NAME/KEY: misc_feature
<222> LOCATION: (20)..(21)
<223> OTHER INFORMATION: n is a, c, g, or t
<220> FEATURE:
<221> NAME/KEY: misc_feature
<222> LOCATION: (23)..(24)
<223> OTHER INFORMATION: n is a, c, g, or t

<400> SEQUENCE: 406
tgctcccagg ctcatgnngn ntnnatccat gttattcgcg atggcccatt 50

<210> SEQ ID NO 407
<211> LENGTH: 46
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (16)..(17)
<223> OTHER INFORMATION: n is a, c, g, or t
<220> FEATURE:
<221> NAME/KEY: misc_feature
<222> LOCATION: (19)..(20)
<223> OTHER INFORMATION: n is a, c, g, or t
<220> FEATURE:
<221> NAME/KEY: misc_feature
<222> LOCATION: (22)..(23)
<223> OTHER INFORMATION: n is a, c, g, or t

<400> SEQUENCE: 407
aataacatgg atgtanncnn cnngagcctg ggagcaccaa gcggca 46

<210> SEQ ID NO 408
<211> LENGTH: 46
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (17)..(18)
<223> OTHER INFORMATION: n is a, c, g, or t
<220> FEATURE:
<221> NAME/KEY: misc_feature
<222> LOCATION: (20)..(21)
<223> OTHER INFORMATION: n is a, c, g, or t
<220> FEATURE:
<221> NAME/KEY: misc_feature
<222> LOCATION: (23)..(24)
<223> OTHER INFORMATION: n is a, c, g, or t

<400> SEQUENCE: 408
tggtgctccc aggctcnngn ngnntacatc catgttattc gcgatg 46

<210> SEQ ID NO 409
<211> LENGTH: 43
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (16)..(17)
<223> OTHER INFORMATION: n is a, c, g, or t
<220> FEATURE:
<221> NAME/KEY: misc_feature
<222> LOCATION: (19)..(20)
<223> OTHER INFORMATION: n is a, c, g, or t
<220> FEATURE:

<221> NAME/KEY: misc_feature
<222> LOCATION: (22)..(23)
<223> OTHER INFORMATION: n is a, c, g, or t

<400> SEQUENCE: 409
aacatggatg taatcnncnn gnncctggga gcaccaagcg gca 43

<210> SEQ ID NO 410
<211> LENGTH: 47
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (17)..(18)
<223> OTHER INFORMATION: n is a, c, g, or t
<220> FEATURE:
<221> NAME/KEY: misc_feature
<222> LOCATION: (20)..(21)
<223> OTHER INFORMATION: n is a, c, g, or t
<220> FEATURE:
<221> NAME/KEY: misc_feature
<222> LOCATION: (23)..(24)
<223> OTHER INFORMATION: n is a, c, g, or t

<400> SEQUENCE: 410
gcttggtgct cccaggnncn ngnngattac atccatgtta ttcgcga 47

<210> SEQ ID NO 411
<211> LENGTH: 43
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (16)..(17)
<223> OTHER INFORMATION: n is a, c, g, or t
<220> FEATURE:
<221> NAME/KEY: misc_feature
<222> LOCATION: (19)..(20)
<223> OTHER INFORMATION: n is a, c, g, or t
<220> FEATURE:
<221> NAME/KEY: misc_feature
<222> LOCATION: (22)..(23)
<223> OTHER INFORMATION: n is a, c, g, or t

<400> SEQUENCE: 411
atggatgtaa tcaacnngnn cnngggagca ccaagcggca gtg 43

<210> SEQ ID NO 412
<211> LENGTH: 47
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (17)..(18)
<223> OTHER INFORMATION: n is a, c, g, or t
<220> FEATURE:
<221> NAME/KEY: misc_feature
<222> LOCATION: (20)..(21)
<223> OTHER INFORMATION: n is a, c, g, or t
<220> FEATURE:
<221> NAME/KEY: misc_feature
<222> LOCATION: (23)..(24)
<223> OTHER INFORMATION: n is a, c, g, or t

<400> SEQUENCE: 412
gccgcttggt gctcccnngn ncnngttgat tacatccatg ttattcg 47

<210> SEQ ID NO 413
<211> LENGTH: 45
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (16)..(17)
<223> OTHER INFORMATION: n is a, c, g, or t
<220> FEATURE:
<221> NAME/KEY: misc_feature
<222> LOCATION: (19)..(20)
<223> OTHER INFORMATION: n is a, c, g, or t
<220> FEATURE:
<221> NAME/KEY: misc_feature
<222> LOCATION: (22)..(23)
<223> OTHER INFORMATION: n is a, c, g, or t

<400> SEQUENCE: 413
gatgtaatca acatgnncnn gnnagcacca agcggcagtg cggca 45

<210> SEQ ID NO 414
<211> LENGTH: 48
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (17)..(18)
<223> OTHER INFORMATION: n is a, c, g, or t
<220> FEATURE:
<221> NAME/KEY: misc_feature
<222> LOCATION: (20)..(21)
<223> OTHER INFORMATION: n is a, c, g, or t
<220> FEATURE:
<221> NAME/KEY: misc_feature
<222> LOCATION: (23)..(24)
<223> OTHER INFORMATION: n is a, c, g, or t

<400> SEQUENCE: 414
actgccgctt ggtgctnncn ngnncatgtt gattacatcc atgttatt 48

<210> SEQ ID NO 415
<211> LENGTH: 44
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (16)..(17)
<223> OTHER INFORMATION: n is a, c, g, or t
<220> FEATURE:
<221> NAME/KEY: misc_feature
<222> LOCATION: (19)..(20)
<223> OTHER INFORMATION: n is a, c, g, or t
<220> FEATURE:
<221> NAME/KEY: misc_feature
<222> LOCATION: (22)..(23)
<223> OTHER INFORMATION: n is a, c, g, or t

<400> SEQUENCE: 415
gtaatcaaca tgagcnngnn annaccaagc ggcagtgcgg cact 44

<210> SEQ ID NO 416
<211> LENGTH: 46
<212> TYPE: DNA
<213> ORGANISM: Artificial Sequence
<220> FEATURE:

<223> OTHER INFORMATION: Primer
<220> FEATURE:
<221> NAME/KEY: misc_feature
<222> LOCATION: (17)..(18)
<223> OTHER INFORMATION: n is a, c, g, or t
<220> FEATURE:
<221> NAME/KEY: misc_feature
<222> LOCATION: (20)..(21)
<223> OTHER INFORMATION: n is a, c, g, or t
<220> FEATURE:
<221> NAME/KEY: misc_feature
<222> LOCATION: (23)..(24)
<223> OTHER INFORMATION: n is a, c, g, or t

<400> SEQUENCE: 416
cgcactgccg cttggtnntn ncnngctcat gttgattaca tccatg 46

<210> SEQ ID NO 417
<211> LENGTH: 45
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (16)..(17)
<223> OTHER INFORMATION: n is a, c, g, or t
<220> FEATURE:
<221> NAME/KEY: misc_feature
<222> LOCATION: (19)..(20)
<223> OTHER INFORMATION: n is a, c, g, or t
<220> FEATURE:
<221> NAME/KEY: misc_feature
<222> LOCATION: (22)..(23)
<223> OTHER INFORMATION: n is a, c, g, or t

<400> SEQUENCE: 417
atgagcctgg gagcannann cnncagtgcg gcacttaaag cagca 45

<210> SEQ ID NO 418
<211> LENGTH: 45
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (17)..(18)
<223> OTHER INFORMATION: n is a, c, g, or t
<220> FEATURE:
<221> NAME/KEY: misc_feature
<222> LOCATION: (20)..(21)
<223> OTHER INFORMATION: n is a, c, g, or t
<220> FEATURE:
<221> NAME/KEY: misc_feature
<222> LOCATION: (23)..(24)
<223> OTHER INFORMATION: n is a, c, g, or t

<400> SEQUENCE: 418
tttaagtgcc gcactgnngn ntnntgctcc caggctcatg ttgat 45

<210> SEQ ID NO 419
<211> LENGTH: 46
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (16)..(17)
<223> OTHER INFORMATION: n is a, c, g, or t
<220> FEATURE:
<221> NAME/KEY: misc_feature
<222> LOCATION: (19)..(20)
<223> OTHER INFORMATION: n is a, c, g, or t
<220> FEATURE:
<221> NAME/KEY: misc_feature
<222> LOCATION: (22)..(23)
<223> OTHER INFORMATION: n is a, c, g, or t

<400> SEQUENCE: 419
ggagcaccaa gcggcnntnn gnnacttaaa gcagcagttg ataaag 46

<210> SEQ ID NO 420
<211> LENGTH: 45
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (17)..(18)
<223> OTHER INFORMATION: n is a, c, g, or t
<220> FEATURE:
<221> NAME/KEY: misc_feature
<222> LOCATION: (20)..(21)
<223> OTHER INFORMATION: n is a, c, g, or t
<220> FEATURE:
<221> NAME/KEY: misc_feature
<222> LOCATION: (23)..(24)
<223> OTHER INFORMATION: n is a, c, g, or t

<400> SEQUENCE: 420
aactgctgct ttaagtnncn nanngccgct tggtgctccc aggct 45

<210> SEQ ID NO 421
<211> LENGTH: 46
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (16)..(17)
<223> OTHER INFORMATION: n is a, c, g, or t
<220> FEATURE:
<221> NAME/KEY: misc_feature
<222> LOCATION: (19)..(20)
<223> OTHER INFORMATION: n is a, c, g, or t
<220> FEATURE:
<221> NAME/KEY: misc_feature
<222> LOCATION: (22)..(23)
<223> OTHER INFORMATION: n is a, c, g, or t

<400> SEQUENCE: 421
gcaccaagcg gcagtnngnn anntaaagca gcagttgata aagctg 46

<210> SEQ ID NO 422
<211> LENGTH: 44
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (17)..(18)
<223> OTHER INFORMATION: n is a, c, g, or t
<220> FEATURE:
<221> NAME/KEY: misc_feature
<222> LOCATION: (20)..(21)
<223> OTHER INFORMATION: n is a, c, g, or t
<220> FEATURE:
<221> NAME/KEY: misc_feature
<222> LOCATION: (23)..(24)
<223> OTHER INFORMATION: n is a, c, g, or t

<400> SEQUENCE: 422
atcaactgct gctttanntn ncnnactgcc gcttggtgct ccca 44

<210> SEQ ID NO 423
<211> LENGTH: 46
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (16)..(17)
<223> OTHER INFORMATION: n is a, c, g, or t
<220> FEATURE:
<221> NAME/KEY: misc_feature
<222> LOCATION: (19)..(20)
<223> OTHER INFORMATION: n is a, c, g, or t
<220> FEATURE:
<221> NAME/KEY: misc_feature
<222> LOCATION: (22)..(23)
<223> OTHER INFORMATION: n is a, c, g, or t

<400> SEQUENCE: 423
ccaagcggca gtgcgnnann tnnagcagca gttgataaag ctgttg 46

<210> SEQ ID NO 424
<211> LENGTH: 44
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (17)..(18)
<223> OTHER INFORMATION: n is a, c, g, or t
<220> FEATURE:
<221> NAME/KEY: misc_feature
<222> LOCATION: (20)..(21)
<223> OTHER INFORMATION: n is a, c, g, or t
<220> FEATURE:
<221> NAME/KEY: misc_feature
<222> LOCATION: (23)..(24)
<223> OTHER INFORMATION: n is a, c, g, or t

<400> SEQUENCE: 424
tttatcaact gctgctnnan ntnncgcact gccgcttggt gctc 44

<210> SEQ ID NO 425
<211> LENGTH: 46
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (16)..(17)
<223> OTHER INFORMATION: n is a, c, g, or t
<220> FEATURE:
<221> NAME/KEY: misc_feature
<222> LOCATION: (19)..(20)
<223> OTHER INFORMATION: n is a, c, g, or t
<220> FEATURE:
<221> NAME/KEY: misc_feature
<222> LOCATION: (22)..(23)
<223> OTHER INFORMATION: n is a, c, g, or t

<400> SEQUENCE: 425
agcggcagtg cggcanntnn annagcagtt gataaagctg ttgcat 46

<210> SEQ ID NO 426
<211> LENGTH: 44

-continued

<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (17)..(18)
<223> OTHER INFORMATION: n is a, c, g, or t
<220> FEATURE:
<221> NAME/KEY: misc_feature
<222> LOCATION: (20)..(21)
<223> OTHER INFORMATION: n is a, c, g, or t
<220> FEATURE:
<221> NAME/KEY: misc_feature
<222> LOCATION: (23)..(24)
<223> OTHER INFORMATION: n is a, c, g, or t

<400> SEQUENCE: 426
agctttatca actgctnntn nanntgccgc actgccgctt ggtg 44

<210> SEQ ID NO 427
<211> LENGTH: 46
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (16)..(17)
<223> OTHER INFORMATION: n is a, c, g, or t
<220> FEATURE:
<221> NAME/KEY: misc_feature
<222> LOCATION: (19)..(20)
<223> OTHER INFORMATION: n is a, c, g, or t
<220> FEATURE:
<221> NAME/KEY: misc_feature
<222> LOCATION: (22)..(23)
<223> OTHER INFORMATION: n is a, c, g, or t

<400> SEQUENCE: 427
ggcagtgcgg cacttnnann annagttgat aaagctgttg catctg 46

<210> SEQ ID NO 428
<211> LENGTH: 44
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (17)..(18)
<223> OTHER INFORMATION: n is a, c, g, or t
<220> FEATURE:
<221> NAME/KEY: misc_feature
<222> LOCATION: (20)..(21)
<223> OTHER INFORMATION: n is a, c, g, or t
<220> FEATURE:
<221> NAME/KEY: misc_feature
<222> LOCATION: (23)..(24)
<223> OTHER INFORMATION: n is a, c, g, or t

<400> SEQUENCE: 428
aacagcttta tcaactnntn ntnnaagtgc cgcactgccg cttg 44

<210> SEQ ID NO 429
<211> LENGTH: 46
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (16)..(17)

<223> OTHER INFORMATION: n is a, c, g, or t
<220> FEATURE:
<221> NAME/KEY: misc_feature
<222> LOCATION: (19)..(20)
<223> OTHER INFORMATION: n is a, c, g, or t
<220> FEATURE:
<221> NAME/KEY: misc_feature
<222> LOCATION: (22)..(23)
<223> OTHER INFORMATION: n is a, c, g, or t

<400> SEQUENCE: 429
agtgcggcac ttaaannann anntgataaa gctgttgcat ctggtg 46

<210> SEQ ID NO 430
<211> LENGTH: 46
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (17)..(18)
<223> OTHER INFORMATION: n is a, c, g, or t
<220> FEATURE:
<221> NAME/KEY: misc_feature
<222> LOCATION: (20)..(21)
<223> OTHER INFORMATION: n is a, c, g, or t
<220> FEATURE:
<221> NAME/KEY: misc_feature
<222> LOCATION: (23)..(24)
<223> OTHER INFORMATION: n is a, c, g, or t

<400> SEQUENCE: 430
tgcaacagct ttatcanntn ntnntttaag tgccgcactg ccgctt 46

<210> SEQ ID NO 431
<211> LENGTH: 45
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (16)..(17)
<223> OTHER INFORMATION: n is a, c, g, or t
<220> FEATURE:
<221> NAME/KEY: misc_feature
<222> LOCATION: (19)..(20)
<223> OTHER INFORMATION: n is a, c, g, or t
<220> FEATURE:
<221> NAME/KEY: misc_feature
<222> LOCATION: (22)..(23)
<223> OTHER INFORMATION: n is a, c, g, or t

<400> SEQUENCE: 431
gcggcactta aagcannann tnntaaagct gttgcatctg gtgtc 45

<210> SEQ ID NO 432
<211> LENGTH: 44
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (17)..(18)
<223> OTHER INFORMATION: n is a, c, g, or t
<220> FEATURE:
<221> NAME/KEY: misc_feature
<222> LOCATION: (20)..(21)
<223> OTHER INFORMATION: n is a, c, g, or t
<220> FEATURE:
<221> NAME/KEY: misc_feature
<222> LOCATION: (23)..(24)
<223> OTHER INFORMATION: n is a, c, g, or t

<400> SEQUENCE: 432
agatgcaaca gctttannan ntnntgcttt aagtgccgca ctgc 44

<210> SEQ ID NO 433
<211> LENGTH: 44
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (16)..(17)
<223> OTHER INFORMATION: n is a, c, g, or t
<220> FEATURE:
<221> NAME/KEY: misc_feature
<222> LOCATION: (19)..(20)
<223> OTHER INFORMATION: n is a, c, g, or t
<220> FEATURE:
<221> NAME/KEY: misc_feature
<222> LOCATION: (22)..(23)
<223> OTHER INFORMATION: n is a, c, g, or t

<400> SEQUENCE: 433
gcacttaaag cagcanntnn tnnagctgtt gcatctggtg tcgt 44

<210> SEQ ID NO 434
<211> LENGTH: 44
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (17)..(18)
<223> OTHER INFORMATION: n is a, c, g, or t
<220> FEATURE:
<221> NAME/KEY: misc_feature
<222> LOCATION: (20)..(21)
<223> OTHER INFORMATION: n is a, c, g, or t
<220> FEATURE:
<221> NAME/KEY: misc_feature
<222> LOCATION: (23)..(24)
<223> OTHER INFORMATION: n is a, c, g, or t

<400> SEQUENCE: 434
accagatgca acagctnnan nanntgctgc tttaagtgcc gcac 44

<210> SEQ ID NO 435
<211> LENGTH: 44
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (16)..(17)
<223> OTHER INFORMATION: n is a, c, g, or t
<220> FEATURE:
<221> NAME/KEY: misc_feature
<222> LOCATION: (19)..(20)
<223> OTHER INFORMATION: n is a, c, g, or t
<220> FEATURE:
<221> NAME/KEY: misc_feature
<222> LOCATION: (22)..(23)
<223> OTHER INFORMATION: n is a, c, g, or t

<400> SEQUENCE: 435
cttaaagcag cagttnntnn anntgttgca tctggtgtcg tcgt 44

<210> SEQ ID NO 436
<211> LENGTH: 46
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (17)..(18)
<223> OTHER INFORMATION: n is a, c, g, or t
<220> FEATURE:
<221> NAME/KEY: misc_feature
<222> LOCATION: (20)..(21)
<223> OTHER INFORMATION: n is a, c, g, or t
<220> FEATURE:
<221> NAME/KEY: misc_feature
<222> LOCATION: (23)..(24)
<223> OTHER INFORMATION: n is a, c, g, or t

<400> SEQUENCE: 436
gacaccagat gcaacanntn nannaactgc tgctttaagt gccgca 46

<210> SEQ ID NO 437
<211> LENGTH: 44
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (16)..(17)
<223> OTHER INFORMATION: n is a, c, g, or t
<220> FEATURE:
<221> NAME/KEY: misc_feature
<222> LOCATION: (19)..(20)
<223> OTHER INFORMATION: n is a, c, g, or t
<220> FEATURE:
<221> NAME/KEY: misc_feature
<222> LOCATION: (22)..(23)
<223> OTHER INFORMATION: n is a, c, g, or t

<400> SEQUENCE: 437
aaagcagcag ttgatnnann tnntgcatct ggtgtcgtcg tagt 44

<210> SEQ ID NO 438
<211> LENGTH: 45
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (17)..(18)
<223> OTHER INFORMATION: n is a, c, g, or t
<220> FEATURE:
<221> NAME/KEY: misc_feature
<222> LOCATION: (20)..(21)
<223> OTHER INFORMATION: n is a, c, g, or t
<220> FEATURE:
<221> NAME/KEY: misc_feature
<222> LOCATION: (23)..(24)
<223> OTHER INFORMATION: n is a, c, g, or t

<400> SEQUENCE: 438
gacgacacca gatgcannan ntnnatcaac tgctgcttta agtgc 45

<210> SEQ ID NO 439
<211> LENGTH: 44
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (16)..(17)
<223> OTHER INFORMATION: n is a, c, g, or t
<220> FEATURE:
<221> NAME/KEY: misc_feature
<222> LOCATION: (19)..(20)
<223> OTHER INFORMATION: n is a, c, g, or t
<220> FEATURE:
<221> NAME/KEY: misc_feature
<222> LOCATION: (22)..(23)
<223> OTHER INFORMATION: n is a, c, g, or t

<400> SEQUENCE: 439
gcagcagttg ataaanntnn tnnatctggt gtcgtcgtag tagc 44

<210> SEQ ID NO 440
<211> LENGTH: 47
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (17)..(18)
<223> OTHER INFORMATION: n is a, c, g, or t
<220> FEATURE:
<221> NAME/KEY: misc_feature
<222> LOCATION: (20)..(21)
<223> OTHER INFORMATION: n is a, c, g, or t
<220> FEATURE:
<221> NAME/KEY: misc_feature
<222> LOCATION: (23)..(24)
<223> OTHER INFORMATION: n is a, c, g, or t

<400> SEQUENCE: 440
tacgacgaca ccagatnnan nanntttatc aactgctgct ttaagtg 47

<210> SEQ ID NO 441
<211> LENGTH: 45
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (16)..(17)
<223> OTHER INFORMATION: n is a, c, g, or t
<220> FEATURE:
<221> NAME/KEY: misc_feature
<222> LOCATION: (19)..(20)
<223> OTHER INFORMATION: n is a, c, g, or t
<220> FEATURE:
<221> NAME/KEY: misc_feature
<222> LOCATION: (22)..(23)
<223> OTHER INFORMATION: n is a, c, g, or t

<400> SEQUENCE: 441
gcagttgata aagctnntnn anntggtgtc gtcgtagtag cggca 45

<210> SEQ ID NO 442
<211> LENGTH: 47
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (17)..(18)
<223> OTHER INFORMATION: n is a, c, g, or t
<220> FEATURE:
<221> NAME/KEY: misc_feature
<222> LOCATION: (20)..(21)

<223> OTHER INFORMATION: n is a, c, g, or t
<220> FEATURE:
<221> NAME/KEY: misc_feature
<222> LOCATION: (23)..(24)
<223> OTHER INFORMATION: n is a, c, g, or t

<400> SEQUENCE: 442
tactacgacg acaccanntn nannagcttt atcaactgct gctttaa 47

<210> SEQ ID NO 443
<211> LENGTH: 45
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (16)..(17)
<223> OTHER INFORMATION: n is a, c, g, or t
<220> FEATURE:
<221> NAME/KEY: misc_feature
<222> LOCATION: (19)..(20)
<223> OTHER INFORMATION: n is a, c, g, or t
<220> FEATURE:
<221> NAME/KEY: misc_feature
<222> LOCATION: (22)..(23)
<223> OTHER INFORMATION: n is a, c, g, or t

<400> SEQUENCE: 443
gttgataaag ctgttnnann tnntgtcgtc gtagtagcgg cagct 45

<210> SEQ ID NO 444
<211> LENGTH: 46
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (17)..(18)
<223> OTHER INFORMATION: n is a, c, g, or t
<220> FEATURE:
<221> NAME/KEY: misc_feature
<222> LOCATION: (20)..(21)
<223> OTHER INFORMATION: n is a, c, g, or t
<220> FEATURE:
<221> NAME/KEY: misc_feature
<222> LOCATION: (23)..(24)
<223> OTHER INFORMATION: n is a, c, g, or t

<400> SEQUENCE: 444
cgctactacg acgacannan ntnnaacagc tttatcaact gctgct 46

<210> SEQ ID NO 445
<211> LENGTH: 43
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (16)..(17)
<223> OTHER INFORMATION: n is a, c, g, or t
<220> FEATURE:
<221> NAME/KEY: misc_feature
<222> LOCATION: (19)..(20)
<223> OTHER INFORMATION: n is a, c, g, or t
<220> FEATURE:
<221> NAME/KEY: misc_feature
<222> LOCATION: (22)..(23)
<223> OTHER INFORMATION: n is a, c, g, or t

<400> SEQUENCE: 445
gataaagctg ttgcanntnn tnncgtcgta gtagcggcag ctg 43

<210> SEQ ID NO 446
<211> LENGTH: 46
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (17)..(18)
<223> OTHER INFORMATION: n is a, c, g, or t
<220> FEATURE:
<221> NAME/KEY: misc_feature
<222> LOCATION: (20)..(21)
<223> OTHER INFORMATION: n is a, c, g, or t
<220> FEATURE:
<221> NAME/KEY: misc_feature
<222> LOCATION: (23)..(24)
<223> OTHER INFORMATION: n is a, c, g, or t

<400> SEQUENCE: 446
tgccgctact acgacgnnan nanntgcaac agctttatca actgct 46

<210> SEQ ID NO 447
<211> LENGTH: 44
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (16)..(17)
<223> OTHER INFORMATION: n is a, c, g, or t
<220> FEATURE:
<221> NAME/KEY: misc_feature
<222> LOCATION: (19)..(20)
<223> OTHER INFORMATION: n is a, c, g, or t
<220> FEATURE:
<221> NAME/KEY: misc_feature
<222> LOCATION: (22)..(23)
<223> OTHER INFORMATION: n is a, c, g, or t

<400> SEQUENCE: 447
aaagctgttg catctnntnn cnncgtagta gcggcagctg ggaa 44

<210> SEQ ID NO 448
<211> LENGTH: 47
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (17)..(18)
<223> OTHER INFORMATION: n is a, c, g, or t
<220> FEATURE:
<221> NAME/KEY: misc_feature
<222> LOCATION: (20)..(21)
<223> OTHER INFORMATION: n is a, c, g, or t
<220> FEATURE:
<221> NAME/KEY: misc_feature
<222> LOCATION: (23)..(24)
<223> OTHER INFORMATION: n is a, c, g, or t

<400> SEQUENCE: 448
agctgccgct actacgnngn nannagatgc aacagcttta tcaactg 47

<210> SEQ ID NO 449
<211> LENGTH: 44
<212> TYPE: DNA

<213> ORGANISM: Artificial Sequence
<220> FEATURE:
<223> OTHER INFORMATION: Primer
<220> FEATURE:
<221> NAME/KEY: misc_feature
<222> LOCATION: (16)..(17)
<223> OTHER INFORMATION: n is a, c, g, or t
<220> FEATURE:
<221> NAME/KEY: misc_feature
<222> LOCATION: (19)..(20)
<223> OTHER INFORMATION: n is a, c, g, or t
<220> FEATURE:
<221> NAME/KEY: misc_feature
<222> LOCATION: (22)..(23)
<223> OTHER INFORMATION: n is a, c, g, or t

<400> SEQUENCE: 449
gctgttgcat ctggtnncnn cnnagtagcg gcagctggga atga 44

<210> SEQ ID NO 450
<211> LENGTH: 46
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (17)..(18)
<223> OTHER INFORMATION: n is a, c, g, or t
<220> FEATURE:
<221> NAME/KEY: misc_feature
<222> LOCATION: (20)..(21)
<223> OTHER INFORMATION: n is a, c, g, or t
<220> FEATURE:
<221> NAME/KEY: misc_feature
<222> LOCATION: (23)..(24)
<223> OTHER INFORMATION: n is a, c, g, or t

<400> SEQUENCE: 450
cccagctgcc gctactnngn ngnnaccaga tgcaacagct ttatca 46

<210> SEQ ID NO 451
<211> LENGTH: 46
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (16)..(17)
<223> OTHER INFORMATION: n is a, c, g, or t
<220> FEATURE:
<221> NAME/KEY: misc_feature
<222> LOCATION: (19)..(20)
<223> OTHER INFORMATION: n is a, c, g, or t
<220> FEATURE:
<221> NAME/KEY: misc_feature
<222> LOCATION: (22)..(23)
<223> OTHER INFORMATION: n is a, c, g, or t

<400> SEQUENCE: 451
gttgcatctg gtgtcnncnn annagcggca gctgggaatg agggaa 46

<210> SEQ ID NO 452
<211> LENGTH: 45
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (17)..(18)
<223> OTHER INFORMATION: n is a, c, g, or t
<220> FEATURE:
<221> NAME/KEY: misc_feature
<222> LOCATION: (20)..(21)
<223> OTHER INFORMATION: n is a, c, g, or t
<220> FEATURE:
<221> NAME/KEY: misc_feature
<222> LOCATION: (23)..(24)
<223> OTHER INFORMATION: n is a, c, g, or t

<400> SEQUENCE: 452
attcccagct gccgctnntn ngnngacacc agatgcaaca gcttt 45

<210> SEQ ID NO 453
<211> LENGTH: 44
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (16)..(17)
<223> OTHER INFORMATION: n is a, c, g, or t
<220> FEATURE:
<221> NAME/KEY: misc_feature
<222> LOCATION: (19)..(20)
<223> OTHER INFORMATION: n is a, c, g, or t
<220> FEATURE:
<221> NAME/KEY: misc_feature
<222> LOCATION: (22)..(23)
<223> OTHER INFORMATION: n is a, c, g, or t

<400> SEQUENCE: 453
gcatctggtg tcgtcnnann annggcagct gggaatgagg gaac 44

<210> SEQ ID NO 454
<211> LENGTH: 44
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (17)..(18)
<223> OTHER INFORMATION: n is a, c, g, or t
<220> FEATURE:
<221> NAME/KEY: misc_feature
<222> LOCATION: (20)..(21)
<223> OTHER INFORMATION: n is a, c, g, or t
<220> FEATURE:
<221> NAME/KEY: misc_feature
<222> LOCATION: (23)..(24)
<223> OTHER INFORMATION: n is a, c, g, or t

<400> SEQUENCE: 454
ctcattccca gctgccnntn ntnngacgac accagatgca acag 44

<210> SEQ ID NO 455
<211> LENGTH: 44
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (16)..(17)
<223> OTHER INFORMATION: n is a, c, g, or t
<220> FEATURE:
<221> NAME/KEY: misc_feature
<222> LOCATION: (19)..(20)
<223> OTHER INFORMATION: n is a, c, g, or t
<220> FEATURE:
<221> NAME/KEY: misc_feature
<222> LOCATION: (22)..(23)

<223> OTHER INFORMATION: n is a, c, g, or t

<400> SEQUENCE: 455
tctggtgtcg tcgtannann gnnagctggg aatgagggaa catc 44

<210> SEQ ID NO 456
<211> LENGTH: 45
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (17)..(18)
<223> OTHER INFORMATION: n is a, c, g, or t
<220> FEATURE:
<221> NAME/KEY: misc_feature
<222> LOCATION: (20)..(21)
<223> OTHER INFORMATION: n is a, c, g, or t
<220> FEATURE:
<221> NAME/KEY: misc_feature
<222> LOCATION: (23)..(24)
<223> OTHER INFORMATION: n is a, c, g, or t

<400> SEQUENCE: 456
tccctcattc ccagctnncn ntnntacgac gacaccagat gcaac 45

<210> SEQ ID NO 457
<211> LENGTH: 46
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (16)..(17)
<223> OTHER INFORMATION: n is a, c, g, or t
<220> FEATURE:
<221> NAME/KEY: misc_feature
<222> LOCATION: (19)..(20)
<223> OTHER INFORMATION: n is a, c, g, or t
<220> FEATURE:
<221> NAME/KEY: misc_feature
<222> LOCATION: (22)..(23)
<223> OTHER INFORMATION: n is a, c, g, or t

<400> SEQUENCE: 457
ggtgtcgtcg tagtanngnn anntgggaat gagggaacat ccggat 46

<210> SEQ ID NO 458
<211> LENGTH: 46
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (17)..(18)
<223> OTHER INFORMATION: n is a, c, g, or t
<220> FEATURE:
<221> NAME/KEY: misc_feature
<222> LOCATION: (20)..(21)
<223> OTHER INFORMATION: n is a, c, g, or t
<220> FEATURE:
<221> NAME/KEY: misc_feature
<222> LOCATION: (23)..(24)
<223> OTHER INFORMATION: n is a, c, g, or t

<400> SEQUENCE: 458
tgttccctca ttcccanntn ncnntactac gacgacacca gatgca 46

<210> SEQ ID NO 459
<211> LENGTH: 45
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (16)..(17)
<223> OTHER INFORMATION: n is a, c, g, or t
<220> FEATURE:
<221> NAME/KEY: misc_feature
<222> LOCATION: (19)..(20)
<223> OTHER INFORMATION: n is a, c, g, or t
<220> FEATURE:
<221> NAME/KEY: misc_feature
<222> LOCATION: (22)..(23)
<223> OTHER INFORMATION: n is a, c, g, or t

<400> SEQUENCE: 459
gctgggaatg agggannann cnnatcatcg agtaccgtcg gttat 45

<210> SEQ ID NO 460
<211> LENGTH: 47
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (17)..(18)
<223> OTHER INFORMATION: n is a, c, g, or t
<220> FEATURE:
<221> NAME/KEY: misc_feature
<222> LOCATION: (20)..(21)
<223> OTHER INFORMATION: n is a, c, g, or t
<220> FEATURE:
<221> NAME/KEY: misc_feature
<222> LOCATION: (23)..(24)
<223> OTHER INFORMATION: n is a, c, g, or t

<400> SEQUENCE: 460
gacggtactc gatgatnngn ntnntccctc attcccagct gccgcta 47

<210> SEQ ID NO 461
<211> LENGTH: 45
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (16)..(17)
<223> OTHER INFORMATION: n is a, c, g, or t
<220> FEATURE:
<221> NAME/KEY: misc_feature
<222> LOCATION: (19)..(20)
<223> OTHER INFORMATION: n is a, c, g, or t
<220> FEATURE:
<221> NAME/KEY: misc_feature
<222> LOCATION: (22)..(23)
<223> OTHER INFORMATION: n is a, c, g, or t

<400> SEQUENCE: 461
gggaatgagg gaacanncnn annatcgagt accgtcggtt atcca 45

<210> SEQ ID NO 462
<211> LENGTH: 44
<212> TYPE: DNA
<213> ORGANISM: Artificial Sequence
<220> FEATURE:
<223> OTHER INFORMATION: Primer
<220> FEATURE:

<221> NAME/KEY: misc_feature
<222> LOCATION: (17)..(18)
<223> OTHER INFORMATION: n is a, c, g, or t
<220> FEATURE:
<221> NAME/KEY: misc_feature
<222> LOCATION: (20)..(21)
<223> OTHER INFORMATION: n is a, c, g, or t
<220> FEATURE:
<221> NAME/KEY: misc_feature
<222> LOCATION: (23)..(24)
<223> OTHER INFORMATION: n is a, c, g, or t

<400> SEQUENCE: 462
accgacggta ctcgatnntn ngnntgttcc ctcattccca gctg 44

<210> SEQ ID NO 463
<211> LENGTH: 44
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (16)..(17)
<223> OTHER INFORMATION: n is a, c, g, or t
<220> FEATURE:
<221> NAME/KEY: misc_feature
<222> LOCATION: (19)..(20)
<223> OTHER INFORMATION: n is a, c, g, or t
<220> FEATURE:
<221> NAME/KEY: misc_feature
<222> LOCATION: (22)..(23)
<223> OTHER INFORMATION: n is a, c, g, or t

<400> SEQUENCE: 463
aatgagggaa catccnnann anngagtacc gtcggttatc cagg 44

<210> SEQ ID NO 464
<211> LENGTH: 44
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (17)..(18)
<223> OTHER INFORMATION: n is a, c, g, or t
<220> FEATURE:
<221> NAME/KEY: misc_feature
<222> LOCATION: (20)..(21)
<223> OTHER INFORMATION: n is a, c, g, or t
<220> FEATURE:
<221> NAME/KEY: misc_feature
<222> LOCATION: (23)..(24)
<223> OTHER INFORMATION: n is a, c, g, or t

<400> SEQUENCE: 464
ataaccgacg gtactcnntn ntnnggatgt tccctcattc ccag 44

<210> SEQ ID NO 465
<211> LENGTH: 46
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (16)..(17)
<223> OTHER INFORMATION: n is a, c, g, or t
<220> FEATURE:
<221> NAME/KEY: misc_feature
<222> LOCATION: (19)..(20)
<223> OTHER INFORMATION: n is a, c, g, or t
<220> FEATURE:
<221> NAME/KEY: misc_feature
<222> LOCATION: (22)..(23)
<223> OTHER INFORMATION: n is a, c, g, or t

<400> SEQUENCE: 465
acatccggat catcgnntnn cnncggttat ccaggcaagt accctt 46

<210> SEQ ID NO 466
<211> LENGTH: 44
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (17)..(18)
<223> OTHER INFORMATION: n is a, c, g, or t
<220> FEATURE:
<221> NAME/KEY: misc_feature
<222> LOCATION: (20)..(21)
<223> OTHER INFORMATION: n is a, c, g, or t
<220> FEATURE:
<221> NAME/KEY: misc_feature
<222> LOCATION: (23)..(24)
<223> OTHER INFORMATION: n is a, c, g, or t

<400> SEQUENCE: 466
cttgcctgga taaccgnngn nanncgatga tccggatgtt ccct 44

<210> SEQ ID NO 467
<211> LENGTH: 45
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (16)..(17)
<223> OTHER INFORMATION: n is a, c, g, or t
<220> FEATURE:
<221> NAME/KEY: misc_feature
<222> LOCATION: (19)..(20)
<223> OTHER INFORMATION: n is a, c, g, or t
<220> FEATURE:
<221> NAME/KEY: misc_feature
<222> LOCATION: (22)..(23)
<223> OTHER INFORMATION: n is a, c, g, or t

<400> SEQUENCE: 467
tccggatcat cgagtnncnn cnnttatcca ggcaagtacc cttca 45

<210> SEQ ID NO 468
<211> LENGTH: 45
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (17)..(18)
<223> OTHER INFORMATION: n is a, c, g, or t
<220> FEATURE:
<221> NAME/KEY: misc_feature
<222> LOCATION: (20)..(21)
<223> OTHER INFORMATION: n is a, c, g, or t
<220> FEATURE:
<221> NAME/KEY: misc_feature
<222> LOCATION: (23)..(24)
<223> OTHER INFORMATION: n is a, c, g, or t

<400> SEQUENCE: 468
gtacttgcct ggataanngn ngnnactcga tgatccggat gttcc 45

<210> SEQ ID NO 469
<211> LENGTH: 45
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (16)..(17)
<223> OTHER INFORMATION: n is a, c, g, or t
<220> FEATURE:
<221> NAME/KEY: misc_feature
<222> LOCATION: (19)..(20)
<223> OTHER INFORMATION: n is a, c, g, or t
<220> FEATURE:
<221> NAME/KEY: misc_feature
<222> LOCATION: (22)..(23)
<223> OTHER INFORMATION: n is a, c, g, or t

<400> SEQUENCE: 469
tcgagtaccg tcggtnntnn anncaagtac ccttcagtga ttgca 45

<210> SEQ ID NO 470
<211> LENGTH: 44
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (17)..(18)
<223> OTHER INFORMATION: n is a, c, g, or t
<220> FEATURE:
<221> NAME/KEY: misc_feature
<222> LOCATION: (20)..(21)
<223> OTHER INFORMATION: n is a, c, g, or t
<220> FEATURE:
<221> NAME/KEY: misc_feature
<222> LOCATION: (23)..(24)
<223> OTHER INFORMATION: n is a, c, g, or t

<400> SEQUENCE: 470
cactgaaggg tacttgnntn nannaccgac ggtactcgat gatc 44

<210> SEQ ID NO 471
<211> LENGTH: 45
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (16)..(17)
<223> OTHER INFORMATION: n is a, c, g, or t
<220> FEATURE:
<221> NAME/KEY: misc_feature
<222> LOCATION: (19)..(20)
<223> OTHER INFORMATION: n is a, c, g, or t
<220> FEATURE:
<221> NAME/KEY: misc_feature
<222> LOCATION: (22)..(23)
<223> OTHER INFORMATION: n is a, c, g, or t

<400> SEQUENCE: 471
agtaccgtcg gttatnnann cnngtaccct tcagtgattg cagtg 45

<210> SEQ ID NO 472
<211> LENGTH: 45
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (17)..(18)
<223> OTHER INFORMATION: n is a, c, g, or t
<220> FEATURE:
<221> NAME/KEY: misc_feature
<222> LOCATION: (20)..(21)
<223> OTHER INFORMATION: n is a, c, g, or t
<220> FEATURE:
<221> NAME/KEY: misc_feature
<222> LOCATION: (23)..(24)
<223> OTHER INFORMATION: n is a, c, g, or t

<400> SEQUENCE: 472
aatcactgaa gggtacnngn ntnnataacc gacggtactc gatga 45

<210> SEQ ID NO 473
<211> LENGTH: 43
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (16)..(17)
<223> OTHER INFORMATION: n is a, c, g, or t
<220> FEATURE:
<221> NAME/KEY: misc_feature
<222> LOCATION: (19)..(20)
<223> OTHER INFORMATION: n is a, c, g, or t
<220> FEATURE:
<221> NAME/KEY: misc_feature
<222> LOCATION: (22)..(23)
<223> OTHER INFORMATION: n is a, c, g, or t

<400> SEQUENCE: 473
accgtcggtt atccanncnn gnncccttca gtgattgcag tgg 43

<210> SEQ ID NO 474
<211> LENGTH: 45
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (17)..(18)
<223> OTHER INFORMATION: n is a, c, g, or t
<220> FEATURE:
<221> NAME/KEY: misc_feature
<222> LOCATION: (20)..(21)
<223> OTHER INFORMATION: n is a, c, g, or t
<220> FEATURE:
<221> NAME/KEY: misc_feature
<222> LOCATION: (23)..(24)
<223> OTHER INFORMATION: n is a, c, g, or t

<400> SEQUENCE: 474
tgcaatcact gaagggnncn ngnntggata accgacggta ctcga 45

<210> SEQ ID NO 475
<211> LENGTH: 45
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (16)..(17)
<223> OTHER INFORMATION: n is a, c, g, or t
<220> FEATURE:

<221> NAME/KEY: misc_feature
<222> LOCATION: (19)..(20)
<223> OTHER INFORMATION: n is a, c, g, or t
<220> FEATURE:
<221> NAME/KEY: misc_feature
<222> LOCATION: (22)..(23)
<223> OTHER INFORMATION: n is a, c, g, or t

<400> SEQUENCE: 475
gtcggttatc caggcnngnn cnnttcagtg attgcagtgg gcgct 45

<210> SEQ ID NO 476
<211> LENGTH: 44
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (17)..(18)
<223> OTHER INFORMATION: n is a, c, g, or t
<220> FEATURE:
<221> NAME/KEY: misc_feature
<222> LOCATION: (20)..(21)
<223> OTHER INFORMATION: n is a, c, g, or t
<220> FEATURE:
<221> NAME/KEY: misc_feature
<222> LOCATION: (23)..(24)
<223> OTHER INFORMATION: n is a, c, g, or t

<400> SEQUENCE: 476
cactgcaatc actgaanngn ncnngcctgg ataaccgacg gtac 44

<210> SEQ ID NO 477
<211> LENGTH: 45
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (16)..(17)
<223> OTHER INFORMATION: n is a, c, g, or t
<220> FEATURE:
<221> NAME/KEY: misc_feature
<222> LOCATION: (19)..(20)
<223> OTHER INFORMATION: n is a, c, g, or t
<220> FEATURE:
<221> NAME/KEY: misc_feature
<222> LOCATION: (22)..(23)
<223> OTHER INFORMATION: n is a, c, g, or t

<400> SEQUENCE: 477
ggttatccag gcaagnncnn tnnagtgatt gcagtgggcg ctgta 45

<210> SEQ ID NO 478
<211> LENGTH: 46
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (17)..(18)
<223> OTHER INFORMATION: n is a, c, g, or t
<220> FEATURE:
<221> NAME/KEY: misc_feature
<222> LOCATION: (20)..(21)
<223> OTHER INFORMATION: n is a, c, g, or t
<220> FEATURE:
<221> NAME/KEY: misc_feature
<222> LOCATION: (23)..(24)
<223> OTHER INFORMATION: n is a, c, g, or t

<400> SEQUENCE: 478
gcccactgca atcactnnan ngnncttgcc tggataaccg acggta 46

<210> SEQ ID NO 479
<211> LENGTH: 44
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (16)..(17)
<223> OTHER INFORMATION: n is a, c, g, or t
<220> FEATURE:
<221> NAME/KEY: misc_feature
<222> LOCATION: (19)..(20)
<223> OTHER INFORMATION: n is a, c, g, or t
<220> FEATURE:
<221> NAME/KEY: misc_feature
<222> LOCATION: (22)..(23)
<223> OTHER INFORMATION: n is a, c, g, or t

<400> SEQUENCE: 479
tatccaggca agtacnntnn anngattgca gtgggcgctg taga 44

<210> SEQ ID NO 480
<211> LENGTH: 45
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (17)..(18)
<223> OTHER INFORMATION: n is a, c, g, or t
<220> FEATURE:
<221> NAME/KEY: misc_feature
<222> LOCATION: (20)..(21)
<223> OTHER INFORMATION: n is a, c, g, or t
<220> FEATURE:
<221> NAME/KEY: misc_feature
<222> LOCATION: (23)..(24)
<223> OTHER INFORMATION: n is a, c, g, or t

<400> SEQUENCE: 480
agcgcccact gcaatcnntn nanngtactt gcctggataa ccgac 45

<210> SEQ ID NO 481
<211> LENGTH: 44
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (16)..(17)
<223> OTHER INFORMATION: n is a, c, g, or t
<220> FEATURE:
<221> NAME/KEY: misc_feature
<222> LOCATION: (19)..(20)
<223> OTHER INFORMATION: n is a, c, g, or t
<220> FEATURE:
<221> NAME/KEY: misc_feature
<222> LOCATION: (22)..(23)
<223> OTHER INFORMATION: n is a, c, g, or t

<400> SEQUENCE: 481
gtgggcgctg tagacnntnn anntcaacgt gcctcttttt cctc 44

<210> SEQ ID NO 482

```
<211> LENGTH: 44
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (17)..(18)
<223> OTHER INFORMATION: n is a, c, g, or t
<220> FEATURE:
<221> NAME/KEY: misc_feature
<222> LOCATION: (20)..(21)
<223> OTHER INFORMATION: n is a, c, g, or t
<220> FEATURE:
<221> NAME/KEY: misc_feature
<222> LOCATION: (23)..(24)
<223> OTHER INFORMATION: n is a, c, g, or t

<400> SEQUENCE: 482

aaaagaggca cgttganntn nanngtctac agcgcccact gcaa         44

<210> SEQ ID NO 483
<211> LENGTH: 44
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (16)..(17)
<223> OTHER INFORMATION: n is a, c, g, or t
<220> FEATURE:
<221> NAME/KEY: misc_feature
<222> LOCATION: (19)..(20)
<223> OTHER INFORMATION: n is a, c, g, or t
<220> FEATURE:
<221> NAME/KEY: misc_feature
<222> LOCATION: (22)..(23)
<223> OTHER INFORMATION: n is a, c, g, or t

<400> SEQUENCE: 483

ggcgctgtag actctnnann tnnacgtgcc tctttttcct ccgt         44

<210> SEQ ID NO 484
<211> LENGTH: 44
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (17)..(18)
<223> OTHER INFORMATION: n is a, c, g, or t
<220> FEATURE:
<221> NAME/KEY: misc_feature
<222> LOCATION: (20)..(21)
<223> OTHER INFORMATION: n is a, c, g, or t
<220> FEATURE:
<221> NAME/KEY: misc_feature
<222> LOCATION: (23)..(24)
<223> OTHER INFORMATION: n is a, c, g, or t

<400> SEQUENCE: 484

ggaaaaagag gcacgtnnan ntnnagagtc tacagcgccc actg         44

<210> SEQ ID NO 485
<211> LENGTH: 45
<212> TYPE: DNA
<213> ORGANISM: Artificial Sequence
<220> FEATURE:
<223> OTHER INFORMATION: Primer
<220> FEATURE:
<221> NAME/KEY: misc_feature
```

-continued

<222> LOCATION: (16)..(17)
<223> OTHER INFORMATION: n is a, c, g, or t
<220> FEATURE:
<221> NAME/KEY: misc_feature
<222> LOCATION: (19)..(20)
<223> OTHER INFORMATION: n is a, c, g, or t
<220> FEATURE:
<221> NAME/KEY: misc_feature
<222> LOCATION: (22)..(23)
<223> OTHER INFORMATION: n is a, c, g, or t

<400> SEQUENCE: 485
gctgtagact cttcanntnn anntgcctct ttttcctccg tggga 45

<210> SEQ ID NO 486
<211> LENGTH: 44
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (17)..(18)
<223> OTHER INFORMATION: n is a, c, g, or t
<220> FEATURE:
<221> NAME/KEY: misc_feature
<222> LOCATION: (20)..(21)
<223> OTHER INFORMATION: n is a, c, g, or t
<220> FEATURE:
<221> NAME/KEY: misc_feature
<222> LOCATION: (23)..(24)
<223> OTHER INFORMATION: n is a, c, g, or t

<400> SEQUENCE: 486
ggaggaaaaa gaggcanntn nanntgaaga gtctacagcg ccca 44

<210> SEQ ID NO 487
<211> LENGTH: 43
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (16)..(17)
<223> OTHER INFORMATION: n is a, c, g, or t
<220> FEATURE:
<221> NAME/KEY: misc_feature
<222> LOCATION: (19)..(20)
<223> OTHER INFORMATION: n is a, c, g, or t
<220> FEATURE:
<221> NAME/KEY: misc_feature
<222> LOCATION: (22)..(23)
<223> OTHER INFORMATION: n is a, c, g, or t

<400> SEQUENCE: 487
gtagactctt caaatnnann tnnctctttt tcctccgtgg gac 43

<210> SEQ ID NO 488
<211> LENGTH: 47
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (17)..(18)
<223> OTHER INFORMATION: n is a, c, g, or t
<220> FEATURE:
<221> NAME/KEY: misc_feature
<222> LOCATION: (20)..(21)
<223> OTHER INFORMATION: n is a, c, g, or t
<220> FEATURE:

<221> NAME/KEY: misc_feature
<222> LOCATION: (23)..(24)
<223> OTHER INFORMATION: n is a, c, g, or t

<400> SEQUENCE: 488
cacggaggaa aaagagnnan ntnnatttga agagtctaca gcgccca 47

<210> SEQ ID NO 489
<211> LENGTH: 44
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (16)..(17)
<223> OTHER INFORMATION: n is a, c, g, or t
<220> FEATURE:
<221> NAME/KEY: misc_feature
<222> LOCATION: (19)..(20)
<223> OTHER INFORMATION: n is a, c, g, or t
<220> FEATURE:
<221> NAME/KEY: misc_feature
<222> LOCATION: (22)..(23)
<223> OTHER INFORMATION: n is a, c, g, or t

<400> SEQUENCE: 489
gactcttcaa atcaanntnn cnntttttcc tccgtgggac cgga 44

<210> SEQ ID NO 490
<211> LENGTH: 50
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (17)..(18)
<223> OTHER INFORMATION: n is a, c, g, or t
<220> FEATURE:
<221> NAME/KEY: misc_feature
<222> LOCATION: (20)..(21)
<223> OTHER INFORMATION: n is a, c, g, or t
<220> FEATURE:
<221> NAME/KEY: misc_feature
<222> LOCATION: (23)..(24)
<223> OTHER INFORMATION: n is a, c, g, or t

<400> SEQUENCE: 490
tcccacggag gaaaaanngn nannttgatt tgaagagtct acagcgccca 50

<210> SEQ ID NO 491
<211> LENGTH: 45
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (16)..(17)
<223> OTHER INFORMATION: n is a, c, g, or t
<220> FEATURE:
<221> NAME/KEY: misc_feature
<222> LOCATION: (19)..(20)
<223> OTHER INFORMATION: n is a, c, g, or t
<220> FEATURE:
<221> NAME/KEY: misc_feature
<222> LOCATION: (22)..(23)
<223> OTHER INFORMATION: n is a, c, g, or t

<400> SEQUENCE: 491
gcctcttttt cctccnngnn annggagctg gatgtcatgg cccct 45

<210> SEQ ID NO 492
<211> LENGTH: 45
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (17)..(18)
<223> OTHER INFORMATION: n is a, c, g, or t
<220> FEATURE:
<221> NAME/KEY: misc_feature
<222> LOCATION: (20)..(21)
<223> OTHER INFORMATION: n is a, c, g, or t
<220> FEATURE:
<221> NAME/KEY: misc_feature
<222> LOCATION: (23)..(24)
<223> OTHER INFORMATION: n is a, c, g, or t

<400> SEQUENCE: 492
catgacatcc agctccnntn ncnnggagga aaaagaggca cgttg 45

<210> SEQ ID NO 493
<211> LENGTH: 45
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (16)..(17)
<223> OTHER INFORMATION: n is a, c, g, or t
<220> FEATURE:
<221> NAME/KEY: misc_feature
<222> LOCATION: (19)..(20)
<223> OTHER INFORMATION: n is a, c, g, or t
<220> FEATURE:
<221> NAME/KEY: misc_feature
<222> LOCATION: (22)..(23)
<223> OTHER INFORMATION: n is a, c, g, or t

<400> SEQUENCE: 493
ttttcctccg tggganngnn gnnggatgtc atggcccctg gcgtt 45

<210> SEQ ID NO 494
<211> LENGTH: 44
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (17)..(18)
<223> OTHER INFORMATION: n is a, c, g, or t
<220> FEATURE:
<221> NAME/KEY: misc_feature
<222> LOCATION: (20)..(21)
<223> OTHER INFORMATION: n is a, c, g, or t
<220> FEATURE:
<221> NAME/KEY: misc_feature
<222> LOCATION: (23)..(24)
<223> OTHER INFORMATION: n is a, c, g, or t

<400> SEQUENCE: 494
aggggccatg acatccnncn ncnntcccac ggaggaaaaa gagg 44

<210> SEQ ID NO 495
<211> LENGTH: 48
<212> TYPE: DNA
<213> ORGANISM: Artificial Sequence
<220> FEATURE:

<223> OTHER INFORMATION: Primer
<220> FEATURE:
<221> NAME/KEY: misc_feature
<222> LOCATION: (16)..(17)
<223> OTHER INFORMATION: n is a, c, g, or t
<220> FEATURE:
<221> NAME/KEY: misc_feature
<222> LOCATION: (19)..(20)
<223> OTHER INFORMATION: n is a, c, g, or t
<220> FEATURE:
<221> NAME/KEY: misc_feature
<222> LOCATION: (22)..(23)
<223> OTHER INFORMATION: n is a, c, g, or t

<400> SEQUENCE: 495
tcctccgtgg gaccgnngnn gnntgtcatg gcccctggcg tttctatt 48

<210> SEQ ID NO 496
<211> LENGTH: 44
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (17)..(18)
<223> OTHER INFORMATION: n is a, c, g, or t
<220> FEATURE:
<221> NAME/KEY: misc_feature
<222> LOCATION: (20)..(21)
<223> OTHER INFORMATION: n is a, c, g, or t
<220> FEATURE:
<221> NAME/KEY: misc_feature
<222> LOCATION: (23)..(24)
<223> OTHER INFORMATION: n is a, c, g, or t

<400> SEQUENCE: 496
gccaggggcc atgacanncn ncnncggtcc cacggaggaa aaag 44

<210> SEQ ID NO 497
<211> LENGTH: 45
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (16)..(17)
<223> OTHER INFORMATION: n is a, c, g, or t
<220> FEATURE:
<221> NAME/KEY: misc_feature
<222> LOCATION: (19)..(20)
<223> OTHER INFORMATION: n is a, c, g, or t
<220> FEATURE:
<221> NAME/KEY: misc_feature
<222> LOCATION: (22)..(23)
<223> OTHER INFORMATION: n is a, c, g, or t

<400> SEQUENCE: 497
tccgtgggac cggagnngnn tnncatggcc cctggcgttt ctatt 45

<210> SEQ ID NO 498
<211> LENGTH: 46
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (17)..(18)
<223> OTHER INFORMATION: n is a, c, g, or t
<220> FEATURE:
<221> NAME/KEY: misc_feature
<222> LOCATION: (20)..(21)
<223> OTHER INFORMATION: n is a, c, g, or t
<220> FEATURE:
<221> NAME/KEY: misc_feature
<222> LOCATION: (23)..(24)
<223> OTHER INFORMATION: n is a, c, g, or t

<400> SEQUENCE: 498
aacgccaggg gccatgnnan ncnnctccgg tcccacggag gaaaaa 46

<210> SEQ ID NO 499
<211> LENGTH: 45
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (16)..(17)
<223> OTHER INFORMATION: n is a, c, g, or t
<220> FEATURE:
<221> NAME/KEY: misc_feature
<222> LOCATION: (19)..(20)
<223> OTHER INFORMATION: n is a, c, g, or t
<220> FEATURE:
<221> NAME/KEY: misc_feature
<222> LOCATION: (22)..(23)
<223> OTHER INFORMATION: n is a, c, g, or t

<400> SEQUENCE: 499
gtgggaccgg agctgnntnn cnnggcccct ggcgtttcta ttcaa 45

<210> SEQ ID NO 500
<211> LENGTH: 47
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (17)..(18)
<223> OTHER INFORMATION: n is a, c, g, or t
<220> FEATURE:
<221> NAME/KEY: misc_feature
<222> LOCATION: (20)..(21)
<223> OTHER INFORMATION: n is a, c, g, or t
<220> FEATURE:
<221> NAME/KEY: misc_feature
<222> LOCATION: (23)..(24)
<223> OTHER INFORMATION: n is a, c, g, or t

<400> SEQUENCE: 500
agaaacgcca ggggccnngn nanncagctc cggtcccacg gaggaaa 47

<210> SEQ ID NO 501
<211> LENGTH: 46
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (16)..(17)
<223> OTHER INFORMATION: n is a, c, g, or t
<220> FEATURE:
<221> NAME/KEY: misc_feature
<222> LOCATION: (19)..(20)
<223> OTHER INFORMATION: n is a, c, g, or t
<220> FEATURE:
<221> NAME/KEY: misc_feature
<222> LOCATION: (22)..(23)
<223> OTHER INFORMATION: n is a, c, g, or t

<400> SEQUENCE: 501
ggaccggagc tggatnncnn gnnccctggc gtttctattc aatcga 46

<210> SEQ ID NO 502
<211> LENGTH: 45
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (17)..(18)
<223> OTHER INFORMATION: n is a, c, g, or t
<220> FEATURE:
<221> NAME/KEY: misc_feature
<222> LOCATION: (20)..(21)
<223> OTHER INFORMATION: n is a, c, g, or t
<220> FEATURE:
<221> NAME/KEY: misc_feature
<222> LOCATION: (23)..(24)
<223> OTHER INFORMATION: n is a, c, g, or t

<400> SEQUENCE: 502
aatagaaacg ccagggnncn ngnnatccag ctccggtccc acgga 45

<210> SEQ ID NO 503
<211> LENGTH: 44
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (16)..(17)
<223> OTHER INFORMATION: n is a, c, g, or t
<220> FEATURE:
<221> NAME/KEY: misc_feature
<222> LOCATION: (19)..(20)
<223> OTHER INFORMATION: n is a, c, g, or t
<220> FEATURE:
<221> NAME/KEY: misc_feature
<222> LOCATION: (22)..(23)
<223> OTHER INFORMATION: n is a, c, g, or t

<400> SEQUENCE: 503
gtcatggccc ctggcnntnn tnntcaatcg acgcttccag ggaa 44

<210> SEQ ID NO 504
<211> LENGTH: 44
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (17)..(18)
<223> OTHER INFORMATION: n is a, c, g, or t
<220> FEATURE:
<221> NAME/KEY: misc_feature
<222> LOCATION: (20)..(21)
<223> OTHER INFORMATION: n is a, c, g, or t
<220> FEATURE:
<221> NAME/KEY: misc_feature
<222> LOCATION: (23)..(24)
<223> OTHER INFORMATION: n is a, c, g, or t

<400> SEQUENCE: 504
tggaagcgtc gattgannan nanngccagg ggccatgaca tcca 44

<210> SEQ ID NO 505
<211> LENGTH: 46

<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (16)..(17)
<223> OTHER INFORMATION: n is a, c, g, or t
<220> FEATURE:
<221> NAME/KEY: misc_feature
<222> LOCATION: (19)..(20)
<223> OTHER INFORMATION: n is a, c, g, or t
<220> FEATURE:
<221> NAME/KEY: misc_feature
<222> LOCATION: (22)..(23)
<223> OTHER INFORMATION: n is a, c, g, or t

<400> SEQUENCE: 505
attcaatcga cgcttnnann gnncaagtat ggtgcgcaaa acggga 46

<210> SEQ ID NO 506
<211> LENGTH: 46
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (17)..(18)
<223> OTHER INFORMATION: n is a, c, g, or t
<220> FEATURE:
<221> NAME/KEY: misc_feature
<222> LOCATION: (20)..(21)
<223> OTHER INFORMATION: n is a, c, g, or t
<220> FEATURE:
<221> NAME/KEY: misc_feature
<222> LOCATION: (23)..(24)
<223> OTHER INFORMATION: n is a, c, g, or t

<400> SEQUENCE: 506
ttgcgcacca tacttgnncn ntnnaagcgt cgattgaata gaaacg 46

<210> SEQ ID NO 507
<211> LENGTH: 45
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (16)..(17)
<223> OTHER INFORMATION: n is a, c, g, or t
<220> FEATURE:
<221> NAME/KEY: misc_feature
<222> LOCATION: (19)..(20)
<223> OTHER INFORMATION: n is a, c, g, or t
<220> FEATURE:
<221> NAME/KEY: misc_feature
<222> LOCATION: (22)..(23)
<223> OTHER INFORMATION: n is a, c, g, or t

<400> SEQUENCE: 507
caatcgacgc ttccanngnn cnngtatggt gcgcaaaacg ggact 45

<210> SEQ ID NO 508
<211> LENGTH: 46
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (17)..(18)

<223> OTHER INFORMATION: n is a, c, g, or t
<220> FEATURE:
<221> NAME/KEY: misc_feature
<222> LOCATION: (20)..(21)
<223> OTHER INFORMATION: n is a, c, g, or t
<220> FEATURE:
<221> NAME/KEY: misc_feature
<222> LOCATION: (23)..(24)
<223> OTHER INFORMATION: n is a, c, g, or t

<400> SEQUENCE: 508
gttttgcgca ccatacnngn ncnntggaag cgtcgattga atagaa 46

<210> SEQ ID NO 509
<211> LENGTH: 48
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (16)..(17)
<223> OTHER INFORMATION: n is a, c, g, or t
<220> FEATURE:
<221> NAME/KEY: misc_feature
<222> LOCATION: (19)..(20)
<223> OTHER INFORMATION: n is a, c, g, or t
<220> FEATURE:
<221> NAME/KEY: misc_feature
<222> LOCATION: (22)..(23)
<223> OTHER INFORMATION: n is a, c, g, or t

<400> SEQUENCE: 509
gggaacaagt atggtnngnn anncgggact tccatggcct cgccgcat 48

<210> SEQ ID NO 510
<211> LENGTH: 45
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (17)..(18)
<223> OTHER INFORMATION: n is a, c, g, or t
<220> FEATURE:
<221> NAME/KEY: misc_feature
<222> LOCATION: (20)..(21)
<223> OTHER INFORMATION: n is a, c, g, or t
<220> FEATURE:
<221> NAME/KEY: misc_feature
<222> LOCATION: (23)..(24)
<223> OTHER INFORMATION: n is a, c, g, or t

<400> SEQUENCE: 510
ggccatggaa gtcccgnntn ncnnaccata cttgttccct ggaag 45

<210> SEQ ID NO 511
<211> LENGTH: 45
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (16)..(17)
<223> OTHER INFORMATION: n is a, c, g, or t
<220> FEATURE:
<221> NAME/KEY: misc_feature
<222> LOCATION: (19)..(20)
<223> OTHER INFORMATION: n is a, c, g, or t
<220> FEATURE:
<221> NAME/KEY: misc_feature
<222> LOCATION: (22)..(23)
<223> OTHER INFORMATION: n is a, c, g, or t

<400> SEQUENCE: 511
aacaagtatg gtgcgnnann cnngacttcc atggcctcgc cgcat 45

<210> SEQ ID NO 512
<211> LENGTH: 44
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (17)..(18)
<223> OTHER INFORMATION: n is a, c, g, or t
<220> FEATURE:
<221> NAME/KEY: misc_feature
<222> LOCATION: (20)..(21)
<223> OTHER INFORMATION: n is a, c, g, or t
<220> FEATURE:
<221> NAME/KEY: misc_feature
<222> LOCATION: (23)..(24)
<223> OTHER INFORMATION: n is a, c, g, or t

<400> SEQUENCE: 512
cgaggccatg gaagtcnngn ntnncgcacc atacttgttc cctg 44

<210> SEQ ID NO 513
<211> LENGTH: 43
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (16)..(17)
<223> OTHER INFORMATION: n is a, c, g, or t
<220> FEATURE:
<221> NAME/KEY: misc_feature
<222> LOCATION: (19)..(20)
<223> OTHER INFORMATION: n is a, c, g, or t
<220> FEATURE:
<221> NAME/KEY: misc_feature
<222> LOCATION: (22)..(23)
<223> OTHER INFORMATION: n is a, c, g, or t

<400> SEQUENCE: 513
aagtatggtg cgcaanncnn gnnttccatg gcctcgccgc atg 43

<210> SEQ ID NO 514
<211> LENGTH: 45
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (17)..(18)
<223> OTHER INFORMATION: n is a, c, g, or t
<220> FEATURE:
<221> NAME/KEY: misc_feature
<222> LOCATION: (20)..(21)
<223> OTHER INFORMATION: n is a, c, g, or t
<220> FEATURE:
<221> NAME/KEY: misc_feature
<222> LOCATION: (23)..(24)
<223> OTHER INFORMATION: n is a, c, g, or t

<400> SEQUENCE: 514
cggcgaggcc atggaanncn ngnnttgcgc accatacttg ttccc 45

<210> SEQ ID NO 515
<211> LENGTH: 43
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (16)..(17)
<223> OTHER INFORMATION: n is a, c, g, or t
<220> FEATURE:
<221> NAME/KEY: misc_feature
<222> LOCATION: (19)..(20)
<223> OTHER INFORMATION: n is a, c, g, or t
<220> FEATURE:
<221> NAME/KEY: misc_feature
<222> LOCATION: (22)..(23)
<223> OTHER INFORMATION: n is a, c, g, or t

<400> SEQUENCE: 515
tatggtgcgc aaaacnngnn tnncatggcc tcgccgcatg tag 43

<210> SEQ ID NO 516
<211> LENGTH: 46
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (17)..(18)
<223> OTHER INFORMATION: n is a, c, g, or t
<220> FEATURE:
<221> NAME/KEY: misc_feature
<222> LOCATION: (20)..(21)
<223> OTHER INFORMATION: n is a, c, g, or t
<220> FEATURE:
<221> NAME/KEY: misc_feature
<222> LOCATION: (23)..(24)
<223> OTHER INFORMATION: n is a, c, g, or t

<400> SEQUENCE: 516
atgcggcgag gccatgnnan ncnngttttg cgcaccatac ttgttc 46

<210> SEQ ID NO 517
<211> LENGTH: 47
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (16)..(17)
<223> OTHER INFORMATION: n is a, c, g, or t
<220> FEATURE:
<221> NAME/KEY: misc_feature
<222> LOCATION: (19)..(20)
<223> OTHER INFORMATION: n is a, c, g, or t
<220> FEATURE:
<221> NAME/KEY: misc_feature
<222> LOCATION: (22)..(23)
<223> OTHER INFORMATION: n is a, c, g, or t

<400> SEQUENCE: 517
ccgcatgtag ctgggnngnn cnnattgatt ctttctaagc acccgaa 47

<210> SEQ ID NO 518
<211> LENGTH: 48
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (17)..(18)
<223> OTHER INFORMATION: n is a, c, g, or t
<220> FEATURE:
<221> NAME/KEY: misc_feature
<222> LOCATION: (20)..(21)
<223> OTHER INFORMATION: n is a, c, g, or t
<220> FEATURE:
<221> NAME/KEY: misc_feature
<222> LOCATION: (23)..(24)
<223> OTHER INFORMATION: n is a, c, g, or t

<400> SEQUENCE: 518
cttagaaaga atcaatnngn ncnncccagc tacatgcggc gaggccat 48

<210> SEQ ID NO 519
<211> LENGTH: 46
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (16)..(17)
<223> OTHER INFORMATION: n is a, c, g, or t
<220> FEATURE:
<221> NAME/KEY: misc_feature
<222> LOCATION: (19)..(20)
<223> OTHER INFORMATION: n is a, c, g, or t
<220> FEATURE:
<221> NAME/KEY: misc_feature
<222> LOCATION: (22)..(23)
<223> OTHER INFORMATION: n is a, c, g, or t

<400> SEQUENCE: 519
catgtagctg gggcgnncnn anngattctt tctaagcacc cgaact 46

<210> SEQ ID NO 520
<211> LENGTH: 51
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (17)..(18)
<223> OTHER INFORMATION: n is a, c, g, or t
<220> FEATURE:
<221> NAME/KEY: misc_feature
<222> LOCATION: (20)..(21)
<223> OTHER INFORMATION: n is a, c, g, or t
<220> FEATURE:
<221> NAME/KEY: misc_feature
<222> LOCATION: (23)..(24)
<223> OTHER INFORMATION: n is a, c, g, or t

<400> SEQUENCE: 520
gtgcttagaa agaatcnntn ngnncgcccc agctacatgc ggcgaggcca t 51

<210> SEQ ID NO 521
<211> LENGTH: 44
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (16)..(17)
<223> OTHER INFORMATION: n is a, c, g, or t
<220> FEATURE:
<221> NAME/KEY: misc_feature
<222> LOCATION: (19)..(20)

<223> OTHER INFORMATION: n is a, c, g, or t
<220> FEATURE:
<221> NAME/KEY: misc_feature
<222> LOCATION: (22)..(23)
<223> OTHER INFORMATION: n is a, c, g, or t

<400> SEQUENCE: 521
gtagctgggg cggccnnann gnntctttct aagcacccga actg         44

<210> SEQ ID NO 522
<211> LENGTH: 43
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (17)..(18)
<223> OTHER INFORMATION: n is a, c, g, or t
<220> FEATURE:
<221> NAME/KEY: misc_feature
<222> LOCATION: (20)..(21)
<223> OTHER INFORMATION: n is a, c, g, or t
<220> FEATURE:
<221> NAME/KEY: misc_feature
<222> LOCATION: (23)..(24)
<223> OTHER INFORMATION: n is a, c, g, or t

<400> SEQUENCE: 522
cgggtgctta gaaaganncn ntnnggccgc cccagctaca tgc          43

<210> SEQ ID NO 523
<211> LENGTH: 46
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (16)..(17)
<223> OTHER INFORMATION: n is a, c, g, or t
<220> FEATURE:
<221> NAME/KEY: misc_feature
<222> LOCATION: (19)..(20)
<223> OTHER INFORMATION: n is a, c, g, or t
<220> FEATURE:
<221> NAME/KEY: misc_feature
<222> LOCATION: (22)..(23)
<223> OTHER INFORMATION: n is a, c, g, or t

<400> SEQUENCE: 523
ttgattcttt ctaagnncnn gnnctggaca aacactcaag tccgca       46

<210> SEQ ID NO 524
<211> LENGTH: 45
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (17)..(18)
<223> OTHER INFORMATION: n is a, c, g, or t
<220> FEATURE:
<221> NAME/KEY: misc_feature
<222> LOCATION: (20)..(21)
<223> OTHER INFORMATION: n is a, c, g, or t
<220> FEATURE:
<221> NAME/KEY: misc_feature
<222> LOCATION: (23)..(24)
<223> OTHER INFORMATION: n is a, c, g, or t

<400> SEQUENCE: 524
ttgagtgttt gtccagnncn ngnncttaga aagaatcaat gcggc       45

<210> SEQ ID NO 525
<211> LENGTH: 45
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (16)..(17)
<223> OTHER INFORMATION: n is a, c, g, or t
<220> FEATURE:
<221> NAME/KEY: misc_feature
<222> LOCATION: (19)..(20)
<223> OTHER INFORMATION: n is a, c, g, or t
<220> FEATURE:
<221> NAME/KEY: misc_feature
<222> LOCATION: (22)..(23)
<223> OTHER INFORMATION: n is a, c, g, or t

<400> SEQUENCE: 525
ctttctaagc acccgnncnn gnnaaacact caagtccgca gcagt       45

<210> SEQ ID NO 526
<211> LENGTH: 46
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (17)..(18)
<223> OTHER INFORMATION: n is a, c, g, or t
<220> FEATURE:
<221> NAME/KEY: misc_feature
<222> LOCATION: (20)..(21)
<223> OTHER INFORMATION: n is a, c, g, or t
<220> FEATURE:
<221> NAME/KEY: misc_feature
<222> LOCATION: (23)..(24)
<223> OTHER INFORMATION: n is a, c, g, or t

<400> SEQUENCE: 526
gcggacttga gtgtttnncn ngnncgggtg cttagaaaga atcaat       46

<210> SEQ ID NO 527
<211> LENGTH: 48
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (16)..(17)
<223> OTHER INFORMATION: n is a, c, g, or t
<220> FEATURE:
<221> NAME/KEY: misc_feature
<222> LOCATION: (19)..(20)
<223> OTHER INFORMATION: n is a, c, g, or t
<220> FEATURE:
<221> NAME/KEY: misc_feature
<222> LOCATION: (22)..(23)
<223> OTHER INFORMATION: n is a, c, g, or t

<400> SEQUENCE: 527
tggacaaaca ctcaanncnn cnncagttta gaaaacacca ctacaaaa       48

<210> SEQ ID NO 528
<211> LENGTH: 47
<212> TYPE: DNA

<213> ORGANISM: Artificial Sequence
<220> FEATURE:
<223> OTHER INFORMATION: Primer
<220> FEATURE:
<221> NAME/KEY: misc_feature
<222> LOCATION: (17)..(18)
<223> OTHER INFORMATION: n is a, c, g, or t
<220> FEATURE:
<221> NAME/KEY: misc_feature
<222> LOCATION: (20)..(21)
<223> OTHER INFORMATION: n is a, c, g, or t
<220> FEATURE:
<221> NAME/KEY: misc_feature
<222> LOCATION: (23)..(24)
<223> OTHER INFORMATION: n is a, c, g, or t

<400> SEQUENCE: 528
ggtgttttct aaactgnngn ngnnttgagt gtttgtccag ttcgggt 47

<210> SEQ ID NO 529
<211> LENGTH: 47
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (16)..(17)
<223> OTHER INFORMATION: n is a, c, g, or t
<220> FEATURE:
<221> NAME/KEY: misc_feature
<222> LOCATION: (19)..(20)
<223> OTHER INFORMATION: n is a, c, g, or t
<220> FEATURE:
<221> NAME/KEY: misc_feature
<222> LOCATION: (22)..(23)
<223> OTHER INFORMATION: n is a, c, g, or t

<400> SEQUENCE: 529
ttagaaaaca ccactnnann anntggtgat tctttctact atggaaa 47

<210> SEQ ID NO 530
<211> LENGTH: 46
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (17)..(18)
<223> OTHER INFORMATION: n is a, c, g, or t
<220> FEATURE:
<221> NAME/KEY: misc_feature
<222> LOCATION: (20)..(21)
<223> OTHER INFORMATION: n is a, c, g, or t
<220> FEATURE:
<221> NAME/KEY: misc_feature
<222> LOCATION: (23)..(24)
<223> OTHER INFORMATION: n is a, c, g, or t

<400> SEQUENCE: 530
gtagaaagaa tcaccanntn ntnnagtggt gttttctaaa ctgctg 46

<210> SEQ ID NO 531
<211> LENGTH: 46
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (16)..(17)
<223> OTHER INFORMATION: n is a, c, g, or t
<220> FEATURE:
<221> NAME/KEY: misc_feature
<222> LOCATION: (19)..(20)
<223> OTHER INFORMATION: n is a, c, g, or t
<220> FEATURE:
<221> NAME/KEY: misc_feature
<222> LOCATION: (22)..(23)
<223> OTHER INFORMATION: n is a, c, g, or t

<400> SEQUENCE: 531
accactacaa aacttnntnn tnntttctac tatggaaaag ggctga 46

<210> SEQ ID NO 532
<211> LENGTH: 48
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (17)..(18)
<223> OTHER INFORMATION: n is a, c, g, or t
<220> FEATURE:
<221> NAME/KEY: misc_feature
<222> LOCATION: (20)..(21)
<223> OTHER INFORMATION: n is a, c, g, or t
<220> FEATURE:
<221> NAME/KEY: misc_feature
<222> LOCATION: (23)..(24)
<223> OTHER INFORMATION: n is a, c, g, or t

<400> SEQUENCE: 532
ttttccatag tagaaannan nannaagttt tgtagtggtg ttttctaa 48

<210> SEQ ID NO 533
<211> LENGTH: 45
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (16)..(17)
<223> OTHER INFORMATION: n is a, c, g, or t
<220> FEATURE:
<221> NAME/KEY: misc_feature
<222> LOCATION: (19)..(20)
<223> OTHER INFORMATION: n is a, c, g, or t
<220> FEATURE:
<221> NAME/KEY: misc_feature
<222> LOCATION: (22)..(23)
<223> OTHER INFORMATION: n is a, c, g, or t

<400> SEQUENCE: 533
gattctttct actatnnann anngctgatc aacgtacagg cggca 45

<210> SEQ ID NO 534
<211> LENGTH: 48
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (17)..(18)
<223> OTHER INFORMATION: n is a, c, g, or t
<220> FEATURE:
<221> NAME/KEY: misc_feature
<222> LOCATION: (20)..(21)
<223> OTHER INFORMATION: n is a, c, g, or t
<220> FEATURE:
<221> NAME/KEY: misc_feature
<222> LOCATION: (23)..(24)

<223> OTHER INFORMATION: n is a, c, g, or t

<400> SEQUENCE: 534
ctgtacgttg atcagcnntn ntnnatagta gaaagaatca ccaagttt 48

<210> SEQ ID NO 535
<211> LENGTH: 42
<212> TYPE: DNA
<213> ORGANISM: Artificial Sequence
<220> FEATURE:
<223> OTHER INFORMATION: Primer

<400> SEQUENCE: 535
tcaaggctac aatggagcaa atgttaaagt agcggttatc ga 42

<210> SEQ ID NO 536
<211> LENGTH: 38
<212> TYPE: DNA
<213> ORGANISM: Artificial Sequence
<220> FEATURE:
<223> OTHER INFORMATION: Primer

<400> SEQUENCE: 536
tttaacattt gctccattgt agccttgaga gtgcagag 38

<210> SEQ ID NO 537
<211> LENGTH: 38
<212> TYPE: DNA
<213> ORGANISM: Artificial Sequence
<220> FEATURE:
<223> OTHER INFORMATION: Primer

<400> SEQUENCE: 537
ctacactgga ggaggtgtta aagtagcggt tatcgaca 38

<210> SEQ ID NO 538
<211> LENGTH: 37
<212> TYPE: DNA
<213> ORGANISM: Artificial Sequence
<220> FEATURE:
<223> OTHER INFORMATION: Primer

<400> SEQUENCE: 538
ctactttaac acctcctcca gtgtagcctt gagagtg 37

<210> SEQ ID NO 539
<211> LENGTH: 40
<212> TYPE: DNA
<213> ORGANISM: Artificial Sequence
<220> FEATURE:
<223> OTHER INFORMATION: Primer

<400> SEQUENCE: 539
aggctacact ggaagaaatg ttaaagtagc ggttatcgac 40

<210> SEQ ID NO 540
<211> LENGTH: 34
<212> TYPE: DNA
<213> ORGANISM: Artificial Sequence
<220> FEATURE:
<223> OTHER INFORMATION: Primer

<400> SEQUENCE: 540
ctttaacatt tcttccagtg tagccttgag agtg 34

<210> SEQ ID NO 541
<211> LENGTH: 42
<212> TYPE: DNA
<213> ORGANISM: Artificial Sequence
<220> FEATURE:
<223> OTHER INFORMATION: Primer

<400> SEQUENCE: 541
aaggctacac tgcaggaggt gttaaagtag cggttatcga ca 42

<210> SEQ ID NO 542
<211> LENGTH: 40
<212> TYPE: DNA
<213> ORGANISM: Artificial Sequence
<220> FEATURE:
<223> OTHER INFORMATION: Primer

<400> SEQUENCE: 542
ctactttaac acctcctgca gtgtagcctt gagagtgcag 40

<210> SEQ ID NO 543
<211> LENGTH: 37
<212> TYPE: DNA
<213> ORGANISM: Artificial Sequence
<220> FEATURE:
<223> OTHER INFORMATION: Primer

<400> SEQUENCE: 543
cgtttcaaga tccctcttct catggcacac acgtcgc 37

<210> SEQ ID NO 544
<211> LENGTH: 40
<212> TYPE: DNA
<213> ORGANISM: Artificial Sequence
<220> FEATURE:
<223> OTHER INFORMATION: Primer

<400> SEQUENCE: 544
tgtgccatga gaagagggat cttgaaacgg gtttgtttcg 40

<210> SEQ ID NO 545
<211> LENGTH: 38
<212> TYPE: DNA
<213> ORGANISM: Artificial Sequence
<220> FEATURE:
<223> OTHER INFORMATION: Primer

<400> SEQUENCE: 545
tgccgtccga accaaacccg tttcaagata acaattct 38

<210> SEQ ID NO 546
<211> LENGTH: 37
<212> TYPE: DNA
<213> ORGANISM: Artificial Sequence
<220> FEATURE:
<223> OTHER INFORMATION: Primer

<400> SEQUENCE: 546
tcttgaaacg ggtttggttc ggacggcacc atagaag 37

<210> SEQ ID NO 547
<211> LENGTH: 40
<212> TYPE: DNA
<213> ORGANISM: Artificial Sequence
<220> FEATURE:
<223> OTHER INFORMATION: Primer

<400> SEQUENCE: 547
ccgtttcaag atcccaatca tcatggcaca cacgtcgcag 40

<210> SEQ ID NO 548
<211> LENGTH: 42
<212> TYPE: DNA
<213> ORGANISM: Artificial Sequence
<220> FEATURE:
<223> OTHER INFORMATION: Primer

<400> SEQUENCE: 548
tgtgtgccat gatgattggg atcttgaaac gggtttgttt cg 42

<210> SEQ ID NO 549
<211> LENGTH: 45
<212> TYPE: DNA
<213> ORGANISM: Artificial Sequence
<220> FEATURE:
<223> OTHER INFORMATION: Primer

<400> SEQUENCE: 549
acaaacccgt tttcagatcc caattctcat ggcacacacg tcgca 45

<210> SEQ ID NO 550
<211> LENGTH: 43
<212> TYPE: DNA
<213> ORGANISM: Artificial Sequence
<220> FEATURE:
<223> OTHER INFORMATION: Primer

<400> SEQUENCE: 550
ccatgagaat tgggatctga aaacgggttt gtttcggacg gca 43

<210> SEQ ID NO 551
<211> LENGTH: 38
<212> TYPE: DNA
<213> ORGANISM: Artificial Sequence
<220> FEATURE:
<223> OTHER INFORMATION: Primer

<400> SEQUENCE: 551
ggttgcggcg tcatacaatt ctattggcgt gcttggtg 38

<210> SEQ ID NO 552
<211> LENGTH: 38
<212> TYPE: DNA
<213> ORGANISM: Artificial Sequence
<220> FEATURE:
<223> OTHER INFORMATION: Primer

<400> SEQUENCE: 552
gccaatagaa ttgtatgacg ccgcaaccgt tcctgcga 38

<210> SEQ ID NO 553
<211> LENGTH: 40
<212> TYPE: DNA
<213> ORGANISM: Artificial Sequence
<220> FEATURE:
<223> OTHER INFORMATION: Primer

<400> SEQUENCE: 553
tggtgtagcc tcgggtgttt cgctctacgc cgttaaagtt 40

<210> SEQ ID NO 554
<211> LENGTH: 39

<212> TYPE: DNA
<213> ORGANISM: Artificial Sequence
<220> FEATURE:
<223> OTHER INFORMATION: Primer

<400> SEQUENCE: 554
cgtagagcga aacacccgag gctacaccaa gcacgccaa 39

<210> SEQ ID NO 555
<211> LENGTH: 42
<212> TYPE: DNA
<213> ORGANISM: Artificial Sequence
<220> FEATURE:
<223> OTHER INFORMATION: Primer

<400> SEQUENCE: 555
gtgtagcccc gggtgttgca ctctacgccg ttaaagttct tg 42

<210> SEQ ID NO 556
<211> LENGTH: 43
<212> TYPE: DNA
<213> ORGANISM: Artificial Sequence
<220> FEATURE:
<223> OTHER INFORMATION: Primer

<400> SEQUENCE: 556
acggcgtaga gtgcaacacc cggggctaca ccaagcacgc caa 43

<210> SEQ ID NO 557
<211> LENGTH: 44
<212> TYPE: DNA
<213> ORGANISM: Artificial Sequence
<220> FEATURE:
<223> OTHER INFORMATION: Primer

<400> SEQUENCE: 557
tggtgtagcc ccgactcttg gactctacgc cgttaaagtt cttg 44

<210> SEQ ID NO 558
<211> LENGTH: 43
<212> TYPE: DNA
<213> ORGANISM: Artificial Sequence
<220> FEATURE:
<223> OTHER INFORMATION: Primer

<400> SEQUENCE: 558
acggcgtaga gtccaagagt cggggctaca ccaagcacgc caa 43

<210> SEQ ID NO 559
<211> LENGTH: 41
<212> TYPE: DNA
<213> ORGANISM: Artificial Sequence
<220> FEATURE:
<223> OTHER INFORMATION: Primer

<400> SEQUENCE: 559
gcctgggagc acaaggctct agtgcggcac ttaaagcagc a 41

<210> SEQ ID NO 560
<211> LENGTH: 41
<212> TYPE: DNA
<213> ORGANISM: Artificial Sequence
<220> FEATURE:
<223> OTHER INFORMATION: Primer

<400> SEQUENCE: 560
agtgccgcac tagagccttg tgctcccagg ctcatgttga t 41

<210> SEQ ID NO 561
<211> LENGTH: 37
<212> TYPE: DNA
<213> ORGANISM: Artificial Sequence
<220> FEATURE:
<223> OTHER INFORMATION: Primer

<400> SEQUENCE: 561
atggcccctg gctattctat tcaatcgacg cttccag 37

<210> SEQ ID NO 562
<211> LENGTH: 36
<212> TYPE: DNA
<213> ORGANISM: Artificial Sequence
<220> FEATURE:
<223> OTHER INFORMATION: Primer

<400> SEQUENCE: 562
tcgattgaat agaatagcca ggggccatga catcca 36

<210> SEQ ID NO 563
<211> LENGTH: 42
<212> TYPE: DNA
<213> ORGANISM: Artificial Sequence
<220> FEATURE:
<223> OTHER INFORMATION: Primer

<400> SEQUENCE: 563
tcgacgcttc caaggtccgt gtatggtgcg caaaacggga ct 42

<210> SEQ ID NO 564
<211> LENGTH: 44
<212> TYPE: DNA
<213> ORGANISM: Artificial Sequence
<220> FEATURE:
<223> OTHER INFORMATION: Primer

<400> SEQUENCE: 564
ttgcgcacca tacacggacc ttggaagcgt cgattgaata gaaa 44

<210> SEQ ID NO 565
<211> LENGTH: 39
<212> TYPE: DNA
<213> ORGANISM: Artificial Sequence
<220> FEATURE:
<223> OTHER INFORMATION: Primer

<400> SEQUENCE: 565
catggcacac actgcggagg aacggttgcg gcgttaaac 39

<210> SEQ ID NO 566
<211> LENGTH: 39
<212> TYPE: DNA
<213> ORGANISM: Artificial Sequence
<220> FEATURE:
<223> OTHER INFORMATION: Primer

<400> SEQUENCE: 566
gcaaccgttc ctccgcagtg tgtgccatga gaattgtta 39

<210> SEQ ID NO 567
<211> LENGTH: 43
<212> TYPE: DNA
<213> ORGANISM: Artificial Sequence
<220> FEATURE:
<223> OTHER INFORMATION: Primer

<400> SEQUENCE: 567
gtcgcaggaa cgattggttc aaacaattct attggcgtgc ttg 43

<210> SEQ ID NO 568
<211> LENGTH: 45
<212> TYPE: DNA
<213> ORGANISM: Artificial Sequence
<220> FEATURE:
<223> OTHER INFORMATION: Primer

<400> SEQUENCE: 568
caatagaatt gtttgaacca atcgttcctg cgacgtgtgt gccat 45

<210> SEQ ID NO 569
<211> LENGTH: 41
<212> TYPE: DNA
<213> ORGANISM: Artificial Sequence
<220> FEATURE:
<223> OTHER INFORMATION: Primer

<400> SEQUENCE: 569
aacggttgcg gcgcatggaa attctattgg cgtgcttggt g 41

<210> SEQ ID NO 570
<211> LENGTH: 41
<212> TYPE: DNA
<213> ORGANISM: Artificial Sequence
<220> FEATURE:
<223> OTHER INFORMATION: Primer

<400> SEQUENCE: 570
caatagaatt tccatgcgcc gcaaccgttc ctgcgacgtg t 41

<210> SEQ ID NO 571
<211> LENGTH: 43
<212> TYPE: DNA
<213> ORGANISM: Artificial Sequence
<220> FEATURE:
<223> OTHER INFORMATION: Primer

<400> SEQUENCE: 571
aacggttgcg gcgagaggag gttctattgg cgtgcttggt gta 43

<210> SEQ ID NO 572
<211> LENGTH: 46
<212> TYPE: DNA
<213> ORGANISM: Artificial Sequence
<220> FEATURE:
<223> OTHER INFORMATION: Primer

<400> SEQUENCE: 572
cacgccaata gaacctcctc tcgccgcaac cgttcctgcg acgtgt 46

<210> SEQ ID NO 573
<211> LENGTH: 43
<212> TYPE: DNA
<213> ORGANISM: Artificial Sequence
<220> FEATURE:
<223> OTHER INFORMATION: Primer

<400> SEQUENCE: 573
aacggttgcg gcgggaggcg gttctattgg cgtgcttggt gta 43

<210> SEQ ID NO 574
<211> LENGTH: 46
<212> TYPE: DNA
<213> ORGANISM: Artificial Sequence
<220> FEATURE:
<223> OTHER INFORMATION: Primer

<400> SEQUENCE: 574
cacgccaata gaaccgcctc ccgccgcaac cgttcctgcg acgtgt 46

<210> SEQ ID NO 575
<211> LENGTH: 37
<212> TYPE: DNA
<213> ORGANISM: Artificial Sequence
<220> FEATURE:
<223> OTHER INFORMATION: Primer

<400> SEQUENCE: 575
tgcttcgctc tacggcgtta aagttcttgc agcagac 37

<210> SEQ ID NO 576
<211> LENGTH: 39
<212> TYPE: DNA
<213> ORGANISM: Artificial Sequence
<220> FEATURE:
<223> OTHER INFORMATION: Primer

<400> SEQUENCE: 576
caagaacttt aacgccgtag agcgaagcag acggggcta 39

<210> SEQ ID NO 577
<211> LENGTH: 43
<212> TYPE: DNA
<213> ORGANISM: Artificial Sequence
<220> FEATURE:
<223> OTHER INFORMATION: Primer

<400> SEQUENCE: 577
ttcgctctac gcctcatgtt ctgcagcaga cggatcaggc caa 43

<210> SEQ ID NO 578
<211> LENGTH: 42
<212> TYPE: DNA
<213> ORGANISM: Artificial Sequence
<220> FEATURE:
<223> OTHER INFORMATION: Primer

<400> SEQUENCE: 578
atccgtctgc tgcagaacat gaggcgtaga gcgaagcaga cg 42

<210> SEQ ID NO 579
<211> LENGTH: 41
<212> TYPE: DNA
<213> ORGANISM: Artificial Sequence
<220> FEATURE:
<223> OTHER INFORMATION: Primer

<400> SEQUENCE: 579
aataacatgg atatatcttg catgagcctg ggagcaccaa g 41

<210> SEQ ID NO 580
<211> LENGTH: 44
<212> TYPE: DNA
<213> ORGANISM: Artificial Sequence
<220> FEATURE:
<223> OTHER INFORMATION: Primer

<400> SEQUENCE: 580
caggctcatg caagatatat ccatgttatt cgcgatggcc catt 44

<210> SEQ ID NO 581
<211> LENGTH: 43
<212> TYPE: DNA
<213> ORGANISM: Artificial Sequence
<220> FEATURE:
<223> OTHER INFORMATION: Primer

<400> SEQUENCE: 581
cgaataacat ggatcttatc tgcatgagcc tgggagcacc aag 43

<210> SEQ ID NO 582
<211> LENGTH: 45
<212> TYPE: DNA
<213> ORGANISM: Artificial Sequence
<220> FEATURE:
<223> OTHER INFORMATION: Primer

<400> SEQUENCE: 582
ccaggctcat gcagataaga tccatgttat tcgcgatggc ccatt 45

<210> SEQ ID NO 583
<211> LENGTH: 44
<212> TYPE: DNA
<213> ORGANISM: Artificial Sequence
<220> FEATURE:
<223> OTHER INFORMATION: Primer

<400> SEQUENCE: 583
taacatggat gtatgctcat tgagcctggg agcaccaagc ggca 44

<210> SEQ ID NO 584
<211> LENGTH: 43
<212> TYPE: DNA
<213> ORGANISM: Artificial Sequence
<220> FEATURE:
<223> OTHER INFORMATION: Primer

<400> SEQUENCE: 584
tgctcccagg ctcaatgagc atacatccat gttattcgcg atg 43

<210> SEQ ID NO 585
<211> LENGTH: 37
<212> TYPE: DNA
<213> ORGANISM: Artificial Sequence
<220> FEATURE:
<223> OTHER INFORMATION: Primer

<400> SEQUENCE: 585
acatggatgt aatctgcatg agcctgggag caccaag 37

<210> SEQ ID NO 586
<211> LENGTH: 39
<212> TYPE: DNA
<213> ORGANISM: Artificial Sequence
<220> FEATURE:
<223> OTHER INFORMATION: Primer

<400> SEQUENCE: 586
tcccaggctc atgcagatta catccatgtt attcgcgat 39

<210> SEQ ID NO 587

<211> LENGTH: 38
<212> TYPE: DNA
<213> ORGANISM: Artificial Sequence
<220> FEATURE:
<223> OTHER INFORMATION: Primer

<400> SEQUENCE: 587
ggatgtaatc aacatcagcc tgggagcacc aagcggca 38

<210> SEQ ID NO 588
<211> LENGTH: 38
<212> TYPE: DNA
<213> ORGANISM: Artificial Sequence
<220> FEATURE:
<223> OTHER INFORMATION: Primer

<400> SEQUENCE: 588
tgctcccagg ctgatgttga ttacatccat gttattcg 38

<210> SEQ ID NO 589
<211> LENGTH: 38
<212> TYPE: DNA
<213> ORGANISM: Artificial Sequence
<220> FEATURE:
<223> OTHER INFORMATION: Primer

<400> SEQUENCE: 589
ggatgtaatc aacgtaagcc tgggagcacc aagcggca 38

<210> SEQ ID NO 590
<211> LENGTH: 38
<212> TYPE: DNA
<213> ORGANISM: Artificial Sequence
<220> FEATURE:
<223> OTHER INFORMATION: Primer

<400> SEQUENCE: 590
tgctcccagg cttacgttga ttacatccat gttattcg 38

<210> SEQ ID NO 591
<211> LENGTH: 41
<212> TYPE: DNA
<213> ORGANISM: Artificial Sequence
<220> FEATURE:
<223> OTHER INFORMATION: Primer

<400> SEQUENCE: 591
ggatgtaatc aacgtaagcg cgggagcacc aagcggcagt g 41

<210> SEQ ID NO 592
<211> LENGTH: 42
<212> TYPE: DNA
<213> ORGANISM: Artificial Sequence
<220> FEATURE:
<223> OTHER INFORMATION: Primer

<400> SEQUENCE: 592
ttggtgctcc cgcgcttacg ttgattacat ccatgttatt cg 42

<210> SEQ ID NO 593
<211> LENGTH: 42
<212> TYPE: DNA
<213> ORGANISM: Artificial Sequence
<220> FEATURE:
<223> OTHER INFORMATION: Primer

<400> SEQUENCE: 593
aatcaacatg agcttcggag caagcggcag tgcggcactt aa 42

<210> SEQ ID NO 594
<211> LENGTH: 42
<212> TYPE: DNA
<213> ORGANISM: Artificial Sequence
<220> FEATURE:
<223> OTHER INFORMATION: Primer

<400> SEQUENCE: 594
cactgccgct tgctccgaag ctcatgttga ttacatccat gt 42

<210> SEQ ID NO 595
<211> LENGTH: 40
<212> TYPE: DNA
<213> ORGANISM: Artificial Sequence
<220> FEATURE:
<223> OTHER INFORMATION: Primer

<400> SEQUENCE: 595
aacatgagcc tgtacgcacc aagcggcagt gcggcactta 40

<210> SEQ ID NO 596
<211> LENGTH: 41
<212> TYPE: DNA
<213> ORGANISM: Artificial Sequence
<220> FEATURE:
<223> OTHER INFORMATION: Primer

<400> SEQUENCE: 596
cactgccgct tggtgcgtac aggctcatgt tgattacatc c 41

<210> SEQ ID NO 597
<211> LENGTH: 43
<212> TYPE: DNA
<213> ORGANISM: Artificial Sequence
<220> FEATURE:
<223> OTHER INFORMATION: Primer

<400> SEQUENCE: 597
caacatgagc ctgtcagcag atagcggcag tgcggcactt aaa 43

<210> SEQ ID NO 598
<211> LENGTH: 42
<212> TYPE: DNA
<213> ORGANISM: Artificial Sequence
<220> FEATURE:
<223> OTHER INFORMATION: Primer

<400> SEQUENCE: 598
gcactgccgc tatctgctga caggctcatg ttgattacat cc 42

<210> SEQ ID NO 599
<211> LENGTH: 43
<212> TYPE: DNA
<213> ORGANISM: Artificial Sequence
<220> FEATURE:
<223> OTHER INFORMATION: Primer

<400> SEQUENCE: 599
caacatgagc ctgaacgcac gtagcggcag tgcggcactt aaa 43

<210> SEQ ID NO 600
<211> LENGTH: 42
<212> TYPE: DNA

<213> ORGANISM: Artificial Sequence
<220> FEATURE:
<223> OTHER INFORMATION: Primer

<400> SEQUENCE: 600
gcactgccgc tacgtgcgtt caggctcatg ttgattacat cc 42

<210> SEQ ID NO 601
<211> LENGTH: 42
<212> TYPE: DNA
<213> ORGANISM: Artificial Sequence
<220> FEATURE:
<223> OTHER INFORMATION: Primer

<400> SEQUENCE: 601
atgagcctgg gaaattcatc tagcggcagt gcggcactta aa 42

<210> SEQ ID NO 602
<211> LENGTH: 41
<212> TYPE: DNA
<213> ORGANISM: Artificial Sequence
<220> FEATURE:
<223> OTHER INFORMATION: Primer

<400> SEQUENCE: 602
gcactgccgc tagatgaatt tcccaggctc atgttgatta c 41

<210> SEQ ID NO 603
<211> LENGTH: 40
<212> TYPE: DNA
<213> ORGANISM: Artificial Sequence
<220> FEATURE:
<223> OTHER INFORMATION: Primer

<400> SEQUENCE: 603
catgagcctg ggatcagtta gcggcagtgc ggcacttaaa 40

<210> SEQ ID NO 604
<211> LENGTH: 38
<212> TYPE: DNA
<213> ORGANISM: Artificial Sequence
<220> FEATURE:
<223> OTHER INFORMATION: Primer

<400> SEQUENCE: 604
gcactgccgc taactgatcc caggctcatg ttgattac 38

<210> SEQ ID NO 605
<211> LENGTH: 40
<212> TYPE: DNA
<213> ORGANISM: Artificial Sequence
<220> FEATURE:
<223> OTHER INFORMATION: Primer

<400> SEQUENCE: 605
catgagcctg ggatcagata gcggcagtgc ggcacttaaa 40

<210> SEQ ID NO 606
<211> LENGTH: 38
<212> TYPE: DNA
<213> ORGANISM: Artificial Sequence
<220> FEATURE:
<223> OTHER INFORMATION: Primer

<400> SEQUENCE: 606
gcactgccgc tatctgatcc caggctcatg ttgattac 38

<210> SEQ ID NO 607
<211> LENGTH: 40
<212> TYPE: DNA
<213> ORGANISM: Artificial Sequence
<220> FEATURE:
<223> OTHER INFORMATION: Primer

<400> SEQUENCE: 607
catgagcctg ggatcaggta gcggcagtgc ggcacttaaa 40

<210> SEQ ID NO 608
<211> LENGTH: 38
<212> TYPE: DNA
<213> ORGANISM: Artificial Sequence
<220> FEATURE:
<223> OTHER INFORMATION: Primer

<400> SEQUENCE: 608
gcactgccgc tacctgatcc caggctcatg ttgattac 38

<210> SEQ ID NO 609
<211> LENGTH: 40
<212> TYPE: DNA
<213> ORGANISM: Artificial Sequence
<220> FEATURE:
<223> OTHER INFORMATION: Primer

<400> SEQUENCE: 609
catgagcctg ggacactata gcggcagtgc ggcacttaaa 40

<210> SEQ ID NO 610
<211> LENGTH: 38
<212> TYPE: DNA
<213> ORGANISM: Artificial Sequence
<220> FEATURE:
<223> OTHER INFORMATION: Primer

<400> SEQUENCE: 610
gcactgccgc tatagtgtcc caggctcatg ttgattac 38

<210> SEQ ID NO 611
<211> LENGTH: 36
<212> TYPE: DNA
<213> ORGANISM: Artificial Sequence
<220> FEATURE:
<223> OTHER INFORMATION: Primer

<400> SEQUENCE: 611
gagcctggga gcagacagcg gcagtgcggc acttaa 36

<210> SEQ ID NO 612
<211> LENGTH: 39
<212> TYPE: DNA
<213> ORGANISM: Artificial Sequence
<220> FEATURE:
<223> OTHER INFORMATION: Primer

<400> SEQUENCE: 612
tgccgcactg ccgctgtctg ctcccaggct catgttgat 39

<210> SEQ ID NO 613
<211> LENGTH: 36
<212> TYPE: DNA
<213> ORGANISM: Artificial Sequence
<220> FEATURE:

<223> OTHER INFORMATION: Primer

<400> SEQUENCE: 613
gagcctggga gcagaaagcg gcagtgcggc acttaa 36

<210> SEQ ID NO 614
<211> LENGTH: 39
<212> TYPE: DNA
<213> ORGANISM: Artificial Sequence
<220> FEATURE:
<223> OTHER INFORMATION: Primer

<400> SEQUENCE: 614
tgccgcactg ccgctttctg ctcccaggct catgttgat 39

<210> SEQ ID NO 615
<211> LENGTH: 36
<212> TYPE: DNA
<213> ORGANISM: Artificial Sequence
<220> FEATURE:
<223> OTHER INFORMATION: Primer

<400> SEQUENCE: 615
gagcctggga gcagtaagcg gcagtgcggc acttaa 36

<210> SEQ ID NO 616
<211> LENGTH: 39
<212> TYPE: DNA
<213> ORGANISM: Artificial Sequence
<220> FEATURE:
<223> OTHER INFORMATION: Primer

<400> SEQUENCE: 616
tgccgcactg ccgcttactg ctcccaggct catgttgat 39

<210> SEQ ID NO 617
<211> LENGTH: 36
<212> TYPE: DNA
<213> ORGANISM: Artificial Sequence
<220> FEATURE:
<223> OTHER INFORMATION: Primer

<400> SEQUENCE: 617
gagcctggga gcaggaggca gtgcggcact taaagc 36

<210> SEQ ID NO 618
<211> LENGTH: 38
<212> TYPE: DNA
<213> ORGANISM: Artificial Sequence
<220> FEATURE:
<223> OTHER INFORMATION: Primer

<400> SEQUENCE: 618
agtgccgcac tgcctcctgc tcccaggctc atgttgat 38

<210> SEQ ID NO 619
<211> LENGTH: 42
<212> TYPE: DNA
<213> ORGANISM: Artificial Sequence
<220> FEATURE:
<223> OTHER INFORMATION: Primer

<400> SEQUENCE: 619
agcctgggag cacacggcaa tgcggcactt aaagcagcag tt 42

<210> SEQ ID NO 620
<211> LENGTH: 42
<212> TYPE: DNA
<213> ORGANISM: Artificial Sequence
<220> FEATURE:
<223> OTHER INFORMATION: Primer

<400> SEQUENCE: 620
tttaagtgcc gcattgccgt gtgctcccag gctcatgttg at 42

<210> SEQ ID NO 621
<211> LENGTH: 38
<212> TYPE: DNA
<213> ORGANISM: Artificial Sequence
<220> FEATURE:
<223> OTHER INFORMATION: Primer

<400> SEQUENCE: 621
aagcggcagt gcgacactta aagcagcagt tgataaag 38

<210> SEQ ID NO 622
<211> LENGTH: 38
<212> TYPE: DNA
<213> ORGANISM: Artificial Sequence
<220> FEATURE:
<223> OTHER INFORMATION: Primer

<400> SEQUENCE: 622
aactgctgct ttaagtgtcg cactgccgct tggtgctc 38

<210> SEQ ID NO 623
<211> LENGTH: 41
<212> TYPE: DNA
<213> ORGANISM: Artificial Sequence
<220> FEATURE:
<223> OTHER INFORMATION: Primer

<400> SEQUENCE: 623
gttaaagttc ttcgtggttg tgacggatca ggccaatact c 41

<210> SEQ ID NO 624
<211> LENGTH: 41
<212> TYPE: DNA
<213> ORGANISM: Artificial Sequence
<220> FEATURE:
<223> OTHER INFORMATION: Primer

<400> SEQUENCE: 624
ctgatccgtc acaaccacga agaactttaa cggcgtagag c 41

<210> SEQ ID NO 625
<211> LENGTH: 40
<212> TYPE: DNA
<213> ORGANISM: Artificial Sequence
<220> FEATURE:
<223> OTHER INFORMATION: Primer

<400> SEQUENCE: 625
ttaaagttct tgcaggaggc ggatcaggcc aatactcatg 40

<210> SEQ ID NO 626
<211> LENGTH: 42
<212> TYPE: DNA
<213> ORGANISM: Artificial Sequence
<220> FEATURE:
<223> OTHER INFORMATION: Primer

<400> SEQUENCE: 626
tattggcctg atccgcctcc tgcaagaact ttaacggcgt ag 42

<210> SEQ ID NO 627
<211> LENGTH: 41
<212> TYPE: DNA
<213> ORGANISM: Artificial Sequence
<220> FEATURE:
<223> OTHER INFORMATION: Primer

<400> SEQUENCE: 627
ttaaagttct tgcaggacgt gacggatcag gccaatactc a 41

<210> SEQ ID NO 628
<211> LENGTH: 38
<212> TYPE: DNA
<213> ORGANISM: Artificial Sequence
<220> FEATURE:
<223> OTHER INFORMATION: Primer

<400> SEQUENCE: 628
ctgatccgtc acgtcctgca agaactttaa cggcgtag 38

<210> SEQ ID NO 629
<211> LENGTH: 40
<212> TYPE: DNA
<213> ORGANISM: Artificial Sequence
<220> FEATURE:
<223> OTHER INFORMATION: Primer

<400> SEQUENCE: 629
ttaaagttct tgcagacggc ggatcaggcc aatactcatg 40

<210> SEQ ID NO 630
<211> LENGTH: 42
<212> TYPE: DNA
<213> ORGANISM: Artificial Sequence
<220> FEATURE:
<223> OTHER INFORMATION: Primer

<400> SEQUENCE: 630
tattggcctg atccgccgtc tgcaagaact ttaacggcgt ag 42

<210> SEQ ID NO 631
<211> LENGTH: 45
<212> TYPE: DNA
<213> ORGANISM: Artificial Sequence
<220> FEATURE:
<223> OTHER INFORMATION: Primer

<400> SEQUENCE: 631
taaagttctt gcacatggag attcaggcca atactcatgg attat 45

<210> SEQ ID NO 632
<211> LENGTH: 44
<212> TYPE: DNA
<213> ORGANISM: Artificial Sequence
<220> FEATURE:
<223> OTHER INFORMATION: Primer

<400> SEQUENCE: 632
agtattggcc tgaatctcca tgtgcaagaa ctttaacggc gtag 44

<210> SEQ ID NO 633
<211> LENGTH: 40

<212> TYPE: DNA
<213> ORGANISM: Artificial Sequence
<220> FEATURE:
<223> OTHER INFORMATION: Primer

<400> SEQUENCE: 633
aagttcttgc agcacgtaac ggatcaggcc aatactcatg 40

<210> SEQ ID NO 634
<211> LENGTH: 44
<212> TYPE: DNA
<213> ORGANISM: Artificial Sequence
<220> FEATURE:
<223> OTHER INFORMATION: Primer

<400> SEQUENCE: 634
tattggcctg atccgttacg tgctgcaaga actttaacgg cgta 44

<210> SEQ ID NO 635
<211> LENGTH: 45
<212> TYPE: DNA
<213> ORGANISM: Artificial Sequence
<220> FEATURE:
<223> OTHER INFORMATION: Primer

<400> SEQUENCE: 635
agttcttgca gcagtaggag atggccaata ctcatggatt atcaa 45

<210> SEQ ID NO 636
<211> LENGTH: 45
<212> TYPE: DNA
<213> ORGANISM: Artificial Sequence
<220> FEATURE:
<223> OTHER INFORMATION: Primer

<400> SEQUENCE: 636
tgagtattgg ccatctccta ctgctgcaag aactttaacg gcgta 45

<210> SEQ ID NO 637
<211> LENGTH: 43
<212> TYPE: DNA
<213> ORGANISM: Artificial Sequence
<220> FEATURE:
<223> OTHER INFORMATION: Primer

<400> SEQUENCE: 637
ttaaagttct tgcagcatgt agcggatcag gccaatactc atg 43

<210> SEQ ID NO 638
<211> LENGTH: 44
<212> TYPE: DNA
<213> ORGANISM: Artificial Sequence
<220> FEATURE:
<223> OTHER INFORMATION: Primer

<400> SEQUENCE: 638
tattggcctg atccgctaca tgctgcaaga actttaacgg cgta 44

<210> SEQ ID NO 639
<211> LENGTH: 43
<212> TYPE: DNA
<213> ORGANISM: Artificial Sequence
<220> FEATURE:
<223> OTHER INFORMATION: Primer

<400> SEQUENCE: 639
aagttcttgc agcagactct tcaggccaat actcatggat tat 43

<210> SEQ ID NO 640
<211> LENGTH: 41
<212> TYPE: DNA
<213> ORGANISM: Artificial Sequence
<220> FEATURE:
<223> OTHER INFORMATION: Primer

<400> SEQUENCE: 640
atgagtattg gcctgaagag tctgctgcaa gaactttaac g 41

<210> SEQ ID NO 641
<211> LENGTH: 42
<212> TYPE: DNA
<213> ORGANISM: Artificial Sequence
<220> FEATURE:
<223> OTHER INFORMATION: Primer

<400> SEQUENCE: 641
ttcttgcagc agactctgta ggccaatact catggattat ca 42

<210> SEQ ID NO 642
<211> LENGTH: 42
<212> TYPE: DNA
<213> ORGANISM: Artificial Sequence
<220> FEATURE:
<223> OTHER INFORMATION: Primer

<400> SEQUENCE: 642
catgagtatt ggcctacaga gtctgctgca agaactttaa cg 42

<210> SEQ ID NO 643
<211> LENGTH: 43
<212> TYPE: DNA
<213> ORGANISM: Artificial Sequence
<220> FEATURE:
<223> OTHER INFORMATION: Primer

<400> SEQUENCE: 643
aagttcttgc agcagacgat tcaggccaat actcatggat tat 43

<210> SEQ ID NO 644
<211> LENGTH: 41
<212> TYPE: DNA
<213> ORGANISM: Artificial Sequence
<220> FEATURE:
<223> OTHER INFORMATION: Primer

<400> SEQUENCE: 644
atgagtattg gcctgaatcg tctgctgcaa gaactttaac g 41

<210> SEQ ID NO 645
<211> LENGTH: 43
<212> TYPE: DNA
<213> ORGANISM: Artificial Sequence
<220> FEATURE:
<223> OTHER INFORMATION: Primer

<400> SEQUENCE: 645
aagttcttgc agcagacaat tcaggccaat actcatggat tat 43

<210> SEQ ID NO 646
<211> LENGTH: 41
<212> TYPE: DNA
<213> ORGANISM: Artificial Sequence
<220> FEATURE:
<223> OTHER INFORMATION: Primer

<400> SEQUENCE: 646
atgagtattg gcctgaattg tctgctgcaa gaactttaac g 41

<210> SEQ ID NO 647
<211> LENGTH: 42
<212> TYPE: DNA
<213> ORGANISM: Artificial Sequence
<220> FEATURE:
<223> OTHER INFORMATION: Primer

<400> SEQUENCE: 647
ttcttgcagc agacaatcta ggccaatact catggattat ca 42

<210> SEQ ID NO 648
<211> LENGTH: 42
<212> TYPE: DNA
<213> ORGANISM: Artificial Sequence
<220> FEATURE:
<223> OTHER INFORMATION: Primer

<400> SEQUENCE: 648
catgagtatt ggcctagatt gtctgctgca agaactttaa cg 42

<210> SEQ ID NO 649
<211> LENGTH: 43
<212> TYPE: DNA
<213> ORGANISM: Artificial Sequence
<220> FEATURE:
<223> OTHER INFORMATION: Primer

<400> SEQUENCE: 649
ttcttgcagc agacggagga ggccaatact catggattat caa 43

<210> SEQ ID NO 650
<211> LENGTH: 38
<212> TYPE: DNA
<213> ORGANISM: Artificial Sequence
<220> FEATURE:
<223> OTHER INFORMATION: Primer

<400> SEQUENCE: 650
atgagtattg gcctcctccg tctgctgcaa gaacttta 38

<210> SEQ ID NO 651
<211> LENGTH: 43
<212> TYPE: DNA
<213> ORGANISM: Artificial Sequence
<220> FEATURE:
<223> OTHER INFORMATION: Primer

<400> SEQUENCE: 651
ttcttgcagc agacggagat ggccaatact catggattat caa 43

<210> SEQ ID NO 652
<211> LENGTH: 38
<212> TYPE: DNA
<213> ORGANISM: Artificial Sequence
<220> FEATURE:
<223> OTHER INFORMATION: Primer

<400> SEQUENCE: 652
atgagtattg gccatctccg tctgctgcaa gaacttta 38

<210> SEQ ID NO 653
<211> LENGTH: 45
<212> TYPE: DNA
<213> ORGANISM: Artificial Sequence
<220> FEATURE:
<223> OTHER INFORMATION: Primer

<400> SEQUENCE: 653
tgcagcagac ggagtaggca actactcatg gattatcaac ggcat 45

<210> SEQ ID NO 654
<211> LENGTH: 45
<212> TYPE: DNA
<213> ORGANISM: Artificial Sequence
<220> FEATURE:
<223> OTHER INFORMATION: Primer

<400> SEQUENCE: 654
ataatccatg agtagttgcc tactccgtct gctgcaagaa cttta 45

<210> SEQ ID NO 655
<211> LENGTH: 43
<212> TYPE: DNA
<213> ORGANISM: Artificial Sequence
<220> FEATURE:
<223> OTHER INFORMATION: Primer

<400> SEQUENCE: 655
ttcttgcagc agacggacgt ggccaatact catggattat caa 43

<210> SEQ ID NO 656
<211> LENGTH: 38
<212> TYPE: DNA
<213> ORGANISM: Artificial Sequence
<220> FEATURE:
<223> OTHER INFORMATION: Primer

<400> SEQUENCE: 656
atgagtattg gccacgtccg tctgctgcaa gaacttta 38

<210> SEQ ID NO 657
<211> LENGTH: 43
<212> TYPE: DNA
<213> ORGANISM: Artificial Sequence
<220> FEATURE:
<223> OTHER INFORMATION: Primer

<400> SEQUENCE: 657
aatgggccat ctctggtaga atggatgtaa tcaacatgag cct 43

<210> SEQ ID NO 658
<211> LENGTH: 42
<212> TYPE: DNA
<213> ORGANISM: Artificial Sequence
<220> FEATURE:
<223> OTHER INFORMATION: Primer

<400> SEQUENCE: 658
gattacatcc attctaccag agatggccca ttcgatgccg tt 42

<210> SEQ ID NO 659
<211> LENGTH: 40
<212> TYPE: DNA
<213> ORGANISM: Artificial Sequence
<220> FEATURE:
<223> OTHER INFORMATION: Primer

<400> SEQUENCE: 659
aatgggccat cggacgtaac atggatgtaa tcaacatgag 40

<210> SEQ ID NO 660
<211> LENGTH: 42
<212> TYPE: DNA
<213> ORGANISM: Artificial Sequence
<220> FEATURE:
<223> OTHER INFORMATION: Primer

<400> SEQUENCE: 660
gattacatcc atgttacgtc cgatggccca ttcgatgccg tt 42

<210> SEQ ID NO 661
<211> LENGTH: 43
<212> TYPE: DNA
<213> ORGANISM: Artificial Sequence
<220> FEATURE:
<223> OTHER INFORMATION: Primer

<400> SEQUENCE: 661
aatgggccat caattctgga atggatgtaa tcaacatgag cct 43

<210> SEQ ID NO 662
<211> LENGTH: 42
<212> TYPE: DNA
<213> ORGANISM: Artificial Sequence
<220> FEATURE:
<223> OTHER INFORMATION: Primer

<400> SEQUENCE: 662
gattacatcc attccagaat tgatggccca ttcgatgccg tt 42

<210> SEQ ID NO 663
<211> LENGTH: 36
<212> TYPE: DNA
<213> ORGANISM: Artificial Sequence
<220> FEATURE:
<223> OTHER INFORMATION: Primer

<400> SEQUENCE: 663
aaaacgggac ttcccaggcc tcgccgcatg tagctg 36

<210> SEQ ID NO 664
<211> LENGTH: 38
<212> TYPE: DNA
<213> ORGANISM: Artificial Sequence
<220> FEATURE:
<223> OTHER INFORMATION: Primer

<400> SEQUENCE: 664
tacatgcggc gaggcctggg aagtcccgtt ttgcgcac 38

<210> SEQ ID NO 665
<211> LENGTH: 40
<212> TYPE: DNA
<213> ORGANISM: Artificial Sequence
<220> FEATURE:
<223> OTHER INFORMATION: Primer

<400> SEQUENCE: 665
aaggctacac tggaagaaat gttaaagtag cggttatcga 40

<210> SEQ ID NO 666

<211> LENGTH: 37
<212> TYPE: DNA
<213> ORGANISM: Artificial Sequence
<220> FEATURE:
<223> OTHER INFORMATION: Primer

<400> SEQUENCE: 666
ctactttaac atttcttcca gtgtagcctt gagagtg 37

<210> SEQ ID NO 667
<211> LENGTH: 38
<212> TYPE: DNA
<213> ORGANISM: Artificial Sequence
<220> FEATURE:
<223> OTHER INFORMATION: Primer

<400> SEQUENCE: 667
ctacactgga tcatatgtta aagtagcggt tatcgaca 38

<210> SEQ ID NO 668
<211> LENGTH: 40
<212> TYPE: DNA
<213> ORGANISM: Artificial Sequence
<220> FEATURE:
<223> OTHER INFORMATION: Primer

<400> SEQUENCE: 668
taaccgctac tttaacatat gatccagtgt agccttgaga 40

<210> SEQ ID NO 669
<211> LENGTH: 36
<212> TYPE: DNA
<213> ORGANISM: Artificial Sequence
<220> FEATURE:
<223> OTHER INFORMATION: Primer

<400> SEQUENCE: 669
cttctatggt ggattccgaa acaaacccgt ttcaag 36

<210> SEQ ID NO 670
<211> LENGTH: 36
<212> TYPE: DNA
<213> ORGANISM: Artificial Sequence
<220> FEATURE:
<223> OTHER INFORMATION: Primer

<400> SEQUENCE: 670
ggtttgtttc ggaatccacc atagaagccc ctccag 36

<210> SEQ ID NO 671
<211> LENGTH: 39
<212> TYPE: DNA
<213> ORGANISM: Artificial Sequence
<220> FEATURE:
<223> OTHER INFORMATION: Primer

<400> SEQUENCE: 671
tttcaagata acaatacaca tggcacacac gtcgcagga 39

<210> SEQ ID NO 672
<211> LENGTH: 38
<212> TYPE: DNA
<213> ORGANISM: Artificial Sequence
<220> FEATURE:
<223> OTHER INFORMATION: Primer

<400> SEQUENCE: 672
tgtgtgccat gtgtattgtt atcttgaaac gggtttgt 38

<210> SEQ ID NO 673
<211> LENGTH: 34
<212> TYPE: DNA
<213> ORGANISM: Artificial Sequence
<220> FEATURE:
<223> OTHER INFORMATION: Primer

<400> SEQUENCE: 673
gtttcaagat gaaaattctc atggcacaca cgtc 34

<210> SEQ ID NO 674
<211> LENGTH: 40
<212> TYPE: DNA
<213> ORGANISM: Artificial Sequence
<220> FEATURE:
<223> OTHER INFORMATION: Primer

<400> SEQUENCE: 674
tgtgccatga gaattttcat cttgaaacgg gtttgtttcg 40

<210> SEQ ID NO 675
<211> LENGTH: 39
<212> TYPE: DNA
<213> ORGANISM: Artificial Sequence
<220> FEATURE:
<223> OTHER INFORMATION: Primer

<400> SEQUENCE: 675
aacccgtttc aagatccaaa ttctcatggc acacacgtc 39

<210> SEQ ID NO 676
<211> LENGTH: 38
<212> TYPE: DNA
<213> ORGANISM: Artificial Sequence
<220> FEATURE:
<223> OTHER INFORMATION: Primer

<400> SEQUENCE: 676
tgccatgaga atttggatct tgaaacgggt ttgtttcg 38

<210> SEQ ID NO 677
<211> LENGTH: 41
<212> TYPE: DNA
<213> ORGANISM: Artificial Sequence
<220> FEATURE:
<223> OTHER INFORMATION: Primer

<400> SEQUENCE: 677
gtttcaagat aaccaatctc atggcacaca cgtcgcagga a 41

<210> SEQ ID NO 678
<211> LENGTH: 40
<212> TYPE: DNA
<213> ORGANISM: Artificial Sequence
<220> FEATURE:
<223> OTHER INFORMATION: Primer

<400> SEQUENCE: 678
tgtgtgccat gagattggtt atcttgaaac gggtttgttt 40

<210> SEQ ID NO 679
<211> LENGTH: 41
<212> TYPE: DNA

<213> ORGANISM: Artificial Sequence
<220> FEATURE:
<223> OTHER INFORMATION: Primer

<400> SEQUENCE: 679
gtttcaagat aacgattctc atggcacaca cgtcgcagga a 41

<210> SEQ ID NO 680
<211> LENGTH: 40
<212> TYPE: DNA
<213> ORGANISM: Artificial Sequence
<220> FEATURE:
<223> OTHER INFORMATION: Primer

<400> SEQUENCE: 680
tgtgtgccat gagaatcgtt atcttgaaac gggtttgttt 40

<210> SEQ ID NO 681
<211> LENGTH: 36
<212> TYPE: DNA
<213> ORGANISM: Artificial Sequence
<220> FEATURE:
<223> OTHER INFORMATION: Primer

<400> SEQUENCE: 681
tcaagataac aatcaacatg gcacacacgt cgcagg 36

<210> SEQ ID NO 682
<211> LENGTH: 40
<212> TYPE: DNA
<213> ORGANISM: Artificial Sequence
<220> FEATURE:
<223> OTHER INFORMATION: Primer

<400> SEQUENCE: 682
acgtgtgtgc catgttgatt gttatcttga aacgggtttg 40

<210> SEQ ID NO 683
<211> LENGTH: 38
<212> TYPE: DNA
<213> ORGANISM: Artificial Sequence
<220> FEATURE:
<223> OTHER INFORMATION: Primer

<400> SEQUENCE: 683
tcatggcaca cacgcagcag gaacggttgc ggcgttaa 38

<210> SEQ ID NO 684
<211> LENGTH: 38
<212> TYPE: DNA
<213> ORGANISM: Artificial Sequence
<220> FEATURE:
<223> OTHER INFORMATION: Primer

<400> SEQUENCE: 684
caaccgttcc tgctgcgtgt gtgccatgag aattgtta 38

<210> SEQ ID NO 685
<211> LENGTH: 33
<212> TYPE: DNA
<213> ORGANISM: Artificial Sequence
<220> FEATURE:
<223> OTHER INFORMATION: Primer

<400> SEQUENCE: 685
tgtagccccg gatgcttcgc tctacgccgt taa 33

<210> SEQ ID NO 686
<211> LENGTH: 35
<212> TYPE: DNA
<213> ORGANISM: Artificial Sequence
<220> FEATURE:
<223> OTHER INFORMATION: Primer

<400> SEQUENCE: 686
cgtagagcga agcatccggg gctacaccaa gcacg 35

<210> SEQ ID NO 687
<211> LENGTH: 36
<212> TYPE: DNA
<213> ORGANISM: Artificial Sequence
<220> FEATURE:
<223> OTHER INFORMATION: Primer

<400> SEQUENCE: 687
cgttaaagtt acagcagcag acggatcagg ccaata 36

<210> SEQ ID NO 688
<211> LENGTH: 40
<212> TYPE: DNA
<213> ORGANISM: Artificial Sequence
<220> FEATURE:
<223> OTHER INFORMATION: Primer

<400> SEQUENCE: 688
tgatccgtct gctgctgtaa ctttaacggc gtagagcgaa 40

<210> SEQ ID NO 689
<211> LENGTH: 36
<212> TYPE: DNA
<213> ORGANISM: Artificial Sequence
<220> FEATURE:
<223> OTHER INFORMATION: Primer

<400> SEQUENCE: 689
taatcaacat gagcgcggga gcaccaagcg gcagtg 36

<210> SEQ ID NO 690
<211> LENGTH: 35
<212> TYPE: DNA
<213> ORGANISM: Artificial Sequence
<220> FEATURE:
<223> OTHER INFORMATION: Primer

<400> SEQUENCE: 690
ttggtgctcc cgcgctcatg ttgattacat ccatg 35

<210> SEQ ID NO 691
<211> LENGTH: 36
<212> TYPE: DNA
<213> ORGANISM: Artificial Sequence
<220> FEATURE:
<223> OTHER INFORMATION: Primer

<400> SEQUENCE: 691
taatcaacat gagcacggga gcaccaagcg gcagtg 36

<210> SEQ ID NO 692
<211> LENGTH: 35
<212> TYPE: DNA
<213> ORGANISM: Artificial Sequence
<220> FEATURE:

<223> OTHER INFORMATION: Primer

<400> SEQUENCE: 692
ttggtgctcc cgtgctcatg ttgattacat ccatg                      35

<210> SEQ ID NO 693
<211> LENGTH: 38
<212> TYPE: DNA
<213> ORGANISM: Artificial Sequence
<220> FEATURE:
<223> OTHER INFORMATION: Primer

<400> SEQUENCE: 693
atgtaatcaa catggcactg ggagcaccaa gcggcagt                   38

<210> SEQ ID NO 694
<211> LENGTH: 40
<212> TYPE: DNA
<213> ORGANISM: Artificial Sequence
<220> FEATURE:
<223> OTHER INFORMATION: Primer

<400> SEQUENCE: 694
ttggtgctcc cagtgccatg ttgattacat ccatgttatt                 40

<210> SEQ ID NO 695
<211> LENGTH: 34
<212> TYPE: DNA
<213> ORGANISM: Artificial Sequence
<220> FEATURE:
<223> OTHER INFORMATION: Primer

<400> SEQUENCE: 695
tgggagcacc accaggcagt gcggcactta aagc                       34

<210> SEQ ID NO 696
<211> LENGTH: 36
<212> TYPE: DNA
<213> ORGANISM: Artificial Sequence
<220> FEATURE:
<223> OTHER INFORMATION: Primer

<400> SEQUENCE: 696
gtgccgcact gcctggtggt gctcccaggc tcatgt                     36

<210> SEQ ID NO 697
<211> LENGTH: 37
<212> TYPE: DNA
<213> ORGANISM: Artificial Sequence
<220> FEATURE:
<223> OTHER INFORMATION: Primer

<400> SEQUENCE: 697
tgagcctggg agcacttagc ggcagtgcgg cacttaa                    37

<210> SEQ ID NO 698
<211> LENGTH: 39
<212> TYPE: DNA
<213> ORGANISM: Artificial Sequence
<220> FEATURE:
<223> OTHER INFORMATION: Primer

<400> SEQUENCE: 698
tgccgcactg ccgctaagtg ctcccaggct catgttgat                  39

<210> SEQ ID NO 699
<211> LENGTH: 37
<212> TYPE: DNA
<213> ORGANISM: Artificial Sequence
<220> FEATURE:
<223> OTHER INFORMATION: Primer

<400> SEQUENCE: 699
tgagcctggg agcagaaagc ggcagtgcgg cacttaa 37

<210> SEQ ID NO 700
<211> LENGTH: 39
<212> TYPE: DNA
<213> ORGANISM: Artificial Sequence
<220> FEATURE:
<223> OTHER INFORMATION: Primer

<400> SEQUENCE: 700
tgccgcactg ccgctttctg ctcccaggct catgttgat 39

<210> SEQ ID NO 701
<211> LENGTH: 37
<212> TYPE: DNA
<213> ORGANISM: Artificial Sequence
<220> FEATURE:
<223> OTHER INFORMATION: Primer

<400> SEQUENCE: 701
tgagcctggg agcatctagc ggcagtgcgg cacttaa 37

<210> SEQ ID NO 702
<211> LENGTH: 39
<212> TYPE: DNA
<213> ORGANISM: Artificial Sequence
<220> FEATURE:
<223> OTHER INFORMATION: Primer

<400> SEQUENCE: 702
tgccgcactg ccgctagatg ctcccaggct catgttgat 39

<210> SEQ ID NO 703
<211> LENGTH: 35
<212> TYPE: DNA
<213> ORGANISM: Artificial Sequence
<220> FEATURE:
<223> OTHER INFORMATION: Primer

<400> SEQUENCE: 703
gactcgagcc atgaagatct taaagtcgct ggagg 35

<210> SEQ ID NO 704
<211> LENGTH: 36
<212> TYPE: DNA
<213> ORGANISM: Artificial Sequence
<220> FEATURE:
<223> OTHER INFORMATION: Primer

<400> SEQUENCE: 704
gactttaaga tcttcatggc tcgagtcgat accgct 36

<210> SEQ ID NO 705
<211> LENGTH: 40
<212> TYPE: DNA
<213> ORGANISM: Artificial Sequence
<220> FEATURE:
<223> OTHER INFORMATION: Primer

<400> SEQUENCE: 705
gcagtccgtg cctcaaggcg tatcacaaat taaagcccct 40

<210> SEQ ID NO 706
<211> LENGTH: 40
<212> TYPE: DNA
<213> ORGANISM: Artificial Sequence
<220> FEATURE:
<223> OTHER INFORMATION: Primer

<400> SEQUENCE: 706
atttgtgata cgccttgagg cacggactgc gcgtacgcat 40

<210> SEQ ID NO 707
<211> LENGTH: 40
<212> TYPE: DNA
<213> ORGANISM: Artificial Sequence
<220> FEATURE:
<223> OTHER INFORMATION: Primer

<400> SEQUENCE: 707
cagacggatc agcacaatac tcatggatta tcaacggcat 40

<210> SEQ ID NO 708
<211> LENGTH: 40
<212> TYPE: DNA
<213> ORGANISM: Artificial Sequence
<220> FEATURE:
<223> OTHER INFORMATION: Primer

<400> SEQUENCE: 708
taatccatga gtattgtgct gatccgtctg ctgcaagaac 40

<210> SEQ ID NO 709
<211> LENGTH: 38
<212> TYPE: DNA
<213> ORGANISM: Artificial Sequence
<220> FEATURE:
<223> OTHER INFORMATION: Primer

<400> SEQUENCE: 709
gcagcagacg gaaacggcca atactcatgg attatcaa 38

<210> SEQ ID NO 710
<211> LENGTH: 39
<212> TYPE: DNA
<213> ORGANISM: Artificial Sequence
<220> FEATURE:
<223> OTHER INFORMATION: Primer

<400> SEQUENCE: 710
catgagtatt ggccgtttcc gtctgctgca agaacttta 39

<210> SEQ ID NO 711
<211> LENGTH: 40
<212> TYPE: DNA
<213> ORGANISM: Artificial Sequence
<220> FEATURE:
<223> OTHER INFORMATION: Primer

<400> SEQUENCE: 711
ttcttgcagc agacgaatca ggccaatact catggattat 40

<210> SEQ ID NO 712
<211> LENGTH: 40

<212> TYPE: DNA
<213> ORGANISM: Artificial Sequence
<220> FEATURE:
<223> OTHER INFORMATION: Primer

<400> SEQUENCE: 712
tgagtattgg cctgattcgt ctgctgcaag aactttaacg 40

<210> SEQ ID NO 713
<211> LENGTH: 38
<212> TYPE: DNA
<213> ORGANISM: Artificial Sequence
<220> FEATURE:
<223> OTHER INFORMATION: Primer

<400> SEQUENCE: 713
atcgaatggg ccgtagcgaa taacatggat gtaatcaa 38

<210> SEQ ID NO 714
<211> LENGTH: 40
<212> TYPE: DNA
<213> ORGANISM: Artificial Sequence
<220> FEATURE:
<223> OTHER INFORMATION: Primer

<400> SEQUENCE: 714
catccatgtt attcgctacg gcccattcga tgccgttgat 40

<210> SEQ ID NO 715
<211> LENGTH: 38
<212> TYPE: DNA
<213> ORGANISM: Artificial Sequence
<220> FEATURE:
<223> OTHER INFORMATION: Primer

<400> SEQUENCE: 715
gttgataaag ctgttaaatc tggtgtcgtc gtagtagc 38

<210> SEQ ID NO 716
<211> LENGTH: 38
<212> TYPE: DNA
<213> ORGANISM: Artificial Sequence
<220> FEATURE:
<223> OTHER INFORMATION: Primer

<400> SEQUENCE: 716
gacgacacca gatttaacag ctttatcaac tgctgctt 38

<210> SEQ ID NO 717
<211> LENGTH: 39
<212> TYPE: DNA
<213> ORGANISM: Artificial Sequence
<220> FEATURE:
<223> OTHER INFORMATION: Primer

<400> SEQUENCE: 717
gataaagctg ttgcagatgg tgtcgtcgta gtagcggca 39

<210> SEQ ID NO 718
<211> LENGTH: 40
<212> TYPE: DNA
<213> ORGANISM: Artificial Sequence
<220> FEATURE:
<223> OTHER INFORMATION: Primer

<400> SEQUENCE: 718
tactacgacg acaccatctg caacagcttt atcaactgct 40

<210> SEQ ID NO 719
<211> LENGTH: 38
<212> TYPE: DNA
<213> ORGANISM: Artificial Sequence
<220> FEATURE:
<223> OTHER INFORMATION: Primer

<400> SEQUENCE: 719
aatgagggaa caaaaggatc atcgagtacc gtcggtta 38

<210> SEQ ID NO 720
<211> LENGTH: 40
<212> TYPE: DNA
<213> ORGANISM: Artificial Sequence
<220> FEATURE:
<223> OTHER INFORMATION: Primer

<400> SEQUENCE: 720
acggtactcg atgatccttt tgttccctca ttcccagctg 40

<210> SEQ ID NO 721
<211> LENGTH: 39
<212> TYPE: DNA
<213> ORGANISM: Artificial Sequence
<220> FEATURE:
<223> OTHER INFORMATION: Primer

<400> SEQUENCE: 721
aacatccgga tcaaaaagta ccgtcggtta tccaggcaa 39

<210> SEQ ID NO 722
<211> LENGTH: 39
<212> TYPE: DNA
<213> ORGANISM: Artificial Sequence
<220> FEATURE:
<223> OTHER INFORMATION: Primer

<400> SEQUENCE: 722
ataaccgacg gtactttttg atccggatgt tccctcatt 39

<210> SEQ ID NO 723
<211> LENGTH: 40
<212> TYPE: DNA
<213> ORGANISM: Artificial Sequence
<220> FEATURE:
<223> OTHER INFORMATION: Primer

<400> SEQUENCE: 723
tgttgcatct ggtccagtcg tagtagcggc agctgggaat 40

<210> SEQ ID NO 724
<211> LENGTH: 40
<212> TYPE: DNA
<213> ORGANISM: Artificial Sequence
<220> FEATURE:
<223> OTHER INFORMATION: Primer

<400> SEQUENCE: 724
tgccgctact acgactggac cagatgcaac agctttatca 40

<210> SEQ ID NO 725
<211> LENGTH: 38
<212> TYPE: DNA
<213> ORGANISM: Artificial Sequence
<220> FEATURE:
<223> OTHER INFORMATION: Primer

<400> SEQUENCE: 725
agggaacatc cggaccatcg agtaccgtcg gttatcca 38

<210> SEQ ID NO 726
<211> LENGTH: 40
<212> TYPE: DNA
<213> ORGANISM: Artificial Sequence
<220> FEATURE:
<223> OTHER INFORMATION: Primer

<400> SEQUENCE: 726
accgacggta ctcgatggtc cggatgttcc ctcattccca 40

<210> SEQ ID NO 727
<211> LENGTH: 40
<212> TYPE: DNA
<213> ORGANISM: Artificial Sequence
<220> FEATURE:
<223> OTHER INFORMATION: Primer

<400> SEQUENCE: 727
cttcaaatca acgtgactct ttttcctccg tgggaccgga 40

<210> SEQ ID NO 728
<211> LENGTH: 40
<212> TYPE: DNA
<213> ORGANISM: Artificial Sequence
<220> FEATURE:
<223> OTHER INFORMATION: Primer

<400> SEQUENCE: 728
acggaggaaa aagagtcacg ttgatttgaa gagtctacag 40

<210> SEQ ID NO 729
<211> LENGTH: 40
<212> TYPE: DNA
<213> ORGANISM: Artificial Sequence
<220> FEATURE:
<223> OTHER INFORMATION: Primer

<400> SEQUENCE: 729
tcaacgtgcc tctgattcct ccgtgggacc ggagctggat 40

<210> SEQ ID NO 730
<211> LENGTH: 37
<212> TYPE: DNA
<213> ORGANISM: Artificial Sequence
<220> FEATURE:
<223> OTHER INFORMATION: Primer

<400> SEQUENCE: 730
tcccacggag gaatcagagg cacgttgatt tgaagag 37

<210> SEQ ID NO 731
<211> LENGTH: 38
<212> TYPE: DNA
<213> ORGANISM: Artificial Sequence
<220> FEATURE:
<223> OTHER INFORMATION: Primer

<400> SEQUENCE: 731
tactatggaa aaggggtaat caacgtacag gcggcagc 38

<210> SEQ ID NO 732
<211> LENGTH: 38
<212> TYPE: DNA
<213> ORGANISM: Artificial Sequence
<220> FEATURE:
<223> OTHER INFORMATION: Primer

<400> SEQUENCE: 732
ctgtacgttg attacccctt ttccatagta gaaagaat 38

<210> SEQ ID NO 733
<211> LENGTH: 36
<212> TYPE: DNA
<213> ORGANISM: Artificial Sequence
<220> FEATURE:
<223> OTHER INFORMATION: Primer

<400> SEQUENCE: 733
tggcgtttct attgaatcga cgcttccagg gaacaa 36

<210> SEQ ID NO 734
<211> LENGTH: 37
<212> TYPE: DNA
<213> ORGANISM: Artificial Sequence
<220> FEATURE:
<223> OTHER INFORMATION: Primer

<400> SEQUENCE: 734
ctggaagcgt cgattcaata gaaacgccag gggccat 37

<210> SEQ ID NO 735
<211> LENGTH: 36
<212> TYPE: DNA
<213> ORGANISM: Artificial Sequence
<220> FEATURE:
<223> OTHER INFORMATION: Primer

<400> SEQUENCE: 735
cttccaggga acacatatgg tgcgcaaaac gggact 36

<210> SEQ ID NO 736
<211> LENGTH: 38
<212> TYPE: DNA
<213> ORGANISM: Artificial Sequence
<220> FEATURE:
<223> OTHER INFORMATION: Primer

<400> SEQUENCE: 736
gttttgcgca ccatatgtgt tccctggaag cgtcgatt 38

<210> SEQ ID NO 737
<211> LENGTH: 36
<212> TYPE: DNA
<213> ORGANISM: Artificial Sequence
<220> FEATURE:
<223> OTHER INFORMATION: Primer

<400> SEQUENCE: 737
cttccaggga acctttatgg tgcgcaaaac gggact 36

<210> SEQ ID NO 738
<211> LENGTH: 38
<212> TYPE: DNA
<213> ORGANISM: Artificial Sequence
<220> FEATURE:
<223> OTHER INFORMATION: Primer

<400> SEQUENCE: 738
gttttgcgca ccataaaggt tccctggaag cgtcgatt 38

<210> SEQ ID NO 739
<211> LENGTH: 40
<212> TYPE: DNA
<213> ORGANISM: Artificial Sequence
<220> FEATURE:
<223> OTHER INFORMATION: Primer

<400> SEQUENCE: 739
tttctactat ggaaacgggc tgatcaacgt acaggcggca 40

<210> SEQ ID NO 740
<211> LENGTH: 40
<212> TYPE: DNA
<213> ORGANISM: Artificial Sequence
<220> FEATURE:
<223> OTHER INFORMATION: Primer

<400> SEQUENCE: 740
acgttgatca gcccgtttcc atagtagaaa gaatcaccaa 40

<210> SEQ ID NO 741
<211> LENGTH: 39
<212> TYPE: DNA
<213> ORGANISM: Artificial Sequence
<220> FEATURE:
<223> OTHER INFORMATION: Primer

<400> SEQUENCE: 741
tttctaagca cccgaaatgg acaaacactc aagtccgca 39

<210> SEQ ID NO 742
<211> LENGTH: 38
<212> TYPE: DNA
<213> ORGANISM: Artificial Sequence
<220> FEATURE:
<223> OTHER INFORMATION: Primer

<400> SEQUENCE: 742
gagtgtttgt ccatttcggg tgcttagaaa gaatcaat 38

<210> SEQ ID NO 743
<211> LENGTH: 39
<212> TYPE: DNA
<213> ORGANISM: Artificial Sequence
<220> FEATURE:
<223> OTHER INFORMATION: Primer

<400> SEQUENCE: 743
ttctttctaa gcaccgtaac tggacaaaca ctcaagtcc 39

<210> SEQ ID NO 744
<211> LENGTH: 38
<212> TYPE: DNA
<213> ORGANISM: Artificial Sequence
<220> FEATURE:
<223> OTHER INFORMATION: Primer

<400> SEQUENCE: 744
tgtttgtcca gttacggtgc ttagaaagaa tcaatgcg 38

<210> SEQ ID NO 745

<211> LENGTH: 36
<212> TYPE: DNA
<213> ORGANISM: Artificial Sequence
<220> FEATURE:
<223> OTHER INFORMATION: Primer

<400> SEQUENCE: 745
cacccgaact ggcgtaacac tcaagtccgc agcagt 36

<210> SEQ ID NO 746
<211> LENGTH: 40
<212> TYPE: DNA
<213> ORGANISM: Artificial Sequence
<220> FEATURE:
<223> OTHER INFORMATION: Primer

<400> SEQUENCE: 746
tgcggacttg agtgttacgc cagttcgggt gcttagaaag 40

<210> SEQ ID NO 747
<211> LENGTH: 33
<212> TYPE: DNA
<213> ORGANISM: Artificial Sequence
<220> FEATURE:
<223> OTHER INFORMATION: Primer

<400> SEQUENCE: 747
cgtctgctta cctctacgcc gttaaagttc ttg 33

<210> SEQ ID NO 748
<211> LENGTH: 40
<212> TYPE: DNA
<213> ORGANISM: Artificial Sequence
<220> FEATURE:
<223> OTHER INFORMATION: Primer

<400> SEQUENCE: 748
actttaacgg cgtagaggta agcagacggg gctacaccaa 40

<210> SEQ ID NO 749
<211> LENGTH: 36
<212> TYPE: DNA
<213> ORGANISM: Artificial Sequence
<220> FEATURE:
<223> OTHER INFORMATION: Primer

<400> SEQUENCE: 749
agcctgggag cacaaagcgg cagtgcggca cttaaa 36

<210> SEQ ID NO 750
<211> LENGTH: 34
<212> TYPE: DNA
<213> ORGANISM: Artificial Sequence
<220> FEATURE:
<223> OTHER INFORMATION: Primer

<400> SEQUENCE: 750
cactgccgct ttgtgctccc aggctcatgt tgat 34

<210> SEQ ID NO 751
<211> LENGTH: 41
<212> TYPE: DNA
<213> ORGANISM: Artificial Sequence
<220> FEATURE:
<223> OTHER INFORMATION: Primer

<400> SEQUENCE: 751
ttcaatcgac gcttccaacg aacaagtatg gtgcgcaaaa c 41

<210> SEQ ID NO 752
<211> LENGTH: 39
<212> TYPE: DNA
<213> ORGANISM: Artificial Sequence
<220> FEATURE:
<223> OTHER INFORMATION: Primer

<400> SEQUENCE: 752
caccatactt gttcgttgga agcgtcgatt gaatagaaa 39

<210> SEQ ID NO 753
<211> LENGTH: 39
<212> TYPE: DNA
<213> ORGANISM: Artificial Sequence
<220> FEATURE:
<223> OTHER INFORMATION: Primer

<400> SEQUENCE: 753
tggattatca acggcgtaga atgggccatc gcgaataac 39

<210> SEQ ID NO 754
<211> LENGTH: 39
<212> TYPE: DNA
<213> ORGANISM: Artificial Sequence
<220> FEATURE:
<223> OTHER INFORMATION: Primer

<400> SEQUENCE: 754
cgatggccca ttctacgccg ttgataatcc atgagtatt 39

<210> SEQ ID NO 755
<211> LENGTH: 269
<212> TYPE: PRT
<213> ORGANISM: Bacillus lentus

<400> SEQUENCE: 755

Ala Gln Ser Val Pro Trp Gly Ile Ser Arg Val Gln Ala Pro Ala Ala
1 5 10 15

His Asn Arg Gly Leu Thr Gly Ser Gly Val Lys Val Ala Val Leu Asp
20 25 30

Thr Gly Ile Ser Thr His Pro Asp Leu Asn Ile Arg Gly Gly Ala Ser
35 40 45

Phe Val Pro Gly Glu Pro Ser Thr Gln Asp Gly Asn Gly His Gly Thr
50 55 60

His Val Ala Gly Thr Ile Ala Ala Leu Asn Asn Ser Ile Gly Val Leu
65 70 75 80

Gly Val Ala Pro Ser Ala Glu Leu Tyr Ala Val Lys Val Leu Gly Ala
85 90 95

Ser Gly Ser Gly Ser Val Ser Ser Ile Ala Gln Gly Leu Glu Trp Ala
100 105 110

Gly Asn Asn Gly Met His Val Ala Asn Leu Ser Leu Gly Ser Pro Ser
115 120 125

Pro Ser Ala Thr Leu Glu Gln Ala Val Asn Ser Ala Thr Ser Arg Gly
130 135 140

Val Leu Val Val Ala Ala Ser Gly Asn Ser Gly Ala Gly Ser Ile Ser
145 150 155 160

Tyr Pro Ala Arg Tyr Ala Asn Ala Met Ala Val Gly Ala Thr Asp Gln
165 170 175

```
Asn Asn Asn Arg Ala Ser Phe Ser Gln Tyr Gly Ala Gly Leu Asp Ile
            180                 185                 190

Val Ala Pro Gly Val Asn Val Gln Ser Thr Tyr Pro Gly Ser Thr Tyr
        195                 200                 205

Ala Ser Leu Asn Gly Thr Ser Met Ala Thr Pro His Val Ala Gly Ala
    210                 215                 220

Ala Ala Leu Val Lys Gln Lys Asn Pro Ser Trp Ser Asn Val Gln Ile
225                 230                 235                 240

Arg Asn His Leu Lys Asn Thr Ala Thr Ser Leu Gly Ser Thr Asn Leu
                245                 250                 255

Tyr Gly Ser Gly Leu Val Asn Ala Glu Ala Ala Thr Arg
            260                 265
```

<210> SEQ ID NO 756
<211> LENGTH: 1143
<212> TYPE: DNA
<213> ORGANISM: Bacillus lentus

<400> SEQUENCE: 756

```
gtgagaagca aaaaattgtg gatcgtcgcg tcgaccgcac tactcatttc tgttgctttc     60

agttcatcga tcgcatcggc tgctgaagaa gcaaaagaaa aatatttaat tggctttaat    120

gagcaggaag ctgtcagtga gtttgtagaa caagtagagg caaatgacga ggtcgccatt    180

ctctctgagg aagaggaagt cgaaattgaa ttgcttcatg aatttgaaac gattcctgtt    240

ttatccgttg agttaagccc agaagatgtg gacgcgcttg agctcgatcc agcgatttct    300

tatattgaag aggatgcaga agtaacgaca atggcgcaat cagtgccatg gggaattagc    360

cgtgtgcaag ccccagctgc ccataaccgt ggattgacag gttctggtgt aaaagttgct    420

gtcctcgata caggtatttc cactcatcca gacttaaata ttcgtggtgg cgctagcttt    480

gtaccagggg aaccatccac tcaagatggg aatgggcatg gcacgcatgt ggccgggacg    540

attgctgctt taaacaattc gattggcgtt cttggcgtag cgccgagcgc ggaactatac    600

gctgttaaag tattaggggc gagcggttca ggttcggtca gctcgattgc ccaaggattg    660

gaatgggcag ggaacaatgg catgcacgtt gctaatttga gtttaggaag cccttcgcca    720

agtgccacac ttgagcaagc tgttaatagc gcgacttcta gaggcgttct tgttgtagcg    780

gcatctggaa attcaggtgc aggctcaatc agctatccgg cccgttatgc gaacgcaatg    840

gcagtcggag ctactgacca aaacaacaac cgcgccagct tttcacagta tggcgcaggg    900

cttgacattg tcgcaccagg tgtaaacgtg cagagcacat acccaggttc aacgtatgcc    960

agcttaaacg gtacatcgat ggctactcct catgttgcag gtgcagcagc ccttgttaaa   1020

caaaagaacc catcttggtc caatgtacaa atccgcaatc atctaaagaa tacggcaacg   1080

agcttaggaa gcacgaactt gtatggaagc ggacttgtca atgcagaagc tgcaactcgt   1140

taa                                                                  1143
```

<210> SEQ ID NO 757
<211> LENGTH: 380
<212> TYPE: PRT
<213> ORGANISM: Artificial Sequence
<220> FEATURE:
<223> OTHER INFORMATION: Mutant of Bacillus lentus subtilisin

<400> SEQUENCE: 757

```
Val Arg Ser Lys Lys Leu Trp Ile Val Ala Ser Thr Ala Leu Leu Ile
1               5                   10                  15
```

```
Ser Val Ala Phe Ser Ser Ser Ile Ala Ser Ala Ala Glu Glu Ala Lys
            20                  25                  30

Glu Lys Tyr Leu Ile Gly Phe Asn Glu Gln Glu Ala Val Ser Glu Phe
        35                  40                  45

Val Glu Gln Val Glu Ala Asn Asp Glu Val Ala Ile Leu Ser Glu Glu
    50                  55                  60

Glu Glu Val Glu Ile Glu Leu Leu His Glu Phe Glu Thr Ile Pro Val
65                  70                  75                  80

Leu Ser Val Glu Leu Ser Pro Glu Asp Val Asp Ala Leu Glu Leu Asp
                85                  90                  95

Pro Ala Ile Ser Tyr Ile Glu Glu Asp Ala Glu Val Thr Thr Met Ala
            100                 105                 110

Gln Ser Val Pro Trp Gly Ile Ser Arg Val Gln Ala Pro Ala Ala His
        115                 120                 125

Asn Arg Gly Leu Thr Gly Ser Gly Val Lys Val Ala Val Leu Asp Thr
    130                 135                 140

Gly Ile Ser Thr His Pro Asp Leu Asn Ile Arg Gly Gly Ala Ser Phe
145                 150                 155                 160

Val Pro Gly Glu Pro Ser Thr Gln Asp Gly Asn Gly His Gly Thr His
                165                 170                 175

Val Ala Gly Thr Ile Ala Ala Leu Asn Asn Ser Ile Gly Val Leu Gly
            180                 185                 190

Val Ala Pro Ser Ala Glu Leu Tyr Ala Val Lys Val Leu Gly Ala Ser
        195                 200                 205

Gly Ser Gly Ser Val Ser Ser Ile Ala Gln Gly Leu Glu Trp Ala Gly
    210                 215                 220

Asn Asn Gly Met His Val Ala Asn Leu Ser Leu Gly Ser Pro Ser Pro
225                 230                 235                 240

Ser Ala Thr Leu Glu Gln Ala Val Asn Ser Ala Thr Ser Arg Gly Val
                245                 250                 255

Leu Val Val Ala Ala Ser Gly Asn Ser Gly Ala Gly Ser Ile Ser Tyr
            260                 265                 270

Pro Ala Arg Tyr Ala Asn Ala Met Ala Val Gly Ala Thr Asp Gln Asn
        275                 280                 285

Asn Asn Arg Ala Ser Phe Ser Gln Tyr Gly Ala Gly Leu Asp Ile Val
    290                 295                 300

Ala Pro Gly Val Asn Val Gln Ser Thr Tyr Pro Gly Ser Thr Tyr Ala
305                 310                 315                 320

Ser Leu Asn Gly Thr Ser Met Ala Thr Pro His Val Ala Gly Ala Ala
                325                 330                 335

Ala Leu Val Lys Gln Lys Asn Pro Ser Trp Ser Asn Val Gln Ile Arg
            340                 345                 350

Asn His Leu Lys Asn Thr Ala Thr Ser Leu Gly Ser Thr Asn Leu Tyr
        355                 360                 365

Gly Ser Gly Leu Val Asn Ala Glu Ala Ala Thr Arg
    370                 375                 380
```

<210> SEQ ID NO 758
<211> LENGTH: 27
<212> TYPE: DNA
<213> ORGANISM: Artificial Sequence
<220> FEATURE:
<223> OTHER INFORMATION: Primer

<400> SEQUENCE: 758
cgcgcttgag ctcgatccag cgatttc 27

<210> SEQ ID NO 759
<211> LENGTH: 25
<212> TYPE: DNA
<213> ORGANISM: Artificial Sequence
<220> FEATURE:
<223> OTHER INFORMATION: Primer

<400> SEQUENCE: 759
gtctccaagc tttaacgagt tgcag 25

<210> SEQ ID NO 760
<211> LENGTH: 30
<212> TYPE: DNA
<213> ORGANISM: Artificial Sequence
<220> FEATURE:
<223> OTHER INFORMATION: Primer

<400> SEQUENCE: 760
gcaattcaga tcttccttca ggttatgacc 30

<210> SEQ ID NO 761
<211> LENGTH: 30
<212> TYPE: DNA
<213> ORGANISM: Artificial Sequence
<220> FEATURE:
<223> OTHER INFORMATION: Primer

<400> SEQUENCE: 761
gcatcgaaga tctgattgct taactgcttc 30

<210> SEQ ID NO 762
<211> LENGTH: 1143
<212> TYPE: DNA
<213> ORGANISM: Artificial Sequence
<220> FEATURE:
<223> OTHER INFORMATION: Mutant of Bacillus lentus subtilisin

<400> SEQUENCE: 762
gtgagaagca aaaaattgtg gatcgtcgcg tcgaccgcac tactcatttc tgttgctttt 60
agttcatcga tcgcatcggc tgctgaagaa gcaaaagaaa aatatttaat tggctttaat 120
gagcaggaag ctgtcagtga gtttgtagaa caagtagagg caaatgacga ggtcgccatt 180
ctctctgagg aagaggaagt cgaaattgaa ttgcttcatg aatttgaaac gattcctgtt 240
ttatccgttg agttaagccc agaagatgtg gacgcgcttg aactcgatcc agcgatttct 300
tatattgaag aggatgcaga agtaacgaca atggcgcaat cagtgccatg gggaattagc 360
cgtgtgcaag ccccggctgc ccataaccgt ggattgacag gttctggtgt aaaagttgct 420
gtcctcgata caggtatttc cactcatcca gacttaaata ttcgtggtgg cgctagcttt 480
gtaccagggg aaccatccac tcaagatggg aatgggcatg gcacgcatgt ggccgggacg 540
attgctgctc taaacaattc gattggcgta cttggcgtag cgccgagcgc ggaactatac 600
gctgttaaag tattaggggc gagcggtggg ggcgccatca gctcgattgc ccaaggattg 660
gaatgggcag ggaacaatgg catgcacgtt gctaatttga gtttaggaag cccttcgcca 720
agtgccacac ttgagcaagc tgttaatagc gcgacttcta ggggcgttct tgttgtagcg 780
gcatctggaa attcgggtgc agactcaatc agctatccgg cccgttatgc gaacgcaatg 840
gcagtcggag ctactgacca aaacaacaac cgcgccagct tttcacagta tggcgcaggg 900

-continued

```
cttgacatcg tcgcaccagg tgtaaacgtg cagagcacat acccaggttc aacgtatgcc    960

agcttaaacg gtacatcgat ggctactcct catgttgcag gtgcagcagt ccttgttaaa   1020

cataagaacc catcttggtc caatgtacga atccgcgatc atctaaagaa aacggcaacg   1080

agcttaggaa gcacgaactt gtatggaagc ggacttgtca atgccgaagc tgcaactcgt   1140

taa                                                                 1143


<210> SEQ ID NO 763
<211> LENGTH: 380
<212> TYPE: PRT
<213> ORGANISM: Artificial Sequence
<220> FEATURE:
<223> OTHER INFORMATION: Mutant of Bacillus Lentus subtilisin

<400> SEQUENCE: 763

Val Arg Ser Lys Lys Leu Trp Ile Val Ala Ser Thr Ala Leu Leu Ile
1               5                   10                  15

Ser Val Ala Phe Ser Ser Ser Ile Ala Ser Ala Ala Glu Glu Ala Lys
            20                  25                  30

Glu Lys Tyr Leu Ile Gly Phe Asn Glu Gln Glu Ala Val Ser Glu Phe
        35                  40                  45

Val Glu Gln Val Glu Ala Asn Asp Glu Val Ala Ile Leu Ser Glu Glu
    50                  55                  60

Glu Glu Val Glu Ile Glu Leu Leu His Glu Phe Glu Thr Ile Pro Val
65                  70                  75                  80

Leu Ser Val Glu Leu Ser Pro Glu Asp Val Asp Ala Leu Glu Leu Asp
                85                  90                  95

Pro Ala Ile Ser Tyr Ile Glu Glu Asp Ala Glu Val Thr Thr Met Ala
            100                 105                 110

Gln Ser Val Pro Trp Gly Ile Ser Arg Val Gln Ala Pro Ala Ala His
        115                 120                 125

Asn Arg Gly Leu Thr Gly Ser Gly Val Lys Val Ala Val Leu Asp Thr
    130                 135                 140

Gly Ile Ser Thr His Pro Asp Leu Asn Ile Arg Gly Gly Ala Ser Phe
145                 150                 155                 160

Val Pro Gly Glu Pro Ser Thr Gln Asp Gly Asn Gly His Gly Thr His
                165                 170                 175

Val Ala Gly Thr Ile Ala Ala Leu Asn Asn Ser Ile Gly Val Leu Gly
            180                 185                 190

Val Ala Pro Ser Ala Glu Leu Tyr Ala Val Lys Val Leu Gly Ala Ser
        195                 200                 205

Gly Gly Gly Ala Ile Ser Ser Ile Ala Gln Gly Leu Glu Trp Ala Gly
    210                 215                 220

Asn Asn Gly Met His Val Ala Asn Leu Ser Leu Gly Ser Pro Ser Pro
225                 230                 235                 240

Ser Ala Thr Leu Glu Gln Ala Val Asn Ser Ala Thr Ser Arg Gly Val
                245                 250                 255

Leu Val Val Ala Ala Ser Gly Asn Ser Gly Ala Asp Ser Ile Ser Tyr
            260                 265                 270

Pro Ala Arg Tyr Ala Asn Ala Met Ala Val Gly Ala Thr Asp Gln Asn
        275                 280                 285

Asn Asn Arg Ala Ser Phe Ser Gln Tyr Gly Ala Gly Leu Asp Ile Val
    290                 295                 300

Ala Pro Gly Val Asn Val Gln Ser Thr Tyr Pro Gly Ser Thr Tyr Ala
305                 310                 315                 320
```

```
Ser Leu Asn Gly Thr Ser Met Ala Thr Pro His Val Ala Gly Ala Ala
                325                 330                 335

Val Leu Val Lys His Lys Asn Pro Ser Trp Ser Asn Val Arg Ile Arg
            340                 345                 350

Asp His Leu Lys Lys Thr Ala Thr Ser Leu Gly Ser Thr Asn Leu Tyr
        355                 360                 365

Gly Ser Gly Leu Val Asn Ala Glu Ala Ala Thr Arg
    370                 375                 380


<210> SEQ ID NO 764
<211> LENGTH: 1140
<212> TYPE: DNA
<213> ORGANISM: Artificial Sequence
<220> FEATURE:
<223> OTHER INFORMATION: Mutant of Bacillus Lentus subtilisisn

<400> SEQUENCE: 764

gtgagaagca aaaaattgtg gatcgtcgcg tcgaccgcac tactcatttc tgttgctttt     60

agttcatcga tcgcatcggc tgctgaagaa gcaaaagaaa aatatttaat tggctttaat    120

gagcaggaag ctgtcagtga gtttgtagaa caagtagagg caaatgacga ggtcgccatt    180

ctctctgagg aagaggaagt cgaaattgaa ttgcttcatg aatttgaaac gattcctgtt    240

ttatccgttg agttaagccc agaagatgtg gacgcgcttg aactcgatcc agcgatttct    300

tatattgaag aggatgcaga agtaacgaca atggcgcaat cagtgccatg gggaattagc    360

cgtgtgcaag ccccggctgc ccataaccgt ggattgacag gttctggtgt aaaagttgct    420

gtcctcgata caggtatttc cactcatcca gacttaaata ttcgtggtgg cgctagcttt    480

gtaccagggg aaccatccac tcaagatggg aatgggcatg gcacgcatgt ggccgggacg    540

attgctgctc taaacaattc gattggcgta cttggcgtag cgccgagcgc ggaactatac    600

gctgttaaag tattaggggc gagcggtggg ggcgccatca gctcgattgc ccaaggattg    660

gaatgggcag ggaacaatgg catgcacgtt gctaatttga gtttaggaag cccttcgcca    720

agtgccacac ttgagcaagc tgttaatagc gcgacttcta ggggcgttct tgttgtagcg    780

gcatctggaa attcgggtgc agactcaatc agctatccgg cccgttatgc gaacgcaatg    840

gcagtcggag ctactgacca aaacaacaac cgcgccagct ttcacagta tggcgcaggg    900

cttgacatcg tcgcaccagg tgtaaacgtg cagagcacat acccaggttc aacgtatgcc    960

agcttaaacg gtacatcgat ggctactcct catgttgcag gtgcagcagt ccttgttaaa   1020

caaaagaacc catcttggtc caatgtacga atccgcgatc atctaaagaa tacggcaacg   1080

agcttaggaa gcacgaactt gtatggaagc ggacttgtca atgccgaagc tgcaactcgt   1140


<210> SEQ ID NO 765
<211> LENGTH: 380
<212> TYPE: PRT
<213> ORGANISM: Artificial Sequence
<220> FEATURE:
<223> OTHER INFORMATION: Mutant of Bacillus lentus subtilisin

<400> SEQUENCE: 765

Val Arg Ser Lys Lys Leu Trp Ile Val Ala Ser Thr Ala Leu Leu Ile
1               5                   10                  15

Ser Val Ala Phe Ser Ser Ser Ile Ala Ser Ala Ala Glu Glu Ala Lys
            20                  25                  30

Glu Lys Tyr Leu Ile Gly Phe Asn Glu Gln Glu Ala Val Ser Glu Phe
        35                  40                  45
```

-continued

```
Val Glu Gln Val Glu Ala Asn Asp Glu Val Ala Ile Leu Ser Glu Glu
    50                  55                  60

Glu Glu Val Glu Ile Glu Leu Leu His Glu Phe Glu Thr Ile Pro Val
65                  70                  75                  80

Leu Ser Val Glu Leu Ser Pro Glu Asp Val Asp Ala Leu Glu Leu Asp
                85                  90                  95

Pro Ala Ile Ser Tyr Ile Glu Glu Asp Ala Glu Val Thr Thr Met Ala
            100                 105                 110

Gln Ser Val Pro Trp Gly Ile Ser Arg Val Gln Ala Pro Ala Ala His
        115                 120                 125

Asn Arg Gly Leu Thr Gly Ser Gly Val Lys Val Ala Val Leu Asp Thr
    130                 135                 140

Gly Ile Ser Thr His Pro Asp Leu Asn Ile Arg Gly Gly Ala Ser Phe
145                 150                 155                 160

Val Pro Gly Glu Pro Ser Thr Gln Asp Gly Asn Gly His Gly Thr His
                165                 170                 175

Val Ala Gly Thr Ile Ala Ala Leu Asn Asn Ser Ile Gly Val Leu Gly
            180                 185                 190

Val Ala Pro Ser Ala Glu Leu Tyr Ala Val Lys Val Leu Gly Ala Ser
        195                 200                 205

Gly Gly Gly Ala Ile Ser Ser Ile Ala Gln Gly Leu Glu Trp Ala Gly
    210                 215                 220

Asn Asn Gly Met His Val Ala Asn Leu Ser Leu Gly Ser Pro Ser Pro
225                 230                 235                 240

Ser Ala Thr Leu Glu Gln Ala Val Asn Ser Ala Thr Ser Arg Gly Val
                245                 250                 255

Leu Val Val Ala Ala Ser Gly Asn Ser Gly Ala Asp Ser Ile Ser Tyr
            260                 265                 270

Pro Ala Arg Tyr Ala Asn Ala Met Ala Val Gly Ala Thr Asp Gln Asn
        275                 280                 285

Asn Asn Arg Ala Ser Phe Ser Gln Tyr Gly Ala Gly Leu Asp Ile Val
    290                 295                 300

Ala Pro Gly Val Asn Val Gln Ser Thr Tyr Pro Gly Ser Thr Tyr Ala
305                 310                 315                 320

Ser Leu Asn Gly Thr Ser Met Ala Thr Pro His Val Ala Gly Ala Ala
                325                 330                 335

Val Leu Val Lys Gln Lys Asn Pro Ser Trp Ser Asn Val Arg Ile Arg
            340                 345                 350

Asp His Leu Lys Asn Thr Ala Thr Ser Leu Gly Ser Thr Asn Leu Tyr
        355                 360                 365

Gly Ser Gly Leu Val Asn Ala Glu Ala Ala Thr Arg
    370                 375                 380
```

FABRIC AND HOME CARE PRODUCTS COMPRISING COLD WATER PROTEASES

CROSS-REFERENCES TO RELATED APPLICATIONS

This application claims priority to and benefit of U.S. Provisional Patent Application No. 61/267,878, filed on Dec. 9, 2009, and U.S. Provisional Patent Application No. 61/392,175, filed on Oct. 12, 2010, the disclosure of each of which is incorporated herein by reference in its entirety for all purposes.

FIELD OF INVENTION

This invention relates to fabric and home care products comprising cold water proteases as well as methods of making and using such fabric and home care products.

BACKGROUND OF THE INVENTION

Detergent manufacturers incorporate proteases into their products to provide good cleaning of stains (such as blood). However, given the sustainability and consumer trends to lower wash temperatures it is proving increasingly difficult to deliver consumer acceptable benefits and there remains a need to improve the cleaning and freshness profile of these laundry detergent compositions. The Inventors have found that additionally incorporating certain cold water proteases into a fabric and home care products, for example, a laundry detergent composition that comprises a hueing agent, a cleaning polymer and/or a perfume capsule, improves the whiteness, whiteness perception, and/or freshness.

SUMMARY OF THE INVENTION

This invention relates to fabric and home care products comprising one or more cold water proteases and processes for making and using such products. Such compositions provide improved cleaning and freshness. Such cold water proteases may be derived from parent enzymes, including BPN' subtilisin and subtilisin derived from *Bacillus lentus*, by substitution, insertion and/or deletion of one or more of the parent enzymes' amino acids.

BRIEF DESCRIPTION OF THE DRAWINGS

FIG. 5 provides an alignment of the mature reference subtilisin proteases including: BPN' (SEQ ID NO:2) and GG36 (SEQ ID NO:755). Each amino acid position of each protease variant described herein, including each cold water protease variant, is numbered according to the numbering of the corresponding amino acid position in the amino acid sequence of *Bacillus amyloliquefaciens* subtilisin protease BPN' (SEQ ID NO:2), as shown in FIG. 5, as determined by alignment of the protease variant amino acid sequence with the *Bacillus amyloliquefaciens* subtilisin protease BPN' amino acid sequence. Thus, unless otherwise specified herein, substitution positions are given in relationship to BPN'.

DETAILED DESCRIPTION OF THE INVENTION

Definitions

Figure 1:
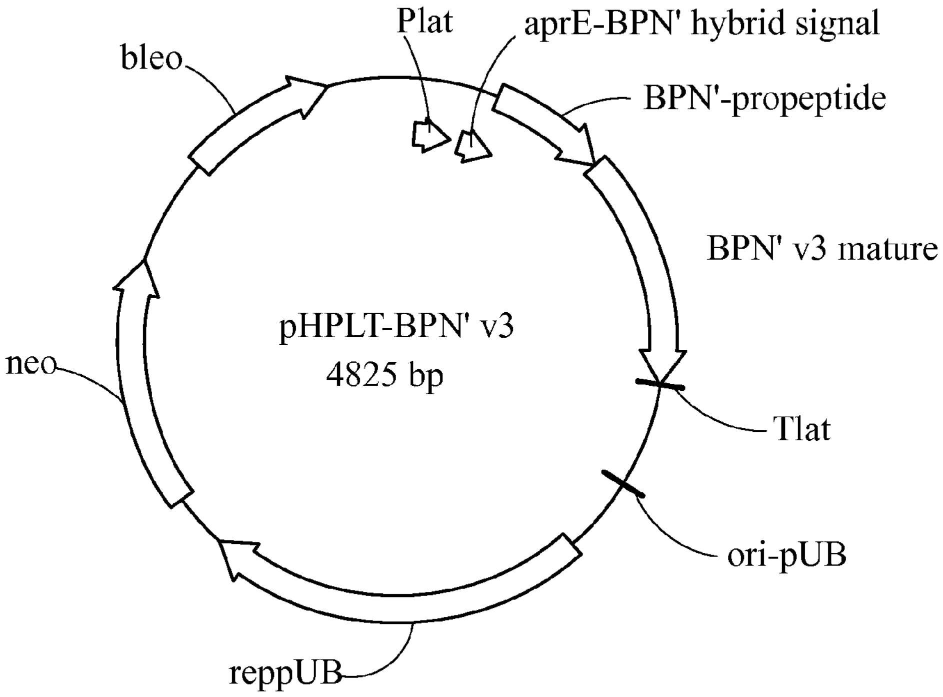
FIG. 1 provides a plasmid map of pHPLT-BPN'-v3.

As used herein "fabric and home products" means products or devices generally intended to be used or consumed in the form in which they are sold and that are for treating fabrics, hard surfaces and any other surfaces in the area of fabric and home care, including: air care including air fresheners and scent delivery systems, car care, dishwashing, fabric conditioning (including softening and/or freshening), laundry detergency, laundry and rinse additive and/or care, hard surface cleaning and/or treatment including floor and toilet bowl cleaners, and other cleaning for consumer or institutional use.

As used herein, the term "cleaning and/or treatment composition" is a subset of fabric and home care products that includes, unless otherwise indicated fabric & home care products. Such products include, but are not limited to, products for treating fabrics, hard surfaces and any other surfaces in the area of fabric and home care, including: air care including air fresheners and scent delivery systems, car care, dishwashing, fabric conditioning (including softening and/or freshening), laundry detergency, laundry and rinse additive and/or care, hard surface cleaning and/or treatment including floor and toilet bowl cleaners, granular or powder-form all-purpose or "heavy-duty" washing agents, especially cleaning detergents; liquid, gel or paste-form all-purpose washing agents, especially the so-called heavy-duty liquid types; liquid fine-fabric detergents; hand dishwashing agents or light duty dishwashing agents, especially those of the high-foaming type; machine dishwashing agents, including the various tablet, granular, liquid and rinse-aid types for household and institutional use: car or carpet shampoos, bathroom cleaners including toilet bowl cleaners; as well as cleaning auxiliaries such as bleach additives and "stain-stick" or pre-treat types, substrate-laden products such as dryer added sheets.

As used herein, the term "fabric and/or hard surface cleaning and/or treatment composition" is a subset of cleaning and treatment compositions that includes, unless otherwise indicated, granular or powder-form all-purpose or "heavy-duty" washing agents, especially cleaning detergents; liquid, gel or paste-form all-purpose washing agents, especially the so-called heavy-duty liquid types; liquid fine-fabric detergents; hand dishwashing agents or light duty dishwashing agents, especially those of the high-foaming type; machine dishwashing agents, including the various tablet, granular, liquid and rinse-aid types for household and institutional use; liquid cleaning and disinfecting agents, car or carpet shampoos, bathroom cleaners including toilet bowl cleaners; fabric conditioning products including softening and/or freshening that may be in liquid, solid and/or dryer sheet form; as well as cleaning auxiliaries such as bleach additives and "stain-stick" or pre-treat types, substrate-laden products such as dryer added sheets. All of such products which are applicable may be in standard, concentrated or even highly concentrated form even to the extent that such products may in certain aspect be non-aqueous.

As used herein, articles such as "a" and "an" when used in a claim, are understood to mean one or more of what is claimed or described.

As used herein, the terms "include", "includes" and "including" are meant to be non-limiting.

As used herein, the term “solid” includes granular, powder, bar and tablet product forms.

As used herein, the term “fluid” includes liquid, gel, paste and gas product forms.

As used herein, the term “situs” includes fabrics, garments, and/or hard surfaces.

Unless otherwise noted, all component or composition levels are in reference to the active portion of that component or composition, and are exclusive of impurities, for example, residual solvents or by-products, which may be present in commercially available sources of such components or compositions.

All percentages and ratios are calculated by weight unless otherwise indicated. All percentages and ratios are calculated based on the total composition unless otherwise indicated.

It should be understood that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

Fabric and Home Products Comprising One or More Proteases

A composition comprising a protease, said protease being selected from the group consisting of:

a) a cold water protease having a performance index greater than 1, at least 1.1, at least 1.2, at least 1.3, at least 1.4, at least 1.5, at least 1.6, at least 1.7, at least 1.8, at least 1.9, at least 2 from 1 to about 10, from 1 to about 8 or even from 1 to about 5 on BMI at pH 8 and 60° F. when compared to an enzyme having SEQ ID NO:4, as defined in Test Method 2 and/or Test Method 3;

b) a cold water protease having a performance index at least 1, at least 1.1, at least 1.2, at least 1.3, at least 1.4, at least 1.5, at least 1.6, at least 1.7, at least 1.8, at least 1.9, at least 2 from 1 to about 10, from 1 to about 8 or even from 1 to about 5 on BMI at pH 8 and 60° F. when compared to an enzyme having SEQ ID NO:6, as defined in Test Method 2 and/or Test Method 3;

c) a cold water protease, said cold water protease being selected from the group consisting of:

(i) a variant of a parent protease, said parent protease having at least 60%, or 80%, or 85% or 90% or 95% or 96% or 97% or 98% or 99% or even 100% identity to SEQ ID NO:4, said variant comprising a group of mutations selected from the following groups of mutations: P210S, P210S-N218A, S063T-S078N-S101A-S183T-T244N, N061A-S078N-S224A, S053G-S078N-P129T-Q185T, S063T-S078N-S101A, S078N-P129T, S063T-S078N-S101A-S183T and S063T-S078N-S101A-T244I;

(ii) a variant of a parent protease, said parent protease having at least 60%, or 80%, or 85% or 90% or 95% or 96% or 97% or 98% or 99% or even 100% identity to SEQ ID NO:2, said variant comprising a group of mutations selected from the following groups of mutations: G097A-I111V-M124V-Y217Q, G097A-I111V-Y167A-Y217Q, S024G-N025G-N061P-G097A-S101N-G128S-Y217Q, S024G-N025G-S053G-N061P-G097A-S101N-G128A-V203Y-Y217Q, S024G-N025G-S053G-T055P-N061P-G097A-S101N-G128S-V203Y-Y217Q, V068A-A092G-Y217Q, N061P-G097A-S101N-G128A-P210S-Y217Q, S024G-N025G-S053G-N061P-G097A-S101N-G128A-P210S-Y217Q, S024G-N025G-S053G-N061P-G097A-S101N-G128S-Y217Q, S024G-N025G-S053G-N061P-S078N-G097A-S101N-I111V-G128S-Y217Q, S024G-N025G-S053G-T055P-N061P-G097A-S101N-G128A-Y217Q, N025G-G097A-S101N-G128A-Y217Q, N025G-S038G-S053G-N061P-S078N-G097A-S101N-G128A-Y217Q, N025G-S053G-N061P-S078N-G128A-Y217Q, N025G-S053G-N061P-S078N-S101N-G128A-Y217Q, N025G-S053G-T055P-N061P-S078N-G097A-S101N-G128A-Y217Q, N025G-S053G-T055P-S078N-G097A-S101N-G128A-Y217Q, N025G-S078N-G097A-S101N-G128A-Y217Q, N025G-T055P-N061P-S078N-G097A-S101N-G128A-Y217Q, N025G-T055P-N061P-S078N-S101N-G128A-Y217Q, N061P-S101N-G128A-Y217Q, S024G-N025G-N061P-G097A-G128A-Y217Q, S024G-N025G-N061P-G097A-S101N-G128A-Y217Q, S024G-N025G-S053G-N061P-S078N-G097A-S101N-G128A-Y217Q, S024G-N025G-S053G-N061P-S078N-S101N-G128A-Y217Q, S024G-N025G-S053G-T055P-G097A-S101N-G128A-Y217Q, S024G-N025G-S053G-T055P-N061P-G128A-Y217Q, S024G-N025G-T055P-G097A-G128A-Y217Q, S024G-N025G-T055P-N061P-S078N-G097A-S101N-G128A-Y217Q, S024G-N061P-S078N-G097A-S101N-G128A-Y217Q, S024G-S053G-N061P-G097A-G128A-Y217Q, S024G-S053G-N061P-S078N-G097A-G128A-Y217Q, S024G-S053G-T055P-G097A-S101N-G128A-Y217Q, S024G-S053G-T055P-N061P-G097A-S101N-G128A-Y217Q, S024G-S053G-T055P-N061P-S078N-G097A-S101N-G128A-Y217Q, S024G-S053G-T055P-N061P-S101N-G128A-Y217Q, S024G-T055P-N061P-G097A-G128A-Y217Q, S053G-G097A-S101N-G128A-Y217Q, S053G-N061P-G097A-S101N-G128A-Y217Q-S249N, S053G-N061P-S078N-G097A-G128A-Y217Q, S053G-S078N-G097A-S101N-G128A-Y217Q, S053G-T055P-G097A-S101N-G128A-Y217Q, S053G-T055P-N061P-S101N-G128A-Y217Q, S053G-T055P-S078N-G097A-S101N-G128A-Y217Q, T055P-G097A-S101N-G128A-Y217Q, T055P-N061P-S078N-G097A-S101N-G128A-Y217Q, S024G-N025G-N061P-S078N-G097A-S101N-G128A-Y217Q, S024G-N025G-S053G-T055P-N061P-G097A-S101N-G128A-Y217Q, S024G-T055P-N061P-S078N-S101N-G128A-Y217Q, T055P-N061P-S078N-G128A-Y217Q and S24G-S53G-S78N-S101N-G128A-Y217Q;

(iii) a variant of a parent protease, said parent having at least 60%, or 80%, or 85% or 90% or 95% or 96% or 97% or 98% or 99% or even 100% identity to SEQ ID NO:2, said variant comprising three, four, five or six of the following mutations X24G/R, X53G, X78N, X101N, X128A/S and X217L/Q; said variant optionally comprising at least one group of mutations selected from the following groups of mutations:

A116V, G160S, I111L, I115V, N109S, N117M, P005G, Q059V, T164S, Y262M, A015Q, A015S, A098E, A098N, A098S, A098T, A098V, A098Y, A114S, A114T, A116G, A116L, A116S, A116T, A116W, A133G, A133H, A133T, A133V, A137G, A137I, A137L, A137S, A137T, A138S, A216E, A216F, A216V, D099S, D181E, F261A, F261Q, G024F, G024I, G024Q, G024Y, G097S,

G160T, G211L, G211V, H017F, H017W, H039V, H226A, I031V, I111V, I268V, K170R, K265R, L016Q, L016T, L135M, L209T, L209V, L233M, L257T, L257V, L267A, L267V, N025A, N025I, N025Q, N025R, N025T, N025V, N101I, N101Q, N101S, N109A, N109G, N109H, N109L, N109M, N109Q, N109T, N117Q, N184A, N184L, N184T, N184W, N212G, N212L, N212V, N243P, N252G, N252M, P005T, P014S, P040G, P040L, P040Q, P129A, P129S, P172G, P172S, P194Q, P210A, P210S, Q185F, Q185G, Q185I, Q185M, Q185N, Q185S, Q275H, R186K, S009A, S009G, S009H, S009M, S018T, S130T, S132N, S145K, S159T, S161I, S161K, S161N, S161T, S162I, S162M, S162Y, S163G, S182F, S182G, S182V, S182W, S183F, S183L, S183M, S183T, S183V, S183W, S224A, S236T, S249V, T022A, T022G, T022Q, T022V, T208V, T242S, T253N, T253S, T254A, T254S, T255L, T255S, T255V, V004A, V004P, V004W, V084C, V139C, V165M, V203F, Y021K, Y021N, Y021T, Y021V, Y167F, Y171F, Y214F, Y262F, Y262T, A088T-L257G, A116T-A128S, N061S-N109G-A128S-N243V-S260P, S009T-N109G-A128S-K141R-N243V, S009T-S018T-Y021N-N109G-A128S-K141R, S162G-K256R, A088T-N243V, G024E-A116T, K043Y, N076D-A116T, N218S-S248N, S033T-N243V, S033T-S063G, S248N-L257G, A001E-S249A, A088T-A116T, A088T-A128S, A088T-G131H, A088T-N109G, A088T-S248N, A088T-S249A, A116T-N243V, A116T-T158S, A128S, A128S-K256R, A128S-L257G, A128S-N243V, A128S-S248N, A128S-T158S, G024E-A088T, G024E-A128S, G024E-G131H, G024E-K256R, G024E-L257G, G024E-N218S, G024E-N243V, G024E-S162G, G024E-S249A, G024E-T158S, G131H, G131H-K256R, G131H-S249A, K043Y-A088T, K043Y-A116T, K256R, N076D-K256R, N109G, N109G-A116T, N109G-A128S, N109G-A128S-N243V-K256R, N109G-A128S-N243V-S248A, N109G-G131H, N109G-K256R, N109G-L257G, N109G-N218S, N109G-N243V, N109G-S248N, N218S-L257G, N243V, N243V-K256R, N243V-L257G, N243V-S248N, N243V-S249A, Q103H-A128S, Q103H-G131H, Q103H-K256R, Q103H-L257G, Q103H-N243V, Q103H-S248N, Q103H-S249A, Q103H-T158S, Q206D-N243V, S033T-A128S, S033T-K256R, S033T-N076D, S033T-N218S, S033T-S248N, S033T-T158S, S063G-A128S, S063G-K256R, S063G-N243V, S063G-S162G, S063G-T158S, S248N-K256R, S249A, T158S-N243V, T158S-S249A, A088T-A116T-N243V-K256R-L257G, A088T-A116T-N243V-L257G, A088T-T158S-N218S-K256R, A088T-T158S-N218S-N243V-L257G, A088T-A116T-T158S-N218S-N243V-K256R-L257G, A088T-N109G-A116T-G131H-A153S-N218S-S248N-L257G, A088T-N109G-A116T-T158S-S248N-K256R-L257G, A088T-N109G-T158S-L257G, A114S-A116T-N218S-N243V-S248N-K256R-L257G, A116T-T158S-K256R, A088T-A116T-G131H-T158S-S248N-L257G, A088T-A116T-T158S, A088T-N109G-A116T-G131H-L257G, A088T-N109G-A116T-T158S-N243V-S248N-L257G, A088T-N109G-N243V-L257G, A088T-N109G-N243V-S248N, A088T-N109G-T158S-N243V-L257G, A088T-N109G-T158S-N243V-S248N-L257G, A116T-T158S-S248N-L257G, Y006H-A116T-G131H-S248N, A088T-A116T-G131H-T158S-N218S-N243V, A088T-A116T-G131H-T158S-N243V, A088T-A116T-G131H-T158S-N243V-K256R-L257G, A088T-A116T-N218S-N243V-K256R-L257G, A088T-A116T-S248N-K256R-L257G,

A088T-A116T-T158S-N218S-N243V, A088T-A116T-T158S-N243V-K256R-L257G, A088T-A116T-T158S-N243V-S248N-L257G, A088T-G131H-N243V-S248N-K256R-L257G, A088T-N109G-A116T-T158S-L257G, A088T-N109G-A116T-T158S-N212D-N243V-K256R-L257G, A088T-N109G-A116T-T158S-N218S-N243V-S248N-K256R, A088T-N109G-A116T-T158S-S248N-L257G, A088T-N109G-G131H-V148A-N218S-N243V-K256R-L257G, A088T-N109G-K256R, A088T-N109G-N243V-S248N-L257G, A088T-N109G-T158S-K256R A088T-N109G-T158S-N243V, A088T-T158S-N243V-K256R-L257G, A116T-N218S-N243V-L257G-N269S, A116T-T158S-K256R-L257G, N109G-A116T-K256R-L257G, N109G-A116T-N243V, N109G-A116T-T158S-N243V-K256R-L257G, N109G-G131H-L257G, N109G-G131H-S248N-K256R-L257G, N109G-G131H-T158S-K256R-L257G, S003P-A116T-T158S-S248N-K256R, T158S-S248N-K256R, A088T-A116T-G131H-N243V-K256R, A088T-A116T-G131H-S248N-K256R-L257G, A088T-A116T-G131H-V147A-T158S-N218S-N243V-S248N-L257G, A088T-A116T-S248N-L257G, A088T-A116T-T158S-N218S, A088T-A116T-T158S-N218S-K256R-L257G, A088T-A116T-T158S-N218S-L257G, A088T-G131H-N243V-L257G, A088T-G131H-T158S-S248N-L257G, A088T-N109G-A116T, A088T-N109G-A116T-G131H-N218S, A088T-N109G-A116T-G131H-N218S-S248N-L257G, A088T-N109G-A116T-G131H-N243V-S248N-K256R-L257G, A088T-N109G-A116T-G131H-T158S-S248N-K256R-L257G, A088T-N109G-A116T-N218S-N243V-K256R, A088T-N109G-A116T-N218S-N243V-L257G, A088T-N109G-A116T-N243V-S248N-K256R, A088T-N109G-A116T-N243V-S248N-K256R-L257G, A088T-N109G-A116T-T158S-N243V-L257G, A088T-N109G-G131H-T158S-N243V-S248N-K256R, A088T-N109G-G131H-T158S-W241R-S248N-K256R, A088T-N109G-K256R-L257G, A088T-N109G-L257G, A088T-N109G-N243V, A088T-N109G-N243V-K256R, A088T-N109G-N243V-K256R-L257G, A088T-N109G-S248N-K256R, A088T-N109G-T158S-N218S-K256R-L257G, A088T-N109G-T158S-N218S-N243V-S248N-K256R, A088T-N109G-T158S-N243V-K256R, A088T-N109G-T158S-N243V-K256R-L257G, A088T-N109G-T158S-N243V-S248N-A274D, A088T-N109G-T158S-S248N-L257G, A088T-T158S-K256R, A088T-T158S-N218S-N243V-K256R-L257G, A088T-T158S-N243V-L257G, A116T-G131H-N218S-N243V-S248N, A116T-G131H-S248N-L257G, A116T-S248N-K256R-L257G, A116T-T158S-N218S-N243V-K256R, A116T-T158S-N218S-S248N-L257G-Q271R, A116T-T158S-N243V-K256R-L257G, A116T-T158S-N243V-S248N-L257G, G131H-S248N, G131H-T158S-I234T-N243V-K256R, G131H-W241L-N243V-S248N-K256R, N109G-A116T-G131H-A137V-T158S-S248N-K256R-L257G, N109G-A116T-G131H-A151S-N218S-K256R-L257G, N109G-A116T-G131H-T158S-N218S-N243V-K256R, N109G-A116T-G131H-T158S-N218S-S248N, N109G-A116T-G131H-T158S-N243V-S248N, N109G-A116T-S248N, N109G-A116T-T158S-L257G, N109G-A116T-T158S-N218S-W241R-N243V, N109G-A116T-T158S-N243V-S248N-L257G, N109G-A116T-T158S-S248N-K256R-L257G, N109G-A116T-T158S-S248N-L257G, N109G-G131H-N218S-L257G,

N109G-G131H-N218S-S248N-K256R-L257G, N109G-G131H-T158S-N218S-S248N-K256R-L257G-A274T, N109G-N243V-L257G, N109G-T158S-N218S-K256R-L257G, N109G-T158S-N218S-L257G, N109G-T158S-S248N-K256R, P014L-A015L-L016C-H017T-S018L-Q019K-G020A-Y021T-T022L-G023E, S003F-A088T-N109G-A116T-T158S-N243V-K256R-L257G, V004A-A088T-A116T-T158S-N218S, V004A-N109G-A116T-G131H-S248N-K256R-L257G, V004L-A116T-N218S-N243V-S248N-L257G, Y006H-N109G-N218S-N243V-S248N, A001T-A116T-T158S-N243V-L257G, A088T-A116T-G131H-L257G, A088T-A116T-G131H-N218S-L257G, A088T-A116T-G131H-N218S-S248N-K256R-L257G, A088T-A116T-G131H-N218S-S248N-L257G, A088T-A116T-G131H-N243V-K256R-L257G, A088T-A116T-G131H-N243V-L257G, A088T-A116T-G131H-N243V-S248N, A088T-A116T-G131H-T158S-K256R-L257G, A088T-A116T-G131H-T158S-L257G, A088T-A116T-G131H-T158S-N218S, A088T-A116T-G131H-T158S-N218S-N243V-K256R-A273T, A088T-A116T-G131H-T158S-N218S-S248N-K256R, A088T-A116T-G131H-T158S-N218S-S248N-L257G, A088T-A116T-G131H-T158S-N243V-S248N-K256R, A088T-A116T-G131H-T158S-S248N, A088T-A116T-K256R, A088T-A116T-K256R-L257G, A088T-A116T-N218S-N243V-L257G, A088T-A116T-N243V-K256R, A088T-A116T-N243V-S248N-K256R-L257G, A088T-A116T-S248N-K256R, A088T-A116T-T158S-K256R, A088T-A116T-T158S-N218S-N243V-K256R, A088T-A116T-T158S-N218S-N243V-K256R-N269S, A088T-A116T-T158S-N218S-N243V-S248N, A088T-A116T-T158S-N218S-N243V-S248N-K256R-L257G, A088T-A116T-T158S-N243V-K256R, A088T-A116T-T158S-N243V-L257G, A088T-A116T-T158S-N243V-S248N-K256R, A088T-A116T-T158S-N243V-S248N-K256R-L257G, A088T-A116T-T158S-S248N-K256R, A088T-A116T-V143A-N218S-S248N-K256R, A088T-A116T-V147I-T158S-N218S-N243V-L257G, A088T-G131H-K256R-L257G, A088T-G131H-N218S-N243V-S248N, A088T-G131H-N218S-S248N-L257G, A088T-G131H-S248N-K256R-L257G, A088T-G131H-T158S-L257G, A088T-G131H-T158S-N218S-K256R, A088T-G131H-T158S-N218S-N243V-K256R-L257G, A088T-G131H-T158S-N218S-N243V-L257G, A088T-G131H-T158S-N218S-S248N, A088T-G131H-T158S-N243V, A088T-G131H-T158S-N243V-S248N, A088T-G131H-T158S-N243V-S248N-K256R, A088T-G131H-T158S-N243V-S248N-L257G, A088T-I107T-N109G-A116T-G131H-T158S-N218S-N243V-S248N, A088T-N109G-A116T-G131H-N218S-L257G, A088T-N109G-A116T-G131H-N218S-N243V, A088T-N109G-A116T-G131H-N218S-N243V-K256R-L257G, A088T-N109G-A116T-G131H-N218S-N243V-L257G, A088T-N109G-A116T-G131H-N218S-S248N-K256R-L257G, A088T-N109G-A116T-G131H-N243V, A088T-N109G-A116T-G131H-N243V-L257G, A088T-N109G-A116T-G131H-N243V-S248N-L257G, A088T-N109G-A116T-G131H-S248N, A088T-N109G-A116T-G131H-S248N-K256R, A088T-N109G-A116T-G131H-S248N-L257G, A088T-N109G-A116T-G131H-T158S-L257G, A088T-N109G-A116T-G131H-T158S-N218S, A088T-N109G-A116T-G131H-T158S-N218S-S248N-K256R, A088T-N109G-A116T-G131H-T158S-N218T-N243V, A088T-N109G-A116T-G131H-T158S-N243V-K256R, A088T-N109G-A116T-G131H-T158S-N243V-K256R-L257G, A088T-N109G-A116T-G131H-T158S-N243V-S248N, A088T-N109G-A116T-G131H-T158S-N243V-S248N-K256R, A088T-N109G-A116T-G131H-T158S-S248N-K256R-L257G, A088T-N109G-A116T-G131H-T158S-S248N-L257G, A088T-N109G-A116T-N218S, A088T-N109G-A116T-N218S-L257G, A088T-N109G-A116T-N218S-N243V, A088T-N109G-A116T-N218S-N243V-S248N-L257G, A088T-N109G-A116T-N218S-S248N-K256R, A088T-N109G-A116T-N218T-K256R, A088T-N109G-A116T-N218T-K256R-L257G, A088T-N109G-A116T-N243V, A088T-N109G-A116T-N243V-K256R-L257G, A088T-N109G-A116T-N243V-K256R-L257G-N269D, A088T-N109G-A116T-S248N-K256R, A088T-N109G-A116T-T158S, A088T-N109G-A116T-T158S-N218S-L257G, A088T-N109G-A116T-T158S-N218S-N243V, A088T-N109G-A116T-T158S-N218S-N243V-K256R, A088T-N109G-A116T-T158S-N218S-N243V-K256R-L257G, A088T-N109G-A116T-T158S-N218S-N243V-L257G, A088T-N109G-A116T-T158S-N218S-S248N, A088T-N109G-A116T-T158S-N243V, A088T-N109G-A116T-T158S-N243V-K256R, A088T-N109G-A116T-T158S-N243V-K256R-L257G, A088T-N109G-G131H-L257G, A088T-N109G-G131H-N218S-K256R-L257G, A088T-N109G-G131H-N218S-N243V-K256R, A088T-N109G-G131H-N218S-N243V-L257G, A088T-N109G-G131H-N218S-N243V-S248N-K256R-L257G, A088T-N109G-G131H-N243V, A088T-N109G-G131H-N243V-L257G, A088T-N109G-G131H-N243V-S248N-K256R, A088T-N109G-G131H-N243V-S248N-L257G, A088T-N109G-G131H-S248N-L257G, A088T-N109G-G131H-T158S-L257G, A088T-N109G-G131H-T158S-N218S-N243V-S248N-K256R, A088T-N109G-G131H-T158S-N243V, A088T-N109G-G131H-T158S-N243V-K256R, A088T-N109G-G131H-T158S-N243V-K256R-L257G, A088T-N109G-G131H-T158S-N243V-L257G, A088T-N109G-N218S-K256R, A088T-N109G-N218S-N243V-S248N-L257G, A088T-N109G-N218S-S248N-K256R-L257G, A088T-N109G-N243V-S248N-K256R-L257G, A088T-N109G-N243V-S248N-L257G-I268V, A088T-N109G-S248N-K256R-L257G, A088T-N109G-T158S-N218S-K256R, A088T-N109G-T158S-N218S-N243V-L257G, A088T-N109G-T158S-N243V-K256R-I268V, A088T-N109G-T158S-N243V-S248N-Q275R, A088T-N218S-N243V, A088T-N218S-N243V-S248N-K256R-L257G, A088T-N218S-S248N, A088T-N218S-S248N-L257G, A088T-N243V-K256R, A088T-N243V-L257G, A088T-S145T-T158S-S248N, A088T-T158S-L257G, A088T-T158S-N218S-S248N-L257G, A088T-T158S-N243V-K256R-L257G-Q271H, A088T-T158S-S248N, A088T-V143A-T158S-K256R, A116T-G131H-K256R, A116T-G131H-N218S, A116T-G131H-N243V, A116T-G131H-N243V-K256R, A116T-G131H-N243V-L257G, A116T-G131H-S248N-K256R, A116T-G131H-T158S-N218S-I234T-N243V-S248N-K256R, A116T-G131H-T158S-N243V-L257G, A116T-G131H-T158S-N243V-S248N-K256R, A116T-G131H-V143F-T158S-N218S, A116T-L257G, A116T-N218S, A116T-N218S-L257G, A116T-N218S-N243V-L257G, A116T-N243V-K256R, A116T-N243V-S248N, A116T-N243V-S248N-K256R-L257G, A116T-S248N,

A116T-T158S-N218S-N243V, A116T-T158S-N218S-S248N, A116T-T158S-N243V, A116T-T158S-N243V-K256R, A116T-T158S-N243V-L257G, A116T-T158S-N243V-S248N, A116T-T158S-S248N-K256R-L257G, A116T-V149I-T158S-N243V-S248N-K256R-Q271H, G131H-N218S-N243V-L257G, G131H-N243V, G131H-N243V-S248N-K256R, G131H-T158S, G131H-T158S-N218S-N243V-K256R, G131H-T158S-N243V-K256R-L257G, G131H-T158S-N243V-S248N-L257G, N109G-A116T-G131H-N218S-K256R-L257G, N109G-A116T-G131H-N218S-L257G, N109G-A116T-G131H-N218S-N243V-K256R-L257G, N109G-A116T-G131H-N218S-S248N-K256R, N109G-A116T-G131H-N243V-K256R, N109G-A116T-G131H-N243V-L257G, N109G-A116T-G131H-N243V-S248N-K256R-L257G, N109G-A116T-G131H-S248N, N109G-A116T-G131H-S248N-I268V, N109G-A116T-G131H-T158S-N218S-N243V-S248N-K256R, N109G-A116T-G131H-T158S-N218S-S248N-L257G, N109G-A116T-G131H-T158S-S248N, N109G-A116T-G131H-T158S-S248N-K256R, N109G-A116T-N218S, N109G-A116T-N218S-N243V-K256R, N109G-A116T-N218S-N243V-K256R-L257G, N109G-A116T-N218S-S248N-L257G, N109G-A116T-N243V-K256R, N109G-A116T-N243V-S248N-K256R-L257G, N109G-A116T-S248N-L257G, N109G-A116T-T158S-G211V-N243V-S248N-K256R, N109G-A116T-T158S-K256R-L257G, N109G-A116T-T158S-N218S, N109G-A116T-T158S-N218S-N243V-K256R-L257G, N109G-A116T-T158S-N218S-N243V-L257G, N109G-A116T-T158S-N218S-N243V-S248N-L257G, N109G-A116T-T158S-N218S-S248N-K256R-L257G, N109G-A116T-T158S-N243V, N109G-A116T-T158S-Q275R, N109G-G131H-A137V-T158S-N218S-S248N, N109G-G131H-N218S-K237N, N109G-G131H-N218S-N243V-K256R-L257G, N109G-G131H-N218S-S248N-K256R, N109G-G131H-N243V-K256R-L257G, N109G-G131H-S145F-N218S-N243V-K256R-L257G, N109G-G131H-S248N-K256R, N109G-G131H-S248N-L257G, N109G-G131H-T158S-K256R, N109G-G131H-T158S-N218S-N243V-K256R, N109G-G131H-T158S-N243V, N109G-G131H-T158S-N243V-K256R-L257G, N109G-G131H-T158S-N243V-L257G, N109G-G131H-T158S-S248N-L257G, N109G-G131H-T158S-S248N-Q271R, N109G-N218S-L257G, N109G-N218S-N243V, N109G-N243V-K256R-L257G, N109G-N243V-S248N-K256R-L257G, N109G-T158S-I268V, N109G-T158S-K256R, N109G-T158S-N218S-N243V-K256R-L257G, N109G-T158S-N218S-S248N-L257G, N109G-T158S-N243V, N109G-T158S-N243V-K256R-L257G, N109G-T158S-N243V-S248N, N109S-A116T-S248N, N218S, N218S-N243V-S248N-K256R-L257G, N218S-S248N-L257G, N243V-K256R, N243V-S248N-K256R, N243V-S248N-K256R-L257G, S105P-A116T-T158S-N218S-N243V-S248N-K256R, S248N, T158S-N243V-K256R, T158S-N243V-L257G, S018F-S162L, S018P-D120N, P014T-S037T, S009T-K141R, S161P-S162L, N61P-S63G-N109Q-A128S-S224A-N243V, A88T-N109G-A114S-A116T-A128S-N243V, A88T-N109G-A114S-A116T-A128S-S183L-S224A-N243V, N109G-A128S-S183V, N109M-A128S-S224A, A88T-N109S-A116T-A128S-S224A-N243V, N109Q-A128S-S224A-N243V, A88T-N109M-A116T-A128S-S224A-N243V, S63G-A128S, N109S-A128S-S224A-N243V, A88T-N109G-A116T-N243V, N61S-N109G-N243V, N101Q-N109Q-A128S-S224A-N243V, A88T-N109G-A116T-T158S-N243V-K256R, N109G-A116T, A88T-N109G, N61G-N109G-N243V, N109G-A128S-P129S-S130T-S224A-N243V, A88T-N109Q-A116T-A128S-S224A-N243V, N062L-S063N-Q217L, N062S-S063R-Q217E, N062S-S063L-Q217L, S063G, S063G-Q217L, S063N and S063N-Q217L;

d) a cold water protease, said cold water protease being selected from the group consisting of:

(i) a variant of a parent protease, said parent protease having at least 60%, or 80%, or 85% or 90% or 95% or 96% or 97% or 98% or 99% or even 100% identity to SEQ ID NO:4, said variant comprising a group of mutations selected from the following groups of mutations: E156S-P210S, P210S-N218S, Y104F-E156S-P210I, E156A-P210S-N218S, N218A, N061A-S078N-S087E-S224A, Q059V-S078N-G211A, Q059V-S078N-V147Q, Q059V-S078N, Q059V-S078N-I108V-N252Q, S053G-S078N-P129T, S078N-G211A, S078N-Q185T, S078N-V147Q, S078N, S078N-S224A, S078N-S224A-A274D, S078N-I108V-V147Q, N061A-S078N-S224A, S053G-S078N-P129T-Q185T and S078N-P129T;

(ii) a variant of a parent protease, said parent protease having at least 60%, or 80%, or 85% or 90% or 95% or 96% or 97% or 98% or 99% or even 100% identity to SEQ ID NO:2, said variant comprising a group of mutations selected from the following groups of mutations: G097A-I111V-Y217Q, I111V-G128A-Y217Q, I111V-M124V-Y167A, I111V-M124V-Y217Q, L096T-G097A-Y217Q, N062Q-G097A-I111V, S053G-N061P-G097A-S101N-G128S-V203Y-Y217Q, S089Y-M124V-Y217Q, V068A-I111V-Y217Q, G097A-I111V-M124V, G097A-L126A-Y217Q, G097A-M124V-Y217Q, I111V-Y167A-Y217Q, M124V-Y167A-Y217Q, P052L-V068A-G097A, S089Y-I111V-M124V, V068A-A092G-G097A, V068A-A092G-I111V, V068A-G097A-I111V, V068A-S089Y-I111V, Y104N-G128A-Y217Q, G097A-G128A-P210S-Y217Q, G097A-G128S-P210S-Y217Q, G097A-I111V-M124I-Y217Q, G097A-I111V-M124V-P210S-Y217Q, G097A-N123Q-P210S-Y217Q, G097A-N123Q-Y217Q, N061P-G097A-G128A-P210S-Y217Q, N061P-G097A-G128S-Y217Q, N061P-G097A-I111V-M124V-Y217Q, N061P-G097A-N123Q-Y217Q, N061P-G097A-S101N-I111V-M124V-Y217Q, N061P-G097A-S101N-N123Q-Y217Q, N061P-G102A-P129S-Y217Q, N061P-N062Q-G097A-G100N-S101N-Y217Q, N061P-N062Q-G097A-G100N-Y217Q, N061P-N062Q-G097A-G100Q-P210S-Y217Q, N061P-N062Q-G097A-I111V-Y217Q, N061P-N062Q-G097A-S101N-I111V-Y217Q, N061P-S078N-G097A-I111V-M124I-Y217Q, N061P-S078N-G102A-I111V-P129S-Y217Q, N062Q-G097A-I111V-P210S-Y217Q, N062Q-G097A-I111V-Y217Q, N062Q-S078N-G097A-I111V-Y217Q, S024G-N025G-N061P-G097A-S101N-G128A-P210S-Y217Q, S024G-N025G-S053G-N061P-G097A-S101N-I111V-M124V-Y217Q, S024G-N025G-S053G-N061P-G097A-S101N-N123Q-Y217Q, S024G-N025G-S053G-N061P-N062Q-G097A-G100N-S101N-Y217Q, S024G-N025G-S053G-N061P-N062Q-G097A-S101N-I111V-Y217Q, S024G-N025G-S053G-N061P-S101N-G102A-P129S-Y217Q, S053G-N061P-G097A-G128S-Y217Q, S053G-N061P-G097A-M124I-Y217Q, S053G-N061P-G097A-S101N-I111V-M124V-Y217Q, S053G-N061P-G102A-P129S-P210S-Y217Q, S053G-N061P-G102A-P129S-Y217Q, S053G-N061P-N062Q-G097A-G100N-S101N-Y217Q, S053G-N061P-N062Q-G097A-S101N-I111V-Y217Q, S053G-N061P-S101N-G102A-P129S-Y217Q, S053G-S078N-G097A-I111V-G128S-Y217Q, S078N-G097A-G128S-Y217Q, S078N-G097A-I111V-M124V-Y217Q, N061P-G097A-M124I-Y217Q, N061P-G097A-M124V-Y217Q, N061P-N062Q-G097A-G100D-Y217Q, N061P-N062Q-G097A-G100Q-S101N-Y217Q, N061P-N062Q-G097A-G100Q-Y217Q, N061P-N062Q-G100N-G102A-Y217Q, N061P-N062Q-S078N-G097A-G100N-I111V-Y217Q, S024G-N025G-S053G-N061P-G097A-S101N-M124I-Y217Q, S053G-N061P-G097A-S101N-M124I-Y217Q, S053G-N061P-G097A-S101N-N123Q-Y217Q, N025G-S078N-G097A-G128A-Y217Q, N025G-T055P-G097A-G128A-Y217Q, S024G-G097A-S101N-G128A-Y217Q, S024G-I035V-T055P-N061P-S078N-G097A-Y217Q, S024G-N025G-N061P-S078N-G097A-S101N-G128A, S024G-N025G-N061P-S078N-G097A-S101N-G128A-Y217Q, S024G-N025G-N061P-S078N-S101N-G128A-Y217Q, S024G-N025G-S053G-N061P-G097A-G128A-S130G-Y217Q, S024G-N025G-S053G-N061P-G128A-Y217Q, S024G-N025G-S053G-T055P-G097A-G128A-Y217Q, S024G-N025G-S053G-T055P-N061P-S078N-G097A-G128A-Y217Q, S024G-N025G-S053G-T055P-N061P-S078N-G128A-Y217Q, S024G-N025G-S053G-T055P-S078N-S101N-G128A-Y217Q, S024G-N025G-S053G-T055P-S101N-G128A-Y217Q, S024G-N025G-T055P-G097A-S101N-G128A-Y217Q, S024G-N025G-T055P-N061P-S078N-G097A-Y217Q, S024G-N061P-G097A-S101N-G128A-Y217Q, S024G-S038G-S053G-S078N-S101N-G128A-Y217Q, S024G-S053G-S078N-G097A-S101N-G128A-Y217Q, S024G-S053G-S078N-S101N-G128A-Y217Q, S024G-S053G-T055P-N061P-S078N-G097A-G128A-Y217Q, S024G-T055P-G097A-G128A-Y217Q, S024G-T055P-N061P-G097A-S101N-G128A, S024G-T055P-N061P-S078N-S101N-G128A-Y217Q, S024G-T055P-S078N-G097A-S101N-G128A-Y217Q, S101N-G128A-Y217Q, T055P-N061P-G097A-A116S-G128A, T055P-N061P-S078N-G128A-Y217Q, N025G-G097A-S101N-G128A-Y217Q, N025G-S038G-S053G-N061P-S078N-G097A-S101N-G128A-Y217Q, N025G-S053G-N061P-S078N-G128A-Y217Q, N025G-S053G-N061P-S078N-S101N-G128A-Y217Q, N025G-S053G-T055P-N061P-S078N-G097A-S101N-G128A-Y217Q, N025G-S053G-T055P-S078N-G097A-S101N-G128A-Y217Q, N025G-S078N-G097A-S101N-G128A-Y217Q, N025G-T055P-N061P-S078N-G097A-S101N-G128A-Y217Q, N025G-T055P-N061P-S078N-S101N-G128A-Y217Q, N061P-S101N-G128A-Y217Q, S024G-N025G-N061P-G097A-G128A-Y217Q, S024G-N025G-N061P-G097A-S101N-G128A-Y217Q, S024G-N025G-S053G-N061P-S078N-G097A-S101N-G128A-Y217Q, S024G-N025G-S053G-T055P-G097A-S101N-G128A-Y217Q, S024G-N025G-S053G-T055P-N061P-G128A-Y217Q, S024G-N025G-T055P-G097A-G128A-Y217Q, S024G-N025G-T055P-N061P-S078N-G097A-S101N-G128A-Y217Q, S024G-N061P-S078N-G097A-S101N-G128A-Y217Q, S024G-S053G-N061P-G097A-G128A-Y217Q, S024G-S053G-N061P-S078N-G097A-G128A-Y217Q, S024G-S053G-T055P-G097A-S101N-G128A-Y217Q, S024G-S053G-T055P-N061P-S101N-G128A-Y217Q, S024G-T055P-N061P-G097A-G128A-Y217Q, S053G-N061P-G097A-S101N-G128A-Y217Q-S249N, S053G-N061P-S078N-G097A-G128A-Y217Q, S053G-S078N-G097A-S101N-G128A-Y217Q, S053G-T055P-G097A-S101N-G128A-Y217Q, S053G-T055P-N061P-S101N-G128A-Y217Q, S053G-T055P-S078N-G097A-S101N-G128A-Y217Q, T055P-G097A-S101N-G128A-Y217Q and T055P-N061P-S078N-G097A-S101N-G128A-Y217Q;

(iii) a variant of a parent protease, said parent protease, having at least 60%, or 80%, or 85% or 90% or 95% or 96% or 97% or 98% or 99% or even 100% identity to SEQ ID NO:2, said variant comprising three, four, five or six of the following mutations X24G/R, X53G, X78N, X101N, X128A/S and X217L/Q, said variant optionally comprising at least one group of mutations selected from the following groups of mutations: A001G, A001Y, A013G, A013V, A015F, A015G, A015K, A015M, A015P, A015T, A015W, A015Y, A029G, A073S, A088C, A088I, A088L, A088T, A088V, A098D, A098K, A098P, A098R, A098W, A116D, A116E, A116R, A128S, A133L, A133M, A133S, A134G, A134S, A137N, A137V, A144M, A144Q, A144S, A144T, A144V, A151C, A176S, A176T, A179S, A216G, A216L, A216P, A216Q, A216S, A216T, A216Y, A228T, A230C, A231C, A272I, A272L, A272Q, A272S, A272T, A272W, A273S, A274G, A274L, A274Q, A274T, A274V, D041E, D099G, D099N, D120A, D120K, D120Q, D120R, D120S, D140E, D181S, D259E, E054D, E156D, E156T, E251V, F261G, F261H, F261L, F261R, F261S, F261T, F261V, F261W, G007A, G007S, G020A, G020D, G020S, G024N, G024R, G024S, G024T, G024V, G024W, G053H, G053K, G053N, G053T, G097A, G097D, G097T, G131A, G131H, G131P, G131Q, G131T, G131V, G160H, G160P, G166A, G166S, G166T, G211A, G211D, G211M, G211N, G211P, G211Q, G211R, G211W, G215A, G215N, G215V, H017L, H017M, H017T, H017V, H017Y, H039A, H039C, H039N, H226F, H226I, H226M, H226S, H226V, H226Y, I035V, I079A, I079S, I079T, I079V, I079W, I108V, I115L, I122A, I234L, I234V, K012R, K027R, K136R, K141F, K213W, K237R, K256R, K265Q, L016A, L016F, L016I, L016S, L016V, L042I, L075A, L075M, L075Q, L075V, L075Y, L082K, L082M, L082Q, L082V, L090I, L196I, L196V, L209Q, L209W, L233A, L233Q, L233V, L235I, L235K, L250I, L257A, L257H, L257Q, L257S, L257Y, L267Q, L267R, L267S, L267T, M199V, N025F, N025G, N025H, N025K, N025L, N025M, N025S, N025Y, N061F, N061H, N061P, N061S, N061T, N061V, N061W, N076G, N076W, N078S, N078T, N078V, N101A, N101H, N101L, N101T, N109K, N109R, N117A, N117E, N117H, N117K, N118G, N184G, N184H, N184I, N184S, N184V, N212A, N212F, N212I, N212K, N212P, N212Q, N212S, N212Y, N218A, N218H, N218L, N218S, N240E, N240H, N240L, N240R, N240T, N243A, N243Q, N243T, N243V, N252A, N252K, N252L, N252Q, N252R, N252S, N252T, N269Q, N269S, P014G, P014Q, P014T, P040A, P040H, P040S, P040T, P040V, P040Y, P086A, P086C, P086F, P086H, P086S, P129D, P129G, P129K, P129T, P172A, P172Q, P194A, P194G, P194L, P194M, P194S, P194V, P194Y, P210G, P210R, P210V, Q002A, Q002S, Q010A, Q010F, Q010H, Q010I, Q010L, Q010N, Q010S, Q010T, Q019A, Q019G, Q019N, Q019S, Q019T, Q019V, Q019W, Q059I, Q103L, Q103S, Q185A, Q185H, Q185L, Q185T, Q185Y, Q206P, Q206S, Q206Y, Q217I, Q217N, Q217S, Q217T, Q245K, Q275D, Q275S, Q275W, S003A, S003G, S003H, S003M, S003P, S003Q, S003T, S003V, S009I, S009L, S009P, S009T, S009W, S018A, S018G, S018I, S018L, S018M, S018N, S018P, S018V, S018W, S033T, S037Q, S037T, S037V, S038G, S038H, S038K, S038Q, S038T, S063K, S063N, S063Q, S063T, S087A, S087F, S087G, S087Q, S087T, S089L, S089M, S089N, S089Q, S089T, S089W, S130A, S130F, S130G, S130L, S130V, S145A, S145H, S145M, S145V, S159A, S159G, S159H, S159Q, S159R, S161A, S161G, S161H, S161L, S161M, S161P, S161Q, S161W, S162A, S162F, S162G, S162L, S162N, S162P, S162R, S162V, S163P, S173A, S173G, S182A, S182H, S182K, S182L, S182N, S182P, S182Q, S182T, S183A, S183G, S183H, S183Q, S188A, S188G, S188T, S188V, S191A, S204A, S204I, S204L, S204Q, S204V, S224C, S236A, S236N, S236Q, S248A, S248F, S248G, S248I, S248K, S248L, S248M, S248N, S248Q, S248T, S248V, S249A, S249C, S249H, S249Q, S249T, S249W, S249Y, S260H, S260N, S260P, S260T, T022H, T022K, T022N, T022R, T022S, T022Y, T055A, T055G, T055L, T055N, T055P, T055Q, T071S, T158H, T158S, T164N, T208C, T208L, T220S, T242N, T244A, T244G, T244H, T244I, T244Q, T244S, T244V, T244W, T253A, T253G, T253H, T253Q, T254V, T255A, T255G, T255H, T255I, T255Q, T255Y, V004G, V004N, V004R, V008A, V008C, V008M, V026I, V044I, V044L, V045H, V045K, V045L, V045M, V045Q, V045S, V045W, V045Y, V051I, V081L, V081Q, V081T, V084A, V084S, V084T, V093I, V121I, V143N, V143S, V143Y, V147C, V147I, V147L, V147T, V180I, V180L, V180T, V192A, V192S, V192T, V198I, V198L, V198M, V203H, V203I, V203L, V203N, V203Q, V203T, V203W, V203Y, V270A, V270S, V270T, W241M, W241Y, Y006G, Y006H, Y006I, Y006K, Y006L, Y006P, Y006Q, Y006T, Y006V, Y006W, Y021A, Y021D, Y021E, Y021L, Y021Q, Y021R, Y021S, Y104F, Y104I, Y214L, Y214V, Y214W, Y262A, Y262G, Y262L, Y262N, Y262S, Y262W, Y263G, Y263W, A001F, A001K, A001L, A001M, A001Q, A001R, A001S, A001T, A001V, A013C, A013S, A015D, A015E, A015L, A015R, A048S, A073N, A073T, A074G, A074S, A085C, A085G, A085S, A085V, A088M, A088S, A092S, A098G, A114G, A133P, A137E, A137H, A144G, A144H, A144K, A144L, A144N, A153S, A153V, A176C, A179G, A187G, A187S, A200G, A216W, A223S, A228S, A230T, A230V, A231V, A232C, A232V, A272E, A272G, A272K, A272P, A273G, A273L, A273V, A274M, A274R, D036E, D099A, D099Q, D120E, D181A, D181G, D259A, D259G, D259Q, D259T, E156A, E156S, E251I, E251L, E251Q, E251T, F058Y, F261C, F261D, F261K, F261P, G020E, G020F, G020H, G020L, G020N, G020Q, G020R, G020T, G020Y, G024A, G024P, G053A, G053D, G053E, G053F, G053L, G053Q, G053S, G053Y, G097K, G097M, G157A, G157S, G160A, G160L, G166C, G166I, G166Q, G169A, G211K, G215H, G215L, G215S, G215T, G215W, G258S, H017I, H039S, H226L, H238N, H238Y, I011L, I011V, I031L, I079F, I079K, I079L, I079M, I079Q, I205A, I205V, I268L, I268M, K012G, K043F, K043H, K043I, K043N, K043Q, K043T, K141A, K141R, K141W, K170A, K213A, K213G, K213H, K213I, K213L, K213N, K213Q, K213R, K213S, K213T, K213V, K237A, K237H, K237I, K237L, K237N, K237S, K256A, K256G, K256H, K256M, K256P, K256Q, K256W, K265H, L016E, L042V, L075G, L075H, L075I, L075T, L082A, L082F, L082H, L082R, L082S, L082T, L090M, L135F, L196M, L209C, L209H, L209S, L233S, L235M, L235R, L235W, L257C, L257G, L267F, M050Y, M119C, M119I, M124L, N025C, N025E, N025P, N061A, N061G, N061I, N061K, N061L, N061Q, N061R, N062S, N062T, N076A, N076P, N076Q, N076S, N076T, N076V, N078G, N078H, N078K, N078P, N078Q, N078R, N101F, N117R, N117S, N118D, N118H, N118Q, N118R, N118S, N118T, N184C, N184E, N184R, N212D, N212R, N212W, N218F, N218G, N218M, N218P, N218T, N218V, N218W, N240A, N240G, N240Q, N240S, N240W, N243C, N243G, N243S, N252V, N269H, P005A, P005D, P005M, P005Q, P014A, P014M, P014R, P014V, P040F, P040R, P040W, P129E, P129R, P172E, P172K, P194H, P194R, P194W, P201A, P201G, P210L, P239K, P239R, Q002D, Q002E, Q002G, Q002I, Q002P, Q002V, Q010D, Q010R, Q019C, Q019D, Q019E, Q019H, Q019L, Q019P, Q019R, Q059A, Q059E, Q059L, Q059S, Q059T, Q103W, Q185D, Q185K, Q185R, Q185W, Q206G, Q206H, Q206L, Q206V, Q206W, Q217E, Q217F, Q217H, Q217L, Q217V, Q245M, Q271A, Q271D, Q271G, Q271L, Q271P, Q271T, Q271Y, Q275F, Q275L, Q275P, Q275R, S003D, S003F, S063A, S063F, S063G, S063M, S063R, S063Y, S087C, S087K, S087L, S087M, S087N, S087Y, S089A, S089D, S089F, S089G, S089H, S089I, S089K, S089R, S089V, S089Y, S130D, S130E, S130K, S130W, S145G, S145L, S145R, S145T, S159D, S159L, S159W, S161E, S161R, S162C, S162E, S162W, S163A, S182E, S182R, S183C, S183D, S183P, S183R, S188D, S188P, S204G, S204Y, S207G, S224G, S224T, S236C, S236G, S248D, S248H, S248R, S249E, S249L, S249R, S260A, S260G, S260K, S260Q, S260V, S260Y, T022L, T055D, T055E, T055I, T055K, T055M, T055S, T055V, T055Y, T158A, T158G, T158L, T158Q, T158V, T164K, T164Q, T208S, T244D, T244E, T244R, T253E, T253R, T253Y, T254G, T255D, T255E, T255K, T255R, V026A, V028I, V028L, V030I, V044C, V044P, V045E, V045G, V045N, V072L, V081A, V081G, V081H, V081S, V084I, V084M, V095A, V095C, V143A, V143F, V143H, V143Q, V143T, V143W, V147A, V147Q, V147S, V148I, V148L, V149C, V149I, V149L, V165L, V180A, V180C, V180M, V192C, V192F, V192I, V192Q, V192Y, V203A, V203G, V203K, V203S, V270C, V270L, V270P, W241F, Y006A, Y006M, Y006N, Y006R, Y006S, Y021C, Y091W, Y104V, Y104W, Y262C, Y262D, Y262E, Y262H, Y262I, Y262R, Y262V, A088T-A116T, A088T-N109G, A088T-N243V, A088T-S249A, A116T, A116T-G131H, A116T-N243V, A116T-S162G, A116T-T158S, A128S-K256R, A128S-L257G, A128S-S248N, A128S-T158S, G024E-A116T, G024E-K256R, G024E-L257G, G024E-N243V, G024E-T158S, G131H-S249A, K043Y-A088T, N076D-K256R, N109G, N109G-A116T, N109G-A128S, N109G-A128S-N243V-K256R, N109G-A128S-N243V-S248A, N109G-L257G, N109G-N243V, N243V-K256R, N243V-S248N, N243V-S249A, Q103H-A128S, Q103H-G131H, Q103H-K256R, Q103H-L257G, Q103H-N243V, Q103H-S248N, Q103H-S249A, Q103H-T158S, S033T-N243V, S033T-T158S, S063G-A128S, S063G-K256R, S063G-S162G, S063G-T158S, S248N-L257G, S249A, T158S-S249A, A001E-A128S-G131H-N243V, A001E-G131H-G169A-N243V, A001E-N109G, A001E-S033T-N109G-N218S, A088T-A128S, A116T-G169A, A116T-Q206D, A128S-N243V, G024E, G024E-A088T, G024E-A128S, G024E-G131H, G024E-N218S, G024E-S162G, G024E-S249A, G169A, G169A-K256R, G169A-L257G, G169A-N218S, G169A-N243V, G169A-Q206D, G169A-S248N, G169A-S249A, K043Y, K043Y-A116T, K043Y-G169A, N076D, N109G-G169A, N218S-L257G, P040E-N109G-A128S-G131H, Q206D-L257G, Q206D-N243V, S033T-A128S, S033T-A128S-G131H-N243P, S033T-K256R, S033T-L257G, S033T-N076D, S033T-N109G, S033T-N218S, S033T-P040E-Q103H-N109G, S033T-Q103H-A128S-G131H, S033T-S063G, S033T-S248N, S063G-N109G-A128S-G131H, S063G-N243V, S063G-Q206D, S248N-K256R, T158S-Q206D, A001E-A128S, A001E-G131H, A001E-K256R, A001E-N218S, A001E-N243V, A001E-S033T, A001E-S063G, A001E-S162G, A088T-K256R, A088T-N218S, A088T-Q103H, A088T-S162G, A088T-T158SA116T-A128SA116T-G131HA116T-K256R, A116T-L257G, A116T-S162G, A116T-S248N, A116T-S249A, A128S-G169A, A128S-N218S, A128S-S162G, A128S-S249A, G024E, G024E-N109G, G024E-Q103H, G024E-S033T, G024E-S063G, G024E-S248N, G131H-L257G, G131H-N243V, G131H-S162G, G131H-T158S, G169A, G169A-L257G, G169A-S248N, K043Y-A128S, K043Y-G131H, K043Y-K256R, K043Y-L257G, K043Y-N109G, K043Y-N243V, K043Y-Q103H, K043Y-S063G, K043Y-S162G, K043Y-S248N, K043Y-S249A, K043Y-T158S, K256R-L257G, N061G-N109G-N243V, N061S-A128S-N243V-S260P, N061S-N109G-A128S-N243V-S260P, N061S-N109G-A128S-S260P, N076D-A088T, N076D-A128S, N076D-G169A, N076D-N218S, N076D-N243V, N076D-S162G, N076D-S248N, N076D-T158S, N109A-A128S-N243V-K256R, N109G-A128S-G131H-N243V-S248N-K256R, N109G-A128S-N243V-S248A-K256R, N109G-A128S-N243V-S248N-K256R-L257G, N109G-A128S-S162G-N243V-S248N-K256R, N109G-A128S-T158S-N243V-S248N-K256R, N109G-Q206D, N109G-S162G, N109G-S249A, N109G-T158S, N109Q-A128S-N243V-K256R, N109S-A128S-N243V-K256R, N218S-K256R, N218S-N243V, P040A-N109G-A128S-N243V-S248N-K256R, Q103H, Q103H-A116T, Q103H-G169A, Q103H-N109G, Q103H-N218S, Q103H-S162G, S009T-A128S-K141R-N243V, S009T-N109G-A128S-K141R, S009T-N109G-A128S-K141R-N243V, S009T-S018T-Y021N-N109G-A128S-K141R, S018T-Y021N-N109G-A128S, S018T-Y021N-N109G-A128S-N243V, S018T-Y021N-N109G-A128S-N243V-S248N-K256R, S033T-A088T, S033T-A116T, S033T-G131H, S033T-K043Y, S033T-L257G, S033T-N109G, S033T-Q103H, S033T-Q206D, S033T-S162G, S033T-S249A, S063G, S063G-A088T, S063G-A116T, S063G-L257G, S063G-N076D, S063G-N109G, S063G-N218S, S063G-Q103H, S063G-S248N, S063G-S249A, S162G-G169A, S162G-L257G, S162G-N218S, S162G-N243V, S162G-S248N, S162G-S249A, S248N-S249A, S249A-K256R, S249A-L257G, T158S-G169A, T158S-K256R, T158S-L257G, T158S-N218S, T158S-S248N, A001E, A001E-A088T, A001E-A116T, A001E-G169A, A001E-L257G, A001E-N109G, A001E-S033T-N109G-N243V, A001E-T158S, A088T-G169A, A088T-Q206D, A116T-N218S, A128S-G131H, A128S-N243V-S248N-K256R, A128S-Q206D, G024E-K043Y, G024E-N076D, G024E-Q206D, G131H-G169A, G131H-N218S, G131H-N243V-K256R, G131H-Q206D, G131H-S248N, G169A-K256R, G169A-N218S, G169A-N243V, G169A-Q206D, K043Y-N076D, K043Y-N218S, N061P-N109G-G131H-N243V, N061P-N109G-N243V, N061S-N109G-A128S-N243V-S248N-K256R-S260P, N061S-N109G-N243V, N076D, N076D-G131H, N076D-L257G, N076D-N109G, N076D-Q103H, N076D-S249A, N109G-A128S-N243V-S248N, N109G-A128S-N243V-S248N-K256R, N109G-A128S-S248N-K256R, N109G-N243P-S248A-K256R, N109G-N243P-S248N-K256R, N109G-N243V-K256R, N109G-N243V-S248A-K256R, N109G-N243V-S248N, N109G-N243V-S248N-K256R, N109G-S248N-K256R, N218S-S249A, N243V-S248N-K256R, Q103H-Q206D, Q206D, Q206D-K256R, Q206D-N218S, Q206D-S248N, Q206D-S249A, S009T-N109G-A128S-K141R-N243V-S248N-K256R, S009T-S018T-Y021N-A128S-K141R-N243V, S018T-Y021N-A128S-N243V, S018T-Y021N-N061S-A128S-N243V-S260P, S018T-Y021N-N061S-N109G-A128S-S260P, S018T-Y021N-S033T-N109G-A128S-N243V-S248N-K256R, S033T, S033T-G169A, S033T-N076D-A128S-N218S, S033T-N076D-N109G-A128S-N218S-N243V-S248N-K256R, S033T-N109G-A128S-N243P-S248N-K256R, S033T-N109G-A128S-N243V-S248N-K256R, S063G-G131H, S063G-G169A, S162G-Q206D, T158S-S162G, A088T-A116T-G131H-L257G, A088T-A116T-G131H-N218S-A274T, A088T-A116T-G131H-N218S-K256R, A088T-A116T-G131H-N218S-K256R-L257G, A088T-A116T-G131H-N218S-N243V, A088T-A116T-G131H-N218S-N243V-L257G, A088T-A116T-G131H-N218S-N243V-S248N-K256R, A088T-A116T-G131H-N218S-N243V-S248N-K256R-L257G, A088T-A116T-G131H-N218S-N243V-S248N-L257G, A088T-A116T-G131H-N218S-S248N, A088T-A116T-G131H-N218S-S248N-L257G, A088T-A116T-G131H-N243V, A088T-A116T-G131H-N243V-K256R, A088T-A116T-G131H-N243V-S248N, A088T-A116T-G131H-N243V-S248N-A274V, A088T-A116T-G131H-N243V-S248N-K256R-L257G, A088T-A116T-G131H-N243V-S248N-K256R-L257G, A088T-A116T-G131H-N243V-S248N-L257G, A088T-A116T-G131H-S248N-K256R, A088T-A116T-G131H-S248N-K256R-L257G, A088T-A116T-G131H-T158S-K256R, A088T-A116T-G131H-T158S-K256R-L257G, A088T-A116T-G131H-T158S-N218S-K256R, A088T-A116T-G131H-T158S-N218S-K256R-L257G, A088T-A116T-G131H-T158S-N218S-L257G, A088T-A116T-G131H-T158S-N218S-N243V-K256R, A088T-A116T-G131H-T158S-N218S-N243V-K256R-L257G, A088T-A116T-G131H-T158S-N218S-N243V-L257G, A088T-A116T-G131H-T158S-N218S-N243V-

S248N, A088T-A116T-G131H-T158S-N218S-N243V-S248N, A088T-A116T-G131H-T158S-N218S-N243V-S248N-K256R, A088T-A116T-G131H-T158S-N243V-K256R, A088T-A116T-G131H-T158S-N243V-K256R, A088T-A116T-G131H-T158S-N243V-K256R-L257G, A088T-A116T-G131H-T158S-N243V-L257G, A088T-A116T-G131H-T158S-N243V-S248N, A088T-A116T-G131H-T158S-N243V-S248N-K256R-L257G, A088T-A116T-G131H-T158S-N243V-S248N-K256R-L257G, A088T-A116T-G131H-T158S-N243V-S248N-L257G, A088T-A116T-G131H-T158S-S248N-K256R, A088T-A116T-G131H-T158S-S248N-K256R-L257G, A088T-A116T-K256R, A088T-A116T-L257G, A088T-A116T-N218S, A088T-A116T-N218S-N243V-K256R, A088T-A116T-N218S-N243V-N269D, A088T-A116T-N218S-N243V-S248N, A088T-A116T-N218S-N243V-S248N-K256R-L257G, A088T-A116T-N218S-N243V-S248N-L257G, A088T-A116T-N218S-S248N, A088T-A116T-N218S-S248N-L257G, A088T-A116T-N243V-K256R-L257G, A088T-A116T-N243V-S248N-K256R, A088T-A116T-S248N, A088T-A116T-S248N-K256R, A088T-A116T-T158S-A216S-N218S-N243V-K256R-L257G, A088T-A116T-T158S-N218S-K256R, A088T-A116T-T158S-N218S-N243V-K256R, A088T-A116T-T158S-N218S-N243V-S248N-K256R-L257G, A088T-A116T-T158S-N218S-S248N, A088T-A116T-T158S-N243V-K256R, A088T-A116T-T158S-N243V-S248N, A088T-A116T-T158S-N243V-S248N-K256R, A088T-A116T-T158S-N243V-S248N-L257G, A088T-A116T-T158S-S248N, A088T-G131D-T158S-N243V-S248N, A088T-G131H-A138V-N218S-L257G, A088T-G131H-K256R, A088T-G131H-N218S-N243V-K256R, A088T-G131H-N218S-N243V-K256R, A088T-G131H-N218S-S248N, A088T-G131H-N218S-S248N-K256R-L257G, A088T-G131H-N218T-L257G, A088T-G131H-N243V-L257G, A088T-G131H-N243V-S248N-K256R, A088T-G131H-S248N, A088T-G131H-S248N-L257G, A088T-G131H-T158S-K256R, A088T-G131H-T158S-K256R-L257G, A088T-G131H-T158S-N218S, A088T-G131H-T158S-N218S, A088T-G131H-T158S-N218S-K256R-L257G, A088T-G131H-T158S-N218S-N243V-K256R, A088T-G131H-T158S-N218S-N243V-K256R, A088T-G131H-T158S-N218S-N243V-S248N, A088T-G131H-T158S-N218S-S248N, A088T-G131H-T158S-N218S-S248N-K256R, A088T-G131H-T158S-N218S-S248N-L257G-I268V, A088T-G131H-T158S-N243V-K256R, A088T-G131H-T158S-N243V-K256R-L257G, A088T-G131H-T158S-N243V-S248N, A088T-G131H-T158S-N243V-S248N-K256R-L257G, A088T-G131H-T158S-S248N, A088T-G131H-T158S-S248N-K256R, A088T-N109G-A116T-G131H-K256R, A088T-N109G-A116T-G131H-K256R-L257G, A088T-N109G-A116T-G131H-K256R-L257G, A088T-N109G-A116T-G131H-N218S-K256R, A088T-N109G-A116T-G131H-N218S-K256R, A088T-N109G-A116T-G131H-N218S-K256R-L257G, A088T-N109G-A116T-G131H-N218S-N243V-L257G, A088T-N109G-A116T-G131H-N218S-S248N, A088T-N109G-A116T-G131H-N218S-S248N-L257G, A088T-N109G-A116T-G131H-N243V-K256R, A088T-N109G-A116T-G131H-N243V-K256R-L257G, A088T-N109G-A116T-G131H-N243V-S248N-K256R, A088T-N109G-A116T-G131H-S248N-K256R-L257G, A088T-N109G-A116T-G131H-S248N-L257G, A088T-N109G-A116T-G131H-T158S-K256R, A088T-N109G-A116T-G131H-T158S-L257G, A088T-N109G-A116T-G131H-T158S-N218S, A088T-N109G-A116T-G131H-T158S-N218S-L257G, A088T-N109G-A116T-G131H-T158S-N218S-N243V, A088T-N109G-A116T-G131H-T158S-N218S-N243V-K256R, A088T-N109G-A116T-G131H-T158S-N218S-N243V-L257G, A088T-N109G-A116T-G131H-T158S-N218S-N243V-S248N-K256R, A088T-N109G-A116T-G131H-T158S-N218S-N243V-S248N-K256R-L257G, A088T-N109G-A116T-G131H-T158S-N218S-S248N, A088T-N109G-A116T-G131H-T158S-N218T-K256R, A088T-N109G-A116T-G131H-T158S-N243V, A088T-N109G-A116T-G131H-T158S-N243V-S248N, A088T-N109G-A116T-G131H-T158S-N243V-S248N-K256R-L257G, A088T-N109G-A116T-G131H-T158S-N243V-S248N-L257G, A088T-N109G-A116T-G131H-V149A-T158S-N218S-K256R, A088T-N109G-A116T-K256R, A088T-N109G-A116T-N218S-K256R, A088T-N109G-A116T-N218S-N243V, A088T-N109G-A116T-N218S-N243V-K256R-L257G, A088T-N109G-A116T-N218S-N243V-L257G, A088T-N109G-A116T-N218S-N243V-S248N-K256R, A088T-N109G-A116T-N218S-S248N, A088T-N109G-A116T-N218S-S248N-K256R-L257G, A088T-N109G-A116T-N243V-K256R, A088T-N109G-A116T-N243V-S248N-K256R-L257G, A088T-N109G-A116T-N243V-S248N-L257G, A088T-N109G-A116T-S248N, A088T-N109G-A116T-S248N-K256R-L257G, A088T-N109G-A116T-S248N-L257G, A088T-N109G-A116T-T158S, A088T-N109G-A116T-T158S-K256R, A088T-N109G-A116T-T158S-N218S, A088T-N109G-A116T-T158S-N218S-L257G, A088T-N109G-A116T-T158S-N218S-N243V-S248N, A088T-N109G-A116T-T158S-N218S-N243V-S248N-K256R, A088T-N109G-A116T-T158S-N218S-N243V-S248N-K256R-L257G, A088T-N109G-A116T-T158S-N218S-S248N, A088T-N109G-A116T-T158S-N218S-S248N-K256R, A088T-N109G-A116T-T158S-N218S-S248N-L257G, A088T-N109G-A116T-T158S-N243V-K256R, A088T-N109G-A116T-T158S-N243V-S248N, A088T-N109G-A116T-T158S-S248N. A088T-N109G-A116T-T158S-S248N-K256R, A088T-N109G-A137E-T158S-N218S-N243V-S248N-K256R-L257G, A088T-N109G-G131H-A152S-T158S-N218S-S248N-K256R, A088T-N109G-G131H-K256R-L257G, A088T-N109G-G131H-N218S, A088T-N109G-G131H-N218S, A088T-N109G-G131H-N218S-K256R, A088T-N109G-G131H-N218S-L257G, A088T-N109G-G131H-N218S-N243V, A088T-N109G-G131H-N218S-N243V-K256R, A088T-N109G-G131H-N218S-N243V-K256R-L257G, A088T-N109G-G131H-N218S-N243V-S248N-K256R, A088T-N109G-G131H-N218S-S248N, A088T-N109G-G131H-N218S-S248N-K256R, A088T-N109G-G131H-N218S-S248N-K256R-L257G, A088T-N109G-G131H-N243V-K256R, A088T-N109G-G131H-N243V-K256R-L257G, A088T-N109G-G131H-N243V-L257G, A088T-N109G-G131H-N243V-S248N-K256R, A088T-N109G-G131H-S248N-K256R, A088T-N109G-G131H-S248N-L257G, A088T-N109G-G131H-T158S, A088T-N109G-G131H-T158S-K256R, A088T-N109G-G131H-T158S-K256R-L257G, A088T-N109G-G131H-T158S-N218S-K256R, A088T-N109G-G131H-T158S-N218S-L257G, A088T-N109G-G131H-T158S-

N218S-N243V, A088T-N109G-G131H-T158S-N218S-N243V-K256R, A088T-N109G-G131H-T158S-N218S-N243V-S248N, A088T-N109G-G131H-T158S-N218S-S248N-L257G, A088T-N109G-G131H-T158S-N243V-K256R-L257G, A088T-N109G-G131H-T158S-N243V-S248N, A088T-N109G-G131H-T158S-N243V-S248N-K256R-L257G, A088T-N109G-G131H-T158S-N243V-S248N-L257G, A088T-N109G-G131H-T158S-S248N, A088T-N109G-G131H-T158S-S248N-L257G, A088T-N109G-G131H-V149A-K256R-L257G, A088T-N109G-G154A-N155P-E156T-G157L-T158M-S159E-G160E-S161L, A088T-N109G-K256R-L257G, A088T-N109G-N218S-K256R, A088T-N109G-N218S-N243V-L257G, A088T-N109G-N218S-N243V-S248N-K256R, A088T-N109G-N218S-S248N, A088T-N109G-N218S-S248N-L257G, A088T-N109G-N243V-S248N-K256R, A088T-N109G-S248N, A088T-N109G-T158S-N218S, A088T-N109G-T158S-N218S-K256R-Q271H, A088T-N109G-T158S-N218S-N243V, A088T-N109G-T158S-N218S-N243V-K256R-Q275R, A088T-N109G-T158S-N218S-N243V-S248N-K256R-L257G, A088T-N109G-T158S-N218S-S248N, A088T-N109G-T158S-N218S-S248N-K256R, A088T-N109G-T158S-N218S-S248N-N269D, A088T-N109G-T158S-N243V-K256R, A088T-N109G-T158S-N243V-S248N-K256R, A088T-N109G-T158S-N243V-S248N-K256R-L257G-N269D, A088T-N109G-T158S-N243V-S248N-L257G, A088T-N109G-T158S-S248N-K256R-L257G, A088T-N109G-T158S-S248N-L257G, A088T-N109G-V147A-N218S-N243V-K256R, A088T-N218S-K256R, A088T-N218S-L257G-I268V, A088T-N218S-N243V, A088T-N218S-N243V-K256R, A088T-N218S-N243V-K256R-L257G, A088T-N218S-N243V-L257G, A088T-N218S-N243V-S248N-K256R-L257G, A088T-N218S-N243V-S248N-L257G, A088T-N218S-N243V-S248N-N269S, A088T-N218S-S248N-K256R, A088T-N243V-S248N, A088T-N243V-S248N-K256R, A088T-N243V-S248N-K256R-L257G, A088T-N243V-S248N-L257G, A088T-S248N, A088T-S248N-K256R-L257G, A088T-S248N-L257G, A088T-S248N-L257G-I268V, A088T-T158S-N218S, A088T-T158S-N218S-K256R, A088T-T158S-N218S-L257G, A088T-T158S-N218S-N243V-K256R-I268V, A088T-T158S-N218S-N243V-K256R-L257G, A088T-T158S-N218S-N243V-S248N-L257G, A088T-T158S-N218S-S248N, A088T-T158S-N243V-K256R, A088T-T158S-N243V-K256R-L257G, A088T-T158S-N243V-S248N-K256R, A088T-T158S-N243V-S248N-L257G, A088T-T158S-S248N, A088T-T158S-S248N-L257G, A088T-V147A-K256R, A098S-G131H-T158S-N218S-N243V-S248N-K256R-L257G, A116T-G131H-N218S-K256R, A116T-G131H-N218S-K256R-L257G, A116T-G131H-N218S-L257G, A116T-G131H-N218S-N243V-S248N-L257G, A116T-G131H-N218S-S248N-K256R-L257G, A116T-G131H-N243V-S248N, A116T-G131H-N243V-S248N-L257G, A116T-G131H-T158S-A231V-N243V-L257G, A116T-G131H-T158S-K256R, A116T-G131H-T158S-K256R-L257G, A116T-G131H-T158S-N218S-K256R, A116T-G131H-T158S-N218S-K256R-L257G, A116T-G131H-T158S-N218S-N243V, A116T-G131H-T158S-N218S-N243V-K256R, A116T-G131H-T158S-N218S-N243V-K256R-L257G, A116T-G131H-T158S-N218S-N243V-L257G, A116T-G131H-T158S-N218S-N243V-S248N-K256R, A116T-G131H-T158S-N218S-N243V-S248N-K256R-L257G, A116T-G131H-T158S-N218S-N243V-S248N-L257G, A116T-G131H-T158S-N218S-S248N-K256R, A116T-G131H-T158S-N218T-L257G, A116T-G131H-T158S-S248N-K256R, A116T-G131H-T158S-S248N-L257G, A116T-N218S-K256R, A116T-N218S-K256R-L257G, A116T-N218S-N243V-S248N-K256R, A116T-N218S-N243V-S248N-K256R-L257G, A116T-N218S-N243V-S248N-L257G, A116T-N218S-S248N, A116T-N218S-S248N-K256R, A116T-N218S-S248N-L257G, A116T-N243V-S248N-L257G, A116T-S248N-L257G, A116T-T158S-L257G-Q271R, A116T-T158S-N218S-L257G, A116T-T158S-N218S-N243V-K256R-L257G, A116T-T158S-N218S-S248N-K256R, A116T-T158S-N218S-S248N-K256R-L257G, A116T-T158S-N243V-S248N-K256R, A116T-T158S-N243V-S248N-K256R-L257G, G024S-G053S-N078S-G097A-N101S-A128S, G131H-N218S, G131H-N218S-K256R, G131H-N218S-N243V-K256R, G131H-N218S-N243V-K256R-L257G, G131H-N218S-N243V-S248N, G131H-N218S-N243V-S248N-K256R, G131H-N218S-S248N-K256R-L257G, G131H-N218S-S248N-L257G, G131H-N243V-K256R-L257G, G131H-N243V-S248N-K256R-L257G, G131H-S248N-K256R, G131H-T158S-K256R, G131H-T158S-K256R-L257G, G131H-T158S-N218S-K256R, G131H-T158S-N218S-K256R-L257G, G131H-T158S-N218S-N243V-K256R-L257G, G131H-T158S-N218S-N243V-S248N, G131H-T158S-N218S-S248N-K256R-L257G, G131H-T158S-N218S-S248N-L257G, G131H-T158S-N243V-K256R, G131H-T158S-N243V-S248N-K256R, G131H-T158S-S248N-L257G, G131H-V147I-N218S-S248N-K256R, I107T-N109G-A116T-G131H-T158S-N218S-N243V-S248N-K256R-L257G, I107T-N109G-G131H-N218S-N243V-K256R-L257G, N109G, N109G-A116T-G131H, N109G-A116T-G131H-A144V-T158S-S248N-K256R-L257G, N109G-A116T-G131H-K256R-L257G, N109G-A116T-G131H-L257G, N109G-A116T-G131H-N218S-N243V-K256R, N109G-A116T-G131H-N218S-N243V-S248N-K256R, N109G-A116T-G131H-N243V, N109G-A116T-G131H-N243V-K256R-L257G, N109G-A116T-G131H-N243V-S248N, N109G-A116T-G131H-N243V-S248N-K256R, N109G-A116T-G131H-S248N-K256R, N109G-A116T-G131H-T158S-K256R, N109G-A116T-G131H-T158S-K256R-L257G, N109G-A116T-G131H-T158S-L257G, N109G-A116T-G131H-T158S-N218S, N109G-A116T-G131H-T158S-N218S-K256R-L257G, N109G-A116T-G131H-T158S-N218S-L257G, N109G-A116T-G131H-T158S-N218S-N243V-S248N-K256R-L257G, N109G-A116T-G131H-T158S-N218S-S248N-K256R, N109G-A116T-G131H-T158S-N218S-S248N-K256R-L257G, N109G-A116T-G131H-T158S-N243V-L257G, N109G-A116T-G131H-T158S-S248N-L257G, N109G-A116T-G131H-V147A-T158S-N218S-K256R-L257G, N109G-A116T-G131H-V149A-T158S-N218S-N243V-S248N-L257G, N109G-A116T-K256R, N109G-A116T-N218S-K256R, N109G-A116T-N218S-N243V, N109G-A116T-N218S-N243V-L257G, N109G-A116T-N218S-N243V-S248N-I268V, N109G-A116T-N218S-N243V-S248N-K256R-L257G, N109G-A116T-N218S-N243V-S248N-L257G, N109G-A116T-N243V-S248N, N109G-A116T-N243V-S248N-K256R, N109G-

A116T-N243V-S248N-L257G, N109G-A116T-S248N-K256R, N109G-A116T-T158S, N109G-A116T-T158S-N218S-N243V-S248N-K256R, N109G-A116T-T158S-N218S-N243V-S248N-K256R-L257G, N109G-A116T-T158S-N218S-S248N-K256R, N109G-A116T-T158S-N243V-L257G, N109G-A116T-T158S-N243V-S248N, N109G-A116T-T158S-S248N, N109G-A116T-T158S-S248N-K256R, N109G-G131H, N109G-G131H-K256R, N109G-G131H-N218S-K256R, N109G-G131H-N218S-K256R-L257G, N109G-G131H-N218S-N243V-L257G, N109G-G131H-N218S-N243V-S248N-K256R, N109G-G131H-N218S-N243V-S248N-K256R-L257G, N109G-G131H-N218S-N243V-S248N-L257G, N109G-G131H-N218S-S248N-L257G, N109G-G131H-N243V, N109G-G131H-N243V-K256R, N109G-G131H-N243V-S248N, N109G-G131H-N243V-S248N-K256R-L257G, N109G-G131H-N243V-S248N-L257G, N109G-G131H-T158S-N218S-K256R-L257G, N109G-G131H-T158S-N218S-L257G, N109G-G131H-T158S-N218S-N243V, N109G-G131H-T158S-N218S-N243V-K256R-L257G, N109G-G131H-T158S-N218S-N243V-S248N, N109G-G131H-T158S-N218S-N243V-S248N-K256R-L257G, N109G-G131H-T158S-N218S-N243V-S248N-L257G, N109G-G131H-T158S-N218S-S248N-K256R-L257G, N109G-G131H-T158S-N243V-K256R-I268V, N109G-G131H-T158S-N243V-S248N, N109G-G131H-T158S-N243V-S248N-K256R, N109G-G131H-T158S-N243V-S248N-L257G, N109G-G131H-T158S-S248N, N109G-G131H-T158S-S248N-K256R-L257G, N109G-K141E-N218S-S248N-L257G, N109G-N218S, N109G-N218S-N243V-K256R, N109G-N218S-N243V-L257G, N109G-N218S-N243V-S248N-S260F, N109G-N218S-S248N, N109G-N218S-S248N-K256R, N109G-N243V-S248N-L257G, N109G-N243V-S248N-L257G-Q275R, N109G-S182F-S204F-S207L-N218S-S236F-S248N-L257G, N109G-T158S-K256R-L257G, N109G-T158S-L257G, N109G-T158S-N218S-N243V-K256R, N109G-T158S-N218S-N243V-S248N, N109G-T158S-N218S-N243V-S248N-L257G, N109G-T158S-N243V-K256R, N109G-T158S-N243V-S248N-K256R, N109G-T158S-N243V-S248N-L257G, N109G-T158S-S248N-L257G, N218S-N243V-L257G, N218S-N243V-S248N-K256R, N243V-K256R-L257G, N243V-S248N-L257G-Q271R, P057Q-A088T-N109G-A116T-G131H-T158S-N218S-S248N, S003P-A116T-N218S-K256R, S003P-N109G-G131H-N218S-N243V-S248N-K256R-L257G, S248N-K256R-L257G, T158S-K256R-L257G, T158S-N218S-A272V, T158S-N218S-K256R-L257G, T158S-N218S-L233S, T158S-N218S-N243V, T158S-N218S-N243V-K256R-L257G, T158S-N218S-N243V-L257G, T158S-N218S-N243V-S248N-K256R, T158S-N218S-S248N-K256R, T158S-N243V, T158S-N243V-K256R-L257G, T158S-N243V-S248N, T158S-N243V-S248N-K256R-N269D, V004A-N109G-A116T-T158S-N218S-S248N-L257G, A088T-A098S-N218S-K256R, A088T-A116T-G131H-K256R, A088T-A116T-G131H-K256R-L257G-L267M, A088T-A116T-G131H-N218S-N243V-K256R, A088T-A116T-G131H-N218S-N243V-K256R-L257G, A088T-A116T-G131H-N218S-N243V-S248N, A088T-A116T-G131H-N218S-S248N, A088T-A116T-G131H-N218S-S248N-K256R, A088T-A116T-G131H-N218S-S248N-K256R, A088T-A116T-G131H-N243V, A088T-A116T-G131H-S248N, A088T-A116T-G131H-S248N-L257G, A088T-A116T-G131H-S248N-L257G, A088T-A116T-G131H-T158S-N218S, A088T-A116T-G131H-T158S-N218S-K256R-L257G, A088T-A116T-G131H-T158S-N218S-N243V-S248N-K256R, A088T-A116T-G131H-T158S-N218S-N243V-S248N-L257G, A088T-A116T-G131H-T158S-N218S-S248N, A088T-A116T-G131H-T158S-N218S-S248N-K256R, A088T-A116T-K256R-L257G, A088T-A116T-N218S-I268V, A088T-A116T-N218S-K256R, A088T-A116T-N218S-N243V-Q271R, A088T-A116T-N218S-N243V-S248N-K256R, A088T-A116T-N218S-N243V-S248N-K256R-Q275R, A088T-A116T-N218S-S248N, A088T-A116T-N218S-S248N-K256R, A088T-A116T-N243V-S248N-K256R, A088T-A116T-T158S, A088T-A116T-T158S-N218S-K256R, A088T-A116T-T158S-N218S-N243V-L257G, A088T-A116T-T158S-N218S-N243V-S248N-L257G, A088T-A116T-T158S-N218S-S248N, A088T-A116T-T158S-N218S-S248N-K256R, A088T-A116T-T158S-N218S-S248N-K256R-L257G, A088T-A116T-T158S-N218S-S248N-L257G, A088T-A116T-T158S-S248N-L257G, A088T-G131H, A088T-G131H, A088T-G131H-N218S-K237R-K256R-L257G, A088T-G131H-N218S-K256R, A088T-G131H-N218S-K256R-L257G, A088T-G131H-N218S-N243V-K256R-L257G, A088T-G131H-N218S-N243V-L257G, A088T-G131H-N218S-N243V-L257G, A088T-G131H-N218S-N243V-S248N, A088T-G131H-N218S-N243V-S248N-K256R, A088T-G131H-N218S-N243V-S248N-K256R-L257G, A088T-G131H-N218S-N243V-S248N-K256R-L257G, A088T-G131H-N218S-S248N, A088T-G131H-N243V, A088T-G131H-N243V-K256R, A088T-G131H-N243V-K256R-L257G, A088T-G131H-N243V-S248N, A088T-G131H-N243V-S248N, A088T-G131H-N243V-S248N-K256R, A088T-G131H-S248N, A088T-G131H-S248N-K256R, A088T-G131H-T158S-N218S-K256R-L257G, A088T-G131H-T158S-N218S-L257G, A088T-G131H-T158S-N218S-N243V, A088T-G131H-T158S-N218S-N243V-K256R-L257G, A088T-G131H-T158S-N218S-N243V-S248N-K256R, A088T-G131H-T158S-N218S-N243V-S248N-K256R-L257G, A088T-G131H-T158S-N218S-N243V-S248N-K256R-L257G, A088T-G131H-T158S-N218S-N243V-S248N-L257G, A088T-G131H-T158S-N218S-S248N-K256R, A088T-G131H-T158S-N218S-S248N-K256R-L257G, A088T-G131H-T158S-S248N-K256R-L257G, A088T-L257G, A088T-N109G-A116T-G131H-N218S-L257G, A088T-N109G-A116T-G131H-N218S-N243V-S248N-K256R, A088T-N109G-A116T-G131H-N218S-N243V-S248N-K256R-L257G, A088T-N109G-A116T-G131H-N218S-N243V-S248N-N269D, A088T-N109G-A116T-G131H-N218S-N243V-S248N-Q275R, A088T-N109G-A116T-G131H-N218S-S248N-K256R-L257G, A088T-N109G-A116T-G131H-N243V-S248N, A088T-N109G-A116T-G131H-T158S, A088T-N109G-A116T-G131H-T158S-N218S-L257G-I268V, A088T-N109G-A116T-G131H-T158S-N218S-N243V-K256R-L257G, A088T-N109G-A116T-G131H-T158S-N218S-N243V-S248N, A088T-N109G-A116T-G131H-T158S-N218S-N243V-S248N-L257G, A088T-N109G-A116T-G131H-T158S-N218S-S248N-L257G, A088T-N109G-A116T-G131H-T158S-S248N, A088T-

N109G-A116T-G131H-W241L-S248N-K256R-L257G, A088T-N109G-A116T-K256R, A088T-N109G-A116T-N218S-K256R-L257G, A088T-N109G-A116T-T158S-N218S-K256R-L257G, A088T-N109G-A116T-T158S-N218S-N243V-S248N-L257G, A088T-N109G-A116T-T158S-N243V-S248N-K256R, A088T-N109G-G131H-A138V-T158S-N218S-N243V-S248N-L257G, A088T-N109G-G131H-N218S-N243V-S248N-L257G, A088T-N109G-G131H-N218S-S248N-K256R-L257G-Q275R, A088T-N109G-G131H-N243V-S248N, A088T-N109G-G131H-N243V-S248N-K256R-L257G, A088T-N109G-G131H-T158S-L233S-N243V-S248N, A088T-N109G-G131H-T158S-N218S-N243V-K256R-L257G, A088T-N109G-G131H-T158S-N218S-N243V-S248N-K256R-L257G, A088T-N109G-G131H-T158S-N218S-N243V-S248N-L257G, A088T-N109G-G131H-T158S-N218S-S248N-K256R, A088T-N109G-G131H-T158S-N243V-S248N-K256R, A088T-N109G-G131H-T158S-S248N-K256R, A088T-N109G-G131H-T158S-S248N-K256R-L257G, A088T-N109G-N218S-K256R-L257G, A088T-N109G-N218S-N243V-K256R, A088T-N109G-N218S-N243V-S248N, A088T-N109G-N218S-N243V-S248N-K256R-L257G, A088T-N109G-N218S-S248N-K256R, A088T-N109G-N243V-K256R, A088T-N109G-S248N-K256R-L257G, A088T-N109G-T158S, A088T-N109G-T158S-K256R-L257G, A088T-N109G-T158S-N218S-N243V-K256R, A088T-N109G-T158S-N218S-N243V-K256R-L257G, A088T-N109G-T158S-N218S-N243V-S248N-K256R, A088T-N109G-T158S-N218S-N243V-S248N-L257G, A088T-N109G-T158S-S248N, A088T-N218S-N243V-S248N, A088T-N218S-N243V-S248N-K256R, A088T-N218S-N243V-S248N-K256R, A088T-N218S-S248N, A088T-N218S-S248N-L257G, A088T-S248N-K256R-L257G, A088T-T158S-K256R, A088T-T158S-N218S-N243V-K256R, A088T-T158S-N218S-N243V-L257G, A088T-T158S-N218S-N243V-S248N, A088T-T158S-N218S-N243V-S248N-K256R, A088T-T158S-N218S-N243V-S248N-K256R-L257G, A088T-T158S-N218S-S248N-K256R, A088T-T158S-N218S-S248N-L257G, A088T-T158S-N218S-S248N-L257G-Q275K, A088T-T158S-N243V, A088T-T158S-N243V-S248N, A088T-T158S-S248N-K256R-L257G, A088T-V147I-N218S-N243V-K256R-L257G, A116T-G131H-L257G, A116T-G131H-N218S-N243V, A116T-G131H-N218S-N243V-K256R-L257G, A116T-G131H-N218S-N243V-S248N-K256R-L257G, A116T-G131H-N218S-S248N, A116T-G131H-N218S-S248N-K256R, A116T-G131H-N243V-S248N-K256R, A116T-G131H-T158S-N218S-N243V-S248N, A116T-G131H-T158S-N218S-S248N, A116T-G131H-T158S-N243V-K256R, A116T-G131H-V139I-N218S-N243V-S248N, A116T-K141E-N218S-N243V-S248N-K256R-L257G, A116T-N218S-N243V-S248N, A116T-N218T-N243V-S248N, A116T-N243V-K256R-L257G, A116T-S248N-K256R, A116T-T158S-N218S-K256R, A116T-T158S-N218S-K256R-L257G, A116T-T158S-N218S-N243V-L257G, A116T-T158S-N218S-N243V-S248N, A116T-T158S-N218S-S248N-L257G, G024S-G053S-N078S-G097A-N101S, G053S-A088T-N109G-A116T-G131H-T158S-G169S-N218S-S248N-K256R-L257G, G131H-K141R-T158S-N218S-K256R, G131H-K256R, G131H-N218S-K256R-L257G, G131H-N218S-N243V-S248N-L257G, G131H-N218S-S248N-K256R, G131H-N243V-S248N, G131H-N243V-S248N-L257G, G131H-T158S-N218S, G131H-T158S-N218S-N240H-N243V-S248N-K256R-L257G, G131H-T158S-N218S-N243V, G131H-T158S-N218S-S248N-K256R-L257G-N269S, G131H-T158S-N243V-L257G, G131H-T158S-N243V-S248N, G131H-T158S-S248N, K256R, N109G-A116T-G131H-N218S-N243V, N109G-A116T-G131H-N218S-N243V-L257G, N109G-A116T-G131H-N218S-S248N-L257G, N109G-A116T-G131H-N218S-W241R-N243V-K256R, N109G-A116T-G131H-S248N-L257G, N109G-A116T-G131H-T158S-N218S-K256R, N109G-A116T-G131H-T158S-N218S-N243V-K256R-L257G, N109G-A116T-G131H-T158S-N218S-N243V-S248N, N109G-A116T-G131H-T158S-N218S-N243V-S248N-L257G, N109G-A116T-G131H-T158S-N243V-K256R-L257G, N109G-A116T-G131H-T158S-N243V-S248N-K256R, N109G-A116T-G131H-T158S-S248N-K256R-L257G, N109G-A116T-I234T-N243V-S248N-K256R-L257G, N109G-A116T-N218S-N243V-S248N, N109G-A116T-N243V-K256R-L257G, N109G-A116T-T158S-N218S-K237R-N243V-S248N, N109G-G131H-N218S-N243V-S248N, N109G-G131H-S248N, N109G-G131H-T158S, N109G-G131H-T158S-L257G, N109G-G131H-T158S-N218S-N243V-S248N-K256R, N109G-G131H-T158S-N218S-S248N-K256R, N109G-G131H-T158S-N218S-S248N-L257G, N109G-G131H-T158S-N243V-S248N-K256R-L257G, N109G-G131H-T158S-S248N-K256R, N109G-N218S-K256R-L257G, N109G-N218S-N243V-S248N-K256R, N109G-N218S-S248N-L257G, N109G-S248N, N109G-T158S-N218S, N109G-T158S-N218S-N243V, N109G-T158S-N243V-L257G, N218S-N243V-K256R, N218S-N243V-S248N, N218S-S248N, N218S-S248N-K256R, N243V-L257G, S003P-N109G-A116T-G131H-N218S-N243V-S248N, S003P-N109G-A116T-G131H-T158S-N218S-K256R, S105H-W106G-I107L-I108S-N109A-G110A-I111S-E112N-W113G-A114P, S248N-L257G, T158S-N218S-K256R, T158S-N218S-L233S-S248N, T158S-N218S-L257G, T158S-N218S-N243V-K256R, T158S-N218S-N243V-S248N, T158S-N218S-N243V-S248N-L257G, T158S-N218S-S248N-K256R-L257G, T158S-N218S-S248N-L257G, T158S-N243V-S248N-L257G, V004L-A088T-G131H-T158S-N218S-S248N-L257G, A133V-S260N, N061S-S260P, P014T-S037T, S009T-K141F, S009T-K141R, S018F-S162L, S018L-Y021S, S018P-D120N, S018T-S162P, S018T-Y021N, S018Y-K213R, S161P-S162L, S161P-S260P, T253A-S260P, A134T-S260G, I115V-N184Y, N025K-S037P, Q010L-S037P, Q019L-S260N, Q019L-S260P, S037P-T254S, S161P-T253A, N061S-S260P, Q010L-S037P, S009T-K141F, S018L-Y021S, S018T-S162P, S018T-Y021N, S018Y-K213R, S037P-T254S, S161P-S260P, S161P-T253A, T253A-S260P, A133V-S260N, A134T-S260G, I115T-S183T, I115V-N184Y, N061D-S260I, Q019L-S260N, Q019L-S260P, S183T-S249R, N61D-Q206R, Y262N-Q275R, K43R-N76S, K170R-D259G, Y6F-S249C, Q19A-N109S, H17L-Q19A, Q19R-Q185R, S18Y-V203A, S161E-S260T, S18K-V203I, V4A-T55A, N252S-L257H, S249R-Y262H, N61L-Q206H, N184Y-Y262N, Q19R-N25D, A74S-P129Q, K27R-D120H, V4A-T55A, Y21H-N252H, K27R-N269D, A98T-T158A, I79V-Q217H, S9L-N218S, V4A-Y6F,

V203A-Q217R, T22S-T242S, N76P-N212S, S37T-S260P, T55A-V147A, V4A-Y6F, Y262N-Q275R, G160R-T244A, N25D-Q185R, G211V-T244A, S9L-N218S, A144H-T244A, Y21H-N252H, A1Y-Q275R, V198L-D259G, K141I-S248N, S183T-R186K, S161E-Q185H, P129S-K136R, K43N-S163T, S37G-Q275H, Y6F-S249C, N62Y-T244A, S260P-Q275R, S33T-T55P-N61P-S63G-A88T-N109G-A116T-A128S-G131H-S224A-N243V, S33T-N61G-S63G-N109G-A128S-N218S-N243V, S33T-S63G-N109G-A128S-N218S-N243V, S33T-T55P-N61P-S63G-N109Q-A128S-G131H-S224A-N243V, N61P-S63G-N109Q-A128S-G131H-G169A-S224A-N243V-S249Q, S33T-N61G-A88T-N109G-A116T-A128S-N218S-N243V, S33T-N109G-A128S-N218S-N243V, S33T-N76D-N109G-A128S-N218S-N243V, S33T-N76D-N109G-A128S-N218S-N243V-S248N-K256R, S33T-N61G-N109G-A128S-N218S-N243V, S33T-A128S-N218S, A1G-N61P-S63G-N109Q-A128S-G131H-S224A-N243V, N61P-S63G-N109Q-A128S-G131H-S224A-N243V-S249Q, N61P-S63G-N109Q-A128S-G131H-S224A-N243V, S63G-N109Q-A128S-G131H-S224A-N243V, N109G-A114S-A128S, N109G-A114S-A128S-S183L-S224A, N109G-A114S-A128S-S224A, N109G-A114S-A128S-S224A-N243V, A88T-N109G-A116T-A128S-S224A-N243V, N61G-A88T-N109G-A116T-A128S-S224A-N243V, N109G-A114S-A128S-N243V, N109G-A128S-S224A-N243V, N109G-A128S-S224A, N109G-A128S-S183L-S224A, N61G-N109G-A128S-S224A, N109G-A128S-S183L, S33T-N76D, N109S-A128S-S224A, N101Q-N109Q-A128S-P129S-S130T-S224A-N243V, S63G-N109Q-A128S-S224A-N243V, N109M-A128S-S224A-N243V, S63G-N109G, N109G-K256R, S63G-N76D, S33T-N109G-A128S-G169A-N218S-N243V, S33T-N109G-A128S-N218S-S224A-N243V, N062L, N062L-S063G, N062S-S063G-Q217L, N062S-S063L-Q217L, N062S-S063N, N062S-S063R, S063G, S063G-Q217L, S063G-Q217L-M222S, S063L-Q217L, S063N, S063N-Q217L, D099N-K141Y-K213Q, D099N-K141Y-K256Q, K043T-K141Y-E156Q, N062L-Q217E, N062L-Q217L, N062L-S063G-Q217E, N062L-S063L, N062L-S063N-Q217L, N062S-Q217L, N062S-S063G, N062S-S063L, N062S-S063N-Q217L, N062S-S063R-Q217E, S063G-Q217E, S063N-Q217E, S063R, S063R-Q217E and S063R-Q217L;

e) a protease, said protease being selected from the group consisting of (i) a variant of a parent protease, said parent protease having at least 60%, or 80%, or 85% or 90% or 95% or 96% or 97% or 98% or 99% or even 100% identity to SEQ ID NO:4, said variant comprising a group of mutations selected from the following groups of mutations: Q059V-S078N-I108V-V147Q-G211A-N252Q, S078N-I108V-V147Q-G211A, S078N-S087E-M124I-S224A, S078N-I108V-V147Q-N252Q, S078N-I108V-V147Q-G211A-N252Q, and Q059V-S078N-I108V-V147Q-G211A-N252Q;

(ii) a variant of a parent protease, said parent protease, having at least 60%, or 80%, or 85% or 90% or 95% or 96% or 97% or 98% or 99% or even 100% identity to SEQ ID NO:2, said variant comprising a group of mutations selected from the following groups of mutations: G097A-M124V-Y167A-Y217Q, V068A-Y167A-Y217Q, G097A-I111V-M124V-Y167A, I111V-M124V-Y167A-Y217Q, V068A-I111V-Y167A-Y217Q, G097A-I111V-M124V-Y167A-Y217Q, P052L-V068A-I111V, G097A-N123A-Y217Q, N061P-N062Q-G097A-G100D-Y217Q, N061P-S101N-G102A-G128S-Y217Q, Y217Q, N061P-G102A-G128S-Y217Q, N061P-S101N-G102A-G128S-Y217Q, S078N-G097A-I111V-N123Q-Y217Q, G102A-N123Q-Y217Q, N061P-G102A-G128S-Y217Q, S078N-G097A-I111V-N123Q-Y217Q, and G102A-N123Q-Y217Q; and (iii) a variant of a parent protease, said parent protease having at least 60%, or 80%, or 85% or 90% or 95% or 96% or 97% or 98% or 99% or even 100% identity to SEQ ID NO:2, said variant comprising three, four, five or six of the following mutations: X24G/R, X53G, X78N, X101N, X128A/S and X217L/Q, said variant optionally comprising at least one group of mutations selected from the following groups of mutations: A001D, A001H, A001N, A015C, A048C, A048E, A085T, A133R, A137R, A142C, A144D, A144R, A152S, A153G, A187P, A187Q, A187T, A187V, A216R, A230S, A272R, A273H, A273T, A274H, D036N, D036S, D181H, D181T, D259N, D259P, D259S, E156G, E156H, E156L, E156Q, E156V, E251C, F189S, F189T, F189W, F189Y, F261E, G020C, G024D, G053M, G053R, G097R, G131D, G131R, G157N, G160R, G160V, G166L, G166W, G211E, G215D, G258A, G258D, G258P, I011T, I031C, I079E, I079R, I175L, I205C, K012H, K012N, K027A, K027N, K027S, K043A, K043D, K043E, K043G, K043L, K043M, K043P, K043V, K043W, K043Y, K136H, K141H, K141L, K141M, K141N, K141Q, K141T, K141V, K170G, K170S, K237T, K237V, K256D, K256S, K256T, K256V, K265N, K265S, L042F, L042M, L082E, L209A, L209E, L209G, L209R, L233G, L235V, L257D, L257E, L257P, L257R, L257W, L267E, M050L, N056D, N056S, N061C, N061D, N062A, N062H, N062L, N062V, N062Y, N076D, N076L, N076M, N078D, N078F, N101D, N101R, N118A, N212C, N212E, N218C, N218D, N218E, N252D, N252E, P014F, P014K, P057A, P057W, P172R, P194E, P201T, P210E, Q059C, Q059D, Q059R, Q185E, Q206D, Q217A, Q217K, Q217R, Q245A, Q245D, Q245E, Q245H, Q245R, Q271E, Q271F, Q271R, Q271W, Q275G, Q275IR186I, R186L, R186V, R186W, S003E, S009C, S009E, S018C, S037D, S037E, S037H, S037R, S037Y, S038D, S038P, S038R, S038Y, S063L, S087D, S087R, S089C, S089E, S130C, S130R, S145D, S159C, S159P, S161C, S173T, S182C, S188E, S188F, S188K, S188L, S188R, S188W, S190A, S190G, S190T, S204R, S236D, S236E, S248C, S248E, S260C, S260E, S260R, T022P, T055C, T055W, T071A, T158D, T158E, T158P, T158R, T158Y, T164R, T242D, T242G, T255C, V004E, V004T, V045C, V045D, V045R, V045T, V051H, V081R, V143C, V143E, V143G, V192G, V203C, V203D, V203E, V203M, V203R, V270G, W241L, Y214H, Y214Q, A001E, A133E, A187L, A187N, A216C, A216H, A273Q, D099H, D259H, E156C, E195G, F189H, G131C, G146A, G166V, G215C, G215E, I107L, K012A, K012S, K012T, K043C, K170C, K256C, K256E, K265G, K265Y, L233EM222F, M222S, N062Q, N076E, N078E, N184P, N218R, P005V, P014D, Q002K, Q002L, Q002R, Q010W, Q271C, R186H, S049C, S063C, S063D, S105T, S188C, S190C, S204E, T055R, T164G, V004D, V044T, V045I, V165C, V180S, Y006C, Y006D, Y006E, Y104T, A001C, A187C, A230G, A273D, A273P, D036Q, F189G, F189L, F189R, G157T, G178A, I031F, I111M, K012F, K012L, K027T, K043R, K136G, K141G, K170Q, M222A, M222L, N062R, N117G, N269C, P005W, P129V, P239A, P239H, P239T, Q059W, Q217G, Q275A, R186A, S191G, T164A, T220A, A001P, A187F, A187W, A273R, D041C, D060G, D197T, F189A, G046D, G157P, K012C, K012E, K012W, L042C, M222T, N062C, P239G, P239N, Q217C, R186M, S049T, S089P, S125A, S173V, V044A, A001E, A001E-A128S, A001E-G024E, A001E-G131H, A001E-G169A, A001E-L257G, A001E-218S, A001E-Q103H, A001E-S063G, A001E-S248N, A001E-S249A, G024E-N076D, K043Y-N076D, K043Y-Q206D, N076D-A116T, N076D-G169A, N076D-Q206D, Q103H-Q206D, S033T-G169A, S033T-S063G-Q103H-N109Q-A128S-G131H-G169A-N243P, S033T-S063G-Q103H-N109Q-A128S-G131H-G169A-N243V, A001E-K043Y, A001E-N076D, A001E-N076D-N109G-A128S, A001E-Q206D, G024E-Q206D, A001E-A128S-G131H-N243V, A001E-G131H-G169A-N243V, A001E-S033T-N109G-N218S, A116T-G169A, A116T-Q206D, G169A-S249A, K043Y-G169A, N109G-G169A, P040E-N109G-128S-G131H, Q206D-L257G, S033T-A128S-G131H-N243P, S033T-A128S-G131H-N243V, S033T-P040E-Q103H-N109G, S033T-Q103H-A128S-G131H, S063G-N109G-A128S-G131H, S063G-Q206D, T158S-Q206D, A001E-N076D-N109G-A128S, A015S-A088T-N109G-G131H-T158S-N218S-S248N, A088T-A098S-G131H-S248N-K256R-L257G, A088T-A116T-G131H-N218S-N243V-K256R-L257G, A088T-A116T-G131H-T158S-L257G, A088T-A116T-G131H-T158S-N218S-L257G, A088T-A116T-G131H-T158S-N218S-N243V-S248N-K256R-L257G, A088T-A116T-G131H-T158S-N218S-N243V-S248N-L257G, A088T-A116T-N218S-L257G, A088T-A116T-T158S-K256R, A088T-A116T-T158S-S248N-K256R-L257G, A088T-G131H-K141E-N218S-N243V-S248N-L257G, A088T-G131H-K256R, A088T-G131H-N218S-K256R, A088T-G131H-N218S-N243V-S248N-K256R, A088T-G131H-N218S-N243V-S248N-L257G, A088T-G131H-N218S-S248N-K256R, A088T-G131H-T158S-S248N-K256R, A088T-G131H-T158S-S248N-K256R-L257G, A088T-I107T-N109G-G131H-N218S-S248N-K256R, A088T-N109G-A116T-G131H-D140G-T158S-N218S-N243V-K256R, A088T-N109G-A116T-G131H-N218S-N243V-K256R, A088T-N109G-A116T-G131H-N218S-N243V-S248N-K256R, A088T-N109G-A116T-G131H-T158S-N218S-S248N-L257G, A088T-N109G-A116T-G131H-T158S-N243V-S248N-K256R-I268V, A088T-N109G-A116T-G131H-V149A-N218S-S248N-K256R-L257G, A088T-N109G-A116T-N218S-N243V-S248N-K256R-L257G, A088T-N109G-A116T-T158S-K256R-L257G, A088T-N109G-A116T-T158S-N218S-N243V-L257G, A088T-N109G-D140G-N243V, A088T-N109G-G131H-D140G-T158S-N243V-S248N-K256R, A088T-N109G-G131H-K141E-T158S-N218S-K256R, A088T-N109G-G131H-N218S-S248N, A088T-N109G-G131H-N218S-S248N-K256R-Q271R, A088T-N109G-G131H-N218S-S248N-L257G, A088T-N109G-G131H-T158S-K256R, A088T-N109G-G131H-T158S-N218S-S248N-K256R, A088T-N109G-G131H-V149L-T158S-K256R-L257G, A088T-N109G-T158S-N218S, A088T-N109G-T158S-N218S-K256R-L257G-Q271K, A088T-N109G-T158S-N218S-L257G, A088T-N109G-T158S-S248N-K256R, A088T-N218S-S248N-L257G-Q27R, A088T-T158S-N218S-K256R-L257G, A088T-T158S-N218S-N243V-K256R, A088T-Y104H-A116T-G131H-N218S-N243V, A116T-G131H-K141E-N218S-N243V-S248N-L257G, A116T-G131H-N218S-N243V-S248N-K256R, A116T-G131H-T158S-N218S-S248N-L257G-N269D, A116T-G131H-T158S-N218S-S248N-Q271R, A116T-G131H-T158S-N243V-S248N, A116T-G157E-T158S-N243V-S248N-K256R, A116T-T158S-N218S, G131H-N218S-L257G, G131H-N218S-S248N, G131H-T158S-N218S-N243V-S248N-K256R-L257G, G131H-T158S-N218S-N243V-S248N-L257G, G131H-T158S-N218S-S248N-I268V, I107T-N109G-G131H-N218S-L257G, L090I-N109G-T158S-N243V, L257G, N109G-A116T-G131H-T158S-N218S-K256R-L257G-Q271R, N109G-A116T-N218S-W241R-N243V-S248N-K256R-L257G, N109G-G131H-K141E-L257G, N109G-G131H-N218S-N243V, N109G-T158S-N218S-N243V-L257G, N109G-T158S-N218S-S248N-K256R, N109G-T158S-N243V-S248N-K256R-L257G, N218S-S248N-K256R-L257G, S003P-N109G-G131H-T158S-L257G, S003P-S248N-L257G, T158S-S248N-K256R-L257G, V004A-A088T-G131H-N218S-N243V-S248N-L257G, Y006H-N218S-N243V-S248N, Y104H-N109G-G131H-N243V-S248N, A088T-A116T-T158S-N218S-N243V-S248N-K256R, A088T-A116T-T158S-N243V, A088T-G131H-T158S-N218S-I234T-S248N-L257G, A088T-G131H-T158S-N218S-N243V-S248N-K256R, A088T-G131H-V149L-T158S-N243V-S248N-K256R-L257G, A088T-I107T-N109G-G131H-N218S-A223G-S248N-K256R, A088T-K213N-N243V-S248N-K256R, A088T-K256R-L257G, A088T-N109G-A116T-G131H-A232S-N243V-K256R, A088T-N109G-A116T-G131H-D140G-S248N-L257G, A088T-N109G-A116T-G131H-N218S-N243V-S248N-K256R-L257G, A088T-N109G-A116T-G131H-T158S-N218S-N243V-S248N, A088T-N109G-A116T-G131H-T158S-N243V-S248N-L257G, A088T-N109G-A116T-M124I-G131H-T158S-N218S-S248N-L257G, A088T-N109G-A116T-V148A-N218S-N243V, A088T-N109G-G131H-N218S-N243V-S248N, A088T-N109G-N218S-S248N-T255K-K256R-L257G, A088T-T158S-N218S-L257G, A088T-T158S-N218S-Q245K-S248N-K256R, A088T-T158S-N218S-S248N-K256R, A116T-G131H-N218S-N243V-K256R, A116T-G131H-N218S-W241R-N243V-S248N-K256R-L257G, A116T-G131H-T158S-N218S-L257G, A116T-G131H-V150A-T158S-N243V-S248N-K256R-L257G, I107T-G131H-T158S-N243V-S248N-K256R-L257G, N109G-A116T-K141E-T158S-N218S-N243V-L257G, N109G-A116T-T158S-N218S-N243V-S248N, T158S-N243V-S248N-K256R, T158S-N243V-S248N-K256R-L257G, A088T-A116T-G131H-G146C, A088T-A116T-N218S, A088T-A116T-T158S-N243V-K256R-L257G, A088T-A138E-N218S-N243V-K256R, A088T-N109G-A116T-G131H-T158S-N218S-N243F-S248N, A088T-T158S-V203I-N218S-K256R-L257G, A116T-D140G-T158S-N218S-N243V-S248N, A088T-A116T-T158S-K256R-L257G, A088T-A116T-T158S-N218S-N243V-S248N-E251K-K256R-L257G, A088T-I108T-N109G-G131H-T158S-N218S-S248N-K256R-L257G, A088T-N109G-A116T-G131H-K141E-N218S, A088T-N109G-W241R-S248N-K256R, G065D-A088T-

G131H-N243V-S248N, A045S-S236G, G024A-S037W, I031V-S038W, N061D-S260I, Q010R-S037T, I115T-S183T, N025K-P129K, N025K-P129R, A045S-S236Y, S162L-D181H, I031V-S038W, N025K-S037P, N025K-P129R, Y21H-D259G, A133V-D259N, I79V-Q217H, S18K-V203I, T158A-D259P, N61K-N252K, K43N-Q217R, Q206R-S260P, V198L-D259G, S161E-S260T, G160A-D259G, A1Y-Q275R, A200T-H226L, Q217R-T244A, S260P-Q275R, T158I-D259N, L75I-N76D, S161E-Q185H, Y21H-S37E, S249R-Q275R, N76T-N212D, S260P-Q275L, G131S-K265N, V4A-S249N, N25D-Q185R, K43R-N76S, S183D-Q206R, Q10R-Q275K, K43N-S163T, N25D-V26A, S260P-Q275L, K141I-S248N, L16Q, Q217H, K27R-N269T, P210S-N212D, N118G-V121A, G215D-D259V, N62Y-G97D, V4E-S260P, K27E-Y91F, Y6D-T55A, N77D-N252T, N25K-H238R, V44A-Q206H, S37P-S260F, V44A-Q206R, I31L-S33T-S63G-N109G-A128S-G169A-N218S-N243V, A1G-I31L-S33T-T55P-N61P-S63G-A88T-N109G-A116T-A128S-G131H-G169A-S224A-N243V-S249Q, S33T-N61G-S63G-N109G-A128S-G131H-G169A-N218S-N243V, S33T-S63G-N109G-A128S-G169A-N218S-N243V, S33T-T55P-N61P-S63G-A88T-N109G-A116T-A128S-G131H-S224A-N243V-S249Q, S33T-N76D-A128S-N218S, N76D-N109G-A128S-S224A, D099N, K141Y-E156Q, N062L-S063L-Q217L, N062L-S063N, N062L-S063N-Q217E, N062L-S063R, N062L-S063R-Q217L, N062S-Q217E, N062S-S063G-Q217E, N062S-S063G-Q217R, N062S-S063N-Q217R, S063G-S125A, D060G-Q217L, D120N-K141Y-K213Q, K043T-D099N-D120N-K141Y, K043T-D099N-K141Y-K256Q, K043T-K237A, N062L-S063G-Q217R, N062L-S063G-S125A, N062L-S063L-Q217E, N062L-S063N-S125A-Q217L, N062S-Q217R, N062S-S063L-Q217E, N062S-S063R-Q217L, S063G-M222S, S063G-Q217R, K141Y-D197N, N062L-Q217R, N062L-S063G-Q217L-M222S, N062L-S063L-Q217R, N062L-S063N-Q217R, N062S-Q217G, N062S-S063G-Q217G, N062S-S063G-Q217L-M222L, N062S-S063G-S125A-Q217L, N062S-S063N-Q217E, Q217G, S033G-N062S-S063G, S063G-Q217G, S063G-Q217L-M222L, S063G-S125A-Q217R, S063L-Q217R, S063N-M222S, S063N-Q217R, S063N-S125A-Q217L, S063R-Q217R, S063R-S125A-Q217L, D099N-E156Q-K256Q, E156Q, K012T-D099N-K213Q, K012T-K256Q, K043T-D099N-K141Y-K213Q, K043T-E156Q, K141Y-K213Q, N062L-Q217G, N062L-Q217L-M222L, N062L-Q217L-M222S, N062L-S063G-M222S, N062L-S063G-Q217L-M222L, N062L-S063G-Q217R-M222S, N062L-S063N-Q217L-M222S, N062L-S063N-S125A, N062L-S063R-S125A, N062L-S125A, N062S-S063G-M222S, N062S-S063G-Q217G-M222S, N062S-S063G-S125A, N062S-S063N-Q217L-M222L, N062S-S063N-S125A-Q217L, N062S-S063R-Q217G, N062S-S063R-Q217L-M222S, Q217G-M222S, Q217L-M222S, Q217R, S033G-S063G-Q217R, S063G-Q217E-M222S, S063G-S125A-Q217G, S063L-Q217E, S063N-Q217G, S063N-Q217G-M222S, S063N-Q217L-M222S, S063R-Q217L-M222S and S063R-S125A.

f) a variant of a parent protease, the variant comprising an amino acid sequence comprising from three to six amino acid substitutions selected from the group consisting of X024G/R, X053G, X078N, X101N, X128A/S, and X217L/Q, wherein the variant has proteolytic activity;

g) a variant of a protease, the variant having proteolytic activity and comprising an amino acid sequence which comprises from two to seven alterations at the amino acid positions corresponding to amino acid positions of SEQ ID NO:2 selected from the group consisting of positions 24, 53, 78, 97, 101, 128, and 217, wherein each alteration is independently (i) an insertion of one or more amino acid residues upstream or downstream of the amino acid residue which occupies the position, (ii) a deletion of the amino acid residue which occupies the position, or (iii) a substitution of the amino acid residue which occupies the position with a different amino acid residue, h) a variant of a parent protease, wherein: the variant comprises an amino acid sequence having no more than 15 alterations relative to, the parent protease, wherein the alterations are independently selected from an insertion, a deletion, or a substitution, and the alterations include a substitution of glycine at positions 24 and 53, a substitution of asparagine at positions 78 and 101, a substitution of alanine or serine at position 128, and a substitution of glutamine at position 217; the parent protease has at least 90% sequence identity to SEQ ID NO:2; and the variant has increased proteolytic activity relative to the parent protease i) a variant of a parent protease, said parent protease at least 90%, 91%, 92%, 93%, 94%, 95%, 96%, or 97% sequence identity to SEQ ID NO:2, said variant having an amino acid sequence having at least 90%, 91%, 92%, 93%, 94%, 95%, 96%, or 97% identity to the sequence of SEQ ID NO:2; said variant comprising an a substitution of glycine at positions 24 and 53, a substitution of asparagine at positions 78 and 101, a substitution of alanine or serine at position 128, and a substitution of glutamine at position 217, and said variant having increased proteolytic activity relative to the parent protease;

j) mixtures thereof and one or more adjunct ingredients, said composition being a fabric and home care product is disclosed.

In one aspect of said composition, said cold water protease has either a performance index greater than 1, at least 1.1, at least 1.2, at least 1.3, at least 1.4, at least 1.5, at least 1.6, at least 1.7, at least 1.8, at least 1.9, at least 2 from at least 1 to about 10, from at least 1 to about 8 or even from at least 1 to about 5 on BMI at pH 8 and 60° F. when compared to an enzyme having SEQ ID NO:4, as defined in Test Method 2 or Test Method 3 or said cold water protease has a performance index at least 1, at least 1.1, at least 1.2, at least 1.3, at least 1.4, at least 1.5, at least 1.6, at least 1.7, at least 1.8, at least 1.9, at least 2 from 1.0 to about 10, from 1.0 to about 8 or even from 1.0 to about 5 on BMI at pH 8 and 60° F. when compared to an enzyme having SEQ ID NO:6, as defined in Test Method 2 or Test Method 3 and said cold water protease is selected from the group consisting of:

a) a variant of a parent protease having SEQ ID NO:4, said variant comprising a group of mutations selected from the following groups of mutations: P210S, P210S-N218A, S063T-S078N-S101A-S183T-T244N, N061A-S078N-S224A, S053G-S078N-P129T-Q185T, S063T-S078N-S101A, S078N-P129T, S063T-S078N-S101A-S183T and S063T-S078N-S101A-T244I;

b) a variant of a parent protease having SEQ ID NO:2, said variant comprising a group of mutations selected from the following groups of mutations: G097A-I111V-M124V-

Y217Q, G097A-I111V-Y167A-Y217Q, S024G-N025G-N061P-G097A-S101N-G128S-Y217Q, S024G-N025G-S053G-N061P-G097A-S101N-G128A-V203Y-Y217Q, S024G-N025G-S053G-T055P-N061P-G097A-S101N-G128S-V203Y-Y217Q, V068A-A092G-Y217Q, N061P-G097A-S101N-G128A-P210S-Y217Q, S024G-N025G-S053G-N061P-G097A-S101N-G128A-P210S-Y217Q, S024G-N025G-S053G-N061P-G097A-S101N-G128S-Y217Q, S024G-N025G-S053G-N061P-S078N-G097A-S101N-I111V-G128S-Y217Q, S024G-N025G-S053G-T055P-N061P-G097A-S101N-G128A-Y217Q, N025G-G097A-S101N-G128A-Y217Q, N025G-S038G-S053G-N061P-S078N-G097A-S101N-G128A-Y217Q, N025G-S053G-N061P-S078N-G128A-Y217Q, N025G-S053G-N061P-S078N-S101N-G128A-Y217Q, N025G-S053G-T055P-N061P-S078N-G097A-S101N-G128A-Y217Q, N025G-S053G-T055P-S078N-G097A-S101N-G128A-Y217Q, N025G-S078N-G097A-S101N-G128A-Y217Q, N025G-T055P-N061P-S078N-G097A-S101N-G128A-Y217Q, N025G-T055P-N061P-S078N-S101N-G128A-Y217Q, N061P-S101N-G128A-Y217Q, S024G-N025G-N061P-G097A-G128A-Y217Q, S024G-N025G-N061P-G097A-S101N-G128A-Y217Q, S024G-N025G-S053G-N061P-S078N-G097A-S101N-G128A-Y217Q, S024G-N025G-S053G-N061P-S078N-S101N-G128A-Y217Q, S024G-N025G-S053G-T055P-G097A-S101N-G128A-Y217Q, S024G-N025G-S053G-T055P-N061P-G128A-Y217Q, S024G-N025G-T055P-G097A-G128A-Y217Q, S024G-N025G-T055P-N061P-S078N-G097A-S101N-G128A-Y217Q, S024G-N061P-S078N-G097A-S101N-G128A-Y217Q, S024G-S053G-N061P-G097A-G128A-Y217Q, S024G-S053G-N061P-S078N-G097A-G128A-Y217Q, S024G-S053G-T055P-G097A-S101N-G128A-Y217Q, S024G-S053G-T055P-N061P-G097A-S101N-G128A-Y217Q, S024G-S053G-T055P-N061P-S078N-G097A-S101N-G128A-Y217Q, S024G-S053G-T055P-N061P-S101N-G128A-Y217Q, S024G-T055P-N061P-G097A-G128A-Y217Q, S053G-G097A-S101N-G128A-Y217Q, S053G-N061P-G097A-S101N-G128A-Y217Q-S249N, S053G-N061P-S078N-G097A-G128A-Y217Q, S053G-S078N-G097A-S101N-G128A-Y217Q, S053G-T055P-G097A-S101N-G128A-Y217Q, S053G-T055P-N061P-S101N-G128A-Y217Q, S053G-T055P-S078N-G097A-S101N-G128A-Y217Q, T055P-G097A-S101N-G128A-Y217Q, T055P-N061P-S078N-G097A-S101N-G128A-Y217Q, S024G-N025G-N061P-S078N-G097A-S101N-G128A-Y217Q, S024G-N025G-S053G-T055P-N061P-G097A-S101N-G128A-Y217Q, S024G-T055P-N061P-S078N-S101N-G128A-Y217Q, T055P-N061P-S078N-G128A-Y217Q and S24G-S53G-S78N-S101N-G128A-Y217Q;

c) a variant of a parent protease having SEQ ID NO:6, said variant comprising a group of mutations selected from the following groups of mutations: A116V, G160S, I111L, I115V, N109S, N117M, P005G, Q059V, T164S, Y262M, A015Q, A015S, A098E, A098N, A098S, A098T, A098V, A098Y, A114S, A114T, A116G, A116L, A116S, A116T, A116W, A133G, A133H, A133T, A133V, A137G, A137I, A137L, A137S, A137T, A138S, A216E, A216F, A216V, D099S, D181E, F261A, F261Q, G024F, G024I, G024Q, G024Y, G097S, G160T, G211L, G211V, H017F, H017W, H039V, H226A, I031V, I111V, I268V, K170R, K265R, L016Q, L016T, L135M, L209T, L209V, L233M, L257T, L257V, L267A, L267V, N025A, N025I, N025Q, N025R, N025T, N025V, N101I, N101Q, N101S, N109A, N109G, N109H, N109L, N109M, N109Q, N109T, N117Q, N184A, N184L, N184T, N184W, N212G, N212L, N212V, N243P, N252G, N252M, P005T, P014S, P040G, P040L, P040Q, P129A, P129S, P172G, P172S, P194Q, P210A, P210S, Q185F, Q185G, Q185I, Q185M, Q185N, Q185S, Q275H, R186K, S009A, S009G, S009H, S009M, S018T, S130T, S132N, S145K, S159T, S161I, S161K, S161N, S161T, S162I, S162M, S162Y, S163G, S182F, S182G, S182V, S182W, S183F, S183L, S183M, S183T, S183V, S183W, S224A, S236T, S249V, T022A, T022G, T022Q, T022V, T208V, T242S, T253N, T253S, T254A, T254S, T255L, T255S, T255V, V004A, V004P, V004W, V084C, V139C, V165M, V203F, Y021K, Y021N, Y021T, Y021V, Y167F, Y171F, Y214F, Y262F, Y262T, A088T-L257G, A116T-A128S, N061S-N109G-A128S-N243V-S260P, S009T-N109G-A128S-K141R-N243V, S009T-S018T-Y021N-N109G-A128S-K141R, S162G-K256R, A088T-N243V, G024E-A116T, K043Y, N076D-A116T, N218S-S248N, S033T-N243V, S033T-S063G, S248N-L257G, A001E-S249A, A088T-A116T, A088T-A128S, A088T-G131H, A088T-N109G, A088T-S248N, A088T-S249A, A116T-N243V, A116T-T158S, A128S, A128S-K256R, A128S-L257G, A128S-N243V, A128S-S248N, A128S-T158S, G024E-A088T, G024E-A128S, G024E-G131H, G024E-K256R, G024E-L257G, G024E-N218S, G024E-N243V, G024E-S162G, G024E-S249A, G024E-T158S, G131H, G131H-K256R, G131H-S249A, K043Y-A088T, K043Y-A116T, K256R, N076D-K256R, N109G, N109G-A116T, N109G-A128S, N109G-A128S-N243V-K256R, N109G-A128S-N243V-S248A, N109G-G131H, N109G-K256R, N109G-L257G, N109G-N218S, N109G-N243V, N109G-S248N, N218S-L257G, N243V, N243V-K256R, N243V-L257G, N243V-S248N, N243V-S249A, Q103H-A128S, Q103H-G131H, Q103H-K256R, Q103H-L257G, Q103H-N243V, Q103H-S248N, Q103H-S249A, Q103H-T158S, Q206D-N243V, S033T-A128S, S033T-K256R, S033T-N076D, S033T-N218S, S033T-S248N, S033T-T158S, S063G-A128S, S063G-K256R, S063G-N243V, S063G-S162G, S063G-T158S, S248N-K256R, S249A, T158S-N243V, T158S-S249A, A088T-A116T-N243V-K256R-L257G, A088T-A116T-N243V-L257G, A088T-T158S-N218S-K256R, A088T-T158S-N218S-N243V-L257G, A088T-A116T-T158S-N218S-N243V-K256R-L257G, A088T-N109G-A116T-G131H-A153S-N218S-S248N-L257G, A088T-N109G-A116T-T158S-S248N-K256R-L257G, A088T-N109G-T158S-L257G, A114S-A116T-N218S-N243V-S248N-K256R-L257G, A116T-T158S-K256R, A088T-A116T-G131H-T158S-S248N-L257G, A088T-A116T-T158S, A088T-N109G-A116T-G131H-L257G, A088T-N109G-A116T-T158S-N243V-S248N-L257G, A088T-N109G-N243V-L257G, A088T-N109G-N243V-S248N, A088T-N109G-T158S-N243V-L257G, A088T-N109G-T158S-N243V-S248N-L257G, A116T-T158S-S248N-L257G, Y006H-A116T-G131H-S248N, A088T-A116T-G131H-T158S-N218S-N243V, A088T-A116T-G131H-T158S-N243V, A088T-A116T-G131H-T158S-N243V-K256R-L257G, A088T-A116T-N218S-N243V-K256R-L257G, A088T-A116T-S248N-K256R-L257G, A088T-A116T-T158S-N218S-N243V, A088T-A116T-T158S-N243V-K256R-L257G, A088T-A116T-T158S-N243V-S248N-L257G, A088T-G131H-N243V-S248N-K256R-L257G, A088T-N109G-A116T-T158S-L257G, A088T-N109G-A116T-T158S-N212D-N243V-K256R-L257G, A088T-N109G-A116T-T158S-N218S-N243V-S248N-K256R, A088T-N109G-A116T-T158S-S248N-L257G, A088T-N109G-G131H-V148A-N218S-N243V-K256R-L257G, A088T-N109G-K256R, A088T-N109G-N243V-S248N-L257G, A088T-N109G-T158S-K256R A088T-N109G-T158S-N243V, A088T-T158S-

N243V-K256R-L257G, A116T-N218S-N243V-L257G-N269S, A116T-T158S-K256R-L257G, N109G-A116T-K256R-L257G, N109G-A116T-N243V, N109G-A116T-T158S-N243V-K256R-L257G, N109G-G131H-L257G, N109G-G131H-S248N-K256R-L257G, N109G-G131H-T158S-K256R-L257G, S003P-A116T-T158S-S248N-K256R, T158S-S248N-K256R, A088T-A116T-G131H-N243V-K256R, A088T-A116T-G131H-S248N-K256R-L257G, A088T-A116T-G131H-V147A-T158S-N218S-N243V-S248N-L257G, A088T-A116T-S248N-L257G, A088T-A116T-T158S-N218S, A088T-A116T-T158S-N218S-K256R-L257G, A088T-A116T-T158S-N218S-L257G, A088T-G131H-N243V-L257G, A088T-G131H-T158S-S248N-L257G, A088T-N109G-A116T, A088T-N109G-A116T-G131H-N218S, A088T-N109G-A116T-G131H-N218S-S248N-L257G, A088T-N109G-A116T-G131H-N243V-S248N-K256R-L257G, A088T-N109G-A116T-G131H-T158S-S248N-K256R-L257G, A088T-N109G-A116T-N218S-N243V-K256R, A088T-N109G-A116T-N218S-N243V-L257G, A088T-N109G-A116T-N243V-S248N-K256R, A088T-N109G-A116T-N243V-S248N-K256R-L257G, A088T-N109G-A116T-T158S-N243V-L257G, A088T-N109G-G131H-T158S-N243V-S248N-K256R, A088T-N109G-G131H-T158S-W241R-S248N-K256R, A088T-N109G-K256R-L257G, A088T-N109G-L257G, A088T-N109G-N243V, A088T-N109G-N243V-K256R, A088T-N109G-N243V-K256R-L257G, A088T-N109G-S248N-K256R, A088T-N109G-T158S-N218S-K256R-L257G, A088T-N109G-T158S-N218S-N243V-S248N-K256R, A088T-N109G-T158S-N243V-K256R, A088T-N109G-T158S-N243V-K256R-L257G, A088T-N109G-T158S-N243V-S248N-A274D, A088T-N109G-T158S-S248N-L257G, A088T-T158S-K256R, A088T-T158S-N218S-N243V-K256R-L257G, A088T-T158S-N243V-L257G, A116T-G131H-N218S-N243V-S248N, A116T-G131H-S248N-L257G, A116T-S248N-K256R-L257G, A116T-T158S-N218S-N243V-K256R, A116T-T158S-N218S-S248N-L257G-Q271R, A116T-T158S-N243V-K256R-L257G, A116T-T158S-N243V-S248N-L257G, G131H-S248N, G131H-T158S-I234T-N243V-K256R, G131H-W241L-N243V-S248N-K256R, N109G-A116T-G131H-A137V-T158S-S248N-K256R-L257G, N109G-A116T-G131H-A151S-N218S-K256R-L257G, N109G-A116T-G131H-T158S-N218S-N243V-K256R, N109G-A116T-G131H-T158S-N218S-S248N, N109G-A116T-G131H-T158S-N243V-S248N, N109G-A116T-S248N, N109G-A116T-T158S-L257G, N109G-A116T-T158S-N218S-W241R-N243V, N109G-A116T-T158S-N243V-S248N-L257G, N109G-A116T-T158S-S248N-K256R-L257G, N109G-A116T-T158S-S248N-L257G, N109G-G131H-N218S-L257G, N109G-G131H-N218S-S248N-K256R-L257G, N109G-G131H-T158S-N218S-S248N-K256R-L257G-A274T, N109G-N243V-L257G, N109G-T158S-N218S-K256R-L257G, N109G-T158S-N218S-L257G, N109G-T158S-S248N-K256R, P014L-A015L-L016C-H017T-S018L-Q019K-G020A-Y021T-T022L-G023E, S003F-A088T-N109G-A116T-T158S-N243V-K256R-L257G, V004A-A088T-A116T-T158S-N218S, V004A-N109G-A116T-G131H-S248N-K256R-L257G, V004L-A116T-N218S-N243V-S248N-L257G, Y006H-N109G-N218S-N243V-S248N, A001T-A116T-T158S-N243V-L257G, A088T-A116T-G131H-L257G, A088T-A116T-G131H-N218S-L257G, A088T-A116T-G131H-N218S-S248N-K256R-L257G, A088T-A116T-G131H-N218S-S248N-L257G, A088T-A116T-G131H-N243V-K256R-L257G, A088T-A116T-G131H-N243V-L257G, A088T-A116T-G131H-N243V-S248N, A088T-A116T-G131H-T158S-K256R-L257G, A088T-A116T-G131H-T158S-L257G, A088T-A116T-G131H-T158S-N218S, A088T-A116T-G131H-T158S-N218S-N243V-K256R-A273T, A088T-A116T-G131H-T158S-N218S-S248N-K256R, A088T-A116T-G131H-T158S-N218S-S248N-L257G, A088T-A116T-G131H-T158S-N243V-S248N-K256R, A088T-A116T-G131H-T158S-S248N, A088T-A116T-K256R, A088T-A116T-K256R-L257G, A088T-A116T-N218S-N243V-L257G, A088T-A116T-N243V-K256R, A088T-A116T-N243V-S248N-K256R-L257G, A088T-A116T-S248N-K256R, A088T-A116T-T158S-K256R, A088T-A116T-T158S-N218S-N243V-K256R, A088T-A116T-T158S-N218S-N243V-K256R-N269S, A088T-A116T-T158S-N218S-N243V-S248N, A088T-A116T-T158S-N218S-N243V-S248N-K256R-L257G, A088T-A116T-T158S-N243V-K256R, A088T-A116T-T158S-N243V-L257G, A088T-A116T-T158S-N243V-S248N-K256R, A088T-A116T-T158S-N243V-S248N-K256R-L257G, A088T-A116T-T158S-S248N-K256R, A088T-A116T-V143A-N218S-S248N-K256R, A088T-A116T-V147I-T158S-N218S-N243V-L257G, A088T-G131H-K256R-L257G, A088T-G131H-N218S-N243V-S248N, A088T-G131H-N218S-S248N-L257G, A088T-G131H-S248N-K256R-L257G, A088T-G131H-T158S-L257G, A088T-G131H-T158S-N218S-K256R, A088T-G131H-T158S-N218S-N243V-K256R-L257G, A088T-G131H-T158S-N218S-N243V-L257G, A088T-G131H-T158S-N218S-S248N, A088T-G131H-T158S-N243V, A088T-G131H-T158S-N243V-S248N, A088T-G131H-T158S-N243V-S248N-K256R, A088T-G131H-T158S-N243V-S248N-L257G, A088T-I107T-N109G-A116T-G131H-T158S-N218S-N243V-S248N, A088T-N109G-A116T-G131H-N218S-L257G, A088T-N109G-A116T-G131H-N218S-N243V, A088T-N109G-A116T-G131H-N218S-N243V-K256R-L257G, A088T-N109G-A116T-G131H-N218S-N243V-L257G, A088T-N109G-A116T-G131H-N218S-S248N-K256R-L257G, A088T-N109G-A116T-G131H-N243V, A088T-N109G-A116T-G131H-N243V-L257G, A088T-N109G-A116T-G131H-N243V-S248N-L257G, A088T-N109G-A116T-G131H-S248N, A088T-N109G-A116T-G131H-S248N-K256R, A088T-N109G-A116T-G131H-S248N-L257G, A088T-N109G-A116T-G131H-T158S-L257G, A088T-N109G-A116T-G131H-T158S-N218S, A088T-N109G-A116T-G131H-T158S-N218S-S248N-K256R, A088T-N109G-A116T-G131H-T158S-N218T-N243V, A088T-N109G-A116T-G131H-T158S-N243V-K256R, A088T-N109G-A116T-G131H-T158S-N243V-K256R-L257G, A088T-N109G-A116T-G131H-T158S-N243V-S248N, A088T-N109G-A116T-G131H-T158S-N243V-S248N-K256R, A088T-N109G-A116T-G131H-T158S-S248N-K256R-L257G, A088T-N109G-A116T-G131H-T158S-S248N-L257G, A088T-N109G-A116T-N218S, A088T-N109G-A116T-N218S-L257G, A088T-N109G-A116T-N218S-N243V, A088T-N109G-A116T-N218S-N243V-S248N-L257G, A088T-N109G-A116T-N218S-S248N-K256R, A088T-N109G-A116T-N218T-K256R, A088T-N109G-A116T-N218T-K256R-L257G, A088T-N109G-A116T-N243V, A088T-N109G-A116T-N243V-K256R-L257G, A088T-N109G-A116T-N243V-K256R-L257G-N269D, A088T-N109G-A116T-S248N-K256R, A088T-N109G-A116T-T158S, A088T-N109G-A116T-T158S-N218S-L257G, A088T-N109G-A116T-T158S-N218S-N243V, A088T-N109G-A116T-T158S-N218S-N243V-K256R, A088T-N109G-A116T-T158S-N218S-N243V-K256R-L257G, A088T-N109G-A116T-T158S-N218S-N243V-L257G, A088T-N109G-A116T-T158S-N218S-

S248N, A088T-N109G-A116T-T158S-N243V, A088T-N109G-A116T-T158S-N243V-K256R, A088T-N109G-A116T-T158S-N243V-K256R-L257G, A088T-N109G-G131H-L257G, A088T-N109G-G131H-N218S-K256R-L257G, A088T-N109G-G131H-N218S-N243V-K256R, A088T-N109G-G131H-N218S-N243V-L257G, A088T-N109G-G131H-N218S-N243V-S248N-K256R-L257G, A088T-N109G-G131H-N243V, A088T-N109G-G131H-N243V-L257G, A088T-N109G-G131H-N243V-S248N-K256R, A088T-N109G-G131H-N243V-S248N-L257G, A088T-N109G-G131H-S248N-L257G, A088T-N109G-G131H-T158S-L257G, A088T-N109G-G131H-T158S-N218S-N243V-S248N-K256R, A088T-N109G-G131H-T158S-N243V, A088T-N109G-G131H-T158S-N243V-K256R, A088T-N109G-G131H-T158S-N243V-K256R-L257G, A088T-N109G-G131H-T158S-N243V-L257G, A088T-N109G-N218S-K256R, A088T-N109G-N218S-N243V-S248N-L257G, A088T-N109G-N218S-S248N-K256R-L257G, A088T-N109G-N243V-S248N-K256R-L257G, A088T-N109G-N243V-S248N-L257G-I268V, A088T-N109G-S248N-K256R-L257G, A088T-N109G-T158S-N218S-K256R, A088T-N109G-T158S-N218S-N243V-L257G, A088T-N109G-T158S-N243V-K256R-I268V, A088T-N109G-T158S-N243V-S248N-Q275R, A088T-N218S-N243V, A088T-N218S-N243V-S248N-K256R-L257G, A088T-N218S-S248N, A088T-N218S-S248N-L257G, A088T-N243V-K256R, A088T-N243V-L257G, A088T-S145T-T158S-S248N, A088T-T158S-L257G, A088T-T158S-N218S-S248N-L257G, A088T-T158S-N243V-K256R-L257G-Q271H, A088T-T158S-S248N, A088T-V143A-T158S-K256R, A116T-G131H-K256R, A116T-G131H-N218S, A116T-G131H-N243V, A116T-G131H-N243V-K256R, A116T-G131H-N243V-L257G, A116T-G131H-S248N-K256R, A116T-G131H-T158S-N218S-I234T-N243V-S248N-K256R, A116T-G131H-T158S-N243V-L257G, A116T-G131H-T158S-N243V-S248N-K256R, A116T-G131H-V143F-T158S-N218S, A116T-L257G, A116T-N218S, A116T-N218S-L257G, A116T-N218S-N243V-L257G, A116T-N243V-K256R, A116T-N243V-S248N, A116T-N243V-S248N-K256R-L257G, A116T-S248N, A116T-T158S-N218S-N243V, A116T-T158S-N218S-S248N, A116T-T158S-N243V, A116T-T158S-N243V-K256R, A116T-T158S-N243V-L257G, A116T-T158S-N243V-S248N, A116T-T158S-S248N-K256R-L257G, A116T-V149I-T158S-N243V-S248N-K256R-Q271H, G131H-N218S-N243V-L257G, G131H-N243V, G131H-N243V-S248N-K256R, G131H-T158S, G131H-T158S-N218S-N243V-K256R, G131H-T158S-N243V-K256R-L257G, G131H-T158S-N243V-S248N-L257G, N109G-A116T-G131H-N218S-K256R-L257G, N109G-A116T-G131H-N218S-L257G, N109G-A116T-G131H-N218S-N243V-K256R-L257G, N109G-A116T-G131H-N218S-S248N-K256R, N109G-A116T-G131H-N243V-K256R, N109G-A116T-G131H-N243V-L257G, N109G-A116T-G131H-N243V-S248N-K256R-L257G, N109G-A116T-G131H-S248N, N109G-A116T-G131H-S248N-I268V, N109G-A116T-G131H-T158S-N218S-N243V-S248N-K256R, N109G-A116T-G131H-T158S-N218S-S248N-L257G, N109G-A116T-G131H-T158S-S248N, N109G-A116T-G131H-T158S-S248N-K256R, N109G-A116T-N218S, N109G-A116T-N218S-N243V-K256R, N109G-A116T-N218S-N243V-K256R-L257G, N109G-A116T-N218S-S248N-L257G, N109G-A116T-N243V-K256R, N109G-A116T-N243V-S248N-K256R-L257G, N109G-A116T-S248N-L257G, N109G-A116T-T158S-G211V-N243V-S248N-K256R, N109G-A116T-T158S-K256R-L257G, N109G-A116T-T158S-N218S, N109G-A116T-T158S-N218S-N243V-K256R-L257G, N109G-A116T-T158S-N218S-N243V-L257G, N109G-A116T-T158S-N218S-N243V-S248N-L257G, N109G-A116T-T158S-N218S-S248N-K256R-L257G, N109G-A116T-T158S-N243V, N109G-A116T-T158S-Q275R, N109G-G131H-A137V-T158S-N218S-S248N, N109G-G131H-N218S-K237N, N109G-G131H-N218S-N243V-K256R-L257G, N109G-G131H-N218S-S248N-K256R, N109G-G131H-N243V-K256R-L257G, N109G-G131H-S145F-N218S-N243V-K256R-L257G, N109G-G131H-S248N-K256R, N109G-G131H-S248N-L257G, N109G-G131H-T158S-K256R, N109G-G131H-T158S-N218S-N243V-K256R, N109G-G131H-T158S-N243V, N109G-G131H-T158S-N243V-K256R-L257G, N109G-G131H-T158S-N243V-L257G, N109G-G131H-T158S-S248N-L257G, N109G-G131H-T158S-S248N-Q271R, N109G-N218S-L257G, N109G-N218S-N243V, N109G-N243V-K256R-L257G, N109G-N243V-S248N-K256R-L257G, N109G-T158S-I268V, N109G-T158S-K256R, N109G-T158S-N218S-N243V-K256R-L257G, N109G-T158S-N218S-S248N-L257G, N109G-T158S-N243V, N109G-T158S-N243V-K256R-L257G, N109G-T158S-N243V-S248N, N109S-A116T-S248N, N218S, N218S-N243V-S248N-K256R-L257G, N218S-S248N-L257G, N243V-K256R, N243V-S248N-K256R, N243V-S248N-K256R-L257G, S105P-A116T-T158S-N218S-N243V-S248N-K256R, S248N, T158S-N243V-K256R, T158S-N243V-L257G, S018F-S162L, S018P-D120N, P014T-S037T, S009T-K141R, S161P-S162L, N61P-S63G-N109Q-A128S-S224A-N243V, A88T-N109G-A114S-A116T-A128S-N243V, A88T-N109G-A114S-A116T-A128S-S183L-S224A-N243V, N109G-A128S-S183V, N109M-A128S-S224A, A88T-N109S-A116T-A128S-S224A-N243V, N109Q-A128S-S224A-N243V, A88T-N109M-A116T-A128S-S224A-N243V, S63G-A128S, N109S-A128S-S224A-N243V, A88T-N109G-A116T-N243V, N61S-N109G-N243V, N101Q-N109Q-A128S-S224A-N243V, A88T-N109G-A116T-T158S-N243V-K256R, N109G-A116T, A88T-N109G, N61G-N109G-N243V, N109G-A128S-P129S-S130T-S224A-N243V, A88T-N109Q-A116T-A128S-S224A-N243V, N062L-S063N-Q217L, N062S-S063R-Q217E, N062S-S063L-Q217L, S063G, S063G-Q217L, S063N and S063N-Q217L.

In one aspect of said composition, said variant of a parent protease, said parent protease having at least 60%, 80%, 85%, 90%, 95%, 96%, 97%, 98%, 99% or 100% identity to SEQ ID NO:2, comprises the amino acid substitutions: S024G+S053G+S078N+S101N+G128A/S+Y217Q/L/D; and optionally one or more groups of substitutions selected from the following groups of mutations: A088T+N109G+A116T+G131H+N243V+L257G, S033T+N076D, S009T+N109G+K141R+N243V, S162G+K256R, N109G+A116T, N109G+L257G, S162G+L257G, N061G+N109G+N243V, N109G+N243V+S248A, S033T+N076D+N109G+N218S+N243V+S248N+K256R, N109G+A116T+N243V+K256R, A088T+N109G+A116T+G131H+N243V, A088T+N109G, N109G+N243V, T158S+L257G, N061S+N109G+N243V, P040A+N109G+N243V+S248N+K256R, S009T+S018T+Y021N+N109G+K141R, A088T+N109G+A116T+T158S+N243V+K256R, A088T+N109G+A116T+T158S+N218S+L257G, N109G+K256R, N109G+N243V+K256R, S063G+K256R, S063G+N109G, S063G, S063G+N076D, S033T+N076D+N218S and N076D+N218S.

In one aspect of said composition, said protease is a variant of a parent protease having SEQ ID NO:6, said variant comprising one or more of the following groups of amino acid substitutions: A088T+N109G+A116T+G131H+N243V+

L257G, S033T+N076D, S009T+N109G+A128S+K141R+N243V, S162G+K256R, N109G+A116T, N109G+L257G, S162G+L257G, N061G+N109G+N243V, N109G+A128S+N243V+S248A, S033T+N076D+N109G+A128S+N218S+N243V+S248N+K256R, N109G+A116T+N243V+K256R, A088T+N109G+A116T+G131H+N243V, A088T+N109G, N109G+N243V, T158S+L257G, N061S+N109G+N243V, P040A+N109G+A128S+N243V+S248N+K256R, S009T+S018T+Y021N+N109G+A128S+K141R, A088T+N109G+A116T+T158S+N243V+K256R, A088T+N109G+A116T+T158S+N218S+L257G, N109G+K256R, N109G+A128S+N243V+K256R, S063G+K256R, S063G+N109G, S063G+A128S, S063G+N076D, S033T+N076D+A128S+N218S and N076D+N218S.

In one aspect of said composition, said parent protease is a subtilisin protease.

In one aspect of said composition, said parent protease is a subtilisin protease selected from the group consisting of *B. amyloliquefaciens* subtilisin protease BPN' (SEQ ID NO:2), *Geobacillus stearothermophilus* (formerly classified as *B. stearothermophilus*), *B. subtilis, B. licheniformis, B. lentus, B. brevis, B. alkalophilus, B. amyloliquefaciens, B. clausii, B. halodurans, B. megaterium, B. coagulans, B. circulans, B. lautus*, and *B. thuringiensis.*

In one aspect of said composition, said cold water protease is a variant of a parent protease, said cold water protease comprising a total of three, four, five, six, seven, eight, nine, 10, 11, 12, 13, 14 or 15 mutations selected from groups (a) and (b) below, wherein at least one mutation is selected from group (a):

a) 1, 9, 14, 15, 16, 17, 18, 19, 20, 21, 22, 23, 33, 43, 76, 102, 109, 137, 141, 158, 169, 204, 210, 218, 243, 248, 249, 256, 257, 260, and 269; and b) 24, 25, 40, 52, 53, 55, 58, 59, 61, 62, 63, 68, 78, 86, 87, 88, 89, 92, 96, 97, 100, 101, 103, 104, 106, 111, 114, 115, 116, 117, 118, 123, 124, 125, 126, 128, 129, 130, 131, 132, 133, 134, 144, 145, 159, 161, 162, 167, 194, 203, 206, 213, 217, 227, 232, 239, 240, 242, 265, 267, and 275.

In one aspect of said composition, said variant of a parent protease, said parent protease having SEQ ID NO:2, comprises a total of three, four, five, six, seven, eight, nine, 10, 11, 12, 13, 14 or 15 mutations selected from groups (a) and (b) below, wherein at least one mutation is selected from group (a):

(a) A1E/T, S9/T, P14L, A15L, L16C, H17T, S18UT, Q19K, G20A, Y21N/T, T22L, G23E, S33T, K43Y, N76D, G102A, N109A/S/G, A137V, K141R, T158S, G169A, S204E, P210S, N218S, N243P/V, S248N/A, S249A, K256R, L257G, S260P, and N269D; and (b) S24G/R/E, N25G, P40A/E, P52L, S53G, T55P, F58G, Q59S, N61E/P/G/S, N62Q/R/S, S63G/H, V68A, S78N, P86S, S87D/G, A88T/V, S89Y, A92G, L96T, G97A, G100N/Q/T, S101N, Q103E/H, Y104N, W106F, I111V, A114G, I115V, A116N/T, N117S, N118G, N123A/G/Q/V, M124IN, S125A, L126A, G128A/S, P129E/Q/S/V, S130G, G131S/H, S132N, A133V, A134T, A144K, S145D, S159K, S161P, S162G/K, Y167A, P194L, V203Y, Q206D/E, K213L, Y217Q/L/D, V227T, A232T, P239R/V, N240K, T242R, K265N, L267V, and Q275E.

In one aspect of said composition, said variant of a parent protease has a total net charge of −1, 0 or +1 relative to the BPN' wild-type.

In one aspect of said composition, said composition comprises an adjunct ingredient selected from the group consisting of: a surfactant, a builder, a chelating agent, a dye transfer inhibiting agent, a dispersant, one or more additional enzymes, an enzyme stabilizer, a catalytic material, a bleach activator, a hydrogen peroxide, a source of hydrogen peroxide, a preformed peracid, a polymeric dispersing agent, a clay soil removal/anti-redeposition agent, a brightener, a suds suppressor, a dye, a perfume, a perfume delivery system, a structure elasticizing agent, a fabric softener, a carrier, a hydrotrope, a processing aid, a solvent, a pigment and mixtures thereof.

In one aspect of said composition, said composition comprises a material selected from the group consisting of an encapsulate comprising a perfume, a hueing agent, an amphiphilic cleaning polymer, a brightener, a chelating agent and mixtures thereof.

In one aspect of said composition, said composition comprises a second non-immunoequivalent protease selected from the group comprising:

a) subtilisins (EC 3.4.21.62);

b) trypsin-like or chymotrypsin-like proteases;

c) metalloproteases; and d) mixtures thereof.

In one aspect of said composition, said composition comprises a second non-immunoequivalent protease that is a subtilisin (EC 3.4.21.62) protease said subtilisin (EC 3.4.21.62) protease being a cold water GG36 variant protease.

In one aspect of said composition, said composition comprises an additional enzyme selected from the group consisting of hemicellulases, peroxidases, proteases, cellulases, cellobiose dehydrogenases, xyloglucanases, xylanases, lipases, phospholipases, esterases, cutinases, pectinases, mannanases, pectate lyases, keratinases, reductases, oxidases, phenoloxidases, lipoxygenases, ligninases, pullulanases, tannases, pentosanases, lichenases glucanases, arabinosidases, hyaluronidase, chondroitinase, laccase, amylases, or mixtures thereof.

In one aspect of said composition, said composition comprises an additional enzyme is selected from the group consisting of:

a) first-wash lipases;

b) alpha-amylases that are greater than 90% identical to the wild-type alkaline alpha-amylases derived from *Bacillus* sp. NCIB 12289, NCIB 12512, NCIB 12513, DSM 9375 DSM 12368, DSMZ no. 12649, KSM AP1378, KSM K36 or KSM K38;

c) microbial-derived endoglucanases; and d) mixtures thereof.

In one aspect of said composition, said composition comprises a material selected from the group consisting of:

a) an alcohol ethoxysulphate surfactant;

b) a chelant selected from the group consisting of DTPA (Diethylene triamine pentaacetic acid), HEDP (Hydroxyethane diphosphonic acid), DTPMP (Diethylene triamine penta(methylene phosphonic acid)), ethylenediaminedisuccinic acid (EDDS), 1,2-Dihydroxybenzene-3,5-disulfonic acid disodium salt hydrate, and derivatives of such chelants; and c) mixtures thereof.

In one aspect of said composition, said composition comprises a material selected from the group consisting of:

a) an alcohol ethoxysulphate surfactant having an alkyl chain length of from 10 to 14 and a degree of ethoxylation from 1 to 4;

b) a chelant selected from the group consisting of DTPA (Diethylene triamine pentaacetic acid), HEDP (Hydroxyethane diphosphonic acid), DTPMP (Diethylene triamine penta(methylene phosphonic acid)), ethylenediaminedisuccinic acid (EDDS), 1,2-Dihydroxybenzene-3,5-disulfonic acid disodium salt hydrate, and derivatives of such chelants; and c) mixtures thereof.

In one aspect of said composition, said composition comprises, based on total composition weight, a chelant level of from about 1% to about 5%.

In one aspect of said composition, said composition comprises a fabric hueing agent selected from the group consisting of a) dyes;

b) dye-clay conjugates comprising at least one cationic-basic dye and a smectite clay; and c) mixtures thereof.

In one aspect of said composition, said composition comprises a fabric hueing agent selected from the group consisting of a) small molecule dyes; polymeric dyes and mixtures thereof;

b) dye-clay conjugates comprising at least one cationic-basic dye and a smectite clay; and c) mixtures thereof.

In one aspect of said composition, said composition comprises, based on total composition weight:

a) from about 0.0005 wt % to about 0.1 wt % of said cold water protease; and b) one or more of the following (i) from about 0.00003 wt % to about 0.1 wt % fabric hueing agent;

(ii) from about 0.001 wt % to about 5 wt %, perfume capsules and/or (iii) from about 0.1 wt % to about 5 wt % amphiphilic cleaning polymer.

In one aspect of said composition, said composition has a single or multi-compartment unit dose form.

In one aspect of said composition, said composition is in the form of a multi-compartment unit dose, wherein at least one protease is in a different compartment to any additional enzymes and/or chelant.

In one aspect, a composition comprising a cold water protease and a material selected from the group consisting of: an encapsulate comprising a perfume, a GG36 variant protease, a hueing agent, an amphiphilic cleaning polymer and mixtures thereof said composition being a fabric and home care product is disclosed.

In one aspect of said composition comprising a cold water protease and a material selected from the group consisting of: an encapsulate comprising a perfume, a GG36 variant protease, a hueing agent, an amphiphilic cleaning polymer and mixtures thereof, said cold water protease is a variant of the protease having SEQ ID NO:2 (subtilisin BPN') said variant comprising one or more of the following sets of mutations, insertions or deletions: S182E, N109I, N109D-Y217L-S248R, N109D-S188R-Y217L, S87D-Y217L-S248R, S87R-N109D-Y217L-S248R, S87R-N109D-S188D-Y217L-S248R, G128A-Y217Q, I111V-M124V, M124V-Y217Q, N62Q-G97A, S89Y-M124V, V68A, V68A-A92G, V68A-G97A, V68A-I111V, V68A-S89Y, V68A-V227T, V68A-Y217Q, W106F-Y217Q, G97A-G128A-Y217Q, G97A-L126A-Y217Q, G97A-M124V-L126A-Y217Q, G97A-N123G-Y217Q, L96T-G97A-Y217Q, M124V-L126A-Y217Q, N62Q-G128A-Y217Q, N62Q-G97A-Y217Q, G97N-G128A-Y217M, G97G-G128S-Y217E, G97A-G128A-Y217Q, G97M-G128S-Y217E, G97A-G128S-Y217Q, G97D-128S-Y217Q, G97M-G128G-Y217M, G97G-G128S-Y217Q, G97S-G128S-Y217Q, G97G-128A-Y217Q, G97S-G128A-Y217E, G97A-G128S-Y217L, G97A-G128A-Y217N, G97Q-G128S-Y217L, G97A-G128A-Y217M, G97A-G128A-Y217S, G97D-G128A-Y217Q, G97M-G128S-Y217Q, G97Q-G128G-Y217D-S87Y, G97S-G128A-Y217N, 097A-128S-Y217T, G97D-G128S-Y217E, G97D-G128A-Y217L, G97G-G128S-Y217E-S78P-A272T, G97T-G128S-Y217D, G97D-G128A-Y217I, G97Q-G128S-Y217Q, G97G-128A-Y217D, G97Q-G128A-Y217N, G97S-G128A-Y217M, 097S-G128S-Y217N, G97S-G128S-Y217M, G97E-G128S-Y217M, G97S-G128P-Y217Q, G97T-G128S-Y217Q, G97D-G128S-Y217Q-A73T, G97E-G128S-Y217N, G97G-G128A-Y217I, G97Q-G128A-Y217D, G97Q-G128S-Y217M, G97R-G128T-Y217Q-S162P, G97S-G128S-Y217D, G97T-G128P-Y217I, G97Q-G128G-Y217E, G97C-G128G-Y217N, G97D-G128S-Y217H, G97M-G128S-Y217L, G97M-G128S-Y217N, G97S-G128S-Y217E, G97M-G128S-Y217I, G97A-G128P-Y217A, G97R-G128S-Y217D, G97A-G128A-Y217Q-S145D, G97A-G128A-Y217Q-P239R, G97A-G128A-Y217Q-N61E-P129E-S162K-K213L-N240K, G97A-G128A-Y217Q-N61E, G97A-G128A-Y217Q-P40E-A144K-K213L, G97A-G128A-Y217Q-P129E, G97A-G128A-Y217Q-N61E-P129E-S159K, G97A-G128A-Y217Q-K213L, G97A-G128A-Y217Q-S87D, G97A-G128A-Y217Q-Q206E, G97A-G128A-Y217Q-S24R-P40E-S145D-S159K-K213L, G97A-G128A-Y217Q-K265N, G97A-G128A-Y217Q-S24R, G97A-G128A-Y217Q-P40E, G97A-G128A-Y217Q-Q275E, G97A-G128A-Y217Q-P129E-S145D-N240K, G97A-G128A-Y217Q-A144K, G97A-G128A-Y217Q-S159K, G97A-G128A-Y217Q-S162K, G97A-G128A-Y217Q-N240K, G97A-G128A-Y217Q-S53G, G97A-G128A-Y217Q-S78N, G97A-G128A-Y217Q-S53G-S78N, G97A-G128A-Y217Q-S53G-I111V, G97A-G128A-Y217Q-S53G-N117S, G97A-G128A-Y217Q-S53G-S132N, G97A-G128A-Y217Q-Y104N-S132N, G97A-G128A-Y217Q-S53G-S78N-I111V, G97A-G128A-Y217Q-S53G-S78N-N117S, G97A-G128A-Y217Q-S53G-S78N-S132N, G97A-G128A-Y217Q-S53G-Y104N-S132N, G97A-G128A-Y217Q-S78N-Y104N-S132N, Y217L-V068C-A069G, Y217L-I079F-A098G, Y217L-P086T-S101D-Q103S-V147I, Y217L-A088T-P129S-G146D, Y217L-V093I-G128D-P129R, Y217L-Z096.01D-A098R, Y217L-Z096.01H-A098G, Y217L-G097S-Z097.01S-A098G-A273T, Y217L-A098S-D099G-G100D, Y217L-Z098.01N, Y217L-D099G-Z099.01N, Y217L-D099G-Z099.01S, Y217L-D099V-S101D, Y217L-Z099.01S, Y217L-G100D, Y217L-S101D-Q103H, Y217L-S101G-A151V, Y217L-S101H-G102S, Y217L-S101H-Q103D, Y217L-G102R-Q103C-Y104C-V192I, Y217L-Q103D, Y217L-V121I-I122S-N123C, Y217L-V121L-N123C, Y217L-I122S-N123S, Y217L-M124I, Y217L-M124V, Y217L-L126F-P129Z-S182N, Y217L-L126Y, Y217L-G127S-P129D, Y217L-Z127.01N-G128S-P129S, Y217L-G128H-P129Y, Y217L-G128S-P129D, Y217L-G128S-P129D-S248R, Y217L-G128S-P129G, Y217L-P129G-G131Z, Y217L-P129G-S130H-S132Z, Y217L-P129H-G131Z, Y217L-P129L, Y217L-P129S-S130H-S132Z, Y217L-P129Z, Y217L-P129Z-S130G, Y217L-P129Z-S130G-G131H-S132H, Y217L-P129Z-S130H, Y217L-S130V-G131D-S132I, S87T-A88L-S89G-G97A-G128A-Y217Q, N61P-S63H-G97A-G128A-Y217Q, S87G-A88V-S89A-G97A-G128A-Y217Q, P86S-S87G-A88V-G97A-G128A-Y217Q, Q59S-N61P-G97A-G128A-Y217Q, S24G-N25G-G97A-G128A-Y217Q, N61P-N62S-G97A-G128A-Y217Q, G97A-G128A-P129Q-S130G-G131S-Y217Q, L75S-N76Y-G97A-G128A-Y217Q, G97A-G128A-V203Y-Y217Q, T55P-G97A-G128A-Y217Q, A88V-L90I-G97A-G128A-Y217Q, G97A-G128A-G211R-N212S-K213V-Y217Q, G23A-S24G-N25G-G97A-G128A-Y217Q, T22N-S24A-G97A-G128A-Y217Q, S24R-G97A-G128A-Y217Q, G97A-A98S-G128A-Y217Q, G97A-G128A-T158G-S159G-Y217Q, Q59E-N61P-G97A-G128A-Y217Q, G97A-A98E-G128A-Y217Q, 097A-G128A-Y217Q-P86S-S87G-A88V-A116N-N117S-N118G, 097A-G128A-Y217Q-S63T-P86S-S87G-A88V, G97A-G128A-Y217Q-P86S-S87G-A88V-P239R, G97A-G128A-Y217Q-S24G-N25G-N61P-N62S-P194L-A232T, G97A-G128A-Y217Q-P129Q-S130G-G131S-A133V-L267V, G97A-G128A-Y217Q-A134T-L267V, G97A-G128A-Y217Q-S24R-P40E-P129E-S159K-K265R, G97A-G128A-Y217Q-A134T-G211T, G97A-G128A-Y217Q-S24R-P129E, G97A-G128A-Y217Q-I111V-S161P, G97A-G128A-Y217Q-T55P-P129Q, G97A-G128A-Y217Q-I115V-L267V, G97A-G128A-Y217Q-P86S-S87G-A88V-A116S-N117G-N118R, G97A-G128A-Y217Q-V203Y-L267V, G97A-G128A-Y217Q-S24G-N25G-S78N-S101N-V203Y, G97A-G128A-Y217Q-P52S-T55P-V203Y, G97A-G128A-Y217Q-Q59S-N61P-A116S-N117G-N118R, G97A-G128A-Y217Q-S24G-N25G-P129Q-S130G-G131S, G97A-G128A-Y217Q-P86S-S87G-A88V-T242R, G97A-G128A-Y217Q-P40E-T55P-N269K, G97A-G128A-Y217Q-G23A-S24G-N25G-A116N-N117S-N118G, G97A-G128A-Y217Q-V8L-N25Y-P129Q-S130G-G131S, G97A-G128A-Y217Q-S24G-N25G-S53G-S78N-S87T-A88L-S89G-S101N, G97A-G128A-Y217Q-G211T-L267V, G97A-G128A-Y217Q-S24R-A116N-N117S-N118G, G97A-G128A-Y217Q-S24R-A128S-P129G, G97A-G128A-Y217Q-P129Q-S130G-G131S-N240K, G97A-G128A-Y217Q-N25Y-P129Q-S130G-G131S, G97A-G128A-Y217Q-S87T-A88L-S89G-A134T, G97A-G128A-Y217Q-P129Q-S130G-G131S-L267V, G97A-G128A-Y217Q-S87G-A88V-S89A-A116N-N117S-N118G, G97A-G128A-Y217Q-N61P-P129Q-S130G-G131S, G97A-G128A-Y217Q-N61P-S78N-S87T-A88L-S89G-S101N, G97A-G128A-Y217Q-T55P-P129V-P194S, G97A-G128A-Y217Q-T55P-P129V, G97A-G128A-Y217Q-S24G-N25G-T55P-S78N-S101N, G97A-G128A-Y217Q-T55P-S78N-I115V, G97A-G128A-Y217Q-N25Y-S87G-A88V-S89A, 097A-G128A-Y217Q-A134T-N240K, G97A-G128A-Y217Q-S24R-Q59S-N61P, G97A-G128A-Y217Q-G23A-S24G-N25G-P239R, G97A-G128A-Y217Q-T55P-A116S-N117G-N118R, G97A-G128A-Y217Q-A134T-S161P, G97A-G128A-Y217Q-S24G-N25G-S53G-N61P-S101N-V203Y, G97A-G128A-Y217Q-N25Y-Q59S-N61P, G97A-G128A-Y217Q-N25Y-P129Q-S130G-G131S-A137T, G97A-G128A-Y217Q-G23A-S24G-N25G-N61P-S63H, G97A-G128A-Y217Q-T55P-N61P-S78N-S101N-V203Y, 097A-G128A-Y217Q-P129Q-N240K, G97A-G128A-Y217Q-T55P-A134T, G97A-G128A-Y217Q-N25Y-N61P-S63H, G97A-G128A-Y217Q-S87T-A88L-S89G-P129S, G97A-G128A-Y217Q-T55P-L75H-N76G, G97A-G128A-Y217Q-S24G-N25G-S53G-S78N-S87T-A88L-S89G-S101N-V203Y, G97A-G128A-Y217Q-T55P-I115V, 097A-G128A-Y217Q-T55P-A116N-N117S-N118G, G97A-G128A-Y217Q-S24G-N25G-A116N-N117S-N118G, G97A-G128A-Y217Q-S24R-P129Q-S130G-G131S, G97A-G128A-Y217Q-G23A-S24G-N25G-G211R-N212S-K213V, G97A-G128A-Y217Q-S24G-N25G-T55P-N61P-S78N-S101N-V203Y, G97A-G128A-Y217Q-T55P-S78N-S87T-A88L-S89G-S101N, G97A-G128A-Y217Q-I115V-A273S, G97A-G128A-Y217Q-N25Y-T55P, 097A-G128A-Y217Q-S24G-N25G-S53G-T55P-N61P-S78N-S87T-A88L-S89G-S101N-V203Y, G97A-G128A-Y217Q-Q59S-N61P-N240K, G97A-G128A-Y217Q-S161P-L267V, G97A-G128A-Y217Q-S24G-N25G-S53G-T55P-N61P-S78N-S87T-A88L-S89G-S101N, G97A-G128A-Y217Q-S87T-A88L-S89G-S101N, G97A-G128A-Y217Q-S24G-N25G-N61P-S101N, G97A-G128A-Y217Q-S24G-N25G-S53G-T55P-S101N-V203Y, G97A-G128A-Y217Q-N240K, G97A-G128A-Y217Q-S24G-N25G-S53G-T55P-S87T-A88L-S89G-S101N-V203Y, 097A-G128A-Y217Q-S24G-N25G-T55P-S101N, G97A-G128A-Y217Q-N61P-S63H-A128S-P129Q, G97A-G128A-Y217Q-S89Y-P129Q-S130G-G131S, 097A-G128A-Y217Q-P129Q-S130G-G131S-V203Y, G97A-G128A-Y217Q-I115V-N240K, G97A-G128A-Y217Q-S53G-N61P-S87T-A88L-S89G-S101N-V203Y, 097A-G128A-Y217Q-S161P-V203Y, 097A-G128A-Y217Q-S87T-A88L-S89G-N240K, G97A-G128A-Y217Q-S87T-A88L-S89G-P239R, G97A-G128A-Y217Q-T55P-N61P-S78N-S87T-A88L-S89G-S101N-V203Y, G97A-G128A-Y217Q-S24G-N25G-I115V-A134T, G97A-G128A-Y217Q-Y6Q-P129Q-S130G-G131S, G97A-G128A-Y217Q-T55P-S78N-S89Y, G97A-G128A-Y217Q-S24G-N25G-T55P-S78N-A88V-S101N, G97A-G128A-Y217Q-N61P-S63H-S78N-I111V-A134T, G97A-G128A-Y217Q-S24G-N25G-S53G-T55P-S78N-S101N, G97A-G128A-Y217Q-S24G-N25G-S53G-S78N-S101N-V203Y, G97A-G128A-Y217Q-S53G-N61P-S101N-V203Y, 097A-G128A-Y217Q-S53G-T55P-S78N-S101N-V203Y, G97A-G128A-Y217Q-S53G-T55P-N61P-S78N-S87T-A88L-S89G-S101N, G97A-G128A-Y217Q-N240K-A273S, G97A-G128A-Y217Q-S78N-S87T-A88L-S89G-S101N, G97A-G128A-Y217Q-Q59S-N61P-S87T-A88L-S89G, G97A-G128A-Y217Q-N61P-S63H-S78N-S161P, G97A-G128A-Y217Q-N61P-S63H-S78N-I111V, 097A-G128A-Y217Q-T55P-A128S-P129Q, G97A-G128A-Y217Q-N61P-S78N-S101N-V203Y, G97A-G128A-Y217Q-N61E-A144K, G97A-G128A-Y217Q-A134T-P239R, G97A-G128A-Y217Q-S24G-N25G-S53G-S78N-S87T-A88L-S101N-V203Y, G97A-G128A-Y217Q-S24G-N25G-S53G-T55P-N61P-S101N-V203Y, G97A-G128A-Y217Q-N61P-S78N-S87T-A88L-S89G-S101N-V203Y, G97A-G128A-Y217Q-T55P-N240K, G97A-G128A-Y217Q-S24G-N25G-S87T-A88L-S89G-S101N, G97A-G128A-Y217Q-P129Q-S130G-G131S-P239R, G97A-G128S-Y217Q, G97A-G128A-Y217Q-S53G-N61P-S101N, G97A-G128A-Y217Q-I111V-P129Q-G211T, G97A-G128A-Y217Q-S24G-N25G-S53G-S101N-V203Y, G97A-G128A-Y217Q-Q59S-N61P-S87G-A88V-S89A, G97A-G128A-Y217Q-S24G-N25G-S78N-S87T-A88L-S89G-S101N, G97A-G128A-Y217Q-P129Q-S130G-G131S-S162K, G97A-G128A-Y217Q-T55P-P129Q-S130G-G131S, G97A-G128A-Y217Q-T55P-V203Y, G97A-G128A-Y217Q-S87G-A88V-S89A-P129Q-S130G-G131S, G97A-G128A-Y217Q-S24G-N25G-S53G-T55P-N61P-S78N-S87T-A88L-S89G, 097A-G128A-Y217Q-I111V-P129Q-S130G-G131S, G97A-G128A-Y217Q-I111V-A273S, G97A-G128A-Y217Q-N61P-S87T-A88L-S89G, G97A-G128A-Y217Q-T22N-S24A-N61P-S63H, G97A-G128A-Y217Q, G97A-G128A-Y217Q-S53G-S78N-S87T-A88L-S89G-S101N-P129S-V203Y, G97A-G128A-Y217Q-S159K-L267V, G97A-G128A-Y217Q-P40E-S53Y-S78Y-P86S-S87G-A88V, G97A-G128A-Y217Q-S24R-S145D, G97A-G128A-Y217Q-I111V-S159K, G97A-G128A-Y217Q-T55P-P129L, G97A-G128A-Y217Q-Q59S-N61P-V203Y, G97A-G128A-Y217Q-T55P-S78N-S87T-A88L-S89G-S101N-V203Y, G97A-G128A-Y217Q-S24G-N25G-S53G-S78N-S101N, G97A-G128A-Y217Q-S53G-N61P-S78N-S87T-A88L-S89G-S101N-V203Y, G97A-G128A-Y217Q-S89Y, G97A-G128A-Y217Q-S24R-P129V, G97A-G128A-Y217Q-S87G-A88V-S89A-A116N-N117S-N118G-P172H, G97A-G128A-Y217Q-I111V-A134T, G97A-G128A-Y217Q-Q59S-N61P-P129Q-S130G-G131S, G97A-G128A-Y217Q-P5S-S87G-A88V-S89A-A116G-N117R, Y217Q-N61P-

A97G-G102A-A128G-P129S, G97A-G128A-Y217Q-S24G-N25G-S53G-N61P-S78N, G97A-G128A-Y217Q-S145D-S159K-N240K-Q275E, G97A-G128A-Y217Q-T55P-A128S-P129D, G97A-G128A-Y217Q-G23A-S24G-N25G-A128S-P129D, G97A-G128A-Y217Q-S24G-N25G-S53G-S78N-S87T-A88L-S89G-V203Y, G97A-G128A-Y217Q-I111V-P239R, G97A-G128A-Y217Q-S87G-A88V-S89A-S162K, G97A-G128A-Y217Q-S87T-A88L-S89G-I115V, G97A-G128A-Y217Q-S24G-N25G-T55P-S78N, G97A-G128A-Y217Q-T55P-A92G, G97A-G128A-Y217Q-S24G-N25G-S53G-S87T-A88L-S89G-V203Y, G97A-G128A-Y217Q-T22N-S24A-T55P, G97A-G128A-Y217Q-S53G-S87T-A88L-S89G-S101N-V203Y, G97A-G128A-Y217Q-S24G-N25G-S53G-T55P-S78N-S87T-A88L-S89G, G97A-G128A-Y217Q-P129Q-S130G-G131S-S159K, G97A-Y217Q-N61P-N62Q-G100N-A128G, G97A-G128A-Y217Q-S24R-S78N-S182P-L267V, G97A-G128A-Y217Q-P239R-A273S, G97A-G128A-Y217Q-S53G-S78N-S87T-A88L-S89G-S101N-V203Y, G97A-G128A-Y217Q-P129Q-S130G-G131S-T242R, G97A-G128A-Y217Q-S3F-S87T-A88L-S89G-G211T, G97A-G128A-Y217Q-S24G-N25G-L75H-N76G, G97A-G128A-Y217Q-S53G-T55P-N61P-S78N-S87T-A88L-S89G, G97A-G128A-Y217Q-S87T-A88L-S89G-A144K, G97A-G128A-Y217Q-S78N-S87T-A88L-S89G-V203Y, G97A-G128A-Y217Q-Q59S-N61P-A116N-N117S-N118G, G97A-G128A-Y217Q-S87T-A88L-S89G-I111V, G97A-G128A-Y217Q-S24R-S145D-P239R-Q275E, G97A-G128A-Y217Q-S145D-A273S, G97A-G128A-Y217Q-S24G-N25G-K141E-T242R, G97A-G128A-Y217Q-S87T-A88L-S89G-S101N-V203Y, G97A-G128A-Y217Q-A116N-N117S-N118G-P129Q-S130G-G131S, G97A-G128A-Y217Q-S89Y-G211T, G97A-G128A-Y217Q-S87G-A88V-S89A-A116N-N117S-N118G-A144T, G97A-G128A-Y217Q-S24G-N25G-S78N-S87T-A88L-S89G-S101N-V203Y, G97A-G128A-Y217Q-S24G-N25G-P129V, G97A-Y217Q-N61P-A128G-P129S-S130P, G97A-G128A-Y217Q-T55P-N61P-S87T-A88L-S89G-G110C-S130P, G97A-Y217Q-N123G-A128G, G97A-G128A-Y217Q-N61P-N62Q-G100N-G102A-M124I, S78N-G97A-G128A-Y217Q, G97A-S101N-G128A-Y217Q, G97A-G128A-A137V-Y217Q, N61P-G97A-G128A-Y217Q, G97A-G128A-S130P-Y217Q, G97A-Q103N-G128A-Y217Q, S63T-G97A-G128A-Y217Q, G97A-G102A-G128A-Y217Q, G97A-N109D-G128A-Y217Q-S248R, S87R-G97A-G128A-Y217Q, G97A-G128A-S188D-Y217Q, S87D-G97A-G128A-Y217Q-S248R, G97A-G128A-S188D-S248R-Y217Q, G97A-G128A-S248D-Y217Q, S78N-G97A-G128A-Y217Q-L267V, S78N-G97A-G128A-Y217Q-S161P, S78N-G97A-G128A-Y217Q-I115V, S78N-G97A-G128A-Y217Q-A273S, S78N-G97A-G128A-Y217Q-G211T, S78N-G97A-G128A-Y217Q, S78N-G97A-G128A-Y217Q-I111V, S78N-G97A-G128A-Y217Q-V147L, S78N-G97A-G128A-Y217Q-I108V, S78N-G97A-G128A-Y217Q-S89Y, S78N-G97A-G128A-Y217Q-A138T, G97A-G128A-Y217Q-A134T-K213L, G97A-G128A-Y217Q-G23A-S24G-N25G-P129V, 097A-G128A-Y217Q-S24R-P239R, G97A-G128A-Y217Q-S24R-S87T-A88L-S89G

In one aspect of said composition comprising a cold water protease and a material selected from the group consisting of: an encapsulate comprising a perfume, a GG36 variant protease, a hueing agent, an amphiphilic cleaning polymer and mixtures thereof, said variant of the protease having SEQ ID NO:2 comprises three, four, five, six, seven, eight, nine, 10, 11, 12, 13, 14 or 15 mutations within the group of positions comprising positions 24, 25, 40, 52. 53, 55, 58, 59, 61, 62, 63, 68, 78, 86, 87, 88, 89, 92, 96, 97, 100, 101, 103, 104, 106, 111, 114, 115, 116, 117, 118, 123, 124, 125, 126, 128, 129, 130, 131, 132, 133, 134, 144, 145, 159, 161, 162, 167, 194, 203, 206, 213, 217, 227, 232, 239, 240, 242, 265, 267, and 275.

In one aspect of said composition comprising a cold water protease and a material selected from the group consisting of: an encapsulate comprising a perfume, a GG36 variant protease, a hueing agent, an amphiphilic cleaning polymer and mixtures thereof, said variant of the protease having SEQ ID NO:2 comprises a total of three, four, five, six, seven, eight, nine, 10, 11, 12, 13, 14 or 15 mutations selected from groups (a) and (b) below:

(a) charged mutations selected from the group consisting of N61E, A144K, P129E, P239R, P40E, Q103E, Q206E, Q275E, S145D, S159K, S162K, S24R, S63H, S87D and T242R; and (b) neutral mutations selected from the group consisting of A114G, A116N, A133V, A134T, A232T, A88V, A92G, F58G, 0100T, G128A, G131S, G97A, I111V, I115V, K213L, K265N, L126A, L267V, L96T, M124V, N117S, N118G, N123G, N240K, N25G, N61P, N62Q, N62R, N62S, P129Q, P129V, P194L, P239V, P52L, P86S, Q59S, S101N, S125A, S130G, S132N, S161P, S24G, S53G, S78N, S87G, S89Y, T55P, V203Y, V227T, V68A, W106F, Y104N, Y167A, and Y217Q.

In one aspect of said composition comprising a cold water protease and a material selected from the group consisting of: an encapsulate comprising a perfume, a GG36 variant protease, a hueing agent, an amphiphilic cleaning polymer and mixtures thereof, said variant of the protease having SEQ ID NO:2 comprises one or more mutations, and having a total net charge of −1, 0 or +1 relative to the BPN' wild-type.

In one aspect of said composition comprising a cold water protease and a material selected from the group consisting of: an encapsulate comprising a perfume, a GG36 variant protease, a hueing agent, an amphiphilic cleaning polymer and mixtures thereof, said composition comprises an adjunct ingredient selected from the group consisting of: a surfactant, a builder, a chelating agent, a dye transfer inhibiting agent, a dispersant, one or more additional enzyme, an enzyme stabilizer, a catalytic material, a bleach activators, a hydrogen peroxide, a source of hydrogen peroxide, a preformed peracid, a polymeric dispersing agent, a clay soil removal/anti-redeposition agent, a brightener, a suds suppressor, a dye, a perfume, a perfume delivery system, a structure elasticizing agent, a fabric softener, a carrier, a hydrotrope, a processing aid, a solvent, a pigment and mixtures thereof.

In one aspect of said composition comprising a cold water protease and a material selected from the group consisting of: an encapsulate comprising a perfume, a GG36 variant protease, a hueing agent, an amphiphilic cleaning polymer and mixtures thereof, said composition comprises a third non-immunoequivalent protease that is a subtilisin (EC 3.4.21.62) protease said subtilisin (EC 3.4.21.62) protease being a cold water GG36 variant protease.

In one aspect of said composition comprising a cold water protease and a material selected from the group consisting of: an encapsulate comprising a perfume, a GG36 variant protease, a hueing agent, an amphiphilic cleaning polymer and mixtures thereof, said composition comprises an additional enzyme selected from the group consisting of hemicellulases, peroxidases, proteases, cellulases, cellobiose dehydrogenases, xyloglucanases, xylanases, lipases, phospholipases, esterases, cutinases, pectinases, mannanases, pectate lyases, keratinases, reductases, oxidases, phenoloxidases, lipoxygenases, ligninases, pullulanases, tannases, pentosanases, lichenases glucanases, arabinosidases, hyaluronidase, chondroitinase, laccase, amylases, or mixtures thereof.

In one aspect of said composition comprising a cold water protease and a material selected from the group consisting of: an encapsulate comprising a perfume, a GG36 variant protease, a hueing agent, an amphiphilic cleaning polymer and mixtures thereof, said composition comprises an additional enzyme is selected from the group consisting of:

a) first-wash lipases;

b) alpha-amylases that are greater than 90% identical to the wild-type alkaline alpha-amylases derived from *Bacillus* sp. NCIB 12289, NCIB 12512, NCIB 12513, DSM 9375 DSM 12368, DSMZ no. 12649, KSM AP1378, KSM K36 or KSM K38;

c) microbial-derived endoglucanases; and d) mixtures thereof.

In one aspect of said composition comprising a cold water protease and a material selected from the group consisting of: an encapsulate comprising a perfume, a GG36 variant protease, a hueing agent, an amphiphilic cleaning polymer and mixtures thereof, said composition comprises a material selected from the group consisting of:

a) an alcohol ethoxysulphate surfactant;

b) a chelant selected from the group consisting of DTPA (Diethylene triamine pentaacetic acid), HEDP (Hydroxyethane diphosphonic acid), DTPMP (Diethylene triamine penta(methylene phosphonic acid)), ethylenediaminedisuccinic acid (EDDS), 1,2-Dihydroxybenzene-3,5-disulfonic acid disodium salt hydrate, and derivatives of such chelants; and c) mixtures thereof.

In one aspect of said composition comprising a cold water protease and a material selected from the group consisting of: an encapsulate comprising a perfume, a GG36 variant protease, a hueing agent, an amphiphilic cleaning polymer and mixtures thereof, said composition comprises a material selected from the group consisting of:

a) an alcohol ethoxysulphate surfactant having an alkyl chain length of from 10 to 14 and a degree of ethoxylation from 1 to 4;

b) a chelant selected from the group consisting of DTPA (Diethylene triamine pentaacetic acid), HEDP (Hydroxyethane diphosphonic acid), DTPMP (Diethylene triamine penta(methylene phosphonic acid)), ethylenediaminedisuccinic acid (EDDS), 1,2-Dihydroxybenzene-3,5-disulfonic acid disodium salt hydrate, and derivatives of such chelants; and c) mixtures thereof.

In one aspect of said composition comprising a cold water protease and a material selected from the group consisting of: an encapsulate comprising a perfume, a GG36 variant protease, a hueing agent, an amphiphilic cleaning polymer and mixtures thereof, said composition comprises, based on total composition weight, a chelant level of from about 1% to about 5%.

In one aspect of said composition comprising a cold water protease and a material selected from the group consisting of: an encapsulate comprising a perfume, a GG36 variant protease, a hueing agent, an amphiphilic cleaning polymer and mixtures thereof, said composition comprises a fabric hueing agent selected from the group consisting of a) dyes;

b) dye-clay conjugates comprising at least one cationic-basic dye and a smectite clay; and c) mixtures thereof.

In one aspect of said composition comprising a cold water protease and a material selected from the group consisting of: an encapsulate comprising a perfume, a GG36 variant protease, a hueing agent, an amphiphilic cleaning polymer and mixtures thereof, said composition comprises a fabric hueing agent selected from the group consisting of a) small molecule dyes; polymeric dyes and mixtures thereof;

b) dye-clay conjugates comprising at least one cationic-basic dye and a smectite clay; and c) mixtures thereof.

In one aspect of said composition comprising a cold water protease and a material selected from the group consisting of: an encapsulate comprising a perfume, a GG36 variant protease, a hueing agent, an amphiphilic cleaning polymer and mixtures thereof, said composition comprises based on total composition weight:

a) from about 0.0005 wt % to about 0.1 wt % of said cold water protease; and b) one or more of the following:

(i) from about 0.00003 wt % to about 0.1 wt % of a fabric hueing agent;

(ii) from about 0.001 wt % to about 5 wt %, of a perfume capsules;

(iii) from about 0.1 wt % to about 5 wt % of a amphiphilic cleaning polymer;

(iv) from about 0.00003 wt % to about 0.1 wt % of a GG36 variant protease.

In one aspect of said composition comprising a cold water protease and a material selected from the group consisting of: an encapsulate comprising a perfume, a GG36 variant protease, a hueing agent, an amphiphilic cleaning polymer and mixtures thereof, said composition has a single or multi-compartment unit dose form.

In one aspect of said composition comprising a cold water protease and a material selected from the group consisting of: an encapsulate comprising a perfume, a GG36 variant protease, a hueing agent, an amphiphilic cleaning polymer and mixtures thereof, said composition is in the form of a multi-compartment unit dose, wherein at least one protease is in a different compartment to any additional enzymes and/or chelant.

A fabric and home product that may comprise one or more cold water proteases and a material selected from the group consisting of: an encapsulate comprising a perfume, a hueing agent, an amphiphilic cleaning polymer and mixtures thereof, with the balance of any aspects of the aforementioned composition is made up of one or more adjunct materials, is disclosed.

In one aspect of the aforementioned fabric and home care product, said fabric and home care product may comprise, based on total fabric and home care product weight, from about 0.0005 wt % to about 0.1 wt %, from about 0.001 wt % to about 0.05 wt %, or even from about 0.002 wt % to about 0.03 wt % of said cold water protease.

In one aspect of the aforementioned fabric and home care product, said fabric and home care product may comprise, based on total fabric and home care product weight, about 0.00003 wt % to about 0.1 wt %, from about 0.00008 wt % to about 0.05 wt %, or even from about 0.0001 wt % to about 0.04 wt %, fabric hueing agent;

In one aspect of the aforementioned fabric and home care product, said fabric and home care product may comprise, based on total fabric and home care product weight, from about 0.001 wt % to about 5 wt %, from about 0.01 wt % to about 2 wt %, or even from about 0.03 wt % to about 0.5 wt %, perfume capsules.

In one aspect of the aforementioned fabric and home care product, said fabric and home care product may comprise, based on total fabric and home care product weight, from about 0.1 wt % to about 5 wt %, from about 0.25 wt % to about 2.5 wt %, or even from about 0.3 wt % to about 1.5 wt % amphiphilic cleaning polymer.

Cold Water Proteases

In addition to the cold water proteases disclosed above in the Fabric and Home Care Products, suitable cold water protease variants are enzymes that exhibit one or more of the following four criteria:

(a) a performance index of at least 1.1, at least 1.2, at least 1.3, at least 1.4, at least 1.5, at least 1.6, at least 1.7, at least 1.8, at least 1.9; at least 2 from 1.1 to about 10, from 1.1 to about 8 or even from 1.1 to about 5 on BMI at pH 8 and 60° F. when compared to Purafect Prime (SEQ ID NO:2 with the mutation Y217L), as defined in Test Method 2 and/or Test Method 3;

(b) a performance index of at least 1.3, at least 1.4, at least 1.5, at least 1.6, at least 1.7, at least 1.8, at least 1.9, at least 2, from 1.3 to about 10, from 1.3 to about 8 or even from 1.3 to about 5 on BMI at pH 8 and 60° F. when compared to BPN' (SEQ ID NO:2), as defined in Test Method 2 and/or Test Method 3;

(c) a performance index of at least 0.9, at least 1.0, at least 1.1, at least 1.2, at least 1.3, at least 1.4, at least 1.5, at least 1.6, at least 1.7, at least 1.8, at least 1.9, at least 2 from 0.9 to about 10, from 0.9 to about 8 or even from 0.9 to about 5 on BMI at pH 8 and 60° F. when compared to SEQ ID NO:4, as defined in Test Method 2 and/or Test Method 3;

(d) a performance index of at least 0.9, at least 1.0, at least 1.1, at least 1.2, at least 1.3, at least 1.4, at least 1.5, at least 1.6, at least 1.7, at least 1.8, at least 1.9, at least 2 from 0.9 to about 10, from 0.9 to about 8 or even from 0.9 to about 5 on BMI at pH 8 and 60° F. when compared to SEQ ID NO:6, as defined in Test Method 2 and/or Test Method 3.

Examples of such proteases can be found in Examples 2-18 and 31 of the present specification. Cold water proteases as defined above may be used in Fabric and Home Care Products. Thus, in pne aspect, Fabric and Home Care Products comprising such cold water proteases are disclosed.

GG36 Proteases of this Invention

Suitable GG36 proteases can be selected from the variants described in Examples 19 to 30. In one aspect, GG36 cold water proteases may be Series 1 GG36 cold water proteases.

Suitable Series 1 GG36 cold water protease variants include enzymes derived from a parent protease, said parent protease's sequence being at least 90%, at least 95%, at least 96%, at least 97%, at least 98%, at least 99%, at least 99.5% or 100% identical to the amino acid sequence of SEQ ID NO:755, said variant having one or more of the following characteristics:

a) a Test Method 4 performance index of at least 1.1, at least 1.2, at least 1.3, at least 1.4, at least 1.5, at least 1.6, at least 1.7, at least 1.8, at least 1.9; at least 2; from 1.1 to about 10, from 1.1 to about 8 or even from 1.1 to about 5;

b) a Test Method 5 performance index of at least 1.1, at least 1.2, at least 1.3, at least 1.4, at least 1.5, at least 1.6, at least 1.7, at least 1.8, at least 1.9, at least 2; from 1.1 to about 10, from 1.1 to about 8 or even from 1.1 to about 5;

c) a Test Method 6 performance index of at least 1.0, at least 1.1, at least 1.2, at least 1.3, at least 1.4, at least 1.5, at least 1.6, at least 1.7, at least 1.8, at least 1.9, at least 2, from 1.0 to about 10, from 1.0 to about 8 or even from 1.0 to about 5.

Suitable Series 1 GG36 cold water proteases can be derived from subtilisins, particularly those derived from subtilisin *Bacillus Lentus* of SEQ ID NO:755 and in one aspect may comprise one or more of the following mutations:

A1R, Q2S, V4R, V4S, S9A, R10S, P14K, A16S, H17R, N18R, G20R, T22A, T22R, S24R, S24W, G25R, G25V, V26F, L42I, N43R, N43A, G46R, P52F, P52E, P52N, T57R, Q59A, N62E, N62Q, V68A, V68C, T71G, 172C, A74C. L75A, L75F, L75R, N76D, S78R, L82R, P86W, E89P, E89T, E89G, E89H, E89I, E89V, E89W, Y91N, K94N, G100S, S101A, S101N, S101G, S101D, S103G, S103N, V104L, V104I, S106V, S106G, A108I, L111V, E112V, G115K, G115R, N117F, G118I, V121F, S128D, S128F, S128L, S128N, P129E, S144R, L148I, A158E. G159E, S160D, S166D, N185E, N185I, R186H, S188E, S188D, D197F, V203E, Y209S, Y209N, Y209F, Y209T, Y209E, Y209H, Y209G, P210R, S212I, S212F, Y214F, A215N, A215D, A215E, L217E, L217N, T224A, A230E, A231I, Q236F, N238R, N238K, P239K, P239G, P239R, P239S, W241R, S242R, S242L, N243R, V244R, N248I, N248V, H249R, L250I, N252R, T253R, L262D, Y263F, S265F, L267V, L267N. N269I, N269R, E271F, E271I, E271H, E271P, E271T, E271V, E271L and/or A272F In one aspect, suitable Series 1 GG36 cold water proteases include subtlisins, particularly *Bacillus Lentus* of SEQ ID NO:755, that may comprise one or more of the following sets of mutations, insertions or deletions:

T022R-S024R, S009A-E271L, N018R-W241R, N018R-G115R, N043R-H249R, G020R-H249R, V004R-H249R, G020R-S024R, N018R-H249R, S009A-G020R, G020R-W241R, S009A-S078R, G020R-G115R, N018R-S024R, S024R-S242R, T022R-G115R, N018R-N043R, G020R-N043R, N018R-S242R, S242R-N269R, N018R-V244R, S024R-N269R, G020R-E271L, S024R-E271L, V004R-S009A, G020R-N269R, A001R-S024R, V244R-E271L, S009A-N018R, W241R-E271L, V004R-S024R, S009A-H249R, S009A-T022R, N062E-P129E, N062E-G159E, A016S-L148I, A158E-H249R, A016S-N062E, L111V-S188D, T022A-N062E, N062E-L148I, T022A-P129E, N062E-E271F, N062E-A158E, A016S-G159E, N062E-R186H, S128N-G159E, N062E-S188D, N062E-S128N, L148I-G159E, S103G-A158E, L111V-G159E, A158E-E271F, A016S-S188D, T022A-L111V, S128N-A158E, A016S-A158E, V104L-A158E, S128N-R186H, G159E-Y209E, N062E-S101A, L111V-Y209E, L148I-S188D, S101A-Y209E, T022A-S188D, A016S-T022A, S128N-P129E, A016S-Y209E, A016S-S128N, T022A-E089P, S128N-Y209E, E089P-A158E, N062E-S103G, R186H-E271F, A016S-P129E, E089P-G159E, L111V-H249R, S101A-P129E, L148I-Y209E, T022A-G159E, P129E-H249R, P129E-Y209E, V104L-P129E, S128N-S188D, L111V-A158E, T022A-A158E, N062E-Y209E, N062E-H249R, S101A-R186H, E089P-P129E, P129E-E271, T22A-L111V-G159E, S101A-S103G-V104L-Y209E, S101A-S103G-V104L-G159E, S101A-S103G-V104L-S188D, S101G-S103A-V104I-G159D, T22A-S103G-G159E, T22A-S128N-E271F-Y209E, T22A-Y209E-E271F, T22A-S101A-Y209E, S101A-Y209E-E271F, T22A-L111V-S128N, T22A-S101A-G159E, S101A-S103G-V104L, T22A-S101A-S103G-V104L, S101A-S103G-V104L, S101G-S103A-V104I, S101A-S103G-V104L-S128N, S103A-V104I-G159D-A232V-Q236H-Q245R-N248D-N252K, S101G-V104I-G159D-A232V-Q236H-Q245R-N248D-N252K, S101G-S103A-G159D-A232V-Q236H-

Q245R-N248D-N252K, S101G-S103A-V104L-A232V-Q236H-Q245R-N248D-N252K, S101G-S103A-V104L-G159D-Q236H-Q245R-N248D-N252K, S101G-S103A-V104L-G159D-A232V-Q245R-N248D-N252K, S101G-S103A-V104L-G159D-A232V-Q236H-N248D-N252K, S101G-S103A-V104L-G159D-A232V-Q236H-Q245R-N252K, S101G-S103A-V104L-G159D-A232V-Q236H-Q245R-N248D, N62E-S101G-S103A-V104I-G159D-A232V-Q245R-N248D-E271F, N62E-S101G-S103A-V104I-G159D-A232V-Q245R-N248D-H249R, T22A-S101G-S103A-V104I-G159D-A232V-Q245R-N248D-H249R, S101G-S103A-V104I-G159D-A232V-Q245R-N248D-S24R, S101G-S103A-V104I-G159D-A232V-Q245R-N248D-T253R, S101G-S103A-V104I-A158E-A232V-Q245R-N248D-H249R, T22A-S101G-S103A-V104I-G159D-A232V-Q245R-N248D-E271F, S101G-S103A-V104I-G159E-A232V-Q245R-N248D-H249R, S101G-S103A-V104I-G159D-A232V-Q245R-N248D-N238R, S101G-S103A-V104I-A158E-A232V-Q245R-N248D-E271F, S101G-S103A-V104I-G159D-A232V-Q245R-N248D, S101G-S103A-V104I-G159D-A232V-Q245R-N248D-E271F, S101G-S103A-V104I-G159D-A232V-Q245R-N248D-N76D, and/or S101G-S103A-V104I-G159E-A232V-Q245R-N248D-E271F.

In one aspect, suitable Series 1 GG36 cold water proteases include variants of subtlisins, particularly *Bacillus Lentus* of SEQ ID NO:755, said variants comprising three, four, five, six, seven, eight, nine, 10, 11, 12, 13, 14 or 15 mutations within the group of positions comprising positions 1, 2, 4, 9, 10, 14, 16, 17, 18, 20, 22, 24, 25, 26, 42, 43, 46, 52, 57, 59, 62, 68, 71, 72, 74, 75, 76, 78, 82, 86, 89, 91, 94, 100, 101, 103, 104, 106, 108, 111, 112, 115, 117, 118, 121, 128, 129, 144, 148, 158, 159, 160, 166, 185, 186, 188, 197, 203, 209, 210, 212, 214, 215, 217, 224, 230, 231, 236, 238, 239, 241, 242, 243, 244, 248, 249, 250, 252, 253, 262, 263, 265, 267, 269, 271 and 272.

In one aspect, suitable Series 1 GG36 cold water proteases include variants of subtlisins, particularly *Bacillus Lentus* of SEQ ID NO:755, said variants comprising a total of three, four, five, six, seven, eight, nine, 10, 11, 12, 13, 14 or 15 mutations selected from the group comprising: A1R, Q2S, V4R, V4S, S9A, R10S, P14K, A16S, H17R, N18R, G20R, T22A, T22R, S24R, S24W, G25R, G25V, V26F, L42I, N43R, N43A, G46R, P52F, P52E, P52N, T57R, Q59A, N62E, N62Q, V68A, V68C, T71G, 172C, A74C. L75A, L75F, L75R, N76D, S78R, L82R, P86W, E89P, E89T, E89G, E89H, E89I, E89V, E89W, Y91N, K94N, G100S, S101A, S101N, S101G, S101D, S103G, S103N, V104L, V104I, S106V, S106G, A108I, L111V, E112V, G115K, G115R, N117F, G118I, V121F, S128D, S128F, S128L, S128N, P129E, S144R, L148I, A158E. G159E, S160D, S166D, N185E, N185I, R186H, S188E, S188D, D197F, V203E, Y209S, Y209N, Y209F, Y209T, Y209E, Y209H, Y209G, P210R, S212I, S212F, Y214F, A215N, A215D, A215E, L217E, L217N, T224A, A230E, A231I, Q236F, N238R, N238K, P239K, P239G, P239R, P239S, W241R, S242R, S242L, N243R, V244R, N248I, N248V, H249R, L250I, N252R, T253R, L262D, Y263F, S265F, L267V, L267N. N269I, N269R, E271F, E271I, E271H, E271P, E271T, E271V, E271L and A272F; and optionally one or more of the following mutations: S103A, G159D, Q236H, Q245R, N248D and N252K.

In one aspect, said Series 1 GG36 cold water protease is variant of subtilisin GG36 having SEQ ID NO:755, said variant comprising one or more mutations, and having a total net charge of −5, −4, −3, −2, −1 or 0 relative to subtilisin GG36 wild-type, is disclosed.

In one aspect, said Series 1 GG36 cold water proteases are low ionic strength cold water proteases. Such low ionic strength proteases are variants of subtilisin GG36 having SEQ ID NO:755, said variants comprising one or more mutations, and having a total net charge of −5, −4, −3, −2, −1 or 0 relative to subtilisin GG36 wild-type, is disclosed. These mutations are selected from:

(a) two or more of the following mutations: A1R, Q2S, V4R, V4S, S9A, R10S, P14K, A16S, T22A, T22R, S24R, G25V, V26F, L42I, P52F, P52E, P52N, N62E, N62Q, V68A, V68C, T71G, 172C, A74C, L75A, L75F, S78R, E89P, E89T, E89G, E89H, E89W, Y91N, K94N, G100S, S101A, S101N, S101G, S101D, S103G, S103N, V104L, V104I, A108I, L111V, E112V, G115K, N117F, V121F, S128D, S128F, S128L, S128N, P129E, L148I, A158E. G159E, S160D, S166D, N185E, R186H, S188E, S188D, V203E, Y209S, Y209N, Y209F, Y209T, Y209E, Y209H, Y209G, P210R, S212I, S212F, Y214F, A215N, A215D, A215E, L217E, L217N, T224A, A230E, A231I, Q236F, N238R, N238K, P239K, P239G, P239R, N248V, H249R, L250I, L262D, Y263F, S265F, L267V, L267N. N269I, N269R, E271F, E271I, E271H and A272F; and/or (b) one or more of the following sets of mutations: N062E-P129E, N062E-G159E, A016S-L148I, A158E-H249R, A016S-N062E, L111V-S188D, T022A-N062E, N062E-L148I, T022A-P129E, N062E-E271F, N062E-A158E, A016S-G159E, N062E-R186H, S128N-G159E, N062E-S188D, N062E-S128N, L148I-G159E, S103G-A158E, L111V-G159E, A158E-E271F, A016S-S188D, T022A-L111V, S128N-A158E, A016S-A158E, V104L-A158E, S128N-R186H, G159E-Y209E, N062E-S101A, L111V-Y209E, L148I-S188D, S101A-Y209E, T022A-S188D, A016S-T022A, S128N-P129E, A016S-Y209E, A016S-S128N, T022A-E089P, S128N-Y209E, E089P-A158E, N062E-S103G, R186H-E271F, A016S-P129E, E089P-G159E, L111V-H249R, S101A-P129E, L148I-Y209E, T022A-G159E, P129E-H249R, P129E-Y209E, V104L-P129E, S128N-S188D, L111V-A158E, T022A-A158E, N062E-Y209E, N062E-H249R, S101A-R186H, E089P-P129E, P129E-E271F, T22A-L111V-G159E, S101A-S103G-V104L-Y209E, S101A-S103G-V104L-G159E, S101A-S103G-V104L-S188D, S101G-S103A-V104I-G159D, T22A-S103G-G159E, T22A-S128N-E271F-Y209E, T22A-Y209E-E271F, T22A-S101A-Y209E, S101A-Y209E-E271F, T22A-L111V-S128N, T22A-S101A-G159E, S101A-S103G-V104L, T22A-S101A-S103G-V104L, S101A-S103G-V104L, S101G-S103A-V104I, S101A-S103G-V104L-S128N, S103A-V104I-G159D-A232V-Q236H-Q245R-N248D-N252K, S101G-V104I-G159D-A232V-Q236H-Q245R-N248D-N252K, S101G-S103A-G159D-A232V-Q236H-Q245R-N248D-N252K, S101G-S103A-V104L-A232V-Q236H-Q245R-N248D-N252K, S101G-S103A-V104L-G159D-Q236H-Q245R-N248D-N252K, S101G-S103A-V104L-G159D-A232V-Q245R-N248D-N252K, S101G-S103A-V104L-G159D-A232V-Q236H-N248D-N252K, S101G-S103A-V104L-G159D-A232V-Q236H-Q245R-N252K, S101G-S103A-V104L-G159D-A232V-Q236H-Q245R-N248D, N62E-S101G-S103A-V104I-G159D-A232V-Q245R-N248D-E271F, N62E-S101G-S103A-V104I-G159D-A232V-Q245R-N248D-H249R, T22A-S101G-S103A-V104I-G159D-A232V-Q245R-N248D-H249R, S101G-S103A-V104I-G159D-A232V-Q245R-N248D-S24R, S101G-S103A-V104I-

G159D-A232V-Q245R-N248D-T253R, S101G-S103A-V104I-A158E-A232V-Q245R-N248D-H249R, T22A-S101G-S103A-V104I-G159D-A232V-Q245R-N248D-E271F, S101G-S103A-V104I-G159E-A232V-Q245R-N248D-H249R, S101G-S103A-V104I-G159D-A232V-Q245R-N248D-N238R, S101G-S103A-V104I-A158E-A232V-Q245R-N248D-E271F, S101G-S103A-V104I-G159D-A232V-Q245R-N248D, S101G-S103A-V104I-G159D-A232V-Q245R-N248D-E271F, S101G-S103A-V104I-G159D-A232V-Q245R-N248D-N76D and S101G-S103A-V104I-G159E-A232V-Q245R-N248D-E271F;

In one aspect the above low ionic strength Series 1 GG36 cold water proteases form part of a detergent composition that is diluted in water, typically within a washing machine, to form a wash liquor, whose conductivity is from about 0.1 mS/cm to about 3 mS/cm, from about 0.3 mS/cm to about 2.5 mS/cm, or even from about 0.5 mS/cm to about 2 mS/cm In one aspect, said Series 1 GG36 cold water proteases are high ionic strength cold water proteases. Such high ionic strength proteases are variants of subtilisin GG36 having SEQ ID NO:755, said variants comprising two or more mutations, and having a total net charge of +5, +4, +3, +2, +1 or 0 relative to subtilisin GG36 wild-type. These mutations are selected from:

a) two or more of the following mutations V4R, H17R, N18R, G20R, T22R, S24R, S24W, G25R, N43R, N43A, G46R, P52F, P52N, T57R, Q59A, N62Q, T71G, L75R, N76D, S78R, L82R, P86W, E89P, E89W, E89T, E89I, E89H, E89V, V104L, S106V, S106G, G115R, G118I, V121F, S144R, N185I, D197F, Y209N, Y209S, L217E, A231I, P239R, P239S, W241R, S242R, S242L, N243R, V244R, N248I, H249R, N252R, T253R, E271T, E271V, E271L, E271H, E271F, E271P, AIR, S9A, S212F and N269R; and/or b) one or more of the following sets of mutations T022R-S024R, S009A-E271L, N018R-W241R, N018R-G115R, N043R-H249R, G020R-H249R, V004R-H249R, G020R-S024R, N018R-H249R, S009A-G020R, G020R-W241R, S009A-S078R, G020R-G115R, N018R-S024R, S024R-S242R, T022R-G115R, N018R-N043R, G020R-N043R, N018R-S242R, S242R-N269R, N018R-V244R, S024R-N269R, G020R-E271L, S024R-E271L, V004R-S009A, G020R-N269R, A001R-S024R, V244R-E271L, S009A-N018R, W241R-E271L, V004R-S024R, S009A-H249R, S009A-T022R, S101G-S103A-V104I-G159D-A232V-Q245R-N248D-E271F, S101G-S103A-V104I-A158E-A232V-Q245R-N248D-E271F, S101G-S103A-V104I-A158E-A232V-Q245R-N248D-H249R, S101G-S103A-V104I-G159D-A232V-Q245R-N248D-S24R, S101G-S103A-V104L-G159D-A232V-Q236H-Q245R-N252K, S101G-S103A-V104L-A232V-Q236H-Q245R-N248D-N252K In one aspect, the above high ionic strength Series 1 GG36 cold water proteases form part of a detergent composition that is diluted in water, typically within a washing machine, to form a wash liquor, whose conductivity is from about 3 mS/cm to about 30 mS/cm, from about 3.5 mS/cm to about 20 mS/cm, or even from about 4 mS/cm to about 10 mS/cm.

The charge of the Series 1 GG36 cold water protease variants is expressed relative to subtilisin GG36 protease wild-type having the amino acid sequence of SEQ ID NO:755. The amino acids that impart a single negative charge are D and E and those that impart a single positive charge are R, H and K. Any amino acid change versus SEQ ID NO:755 that changes a charge is used to calculate the charge of the Series 1 GG36 cold water protease variant. For example, introducing a negative charge mutation from a wild-type neutral position will add a net charge of −1 to the Series 1 GG36 cold water protease variant, whereas introducing a negative charge mutation (D or E) from a wild-type positive amino acid residue (R, H or K) will add a net charge of −2. Summing the charge changes from all the amino acid residues that are different for the Series 1 GG36 cold water protease variant versus subtilisin GG36 protease wild-type having the amino acid sequence of SEQ ID NO:755 gives the charge change of the Series 1 GG36 cold water protease variant. Without wishing to be bound by theory, it is believed that:

(a) the preferred charge range for Series 1 GG36 cold water proteases to be used in low conductivity laundry detergent solutions is −5, −4, −3, −2, −1, 0, particularly −2, −1;

(b) the preferred charge range for Series 1 GG36 cold water proteases to be used in high conductivity laundry detergent solutions is +5, +4, +3, +2, +1, 0, particularly +2, +1. By correctly selecting the charge unexpectedly improved levels of cold water cleaning performance can be obtained.

Low conductivity solutions are defined as having a conductivity of from about 0.1 mS/cm to about 3 mS/cm, from about 0.3 mS/cm to about 2.5 mS/cm, or even from about 0.5 mS/cm to about 2 mS/cm.

High conductivity having conductivity solutions are defined as having a conductivity of from about 3 mS/cm to about 30 mS/cm, from about 3.5 mS/cm to about 20 mS/cm, or even from about 4 mS/cm to about 10 mS/cm The above examples should be viewed as non-limiting. Once mutations are combined to optimize cold water performance, the enzyme charge can also be balanced by mutations in further positions.

Protease Amino Acid Numbering, Enzyme Nomenclature and Additional Definitions

The numbering of amino acid positions used in this patent is the *Bacillus amyloliquefaciens* subtilisin BPN' numbering system. Each amino acid position of each protease variant, including each Series 1 GG36 cold water protease variant, is numbered according to the numbering of corresponding amino acid position in the amino acid sequence of *Bacillus amyloliquefaciens* subtilisin BPN' as determined by alignment of the variant protease amino acid sequence with the *Bacillus amyloliquefaciens* subtilisin BPN' amino acid sequence.

An alternative numbering scheme is numbering the specific amino acid sequence of the *B. lentus* subtilisin GG36 protease, having the amino acid sequence of SEQ ID NO:755. None of the amino acid positions of the protease variants, including the Series 1 GG36 cold water protease variants, described herein are numbered using this alternative numbering scheme.

In describing Series 1 GG36 cold water protease variants herein, the following nomenclature is used for ease of reference: Original amino acid(s):position(s):substituted amino acid(s).

Mutations are named by the one letter code for the parent amino acid, followed by a three digit position number and then the one letter code for the variant amino acid. For example, mutating glycine (G) at position 87 to serine (S) is represented as "G087S" or "G87S". Multiple mutations are indicated by inserting a "-" between the mutations. Mutations at positions 87 and 90 are represented as either "G087S-A090Y" or "G87S-A90Y" or "G87S+A90Y" or "G087S+A090Y". For deletions, the one letter code "Z" is used. For an insertion relative to the parent sequence, the one letter code "Z" is on the left side of the position number. For a deletion, the one letter code "Z" is on the right side of the position number. For insertions, the position number is the position number before the inserted amino acid(s), plus 0.01 for each amino acid. For example, an insertion of three amino acids alanine (A), serine (S) and tyrosine (Y) between position 87 and 88 is shown as "Z087.01A-Z087.02S-Z087.03Y." Thus, combining all the mutations above plus a deletion at position 100 is: "G087S-Z087.01A-Z087.02S-Z087.03Y-A090Y-A100Z."

In all cases, the accepted IUPAC single letter or triple letter amino acid abbreviation is employed. The single letter X refers to any of the twenty amino acids.

The term "wild-type" in reference to an amino acid sequence or nucleic acid sequence indicates that the amino acid sequence or nucleic acid sequence is native or naturally occurring sequence. As used herein, the term "naturally-occurring" refers to anything (e.g., proteins, amino acids, or nucleic acid sequences) that are found in nature (i.e., have not been manipulated by means of recombinant methods). As used herein, the term, "non-naturally occurring" refers to anything that is not found in nature (e.g., recombinant nucleic acids produced in the laboratory).

As used herein with regard to amino acid residue positions, "corresponding to" or "corresponds to" or "corresponds" refers to an amino acid residue at the enumerated position in a protein or peptide, or an amino acid residue that is analogous, homologous, or equivalent to an enumerated residue in a protein or peptide. As used herein, "corresponding region" generally refers to an analogous position along related proteins or a reference protein.

The terms "derived from" and "obtained from" refer to not only a protease produced or producible by a strain of the organism in question, but also a protease encoded by a DNA sequence isolated from such strain and produced in a host organism containing such DNA sequence. Additionally, the term refers to a protease which is encoded by a DNA sequence of synthetic and/or cDNA origin and which has the identifying characteristics of the protease in question. To exemplify, "proteases derived from *Bacillus*" refers to those enzymes having proteolytic activity which are naturally-produced by *Bacillus*, as well as to serine proteases like those produced by *Bacillus* sources but which through the use of genetic engineering techniques are produced by non-*Bacillus* organisms transformed with a nucleic acid encoding the serine proteases.

The term "identical" in the context of two nucleic acids or polypeptide sequences refers to the residues in the two sequences that are the same when aligned for maximum correspondence, as measured using one of the following sequence comparison or analysis algorithms.

As used herein, "homologous genes" refers to a pair of genes from different, but usually related species, which correspond to each other and which are identical or very similar to each other. The term encompasses genes that are separated by speciation (i.e., the development of new species) (e.g., orthologous genes), as well as genes that have been separated by genetic duplication (e.g., paralogous genes).

The term "mature" form of a protein, polypeptide, or peptide refers to the functional form of the protein, polypeptide, or peptide without the signal peptide sequence and propeptide sequence.

As used herein, "homology" refers to sequence similarity or identity, with identity being preferred. Homology may be determined using standard techniques known in the art (See e.g., Smith and Waterman, Adv. Appl. Math. 2:482 [1981]; Needleman and Wunsch, J. Mol. Biol. 48:443 [1970\; Pearson and Lipman, Proc. Natl. Acad. Sci. USA 85:2444 [1988]; software programs such as GAP, BESTFIT, FASTA, and TFASTA in the Wisconsin Genetics Software Package (Genetics Computer Group, Madison, Wis.); and Devereux et al., Nucl. Acid Res. 12:387-395 [1984]). One example of a useful algorithm is PILEUP. PILEUP creates a multiple sequence alignment from a group of related sequences using progressive, pair-wise alignments. It can also plot a tree showing the clustering relationships used to create the alignment. PILEUP uses a simplification of the progressive alignment method of Feng and Doolittle (See, Feng and Doolittle, J. Mol. Evol. 35:351-360 [1987]). The method is similar to that described by Higgins and Sharp (See, Higgins and Sharp, CABIOS 5:151-153 [1989]). Useful PILEUP parameters including a default gap weight of 3.00, a default gap length weight of 0.10, and weighted end gaps. Another example of a useful algorithm is the BLAST algorithm, described by Altschul et al., (See, Altschul et al., J. Mol. Biol. 215:403-410 [1990]; and Karlin and Altschul, Proc. Natl. Acad. Sci. USA 90:5873-5787 [1993]). A particularly useful BLAST program is the WU-BLAST-2 program (See, Altschul et al., Meth. Enzymol. 266:460-480 [1996]). WU-BLAST-2 uses several search parameters, most of which are set to the default values. The adjustable parameters are set with the following values: overlap span=1, overlap fraction=0.125, word threshold (T)=11. The HSP S and HSP S2 parameters are dynamic values and are established by the program itself depending upon the composition of the particular sequence and composition of the particular database against which the sequence of interest is being searched. However, the values may be adjusted to increase sensitivity.

The percent sequence identity between a reference sequence and a test sequence of interest may be readily determined by one skilled in the art. The percent identity shared by polynucleotide or polypeptide sequences is determined by direct comparison of the sequence information between the molecules by aligning the sequences and determining the identity by methods known in the art. An example of an algorithm that is suitable for determining sequence similarity is the BLAST algorithm, (See, Altschul, et al., J. Mol. Biol., 215:403-410 [1990]). Software for performing BLAST analyses is publicly available through the National Center for Biotechnology Information. This algorithm involves first identifying high scoring sequence pairs (HSPs) by identifying short words of length W in the query sequence that either match or satisfy some positive-valued threshold score T when aligned with a word of the same length in a database sequence. These initial neighborhood word hits act as starting points to find longer HSPs containing them. The word hits are expanded in both directions along each of the two sequences being compared for as far as the cumulative alignment score can be increased. Extension of the word hits is stopped when: the cumulative alignment score falls off by the quantity X from a maximum achieved value; the cumulative score goes to zero or below; or the end of either sequence is reached. The BLAST algorithm parameters W, T, and X determine the sensitivity and speed of the alignment. The BLAST program uses as defaults a wordlength (W) of 11, the BLOSUM62 scoring matrix (See, Henikoff and Henikoff, Proc. Natl. Acad. Sci. USA 89:10915 [1992]) alignments (B) of 50, expectation (E) of 10, M'S, N'-4, and a comparison of both strands.

The BLAST algorithm then performs a statistical analysis of the similarity between two sequences (See e.g., Karlin and Altschul, supra). One measure of similarity provided by the BLAST algorithm is the smallest sum probability (P(N)), which provides an indication of the probability by which a match between two nucleotide or amino acid sequences would occur by chance. For example, a nucleic acid is considered similar to a serine protease nucleic acid of this invention if the smallest sum probability in a comparison of the test nucleic acid to a serine protease nucleic acid is less than about 0.1, more preferably less than about 0.01, and most preferably less than about 0.001. Where the test nucleic acid encodes a serine protease polypeptide, it is considered similar to a specified serine protease nucleic acid if the comparison results in a smallest sum probability of less than about 0.5, and more preferably less than about 0.2.

Percent "identical" or "identity" in the context of two or more nucleic acid or polypeptide sequences refers to two or more sequences that are the same or have a specified percentage of nucleic acid residues or amino acid residues, respectively, that are the same, when compared and aligned for maximum similarity, as determined using a sequence comparison algorithm or by visual inspection. "Percent sequence identity" or "% identity" or "% sequence identity or "% amino acid sequence identity" of a subject amino acid sequence to a reference (i.e., query) amino acid sequence means that the subject amino acid sequence is identical (i.e., on an amino acid-by-amino acid basis) by a specified percentage to the query amino acid sequence over a comparison length when the sequences are optimally aligned. Thus, 80% amino acid sequence identity or 80% identity with respect to two amino acid sequences means that 80% of the amino acid residues in two optimally aligned amino acid sequences are identical.

"Percent sequence identity" or "% identity" or "% sequence identity or "% nucleotide sequence identity" of a subject nucleic acid sequence to a reference (i.e. query) nucleic acid sequence means that the subject nucleic acid sequence is identical (i.e., on a nucleotide-by-nucleotide basis for a polynucleotide sequence) by a specified percentage to the query sequence over a comparison length when the sequences are optimally aligned. Thus, 80% nucleotide sequence identity or 80% identity with respect to two nucleic acid sequences means that 80% of the nucleotide residues in two optimally aligned nucleic acid sequences are identical.

In some embodiments, the percent sequence identity or % sequence identity" or "% identity" of a subject sequence to a query sequence can be calculated by optimally aligning the two sequences and comparing the two optimally aligned sequences over the comparison length. The number of positions in the optimal alignment at which identical residues occur in both sequences are determined, thereby providing the number of matched positions, and the number of matched positions is then divided by the total number of positions of the comparison length (which, unless otherwise specified, is the length of the query sequence). The resulting number is multiplied by 100 to yield the percent sequence identity of the subject sequence to the query sequence.

"Optimal alignment" or "optimally aligned" refers to the alignment of two (or more) sequences giving the highest percent identity score. For example, optimal alignment of two protein sequences can be achieved by manually aligning the sequences such that the maximum number of identical amino acid residues in each sequence are aligned together or by using software programs or procedures described herein or known in the art. Optimal alignment of two nucleic acid sequences can be achieved by manually aligning the sequences such that the maximum number of identical nucleotide residues in each sequence are aligned together or by using software programs or procedures described herein or known in the art.

In some embodiments, two polypeptide sequences are deemed "optimally aligned" when they are aligned using defined parameters, such as a defined amino acid substitution matrix, gap existence penalty (also termed gap open penalty), and gap extension penalty, so as to achieve the highest similarity score possible for that pair of sequences. The BLOSUM62 scoring matrix (See, Henikoff and Henikoff, supra) is often used as a default scoring substitution matrix in polypeptide sequence alignment algorithms (e.g., BLASTP). The gap existence penalty is imposed for the introduction of a single amino acid gap in one of the aligned sequences, and the gap extension penalty is imposed for each residue position in the gap. Exemplary alignment parameters employed are: BLOSUM62 scoring matrix, gap existence penalty=11, and gap extension penalty=1. The alignment score is defined by the amino acid positions of each sequence at which the alignment begins and ends (e.g., the alignment window), and optionally by the insertion of a gap or multiple gaps into one or both sequences, so as to achieve the highest possible similarity score.

Optimal alignment between two or more sequences can be determined manually by visual inspection or by using a computer, such as, but not limited to for example, the BLASTP program for amino acid sequences and the BLASTN program for nucleic acid sequences (See e.g., Altschul et al., Nucleic Acids Res. 25(17):3389-3402 (1997); See also, the National Center for Biotechnology Information (NCBI) website).

Suitable Fabric Hueing Agents

Fluorescent optical brighteners emit at least some visible light. In contrast, fabric hueing agents can alter the tint of a surface as they absorb at least a portion of the visible light spectrum. Suitable fabric hueing agents include dyes, dye-clay conjugates, and pigments that satisfy the requirements of Test Method 1 in the Test Method Section of the present specification. Suitable dyes include small molecule dyes and polymeric dyes. Suitable small molecule dyes include small molecule dyes selected from the group consisting of dyes falling into the Colour Index (C.I.) classifications of Direct Blue, Direct Red, Direct Violet, Acid Blue, Acid Red, Acid Violet, Basic Blue, Basic Violet and Basic Red, or mixtures thereof, for example:

(1) Tris-Azo Direct Blue Dyes of the Formula

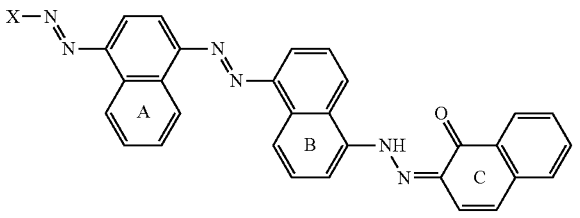

where at least two of the A, B and C napthyl rings are substituted by a sulfonate group, the C ring may be substituted at the 5 position by an $NH_2$ or NHPh group, X is a benzyl or naphthyl ring substituted with up to 2 sulfonate groups and may be substituted at the 2 position with an OH group and may also be substituted with an $NH_2$ or NHPh group.

(2) Bis-Azo Direct Violet Dyes of the Formula:

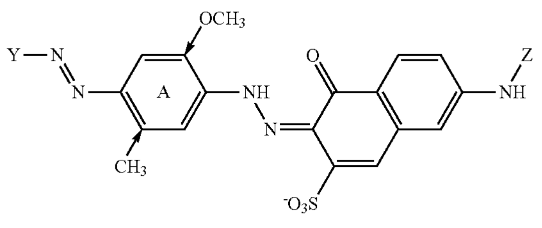

where Z is H or phenyl, the A ring is preferably substituted by a methyl and methoxy group at the positions indicated by arrows, the A ring may also be a naphthyl ring, the Y group is a benzyl or naphthyl ring, which is substituted by sulfate group and may be mono or disubstituted by methyl groups.

(3) Blue or Red Acid Dyes of the Formula

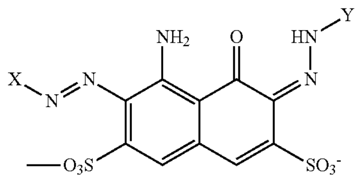

where at least one of X and Y must be an aromatic group. In one aspect, both the aromatic groups may be a substituted benzyl or naphthyl group, which may be substituted with non water-solubilising groups such as alkyl or alkyloxy or aryloxy groups, X and Y may not be substituted with water solubilising groups such as sulfonates or carboxylates. In another aspect, X is a nitro substituted benzyl group and Y is a benzyl group (4) Red Acid Dyes of the Structure

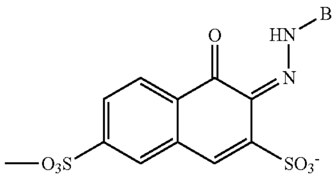

or

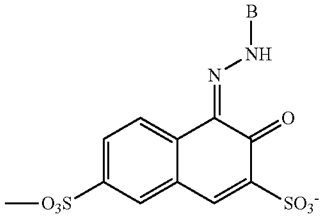

where B is a naphthyl or benzyl group that may be substituted with non water solubilising groups such as alkyl or alkyloxy or aryloxy groups, B may not be substituted with water solubilising groups such as sulfonates or carboxylates.

(5) Dis-Azo Dyes of the Structure

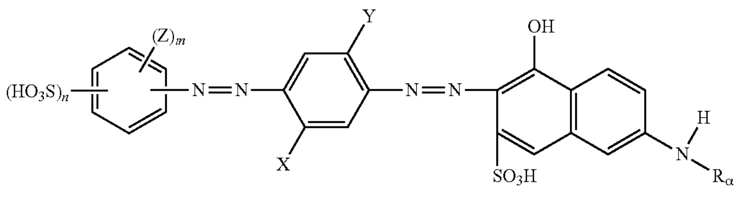

or

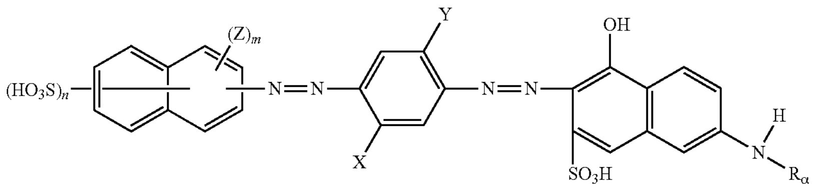

wherein X and Y, independently of one another, are each hydrogen, $C_1$-$C_4$ alkyl or $C_1$-$C_4$-alkoxy, Rα is hydrogen or aryl, Z is $C_1$-$C_4$ alkyl; $C_1$-$C_4$-alkoxy; halogen; hydroxyl or carboxyl, n is 1 or 2 and m is 0, 1 or 2, as well as corresponding salts thereof and mixtures thereof.

(6) Triphenylmethane Dyes of the Following Structures

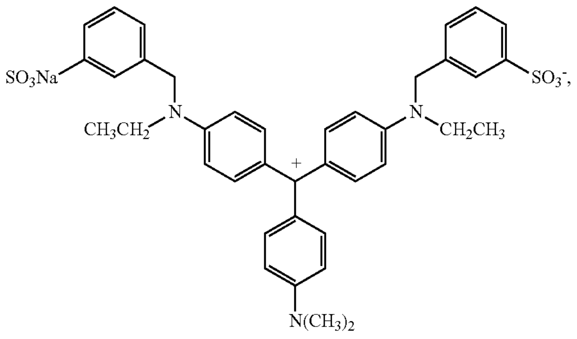

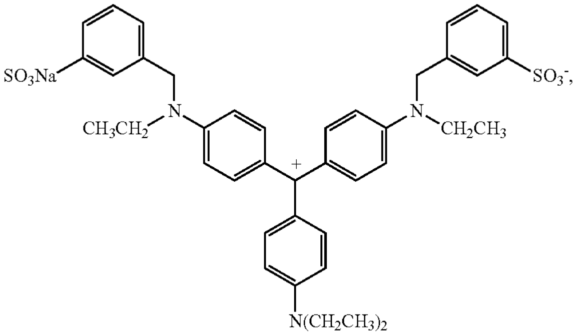

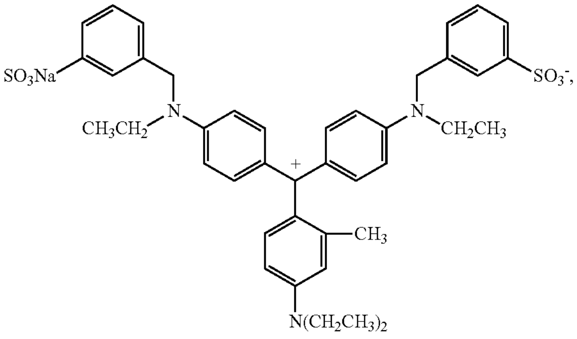

-continued

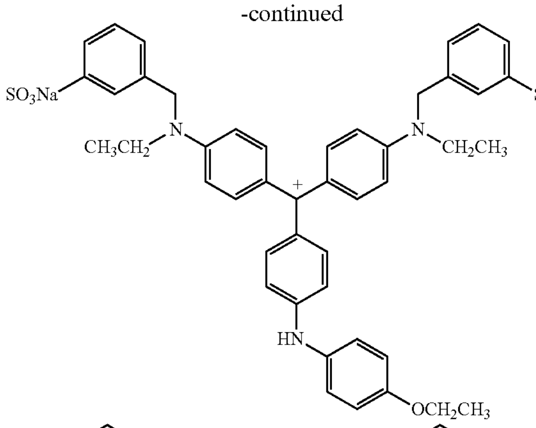

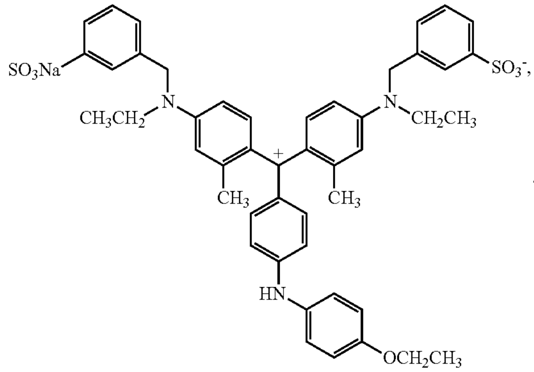

and/or

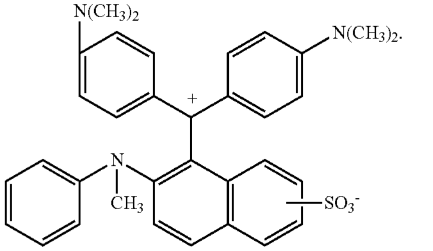

and mixtures thereof.

In another aspect, suitable small molecule dyes include small molecule dyes selected from the group consisting of Colour Index (Society of Dyers and Colourists, Bradford, UK) numbers 1,4-Naphthalenedione, 1-[2-[2-[4-[[4-(acetyloxy)butyl]ethylamino]-2-methylphenyl]diazenyl]-5-nitro-3-thienyl]-Ethanone, 1-hydroxy-2-(1-naphthalenylazo)-Naphthalenedisulfonic acid, ion(2-), 1-hydroxy-2-[[4-(phenylazo)phenyl]azo]-Naphthalenedisulfonic acid, ion (2-), 2-[(1E)-[4-[bis(3-methoxy-3-oxopropyl)amino]-2-methylphenyl]azo]-5-nitro-3-Thiophenecarboxylic acid, ethyl ester, 2-[[4-[(2-cyanoethyl)ethylamino]phenyl]azo]-5-(phenylazo)-3-Thiophenecarbonitrile, 2-[2-[4-[(2-cyanoethyl)ethylamino]phenyl]diazenyl]-5-[2-(4-nitrophenyl)diazenyl]-3-Thiophenecarbonitrile, 2-hydroxy-1-(1-naphthalenylazo)-Naphthalenedisulfonic acid, ion(2-), 2-hydroxy-1-[[4-(phenylazo)phenyl]azo]-Naphthalenedisulfonic acid, ion(2-), 4,4'-[[4-(dimethylamino)-2,5-cyclohexadien-1-ylidene]methylene]bis[N,N-dimethyl-Benzenamine, 6-hydroxy-5-[(4-methoxyphenyl)azo]-2-Naphthalenesulfonic acid, monosodium salt, 6-hydroxy-5-[(4-methylphenyl)azo]-2-Naphthalenesulfonic acid, monosodium salt, 7-hydroxy-8-[[4-(phenylazo)phenyl]azo]-1,3-Naphthalenedisulfonic acid, ion(2-), 7-hydroxy-8-[2-(1-naphthalenyl)diazenyl]-1,3-Naphthalenedisulfonic acid, ion (2-), 8-hydroxy-7-[2-(1-naphthalenyl)diazenyl]-1,3-Naphthalenedisulfonic acid, ion(2-), 8-hydroxy-7-[2-[4-(2-phenyldiazenyl)phenyl]diazenyl]-1,3-Naphthalenedisulfonic acid, ion(2-), Acid Black 1, Acid black 24, Acid Blue 113, Acid Blue 15, Acid Blue 17, Acid Blue 25, Acid blue 29, Acid blue 3, Acid blue 40, Acid blue 45, Acid blue 62, Acid blue 7, Acid blue 75, Acid Blue 80, Acid Blue 83, Acid blue 9, Acid Blue 90, Acid green 27, Acid orange 12, Acid orange 7, Acid red 14, Acid red 150,Acid red 151, Acid red 17, Acid red 18, Acid red 266, Acid red 27, Acid red 4, Acid red 51, Acid red 52, Acid red 73, Acid red 87, Acid red 88, Acid red 92, Acid red 94, Acid red 97, Acid Violet 15, Acid Violet 17, Acid Violet 24, Acid violet 43, Acid Violet 49, Basic blue 159, Basic blue 16, Basic blue 22, Basic blue 3, Basic blue 47, Basic blue 66, Basic blue 75, Basic blue 9, Basic violet 1, Basic violet 2, Basic violet 3, Basic violet 4, Basic violet 10, Basic violet 35, C.I. Acid black 1, C.I. Acid Blue 10, C.I. Acid Blue 113, C.I. Acid Blue 25, C.I. Acid Blue 29, C.I. Acid Blue 290 C.I. Acid Red 103, C.I. Acid red 150, C.I. Acid red 52, C.I. Acid red 73, C.I. Acid red 88, C.I. Acid red 91, C.I. Acid violet 17, C.I. Acid violet 43, C.I. Direct Blue 1, C.I. Direct Blue 120, C.I. Direct Blue 34, C.I. Direct Blue 70, C.I. Direct Blue 71, C.I. Direct Blue 72, C.I. Direct Blue 82, C.I. Direct violet 51, C.I. Disperse Blue 10, C.I. Disperse Blue 100, C.I. Disperse Blue 101, C.I. Disperse Blue 102, C.I. Disperse Blue 106:1, C.I. Disperse Blue 11, C.I. Disperse Blue 12, C.I. Disperse Blue 121, C.I. Disperse Blue 122, C.I. Disperse Blue 124, C.I. Disperse Blue 125, C.I. Disperse Blue 128, C.I. Disperse Blue 130, C.I. Disperse Blue 133, C.I. Disperse Blue 137, C.I. Disperse Blue 138, C.I. Disperse Blue 139, C.I. Disperse Blue 142, C.I. Disperse Blue 146, C.I. Disperse Blue 148, C.I. Disperse Blue 149, C.I. Disperse Blue 165, C.I. Disperse Blue 165:1, C.I. Disperse Blue 165:2, C.I. Disperse Blue 165:3, C.I. Disperse Blue 171, C.I. Disperse Blue 173, C.I. Disperse Blue 174, C.I. Disperse Blue 175, C.I. Disperse Blue 177, C.I. Disperse Blue 183, C.I. Disperse Blue 187, C.I. Disperse Blue 189, C.I. Disperse Blue 193, C.I. Disperse Blue 194, C.I. Disperse Blue 200, C.I. Disperse Blue 201, C.I. Disperse Blue 202, C.I. Disperse Blue 205, C.I. Disperse Blue 206, C.I. Disperse Blue 207, C.I. Disperse Blue 209, C.I. Disperse Blue 21, C.I. Disperse Blue 210, C.I. Disperse Blue 211, C.I. Disperse Blue 212, C.I. Disperse Blue 219, C.I. Disperse Blue 220, C.I. Disperse Blue 222, C.I. Disperse Blue 224, C.I. Disperse Blue 225, C.I. Disperse Blue 248, C.I. Disperse Blue 252, C.I. Disperse Blue 253, C.I. Disperse Blue 254, C.I. Disperse Blue 255, C.I. Disperse Blue 256, C.I. Disperse Blue 257, C.I. Disperse Blue 258, C.I. Disperse Blue 259, C.I. Disperse Blue 260, C.I. Disperse Blue 264, C.I. Disperse Blue 265, C.I. Disperse Blue 266, C.I. Disperse Blue 267, C.I. Disperse Blue 268, C.I. Disperse Blue 269, C.I. Disperse Blue 270, C.I. Disperse Blue 278, C.I. Disperse Blue 279, C.I. Disperse Blue 281, C.I. Disperse Blue 283, C.I. Disperse Blue 284, C.I. Disperse Blue 285, C.I. Disperse Blue 286, C.I. Disperse Blue 287, C.I. Disperse Blue 290, C.I. Disperse Blue 291, C.I. Disperse Blue 294, C.I. Disperse Blue 295, C.I. Disperse Blue 30, C.I. Disperse Blue 301, C.I. Disperse Blue 303, C.I. Disperse Blue 304, C.I. Disperse Blue 305, C.I. Disperse Blue 313, C.I. Disperse Blue 315, C.I. Disperse Blue 316, C.I. Disperse Blue 317, C.I. Disperse Blue 321, C.I. Disperse Blue 322, C.I. Disperse Blue 324, C.I. Disperse Blue 328, C.I. Disperse Blue 33, C.I. Disperse Blue 330, C.I. Disperse Blue 333, C.I. Disperse Blue 335, C.I. Disperse Blue 336, C.I. Disperse Blue 337, C.I. Disperse Blue 338, C.I. Disperse Blue 339, C.I. Disperse Blue 340, C.I. Disperse Blue 341, C.I. Disperse Blue 342, C.I. Disperse Blue 343, C.I. Disperse Blue 344, C.I. Disperse Blue 345, C.I. Disperse Blue 346, C.I. Disperse Blue 351, C.I. Disperse Blue 352, C.I. Disperse Blue 353, C.I.

Disperse Blue 355, C.I. Disperse Blue 356, C.I. Disperse Blue 357C.I. Disperse Blue 358, C.I. Disperse Blue 36, C.I. Disperse Blue 360, C.I. Disperse Blue 366, C.I. Disperse Blue 368, C.I. Disperse Blue 369, C.I. Disperse Blue 371, C.I. Disperse Blue 373, C.I. Disperse Blue 374, C.I. Disperse Blue 375, C.I. Disperse Blue 376, C.I. Disperse Blue 378, C.I. Disperse Blue 38, C.I. Disperse Blue 42, C.I. Disperse Blue 43, C.I. Disperse Blue 44, C.I. Disperse Blue 47, C.I. Disperse Blue 79, C.I. Disperse Blue 79:1, C.I. Disperse Blue 79:2, C.I. Disperse Blue 79:3, C.I. Disperse Blue 82, C.I. Disperse Blue 85, C.I. Disperse Blue 88, C.I. Disperse Blue 90, C.I. Disperse Blue 94, C.I. Disperse Blue 96, C.I. Disperse Violet 10, C.I. Disperse Violet 100, C.I. Disperse Violet 102, C.I. Disperse Violet 103, C.I. Disperse Violet 104, C.I. Disperse Violet 106, C.I. Disperse Violet 107, C.I. Disperse Violet 12, C.I. Disperse Violet 13, C.I. Disperse Violet 16, C.I. Disperse Violet 2, C.I. Disperse Violet 24, C.I. Disperse Violet 25, C.I. Disperse Violet 3, C.I. Disperse Violet 33, C.I. Disperse Violet 39, C.I. Disperse Violet 42, C.I. Disperse Violet 43, C.I. Disperse Violet 45, C.I. Disperse Violet 48, C.I. Disperse Violet 49, C.I. Disperse Violet 5, C.I. Disperse Violet 50, C.I. Disperse Violet 53, C.I. Disperse Violet 54, C.I. Disperse Violet 55, C.I. Disperse Violet 58, C.I. Disperse Violet 6, C.I. Disperse Violet 60, C.I. Disperse Violet 63, C.I. Disperse Violet 66, C.I. Disperse Violet 69, C.I. Disperse Violet 7, C.I. Disperse Violet 75, C.I. Disperse Violet 76, C.I. Disperse Violet 77, C.I. Disperse Violet 82, C.I. Disperse Violet 86, C.I. Disperse Violet 88, C.I. Disperse Violet 9, C.I. Disperse Violet 91, C.I. Disperse Violet 92, C.I. Disperse Violet 93, C.I. Disperse Violet 93:1, C.I. Disperse Violet 94, C.I. Disperse Violet 95, C.I. Disperse Violet 96, C.I. Disperse Violet 97, C.I. Disperse Violet 98, C.I. Disperse Violet 99, C.I. Reactive Black 5, C.I. Reactive Blue 19, C.I. Reactive Blue 4, C.I. Reactive Red 2, C.I. Solvent Blue 43, C.I. Solvent Blue 43, C.I. Solvent Red 14, C.I. Acid black 24, C.I. Acid blue 113, C.I. Acid Blue 29, C.I. Direct violet 7, C.I. Food Red 14, Dianix Violet CC, Direct blue 1, Direct Blue 71, Direct blue 75, Direct blue 78, Direct blue 80, Direct blue 279, Direct violet 11, Direct violet 31, Direct violet 35, Direct violet 48, Direct violet 5, Direct Violet 51, Direct violet 66, Direct violet 9, Disperse Blue 106, Disperse blue 148, Disperse blue 165, Disperse Blue 3, Disperse Blue 354, Disperse Blue 364, Disperse blue 367, Disperse Blue 56, Disperse Blue 77, Disperse Blue 79, Disperse blue 79:1, Disperse Red 1, Disperse Red 15, Disperse Violet 26, Disperse Violet 27, Disperse Violet 28, Disperse violet 63, Disperse violet 77, Eosin Y, Ethanol, 2,2'-[[4-[(3,5-dinitro-2-thienyl)azo]phenyl]imino] bis-, diacetate (ester), Lumogen F Blue 650, Lumogen F Violet 570, N-[2-[2-(3-acetyl-5-nitro-2-thienyl)diazenyl]-5-(diethylamino)phenyl]-Acetamide, N-[2-[2-(4-chloro-3-cyano-5-formyl-2-thienyl)diazenyl]-5-(diethylamino)phenyl]-Acetamide, N-[5-[bis(2-methoxyethyl)amino]-2-[2-(5-nitro-2,1-benzisothiazol-3-yl)diazenyl]phenyl]-Acetamide, N-[5-[bis[2-(acetyloxy)ethyl]amino]-2-[(2-bromo-4,6-dinitrophenyl)azo]phenyl]-Acetamide, Naphthalimide, derivatives, Oil Black 860, Phloxine B, Pyrazole, Rose Bengal, Sodium 6-hydroxy-5-(4-isopropylphenylazo)-2-naphthalenesulfonate, Solvent Black 3, Solvent Blue 14, Solvent Blue 35, Solvent Blue 58, Solvent Blue 59, Solvent Red 24, Solvent Violet 13, Solvent Violet 8, Sudan Red 380, Triphenylmethane, and Triphenylmethane, derivatives or mixtures thereof.

Suitable polymeric dyes include polymeric dyes selected from the group consisting of polymers containing conjugated chromogens (dye-polymer conjugates) and polymers with chromogens co-polymerized into the backbone of the polymer and mixtures thereof.

In another aspect, suitable polymeric dyes include polymeric dyes selected from the group consisting of fabric-substantive colorants sold under the name of Liquitint® (Milliken, Spartanburg, S.C., USA), dye-polymer conjugates formed from at least one reactive dye and a polymer selected from the group consisting of polymers comprising a moiety selected from the group consisting of a hydroxyl moiety, a primary amine moiety, a secondary amine moiety, a thiol moiety and mixtures thereof. In still another aspect, suitable polymeric dyes include polymeric dyes selected from the group consisting of Liquitint® (Milliken, Spartanburg, S.C., USA) Violet CT, carboxymethyl cellulose (CMC) conjugated with a reactive blue, reactive violet or reactive red dye such as CMC conjugated with C.I. Reactive Blue 19, sold by Megazyme, Wicklow, Ireland under the product name AZO-CM-CELLULOSE, product code S-ACMC, alkoxylated triphenyl-methane polymeric colourants, alkoxylated thiophene polymeric colourants, and mixtures thereof.

Suitable dye clay conjugates include dye clay conjugates selected from the group comprising at least one cationic/basic dye and a smectite clay, and mixtures thereof. In another aspect, suitable dye clay conjugates include dye clay conjugates selected from the group consisting of one cationic/basic dye selected from the group consisting of C.I. Basic Yellow 1 through 108, C.I. Basic Orange 1 through 69, C.I. Basic Red 1 through 118, C.I. Basic Violet 1 through 51, C.I. Basic Blue 1 through 164, C.I. Basic Green 1 through 14, C.I. Basic Brown 1 through 23, CI Basic Black 1 through 11, and a clay selected from the group consisting of Montmorillonite clay, Hectorite clay, Saponite clay and mixtures thereof. In still another aspect, suitable dye clay conjugates include dye clay conjugates selected from the group consisting of: Montmorillonite Basic Blue B7 C.I. 42595 conjugate, Montmorillonite Basic Blue B9 C.I. 52015 conjugate, Montmorillonite Basic Violet V3 C.I. 42555 conjugate, Montmorillonite Basic Green G1 C.I. 42040 conjugate, Montmorillonite Basic Red R1 C.I. 45160 conjugate, Montmorillonite C.I. Basic Black 2 conjugate, Hectorite Basic Blue B7 C.I. 42595 conjugate, Hectorite Basic Blue B9 C.I. 52015 conjugate, Hectorite Basic Violet V3 C.I. 42555 conjugate, Hectorite Basic Green G1 C.I. 42040 conjugate, Hectorite Basic Red R1 C.I. 45160 conjugate, Hectorite C.I. Basic Black 2 conjugate, Saponite Basic Blue B7 C.I. 42595 conjugate, Saponite Basic Blue B9 C.I. 52015 conjugate, Saponite Basic Violet V3 C.I. 42555 conjugate, Saponite Basic Green G1 C.I. 42040 conjugate, Saponite Basic Red R1 C.I. 45160 conjugate, Saponite C.I. Basic Black 2 conjugate and mixtures thereof.

Suitable pigments include pigments selected from the group consisting of flavanthrone, indanthrone, chlorinated indanthrone containing from 1 to 4 chlorine atoms, pyranthrone, dichloropyranthrone, monobromodichloropyranthrone, dibromodichloropyranthrone, tetrabromopyranthrone, perylene-3,4,9,10-tetracarboxylic acid diimide, wherein the imide groups may be unsubstituted or substituted by C1-C3-alkyl or a phenyl or heterocyclic radical, and wherein the phenyl and heterocyclic radicals may additionally carry substituents which do not confer solubility in water, anthrapyrimidinecarboxylic acid amides, violanthrone, isoviolanthrone, dioxazine pigments, copper phthalocyanine which may contain up to 2 chlorine atoms per molecule, polychloro-copper phthalocyanine or polybromochloro-copper phthalocyanine containing up to 14 bromine atoms per molecule and mixtures thereof. In another aspect, suitable pigments include pigments selected from the group consisting of Ultramarine Blue (C.I. Pigment Blue 29), Ultramarine Violet (C.I. Pigment Violet 15) and mixtures thereof.

The aforementioned fabric hueing agents can be used in combination (any mixture of fabric hueing agents can be used). Suitable fabric hueing agents can be purchased from Aldrich, Milwaukee, Wis., USA; Ciba Specialty Chemicals, Basel, Switzerland; BASF, Ludwigshafen, Germany; Dayglo Color Corporation, Mumbai, India; Organic Dyestuffs Corp., East Providence, R.I., USA; Dystar, Frankfurt, Germany; Lanxess, Leverkusen, Germany; Megazyme, Wicklow, Ireland; Clariant, Muttenz, Switzerland; Avecia, Manchester, UK and/or made in accordance with the examples contained herein.

Suitable hueing agents are described in more detail in U.S. Pat. No. 7,208,459 B2.

Encapsulates

In one aspect, an encapsulate comprising a core, a shell having an inner and outer surface, said shell encapsulating said core.

In one aspect of said encapsulate, said core may comprise a material selected from the group consisting of perfumes; brighteners; dyes; insect repellants; silicones; waxes; flavors; vitamins; fabric softening agents; skin care agents in one aspect, paraffins; enzymes; anti-bacterial agents; bleaches; sensates; and mixtures thereof; and said shell may comprise a material selected from the group consisting of polyethylenes; polyamides; polystyrenes; polyisoprenes; polycarbonates; polyesters; polyacrylates; aminoplasts, in one aspect said aminoplast may comprise a polyureas, polyurethane, and/or polyureaurethane, in one aspect said polyurea may comprise polyoxymethyleneurea and/or melamine formaldehyde; polyolefins; polysaccharides, in one aspect said polysaccharide may comprise alginate and/or chitosan; gelatin; shellac; epoxy resins; vinyl polymers; water insoluble inorganics; silicone; and mixtures thereof.

In one aspect of said encapsulate, said core may comprise perfume.

In one aspect of said encapsulate, said shell may comprise melamine formaldehyde and/or cross linked melamine formaldehyde.

In a one aspect, suitable encapsulates may comprise a core material and a shell, said shell at least partially surrounding said core material, is disclosed. At least 75%, 85% or even 90% of said encapsulates may have a fracture strength of from about 0.2 MPa to about 10 MPa, from about 0.4 MPa to about 5 MPa, from about 0.6 MPa to about 3.5 MPa, or even from about 0.7 MPa to about 3 MPa; and a benefit agent leakage of from 0% to about 30%, from 0% to about 20%, or even from 0% to about 5%.

In one aspect, at least 75%, 85% or even 90% of said encapsulates may have a particle size of from about 1 microns to about 80 microns, about 5 microns to 60 microns, from about 10 microns to about 50 microns, or even from about 15 microns to about 40 microns.

In one aspect, at least 75%, 85% or even 90% of said encapsulates may have a particle wall thickness of from about 30 nm to about 250 nm, from about 80 nm to about 180 nm, or even from about 100 nm to about 160 nm.

In one aspect, said encapsulates' core material may comprise a material selected from the group consisting of a perfume raw material and/or optionally a material selected from the group consisting of vegetable oil, including neat and/or blended vegetable oils including caster oil, coconut oil, cottonseed oil, grape oil, rapeseed, soybean oil, corn oil, palm oil, linseed oil, safflower oil, olive oil, peanut oil, coconut oil, palm kernel oil, castor oil, lemon oil and mixtures thereof; esters of vegetable oils, esters, including dibutyl adipate, dibutyl phthalate, butyl benzyl adipate, benzyl octyl adipate, tricresyl phosphate, trioctyl phosphate and mixtures thereof; straight or branched chain hydrocarbons, including those straight or branched chain hydrocarbons having a boiling point of greater than about 80° C.; partially hydrogenated terphenyls, dialkyl phthalates, alkyl biphenyls, including monoisopropylbiphenyl, alkylated naphthalene, including dipropylnaphthalene, petroleum spirits, including kerosene, mineral oil and mixtures thereof; aromatic solvents, including benzene, toluene and mixtures thereof; silicone oils; and mixtures thereof.

In one aspect, said encapsulates' wall material may comprise a suitable resin including the reaction product of an aldehyde and an amine, suitable aldehydes include, formaldehyde. Suitable amines include melamine, urea, benzoguanamine, glycoluril, and mixtures thereof. Suitable melamines include, methylol melamine, methylated methylol melamine, imino melamine and mixtures thereof. Suitable ureas include, dimethylol urea, methylated dimethylol urea, urea-resorcinol, and mixtures thereof.

In one aspect, suitable formaldehyde scavengers may be employed with the encapsulates, for example, in a capsule slurry and/or added to a fabric and home care product before, during or after the encapsulates are added to such fabric and home care product.

Suitable capsules that can be made by following the teaching of USPA 2008/0305982 A1; and/or USPA 2009/0247449 A1. Alternatively, suitable capsules can be purchased from Appleton Papers Inc. of Appleton, Wis. USA.

In addition, the materials for making the aforementioned encapsulates can be obtained from Solutia Inc. (St Louis, Mo. U.S.A.), Cytec Industries (West Paterson, N.J. U.S.A.), sigma-Aldrich (St. Louis, Mo. U.S.A.), CP Kelco Corp. of San Diego, Calif., USA; BASF AG of Ludwigshafen, Germany; Rhodia Corp. of Cranbury, N.J., USA; Hercules Corp. of Wilmington, Del., USA; Agrium Inc. of Calgary, Alberta, Canada, ISP of New Jersey U.S.A., Akzo Nobel of Chicago, Ill., USA; Stroever Shellac Bremen of Bremen, Germany; Dow Chemical Company of Midland, Mich., USA; Bayer AG of Leverkusen, Germany; Sigma-Aldrich Corp., St. Louis, Mo., USA.

Amphiphilic Cleaning Polymers

Preferably, the amphiphilic cleaning polymer is a compound having the following general structure: bis$((C_2H_5O)(C_2H_4O)n)(CH_3)$—$N^+$—$C_xH_{2x}$—$N^+$—$(CH_3)$-bis$((C_2H_5O)(C_2H_4O)n)$, wherein n=from 20 to 30, and x=from 3 to 8, or sulphated or sulphonated variants thereof.

Amphiphilic alkoxylated grease cleaning polymers of the present invention refer to any alkoxylated polymers having balanced hydrophilic and hydrophobic properties such that they remove grease particles from fabrics and surfaces. Specific embodiments of the amphiphilic alkoxylated grease cleaning polymers of the present invention comprise a core structure and a plurality of alkoxylate groups attached to that core structure.

The core structure may comprise a polyalkylenimine structure comprising, in condensed form, repeating units of formulae (I), (II), (III) and (IV):

(I)

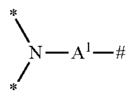

-continued (II)

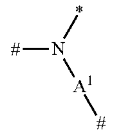

(III)

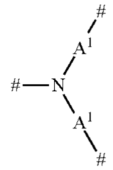

(IV)

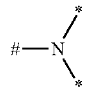

wherein # in each case denotes one-half of a bond between a nitrogen atom and the free binding position of a group $A^1$ of two adjacent repeating units of formulae (I), (II), (III) or (IV); * in each case denotes one-half of a bond to one of the alkoxylate groups; and $A^1$ is independently selected from linear or branched $C_2$-$C_6$-alkylene; wherein the polyalkylenimine structure consists of 1 repeating unit of formula (I), x repeating units of formula (II), y repeating units of formula (III) and y+1 repeating units of formula (IV), wherein x and y in each case have a value in the range of from 0 to about 150; where the average weight average molecular weight, Mw, of the polyalkylenimine core structure is a value in the range of from about 60 to about 10,000 g/mol.

The core structure may alternatively comprise a polyalkanolamine structure of the condensation products of at least one compound selected from N-(hydroxyalkyl)amines of formulae (I.a) and/or (I.b), (I.a)

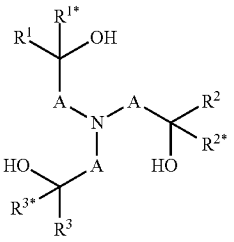

(I.b)

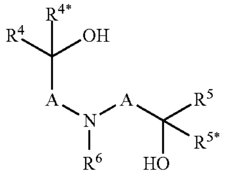

wherein A are independently selected from $C_1$-$C_6$-alkylene; $R^1$, $R^{1*}$, $R^2$, $R^{2*}$, $R^3$, $R^{3*}$, $R^4$, $R^{4*}$, $R^5$ and $R^{5*}$ are independently selected from hydrogen, alkyl, cycloalkyl or aryl, wherein the last three mentioned radicals may be optionally substituted; and $R^6$ is selected from hydrogen, alkyl, cycloalkyl or aryl, wherein the last three mentioned radicals may be optionally substituted.

The plurality of alkylenoxy groups attached to the core structure are independently selected from alkylenoxy units of the formula (V)

$$*-[A^2-O]_m-[CH_2-CH_2-O]_n-[A^3-O]_p-R \quad (V)$$

wherein * in each case denotes one-half of a bond to the nitrogen atom of the repeating unit of formula (I), (II) or (IV); $A^2$ is in each case independently selected from 1,2-propylene, 1,2-butylene and 1,2-isobutylene; $A^3$ is 1,2-propylene; R is in each case independently selected from hydrogen and $C_1$-$C_4$-alkyl; m has an average value in the range of from 0 to about 2; n has an average value in the range of from about 20 to about 50; and p has an average value in the range of from about 10 to about 50.

Specific embodiments of the amphiphilic alkoxylated grease cleaning polymers may be selected from alkoxylated polyalkylenimines having an inner polyethylene oxide block and an outer polypropylene oxide block, the degree of ethoxylation and the degree of propoxylation not going above or below specific limiting values. Specific embodiments of the alkoxylated polyalkylenimines according to the present invention have a minimum ratio of polyethylene blocks to polypropylene blocks (n/p) of about 0.6 and a maximum of about $1.5(x+2y+1)^{1/2}$. Alkoxykated polyalkyenimines having an n/p ratio of from about 0.8 to about $1.2(x+2y+1)^{1/2}$ have been found to have especially beneficial properties.

The alkoxylated polyalkylenimines according to the present invention have a backbone which consists of primary, secondary and tertiary amine nitrogen atoms which are attached to one another by alkylene radicals A and are randomly arranged. Primary amino moieties which start or terminate the main chain and the side chains of the polyalkylenimine backbone and whose remaining hydrogen atoms are subsequently replaced by alkylenoxy units are referred to as repeating units of formulae (I) or (IV), respectively. Secondary amino moieties whose remaining hydrogen atom is subsequently replaced by alkylenoxy units are referred to as repeating units of formula (II). Tertiary amino moieties which branch the main chain and the side chains are referred to as repeating units of formula (III).

Since cyclization can occur in the formation of the polyalkylenimine backbone, it is also possible for cyclic amino moieties to be present to a small extent in the backbone. Such polyalkylenimines containing cyclic amino moieties are of course alkoxylated in the same way as those consisting of the noncyclic primary and secondary amino moieties.

The polyalkylenimine backbone consisting of the nitrogen atoms and the groups $A^1$, has an average molecular weight Mw of from about 60 to about 10,000 g/mole, preferably from about 100 to about 8,000 g/mole and more preferably from about 500 to about 6,000 g/mole.

The sum (x+2y+1) corresponds to the total number of alkylenimine units present in one individual polyalkylenimine backbone and thus is directly related to the molecular weight of the polyalkylenimine backbone. The values given in the specification however relate to the number average of all polyalkylenimines present in the mixture. The sum (x+2y+2) corresponds to the total number amino groups present in one individual polyalkylenimine backbone.

The radicals $A^1$ connecting the amino nitrogen atoms may be identical or different, linear or branched $C_2$-$C_6$-alkylene radicals, such as 1,2-ethylene, 1,2-propylene, 1,2-butylene, 1,2-isobutylene, 1,2-pentanediyl, 1,2-hexanediyl or hexamethylen. A preferred branched alkylene is 1,2-propylene. Preferred linear alkylene are ethylene and hexamethylene. A more preferred alkylene is 1,2-ethylene.

The hydrogen atoms of the primary and secondary amino groups of the polyalkylenimine backbone are replaced by alkylenoxy units of the formula (V).

$$*-[A^2-O]_m-[CH_2-CH_2-O]_n-[A^3-O]_p-R \quad (V)$$

In this formula, the variables preferably have one of the meanings given below:

$A^2$ in each case is selected from 1,2-propylene, 1,2-butylene and 1,2-isobutylene; preferably $A^2$ is 1,2-propylene. $A^3$ is 1,2-propylene; R in each case is selected from hydrogen and $C_1$-$C_4$-alkyl, such as methyl, ethyl, n-propyl, isopropyl, n-butyl, isobutyl and tert.-butyl; preferably R is hydrogen. The index m in each case has a value of 0 to about 2; preferably m is 0 or approximately 1; more preferably m is 0. The index n has an average value in the range of from about 20 to about 50, preferably in the range of from about 22 to about 40, and more preferably in the range of from about 24 to about 30. The index p has an average value in the range of from about 10 to about 50, preferably in the range of from about 11 to about 40, and more preferably in the range of from about 12 to about 30.

Preferably the alkylenoxy unit of formula (V) is a non-random sequence of alkoxylate blocks. By non-random sequence it is meant that the $[-A^2-O-]_m$ is added first (i.e., closest to the bond to the nitrogen atom of the repeating unit of formula (I), (II), or (III)), the $[-CH_2-CH_2-O-]_n$ is added second, and the $[-A^3-O-]_p$ is added third. This orientation provides the alkoxylated polyalkylenimine with an inner polyethylene oxide block and an outer polypropylene oxide block.

The substantial part of these alkylenoxy units of formula (V) is formed by the ethylenoxy units $-[CH_2-CH_2-O]_n-$ and the propylenoxy units $-[CH_2-CH_2(CH_3)-O]_p-$. The alkylenoxy units may additionally also have a small proportion of propylenoxy or butylenoxy units $-[A^2-O]_m-$, i.e. the polyalkylenimine backbone saturated with hydrogen atoms may be reacted initially with small amounts of up to about 2 mol, especially from about 0.5 to about 1.5 mol, in particular from about 0.8 to about 1.2 mol, of propylene oxide or butylene oxide per mole of NH— moieties present, i.e. incipiently alkoxylated.

This initial modification of the polyalkylenimine backbone allows, if necessary, the viscosity of the reaction mixture in the alkoxylation to be lowered. However, the modification generally does not influence the performance properties of the alkoxylated polyalkylenimine and therefore does not constitute a preferred measure.

The amphiphilic alkoxylated grease cleaning polymers are present in the fabric and home care products, including but not limited to detergents, of the present invention at levels ranging from about 0.05% to 10% by weight of the fabric and home care product. Embodiments of the fabric and home care products may comprise from about 0.1% to about 5% by weight. More specifically, the embodiments may comprise from about 0.25 to about 2.5% of the grease cleaning polymer.

Non-Immunoequivalent Enzyme and/or Additional Enzymes

The fabric and home care products can comprise one or more enzymes which provide cleaning performance and/or fabric care benefits. Examples of suitable enzymes include, but are not limited to, hemicellulases, peroxidases, proteases, cellulases, xylanases, lipases, phospholipases, esterases, cutinases, pectinases, mannanases, pectate lyases, keratinases, reductases, oxidases, phenoloxidases, lipoxygenases, ligninases, pullulanases, tannases, pentosanases, malanases, β-glucanases, arabinosidases, hyaluronidase, chondroitinase, laccase, and amylases, or mixtures thereof. A typical combination is an enzyme cocktail that may comprise, for example, a protease and lipase in conjunction with amylase. When present in a fabric and home care product, the aforementioned additional enzymes may be present at levels from about 0.00001% to about 2%, from about 0.0001% to about 1% or even from about 0.001% to about 0.5% enzyme protein by weight of the fabric and home care product.

In one aspect preferred enzymes would include a protease. Suitable proteases include metalloproteases and serine proteases, including neutral or alkaline microbial serine proteases, such as subtilisins (EC 3.4.21.62). Suitable proteases include those of animal, vegetable or microbial origin. In one aspect, such suitable protease may be of microbial origin. The suitable proteases include chemically or genetically modified mutants of the aforementioned suitable proteases. In one aspect, the suitable protease may be a serine protease, such as an alkaline microbial protease or/and a trypsin-type protease. Examples of suitable neutral or alkaline proteases include:

(a) subtilisins (EC 3.4.21.62), including those derived from *Bacillus*, such as *Bacillus lentus, B. alkalophilus, B. subtilis, B. amyloliquefaciens, Bacillus pumilus* and *Bacillus gibsonii* described in U.S. Pat. No. 6,312,936 B1, U.S. Pat. No. 5,679,630, U.S. Pat. No. 4,760,025, U.S. Pat. No. 7,262,042 and WO09/021,867.

(b) trypsin-type or chymotrypsin-type proteases, such as trypsin (e.g., of porcine or bovine origin), including the *Fusarium* protease described in WO 89/06270 and the chymotrypsin proteases derived from *Cellumonas* described in WO 05/052161 and WO 05/052146.

(c) metalloproteases, including those derived from *Bacillus amyloliquefaciens* described in WO 07/044993A2.

Preferred proteases include those derived from *Bacillus gibsonii* or *Bacillus Lentus.*

Suitable commercially available protease enzymes include those sold under the trade names Alcalase®, Savinase®, Primase®, Durazym®, Polarzyme®, Kannase®, Liquanase®, Liquanase Ultra®, Savinase Ultra®, Ovozyme®, Neutrase®, Everlase® and Esperase® by Novozymes A/S (Denmark), those sold under the tradename Maxatase®, Maxacal®, Maxapem®, Properase®, Purafect®, Purafect Prime®, Purafect Ox®, FN3®, FN4®, Excellase® and Purafect OXP® by Genencor International, those sold under the tradename Opticlean® and Optimase® by Solvay Enzymes, those available from Henkel/Kemira, namely BLAP (sequence shown in FIG. 29 of U.S. Pat. No. 5,352,604 with the following mutations S99D+S101 R+S103A+V104I+G159S, hereinafter referred to as BLAP), BLAP R (BLAP with S3T+V4I+V199M+V205I+L217D), BLAP X (BLAP with S3T+V4I+V205I) and BLAP F49 (BLAP with S3T+V4I+A194P+V199M+V205I+L217D)—all from Henkel/Kemira; and KAP (*Bacillus alkalophilus* subtilisin with mutations A230V+S256G+S259N) from Kao.

In one aspect, the fabric and home care product may comprise a protease that is not immunoequivalent to the cold water protease of this invention. For the purposes of this invention, an immunoequivalent protease will have a high degree of identity (>80%) with BPN' and will cross-react with the same antibody. Suitable non-immunoequivalent enzymes will include those derived from *Bacillus Lentus, Bacillus gibsonii* and the metalloprotease derived from *Bacillus amyloliquefaciens.*

Suitable alpha-amylases include those of bacterial or fungal origin. Chemically or genetically modified mutants (variants) are included. A preferred alkaline alpha-amylase is derived from a strain of *Bacillus*, such as *Bacillus licheniformis, Bacillus amyloliquefaciens, Bacillus stearothermophilus, Bacillus subtilis*, or other *Bacillus* sp., such as *Bacillus* sp. NCIB 12289, NCIB 12512, NCIB 12513, DSM 9375 (U.S. Pat. No. 7,153,818) DSM 12368, DSMZ no. 12649, KSM AP1378 (WO 97/00324), KSM K36 or KSM K38 (EP 1,022, 334). Preferred amylases include:

(a) the variants described in WO 94/02597, WO 94/18314, WO96/23874 and WO 97/43424, especially the variants with substitutions in one or more of the following positions versus the enzyme listed as SEQ ID No. 2 in WO 96/23874: 15, 23, 105, 106, 124, 128, 133, 154, 156, 181, 188, 190, 197, 202, 208, 209, 243, 264, 304, 305, 391, 408, and 444.

(b) the variants described in U.S. Pat. No. 5,856,164 and WO99/23211, WO 96/23873, WO00/60060 and WO 06/002643, especially the variants with one or more substitutions in the following positions versus the AA560 enzyme listed as SEQ ID No. 12 in WO 06/002643:

26, 30, 33, 82, 37, 106, 118, 128, 133, 149, 150, 160, 178, 182, 186, 193, 203, 214, 231, 256, 257, 258, 269, 270, 272, 283, 295, 296, 298, 299, 303, 304, 305, 311, 314, 315, 318, 319, 339, 345, 361, 378, 383, 419, 421, 437, 441, 444, 445, 446, 447, 450, 461, 471, 482, 484, preferably that also contain the deletions of D183* and G184*.

(c) variants exhibiting at least 90% identity with SEQ ID No. 4 in WO06/002643, the wild-type enzyme from *Bacillus* SP722, especially variants with deletions in the 183 and 184 positions and variants described in WO 00/60060, which is incorporated herein by reference.

(d) variants exhibiting at least 95% identity with the wild-type enzyme from *Bacillus* sp.707 (SEQ ID NO:7 in U.S. Pat. No. 6,093,562), especially those comprising one or more of the following mutations M202, M208, S255, R172, and/or M261. Preferably said amylase comprises one or more of M202L, M202V, M202S, M202T, M202I, M202Q, M202W, S255N and/or R172Q. Particularly preferred are those comprising the M202L or M202T mutations.

Suitable commercially available alpha-amylases include DURAMYL®, LIQUEZYME®, TERMAMYL®, TERMAMYL ULTRA®, NATALASE®, SUPRAMYL®, STAINZYME®, STAINZYME PLUS®, FUNGAMYL® and BAN® (Novozymes A/S, Bagsvaerd, Denmark), KEMZYM® AT 9000 Biozym Biotech Trading GmbH Wehlistrasse 27b A-1200 Wien Austria, RAPIDASE®, PURASTAR®, ENZYSIZE®, OPTISIZE HT PLUS® and PURASTAR OXAM® (Genencor International Inc., Palo Alto, Calif.) and KAM® (Kao, 14-10 Nihonbashi Kayabacho, 1-chome, Chuo-ku Tokyo 103-8210, Japan). In one aspect, suitable amylases include NATALASE®, STAINZYME® and STAINZYME PLUS® and mixtures thereof.

In one aspect, such additional enzyme may be selected from the group consisting of: lipases, including "first cycle lipases" such as those described in U.S. Pat. No. 6,939,702 B1 and US PA 2009/0217464. In one aspect, the lipase is a first-wash lipase, preferably a variant of the wild-type lipase from *Thermomyces lanuginosus* comprising T231R and N233R mutations. The wild-type sequence is the 269 amino acids (amino acids 23-291) of the Swissprot accession number Swiss-Prot O59952 (derived from *Thermomyces lanuginosus* (*Humicola lanuginosa*)). Preferred lipases would include those sold under the tradenames Lipex® and Lipolex®.

In one aspect, other preferred enzymes include microbial-derived endoglucanases exhibiting endo-beta-1,4-glucanase activity (E.C. 3.2.1.4), including a bacterial polypeptide endogenous to a member of the genus *Bacillus* which has a sequence of at least 90%, 94%, 97% and even 99% identity to the amino acid sequence SEQ ID NO:2 in U.S. Pat. No. 7,141,403B2) and mixtures thereof. Suitable endoglucanases are sold under the tradenames Celluclean® and Whitezyme® (Novozymes A/S, Bagsvaerd, Denmark).

Other preferred enzymes include pectate lyases sold under the tradenames Pectawash®, Pectaway® and mannanases sold under the tradenames Mannaway® (all from Novozymes A/S, Bagsvaerd, Denmark), and Purabrite® (Genencor International Inc., Palo Alto, Calif.).

Adjunct Materials

While not essential for the purposes of the present invention, the non-limiting list of adjuncts illustrated hereinafter are suitable for use in the instant fabric and home care products and may be desirably incorporated in certain embodiments of the invention, for example to assist or enhance cleaning performance, for treatment of the substrate to be cleaned, or to modify the aesthetics of the fabric and home care product as is the case with perfumes, colorants, dyes or the like. The levels of any such adjuncts incorporated in any fabric and home care product are in addition to any materials previously recited for incorporation. The precise nature of these additional components, and levels of incorporation thereof, will depend on the physical form of the fabric and home care product and the nature of the cleaning operation for which it is to be used. Suitable adjunct materials include, but are not limited to, surfactants, builders, chelating agents, dye transfer inhibiting agents, dispersants, additional enzymes, and enzyme stabilizers, catalytic materials, bleach activators, hydrogen peroxide, sources of hydrogen peroxide, preformed peracids, polymeric dispersing agents, clay soil removal/anti-redeposition agents, brighteners, suds suppressors, dyes, perfumes, perfume delivery systems, structure elasticizing agents, fabric softeners, carriers, hydrotropes, processing aids, solvents and/or pigments. In addition to the disclosure below, suitable examples of such other adjuncts and levels of use are found in U.S. Pat. Nos. 5,576,282, 6,306,812 B1 and 6,326,348 B1 that are incorporated by reference.

As stated, the adjunct ingredients are not essential to Applicants' fabric and home care products. Thus, certain embodiments of Applicants' fabric and home care products do not contain one or more of the following adjuncts materials: surfactants, builders, chelating agents, dye transfer inhibiting agents, dispersants, additional enzymes, and enzyme stabilizers, catalytic materials, bleach activators, hydrogen peroxide, sources of hydrogen peroxide, preformed peracids, polymeric dispersing agents, clay soil removal/anti-redeposition agents, brighteners, suds suppressors, dyes, perfumes, perfume delivery systems, structure elasticizing agents, fabric softeners, carriers, hydrotropes, processing aids, solvents and/or pigments. However, when one or more adjuncts are present, such one or more adjuncts may be present as detailed below:

Perfume Delivery Systems and Perfumes—The compositions of the present invention may comprise a neat perfume and/or perfume technology systems that can be combined to yield the desired scent experience from the store shelf stage of a product, through its total performance cycle. Suitable perfumes include those perfumes that are enduring perfumes and/or quadrant perfumes. Examples of such neat perfumes are disclosed U.S. Pat. Nos. 5,500,138; 5,500,154; 6,491,728; 5,500,137 and 5,780,404. Suitable perfume delivery systems, methods of making certain perfume delivery systems and the uses of such perfume delivery systems are disclosed in USPA 2007/0275866 A1. Such perfume delivery systems include:

Polymer Assisted Delivery (PAD): This perfume delivery technology uses polymeric materials to deliver perfume materials. Classical coacervation, water soluble or partly soluble to insoluble charged or neutral polymers, liquid crystals, hot melts, hydrogels, perfumed plastics, microcapsules, nano- and micro-latexes, polymeric film formers, and polymeric absorbents, polymeric adsorbents, etc. are some examples. PAD includes but is not limited to:

a.) Matrix Systems: The fragrance is dissolved or dispersed in a polymer matrix or particle. Perfumes, for example, may be 1) dispersed into the polymer prior to formulating into the product or 2) added separately from the polymer during or after formulation of the product. Diffusion of perfume from the polymer is a common trigger that allows or increases the rate of perfume release from a polymeric matrix system that is deposited or applied to the desired surface (situs), although many other triggers are know that may control perfume release. Absorption and/or adsorption into or onto polymeric particles, films, solutions, and the like are aspects of this technology. Nano- or micro-particles composed of organic materials (e.g., latexes) are examples. Suitable particles include a wide range of materials including, but not limited to polyacetal, polyacrylate, polyacrylic, polyacrylonitrile, polyamide, polyaryletherketone, polybutadiene, polybutylene, polybutylene terephthalate, polychloroprene, poly ethylene, polyethylene terephthalate, polycyclohexylene dimethylene terephthalate, polycarbonate, polychloroprene, polyhydroxyalkanoate, polyketone, polyester, polyethylene, polyetherimide, polyethersulfone, polyethylenechlorinates, polyimide, polyisoprene, polylactic acid, polymethylpentene, polyphenylene oxide, polyphenylene sulfide, polyphthalamide, polypropylene, polystyrene, polysulfone, polyvinyl acetate, polyvinyl chloride, as well as polymers or copolymers based on acrylonitrile-butadiene, cellulose acetate, ethylene-vinyl acetate, ethylene vinyl alcohol, styrene-butadiene, vinyl acetate-ethylene, and mixtures thereof.

"Standard" systems refer to those that are "pre-loaded" with the intent of keeping the pre-loaded perfume associated with the polymer until the moment or moments of perfume release. Such polymers may also suppress the neat product odor and provide a bloom and/or longevity benefit depending on the rate of perfume release. One challenge with such systems is to achieve the ideal balance between 1) in-product stability (keeping perfume inside carrier until you need it) and 2) timely release (during use or from dry situs). Achieving such stability is particularly important during in-product storage and product aging. This challenge is particularly apparent for aqueous-based, surfactant-containing products, such as heavy duty liquid laundry detergents. Many "Standard" matrix systems available effectively become "Equilibrium" systems when formulated into aqueous-based products. One may select an "Equilibrium" system or a Reservoir system, which has acceptable in-product diffusion stability and available triggers for release (e.g., friction). "Equilibrium" systems are those in which the perfume and polymer may be added separately to the product, and the equilibrium interaction between perfume and polymer leads to a benefit at one or more consumer touch points (versus a free perfume control that has no polymer-assisted delivery technology). The polymer may also be pre-loaded with perfume; however, part or all of the perfume may diffuse during in-product storage reaching an equilibrium that includes having desired perfume raw materials (PRMs) associated with the polymer. The polymer then carries the perfume to the surface, and release is typically via perfume diffusion. The use of such equilibrium system polymers has the potential to decrease the neat product odor intensity of the neat product (usually more so in the case of pre-loaded standard system). Deposition of such polymers may serve to "flatten" the release profile and provide increased longevity. As indicated above, such longevity would be achieved by suppressing the initial intensity and may enable the formulator to use more high impact or low odor detection threshold (ODT) or low Kovats Index (KI) PRMs to achieve FMOT benefits without initial intensity that is too strong or distorted. It is important that perfume release occurs within the time frame of the application to impact the desired consumer touch point or touch points. Suitable micro-particles and micro-latexes as well as methods of making same may be found in USPA 2005/0003980 A1. Matrix systems also include hot melt adhesives and perfume plastics. In addition, hydrophobically modified polysaccharides may be formulated into the perfumed product to increase perfume deposition and/or modify perfume release. All such matrix systems, including for example polysaccharides and nanolatexes may be combined with other PDTs, including other PAD systems such as PAD reservoir systems in the form of a perfume microcapsule (PMC). Polymer Assisted Delivery (PAD) matrix systems may include those described in the following references: US Patent Applications 2004/0110648 A1; 2004/0092414 A1; 2004/0091445 A1 and 2004/0087476 A1; and U.S. Pat. Nos. 6,531,444; 6,024,943; 6,042,792; 6,051,540; 4,540,721 and 4,973,422.

Silicones are also examples of polymers that may be used as PDT, and can provide perfume benefits in a manner similar to the polymer-assisted delivery "matrix system". Such a PDT is referred to as silicone-assisted delivery (SAD). One may pre-load silicones with perfume, or use them as an equilibrium system as described for PAD. Suitable silicones as well as making same may be found in WO 2005/102261; USPA 20050124530A1; USPA 20050143282A1; and WO 2003/015736. Functionalized silicones may also be used as described in USPA 2006/003913 A1. Examples of silicones include polydimethylsiloxane and polyalkyldimethylsiloxanes. Other examples include those with amine functionality, which may be used to provide benefits associated with amine-assisted delivery (AAD) and/or polymer-assisted delivery (PAD) and/or amine-reaction products (ARP). Other such examples may be found in U.S. Pat. No. 4,911,852; USPA 2004/0058845 A1; USPA 2004/0092425 A1 and USPA 2005/0003980 A1.

b.) Reservoir Systems: Reservoir systems are also known as a core-shell type technology, or one in which the fragrance is surrounded by a perfume release controlling membrane, which may serve as a protective shell. The material inside the microcapsule is referred to as the core, internal phase, or fill, whereas the wall is sometimes called a shell, coating, or membrane. Microparticles or pressure sensitive capsules or microcapsules are examples of this technology. Microcapsules of the current invention are formed by a variety of procedures that include, but are not limited to, coating, extrusion, spray-drying, interfacial, in-situ and matrix polymerization. The possible shell materials vary widely in their stability toward water. Among the most stable are polyoxymethyleneurea (PMU)-based materials, which may hold certain PRMs for even long periods of time in aqueous solution (or product). Such systems include but are not limited to urea-formaldehyde and/or melamine-formaldehyde. Gelatin-based microcapsules may be prepared so that they dissolve quickly or slowly in water, depending for example on the degree of cross-linking. Many other capsule wall materials are available and vary in the degree of perfume diffusion stability observed. Without wishing to be bound by theory, the rate of release of perfume from a capsule, for example, once deposited on a surface is typically in reverse order of in-product perfume diffusion stability. As such, urea-formaldehyde and melamine-formaldehyde microcapsules for example, typically require a release mechanism other than, or in addition to, diffusion for release, such as mechanical force (e.g., friction, pressure, shear stress) that serves to break the capsule and increase the rate of perfume (fragrance) release. Other triggers include melting, dissolution, hydrolysis or other chemical reaction, electromagnetic radiation, and the like. The use of pre-loaded microcapsules requires the proper ratio of in-product stability and in-use and/or on-surface (on-situs) release, as well as proper selection of PRMs. Microcapsules that are based on urea-formaldehyde and/or melamine-formaldehyde are relatively stable, especially in near neutral aqueous-based solutions. Other suitable microcapsules include microcapsules having shells that comprise urethane materials, acrylics and/or vinyl alcohols. These materials may require a friction trigger which may not be applicable to all product applications. Other microcapsule materials (e.g., gelatin) may be unstable in aqueous-based products and may even provide reduced benefit (versus free perfume control) when in-product aged. Scratch and sniff technologies are yet another example of PAD. Perfume microcapsules (PMC) may include those described in the following references: US Patent Applications: 2003/0125222 A1; 2003/215417 A1; 2003/216488 A1; 2003/158344 A1; 2003/165692 A1; 2004/071742 A1; 2004/071746 A1; 2004/072719 A1; 2004/072720 A1; 2006/0039934 A1; 2003/203829 A1; 2003/195133 A1; 2004/087477 A1; 2004/0106536 A1; and U.S. Pat. Nos. 6,645,479 B1; 6,200,949 B1; 4,882,220; 4,917,920; 4,514,461; 6,106,875 and 4,234,627, 3,594,328 and U.S. RE 32713.

Molecule-Assisted Delivery (MAD): Non-polymer materials or molecules may also serve to improve the delivery of perfume. Without wishing to be bound by theory, perfume may non-covalently interact with organic materials, resulting in altered deposition and/or release. Non-limiting examples of such organic materials include but are not limited to hydrophobic materials such as organic oils, waxes, mineral oils, petrolatum, fatty acids or esters, sugars, surfactants, liposomes and even other perfume raw material (perfume oils), as well as natural oils, including body and/or other soils. Perfume fixatives are yet another example. In one aspect, non-polymeric materials or molecules have a CLogP greater than about 2. Molecule-Assisted Delivery (MAD) may also include those described in U.S. Pat. No. 7,119,060 and U.S. Pat. No. 5,506,201.

Fiber-Assisted Delivery (FAD): The choice or use of a situs itself may serve to improve the delivery of perfume. In fact, the situs itself may be a perfume delivery technology. For example, different fabric types such as cotton or polyester will have different properties with respect to ability to attract and/or retain and/or release perfume. The amount of perfume deposited on or in fibers may be altered by the choice of fiber, and also by the history or treatment of the fiber, as well as by any fiber coatings or treatments. Fibers may be woven and non-woven as well as natural or synthetic. Natural fibers include those produced by plants, animals, and geological processes, and include but are not limited to cellulose materials such as cotton, linen, hemp jute, flax, ramie, and sisal, and fibers used to manufacture paper and cloth. Fiber-Assisted Delivery may consist of the use of wood fiber, such as thermomechanical pulp and bleached or unbleached kraft or sulfite pulps. Animal fibers consist largely of particular proteins, such as silk, sinew, catgut and hair (including wool). Polymer fibers based on synthetic chemicals include but are not limited to polyamide nylon, PET or PBT polyester, phenol-formaldehyde (PF), polyvinyl alcohol fiber (PVOH), polyvinyl chloride fiber (PVC), polyolefins (PP and PE), and acrylic polymers. All such fibers may be pre-loaded with a perfume, and then added to a product that may or may not contain free perfume and/or one or more perfume delivery technologies. In one aspect, the fibers may be added to a product prior to being loaded with a perfume, and then loaded with a perfume by adding a perfume that may diffuse into the fiber, to the product. Without wishing to be bound by theory, the perfume may absorb onto or be adsorbed into the fiber, for example, during product storage, and then be released at one or more moments of truth or consumer touch points.

Amine Assisted Delivery (AAD): The amine-assisted delivery technology approach utilizes materials that contain an amine group to increase perfume deposition or modify perfume release during product use. There is no requirement in this approach to pre-complex or pre-react the perfume raw material(s) and amine prior to addition to the product. In one aspect, amine-containing AAD materials suitable for use herein may be non-aromatic; for example, polyalkylimine, such as polyethyleneimine (PEI), or polyvinylamine (PVAm), or aromatic, for example, anthranilates. Such materials may also be polymeric or non-polymeric. In one aspect, such materials contain at least one primary amine. This technology will allow increased longevity and controlled release also of low ODT perfume notes (e.g., aldehydes, ketones, enones) via amine functionality, and delivery of other PRMs, without being bound by theory, via polymer-assisted delivery for polymeric amines. Without technology, volatile top notes can be lost too quickly, leaving a higher ratio of middle and base notes to top notes. The use of a polymeric amine allows higher levels of top notes and other PRMS to be used to obtain freshness longevity without causing neat product odor to be more intense than desired, or allows top notes and other PRMs to be used more efficiently. In one aspect, AAD systems are effective at delivering PRMs at pH greater than about neutral. Without wishing to be bound by theory, conditions in which more of the amines of the AAD system are deprotonated may result in an increased affinity of the deprotonated amines for PRMs such as aldehydes and ketones, including unsaturated ketones and enones such as damascone. In another aspect, polymeric amines are effective at delivering PRMs at pH less than about neutral. Without wishing to be bound by theory, conditions in which more of the amines of the AAD system are protonated may result in a decreased affinity of the protonated amines for PRMs such as aldehydes and ketones, and a strong affinity of the polymer framework for a broad range of PRMs. In such an aspect, polymer-assisted delivery may be delivering more of the perfume benefit; such systems are a subspecies of AAD and may be referred to as Amine-Polymer-Assisted Delivery or APAD. In some cases when the APAD is employed in a composition that has a pH of less than seven, such APAD systems may also be considered Polymer-Assisted Delivery (PAD). In yet another aspect, AAD and PAD systems may interact with other materials, such as anionic surfactants or polymers to form coacervate and/or coacervates-like systems. In another aspect, a material that contains a heteroatom other than nitrogen, for example sulfur, phosphorus or selenium, may be used as an alternative to amine compounds. In yet another aspect, the aforementioned alternative compounds can be used in combination with amine compounds. In yet another aspect, a single molecule may comprise an amine moiety and one or more of the alternative heteroatom moieties, for example, thiols, phosphines and selenols. Suitable AAD systems as well as methods of making same may be found in US Patent Applications 2005/0003980 A1; 2003/0199422 A1; 2003/0036489 A1; 2004/0220074 A1 and U.S. Pat. No. 6,103,678.

Cyclodextrin Delivery System (CD): This technology approach uses a cyclic oligosaccharide or cyclodextrin to improve the delivery of perfume. Typically a perfume and cyclodextrin (CD) complex is formed. Such complexes may be preformed, formed in-situ, or formed on or in the situs. Without wishing to be bound by theory, loss of water may serve to shift the equilibrium toward the CD-Perfume complex, especially if other adjunct ingredients (e.g., surfactant) are not present at high concentration to compete with the perfume for the cyclodextrin cavity. A bloom benefit may be achieved if water exposure or an increase in moisture content occurs at a later time point. In addition, cyclodextrin allows the perfume formulator increased flexibility in selection of PRMs. Cyclodextrin may be pre-loaded with perfume or added separately from perfume to obtain the desired perfume stability, deposition or release benefit. Suitable CDs as well as methods of making same may be found in USPA 2005/0003980 A1 and 2006/0263313 A1 and U.S. Pat. Nos. 5,552,378; 3,812,011; 4,317,881; 4,418,144 and 4,378,923.

Starch Encapsulated Accord (SEA): The use of a starch encapsulated accord (SEA) technology allows one to modify the properties of the perfume, for example, by converting a liquid perfume into a solid by adding ingredients such as starch. The benefit includes increased perfume retention during product storage, especially under non-aqueous conditions. Upon exposure to moisture, a perfume bloom may be triggered. Benefits at other moments of truth may also be achieved because the starch allows the product formulator to select PRMs or PRM concentrations that normally cannot be used without the presence of SEA. Another technology example includes the use of other organic and inorganic materials, such as silica to convert perfume from liquid to solid. Suitable SEAs as well as methods of making same may be found in USPA 2005/0003980 A1 and U.S. Pat. No. 6,458,754 B1.

In one aspect, SEA's may be made by preparing a mixture comprising starch, water, acid and a perfume, the acid being incorporated in the mixture in an amount sufficient to lower the pH of the starch-water mixture by at least 0.25 units; and atomising and drying the mixture thereby forming encapsulated perfume. In the first step in the process of perfume encapsulation, an aqueous mixture is prepared comprising starch, water, perfume and acid. These ingredients may be added in any order, but usually the starch-water mixture is prepared first and subsequently, either sequentially or together, the acid and perfume are added. When they are added sequentially, the acid may be added prior to the ingredient for encapsulation. Alternatively, the acid is added after the ingredient for encapsulation. The concentration of starch in the aqueous mixture may be from as low as 5 or 10 wt % to as high as 60 or even 75 wt %. Generally the concentration of starch in the mixture is from 20 to 50 wt %, more usually around 25 to 40 wt % in the aqueous mixture.

Suitable starches can be made from raw starch, pregelatinized starch, modified starch derived from tubers, legumes, cereal and grains for example corn starch, wheat starch, rice starch, waxy corn starch, oat starch, cassava starch, waxy barley starch, waxy rice starch, sweet rice starch, amioca, potato starch, tapioca starch and mixtures thereof. Modified starches may be particularly suitable for use in the present invention, and these include hydrolyzed starch, acid thinned starch, starch having hydrophobic groups, such as starch esters of long chain hydrocarbons ($C_5$ or greater), starch acetates, starch octenyl succinate and mixtures thereof. In one aspect, starch esters, such as starch octenyl succinates are employed.

The term "hydrolyzed starch" refers to oligosaccharide-type materials that are typically obtained by acid and/or enzymatic hydrolysis of starches, preferably corn starch. It may be preferred to include in the starch water-mixture, a starch ester. Particularly preferred are the modified starches comprising a starch derivative containing a hydrophobic group or both a hydrophobic and a hydrophilic group which has been degraded by at least one enzyme capable of cleaving the 1,4 linkages of the starch molecule from the non-reducing ends to produce short chained saccharides to provide high oxidation resistance while maintaining substantially high molecular weight portions of the starch base. The aqueous starch mixture may also include a plasticizer for the starch. Suitable examples include monosaccharides, disaccharides, oligosaccharides and maltodextrins, such as glucose, sucrose, sorbitol, gum arabic, guar gums and maltodextrin.

The acid used in the process of the invention may be any acid. Examples include sulphuric acid, nitric acid, hydrochloric acid, sulphamic acid and phosphonic acid. In one aspect, carboxylic organic acids are employed. In another aspect, organic acids comprising more than one carboxylic acid groups are employed. Examples of suitable organic acids include citric acid, tartaric acid, maleic acid, malic acid, succinic acid, sebacic acid, adipic acid, itaconic acid, acetic acid and ascorbic acid, etc. In one aspect, saturated acids, such as citric acid, are employed.

Suitable perfumes for encapsulation include the HIA perfumes including those having a boiling point determined at the normal standard pressure of about 760 mmHg of 275° C. or lower, an octanol/water partition coefficient P of about 2000 or higher and an odour detection threshold of less than or equal 50 parts per billion (ppb). In one aspect, the perfume may have logP of 2 or higher. Suitable perfumes may be selected from the group consisting of 3-(4-t-butylphenyl)-2-methylpropanal, 3-(4-t-butylphenyl)-propanal, 3-(4-isopropylphenyl)-2-methylpropanal, methylenedioxyphenyl)-2-methylpropanal, and 2,6-dimethyl-5-heptenal, Alpha-damascone, Delta-damascone, Iso-damascone, Beta-damascenone, 6,7-dihydro-1,1,2,3,3-pentamethyl-4(5H)-indanone, methyl-7,3-dihydro-2H-1,5-benzodioxepine-3-one, 2-[2-(4-methyl-3-cyclohexenyl-1-yl)propyl]cyclopentan-2-one, 2-sec-butylcyclohexanone, and Alpha-dihydro ionone, linalool, ethyllinalool, tetrahydrolinalool, and dihydromyrcenol.

Suitable ingredients can be obtained from Givaudan of Mount Olive, N.J., USA, International Flavors & Fragrances of South Brunswick, N.J., USA, or Quest of Naarden, Netherlands.

Following the formation of the aqueous mixture comprising starch, water, perfumes and acid, the mixture is mixed under high shear to form an emulsion or dispersion of ingredient for encapsulation in the aqueous starch solution.

Any suitable technique may then be used for the final stage of processing where the aqueous mixture including acid and perfumes is atomised and dried. Suitable techniques include, but are not limited to those known in the art including spray drying, extrusion, spray chilling/crystallisation methods, fluid bed coating and the use of phase transfer catalysts to promote interfacial polymerization. Spray efficiencies may be increased by methods known in the art, such as by using high drying towers, lightly oiling the chamber walls, or using preconditioned air in which the moisture has been substantially removed.

Inorganic Carrier Delivery System (ZIC): This technology relates to the use of porous zeolites or other inorganic materials to deliver perfumes. Perfume-loaded zeolite may be used with or without adjunct ingredients used for example to coat the perfume-loaded zeolite (PLZ) to change its perfume release properties during product storage or during use or from the dry situs. Suitable zeolite and inorganic carriers as well as methods of making same may be found in USPA 2005/0003980 A1 and U.S. Pat. Nos. 5,858,959; 6,245,732 B1; 6,048,830 and 4,539,135. Silica is another form of ZIC. Another example of a suitable inorganic carrier includes inorganic tubules, where the perfume or other active material is contained within the lumen of the nano- or micro-tubules. Preferably, the perfume-loaded inorganic tubule (or Perfume-Loaded Tubule or PLT) is a mineral nano- or micro-tubule, such as halloysite or mixtures of halloysite with other inorganic materials, including other clays. The PLT technology may also comprise additional ingredients on the inside and/or outside of the tubule for the purpose of improving in-product diffusion stability, deposition on the desired situs or for controlling the release rate of the loaded perfume. Monomeric and/or polymeric materials, including starch encapsulation, may be used to coat, plug, cap, or otherwise encapsulate the PLT. Suitable PLT systems as well as methods of making same may be found in U.S. Pat. No. 5,651,976.

Pro-Perfume (PP): This technology refers to perfume technologies that result from the reaction of perfume materials with other substrates or chemicals to form materials that have a covalent bond between one or more PRMs and one or more carriers. The PRM is converted into a new material called a pro-PRM (i.e., pro-perfume), which then may release the original PRM upon exposure to a trigger such as water or light. Pro-perfumes may provide enhanced perfume delivery properties such as increased perfume deposition, longevity, stability, retention, and the like. Pro-perfumes include Those that are monomeric (non-polymeric) or polymeric, and may be pre-formed or may be formed in-situ under equilibrium conditions, such as those that may be present during in-product storage or on the wet or dry situs. Nonlimiting examples of pro-perfumes include Michael adducts (e.g., beta-amino ketones), aromatic or non-aromatic imines (Schiffs Bases), oxazolidines, beta-keto esters, and orthoesters. Another aspect includes compounds comprising one or more beta-oxy or beta-thio carbonyl moieties capable of releasing a PRM, for example, an alpha, beta-unsaturated ketone, aldehyde or carboxylic ester. The typical trigger for perfume release is exposure to water; although other triggers may include enzymes, heat, light, pH change, autoxidation, a shift of equilibrium, change in concentration or ionic strength and others. For aqueous-based products, light-triggered pro-perfumes are particularly suited. Such photo-pro-perfumes (PPPs) include but are not limited to those that release coumarin derivatives and perfumes and/or pro-perfumes upon being triggered. The released pro-perfume may release one or more PRMs by means of any of the above mentioned triggers. In one aspect, the photo-pro-perfume releases a nitrogen-based pro-perfume when exposed to a light and/or moisture trigger. In another aspect, the nitrogen-based pro perfume, released from the photo-pro-perfume, releases one or more PRMs selected, for example, from aldehydes, ketones (including enones) and alcohols. In still another aspect, the PPP releases a dihydroxy coumarin derivative. The light-triggered pro-perfume may also be an ester that releases a coumarin derivative and a perfume alcohol. In one aspect the pro-perfume is a dimethoxybenzoin derivative as described in USPA 2006/0020459 A1. In another aspect the pro-perfume is a 3',5'-dimethoxybenzoin (DMB) derivative that releases an alcohol upon exposure to electromagnetic radiation. In yet another aspect, the pro-perfume releases one or more low ODT PRMs, including tertiary alcohols such as linalool, tetrahydrolinalool, or dihydromyrcenol. Suitable pro-perfumes and methods of making same can be found in U.S. Pat. Nos. 7,018,978 B2; 6,987,084 B2; 6,956,013 B2; 6,861,402 B1; 6,544,945 B1; 6,093,691; 6,277,796 B1; 6,165,953; 6,316,397 B1; 6,437,150 B1; 6,479,682 B1; 6,096,918; 6,218,355 B1; 6,133,228; 6,147,037; 7,109,153 B2; 7,071,151 B2; 6,987,084 B2; 6,610,646 B2 and 5,958,870, as well as can be found in USPA 2005/0003980 A1 and USPA 2006/0223726 A1.

a.) Amine Reaction Product (ARP): For purposes of the present application, ARP is a subclass or species of PP. One may also use "reactive" polymeric amines in which the amine functionality is pre-reacted with one or more PRMs to form an amine reaction product (ARP). Typically the reactive amines are primary and/or secondary amines, and may be part of a polymer or a monomer (non-polymer). Such ARPs may also be mixed with additional PRMs to provide benefits of polymer-assisted delivery and/or amine-assisted delivery. Nonlimiting examples of polymeric amines include polymers based on polyalkylimines, such as polyethyleneimine (PEI), or polyvinylamine (PVAm). Nonlimiting examples of monomeric (non-polymeric) amines include hydroxylamines, such as 2-aminoethanol and its alkyl substituted derivatives, and aromatic amines such as anthranilates. The ARPs may be premixed with perfume or added separately in leave-on or rinse-off applications. In another aspect, a material that contains a heteroatom other than nitrogen, for example oxygen, sulfur, phosphorus or selenium, may be used as an alternative to amine compounds. In yet another aspect, the aforementioned alternative compounds can be used in combination with amine compounds. In yet another aspect, a single molecule may comprise an amine moiety and one or more of the alternative heteroatom moieties, for example, thiols, phosphines and selenols. The benefit may include improved delivery of perfume as well as controlled perfume release. Suitable ARPs as well as methods of making same can be found in USPA 2005/0003980 A1 and U.S. Pat. No. 6,413,920 B1.

In one aspect, the amine reaction product's perfume component, which is reacted with the amine to form the amine reaction product, is selected from a perfume comprising a ketone moiety and/or an aldehyde moiety. In one aspect, such perfumes comprise a chain containing at least 5 carbon atoms. In one aspect, suitable perfumes comprising a ketone moiety may be selected from Alpha Damascone, Delta Damascone, Iso Damascone, Carvone, Gamma-Methyl-Ionone, Iso-E-Super, 2,4,4,7-Tetramethyl-oct-6-en-3-one, Benzyl Acetone, Beta Damascone, Damascenone, methyl dihydrojasmonate, methyl cedrylone, and mixtures thereof. In one aspect, suitable perfumes comprising an aldehyde moiety may be selected from 1-decanal, benzaldehyde, florhydral, 2,4-dimethyl-3-cyclohexen-1-carboxaldehyde; cis/trans-3,7-dimethyl-2,6-octadien-1-al; heliotropin; 2,4,6-trimethyl-3-cyclohexene-1-carboxaldehyde; 2,6-nonadienal; alpha-n-amyl cinnamic aldehyde, alpha-n-hexyl cinnamic aldehyde, P.T. Bucinal, lyral, cymal, methyl nonyl acetaldehyde, hexanal, trans-2-hexenal, and mixture thereof. In one aspect, the suitable perfume mat be selected from undecylenic aldehyde, undecalactone gamma, heliotropin, dodecalactone gamma, p-anisic aldehyde, para hydroxy-phenyl-butanone, cymal, benzyl acetone, ionone alpha, p.t. bucinal, damascenone, ionone beta and methyl-nonyl ketone, and/or mixtures thereof. Typically the level of perfume may be from 10% to 90%, from 30% to 85%, or even from 45% to 80% by weight of the amine reaction product. In one aspect, suitable amine reaction products are those resulting from the reaction of polethyleneimine polymer like Lupasol polymers, with one or more of the following Alpha Damascone, Delta Damascone, Carvone, Hedione, Florhydral, Lilial, Heliotropine, Gamma-Methyl-Ionone and 2,4-dimethyl-3-10' cyclohexen-1-carboxaldehyde; amine reaction products are those resulting from the reaction of Astramol Dendrimers with Carvone and amine reaction products resulting from the reaction of ethyl-4-amino benzoate with 2,4-dimethyl-3-cyclohexen-1-carboxaldehyde. In one aspect, suitable amine reaction products are those resulting from the reaction of Lupasol HF with Delta Damascone; LupasolG35 with Alpha Damascone; LupasolG100 with 2,4-dimethyl-3-cyclohexen-1-carboxaldehyde, ethyl-4-amino benzoate with 2,4-dimethyl-3-cyclohexen-1-carboxaldehyde.

In one aspect, suitable primary and/or secondary amine containing compounds are characterized by an Odor Intensity Index of less than that of a 1% solution of methylanthranilate in dipropylene glycol.

A general structure for a suitable primary amine compound is as follows:

$$B\text{-}(NH_2)_n$$

wherein B is a carrier material, and n is an index of value of at least 1.

Suitable compounds comprising a secondary amine group may have a structure similar to the above excepted that the compound comprises one or more —NH— moieties in addition to any —NH2 moieties. Thus, such an amine compound may have the formula:

$$B\text{-}(NH_2)_n;\ B\text{-}(NH)_n;\ B\text{-}(NH)_n\text{—}(NH_2)_n$$

wherein B is a carrier material, and each n is independently an index of value of at least 1.

In one aspect, B carriers may be inorganic having non- or substantially non carbon based backbones, or organic carriers having essentially carbon bond backbones.

Suitable inorganic carriers include mono or polymers or organic-organosilicon copolymers of amino derivatised organo silane, siloxane, silazane, alumane, aluminum siloxane, or aluminum silicate compounds. Typical examples of such carriers are: organosiloxanes with at least one primary amine moiety like the diaminoalkylsiloxane $[H_2NCH_2(CH_3)_2\ Si]O$, or the organoaminosilane $(C_6H_5)\ 3SiNH_2$ (described in: Chemistry and Technology of Silicone, W. Noll, Academic Press Inc. 1998, London, pp 209, 106). Mono or polymer or organic-organosilicon copolymers containing one or more organosilylhydrasine moiety are also suitable. A typical example of such a carrier material is N,N'-bis(trimethylsilyl)hydrazine $(Me_3Si)_2NNH_2$. Typical suitable amines comprising an organic carrier include aminoaryl derivatives, polyamines, aminoacids and derivatives, substituted amines and amides, glucamines, dendrimers and amino-substituted mono-, di-, oligo-, poly-saccharides.

The amine compound may be interrupted or substituted by linkers or cellulose substantive group. A general formula for this amine compound is as follows:

$$NH_{2n}\text{-}L_m\text{-}B\text{-}L_m\text{-}R^*_m;$$

wherein each m is an index of value 0 or at least 1, and n is an index of value of at least 1 as defined herein before. As can be seen above, the amine group is linked to a carrier molecule as defined by classes hereinafter described. The primary and/or secondary amine group is either directly linked to the carrier group or via a linker group L. The carrier can also be substituted by a R* substituent, and R* can be linked to the carrier either directly or via a linker group L. R* can also contain branching groups like e.g. tertiary amine and amide groups. It is important for the purpose of the invention that the amine compound comprises at least one primary and/or secondary amine group to react with the perfume aldehyde and/or ketone to form the reaction products. Such reaction is typically known as a Schiff base reaction as a Schiff base is formed. The amine compound is not limited to having only one amine function. Indeed, more preferably, the amine compound comprises more than one amine function, thereby enabling the amine compound to react with several aldehydes and/or ketones. Accordingly, reaction products carrying mixed aldehyde(s) and/or ketone(s) can be achieved, thereby resulting in a mixed release of such fragrances.

Bleaching Agents—The fabric and home care products of the present invention may comprise one or more bleaching agents. Suitable bleaching agents other than bleaching catalysts include photobleaches, bleach activators, hydrogen peroxide, sources of hydrogen peroxide, pre-formed peracids and mixtures thereof. In general, when a bleaching agent is used, the fabric and home care products of the present invention may comprise from about 0.1% to about 50% or even from about 0.1% to about 25% bleaching agent by weight of the subject fabric and home care product. Examples of suitable bleaching agents include:

(1) photobleaches for example sulfonated zinc phthalocyanine sulfonated aluminium phthalocyanines, xanthene dyes and mixtures thereof;

(2) preformed peracids: Suitable preformed peracids include, but are not limited to, compounds selected from the group consisting of percarboxylic acids and salts, percarbonic acids and salts, perimidic acids and salts, peroxymonosulfuric acids and salts, for example, Oxone®, and mixtures thereof. Suitable percarboxylic acids include hydrophobic and hydrophilic peracids having the formula R—(C═O)O—O-M wherein R is an alkyl group, optionally branched, having, when the peracid is hydrophobic, from 6 to 14 carbon atoms, or from 8 to 12 carbon atoms and, when the peracid is hydrophilic, less than 6 carbon atoms or even less than 4 carbon atoms; and M is a counterion, for example, sodium, potassium or hydrogen;

(3) sources of hydrogen peroxide, for example, inorganic perhydrate salts, including alkali metal salts such as sodium salts of perborate (usually mono- or tetra-hydrate), percarbonate, persulphate, perphosphate, persilicate salts and mixtures thereof. In one aspect of the invention the inorganic perhydrate salts are selected from the group consisting of sodium salts of perborate, percarbonate and mixtures thereof. When employed, inorganic perhydrate salts are typically present in amounts of from 0.05 to 40 wt %, or 1 to 30 wt % of the overall fabric and home care product and are typically incorporated into such fabric and home care products as a crystalline solid that may be coated. Suitable coatings include, inorganic salts such as alkali metal silicate, carbonate or borate salts or mixtures thereof, or organic materials such as water-soluble or dispersible polymers, waxes, oils or fatty soaps; and (4) bleach activators having R—(C═O)-L wherein R is an alkyl group, optionally branched, having, when the bleach activator is hydrophobic, from 6 to 14 carbon atoms, or from 8 to 12 carbon atoms and, when the bleach activator is hydrophilic, less than 6 carbon atoms or even less than 4 carbon atoms; and L is leaving group. Examples of suitable leaving groups are benzoic acid and derivatives thereof—especially benzene sulphonate. Suitable bleach activators include dodecanoyl oxybenzene sulphonate, decanoyl oxybenzene sulphonate, decanoyl oxybenzoic acid or salts thereof, 3,5,5-trimethyl hexanoyloxybenzene sulphonate, tetraacetyl ethylene diamine (TAED) and nonanoyloxybenzene sulphonate (NOBS). Suitable bleach activators are also disclosed in WO 98/17767. While any suitable bleach activator may be employed, in one aspect of the invention the subject fabric and home care product may comprise NOBS, TAED or mixtures thereof.

When present, the peracid and/or bleach activator is generally present in the fabric and home care product in an amount of from about 0.1 to about 60 wt %, from about 0.5 to about 40 wt % or even from about 0.6 to about 10 wt % based on the fabric and home care product. One or more hydrophobic peracids or precursors thereof may be used in combination with one or more hydrophilic peracid or precursor thereof.

The amounts of hydrogen peroxide source and peracid or bleach activator may be selected such that the molar ratio of available oxygen (from the peroxide source) to peracid is from 1:1 to 35:1, or even 2:1 to 10:1.

Surfactants—The fabric and home care products according to the present invention may comprise a surfactant or surfactant system wherein the surfactant can be selected from nonionic surfactants, anionic surfactants, cationic surfactants, ampholytic surfactants, zwitterionic surfactants, semi-polar nonionic surfactants and mixtures thereof. When present, surfactant is typically present at a level of from about 0.1% to about 60%, from about 1% to about 50% or even from about 5% to about 40% by weight of the subject fabric and home care product.

Builders—The fabric and home care products of the present invention may comprise one or more detergent builders or builder systems. When a builder is used, the subject fabric and home care product will typically comprise at least about 1%, from about 5% to about 60% or even from about 10% to about 40% builder by weight of the subject fabric and home care product.

Builders include, but are not limited to, the alkali metal, ammonium and alkanolammonium salts of polyphosphates, alkali metal silicates, alkaline earth and alkali metal carbonates, aluminosilicate builders and polycarboxylate compounds, ether hydroxypolycarboxylates, copolymers of maleic anhydride with ethylene or vinyl methyl ether, 1,3,5-trihydroxy benzene-2,4,6-trisulphonic acid, and carboxymethyloxysuccinic acid, the various alkali metal, ammonium and substituted ammonium salts of polyacetic acids such as ethylenediamine tetraacetic acid and nitrilotriacetic acid, as well as polycarboxylates such as mellitic acid, succinic acid, citric acid, oxydisuccinic acid, polymaleic acid, benzene 1,3,5-tricarboxylic acid, carboxymethyloxysuccinic acid, and soluble salts thereof.

Chelating Agents—The fabric and home care products herein may contain a chelating agent. Suitable chelating agents include copper, iron and/or manganese chelating agents and mixtures thereof. When a chelating agent is used, the subject fabric and home care product may comprise from about 0.005% to about 15% or even from about 3.0% to about 10% chelating agent by weight of the subject fabric and home care product. Suitable chelants include DTPA (Diethylene triamine pentaacetic acid), HEDP (Hydroxyethane diphosphonic acid), DTPMP (Diethylene triamine penta(methylene phosphonic acid)), 1,2-Dihydroxybenzene-3,5-disulfonic acid disodium salt hydrate, ethylenediamine, diethylene triamine, ethylenediaminedisuccinic acid (EDDS), N-hydroxyethylethylenediaminetri-acetic acid (HEDTA), triethylenetetraaminehexaacetic acid (TTHA), N-hydroxyethyliminodiacetic acid (HEIDA), dihydroxyethylglycine (DHEG), ethylenediaminetetrapropionic acid (EDTP) and derivatives thereof.

Dye Transfer Inhibiting Agents—The fabric and home care products of the present invention may also include one or more dye transfer inhibiting agents. Suitable polymeric dye transfer inhibiting agents include, but are not limited to, polyvinylpyrrolidone polymers, polyamine N-oxide polymers, copolymers of N-vinylpyrrolidone and N-vinylimidazole, polyvinyloxazolidones and polyvinylimidazoles or mixtures thereof. When present in a subject fabric and home care product, the dye transfer inhibiting agents may be present at levels from about 0.0001% to about 10%, from about 0.01% to about 5% or even from about 0.1% to about 3% by weight of the fabric and home care product.

Brighteners—The fabric and home care products of the present invention can also contain additional components that may tint articles being cleaned, such as fluorescent brighteners. Suitable fluorescent brightener levels include lower levels of from about 0.01, from about 0.05, from about 0.1 or even from about 0.2 wt % to upper levels of 0.5 or even 0.75 wt %.

Dispersants—The fabric and home care products of the present invention can also contain dispersants. Suitable water-soluble organic materials include the homo- or co-polymeric acids or their salts, in which the polycarboxylic acid comprises at least two carboxyl radicals separated from each other by not more than two carbon atoms.

Enzyme Stabilizers—Enzymes for use in detergents can be stabilized by various techniques. The enzymes employed herein can be stabilized by the presence of water-soluble sources of calcium and/or magnesium ions in the finished fabric and home care products that provide such ions to the enzymes. In case of aqueous fabric and home care products comprising protease, a reversible protease inhibitor, such as a boron compound, or compounds such as calcium formate, sodium formate and 1,2-propane diol can be added to further improve stability.

Catalytic Metal Complexes—Applicants' compositions may include catalytic metal complexes. One type of metal-containing bleach catalyst is a catalyst system comprising a transition metal cation of defined bleach catalytic activity, such as copper, iron, titanium, ruthenium, tungsten, molybdenum, or manganese cations, an auxiliary metal cation having little or no bleach catalytic activity, such as zinc or aluminum cations, and a sequestrate having defined stability constants for the catalytic and auxiliary metal cations, particularly ethylenediaminetetraacetic acid, ethylenediaminetetra(methylenephosphonic acid) and water-soluble salts thereof. Such catalysts are disclosed in U.S. Pat. No. 4,430,243.

If desired, the compositions herein can be catalyzed by means of a manganese compound. Such compounds and levels of use are well known in the art and include, for example, the manganese-based catalysts disclosed in U.S. Pat. No. 5,576,282.

Cobalt bleach catalysts useful herein are known, and are described, for example, in U.S. Pat. No. 5,597,936; U.S. Pat. No. 5,595,967. Such cobalt catalysts are readily prepared by known procedures, such as taught for example in U.S. Pat. No. 5,597,936, and U.S. Pat. No. 5,595,967.

Compositions herein may also suitably include a transition metal complex of ligands such as bispidones (WO 05/042532 A1) and/or macropolycyclic rigid ligands—abbreviated as "MRLs". As a practical matter, and not by way of limitation, the compositions and processes herein can be adjusted to provide on the order of at least one part per hundred million of the active MRL species in the aqueous washing medium, and will typically provide from about 0.005 ppm to about 25 ppm, from about 0.05 ppm to about 10 ppm, or even from about 0.1 ppm to about 5 ppm, of the MRL in the wash liquor.

Suitable transition-metals in the instant transition-metal bleach catalyst include, for example, manganese, iron and chromium. Suitable MRLs include 5,12-diethyl-1,5,8,12-tetraazabicyclo[6.6.2]hexadecane.

Suitable transition metal MRLs are readily prepared by known procedures, such as taught for example in WO 00/32601, and U.S. Pat. No. 6,225,464.

Solvents—Suitable solvents include water and other solvents such as lipophilic fluids. Examples of suitable lipophilic fluids include siloxanes, other silicones, hydrocarbons, glycol ethers, glycerine derivatives such as glycerine ethers, perfluorinated amines, perfluorinated and hydrofluoroether solvents, low-volatility nonfluorinated organic solvents, diol solvents, other environmentally-friendly solvents and mixtures thereof.

Processes of Making Fabric and Home Care Products

The fabric and home care products of the present invention can be formulated into any suitable form and prepared by any process chosen by the formulator, non-limiting examples of which are described in Applicants' examples and in U.S. Pat. No. 4,990,280; U.S. 20030087791A1; U.S. 20030087790A1; U.S. 20050003983A1; U.S. 20040048764A1; U.S. Pat. No. 4,762,636; U.S. Pat. No. 6,291,412; U.S. 20050227891A1; EP 1070115A2; U.S. Pat. No. 5,879,584; U.S. Pat. No. 5,691,297; U.S. Pat. No. 5,574,005; U.S. 5,569,645; U.S. Pat. No. 5,565,422; U.S. Pat. No. 5,516,448; U.S. Pat. No. 5,489,392; U.S. Pat. No. 5,486,303 all of which are incorporated herein by reference.

Method of Use

The present invention includes a method for cleaning and/or treating a situs inter alia a surface or fabric. In one aspect, such method comprises the steps of optionally washing and/or rinsing said surface or fabric, contacting said surface or fabric with any fabric and home care product disclosed in this specification then optionally washing and/or rinsing said surface or fabric is disclosed.

As used herein, washing includes but is not limited to, scrubbing, and mechanical agitation. Drying of such surfaces or fabrics may be accomplished by any one of the common means employed either in domestic or industrial settings. Such means include but are not limited to forced air or still air drying at ambient or elevated temperatures at pressures between 5 and 0.01 atmospheres in the presence or absence of electromagnetic radiation, including sunlight, infrared, ultraviolet and microwave irradiation. In one aspect, said drying may be accomplished at temperatures above ambient by employing an iron wherein, for example, said fabric may be in direct contact with said iron for relatively short or even extended periods of time and wherein pressure may be exerted beyond that otherwise normally present due to gravitational force. In another aspect, said drying may be accomplished at temperatures above ambient by employing a dryer. Apparatus for drying fabric is well known and it is frequently referred to as a clothes dryer. In addition to clothes such appliances are used to dry many other items including towels, sheets, pillowcases, diapers and so forth and such equipment has been accepted as a standard convenience in many nations of the world substantially replacing the use of clothes lines for drying of fabric. Most dryers in use today use heated air which is passed over and or through the fabric as it is tumbled within the dryer. The air may be heated, for example, either electronically, via gas flame, or even with microwave radiation. Such air may be heated from about 15° C. to about 400° C., from about 25° C. to about 200° C., from about 35° C. to about 100° C., or even from about 40° C. to about 85° C. and used in the dryer to dry a surface and/or a fabric. As will be appreciated by one skilled in the art, the cleaning compositions of the present invention are ideally suited for use in laundry applications. Accordingly, the present invention includes a method for laundering a fabric. The method comprises the steps of contacting a fabric to be laundered with a said cleaning laundry solution comprising at least one embodiment of Applicants' cleaning composition, cleaning additive or mixture thereof. The fabric may comprise most any fabric capable of being laundered in normal consumer or institutional use conditions. The solution preferably has a pH of from about 8 to about 10.5. The compositions may be employed at concentrations of from about 500 ppm to about 15,000 ppm in solution. The water temperatures typically range from about 5° C. to about 90° C. The water to fabric ratio is typically from about 1:1 to about 30:1.

Test Methods

Test Method 1

A protocol to define whether a dye or pigment material is a fabric hueing agent for the purpose of the invention is given here:

1.) Fill two tergotometer pots with 800 ml of Newcastle upon Tyne, UK, City Water (~12 grains per US gallon total hardness, supplied by Northumbrian Water, Pity Me, Durham, Co. Durham, UK).
2) Insert pots into tergotometer, with water temperature controlled at 30° C. and agitation set at 40 rpm for the duration of the experiment.
3) Add 4.8 g of IEC-B detergent (IEC 60456 Washing Machine Reference Base Detergent Type B), supplied by wfk, Brüggen-Bracht, Germany, to each pot.
4) After two minutes, add 2.0 mg active colorant to the first pot.
5) After one minute, add 50 g of flat cotton vest (supplied by Warwick Equest, Consett, County Durham, UK), cut into 5 cm×5 cm swatches, to each pot.
6) After 10 minutes, drain the pots and re-fill with cold Water (16° C.) having a water hardness of 14.4 English Clark Degrees Hardness with a 3:1 Calcium to Magnesium molar ratio.
7) After 2 minutes rinsing, remove fabrics.
8) Repeat steps 3-7 for a further three cycles using the same treatments.
9) Collect and line dry the fabrics indoors for 12 hours.

10) Analyse the swatches using a Hunter Miniscan spectrometer fitted with D65 illuminant and UVA cutting filter, to obtain Hunter a (red-green axis) and Hunter b (yellow-blue axis) values.

11) Average the Hunter a and Hunter b values for each set of fabrics. If the fabrics treated with colorant under assessment show an average difference in hue of greater than 0.2 units on either the a axis or b axis, it is deemed to be a fabric hueing agent for the purpose of the invention.

Test Method 2

For Test Method 2, the BMI microswatch assay is run using the detergent compositions 1, 2 or 4 from Table 1-3. The detergent is dissolved in water that has a hardness of 6 gpg and adjusted to a temperature of 16° C. Performance of the variant enzymes is then determined as per the BMI microswatch assay described. The performance index is determined by comparing the performance of the variant with that of the enzyme of SEQ ID NO:2, SEQ ID NO:4 or SEQ ID NO:6, with in all cases the enzyme dosage being 1 ppm. This Method is described in further detail in Example 31.

Test Method 3

For Test Method 3 the BMI microswatch assay is run using the detergent compositions 1, 2 or 4 from Table 1-3. The detergent is dissolved in water that has a hardness of 6 gpg and adjusted to a temperature of 16° C. Performance of the variant enzymes is then determined as per the BMI microswatch assay described. The performance index is determined by comparing the performance of the variant with that of the enzyme of SEQ ID NO:2, SEQ ID NO:4 or SEQ ID NO:6, with in all cases the enzyme dosage being 0.4 ppm. This Method is described in further detail in Example 1.

Test Method 4

For Test Method 4, the BMI microswatch assay is run using the detergent composition 10 from Table 19-4. The detergent is dissolved in water that has a hardness of 12 gpg and adjusted to a temperature of 16° C. Performance of the variant enzymes is then determined as per the BMI microswatch assay described. The performance index is determined by comparing the performance of the variant with that of the enzyme of SEQ ID NO:755, with in all cases the enzyme dosage being 1.6 ppm. Enzymes having a performance index of 1.1 or greater are viewed to be Series 1 GG36 cold water proteases. This Method is described in further detail in Example 19.

Test Method 5

For Test Method 5, the BMI microswatch assay is run using the detergent composition 7 from Table 19-4. The detergent is dissolved in water that has a hardness of 6 gpg and adjusted to a temperature of 16° C. Performance of the variant enzymes is then determined as per the BMI microswatch assay described. The performance index is determined by comparing the performance of the variant with that of the enzyme of SEQ ID NO:755, with in all cases the enzyme dosage being 4 ppm. Enzymes having a performance index of 1.1 or greater are viewed to be Series 1 GG36 cold water proteases. This Method is described in further detail in Example 19.

Test Method 6

For Test Method 6 the BMI microswatch assay is run using the detergent composition 7 from Table 19-4. The detergent is dissolved in water that has a hardness of 6 gpg and adjusted to a temperature of 16° C. Performance of the variant enzymes is then determined as per the BMI microswatch assay described. The performance index is determined by comparing the performance of the variant with that of a reference enzyme, said reference enzyme being the enzyme of SEQ ID NO:755 consisting the A158E mutation, with in all cases the enzyme dosage being 4 ppm. Enzymes having a performance index of 1.0 or greater are viewed to be Series 1 GG36 cold water proteases. This Method is described in further detail in Example 19.

Test Method 7

Electrical conductivity of an aqueous solution is assayed according to the standard method ASTM D1125 and reported in units of milliSiemens/cm, abbreviated to mS/cm in this patent.

EXPERIMENTAL

In the experimental disclosure which follow, the following abbreviations apply: PI (Performance Index), ppm (parts per million); M (molar); mM (millimolar); µM (micromolar); nM (nanomolar); mol (moles); mmol (millimoles); µmol (micromoles); nmol (nanomoles); gm (grams); mg (milligrams); µg (micrograms); pg (picograms); L (liters); ml and mL (milliliters); µl and µL (microliters); cm (centimeters); mm (millimeters); µm (micrometers); nm (nanometers); U (units); V (volts); MW (molecular weight); sec (seconds); min(s) (minute/minutes); h(s) and hr(s) (hour/hours); ° C. (degrees Centigrade); QS (quantity sufficient); ND (not done); rpm (revolutions per minute); GH (degrees German hardness); $H_2O$ (water); $dH_2O$ (deionized water); HCl (hydrochloric acid); aa (amino acid); bp (base pair); kb (kilobase pair); kD (kilodaltons); cDNA (copy or complementary DNA); DNA (deoxyribonucleic acid); ssDNA (single stranded DNA); dsDNA (double stranded DNA); dNTP (deoxyribonucleotide triphosphate); RNA (ribonucleic acid); $MgCl_2$ (magnesium chloride); NaCl (sodium chloride); w/v (weight to volume); v/v (volume to volume); w/w (weight to weight); g (gravity); OD (optical density); ppm (parts per million); Dulbecco's phosphate buffered solution (DPBS); SOC (2% Bacto-Tryptone, 0.5% Bacto Yeast Extract, 10 mM NaCl, 2.5 mM KCl); Terrific Broth (TB; 12 g/l Bacto-Tryptone, 24 g/l glycerol, 2.31 g/l $KH_2PO_4$, and 12.54 g/l $K_2HPO_4$); $OD_{280}$ (optical density at 280 nm); $OD_{600}$ (optical density at 600 nm); $A_{405}$ (absorbance at 405 nm); Vmax (the maximum initial velocity of an enzyme catalyzed reaction); PAGE (polyacrylamide gel electrophoresis); PBS (phosphate buffered saline [150 mM NaCl, 10 mM sodium phosphate buffer, pH 7.2]); PBST (PBS+0.25% TWEEN®-20); PEG (polyethylene glycol); PCR (polymerase chain reaction); RT-PCR (reverse transcription PCR); SDS (sodium dodecyl sulfate); Tris (tris(hydroxymethyl)aminomethane); HEPES (N-[2-Hydroxyethyl] piperazine-N-[2-ethanesulfonic acid]); HBS (HEPES buffered saline); Tris-HCl (tris[Hydroxymethyl]aminomethane-hydrochloride); Tricine (N-[tris-(hydroxymethyl)-methyl]-glycine); CHES (2-(N-cyclo-hexylamino) ethane-sulfonic acid); TAPS (3-{[tris-(hydroxymethyl)-methyl]-amino}-propanesulfonic acid); CAPS (3-(cyclo-hexylamino)-propane-sulfonic acid; DMSO (dimethyl sulfoxide); DTT (1,4-dithio-DL-threitol); SA (sinapinic acid (s,5-dimethoxy-4-hydroxy cinnamic acid); TCA (trichloroacetic acid); Glut and GSH (reduced glutathione); GSSG (oxidized glutathione); TCEP (Tris[2-carboxyethyl]phosphine); Ci (Curies); mCi (milliCuries); µCi (microCuries); HPLC (high-performance liquid chromatography); RP-HPLC (reverse phase high pressure liquid chromatography); TLC (thin layer chromatography); MALDI-TOF (matrix-assisted laser desorption/ionization—time of flight); Ts (tosyl); Bn (benzyl); Ph (phenyl); Ms (mesyl); Et (ethyl), Me (methyl); Taq (*Thermus aquaticus* DNA polymerase); Klenow (DNA polymerase I large (Klenow) fragment); EGTA (ethylene glycol-bis(B-aminoethyl ether) N,N,N',N'-tetraacetic acid); EDTA (ethylenediaminetetracetic acid); bla (β-lactamase or ampicillin-resistance gene); HDL (heavy duty liquid); HDD (heavy duty powder detergent); HSG (high suds granular detergent); CEE (Central and Eastern Europe); WE (Western Europe); NA, when used in reference to detergents (North America); Japan and JPN, when used in reference to detergents (Japan); MTP (microtiter plate); MJ Research (MJ Research, Reno, Nev.); Baseclear (Baseclear BV, Inc., Leiden, The Netherlands); PerSeptive (PerSeptive Biosystems, Framingham, Mass.); ThermoFinnigan (ThermoFinnigan, San Jose, Calif.); Argo (Argo BioAnalytica, Morris Plains, N.J.); Seitz EKS (SeitzSchenk Filtersystems GmbH, Bad Kreuznach, Germany); Pall (Pall Corp., East Hills, N.Y. and Bad Kreuznach, Germany); Spectrum (Spectrum Laboratories, Dominguez Rancho, Calif.); Molecular Structure (Molecular Structure Corp., Woodlands, Tex.); Accelrys (Accelrys, Inc., San Diego, Calif.); Chemical Computing (Chemical Computing Corp., Montreal, Canada); New Brunswick (New Brunswick Scientific, Co., Edison, N.J.); CFT (Center for Test Materials, Vlaardingen, The Netherlands); P&G and Procter & Gamble (Procter & Gamble, Inc., Cincinnati, Ohio); GE Healthcare (GE Healthcare, Chalfont St. Giles, United Kingdom); DNA2.0 (DNA2.0, Menlo Park, Calif.); OXOID (Oxoid, Basingstoke, Hampshire, UK); Megazyme (Megazyme International Ireland Ltd., Bray Business Park, Bray, Co., Wicklow, Ireland); Finnzymes (Finnzymes Oy, Espoo, Finland); Kelco (CP Kelco, Wilmington, Del.); Corning (Corning Life Sciences, Corning, N.Y.); (NEN (NEN Life Science Products, Boston, Mass.); Pharma AS (Pharma AS, Oslo, Norway); Dynal (Dynal, Oslo, Norway); Bio-Synthesis (Bio-Synthesis, Lewisville, Tex.); ATCC (American Type Culture Collection, Rockville, Md.); Gibco/BRL (Gibco/BRL, Grand Island, N.Y.); Sigma (Sigma Chemical Co., St. Louis, Mo.); Pharmacia (Pharmacia Biotech, Piscataway, N.J.); NCBI (National Center for Biotechnology Information); Applied Biosystems (Applied Biosystems, Foster City, Calif.); BD Biosciences and/or Clontech (BD Biosciences CLONTECH Laboratories, Palo Alto, Calif.); Operon Technologies (Operon Technologies, Inc., Alameda, Calif.); MWG Biotech (MWG Biotech, High Point, N.C.); Oligos Etc (Oligos Etc. Inc, Wilsonville, Oreg.); Bachem (Bachem Bioscience, Inc., King of Prussia, Pa.); Difco (Difco Laboratories, Detroit, Mich.); Mediatech (Mediatech, Herndon, Va.; Santa Cruz (Santa Cruz Biotechnology, Inc., Santa Cruz, Calif.); Oxoid (Oxoid Inc., Ogdensburg, N.Y.); Worthington (Worthington Biochemical Corp., Freehold, N.J.); GIBCO BRL or Gibco BRL (Life Technologies, Inc., Gaithersburg, Md.); Millipore (Millipore, Billerica, Mass.); Bio-Rad (Bio-Rad, Hercules, Calif.); Invitrogen (Invitrogen Corp., San Diego, Calif.); NEB (New England Biolabs, Beverly, Mass.); Sigma (Sigma Chemical Co., St. Louis, Mo.); Pierce (Pierce Biotechnology, Rockford, Ill.); Takara (Takara Bio Inc. Otsu, Japan); Roche (Hoffmann-La Roche, Basel, Switzerland); Gene Oracle (Gene Oracle, Inc., Mountain View, Calif.); EM Science (EM Science, Gibbstown, N.J.); Qiagen (Qiagen, Inc., Valencia, Calif.); Biodesign (Biodesign Intl., Saco, Me.); Aptagen (Aptagen, Inc., Herndon, Va.); Sorvall (Sorvall brand, from Kendro Laboratory Products, Asheville, N.C.); Molecular Devices (Molecular Devices, Corp., Sunnyvale, Calif.); R&D Systems (R&D Systems, Minneapolis, Minn.); Siegfried Handel (Siegfried Handel AG, Zofingen, Switzerland); Stratagene (Stratagene Cloning Systems, La Jolla, Calif.); Marsh (Marsh Biosciences, Rochester, N.Y.); Geneart (Geneart GmbH, Regensburg, Germany); Bio-Tek (Bio-Tek Instruments, Winooski, Vt.); (Biacore (Biacore, Inc., Piscataway, N.J.); PeproTech (PeproTech, Rocky Hill, N.J.); SynPep (SynPep, Dublin, Calif.); New Objective (New Objective brand; Scientific Instrument Services, Inc., Ringoes, N.J.); Waters (Waters, Inc., Milford, Mass.); Matrix Science (Matrix Science, Boston, Mass.); Dionex (Dionex, Corp., Sunnyvale, Calif.); Monsanto (Monsanto Co., St. Louis, Mo.); Wintershall (Wintershall AG, Kassel, Germany); BASF (BASF Co., Florham Park, N.J.); Huntsman (Huntsman Petrochemical Corp., Salt Lake City, Utah); Shell Chemicals (Shell Chemicals, Inc., London, UK); (Stepan, Northfield, Ill.); Clariant (Clariant, Sulzbach, Germany); Industrial Zeolite (Industrial Zeolite Ltd., Grays, Essex, UK); Jungbunzlauer (Jungbunzlauer, Basel, Switzerland); Solvay (Solvay, Brussels, Belgium); 3V Sigma (3V Sigma, Bergamo, Italy); Innospec (Innospec, Ellesmere Port, UK); Thermphos (Thermphos, Vlissiggen-Ost, The Netherlands); Ciba Specialty (Ciba Specialty Chemicals, Basel, Switzerland); Dow Corning (Dow Corning, Barry, UK); Enichem (Enichem Iberica, Barcelona, Spain); Fluka Chemie AG (Fluka Chemie AG, Buchs, Switzerland); Gist-Brocades (Gist-Brocades, NV, Delft, The Netherlands); Dow Corning (Dow Corning Corp., Midland, Mich.); Mettler-Toledo (Mettler-Toledo Inc, Columbus, Ohio); RB (Reckitt-Benckiser, Slough, UK); and Microsoft (Microsoft, Inc., Redmond, Wash.).

For North American (NA) and Western European (WE) heavy duty liquid laundry (HDL) detergents, heat inactivation of the enzymes present in commercially-available detergents is performed by placing pre-weighed liquid detergent (in a glass bottle) in a water bath at 95° C. for 2 hours. The incubation time for heat inactivation of NA and WE auto dish washing (ADW) detergents is 8 hours. Both un-heated and heated detergents are assayed within 5 minutes of dissolving the detergent to accurately determine percentage deactivated. Enzyme activity is tested by the AAPF assay.

For testing of enzyme activity in heat-inactivated detergents, working solutions of detergents are made from the heat inactivated stocks. Appropriate amounts of water hardness (e.g., 6 gpg or 12 gpg) and buffer are added to the detergent solutions to match the desired conditions. The solutions are mixed by vortexing or inverting the bottles. The following Table provides information regarding some of the commercially-available detergents and test conditions used herein. In some experiments, additional and/or other commercially available detergents find use in the following Examples.

TABLE 1.1

Laundry and Dish Washing Conditions

| Region | Form | Dose | Detergent* | Buffer | gpg | pH | T (° C.) |
|---|---|---|---|---|---|---|---|
| Laundry (Heavy Duty Liquid and Granular) | | | | | | | |
| NA | HDL | 0.78 g/l | P&G TIDE ® 2X | 5 mM HEPES | 6 | 8.0 | 20 |
| WE | HDL | 5.0 g/L | Henkel PERSIL ™ | 5 mM HEPES | 12 | 8.2 | 40 |
| WE | HDG | 8.0 g/L | P&G ARIEL ® | 2 mM $Na_2CO_3$ | 12 | 10.5 | 40 |
| JPN | HDG | 0.7 g/L | P&G TIDE ® | 2 mM $Na_2CO_3$ | 6 | 10.0 | 20 |
| NA | HDG | 1.0 g/L | P&G TIDE ® | 2 mM $Na_2CO_3$ | 6 | 10.0 | 20 |
| Automatic Dish Washing | | | | | | | |
| WE | ADW | 3.0 g/L | RB CALGONIT ™ | 2 mM $Na_2CO_3$ | 21 | 10.0 | 40 |

TABLE 1.1-continued

| Laundry and Dish Washing Conditions | | | | | | | |
|---|---|---|---|---|---|---|---|
| Region | Form | Dose | Detergent* | Buffer | gpg | pH | T (° C.) |
| NA | ADW | 3.0 g/L | P&G CASCADE ® | 2 mM $Na_2CO_3$ | 9 | 10.0 | 40 |

In some additional aspects, the following solutions find use:

TABLE 1-2

| Working Detergent Solutions | | | | | |
|---|---|---|---|---|---|
| Detergent | Temp (C.) | Detergent g/L | pH | Buffer | gpg |
| TIDE ® 2X Cold | 16 | 0.98 | 8 | 5 mM HEPES | 6 |
| TIDE ® 2X Cold | 32 | 0.98 | 8 | 5 mM HEPES | 6 |
| TIDE ® 2X Cold | 16 | 0.98 | 7 | 5 mM MOPS | 6 |

The examples, which are intended to be purely exemplary of the invention and should therefore not be considered to limit the invention in any way, also describe and detail aspects and embodiments of the invention discussed above. The foregoing examples and detailed description are offered by way of illustration and not by way of limitation.

BPN' Variant or Part I Examples

Table of Detergents

The compositions of the detergents used in the assays in BPN' Variant (or Part I) Examples are shown in Table 1-3. BPN' variant protein samples were added to the detergent compositions as described in Part I Example 1 to assay for the various properties tested.

The following are liquid laundry detergent compositions suitable for top-loading automatic washing machines (1, 2 & 4) and front loading washing machines (3).

TABLE 1-3

Composition of Detergents Used in the Assays to Test BPN' Variants

| | Composition (wt % of composition) | | | |
|---|---|---|---|---|
| Ingredient | 1 | 2 | 3 | 4 |
| $C_{12-15}$ Alkylethoxy(1.8)sulfate | 14.7 | 11.6 | | 16.31 |
| $C_{11.8}$ Alkylbenzene sulfonate | 4.3 | 11.6 | 8.3 | 7.73 |
| $C_{16-17}$ Branched alkyl sulfate | 1.7 | 1.29 | | 3.09 |
| $C_{12-14}$ Alkyl-9-ethoxylate | 0.9 | 1.07 | | 1.31 |
| $C_{12}$ dimethylamine oxide | 0.6 | 0.64 | | 1.03 |
| Citric acid | 3.5 | 0.65 | 3 | 0.66 |
| $C_{12-18}$ fatty acid | 1.5 | 2.32 | 3.6 | 1.52 |
| Sodium Borate (Borax) | 2.5 | 2.46 | 1.2 | 2.53 |
| Sodium $C_{12-14}$ alkyl ethoxy 3 sulfate | | | 2.9 | |
| $C_{14-15}$ alkyl 7-ethoxylate | | | 4.2 | |
| $C_{12-14}$ Alkyl-7-ethoxylate | | | 1.7 | |
| Ca formate | 0.09 | 0.09 | | 0.09 |
| A compound having the following general structure: bis(($C_2H_5O$)($C_2H_4O$)*n*)($CH_3$)—$N^+$—$C_xH_{2x}$—$N^+$—($CH_3$)-bis(($C_2H_5O$)($C_2H_4O$)*n*), wherein n = from 20 to 30, and x = from 3 to 8, or sulphated or sulphonated variants thereof | | | 1.2 | |
| Random graft co-polymer[1] | | 1.46 | 0.5 | |
| Ethoxylated Polyethylenimine[2] | 1.5 | 1.29 | | 1.44 |
| Diethylene triamine pentaacetic acid | 0.34 | 0.64 | | 0.34 |
| Diethylene triamine penta(methylene phosphonic acid) | | | 0.3 | |
| Tinopal AMS-GX | | 0.06 | | |
| Tinopal CBS-X | 0.2 | 0.17 | | 0.29 |
| Amphiphilic alkoxylated grease cleaning polymer[3] | 1.28 | 1 | 0.4 | 1.93 |
| Ethanol | 2 | 1.58 | 1.6 | 5.4 |
| Propylene Glycol | 3.9 | 3.59 | 1.3 | 4.3 |
| Diethylene glycol | 1.05 | 1.54 | | 1.15 |
| Polyethylene glycol | 0.06 | 0.04 | | 0.1 |
| Monoethanolamine | 3.05 | 2.41 | 0.4 | 1.26 |
| NaOH | 2.44 | 1.8 | | 3.01 |
| Sodium Cumene Sulphonate | | | 1 | |
| Sodium Formate | | 0.11 | | 0.09 |
| Water, Aesthetics (Dyes, perfumes) and Minors (Enzymes, solvents, structurants) | balance | balance | balance | |

[1]Random graft copolymer is a polyvinyl acetate grafted polyethylene oxide copolymer having a polyethylene oxide backbone and multiple polyvinyl acetate side chains. The molecular weight of the polyethylene oxide backbone is about 6000 and the weight ratio of the polyethylene oxide to polyvinyl acetate is about 40 to 60 and no more than 1 grafting point per 50 ethylene oxide units.

[2]Polyethylenimine (MW = 600) with 20 ethoxylate groups per —NH.

[3]Amphiphilic alkoxylated grease cleaning polymer is a polyethylenimine (MW = 600) with 24 ethoxylate groups per —NH and 16 propoxylate groups per —NH Vectors, Cells, and Methods for Making Protease Variant Polypeptides of the Invention A variety of methods are known in the art that are suitable for generating modified polynucleotides of the invention that encode protease variants of the invention (such as cold water proteases of the invention), including, but not limited to, e.g., site-saturation mutagenesis, scanning mutagenesis, insertional mutagenesis, deletion mutagenesis, random mutagenesis, site-directed mutagenesis, and directed-evolution, as well as various other recombinatorial approaches. Methods for making modified polynucleotides and proteins (e.g., protease variants) include DNA shuffling methodologies (see, e.g., Stemmer W P, Proc. Natl. Acad. Sci. USA 91(22):10747-51 (1994)); methods based on non-homologous recombination of genes, e.g., ITCHY (Ostermeier et al., Bioorg. Med. Chem. 7:2139-44 [1999]); SCRATCHY (Lutz et al. Proc. Natl. Acad. Sci. USA 98:11248-53 [2001]); SHIPREC (Sieber et al., Nat. Biotechnol. 19:456-60 [2001]); NRR (Bittker et al., Nat. Biotechnol. 20:1024-9 [2001]; Bittker et al., Proc Natl. Acad. Sci. USA 101:7011-6 [2004]); methods that rely on the use of oligonucleotides to insert random and targeted mutations, deletions and/or insertions (Ness et al., Nat. Biotechnol. 20:1251-5 [2002]; Coco et al., Nat. Biotechnol. 20:1246-50 [2002]; Zha et al., Chembiochem. 4:34-9 [2003]; Glaser et al., J. Immunol. 149:3903-13 [1992]); see also Arkin and Youvan, Biotechnology 10:297-300 (1992); Reidhaar-Olson et al., Methods Enzymol. 208:564-86 (1991).

In one aspect, a full-length parent polynucleotide is ligated into an appropriate expression plasmid, and the following mutagenesis method is used to facilitate the construction of the modified protease of the present invention, although other methods may be used. The method is based on that described by Pisarchik et al. (Pisarchik et al., Prot. Eng. Des. Select. 20:257-265 [2007]). In one aspect, an added advantage is provided in that the restriction enzyme cuts outside its recognition sequence, which allows digestion of practically any nucleotide sequence and precludes formation of a restriction site scar.

In one approach, a naturally-occurring gene encoding a full-length protease is obtained and sequenced and scanned for one or more points at which it is desired to make a mutation (e.g., deletion, insertion, substitution) at one or more amino acids. Mutation of the gene in order to change its sequence to conform to the desired sequence is accomplished by primer extension in accord with generally known methods. Fragments to the left and to the right of the desired point(s) of mutation are amplified by PCR and to include the Eam1104I restriction site. The left and right fragments are digested with Eam1104I to generate a plurality of fragments having complementary three base overhangs, which are then pooled and ligated to generate a library of modified sequences containing one or more mutations. This method avoids the occurrence of frame-shift mutations. This method also simplifies the mutagenesis process because all of the oligonucleotides can be synthesized so as to have the same restriction site, and no synthetic linkers are necessary to create the restriction sites as is required by some other methods.

PART I EXAMPLES

Example 1

Assays

Various assays were used as set forth below. Any deviations from the protocols provided below are indicated in the subsequent Examples.

A. TCA Assay for Protein Content Determination in 96-Well Microtiter Plates

For BPN' and BPN' variants, this assay was started using filtered *B. subtilis* bacterial culture supernatant from microtiter plates grown 3-4 days at 33-37° C. with shaking at 230-250 rpm and humidified aeration. A fresh 96-well flat bottom microtiter plate (MTP) was used for the assay. First, 100 μL/well of 0.25N HCl was placed in each well. Then, 25 μL of filtered culture broth was added. The light scattering/absorbance at 405 nm (use 5 sec mixing mode in the plate reader) was then determined in order to provide the "blank" reading. For the test, 100 μL/well of 30% (w/v) trichloroacetic acid (TCA) was placed in the plates and incubated for 10 minutes at room temperature. The light scattering/absorbance at 405 nm (use 5 sec mixing mode in the plate reader) was then determined. The equipment used was a Biomek FX Robot (Beckman Coulter) and a SpectraMAX (type 340; Molecular Devices) MTP Reader; the MTPs were from Costar (type 9017).

The calculations were performed by subtracting the blank (no TCA) from the test reading with TCA to provide a relative measure of the protein content in the samples. If desired, a standard curve can be created by calibrating the TCA readings with AAPF assays of clones with known conversion factors. However, the TCA results are linear with respect to protein concentration from 250 to 2500 micrograms protein per ml (ppm) and can thus be plotted directly against enzyme performance for the purpose of choosing good-performing variants. The turbidity/light scatter increase in the samples correlates to the total amount of precipitable protein in the culture supernatant.

B. AAPF Protease Assay in 96-Well Microtiter Plates

In order to determine the protease activity of the proteases and variants thereof of the present invention, the hydrolysis of N-succinyl-L-alanyl-L-alanyl-L-prolyl-L-phenyl-p-nitroanilide (suc-AAPF-pNA) was measured. The reagent solutions used were: 100 mM Tris/HCl, pH 8.6, containing 0.005% TWEEN®-80 (Tris dilution buffer); 100 mM Tris buffer, pH 8.6, containing 10 mM $CaCl_2$ and 0.005% TWEEN®-80 (Tris/Ca buffer); and 160 mM suc-AAPF-pNA in DMSO (suc-AAPF-pNA stock solution) (Sigma: S-7388). To prepare a suc-AAPF-pNA working solution, 1 ml suc-AAPF-pNA stock solution was added to 100 ml Tris/Ca buffer and mixed well for at least 10 seconds. The assay was performed by adding 10 μl of diluted protease solution to each well, immediately followed by the addition of 190 μl 1 mg/ml suc-AAPF-pNA working solution. The solutions were mixed for 5 sec., and the absorbance change in kinetic mode (25 readings in 5 minutes) was read at 405 nm in an MTP reader, at 25° C. The protease activity was expressed as AU (activity=$\Delta OD \cdot min^{-1} ml^{-1}$).

C. BMI Microswatch Assay of Test Method 3

Blood milk and ink (BMI) stained microswatches of 5.5 millimeter circular diameter were obtained from CFT. Before cutting the swatches, the fabric (EMPA 116) was washed with water. One microswatch was placed in each well of a 96-well non-binding microtiter plate (Corning 3641). The detergents used for the assays included Detergent Composition 1, Detergent Composition 2, and Detergent Composition 4. The detergents were diluted in Milli-Q (deionized) water to a working strength concentration of 0.788 g/L. These detergents were buffered with 5 mM HEPES pH 8.2 or pH 7.2, which upon addition to detergent, buffers at pH 8 or pH 7, respectively. Additionally, 6 grains per gallon (gpg) water hardness (3:1 Ca:Mg—$CaCl_2$:$MgCl_2$.$6H_2O$) was added. The detergent solution was pre-equilibrated in an ice-water bath for 16° C. assays (room temperature for 32° C. assays) and pumped into a circulating reservoir (Beckman FX). Then, 190 μl of the desired detergent solution was added to each well of the MTP that contained microswatches. To this mixture, 10 μl of the diluted enzyme master dilution solution was added, providing an approximate enzyme concentration of 0.4-0.5 μg/mL. The master dilution was prepared from the culture supernatants at 8 μg/mL, where the approximate enzyme concentration of the culture supernatants and BPN'-v3 or BPN'-v36 parent controls was determined using the AAPF protease activity assay, basing the concentration on a purified BPN'-v3 or BPN'-v36 standard of known concentration. The MTP was sealed with tape and placed in the iEMS incubator/shaker (Thermo/Labsystems) pre-set at 16° C. in a refrigerated dairy case or at 32° C. on the benchtop for 20 minutes, with agitation at 1400 rpm. Following incubation under the appropriate conditions, the sealing tape was removed from each plate and 125 μl (150 μl if pipetting by hand for smaller screens) of the solution from each well was transferred into a fresh MTP (Corning 9017). The new MTP containing 125 μl-150 μl of solution/well was read at 600 nm (with 5 sec mixing mode in the plate reader) using a MTP SpectraMax reader (type 340; Molecular Devices). Blank controls containing a microswatch and detergent but no enzyme were also included. The absorbance value obtained was corrected for the blank value (substrate without enzyme), providing a measure of hydrolytic activity. For each sample (variant), the performance index was calculated as described below. This BMI Microswatch Assay, run at 60° F. (16° C.) and pH 8, is referred to herein as "Test Method. 3"

D. Stability Assay

The stability of protease variants was determined in the presence of 40% concentrated Detergent Composition 3 diluted in water. The reagents used were Detergent Composition 3 diluted to 50% in Milli-Q water, 10 mM MES 0.01% TWEEN®-80 pH 5.8 master dilution buffer, AAPF reagents: see protocol AAPF assay. The equipment used was F-bottom MTP (Corning 9017) for dilution of diluted enzyme into detergent as well as for suc-AAPF-pNA plates, Biomek FX (Beckman Coulter), Spectramax Plus 384 MTP Reader (Molecular Devices), iEMS Incubator/Shaker (1 mm amplitude) (Thermo Electron Corporation), sealing tape: Nunc (236366), circulating reservoir (Beckman Fx).

Detergent Composition 3 was initially diluted to 50% in water. This detergent was kept at room temperature and cycled through the circulating reservoir. The iEMS incubators/shakers (Thermo/Labsystems) were pre-set at 43° C. Culture supernatants were diluted into plates containing master dilution buffer to a concentration of ~20 ppm (master dilution plate). Then, 40 μl of sample from the master dilution plate was added to plates containing 160 μl 50% Detergent Composition 3 to give a final incubation concentration of 4 ppm. The contents were mixed and kept at room temperature and triplicate AAPF assays were performed immediately on these plates and recorded as unstressed reads. The AAPF assay was modified such that 20 μL of sample from the step above was added to 190 μL of suc-AAPF-pNA working solution. The plates were immediately covered with sealing tape and placed in 43° C. iEMS shakers for 30 min at 650 rpm. Following 30 minutes of incubation, triplicate AAPF assays were performed on these stress plates and recorded as stressed reads. The stability of the samples was determined by calculating the ratio of the residual and initial AAPF activity as follows: Residual Activity (%)=[mOD·min$^{-1}$ stressed]*100/[mOD·min$^{-1}$ unstressed]. For each sample (variant), the performance index was calculated as described below.

E. LAS/EDTA Stability Assay

The stability of protease variants in the presence of a representative anionic surfactant (LAS=linear alkylbenzene sulfonate, specifically, sodium dodecylbenzenesulfonate-DOBS) and di-sodium EDTA was measured after incubation under defined conditions and the residual activity was determined using the AAPF assay. The reagents used were dodecyllbenzene sulfonate, sodium salt (DOBS, Sigma No. D-2525), TWEEN®-80 (Sigma No. P-8074), di-sodium EDTA (Siegfried Handel No. 164599-02), HEPES (Sigma No. H-7523), unstressed buffer: 50 mM HEPES (11.9 g/l)+0.005% TWEEN®-80, pH 8.0, Stress buffer: 50 mM HEPES (11.9 g/l), 0.1% (w/v) DOBS (1 g/l), 10 mM EDTA (3.36 g/l), pH 8.0, reference protease and protease variant culture supernatants, containing 200-400 μg/ml protein. The equipment used was V- or U-bottom MTPs as dilution plates (Greiner 651101 and 650161, respectively), F-bottom MTPs (Corning 9017) for unstressed and LAS/EDTA buffer as well as for suc-AAPF-pNA plates, Biomek FX (Beckman Coulter), Spectramax Plus 384 MTP Reader (Molecular Devices), iEMS Incubator/Shaker (1 mm amplitude) (Thermo Electron Corporation), and Nunc sealing tape (236366).

The iEMS incubator/shaker (Thermo/Labsystems) was set at 29° C. Culture supernatants were diluted into plates containing unstressed buffer to a concentration of ~25 ppm (master dilution plate). Then, 20 μl of sample from the master dilution plate was added to plates containing 180 μl unstressed buffer to give a final incubation concentration of 2.5 ppm. The contents were mixed and kept at room temperature and an AAPF assay was performed on this plate. Then, 20 μl of sample from the master dilution plate was also added to plates containing 180 μl stress buffer (50 mM HEPES (11.9 g/l), 0.1% (w/v) DOBS (1 g/l), 10 mM EDTA (3.36 g/l), pH 8.0). The solutions were mixed and immediately placed in 29° C. iEMS shaker for 30 min at 400 rpm. Following 30 minutes of incubation, an AAPF assay was performed on the stress plate. The stability of the samples was determined by calculating the ratio of the residual and initial AAPF activity as follows: Residual Activity (%)=[mOD·min-1 stressed]*100/[mOD·min-1 unstressed]. For each sample (variant), the performance index was calculated as described below.

Performance Index

The performance index provides a comparison of the performance of a variant (actual value) and a standard or reference protease enzyme (theoretical value) at the same protein concentration. The theoretical values can be calculated using the parameters of a performance dose response curve (i.e. using a Langmuir equation to generate the performance curve) of the standard/reference protease. A performance index (PI) that is greater than 1 (PI>1) identifies a better variant as compared to the standard or reference protease (which may be, e.g., wild-type protease or another protease variant), while a PI of 1 (PI=1) identifies a variant that performs the same as the standard or reference protease, and a PI that is less than 1 (PI<1) identifies a variant that performs worse than the standard or reference protease. Thus, the PI identifies winners (e.g., variants having enhanced proteolytic activity compared to that of the standard/reference protease) as well as variants that may be less desirable for use under certain circumstances (e.g., variants having proteolytic activity lower than the proteolytic activity of the standard/reference protease).

It is important to note that protease variants of the invention having performance index values lower than that of a reference or standard protease are nevertheless useful in the applications and methods described herein. For example, protease variants of the invention having performance index values lower than that of a reference or standard protease have proteolytic activity and thus are useful in the compositions of the invention, such as, but not limited to, e.g., cleaning compositions (including, but not limited, to, e.g., detergent cleaning compositions) for cleaning a variety of surfaces and items, including, but not limited to, e.g., laundry, fabrics, and dishware, and in personal care applications and compositions as described elsewhere herein; such protease variants are also useful in fabric and home care products and compositions and in non-fabric and home care products and compositions described elsewhere herein and in methods of the invention, including, but not limited, to, e.g., cleaning methods, methods for personal care, etc., described elsewhere herein.

Various terms set forth below are used to describe the variant: non-deleterious variants have a PI>0.05; deleterious variants have a PI less than or equal to 0.05; combinable variants are those for which the variant has performance index values greater than or equal to 0.2 for at least one property, and >0.05 for all properties. Combinable variants are those that can be combined to deliver proteins with appropriate performance indices for one or more desired properties. These data find use in engineering any subtilisin/subtilase or protease. Even if the subtilase or protease to be engineered has an amino acid different from that of subtilisin BPN' at one or more particular positions, these data find use in identifying amino acid substitutions that alter the desired properties by identifying the best choices for substitutions, including substitutions of the BPN' wild type amino acid.

Example 2

Construction of BPN' Library and Cleaning Performance of BPN' Variants a) Description of the BPN'-v3 Expression Cassette Used for Library Construction The BPN'-v3 (BPN' protease containing G097A-G128A-Y217Q substitutions) expression cassette used for combinatorial library construction was generated using the BPN' expression cassette, which comprises the aprE-BPN' hybrid leader sequence (i.e., signal sequence), BPN' pro and BPN' mature sequence from *B. amyloliquefaciens*. The DNA sequence is shown below as SEQ ID NO:1 and encodes the BPN' precursor protein shown below as SEQ ID NO:168.

(SEQ ID NO: 1)

GTGAGAAGCAAAAAATTGTGGATCAGTTTGCTGTTTGCTTTAGCGTTAAT

CTTTACGATGGCGTTCGGCAGCACATCCTCTGCCCAGGCGGCAGGGAAAT

CAAACGGGGAAAAGAAATATATTGTCGGGTTTAAACAGACAATGAGCACG

ATGAGCGCCGCTAAGAAGAAAGATGTCATTTCTGAAAAAGGCGGGAAAGT

GCAAAAGCAATTCAAATATGTAGACGCAGCTTCAGCTACATTAAACGAAA

AAGCTGTAAAAGAATTGAAAAAAGACCCGAGCGTCGCTTACGTTGAAGAA

GATCACGTAGCACATGCGTACGCGCAGTCCGTGCCTTACGGCGTATCACA

AATTAAAGCCCCTGCTCTGCACTCTCAAGGCTACACTGGATCAAATGTTA

AAGTAGCGGTTATCGACAGCGGTATCGACTCGAGCCATCCAGATCTTAAA

GTCGCTGGAGGGGCTTCTATGGTGCCGTCCGAAACAAACCCGTTTCAAGA

TAACAATTCTCATGGCACACACGTCGCAGGAACGGTTGCGGCGTTAAACA

ATTCTATTGGCGTGCTTGGTGTAGCCCCGTCTGCTTCGCTCTACGCCGTT

AAAGTTCTTGGCGCAGACGGATCAGGCCAATACTCATGGATTATCAACGG

CATCGAATGGGCCATCGCGAATAACATGGATGTAATCAACATGAGCCTGG

-continued

GAGGACCAAGCGGCAGTGCGGCACTTAAAGCAGCAGTTGATAAAGCTGTT

GCATCTGGTGTCGTCGTAGTAGCGGCAGCTGGGAATGAGGGAACATCCGG

ATCATCGAGTACCGTCGGTTATCCAGGCAAGTACCCTTCAGTGATTGCAG

TGGGCGCTGTAGACTCTTCAAATCAACGTGCCTCTTTTTCCTCCGTGGGA

CCGGAGCTGGATGTCATGGCCCCTGGCGTTTCTATTCAATCGACGCTTCC

AGGGAACAAGTATGGTGCGTATAACGGGACTTCCATGGCCTCGCCGCATG

TAGCTGGGGCGGCCGCATTGATTCTTTCTAAGCACCCGAACTGGACAAAC

ACTCAAGTCCGCAGCAGTTTAGAAAACACCACTACAAAACTTGGTGATTC

TTTCTACTATGGAAAAGGGCTGATCAACGTACAGGCGGCAGCTCAG

In the nucleotide sequence of SEQ ID NO:1, the DNA sequence encoding the mature protease is shown in bold, the nucleotide sequence encoding leader sequence (aprE-BPN' hybrid leader sequence) is shown in standard (non-underlined) text, and the nucleotide sequence encoding the pro sequence (BPN') is underlined. In the amino acid sequence (aprE-BPN' hybrid leader sequence, BPN' pro sequence, and BPN' mature protein sequence) of the BPN' precursor protein set forth in SEQ ID NO:168, the bolded portion indicates the mature BPN' subtilisin protease.

(SEQ ID NO: 168)

VRSKKLWISLLFALALIFTMAFGSTSSAQAAGKSNGEKKYIVGFKQTMS

TMSAAKKKDVISEKGGKVQKQFKYVDAASATLNEKAVKELKKDPSVAYV

EEDHVAHAYAQSVPYGVSQIKAPALHSQGYTGSNVKVAVIDSGIDSSHP

DLKVAGGASMVPSETNPFQDNNSHGTHVAGTVAALNNSIGVLGVAPSAS

LYAVKVLGADGSGQYSWIINGIEWAIANNMDVINMSLGGPSGSAALKAA

VDKAVASGVVVVAAAGNEGTSGSSSTVGYPGKYPSVIAVGAVDSSNQRA

SFSSVGPELDVMAPGVSIQSTLPGNKYGAYNGTSMASPHVAGAAALILS

KHPNWTNTQVRSSLENTTTKLGDSFYYGKGLINVQAAAQ

The amino acid sequence of the mature BPN' subtilisin protease is shown as SEQ ID NO:2.

The nucleotide sequence of the mature BPN'-v3 gene is that of SEQ ID NO:3 (the signal sequence and propeptide sequence used in the BPN'-v3 expression cassette is the same as that for BPN' shown in SEQ ID NO:1). The protein sequence of the mature BPN'-v3 protease variant is that of SEQ ID NO:4 (the signal sequence and propeptide sequence used in the BPN'-v3 expression cassette is the same as that for BPN' shown in SEQ ID NO:168).

b) Construction of Combinatorial Library Using pHPLT-BPN'-v3 Plasmid

The pHPLT-BPN'-v3 plasmid (see FIG. 1) containing the BPN'-v3 expression cassette described above served as template DNA for cloning to provide variants derived from BPN'-v3. The vector pHPLT (FIG. 4 in U.S. Pat. No. 6,566,112) contains the *B. licheniformis* LAT promoter ("Plat"); a sequence encoding the LAT signal peptide ("preLAT"). Additional plasmid elements from plasmid pUB110 disclosed in McKenzie et al., *Plasmid* 15(2): 93-103 (1986): "ori-pUB" is the origin of replication from pUB110; "neo" is the neomycin/kanamycin resistance gene from pUB110; "Terminator" is the transcriptional terminator from *B. licheniformis* amylase.

A combinatorial DNA library was synthesized at DNA 2.0 and delivered as individual ligation reactions. In some instances for efficient transformation of *B. subtilis*, the DNA from the ligation reaction mixtures was amplified by rolling circle amplification (RCA) using the Illustra Templiphi kit (GE Healthcare). The reaction was performed according to the manufacturer's protocol. One microliter of ten-fold diluted amplified DNA was used to transform 50 μL of competent *B. subtilis* cells (ΔaprE, ΔnprE, amyE::xylRPxylA-comK-phleo). The transformation mixture was shaken at 37° C. for 1 hour. Ten micro-liter aliquots of the transformation mixture were plated on skim milk (1.6%) Luria agar plates supplemented with 10 μg/ml of neomycin (Teknova).

The transformants that formed halos on the skim milk plates were picked into microtiter plates containing 150 μl Luria broth (LB) medium supplemented with 10 μg/ml neomycin. Plates were grown overnight at 37° C. with 250-300 rpm shaking and 70-80% humidity using Enzyscreen lids for microtiter plates (Enzyscreen). Using a 96 pin replicating tool, (Enzyscreen) the overnight culture plate was used to inoculate a new microtiter plate containing 180 μl of MBD medium (a MOPS based defined medium) with 2.5 μg/ml neomycin. MBD medium was prepared essentially as known in the art (see Neidhardt et al., J. Bacteriol. 119:736-747 [1974]), except that $NH_4Cl$, $FeSO_4$, and $CaCl_2$ were omitted from the base medium, 3 mM $K_2HPO_4$ was used, and the base medium was supplemented with 60 mM urea, and 100 ml of a solution made of 210 g/L glucose, and 350 g/L maltodextrin. 1 g/L of BD Bacto Yeast Extract was added and the pH was adjusted to 7.4 with KOH. The micronutrients were made up as a 100x stock solution containing in one liter, 400 mg $FeSO_4.7H_2O$, 100 mg $MnSO_4.H_2O$, 100 mg $ZnSO_4.7H_2O$, 50 mg $CuCl_2.2H_2O$, 100 mg $CoCl_2.6H_2O$, 100 mg $NaMoO_4.2H_2O$, 100 mg $Na_2B_4O_7.10H_2O$, 10 ml of 1M $CaCl_2$, and 10 ml of 0.5 M sodium citrate. The MBD medium containing microtiter plates were grown for 64 hours at 37° C., 250-300 rpm, and 70-80% humidity using Enzyscreen lids (Enzyscreen) for protease variant expression. The next day, cultures were filtered through a micro-filter plate (0.22 um; Millipore) and the resulting filtrates containing protease variants were used for biochemical analysis.

The protease variants were tested for cleaning performance using a BMI microswatch assay in Detergent Composition 1 at 16° C. and pH 8 and BMI microswatch assay in Detergent Composition 2 at 16° C. and pH 8. Protein content was determined using the TCA assay. Assays were performed as described in Example 1 and Performance Indices were calculated relative to BPN'-v3 (with a PI value of 1) as per Test Method 3.

The following BPN' subtilisin protease variant was determined to have a PI value greater than 1.0, at least 1.1, or from greater than 1.0 to about 5 relative to BPN'-v3 in a BMI microswatch cleaning assay in Detergent Composition 1 at pH 8 and 16° C.: BPN' amino acid sequence (SEQ ID NO:2) comprising the set of amino acid substitutions G097A-G128A-P210S-Y217Q, wherein amino acid positions of the variant are numbered by correspondence with the sequence of SEQ ID NO:2. Such variant has a PI value of 1.1 relative to BPN'-v3 in this BMI microswatch cleaning assay, and enhanced proteolytic activity compared to BPN' (SEQ ID NO:2) and a greater PI value than BPN' in this assay. The invention includes a protease variant having enhanced proteolytic activity compared to BPN' (SEQ ID NO:2) in this assay, the variant having an amino acid sequence comprising amino acid substitutions G097A-G128A-P210S-Y217Q, wherein amino acid positions of the variant are numbered by correspondence with the sequence of SEQ ID NO:2. Also included is a protease variant having enhanced proteolytic activity compared to SEQ ID NO:2 in this assay, the variant comprising an amino acid sequence having at least 60%, 70%, 80%, 85%, 90%, 91%, 92%, 93%, 94%, 95%, 96%, 97%, 98% or 99% identity to the sequence of SEQ ID NO:2 and comprising amino acid substitutions G097A-G128A-P210S-Y217Q, wherein amino acid positions of the variant are numbered by correspondence with amino acid positions of the SEQ ID NO:2 sequence. Also provided is a subtilisin protease variant having enhanced proteolytic activity compared to BPN' and/or a PI value greater than that of BPN' (SEQ ID NO:2) and/or BPN'-v3 in a BMI microswatch cleaning assay, the variant comprising an amino acid sequence having at least 90%, 91%, 92%, 93%, 94%, 95%, 96%, 97%, or 98% identity to SEQ ID NO:2, wherein the variant comprises substitutions X097A-X128A-X210S-X217Q, wherein positions of the variant are numbered by correspondence with the sequence of SEQ ID NO:2, and optionally wherein the variant comprises at least one substitution selected from the group of G097A, G128A, P210S, and Y217Q. Such protease variant may be an isolated, recombinant, substantially pure, or non-naturally occurring protease variant. Also included are compositions, including, but not limited to, e.g., cleaning compositions, comprising such protease variant and methods for cleaning utilizing such variant as described in greater detail elsewhere herein.

The following BPN' variants were determined to have a PI value equal to about 1.0 relative to BPN'-v3 (i.e., having a PI value approximately equivalent to that of BPN'-v3) in a BMI microswatch cleaning assay in Detergent Composition 1 at pH 8 and 16° C.: BPN' amino acid sequence (SEQ ID NO:2) comprising at least one set of amino acid substitutions selected from the group consisting of G097A-G128A-Y217Q, G097A-G128A-E156S-P210S-Y217Q, G097A-G128A-P210S-Y217Q-N218A, G097A-G128A-P210S-Y217Q-N218S, and G097A-Y104F-G128A-E156S-P210I-Y217Q, wherein amino acid positions of the variant are numbered by correspondence with the sequence of SEQ ID NO:2. Such variants have enhanced proteolytic activity compared to BPN' (SEQ ID NO:2) and a greater PI value than BPN' in this assay. The invention includes a protease variant having enhanced proteolytic activity compared to BPN' (SEQ ID NO:2) or a PI value of 1.0 relative to BPN'-v3 in this BMI microswatch cleaning assay, the variant comprising an amino acid sequence having at least 60%, 70%, 80%, 85%, 90%, 91%, 92%, 93%, 94%, 95%, 96%, 97%, 98% or 99% identity to the sequence of SEQ ID NO:2 and comprising at least one set of amino acid substitutions selected from said group above, wherein amino acid positions of the variant are numbered by correspondence with amino acid positions of the SEQ ID NO:2 sequence. Also provided is a subtilisin protease variant having enhanced proteolytic activity compared to BPN' and/or a PI value of 1.0 compared to BPN'-v3 in this BMI microswatch cleaning assay, the variant comprising an amino acid sequence having at least 90%, 91%, 92%, 93%, 94%, 95%, 96%, 97%, or 98% identity to SEQ ID NO:2, wherein the variant comprises at least one substitution selected from the group of X097A, X104F, X128A, X156A/S, X210I/S, X217Q, X218A/S, and optionally at least one substitution selected from the group of G097A, Y104F, G128A, E156A/S, P210I/S, Y217Q, and N218A/S, wherein positions of the variant are numbered by correspondence with the sequence of SEQ ID NO:2. Also included are compositions, including, but not limited to, e.g., cleaning compositions, comprising at least one such variant and methods for cleaning utilizing at least one such variant as described in greater detail elsewhere herein.

The following BPN' variants were determined to have a PI value of about 0.9 relative to BPN'-v3 in a BMI microswatch cleaning assay in Detergent Composition 1 at pH 8 and 16° C.: BPN' amino acid sequence (SEQ ID NO:2) comprising at least one set of amino acid substitutions selected from the group consisting of G097A-G128A-E156A-P210S-Y217Q-N218S and G097A-G128A-Y217Q-N218A, wherein positions of the variant are numbered by correspondence with the sequence of SEQ ID NO:2. Such variants have proteolytic activity. The invention includes a protease variant having proteolytic activity, a PI value of 0.9 relative to BPN'-v3, and/or enhanced proteolytic activity compared to BPN' in this assay, the variant comprising an amino acid sequence having at least 60%, 70%, 80%, 85%, 90%, 91%, 92%, 93%, 94%, 95%, 96%, 97%, 98% or 99% identity to the sequence of SEQ ID NO:2 and at least one set of amino acid substitutions selected from said group above, wherein amino acid positions of the variant are numbered by correspondence with positions of the SEQ ID NO:2 sequence. Also included are compositions, including, but not limited to, e.g., cleaning compositions, comprising at least one such variant and methods for cleaning utilizing at least one such variant as described in greater detail elsewhere herein.

The following BPN' variants were determined to have a PI value of greater than 1.0 to about 5 relative to BPN'-v3 in a BMI microswatch cleaning assay in Detergent Composition 2 at pH 8 and 16° C.: BPN' amino acid sequence (SEQ ID NO:2) comprising at least one set of amino acid substitutions selected from the group consisting of G097A-G128A-P210S-Y217Q-N218A and G097A-G128A-P210S-Y217Q, wherein amino acid positions of the variant are numbered by correspondence with the sequence of SEQ ID NO:2. The invention includes a protease variant having enhanced proteolytic activity compared to BPN' (SEQ ID NO:2) and/or a PI value of greater than 1.0 to about 5 relative to BPN'-v3 in this BMI microswatch cleaning assay, the variant comprising an amino acid sequence having at least 60%, 70%, 80%, 85%, 90%, 91%, 92%, 93%, 94%, 95%, 96%, 97%, 98% or 99% identity to the sequence of SEQ ID NO:2 and comprising at least one set of amino acid substitutions selected from said group above, wherein amino acid positions of the variant are numbered by correspondence with amino acid positions of the SEQ ID NO:2 sequence. Such variants have enhanced proteolytic activity compared to BPN' (SEQ ID NO:2) and a greater PI value than BPN' in this assay. Also provided is a subtilisin protease variant having enhanced proteolytic activity compared to BPN' and/or a PI value of greater than 1 compared to BPN'-v3 in this BMI microswatch cleaning assay, the variant comprising an amino acid sequence having at least 85%, 90%, 91%, 92%, 93%, 94%, 95%, 96%, 97%, 98% or 99% identity to SEQ ID NO:2, wherein the variant comprises at least one substitution selected from the group of X097A, X104F, X128A, X156A/S, X210I/S, X217Q, X218A/S, and optionally at least one substitution selected from the group of G097A, Y104F, G128A, E156A/S, P210I/S, Y217Q, and N218A/S, wherein amino acid positions of the variant are numbered by correspondence with position of the sequence of SEQ ID NO:2. Such variants have enhanced proteolytic activity compared to BPN' (SEQ ID NO:2) and a greater PI value than BPN' in this assay. Also included are compositions, including, but not limited to, e.g., cleaning compositions, comprising at least one such variant and methods for cleaning utilizing at least one such variant as described in greater detail elsewhere herein.

The following BPN' variants were determined to have a PI value equal to about 1.0 relative to BPN'-v3 in a BMI microswatch cleaning assay in Detergent Composition 2 at pH 8 and 16° C.: BPN' amino acid sequence (SEQ ID NO:2) comprising at least one set of amino acid substitutions selected from the group consisting of G097A-G128A-Y217Q (i.e., BPN'-v3), G097A-G128A-E156S-P210S-Y217Q, and G097A-G128A-P210S-Y217Q-N218S, wherein positions of the variant are numbered by correspondence with the sequence of SEQ ID NO:2. Such variants have proteolytic activity and enhanced proteolytic activity compared to BPN' in this assay. The invention includes a protease variant having proteolytic activity, PI value of 1.0 relative to BPN'-v3, and/or enhanced proteolytic activity compared to BPN' in this assay, the variant comprising an amino acid sequence having at least 60%, 70%, 80%, 85%, 90%, 91%, 92%, 93%, 94%, 95%, 96%, 97%, 98% or 99% identity to the sequence of SEQ ID NO:2 and at least one set of amino acid substitutions selected from said group above, wherein positions of the variant are numbered by correspondence with positions of the SEQ ID NO:2 sequence. Also included are compositions, including, but not limited to, e.g., cleaning compositions, comprising at least one such variant and methods for cleaning utilizing at least one such variant as described in greater detail elsewhere herein.

The following BPN' variants were determined to have a PI value of about 0.9 relative to BPN'-v3 in a BMI microswatch cleaning assay in Detergent Composition 2 at pH 8 and 16° C.: BPN' amino acid sequence (SEQ ID NO:2) comprising at least one set of amino acid substitutions selected from the group consisting of G097A-G128A-E156A-P210S-Y217Q-N218S, G097A-G128A-Y217Q-N218A, and G097A-Y104F-G128A-E156S-P210I-Y217Q, wherein positions of the variant are numbered by correspondence with the sequence of SEQ ID NO:2. Such variants have proteolytic activity. The invention includes a protease variant having proteolytic activity, a PI value of 0.9 relative to BPN'-v3, and/or enhanced proteolytic activity compared to BPN' in this assay, the variant comprising an amino acid sequence having at least 60%, 70%, 80%, 85%, 90%, 91%, 92%, 93%, 94%, 95%, 96%, 97%, 98% or 99% identity to the sequence of SEQ ID NO:2 and at least one set of amino acid substitutions selected from said group above, wherein amino acid positions of the variant are numbered by correspondence with positions of the SEQ ID NO:2 sequence. Also included are compositions, including, but not limited to, e.g., cleaning compositions, comprising at least one such variant and methods for cleaning utilizing at least one such variant as described in greater detail elsewhere herein.

Example 3

Figure 2:
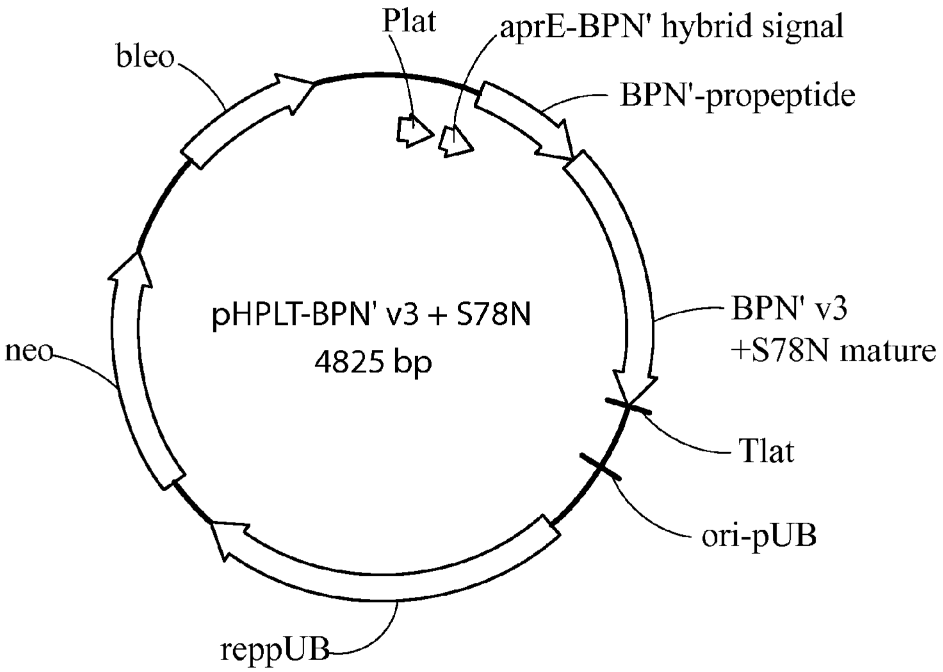
FIG. 2 provides a plasmid map of pHPLT-BPN'-v3+S78N.

Generation of Combinatorial Libraries and Cleaning Performance of Variants of BPN'-v3+S78N a) Description of BPN'-v3+S78N Variant and Synthetic Gene Sequences Derived From this Variant Gene Oracle synthesized and cloned eight genes into the pHPLT-BPN'-v3+S78N (BPN'-S78N-G97A-G128A-Y217Q) parent plasmid (see FIG. 2). Some of these genes were used as templates (parents) to create combinatorial libraries. The BPN'-v3+S78N variant was generated using standard molecular biology methods known in the art. The nucleotide sequence encoding the BPN'-v3+S78N variant is that of SEQ ID NO:7 and the amino acid sequence of the BPN'-v3+S78N variant is that of SEQ ID NO:8. The nucleotide and protein sequences of genes GcM90-96, and GcM100 are shown below.

| Genes | Nucleotide Sequence | Protein Sequence |
|---|---|---|
| GcM90 | SEQ ID NO: 9 | SEQ ID NO: 10 |
| GcM91 | SEQ ID NO: 11 | SEQ ID NO: 12 |
| GcM92 | SEQ ID NO: 13 | SEQ ID NO: 14 |
| GcM93 | SEQ ID NO: 15 | SEQ ID NO: 16 |
| GcM94 | SEQ ID NO: 17 | SEQ ID NO: 18 |
| GcM95 | SEQ ID NO: 19 | SEQ ID NO: 20 |

-continued

| Genes | Nucleotide Sequence | Protein Sequence |
|---|---|---|
| GcM96 | SEQ ID NO: 21 | SEQ ID NO: 22 |
| GcM100 | SEQ ID NO: 23 | SEQ ID NO: 24 |

b) Construction of Combinatorial Libraries CG1-CG5 and CG8 Using the Synthetic Genes GcM90-94 and GcM100

TABLE 3-1

List of Possible Substitutions Introduced and Primers Used for the Construction of Combinatorial Libraries CG1-CG5 and CG8

| Synthesized Genes (template or parent) | Library Name | Substitutions Introduced | Primer Name | Primer Sequence |
|---|---|---|---|---|
| GcM90 | CG1 | G53S | 1 S53 f | /5Phos/CTTCTATGGTGCCGTCCGAAA CAAACCCGTTTCAAG (SEQ ID NO: 25) |
| | | A68V | 1 V68 f | /5Phos/TCATGGCACACACGTCGCAGG AACGGTTGCGGCG (SEQ ID NO: 26) |
| | | A102G | 1 G102 f | /5Phos/AGCAGACGGATCAGGCCAAT ACTCATGGATTATCAAC (SEQ ID NO: 27) |
| | | T129P | 1 P129 f | /5Phos/TGAGCCTGGGAGCACCAAGC GGCAGTGCGGCACTTAAAG (SEQ ID NO: 28) |
| | | T185Q | 1 Q185 f | /5Phos/TAGACTCTTCAAATCAACGTG CCTCTTTTTCCTCCGTG (SEQ ID NO: 29) |
| GcM91 | CG2 | V59Q | 2 Q59 f | /5Phos/GAAACAAACCCGTTTCAAGAT AACAATTCTCATG (SEQ ID NO: 30) |
| | | V1081 | 2 I108 f | /5Phos/ATACTCATGGATTATCAACGG CATCGAATGGGCCATC (SEQ ID NO: 31) |
| | | Q147V | 2 V147 f | /5Phos/TGTTGCATCTGGTGTCGTCGT AGTAGCGGCAGCTGG (SEQ ID NO: 32) |
| | | A211G | 2 G211 f | /5Phos/ATCGACGCTTCCAGGGAACA AGTATGGTGCGCAAAAC (SEQ ID NO: 33) |
| | | Q252N | 2 N252 f | /5Phos/CAGCAGTTTAGAAAACACCA CTACAAAACTTGGTG (SEQ ID NO: 34) |
| GcM92 | CG3 | A61N | 3 N61 f | /5Phos/CAAACCCGTTTCAAGATAACA ATTCTCATGGCACACAC (SEQ ID NO: 35) |
| | | E87S | 3 S87 f | /5Phos/TTGGTGTAGCCCCGTCTGCTT CGCTCTACGCCGTTAAAG (SEQ ID NO: 36) |
| | | I124M | 3 M124 f | /5Phos/TGGATGTAATCAACATGAGCC TGGGAGCACCAAGCG (SEQ ID NO: 37) |
| | | P161S | 3 S161 f | /5Phos/AGGGAACATCCGGATCATCG AGTACCGTCGGTTATCCAG (SEQ ID NO: 38) |
| | | A224S | 3 S224 f | /5Phos/GACTTCCATGGCCTCGCCGCA TGTAGCTGGGGCGGC (SEQ ID NO: 39) |
| GcM93 | CG4 | Q62N | 4 N62 f | /5Phos/GTTTCAAGATAACAATTCTCA TGGCACACACGTCGC (SEQ ID NO: 40) |
| | | N100G | 4 G100 f | /5Phos/GTTCTTGCAGCAGACGGATCA GGCCAATACTCATG (SEQ ID NO: 41) |
| | | A125S | 4 S125 f | /5Phos/ATGTAATCAACATGAGCCTGG GAGCACCAAGCGGCAG (SEQ ID NO: 42) |
| | | D159S | 4 S159 f | /5Phos/GGAATGAGGGAACATCCGGA TCATCGAGTACCGTCGG (SEQ ID NO: 43) |
| | | S240N | 4 N240 f | /5Phos/CTTTCTAAGCACCCGAACTGG ACAAACACTCAAGTCCG (SEQ ID NO: 44) |

TABLE 3-1-continued

List of Possible Substitutions Introduced and Primers Used for the Construction of Combinatorial Libraries CG1-CG5 and CG8

| Synthesized Genes (template or parent) | Library Name | Substitutions Introduced | Primer Name | Primer Sequence |
|---|---|---|---|---|
| GcM94 | CG5 | T63S | 5 S63 f | /5Phos/TCAAGATAACAATTCTCATGG CACACACGTCGCAGG (SEQ ID NO: 45) |
| | | A101S | 5 S101 f | /5Phos/TGCAGCAGACGGATCAGGCC AATACTCATGGATTATC (SEQ ID NO: 46) |
| | | V126L | 5 L126 f | /5Phos/AATCAACATGAGCCTGGGAG CACCAAGCGGCAGTG (SEQ ID NO: 47) |
| | | T183S | 5 S183 f | /5Phos/CGCTGTAGACTCTTCAAATCA ACGTGCCTCTTTTTCC (SEQ ID NO: 48) |
| | | N244T | 5 T244 f | /5Phos/GAACTGGACAAACACTCAAG TCCGCAGCAGTTTAG (SEQ ID NO: 49) |
| GcM100 | CG8 | A68V | 1 V68 f | /5Phos/TCATGGCACACACGTCGCAGG AACGGTTGCGGCG (SEQ ID NO: 50) |
| | | A102G | 1 G102 f | /5Phos/AGCAGACGGATCAGGCCAAT ACTCATGGATTATCAAC (SEQ ID NO: 51) |
| | | A211G | 2 G211 f | /5Phos/ATCGACGCTTCCAGGGAACA AGTATGGTGCGCAAAAC (SEQ ID NO: 52) |
| | | A125S | 4 S125 f | /5Phos/ATGTAATCAACATGAGCCTGG GAGCACCAAGCGGCAG (SEQ ID NO: 53) |

Each synthesized gene was built into the pHPLT-BPN'-S78N-G97A-G128A-Y217Q parent molecule. Resulting plasmids containing the six synthesized genes GcM90-94, and GcM100 served as templates to make combinatorial libraries at the respective positions (Table 3-1). Two additional genes, GcM95 and GcM96, were also synthesized for analysis, but did not serve as parental DNA for libraries. These genes each have nine mutations on top of the pHPLT-BPN'-S78N-G97A-G128A-Y217Q parent molecule.

The parent plasmids (template DNA) containing the synthetic genes GcM90-94, and GcM100 were methylated were methylated using two micrograms of DNA and methylase (NEB), according to the NEB protocol. Methylated DNA was then purified using DNA Clean and Concentrator kit (Zymo Research). Combinatorial libraries CG1-5 and CG8 were made using a QUIKCHANGE® Multi Site-Directed Mutagenesis kit ("QCMS kit"; Stratagene) following the manufacturer's protocol (see Table 3-1 for respective template and primer combinations), with the exception of libraries CG3 and CG4, which used 86.5 ng of each primer in place of the 50 ng suggested in the protocol. All primers used for introducing the desired substitutions in each library are listed in Table 3-1. They were synthesized and provided by Integrated DNA Technologies. After the QCMS reactions were completed for each library, the template DNA was digested by the addition of 0.5-1 μl DpnI (from the QCMS kit) and incubated at 37° C. for 1-4 hours, followed by another addition of 0.5-1 μl DpnI and another incubation at 37° C. for 1-4 hours. For efficient transformation of *B. subtilis*, DNA from the QCMS reaction mixtures were amplified before transformation and transformants grown as described in Example 2.

Additional variants of BPN'-v3+S78N were produced by DNA2.0. The following substitutions were introduced individually into the BPN'-v3+S78N parent molecule: Q59G, N62Q, V68A, S89Y, A92G, I108V, I115V, M124T, P129L, A138T, V147L, S161P, Y167A, P172V, G211T, L267V, and A273S.

All of the combinatorial library variants described above and the variants synthesized at DNA2.0 were tested for cleaning performance using a BMI microswatch assay of Test Method 3 in Detergent Composition 1 at 16° C. and pH 8 and BMI microswatch assay in Detergent Composition 2 at 16° C. and pH 8. Protein content was determined using the TCA assay. Assays were performed as described in Example 1 and Performance Indices were calculated relative to the enzyme of SEQ ID NO:4 (with a PI value of 1.0).

The following BPN' variants were determined to have a PI value greater than 1.0, at least 1.1, at least 1.2, at least 1.3, at least 1.4, at least 1.5, at least 1.6, at least 1.7, at least 1.8, at least 1.9, at least 2, from greater than 1.0 to about 10, from greater than 1.0 to about 8, or from greater than 1.0 to about 5 relative to the enzyme of SEQ ID NO:4 in a BMI microswatch cleaning assay in Detergent Composition 1 at pH 8 and 16° C.: BPN' amino acid sequence (SEQ ID NO:2) comprising at least one set of amino acid substitutions selected from the group consisting of S063T-S078N-G097A-S101A-G128A-S183T-Y217Q-T244N, N061A-S078N-G097A-G128A-Y217Q-S224A, S053G-S078N-G097A-G128A-P129T-Q185T-Y217Q, S063T-S078N-G097A-S101A-G128A-S183T-Y217Q, S063T-S078N-G097A-S101A-G128A-Y217Q, S063T-S078N-G097A-S101A-G128A-Y217Q-T244I, and S078N-G097A-G128A-P129T-Y217Q, wherein amino acid positions of the variant are numbered by correspondence with the sequence of SEQ ID NO:2. Such variants have enhanced proteolytic activity compared to BPN' (SEQ ID NO:2) and a greater PI value than BPN' and BPN'-v3 in this assay. The invention includes a protease variant having enhanced proteolytic activity compared to BPN' (SEQ ID NO:2) and/or a PI value of greater than 1 to about 5 relative to BPN'-v3 in this BMI microswatch cleaning assay, the variant comprising an amino acid sequence having at least 85%, 90%, 91%, 92%, 93%, 94%, 95%, 96%, 97%, 98% or 99% identity to SEQ ID NO:2 and comprising at least one set of amino acid substitutions selected from said group above, wherein amino acid positions of the variant are numbered by correspondence with amino acid positions of the SEQ ID NO:2 sequence. Also included are compositions, including, but not limited to, e.g., cleaning compositions, comprising at least one such variant and methods for cleaning utilizing at least one such variant as described in greater detail elsewhere herein.

Also provided is a subtilisin protease variant having enhanced proteolytic activity compared to BPN' and/or a PI value of greater than 1.0 to about 5 relative to BPN'-v3 in this BMI microswatch cleaning assay, the variant comprising an amino acid sequence having at least 85%, 90%, 91%, 92%, 93%, 94%, 95%, 96%, 97%, or 98% identity to SEQ ID NO:2, wherein the variant comprises at least one substitution selected from the group of X040E, X053G, X059V, X061A, X062H/Q, X068A, X078N, X087E, X101A, X102A, X108V, X124I, X125A, X126V, X129T, X147Q, X159D, X183T, X185T, X211A, X224A, X244I/N, X252Q, and X274D, and optionally at least one substitution selected from the group of X040E, X053G, X059V, X061A, X062H/Q, X068A, X078N, X087E, X101A, X102A, X108V, M124I, S125A, L126V, P129T, V147Q, S159D, S183T, Q185T, G211A, S224A, T244I/N, N252Q, and A274D, wherein amino acid positions of the variant are numbered by correspondence with positions of the sequence of SEQ ID NO:2. Also included are compositions, including, but not limited to, e.g., cleaning compositions, comprising at least one such variant and methods for cleaning utilizing at least one such variant as described in greater detail elsewhere herein.

The following BPN' variants were determined to have a PI value equal to about 1.0 relative to the enzyme of SEQ ID NO:4 (alternatively referred to as BPN'-v3) in a BMI microswatch cleaning assay in Detergent Composition 1 at pH 8 and 16° C.: BPN' amino acid sequence (SEQ ID NO:2) comprising at least one set of amino acid substitutions selected from the group consisting of G097A-G128A-Y217Q, N061A-S078N-S087E-G097A-G128A-Y217Q-S224A, Q059V-S078N-G097A-G128A-G211A-Y217Q, Q059V-S078N-G097A-G128A-V147Q-Y217Q, Q059V-S078N-G097A-G128A-Y217Q, Q059V-S078N-G097A-I108V-G128A-Y217Q-N252Q, S053G-S078N-G097A-G128A-P129T-Y217Q, S078N-G097A-G128A-G211A-Y217Q, S078N-G097A-G128A-Q185T-Y217Q, S078N-G097A-G128A-V147Q-Y217Q, S078N-G097A-G128A-Y217Q, S078N-G097A-G128A-Y217Q-S224A, and S078N-G097A-G128A-Y217Q-S224A-A274D, wherein amino acid positions of the variant are numbered by correspondence with the sequence of SEQ ID NO:2. Such variants have enhanced proteolytic activity compared to BPN' (SEQ ID NO:2) and a greater PI value than BPN' in this assay. The invention includes a protease variant having enhanced proteolytic activity compared to BPN' (SEQ ID NO:2) and/or a PI value of 1.0 relative to BPN'-v3 in this BMI microswatch cleaning assay, the variant comprising an amino acid sequence having at least 60%, 70%, 80%, 85%, 90%, 91%, 92%, 93%, 94%, 95%, 96%, 97%, 98% or 99% identity to the sequence of SEQ ID NO:2 and comprising at least one set of amino acid substitutions selected from said group above, wherein amino acid positions of the variant are numbered by correspondence with amino acid positions of the SEQ ID NO:2 sequence. Also included are compositions, including, but not limited to, e.g., cleaning compositions, comprising at least one such variant and methods for cleaning utilizing at least one such variant as described in greater detail elsewhere herein.

The following BPN' variant was determined to have a PI value of about 0.9 relative to BPN'-v3 in a BMI microswatch cleaning assay in Detergent Composition 1 at pH 8 and 16° C.: BPN' amino acid sequence (SEQ ID NO:2) comprising the set of amino acid substitutions S078N-G097A-I108V-G128A-V147Q-Y217Q, wherein positions of the variant are numbered by correspondence with the sequence of SEQ ID NO:2. Such variants have proteolytic activity. The invention includes a protease variant having proteolytic activity, a PI value of 0.9 relative to BPN'-v3, and/or enhanced proteolytic activity compared to BPN' in this assay, the variant comprising an amino acid sequence having at least 60%, 70%, 80%, 85%, 90%, 91%, 92%, 93%, 94%, 95%, 96%, 97%, or 98% or 99% identity to SEQ ID NO:2 and comprising said set of amino acid substitutions above, wherein amino acid positions of the variant are numbered by correspondence with positions of the SEQ ID NO:2 sequence. Also included are compositions, including, but not limited to, e.g., cleaning compositions, comprising at least one such variant and methods for cleaning utilizing at least one such variant as described in greater detail elsewhere herein.

The following BPN' variants were determined to a PI value equal to or greater than 0.5 and less than 0.9 relative to BPN'-v3 in a BMI microswatch cleaning assay in Detergent Composition 1 at pH 8 and 16° C.: BPN' amino acid sequence (SEQ ID NO:2) comprising at least one set of amino acid substitutions selected from the group consisting of Q059V-S078N-G097A-I108V-G128A-V147Q-G211A-Y217Q-N252Q, S078N-G097A-I108V-G128A-V147Q-G211A-Y217Q, S078N-G097A-I108V-G128A-V147Q-G211A-Y217Q-N252Q, S078N-G097A-I108V-G128A-V147Q-Y217Q-N252Q, and S078N-S087E-G097A-M124I-G128A-Y217Q-S224A, wherein amino acid positions of the variant are numbered by correspondence with positions of the SEQ ID NO:2 sequence. Such variants have proteolytic activity. The invention includes a protease variant having proteolytic activity, the variant comprising an amino acid sequence having at least 60%, 70%, 80%, 85%, 90%, 91%, 92%, 93%, 94%, 95%, 96%, 97%, or 98% or 99% identity to SEQ ID NO:2 and at least one set of amino acid substitutions selected from said group above, wherein positions of the variant are numbered by correspondence with positions of the SEQ ID NO:2 sequence. Also included are compositions, including, but not limited to, e.g., cleaning compositions, comprising at least one such variant and methods for cleaning utilizing at least one such variant as described in greater detail elsewhere herein.

The following BPN' variants were determined to have a PI value greater than 1.0, at least 1.1, at least 1.2, at least 1.3, at least 1.4, at least 1.5, at least 1.6, at least 1.7, at least 1.8, at least 1.9, at least 2, from greater than 1.0 to about 10, from greater than 1.0 to about 8, or from greater than 1.0 to about 5 relative to BPN'-v3 in a BMI microswatch cleaning assay in Detergent Composition 2 at pH 8 and 16° C.: BPN' amino acid sequence (SEQ ID NO:2) comprising at least one set of amino acid substitutions selected from the group consisting of S063T-S078N-G097A-S101A-G128A-S183T-Y217Q, S063T-S078N-G097A-S101A-G128A-S183T-Y217Q-T244N, S063T-S078N-G097A-S101A-G128A-Y217Q, and S063T-S078N-G097A-S101A-G128A-Y217Q-T244I, wherein amino acid positions of the variant are numbered by correspondence with the sequence of SEQ ID NO:2. Such variants have enhanced proteolytic activity compared to BPN' (SEQ ID NO:2) and a greater PI value than BPN' in this assay. The invention includes a protease variant having enhanced proteolytic activity compared to BPN' (SEQ ID NO:2) and/or a PI value of greater than 1.0 to about 5 relative to BPN'-v3 in this BMI microswatch cleaning assay, the variant comprising an amino acid sequence having at least 60%, 70%, 80%, 85%, 90%, 91%, 92%, 93%, 94%, 95%, 96%, 97%, or 98% or 99% identity to SEQ ID NO:2 or SEQ ID NO:6 and comprising at least one set of amino acid substitutions selected from said group above, wherein amino acid positions of the variant are numbered by correspondence with amino acid positions of the SEQ ID NO:2 sequence. Also included are compositions, including, but not limited to, e.g., cleaning compositions, comprising at least one such variant and methods for cleaning utilizing at least one such variant as described in greater detail elsewhere herein.

The following BPN' variants were determined to have a PI value equal to about 1.0 relative to BPN'-v3 in a BMI microswatch cleaning assay in Detergent Composition 2 at pH 8 and 16° C.: BPN' amino acid sequence (SEQ ID NO:2) comprising at least one set of amino acid substitutions selected from the group consisting of G097A-G128A-Y217Q, N061A-S078N-G097A-G128A-Y217Q-S224A, N061A-S078N-S087E-G097A-G128A-Y217Q-S224A, Q059V-S078N-G097A-G128A-G211A-Y217Q, Q059V-S078N-G097A-G128A-V147Q-Y217Q, Q059V-S078N-G097A-G128A-Y217Q, Q059V-S078N-G097A-I108V-G128A-Y217Q-N252Q, S053G-S078N-G097A-G128A-P129T-Q185T-Y217Q, S053G-S078N-G097A-G128A-P129T-Y217Q, S078N-G097A-G128A-G211A-Y217Q, S078N-G097A-G128A-P129T-Y217Q, S078N-G097A-G128A-Q185T-Y217Q, S078N-G097A-G128A-Y217Q, S078N-G097A-G128A-Y217Q-S224A, and S078N-G097A-G128A-Y217Q-S224A-A274D, wherein amino acid positions of the variant are numbered by correspondence with the sequence of SEQ ID NO:2. Such variants have enhanced proteolytic activity compared to BPN' (SEQ ID NO:2) and a greater PI value than BPN' in this assay. The invention includes a protease variant having enhanced proteolytic activity compared to BPN' (SEQ ID NO:2) and/or a PI value of about 1 relative to BPN'-v3 in this BMI microswatch cleaning assay, the variant comprising an amino acid sequence having at least 60%, 70%, 80%, 85%, 90%, 91%, 92%, 93%, 94%, 95%, 96%, 97%, or 98% or 99% identity to SEQ ID NO:2 and comprising at least one set of amino acid substitutions selected from said group above, wherein amino acid positions of the variant are numbered by correspondence with amino acid positions of the SEQ ID NO:2 sequence. Also included are compositions, including, but not limited to, e.g., cleaning compositions, comprising at least one such variant and methods for cleaning utilizing at least one such variant as described in greater detail elsewhere herein.

The following BPN' variants were determined to have a PI value of about 0.9 relative to BPN'-v3 in a BMI microswatch cleaning assay in Detergent Composition 2 at pH 8 and 16° C.: BPN' amino acid sequence (SEQ ID NO:2) comprising at least one set of amino acid substitutions selected from the group consisting of S078N-G097A-G128A-V147Q-Y217Q and S078N-G097A-I108V-G128A-V147Q-Y217Q, wherein positions of the variant are numbered by correspondence with the sequence of SEQ ID NO:2. Such variants have proteolytic activity. The invention includes a protease variant having proteolytic activity, a PI value of 0.9 relative to BPN'-v3, and/or an enhanced proteolytic activity compared to BPN' in this assay, the variant comprising an amino acid sequence having at least 60%, 70%, 80%, 85%, 90%, 91%, 92%, 93%, 94%, 95%, 96%, 97%, or 98% or 99% identity to SEQ ID NO:2 and at least one set of amino acid substitutions selected from said group above, wherein amino acid positions of the variant are numbered by correspondence with positions of the SEQ ID NO:2 sequence. Also included are compositions, including cleaning compositions, comprising at least one such variant and methods for cleaning an item or surface in need of cleaning utilizing at least one such variant as described in greater detail elsewhere herein.

The following BPN' variants were determined to a PI value equal to or greater than 0.5 and less than 0.9 relative to BPN'-v3 in a BMI microswatch cleaning assay in Detergent Composition 2 at pH 8 and 16° C.: BPN' amino acid sequence (SEQ ID NO:2) comprising at least one set of amino acid substitutions selected from the group consisting of Q059V-S078N-G097A-I108V-G128A-V147Q-G211A-Y217Q-N252Q, S078N-G097A-I108V-G128A-V147Q-G211A-Y217Q, S078N-G097A-I108V-G128A-V147Q-G211A-Y217Q-N252Q, S078N-G097A-I108V-G128A-V147Q-Y217Q-N252Q, and S078N-S087E-G097A-M124I-G128A-Y217Q-S224A, wherein amino acid positions of the variant are numbered by correspondence with positions of the SEQ ID NO:2 sequence. Such variants have proteolytic activity. The invention includes a protease variant having proteolytic activity, the variant comprising an amino acid sequence having at least 60%, 70%, 80%, 85%, 90%, 91%, 92%, 93%, 94%, 95%, 96%, 97%, or 98% or 99% identity to SEQ ID NO:2 and at least one set of amino acid substitutions selected from said group above, wherein positions of the variant are numbered by correspondence with positions of the SEQ ID NO:2 sequence. Also included are compositions, including cleaning compositions, comprising at least one such variant and methods for cleaning an item or surface in need of cleaning utilizing at least one such variant as described in greater detail elsewhere herein.

Example 4

Generation and Cleaning Performance of BPN' Variants

Generation of BPN' Variants LC1-LC4 Via QUIKCHANGE® Multi Site-Directed Mutagenesis BPN' variants were constructed from different parental plasmids using QUIKCHANGE® Multi Site-Directed Mutagenesis kits. The parental plasmids (Table 4-1) were methylated using a NEB Dam Methylase Kit in a reaction containing 77.5 μL H2O+10 μL Buffer 10X+0.25 μL SAM+2 uL DAM methylase+10 uL miniprep DNA (~150 ng/μL) at 37° C. overnight. The methylated plasmid DNA was purified using a QIAGEN® PCR purification kit. QUIKCHANGE® Multi Site-Directed Mutagenesis reactions were set up for each of the DNA templates in a reaction mix containing 2.5 μL Buffer 5X+0.5 μL primer 1 (25 μM)+0.5 μL primer 2 (25 μM)+1 μL dNTP's+1 μL enzyme blend+18 μL $H_2O$+1.5 μL DNA. The PCR program used was: 95° C. for 1 min; (95° C. for 1 min, 53° C. for 1 min, 65° C. for 9:39 min)×29 cycles; 65° C. for 10 min, 4° C. hold. Primer sequences are shown in Table 4-2. In all reactions, PCR was performed using a MJ Research PTC-200 Peltier thermal cycler. Parental DNA from the PCR samples was removed by addition of 1 μL of DpnI to QUIKCHANGE® Multi Site-Directed Mutagenesis reactions at 37° C. overnight. To increase transformation frequency, the DpnI-digested reactions were amplified using rolling circle amplification (RCA) using the Illustra TempliPhi kit according to the manufacturer's protocol. *B. subtilis* cells (ΔaprE, ΔnprE, amyE::xylRPxylAcomK-phleo) were transformed with 1 μL each of the RCA reaction and the transformed cells were plated onto LA+116% skim milk plates containing 10 ppm neomycin and incubated at 37° C.

overnight. Colonies from overnight growth were selected to perform colony PCR for sequencing using "puReTaq Ready-To-Go PCR Beads" (Amersham). The PCR and sequencing primers used were pHPLT F1 (/5PHOS/TACATATGAGTTATGCAGTTTG (SEQ. ID NO:54)) and pHPLT seq R1 (/5PHOS/TTATCCTTTACCTTGTCTC (SEQ ID NO:55)). Clones with appropriate sequences were frozen. BPN' variant proteins were produced by growing *B. subtilis* transformants in 96 well microtiter plates at 37° C. for 68 hours in a MOPS based medium containing urea as described in Example 2.

TABLE 4-1

Parental Plasmids and Primers Used for Generation of BPN' Variants LC1-LC4

| Parental Plasmid | Mutations Introduced | Primers Used |
|---|---|---|
| BPN'-G097A-G128A-Y217Q-S024G-N025G-N061P-S101N (termed LC1) | A128S | A128Sf, A128Sr |
| BPN'-G097A-G128A-Y217Q-S053G-N061P-S101N-V203Y (termed LC2) | A128S | A128Sf, A128Sr |
| BPN'-G097A-G128A-Y217Q-S024G-N025G-S053G-T055P-N061P-S101N-V203Y (termed LC3) | A128S | A128Sf, A128Sr |
| BPN'-G097A-G128A-Y217Q-S024G-N025G-S053G-T055P-N061P-S101N-V203Y (termed LC4) | P55T | P55Tf, P55Tr |

TABLE 4-2

Sequences of Primers Used for QUIKCHANGE ® Multi Site-Directed Mutagenesis Reactions to Make BPN' variants LC1-LC4

| Primer Name | Primer Sequence (5' to 3') |
|---|---|
| A128Sf | /5Phos/CAACATGAGCCTGGGATCACCAAGCGGCAGTGCGG (SEQ ID NO: 56) |
| A128Sr | /5Phos/CCGCACTGCCGCTTGGTGATCCCAGGCTCATGTTG (SEQ ID NO: 57) |
| P55Tf | /5Phos/CTATGGTGCCGGGCGAAACAAACCCGTTTCAAGATCCG (SEQ ID NO: 58) |
| P55Tr | /5Phos/CGGATCTTGAAACGGGTTTGTTTCGCCCGGCACCATAG (SEQ ID NO: 59) |

Generation of Additional BPN' Variants LC5-LC37

Figure 3:
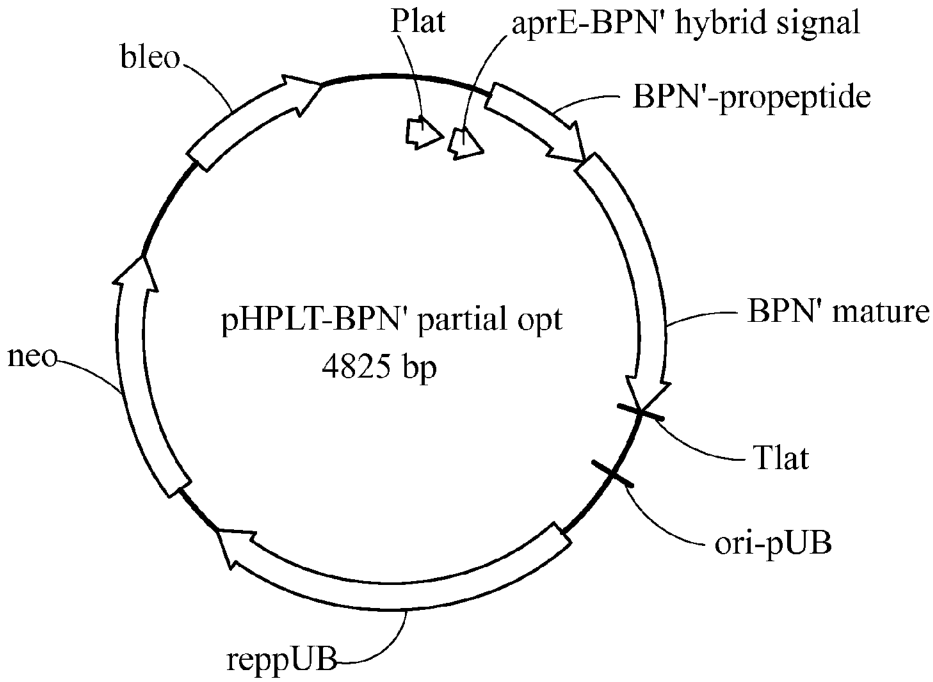
FIG. 3 provides a plasmid map of pHPLT-BPN' partial opt.

An additional 33 BPN' variants termed successively LC5 through LC37 were produced by DNA 2.0 using the BPN' nucleic acid as the parent gene contained in the expression plasmid pHPLT-BPN' partial opt (see FIG. 3). LC5 through LC37 BPN' variants are as follows, respectively: BPN'-P52L-V68A-G97A-I111V, BPN'-I111V-M124V-Y167A-Y217Q, BPN'-Y104N-G128A-Y217Q, BPN'-M124V-Y167A-Y217Q, BPN'-I111V-M124V-Y217Q, BPN'-P52L-V68A-G97A, BPN'-G97A-I111V-M124V, BPN'-V68A-A92G-G97A, BPN'-G97A-I111V-M124V-Y167A-Y217Q, BPN'-P52L-V68A-I111V-Y217Q, BPN'-P52L-V68A-I111V, BPN'-V68A-A92G-I111V, BPN'-P52L-V68A-G97A-I111V-Y217Q, BPN'-V68A-G97A-I111V, BPN'-G97A-I111V-Y217Q, BPN'-G97A-I111V-M124V-Y167A, BPN'-S89Y-I111V-M124V, BPN'-V68A-S89Y-I111V, BPN'-V68A-A92G-Y217Q, BPN'-I111V-Y167A-Y217Q, BPN'-G97A-1111V-Y167A-Y217Q, BPN'-G97A-I111V-M124V-Y217Q, BPN'-V68A-I111V-Y167A-Y217Q, BPN'-I111V-G128A-Y217Q, BPN'-G97A-M124V-Y217Q, BPN'-V68A-Y167A-Y217Q, BPN'-I111V-M124V-Y167A, BPN'-N62Q-G97A-I111V, BPN'-G97A-M124V-Y167A-Y217Q, BPN'-G97A-L126A-Y217Q, BPN'-V68A-I111V-Y217Q, BPN'-S89Y-M124V-Y217Q, and BPN'-L96T-G97A-Y217Q. Plasmid pHPLT-BPN' partial opt was also created by DNA 2.0.

Transformants were picked into microtiter plates and grown as described in Example 2. The variants were assayed for cleaning performance using a BMI microswatch assay in Detergent Composition 2 at 16° C. and pH 8. Protein content was determined using the TCA assay. The assays were performed as described in Example 1 and the Performance Indices were calculated relative to BPN'-v3 (with a PI value of 1.0).

The following BPN' variants were determined to have a PI value greater than 1.0, at least 1.1, at least 1.2, at least 1.3, at least 1.4, at least 1.5, at least 1.6, at least 1.7, at least 1.8, at least 1.9, at least 2, from greater than 1.0 to about 10, from greater than 1.0 to about 8, or from greater than 1.0 to about 5 relative to BPN'-v3 in a BMI microswatch cleaning assay in Detergent Composition 2 at pH 8 and 16° C.: BPN' amino acid sequence (SEQ ID NO:2) comprising at least one set of amino acid substitutions selected from the group consisting of G097A-I111V-M124V-Y217Q, G097A-I111V-Y167A-Y217Q, S024G-N025G-N061P-G097A-S101N-G128S-Y217Q, S024G-N025G-S053G-N061P-G097A-S101N-G128A-V203Y-Y217Q, S024G-N025G-S053G-T055P-N061P-G097A-S101N-G128S-V203Y-Y217Q, and V068A-A092G-Y217Q, wherein amino acid positions of the variant are numbered by correspondence with the sequence of SEQ ID NO:2. Such variants have enhanced proteolytic activity compared to BPN' (SEQ ID NO:2) and a greater PI value than BPN' in this assay. The invention includes a protease variant having enhanced proteolytic activity compared to BPN' (SEQ ID NO:2) and/or a PI value of greater than 1.0 to about 5 relative to BPN'-v3 in this BMI microswatch cleaning assay, the variant comprising an amino acid sequence having at least 60%, 70%, 80%, 85%, 90%, 91%, 92%, 93%, 94%, 95%, 96%, 97%, or 98% or 99% identity to SEQ ID NO:2 and comprising at least one set of amino acid substitutions selected from said group above, wherein amino acid positions of the variant are numbered by correspondence with amino acid positions of the SEQ ID NO:2 sequence. Also provided is a subtilisin protease variant having enhanced proteolytic activity compared to BPN' and/or a PI value of greater than 1.0 compared to BPN'-v3 in this BMI microswatch cleaning assay, the variant comprising an amino acid sequence having at least 85%, 90%, 91%, 92%, 93%, 94%, 95%, 96%, 97%, or 98% identity to SEQ ID NO:2, wherein the variant comprises at least one substitution selected from the group of X024G, X025G, X052L, X053G, X055P, X061P, X062Q, X068A, X089Y, X092G, X096T, X097A, X101N, X104N, X111V, X124V, X126A, X128A/S, X167A, X203Y, and X217Q, and optionally at least one substitution selected from the group of S024G, N025G, P052L, S053G, T055P, N061P, N062Q, V068A, S089Y, A092G, L096T, G097A, S101N, Y104N, I111V, M124V, L126A, G128A/S, Y167A, V203Y, Y217Q, wherein amino acid positions of the variant are numbered by correspondence with positions of the sequence of SEQ ID NO:2. Also included are compositions, including, but not limited to, e.g., cleaning compositions, comprising at least one such variant and methods for cleaning utilizing at least one such variant as described in greater detail elsewhere herein.

The following BPN' variants were determined to have a PI value equal to about 1.0 relative to BPN'-v3 in a BMI microswatch cleaning assay in Detergent Composition 2 at pH 8 and 16° C.: BPN' amino acid sequence (SEQ ID NO:2) comprising at least one set of amino acid substitutions selected from the group consisting of G097A-G128A-Y217Q, G097A-G128S-Y217Q, G097A-I111V-Y217Q, I111V-G128A-Y217Q, I111V-M124V-Y167A, I111V-M124V-Y217Q, L096T-G097A-Y217Q, N062Q-G097A-I111V, S053G-N061P-G097A-S101N-G128S-V203Y-Y217Q, S089Y-M124V-Y217Q, and V068A-I111V-Y217Q, wherein amino acid positions of the variant are numbered by correspondence with the sequence of SEQ ID NO:2. The invention includes a protease variant having enhanced proteolytic activity compared to BPN'(SEQ ID NO:2) and/or a PI value of 1.0 relative to BPN'-v3 in this BMI microswatch cleaning assay, the variant comprising an amino acid sequence having at least 60%, 70%, 80%, 85%, 90%, 91%, 92%, 93%, 94%, 95%, 96%, 97%, or 98% identity to the sequence of SEQ ID NO:2 and comprising at least one set of amino acid substitutions selected from said group above, wherein amino acid positions of the variant are numbered by correspondence with amino acid positions of the SEQ ID NO:2 sequence. Such variants have enhanced proteolytic activity compared to BPN' (SEQ ID NO:2), a greater PI value than BPN', and a PI value of 1.0 compared to BPN'-v3 in this assay. Also included are compositions, including, but not limited to, e.g., cleaning compositions, comprising at least one such variant and methods for cleaning utilizing at least one such variant as described in greater detail elsewhere herein.

The following BPN' variants were determined to have a PI value of about 0.9 relative to BPN'-v3 in a BMI microswatch cleaning assay in Detergent Composition 2 at pH 8 and 16° C.: BPN' amino acid sequence (SEQ ID NO:2) comprising at least one set of amino acid substitutions selected from the group consisting of G097A-I111V-M124V, G097A-L126A-Y217Q, G097A-M124V-Y217Q, I111V-Y167A-Y217Q, M124V-Y167A-Y217Q, P052L-V068A-G097A, S089Y-I111V-M124V, V068A-A092G-G097A, V068A-A092G-I111V, V068A-G097A-I111V, V068A-S089Y-I111V, and Y104N-G128A-Y217Q, wherein positions of the variant are numbered by correspondence with the sequence of SEQ ID NO:2. Such variants have proteolytic activity. The invention includes a protease variant having proteolytic activity, a PI value of 0.9 relative to BPN'-v3, and/or an enhanced proteolytic activity compared to BPN' in this assay, the variant comprising an amino acid sequence having at least 60%, 70%, 80%, 85%, 90%, 91%, 92%, 93%, 94%, 95%, 96%, 97%, or 98% or 99% identity to SEQ ID NO:2 and at least one set of amino acid substitutions selected from said group above, wherein amino acid positions of the variant are numbered by correspondence with positions of the SEQ ID NO:2 sequence. Also included are compositions, including, but not limited to, e.g., cleaning compositions, comprising at least one such variant and methods for cleaning utilizing at least one such variant as described in greater detail elsewhere herein.

The following BPN' variants were determined to a PI value equal to or greater than 0.5 and less than 0.9 relative to BPN'-v3 in a BMI microswatch cleaning assay in Detergent Composition 2 at pH 8 and 16° C.: BPN' amino acid sequence (SEQ ID NO:2) comprising at least one set of amino acid substitutions selected from the group consisting of G097A-M124V-Y167A-Y217Q, V068A-Y167A-Y217Q, G097A-I111V-M124V-Y167A, I111V-M124V-Y167A-Y217Q, V068A-I111V-Y167A-Y217Q, G097A-I111V-M124V-Y167A-Y217Q, P052L-V068A-I111V, wherein positions of the variant are numbered by correspondence with the sequence of SEQ ID NO:2. Such variants have proteolytic activity. The invention includes a protease variant having proteolytic activity, the variant comprising an amino acid sequence having at least 60%, 70%, 80%, 85%, 90%, 91%, 92%, 93%, 94%, 95%, 96%, 97%, or 98% or 99% identity to SEQ ID NO:2 and at least one set of amino acid substitutions selected from said group above, wherein positions of the variant are numbered by correspondence with positions of the SEQ ID NO:2 sequence. Such variants have proteolytic activity. Also included are compositions, including, but not limited to, e.g., cleaning compositions, comprising at least one such variant and methods for cleaning utilizing at least one such variant as described in greater detail elsewhere herein.

Example 5

Cleaning Performance of BPN' Variants

Variants based on parent BPN' were made by DNA 2.0. The variants were grown as described in Example 2 and tested for cleaning performance on BMI microswatch assay in Detergent Composition 1 at 16° C. and pH 8, BMI microswatch assay in Detergent Composition 4 at 16° C. and pH 8, and egg microswatch assay in Detergent Composition 4 at 16° C. and pH 8. The protein content was determined using the TCA assay. The assays were performed as described in Example 1 and the Performance Indices were calculated relative to BPN'-v3 (with a PI value of 1.0).

The following BPN' variants were determined to have a PI value greater than 1.0, at least 1.1, at least 1.2, at least 1.3, at least 1.4, at least 1.5, at least 1.6, at least 1.7, at least 1.8, at least 1.9, at least 2, from greater than 1.0 to about 10, from greater than 1.0 to about 8, or from greater than 1.0 to about 5 relative to BPN'-v3 in a BMI microswatch cleaning assay in Detergent Composition 4 at pH 8 and 16° C.: BPN' amino acid sequence (SEQ ID NO:2) comprising at least one set of amino acid substitutions selected from the group consisting of N061P-G097A-S101N-G128A-P210S-Y217Q, S024G-N025G-S053G-N061P-G097A-S101N-G128A-P210S-Y217Q, S024G-N025G-S053G-N061P-G097A-S101N-G128S-Y217Q, S024G-N025G-S053G-N061P-S078N-G097A-S101N-I111V-G128S-Y217Q, wherein amino acid positions of the variant are numbered by correspondence with the sequence of SEQ ID NO:2. Such variants have enhanced proteolytic activity compared to BPN' (SEQ ID NO:2) and a greater PI value than BPN' in this assay. The invention includes a protease variant having enhanced proteolytic activity compared to BPN' (SEQ ID NO:2) and/or a PI value of greater than 1.0 to about 5 relative to BPN'-v3 in this BMI microswatch cleaning assay, the variant comprising an amino acid sequence having at least 60%, 70%, 80%, 85%, 90%, 91%, 92%, 93%, 94%, 95%, 96%, 97%, or 98% or 99% identity to SEQ ID NO:2 and comprising at least one set of amino acid substitutions selected from said group above, wherein amino acid positions of the variant are numbered by correspondence with amino acid positions of the SEQ ID NO:2 sequence. Also included are compositions, including, but not limited to, e.g., cleaning compositions, comprising at least one such variant and methods for cleaning utilizing at least one such variant as described in greater detail elsewhere herein.

The following BPN' variants were determined to have a PI value equal to about 1.0 relative to BPN'-v3 in a BMI microswatch cleaning assay in Detergent Composition 4 at pH 8 and 16° C.: BPN' amino acid sequence (SEQ ID NO:2) comprising at least one set of amino acid substitutions selected from the group consisting of G097A-G128A-Y217Q, G097A-G128A-P210S-Y217Q, G097A-G128S-P210S-Y217Q, G097A-I111V-M124I-Y217Q, G097A-I111V-M124V-P210S-Y217Q, G097A-N123Q-P210S-Y217Q, G097A-

N123Q-Y217Q, N061P-G097A-G128A-P210S-Y217Q, N061P-G097A-G128S-Y217Q, N061P-G097A-I111V-M124V-Y217Q, N061P-G097A-N123Q-Y217Q, N061P-G097A-S101N-I111V-M124V-Y217Q, N061P-G097A-S101N-N123Q-Y217Q, N061P-G102A-P129S-Y217Q, N061P-N062Q-G097A-G100N-S101N-Y217Q, N061P-N062Q-G097A-G100N-Y217Q, N061P-N062Q-G097A-G100Q-P210S-Y217Q, N061P-N062Q-G097A-I111V-Y217Q, N061P-N062Q-G097A-S101N-I111V-Y217Q, N061P-S078N-G097A-I111V-M124I-Y217Q, N061P-S078N-G102A-I111V-P129S-Y217Q, N062Q-G097A-I111V-P210S-Y217Q, N062Q-G097A-I111V-Y217Q, N062Q-S078N-G097A-I111V-Y217Q, S024G-N025G-N061P-G097A-S101N-G128A-P210S-Y217Q, S024G-N025G-S053G-N061P-G097A-S101N-I111V-M124V-Y217Q, S024G-N025G-S053G-N061P-G097A-S101N-N123Q-Y217Q, S024G-N025G-S053G-N061P-N062Q-G097A-G100N-S101N-Y217Q, S024G-N025G-S053G-N061P-N062Q-G097A-S101N-I111V-Y217Q, S024G-N025G-S053G-N061P-S101N-G102A-P129S-Y217Q, S053G-N061P-G097A-G128S-Y217Q, S053G-N061P-G097A-M124I-Y217Q, S053G-N061P-G097A-S101N-I111V-M124V-Y217Q, S053G-N061P-G102A-P129S-P210S-Y217Q, S053G-N061P-G102A-P129S-Y217Q, S053G-N061P-N062Q-G097A-G100N-S101N-Y217Q, S053G-N061P-N062Q-G097A-S101N-I111V-Y217Q, S053-N061P-S101N-G102A-P129S-Y217Q, S053G-S078N-G097A-I111V-G128S-Y217Q, S078N-G097A-G128S-Y217Q, S078N-G097A-I111V-M124V-Y217Q, wherein amino acid positions of the variant are numbered by correspondence with the sequence of SEQ ID NO:2. Such variants have enhanced proteolytic activity compared to BPN' (SEQ ID NO:2) and a greater PI value than BPN' in this assay. The invention includes a protease variant having enhanced proteolytic activity compared to BPN' (SEQ ID NO:2) and/or a PI value of 1.0 relative to BPN'-v3 in this BMI microswatch cleaning assay, the variant comprising an amino acid sequence having at least 60%, 70%, 80%, 85%, 90%, 91%, 92%, 93%, 94%, 95%, 96%, 97%, or 98% or 99% identity to SEQ ID NO:2 and comprising at least one set of amino acid substitutions selected from said group above, wherein amino acid positions of the variant are numbered by correspondence with amino acid positions of the SEQ ID NO:2 sequence. Also included are compositions, including, but not limited to, e.g., cleaning compositions, comprising at least one such variant and methods for cleaning utilizing at least one such variant as described in greater detail elsewhere herein.

The following BPN' variants were determined to have a PI value of about 0.9 relative to BPN'-v3 in a BMI microswatch cleaning assay in Detergent Composition 4 at pH 8 and 16° C.: BPN' amino acid sequence (SEQ ID NO:2) comprising at least one set of amino acid substitutions selected from the group consisting of N061P-G097A-M124I-Y217Q, N061P-G097A-M124V-Y217Q, N061P-N062Q-G097A-G100D-Y217Q, N061P-N062Q-G097A-G100Q-S101N-Y217Q, N061P-N062Q-G097A-G100Q-Y217Q, N061P-N062Q-G100N-G102A-Y217Q, N061P-N062Q-S078N-G097A-G100N-I111V-Y217Q, S024G-N025G-S053G-N061P-G097A-S101N-M124I-Y217Q, S053G-N061P-G097A-S101N-M124I-Y217Q, S053G-N061P-G097A-S101N-N123Q-Y217Q, wherein positions of the variant are numbered by correspondence with the sequence of SEQ ID NO:2. Such variants have proteolytic activity. The invention includes a protease variant having proteolytic activity, a PI value of 0.9 relative to BPN'-v3, and/or an enhanced proteolytic activity compared to BPN' in this assay, the variant comprising an amino acid sequence having at least 60%, 70%, 80%, 85%, 90%, 91%, 92%, 93%, 94%, 95%, 96%, 97%, or 98% or 99% identity to SEQ ID NO:2 and at least one set of amino acid substitutions selected from said group above, wherein amino acid positions of the variant are numbered by correspondence with positions of the SEQ ID NO:2 sequence. Also included are compositions, including, but not limited to, e.g., cleaning compositions, comprising at least one such variant and methods for cleaning utilizing at least one such variant as described in greater detail elsewhere herein.

Also provided is a subtilisin protease variant having enhanced proteolytic activity compared to BPN' and/or a PI value of greater than 1.0 compared to BPN'-v3 in a BMI microswatch cleaning assay in Detergent Composition 1 or 4 at pH 8 and 16° C., the variant comprising an amino acid sequence having at least 85%, 90%, 91%, 92%, 93%, 94%, 95%, 96%, 97%, or 98% identity to SEQ ID NO:2, wherein the variant comprises at least one substitution selected from the group of X024G, X025G, X053G, X061P, X062Q, X078N, X097A, X100D/N/Q, X101N, X102A, X111V, X123A/Q/V, X124I/V, X128A/S, X129S, X210S, X217Q, and optionally at least one substitution selected from the group of S024G, N025G, S053G, N061P, N062Q, S078N, G097A, G100D/N/Q, S101N, G102A, I111V, N123A/Q/V, M124UV, G128A/S, P129S, P210S, and Y217Q, wherein amino acid positions of the variant are numbered by correspondence with positions of the sequence of SEQ ID NO:2. Such variants have enhanced proteolytic activity compared to BPN' (SEQ ID NO:2) and a greater PI value than BPN' in this assay. Also included are compositions, including, but not limited to, e.g., cleaning compositions, comprising at least one such variant and methods for cleaning utilizing at least one such variant as described in greater detail elsewhere herein.

The following BPN' variants were determined to have a PI value equal to or greater than 0.5 and less than 0.9 relative to BPN'-v3 in a BMI microswatch cleaning assay in Detergent Composition 4 at pH 8 and 16° C.: BPN' amino acid sequence (SEQ ID NO:2) comprising at least one set of amino acid substitutions selected from the group consisting of G097A-N123A-Y217Q, G097A-N123V-Y217Q, N061P-G102A-G128S-Y217Q, N061P-S101N-G102A-G128S-Y217Q, Y217Q, S078N-G097A-I111V-N123Q-Y217Q, and G102A-N123Q-Y217Q, wherein positions of the variant are numbered by correspondence with positions of the SEQ ID NO:2 sequence. Such variants have proteolytic activity. The invention includes a protease variant having proteolytic activity, the variant comprising an amino acid sequence having at least 60%, 70%, 80%, 85%, 90%, 91%, 92%, 93%, 94%, 95%, 96%, 97%, or 98% or 99% identity to SEQ ID NO:2 and at least one set of amino acid substitutions selected from said group above, wherein positions of the variant are numbered by correspondence with positions of the SEQ ID NO:2 sequence. Also included are compositions, including, but not limited to, e.g., cleaning compositions, comprising at least one such variant and methods for cleaning utilizing at least one such variant as described in greater detail elsewhere herein.

The following BPN' variants were determined to have a PI value greater than 1.0, at least 1.1, at least 1.2, at least 1.3, at least 1.4, at least 1.5, at least 1.6, at least 1.7, at least 1.8, at least 1.9, at least 2, from greater than 1.0 to about 10, from greater than 1.0 to about 8, or from greater than 1.0 to about 5 relative to BPN'-v3 in a BMI microswatch cleaning assay in Detergent Composition 1 at pH 8 and 16° C.: BPN' amino acid sequence (SEQ ID NO:2) comprising at least one set of amino acid substitutions selected from the group consisting of N061P-G097A-G128S-Y217Q, N061P-G097A-S101N-G128A-P210S-Y217Q, N061P-N062Q-G097A-S101N-I111V-Y217Q, S024G-N025G-N061P-G097A-S101N-G128A-P210S-Y217Q, S024G-N025G-S053G-N061P-G097A-S101N-G128A-P210S-Y217Q, S024G-N025G-S053G-N061P-G097A-S101N-G128S-Y217Q, and S024G-N025G-S053G-N061P-S078N-G097A-S101N-I111V-G128S-Y217Q, wherein amino acid positions of the variant are numbered by correspondence with the sequence of SEQ ID NO:2. Such variants have enhanced proteolytic activity compared to BPN' (SEQ ID NO:2) and a greater PI value than BPN' in this assay. The invention includes a protease variant having enhanced proteolytic activity compared to BPN' (SEQ ID NO:2) and/or a PI value of greater than 1.0 to about 5 relative to BPN'-v3 in this BMI microswatch cleaning assay, the variant comprising an amino acid sequence having at least 60%, 70%, 80%, 85%, 90%, 91%, 92%, 93%, 94%, 95%, 96%, 97%, or 98% or 99% identity to SEQ ID NO:2 and comprising at least one set of amino acid substitutions selected from said group above, wherein amino acid positions of the variant are numbered by correspondence with amino acid positions of the SEQ ID NO:2 sequence. Also included are compositions, including, but not limited to, e.g., cleaning compositions, comprising at least one such variant and methods for cleaning utilizing at least one such variant as described in greater detail elsewhere herein.

The following BPN' variants were determined to have a PI value equal to about 1.0 relative to BPN'-v3 in a BMI microswatch cleaning assay in Detergent Composition 1 at pH 8 and 16° C.: BPN' amino acid sequence (SEQ ID NO:2) comprising at least one set of amino acid substitutions selected from the group consisting of G097A-G128A-Y217Q, G097A-G128A-P210S-Y217Q, G097A-G128S-P210S-Y217Q, G097A-I111V-M124I-Y217Q, G097A-I111V-M124V-P210S-Y217Q, G097A-N123Q-P210S-Y217Q, G097A-N123Q-Y217Q, N061P-G097A-G128A-P210S-Y217Q, N061P-G097A-I111V-M124V-Y217Q, N061P-G097A-M124V-Y217Q, N061P-G097A-N123Q-Y217Q, N061P-G097A-S101N-I111V-M124V-Y217Q, N061P-G102A-P129S-Y217Q, N061P-N062Q-G097A-G100N-S101N-Y217Q, N061P-N062Q-G097A-G100Q-Y217Q, N061P-N062Q-G097A-I111V-Y217Q, N061P-N062Q-S078N-G097A-G100N-I111V-Y217Q, N061P-S078N-G097A-I111V-M124I-Y217Q, N061P-S078N-G102A-I111V-P129S-Y217Q, N062Q-G097A-I111V-P210S-Y217Q, N062Q-G097A-I111V-Y217Q, N062Q-S078N-G097A-I111V-Y217Q, S024G-N025G-S053G-N061P-G097A-S101N-I111V-M124V-Y217Q, S024G-N025G-S053G-N061P-G097A-S101N-N123Q-Y217Q, S024G-N025G-S053G-N061P-N062Q-G097A-G100N-S101N-Y217Q, S024G-N025G-S053G-N061P-N062Q-G097A-S101N-I111V-Y217Q, S024G-N025G-S053G-N061P-S101N-G102A-P129S-Y217Q, S053G-N061P-G097A-G128S-Y217Q, S053G-N061P-G102A-P129S-P210S-Y217Q, S053G-N061P-G102A-P129S-Y217Q, S053G-N061P-N062Q-G097A-S101N-I111V-Y217Q, S053G-N061P-S101N-G102A-P129S-Y217Q, S053G-S078N-G097A-I111V-G128S-Y217Q, S078N-G097A-G128S-Y217Q, and S078N-G097A-I111V-M124V-Y217Q, wherein amino acid positions of the variant are numbered by correspondence with the sequence of SEQ ID NO:2. Such variants have enhanced proteolytic activity compared to BPN' (SEQ ID NO:2) and a greater PI value than BPN' in this assay. The invention includes a protease variant having enhanced proteolytic activity compared to BPN' (SEQ ID NO:2) and/or a PI value of 1.0 relative to BPN'-v3 in this BMI microswatch cleaning assay, the variant comprising an amino acid sequence having at least 60%, 70%, 80%, 85%, 90%, 91%, 92%, 93%, 94%, 95%, 96%, 97%, or 98% or 99% identity to SEQ ID NO:2 and comprising at least one set of amino acid substitutions selected from said group above, wherein amino acid positions of the variant are numbered by correspondence with amino acid positions of the SEQ ID NO:2 sequence. Also included are compositions, including, but not limited to, e.g., cleaning compositions, comprising at least one such variant and methods for cleaning utilizing at least one such variant as described in greater detail elsewhere herein.

The following BPN' variants were determined to have a PI value of about 0.9 relative to BPN'-v3 in a BMI microswatch cleaning assay in Detergent Composition 1 at pH 8 and 16° C.: BPN' amino acid sequence (SEQ ID NO:2) comprising at least one set of amino acid substitutions selected from the group consisting of N061P-G097A-M124I-Y217Q, N061P-G097A-S101N-N123Q-Y217Q, N061P-N062Q-G097A-G100N-Y217Q, N061P-N062Q-G097A-G100Q-P210S-Y217Q, N061P-N062Q-G097A-G100Q-S101N-Y217Q, N061P-N062Q-G100N-G102A-Y217Q, S024G-N025G-S053G-N061P-G097A-S101N-M124I-Y217Q, S053G-N061P-G097A-M124I-Y217Q, S053G-N061P-G097A-S101N-I111V-M124V-Y217Q, S053G-N061P-G097A-S101N-M124I-Y217Q, S053G-N061P-G097A-S101N-N123Q-Y217Q, and S053G-N061P-N062Q-G097A-G100N-S101N-Y217Q, wherein positions of the variant are numbered by correspondence with the sequence of SEQ ID NO:2. Such variants have proteolytic activity. The invention includes a protease variant having proteolytic activity, a PI value of 0.9 relative to BPN'-v3, and/or an enhanced proteolytic activity compared to BPN' in this assay, the variant comprising an amino acid sequence having at least 60%, 70%, 80%, 85%, 90%, 91%, 92%, 93%, 94%, 95%, 96%, 97%, or 98% or 99% identity to SEQ ID NO:2 and at least one set of amino acid substitutions selected from said group above, wherein amino acid positions of the variant are numbered by correspondence with positions of the SEQ ID NO:2 sequence. Also included are compositions, including, but not limited to, e.g., cleaning compositions, comprising at least one such variant and methods for cleaning utilizing at least one such variant as described in greater detail elsewhere herein.

The following BPN' variants were determined to have a PI value equal to or greater than 0.5 and less than 0.9 relative to BPN'-v3 in a BMI microswatch cleaning assay in Detergent Composition 1 at pH 8 and 16° C.: BPN' amino acid sequence (SEQ ID NO:2) comprising at least one set of amino acid substitutions selected from the group consisting of G097A-N123A-Y217Q, G097A-N123V-Y217Q, N061P-N062Q-G097A-G100D-Y217Q, N061P-S101N-G102A-G128S-Y217Q, Y217Q, N061P-G102A-G128S-Y217Q, S078N-G097A-I111V-N123Q-Y217Q, and G102A-N123Q-Y217Q, wherein positions of the variant are numbered by correspondence with positions of the SEQ ID NO:2 sequence. Such variants have proteolytic activity. The invention includes a protease variant having proteolytic activity, the variant comprising an amino acid sequence having at least 60%, 70%, 80%, 85%, 90%, 91%, 92%, 93%, 94%, 95%, 96%, 97%, or 98% or 99% identity to SEQ ID NO:2 and at least one set of amino acid substitutions selected from said group above, wherein positions of the variant are numbered by correspondence with positions of the SEQ ID NO:2 sequence. Also included are compositions, including, but not limited to, e.g., cleaning compositions, comprising at least one such variant and methods for cleaning utilizing at least one such variant as described in greater detail elsewhere herein.

The following BPN' variants were determined to have a PI value greater than 1.0 to about 5 relative to BPN'-v3 in an egg microswatch cleaning assay in Detergent Composition 4 at 16° C. and pH 8: BPN' amino acid sequence (SEQ ID NO:2) comprising the set of amino acid substitutions N061P-G097A-S101N-G128A-P210S-Y217Q, wherein amino acid positions of the variant are numbered by correspondence with the sequence of SEQ ID NO:2. Such variants have enhanced proteolytic activity compared to BPN' (SEQ ID NO:2) and a greater PI value than BPN' in this assay. The invention includes a protease variant having enhanced proteolytic activity compared to BPN' (SEQ ID NO:2) and/or a PI value of greater than 1.0 to about 5 relative to BPN'-v3 in this egg microswatch cleaning assay, the variant comprising an amino acid sequence having at least 60%, 70%, 80%, 85%, 90%, 91%, 92%, 93%, 94%, 95%, 96%, 97%, or 98% or 99% identity to SEQ ID NO:2 and comprising amino acid substitutions N061P-G097A-S101N-G128A-P210S-Y217Q, wherein amino acid positions of the variant are numbered by correspondence with the sequence of SEQ ID NO:2. Also included are compositions, including, but not limited to, e.g., cleaning compositions, comprising at least one such variant and methods for cleaning utilizing at least one such variant as described in greater detail elsewhere herein.

The following BPN' variants were determined to have a PI value equal to about 1.0 relative to BPN'-v3 in an egg microswatch cleaning assay in Detergent Composition 4 at pH 8 and 16° C.: BPN' amino acid sequence (SEQ ID NO:2) comprising at least one set of amino acid substitutions selected from the group consisting of G097A-G128A-Y217Q, N061P-G102A-P129S-Y217Q, N062Q-G097A-I111V-P210S-Y217Q, S024G-N025G-S053G-N061P-G097A-S101N-G128A-P210S-Y217Q, S024G-N025G-N061P-G097A-S101N-G128A-P210S-Y217Q, N061P-G097A-G128A-P210S-Y217Q, G097A-G128S-P210S-Y217Q, S024G-N025G-S063G-N061P-S078N-G097A-S101N-I111V-G128S-Y217Q, S024G-N025G-S053G-N061P-G097A-S101N-G128S-Y217Q, N061P-G097A-G128S-Y217Q, G097A-G128A-P210S-Y217Q, wherein amino acid positions of the variant are numbered by correspondence with the sequence of SEQ ID NO:2. Such variants have enhanced proteolytic activity compared to BPN' (SEQ ID NO:2) and a greater PI value than BPN' in this assay. The invention includes a protease variant having enhanced proteolytic activity compared to BPN' (SEQ ID NO:2) and/or a PI value of 1.0 relative to BPN'-v3 in this egg microswatch cleaning assay, the variant comprising an amino acid sequence having at least 60%, 70%, 80%, 85%, 90%, 91%, 92%, 93%, 94%, 95%, 96%, 97%, or 98% or 99% identity to SEQ ID NO:2 and comprising at least one set of amino acid substitutions selected from said group above, wherein amino acid positions of the variant are numbered by correspondence with amino acid positions of the SEQ ID NO:2 sequence. Also included are compositions, including, but not limited to, e.g., cleaning compositions, comprising at least one such variant and methods for cleaning utilizing at least one such variant as described in greater detail elsewhere herein.

The following BPN' variants were determined to have a PI value equal to or greater than 0.5 and equal to or less than 0.9 relative to BPN'-v3 in an egg microswatch cleaning assay in Detergent Composition 4 at pH 8 and 16° C.: BPN' amino acid sequence (SEQ ID NO:2) comprising at least one set of amino acid substitutions selected from the group consisting of N061P-G097A-M124I-Y217Q, S053G-N061P-G097A-S101N-N123Q-Y217Q, S053G-N061P-G102A-P129S-P210S-Y217Q, G097A-I111V-M124V-P210S-Y217Q, G097A-N123Q-P210S-Y217Q, S053G-N061P-S101N-G102A-P129S-Y217Q, S053G-N061P-N062Q-G097A-S101N-I111V-Y217Q, N061P-N062Q-G097A-S101N-I111V-Y217Q, N061P-N062Q-G097A-I111V-Y217Q, N062Q-G097A-I111V-Y217Q, N061P-G097A-S101N-I111V-M124V-Y217Q, G097A-N123Q-Y217Q, N061P-G097A-I111V-M124V-Y217Q, S078N-G097A-I111V-M124V-Y217Q, S053G-S078N-G097A-I111V-G128S-Y217Q, S078N-G097A-G128S-Y217Q, S053G-N061P-G097A-G128S-Y217Q, N061P-N062Q-G097A-G100N-Y217Q, S024G-N025G-S053G-N061P-G097A-S101N-N123Q-Y217Q, N061P-G097A-S101N-N123Q-Y217Q, N061P-N062Q-G097A-G100Q-P210S-Y217Q, N061P-G097A-N123Q-Y217Q, S024G-N025G-S053G-N061P-G097A-S101N-M124I-Y217Q, S053G-N061P-G097A-S101N-M124I-Y217Q, S053G-N061P-G097A-M124I-Y217Q, N061P-S078N-G097A-I111V-M124I-Y217Q, N061P-G097A-M124V-Y217Q, S024G-N025G-S053G-N061P-N062Q-G097A-G100N-S101N-Y217Q, S024G-N025G-S053G-N061P-S101N-G102A-P129S-Y217Q, N061P-S078N-G102A-I111V-P129S-Y217Q, S053G-N061P-G102A-P129S-Y217Q, S024G-N025G-S053G-N061P-N062Q-G097A-S101N-I111V-Y217Q, N062Q-S078N-G097A-I111V-Y217Q, S024G-N025G-S053G-N061P-G097A-S101N-I111V-M124V-Y217Q, S053G-N061P-G097A-S101N-I111V-M124V-Y217Q, G097A-I111V-M124I-Y217Q, Y217Q, N061P-N062Q-G100N-G102A-Y217Q, S053G-N061P-N062Q-G097A-G100N-S101N-Y217Q, N061P-N062Q-G097A-G100N-S101N-Y217Q, N061P-N062Q-S078N-G097A-G100N-I111V-Y217Q, N061P-N062Q-G097A-G100Q-Y217Q, N061P-S101N-G102A-G128S-Y217Q, G097A-N123V-Y217Q, G097A-N123A-Y217Q, G102A-N123Q-Y217Q, N061P-N062Q-G097A-G100Q-S101N-Y217Q, S078N-G097A-I111V-N123Q-Y217Q, N061P-N062Q-G097A-G100D-Y217Q, and N061P-G102A-G128S-Y217Q, wherein positions of the variant are numbered by correspondence with the sequence of SEQ ID NO:2. Such variants have proteolytic activity. The invention includes a protease variant having proteolytic activity and/or a PI value of equal to or greater than 0.5 and equal to or less than 0.9 relative to BPN'-v3 in this egg microswatch cleaning assay, the variant comprising an amino acid sequence having at least 60%, 70%, 80%, 85%, 90%, 91%, 92%, 93%, 94%, 95%, 96%, 97%, or 98% or 99% identity to SEQ ID NO:2 and at least one set of amino acid substitutions selected from said group above, wherein amino acid positions of the variant are numbered by correspondence with positions of the SEQ ID NO:2 sequence. Also included are compositions, including, but not limited to, e.g., cleaning compositions, comprising at least one such variant and methods for cleaning utilizing at least one such variant as described in greater detail elsewhere herein.

Also provided is a subtilisin protease variant having enhanced proteolytic activity compared to BPN' and/or a PI value of greater than 1.0 and to about 5 compared to BPN'-v3 in this egg microswatch cleaning assay in Detergent Composition 4 at pH 8 and 16° C., the variant comprising an amino acid sequence having at least 85%, 90%, 91%, 92%, 93%, 94%, 95%, 96%, 97%, or 98% identity to SEQ ID NO:2, wherein the variant comprises at least one substitution selected from the group of X024G, X025G, X053G, X061P, X062Q, X078N, X097A, X100D/N/Q, X101N, X102A, X111V, X123A/Q/V, X124UV, X128A/S, X129S, X210S, and X217Q, and optionally at least one substitution selected from the group of S024G, N025G, S053G, N061P, N062Q, S078N, G097A, G100D/N/Q, S101N, G102A, I111V, N123A/Q/V, M124I/V, G128A/S, P129S, P210S, and Y217Q, wherein amino acid positions of the variant are numbered by correspondence with positions of the sequence of SEQ ID NO:2. Such variants have enhanced proteolytic activity compared to BPN' (SEQ ID NO:2) and a greater PI value than BPN' in this assay. Also included are compositions, including, but not limited to, e.g., cleaning compositions, comprising at least one such variant and methods for cleaning utilizing at least one such variant as described in greater detail elsewhere herein.

Example 6

Construction and Cleaning Performance of BPN' Variants

A BPN' combinatorial library based on BPN' parent was made by DNA2.0 and delivered as a ligation reaction. For efficient transformation of *B. subtilis*, DNA from the ligation reaction mixtures was amplified before transformation and transformants grown as described in Example 2. These variants were tested for cleaning performance using BMI microswatch assay of Test Method 3 in Detergent Composition 1 and Detergent Composition 4 at 16° C. and pH 8 as well as egg microswatch assay in Detergent Composition 4 at 16° C. and pH 8. Protein content was determined using the TCA assay and protease activity was assayed using the AAPF assay. The assays were performed as described in Example 1 and the Performance Indices were calculated relative to BPN'-v3 (with a PI value of 1.0).

The following BPN' variants were determined to have a PI value greater than 1.0, at least 1.1, at least 1.2, at least 1.3, at least 1.4, at least 1.5, at least 1.6, at least 1.7, at least 1.8, at least 1.9, at least 2, from greater than 1.0 to about 10, from greater than 1.0 to about 8, or from greater than 1.0 to about 5 relative to BPN'-v3 in a BMI microswatch cleaning assay in Detergent Composition 1 at pH 8 and 16° C.: BPN' amino acid sequence (SEQ ID NO:2) comprising at least one set of amino acid substitutions selected from the group consisting of S024G-N025G-S053G-T055P-N061P-G097A-S101N-G128A-Y217Q, N025G-G097A-S101N-G128A-Y217Q, N025G-S038G-S053G-N061P-S078N-G097A-S101N-G128A-Y217Q, N025G-S053G-N061P-S078N-G128A-Y217Q, N025G-S053G-N061P-S078N-S101N-G128A-Y217Q, N025G-S053G-T055P-N061P-S078N-G097A-S101N-G128A-Y217Q, N025G-S053G-T055P-S078N-G097A-S101N-G128A-Y217Q, N025G-S078N-G097A-S101N-G128A-Y217Q, N025G-T055P-N061P-S078N-G097A-S101N-G128A-Y217Q, N025G-T055P-N061P-S078N-S101N-G128A-Y217Q, N061P-S101N-G128A-Y217Q, S024G-N025G-N061P-G097A-G128A-Y217Q, S024G-N025G-N061P-G097A-S101N-G128A-Y217Q, S024G-N025G-S053G-N061P-S078N-G097A-S101N-G128A-Y217Q, S024G-N025G-S053G-N061P-S078N-S101N-G128A-Y217Q, S024G-N025G-S053G-T055P-G097A-S101N-G128A-Y217Q, S024G-N025G-S053G-T055P-N061P-G128A-Y217Q, S024G-N025G-T055P-G097A-G128A-Y217Q, S024G-N025G-T055P-N061P-S078N-G097A-S101N-G128A-Y217Q, S024G-N061P-S078N-G097A-S101N-G128A-Y217Q, S024G-S053G-N061P-G097A-G128A-Y217Q, S024G-S053G-N061P-S078N-G097A-G128A-Y217Q, S024G-S053G-T055P-G097A-S101N-G128A-Y217Q, S024G-S053G-T055P-N061P-G097A-S101N-G128A-Y217Q, S024G-S053G-T055P-N061P-S078N-G097A-S101N-G128A-Y217Q, S024G-S053G-T055P-N061P-S101N-G128A-Y217Q, S024G-T055P-N061P-G097A-G128A-Y217Q, S053G-G097A-S101N-G128A-Y217Q, S053G-N061P-G097A-S101N-G128A-Y217Q-S249N, S053G-N061P-S078N-G097A-G128A-Y217Q, S053G-S078N-G097A-S101N-G128A-Y217Q, S053G-T055P-G097A-S101N-G128A-Y217Q, S053G-T055P-N061P-S101N-G128A-Y217Q, S053G-T055P-S078N-G097A-S101N-G128A-Y217Q, T055P-G097A-S101N-G128A-Y217Q, and T055P-N061P-S078N-G097A-S101N-G128A-Y217Q, wherein amino acid positions of the variant are numbered by correspondence with the sequence of SEQ ID NO:2. Such variants have enhanced proteolytic activity compared to BPN' (SEQ ID NO:2) and a greater PI value than BPN' in this assay. The invention includes a protease variant having enhanced proteolytic activity compared to BPN' (SEQ ID NO:2) and/or a PI value of greater than 1.0 to about 5 relative to BPN'-v3 in this BMI microswatch cleaning assay, the variant comprising an amino acid sequence having at least 60%, 70%, 80%, 85%, 90%, 91%, 92%, 93%, 94%, 95%, 96%, 97%, or 98% or 99% identity to SEQ ID NO:2 and comprising at least one set of amino acid substitutions selected from said group above, wherein amino acid positions of the variant are numbered by correspondence with amino acid positions of the SEQ ID NO:2 sequence.

The following BPN' variants were determined to have a PI value equal to about 1.0 relative to BPN'-v3 in a BMI microswatch cleaning assay in Detergent Composition 1 at pH 8 and 16° C.: BPN' amino acid sequence (SEQ ID NO:2) comprising at least one set of amino acid substitutions selected from the group consisting of G097A-G128S-Y217Q, G097A-G128A-Y217Q, N025G-S078N-G097A-G128A-Y217Q, N025G-T055P-G097A-G128A-Y217Q, S024G-G097A-S101N-G128A-Y217Q, S024G-I035V-T055P-N061P-S078N-G097A-Y217Q, S024G-N025G-N061P-S078N-G097A-S101N-G128A, S024G-N025G-N061P-S078N-G097A-S101N-G128A-Y217Q, S024G-N025G-N061P-S078N-S101N-G128A-Y217Q, S024G-N025G-S053G-N061P-G097A-G128A-S130G-Y217Q, S024G-N025G-S053G-N061P-G128A-Y217Q, S024G-N025G-S053G-T055P-G097A-G128A-Y217Q, S024G-N025G-S053G-T055P-N061P-S078N-G097A-G128A-Y217Q, S024G-N025G-S053G-T055P-N061P-S078N-G128A-Y217Q, S024G-N025G-S053G-T055P-S078N-S101N-G128A-Y217Q, S024G-N025G-S053G-T055P-S101N-G128A-Y217Q, S024G-N025G-T055P-G097A-S101N-G128A-Y217Q, S024G-N025G-T055P-N061P-S078N-G097A-Y217Q, S024G-N061P-G097A-S101N-G128A-Y217Q, S024G-S038G-S053G-S078N-S101N-G128A-Y217Q, S024G-S053G-S078N-G097A-S101N-G128A-Y217Q, S024G-S053G-S078N-S101N-G128A-Y217Q, S024G-S053G-T055P-N061P-S078N-G097A-G128A-Y217Q, S024G-T055P-G097A-G128A-Y217Q, S024G-T055P-N061P-G097A-S101N-G128A, S024G-T055P-N061P-S078N-S101N-G128A-Y217Q, S024G-T055P-S078N-G097A-S101N-G128A-Y217Q, S101N-G128A-Y217Q, T055P-N061P-G097A-A116S-G128A, and T055P-N061P-S078N-G128A-Y217Q, wherein amino acid positions of the variant are numbered by correspondence with the sequence of SEQ ID NO:2. Such variants have enhanced proteolytic activity compared to BPN' and a greater PI value than BPN' in this assay. The invention includes a protease variant having enhanced proteolytic activity compared to BPN' (SEQ ID NO:2) and/or a PI value of 1.0 relative to BPN'-v3 in this BMI microswatch cleaning assay, the variant comprising an amino acid sequence having at least 60%, 70%, 80%, 85%, 90%, 91%, 92%, 93%, 94%, 95%, 96%, 97%, or 98% or 99% identity to SEQ ID NO:2 and comprising at least one set of amino acid substitutions selected from said group above, wherein amino acid positions of the variant are numbered by correspondence with amino acid positions of the SEQ ID NO:2 sequence. Also included are compositions, including, but not limited to, e.g., cleaning compositions, comprising at least one such variant and methods for cleaning utilizing at least one such variant as described in greater detail elsewhere herein.

Also provided is a subtilisin protease variant having enhanced proteolytic activity compared to BPN' and/or a PI value of greater than 1.0 compared to BPN'-v3 in this BMI microswatch cleaning assay in Detergent Composition 1 at pH 8 and 16° C., the variant comprising an amino acid sequence having at least 85%, 90%, 91%, 92%, 93%, 94%, 95%, 96%, 97%, or 98% identity to SEQ ID NO:2, wherein the variant comprises at least one substitution selected from the group of X024G, X025G, X035V, X038G, X053G, X055P, X061P, X078N, X097A, X101N, X116S, X128A/S, X130G, X216Q, X217Q, and X249N, and optionally at least one substitution selected from the group of S024G, N025G, I035V, S038G, S053G, T055P, N061P, S078N, G097A, S101N, A116S, G128A/S, S130G, Y216Q, Y217Q, and S249N, wherein amino acid positions of the variant are numbered by correspondence with positions of the sequence of SEQ ID NO:2. Also included are compositions, including, but not limited to, e.g., cleaning compositions, comprising at least one such variant and methods for cleaning utilizing at least one such variant as described in greater detail elsewhere herein.

The following BPN' variants were determined to have a PI value greater than 1.0, at least 1.1, at least 1.2, at least 1.3, at least 1.4, at least 1.5, at least 1.6, at least 1.7, at least 1.8, at least 1.9, at least 2, from greater than 1.0 to about 10, from greater than 1.0 to about 8, or from greater than 1.0 to about 5 relative to BPN'-v3 in a BMI microswatch cleaning assay in Detergent Composition 4 at pH 8 and 16° C.: BPN' amino acid sequence (SEQ ID NO:2) comprising at least one set of amino acid substitutions selected from the group consisting of S024G-N025G-N061P-S078N-G097A-S101N-G128A-Y217Q, S024G-N025G-S053G-N061P-S078N-S101N-G128A-Y217Q, S024G-N025G-S053G-T055P-N061P-G097A-S101N-G128A-Y217Q, S024G-S053G-T055P-N061P-G097A-S101N-G128A-Y217Q, S024G-S053G-T055P-N061P-S078N-G097A-S101N-G128A-Y217Q, S024G-T055P-N061P-S078N-S101N-G128A-Y217Q, S053G-G097A-S101N-G128A-Y217Q, and T055P-N061P-S078N-G128A-Y217Q, wherein amino acid positions of the variant are numbered by correspondence with the sequence of SEQ ID NO:2. Such variants have enhanced proteolytic activity compared to BPN' (SEQ ID NO:2) and a greater PI value than BPN' in this assay. The invention includes a protease variant having enhanced proteolytic activity compared to BPN' (SEQ ID NO:2) and/or a PI value of greater than 1.0 to about 5 relative to BPN'-v3 in this BMI microswatch cleaning assay, the variant comprising an amino acid sequence having at least 60%, 70%, 80%, 85%, 90%, 91%, 92%, 93%, 94%, 95%, 96%, 97%, or 98% or 99% identity to SEQ ID NO:2 and comprising at least one set of amino acid substitutions selected from said group above, wherein amino acid positions of the variant are numbered by correspondence with amino acid positions of the SEQ ID NO:2 sequence.

The following BPN' variants were determined to have a PI value equal to about 1.0 relative to BPN'-v3 in a BMI microswatch cleaning assay of Test Method 3 in Detergent Composition 4 at pH 8 and 16° C.: BPN' amino acid sequence (SEQ ID NO:2) comprising at least one set of amino acid substitutions selected from the group consisting of G097A-G128S-Y217Q, G097A-G128A-Y217Q, N025G-G097A-S101N-G128A-Y217Q, N025G-S038G-S053G-N061P-S078N-G097A-S101N-G128A-Y217Q, N025G-S053G-N061P-S078N-G128A-Y217Q, N025G-S053G-N061P-S078N-S101N-G128A-Y217Q, N025G-S053G-T055P-N061P-S078N-G097A-S101N-G128A-Y217Q, N025G-S053G-T055P-S078N-G097A-S101N-G128A-Y217Q, N025G-S078N-G097A-G128A-Y217Q, N025G-S078N-G097A-S101N-G128A-Y217Q, N025G-T055P-G097A-G128A-Y217Q, N025G-T055P-N061P-S078N-G097A-S101N-G128A-Y217Q, N025G-T055P-N061P-S078N-S101N-G128A-Y217Q, N061P-S101N-G128A-Y217Q, S024G-G097A-S101N-G128A-Y217Q, S024G-I035V-T055P-N061P-S078N-G097A-Y217Q, S024G-N025G-N061P-G097A-G128A-Y217Q, S024G-N025G-N061P-G097A-S101N-G128A-Y217Q, S024G-N025G-N061P-S078N-G097A-S101N-G128A, S024G-N025G-N061P-S078N-S101N-G128A-Y217Q, S024G-N025G-S053G-N061P-G097A-G128A-S130G-Y217Q, S024G-N025G-S053G-N061P-G128A-Y217Q, S024G-N025G-S053G-N061P-S078N-G097A-S101N-G128A-Y217Q, S024G-N025G-S053G-T055P-G097A-G128A-Y217Q, S024G-N025G-S053G-T055P-G097A-S101N-G128A-Y217Q, S024G-N025G-S053G-T055P-N061P-G128A-Y217Q, S024G-N025G-S053G-T055P-N061P-S078N-G097A-G128A-Y217Q, S024G-N025G-S053G-T055P-N061P-S078N-G128A-Y217Q, S024G-N025G-S053G-T055P-S078N-S101N-G128A-Y217Q, S024G-N025G-S053G-T055P-S101N-G128A-Y217Q, S024G-N025G-T055P-G097A-G128A-Y217Q, S024G-N025G-T055P-G097A-S101N-G128A-Y217Q, S024G-N025G-T055P-N061P-S078N-G097A-S101N-G128A-Y217Q, S024G-N061P-G097A-S101N-G128A-Y217Q, S024G-N061P-S078N-G097A-S101N-G128A-Y217Q, S024G-S038G-S053G-S078N-S101N-G128A-Y217Q, S024G-S053G-N061P-G097A-G128A-Y217Q, S024G-S053G-N061P-S078N-G097A-G128A-Y217Q, S024G-S053G-S078N-G097A-S101N-G128A-Y217Q, S024G-S053G-S078N-S101N-G128A-Y217Q, S024G-S053G-T055P-G097A-S101N-G128A-Y217Q, S024G-S053G-T055P-N061P-S078N-G097A-G128A-Y217Q, S024G-S053G-T055P-N061P-S101N-G128A-Y217Q, S024G-T055P-G097A-G128A-Y217Q, S024G-T055P-N061P-G097A-G128A-Y217Q, S024G-T055P-N061P-G097A-S101N-G128A, S024G-T055P-S078N-G097A-S101N-G128A-Y217Q, S053G-N061P-G097A-S101N-G128A-Y217Q-S249N, S053G-N061P-S078N-G097A-G128A-Y217Q, S053G-S078N-G097A-S101N-G128A-Y217Q, S053G-T055P-G097A-S101N-G128A-Y217Q, S053G-T055P-N061P-S101N-G128A-Y217Q, S053G-T055P-S078N-G097A-S101N-G128A-Y217Q, S101N-G128A-Y217Q, T055P-G097A-S101N-G128A-Y217Q, and T055P-N061P-S078N-G097A-S101N-G128A-Y217Q, wherein amino acid positions of the variant are numbered by correspondence with the sequence of SEQ ID NO:2. Such variants have enhanced proteolytic activity compared to BPN' (SEQ ID NO:2) and a greater PI value than BPN' in this assay. The invention includes a protease variant having enhanced proteolytic activity compared to BPN' (SEQ ID NO:2) and/or a PI value of 1.0 relative to BPN'-v3 in this BMI microswatch cleaning assay, the variant comprising an amino acid sequence having at least 60%, 70%, 80%, 85%, 90%, 91%, 92%, 93%, 94%, 95%, 96%, 97%, or 98% or 99% identity to SEQ ID NO:2 and comprising at least one set of amino acid substitutions selected from said group above, wherein amino acid positions of the variant are numbered by correspondence with amino acid positions of the SEQ ID NO:2 sequence. Also included are compositions, including, but not limited to, e.g., cleaning compositions, comprising at least one such variant and methods for cleaning utilizing at least one such variant as described in greater detail elsewhere herein.

The following BPN' variants were determined to have a PI value of about 0.9 relative to BPN'-v3 in a BMI microswatch cleaning assay of Test Method 3 in Detergent Composition 4 at pH 8 and 16° C.: BPN' amino acid sequence (SEQ ID NO:2) comprising at least one set of amino acid substitutions selected from the group consisting of T055P-N061P-G097A-A116S-G128A, S024G-N025G-T055P-N061P-S078N-G097A-Y217Q, wherein positions of the variant are numbered by correspondence with the sequence of SEQ ID NO:2. Such variants have proteolytic activity and may have enhanced proteolytic activity compared to BPN' (SEQ ID NO:2) in this assay. The invention includes a protease variant having proteolytic activity, a PI value of 0.9 relative to BPN'-v3, and/or an enhanced proteolytic activity compared to BPN' in this assay, the variant comprising an amino acid sequence having at least 60%, 70%, 80%, 85%, 90%, 91%, 92%, 93%, 94%, 95%, 96%, 97%, or 98% or 99% identity to SEQ ID NO:2 and at least one set of amino acid substitutions selected from said group above, wherein amino acid positions of the variant are numbered by correspondence with positions of the SEQ ID NO:2 sequence. Also included are compositions, including, but not limited to, e.g., cleaning compositions, comprising at least one such variant and methods for cleaning utilizing at least one such variant as described in greater detail elsewhere herein.

The following BPN' variants were determined to have a PI value greater than 1.0, at least 1.1, at least 1.2, at least 1.3, at least 1.4, at least 1.5, at least 1.6, at least 1.7, at least 1.8, at least 1.9, at least 2, from greater than 1.0 to about 10, from greater than 1.0 to about 8, or from greater than 1.0 to about 5 relative to BPN'-v3 in an egg microswatch cleaning assay in Detergent Composition 4 at pH 8 and 16° C.: BPN' amino acid sequence (SEQ ID NO:2) comprising at least one set of amino acid substitutions selected from the group consisting of N025G-T055P-N061P-S078N-G097A-S101N-G128A-Y217Q, N061P-S101N-G128A-Y217Q, S024G-N025G-S053G-N061P-S078N-S101N-G128A-Y217Q, S024G-N025G-S053G-T055P-S101N-G128A-Y217Q, S024G-N025G-S053G-T055P-N061P-G128A-Y217Q, S024G-N025G-T055P-N061P-S078N-G097A-S101N-G128A-Y217Q, N025G-S053G-N061P-S078N-G128A-Y217Q, S024G-N025G-S053G-T055P-G097A-S101N-G128A-Y217Q, S024G-N025G-N061P-S078N-G097A-S101N-G128A-Y217Q, S024G-S053G-T055P-G097A-S101N-G128A-Y217Q, S053G-N061P-S078N-G097A-G128A-Y217Q, S024G-N025G-T055P-G097A-G128A-Y217Q, S024G-N025G-S053G-T055P-G097A-G128A-Y217Q, wherein amino acid positions of the variant are numbered by correspondence with the sequence of SEQ ID NO:2. Such variants have enhanced proteolytic activity compared to BPN' (SEQ ID NO:2) and a greater PI value than BPN' in this assay. The invention includes a protease variant having enhanced proteolytic activity compared to BPN'(SEQ ID NO:2) and/or a PI value of greater than 1.0 to about 5 relative to BPN'-v3 in this egg microswatch cleaning assay, the variant comprising an amino acid sequence having at least 60%, 70%, 80%, 85%, 90%, 91%, 92%, 93%, 94%, 95%, 96%, 97%, or 98% or 99% identity to SEQ ID NO:2 and comprising at least one set of amino acid substitutions selected from said group above, wherein amino acid positions of the variant are numbered by correspondence with amino acid positions of the SEQ ID NO:2 sequence.

The following BPN' variants were determined to have a PI value equal to about 1.0 relative to BPN'-v3 in an egg microswatch cleaning assay in Detergent Composition 4 at pH 8 and 16° C.: BPN' amino acid sequence (SEQ ID NO:2) comprising at least one set of amino acid substitutions selected from the group consisting of G097A-G128S-Y217Q, G097A-G128A-Y217Q, S024G-G097A-S101N-G128A-Y217Q, N025G-T055P-N061P-S078N-S101N-G128A-Y217Q, S053G-T055P-N061P-S101N-G128A-Y217Q, S053G-T055P-S078N-G097A-S101N-G128A-Y217Q, N025G-S053G-N061P-S078N-S101N-G128A-Y217Q, S024G-S053G-T055P-N061P-S101N-G128A-Y217Q, S024G-N025G-S053G-T055P-N061P-G097A-S101N-G128A-Y217Q, N025G-S053G-T055P-N061P-S078N-G097A-S101N-G128A-Y217Q, S024G-N025G-N061P-S078N-S101N-G128A-Y217Q, S024G-S053G-T055P-N061P-G097A-S101N-G128A-Y217Q, T055P-N061P-S078N-G128A-Y217Q, N025G-S038G-S053G-N061P-S078N-G097A-S101N-G128A-Y217Q, S024G-N025G-S053G-N061P-G128A-Y217Q, S024G-N025G-S053G-T055P-S078N-S101N-G128A-Y217Q, T055P-N061P-S078N-G097A-S101N-G128A-Y217Q, S024G-N025G-S053G-T055P-N061P-S078N-G128A-Y217Q, S024G-N025G-N061P-G097A-S101N-G128A-Y217Q, S024G-T055P-G097A-G128A-Y217Q, T055P-N061P-G097A-A116S-G128A, S053G-T055P-G097A-S101N-G128A-Y217Q, T055P-G097A-S101N-G128A-Y217Q, S024G-N061P-G097A-S101N-G128A-Y217Q, S024G-N025G-N061P-G097A-G128A-Y217Q, S024G-S053G-S078N-S101N-G128A-Y217Q, S024G-N025G-S053G-T055P-N061P-S078N-G097A-G128A-Y217Q, S053G-G097A-S101N-G128A-Y217Q, N025G-T055P-G097A-G128A-Y217Q, S024G-T055P-S078N-G097A-S101N-G128A-Y217Q, N025G-S078N-G097A-S101N-G128A-Y217Q, N025G-G097A-S101N-G128A-Y217Q, S024G-S053G-N061P-S078N-G097A-G128A-Y217Q, S024G-N025G-T055P-N061P-S078N-G097A-Y217Q, S024G-I035V-T055P-N061P-S078N-G097A-Y217Q, wherein amino acid positions of the variant are numbered by correspondence with the sequence of SEQ ID NO:2. Such variants have enhanced proteolytic activity compared to BPN' (SEQ ID NO:2) and a greater PI value than BPN' in this assay. The invention includes a protease variant having enhanced proteolytic activity compared to BPN' (SEQ ID NO:2) and/or a PI value of 1.0 relative to BPN'-v3 in this egg microswatch cleaning assay, the variant comprising an amino acid sequence having at least 60%, 70%, 80%, 85%, 90%, 91%, 92%, 93%, 94%, 95%, 96%, 97%, or 98% or 99% identity to SEQ ID NO:2 and comprising at least one set of amino acid substitutions selected from said group above, wherein amino acid positions of the variant are numbered by correspondence with amino acid positions of the SEQ ID NO:2 sequence. Also included are compositions, including, but not limited to, e.g., cleaning compositions, comprising at least one such variant and methods for cleaning comprising utilizing at least one such variant as described in greater detail elsewhere herein.

The following BPN' variants were determined to have a PI value of about 0.9 relative to BPN'-v3 in an egg microswatch cleaning assay in Detergent Composition 4 at pH 8 and 16° C.: BPN' amino acid sequence (SEQ ID NO:2) comprising at least one set of amino acid substitutions selected from the group consisting of S101N-G128A-Y217Q, S024G-T055P-N061P-G097A-S101N-G128A, S024G-N025G-N061P-S078N-G097A-S101N-G128A, S024G-T055P-N061P-S078N-S101N-G128A-Y217Q, S024G-N025G-S053G-N061P-S078N-G097A-S101N-G128A-Y217Q, S024G-S053G-T055P-N061P-S078N-G097A-S101N-G128A-Y217Q, S053G-N061P-G097A-S101N-G128A-Y217Q-S249N, N025G-S053G-T055P-S078N-G097A-S101N-

G128A-Y217Q, S024G-N025G-T055P-G097A-S101N-G128A-Y217Q, S024G-S053G-N061P-G097A-G128A-Y217Q, S024G-N061P-S078N-G097A-S101N-G128A-Y217Q, S024G-S053G-T055P-N061P-S078N-G097A-G128A-Y217Q, S024G-T055P-N061P-G097A-G128A-Y217Q, S024G-S038G-S053G-S078N-S101N-G128A-Y217Q, S053G-S078N-G097A-S101N-G128A-Y217Q, N025G-S078N-G097A-G128A-Y217Q, and S024G-N025G-S053G-N061P-G097A-G128A-S130G-Y217Q, wherein positions of the variant are numbered by correspondence with the sequence of SEQ ID NO:2. Such variants have proteolytic activity. The invention includes a protease variant having proteolytic activity, a PI value of 0.9 relative to BPN'-v3, and/or an enhanced proteolytic activity compared to BPN' in this assay, the variant comprising an amino acid sequence having at least 60%, 70%, 80%, 85%, 90%, 91%, 92%, 93%, 94%, 95%, 96%, 97%, or 98% or 99% identity to SEQ ID NO:2 and at least one set of amino acid substitutions selected from said group above, wherein amino acid positions of the variant are numbered by correspondence with positions of the SEQ ID NO:2 sequence. Also included are compositions, including, but not limited to, e.g., cleaning compositions, comprising at least one such variant and methods for cleaning utilizing at least one such variant as described in greater detail elsewhere herein.

The following BPN' variant was determined to have a PI value of about 0.8 relative to BPN'-v3 in an egg microswatch cleaning assay in Detergent Composition 4 at pH 8 and 16° C.: BPN' amino acid sequence (SEQ ID NO:2) comprising amino acid substitutions S024G-S053G-S078N-G097A-S101N-G128A-Y217Q, wherein positions of the variant are numbered by correspondence with the sequence of SEQ ID NO:2. The invention includes a protease variant having proteolytic activity, a PI value of 0.8 relative to BPN'-v3, and/or an enhanced proteolytic activity compared to BPN' in this assay, the variant comprising an amino acid sequence having at least 60%, 70%, 80%, 85%, 90%, 91%, 92%, 93%, 94%, 95%, 96%, 97%, or 98% or 99% identity to SEQ ID NO:2 and comprising amino acid substitutions S024G-S053G-S078N-G097A-S101N-G128A-Y217Q, wherein amino acid positions of the variant are numbered by correspondence with positions of the SEQ ID NO:2 sequence. Also included are compositions, including, but not limited to, e.g., cleaning compositions, comprising at least one such variant and methods for cleaning utilizing at least one such variant as described in greater detail elsewhere herein.

The following BPN' variants were determined to have a PI value greater than 1.0, at least 1.1, at least 1.2, at least 1.3, at least 1.4, at least 1.5, at least 1.6, at least 1.7, at least 1.8, at least 1.9, at least 2, from greater than 1.0 to about 10, from greater than 1 to about 12, from greater than 4 to about 12, from greater than 1.0 to about 8, or from greater than 1.0 to about 5 relative to BPN'-v3 in an AAPF proteolytic assay: BPN' amino acid sequence (SEQ ID NO:2) comprising at least one set of amino acid substitutions selected from the group consisting of S024G-G097A-S101N-G128A-Y217Q, S101N-G128A-Y217Q, N025G-T055P-N061P-S078N-S101N-G128A-Y217Q, S053G-T055P-N061P-S101N-G128A-Y217Q, S024G-T055P-N061P-G097A-S101N-G128A, S053G-T055P-S078N-G097A-S101N-G128A-Y217Q, N025G-S053G-N061P-S078N-S101N-G128A-Y217Q, S024G-S053G-T055P-N061P-S101N-G128A-Y217Q, S024G-N025G-S053G-T055P-N061P-G097A-S101N-G128A-Y217Q, S024G-N025G-N061P-S078N-G097A-S101N-G128A, N061P-S101N-G128A-Y217Q, S024G-N025G-S053G-N061P-S078N-S101N-G128A-Y217Q, S024G-T055P-N061P-S078N-S101N-G128A-Y217Q, N025G-S053G-T055P-N061P-S078N-G097A-S101N-G128A-Y217Q, S024G-N025G-S053G-T055P-S101N-G128A-Y217Q, N025G-T055P-N061P-S078N-G097A-S101N-G128A-Y217Q, S024G-N025G-N061P-S078N-S101N-G128A-Y217Q, S024G-N025G-S053G-T055P-N061P-G128A-Y217Q, S024G-S053G-T055P-N061P-G097A-S101N-G128A-Y217Q, S024G-N025G-S053G-N061P-S078N-G097A-S101N-G128A-Y217Q, T055P-N061P-S078N-G128A-Y217Q, S024G-S053G-T055P-N061P-S078N-G097A-S101N-G128A-Y217Q, N025G-S038G-S053G-N061P-S078N-G097A-S101N-G128A-Y217Q, S024G-N025G-T055P-N061P-S078N-G097A-S101N-G128A-Y217Q, S024G-N025G-S053G-N061P-G128A-Y217Q, N025G-S053G-N061P-S078N-G128A-Y217Q, S024G-N025G-S053G-T055P-G097A-S101N-G128A-Y217Q, S024G-N025G-S053G-T055P-S078N-S101N-G128A-Y217Q, T055P-N061P-S078N-G097A-S101N-G128A-Y217Q, S024G-N025G-S053G-T055P-N061P-S078N-G128A-Y217Q, S024G-N025G-N061P-G097A-S101N-G128A-Y217Q, S053G-N061P-G097A-S101N-G128A-Y217Q-S249N, N025G-S 053G-T055P-S078N-G097A-S101N-G128A-Y217Q, S024G-T055P-G097A-G128A-Y217Q, T055P-N061P-G097A-A116S-G128A, S024G-N025G-T055P-G097A-S101N-G128A-Y217Q, S024G-N025G-N061P-S078N-G097A-S101N-G128A-Y217Q, S053G-T055P-G097A-S101N-G128A-Y217Q, T055P-G097A-S101N-G128A-Y217Q, S024G-N061P-G097A-S101N-G128A-Y217Q, S024G-S053G-T055P-G097A-S101N-G128A-Y217Q, G097A-G128S-Y217Q, S024G-S053G-N061P-G097A-G128A-Y217Q, S024G-N025G-N061P-G097A-G128A-Y217Q, S024G-N061P-S078N-G097A-S101N-G128A-Y217Q, S024G-S053G-T055P-N061P-S078N-G097A-G128A-Y217Q, S024G-S053G-S078N-S101N-G128A-Y217Q, S024G-N025G-S053G-T055P-N061P-S078N-G097A-G128A-Y217Q, S053G-N061P-S078N-G097A-G128A-Y217Q, S024G-T055P-N061P-G097A-G128A-Y217Q, S024G-S038G-S053G-S078N-S101N-G128A-Y217Q, S053G-G097A-S101N-G128A-Y217Q, N025G-T055P-G097A-G128A-Y217Q, S024G-T055P-S078N-G097A-S101N-G128A-Y217Q, S053G-S078N-G097A-S101N-G128A-Y217Q, S024G-N025G-T055P-S024G-N025G-S053G-T055P-G097A-G128A-Y217Q, N025G-S078N-G097A-S101N-G128A-Y217Q, N025G-G097A-S101N-G128A-Y217Q, S024G-S053G-N061P-S078N-G097A-G128A-Y217Q, S024G-S053G-S078N-G097A-S101N-G128A-Y217Q, N025G-S078N-G097A-G128A-Y217Q, and S024G-N025G-S053G-N061P-G097A-G128A-S130G-Y217Q, wherein amino acid positions of the variant are numbered by correspondence with the sequence of SEQ ID NO:2. Such variants have enhanced proteolytic activity compared to BPN' protease (SEQ ID NO:2) and a greater PI value than BPN' in this assay. The invention includes a protease variant having enhanced proteolytic activity compared to BPN' (SEQ ID NO:2) and/or a PI value of greater than 1.0 to about 5 relative to BPN'-v3 in this AAPF assay, the variant comprising an amino acid sequence having at least 60%, 70%, 80%, 85%, 90%, 91%, 92%, 93%, 94%, 95%, 96%, 97%, or 98% or 99% identity to SEQ ID NO:2 and comprising at least one set of amino acid substitutions selected from said group above, wherein amino acid positions of the variant are numbered by correspondence with amino acid positions of the SEQ ID NO:2 sequence.

The following BPN' variant was determined to have a PI value equal to about 1.0 relative to BPN'-v3 in an AAPF proteolytic assay: BPN' amino acid sequence (SEQ ID NO:2) comprising amino acid substitutions G097A-G128A-

Y217Q, wherein amino acid positions of the variant are numbered by correspondence with the sequence of SEQ ID NO:2. Such variants have enhanced proteolytic activity compared to BPN' protease (SEQ ID NO:2) and a greater PI value than BPN' in this assay. The invention includes a protease variant having enhanced proteolytic activity compared to BPN' (SEQ ID NO:2) and/or a PI value of 1.0 relative to BPN'-v3 in this AAPF assay, the variant comprising an amino acid sequence having at least 60%, 70%, 80%, 85%, 90%, 91%, 92%, 93%, 94%, 95%, 96%, 97%, or 98% or 99% identity to SEQ ID NO:2 and comprising amino acid substitutions G097A-G128A-Y217Q, wherein amino acid positions of the variant are numbered by correspondence with amino acid positions of the SEQ ID NO:2 sequence. Also included are compositions, including, but not limited to, e.g., cleaning compositions, comprising at least one such variant and methods for cleaning utilizing at least one such variant as described in greater detail elsewhere herein.

Example 7

Construction of Site Evaluation Libraries of BPN'-v36 and Cleaning Performance of BPN'-v36 Variants Construction of the Site Evaluation Libraries of BPN'-v36

The amino acid sequence of BPN'-v36 is that of SEQ ID NO:6 and the nucleic acid sequence encoding the BPN'-v36 protease variant is that of SEQ ID NO:5.

The amino acid sequence of BPN'-v36 may be represented by reference to the subtilisin BPN' amino acid sequence of SEQ ID NO:2. That is, BPN'-v36 may be represented as the subtilisin BPN' sequence of SEQ ID NO:2 with the six amino acid substitutions S024G-S053G-S078N-S101N-G128A-Y217Q. The BPN'-v36 amino acid sequence may be conveniently designated as BPN'-S024G-S053G-S078N-S101N-G128A-Y217Q or BPN'+S024G+S053G+S078N+S101N+G128A+Y217Q. Throughout this specification, unless otherwise indicated, each amino acid position of an amino acid sequence is numbered according to the numbering of a corresponding amino acid position in the amino acid sequence of *Bacillus amyloliquefaciens* subtilisin BPN' shown in SEQ ID NO:2 as determined by alignment of the variant amino acid sequence with the *Bacillus amyloliquefaciens* subtilisin BPN' amino acid sequence.

Site evaluation libraries (SELs) were created at every single amino acid position in mature BPN'-v36 (i.e., BPN'-S24G-S53G-S78N-S101N-G128A-Y217Q) protein by PCR fusion.

For each codon to be mutated in the BPN'-v36 protease, a pair of partially overlapping, complementary (mutagenic forward and reverse) primers were designed. Each mutagenic primer contained the NNS (N=A,C,G, or T and S=G or C) mutagenic codon in the center flanked by at least 15 nucleotides on each side. To create a library at a given position, two PCR reactions were carried out using either a common forward gene-flanking primer (P4974, SEQ ID NO:60) and a mutagenic NNS reverse primer, or the common reverse gene-flanking primer (P4976, SEQ ID NO:61) and a mutagenic NNS forward primer. These PCR reactions generated two PCR fragments, one encoding the 5' half of the mutant BPN'-v36 gene (5' gene fragment) and the other encoding the 3' half of the mutant BPN'-v36 gene (3' gene fragment).

Figure 4:
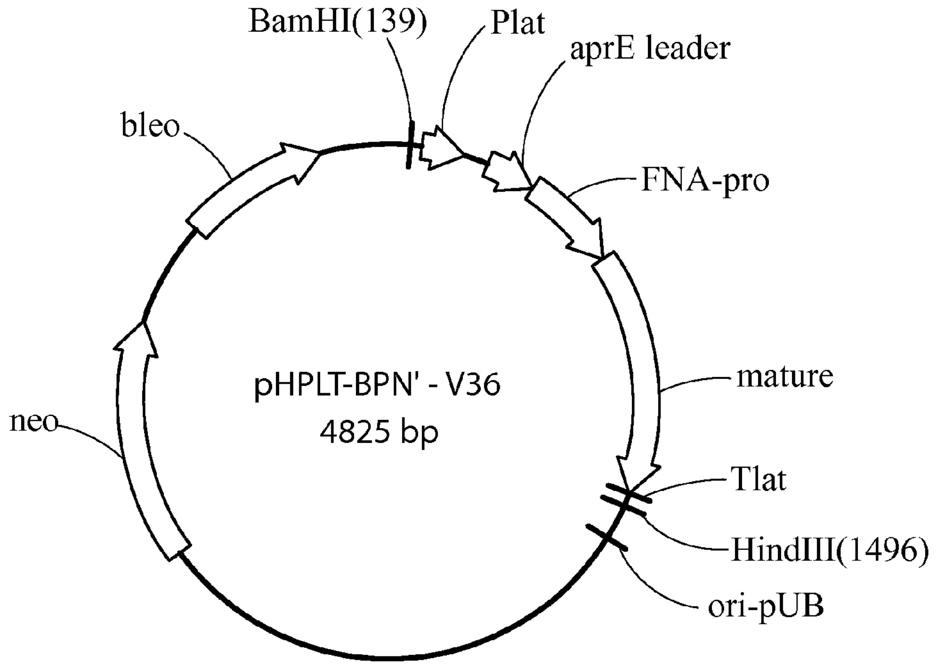
FIG. 4 provides a plasmid map of pHPLT-BPN'-v36.

Each PCR amplification reaction contained 30 pmol of each primer and 100 ng of the BPN'-v36 parent template DNA (plasmid pHPLT-BPN'-v36, see FIG. 4). Amplifications were carried out using Vent DNA polymerase (NEB). The PCR reaction (20 μL) was initially heated at 95° C. for 2.5 min followed by 30 cycles of denaturation at 94° C. for 15 sec., annealing at 55° C. for 15 sec. and extension at 72° C. for 40 sec. Following amplification, the 5' and 3' gene fragments were gel-purified by the QIAGEN® gel-band purification kit, mixed (50 ng of each fragment), mixed and amplified by PCR once again using the primers P4973 (SEQ ID NO:62) and P4950 (SEQ ID NO:63) to generate the full-length gene fragment. The PCR conditions were same as described above, except the extension phase, which was carried out at 72° C. for 2 min. The full-length DNA fragment was gel-purified by the QIAGEN® gel-band purification kit, digested by the BamHI and HindIII restriction enzymes and ligated with the pHPLT-BPN' partial opt vector that also was digested with the same restriction enzymes. Ligation mixtures were amplified using rolling circle amplification in an Illustra Templiphi kit according to the manufacturer's recommendation (GE Healthcare) to generate multimeric DNA for transformation into *Bacillus subtilis*. For this purpose, 1 μl of the ligation mixture was mixed with 5 μl of the sample buffer, heated to 95° C. for 3 min and cooled on ice. Next, 5 μl of the reaction buffer and 0.2 μl of the enzyme were added to each tube, followed by incubation at 30° C. for 10 hours. Products of the rolling circle amplification were diluted 100 times and used to transform *B. subtilis* cells (ΔaprE, ΔnprE, amyE::xylRPxylAcomK-phleo). An aliquot of the transformation mix was plated on LB plates containing 1.6% skim milk and 10 μg/mL neomycin and incubated overnight at 37° C. Subsequently, the colonies with halos were inoculated in 150 μl of LB media containing 10 μg/mL neomycin. The next day, cultures were either frozen with 15% glycerol or grown in MBD medium for biochemical analysis as described in Example 2.

Cleaning Performance of the BPN'-v36 Variants

Protein variants from BPN'-v36 SEL were tested for cleaning performance using a BMI microswatch assay in Detergent Composition 4 at 16° C. and pH 8 and egg microswatch assay in Detergent Composition 4 at 16° C. and pH 8. Protein content was determined using the TCA assay. The assays were performed as described in Example 1 and the Performance Indices were calculated relative to BPN'-v36 (i.e., BPN'-S24G-S53G-S78N-S101N-G128A-Y217Q).

The following BPN'-v36 variants were determined to have a PI value greater than 1.0, at least 1.1, at least 1.2, at least 1.3, at least 1.4, at least 1.5, at least 1.6, at least 1.7, at least 1.8, at least 1.9, at least 2, from greater than 1.0 to about 10, from greater than 1.0 to about 8, or from greater than 1.0 to about 5 relative to BPN'-v36 in a BMI microswatch cleaning assay in Detergent Composition 4 at pH 8 and 16° C.: BPN'-S024G-S053G-S078N-S101N-G128A-Y217Q (SEQ ID NO:6) (i.e., BPN'-v36) comprising at least one amino acid substitution selected from the group consisting of A116V, G160S, I111L, I115V, N109S, N117M, P005G, Q059V, T164S, Y262M, A015Q, A015S, A098E, A098N, A098S, A098T, A098V, A098Y, A114S, A114T, A116G, A116L, A116S, A116T, A116W, A133G, A133H, A133T, A133V, A137G, A137I, A137L, A137S, A137T, A138S, A216E, A216F, A216V, D099S, D181E, F261A, F261Q, G024F, G024I, G024Q, G024Y, G097S, G160T, G211L, G211V, H017F, H017W, H039V, H226A, I031V, I111V, I268V, K170R, K265R, L016Q, L016T, L135M, L209T, L209V, L233M, L257T, L257V, L267A, L267V, N025A, N025I, N025Q, N025R, N025T, N025V, N101I, N101Q, N101S, N109A, N109G, N109H, N109L, N109M, N109Q, N109T, N117Q, N184A, N184L, N184T, N184W, N212G, N212L, N212V, N243P, N252G, N252M, P005T, P014S, P040G, P040L, P040Q, P129A, P129S, P172G, P172S, P194Q, P210A, P210S, Q185F, -Q185G, Q185I, Q185M, Q185N, Q185S, Q275H, R186K, S009A, S009G, S009H, S009M, S018T, S130T, S132N, S145K, S159T, S161I, S161K, S161N, S161T, S162I, S162M, S162Y, S163G, S182F, S182G, S182V, S182W, S183F, S183L, S183M, S183T, S183V, S183W, S224A, S236T, S249V, T022A, T022G, T022Q, T022V, T208V, T242S, T253N, T253S, T254A, T254S, T255L, T255S, T255V, V004A, V004P, V004W, V084C, V139C, V165M, V203F, Y021K, Y021N, Y021T, Y021V, Y167F, Y171F, Y214F, Y262F, and Y262T, wherein amino acid positions of the variant are numbered by correspondence with the sequence of SEQ ID NO:2. Such variants have enhanced proteolytic activity compared to BPN' (SEQ ID NO:2) and a greater PI value than BPN' in this assay. The invention includes a protease variant having enhanced proteolytic activity compared to BPN' (SEQ ID NO:2), enhanced proteolytic activity compared to BPN'-v3 and BPN'-v36, a PI value greater than that of BPN'-v3, and/or a PI value greater than 1 to about 5 relative to BPN'-v36 in this BMI microswatch cleaning assay, the variant comprising an amino acid sequence having at least 60%, 70%, 80%, 85%, 90%, 91%, 92%, 93%, 94%, 95%, 96%, 97%, or 98% or 99% identity to SEQ ID NO:2 or SEQ ID NO:6 and comprising at least one, two, three, four, five, six or more amino acid substitutions selected from said group above, wherein amino acid positions of the variant are numbered by correspondence with amino acid positions of the SEQ ID NO:2 sequence. Also included are compositions, including, but not limited to, e.g., cleaning compositions, comprising at least one such variant and methods for cleaning utilizing at least one such variant as described in greater detail elsewhere herein.

The following BPN'-v36 variants were determined to have a PI value equal to about 1.0 relative to BPN'-v36 in a BMI microswatch cleaning assay in Detergent Composition 4 at pH 8 and 16° C.: BPN'-S024G-S053G-S078N-S101N-G128A-Y217Q amino acid sequence (SEQ ID NO:6) comprising at least one amino acid substitution selected from the group consisting of BPN'-v36, A001G, A001Y, A013G, A013V, A015F, A015G, A015K, A015M, A015P, A015T, A015W, A015Y, A029G, A073S, A088C, A088I, A088L, A088T, A088V, A098D, A098K, A098P, A098R, A098W, A116D, A116E, A116R, A128S, A133L, A133M, A133S, A134G, A134S, A137N, A137V, A144M, A144Q, A144S, A144T, A144V, A151C, A176S, A176T, A179S, A216G, A216L, A216P, A216Q, A216S, A216T, A216Y, A228T, A230C, A231C, A272I, A272L, A272Q, A272S, A272T, A272W, A273S, A274G, A274L, A274Q, A274T, A274V, D041E, D099G, D099N, D120A, D120K, D120Q, D120R, D120S, D140E, D181S, D259E, E054D, E156D, E156T, E251V, F261G, F261H, F261L, F261R, F261S, F261T, F261V, F261W, G007A, G007S, G020A, G020D, G020S, G024N, G024R, G024S, G024T, G024V, G024W, G053H, G053K, G053N, G053T, G097A, G097D, G097T, G131A, G131H, G131P, G131Q, G131T, G131V, G160H, G160P, G166A, G166S, G166T, G211A, G211D, G211M, G211N, G211P, G211Q, G211R, G211W, G215A, G215N, G215V, H017L, H017M, H017T, H017V, H017Y, H039A, H039C, H039N, H226F, H226I, H226M, H226S, H226V, H226Y, I035V, I079A, I079S, I079T, I079V, I079W, I108V, I115L, I122A, I234L, I234V, K012R, K027R, K136R, K141F, K213W, K237R, K256R, K265Q, L016A, L016F, L016I, L016S, L016V, L042I, L075A, L075M, L075Q, L075V, L075Y, L082K, L082M, L082Q, L082V, L090I, L196I, L196V, L209Q, L209W, L233A, L233Q, L233V, L235I, L235K, L250I, L257A, L257H, L257Q, L257S, L257Y, L267Q, L267R, L267S, L267T, M199V, N025F, N025G, N025H, N025K, N025L, N025M, N025S, N025Y, N061F, N061H, N061P, N061S, N061T, N061V, N061W, N076G, N076W, N078S, N078T, N078V, N101A, N101H, N101L, N101T, N109K, N109R, N117A, N117E, N117H, N117K, N118G, N184G, N184H, N184I, N184S, N184V, N212A, N212F, N212I, N212K, N212P, N212Q, N212S, N212Y, N218A, N218H, N218L, N218S, N240E, N240H, N240L, N240R, N240T, N243A, N243Q, N243T, N243V, N252A, N252K, N252L, N252Q, N252R, N252S, N252T, N269Q, N269S, P014G, P014Q, P014T, P040A, P040H, P040S, P040T, P040V, P040Y, P086A, P086C, P086F, P086H, P086S, P129D, P129G, P129K, P129T, P172A, P172Q, P194A, P194G, P194L, P194M, P194S, P194V, P194Y, P210G, P210R, P210V, Q002A, Q002S, Q010A, Q010F, Q010H, Q010I, Q010L, Q010N, Q010S, Q010T, Q019A, Q019G, Q019N, Q019S, Q019T, Q019V, Q019W, Q059I, Q103L, Q103S, Q185A, Q185H, Q185L, Q185T, Q185Y, Q206P, Q206S, Q206Y, Q217I, Q217N, Q217S, Q217T, Q245K, Q275D, Q275S, Q275W, S003A, S003G, S003H, S003M, S003P, S003Q, S003T, S003V, S009I, S009L, S009P, S009T, S009W, S018A, S018G, S018I, S018L, S018M, S018N, S018P, S018V, S018W, S033T, S037Q, S037T, S037V, S038G, S038H, S038K, S038Q, S038T, S063K, S063N, S063Q, S063T, S087A, S087F, S087G, S087Q, S087T, S089L, S089M, S089N, S089Q, S089T, S089W, S130A, S130F, S130G, S130L, S130V, S145A, S145H, S145M, S145V, S159A, S159G, S159H, S159Q, S159R, S161A, S161G, S161H, S161L, S161M, S161P, S161Q, S161W, S162A, S162F, S162G, S162L, S162N, S162P, S162R, S162V, S163P, S173A, S173G, S182A, S182H, S182K, S182L, S182N, S182P, S182Q, S182T, S183A, S183G, S183H, S183Q, S188A, S188G, S188T, S188V, S191A, S204A, S204I, S204L, S204Q, S204V, S224C, S236A, S236N, S236Q, S248A, S248F, S248G, S248I, S248K, S248L, S248M, S248N, S248Q, S248T, S248V, S249A, S249C, S249H, S249Q, S249T, S249W, S249Y, S260H, S260N, S260P, S260T, T022H, T022K, T022N, T022R, T022S, T022Y, T055A, T055G, T055L, T055N, T055P, T055Q, T071S, T158H, T158S, T164N, T208C, T208L, T220S, T242N, T244A, T244G, T244H, T244I, T244Q, T244S, T244V, T244W, T253A, T253G, T253H, T253Q, T254V, T255A, T255G, T255H, T255I, T255Q, T255Y, V004G, V004N, V004R, V008A, V008C, V008M, V026I, V044I, V044L, V045H, V045K, V045L, V045M, V045Q, V045S, V045V, V045W, V045Y, V051I, V081L, V081Q, V081T, V084A, V084S, V084T, V093I, V121I, V143N, V143S, V143Y, V147C, V147I, V147L, V147T, V180I, V180L, V180T, V192A, V192S, V192T, V198I, V198L, V198M, V203H, V203I, V203L, V203N, V203Q, V203T, V203W, V203Y, V270A, V270S, V270T, W241M, W241Y, Y006G, Y006H, Y006I, Y006K, Y006L, Y006P, Y006Q, Y006T, Y006V, Y006W, Y021A, Y021D, Y021E, Y021L, Y021Q, Y021R, Y021S, Y104F, Y104I, Y214L, Y214V, Y214W, Y262A, Y262G, Y262L, Y262N, Y262S, Y262W, Y263G, and Y263W, wherein amino acid positions of the variant are numbered by correspondence with the sequence of SEQ ID NO:2. Thus, e.g., the invention includes BPN'-S024G-S053G-S078N-S101N-G128A-Y217Q amino acid sequence (SEQ ID NO:6) comprising substitution A128S, e.g., BPN'-S024G-S053G-S078N-S101N-G128S-Y217Q. Such variants have enhanced proteolytic activity compared to BPN' (SEQ ID NO:2) and a greater PI value than BPN' in this assay. The invention includes a protease variant having enhanced proteolytic activity compared to BPN' (SEQ ID NO:2), a PI value of about 1.0 relative to BPN'-v3, and/or a PI value of 1.0 relative to BPN'-v36 in this BMI microswatch cleaning assay, the variant comprising an amino acid sequence having at least 60%, 70%, 80%, 85%, 90%, 91%, 92%, 93%, 94%, 95%, 96%, 97%, or 98% or 99% identity to SEQ ID NO:2 or SEQ ID NO:6 and comprising at least one, two, three, four, five, six or more amino acid substitutions selected from said group above, wherein amino acid positions of the variant are numbered by correspondence with amino acid positions of the SEQ ID NO:2 sequence. Also included are compositions, including, but not limited to, e.g., cleaning compositions, comprising at least one such variant and methods for cleaning utilizing at least one such variant as described in greater detail elsewhere herein.

The following BPN'-v36 variants were determined using Test Method 3 to have a PI value equal to about 0.9 relative to BPN'-v36 in a BMI microswatch cleaning assay in Detergent Composition 4 at pH 8 and 16° C.: BPN'-S024G-S053G-S078N-S101N-G128A-Y217Q amino acid sequence (SEQ ID NO:6) comprising at least one amino acid substitution selected from the group consisting of A001F, A001K, A001L, A001M, A001Q, A001R, A001S, A001T, A001V, A013C, A013S, A015D, A015E, A015L, A015R, A048S, A073N, A073T, A074G, A074S, A085C, A085G, A085S, A085V, A088M, A088S, A092S, A098G, A114G, A133P, A137E, A137H, A144G, A144H, A144K, A144L, A144N, A153S, A153V, A176C, A179G, A187G, A187S, A200G, A216W, A223S, A228S, A230T, A230V, A231V, A232C, A232V, A272E, A272G, A272K, A272P, A273G, A273L, A273V, A274M, A274R, D036E, D099A, D099Q, D120E, D181A, D181G, D259A, D259G, D259Q, D259T, E156A, E156S, E251I, E251L, E251Q, E251T, F058Y, F261C, F261D, F261K, F261P, G020E, G020F, G020H, G020L, G020N, G020Q, G020R, G020T, G020Y, G024A, G024P, G053A, G053D, G053E, G053F, G053L, G053Q, G053S, G053Y, G097K, G097M, G157A, G157S, G160A, G160L, G166C, G166I, G166Q, G169A, G211K, G215H, G215L, G215S, G215T, G215W, G258S, H017I, H039S, H226L, H238N, H238Y, I011L, I011V, I031L, I079F, I079K, I079L, I079M, I079Q, I205A, I205V, I268L, I268M, K012G, K043F, K043H, K043I, K043N, K043Q, K043T, K141A, K141R, K141W, K170A, K213A, K213G, K213H, K213I, K213L, K213N, K213Q, K213R, K213S, K213T, K213V, K237A, K237H, K237I, K237L, K237N, K237S, K256A, K256G, K256H, K256M, K256P, K256Q, K256W, K265H, L016E, L042V, L075G, L075H, L075I, L075T, L082A, L082F, L082H, L082R, L082S, L082T, L090M, L135F, L196M, L209C, L209H, L209S, L233S, L235M, L235R, L235W, L257C, L257G, L267F, M050Y, M119C, M119I, M124L, N025C, N025E, N025P, N061A, N061G, N061I, N061K, N061L, N061Q, N061R, N062S, N062T, N076A, N076P, N076Q, N076S, N076T, N076V, N078G, N078H, N078K, N078P, N078Q, N078R, N101F, N117R, N117S, N118D, N118H, N118Q, N118R, N118S, N118T, N184C, N184E, N184R, N212D, N212R, N212W, N218F, N218G, N218M, N218P, N218T, N218V, N218W, N240A, N240G, N240Q, N240S, N240W, N243C, N243G, N243S, N252V, N269H, P005A, P005D, P005M, P005Q, P014A, P014M, P014R, P014V, P040F, P040R, P040W, P129E, P129R, P172E, P172K, P194H, P194R, P194W, P201A, P201G, P210L, P239K, P239R, Q002D, Q002E, Q002G, Q002I, Q002P, Q002V, Q010D, Q010R, Q019C, Q019D, Q019E, Q019H, Q019L, Q019P, Q019R, Q059A, Q059E, Q059L, Q059S, Q059T, Q103W, Q185D, Q185K, Q185R, Q185W, Q206G, Q206H, Q206L, Q206V, Q206W, Q217E, Q217F, Q217H, Q217L, Q217V, Q245M, Q271A, Q271D, Q271G, Q271L, Q271P, Q271T, Q271Y, Q275F, Q275L, Q275P, Q275R, S003D, S003F, S003K, S003R, S009K, S018D, S018R, S037A, S037G, S037K, S037L, S037P, S038M, S063A, S063F, S063G, S063M, S063R, S063Y, S087C, S087K, S087L, S087M, S087N, S087Y, S089A, S089D, S089F, S089G, S089H, S089I, S089K, S089R, S089V, S089Y, S130D, S130E, S130K, S130W, S145G, S145L, S145R, S145T, S159D, S159L, S159W, S161E, S161R, S162C, S162E, S162W, S163A, S182E, S182R, S183C, S183D, S183P, S183R, S188D, S188P, S204G, S204Y, S207G, S224G, S224T, S236C, S236G, S248D, S248H, S248R, S249E, S249L, S249R, S260A, S260G, S260K, S260Q, S260V, S260Y, T022L, T055D, T055E, T055I, T055K, T055M, T055S, T055V, T055Y, T158A, T158G, T158L, T158Q, T158V, T164K, T164Q, T208S, T244D, T244E, T244R, T253E, T253R, T253Y, T254G, T255D, T255E, T255K, T255R, V026A, V028I, V028L, V030I, V044C, V044P, V045E, V045G, V045N, V072L, V081A, V081G, V081H, V081S, V084I, V084M, V095A, V095C, V143A, V143F, V143H, V143Q, V143T, V143W, V147A, V147Q, V147S, V148I, V148L, V149C, V149I, V149L, V165L, V180A, V180C, V180M, V192C, V192F, V192I, V192Q, V192Y, V203A, V203G, V203K, V203S, V270C, V270L, V270P, W241F, Y006A, Y006M, Y006N, Y006R, Y006S, Y021C, Y091W, Y104V, Y104W, Y262C, Y262D, Y262E, Y262H, Y262I, Y262R, and Y262V, wherein amino acid positions of the variant are numbered by correspondence with the sequence of SEQ ID NO:2. Such variants may have enhanced proteolytic activity compared to BPN' (SEQ ID NO:2) and/or a greater PI value than BPN' in this assay. The invention includes a protease variant having proteolytic activity and/or a PI value of 0.9 relative to BPN'-v36 in this BMI microswatch cleaning assay, the variant comprising an amino acid sequence having at least 60%, 70%, 80%, 85%, 90%, 91%, 92%, 93%, 94%, 95%, 96%, 97%, or 98% or 99% identity to SEQ ID NO:2 or SEQ ID NO:6 and comprising at least one, two, three, four, five, six or more amino acid substitutions selected from said group above, wherein amino acid positions of the variant are numbered by correspondence with amino acid positions of the SEQ ID NO:2 sequence. Also included are compositions, including, but not limited to, e.g., cleaning compositions, comprising at least one such variant and methods for cleaning utilizing at least one such variant as described in greater detail elsewhere herein.

The following BPN'-v36 variants were determined to have a PI value equal to or greater than 0.5 and less than 0.9 relative to BPN'-v36 in the BMI microswatch cleaning assay of Test Method 3 in Detergent Composition 4 at pH 8 and 16° C.: BPN'-S24G-S53G-S78N-S101N-G128A-Y217Q amino acid sequence (SEQ ID NO:6) comprising at least one amino acid substitution selected from the group consisting of A001D, A001H, A001N, A015C, A048C, A048E, A085T, A133R, A137R, A142C, A144D, A144R, A152S, A153G, A187P, A187Q, A187T, A187V, A216R, A230S, A272R, A273H, A273T, A274H, D036N, D036S, D181H, D181T, D259N, D259P, D259S, E156G, E156H, E156L, E156Q, E156V, E251C, F189S, F189T, F189W, F189Y, F261E, G020C, G024D, G053M, G053R, G097R, G131D, G131R, G157N, G160R, G160V, G166L, G166W, G211E, G215D, G258A, G258D, G258P, I011T, I031C, I079E, I079R, I175L, I205C, K012H, K102N, K027A, K027N, K027S, K043A, K043D, K043E, K043G, K043L, K043M, K043P, K043V, K043W, K043Y, K136H, K141H, K141L, K141M, K141N, K141Q, K141T, K141V, K170G, K170S, K237T, K237V, K256D, K256S, K256T, K256V, K265N, K265S, L042F, L042M, L082E, L209A, L209E, L209G, L209R, L233G, L235V, L257D, L257E, L257P, L257R, L257W, L267E, M050L, N056D, N056S, N061C, N061D, N062A, N062H, N062L, N062V, N062Y, N076D, N076L, N076M, N078D, N078F, N101D, N101R, N118A, N212C, N212E, N218C, N218D, N218E, N252D, N252E, P014F, P014K, P057A, P057W, P172R, P194E, P201T, P210E, Q059C, Q059D, Q059R, Q185E, Q206D, Q217A, Q217K, Q217R, Q245A, Q245D, Q245E, Q245H, Q245R, Q271E, Q271F, Q271R, Q271W, Q275G, Q275I, R186I, R186L, R186V, R186W, S003E, S009C, S009E, S018C, S037D, S037E, S037H, S037R, S037Y, S038D, S038P, S038R, S038Y, S063L, S087D, S087R, S089C, S089E, S130C, S130R, S145D, S159C, S159P, S161C, S173T, S182C, S188E, S188F, S188K, S188L, S188R, S188W, S190A, S190G, S190T, S204R, S236D, S236E, S248C, S248E, S260C, S260E, S260R, T022P, T055C, T055W, T071A, T158D, T158E, T158P, T158R, T159Y, T164R, T242D, T242G, T255C, V004E, V004T, V045C, V045D, V045R, V045T, V051H, V081R, V143C, V143E, V143G, V192G, V203C, V203D, V203E, V203M, V203R, V270G, W241L, Y214H, Y214Q, A001E, A133E, A187L, A187N, A216C, A216H, A273Q, D099H, D259H, E156C, E195G, F189H, G131C, G146A, G166V, G215C, G215E, I107L, K012A, K012S, K012T, K043C, K170C, K256C, K256E, K265G, K265Y, L233E, M222F, M222S, N062Q, N076E, N078E, N184P, N218R, P005V, P014D, Q002K, Q002L, Q002R, Q010W, Q271C, R186H, S049C, S063C, S063D, S105T, S188C, S190C, S204E, T055R, T164G, V004D, V044T, V045I, V165C, V180S, Y006C, Y006D, Y006E, Y104T, A001C, A187C, A230G, A273D, A273P, D036Q, F189G, F189L, F189R, G157T, G178A, I031F, I111M, K012F, K012L, K027T, K043R, K136G, K141G, K170Q, M222A, M222L, N062R, N117G, N269C, P005W, P129V, P239A, P239H, P239T, Q059W, Q217G, Q275A, R186A, S191G, T164A, T220A, A001P, A187F, A187W, A273R, D041C, D060G, D197T, F189A, G046D, G157P, K012C, K012E, K012W, L042C, M222T, N062C, P239G, P239N, Q217C, R186M, S049T, S089P, S125A, S173V, and V044A, wherein amino acid positions of the variant are numbered by correspondence with amino acid positions of the SEQ ID NO:2 sequence. Such variants have proteolytic activity. The invention includes a protease variant having proteolytic activity and/or a PI value equal to or greater than 0.5 and less than 0.9 relative to BPN'-v36 in this BMI microswatch cleaning assay (Test Method 3), the variant comprising an amino acid sequence having at least 60%, 70%, 80%, 85%, 90%, 91%, 92%, 93%, 94%, 95%, 96%, 97%, or 98% or 99% identity to SEQ ID NO:2 or SEQ ID NO:6 and comprising at least one, two, three, four, five, six or more amino acid substitutions selected from said group above, wherein amino acid positions of the variant are numbered by correspondence with amino acid positions of the SEQ ID NO:2 sequence. Also included are compositions, including, but not limited to, e.g., cleaning compositions, comprising at least one such variant and methods for cleaning utilizing at least one such variant as described in greater detail elsewhere herein.

The following BPN'-v36 variants were determined to have a PI value greater than 1.0, at least 1:1, at least 1.2, at least 1.3, at least 1.4, at least 1.5, at least 1.6, at least 1.7, at least 1.8, at least 1.9, at least 2, from greater than 1.0 to about 10, from greater than 1.0 to about 8, or from greater than 1.0 to about 5 relative to BPN'-v36 in an egg microswatch cleaning assay in Detergent Composition 4 at 16° C. and pH 8: BPN'-S024G-S053G-S078N-S101N-G128A-Y217Q amino acid sequence (SEQ ID NO:6) comprising at least one amino acid substitution selected from the group consisting of A216E, L090I, A098R, A098W, A098Y, A116G, A116R, A116S, A133M, I107L, I115V, M124L, N101I, N109H, N109S, N109T, N117R, P005G, Q185L, S089V, V095A, A015Y, A029G, A098D, A098E, A098G, A098N, A098S, A098T, A098V, A114S, A114T, A116E, A116L, A116T, A116V, A133H, A133L, A133S, A137G, A137I, A137L, A137S, A137V, A138S, A144S, A144V, A176S, A176T, A187T, A216F, A216P, A216Q, A216R, A216S, A216T, A216V, A216Y, D041E, D120A, D120E, D120Q, D120R, D120S, D181S, G020A, G020S, G024A, G097A, G097D, G097S, G131Q, G160S, G0166I, G211L, G215N, H039N, H238N, I111L, I111V, I122A, L075I, L075Q, L135M, L209T, L209V, L233V, L235M, L235R; L257A, M119I, N025A, N025G, N025T, N061K, N101F, N101H, N101L, N101Q, N101R, N101S, N101T, N109A, N109G, N109K, N109L, N117E, N117H, N117K, N117S, N212G, N212S, N218F, N218G, N218H, N218L, N218S, N218W, N240Q, N252M, N252R, N252S, P005T, P040A, P040G, P040T, P129D, P129S, P194S, P210R, Q019R, Q019W, Q103L, Q103W, Q185A, Q185G, Q185M, Q185R, Q185T, Q206G, Q206Y, Q217A, Q217E, Q217R, Q217S, Q217T, S003Q, S009H, S018M, S033T, S130A, S130F, S130G, S130T, S130V, S145T, S159A, S161N, S161T, S162V, S162Y, S182L, S182W, S183F, S183L, S183V, S183W, S188K, S188W, S236Q, S236T, S248L, T022H, T022K, T208C, T253H, T255V, V044I, V121I, V139C, V143H, V143Q, V143T, V143W, V143Y, Y006K, Y021A, Y104W, A001F, A001G, A001H, A001K, A001L, A001Q, A001S, A001Y, A013V, A015G, A015K, A015R, A015S, A015T, A015W, A048S, A073N, A073S, A092S, A098K, A098P, A116D, A116W, A128S, A133P, A133T, A133V, A134G, A134S, A137H, A137N, A137T, A144D, A144K, A144L, A144M, A144N, A144R, A179G, A179S, A187V, A216G, A216L, A216W, A223S, A230C, A272K, A272L, A272P, A272S, A272T, A272W, A273G, A273S, A274G, A274M, A274T, D120K, D140E, D181A, D181E, D181G, D181H, D181T, D259E, D259N, D259Q, E054D, E156D, E156T, E251L, E251T, E251V, F058Y, F189W, F261K, F261Q, F261R, G007A, G007S, G020F, G020H, G020N, G020Q, G020T, G020Y, G024F, G024Q, G024R, G024T, G024V, G024W, G024Y, G053T, G097K, G097M, G097R, G097T, G131A, G131H, G131P, G131R, G131T, G131V, G160H, G160T, G166C, G166Q, G166S, G166T, G211A, G211D, G211K, G211M, G211N, G211Q, G211R, G211V, G211W, G215S, G215T, G215W, H017T, H017W, H017Y, H039V, H226A, H226F, H226I, H226L, H226M, H226V, I035V, I079A, I079S, I108V, I205V, I234L, I234V, I268V, K012S, K043P, K136H, K136R, K141A, K141F, K141T, K141W, K170A, K170G, K170R, K213A, K213R, K213S, K237A, K237H, K237L, K237S, K237V, K256A, K256G, K256H, K256M, K256P, K256Q, K256R, L016A, L016Q, L016T, L016V, L042V, L075M, L075T, L082M, L082V, L135F, L196I, L209H, L209Q, L209R, L209S, L209W, L233A, L233M, L233Q, L235I, L235K, L250I, L257S, L257T, L257V, L267A, L267Q, L267T, L267V, M119C, M199V, N025C, N025E, N025F, N025I, N025K, N025L, N025M, N025Q, N025V, N025Y, N061F, N061P, N061S, N061T, N076G, N078S, N101A, N109M, N109Q, N109R, N117A, N117M, N117Q, N118D, N118G, N118H, N118Q, N118R, N118S, N184A, N184C, N184G, N184L, N184R, N184S, N184T, N184V, N184W, N212C, N212F, N212I, N212K, N212L, N212P, N212Q, N212R, N212V, N212W, N212Y, N218A, N218P, N218T, N240A, N240E, N240G, N240H, N240L, N240R, N240S, N240T, N243C, N243Q, N243T, N243V, N252A, N252G, N252K, N252Q, P014G, P014Q, P014R, P014S, P014T, P040F, P040L, P040Q, P040S, P040V, P086C, P086H, P086S, P129A, P129E, P129G, P129K, P129R, P172A, P172K, P172Q, P172S, P194A, P194G, P194H, P194L, P194M, P194Q, P194R, P194V, P194W, P194Y, P210A, P210G, P210L, P210S, P239K, P239R, Q002A, Q002S, Q010A, Q010N, Q010R, Q010T, Q019A, Q019C, Q019D, Q019G, Q019S, Q019T, Q019V, Q059I, Q059V, Q103S, Q185F, Q185H, Q185I, Q185K, Q185N, Q185S, Q185Y, Q206H, Q206L, Q206P, Q206W, Q217F, Q217H, Q217I, Q217K, Q217L, Q217N, Q217V, Q271G, Q271R, Q271T, Q275F, Q275P, Q275R, R186A, R186I, R186K, S003A, S003F, S003G, S003H, S003K, S003R, S003T, S009T, S018N, S018T, S037G, S037T, S037V, S038G, S038Q, S063N, S063Q, S063T, S089M, S089N, S130K, S130L, S130R, S130W, S132N, S145G, S145K, S145M, S145R, S145V, S159C, S159H, S159L, S159Q, S159R, S159T, S159W, S161A, S161C, S161G, S161H, S161I, S161K, S161P, S161Q, S161R, S162F, S162G, S162I, S162L, S162M, S162N, S162P, S162R, S163G, S173A, S173G, S182F, S182G, S182K, S182N, S182Q, S182V, S183A, S183M, S183Q, S183R, S183T, S188A, S188F, S188G, S188P, S188R, S188T, S188V, S190C, S204A, S204G, S204I, S204L, S204Q, S204R, S204V, S207G, S224A, S224T, S236C, S236D, S236E, S236G, S236N, S248A, S248F, S248K, S248M, S248T, S249A, S249R, S249T, S249V, S249W, S249Y, S260G, S260H, S260K, S260N, T022A, T022G, T022Q, T022S, T022V, T022Y, T055A, T055K, T158A, T158S, T208L, T208S, T208V, T220S, T242D, T242N, T242S, T244E, T244G, T244I, T244R, T244V, T244W, T253A, T253G, T253N, T253S, T254S, T254V, T255H, T255I, T255K, T255L, T255Q, T255R, T255S, T255Y, V004A, V004N, V004P, V004W, V008A, V008M, V026I, V045S, V045W, V051I, V081Q, V081T, V084C, V093I, V095C, V143A, V143E, V143F, V143N, V143S, V147I, V147L, V147S, V147T, V148I, V149C, V149I, V165M, V180A, V180C, V180I, V180L, V180T, V192A, V192C, V192I, V192S, V192T, V192Y, V198L, V203A, V203F, V203K, V203L, V203M, V203N, V203Y, W241Y, Y006A, Y006G, Y006H, Y006L, Y006N, Y006P, Y006Q, Y006T, Y021E, Y021K, Y021L, Y021N, Y021Q, Y021R, Y021S, Y021T, Y104F, Y104I, Y104V, Y171F, Y214F, Y214L, Y214W, Y262F, and Y262S, wherein amino acid positions of the variant are numbered by correspondence with the sequence of SEQ ID NO:2. Such variants have enhanced proteolytic activity compared to BPN' (SEQ ID NO:2) and a greater PI value than BPN' in this assay. The invention includes a protease variant having enhanced proteolytic activity compared to BPN' (SEQ ID NO:2), enhanced proteolytic activity compared to BPN'-v3 and BPN'-v36, a PI value greater than that of BPN'-v3, and/or a PI value of greater than 1.0 to about 5 relative to BPN'-v36 in this egg microswatch cleaning assay, the variant comprising an amino acid sequence having at least 60%, 70%, 80%, 85%, 90%, 91%, 92%, 93%, 94%, 95%, 96%, 97%, or 98% or 99% identity to SEQ ID NO:2 or SEQ ID NO:6 and comprising at least one, two, three, four, five, six or more amino acid substitutions selected from said group above, wherein amino acid positions of the variant are numbered by correspondence with amino acid positions of the SEQ ID NO:2 sequence. Also included are compositions, including, but not limited to, e.g., cleaning compositions, comprising at least one such variant and methods for cleaning utilizing at least one such variant as described in greater detail elsewhere herein.

The following BPN'-v36 variants were determined to have a PI value equal to about 1.0 relative to BPN'-v36 in an egg microswatch cleaning assay in Detergent Composition 4 at pH 8 and 16° C.: BPN'-S024G-S053G-S078N-S101N-G128A-Y217Q amino acid sequence (SEQ ID NO:6) comprising at least one amino acid substitution selected from the group consisting of BPN'-v36, A001D, A001M, A001N, A001R, A001T, A001V, A013C, A013G, A013S, A015D, A015F, A015L, A015M, A015P, A015Q, A074G, A074S, A085S, A085T, A085V, A088C, A088L, A088S, A088T, A088V, A133E, A133G, A133R, A137E, A144G, A144H, A144Q, A144T, A151C, A152S, A153G, A153S, A153V, A176C, A187G, A187Q, A187S, A200G, A228S, A228T, A230T, A230V, A231C, A231V, A232C, A232V, A272E, A272G, A272I, A272Q, A272R, A273L, A273V, A274L, A274Q, A274R, A274V, D036E, D259A, D259G, D259P, D259S, D259T, E156A, E156S, E156V, E195G, E251C, E251I, E251Q, F189Y, F261A, F261G, F261H, F261L, F261P, F261S, F261T, F261V, F261W, G020C, G020D, G020E, G020L, G020R, G024D, G024I, G024N, G024P, G024S, G053A, G053D, G053F, G053H, G053K, G053N, G053S, G053Y, G157A, G157S, G160A, G160L, G160P, G160R, G166A, G166L, G166V, G166W, G169A, G211E, G211P, G215A, G215D, G215E, G215H, G215V, G258D, G258S, H017F, H017I, H017L, H017M, H017V, H039C, H226S, H226Y, I011T, V, I031C, I031L, I031V, I079F, I079K, I079L, I079M, I079Q, I079R, I079T, I079V, I079W, I115L, I205A, I205C, I268L, K012R, K012T, K027R, K043A, K043E, K043F, K043H, K043I, K043M, K043N, K043Q, K043T, K043V, K043Y, K141H, K141Q, K141V, K170S, K213G, K213H, K213I, K213L, K213N, K213Q, K213T, K213W, K237I, K237N, K237R, K237T, K256C, K256E, K256S, K256T, K256V, K256W, K265H, K265R, L016E, L016F, L016I, L016S, L042I, L042M, L075A, L075H, L075Y, L082K, L082Q, L082T, L196M, L196V, L209A, L209C, L209E, L209G, L235W, L257C, L257H, L257Q, L257Y, L267E, L267F, L267R, L267S, M050Y, N025H, N025P, N025S, N056D, N061A, N061C, N061D, N061G, N061H, N061I, N061L, N061Q, N061R, N061V, N061W, N062A, N062S, N062V, N076A, N076E, N076L, N076M, N076Q, N076S, N076T, N076W, N078G, N078H, N078K, N078P, N078Q, N078T, N101D, N118A, N118T, N184E, N184H, N184I, N212A, N212D, N212E, N218C, N218D, N218E, N218M, N218R, N218V, N240W, N243A, N243G, N243P, N243S, N252D, N252E, N252L, N252T, N252V, N269S, P005A, P005D, P005M, P005Q, P014A, P014D, P014F, P014M, P014V, P040H, P040R, P040W, P040Y, P086A, P129T, P172E, P172G, P172R, P194E, P201A, P201G, P210E, P210V, Q002E, Q002G, Q010D, Q010F, Q010H, Q010I, Q010L, Q010S, Q019E, Q019H, Q019N, Q059A, Q059L, Q059R, Q059S, Q059T, Q185D, Q185E, Q206D, Q206S, Q206V, Q217G, Q245D, Q245E, Q245K, Q245M, Q245R, Q271A, Q271F, Q271P, Q271Y, Q275D, Q275H, Q275I, Q275L, Q275S, Q275W, R186H, R186L, R186V, R186W, S003D, S003E, S003M, S003P, S003V, S009A, S009E, S009G, S009I, S009K, S009M, S009P, S009W, S018A, S018G, S018I, S018L, S018P, S018R, S018V, S018W, S037A, S037D, S037Q, S037R, S037Y, S038D, S038H, S038K, S038M, S038R, S038T, S063A, S063G, S063K, S063M, S063R, S087A, S087D, S087F, S087G, S087Q, S087T, S089A, S089C, S089H, S089I, S089K, S089L, S089Q, S089R, S089T, S089Y, S130D, S130E, S145A, S145H, S145L, S159G, S161E, S161L, S161M, S161W, S162A, S162C, S162E, S162W, S163P, S173T, S182A, S182C, S182E, S182H, S182R, S182T, S183C, S183D, S183G, S183H, S188C, S188D, S188E, S188L, S190T, S191A, S204Y, S224C, S236A, S248C, S248D, S248G, S248I, S248N, S248Q, S248R, S248V, S249C, S249H, S249L, S249Q, S260A, S260C, S260E, S260P, S260Q, S260R, S260T, T022L, T022N, T022R, T055C, T055D, T055G, T055I, T055L, T055N, T055Q, T055S, T055V, T055Y, T071A, T071S, T158G, T158H, T158L, T158P, T158Q, T158R, T158V, T158Y, T164N, T164S, T244A, T244D, T244H, T244Q, T244S, T253Q, T253R, T253Y, T254A, T254G, T255A, T255D, T255E, V004E, V004G, V004R, V008C, V026A, V028L, V030I, V044C, V045D, V045E, V045H, V045M, V045Q, V045Y, V072L, V081L, V081S, V084A, V084I, V084M, V084T, V143C, V147C, V147Q, V149L, V165L, V180M, V192F, V192G, V192Q, V198I, V198M, V203C, V203E, V203H, V203I, V203Q, V203R, V203T, V203W, V270A, V270L, V270T, W241F, W241M, Y006C, Y006D, Y006E, Y006I, Y006M, Y006R, Y006S, Y006V, Y006W, Y021C, Y021D, Y021V, Y091W, Y167F, Y214V, Y262A, Y262C, Y262I, Y262M, Y262R, Y262T, Y262V, and Y262W, wherein amino acid positions of the variant are numbered by correspondence with the sequence of SEQ ID NO:2. Such variants have enhanced proteolytic activity compared to BPN' (SEQ ID NO:2) and a greater PI value than BPN' in this assay. The invention includes a protease variant having enhanced proteolytic activity compared to BPN' (SEQ ID NO:2), a PI value of about 1.0 relative to BPN'-v3, and/or a PI value of 1.0 relative to BPN'-v36 in this egg microswatch cleaning assay, the variant comprising an amino acid sequence having at least 60%, 70%, 80%, 85%, 90%, 91%, 92%, 93%, 94%, 95%, 96%, 97%, or 98% or 99% identity to SEQ ID NO:2 or SEQ ID NO:6 and comprising at least one, two, three, four, five, six or more amino acid substitutions selected from said group above, wherein amino acid positions of the variant are numbered by correspondence with amino acid positions of the SEQ ID NO:2 sequence. Also included are compositions, including, but not limited to, e.g., cleaning compositions, comprising at least one such variant and methods for cleaning utilizing at least one such variant as described in greater detail elsewhere herein. The following BPN'-v36 variants were determined to have a PI value equal to about 0.9 relative to BPN'-v36 in an egg microswatch cleaning assay in Detergent Composition 4 at pH 8 and 16° C.: BPN'-S024G-S053G-S078N-S101N-G128A-Y217Q amino acid sequence (SEQ ID NO:6) comprising at least one amino acid substitution selected from the group consisting of A001E, A015C, A015E, A048C, A048E, A073T, A085C, A085G, A088I, A088M, A114G, A137R, A187L, A187N, A187P, A187W, A216C, A230S, A273D, A273H, A273T, D036N, D099N, D259H, E156C, E156G, E156H, E156Q, F189H, F189R, F189S, F189T, F261C, F261D, F261E, G053E, G053M, G053Q, G131C, G131D, G157N, G160V, G215C, G215L, G258A, H039A, I011L, I079E, I268M, K012A, K012G, K012H, K012N, K027N, K043C, K043D, K043G, K043L, K043W, K136G, K141G, K141L, K141M, K141N, K141R, K170C, K170Q, K213V, K256D, K265G, K265N, K265Q, K265S, L082A, L082F, L082H, L082R, L082S, L090M, L233S, L235V, L257E, L257G, L257R, L257W, M222S, N025R, N062H, N062T, N076D, N076P, N078D, N078E, N078F, N078R, N078V, N269H, N269Q, P014K, P057A, P086F, P201T, Q002D, Q002I, Q002P, Q002V, Q019L, Q019P, Q059C, Q059D, Q059E, Q185W, Q271C, Q271D, Q271E, Q271L, Q271W, Q275G, R186M, S009C, S009L, S018D, S037E, S037H, S037K, S037L, S037P, S038P, S063C, S063D, S063F, S063L, S063Y, S087L, S087N, S087R, S087Y, S089D, S089F, S089G, S089W, S105T, S125A, S130C, S159D, S159P, S163A, S182P, S183P, S190A, S190G, S204E, S224G, S248E, S248H, S249E, S260V, S260Y, T055M, T055R, T055W, T158D, T158E, T164G, T164K, T164Q, T220A, T242G, T253E, T255C, T255G, V004D, V044L, V044P, V045C, V045G, V045L, V045N, V045R, V045V, V081A, V081G, V081H, V084S, V147A, V203D, V203G, V270C, V270P, V270S, W241L, Y104T, Y214Q, Y262D, Y262E, Y262G, Y262H, Y262L, Y262N, Y263G, and Y263W, wherein amino acid positions of the variant are numbered by correspondence with the sequence of SEQ ID NO:2. Such variants have proteolytic activity. The invention includes a protease variant having enhanced proteolytic activity compared to BPN' (SEQ ID NO:2), and/or a PI value of 0.9 relative to BPN'-v36 in this egg microswatch cleaning assay, the variant comprising an amino acid sequence having at least 60%, 70%, 80%, 85%, 90%, 91%, 92%, 93%, 94%, 95%, 96%, 97%, or 98% or 99% identity to SEQ ID NO:2 or SEQ ID NO:6 and comprising at least one, two, three, four, five, six or more amino acid substitutions selected from said group above, wherein amino acid positions of the variant are numbered by correspondence with amino acid positions of the SEQ ID NO:2 sequence. Also included are compositions, including, but not limited to, e.g., cleaning compositions, comprising at least one such variant and methods for cleaning utilizing at least one such variant as described in greater detail elsewhere herein.

The following BPN'-v36 variants were determined to have a PI value equal to or greater than 0.5 and less than 0.9 relative to BPN'-v36 in an egg microswatch cleaning assay in Detergent Composition 4 at pH 8 and 16° C.: BPN'-S024G-S053G-S078N-S101N-G128A-Y217Q amino acid sequence (SEQ ID NO:6) comprising at least one amino acid substitution selected from the group consisting of A001C, A142C, A187C, A216H, A273Q, A274H, D036Q, D036S, D099S, D197T, E156L, F189A, F189L, G053L, G053R, G157P, G178A, G258P, H039S, H238Y, K012C, K012E, K012L, K012W, K136E, K265Y, L075G, L075V, L082E, L126W, L257D, L257P, M050L, M222A, M222F, M222L, N056S, N062C, N062L, N062Y, N269C, P057W, Q002K, Q002L, Q217C, Q245A, Q245H, S018C, S038Y, S049C, S087C, S087K, S145D, S191G, T022P, T055E, T164A, T164R, V045K, V051H, V081R, V143G, V148L, V180S, V203S, V270G, Y214H, A187F, A273P, F189G, G046D, G146A, G157T, I031F, I175L, K012F, K027T, L042F, L233E, L233G, M222T, N062R, N184P, P005V, P005W, P129V, P239N, P239T, Q010W, Q059W, Q275A, V004T, V165C, A128H, A230G, D041C, H067T, K027S, K043R, L090T, N062Q, N117G, P225G, P225S, P239G, P239H, Q002R, S089E, V044A, V045I, A001P, A273R, D041N, D099A, D099H, D099Q, F058G, I111M, L042C, N118L, P239A, S049N, S089P, S173V, T242P, V044T, and V045T, wherein amino acid positions of the variant are numbered by correspondence with the sequence of SEQ ID NO:2. Such variants have proteolytic activity. The invention includes a protease variant having proteolytic activity and/or a PI value of equal to or greater than 0.5 and less than 0.9 relative to BPN'-v36 in this egg microswatch cleaning assay, the variant comprising an amino acid sequence having at least 60%, 70%, 80%, 85%, 90%, 91%, 92%, 93%, 94%, 95%, 96%, 97%, or 98% or 99% identity to SEQ ID NO:2 or SEQ ID NO:6 and comprising at least one, two, three, four, five, six or more amino acid substitutions selected from said group above, wherein amino acid positions of the variant are numbered by correspondence with amino acid positions of the SEQ ID NO:2 sequence. Also included are compositions, including, but not limited to, e.g., cleaning compositions, comprising at least one such variant and methods for cleaning utilizing at least one such variant as described in greater detail elsewhere herein.

Example 8

Cleaning Performance of Additional Combinatorial Variants Based on BPN'-v36 Parent Additional combinatorial variants based on parent BPN'-v36 (BPN'-S24G-S53G-S78N-S101N-G128A-Y217Q) were made and provided by DNA 2.0. These variants were tested for their cleaning performance using BMI microswatch assay in Detergent Composition 4 at 16° C. and pH 8, BMI microswatch assay in Detergent Composition 4 at 16° C. and pH 7, Egg microswatch assay in Detergent Composition 4 at 16° C. and pH 8, and Grass microswatch assay in Detergent Composition 4 at 16° C. and pH 8. Protein content was determined using TCA assay and protease activity was assayed using AAPF assay. All assays were performed as described in Example 1 and the Performance Indices were calculated relative to BPN'-v36.

The following BPN'-v36 variants were determined to have a PI value greater than 1.0, at least 1.1, at least 1.2, at least 1.3, at least 1.4, at least 1.5, at least 1.6, at least 1.7, at least 1.8, at least 1.9, at least 2, from greater than 1.0 to about 10, from greater than 1.0 to about 8, or from greater than 1.0 to about 5 relative to BPN'-v36 in a BMI microswatch cleaning assay in Detergent Composition 4 at pH 8 and 16° C.: BPN'-S024G-S053G-S078N-S101N-G128A-Y217Q amino acid sequence (SEQ ID NO:6) comprising at least one set of amino acid substitutions selected from the group consisting of A088T-L257G, A116T-A128S, N061S-N109G-A128S-N243V-S260P, S009T-N109G-A128S-K141R-N243V, S009T-S018T-Y021N-N109G-A128S-K141R, and S162G-K256R, wherein amino acid positions of the variant are numbered by correspondence with the sequence of SEQ ID NO:2. Such variants have enhanced proteolytic activity compared to BPN', BPN'-v3, and BPN'-v36, and a greater PI value than BPN', BPN'-v3 and BPN'-v36 in this assay. The invention includes a protease variant having enhanced proteolytic activity compared to BPN', BPN'-v3, and BPN'-v36, a PI value of greater than 1.0 to about 5 relative to BPN'-v3, and/or a PI value of greater than 1.0 to about 5 relative to BPN'-v36 in this BMI microswatch cleaning assay, the variant comprising an amino acid sequence having at least 60%, 70%, 80%, 85%, 90%, 91%, 92%, 93%, 94%, 95%, 96%, 97%, or 98% or 99% identity to SEQ ID NO:2 or SEQ ID NO:6 and comprising at least one set of amino acid substitutions selected from said group above, wherein amino acid positions of the variant are numbered by correspondence with amino acid positions of the SEQ ID NO:2 sequence.

The following BPN'-v36 variants were determined to have a PI value equal to about 1.0 relative to BPN'-v36 in a BMI microswatch cleaning assay in Detergent Composition 4 at pH 8 and 16° C.: BPN'-S024G-S053G-S078N-S101N-G128A-Y217Q amino acid sequence (SEQ ID NO:6) comprising at least one set of amino acid substitutions selected from the group consisting of BPN'-v36, A088T, A088T-A116T, A088T-G131H, A088T-K256R, A088T-N109G, A088T-N243V, A088T-Q103H, A088T-S162G, A088T-S248N, A088T-S249A, A088T-T158S, A116T, A116T-G131H, A116T-K256R, A116T-L257G, A116T-N243V, A116T-S162G, A116T-S248N, A116T-S249A, A116T-T158S, A128S-K256R, A128S-L257G, A128S-N243V-S248N-K256R, A128S-S162G, A128S-S248N, A128S-S249A, A128S-T158S, G024E-A116T, G024E-K256R, G024E-L257G, G024E-N109G, G024E-N243V, G024E-T158S, G131H, G131H-K256R, G131H-L257G, G131H-N243V-K256R, G131H-S162G, G131H-S248N, G131H-S249A, G131H-T158S, K043Y-A088T, K043Y-K256R, K043Y-N243V, K256R, K256R-L257G, L257G, N061G-N109G-N243V, N061P-N109G-G131H-N243V, N061P-N109G-N243V, N061S-A128S-N243V-S260P, N061S-N109G-A128S-N243V-S248N-K256R-S260P, N061S-N109G-A128S-S260P, N061S-N109G-N243V, N076D-K256R, N076D-L257G, N076D-N109G, N076D-T158S, N109A-A128S-N243V-K256R, N109G, N109G-A116T, N109G-A128S, N109G-A128S-G131H-N243V-S248N-K256R, N109G-A128S-N243V-K256R, N109G-A128S-N243V-S248A, N109G-A128S-N243V-S248A-K256R, N109G-A128S-N243V-S248N, N109G-A128S-N243V-S248N-K256R, N109G-A128S-N243V-S248N-K256R-L257G, N109G-A128S-S162G-N243V-S248N-K256R, N109G-A128S-S248N-K256R, N109G-A128S-T158S-N243V-S248N-K256R, N109G-G131H, N109G-K256R, N109G-L257G, N109G-N218S, N109G-N243P-S248A-K256R, N109G-N243P-S248N-K256R, N109G-N243V, N109G-N243V-K256R, N109G-N243V-S248A-K256R, N109G-N243V-S248N, N109G-N243V-S248N-K256R, N109G-S162G, N109G-S248N-K256R, N109G-S249A, N109G-T158S, N109Q-A128S-N243V-K256R, N109S-A128S-N243V-K256R, N218S-N243V, N243V, N243V-K256R, N243V-L257G, N243V-S248N, N243V-S248N-K256R, N243V-S249A, P040A-N109G-A128S-N243V-S248N-K256R, Q103H-A116T, Q103H-A128S, Q103H-G131H, Q103H-K256R, Q103H-L257G, Q103H-N109G, Q103H-N218S, Q103H-N243V, Q103H-S162G, Q103H-S248N, Q103H-S249A, Q103H-T158S, S009T-A128S-K141R-N243V, S009T-N109G-A128S-K141R, S009T-N109G-A128S-K141R-N243V-S248N-K256R, S009T-S018T-Y021N-A128S-K141R-N243V, S018T-Y021N-A128S-N243V, S018T-Y021N-N061S-A128S-N243V-S260P, S018T-Y021N-N061S-N109G-A128S-S260P, S018T-Y021N-N109G-A128S, S018T-Y021N-N109G-A128S-N243V, S018T-Y021N-N109G-A128S-N243V-S248N-K256R, S033T-N109G-A128S-N243P-S248N-K256R, S033T-N243V, S033T-Q103H, S033T-T158S, S063G, S063G-A088T, S063G-A128S, S063G-K256R, S063G-L257G, S063G-N076D, S063G-N109G, S063G-Q103H, S063G-S162G, S063G-S248N, S063G-T158S, S162G, S162G-L257G, S162G-N243V, S162G-S248N, S248N, S248N-L257G, S249A, T158S, T158S-L257G, T158S-N218S, T158S-N243V, T158S-S248N, and T158S-S249A, wherein amino acid positions of the variant are numbered by correspondence with the sequence of SEQ ID NO:2. Such variants have enhanced proteolytic activity compared to BPN' (SEQ ID NO:2) and a greater PI value than BPN' in this assay. The invention includes a protease variant having enhanced proteolytic activity compared to BPN' (SEQ ID NO:2), a PI value of 1.0 relative to BPN'-v3, and a PI value of 1.0 relative to BPN'-v36 in this BMI microswatch cleaning assay Test Method 3), the variant comprising an amino acid sequence having at least 60%, 70%, 80%, 85%, 90%, 91%, 92%, 93%, 94%, 95%, 96%, 97%, or 98% or 99% identity to SEQ ID NO:2 or SEQ ID NO:6 and comprising at least one set of amino acid substitutions selected from said group above, wherein amino acid positions of the variant are numbered by correspondence with amino acid positions of the SEQ ID NO:2 sequence. Also included are compositions, including, but not limited to, e.g., cleaning compositions, comprising at least one such variant and methods for cleaning utilizing at least one such variant as described in greater detail elsewhere herein.

The following BPN'-v36 variants were determined to have a PI value equal to about 0.9 relative to BPN'-v36 in a BMI microswatch cleaning assay (test Method 3) in Detergent Composition 4 at pH 8 and 16° C.: BPN'-S024G-S053G-S078N-S101N-G128A-Y217Q amino acid sequence (SEQ ID NO:6) comprising at least one set of amino acid substitutions selected from the group consisting of A001E-A088T, A001E-A116T, A001E-A128S-G131H-N243V, A001E-G131H-G169A-N243V, A001E-K256R, A001E-N109G, A001E-N243V, A001E-S033T, A001E-S033T-N109G-N218S, A001E-S033T-N109G-N243V, A001E-S162G, A001E-T158S, A088T-A128S, A088T-G169A, A088T-N218S, A088T-Q206D, A116T-G169A, A116T-N218S, A116T-Q206D, A128S, A128S-G131H, A128S-G169A, A128S-N218S, A128S-N243V, A128S-Q206D, G024E, G024E-A088T, G024E-A128S, G024E-G131H, G024E-K043Y, G024E-N218S, G024E-Q103H, G024E-S033T, G024E-S063G, G024E-S162G, G024E-S248N, G024E-

S249A, G131H-G169A, G131H-N218S, G131H-N243V, G131H-Q206D, G169A, G169A-K256R, G169A-L257G, G169A-N218S, G169A-N243V, G169A-Q206D, G169A-S248N, G169A-S249A, K043Y, K043Y-A116T, K043Y-A128S, K043Y-G131H, K043Y-G169A, K043Y-L257G, K043Y-N109G, K043Y-N218S, K043Y-Q103H, K043Y-S063G, K043Y-S162G, K043Y-S248N, K043Y-S249A, K043Y-T158S, N076D, N076D-A088T, N076D-A128S, N076D-G131H, N076D-N218S, N076D-N243V, N076D-Q103H, N076D-S162G, N076D-S248N, N076D-S249A, N109G-G169A, N109G-Q206D, N109G-S248N, N218S, N218S-K256R, N218S-L257G, N218S-S248N, N218S-S249A, P040E-N109G-A128S-G131H, Q103H, Q103H-G169A, Q206D, Q206D-K256R, Q206D-L257G, Q206D-N218S, Q206D-N243V, Q206D-S248N, Q206D-S249A, S018T-Y021N-S033T-N109G-A128S-N243V-S248N-K256R, S033T, S033T-A088T, S033T-A116T, S033T-A128S, S033T-A128S-G131H-N243P, S033T-G131H, S033T-K043Y, S033T-K256R, S033T-L257G, S033T-N076D, S033T-N076D-A128S-N218S, S033T-N076D-N109G-A128S-N218S-N243V-S248N-K256R, S033T-N109G, S033T-N109G-A128S-N243V-S248N-K256R, S033T-N218S, S033T-P040E-Q103H-N109G, S033T-Q103H-A128S-G131H, S033T-Q206D, S033T-S063G, S033T-S162G, S033T-S248N, S033T-S249A, S063G-A116T, S063G-G131H, S063G-G169A, S063G-N109G-A128S-G131H, S063G-N218S, S063G-N243V, S063G-Q206D, S063G-S249A, S162G-G169A, S162G-N218S, S162G-Q206D, S162G-S249A, S248N-K256R, S248N-S249A, S249A-K256R, S249A-L257G, T158S-G169A, T158S-K256R, T158S-Q206D, and T158S-S162G, wherein amino acid positions of the variant are numbered by correspondence with the sequence of SEQ ID NO:2. Such variants have proteolytic activity. The invention includes a protease variant having enhanced proteolytic activity compared to BPN' (SEQ ID NO:2), and/or a PI value of 0.9 relative to BPN'-v36 in this BMI microswatch cleaning assay, the variant comprising an amino acid sequence having at least 60%, 70%, 80%, 85%, 90%, 91%, 92%, 93%, 94%, 95%, 96%, 97%, or 98% or 99% identity to SEQ ID NO:2 or SEQ ID NO:6 and comprising at least one set of acid substitutions selected from said group above, wherein amino acid positions of the variant are numbered by correspondence with amino acid positions of the SEQ ID NO:2 sequence. Also included are compositions, including, but not limited to, e.g., cleaning compositions, comprising at least one such variant and methods for cleaning utilizing at least one such variant as described in greater detail elsewhere herein.

The following BPN'-v36 variants were determined to have a PI value equal to or greater than 0.5 and less than 0.9 relative to BPN'-v36 in a BMI microswatch cleaning assay (Test Method 3) in Detergent Composition 4 at pH 8 and 16° C.: BPN'-S024G-S053G-S078N-S101N-G128A-Y217Q amino acid sequence (SEQ ID NO:6) comprising at least one set of amino acid substitutions selected from the group consisting of A001E, A001E-A128S, A001E-G024E, A001E-G131H, A001E-G169A, A001E-L257G, A001E-N218S, A001E-Q103H, A001E-S063G, A001E-S248N, A001E-S249A, G024E-N076D, K043Y-N076D, K043Y-Q206D, N076D-A116T, N076D-G169A, N076D-Q206D, Q103H-Q206D, S033T-G169A, S033T-S063G-Q103H-N109Q-A128S-G131H-G169A-N243P, S033T-S063G-Q103H-N109Q-A128S-G131H-G169A-N243V, A001E-K043Y, A001E-N076D, A001E-N076D-N109G-A128S, A001E-Q206D, and G024E-Q206D, wherein amino acid positions of the variant are numbered by correspondence with the sequence of SEQ ID NO:2. Such variants have proteolytic activity. The invention includes a protease variant having proteolytic activity and/or a PI value equal to or greater than 0.5 and less than 0.9 relative to BPN'-v36 in this BMI microswatch cleaning assay, the variant comprising an amino acid sequence having at least 60%, 70%, 80%, 85%, 90%, 91%, 92%, 93%, 94%, 95%, 96%, 97%, or 98% or 99% identity to SEQ ID NO:2 or SEQ ID NO:6 and comprising at least one set of acid substitutions selected from said group above, wherein amino acid positions of the variant are numbered by correspondence with amino acid positions of the SEQ ID NO:2 sequence. Also included are compositions, including, but not limited to, e.g., cleaning compositions, comprising at least one such variant and methods for cleaning utilizing at least one such variant as described in greater detail elsewhere herein.

The following BPN'-v36 variants were determined to have a PI value greater than 1.0, at least 1.1, at least 1.2, at least 1.3, at least 1.4, at least 1.5, at least 1.6, at least 1.7, at least 1.8, at least 1.9, at least 2, from greater than 1.0 to about 10, from greater than 1.0 to about 8, or from greater than 1.0 to about 5 relative to BPN'-v36 in a BMI microswatch cleaning assay (test Method 3) in Detergent Composition 4 at pH 7 and 16° C.: BPN'-S024G-S053G-S078N-S101N-G128A-Y217Q amino acid sequence (SEQ ID NO:6) comprising at least one set of amino acid substitutions selected from the group consisting of A116T, A088T-N243V, G024E-A116T, K043Y, N076D-A116T, N218S-S248N, S033T-N243V, S033T-S063G, S248N-L257G, A001E-S249A, A088T-A116T, A088T-A128S, A088T-G131H, A088T-L257G, A088T-N109G, A088T-S248N, A088T-S249A, A116T-N243V, A116T-T158S, A128S, A128S-K256R, A128S-L257G, A128S-N243V, A128S-S248N, A128S-T158S, G024E-A088T, G024E-A128S, G024E-G131H, G024E-K256R, G024E-L257G, G024E-N218S, G024E-N243V, G024E-S162G, G024E-S249A, G024E-T158S, G131H, G131H-K256R, G131H-S249A, K043Y-A088T, K043Y-A116T, K256R, N076D-K256R, N109G, N109G-A116T, N109G-A128S, N109G-A128S-N243V-K256R, N109G-A128S-N243V-S248A, N109G-G131H, N109G-K256R, N109G-L257G, N109G-N218S, N109G-N243V, N109G-S248N, N218S-L257G, N243V, N243V-K256R, N243V-L257G, N243V-S248N, N243V-S249A, Q103H-A128S, Q103H-G131H, Q103H-K256R, Q103H-L257G, Q103H-N243V, Q103H-S248N, Q103H-S249A, Q103H-T158S, Q206D-N243V, S033T-A128S, S033T-K256R, S033T-N076D, S033T-N218S, S033T-S248N, S033T-T158S, S063G-A128S, S063G-K256R, S063G-N243V, S063G-S162G, S063G-T158S, S162G-K256R, S248N-K256R, S249A, T158S-N243V, and T158S-S249A, wherein amino acid positions of the variant are numbered by correspondence with the sequence of SEQ ID NO:2. Such variants have enhanced proteolytic activity compared to BPN', BPN'-v3, and BPN'-v36, and a greater PI value than BPN', BPN'-v3 and BPN'-v36 in this assay. The invention includes a protease variant having enhanced proteolytic activity compared to BPN' (SEQ ID NO:2), enhanced proteolytic activity compared to BPN', BPN'-v3, and BPN'-v36, a PI value of greater than 1.0 to about 5 relative to BPN'-v3, and/or a PI value of greater than 1.0 to about 5 relative to BPN'-v36 in this BMI microswatch cleaning assay, the variant comprising an amino acid sequence having at least 60%, 70%, 80%, 85%, 90%, 91%, 92%, 93%, 94%, 95%, 96%, 97%, or 98% or 99% identity to SEQ ID NO:2 or SEQ ID NO:6 and comprising at least one set of amino acid substitutions selected from said group above, wherein amino acid positions of the variant are numbered by correspondence with amino acid positions of the SEQ ID NO:2 sequence. Also included are compositions, including, but not limited to, e.g., cleaning compositions, comprising at least one such variant and methods for cleaning utilizing at least one such variant as described in greater detail elsewhere herein.

The following BPN'-v36 variants were determined to have a PI value equal to about 1.0 relative to BPN'-v36 in a BMI microswatch cleaning assay (Test Method 3) in Detergent Composition 4 at pH 7 and 16° C.: BPN'-S024G-S053G-S078N-S101N-G128A-Y217Q amino acid sequence (SEQ ID NO:6) comprising at least one set of amino acid substitutions selected from the group consisting of BPN'-v36, A001E-A128S, A001E-G131H, A001E-K256R, A001E-N218S, A001E-N243V, A001E-S033T, A001E-S063G, A001E-S162G, A088T, A088T-K256R, A088T-N218S, A088T-Q103H, A088T-S162G, A088T-T158S, A116T-A128S, A116T-G131H, A116T-K256R, A116T-L257G, A116T-S162G, A116T-S248N, A116T-S249A, A128S-G169A, A128S-N218S, A128S-S162G, A128S-S249A, G024E, G024E-N109G, G024E-Q103H, G024E-S033T, G024E-S063G, G024E-S248N, G131H-L257G, G131H-N243V, G131H-S162G, G131H-T158S, G169A, G169A-L257G, G169A-S248N, K043Y-A128S, K043Y-G131H, K043Y-K256R, K043Y-L257G, K043Y-N109G, K043Y-N243V, K043Y-Q103H, K043Y-S063G, K043Y-S162G, K043Y-S248N, K043Y-S249A, K043Y-T158S, K256R-L257G, L257G, N061G-N109G-N243V, N061S-A128S-N243V-S260P, N061S-N109G-A128S-N243V-S260P, N061S-N109G-A128S-S260P, N076D-A088T, N076D-A128S, N076D-G169A, N076D-N218S, N076D-N243V, N076D-S162G, N076D-S248N, N076D-T158S, N109A-A128S-N243V-K256R, N109G-A128S-G131H-N243V-S248N-K256R, N109G-A128S-N243V-S248A-K256R, N109G-A128S-N243V-S248N-K256R-L257G, N109G-A128S-S162G-N243V-S248N-K256R, N109G-A128S-T158S-N243V-S248N-K256R, N109G-Q206D, N109G-S162G, N109G-S249A, N109G-T158S, N109Q-A128S-N243V-K256R, N109S-A128S-N243V-K256R, N218S, N218S-K256R, N218S-N243V, P040A-N109G-A128S-N243V-S248N-K256R, Q103H, Q103H-A116T, Q103H-G169A, Q103H-N109G, Q103H-N218S, Q103H-S162G, S009T-A128S-K141R-N243V, S009T-N109G-A128S-K141R, S009T-N109G-A128S-K141R-N243V, S009T-S018T-Y021N-N109G-A128S-K141R, S018T-Y021N-N109G-A128S, S018T-Y021N-N109G-A128S-N243V, S018T-Y021N-N109G-A128S-N243V-S248N-K256R, S033T-A088T, S033T-A116T, S033T-G131H, S033T-K043Y, S033T-L257G, S033T-N109G, S033T-Q103H, S033T-Q206D, S033T-S162G, S033T-S249A, S063G, S063G-A088T, S063G-A116T, S063G-L257G, S063G-N076D, S063G-N109G, S063G-N218S, S063G-Q103H, S063G-S248N, S063G-S249A, S162G, S162G-G169A, S162G-L257G, S162G-N218S, S162G-N243V, S162G-S248N, S162G-S249A, S248N, S248N-S249A, S249A-K256R, S249A-L257G, T158S, T158S-G169A, T158S-K256R, T158S-L257G, T158S-N218S, and T158S-S248N, wherein amino acid positions of the variant are numbered by correspondence with the sequence of SEQ ID NO:2. Such variants have enhanced proteolytic activity compared to BPN' protease (SEQ ID NO:2) and a greater PI value than BPN' in this assay. The invention includes a protease variant having enhanced proteolytic activity compared to BPN' (SEQ ID NO:2), a PI value of 1.0 relative to BPN'-v3, and a PI value of 1.0 relative to BPN'-v36 in this BMI microswatch cleaning assay, the variant comprising an amino acid sequence having at least 60%, 70%, 80%, 85%, 90%, 91%, 92%, 93%, 94%, 95%, 96%, 97%, or 98% or 99% identity to SEQ ID NO:2 or SEQ ID NO:6 and comprising at least one set of amino acid substitutions selected from said group above, wherein amino acid positions of the variant are numbered by correspondence with amino acid positions of the SEQ ID NO:2 sequence. Also included are compositions, including, but not limited to, e.g., cleaning compositions, comprising at least one such variant and methods for cleaning utilizing at least one such variant as described in greater detail elsewhere herein.

The following BPN'-v36 variants were determined to have a PI value equal to about 0.9 relative to BPN'-v36 in a BMI microswatch cleaning assay (Test Method 3) in Detergent Composition 4 at pH 7 and 16° C.: BPN'-S024G-S053G-S078N-S101N-G128A-Y217Q amino acid sequence (SEQ ID NO:6) comprising at least one set of amino acid substitutions selected from the group consisting of A001E, A001E-A088T, A001E-A116T, A001E-G169A, A001E-L257G, A001E-N109G, A001E-S033T-N109G-N243V, A001E-T158S, A088T-G169A, A088T-Q206D, A116T-N218S, A128S-G131H, A128S-N243V-S248N-K256R, A128S-Q206D, G024E-K043Y, G024E-N076D, G024E-Q206D, G131H-G169A, G131H-N218S, G131H-N243V-K256R, G131H-Q206D, G131H-S248N, G169A-K256R, G169A-N218S, G169A-N243V, G169A-Q206D, K043Y-N076D, K043Y-N218S, N061P-N109G-G131H-N243V, N061P-N109G-N243V, N061S-N109G-A128S-N243V-S248N-K256R-S260P, N061S-N109G-N243V, N076D, N076D-G131H, N076D-L257G, N076D-N109G, N076D-Q103H, N076D-S249A, N109G-A128S-N243V-S248N, N109G-A128S-N243V-S248N-K256R, N109G-A128S-S248N-K256R, N109G-N243P-S248A-K256R, N109G-N243P-S248N-K256R, N109G-N243V-K256R, N109G-N243V-S248A-K256R, N109G-N243V-S248N, N109G-N243V-S248N-K256R, N109G-S248N-K256R, N218S-S249A, N243V-S248N-K256R, Q103H-Q206D, Q206D, Q206D-K256R, Q206D-N218S, Q206D-S248N, Q206D-S249A, S009T-N109G-A128S-K141R-N243V-S248N-K256R, S009T-S018T-Y021N-A128S-K141R-N243V, S018T-Y021N-A128S-N243V, S018T-Y021N-N061S-A128S-N243V-S260P, S018T-Y021N-N061S-N109G-A128S-S260P, S018T-Y021N-S033T-N109G-A128S-N243V-S248N-K256R, S033T, S033T-G169A, S033T-N076D-A128S-N218S, S033T-N076D-N109G-A128S-N218S-N243V-S248N-K256R, S033T-N109G-A128S-N243P-S248N-K256R, S033T-N109G-A128S-N243V-S248N-K256R, S063G-G131H, S063G-G169A, S162G-Q206D, and T158S-S162G, wherein amino acid positions of the variant are numbered by correspondence with the sequence of SEQ ID NO:2. Such variants have proteolytic activity. The invention includes a protease variant having proteolytic activity and/or a PI value of 0.9 relative to BPN'-v36 in this BMI microswatch cleaning assay, the variant comprising an amino acid sequence having at least 60%, 70%, 80%, 85%, 90%, 91%, 92%, 93%, 94%, 95%, 96%, 97%, or 98% or 99% identity to SEQ ID NO:2 or SEQ ID NO:6 and comprising at least one set of acid substitutions selected from said group above, wherein amino acid positions of the variant are numbered by correspondence with amino acid positions of the SEQ ID NO:2 sequence. Also included are compositions, including, but not limited to, e.g., cleaning compositions, comprising at least one such variant and methods for cleaning utilizing at least one such variant as described in greater detail elsewhere herein.

The following BPN'-v36 variants were determined to have a PI value equal to or greater than 0.5 and less than 0.9 relative to BPN'-v36 in a BMI microswatch cleaning assay in Detergent Composition 4 at pH 7 and 16° C.: BPN'-S024G-S053G-S078N-S101N-G128A-Y217Q amino acid sequence (SEQ ID NO:6) comprising at least one set of amino acid substitutions selected from the group consisting of A001E-A128S-

G131H-N243V, A001E-G024E, A001E-G131H-G169A-N243V, A001E-Q103H, A001E-S033T-N109G-N218S, A001E-S248N, A116T-G169A, A116T-Q206D, G169A-S249A, K043Y-G169A, N109G-G169A, P040E-N109G-A128S-G131H, Q206D-L257G, S033T-A128S-G131H-N243P, S033T-A128S-G131H-N243V, S033T-P040E-Q103H-N109G, S033T-Q103H-A128S-G131H, S063G-N109G-A128S-G131H, S063G-Q206D, T158S-Q206D, A001E-K043Y, A001E-N076D, A001E-Q206D, S033T-S063G-Q103H-N109Q-A128S-G131H-G169A-N243P, S033T-S063G-Q103H-N109Q-A128S-G131H-G169A-N243V, A001E-N076D-N109G-A128S, K043Y-Q206D, and N076D-Q206D, wherein amino acid positions of the variant are numbered by correspondence with the sequence of SEQ ID NO:2. Such variants have proteolytic activity. The invention includes a protease variant having proteolytic activity and/or a PI value equal to or greater than 0.5 and less than 0.9 relative to BPN'-v36 in this assay, the variant comprising an amino acid sequence having at least 60%, 70%, 80%, 85%, 90%, 91%, 92%, 93%, 94%, 95%, 96%, 97%, or 98% or 99% identity to SEQ ID NO:2 or SEQ ID NO:6 and comprising at least one set of acid substitutions selected from said group above, wherein amino acid positions of the variant are numbered by correspondence with amino acid positions of the SEQ ID NO:2 sequence. Also included are compositions, including, but not limited to, e.g., cleaning compositions, comprising at least one such variant and methods for cleaning utilizing at least one such variant as described in greater detail elsewhere herein.

The following BPN'-v36 variants were determined to have a PI value greater than 1.0, at least 1.1, at least 1.2, at least 1.3, at least 1.4, at least 1.5, at least 1.6, at least 1.7, at least 1.8, at least 1.9, at least 2, from greater than 1.0 to about 10, from greater than 1.0 to about 8, or from greater than 1.0 to about 5 relative to BPN'-v36 in an egg microswatch cleaning assay in Detergent Composition 4 at pH 8 and 16° C.: BPN'-S024G-S053G-S078N-S101N-G128A-Y217Q amino acid sequence (SEQ ID NO:6) comprising at least one set of amino acid substitutions selected from the group consisting of A088T-L257G, G024E-K256R, G024E-L257G, N109G-A116T, N109G-L257G, N243V-K256R, S033T-N109G, S033T-T158S, S063G-L257G, A001E-L257G, A088T-A128S, A088T-G169A, A088T-K256R, A088T-N109G, A088T-N218S, A088T-N243V, A088T-S248N, A088T-T158S, A116T, A116T-A128S, A116T-G131H, A116T-K256R, A116T-L257G, A116T-N218S, A116T-S162G, A116T-T158S, A128S, A128S-G169A, A128S-K256R, A128S-L257G, A128S-N218S, G024E, G024E-A128S, G024E-G131H, G024E-N109G, G024E-N243V, G024E-S033T, G024E-S063G, G024E-S248N, G024E-S249A, G024E-T158S, G131H, G131H-G169A, G131H-K256R, G131H-N218S, G131H-S249A, G169A, G169A-L257G, G169A-N243V, K043Y-A088T, K043Y-N109G, K256R, K256R-L257G, N061G-N109G-N243V, N076D-N109G, N109G, N109G-A128S, N109G-G131H, N109G-K256R, N109G-N218S, N109G-S162G, N109G-S248N, N109G-S249A, N109G-T158S, N218S, N218S-K256R, N218S-L257G, N218S-S248N, N243V, N243V-L257G, N243V-S248N, N243V-S249A, P040A-N109G-A128S-N243V-S248N-K256R, Q103H-K256R, Q103H-L257G, Q103H-N109G, S009T-S018T-Y021N-N109G-A128S-K141R, S033T-A088T, S033T-A116T, S033T-A128S, S033T-G131H, S033T-K043Y, S033T-K256R, S033T-L257G, S033T-N076D, S033T-N218S, S033T-N243V, S033T-Q103H, S033T-S063G, S033T-S162G, S033T-S248N, S033T-S249A, S063G, S063G-A088T, S063G-A116T, S063G-A128S, S063G-G131H, S063G-K256R, S063G-N109G, S063G-N218S, S063G-N243V, S063G-S248N, S063G-S249A, S063G-T158S, S162G-K256R, S162G-N218S, S162G-N243V, S162G-S248N, S162G-S249A, S248N, S249A, S249A-L257G, T158S, T158S-L257G, and T158S-N243V, wherein amino acid positions of the variant are numbered by correspondence with the sequence of SEQ ID NO:2. Such variants have enhanced proteolytic activity compared to BPN', BPN'-v3, and BPN'-v36, and a greater PI value than BPN', BPN'-v3 and BPN'-v36 in this assay. The invention includes a protease variant having enhanced proteolytic activity compared to BPN' (SEQ ID NO:2), enhanced proteolytic activity compared to BPN', BPN'-v3, and BPN'-v36, a PI value of greater than 1.0 to about 5 relative to BPN'-v3, and/or a PI value of greater than 1.0 to about 5 relative to BPN'-v36 in this egg microswatch cleaning assay, the variant comprising an amino acid sequence having at least 60%, 70%, 80%, 85%, 90%, 91%, 92%, 93%, 94%, 95%, 96%, 97%, or 98% or 99% identity to SEQ ID NO:2 or SEQ ID NO:6 and comprising at least one set of amino acid substitutions selected from said group above, wherein amino acid positions of the variant are numbered by correspondence with amino acid positions of the SEQ ID NO:2 sequence. Also included are compositions, including, but not limited to, e.g., cleaning compositions, comprising at least one such variant and methods for cleaning utilizing at least one such variant as described in greater detail elsewhere herein.

The following BPN'-v36 variants were determined to have a PI value equal to about 1.0 relative to BPN'-v36 in an egg microswatch cleaning assay in Detergent Composition 4 at pH 8 and 16° C.: BPN'-S024G-S053G-S078N-S101N-G128A-Y217Q amino acid sequence (SEQ ID NO:6) comprising at least one set of amino acid substitutions selected from the group consisting of BPN'-v36, A001E, A001E-A116T, A001E-G131H, A001E-G169A, A001E-K256R, A001E-N109G, A001E-S033T-N109G-N243V, A001E-S063G, A001E-S248N, A001E-S249A, A001E-T158S, A088T, A088T-A116T, A088T-G131H, A088T-Q103H, A088T-Q206D, A088T-S162G, A088T-S249A, A116T-G169A, A116T-N243V, A116T-S248N, A116T-S249A, A128S-G131H, A128S-N243V, A128S-S162G, A128S-S248N, A128S-S249A, A128S-T158S, G024E-A088T, G024E-A116T, G024E-K043Y, G024E-N076D, G024E-N218S, G024E-Q103H, G024E-S162G, G131H-L257G, G131H-N243V, G131H-N243V-K256R, G131H-S162G, G131H-S248N, G131H-T158S, G169A-K256R, G169A-N218S, G169A-Q206D, G169A-S248N, G169A-S249A, K043Y, K043Y-A116T, K043Y-A128S, K043Y-G169A, K043Y-K256R, K043Y-L257G, K043Y-N076D, K043Y-N218S, K043Y-N243V, K043Y-S063G, K043Y-S248N, K043Y-S249A, K043Y-T158S, L257G, N061P-N109G-G131H-N243V, N061P-N109G-N243V, N061S-A128S-N243V-S260P, N061S-N109G-A128S-N243V-S248N-K256R-S260P, N061S-N109G-A128S-S260P, N061S-N109G-N243V, N076D, N076D-A088T, N076D-A116T, N076D-G131H, N076D-G169A, N076D-K256R, N076D-L257G, N076D-N218S, N076D-N243V, N076D-Q103H, N076D-S249A, N076D-T158S, N109A-A128S-N243V-K256R, N109G-A128S-G131H-N243V-S248N-K256R, N109G-A128S-N243V-K256R, N109G-A128S-N243V-S248A, N109G-A128S-N243V-S248A-K256R, N109G-A128S-N243V-S248N, N109G-A128S-N243V-S248N-K256R, N109G-A128S-N243V-S248N-K256R-L257G, N109G-A128S-S162G-N243V-S248N-K256R, N109G-G169A, N109G-N243P-S248A-K256R, N109G-N243V-K256R, N109G-N243V-S248A-K256R, N109G-N243V-S248N, N109G-N243V-S248N-K256R, N109G-S248N-K256R, N109Q-A128S-N243V-K256R, N109S-A128S-

N243V-K256R, N218S-N243V, N218S-S249A, Q103H, Q103H-A116T, Q103H-A128S, Q103H-G131H, Q103H-G169A, Q103H-N218S, Q103H-N243V, Q103H-S162G, Q103H-S248N, Q103H-S249A, Q103H-T158S, Q206D, Q206D-L257G, Q206D-N218S, S009T-A128S-K141R-N243V, S009T-N109G-A128S-K141R, S009T-N109G-A128S-K141R-N243V, S009T-N109G-A128S-K141R-N243V-S248N-K256R, S009T-S018T-Y021N-A128S-K141R-N243V, S018T-Y021N-A128S-N243V, S018T-Y021N-N109G-A128S, S018T-Y021N-N109G-A128S-N243V, S018T-Y021N-N109G-A128S-N243V-S248N-K256R, S018T-Y021N-S033T-N109G-A128S-N243V-S248N-K256R, S033T, S033T-A128S-G131H-N243V, S033T-G169A, S033T-N109G-A128S-N243P-S248N-K256R, S033T-N109G-A128S-N243V-S248N-K256R, S033T-Q103H-A128S-G131H, S033T-Q206D, S033T-S063G-Q103H-N109Q-A128S-G131H-G169A-N243V, S063G-G169A, S063G-N076D, S063G-N109G-A128S-G131H, S063G-Q103H, S063G-S162G, S162G, S162G-G169A, S162G-L257G, S248N-K256R, S248N-L257G, S248N-S249A, S249A-K256R, T158S-G169A, T158S-K256R, T158S-N218S, T158S-S162G, T158S-S248N, and T158S-S249A, wherein amino acid positions of the variant are numbered by correspondence with the sequence of SEQ ID NO:2. Such variants have enhanced proteolytic activity compared to BPN' protease (SEQ ID NO:2) and a greater PI value than BPN' in this assay. The invention includes a protease variant having enhanced proteolytic activity compared to BPN' (SEQ ID NO:2), a PI value of 1.0 relative to BPN'-v3, and a PI value of 1.0 relative to BPN'-v36 in this egg microswatch cleaning assay, the variant comprising an amino acid sequence having at least 60%, 70%, 80%, 85%, 90%, 91%, 92%, 93%, 94%, 95%, 96%, 97%, or 98% or 99% identity to SEQ ID NO:2 or SEQ ID NO:6 and comprising at least one set of amino acid substitutions selected from said group above, wherein amino acid positions of the variant are numbered by correspondence with amino acid positions of the SEQ ID NO:2 sequence. Also included are compositions, including, but not limited to, e.g., cleaning compositions, comprising at least one such variant and methods for cleaning utilizing at least one such variant as described in greater detail elsewhere herein.

The following BPN'-v36 variants were determined to have a PI value equal to or greater than 0.5 and less than 0.9 relative to BPN'-v36 in an egg microswatch cleaning assay in Detergent Composition 4 at pH 8 and 16° C.: BPN'-S024G-S053G-S078N-S101N-G128A-Y217Q amino acid sequence (SEQ ID NO:6) comprising at least one set of amino acid substitutions selected from the group consisting of A001E-A088T, A001E-A128S, A001E-A128S-G131H-N243V, A001E-G024E, A001E-G024E-S204E-Q206D, A001E-G131H-G169A-N243V, A001E-K043Y, A001E-N076D, A001E-N076D-N109G-A128S, A001E-N218S, A001E-N243V, A001E-Q103H, A001E-Q206D, A001E-S033T, A001E-S033T-N109G-N218S, A001E-S162G, A116T-Q206D, A128S-N243V-S248N-K256R, A128S-Q206D, G024E-Q206D, G131H-Q206D, K043Y-G131H, K043Y-Q103H, K043Y-Q206D, K043Y-S162G, N061S-N109G-A128S-N243V-S260P, N076D-A128S, N076D-Q206D, N076D-S162G, N076D-S248N, N109G-A128S-S248N-K256R, N109G-A128S-T158S-N243V-S248N-K256R, N109G-N243P-S248N-K256R, N109G-Q206D, N243V-S248N-K256R, P040E-N109G-A128S-G131H, Q103H-Q206D, Q206D-K256R, Q206D-N243V, Q206D-S248N, Q206D-S249A, S018T-Y021N-N061S-A128S-N243V-S260P, S018T-Y021N-N061S-N109G-A128S-S260P, S033T-A128S-G131H-N243P, S033T-N076D-A128S-N218S, S033T-N076D-N109G-A128S-N218S-N243V-S248N-K256R, S033T-P040E-Q103H-N109G, S033T-S063G-Q103H-N109Q-A128S-G131H-G169A-N243P, S063G-Q206D, S162G-Q206D, and T158S-Q206D, wherein amino acid positions of the variant are numbered by correspondence with the sequence of SEQ ID NO:2. Such variants have proteolytic activity. The invention includes a protease variant having proteolytic activity and/or a PI value equal to or greater than 0.5 and less than 0.9 relative to BPN'-v36 in this assay, the variant comprising an amino acid sequence having at least 60%, 70%, 80%, 85%, 90%, 91%, 92%, 93%, 94%, 95%, 96%, 97%, or 98% or 99% identity to SEQ ID NO:2 or SEQ ID NO:6 and comprising at least one set of acid substitutions selected from said group above, wherein amino acid positions of the variant are numbered by correspondence with amino acid positions of the SEQ ID NO:2 sequence. Also included are compositions, including, but not limited to, e.g., cleaning compositions, comprising at least one such variant and methods for cleaning utilizing at least one such variant as described in greater detail elsewhere herein.

The following BPN'-v36 variants were determined to have a PI value greater than 1.0, at least 1.1, at least 1.2, at least 1.3, at least 1.4, at least 1.5, at least 1.6, at least 1.7, at least 1.8, at least 1.9, at least 2, from greater than 1.0 to about 10, from greater than 1.0 to about 8, or from greater than 1.0 to about 5 relative to BPN'-v36 in a grass microswatch cleaning assay in Detergent Composition 4 at pH 8 and 16° C.: BPN'-S024G-S053G-S078N-S101N-G128A-Y217Q amino acid sequence (SEQ ID NO:6) comprising at least one set of amino acid substitutions selected from the group consisting of T158S-L257G, K256R, L257G, S033T-N109G, S162G-K256R, S162G-L257G, G024E-K256R, G024E-L257G, G024E-S033T, N109G-A116T, N218S-L257G, S033T-A088T, S033T-A116T, S033T-N243V, S033T-Q103H, S162G-N218S, S162G-N243V, T158S, T158S-N218S, T158S-N243V, A088T, A088T-G169A, A088T-K256R, A088T-L257G, A088T-S162G, A088T-T158S, A116T-K256R, A116T-L257G, A116T-N243V, A128S-L257G, A128S-N218S, A128S-N243V, A128S-S248N, G024E-A116T, G024E-A128S, G024E-G131H, G024E-N243V, G024E-S248N, G024E-S249A, G024E-T158S, G131H-N243V, G131H-T158S, G169A-N218S, G169A-N243V, G169A-S248N, K256R-L257G, N109G-A128S, N109G-G131H, N109G-N218S, N109G-N243V, N109G-S249A, N218S, N218S-K256R, N218S-N243V, N218S-S249A, N243V, N243V-K256R, N243V-L257G, N243V-S248N, Q103H-N109G, Q103H-N218S, S033T-A128S, S033T-L257G, S033T-N218S, S033T-S162G, S033T-S248N, S033T-T158S, S063G-K256R, S063G-L257G, S162G, S162G-G169A, S162G-S248N, S248N, S248N-K256R, S248N-L257G, S249A, T158S-S162G, and T158S-S248N, wherein amino acid positions of the variant are numbered by correspondence with the sequence of SEQ ID NO:2. Such variants have enhanced proteolytic activity compared to BPN', BPN'-v3, and BPN'-v36, and a greater PI value than BPN', BPN'-v3 and BPN'-v36 in this assay. The invention includes a protease variant having enhanced proteolytic activity compared to BPN' (SEQ ID NO:2), enhanced proteolytic activity compared to BPN', BPN'-v3, and BPN'-v36, a PI value of greater than 1.0 to about 5 relative to BPN'-v3, and/or a PI value of greater than 1.0 to about 5 relative to BPN'-v36 in this BMI microswatch cleaning assay, the variant comprising an amino acid sequence having at least 60%, 70%, 80%, 85%, 90%, 91%, 92%, 93%, 94%, 95%, 96%, 97%, or 98% or 99% identity to SEQ ID NO:2 or SEQ ID NO:6 and comprising at least one set of amino acid substitutions selected from said group above, wherein amino acid positions of the variant are numbered by correspondence with amino acid positions of the SEQ ID NO:2 sequence. Also included are compositions, including, but not limited to, e.g., cleaning compositions, comprising at least one such variant and methods for cleaning utilizing at least one such variant as described in greater detail elsewhere herein.

The following BPN'-v36 variants were determined to have a PI value equal to about 1.0 relative to BPN'-v36 in a grass microswatch cleaning assay in Detergent Composition 4 at pH 8 and 16° C.: BPN'-S024G-S053G-S078N-S101N-G128A-Y217Q amino acid sequence (SEQ ID NO:6) comprising at least one set of amino acid substitutions selected from the group consisting of BPN'-v36, A001E-A088T, A001E-A116T, A088T-A128S, A088T-N243V, A088T-Q103H, A088T-S248N, A088T-S249A, A116T, A116T-G169A, A116T-N218S, A116T-S162G, A116T-S249A, A116T-T158S, A128S-G169A, A128S-K256R, A128S-S162G, A128S-S249A, A128S-T158S, G024E-A088T, G024E-K043Y, G024E-N218S, G024E-Q103H, G024E-S063G, G024E-S162G, G131H-G169A, G131H-K256R, G131H-N218S, G131H-S162G, G131H-S248N, G131H-S249A, G169A, G169A-L257G, G169A-S249A, N076D, N076D-K256R, N076D-L257G, N076D-S162G, N076D-S249A, N109G-K256R, N109G-L257G, N109G-S248N, N243V-S249A, Q103H-A116T, Q103H-G169A, Q103H-K256R, Q103H-L257G, Q103H-N243V, Q103H-S162G, S033T-G131H, S033T-G169A, S033T-K043Y, S033T-N076D, S033T-Q206D, S063G, S063G-A116T, S063G-A128S, S063G-N243V, S063G-S162G, S063G-S248N, S063G-S249A, S063G-T158S, S249A-L257G, T158S-G169A, and T158S-K256R, wherein amino acid positions of the variant are numbered by correspondence with the sequence of SEQ ID NO:2. Such variants have enhanced proteolytic activity compared to BPN' (SEQ ID NO:2) and a greater PI value than BPN' in this assay. The invention includes a protease variant having enhanced proteolytic activity compared to BPN' (SEQ ID NO:2), a PI value of 1.0 relative to BPN'-v3, and a PI value of 1.0 relative to BPN'-v36 in this BMI microswatch cleaning assay, the variant comprising an amino acid sequence having at least 60%, 70%, 80%, 85%, 90%, 91%, 92%, 93%, 94%, 95%, 96%, 97%, or 98% or 99% identity to SEQ ID NO:2 or SEQ ID NO:6 and comprising at least one set of amino acid substitutions selected from said group above, wherein amino acid positions of the variant are numbered by correspondence with amino acid positions of the SEQ ID NO:2 sequence. Also included are compositions, including, but not limited to, e.g., cleaning compositions, comprising at least one such variant and methods for cleaning utilizing at least one such variant as described in greater detail elsewhere herein.

The following BPN'-v36 variants were determined to have a PI value equal to or greater than 0.5 and less than 0.9 relative to BPN'-v36 in a grass microswatch cleaning assay in Detergent Composition 4 at pH 8 and 16° C.: BPN'-S024G-S053G-S078N-S101N-G128A-Y217Q amino acid sequence (SEQ ID NO:6) comprising at least one set of amino acid substitutions selected from the group consisting of A001E-G169A, A001E-K256R, A001E-N109G, A001E-N218S, A088T-A116T, A088T-G131H, A088T-N109G, A088T-N218S, A116T-A128S, A116T-G131H, A116T-S248N, A128S, A128S-G131H, G024E, G024E-N109G, G131H, G131H-L257G, G169A-K256R, G169A-Q206D, K043Y, K043Y-A088T, K043Y-L257G, K043Y-N109G, N076D-A088T, N076D-G131H, N076D-G169A, N076D-N243V, N076D-T158S, N109G, N109G-S162G, N109G-T158S, N218S-S248N, Q103H-A128S, Q103H-S248N, Q103H-S249A, Q103H-T158S, Q206D-K256R, Q206D-L257G, Q206D-N218S, Q206D-N243V, Q206D-S248N, S033T, S033T-K256R, S033T-S063G, S033T-S249A, S063G-A088T, S063G-G131H, S063G-G169A, S063G-N109G, S162G-Q206D, S162G-S249A, S248N-S249A, S249A-K256R, T158S-Q206D, T158S-S249A, A001E-L257G, A001E-N243V, A001E-Q103H, A001E-S063G, A001E-S162G, A001E-T158S, G024E-N076D, G131H-Q206D, K043Y-A116T, K043Y-G169A, K043Y-K256R, K043Y-N076D, K043Y-S063G, K043Y-S162G, K043Y-S248N, K043Y-S249A, K043Y-T158S, N076D-A116T, N076D-A128S, N076D-S248N, N109G-G169A, Q103H, Q103H-G131H, Q206D-S249A, S063G-N076D, S063G-N218S, S063G-Q103H, A001E-A128S, A001E-G024E, A001E-G131H, A001E-N076D, A001E-Q206D, A001E-S033T, A001E-S248N, A001E-S249A, A088T-Q206D, A116T-Q206D, A128S-Q206D, G024E-Q206D, K043Y-A128S, K043Y-G131H, K043Y-N218S, K043Y-Q103H, N076D-N109G, N076D-N218S, N076D-Q103H, N109G-Q206D, Q103H-Q206D, Q206D, A001E, A001E-K043Y, K043Y-N243V, S063G-Q206D, N076D-Q206D, wherein amino acid positions of the variant are numbered by correspondence with the sequence of SEQ ID NO:2. Such variants have proteolytic activity. The invention includes a protease variant having proteolytic activity and/or a PI value equal to or greater than 0.5 and less than 0.9 relative to BPN'-v36 in this grass microswatch cleaning assay, the variant comprising an amino acid sequence having at least 60%, 70%, 80%, 85%, 90%, 91%, 92%, 93%, 94%, 95%, 96%, 97%, or 98% or 99% identity to SEQ ID NO:2 or SEQ ID NO:6 and comprising at least one set of acid substitutions selected from said group above, wherein amino acid positions of the variant are numbered by correspondence with amino acid positions of the SEQ ID NO:2 sequence. Also included are compositions, including, but not limited to, e.g., cleaning compositions, comprising at least one such variant and methods for cleaning utilizing at least one such variant as described in greater detail elsewhere herein.

The following BPN'-v36 variants were determined to have a PI value greater than 1.0, at least 1.1, at least 1.2, at least 1.3, at least 1.4, at least 1.5, at least 1.6, at least 1.7, at least 1.8, at least 1.9, at least 2, from greater than 1.0 to about 10, from greater than 1.0 to about 8, or from greater than 1.0 to about 5 relative to BPN'-v36 in an AAPF proteolytic assay: BPN'-S024G-S053G-S078N-S101N-G128A-Y217Q amino acid sequence (SEQ ID NO:6) comprising at least one set of amino acid substitutions selected from the group consisting of S033T-N076D-A128S-N218S, A001E-S033T-N109G-N218S, S033T-N218S, S033T-S063G-Q103H-N109Q-A128S-G131H-G169A-N243V, A128S-G169A, S033T-S063G-Q103H-N109Q-A128S-G131H-G169A-N243P, S018T-Y021N-S033T-N109G-A128S-N243V-S248N-K256R, S033T-A128S-G131H-N243P, P040E-N109G-A128S-G131H, S033T-A128S, S033T-N109G-A128S-N243V-S248N-K256R, N109G-G169A, S063G-N109G-A128S-G131H, G169A, N109G-A128S-G131H-N243V-S248N-K256R, S033T-A128S-G131H-N243V, A128S-N218S, A001E-G169A, A088T-G169A, G169A-L257G, N109G-N218S, S033T-N109G-A128S-N243P-S248N-K256R, G169A-K256R, N076D-G169A, A001E-G131H-G169A-N243V, G169A-S249A, S033T-N109G, G169A-S248N, K043Y-G169A, K043Y-N218S, N218S-L257G, N218S-N243V, S063G-G169A, A001E-A128S-G131H-N243V, A001E-S033T-N109G-N243V, A088T-N218S, G024E-N218S, G024E-S033T, G169A-Q206D, N076D-N218S, S033T-L257G, S162G-G169A, A001E-N218S, A116T-N218S, G169A-N243V, N218S, P040A-N109G-A128S-N243V-S248N-K256R, S033T-N076D, A001E-

S033T, A128S-G131H, N218S-S248N, S018T-Y021N-N109G-A128S, S033T-K043Y, S033T-N243V, S033T-Q206D, S063G-N218S, S162G-N218S, T158S-G169A, A116T-G169A, G131H-G169A, N061S-N109G-A128S-S260P, N109G-A128S-N243V-K256R, N109G-A128S-N243V-S248A, N109G-A128S-N243V-S248A-K256R, N109G-A128S-N243V-S248N-K256R-L257G, N218S-K256R, S009T-N109G-A128S-K141R, S009T-S018T-Y021N-N109G-A128S-K141R, S033T-A088T, S033T-S063G, S033T-S162G, T158S-N218S, A001E-N076D-N109G-A128S, N109G-A128S-N243V-S248N-K256R, N109G-A128S-S248N-K256R, S009T-N109G-A128S-K141R-N243V, S018T-Y021N-N061S-N109G-A128S-S260P, S033T-A116T, S033T-S248N, S033T-S249A, S033T-T158S, G131H-N218S, N109A-A128S-N243V-K256R, N109G-A128S, N109G-A128S-S162G-N243V-S248N-K256R, N109G-A128S-T158S-N243V-S248N-K256R, N218S-S249A, Q206D-N218S, S018T-Y021N-N109G-A128S-N243V, S018T-Y021N-N109G-A128S-N243V-S248N-K256R, S033T-K256R, A116T-A128S, N061S-N109G-A128S-N243V-S260P, N109G-A128S-N243V-S248N, S009T-N109G-A128S-K141R N243V-S248N-K256R, G024E-A128S, N061S-N109G-A128S-N243V-S248N-K256R-S260P, N109S-A128S-N243V-K256R, S033T, S033T-G131H, A001E-A128S, A128S, A128S-L257G, A128S-Q206D, N109Q-A128S-N243V-K256R, S009T-A128S-K141R-N243V, S009T-S018T-Y021N-A128S-K141R-N243V, A088T-A128S, A128S-K256R, A128S-N243V, N061P-N1090-N243V, N061S-A128S-N243V-S260P, S018T-Y021N-A128S-N243V, A128S-N243V-S248N-K256R, A128S-S248N, A128S-S249A, N076D-A128S, S063G-A128S, A128S-S162G, A128S-T158S, S018T-Y021N-N061S-A128S-N243V-S260P, S033T-Q103H-A128S-G131H, N061S-N109G-N243V, K043Y-A128S, N061P-N109G-G131H-N243V, N109G-L257G, A001E-G024E-S204E-Q206D, A001E-L257G, A088T-N109G, G024E-N109G, K043Y-N109G, N061G-N109G-N243V, N076D-N109G, N109G, N109G-A116T, N109G-K256R, N109G-N243V-K256R, N109G-N243V-S248A-K256R, N109G-Q206D, S063G-N109G, A001E-A116T, A001E-N109G, A001E-Q206D, A088T-A116T, A088T-N243V, A116T-L257G, G024E-A116T, G024E-L257G, G024E-N243V, G024E-Q206D, N109G-G131H, N109G-N243V, N109G-S162G, N109G-S248N, N109G-S248N-K256R, N109G-S249A, N109G-T158S, N243V-L257G, A001E-A088T, A001E-G024E, A001E-K256R, A001E-N076D, A001E-N243V, A088T, A088T-L257G, A088T-Q206D, A116T, A116T-K256R, A116T-N243V, G024E-A088T, G024E-K043Y, G024E-K256R, G024E-N076D, G024E-S162G, G024E-S248N, K043Y-A088T, K043Y-A116T, K043Y-L257G, K043Y-N243V, K043Y-Q206D, K256R-L257G, N076D-A116T, N076D-L257G, N076D-N243V, N076D-Q206D, N109G-N243V-S248N, N109G-N243V-S248N-K256R, N243V-K256R, Q206D, Q206D-L257G, Q206D-N243V, Q206D-S248N, S063G-K256R, S063G-L257G, T158S-L257G, A001E, A001E-K043Y, A001E-S162G, A001E-S248N, A001E-S249A, A001E-T158S, A088T-K256R, A088T-S162G, A088T-S248N, A088T-S249A, A116T-Q206D, A116T-S248N, A116T-S249A, G024E, G024E-G131H, G024E-S249A, G024E-T158S, G131H, G131H-K256R, G131H-L257G, K043Y-K256R, K043Y-N076D, K256R, L257G, N076D-A088T, N076D-K256R, N076D-S162G, N076D-S248N, N076D-S249A, N109G-N243P-S248A-K256R, N109G-N243P-S248N-K256R, N243V, Q206D-K256R, S033T-P040E-Q103H-N109G, S063G, S063G-A116T, S063G-Q206D, S162G-K256R, S162G-L257G, S162G-N243V, S162G-Q206D, S162G-S248N, S248N, S248N-L257G, S249A, S249A-L257G, T158S, T158S-N243V, and T158S-Q206D, wherein amino acid positions of the variant are numbered by correspondence with the sequence of SEQ ID NO:2. Such variants have enhanced proteolytic activity compared to BPN', BPN'-v3, and BPN'-v36, and a greater PI value than BPN', BPN'-v3 and BPN'-v36 in this assay. The invention includes a protease variant having enhanced proteolytic activity compared to BPN' (SEQ ID NO:2), enhanced proteolytic. activity compared to BPN', BPN'-v3, and BPN'-v36, a PI value of greater than 1.0 to about 5 relative to BPN'-v3, and/or a PI value of greater than 1.0 to about 5 relative to BPN'-v36 in this assay, the variant comprising an amino acid sequence having at least 60%, 70%, 80%, 85%, 90%, 91%, 92%, 93%, 94%, 95%, 96%, 97%, or 98% or 99% identity to SEQ ID NO:2 or SEQ ID NO:6 and comprising at least one set of amino acid substitutions selected from said group above, wherein amino acid positions of the variant are numbered by correspondence with amino acid positions of the SEQ ID NO:2 sequence. Also included are compositions, including, but not limited to, e.g., cleaning compositions, comprising at least one such variant and methods for cleaning utilizing at least one such variant as described in greater detail elsewhere herein.

The following BPN'-v36 variants were determined to have a PI value equal to about 1.0 relative to BPN'-v36 in an AAPF proteolytic assay: BPN'-S024G-S053G-S078N-S101N-G128A-Y217Q amino acid sequence (SEQ ID NO:6) comprising at least one set of amino acid substitutions selected from the group consisting of BPN'-v36, A001E-G131H, A001E-S063G, A088T-G131H, A088T-T158S, A116T-G131H, A116T-S162G, A116T-T158S, G024E-S063G, G131H-N243V, G131H-N243V-K256R, G131H-Q206D, G131H-S249A, K043Y, K043Y-S063G, K043Y-S248N, K043Y-S249A, K043Y-T158S, N076D, N076D-G131H, N076D-T158S, N243V-S248N, N243V-S248N-K256R, N243V-S249A, Q103H-G169A, Q206D-S249A, S063G-N076D, S063G-N243V, S063G-S162G, S063G-S249A, S063G-T158S, S162G, S162G-S249A, S248N-K256R, S248N-S249A, S249A-K256R, T158S-K256R, T158S-S248N, and T158S-S249A, wherein amino acid positions of the variant are numbered by correspondence with the sequence of SEQ ID NO:2. Such variants have enhanced proteolytic activity compared to BPN' (SEQ ID NO:2) and a greater PI value than BPN' in this assay. The invention includes a protease variant having enhanced proteolytic activity compared to BPN' (SEQ ID NO:2), a PI value of 1.0 relative to BPN'-v3, and a PI value of 1.0 relative to BPN'-v36 in this assay, the variant comprising an amino acid sequence having at least 60%, 70%, 80%, 85%, 90%, 91%, 92%, 93%, 94%, 95%, 96%, 97%, or 98% or 99% identity to SEQ ID NO:2 or SEQ ID NO:6 and comprising at least one set of amino acid substitutions selected from said group above, wherein amino acid positions of the variant are numbered by correspondence with amino acid positions of the SEQ ID NO:2 sequence. Also included are compositions, including, but not limited to, e.g., cleaning compositions, comprising at least one such variant and methods for cleaning utilizing at least one such variant as described in greater detail elsewhere herein.

The following BPN'-v36 variants were determined to have a PI value equal to about 0.9 relative to BPN'-v36 in an AAPF proteolytic assay: BPN'-S024G-S053G-S078N-S101N-G128A-Y217Q amino acid sequence (SEQ ID NO:6) comprising at least one set of amino acid substitutions selected from the group consisting of G131H-S162G, G131H-S248N, G131H-T158S, K043Y-G131H, K043Y-S162G, S063G-

A088T, S063G-G131H, S063G-S248N, T158S-S162G, Q103H-N218S, S033T-Q103H, and Q103H-A128S, wherein amino acid positions of the variant are numbered by correspondence with the sequence of SEQ ID NO:2. Such variants have proteolytic activity. The invention includes a protease variant having proteolytic activity and/or a PI value of 0.9 relative to BPN'-v36 in this assay, the variant comprising an amino acid sequence having at least 60%, 70%, 80%, 85%, 90%, 91%, 92%, 93%, 94%, 95%, 96%, 97%, or 98% or 99% identity to SEQ ID NO:2 or SEQ ID NO:6 and comprising at least one set of acid substitutions selected from said group above, wherein amino acid positions of the variant are numbered by correspondence with amino acid positions of the SEQ ID NO:2 sequence. Also included are compositions, including, but not limited to, e.g., cleaning compositions, comprising at least one such variant and methods for cleaning utilizing at least one such variant as described in greater detail elsewhere herein.

Also provided is a subtilisin protease variant having proteolytic activity, enhanced proteolytic activity compared to BPN', or a PI value greater than that of BPN' (SEQ ID NO:2) in a BMI microswatch cleaning assay, the variant comprising an amino acid sequence having at least 90%, 91%, 92%, 93%, 94%, 95%, 96%, 97%, or 98% identity to SEQ ID NO:2, wherein the variant comprises at least one substitution selected from the group of X001E, X009T, X018T, X021N, X024G, X033T, X040A, X043Y, X061G/P/S, X063G, X076D, X088T, X103H, X109A/G/Q/S, X116T, X128S, X131H, X141R, X158S, X162G, X169A, X204E, X206D, X218S, X243P/V, X248A/N, X249A, X256R, X257G, and X260P, wherein positions of the variant are numbered by correspondence with the sequence of SEQ ID NO:2, and optionally wherein the variant comprises at least one substitution selected from the group of A001E, S009T, S018T, Y021N, S024G, S033T, P040A, K043Y, N061G/P/S, S063G, N076D, A088T, Q103H, N109A/G/Q/S, A116T, G128S, G131H, K141R, T158S, S162G, G169A, S204E, Q206D, N218S, N243P/V, S248A/N, S249A, K256R, L257G, and S260P. Also included are compositions, including cleaning compositions, comprising at least one such protease variant and methods for cleaning utilizing at least one such protease variant as described in greater detail elsewhere herein.

Example 9

Construction and Cleaning Performance of Variants from a Combinatorial Library Based on BPN'-v36 Parent A BPN' combinatorial library based on the BPN'-v36 parent molecule was made by DNA 2.0 and delivered as a ligation reaction. For efficient transformation of *B. subtilis*, DNA from the ligation reaction mixture was amplified before transformation and transformants grown as described in Example 2. The variants were tested for cleaning performance using BMI microswatch assay in Detergent Composition 4 at 16° C. and pH 8 and egg microswatch assay in Detergent Composition 4 at 16° C. and pH 8. Protein content was determined using the TCA assay. Assays were performed as in Example 1 and Performance Indices were calculated relative to BPN'-v36 (i.e., BPN'-S24G-S53G-S78N-S101N-G128A-Y217Q).

The following BPN'-v36 variants were determined to have a PI value greater than 1.0, at least 1.1, at least 1.2, at least 1.3, at least 1.4, at least 1.5, at least 1.6, at least 1.7, at least 1.8, at least 1.9, at least 2, from greater than 1.0 to about 10, from greater than 1.0 to about 8, or from greater than 1.0 to about 5 relative to BPN'-v36 in a BMI microswatch cleaning assay in Detergent Composition 4 at pH 8 and 16° C.: BPN'-S024G-S053G-S078N-S101N-G128A-Y217Q amino acid sequence (SEQ ID NO:6) comprising at least one set of amino acid substitutions selected from the group consisting of A088T-A116T-N243V-K256R-L257G, A088T-A116T-N243V-L257G, A088T-T158S-N218S-K256R, A088T-T158S-N218S-N243V-L257G, A088T-A116T-T158S-N218S-N243V-K256R-L257G, A088T-N109G-A116T-G131H-A153S-N218S-S248N-L257G, A088T-N109G-A116T-T158S-S248N-K256R-L257G, A088T-N109G-T158S-L257G, A114S-A116T-N218S-N243V-S248N-K256R-L257G, A116T-T158S-K256R, A088T-A116T-G131H-T158S-S248N-L257G, A088T-A116T-T158S, A088T-N109G-A116T-G131H-L257G, A088T-N109G-A116T-T158S-N243V-S248N-L257G, A088T-N109G-N243V-L257G, A088T-N109G-N243V-S248N, A088T-N109G-T158S-N243V-L257G, A088T-N109G-T158S-N243V-S248N-L257G, A116T-T158S-S248N-L257G, Y006H-A116T-G131H-S248N, A088T-A116T-G131H-T158S-N218S-N243V, A088T-A116T-G131H-T158S-N243V, A088T-A116T-G131H-T158S-N243V-K256R-L257G, A088T-A116T-N218S-N243V-K256R-L257G, A088T-A116T-S248N-K256R-L257G, A088T-A116T-T158S-N218S-N243V, A088T-A116T-T158S-N243V-K256R-L257G, A088T-A116T-T158S-N243V-S248N-L257G, A088T-G131H-N243V-S248N-K256R-L257G, A088T-N109G-A116T-T158S-L257G, A088T-N109G-A116T-T158S-N212D-N243V-K256R-L257G, A088T-N109G-A116T-T158S-N218S-N243V-S248N-K256R, A088T-N109G-A116T-T158S-S248N-L257G, A088T-N109G-G131H-V148A-N218S-N243V-K256R-L257G, A088T-N109G-K256R, A088T-N109G-N243V-S248N-L257G, A088T-N109G-T158S-K256R, A088T-N109G-T158S-N243V, A088T-T158S-N243V-K256R-L257G, A116T, A116T-N218S-N243V-L257G-N269S, A116T-T158S-K256R-L257G, N109G-A116T-K256R-L257G, N109G-A116T-N243V, N109G-A116T-T158S-N243V-K256R-L257G, N109G-G131H-L257G, N109G-G131H-S248N-K256R-L257G, N109G-G131H-T158S-K256R-L257G, S003P-A116T-T158S-S248N-K256R, T158S-S248N-K256R, A088T-A116T-G131H-N243V-K256R, A088T-A116T-G131H-S248N-K256R-L257G, A088T-A116T-G131H-V147A-T158S-N218S-N243V-S248N-L257G, A088T-A116T-S248N-L257G, A088T-A116T-T158S-N218S, A088T-A116T-T158S-N218S-K256R-L257G, A088T-A116T-T158S-N218S-L257G, A088T-G131H-N243V-L257G, A088T-G131H-T158S-S248N-L257G, A088T-L257G, A088T-N109G-A116T, A088T-N109G-A116T-G131H-N218S, A088T-N109G-A116T-G131H-N218S-S248N-L257G, A088T-N109G-A116T-G131H-N243V-S248N-K256R-L257G, A088T-N109G-A116T-G131H-T158S-S248N-K256R-L257G, A088T-N109G-A116T-N218S-N243V-K256R, A088T-N109G-A116T-N218S-N243V-L257G, A088T-N109G-A116T-N243V-S248N-K256R, A088T-N109G-A116T-N243V-S248N-K256R-L257G, A088T-N109G-A116T-T158S-L257G, A088T-N109G-A116T-T158S-N243V-L257G, A088T-N109G-G131H-T158S-N243V-S248N-K256R, A088T-N109G-G131H-T158S-W241R-S248N-K256R, A088T-N109G-K256R-L257G, A088T-N109G-L257G, A088T-N109G-N243V, A088T-N109G-N243V-K256R, A088T-N109G-N243V-K256R-L257G, A088T-N109G-S248N-K256R, A088T-N109G-T158S-N218S-K256R-L257G, A088T-N109G-T158S-N218S-N243V-S248N-K256R, A088T-N109G-T158S-N243V-K256R, A088T-N109G-T158S-N243V-K256R-L257G, A088T-N109G-T158S-N243V-S248N-A274D, A088T-N109G-T158S-S248N-

L257G, A088T-T158S-K256R, A088T-T158S-N218S-N243V-K256R-L257G, A088T-T158S-N243V-L257G, A116T-G131H-N218S-N243V-S248N, A116T-G131H-S248N-L257G, A116T-S248N-K256R-L257G, A116T-T158S-N218S-N243V-K256R, A116T-T158S-N218S-S248N-L257G-Q271R, A116T-T158S-N243V-K256R-L257G, A116T-T158S-N243V-S248N-L257G, G131H-S248N, G131H-T158S-I234T-N243V-K256R, G131H-W241L-N243V-S248N-K256R, N109G-A116T-G131H-A137V-T158S-S248N-K256R-L257G, N109G-A116T-G131H-A151S-N218S-K256R-L257G, N109G-A116T-G131H-T158S-N218S-N243V-K256R, N109G-A116T-G131H-T158S-N218S-S248N, N109G-A116T-G131H-T158S-N243V-S248N, N109G-A116T-S248N, N109G-A116T-T158S-L257G, N109G-A116T-T158S-N218S-W241R-N243V, N109G-A116T-T158S-N243V-S248N-L257G, N109G-A116T-T158S-S248N-K256R-L257G, N109G-A116T-T158S-S248N-L257G, N109G-G131H-N218S-L257G, N109G-G131H-N218S-S248N-K256R-L257G, N109G-G131H-T158S-N218S-S248N-K256R-L257G-A274T, N109G-K256R, N109G-N243V-L257G, N109G-T158S-N218S-K256R-L257G, N109G-T158S-N218S-L257G, N109G-T158S-S248N-K256R, P014L-A015L-L016C-H017T-S018L-Q019K-G020A-Y021T-T022L-G023E, S003F-A088T-N109G-A116T-T158S-N243V-K256R-L257G, V004A-A088T-A116T-T158S-N218S, V004A-N109G-A116T-G131H-S248N-K256R-L257G, V004L-A116T-N218S-N243V-S248N-L257G, Y006H-N109G-N218S-N243V-S248N, A001T-A116T-T158S-N243V-L257G, A088T-A116T, A088T-A116T-G131H-L257G, A088T-A116T-G131H-N218S-L257G, A088T-A116T-G131H-N218S-S248N-K256R-L257G, A088T-A116T-G131H-N218S-S248N-L257G, A088T-A116T-G131H-N243V-K256R-L257G, A088T-A116T-G131H-N243V-L257G, A088T-A116T-G131H-N243V-S248N, A088T-A116T-G131H-T158S-K256R-L257G, A088T-A116T-G131H-T158S-L257G, A088T-A116T-G131H-T158S-N218S, A088T-A116T-G131H-T158S-N218S-N243V-K256R-A273T, A088T-A116T-G131H-T158S-N218S-S248N-K256R, A088T-A116T-G131H-T158S-N218S-S248N-L257G, A088T-A116T-G131H-T158S-N243V-S248N-K256R, A088T-A116T-G131H-T158S-S248N, A088T-A116T-G131H-T158S-S248N-L257G, A088T-A116T-K256R, A088T-A116T-K256R-L257G, A088T-A116T-N218S-N243V-L257G, A088T-A116T-N243V-K256R, A088T-A116T-N243V-L257G, A088T-A116T-N243V-S248N-K256R-L257G, A088T-A116T-S248N-K256R, A088T-A116T-T158S-K256R, A088T-A116T-T158S-N218S, A088T-A116T-T158S-N218S-N243V-K256R, A088T-A116T-T158S-N218S-N243V-K256R-N269S, A088T-A116T-T158S-N218S-N243V-S248N, A088T-A116T-T158S-N218S-N243V-S248N, A088T-A116T-T158S-N218S-N243V-S248N-K256R-L257G, A088T-A116T-T158S-N243V-K256R, A088T-A116T-T158S-N243V-L257G, A088T-A116T-T158S-N243V-S248N-K256R, A088T-A116T-T158S-N243V-S248N-K256R-L257G, A088T-A116T-T158S-S248N-K256R, A088T-A116T-V143A-N218S-S248N-K256R, A088T-A116T-V147I-T158S-N218S-N243V-L257G, A088T-G131H-K256R-L257G, A088T-G131H-N218S-N243V-S248N, A088T-G131H-N218S-S248N-L257G, A088T-G131H-S248N-K256R-L257G, A088T-G131H-T158S-L257G, A088T-G131H-T158S-N218S-K256R, A088T-G131H-T158S-N218S-N243V-K256R-L257G, A088T-G131H-T158S-N218S-N243V-L257G, A088T-G131H-T158S-N218S-S248N, A088T-G131H-T158S-N243V, A088T-G131H-T158S-N243V, A088T-G131H-T158S-N243V-S248N, A088T-G131H-T158S-N243V-S248N-K256R, A088T-G131H-T158S-N243V-S248N-L257G, A088T-I107T-N109G-A116T-G131H-T158S-N218S-N243V-S248N, A088T-N109G-A116T-G131H-L257G, A088T-N109G-A116T-G131H-N218S, A088T-N109G-A116T-G131H-N218S-L257G, A088T-N109G-A116T-G131H-N218S-N243V, A088T-N109G-A116T-G131H-N218S-N243V-K256R-L257G, A088T-N109G-A116T-G131H-N218S-N243V-L257G, A088T-N109G-A116T-G131H-N218S-S248N-K256R-L257G, A088T-N109G-A116T-G131H-N243V, A088T-N109G-A116T-G131H-N243V-L257G, A088T-N109G-A116T-G131H-N243V-S248N-L257G, A088T-N109G-A116T-G131H-S248N, A088T-N109G-A116T-G131H-S248N-K256R, A088T-N109G-A116T-G131H-S248N-L257G, A088T-N109G-A116T-G131H-T158S-L257G, A088T-N109G-A116T-G131H-T158S-N218S, A088T-N109G-A116T-G131H-T158S-N218S-S248N-K256R, A088T-N109G-A116T-G131H-T158S-N218T-N243V, A088T-N109G-A116T-G131H-T158S-N243V-K256R, A088T-N109G-A116T-G131H-T158S-N243V-K256R-L257G, A088T-N109G-A116T-G131H-T158S-N243V-S248N, A088T-N109G-A116T-G131H-T158S-N243V-S248N-K256R, A088T-N109G-A116T-G131H-T158S-S248N-K256R-L257G, A088T-N109G-A116T-G131H-T158S-S248N-L257G, A088T-N109G-A116T-N218S, A088T-N109G-A116T-N218S-L257G, A088T-N109G-A116T-N218S-N243V, A088T-N109G-A116T-N218S-N243V-S248N-L257G, A088T-A088T-N109G-A116T-N218T-K256R, A088T-N109G-A116T-N218T-K256R-L257G, A088T-N109G-A116T-N243V, A088T-N109G-A116T-N243V-K256R-L257G, A088T-N109G-A116T-N243V-K256R-L257G-N269D, A088T-N109G-A116T-S248N-K256R, A088T-N109G-A116T-T158S, A088T-N109G-A116T-T158S-N218S-L257G, A088T-N109G-A116T-T158S-N218S-N243V, A088T-N109G-A116T-T158S-N218S-N243V-K256R, A088T-N109G-A116T-T158S-N218S-N243V-K256R-L257G, A088T-N109G-A116T-T158S-N218S-N243V-K256R-L257G, A088T-N109G-A116T-T158S-N218S-N243V-L257G, A088T-N109G-A116T-T158S-N218S-S248N, A088T-N109G-A116T-T158S-N243V, A088T-N109G-A116T-T158S-N243V-K256R, A088T-N109G-A116T-T158S-N243V-K256R-L257G, A088T-N109G-A116T-T158S-S248N-L257G, A088T-N109G-G131H-L257G, A088T-N109G-G131H-N218S-K256R-L257G, A088T-N109G-G131H-N218S-N243V-K256R, A088T-N109G-G131H-N218S-N243V-L257G, A088T-N109G-G131H-N218S-N243V-S248N-K256R-L257G, A088T-N109G-G131H-N243V, A088T-N109G-G131H-N243V-L257G, A088T-N109G-G131H-N243V-S248N-K256R, A088T-N109G-G131H-N243V-S248N-L257G, A088T-N109G-G131H-S248N-L257G, A088T-N109G-G131H-T158S-L257G, A088T-N109G-G131H-T158S-N218S-N243V-S248N-K256R, A088T-N109G-G131H-T158S-N243V, A088T-N109G-G131H-T158S-N243V-K256R, A088T-N109G-G131H-T158S-N243V-K256R-L257G, A088T-N109G-G131H-T158S-N243V-L257G, A088T-N109G-L257G, A088T-N109G-N218S-K256R, A088T-N109G-N218S-N243V-S248N-L257G, A088T-N109G-N218S-S248N-K256R-L257G, A088T-N109G-N243V-K256R-L257G, A088T-N109G-N243V-S248N-K256R-L257G, A088T-N109G-N243V-S248N-L257G-I268V, A088T-N109G-S248N-K256R-L257G, A088T-N109G-T158S-N218S-K256R, A088T-N109G-T158S-N218S-N243V-L257G, A088T-N109G-T158S-N218S-N243V-L257G, A088T-N109G-T158S-N243V-K256R-I268V, A088T-N109G-T158S-N243V-

S248N-Q275R, A088T-N218S-N243V, A088T-N218S-N243V-S248N-K256R-L257G, A088T-N218S-S248N, A088T-N218S-S248N-L257G, A088T-N243V, A088T-N243V, A088T-N243V-K256R, A088T-N243V-L257G, A088T-S145T-T158S-S248N, A088T-T158S-L257G, A088T-T158S-N218S-S248N-L257G, A088T-T158S-N243V-K256R-L257G-Q271H, A088T-T158S-S248N, A088T-V143A-T158S-K256R, A116T-G131H-K256R, A116T-G131H-N218S, A116T-G131H-N243V, A116T-G131H-N243V-K256R, A116T-G131H-N243V-L257G, A116T-G131H-S248N-K256R, A116T-G131H-T158S-N218S-I234T-N243V-S248N-K256R, A116T-G131H-T158S-N243V-L257G, A116T-G131H-T158S-N243V-S248N-K256R, A116T-G131H-V143F-T158S-N218S, A116T-L257G, A116T-N218S, A116T-N218S-L257G, A116T-N218S-N243V-L257G, A116T-N243V, A116T-N243V-K256R, A116T-N243V-S248N, A116T-N243V-S248N-K256R-L257G, A116T-S248N, A116T-T158S, A116T-T158S-N218S-N243V, A116T-T158S-N218S-S248N, A116T-T158S-N243V, A116T-T158S-N243V-K256R, A116T-T158S-N243V-L257G, A116T-T158S-N243V-S248N, A116T-T158S-S248N-K256R-L257G, A116T-V149I-T158S-N243V-S248N-K256R-Q271H, G131H-N218S-N243V-L257G, G131H-N243V, G131H-N243V-S248N-K256R, G131H-T158S, G131H-T158S-N218S-N243V-K256R, G131H-T158S-N243V-K256R-L257G, G131H-T158S-N243V-S248N-L257G, N109G-A116T-G131H-N218S-K256R-L257G, N109G-A116T-G131H-N218S-L257G, N109G-A116T-G131H-N218S-N243V-K256R-L257G, N109G-A116T-G131H-N218S-S248N-K256R, N109G-A116T-G131H-N243V-K256R, N109G-A116T-G131H-N243V-L257G, N109G-A116T-G131H-N243V-S248N-K256R-L257G, N109G-A116T-G131H-S248N, N109G-A116T-G131H-S248N-I268V, N109G-A116T-G131H-T158S-N218S-N243V-S248N-K256R, N109G-A116T-G131H-T158S-N218S-S248N-L257G, N109G-A116T-G131H-T158S-S248N, N109G-A116T-G131H-T158S-S248N-K256R, N109G-A116T-N218S, N109G-A116T-N218S-N243V-K256R, N109G-A116T-N218S-N243V-K256R-L257G, N109G-A116T-N218S-S248N-L257G, N109G-A116T-N243V-K256R, N109G-A116T-N243V-S248N-K256R-L257G, N109G-A116T-S248N-L257G, N109G-A116T-T158S-G211V-N243V-S248N-K256R, N109G-A116T-T158S-K256R-L257G, N109G-A116T-T158S-N218S, N109G-A116T-T158S-N218S-N243V-K256R-L257G, N109G-A116T-T158S-N218S-N243V-L257G, N109G-A116T-T158S-N218S-N243V-S248N-L257G, N109G-A116T-T158S-N218S-S248N-K256R-L257G, N109G-A116T-T158S-N243V, N109G-A116T-T158S-Q275R, N109G-G131H-A137V-T158S-N218S-S248N, N109G-G131H-N218S-K237N, N109G-G131H-N218S-N243V-K256R-L257G, N109G-G131H-N218S-S248N-K256R, N109G-G131H-N243V-K256R-L257G, N109G-G131H-S145F-N218S-N243V-K256R-L257G, N109G-G131H-S248N-K256R, N109G-G131H-S248N-L257G, N109G-G131H-T158S-K256R, N109G-G131H-T158S-N218S-N243V-K256R, N109G-G131H-T158S-N243V, N109G-G131H-T158S-N243V-K256R-L257G, N109G-G131H-T158S-N243V-L257G, N109G-G131H-T158S-S248N-L257G, N109G-G131H-T158S-S248N-Q271R, N109G-N218S-L257G, N109G-N218S-N243V, N109G-N243V-K256R-L257G, N109G-N243V-S248N-K256R-L257G, N109G-T158S-I268V, N109G-T158S-K256R, N109G-T158S-N218S-N243V-K256R-L257G, N109G-T158S-N218S-S248N-L257G, N109G-T158S-N243V, N109G-T158S-N243V-K256R-L257G, N109G-T158S-N243V-S248N, N109S-A116T-S248N, N218S, N218S-N243V-S248N-K256R-L257G, N218S-S248N-L257G, N243V, N243V-K256R, N243V-S248N-K256R, N243V-S248N-K256R-L257G, S105P-A116T-T158S-N218S-N243V-S248N-K256R, S248N, T158S-N243V-K256R, and T158S-N243V-L257G, wherein amino acid positions of the variant are numbered by correspondence with the sequence of SEQ ID NO:2. Such variants have enhanced proteolytic activity compared to BPN', BPN'-v3, and BPN'-v36, and a greater PI value than BPN', BPN'-v3 and BPN'-v36 in this assay. The invention includes a protease variant having enhanced proteolytic activity compared to BPN' (SEQ ID NO:2), enhanced proteolytic activity compared to BPN', BPN'-v3, and BPN'-v36, a PI value of greater than 1.0 to about 5 relative to BPN'-v3, and/or a PI value of greater than 1.0 to about 5 relative to BPN'-v36 in this assay, the variant comprising an amino acid sequence having at least 60%, 70%, 80%, 85%, 90%, 91%, 92%, 93%, 94%, 95%, 96%, 97%, or 98% or 99% identity to SEQ ID NO:2 or SEQ ID NO:6 and comprising at least one set of amino acid substitutions selected from said group above, wherein amino acid positions of the variant are numbered by correspondence with amino acid positions of the SEQ ID NO:2 sequence. Also included are compositions, including, but not limited to, e.g., cleaning compositions, comprising at least one such variant and methods for cleaning utilizing at least one such variant as described in greater detail elsewhere herein.

The following BPN'-v36 variants were determined to have a PI value equal to about 1.0 relative to BPN'-v36 in a BMI microswatch cleaning assay (Test Method 3) in Detergent Composition 4 at pH 8 and 16° C.: BPN'-S024G-S053G-S078N-S101N-G128A-Y217Q amino acid sequence (SEQ ID NO:6) comprising at least one set of amino acid substitutions selected from the group consisting of BPN'-v36, A088T, A088T-A116T-G131H-L257G, A088T-A116T-G131H-N218S-A274T, A088T-A116T-G131H-N218S-K256R, A088T-A116T-G131H-N218S-K256R-L257G, A088T-A116T-G131H-N218S-N243V, A088T-A116T-G131H-N218S-N243V-L257G, A088T-A116T-G131H-N218S-N243V-S248N-K256R, A088T-A116T-G131H-N218S-N243V-S248N-K256R-L257G, A088T-A116T-G131H-N218S-N243V-S248N-L257G, A088T-A116T-G131H-N218S-S248N, A088T-A116T-G131H-N218S-S248N-L257G, A088T-A116T-G131H-N243V, A088T-A116T-G131H-N243V-K256R, A088T-A116T-G131H-N243V-S248N, A088T-A116T-G131H-N243V-S248N-A274V, A088T-A116T-G131H-N243V-S248N-K256R-L257G, A088T-A116T-G131H-N243V-S248N-K256R-L257G, A088T-A116T-G131H-N243V-S248N-L257G, A088T-A116T-G131H-S248N-K256R, A088T-A116T-G131H-S248N-K256R-L257G, A088T-A116T-G131H-T158S-K256R, A088T-A116T-G131H-T158S-K256R-L257G, A088T-A116T-G131H-T158S-N218S-K256R, A088T-A116T-G131H-T158S-N218S-K256R-L257G, A088T-A116T-G131H-T158S-N218S-L257G, A088T-A116T-G131H-T158S-N218S-N243V-K256R, A088T-A116T-G131H-T158S-N218S-N243V-K256R-L257G, A088T-A116T-G131H-T158S-N218S-N243V-L257G, A088T-A116T-G131H-T158S-N218S-N243V-S248N, A088T-A116T-G131H-T158S-N218S-N243V-S248N, A088T-A116T-G131H-T158S-N218S-N243V-S248N-K256R, A088T-A116T-G131H-T158S-N243V-K256R, A088T-A116T-G131H-T158S-N243V-K256R, A088T-A116T-G131H-T158S-N243V-K256R-L257G, A088T-A116T-G131H-T158S-N243V-L257G, A088T-A116T-G131H-T158S-N243V-S248N, A088T-A116T-G131H-T158S-N243V-S248N-K256R-L257G, A088T-A116T-G131H-

T158S-N243V-S248N-K256R-L257G, A088T-A116T-G131H-T158S-N243V-S248N-L257G, A088T-A116T-G131H-T158S-S248N-K256R, A088T-A116T-G131H-T158S-S248N-K256R-L257G, A088T-A116T-K256R, A088T-A116T-L257G, A088T-A116T-N218S, A088T-A116T-N218S-N243V-K256R, A088T-A116T-N218S-N243V-N269D, A088T-A116T-N218S-N243V-S248N, A088T-A116T-N218S-N243V-S248N-K256R-L257G, A088T-A116T-N218S-N243V-S248N-L257G, A088T-A116T-N218S-S248N, A088T-A116T-N218S-S248N-L257G, A088T-A116T-N243V-K256R-L257G, A088T-A116T-N243V-S248N-K256R, A088T-A116T-S248N, A088T-A116T-S248N-K256R, A088T-A116T-T158S-A216S-N218S-N243V-K256R-L257G, A088T-A116T-T158S-N218S-K256R, A088T-A116T-T158S-N218S-N243V-K256R, A088T-A116T-T158S-N218S-N243V-S248N-K256R-L257G, A088T-A116T-T158S-N218S-S248N, A088T-A116T-T158S-N243V-K256R, A088T-A116T-T158S-N243V-S248N, A088T-A116T-T158S-N243V-S248N-K256R, A088T-A116T-T158S-N243V-S248N-L257G, A088T-A116T-T158S-S248N, A088T-G131D-T158S-N243V-S248N, A088T-G131H-A138V-N218S-L257G, A088T-G131H-K256R, A088T-G131H-N218S-N243V-K256R, A088T-G131H-N218S-N243V-K256R, A088T-G131H-N218S-S248N, A088T-G131H-N218S-S248N-K256R-L257G, A088T-G131H-N218T-L257G, A088T-G131H-N243V-L257G, A088T-G131H-N243V-S248N-K256R, A088T-G131H-S248N, A088T-G131H-S248N-L257G, A088T-G131H-T158S-K256R, A088T-G131H-T158S-K256R-L257G, A088T-G131H-T158S-N218S, A088T-G131H-T158S-N218S, A088T-G131H-T158S-N218S-K256R-L257G, A088T-G131H-T158S-N218S-N243V-K256R, A088T-G131H-T158S-N218S-N243V-K256R, A088T-G131H-T158S-N218S-N243V-S248N, A088T-G131H-T158S-N218S-S248N, A088T-G131H-T158S-N218S-S248N-K256R, A088T-G131H-T158S-N218S-S248N-L257G-I268V, A088T-G131H-T158S-N243V-K256R, A088T-G131H-T158S-N243V-K256R-L257G, A088T-G131H-T158S-N243V-S248N, A088T-G131H-T158S-N243V-S248N-K256R-L257G, A088T-G131H-T158S-S248N, A088T-G131H-T158S-S248N-K256R, A088T-N109G-A116T-G131H-K256R, A088T-N109G-A116T-G131H-K256R-L257G, A088T-N109G-A116T-G131H-K256R-L257G, A088T-N109G-A116T-G131H-N218S-K256R, A088T-N109G-A116T-G131H-N218S-K256R, A088T-N109G-A116T-G131H-N218S-K256R-L257G, A088T-N109G-A116T-G131H-N218S-N243V-L257G, A088T-N109G-A116T-G131H-N218S-S248N, A088T-N109G-A116T-G131H-N218S-S248N-L257G, A088T-N109G-A116T-G131H-N243V-K256R, A088T-N109G-A116T-G131H-N243V-K256R-L257G, A088T-N109G-A116T-G131H-N243V-S248N-K256R, A088T-N109G-A116T-G131H-N243V-S248N-K256R, A088T-N109G-A116T-G131H-S248N-K256R-L257G, A088T-N109G-A116T-G131H-S248N-K256R-L257G, A088T-N109G-A116T-G131H-S248N-L257G, A088T-N109G-A116T-G131H-T158S-K256R, A088T-N109G-A116T-G131H-T158S-L257G, A088T-N109G-A116T-G131H-T158S-N218S, A088T-N109G-A116T-G131H-T158S-N218S-L257G, A088T-N109G-A116T-G131H-T158S-N218S-N243V, A088T-N109G-A116T-G131H-T158S-N218S-N243V-K256R, A088T-N109G-A116T-G131H-T158S-N218S-N243V-L257G, A088T-N109G-A116T-G131H-T158S-N218S-N243V-S248N-K256R, A088T-N109G-A116T-G131H-T158S-N218S-N243V-S248N-K256R, A088T-N109G-A116T-G131H-T158S-N218S-N243V-S248N-K256R-L257G,

A088T-N109G-A116T-G131H-T158S-N218S-S248N, A088T-N109G-A116T-G131H-T158S-N218T-K256R, A088T-N109G-A116T-G131H-T158S-N243V, A088T-N109G-A116T-G131H-T158S-N243V-S248N, A088T-N109G-A116T-G131H-T158S-N243V-S248N-K256R-L257G, A088T-N109G-A116T-G131H-T158S-N243V-S248N-L257G, A088T-N109G-A116T-G131H-V149A-T158S-N218S-K256R, A088T-N109G-A116T-K256R, A088T-N109G-A116T-N218S-K256R, A088T-N109G-A116T-N218S-N243V, A088T-N109G-A116T-N218S-N243V-K256R-L257G, A088T-N109G-A116T-N218S-N243V-L257G, A088T-N109G-A116T-N218S-N243V-S248N-K256R, A088T-N109G-A116T-N218S-S248N, A088T-N109G-A116T-N218S-S248N-K256R-L257G, A088T-N109G-A116T-N243V-K256R, A088T-N109G-A116T-N243V-S248N-K256R-L257G, A088T-N109G-A116T-N243V-S248N-L257G, A088T-N109G-A116T-N243V-S248N-L257G, A088T-N109G-A116T-S248N, A088T-N109G-A116T-S248N-K256R-L257G, A088T-N109G-A116T-S248N-L257G, A088T-N109G-A116T-T158S, A088T-N109G-A116T-T158S-K256R, A088T-N109G-A116T-T158S-N218S, A088T-N109G-A116T-T158S-N218S-L257G, A088T-N109G-A116T-T158S-N218S-N243V-S248N, A088T-N109G-A116T-T158S-N218S-N243V-S248N, A088T-N109G-A116T-T158S-N218S-N243V-S248N-K256R, A088T-N109G-A116T-T158S-N218S-N243V-S248N-K256R-L257G, A088T-N109G-A116T-T158S-N218S-S248N, A088T-N109G-A116T-T158S-N218S-S248N-K256R, A088T-N109G-A116T-T158S-N218S-S248N-L257G, A088T-N109G-A116T-T158S-N218S-S248N-L257G, A088T-N109G-A116T-T158S-N243V-K256R, A088T-N109G-A116T-T158S-N243V-S248N, A088T-N109G-A116T-T158S-S248N, A088T-N109G-A116T-T158S-S248N-K256R, A088T-N109G-A137E-T158S-N218S-N243V-S248N-K256R-L257G, A088T-N109G-G131H-A152S-T158S-N218S-S248N-K256R, A088T-N109G-G131H-K256R-L257G, A088T-N109G-G131H-N218S, A088T-N109G-G131H-N218S, A088T-N109G-G131H-N218S-K256R, A088T-N109G-G131H-N218S-K256R, A088T-N109G-G131H-N218S-L257G, A088T-N109G-G131H-N218S-N243V, A088T-N109G-G131H-N218S-N243V-K256R, A088T-N109G-G131H-N218S-N243V-K256R-L257G, A088T-N109G-G131H-N218S-N243V-S248N-K256R, A088T-N109G-G131H-N218S-S248N, A088T-N109G-G131H-N218S-S248N-K256R, A088T-N109G-G131H-N218S-S248N-K256R, A088T-N109G-G131H-N218S-S248N-K256R-L257G, A088T-N109G-G131H-N243V-K256R, A088T-N109G-G131H-N243V-K256R-L257G, A088T-N109G-G131H-N243V-K256R-L257G, A088T-N109G-G131H-N243V-L257G, A088T-N109G-G131H-N243V-S248N-K256R, A088T-N109G-G131H-S248N-K256R, A088T-N109G-G131H-S248N-L257G, A088T-N109G-G131H-T158S, A088T-N109G-G131H-T158S-K256R, A088T-N109G-G131H-T158S-K256R-L257G, A088T-N109G-G131H-T158S-N218S-K256R, A088T-N109G-G131H-T158S-N218S-K256R, A088T-N109G-G131H-T158S-N218S-L257G, A088T-N109G-G131H-T158S-N218S-L257G, A088T-N109G-G131H-T158S-N218S-N243V, A088T-N109G-G131H-T158S-N218S-N243V-K256R, A088T-N109G-G131H-T158S-N218S-N243V-S248N, A088T-N109G-G131H-T158S-N218S-S248N-L257G, A088T-N109G-G131H-T158S-N243V-K256R-L257G, A088T-N109G-G131H-T158S-N243V-S248N, A088T-N109G-G131H-T158S-N243V-S248N-K256R-L257G, A088T-N109G-G131H-T158S-N243V-S248N-K256R-L257G, A088T-N109G-G131H-T158S-

N243V-S248N-L257G, A088T-N109G-G131H-T158S-N243V-S248N-L257G, A088T-N109G-G131H-T158S-S248N, A088T-N109G-G131H-T158S-S248N-L257G, A088T-N109G-G131H-V149A-K256R-L257G, A088T-N109G-G154A-N155P-E156T-G157L-T158M-S159E-G160E-S161L, A088T-N109G-K256R-L257G, A088T-N109G-N218S-K256R, A088T-N109G-N218S-N243V-L257G, A088T-N109G-N218S-N243V-S248N-K256R, A088T-N109G-N218S-N243V-S248N-K256R, A088T-N109G-N218S-S248N, A088T-N109G-N218S-S248N-L257G, A088T-N109G-N218S-S248N-L257G, A088T-N109G-N243V-S248N-K256R, A088T-N109G-S248N, A088T-N109G-S248N, A088T-N109G-T158S-N218S, A088T-N109G-T158S-N218S-K256R-Q271H, A088T-N109G-T158S-N218S-N243V, A088T-N109G-T158S-N218S-N243V-K256R-Q275R, A088T-N109G-T158S-N218S-N243V-S248N-K256R-L257G, A088T-N109G-T158S-N218S-S248N, A088T-N109G-T158S-N218S-S248N-K256R, A088T-N109G-T158S-N218S-S248N-N269D, A088T-N109G-T158S-N243V-K256R, A088T-N109G-T158S-N243V-S248N-K256R, A088T-N109G-T158S-N243V-S248N-K256R-L257G-N269D, A088T-N109G-T158S-N243V-S248N-L257G, A088T-N109G-T158S-S248N-K256R-L257G, A088T-N109G-T158S-S248N-L257G, A088T-N109G-V147A-N218S-N243V-K256R, A088T-N218S, A088T-N218S-K256R, A088T-N218S-L257G-I268V, A088T-N218S-N243V, A088T-N218S-N243V-K256R, A088T-N218S-N243V-K256R-L257G, A088T-N218S-N243V-L257G, A088T-N218S-N243V-S248N-K256R-L257G, A088T-N218S-N243V-S248N-L257G, A088T-N218S-N243V-S248N-N269S, A088T-N218S-S248N-K256R, A088T-N243V-S248N, A088T-N243V-S248N-K256R, A088T-N243V-S248N-K256R, A088T-N243V-S248N-K256R-L257G, A088T-N243V-S248N-L257G, A088T-S248N, A088T-S248N, A088T-S248N-K256R-L257G, A088T-S248N-L257G, A088T-S248N-L257G-I268V, A088T-T158S, A088T-T158S, A088T-T158S-N218S, A088T-T158S-N218S-K256R, A088T-T158S-N218S-L257G, A088T-T158S-N218S-N243V-K256R-I268V, A088T-T158S-N218S-N243V-K256R-L257G, A088T-T158S-N218S-N243V-S248N-L257G, A088T-T158S-N218S-S248N, A088T-T158S-N243V-K256R, A088T-T158S-N243V-K256R-L257G, A088T-T158S-N243V-S248N-K256R, A088T-T158S-N243V-S248N-L257G, A088T-T158S-N243V-S248N-L257G, A088T-T158S-S248N, A088T-T158S-S248N-L257G, A088T-V147A-K256R, A098S-G131H-T158S-N218S-N243V-S248N-K256R-L257G, A116T-G131H-N218S-K256R, A116T-G131H-N218S-K256R-L257G, A116T-G131H-N218S-L257G, A116T-G131H-N218S-N243V-S248N-L257G, A116T-G131H-N218S-S248N-K256R-L257G, A116T-G131H-N243V-S248N, A116T-G131H-N243V-S248N-L257G, A116T-G131H-T158S-A231V-N243V-L257G, A116T-G131H-T158S-K256R, A116T-G131H-T158S-K256R-L257G, A116T-G131H-T158S-N218S-K256R, A116T-G131H-T158S-N218S-K256R-L257G, A116T-G131H-T158S-N218S-N243V, A116T-G131H-T158S-N218S-N243V-K256R, A116T-G131H-T158S-N218S-N243V-K256R-L257G, A116T-G131H-T158S-N218S-N243V-L257G, A116T-G131H-T158S-N218S-N243V-S248N-K256R, A116T-G131H-T158S-N218S-N243V-S248N-K256R-L257G, A116T-G131H-T158S-N218S-N243V-S248N-L257G, A116T-G131H-T158S-N218S-S248N-K256R, A116T-G131H-T158S-N218T-L257G, A116T-G131H-T158S-S248N-K256R, A116T-G131H-T158S-S248N-L257G, A116T-N218S-K256R, A116T-N218S-K256R-L257G, A116T-N218S-N243V-S248N-K256R, A116T-N218S-N243V-S248N-K256R-L257G, A116T-N218S-N243V-S248N-L257G, A116T-N218S-S248N, A116T-N218S-S248N-K256R, A116T-N218S-S248N-L257G, A116T-N243V-S248N-L257G, A116T-S248N-L257G, A116T-T158S-L257G-Q271R, A116T-T158S-N218S-L257G, A116T-T158S-N218S-N243V-K256R-L257G, A116T-T158S-N218S-S248N-K256R, A116T-T158S-N218S-S248N-K256R-L257G, A116T-T158S-N243V-S248N-K256R, A116T-T158S-N243V-S248N-K256R-L257G, G024S-G053S-N078S-G097A-N101S-A128S, G131H, G131H-N218S, G131H-N218S-K256R, G131H-N218S-N243V-K256R, G131H-N218S-N243V-K256R-L257G, G131H-N218S-N243V-S248N, G131H-N218S-N243V-S248N-K256R, G131H-N218S-S248N-K256R-L257G, G131H-N218S-S248N-L257G, G131H-N243V-K256R, G131H-N243V-K256R-L257G, G131H-N243V-S248N-K256R-L257G, G131H-S248N-K256R, G131H-T158S-K256R, G131H-T158S-K256R-L257G, G131H-T158S-N218S-K256R, G131H-T158S-N218S-K256R-L257G, G131H-T158S-N218S-N243V-K256R-L257G, G131H-T158S-N218S-N243V-S248N, G131H-T158S-N218S-S248N-K256R-L257G, G131H-T158S-N218S-S248N-L257G, G131H-T158S-N243V-K256R, G131H-T158S-N243V-S248N-K256R, G131H-T158S-S248N-L257G, G131H-V147I-N218S-S248N-K256R, I107T-N109G-A116T-G131H-T158S-N218S-N243V-S248N-K256R-L257G, I107T-N109G-G131H-N218S-N243V-K256R-L257G, N109G, N109G-A116T-G131H, N109G-A116T-G131H-A144V-T158S-S248N-K256R-L257G, N109G-A116T-G131H-K256R-L257G, N109G-A116T-G131H-L257G, N109G-A116T-G131H-N218S-N243V-K256R, N109G-A116T-G131H-N218S-N243V-S248N-K256R, N109G-A116T-G131H-N243V, N109G-A116T-G131H-N243V-K256R-L257G, N109G-A116T-G131H-N243V-S248N, N109G-A116T-G131H-N243V-S248N-K256R, N109G-A116T-G131H-S248N-K256R, N109G-A116T-G131H-T158S-K256R, N109G-A116T-G131H-T158S-K256R-L257G, N109G-A116T-G131H-T158S-L257G, N109G-A116T-G131H-T158S-N218S, N109G-A116T-G131H-T158S-N218S-K256R-L257G, N109G-A116T-G131H-T158S-N218S-L257G, N109G-A116T-G131H-T158S-N218S-N243V-S248N-K256R-L257G, N109G-A116T-G131H-T158S-N218S-S248N-K256R, N109G-A116T-G131H-T158S-N218S-S248N-K256R-L257G, N109G-A116T-G131H-T158S-N243V-L257G, N109G-A116T-G131H-T158S-S248N-L257G, N109G-A116T-G131H-V147A-T158S-N218S-K256R-L257G, N109G-A116T-G131H-V149A-T158S-N218S-N243V-S248N-L257G, N109G-A116T-K256R, N109G-A116T-N218S-K256R, N109G-A116T-N218S-N243V, N109G-A116T-N218S-N243V-L257G, N109G-A116T-N218S-N243V-S248N-I268V, N109G-A116T-N218S-N243V-S248N-K256R-L257G, N109G-A116T-N218S-N243V-S248N-L257G, N109G-A116T-N243V-S248N, N109G-A116T-N243V-S248N-K256R, N109G-A116T-N243V-S248N-L257G, N109G-A116T-S248N-K256R, N109G-A116T-T158S, N109G-A116T-T158S-N218S-N243V-S248N-K256R, N109G-A116T-T158S-N218S-N243V-S248N-K256R-L257G, N109G-A116T-T158S-N218S-S248N-K256R, N109G-A116T-T158S-N243V-L257G, N109G-A116T-T158S-N243V-S248N, N109G-A116T-T158S-S248N, N109G-A116T-T158S-S248N-K256R, N109G-G131H, N109G-G131H-K256R, N109G-G131H-N218S-K256R, N109G-G131H-N218S-K256R-L257G, N109G-G131H-N218S-N243V-L257G, N109G-G131H-N218S-N243V-S248N-K256R, N109G-G131H-N218S-N243V-

S248N-K256R-L257G, N109G-G131H-N218S-N243V-S248N-L257G, N109G-G131H-N218S-S248N-L257G, N109G-G131H-N243V, N109G-G131H-N243V-K256R, N109G-G131H-N243V-S248N, N109G-G131H-N243V-S248N-K256R-L257G, N109G-G131H-N243V-S248N-L257G, N109G-G131H-T158S-N218S-K256R-L257G, N109G-G131H-T158S-N218S-L257G, N109G-G131H-T158S-N218S-N243V, N109G-G131H-T158S-N218S-N243V-K256R-L257G, N109G-G131H-T158S-N218S-N243V-S248N, N109G-G131H-T158S-N218S-N243V-S248N-K256R-L257G, N109G-G131H-T158S-N218S-N243V-S248N-L257G, N109G-G131H-T158S-N218S-S248N-K256R-L257G, N109G-G131H-T158S-N243V-K256R-I268V, N109G-G131H-T158S-N243V-S248N, N109G-G131H-T158S-N243V-S248N-K256R, N109G-G131H-T158S-N243V-S248N-L257G, N109G-G131H-T158S-S248N, N109G-G131H-T158S-S248N-K256R-L257G, N109G-K141E-N218S-S248N-L257G, N109G-N218S, N109G-N218S-N243V-K256R, N109G-N218S-N243V-L257G, N109G-N218S-N243V-S248N-S260F, N109G-N218S-S248N, N109G-N218S-S248N-K256R, N109G-N243V-K256R, N109G-N243V-S248N, N109G-N243V-S248N-K256R, N109G-N243V-S248N-L257G, N109G-N243V-S248N-L257G-Q275R, N109G-S182F-S204F-S207L-N218S-S236F-S248N-L257G, N109G-S248N-K256R, N109G-T158S-K256R-L257G, N109G-T158S-L257G, N109G-T158S-N218S-N243V-K256R, N109G-T158S-N218S-N243V-S248N, N109G-T158S-N218S-N243V-S248N-L257G, N109G-T158S-N243V-K256R, N109G-T158S-N243V-S248N-K256R, N109G-T158S-N243V-S248N-L257G, N109G-T158S-S248N-L257G, N218S-N243V-L257G, N218S-N243V-S248N-K256R, N243V-K256R-L257G, N243V-S248N-L257G-Q271R, P057Q-A088T-N109G-A116T-G131H-T158S-N218S-S248N, S003P-A116T-N218S-K256R, S003P-N109G-G131H-N218S-N243V-S248N-K256R-L257G, S248N-K256R-L257G, T158S-K256R-L257G, T158S-N218S-A272V, T158S-N218S-K256R-L257G, T158S-N218S-L233S, T158S-N218S-N243V, T158S-N218S-N243V-K256R-L257G, T158S-N218S-N243V-L257G, T158S-N218S-N243V-S248N-K256R, T158S-N218S-S248N-K256R, T158S-N243V, T158S-N243V-K256R-L257G, T158S-N243V-S248N, T158S-N243V-S248N-K256R-N269D, and V004A-N109G-A116T-T158S-N218S-S248N-L257G, wherein amino acid positions of the variant are numbered by correspondence with the sequence of SEQ ID NO:2. Such variants have enhanced proteolytic activity compared to BPN' (SEQ ID NO:2) and a greater PI value than BPN' in this assay. The invention includes a protease variant having enhanced proteolytic activity compared to BPN' (SEQ ID NO:2), a PI value of 1.0 relative to BPN'-v3, and a PI value of 1.0 relative to BPN'-v36 in this assay, the variant comprising an amino acid sequence having at least 60%, 70%, 80%, 85%, 90%, 91%, 92%, 93%, 94%, 95%, 96%, 97%, or 98% or 99% identity to SEQ ID NO:2 or SEQ ID NO:6 and comprising at least one set of amino acid substitutions selected from said group above, wherein amino acid positions of the variant are numbered by correspondence with amino acid positions of the SEQ ID NO:2 sequence. Also included are compositions, including, but not limited to, e.g., cleaning compositions, comprising at least one such variant and methods for cleaning utilizing at least one such variant as described in greater detail elsewhere herein.

The following BPN'-v36 variants were determined to have a PI value equal to about 0.9 relative to BPN'-v36 in a BMI microswatch cleaning assay (Test Method 3) in Detergent Composition 4 at pH 8 and 16° C.: BPN'-S024G-S053G-S078N-S101N-G128A-Y217Q amino acid sequence (SEQ ID NO:6) comprising at least one set of amino acid substitutions selected from the group consisting of A088T-A098S-N218S-K256R, A088T-A116T-G131H-K256R, A088T-A116T-G131H-K256R-L257G-L267M, A088T-A116T-G131H-N218S-N243V-K256R, A088T-A116T-G131H-N218S-N243V-K256R-L257G, A088T-A116T-G131H-N218S-N243V-S248N, A088T-A116T-G131H-N218S-S248N, A088T-A116T-G131H-N218S-S248N-K256R, A088T-A116T-G131H-N218S-S248N-K256R, A088T-A116T-G131H-N243V, A088T-A116T-G131H-S248N, A088T-A116T-G131H-S248N-L257G, A088T-A116T-G131H-S248N-L257G, A088T-A116T-G131H-T158S-N218S, A088T-A116T-G131H-T158S-N218S-K256R-L257G, A088T-A116T-G131H-T158S-N218S-N243V-S248N-K256R, A088T-A116T-G131H-T158S-N218S-N243V-S248N-L257G, A088T-A116T-G131H-T158S-N218S-S248N, A088T-A116T-G131H-T158S-N218S-S248N-K256R, A088T-A116T-K256R-L257G, A088T-A116T-N218S-I268V, A088T-A116T-N218S-K256R, A088T-A116T-N218S-N243V-Q271R, A088T-A116T-N218S-N243V-S248N-K256R, A088T-A116T-N218S-N243V-S248N-K256R-Q275R, A088T-A116T-N218S-S248N, A088T-A116T-N218S-S248N-K256R, A088T-A116T-N243V-S248N-K256R, A088T-A116T-T158S, A088T-A116T-T158S-N218S-K256R, A088T-A116T-T158S-N218S-N243V-L257G, A088T-A116T-T158S-N218S-N243V-S248N-L257G, A088T-A116T-T158S-N218S-S248N, A088T-A116T-T158S-N218S-S248N-K256R, A088T-A116T-T158S-N218S-S248N-K256R-L257G, A088T-A116T-T158S-N218S-S248N-L257G, A088T-A116T-T158S-S248N-L257G, A088T-G131H, A088T-G131H, A088T-G131H-N218S-K237R-K256R-L257G, A088T-G131H-N218S-K256R, A088T-G131H-N218S-K256R-L257G, A088T-G131H-N218S-N243V-K256R-L257G, A088T-G131H-N218S-N243V-L257G, A088T-G131H-N218S-N243V-L257G, A088T-G131H-N218S-N243V-S248N, A088T-G131H-N218S-N243V-S248N-K256R, A088T-G131H-N218S-N243V-S248N-K256R-L257G, A088T-G131H-N218S-N243V-S248N-K256R-L257G, A088T-G131H-N218S-S248N, A088T-G131H-N243V, A088T-G131H-N243V-K256R, A088T-G131H-N243V-K256R-L257G, A088T-G131H-N243V-S248N, A088T-G131H-N243V-S248N, A088T-G131H-N243V-S248N-K256R, A088T-G131H-S248N, A088T-G131H-S248N-K256R, A088T-G131H-T158S-N218S-K256R-L257G, A088T-G131H-T158S-N218S-L257G, A088T-G131H-T158S-N218S-N243V, A088T-G131H-T158S-N218S-N243V-K256R-L257G, A088T-G131H-T158S-N218S-N243V-S248N-K256R, A088T-G131H-T158S-N218S-N243V-S248N-K256R-L257G, A088T-G131H-T158S-N218S-N243V-S248N-K256R-L257G, A088T-G131H-T158S-N218S-N243V-S248N-L257G, A088T-G131H-T158S-N218S-S248N-K256R, A088T-G131H-T158S-N218S-S248N-K256R-L257G, A088T-G131H-T158S-S248N-K256R-L257G, A088T-L257G, A088T-N109G-A116T-G131H-N218S-L257G, A088T-N109G-A116T-G131H-N218S-N243V-S248N-K256R, A088T-N109G-A116T-G131H-N218S-N243V-S248N-K256R-L257G, A088T-N109G-A116T-G131H-N218S-N243V-S248N-N269D, A088T-N109G-A116T-G131H-N218S-N243V-S248N-Q275R, A088T-N109G-A116T-G131H-N218S-S248N-K256R-L257G, A088T-N109G-A116T-G131H-N243V-S248N, A088T-N109G-A116T-G131H-T158S, A088T-N109G-A116T-G131H-T158S-N218S-L257G-I268V, A088T-N109G-A116T-G131H-T158S-N218S-N243V-K256R, A088T-N109G-A116T-

G131H-T158S-N218S-N243V-K256R-L257G, A088T-N109G-A116T-G131H-T158S-N218S-N243V-S248N, A088T-N109G-A116T-G131H-T158S-N218S-N243V-S248N-L257G, A088T-N109G-A116T-G131H-T158S-N218S-S248N-L257G, A088T-N109G-A116T-G131H-T158S-S248N, A088T-N109G-A116T-G131H-T158S-S248N, A088T-N109G-A116T-G131H-W241L-S248N-K256R-L257G, A088T-N109G-A116T-K256R, A088T-N109G-A116T-N218S-K256R-L257G, A088T-N109G-A116T-N218S-N243V-S248N-K256R, A088T-N109G-A116T-N218S-S248N, A088T-N109G-A116T-T158S-N218S, A088T-N109G-A116T-T158S-N218S-K256R-L257G, A088T-N109G-A116T-T158S-N218S-N243V-S248N-L257G, A088T-N109G-A116T-T158S-N243V-S248N, A088T-N109G-A116T-T158S-N243V-S248N-K256R, A088T-N109G-G131H-A138V-T158S-N218S-N243V-S248N-L257G, A088T-N109G-G131H-K256R-L257G, A088T-N109G-G131H-N218S-N243V, A088T-N109G-G131H-N218S-N243V-S248N-L257G, A088T-N109G-G131H-N218S-S248N-K256R-L257G, A088T-N109G-G131H-N218S-S248N-K256R-L257G-Q275R, A088T-N109G-G131H-N243V-S248N, A088T-N109G-G131H-N243V-S248N-K256R-L257G, A088T-N109G-G131H-T158S, A088T-N109G-G131H-T158S-L233S-N243V-S248N, A088T-N109G-G131H-T158S-N218S-N243V-K256R, A088T-N109G-G131H-T158S-N218S-N243V-K256R-L257G, A088T-N109G-G131H-T158S-N218S-N243V-S248N-K256R-L257G, A088T-N109G-G131H-T158S-N218S-N243V-S248N-K256R-L257G, A088T-N109G-G131H-T158S-N218S-N243V-S248N-L257G, A088T-N109G-G131H-T158S-N218S-S248N-K256R, A088T-N109G-G131H-T158S-N243V-S248N-K256R, A088T-N109G-G131H-T158S-S248N-K256R, A088T-N109G-G131H-T158S-S248N-K256R-L257G, A088T-N109G-G131H-V149A-K256R-L257G, A088T-N109G-N218S-K256R-L257G, A088T-N109G-N218S-N243V-K256R, A088T-N109G-N218S-N243V-L257G, A088T-N109G-N218S-N243V-S248N, A088T-N109G-N218S-N243V-S248N-K256R-L257G, A088T-N109G-N218S-S248N-K256R, A088T-N109G-N243V-K256R, A088T-N109G-N243V-S248N-K256R, A088T-N109G-S248N-K256R-L257G, A088T-N109G-T158S, A088T-N109G-T158S-K256R-L257G, A088T-N109G-T158S-N218S-N243V-K256R, A088T-N109G-T158S-N218S-N243V-K256R-L257G, A088T-N109G-T158S-N218S-N243V-S248N-K256R, A088T-N109G-T158S-N218S-N243V-S248N-L257G, A088T-N109G-T158S-N218S-S248N, A088T-N109G-T158S-S248N, A088T-N109G-T158S-S248N, A088T-N218S-N243V-K256R, A088T-N218S-N243V-L257G, A088T-N218S-N243V-S248N, A088T-N218S-N243V-S248N-K256R, A088T-N218S-N243V-S248N-K256R, A088T-N218S-S248N, A088T-N218S-S248N-L257G, A088T-S248N-K256R-L257G, A088T-T158S-K256R, A088T-T158S-N218S-N243V-K256R, A088T-T158S-N218S-N243V-L257G, A088T-T158S-N218S-N243V-S248N, A088T-T158S-N218S-N243V-S248N-K256R, A088T-T158S-N218S-N243V-S248N-K256R-L257G, A088T-T158S-N218S-N243V-S248N-K256R-L257G, A088T-T158S-N218S-N243V-S248N-L257G, A088T-T158S-N218S-S248N, A088T-T158S-N218S-S248N-K256R, A088T-T158S-N218S-S248N-L257G, A088T-T158S-N218S-S248N-L257G-Q275K, A088T-T158S-N243V, A088T-T158S-N243V-K256R, A088T-T158S-N243V-S248N, A088T-T158S-S248N-K256R-L257G, A088T-T158S-S248N-L257G, A088T-V147I-N218S-N243V-K256R-L257G, A116T-G131H-L257G, A116T-G131H-N218S-N243V, A116T-G131H-N218S-N243V-K256R-L257G, A116T-G131H-N218S-N243V-S248N-K256R-L257G, A116T-G131H-N218S-S248N, A116T-G131H-N218S-S248N-K256R, A116T-G131H-N243V-S248N-K256R, A116T-G131H-T158S-N218S-N243V-S248N, A116T-G131H-T158S-N218S-S248N, A116T-G131H-T158S-N243V-K256R, A116T-G131H-V139I-N218S-N243V-S248N, A116T-K141E-N218S-N243V-S248N-K256R-L257G, A116T-K256R, A116T-N218S-N243V-S248N, A116T-N218T-N243V-S248N, A116T-N243V-K256R-L257G, A116T-S248N-K256R, A116T-T158S-N218S-K256R, A116T-T158S-N218S-K256R-L257G, A116T-T158S-N218S-N243V-L257G, A116T-T158S-N218S-N243V-S248N, A116T-T158S-N218S-S248N-L257G, G024S-G053S-N078S-G097A-N101S, G053S-A088T-N109G-A116T-G131H-T158S-G169S-N218S-S248N-K256R-L257G, G131H-K141R-T158S-N218S-K256R, G131H-K256R, G131H-N218S-K256R-L257G, G131H-N218S-N243V-S248N-L257G, G131H-N218S-S248N-K256R, G131H-N243V-S248N, G131H-N243V-S248N-L257G, G131H-T158S-N218S, G131H-T158S-N218S-N240H-N243V-S248N-K256R-L257G, G131H-T158S-N218S-N243V, G131H-T158S-N218S-S248N-K256R-L257G-N269S, G131H-T158S-N243V-L257G, G131H-T158S-N243V-S248N, G131H-T158S-S248N, K256R, K256R-L257G, N109G-A116T-G131H-N218S-N243V, N109G-A116T-G131H-N218S-N243V-L257G, N109G-A116T-G131H-N218S-S248N-L257G, N109G-A116T-G131H-N218S-W241R-N243V-K256R, N109G-A116T-G131H-S248N-L257G, N109G-A116T-G131H-T158S-N218S-K256R, N109G-A116T-G131H-T158S-N218S-N243V-K256R-L257G, N109G-A116T-G131H-T158S-N218S-N243V-S248N, N109G-A116T-G131H-T158S-N218S-N243V-S248N-L257G, N109G-A116T-G131H-T158S-N243V-K256R-L257G, N109G-A116T-G131H-T158S-N243V-S248N-K256R, N109G-A116T-G131H-T158S-S248N-K256R-L257G, N109G-A116T-I234T-N243V-S248N-K256R-L257G, N109G-A116T-N218S-N243V-S248N, N109G-A116T-N243V-K256R-L257G, N109G-A116T-T158S-N218S-K237R-N243V-S248N, N109G-G131H-N218S-N243V-S248N, N109G-G131H-S248N, N109G-G131H-T158S, N109G-G131H-T158S-L257G, N109G-G131H-T158S-N218S-N243V-S248N-K256R, N109G-G131H-T158S-N218S-S248N-K256R, N109G-G131H-T158S-N218S-S248N-L257G, N109G-G131H-T158S-N243V-S248N-K256R-L257G, N109G-G131H-T158S-S248N-K256R, N109G-N218S-K256R-L257G, N109G-N218S-N243V-S248N-K256R, N109G-N218S-S248N-L257G, N109G-S248N, N109G-T158S-N218S, N109G-T158S-N218S-N243V, N109G-T158S-N243V-L257G, N218S-K256R, N218S-N243V-K256R, N218S-N243V-S248N, N218S-S248N, N218S-S248N-K256R, N243V-L257G, S003P-N109G-A116T-G131H-N218S-N243V-S248N, S003P-N109G-A116T-G131H-T158S-N218S-K256R, S105H-W106G-I107L-I108S-N109A-G110A-I111S-E112N-W113G-A114P, S248N-L257G, T158S, T158S-K256R, T158S-N218S, T158S-N218S-K256R, T158S-N218S-L233S-S248N, T158S-N218S-L257G, T158S-N218S-N243V-K256R, T158S-N218S-N243V-S248N, T158S-N218S-N243V-S248N-L257G, T158S-N218S-S248N-K256R-L257G, T158S-N218S-S248N-L257G, T158S-N243V-S248N-L257G, T158S-S248N, and V004L-A088T-G131H-T158S-N218S-S248N-L257G, wherein amino acid positions of the variant are numbered by correspondence with the sequence of SEQ ID NO:2. Such variants have proteolytic activity. The invention includes a protease variant having proteolytic activity and/or a PI value of 0.9 relative to BPN'-v36 in this assay, the variant comprising an amino acid sequence having at least 60%, 70%, 80%, 85%, 90%, 91%, 92%, 93%, 94%, 95%, 96%, 97%, or 98% or 99% identity to SEQ ID NO:2 or SEQ ID NO:6 and comprising at least one set of acid substitutions selected from said group above, wherein amino acid positions of the variant are numbered by correspondence with amino acid positions of the SEQ ID NO:2 sequence. Also included are compositions, including, but not limited to, e.g., cleaning compositions, comprising at least one such variant and methods for cleaning utilizing at least one such variant as described in greater detail elsewhere herein.

The following BPN'-v36 variants were determined to have a PI value equal to or greater than 0.5 and less than 0.9 relative to BPN'-v36 in a BMI microswatch cleaning assay (Test Method 3) in Detergent Composition 4 at pH 8 and 16° C.: BPN'-S024G-S053G-S078N-S101N-G128A-Y217Q amino acid sequence (SEQ ID NO:6) comprising at least one set of amino acid substitutions selected from the group consisting of A015S-A088T-N109G-G131H-T158S-N218S-S248N, A088T-A098S-G131H-S248N-K256R-L257G, A088T-A116T-G131H-N218S-N243V-K256R-L257G, A088T-A116T-G131H-T158S-L257G, A088T-A116T-G131H-T158S-N218S-L257G, A088T-A116T-G131H-T158S-N218S-N243V-S248N-K256R-L257G, A088T-A116T-G131H-T158S-N218S-N243V-S248N-L257G, A088T-A116T-N218S-L257G, A088T-A116T-T158S-K256R, A088T-A116T-T158S-S248N-K256R-L257G, A088T-G131H-K141E-N218S-N243V-S248N-L257G, A088T-G131H-K256R, A088T-G131H-N218S-K256R, A088T-G131H-N218S-N243V-S248N-K256R, A088T-G131H-N218S-N243V-S248N-L257G, A088T-G131H-N218S-S248N-K256R, A088T-G131H-N218S-S248N-K256R, A088T-G131H-T158S-S248N-K256R, A088T-G131H-T158S-S248N-K256R-L257G, A088T-I107T-N109G-G131H-N218S-S248N-K256R, A088T-N109G-A116T-G131H-D140G-T158S-N218S-N243V-K256R, A088T-N109G-A116T-G131H-N218S-N243V-K256R, A088T-N109G-A116T-G131H-N218S-N243V-S248N-K256R, A088T-N109G-A116T-G131H-T158S-N218S-S248N-L257G, A088T-N109G-A116T-G131H-T158S-N243V-S248N-K256R-I268V, A088T-N109G-A116T-G131H-V149A-N218S-S248N-K256R-L257G, A088T-N109G-A116T-N218S-N243V-S248N-K256R-L257G, A088T-N109G-A116T-T158S-K256R-L257G, A088T-N109G-A116T-T158S-N218S-N243V-L257G, A088T-N109G-D140G-N243V, A088T-N109G-G131H-D140G-T158S-N243V-S248N-K256R, A088T-N109G-G131H-K141E-T158S-N218S-K256R, A088T-N109G-G131H-N218S-S248N, A088T-N109G-G131H-N218S-S248N-K256R-Q271R, A088T-N109G-G131H-N218S-S248N-L257G, A088T-N109G-G131H-T158S-K256R, A088T-N109G-G131H-T158S-N218S-S248N-K256R, A088T-N109G-G131H-V149L-T158S-K256R-L257G, A088T-N109G-T158S-N218S, A088T-N109G-T158S-N218S-K256R-L257G-Q271K, A088T-N109G-T158S-N218S-L257G, A088T-N109G-T158S-S248N-K256R, A088T-N218S-S248N-L257G-Q271R, A088T-T158S-N218S-K256R-L257G, A088T-T158S-N218S-N243V-K256R, A088T-Y104H-A116T-G131H-N218S-N243V, A116T-G131H-K141E-N218S-N243V-S248N-L257G, A116T-G131H-N218S-N243V-S248N-K256R, A116T-G131H-T158S-N218S-S248N-L257G-N269D, A116T-G131H-T158S-N218S-S248N-Q271R, A116T-G131H-T158S-N243V-S248N, A116T-G157E-T158S-N243V-S248N-K256R, A116T-T158S-N218S, G131H-N218S-L257G, G131H-N218S-S248N, G131H-T158S-N218S-N243V-S248N-K256R-L257G, G131H-T158S-N218S-N243V-S248N-L257G, G131H-T158S-N218S-S248N-I268V, I107T-N109G-G131H-N218S-L257G, L090I-N109G-T158S-N243V, L257G, N109G-A116T-G131H-T158S-N218S-K256R-L257G-Q271R, N109G-A116T-N218S-W241R-N243V-S248N-K256R-L257G, N109G-G131H-K141E-L257G, N109G-G131H-N218S-N243V, N109G-T158S-N218S-N243V-L257G, N109G-T158S-N218S-S248N-K256R, N109G-T158S-N243V-S248N-K256R-L257G, N218S-S248N-K256R-L257G, S003P-N109G-G131H-T158S-L257G, S003P-S248N-L257G, T158S-S248N-K256R-L257G, V004A-A088T-G131H-N218S-N243V-S248N-L257G, Y006H-N218S-N243V-S248N, Y104H-N109G-G131H-N243V-S248N, A088T-A116T-T158S-N218S-N243V-S248N-K256R, A088T-A116T-T158S-N243V, A088T-G131H-T158S-N218S-I234T-S248N-L257G, A088T-G131H-T158S-N218S-N243V-S248N-K256R, A088T-G131H-V149L-T158S-N243V-S248N-K256R-L257G, A088T-I107T-N109G-G131H-N218S-A223G-S248N-K256R, A088T-K213N-N243V-S248N-K256R, A088T-K256R-L257G, A088T-N109G-A116T-G131H-A232S-N243V-K256R, A088T-N109G-A116T-G131H-D140G-S248N-L257G, A088T-N109G-A116T-G131H-N218S-N243V-S248N-K256R-L257G, A088T-N109G-A116T-G131H-T158S-N218S-N243V-S248N, A088T-N109G-A116T-G131H-T158S-N243V-S248N-L257G, A088T-N109G-A116T-M124I-G131H-T158S-N218S-S248N-L257G, A088T-N109G-A116T-V148A-N218S-N243V, A088T-N109G-G131H-N218S-N243V-S248N, A088T-N109G-N218S-S248N-T255K-K256R-L257G, A088T-T158S-N218S-L257G, A088T-T158S-N218S-Q245K-S248N-K256R, A088T-T158S-N218S-S248N-K256R, A116T-G131H-N218S-N243V-K256R, A116T-G131H-N218S-W241R-N243V-S248N-K256R-L257G, A116T-G131H-T158S-N218S-L257G, A116T-G131H-V150A-T158S-N243V-S248N-K256R-L257G, I107T-G131H-T158S-N243V-S248N-K256R-L257G, N109G-A116T-K141E-T158S-N218S-N243V-L257G, N109G-A116T-T158S-N218S-N243V-S248N, T158S-N243V-S248N-K256R, T158S-N243V-S248N-K256R-L257G, A088T-A116T-G131H-G146C, A088T-A116T-N218S, A088T-A116T-T158S-N243V-K256R-L257G, A088T-A138E-N218S-N243V-K256R, A088T-N109G-A116T-G131H-T158S-N218S-N243F-S248N, A088T-T158S-V203I-N218S-K256R-L257G, A116T-D140G-T158S-N218S-N243V-S248N, A088T-A116T-T158S-K256R-L257G, A088T-A116T-T158S-N218S-N243V-S248N-E251K-K256R-L257G, A088T-I108T-N109G-G131H-T158S-N218S-S248N-K256R-L257G, A088T-N109G-A116T-G131H-K141E-N218S, A088T-N109G-W241R-S248N-K256R, and G065D-A088T-G131H-N243V-S248N, wherein amino acid positions of the variant are numbered by correspondence with the sequence of SEQ ID NO:2. Such variants have proteolytic activity. The invention includes a protease variant having proteolytic activity and/or a PI value equal to or greater than 0.5 and less than 0.9 relative to BPN'-v36 in this assay, the variant comprising an amino acid sequence having at least 60%, 70%, 80%, 85%, 90%, 91%, 92%, 93%, 94%, 95%, 96%, 97%, or 98% or 99% identity to SEQ ID NO:2 or SEQ ID NO:6 and comprising at least one set of acid substitutions selected from said group above, wherein amino acid positions of the variant are numbered by correspondence with amino acid positions of the SEQ ID NO:2 sequence. Also included are compositions, including, but not limited to, e.g., cleaning compositions, comprising at least one such variant and methods for cleaning utilizing at least one such variant as described in greater detail elsewhere herein.

The following BPN'-v36 variants were determined to have a PI value greater than 1.0, at least 1.1, at least 1.2, at least 1.3, at least 1.4, at least 1.5, at least 1.6, at least 1.7, at least 1.8, at least 1.9, at least 2, from greater than 1.0 to about 10, from greater than 1.0 to about 8, or from greater than 1.0 to about 5 relative to BPN'-v36 in an egg microswatch cleaning assay in Detergent Composition 4 at pH 8 and 16° C.: BPN'-S024G-S053G-S078N-S101N-G128A-Y217Q amino acid sequence (SEQ ID NO:6) comprising at least one set of amino acid substitutions selected from the group consisting of A088T-N109G-A116T-T158S-N243V-L257G, A116T-N218S-N243V-L257G-N269S, A088T-A116T-K256R, A088T-G131H-K256R, A088T-N109G-A116T-T158S-S248N-K256R-L257G, A088T-N109G-T158S-L257G, A088T-A116T-G131H-T158S-N218S-N243V-K256R-A273T, A088T-A116T-N243V-L257G, A088T-A116T-S248N-K256R-L257G, A088T-A116T-T158S-N243V-L257G, A088T-A116T-T158S-N243V-S248N-L257G, A088T-N109G-A116T-G131H-N218S-N243V-S248N-K256R-L257G, A088T-N109G-A116T-G131H-N243V-L257G, A088T-N109G-A116T-G131H-T158S-L257G, A088T-N109G-A116T-T158S-N218S-L257G, A088T-N109G-A116T-T158S-N218S-N243V-S248N-K256R-L257G, A088T-N109G-G131H-N218S-K256R-L257G, A088T-N109G-N218S-S248N-L257G, A088T-T158S-N218S-N243V-K256R-I268V, A088T-T158S-N218S-S248N-L257G, A116T-N218S-K256R-L257G, N109G-A116T, N109G-A116T-G131H-T158S-L257G, N109G-A116T-N243V, N109G-A116T-N243V-K256R, N109G-A116T-T158S-L257G, N109G-K256R, N109G-N243V-K256R-L257G, S003P-N109G-G131H-T158S-K256R, A088T-A116T, A088T-A116T-G131H-N218S-K256R-L257G, A088T-A116T-G131H-N218S-L257G, A088T-A116T-G131H-N218S-N243V-S248N-L257G, A088T-A116T-G131H-N243V-K256R-L257G, A088T-A116T-G131H-N243V-S248N-K256R-L257G, A088T-A116T-G131H-T158S-N218S-N243V, A088T-A116T-G131H-T158S-N218S-N243V-K256R-L257G, A088T-A116T-G131H-T158S-N218S-N243V-S248N, A088T-A116T-G131H-T158S-S248N-K256R-L257G, A088T-A116T-G131H-T158S-S248N-L257G, A088T-A116T-N218S-N243V-L257G, A088T-A116T-N218S-N243V-S248N-K256R-L257G, A088T-A116T-N218S-N243V-S248N-K256R-Q275R, A088T-A116T-T158S-A216S-N218S-N243V-K256R-L257G, A088T-A116T-T158S-K256R, A088T-A116T-T158S-N218S-L257G, A088T-A116T-T158S-N218S-N243V, A088T-A116T-T158S-N218S-N243V-K256R, A088T-A116T-T158S-N218S-N243V-K256R-L257G, A088T-A116T-T158S-N218S-N243V-K256R-N269S, A088T-A116T-T158S-N243V, A088T-A116T-T158S-N243V-K256R, A088T-A116T-V147I-T158S-N218S-N243V-L257G, A088T-G131H-K256R-L257G, A088T-G131H-N218S-N243V-S248N-K256R-L257G, A088T-G131H-S248N-K256R-L257G, A088T-G131H-T158S-N218S-L257G, A088T-G131H-T158S-N218S-N243V-L257G, A088T-I107T-N109G-A116T-G131H-T158S-N218S-N243V-S248N, A088T-I107T-N109G-G131H-N218S-S248N-K256R, A088T-N109G-A116T-G131H-A153S-N218S-S248N-L257G, A088T-N109G-A116T-G131H-K256R-L257G, A088T-N109G-A116T-G131H-N218S-K256R-L257G, A088T-N109G-A116T-G131H-N218S-L257G, A088T-N109G-A116T-G131H-N218S-N243V-K256R, A088T-N109G-A116T-G131H-N218S-N243V-L257G, A088T-N109G-A116T-G131H-N243V-L257G, A088T-N109G-A116T-G131H-S248N-L257G, A088T-N109G-A116T-G131H-T158S-N218S, A088T-N109G-A116T-G131H-T158S-N218S-N243V-S248N-K256R, A088T-N109G-A116T-G131H-T158S-N218S-N243V-S248N-L257G, A088T-N109G-A116T-N218S-K256R-L257G, A088T-N109G-A116T-N218S-L257G, A088T-N109G-A116T-N218S-N243V, A088T-N109G-A116T-N218S-N243V-L257G, A088T-N109G-A116T-N218T-K256R, A088T-N109G-A116T-N218T-K256R-L257G, A088T-N109G-A116T-N243V, A088T-N109G-A116T-N243V-K256R-L257G, A088T-N109G-A116T-N243V-K256R-L257G-N269D, A088T-N109G-A116T-T158S, A088T-N109G-A116T-T158S, A088T-N109G-A116T-T158S-L257G, A088T-N109G-A116T-T158S-N218S-N243V-K256R-L257G, A088T-N109G-A116T-T158S-N218S-N243V-K256R-L257G, A088T-N109G-A116T-T158S-N218S-N243V-S248N, A088T-N109G-A116T-T158S-N243V-S248N-L257G, A088T-N109G-G131H-A138V-T158S-N218S-N243V-S248N-L257G, A088T-N109G-G131H-L257G, A088T-N109G-G131H-N218S, A088T-N109G-G131H-N218S-N243V-L257G, A088T-N109G-G131H-N218S-N243V-S248N-K256R-L257G, A088T-N109G-G131H-N218S-S248N-K256R-L257G, A088T-N109G-G131H-T158S-N218S-K256R, A088T-N109G-G131H-T158S-N218S-N243V, A088T-N109G-G131H-T158S-N243V-K256R-L257G, A088T-N109G-G131H-T158S-N243V-L257G, A088T-N109G-G131H-T158S-N243V-S248N-L257G, A088T-N109G-G131H-V149A-K256R-L257G, A088T-N109G-N218S-N243V-L257G, A088T-N109G-N218S-N243V-S248N-L257G, A088T-N109G-N218S-S248N-K256R-L257G, A088T-N109G-N243V, A088T-N109G-N243V-K256R-L257G, A088T-N109G-N243V-L257G, A088T-N109G-N243V-S248N-L257G, A088T-N109G-S248N-K256R-L257G, A088T-N109G-T158S-K256R, A088T-N109G-T158S-N218S-N243V-K256R-Q275R, A088T-N109G-T158S-N243V, A088T-N109G-T158S-N243V-K256R-I268V, A088T-N109G-T158S-N243V-L257G, A088T-N109G-T158S-N243V-S248N-L257G, A088T-N218S-N243V-L257G, A088T-N218S-N243V-S248N-K256R-L257G, A088T-N218S-S248N, A088T-T158S-N218S-N243V-K256R-L257G, A088T-V143A-T158S-K256R, A088T-V147I-N218S-N243V-K256R-L257G, A114S-A116T-N218S-N243V-S248N-K256R-L257G, A116T-G131H-N218S-N243V-S248N-K256R-L257G, A116T-G131H-N218S-N243V-S248N-L257G, A116T-G131H-N243V-K256R, A116T-G131H-N243V-L257G, A116T-G131H-N243V-S248N-K256R, A116T-G131H-S248N-L257G, A116T-G131H-T158S-N218S-I234T-N243V-S248N-K256R, A116T-G131H-T158S-N218S-N243V-S248N-L257G, A116T-N218S-L257G, A116T-T158S-N218S-K256R-L257G, A116T-T158S-N218S-S248N, A116T-T158S-N218S-S248N-L257G-Q271R, A116T-T158S-N243V-S248N-L257G, A116T-T158S-S248N-L257G, G131H-N218S-S248N-K256R-L257G, I107T-N109G-A116T-G131H-T158S-N218S-N243V-S248N-K256R-L257G, N109G-A116T-G131H-A137V-T158S-S248N-K256R-L257G, N109G-A116T-G131H-A151S-N218S-K256R-L257G, N109G-A116T-G131H-N218S-K256R-L257G, N109G-A116T-G131H-N218S-N243V-L257G, N109G-A116T-G131H-N243V-L257G, N109G-A116T-G131H-S248N-L257G, N109G-A116T-G131H-T158S-N218S-N243V-K256R-L257G, N109G-A116T-G131H-T158S-N218S-N243V-S248N-K256R-L257G, N109G-A116T-K256R-L257G, N109G-A116T-N218S-N243V-K256R, N109G-A116T-N218S-N243V-S248N-K256R-L257G, N109G-A116T-N218S-N243V-

S248N-L257G, N109G-A116T-N243V-S248N-K256R, N109G-A116T-S248N-L257G, N109G-A116T-T158S-G211V-N243V-S248N-K256R, N109G-A116T-T158S-N218S, N109G-A116T-T158S-N218S-N243V-L257G, N109G-A116T-T158S-N218S-N243V-S248N, N109G-G131H-N218S-K237N, N109G-G131H-N218S-K256R-L257G, N109G-G131H-N218S-L257G, N109G-G131H-N218S-N243V-L257G, N109G-G131H-N243V-K256R-L257G, N109G-G131H-N243V-S248N-L257G, N109G-G131H-S248N-K256R, N109G-G131H-T158S-K256R-L257G, N109G-G131H-T158S-N218S-K256R-L257G, N109G-G131H-T158S-N243V, N109G-N218S, N109G-N218S-N243V-L257G, N109G-T158S-N218S-K256R-L257G, N109G-T158S-N218S-L257G, N109G-T158S-N218S-N243V-K256R, N109G-T158S-N243V-L257G, N243V-K256R-L257G, N243V-L257G, S003F-A088T-N109G-A116T-T158S-N243V-K256R-L257G, T158S-N218S-L233S, T158S-N218S-N243V-S248N-K256R, V004A-N109G-A116T-T158S-N218S-S248N-L257G, Y006H-A116T-G131H-T158S-N218S-N243V-S248N-K256R-A272G, A088T-A098S-N218S-K256R, A088T-A116T-G131H-K256R-L257G-L267M, A088T-A116T-G131H-L257G, A088T-A116T-G131H-N218S-A274T, A088T-A116T-G131H-N218S-K256R, A088T-A116T-G131H-N218S-N243V-K256R, A088T-A116T-G131H-N218S-N243V-K256R-L257G, A088T-A116T-G131H-N218S-N243V-K256R-L257G, A088T-A116T-G131H-N218S-N243V-L257G, A088T-A116T-G131H-N218S-N243V-S248N-K256R, A088T-A116T-G131H-N218S-N243V-S248N-K256R-L257G, A088T-A116T-G131H-N218S-S248N-L257G, A088T-A116T-G131H-N243V-K256R, A088T-A116T-G131H-N243V-L257G, A088T-A116T-G131H-N243V-S248N, A088T-A116T-G131H-N243V-S248N-A274V, A088T-A116T-G131H-N243V-S248N-K256R-L257G, A088T-A116T-G131H-S248N-K256R-L257G, A088T-A116T-G131H-S248N-L257G, A088T-A116T-G131H-T158S-K256R-L257G, A088T-A116T-G131H-T158S-K256R-L257G, A088T-A116T-G131H-T158S-L257G, A088T-A116T-G131H-T158S-N218S, A088T-A116T-G131H-T158S-N218S-K256R, A088T-A116T-G131H-T158S-N218S-K256R-L257G, A088T-A116T-G131H-T158S-N218S-K256R-L257G, A088T-A116T-G131H-T158S-N218S-L257G, A088T-A116T-G131H-T158S-N218S-N243V-K256R, A088T-A116T-G131H-T158S-N218S-N243V-S248N-K256R, A088T-A116T-G131H-T158S-N218S-S248N-K256R, A088T-A116T-G131H-T158S-N218S-S248N-L257G, A088T-A116T-G131H-T158S-N243V-K256R-L257G, A088T-A116T-G131H-T158S-N243V-L257G, A088T-A116T-G131H-T158S-N243V-S248N-K256R, A088T-A116T-G131H-T158S-N243V-S248N-K256R-L257G, A088T-A116T-K256R, A088T-A116T-N218S-K256R, A088T-A116T-N218S-N243V-K256R, A088T-A116T-N218S-N243V-K256R-L257G, A088T-A116T-N218S-N243V-S248N-K256R, A088T-A116T-N218S-N243V-S248N-L257G, A088T-A116T-N243V-K256R, A088T-A116T-N243V-L257G, A088T-A116T-N243V-S248N-K256R, A088T-A116T-N243V-S248N-K256R-L257G, A088T-A116T-S248N, A088T-A116T-S248N-K256R, A088T-A116T-S248N-L257G, A088T-A116T-T158S-N218S, A088T-A116T-T158S-N218S-K256R, A088T-A116T-T158S-N218S-K256R, A088T-A116T-T158S-N218S-K256R-L257G, A088T-A116T-T158S-N218S-N243V-K256R, A088T-A116T-T158S-N218S-N243V-S248N, A088T-A116T-T158S-N218S-N243V-S248N, A088T-A116T-T158S-N218S-N243V-S248N-K256R, A088T-A116T-T158S-N218S-N243V-S248N-K256R-L257G, A088T-A116T-T158S-N218S-N243V-S248N-L257G, A088T-A116T-T158S-N243V-K256R-L257G, A088T-G131H, A088T-G131H-N218S-K256R-L257G, A088T-G131H-N218S-N243V-K256R, A088T-G131H-N218S-N243V-K256R, A088T-G131H-N218S-N243V-L257G, A088T-G131H-N218S-N243V-L257G, A088T-G131H-N218S-S248N, A088T-G131H-N218S-S248N-K256R, A088T-G131H-N218S-S248N-K256R-L257G, A088T-G131H-N218S-S248N-L257G, A088T-G131H-N218T-L257G, A088T-G131H-N243V-L257G, A088T-G131H-N243V-S248N-K256R, A088T-G131H-S248N, A088T-G131H-S248N-L257G, A088T-G131H-T158S-N218S-K256R, A088T-G131H-T158S-N218S-K256R-L257G, A088T-G131H-T158S-N218S-N243V-K256R, A088T-G131H-T158S-N218S-N243V-K256R, A088T-G131H-T158S-N218S-N243V-K256R-L257G, A088T-G131H-T158S-N218S-N243V-K256R-L257G, A088T-G131H-T158S-N218S-S248N, A088T-G131H-T158S-N218S-S248N-K256R, A088T-G131H-T158S-N218S-S248N-K256R, A088T-G131H-T158S-N218S-S248N-L257G-I268V, A088T-G131H-T158S-N243V, A088T-G131H-T158S-N243V-S248N, A088T-G131H-T158S-N243V-S248N, A088T-G131H-T158S-N243V-S248N-K256R-L257G, A088T-N109G-A116T, A088T-N109G-A116T-G131H-D140G-T158S-N218S-N243V-K256R, A088T-N109G-A116T-G131H-K256R, A088T-N109G-A116T-G131H-N218S, A088T-N109G-A116T-G131H-N218S, A088T-N109G-A116T-G131H-N218S-K256R, A088T-N109G-A116T-G131H-N218S-L257G, A088T-N109G-A116T-G131H-N218S-N243V, A088T-N109G-A116T-G131H-N218S-N243V-K256R-L257G, A088T-N109G-A116T-G131H-N218S-N243V-L257G, A088T-N109G-A116T-G131H-N218S-N243V-S248N-K256R, A088T-N109G-A116T-G131H-N218S-S248N-K256R-L257G, A088T-N109G-A116T-G131H-N218S-S248N-L257G, A088T-N109G-A116T-G131H-N218S-S248N-L257G, A088T-N109G-A116T-G131H-N243V-K256R-L257G, A088T-N109G-A116T-G131H-N243V-S248N, A088T-N109G-A116T-G131H-N243V-S248N-K256R-L257G, A088T-N109G-A116T-G131H-N243V-S248N-L257G, A088T-N109G-A116T-G131H-S248N-K256R, A088T-N109G-A116T-G131H-S248N-K256R-L257G, A088T-N109G-A116T-G131H-S248N-L257G, A088T-N109G-A116T-G131H-T158S, A088T-N109G-A116T-G131H-T158S-N218S, A088T-N109G-A116T-G131H-T158S-N218S-L257G, A088T-N109G-A116T-G131H-T158S-N218S-N243V-K256R, A088T-N109G-A116T-G131H-T158S-N218S-N243V-K256R, A088T-N109G-A116T-G131H-T158S-N218S-N243V-K256R-L257G, A088T-N109G-A116T-G131H-T158S-N218S-N243V-S248N-K256R, A088T-N109G-A116T-G131H-T158S-N218S-S248N, A088T-N109G-A116T-G131H-T158S-N218S-S248N-K256R, A088T-N109G-A116T-G131H-T158S-N218S-S248N-L257G, A088T-N109G-A116T-G131H-T158S-N218S-S248N-L257G, A088T-N109G-A116T-G131H-T158S-N218T-N243V, A088T-N109G-A116T-G131H-T158S-N243V-K256R-L257G, A088T-N109G-A116T-G131H-T158S-N243V-S248N, A088T-N109G-A116T-G131H-T158S-N243V-S248N-K256R, A088T-N109G-A116T-G131H-T158S-N243V-S248N-L257G, A088T-N109G-A116T-G131H-T158S-S248N-K256R-L257G, A088T-N109G-A116T-G131H-T158S-S248N-L257G, A088T-N109G-A116T-K256R, A088T-N109G-A116T-N218S, A088T-N109G-A116T-N218S-N243V, A088T-N109G-A116T-N218S-N243V-K256R, A088T-N109G-A116T-N218S-N243V-K256R-L257G, A088T-N109G-A116T-N218S-N243V-L257G, A088T-

N109G-A116T-N218S-N243V-S248N-K256R-L257G, A088T-N109G-A116T-N243V-S248N, A088T-N109G-A116T-N243V-S248N-K256R, A088T-N109G-A116T-N243V-S248N-K256R-L257G, A088T-N109G-A116T-N243V-S248N-K256R-L257G, A088T-N109G-A116T-N243V-S248N-L257G, A088T-N109G-A116T-S248N-K256R, A088T-N109G-A116T-S248N-K256R-L257G, A088T-N109G-A116T-T158S-K256R, A088T-N109G-A116T-T158S-N218S, A088T-N109G-A116T-T158S-N218S-K256R-L257G, A088T-N109G-A116T-T158S-N218S-L257G, A088T-N109G-A116T-T158S-N218S-N243V, A088T-N109G-A116T-T158S-N218S-N243V-L257G, A088T-N109G-A116T-T158S-N218S-N243V-S248N, A088T-N109G-A116T-T158S-N218S-N243V-S248N-K256R, A088T-N109G-A116T-T158S-N218S-N243V-S248N-L257G, A088T-N109G-A116T-T158S-N218S-S248N, A088T-N109G-A116T-T158S-N218S-S248N-K256R, A088T-N109G-A116T-T158S-N218S-S248N-L257G, A088T-N109G-A116T-T158S-N243V-K256R, A088T-N109G-A116T-T158S-N243V-S248N, A088T-N109G-A116T-T158S-S248N, A088T-N109G-A116T-T158S-S248N-K256R, A088T-N109G-A116T-T158S-S248N-L257G, A088T-N109G-G131H-N218S-K256R, A088T-N109G-G131H-N218S-K256R, A088T-N109G-G131H-N218S-N243V-K256R, A088T-N109G-G131H-N218S-N243V-K256R, A088T-N109G-G131H-N218S-N243V-K256R-L257G, A088T-N109G-G131H-N218S-N243V-S248N-K256R, A088T-N109G-G131H-N218S-S248N, A088T-N109G-G131H-N218S-S248N-L257G, A088T-N109G-G131H-N243V-K256R-L257G, A088T-N109G-G131H-N243V-K256R-L257G, A088T-N109G-G131H-N243V-L257G, A088T-N109G-G131H-N243V-L257G, A088T-N109G-G131H-N243V-S248N-K256R, A088T-N109G-G131H-N243V-S248N-K256R-L257G, A088T-N109G-G131H-N243V-S248N-L257G, A088T-N109G-G131H-S248N-L257G, A088T-N109G-G131H-T158S-K256R-L257G, A088T-N109G-G131H-T158S-N218S-L257G, A088T-N109G-G131H-T158S-N218S-L257G, A088T-N109G-G131H-T158S-N218S-N243V-S248N, A088T-N109G-G131H-T158S-N218S-N243V-S248N-K256R, A088T-N109G-G131H-T158S-N218S-S248N-K256R, A088T-N109G-G131H-T158S-N218S-S248N-L257G, A088T-N109G-G131H-T158S-N243V, A088T-N109G-G131H-T158S-N243V-S248N, A088T-N109G-G131H-T158S-N243V-S248N-K256R, A088T-N109G-G131H-T158S-N243V-S248N-K256R, A088T-N109G-G131H-T158S-N243V-S248N-K256R-L257G, A088T-N109G-G131H-T158S-S248N-K256R-L257G, A088T-N109G-G131H-T158S-W241R-S248N-K256R, A088T-N109G-G131H-V148A-N218S-N243V-K256R-L257G, A088T-N109G-G154A-N155P-E156T-G157L-T158M-S159E-G160E-S161L, A088T-N109G-N218S-K256R, A088T-N109G-N218S-N243V-L257G, A088T-N109G-N218S-N243V-S248N, A088T-N109G-N243V-K256R, A088T-N109G-N243V-S248N, A088T-N109G-N243V-S248N-K256R-L257G, A088T-N109G-S248N, A088T-N109G-T158S-N218S, A088T-N109G-T158S-N218S-K256R, A088T-N109G-T158S-N218S-K256R-L257G, A088T-N109G-T158S-N218S-L257G, A088T-N109G-T158S-N218S-N243V-S248N-K256R, A088T-N109G-T158S-N218S-N243V-S248N-K256R-L257G, A088T-N109G-T158S-N218S-S248N-K256R, A088T-N109G-T158S-N218S-S248N-K256R-L257G, A088T-N109G-T158S-N243V-K256R, A088T-N109G-T158S-N243V-K256R, A088T-N109G-T158S-N243V-S248N-L257G, A088T-N109G-T158S-S248N-K256R-L257G, A088T-N109G-T158S-S248N-L257G, A088T-N109G-T158S-S248N-L257G, A088T-N109G-V147A-N218S-N243V-K256R, A088T-N218S-L257G-I268V, A088T-N218S-N243V, A088T-N218S-N243V-S248N, A088T-N218S-N243V-S248N-N269S, A088T-N218S-S248N-K256R, A088T-N218S-S248N-L257G-Q271R, A088T-N243V, A088T-N243V, A088T-N243V-K256R, A088T-N243V-S248N-K256R, A088T-N243V-S248N-K256R-L257G, A088T-S248N, A088T-T158S-N218S-K256R-L257G, A088T-T158S-N218S-N243V-K256R, A088T-T158S-N218S-N243V-L257G, A088T-T158S-N218S-N243V-S248N-K256R-L257G, A088T-T158S-N218S-N243V-S248N-K256R-L257G, A088T-T158S-N243V-K256R-L257G, A088T-T158S-N243V-K256R-L257G-Q271H, A088T-T158S-N243V-S248N, A088T-T158S-N243V-S248N-L257G, A088T-T158S-S248N, A088T-V147A-K256R, A116T-G131H-K256R, A116T-G131H-N218S, A116T-G131H-N218S-K256R-L257G, A116T-G131H-N218S-L257G, A116T-G131H-N218S-N243V, A116T-G131H-N218S-S248N-K256R, A116T-G131H-N218S-S248N-K256R-L257G, A116T-G131H-N243V-S248N, A116T-G131H-N243V-S248N-L257G, A116T-G131H-S248N-K256R, A116T-G131H-T158S-A231V-N243V-L257G, A116T-G131H-T158S-N218S-K256R, A116T-G131H-T158S-N218S-K256R-L257G, A116T-G131H-T158S-N218S-N243V-K256R-L257G, A116T-G131H-T158S-N218S-N243V-S248N-K256R, A116T-G131H-T158S-N218S-N243V-S248N-K256R-L257G, A116T-G131H-T158S-N218S-S248N, A116T-G131H-T158S-N243V-L257G, A116T-G131H-T158S-N243V-S248N-K256R, A116T-G131H-T158S-S248N-K256R, A116T-G131H-T158S-S248N-L257G, A116T-G131H-V143F-T158S-N218S, A116T-K256R, A116T-N218S, A116T-N218S-K256R, A116T-N218S-N243V-L257G, A116T-N218S-N243V-S248N-K256R, A116T-N218S-N243V-S248N-K256R-L257G, A116T-N218S-N243V-S248N-L257G, A116T-N218S-S248N-L257G, A116T-N243V, A116T-N243V-K256R-L257G, A116T-N243V-S248N, A116T-N243V-S248N-K256R-L257G, A116T-S248N-K256R-L257G, A116T-T158S-K256R-L257G, A116T-T158S-N218S, A116T-T158S-N218S-K256R, A116T-T158S-N218S-N243V, A116T-T158S-N218S-N243V-S248N, A116T-T158S-N218S-S248N-K256R, A116T-T158S-N218S-S248N-K256R-L257G, A116T-T158S-N243V-K256R, A116T-T158S-N243V-L257G, A116T-T158S-N243V-S248N, A116T-T158S-S248N-K256R-L257G, G131H-K141R-T158S-N218S-K256R, G131H-N218S, G131H-N218S-K256R, G131H-N218S-N243V-K256R-L257G, G131H-N218S-N243V-S248N, G131H-N218S-N243V-S248N-L257G, G131H-N243V-S248N-K256R, G131H-N243V-S248N-K256R-L257G, G131H-S248N, G131H-T158S-I234T-N243V-K256R, G131H-T158S-N218S-K256R-L257G, G131H-T158S-N218S-N243V, G131H-T158S-N218S-N243V-S248N-L257G, G131H-T158S-N218S-S248N-K256R-L257G, G131H-T158S-N218S-S248N-L257G, G131H-T158S-N243V-K256R, G131H-T158S-N243V-S248N-L257G, N109G, N109G-A116T-G131H-A144V-T158S-S248N-K256R-L257G, N109G-A116T-G131H-K256R-L257G, N109G-A116T-G131H-N218S-N243V-K256R, N109G-A116T-G131H-N218S-N243V-K256R-L257G, N109G-A116T-G131H-N218S-S248N-K256R, N109G-A116T-G131H-N218S-S248N-L257G, N109G-A116T-G131H-N243V-K256R, N109G-A116T-G131H-N243V-S248N, N109G-A116T-G131H-N243V-S248N-K256R-L257G, N109G-A116T-G131H-S248N, N109G-A116T-G131H-S248N-K256R, N109G-A116T-G131H-T158S-K256R, N109G-A116T-G131H-T158S-K256R-L257G,

N109G-A116T-G131H-T158S-N218S-K256R, N109G-A116T-G131H-T158S-N218S-K256R-L257G, N109G-A116T-G131H-T158S-N218S-L257G, N109G-A116T-G131H-T158S-N218S-N243V-K256R, N109G-A116T-G131H-T158S-N218S-N243V-S248N-L257G, N109G-A116T-G131H-T158S-N218S-S248N, N109G-A116T-G131H-T158S-N243V-L257G, N109G-A116T-G131H-T158S-N243V-S248N, N109G-A116T-G131H-T158S-S248N, N109G-A116T-G131H-T158S-S248N-K256R, N109G-A116T-G131H-T158S-S248N-K256R-L257G, N109G-A116T-G131H-V149A-T158S-N218S-N243V-S248N-L257G, N109G-A116T-N218S, N109G-A116T-N218S-K256R, N109G-A116T-N218S-N243V-K256R-L257G, N109G-A116T-N218S-N243V-S248N-I268V, N109G-A116T-N243V-K256R-L257G, N109G-A116T-N243V-S248N, N109G-A116T-N243V-S248N-L257G, N109G-A116T-T158S, N109G-A116T-T158S-N218S-N243V-K256R-L257G, N109G-A116T-T158S-N218S-N243V-S248N-K256R-L257G, N109G-A116T-T158S-N218S-N243V-S248N-L257G, N109G-A116T-T158S-N218S-S248N-K256R-L257G, N109G-A116T-T158S-N243V-K256R-L257G, N109G-A116T-T158S-N243V-L257G, N109G-A116T-T158S-N243V-S248N-L257G, N109G-A116T-T158S-Q275R, N109G-A116T-T158S-S248N-K256R-L257G, N109G-G131H-L257G, N109G-G131H-N218S-N243V-S248N-K256R-L257G, N109G-G131H-N218S-N243V-S248N-L257G, N109G-G131H-N218S-S248N-K256R-L257G, N109G-G131H-N243V-K256R, N109G-G131H-S145F-N218S-N243V-K256R-L257G, N109G-G131H-S248N-K256R-L257G, N109G-G131H-S248N-L257G, N109G-G131H-T158S-K256R, N109G-G131H-T158S-N218S-L257G, N109G-G131H-T158S-N218S-N243V, N109G-G131H-T158S-N218S-N243V-K256R, N109G-G131H-T158S-N218S-N243V-K256R-L257G, N109G-G131H-T158S-N218S-N243V-S248N-L257G, N109G-G131H-T158S-N218S-S248N-K256R, N109G-G131H-T158S-N218S-S248N-K256R-L257G-A274T, N109G-G131H-T158S-N218S-S248N-L257G, N109G-G131H-T158S-N243V-S248N, N109G-G131H-T158S-N243V-S248N-K256R-L257G, N109G-G131H-T158S-S248N-K256R-L257G, N109G-G131H-T158S-S248N-L257G, N109G-N218S-K256R-L257G, N109G-N218S-L257G, N109G-N218S-N243V-K256R, N109G-N218S-N243V-S248N-S260F, N109G-N218S-S248N, N109G-N243V-K256R, N109G-N243V-L257G, N109G-N243V-S248N, N109G-N243V-S248N-K256R-L257G, N109G-S182F-S204F-S207L-N218S-S236F-S248N-L257G, N109G-S248N-K256R, N109G-T158S-K256R, N109G-T158S-N218S-N243V-K256R-L257G, N109G-T158S-N218S-S248N-L257G, N109G-T158S-N243V, N109G-T158S-N243V-K256R, N109G-T158S-N243V-S248N, N109G-T158S-N243V-S248N-K256R, N109G-T158S-S248N-K256R, N109G-T158S-S248N-L257G, N218S, N218S-N243V-S248N-K256R, N218S-S248N-L257G, N243V-K256R, N243V-S248N-K256R, N243V-S248N-K256R-L257G, N243V-S248N-L257G-Q271R, S003P-A116T-T158S-S248N-K256R, S248N, T158S-N218S, T158S-N218S-A272V, T158S-N218S-L257G, T158S-N218S-N243V-K256R-L257G, T158S-N218S-N243V-L257G, T158S-N218S-S248N-K256R-L257G, T158S-N243V-K256R, T158S-N243V-K256R-L257G, T158S-N243V-S248N-K256R, V004A-N109G-A116T-G131H-S248N-K256R-L257G, and Y006H-A116T-G131H-S248N, wherein amino acid positions of the variant are numbered by correspondence with the sequence of SEQ ID NO:2. Such variants have enhanced proteolytic activity compared to BPN', BPN'-v3, and BPN'-v36, and a greater PI value than BPN', BPN'-v3 and BPN'-v36 in this assay. The invention includes a protease variant having enhanced proteolytic activity compared to BPN' (SEQ ID NO:2), enhanced proteolytic activity compared to BPN', BPN'-v3, and BPN'-v36, a PI value of greater than 1.0 to about 5 relative to BPN'-v3, and/or a PI value of greater than 1.0 to about 5 relative to BPN'-v36 in this assay, the variant comprising an amino acid sequence having at least 60%, 70%, 80%, 85%, 90%, 91%, 92%, 93%, 94%, 95%, 96%, 97%, or 98% or 99% identity to SEQ ID NO:2 or SEQ ID NO:6 and comprising at least one set of amino acid substitutions selected from said group above, wherein amino acid positions of the variant are numbered by correspondence with amino acid positions of the SEQ ID NO:2 sequence. Also included are compositions, including, but not limited to, e.g., cleaning compositions, comprising at least one such variant and methods for cleaning utilizing at least one such variant as described in greater detail elsewhere herein.

The following BPN'-v36 variants were determined to have a PI value equal to about 1.0 relative to BPN'-v36 in an egg microswatch cleaning assay in Detergent Composition 4 at pH 8 and 16° C.: BPN'-S024G-S053G-S078N-S101N-G128A-Y217Q amino acid sequence (SEQ ID NO:6) comprising at least one set of amino acid substitutions selected from the group consisting of BPN'-v36, A015S-A088T-N109G-G131H-T158S-N218S-S248N, A088T, A088T-A116T-G131H-N218S-N243V-S248N, A088T-A116T-G131H-N218S-S248N, A088T-A116T-G131H-N218S-S248N, A088T-A116T-G131H-N218S-S248N-K256R-L257G, A088T-A116T-G131H-N243V, A088T-A116T-G131H-N243V-K256R, A088T-A116T-G131H-N243V-S248N, A088T-A116T-G131H-S248N-K256R, A088T-A116T-G131H-T158S-N218S-N243V-S248N, A088T-A116T-G131H-T158S-N218S-N243V-S248N-K256R, A088T-A116T-G131H-T158S-N218S-N243V-S248N-L257G, A088T-A116T-G131H-T158S-N218S-N243V-S248N-L257G, A088T-A116T-G131H-T158S-N218S-S248N, A088T-A116T-G131H-T158S-N218S-S248N-K256R, A088T-A116T-G131H-T158S-N243V, A088T-A116T-G131H-T158S-N243V-K256R, A088T-A116T-G131H-T158S-N243V-S248N, A088T-A116T-G131H-T158S-N243V-S248N-K256R-L257G, A088T-A116T-G131H-T158S-S248N, A088T-A116T-G131H-T158S-S248N-K256R, A088T-A116T-G131H-T158S-S248N-L257G, A088T-A116T-G131H-V147A-T158S-N218S-N243V-S248N-L257G, A088T-A116T-N218S-I268V, A088T-A116T-N218S-L257G, A088T-A116T-N218S-N243V-N269D, A088T-A116T-N218S-S248N, A088T-A116T-N218S-S248N, A088T-A116T-N218S-S248N-L257G, A088T-A116T-N243V-K256R-L257G, A088T-A116T-N243V-S248N-K256R, A088T-A116T-S248N-K256R, A088T-A116T-T158S-N218S, A088T-A116T-T158S-N218S-N243V-S248N-K256R-L257G, A088T-A116T-T158S-N218S-S248N, A088T-A116T-T158S-N218S-S248N-K256R-L257G, A088T-A116T-T158S-N243V-S248N, A088T-A116T-T158S-N243V-S248N-K256R, A088T-A116T-T158S-N243V-S248N-K256R-L257G, A088T-A116T-T158S-N243V-S248N-L257G, A088T-A116T-T158S-S248N, A088T-A116T-T158S-S248N-K256R-L257G, A088T-A116T-T158S-S248N-L257G, A088T-A116T-V143A-N218S-S248N-K256R, A088T-G131H-A138V-N218S-L257G, A088T-G131H-K141E-N218S-N243V-S248N-L257G, A088T-G131H-K256R, A088T-G131H-N218S-K256R, A088T-G131H-N218S-N243V-K256R-L257G, A088T-G131H-N218S-N243V-S248N, A088T-G131H-N218S-N243V-S248N, A088T-G131H-N218S-N243V-S248N-K256R, A088T-

G131H-N218S-N243V-S248N-K256R-L257G, A088T-G131H-N218S-S248N, A088T-G131H-N218S-S248N-K256R, A088T-G131H-N243V-K256R-L257G, A088T-G131H-N243V-S248N, A088T-G131H-N243V-S248N-K256R-L257G, A088T-G131H-S248N, A088T-G131H-S248N-K256R, A088T-G131H-T158S-K256R, A088T-G131H-T158S-L257G, A088T-G131H-T158S-N218S, A088T-G131H-T158S-N218S-N243V-S248N, A088T-G131H-T158S-N218S-N243V-S248N-K256R, A088T-G131H-T158S-N218S-N243V-S248N-K256R-L257G, A088T-G131H-T158S-N218S-N243V-S248N-L257G, A088T-G131H-T158S-N218S-S248N, A088T-G131H-T158S-N218S-S248N-K256R-L257G, A088T-G131H-T158S-N243V, A088T-G131H-T158S-N243V-K256R, A088T-G131H-T158S-N243V-S248N-K256R, A088T-G131H-T158S-N243V-S248N-L257G, A088T-G131H-T158S-S248N-K256R-L257G, A088T-G131H-T158S-S248N-L257G, A088T-I107T-N109G-G131H-N218S-A223G-S248N-K256R, A088T-L257G, A088T-L257G, A088T-N109G-A116T-G131H-A232S-N243V-K256R, A088T-N109G-A116T-G131H-K256R-L257G, A088T-N109G-A116T-G131H-L257G, A088T-N109G-A116T-G131H-N218S-K256R, A088T-N109G-A116T-G131H-N218S-N243V-S248N-K256R, A088T-N109G-A116T-G131H-N218S-N243V-S248N-N269D, A088T-N109G-A116T-G131H-N243V-K256R, A088T-N109G-A116T-G131H-S248N, A088T-N109G-A116T-G131H-T158S-L257G, A088T-N109G-A116T-G131H-T158S-N218S-N243F-S248N, A088T-N109G-A116T-G131H-T158S-N218S-N243V, A088T-N109G-A116T-G131H-T158S-N218S-N243V-S248N-K256R-L257G, A088T-N109G-A116T-G131H-T158S-N218T-K256R, A088T-N109G-A116T-G131H-T158S-N243V, A088T-N109G-A116T-G131H-T158S-N243V-K256R, A088T-N109G-A116T-G131H-T158S-N243V-S248N, A088T-N109G-A116T-G131H-T158S-N243V-S248N-K256R-I268V, A088T-N109G-A116T-G131H-T158S-N243V-S248N-L257G, A088T-N109G-A116T-G131H-T158S-S248N, A088T-N109G-A116T-G131H-T158S-S248N-K256R-L257G, A088T-N109G-A116T-G131H-V149A-N218S-S248N-K256R-L257G, A088T-N109G-A116T-K256R, A088T-N109G-A116T-N218S-K256R, A088T-N109G-A116T-N218S-N243V-S248N-K256R, A088T-N109G-A116T-N218S-N243V-S248N-L257G, A088T-N109G-A116T-N218S-S248N, A088T-N109G-A116T-N218S-S248N-K256R, A088T-N109G-A116T-S248N, A088T-N109G-A116T-T158S-L257G, A088T-N109G-A116T-T158S-N218S, A088T-N109G-A116T-T158S-N243V, A088T-N109G-A116T-T158S-N243V-K256R, A088T-N109G-A116T-T158S-N243V-S248N-K256R, A088T-N109G-G131H-N218S-N243V-S248N, A088T-N109G-G131H-N218S-S248N-K256R, A088T-N109G-G131H-N218S-S248N-K256R-L257G, A088T-N109G-G131H-N218S-S248N-K256R-L257G-Q275R, A088T-N109G-G131H-N218S-S248N-K256R-Q271R, A088T-N109G-G131H-N243V, A088T-N109G-G131H-N243V-K256R, A088T-N109G-G131H-N243V-S248N-K256R, A088T-N109G-G131H-S248N-K256R, A088T-N109G-G131H-S248N-L257G, A088T-N109G-G131H-T158S, A088T-N109G-G131H-T158S, A088T-N109G-G131H-T158S-K256R, A088T-N109G-G131H-T158S-K256R, A088T-N109G-G131H-T158S-N218S-N243V-K256R, A088T-N109G-G131H-T158S-N218S-N243V-K256R, A088T-N109G-G131H-T158S-N218S-N243V-K256R-L257G, A088T-N109G-G131H-T158S-N218S-N243V-S248N-K256R-L257G, A088T-N109G-G131H-T158S-N218S-N243V-S248N-L257G, A088T-N109G-G131H-T158S-N243V-K256R, A088T-N109G-G131H-T158S-N243V-K256R-L257G, A088T-N109G-G131H-T158S-N243V-S248N-K256R-L257G, A088T-N109G-G131H-T158S-S248N, A088T-N109G-G131H-T158S-S248N-L257G, A088T-N109G-G131H-V149A-K256R-L257G, A088T-N109G-G131H-V149L-T158S-K256R-L257G, A088T-N109G-K256R, A088T-N109G-K256R-L257G, A088T-N109G-K256R-L257G, A088T-N109G-L257G, A088T-N109G-N218S-K256R, A088T-N109G-N218S-N243V-K256R, A088T-N109G-N218S-N243V-S248N-K256R, A088T-N109G-N218S-N243V-S248N-K256R, A088T-N109G-N218S-S248N, A088T-N109G-N218S-S248N-L257G, A088T-N109G-N243V-K256R, A088T-N109G-N243V-S248N-L257G-I268V, A088T-N109G-S248N, A088T-N109G-S248N-K256R, A088T-N109G-T158S-K256R-L257G, A088T-N109G-T158S-N218S, A088T-N109G-T158S-N218S-K256R-Q271H, A088T-N109G-T158S-N218S-N243V-K256R, A088T-N109G-T158S-N218S-N243V-K256R-L257G, A088T-N109G-T158S-N218S-N243V-L257G, A088T-N109G-T158S-N218S-N243V-S248N-K256R, A088T-N109G-T158S-N218S-S248N-N269D, A088T-N109G-T158S-N243V-K256R-L257G, A088T-N109G-T158S-N243V-S248N-A274D, A088T-N109G-T158S-N243V-S248N-K256R-L257G-N269D, A088T-N218S-K256R, A088T-N218S-N243V, A088T-N218S-N243V-K256R, A088T-N218S-N243V-K256R-L257G, A088T-N218S-N243V-S248N-K256R, A088T-N218S-N243V-S248N-L257G, A088T-N218S-S248N-L257G, A088T-N243V-S248N, A088T-N243V-S248N-K256R, A088T-N243V-S248N-L257G, A088T-S145T-T158S-S248N, A088T-S248N-K256R-L257G, A088T-S248N-L257G, A088T-T158S, A088T-T158S, A088T-T158S-K256R, A088T-T158S-L257G, A088T-T158S-N218S, A088T-T158S-N218S-K256R, A088T-T158S-N218S-N243V-K256R, A088T-T158S-N218S-N243V-K256R-L257G, A088T-T158S-N218S-N243V-L257G, A088T-T158S-N218S-S248N, A088T-T158S-N218S-S248N, A088T-T158S-N243V, A088T-T158S-N243V-K256R, A088T-T158S-N243V-S248N-L257G, A116T, A116T-G131H-L257G, A116T-G131H-N218S-K256R, A116T-G131H-N218S-N243V-K256R, A116T-G131H-N218S-N243V-K256R-L257G, A116T-G131H-N218S-N243V-S248N, A116T-G131H-N218S-N243V-S248N-K256R, A116T-G131H-N218S-S248N, A116T-G131H-T158S-K256R, A116T-G131H-T158S-N218S-L257G, A116T-G131H-T158S-N218S-N243V-K256R, A116T-G131H-T158S-N218S-N243V-L257G, A116T-G131H-T158S-N218S-N243V-S248N, A116T-G131H-T158S-N218S-S248N-L257G-N269D, A116T-G131H-T158S-N218S-S248N-Q271R, A116T-G131H-T158S-N218T-L257G, A116T-G131H-T158S-N243V-K256R, A116T-G131H-V150A-T158S-N243V-S248N-K256R-L257G, A116T-K141E-N218S-N243V-S248N-K256R-L257G, A116T-L257G, A116T-N218S-N243V-S248N, A116T-N218T-N243V-S248N, A116T-N243V-S248N-L257G, A116T-S248N, A116T-S248N-L257G, A116T-T158S-K256R, A116T-T158S-N218S-L257G, A116T-T158S-N218S-N243V-K256R, A116T-T158S-N218S-N243V-L257G, A116T-T158S-N243V, A116T-T158S-N243V-K256R-L257G, A116T-T158S-N243V-S248N-K256R, A116T-T158S-N243V-S248N-K256R-L257G, A116T-V149I-T158S-N243V-S248N-K256R-Q271H, G024S-G053S-N078S-G097A-N101S, G024S-G053S-N078S-G097A-N101S-A128S, G131H-K256R, G131H-N218S-K256R-L257G, G131H-N218S-N243V-L257G, G131H-N218S-N243V-S248N-K256R, G131H-N218S-S248N-K256R, G131H-N218S-S248N-L257G, G131H-N243V,

G131H-N243V-S248N, G131H-N243V-S248N-L257G, G131H-T158S-K256R-L257G, G131H-T158S-N218S, G131H-T158S-N218S-K256R, G131H-T158S-N218S-N240H-N243V-S248N-K256R-L257G, G131H-T158S-N218S-N243V-K256R, G131H-T158S-N218S-N243V-K256R-L257G, G131H-T158S-N218S-N243V-S248N, G131H-T158S-N218S-N243V-S248N-K256R-L257G, G131H-T158S-N218S-S248N-I268V, G131H-T158S-N218S-S248N-K256R-L257G-N269S, G131H-T158S-N243V-K256R-L257G, G131H-T158S-N243V-S248N, G131H-T158S-N243V-S248N-K256R, G131H-T158S-S248N, G131H-T158S-S248N-L257G, G131H-W241L-N243V-S248N-K256R, I107T-G131H-T158S-N243V-S248N-K256R-L257G, I107T-N109G-G131H-N218S-L257G, N109G-A116T-G131H-L257G, N109G-A116T-G131H-N218S-L257G, N109G-A116T-G131H-N218S-N243V, N109G-A116T-G131H-N218S-N243V-S248N-K256R, N109G-A116T-G131H-N218S-W241R-N243V-K256R, N109G-A116T-G131H-N243V-S248N-K256R, N109G-A116T-G131H-S248N-I268V, N109G-A116T-G131H-T158S-N218S, N109G-A116T-G131H-T158S-N218S-S248N-K256R, N109G-A116T-G131H-T158S-N218S-S248N-K256R-L257G, N109G-A116T-G131H-T158S-N218S-S248N-L257G, N109G-A116T-G131H-T158S-N243V-K256R-L257G, N109G-A116T-G131H-T158S-S248N-L257G, N109G-A116T-K141E-T158S-N218S-N243V-L257G, N109G-A116T-K256R, N109G-A116T-N218S-N243V, N109G-A116T-N218S-N243V-S248N, N109G-A116T-N218S-S248N-L257G, N109G-A116T-N243V-S248N-K256R-L257G, N109G-A116T-S248N, N109G-A116T-T158S-N218S-N243V-S248N-K256R, N109G-A116T-T158S-N218S-W241R-N243V, N109G-A116T-T158S-N243V-S248N, N109G-A116T-T158S-S248N-L257G, N109G-G131H-K256R, N109G-G131H-N218S-K256R, N109G-G131H-N218S-N243V, N109G-G131H-N218S-N243V-K256R-L257G, N109G-G131H-N218S-N243V-S248N-K256R, N109G-G131H-N218S-S248N-K256R, N109G-G131H-N243V, N109G-G131H-N243V-S248N, N109G-G131H-N243V-S248N-K256R-L257G, N109G-G131H-S248N, N109G-G131H-T158S-L257G, N109G-G131H-T158S-N218S-N243V-S248N, N109G-G131H-T158S-N218S-N243V-S248N-K256R, N109G-G131H-T158S-N218S-N243V-S248N-K256R-L257G, N109G-G131H-T158S-N243V-L257G, N109G-G131H-T158S-N243V-S248N-K256R, N109G-G131H-T158S-S248N-K256R, N109G-K141E-N218S-S248N-L257G, N109G-N218S-N243V, N109G-N218S-N243V-S248N-K256R, N109G-N218S-S248N-K256R-L257G, N109G-N218S-S248N-L257G, N109G-N243V-S248N-L257G-Q275R, N109G-T158S-I268V, N109G-T158S-N218S, N109G-T158S-N218S-N243V, N109G-T158S-N218S-N243V-S248N, N109G-T158S-N218S-S248N-K256R, N109S-A116T-S248N, N218S-K256R, N218S-N243V-K256R, N218S-N243V-L257G, N218S-N243V-S248N, N218S-S248N, N218S-S248N-K256R, N218S-S248N-K256R-L257G, S003P-N109G-G131H-N218S-N243V-S248N-K256R-L257G, S248N-K256R-L257G, T158S-K256R, T158S-K256R-L257G, T158S-N218S-K256R-L257G, T158S-N218S-L233S-S248N, T158S-N243V, T158S-N243V-S248N-K256R-N269D, T158S-N243V-S248N-L257G, V004L-A116T-N218S-N243V-S248N-L257G, and Y006H-N218S-N243V-S248N, wherein amino acid positions of the variant are numbered by correspondence with the sequence of SEQ ID NO:2. Such variants have enhanced proteolytic activity compared to BPN' (SEQ ID NO:2) and a greater PI value than BPN' in this assay. The invention includes a protease variant having enhanced proteolytic activity compared to BPN' (SEQ ID NO:2), a PI value of 1.0 relative to BPN'-v3, and a PI value of 1.0 relative to BPN'-v36 in this assay, the variant comprising an amino acid sequence having at least 60%, 70%, 80%, 85%, 90%, 91%, 92%, 93%, 94%, 95%, 96%, 97%, or 98% or 99% identity to SEQ ID NO:2 or SEQ ID NO:6 and comprising at least one set of amino acid substitutions selected from said group above, wherein amino acid positions of the variant are numbered by correspondence with amino acid positions of the SEQ ID NO:2 sequence. Also included are compositions, including, but not limited to, e.g., cleaning compositions, comprising at least one such variant and methods for cleaning utilizing at least one such variant as described in greater detail elsewhere herein.

The following BPN'-v36 variants were determined to have a PI value equal to or greater than 0.5 and less than 0.9 relative to BPN'-v36 in an egg microswatch cleaning assay in Detergent Composition 4 at pH 8 and 16° C.: BPN'-S024G-S053G-S078N-S101N-G128A-Y217Q amino acid sequence (SEQ ID NO:6) comprising at least one set of amino acid substitutions selected from the group consisting of A088T-A098S-G131H-S248N-K256R-L257G, A088T-A116T-G131H-K256R, A088T-A116T-G131H-N218S-S248N-K256R, A088T-A116T-G131H-N243V-S248N-L257G, A088T-A116T-G131H-S248N, A088T-A116T-G131H-S248N-K256R-L257G, A088T-A116T-G131H-T158S-K256R, A088T-A116T-G131H-T158S-L257G, A088T-A116T-G131H-T158S-N218S-L257G, A088T-A116T-G131H-T158S-N218S-N243V-S248N-K256R-L257G, A088T-A116T-K256R-L257G, A088T-A116T-K256R-L257G, A088T-A116T-N218S-N243V-Q271R, A088T-A116T-N218S-S248N-K256R, A088T-A116T-T158S, A088T-A116T-T158S, A088T-A116T-T158S-K256R, A088T-A116T-T158S-N218S-N243V-L257G, A088T-A116T-T158S-N218S-S248N-K256R, A088T-G131H, A088T-G131H-L257G, A088T-G131H-N218S-N243V-S248N-L257G, A088T-G131H-N243V-K256R, A088T-G131H-N243V-L257G, A088T-G131H-N243V-S248N, A088T-G131H-N243V-S248N-K256R, A088T-G131H-T158S-N218S-I234T-S248N-L257G, A088T-G131H-T158S-N218S-N243V-S248N-K256R-L257G, A088T-G131H-T158S-N243V-K256R-L257G, A088T-G131H-T158S-S248N, A088T-G131H-T158S-S248N-K256R, A088T-G131H-T158S-S248N-K256R-L257G, A088T-G131H-V149L-T158S-N243V-S248N-K256R-L257G, A088T-N109G-A116T-G131H-K141E-N218S, A088T-N109G-A116T-G131H-N218S-N243V-S248N-Q275R, A088T-N109G-A116T-G131H-N218S-S248N, A088T-N109G-A116T-G131H-N243V-S248N-K256R, A088T-N109G-A116T-G131H-S248N-K256R-L257G, A088T-N109G-A116T-G131H-T158S-K256R, A088T-N109G-A116T-G131H-T158S-N218S-N243V-S248N, A088T-N109G-A116T-G131H-T158S-N243V-S248N-K256R-L257G, A088T-N109G-A116T-G131H-T158S-S248N, A088T-N109G-A116T-G131H-V149A-T158S-N218S-K256R, A088T-N109G-A116T-N218S-S248N-K256R-L257G, A088T-N109G-A116T-N243V-K256R, A088T-N109G-A116T-N243V-S248N-L257G, A088T-N109G-A116T-S248N-L257G, A088T-N109G-A116T-T158S-N212D-N243V-K256R-L257G, A088T-N109G-A137E-T158S-N218S-N243V-S248N-K256R-L257G, A088T-N109G-D140G-N243V, A088T-N109G-G131H-A152S-T158S-N218S-S248N-K256R, A088T-N109G-G131H-D140G-T158S-N243V-S248N-K256R, A088T-N109G-G131H-K256R-L257G, A088T-N109G-G131H-N218S, A088T-N109G-G131H-N218S-N243V, A088T-N109G-G131H-T158S-L257G, A088T-N109G-G131H-T158S-N218S-

N243V-S248N-K256R-L257G, A088T-N109G-G131H-T158S-N218S-W241R-S248N-L257G, A088T-N109G-G131H-T158S-S248N-K256R, A088T-N109G-N218S-S248N-K256R, A088T-N109G-N243V-S248N-K256R, A088T-N109G-T158S, A088T-N109G-T158S-N243V-S248N-K256R, A088T-N109G-T158S-N243V-S248N-Q275R, A088T-N109G-T158S-S248N, A088T-N218S-N243V-S248N-K256R-L257G, A088T-N243V-L257G, A088T-S248N, A088T-T158S-K256R, A088T-T158S-N218S-K256R, A088T-T158S-N218S-L257G, A088T-T158S-N218S-L257G, A088T-T158S-N218S-N243V-S248N, A088T-T158S-N218S-N243V-S248N-L257G, A088T-T158S-N218S-Q245K-S248N-K256R, A088T-T158S-N218S-S248N-L257G-Q275K, A088T-T158S-N243V-K256R, A088T-T158S-N243V-K256R-L257G, A088T-T158S-N243V-S248N-K256R, A088T-T158S-S248N, A088T-T158S-S248N-K256R-L257G, A088T-T158S-S248N-L257G, A088T-T158S-S248N-L257G, A098S-G131H-T158S-N218S-N243V-S248N-K256R-L257G, A116T-G131H-K141E-N218S-N243V-S248N-L257G, A116T-G131H-N218S-W241R-N243V-S248N-K256R-L257G, A116T-G131H-N243V, A116T-G131H-T158S-N218S-S248N-K256R, A116T-G131H-V139I-N218S-N243V-S248N, A116T-N218S-S248N-K256R, A116T-T158S-L257G-Q271R, A116T-T158S-N218S-N243V-K256R-L257G, G053S-A088T-N109G-A116T-G131H-T158S-G169S-N218S-S248N-K256R-L257G, G131H-N218S-L257G, G131H-T158S, G131H-T158S-K256R, K256R, L090I-N109G-T158S-N243V, L257G, N109G-A116T-G131H, N109G-A116T-G131H-N243V, N109G-A116T-G131H-T158S-N218S-N243V-S248N-K256R, N109G-A116T-S248N-K256R, N109G-A116T-T158S-N218S-K237R-N243V-S248N, N109G-A116T-T158S-S248N, N109G-G131H-T158S, N109G-G131H-T158S-N243V-K256R-L257G, N109G-G131H-T158S-S248N-Q271R, N109G-N218S-S248N-K256R, N109G-N243V-S248N-L257G, N109G-S248N, N109G-T158S-N218S-N243V-L257G, N109G-T158S-N243V-K256R-L257G, N109G-T158S-N243V-S248N-K256R-L257G, N218S-N243V-S248N-K256R-L257G, S003P-N109G-A116T-G131H-T158S-N218S-K256R, S003P-N109G-G131H-T158S-L257G, S105H-W106G-I107L-I108S-N109A-G110A-I111S-E112N-W113G-A114P, T158S-N218S-S248N-K256R, T158S-N243V-S248N, T158S-S248N, T158S-S248N-K256R-L257G, V004A-A088T-A116T-T158S-N218S, V004A-A088T-G131H-N218S-N243V-S248N-L257G, Y006H-N109G-N218S-N243V-S248N, Y104H-A116T-T158S-S248N, A088T-A116T-G131H-N218S-S248N-L257G, A088T-A116T-G131H-T158S-N218S-N243V-L257G, A088T-A116T-G131H-T158S-N243V-K256R-L257G, A088T-A116T-N218S, A088T-G131D-T158S-N243V-S248N, A088T-G131H-N218S-K237R-K256R-L257G, A088T-G131H-N218S-K256R, A088T-K213N-N243V-S248N-K256R, A088T-K256R-L257G, A088T-N109G-A116T-G131H-D140G-S248N-L257G, A088T-N109G-A116T-G131H-L257G, A088T-N109G-A116T-G131H-N218S-N243V-S248N-K256R-L257G, A088T-N109G-A116T-G131H-T158S-N218S-N243V-S248N, A088T-N109G-A116T-M124I-G131H-T158S-N218S-S248N-L257G, A088T-N109G-A116T-T158S-N218S-N243V-K256R, A088T-N109G-A116T-T158S-N218S-N243V-L257G, A088T-N109G-A116T-T158S-N218S-S248N, A088T-N109G-G131H-K256R-L257G, A088T-N109G-G131H-N218S-N243V-S248N-L257G, A088T-N109G-G131H-N243V-S248N, A088T-N109G-G131H-T158S-L233S-N243V-S248N, A088T-N109G-G131H-T158S-N218S-S248N-K256R, A088T-N109G-L257G, A088T-N109G-N218S-K256R-L257G, A088T-N109G-N218S-S248N-T255K-K256R-L257G, A088T-N109G-S248N-K256R-L257G, A088T-N109G-T158S-N218S-N243V, A088T-N109G-T158S-N218S-N243V-L257G, A088T-N109G-T158S-N218S-N243V-S248N-L257G, A088T-N109G-T158S-N218S-S248N, A088T-S248N-K256R-L257G, A088T-S248N-L257G-I268V, A088T-T158S-N243V-L257G, A088T-T158S-V203I-N218S-K256R-L257G, A088T-Y104H-A116T-G131H-N218S-N243V, A116T-D140G-T158S-N218S-N243V-S248N, A116T-G131H-T158S-K256R-L257G, A116T-G131H-T158S-N243V-S248N, A116T-G157E-T158S-N243V-S248N-K256R, A116T-S248N-K256R, G131H-N218S-S248N, G131H-N243V-K256R, G131H-T158S-N243V-L257G, K256R-L257G, N109G-A116T-G131H-T158S-N218S-N243V-S248N, N109G-A116T-N218S-N243V-L257G, N109G-A116T-N218S-W241R-N243V-S248N-K256R-L257G, N109G-A116T-T158S-N243V, N109G-A116T-T158S-S248N-K256R, N109G-N243V, N109G-T158S-K256R-L257G, N243V, P014L-A015L-L016C-H017T-S018L-Q019K-G020A-Y021T-T022L-G023E, S003P-S248N-L257G, T158S-N218S-N243V-S248N, T158S-S248N-K256R, Y104H-N109G-G131H-N243V-S248N, A088T-A116T-G131H-L257G, A088T-A116T-G131H-N218S-N243V, A088T-A116T-G131H-N218S-S248N-K256R, A088T-A116T-G131H-T158S-N243V-S248N-L257G, A088T-A116T-L257G, A088T-A116T-N218S, A088T-A116T-N218S-N243V-S248N, A088T-A116T-T158S-N218S-S248N, A088T-A116T-T158S-N243V-S248N-K256R, A088T-A138E-N218S-N243V-K256R, A088T-G131H-N218S-N243V-S248N-K256R, A088T-G131H-T158S-S248N-K256R, A088T-N109G-A116T-G131H-N218S-S248N-K256R-L257G, A088T-N109G-A116T-G131H-N243V-S248N-K256R, A088T-N109G-A116T-G131H-T158S-N218S-L257G-I268V, A088T-N109G-A116T-G131H-W241L-S248N-K256R-L257G, A088T-N109G-A116T-N218S-N243V-S248N-K256R, A088T-N109G-A116T-T158S-N243V-K256R-L257G, A088T-N109G-A116T-T158S-N243V-S248N, A088T-N109G-G131H-N218S-L257G, A088T-N109G-G131H-N218S-S248N, A088T-N109G-G131H-T158S-N243V-S248N-L257G, A088T-N109G-N243V-K256R-L257G, A088T-N109G-T158S-S248N-K256R, A088T-N109G-W241R-S248N-K256R, A088T-N218S-S248N-L257G, A088T-T158S-N218S-S248N-K256R, A088T-T158S-N218S-S248N-L257G, A116T-G01H-T158S-N218S-N243V, A116T-N218S-S248N, A116T-N243V-K256R, A116T-T158S, G131H-S248N-K256R, N109G-A116T-G131H-N243V-K256R-L257G, N109G-A116T-I234T-N243V-S248N-K256R-L257G, N109G-A116T-T158S-K256R-L257G, N109G-A116T-T158S-N218S-S248N-K256R, N109G-G131H, N109G-G131H-A137V-T158S-N218S-S248N, N109G-G131H-K141E-L257G, N109G-G131H-T158S-N243V-S248N-L257G, T158S-N218S-N243V-K256R, A088T-A116T-T158S-N243V-K256R-L257G, A088T-N109G-A116T-T158S-K256R-L257G, A088T-N109G-T158S-N218S-S248N, A088T-S248N-L257G, A088T-Y104H-N109G-G131H-A137E-T158S-N218S-N243V-S248N-K256R, G065D-A088T-G131H-N243V-S248N, Y104H-N218S-L257G, A088T-A116T-G131H-V150A-N218S-S248N-L257G, A088T-A116T-T158S-K256R-L257G, A088T-I108T-N109G-G131H-T158S-N218S-S248N-K256R-L257G, A088T-N109G-A116T-T158S-S248N-L257G-Q271P, A088T-N109G-A116T-V148A-N218S-N243V, A088T-Y104H-N109G-A116T-A153S-N218S-N243V-S248N-L257G-N269D, and V004M-A116T-

V148A-T158S-N243V-S248N-K256R, wherein amino acid positions of the variant are numbered by correspondence with the sequence of SEQ ID NO:2. Such variants have proteolytic activity. The invention includes a protease variant having proteolytic activity and/or a PI value equal to or greater than 0.5 and less than 0.9 relative to BPN'-v36 in this assay, the variant comprising an amino acid sequence having at least 60%, 70%, 80%, 85%, 90%, 91%, 92%, 93%, 94%, 95%, 96%, 97%, or 98% or 99% identity to SEQ ID NO:2 or SEQ ID NO:6 and comprising at least one set of acid substitutions selected from said group above, wherein amino acid positions of the variant are numbered by correspondence with amino acid positions of the SEQ ID NO:2 sequence. Also included are compositions, including, but not limited to, e.g., cleaning compositions, comprising at least one such variant and methods for cleaning utilizing at least one such variant as described in greater detail elsewhere herein.

Also provided is a subtilisin protease variant having enhanced proteolytic activity compared to BPN'-v36 and/or BPN-'v3 and/or a PI value of greater than 1.0 compared to BPN'-v36 in a BMI microswatch or egg microswatch cleaning assay in Detergent Composition 4 at pH 8 and 16° C., the variant comprising an amino acid sequence having at least 85%, 90%, 91%, 92%, 93%, 94%, 95%, 96%, 97%, or 98% identity to SEQ ID NO:2, wherein the variant comprises at least one substitution selected from the group of X001R/T, X002R, X003F/P, X004A/L/M/P, X005S, X006H, X014L, X015L/S, X016C, X017T, X018L, X019K, X020A, X021T, X022L, X023E, X024S, X034S, X053S, X057Q, X065D, X078S, X086L, X088T, X090I, X097A, X098S, X101S, X104H, X105H/P, X106G, X107L/T, X108S/T, X109A/G/S, X110A, X111S, X112N, X113G, X114P/S, X116T, X124I, X128S, X131D/H, X137E/V, X138E/V, X139I, X140G, X141E/R, X143A/F, X144V, X145F/P/T, X146C, X147A/I, X148A, X149A/I/L, X150A, X151S, X152S, X153S, X154A, X155P, X156T, X157E/L, X158M/S, X159E, X160E, X161L, X169S, X182F, X203I, X204F, X207L, X211V, X212D, X213N, X216S, X218S/T, X223G, X231V, X232S, X233S, X234T, X235P, X236F/P, X237N/R, X240H, X241L/R, X243F/V, X245K, X248N, X251K, X255K, X256R, X257G, X260F, X267M, X268V, X269D/S, X271H/K/P/R, X272G/V, X273T, X274D/L/T/V, and X275K/R/S, and optionally at least one substitution selected from the group of A001R/T, Q002R, S003F/P, V004A/L/M/P, P005S, Y006H, P014L, A015L/S, L016C, H017T, S018L, Q019K, G020A, Y021T, T022L, G023E, G024S, G034S, G053S, P057Q, G065D, N078S, P086L, A088T, L090I, G097A, A098S, N101S, Y104H, S105H/P, W106G, I107UT, I108S/T, N109A/G/S, G110A, I111S, E112N, W113G, A114P/S, A116T, M124I, A128S, G131D/H, A137E/V, A138E/V, V139I, D140G, K141E/R, V143A/F, A144V, S145F/P/T, G146C, V147A/I, V148A, V149A/I/L, V150A, A151S, A152S, A153S, G154A, N155P, E156T, G157E/L, T158M/S, S159E, G160E, S161L, G169S, S182F, V203I, S204F, S207L, G211V, N212D, K213N, A216S, N218S/T, A223G, A231V, A232S, L233S, I234T, L235P, S236F/P, K237N/R, N240H, W241L/R, N243F/V, Q245K, S248N, E251K, T255K, K256R, L257G, S260F, L267M, I268V, N269D/S, Q271H/K/P/R, A272G/V, A273T, A274D/L/TN, Q275K/R/S, wherein amino acid positions of the variant are numbered by correspondence with positions of the sequence of SEQ ID NO:2. Such variants have enhanced proteolytic activity compared to BPN' (SEQ ID NO:2) BPN'-v3, and BPN'-v36 and a PI value greater than that of BPN', BPN'-v3, and BPN'-v36 in this assay. Also included are compositions, including, but not limited to, e.g., cleaning compositions, comprising at least one such variant and methods for cleaning utilizing at least one such variant as described in greater detail elsewhere herein.

Example 10

Construction and Cleaning Performance of Additional Variants of BPN'-v36

The DNA from the site evaluation libraries of the BPN'-v36 (described in Example 7) was further mutagenized by error-prone PCR. These libraries were amplified with primers P4973 and P4950 (described in Example 7) using Taq DNA polymerase (Promega). Each PCR amplification reaction contained 30 pmol of each primer, 100 ng of the template DNA (SELs of the BPN'-v36) and various amount of $MnCl_2$. The PCR reaction (20 µL) was initially heated at 95° C. for 2.5 min followed by 30 cycles of denaturation at 94° C. for 15 sec., annealing at 55° C. for 15 sec. and extension at 72° C. for 2 min. The DNA fragment was gel-purified by the QIAGEN® gel-band purification kit, digested by the BamHI and HindIII restriction enzymes and ligated with the pHPLT-BPN' partial opt vector that also was digested with the same restriction enzymes. Ligation mixtures were amplified using rolling circle amplification in an Illustra Templiphi kit according to the manufacturer's recommendation (GE Healthcare) to generate multimeric DNA for transformation into *Bacillus subtilis*. For this purpose, 1 µl of the ligation mixture was mixed with 5 µl of the sample buffer, heated to 95° C. for 3 min and cooled on ice. Next, 5 µl of the reaction buffer and 0.2 µl of the enzyme were added to each tube, followed by incubation at 30° C. for 10 hours. Products of the rolling circle amplification were diluted 100 times and used to transform *B. subtilis* cells (ΔaprE, ΔnprE, amyE::xylRPxylAcomK-phleo). An aliquot of the transformation mix was plated on LB plates containing 1.6% skim milk and 10 µg/mL neomycin and incubated overnight at 37° C.

About 500,000 clones were pre-screened on skim milk plates. Very few of them formed halos (i.e., indicative of the presence of functional protease). Colonies with halos were picked, inoculated in 150 µl of LB media containing 10 µg/mL neomycin and sequenced (Quintara). Sequences of these clones were analyzed by looking for combination of mutations, which occurred in this pool multiple times and might provide performance benefits. In order to assess the performance of these mutation combinations, double mutants were created in the BPN'-v36 background by PCR fusion as described below. For this purpose, two or three partially overlapping fragments were amplified by mutagenic primers. Primer combinations used to generate the respective variants are shown in Table 10-1 and primer sequences are shown in Table 10-2.

TABLE 10-1

| Primers Pairs Used to Amplify Fragments | | | | | |
|---|---|---|---|---|---|
| Variant | Mutation 1 | Mutation 2 | Fragment 1 | Fragment 2 | Fragment 3 |
| 1 | A45S | S236Y | P4974, P6645 | P6644, P6647 | P6646, P4976 |

TABLE 10-1-continued

| Primers Pairs Used to Amplify Fragments | | | | | |
|---|---|---|---|---|---|
| Variant | Mutation 1 | Mutation 2 | Fragment 1 | Fragment 2 | Fragment 3 |
| 2 | A45S | S236G | P4974, P6645 | P6644, P6649 | P6648, P4976 |
| 3 | I115T | S183T | P4974, P6651 | P6650, P6655 | P6654, P4976 |
| 4 | I115V | N184Y | P4974, P6653 | P6652, P6657 | P6656, P4976 |
| 5 | I31T | S37P | P4974, P6659 | P6658, P4976 | |
| 6 | I31T | I35L | P4974, P6661 | P6660, P4976 | |
| 7 | I31V | S38W | P4974, P6663 | P6662, P4976 | |
| 8 | *N25K* | P129R | P4974, P6665 | P6664, P6667 | P6666, P4976 |
| 9 | *N25K* | P129K | P4974, P6665 | P6664, P6669 | P6668, P4976 |
| 10 | P14T | S37T | P4974, P6671 | P6670, P6673 | P6672, P4976 |
| 11 | P5L | Q217K | P4974, P6679 | P6678, P6681 | P6680, P4976 |
| 12 | P5L | Q217G | P4974, P6679 | P6678, P6683 | P6682, P4976 |
| 13 | Q10L | S37P | P4974, P6685 | P6684, P6675 | P6674, P4976 |
| 14 | Q10R | S37T | P4974, P6687 | P6686, P6673 | P6672, P4976 |
| 15 | S37P | T254S | P4974, P6675 | P6674, P6689 | P6688, P4976 |
| 16 | *N25K* | S37P | P4974, P6665 | P6664, P6675 | P6674, P4976 |
| 17 | G24A | S37W | P4974, P6691 | P6690, P6677 | P6676, P4976 |
| 18 | *N25K* | P129R | P4974, P6665 | P6664, P6667 | P6666, P4976 |
| 20 | S161P | S162L | P4974, P6695 | P6694, P4976 | |
| 21 | S161P | T253A | P4974, P6693 | P6692, P6701 | P6700, P4976 |
| 22 | S161P | S260P | P4974, P6693 | P6692, P6703 | P6702, P4976 |
| 23 | S162L | D181H | P4974, P6697 | P6696, P6711 | P6710, P4976 |
| 24 | S162L | D181G | P4974, P6697 | P6696, P6713 | P6712, P4976 |
| 25 | S18F | S162L | P4974, P6715 | P6714, P6697 | P6696, P4976 |
| 26 | S18T | S162P | P4974, P6717 | P6716, P6699 | P6698, P4976 |
| 27 | S18P | D120N | P4974, P6719 | P6718, P6727 | P6726, P4976 |
| 28 | S18Y | K213R | P4974, P6721 | P6720, P6729 | P6728, P4976 |
| 29 | S18L | Y21S | P4974, P6731 | P6730, P4976 | |
| 30 | S18T | Y21N | P4974, P6733 | P6732, P4976 | |
| 31 | S9T | K141F | P4974, P6635 | P6734, P6737 | P6736, P4976 |
| 32 | S9T | K141R | P4974, P6635 | P6734, P6739 | P6738, P4976 |
| 33 | Q19L | S260N | P4974, P6725 | P6724, P6705 | P6704, P4976 |
| 34 | Q19L | S260P | P4974, P6725 | P6724, P6703 | P6702, P4976 |
| 35 | N61S | S260P | P4974, P6741 | P6740, P6703 | P6702, P4976 |
| 36 | N61D | S260I | P4974, P6743 | P6742, P6707 | P6706, P4976 |
| 37 | T253A | S260P | P4974, P6701 | P6700, P6703 | P6702, P4976 |
| 38 | A134T | S260G | P4974, P6745 | P6744, P6709 | P6708, P4976 |
| 39 | A133V | S260N | P4974, P6648 | P6746, P6705 | P6704, P4976 |

TABLE 10-2

| Primer Sequences Used for Generation of Double Mutants of BPN'-v36 | |
|---|---|
| Primer Name | SEQ ID NO: |
| P6644 | SEQ ID NO: 64 |
| P6645 | SEQ ID NO: 65 |
| P6646 | SEQ ID NO: 66 |
| P6647 | SEQ ID NO: 67 |
| P6648 | SEQ ID NO: 68 |
| P6649 | SEQ ID NO: 69 |
| P6650 | SEQ ID NO: 70 |
| P6651 | SEQ ID NO: 71 |
| P6652 | SEQ ID NO: 72 |
| P6653 | SEQ ID NO: 73 |
| P6654 | SEQ ID NO: 74 |
| P6655 | SEQ ID NO: 75 |
| P6656 | SEQ ID NO: 76 |
| P6657 | SEQ ID NO: 77 |
| P6658 | SEQ ID NO: 78 |
| P6659 | SEQ ID NO: 79 |
| P6660 | SEQ ID NO: 80 |
| P6661 | SEQ ID NO: 81 |
| P6662 | SEQ ID NO: 82 |
| P6663 | SEQ ID NO: 83 |
| P6664 | SEQ ID NO: 84 |
| P6665 | SEQ ID NO: 85 |
| P6666 | SEQ ID NO: 86 |
| P6667 | SEQ ID NO: 87 |
| P6668 | SEQ ID NO: 88 |
| P6669 | SEQ ID NO: 89 |
| P6670 | SEQ ID NO: 90 |
| P6671 | SEQ ID NO: 91 |
| P6672 | SEQ ID NO: 92 |
| P6673 | SEQ ID NO: 93 |
| P6674 | SEQ ID NO: 94 |
| P6675 | SEQ ID NO: 95 |
| P6676 | SEQ ID NO: 96 |
| P6677 | SEQ ID NO: 97 |
| P6678 | SEQ ID NO: 98 |
| P6679 | SEQ ID NO: 99 |
| P6680 | SEQ ID NO: 100 |
| P6681 | SEQ ID NO: 101 |
| P6682 | SEQ ID NO: 102 |
| P6683 | SEQ ID NO: 103 |
| P6684 | SEQ ID NO: 104 |
| P6685 | SEQ ID NO: 105 |
| P6686 | SEQ ID NO: 106 |
| P6687 | SEQ ID NO: 107 |
| P6688 | SEQ ID NO: 108 |
| P6689 | SEQ ID NO: 109 |
| P6690 | SEQ ID NO: 110 |
| P6691 | SEQ ID NO: 111 |
| P6692 | SEQ ID NO: 112 |
| P6693 | SEQ ID NO: 113 |
| P6694 | SEQ ID NO: 114 |
| P6695 | SEQ ID NO: 115 |
| P6696 | SEQ ID NO: 116 |
| P6697 | SEQ ID NO: 117 |
| P6698 | SEQ ID NO: 118 |
| P6699 | SEQ ID NO: 119 |
| P6700 | SEQ ID NO: 120 |
| P6701 | SEQ ID NO: 121 |
| P6702 | SEQ ID NO: 122 |
| P6703 | SEQ ID NO: 123 |
| P6704 | SEQ ID NO: 124 |
| P6705 | SEQ ID NO: 125 |
| P6706 | SEQ ID NO: 126 |
| P6707 | SEQ ID NO: 127 |
| P6708 | SEQ ID NO: 128 |
| P6709 | SEQ ID NO: 129 |
| P6710 | SEQ ID NO: 130 |
| P6711 | SEQ ID NO: 131 |
| P6712 | SEQ ID NO: 132 |
| P6713 | SEQ ID NO: 133 |
| P6714 | SEQ ID NO: 134 |
| P6715 | SEQ ID NO: 135 |
| P6716 | SEQ ID NO: 136 |
| P6717 | SEQ ID NO: 137 |
| P6718 | SEQ ID NO: 138 |

TABLE 10-2-continued

| Primer Sequences Used for Generation of Double Mutants of BPN'-v36 | |
|---|---|
| Primer Name | SEQ ID NO: |
| P6719 | SEQ ID NO: 139 |
| P6720 | SEQ ID NO: 140 |
| P6721 | SEQ ID NO: 141 |
| P6722 | SEQ ID NO: 142 |
| P6723 | SEQ ID NO: 143 |
| P6724 | SEQ ID NO: 144 |
| P6725 | SEQ ID NO: 145 |
| P6726 | SEQ ID NO: 146 |
| P6727 | SEQ ID NO: 147 |
| P6728 | SEQ ID NO: 148 |
| P6729 | SEQ ID NO: 149 |
| P6730 | SEQ ID NO: 150 |
| P6731 | SEQ ID NO: 151 |
| P6732 | SEQ ID NO: 152 |
| P6733 | SEQ ID NO: 153 |
| P6734 | SEQ ID NO: 154 |
| P6735 | SEQ ID NO: 155 |
| P6736 | SEQ ID NO: 156 |
| P6737 | SEQ ID NO: 157 |
| P6738 | SEQ ID NO: 158 |
| P6739 | SEQ ID NO: 159 |
| P6740 | SEQ ID NO: 160 |
| P6741 | SEQ ID NO: 161 |
| P6742 | SEQ ID NO: 162 |
| P6743 | SEQ ID NO: 163 |
| P6744 | SEQ ID NO: 164 |
| P6745 | SEQ ID NO: 165 |
| P6746 | SEQ ID NO: 166 |
| P6747 | SEQ ID NO: 167 |

Each PCR amplification reaction contained 30 pmol of each primer and 100 ng of the BPN'-v36 parent template DNA (plasmid pHPLT-BPN'-v36) (see FIG. 4). Amplifications were carried out using Vent DNA polymerase (NEB). The PCR reaction (20 μL) was initially heated at 95° C. for 2.5 min followed by 30 cycles of denaturation at 94° C. for 15 sec., annealing at 55° C. for 15 sec. and extension at 72° C. for 40 sec. Following amplification, the 5' and 3' gene fragments were gel-purified by the QIAGEN® gel-band purification kit, mixed (50 ng of each fragment), mixed and amplified by PCR once again using the primers P4973 and P4950 to generate the full-length gene fragment. The PCR conditions were same as described above, except the extension phase, which was carried out at 72° C. for 2 min. The full-length DNA fragment was gel-purified by the QIAGEN® gel-band purification kit, digested by the BamHI and HindIII restriction enzymes and ligated with the pHPLT-BPN' partial opt vector that also was digested with the same restriction enzymes. Ligation mixtures were amplified using rolling circle amplification in an Illustra Templiphi kit according to the manufacturer's recommendation (GE Healthcare) to generate multimeric DNA for transformation into *Bacillus subtilis*. For this purpose, 1 μl of the ligation mixture was mixed with 5 μl of the sample buffer, heated to 95° C. for 3 min and cooled on ice. Next, 5 μl of the reaction buffer and 0.2 μl of the enzyme were added to each tube, followed by incubation at 30° C. for 10 hours. Products of the rolling circle amplification were diluted 100 times and used to transform *B. subtilis* cells (ΔaprE, ΔnprE, amyE::xylRPxylAcomK-phleo). An aliquot of the transformation mix was plated on LB plates containing 1.6% skim milk and 10 μg/mL neomycin and incubated overnight at 37° C. Subsequently, the colonies with halos were inoculated in 150 μl of LB media containing 10 μg/mL neomycin. The next day, the cultures were either frozen with 15% glycerol or grown in MBD medium for biochemical analysis as described in Example 2.

The variants were tested for cleaning performance using BMI microswatch assay in Detergent Composition 4 at 16° C. and pH 8, BMI microswatch assay in Detergent Composition 4 at 16° C. and pH 7, and Egg microswatch assay in Detergent Composition 4 at 16° C. and pH 8. Protein content was determined using TCA assay. All assays were performed as described in Example 1 and Performance Indices were calculated relative to BPN'-v36 (i.e., BPN'-S24G-S53G-S78N-S101N-G128A-Y217Q).

The following BPN'-v36 variants were determined to have a PI value equal to about 1.0 relative to BPN'-v36 in a BMI microswatch cleaning assay in Detergent Composition 4 at pH 8 and 16° C.: BPN'-S024G-S053G-S078N-S101N-G128A-Y217Q amino acid sequence (SEQ ID NO:6) comprising at least one set of amino acid substitutions selected from the group consisting of BPN'-v36, A133V-S260N, N061S-S260P, P014T-S037T, S009T-K141F, S009T-K141R, S018F-S162L, S018L-Y021S, S018P-D120N, S018T-S162P, S018T-Y021N, S018Y-K213R, S161P-S162L, S161P-S260P, and T253A-S260P, wherein amino acid positions of the variant are numbered by correspondence with the sequence of SEQ ID NO:2. Such variants have enhanced proteolytic activity compared to BPN' (SEQ ID NO:2) and a greater PI value than BPN' in this assay. The invention includes a protease variant having enhanced proteolytic activity compared to BPN' (SEQ ID NO:2), a PI value of 1.0 relative to BPN'-v3, and a PI value of 1.0 relative to BPN'-v36 in this assay, the variant comprising an amino acid sequence having at least 60%, 70%, 80%, 85%, 90%, 91%, 92%, 93%, 94%, 95%, 96%, 97%, or 98% or 99% identity to SEQ ID NO:2 or SEQ ID NO:6 and comprising at least one set of amino acid substitutions selected from said group above, wherein amino acid positions of the variant are numbered by correspondence with amino acid positions of the SEQ ID NO:2 sequence. Also included are compositions, including, but not limited to, e.g., cleaning compositions, comprising at least one such variant and methods for cleaning utilizing at least one such variant as described in greater detail elsewhere herein.

The following BPN'-v36 variants were determined to have a PI value equal to about 0.9 relative to BPN'-v36 in a BMI microswatch cleaning assay in Detergent Composition 4 at pH 8 and 16° C.: BPN'-S024G-S053G-S078N-S101N-G128A-Y217Q amino acid sequence (SEQ ID NO:6) comprising at least one set of amino acid substitutions selected from the group consisting of A134T-S260G, I115V-N184Y, N025K-S037P, Q010L-S037P, Q019L-S260N, Q019L-S260P, S037P-T254S, and S161P-T253A, wherein amino acid positions of the variant are numbered by correspondence with the sequence of SEQ ID NO:2. Such variants have proteolytic activity. The invention includes a protease variant having proteolytic activity and/or a PI value of 0.9 relative to BPN'-v36 in this assay, the variant comprising an amino acid sequence having at least 60%, 70%, 80%, 85%, 90%, 91%, 92%, 93%, 94%, 95%, 96%, 97%, or 98% or 99% identity to SEQ ID NO:2 or SEQ ID NO:6 and comprising at least one set of acid substitutions selected from said group above, wherein amino acid positions of the variant are numbered by correspondence with amino acid positions of the SEQ ID NO:2 sequence. Also included are compositions, including, but not limited to, e.g., cleaning compositions, comprising at least one such variant and methods for cleaning utilizing at least one such variant as described in greater detail elsewhere herein.

The following BPN'-v36 variants were determined to have a PI value equal to or greater than 0.5 and less than 0.9 relative to BPN'-v36 in a BMI microswatch cleaning assay in Detergent Composition 4 at pH 8 and 16° C.: BPN'-S024G-S053G-S078N-S101N-G128A-Y217Q amino acid sequence (SEQ ID NO:6) comprising at least one set of amino acid substitutions selected from the group consisting of A045S-S236G, G024A-S037W, I031V-S038W, N061D-S260I, Q010R-S037T, I115T-S183T, N025K-P129K, N025K-P129R, A045S-S236Y, and S162L-D181H, wherein amino acid positions of the variant are numbered by correspondence with the sequence of SEQ ID NO:2. Such variants have proteolytic activity. The invention includes a protease variant having proteolytic activity and/or a PI value equal to or greater than 0.5 and less than 0.9 relative to BPN'-v36 in this assay, the variant comprising an amino acid sequence having at least 60%, 70%, 80%, 85%, 90%, 91%, 92%, 93%, 94%, 95%, 96%, 97%, or 98% or 99% identity to SEQ ID NO:2 or SEQ ID NO:6 and comprising at least one set of acid substitutions selected from said group above, wherein amino acid positions of the variant are numbered by correspondence with amino acid positions of the SEQ ID NO:2 sequence. Also included are compositions, including, but not limited to, e.g., cleaning compositions, comprising at least one such variant and methods for cleaning utilizing at least one such variant as described in greater detail elsewhere herein.

The following BPN'-v36 variants were determined to have a PI value greater than 1.0, at least 1.1, at least 1.2, at least 1.3, at least 1.4, at least 1.5, at least 1.6, at least 1.7, at least 1.8, at least 1.9, at least 2, from greater than 1.0 to about 10, from greater than 1.0 to about 8, or from greater than 1.0 to about 5 relative to BPN'-v36 in a BMI microswatch cleaning assay in Detergent Composition 4 at pH 7 and 16° C.: BPN'-S024G-S053G-S078N-S101N-G128A-Y217Q amino acid sequence (SEQ ID NO:6) comprising at least one set of amino acid substitutions selected from the group consisting of S018F-S162L, S108P-D120N, P014T-S037T, S009T-K141R, and S161P-S162L, wherein amino acid positions of the variant are numbered by correspondence with the sequence of SEQ ID NO:2. Such variants have enhanced proteolytic activity compared to BPN', BPN'-v3, and BPN'-v36, and a greater PI value than BPN', BPN'-v3 and BPN'-v36 in this assay. The invention includes a protease variant having enhanced proteolytic activity compared to BPN' (SEQ ID NO:2), enhanced proteolytic activity compared to BPN', BPN'-v3, and BPN'-v36, a PI value of greater than 1.0 to about 5 relative to BPN'-v3, and/or a PI value of greater than 1.0 to about 5 relative to BPN'-v36 in this assay, the variant comprising an amino acid sequence having at least 60%, 70%, 80%, 85%, 90%, 91%, 92%, 93%, 94%,95%, 96%, 97%, or 98% or 99% identity to SEQ ID NO:2 or SEQ ID NO:6 and comprising at least one set of amino acid substitutions selected from said group above, wherein amino acid positions of the variant are numbered by correspondence with amino acid positions of the SEQ ID NO:2 sequence. Also included are compositions, including, but not limited to, e.g., cleaning compositions, comprising at least one such variant and methods for cleaning utilizing at least one such variant as described in greater detail elsewhere herein.

The following BPN'-v36 variants were determined to have a PI value equal to about 1.0 relative to BPN'-v36 in a BMI microswatch cleaning assay in Detergent Composition 4 at pH 7 and 16° C.: BPN'-S024G-S053G-S078N-S101N-G128A-Y217Q amino acid sequence (SEQ ID NO:6) comprising at least one set of amino acid substitutions selected from the group consisting of BPN'-v36, N061S-S260P, Q010L-S037P, S009T-K141F, S018L-Y021S, S018T-S162P, S018T-Y021N, S018Y-K213R, S037P-T254S, S161P-S260P, S161P-T253A, and T253A-S260P, wherein amino acid positions of the variant are numbered by correspondence with the sequence of SEQ ID NO:2. Such variants have enhanced proteolytic activity compared to BPN' (SEQ ID NO:2) and a greater PI value than BPN' in this assay. The invention includes a protease variant having enhanced proteolytic activity compared to BPN' (SEQ ID NO:2), a PI value of 1.0 relative to BPN'-v3, and a PI value of 1.0 relative to BPN'-v36 in this assay, the variant comprising an amino acid sequence having at least 60%, 70%, 80%, 85%, 90%, 91%, 92%, 93%, 94%, 95%, 96%, 97%, or 98% or 99% identity to SEQ ID NO:2 or SEQ ID NO:6 and comprising at least one set of amino acid substitutions selected from said group above, wherein amino acid positions of the variant are numbered by correspondence with amino acid positions of the SEQ ID NO:2 sequence. Also included are compositions, including, but not limited to, e.g., cleaning compositions, comprising at least one such variant and methods for cleaning utilizing at least one such variant as described in greater detail elsewhere herein.

The following BPN' variants were determined to have a PI value of about 0.9 relative to BPN'-v3 in a BMI microswatch cleaning assay in Detergent Composition 4 at pH 7 and 16° C.: BPN' amino acid sequence (SEQ ID NO:2) comprising at least one set of amino acid substitutions selected from the group consisting of A133V-S260N, A134T-S260G, I115T-S183T, I115V-N184Y, N061D-S260I, Q019L-S260N, and Q019L-S260P, wherein positions of the variant are numbered by correspondence with the sequence of SEQ ID NO:2. Such variants have proteolytic activity. The invention includes a protease variant having proteolytic activity, a PI value of 0.9 relative to BPN'-v3, and/or an enhanced proteolytic activity compared to BPN' in this assay, the variant comprising an amino acid sequence having at least 60%, 70%, 80%, 85%, 90%, 91%, 92%, 93%, 94%, 95%, 96%, 97%, or 98% or 99% identity to SEQ ID NO:2 or SEQ ID NO:6 and at least one set of amino acid substitutions selected from said group above, wherein amino acid positions of the variant are numbered by correspondence with positions of the SEQ ID NO:2 sequence. Also included are compositions, including, but not limited to, e.g., cleaning compositions, comprising at least one such variant and methods for cleaning utilizing at least one such variant as described in greater detail elsewhere herein.

The following BPN'-v36 variants were determined to have a PI value equal to or greater than 0.5 and less than 0.9 relative to BPN'-v36 in a BMI microswatch cleaning assay in Detergent Composition 4 at pH 7 and 16° C.: BPN'-S024G-S053G-S078N-S101N-G128A-Y217Q amino acid sequence (SEQ ID NO:6) comprising at least one set of amino acid substitutions selected from the group consisting of A045S-S236G, G024A-S037W, Q010R-S037T, A045S-S236Y, I031V-S038W, N025K-S037P, S162L-D181H, and N025K-P129R, wherein amino acid positions of the variant are numbered by correspondence with the sequence of SEQ ID NO:2. Such variants have proteolytic activity. The invention includes a protease variant having proteolytic activity and/or a PI value equal to or greater than 0.5 and less than 0.9 relative to BPN'-v36 in this assay, the variant comprising an amino acid sequence having at least 60%, 70%, 80%, 85%, 90%, 91%, 92%, 93%, 94%, 95%, 96%, 97%, or 98% or 99% identity to SEQ ID NO:2 or SEQ ID NO:6 and comprising at least one set of acid substitutions selected from said group above, wherein amino acid positions of the variant are numbered by correspondence with amino acid positions of the SEQ ID NO:2 sequence. Also included are compositions, including, but not limited to, e.g., cleaning compositions, comprising at least one such variant and methods for cleaning utilizing at least one such variant as described in greater detail elsewhere herein.

The following BPN'-v36 variants were determined to have a PI value greater than 1.0, at least 1.1, at least 1.2, at least 1.3, at least 1.4, at least 1.5, at least 1.6, at least 1.7, at least 1.8, at least 1.9, at least 2, from greater than 1.0 to about 10, from greater than 1.0 to about 8, or from greater than 1.0 to about 5 relative to BPN'-v36 in an egg microswatch cleaning assay in Detergent Composition 4 at pH 8 and 16° C.: BPN'-S024G-S053G-S078N-S101N-G128A-Y217Q amino acid sequence (SEQ ID NO:6) comprising at least one set of amino acid substitutions selected from the group consisting of I031V-S038W, P014T-S037T, S018F-S162L, S018P-D120N, and S162L-D181H, wherein amino acid positions of the variant are numbered by correspondence with the sequence of SEQ ID NO:2. Such variants have enhanced proteolytic activity compared to BPN', BPN'-v3, and BPN'-v36, and a greater PI value than BPN', BPN'-v3 and BPN'-v36 in this assay. The invention includes a protease variant having enhanced proteolytic activity compared to BPN' (SEQ ID NO:2), enhanced proteolytic activity compared to BPN', BPN'-v3, and BPN'-v36, a PI value of greater than 1.0 to about 5 relative to BPN'-v3, and/or a PI value of greater than 1.0 to about 5 relative to BPN'-v36 in this assay, the variant comprising an amino acid sequence having at least 60%, 70%, 80%, 85%, 90%, 91%, 92%, 93%, 94%, 95%, 96%, 97%, or 98% or 99% identity to SEQ ID NO:2 or SEQ ID NO:6 and comprising at least one set of amino acid substitutions selected from said group above, wherein amino acid positions of the variant are numbered by correspondence with amino acid positions of the SEQ ID NO:2 sequence. Also included are compositions, including, but not limited to, e.g., cleaning compositions, comprising at least one such variant and methods for cleaning utilizing at least one such variant as described in greater detail elsewhere herein.

The following BPN'-v36 variants were determined to have a PI value equal to about 1.0 relative to BPN'-v36 in an egg microswatch cleaning assay in Detergent Composition 4 at pH 8 and 16° C.: BPN'-S024G-S053G-S078N-S101N-G128A-Y217Q amino acid sequence (SEQ ID NO:6) comprising at least one set of amino acid substitutions selected from the group consisting of BPN'-v36, A133V-S260N, A134T-S260G, G024A-S037W, I115V-N184Y, N025K-P129K, N025K-P129R, N061D-S260I, Q019L-S260P, S009T-K141F, S009T-K141R, S018L-Y021S, S018T-S162P, S018T-Y021N, S018Y-K213R, S161P-S162L, S161P-T253A, and T253A-S260P, wherein amino acid positions of the variant are numbered by correspondence with the sequence of SEQ ID NO:2. Such variants have enhanced proteolytic activity compared to BPN'(SEQ ID NO:2) and a greater PI value than BPN' in this assay. The invention includes a protease variant having enhanced proteolytic activity compared to BPN' (SEQ ID NO:2), a PI value of 1.0 relative to BPN'-v3, and a PI value of 1.0 relative to BPN'-v36 in this assay, the variant comprising an amino acid sequence having at least 60%, 70%, 80%, 85%, 90%, 91%, 92%, 93%, 94%, 95%, 96%, 97%, or 98% or 99% identity to SEQ ID NO:2 or SEQ ID NO:6 and comprising at least one set of amino acid substitutions selected from said group above, wherein amino acid positions of the variant are numbered by correspondence with amino acid positions of the SEQ ID NO:2 sequence. Also included are compositions, including, but not limited to, e.g., cleaning compositions, comprising at least one such variant and methods for cleaning utilizing at least one such variant as described in greater detail elsewhere herein.

The following BPN'-v36 variants were determined to have a PI value equal to or greater than 0.8 and equal to or less than 0.9 relative to BPN'-v36 in an egg microswatch cleaning assay in Detergent Composition 4 at pH 8 and 16° C.: BPN'-S024G-S053G-S078N-S101N-G128A-Y217Q amino acid sequence (SEQ ID NO:6) comprising at least one set of amino acid substitutions selected from the group consisting of A045S-S236G, A045S-S236Y, I115T-S183T, N025K-S037P, N061S-S260P, Q010L-S037P, Q010R-S037T, Q019L-S260N, S037P-T254S, and S161P-S260P, wherein amino acid positions of the variant are numbered by correspondence with the sequence of SEQ ID NO:2. Such variants have proteolytic activity. The invention includes a protease variant having proteolytic activity and/or a PI value equal to or greater than 0.5 and less than 0.9 relative to BPN'-v36 in this assay, the variant comprising an amino acid sequence having at least 60%, 70%, 80%, 85%, 90%, 91%, 92%, 93%, 94%, 95%, 96%, 97%, or 98% or 99% identity to SEQ ID NO:2 or SEQ ID NO:6 and comprising at least one set of acid substitutions selected from said group above, wherein amino acid positions of the variant are numbered by correspondence with amino acid positions of the SEQ ID NO:2 sequence. Also included are compositions, including, but not limited to, e.g., cleaning compositions, comprising at least one such variant and methods for cleaning utilizing at least one such variant as described in greater detail elsewhere herein.

Also provided is a subtilisin protease variant having enhanced proteolytic activity compared to BPN'-v36 and/or a PI value of greater than 1.0 compared to BPN'-v36 in a BMI or egg microswatch cleaning assay in Detergent Composition 4 at pH 8 and 16° C., the variant comprising an amino acid sequence having at least 85%, 90%, 91%, 92%, 93%, 94%, 95%, 96%, 97%, or 98% identity to SEQ ID NO:2, wherein the variant comprises at least one substitution comprising at least one substitution selected from the group of X009T, X010L/R, X014T, X018F/L/P/T/Y, X019L, X021N/S, X024A, X025K, X031V, X037P/T/W, X038W, X045S, X061D/S, X115T/V, X120N, X129K/R, X133V, X134T, X141F/R, X161P, X162L/P, X181H, X183T, X184Y, X213R, X236G/Y, X253A, X254S, and X260G/I/N/P, and optionally at least one substitution selected from the group of S009T, Q010L/R, P014T, S018F/L/P/T/Y, Q019L, Y021N/S, G024A, N025K, I031V, S037P/T/W, S038W, A045S, N061D/S, I115T/V, D120N, P129K/R, A133V, A134T, K141F/R, S161P, S162L/P, D181H, S183T, N184Y, K213R, S236G/Y, T253A, T254S, and S260G/I/N/P, wherein amino acid positions of the variant are numbered by correspondence with positions of the sequence of SEQ ID NO:2. Such variants have enhanced proteolytic activity compared to BPN' (SEQ ID NO:2) BPN'-v3, and BPN'-v36 and a PI value greater than that of BPN', BPN'-v3, and BPN'-v36 in this assay. Also included are compositions, including, but not limited to, e.g., cleaning compositions, comprising at least one such variant and methods for cleaning utilizing at least one such variant as described in greater detail elsewhere herein.

Example 11

1. Generation of Combinatorial Libraries FS1-FS3

The pHPLT-BPN'-v3 plasmid containing the BPN' expression cassette served as template DNA (parent plasmid) for cloning. Three separate combinatorial libraries (FS1, FS2, and FS3) were synthesized by DNA2.0, and were delivered as individual ligation reactions. A list of libraries and possible substitutions are shown in Table 11-1. The libraries were designed to allow the incorporation of either the wild type residues or the substitutions at each site described in Table 11-1.

For efficient transformation of *B. subtilis*, the DNA from the ligation reaction was amplified by rolling circle amplification (RCA) using the Illustra Templiphi kit (GE Healthcare). Reactions were performed according to the manufacturer's protocol. One microliter of ten-fold diluted amplified DNA was used to transform 50 μL of competent *B. subtilis* cells (ΔaprE, ΔnprE, amyE::xylRPxylAcomK-phleo). The transformation mixture was shaken at 37° C. for 1 hour. Ten microliter aliquots of the transformation mixture were plated on skim milk (1.6%) Luria Agar plates supplemented with 10 μg/ml of neomycin (Teknova).

Transformants were picked into microtiter plates containing 125-150 μl Luria broth medium supplemented with 10 μg/ml neomycin. Plates were grown overnight at 37° C. with 250-300 rpm shaking and 70-80% humidity using Enzyscreen lids for microtiter plates (Enzyscreen). Between 7 and 10 microliters from the overnight culture plate were used to inoculate a new microtiter plate containing 190 μl of MBD medium (a MOPS based defined medium) with 10 μg/ml neomycin. MBD medium was prepared essentially as known in the art (see Neidhardt et al., J. Bacteriol. 119:736-747 (1974)), except that $NH_4Cl$, $FeSO_4$, and $CaCl_2$ were omitted from the base medium, 3 mM $K_2HPO_4$ was used, and the base medium was supplemented with 60 mM urea, and 100 ml of a solution made of 210 g/L glucose, and 350 g/L maltodextrin. The micronutrients were made up as a 100x stock solution containing in one liter, 400 mg $FeSO_4.7H_2O$, 100 mg $MnSO_4.H_2O$, 100 mg $ZnSO_4.7H_2O$, 50 mg $CuCl_2.2H_2O$, 100 mg $CoCl_2.6H_2O$, 100 mg $NaMoO_4.2H_2O$, 100 mg $Na_2B_4O_7.10H_2O$, 10 ml of 1 M $CaCl_2$, and 10 ml of 0.5 M sodium citrate. The MBD medium containing microtiter plates were grown for 60-70 hours at 37° C., 250-300 rpm, and 70-80% humidity using Enzyscreen lids (Enzyscreen) for determining protein expression. The next day, cultures were filtered through a micro-filter plate (0.22 μm; Millipore) and the resulting filtrate was used for biochemical analysis.

TABLE 11-1

Possible Substitutions for Combinatorial Libraries FS1-FS3

| | FS1 | FS2 | FS3 |
|---|---|---|---|
| 1 | G102A | A97G | N61E |
| 2 | S130P | A128G | P129E |
| 3 | T55P | N123G | K213L |
| 4 | V203Y | G102A | S145D |
| 5 | N61P | L126V | Q275E |
| 6 | S101N | G100N | P40E |
| 7 | S53G | N62Q | S159K |
| 8 | S78N | M124I | S24R |
| 9 | S87T-A88L-S89G | N61P | A144K |
| 10 | S24G-N25G | S130P | N240K |
| 11 | L75S-N76Y | P129S | P239R |

2. Generation of Variants to Improve BPN' Stability

To improve BPN' stability, variants were constructed using either parent molecules pHPLT-BPN' G97A-G128A-Y217Q-S87D or pHPLT-BPN' G97A-G128A-Y217Q-P40E, both synthesized by Gene Oracle, or parent molecules pHPLT-BPN' G97A-G128A-Y217Q-S78N and pHPLT-partial opt FNA (*B. amyloliquefaciens* subtilisin BPN'-Y217L) synthesized by GeneArt.

The information listed in Tables 11-2 and 11-3 summarizes the parent molecule used, the mutations added, and the primers used to construct variants provided herein.

TABLE 11-2

Primer Sequences Used for the Generation of BPN' Stability Mutants

| Primer Name | SEQ ID NO: |
|---|---|
| p31 | 169 |
| p32 | 170 |
| p25 | 171 |
| p26 | 172 |
| p33 | 173 |
| p34 | 174 |
| p29 | 175 |
| p30 | 176 |
| p27 | 177 |
| p28 | 178 |
| p7 | 179 |
| p8 | 180 |
| p21 | 181 |
| p22 | 182 |
| p11 | 183 |
| p12 | 184 |
| p13 | 185 |
| p14 | 186 |
| p15 | 187 |
| p16 | 188 |
| p17 | 189 |
| p18 | 190 |

TABLE 11-3

Templates Used, Mutations to be Incorporated, and Primers Used in the Generation of Variants for Improved Stability

| | Parent Molecules (Templates) | Mutation to Incorporate | Primers Used |
|---|---|---|---|
| 1 | pHPLT-BPN' G97A-G128A-Y217Q-S87D | S78N | p31, p32 |
| 2 | pHPLT-BPN' G97A-G128A-Y217Q-S78N | P40E | p25, p26 |
| 3 | pHPLT-BPN' G97A-G128A-Y217Q-P40E | S87D | p33, p34 |
| 4 | pHPLT-BPN' G97A-G128A-Y217Q-S78N | P40E, S87D | p25, p33 |
| 5 | pHPLT-BPN' G97A-G128A-Y217Q-S87D | N76D | p29, p30 |
| 6 | pHPLT-BPN' G97A-G128A-Y217Q-S87D | N76D, S78N | p27, p28 |
| 7 | pHPLT-partial opt FNA | S78N | p7, p8 |
| 8 | pHPLT-partial opt FNA | S87D | p21, p22 |
| 9 | pHPLT-partial opt FNA | P40E | p11, p12 |
| 10 | pHPLT-partial opt FNA | K213N | p13, p14 |
| 11 | pHPLT-partial opt FNA | T22V | p15, p16 |
| 12 | pHPLT-partial opt FNA | Q206E | p17, p18 |
| 13 | pHPLT-partial opt FNA | P40E, S87D, S78N | p11, p21, p7 |

*Bacillus subtilis* strains expressing plasmids were streaked onto 1.6% skim milk plates containing 10 ppm neomycin and grown overnight at 37° C. Single colonies from the plates were grown overnight at 37° C. with shaking at 250 rpm in 5 mL Luria broth containing 10 ppm neomycin. Plasmids were isolated using the QIAGEN® Miniprep kit protocol adding 1 microliter of Ready Lyse lysozyme (Epicentre) for 15 minutes at 37° C. in buffer P1 to aid in cell lysis. The plasmids were sequenced to ensure correct DNA sequences before proceeding. The plasmids were methylated using NEB's Dam Methylase Kit in a reaction containing 77.5 µL water+10 µl., Buffer 10X+0.25 µL SAM+2 µl. DAM methylase+10 µL miniprep DNA (~150 ng/µL) at 37° C. overnight. The methylated plasmid DNA was purified using a DNA Clean and Concentrator Kit (Zymo) or with a QIAGEN® PCR purification kit. Multi-Site QUIKCHANGE® mutagenesis reactions were set up for each of the DNA templates in a reaction mix containing 2.5 µL Buffer 5X+0.75 µL Quik Solution+0.5 µL primer 1 (25 µM)+0.5 µL primer 2 (25 µM)+1.5 µL dNTP's+1 µL enzyme blend+16.25 µL $H_2O$+2 µL, DNA. The PCR program used was: 95° C. for 1 min; (95° C. for 1 min, 53° C. for 1 min, 65° C. for 10 min)×29 cycles; 65° C. for 10 min, 4° C. hold. In all reactions, PCR was performed using a MJ Research PTC-200 Peltier thermal cycler. The parental DNA from the PCR samples was removed by addition of 1 µL of DpnI to QUIKCHANGE® mutagenesis kit reactions at 37° C. overnight. To increase the transformation frequency, the DpnI digested reactions were amplified using rolling circle amplification (RCA) using the Illustra TempliPhi kit according to the manufacturer's protocol. *B. subtilis* cells (ΔaprE, ΔnprE, amyE::xylRPxylAcomK-phleo) were transformed with 1 µL each of the RCA reaction and the transformed cells were plated onto LA+1.6% skim milk plates containing 10 ppm neomycin and incubated at 37° C. overnight. Colonies from overnight growth were selected to perform colony PCR for sequencing using "puReTaq Ready-To-Go PCR Beads" (Amersham). The PCR and sequencing primers used were pHPLT F1 (SEQ ID NO:54) and pHPLT seq R1 (SEQ ID NO:55). Clones with appropriate sequences were frozen. The BPN' variant proteins were produced by growing the *B. subtilis* transformants in 96 well microtiter plates at 37° C. for 68 hours in a MOPS based medium containing urea.

3. Generation of BPN' Variants Derived from Five Different Parent Plasmids

BPN' variants were constructed using a total of five different templates: BPN'-v3 (G97A-G128A-Y217Q), BPN'-v4 (G97A-N123G-Y217Q), BPN' variant 8, (S87D-G97A-N109D-G128A-S188D-S248R-Y217Q), BPN' variant 16 (S87D-G97A-N109D-G128A-S188D-Y217Q), and BPN' variant 21 (S87R-G97A-N109R-G128A-S188R-Y217Q-S248R) as shown in Table 11-4. The generation of BPN'-v4 and BPN'-v3 are described in PCT App. No. PCT/US09/46066 (WO 09/149,144), filed on Jun. 3, 2009, hereby incorporated herein by reference for such description. BPN' variants 8, 16, 21 were synthesized by Gene Oracle and served as parent plasmids to build additional variants. All variants were generated using QUIKCHANGE® mutagenesis kits, except two (variants 5 and 33), which were generated using fusion PCR as described below. Primers (listed in Table 11-5) for the generation of variants were synthesized at Integrated DNA Technologies. The mutations introduced (shown in bold) and the primers and template used are shown in Table 11-4.

TABLE 11-4

Mutations Introduced (bold) & Parent Plasmids Used to Generate BPN' Variants

| Variant | Variants Constructed | Parent Plasmid | Primers Used |
|---|---|---|---|
| 1 | G97A-**N123C**-Y217Q | G97A-N123G-Y217Q | N123C f, N123C r |
| 2 | **N76D**-G97A-G128A-Y217Q | G97A-G128A-Y217Q | N76D f, N76D r |

TABLE 11-4-continued

Mutations Introduced (bold) & Parent Plasmids Used to Generate BPN' Variants

| Variant | Variants Constructed | Parent Plasmid | Primers Used |
|---|---|---|---|
| 3 | G97A-**N109D**-G128A-Y217Q | G97A-G128A-Y217Q | N109D f1, N109D r |
| 4 | G97A-G128A-**S188D**-Y217Q | G97A-G128A-Y217Q | S188D f, S188D r |
| 5 | G97A-G128A-**S248D**-Y217Q | G97A-G128A-Y217Q | pHPLT F1, S248D forfus, pHPLT R1, S248D revfus |
| 6 | G97A-G128A-**S188D**-**S248R**-Y217Q | G97A-G128A-Y217Q | S188D f, S248R f1 |
| 7 | G97A-**N109D**-G128A-**S188D-S248R**-Y217Q | S87D-G97A-N109D-G128A-S188D-S248R-Y217Q | D87S f, D87S r |
| 8 | **S87D**-G97A-**N109D**-G128A-**S188D-S248R**-Y217Q | Synthesized by Gene Oracle | Synthesized by Gene Oracle |
| 9 | **S87R**-G97A-G128A-**S188D-S248D**-Y217Q | S87D-G97A-N109D-G128A-S188D-Y217Q | S87R f, S248D f1, D109N f |
| 10 | **S87R**-G97A-**N109D**-G128A-**S188D**-Y217Q | S87D-G97A-N109D-G128A-S188D-S248R-Y217Q | R248Sfor, R248Srev |
| 11 | G97A-**N109D**-G128A-**S188R**-Y217Q | G97A-G128A-Y217Q | N109D f2, S188R f |
| 12 | **S87R**-G97A-**N109D**-G128A-**S188D**-Y217Q-**S248R** | S87D-G97A-N109D-G128A-S188D-S248R-Y217Q | S87R f, S87R r |
| 13 | G97A-**N109D**-G128A-Y217Q-**S248R** | G97A-G128A-Y217Q | N109D f2, S248R f2 |
| 14 | **S87D**-G97A-G128A-Y217Q-**S248R** | G97A-G128A-Y217Q | S87D f, S248R f1 |
| 15 | **S87D**-G97A-**N109D**-G128A-**S188D**-Y217Q-**S248D** | S87D-G97A-N109D-G128A-S188D-Y217Q | S248D f1, S248D r |
| 16 | **S87D**-G97A-**N109D**-G128A-**S188D**-Y217Q | Synthesized by Gene Oracle | Synthesized by Gene Oracle |
| 17 | G97A-**N109D**-G128A-Y217Q-**S248D** | G97A-G128A-Y217Q | N109D f2, S248D f2 |
| 18 | **S87R**-G97A-G128A-Y217Q | G97A-G128A-Y217Q | S87R f, S87R r |
| 19 | **S87R**-G97A-G128A-Y217Q-**S248R** | G97A-G128A-Y217Q | S87R f, S248R f1 |
| 20 | **S87R**-G97A-G128A-**S188R**-Y217Q-**S248R.** | S87R-G97A-N109R-G128A-S188R-Y217Q-S248R | D109N f, D109N r |
| 21 | **S87R**-G97A-**N109R**-G128A-**S188R**-Y217Q-**S248R** | Synthesized by Gene Oracle | Synthesized by Gene Oracle |
| 22 | G97A-**G102A**-G128A-Y217Q | G97A-G128A-Y217Q | G102A f, G102A r |
| 23 | G97A-G128A-**S130P**-Y217Q | G97A-G128A-Y217Q | S130P f, S130P r |
| 24 | G97A-**S101N**-G128A-Y217Q | G97A-G128A-Y217Q | S101N f, S101N r |
| 25 | G97A-**G100N**-G128A-Y217Q | G97A-G128A-Y217Q | G100N f, G100N r |
| 26 | **N61P**-G97A-G128A-Y217Q | G97A-G128A-Y217Q | N61P f, N61P r |
| 27 | G97A-G128A-**A187D**-Y217Q | G97A-G128A-Y217Q | A187D f, A187D r |
| 28 | G97A-G128A-**F189D**-Y217Q | G97A-G128A-Y217Q | f189D f, f189D r |
| 29 | G97A-G128A-**A137V**-Y217Q | G97A-G128A-Y217Q | A137V f, A137V r |
| 30 | **S63T**-G97A-G128A-Y217Q | G97A-G128A-Y217Q | S63T f, S63T r |
| 31 | G97A-**Q103N**-G128A-Y217Q | G97A-G128A-Y217Q | Q103N f, Q103N r |
| 32 | **N62D**-G97A-G128A-Y217Q | G97A-G128A-Y217Q | N62D f, N62D r |
| 33 | G97A-**G100E**-G128A-Y217Q | G97A-G128A-Y217Q | G100E Fsfor, pHPLT F1, G100E Fsrev, pHPLT R1 |

Generation of BPN' Variants Via QUIKCHANGE® Mutagenesis

*Bacillus subtilis* strains containing plasmids expressing BPN'-v3, BPN'-v4, BPN' variant 8, BPN' variant 16, and BPN' variant 21 were streaked onto 1.6% skim milk plates containing 10 ppm neomycin and grown overnight at 37° C. Single colonies from the plates were grown overnight at 37° C. with shaking at 250 rpm in 5 mL Luria broth containing 10 ppm neomycin. Plasmids expressing BPN'-v3, BPN'-v4, BPN' variant 8, BPN' variant 16, and BPN' variant 21 were isolated using QIAGEN® Miniprep kit protocol except following cell lysis, 1 microliter of Ready Lyse lysozyme was added and incubated for 15 minutes at 37° C. The plasmids were methylated using NEB's Dam Methylase Kit in a reaction containing 77.75 μL $H_20$+10 μL Buffer 10X+0.25 μL SAM+2 μL DAM methylase+10 μL miniprep DNA at 37° C. overnight. The methylated DNA was purified using the QIAGEN® PCR purification kit. Variants 14, 18, and 19 listed in Table 11-4 were generated using QUIKCHANGE LIGHTNING™ Multi Site-Directed Mutagenesis kits (Stratagene) in a reaction mix containing 2.5 μL Buffer 5X+0.75 μL Quik Solution+0.5 μL primer 1 (25 μM)+0.5 μL primer 2 (25 μM)+1.5 μL dNTP's+1 μL enzyme blend+16.25 μL $H_2O$+2 μL DNA. The PCR program used was as follows: 95° C. for 2 min; (95° C. for 20 sec, 55° C. for 30 sec, 64° C. for 2 min 30 sec)×29 cycles; 64° C. for 5 min, 4° C. hold.

The remaining variants were created using QUIKCHANGE® Multi Site-Directed Mutagenesis kits in a reaction mix containing 2.5 μL Buffer 5X+0.75 μL Quik Solution+0.5 μL primer 1 (25 μM)+0.5 μL primer 2 (25 μM)+1.5 μL dNTP's+1 μL enzyme blend+16.25 μL $H_2O$+2 μL DNA. The PCR program used was as follows: 95° C. for 1 min; (95° C. for 1 min, 53° C. for 1 min, 65° C. for 10 min)×29 cycles; 65° C. for 10 min, 4° C. hold. In all reactions, PCR was performed using a MJ Research PTC-200 Peltier thermal cycler. The primers used for the Quik-Change reactions are provided in Table 11-5. The primers are shown in primer sequence (5' to 3').

TABLE 11-5

Primers Used for Quik-Change Reactions

| Primer Name | SEQ ID NO: |
|---|---|
| N76D f | 191 |
| N76D r | 192 |
| S87D f | 193 |
| S87D r | 194 |
| G102A f | 195 |
| G102A r | 196 |
| S130P f | 197 |
| S130P r | 198 |
| S101N f | 199 |
| S101N r | 200 |
| G100N f | 201 |
| G100N r | 202 |
| N61P f | 203 |
| N61P r | 204 |
| A187D f | 205 |
| A187D r | 206 |
| F189D f | 207 |
| F189D r | 208 |
| A137V f | 209 |
| A137V r | 210 |
| S63T f | 211 |
| S63T r | 212 |
| Q103N f | 213 |
| Q103N r | 214 |
| N62D f | 215 |
| N62D r | 216 |
| N109D f1 | 217 |

TABLE 11-5-continued

Primers Used for Quik-Change Reactions

| Primer Name | SEQ ID NO: |
|---|---|
| N109D r | 218 |
| S188D f | 219 |
| S188D r | 220 |
| S248R f1 | 221 |
| S87R f | 222 |
| S87R r | 223 |
| S248D f1 | 224 |
| S248D r | 225 |
| D87S f | 226 |
| D87S r | 227 |
| D109N f | 228 |
| D109N r | 229 |
| N109D f2 | 230 |
| S248R f2 | 231 |
| S248D f2 | 232 |
| S188R f | 233 |
| QC FUSION_For1 | 234 |
| QC FUSION_Rev1 | 235 |
| S248D forfus | 236 |
| S248D revfus | 237 |
| R248Sfor | 238 |
| R248S rev | 239 |
| G100E_Fsfor | 240 |
| G100E_Fsrev | 241 |
| N123C f | 242 |
| N123C r | 243 |
| pHpLT R1 | 244 |

The parental DNA from the PCR samples was removed by addition of 1 μL of DpnI to Quik-Change reactions at 37° C. overnight. One micro-liter of the DpnI-digested reactions were amplified using rolling circle amplification (RCA) using the Illustra TempliPhi kit according to the manufacturer's protocol. *B. subtilis* cells (ΔaprE, ΔnprE, amyE::xylRPxylA-comK-phleo) were transformed with 1 μL each of the RCA reaction and the transformed cells were plated onto LA+1.6% skim milk plates containing 10 ppm neomycin and incubated at 37° C. overnight. Colonies from overnight growth were selected to perform colony PCR using "puReTaq Ready-To-Go PCR Beads" (Amersham). The PCR primers used were pHPLT F1 (SEQ ID NO:54) and pHPLT seq R1 (SEQ ID NO:55). Clones with appropriate sequences were frozen. BPN' variants were expressed by growing the *B. subtilis* transformants in 96 well microtiter plates at 37° C. for 68 hours in a MOPS based medium containing urea.

Generation of BPN' Variants Via Fusion PCR

Variants 5 and 33 were generated using Fusion PCR, with fragments amplified from template pHPLT-BPN'-v3. The PCR primers used to generate these variants are included in Table 11-5. For Variant 5, a 5' fragment of the BPN' gene was amplified using forward primer pHPLT F1 (SEQ ID NO:54), and reverse primer S248D revfus. The 3' fragment of the BPN' gene was amplified using the forward primer S248D forfus containing the mutation of interest and the reverse primer pHPLT R1. The two products contained 20 bp of overlapping sequence, and were fused by combining 1 μL of each fragment and fusion primers QC FUSION_For1 and QC FUSION_Rev1 in a final PCR reaction. All PCR reactions were performed using standard conditions of the Herculase II PCR Kit (Stratagene). The PCR mix contained 1 μL DNA polymerase, 1 μL plasmid DNA (or fragment DNA for fusion), 0.5 μL dNTP's, 1.25 μL 25 μM forward primer, 1.25 μL 25 μM reverse primer, 10 μL Buffer 5×, 35 μL $H_2O$ and the PCR program used was as follows: 95° C. for 2 min, (95° C. for 30 sec, 55° C. for 30 sec, 72° C. for "X" sec) for 29 cycles, 72° C. for 1 min, 4° C. hold (the "X" is 15 seconds per 1 kB of DNA to amplify).

For Variant 33, a 5' fragment of the BPN' gene was amplified using the template pHPLT-BPN'-v3 and primers pHPLT F1 (SEQ ID NO:54), and G100E_Fsrev. The 3' fragment that contained the variant was amplified using primers G100E_Fsfor and pHPLT R1. The two products contained 20 bp of overlapping sequence, and were fused by combining 1 μl of each fragment and fusion primers QC FUSION_For1 and QC FUSION_Rev1 in a final PCR reaction. The PCR conditions were the same as listed above.

The two fusion products were purified using a QIAGEN® PCR purification column with conditions provided by the manufacturer, and digested overnight using Bgl I and HindIII enzymes. The plasmid pHPLT-BPN' partial opt was digested using the same enzymes and the vector band was gel extracted and purified over a QIAGEN® gel purification column using the manufacturer's recommendations. The restriction enzyme mix contained: 10 μL purified DNA, 5 μL Roche Buffer B, 0.5 μL HindIII, 0.5 μL Bgl I 34 μL $H_2O$ and the reactions were carried out at 37° C. for 8 hours followed by 65° C. for 20 min. The digest was purified using a QIAGEN® PCR purification column and ligated to the cut vector backbone overnight at 16° C. using the Mighty Mix Ligase kit (Tekara). Following incubation, 1 μL of the ligation mix was amplified using the Illustra TempliPhi kit.

For the amplification reaction, 1 μL of the ligation reaction mix was mixed with 5 μL of sample buffer from the TempliPhi kit and heated for 3 minutes at 95° C. to denature the DNA. The reaction was placed on ice to cool for 2 minutes and then spun down briefly. Five microliters of reaction buffer and 0.2 μL of phi29 polymerase from the TempliPhi kit were added, and the reactions were incubated at 30° C. in an MJ Research PCR machine for 4 hours. The phi29 enzyme was heat inactivated in the reactions by incubation at 65° C. for 10 min in the PCR machine. *Bacillus subtilis* cells (ΔaprE, ΔnprE, amyE::xylRPxylAcomK-phleo) were transformed using 1 μL of the reaction mix and the transformants were grown overnight at 37° C. on 1.6% skim milk plates containing 10 ppm neomycin. Transformants were selected to perform colony PCR and sequencing using "puReTaq Ready-To-Go PCR Beads" (Amersham) and primers pHPLT F1 (SEQ ID NO:54) and pHPLT seqR1 (SEQ ID NO:55).

4. Generation of BPN' Variants from Libraries RCL4-RCL7

RCL4 Library

"RCL4" refers to a group of site saturation libraries created by PCR fusion that simultaneously randomize three contiguous codons in the BPN'-v3-encoding (BPN'-G97A-G128A-Y217Q) gene. The amino acid positions corresponding to the three mutated codons in each library are provided in Table 11-6. Two partially overlapping, complementary mutagenic primers, each containing three degenerate codons were used to introduce mutations within each library as shown in Table 11-6 below. Only the first two nucleotides of each degenerate codon (NNX, N=A, C, T, or G and X is unchanged nucleotide) of interest were mutated in each primer (Table 11-6).

To create each library, two PCR reactions were carried out using either the common 3' gene-flanking primer (P4976, CCTCTCGGTTATGAGTTAGTTC; (SEQ ID NO:61)) and mutagenic primer, or the common 5' gene-flanking primer (P4974, GCCTCACATTTGTGCCACCTA; (SEQ ID NO:60)) and mutagenic primer as shown for each library in Table 11-6. These PCR reactions generated two PCR fragments, one encoding the 5' half of the mutant BPN'-v3 gene (5' gene fragment) and the other encoding the 3' half of the mutant BPN'-v3 gene (3' gene fragment). Each PCR amplification reaction contained 30 pmol of each primer and 100 ng of the BPN'-v3 parent template DNA (plasmid pHPLT-BPN'-v3) (see FIG. 1). Amplifications were carried out using Vent DNA polymerase (NEB). The PCR reaction (20 μL) was initially heated at 95° C. for 2.5 min followed by 30 cycles of denaturation at 94° C. for 15 sec., annealing at 55° C. for 15 sec. and extension at 72° C. for 40 sec. Following amplification, the 5' and 3' gene fragments were gel-purified by the QIAGEN® gel-band purification kit, mixed (50 ng of each fragment) and amplified by PCR once again using the primers P4973 (AAAGGATCCTAATCGGCGCTTTTC; SEQ ID NO:62) and P4950 (CTTGTCTCCAAGCTTAAAATAAAA; SEQ ID NO:63) to generate the full-length gene fragment. The PCR conditions were same as described above, except the extension phase, which was carried out at 72° C. for 2 min. The full-length DNA fragment was gel-purified by the QIAGEN® gel-band purification kit, digested by the BamHI and HindIII restriction enzymes and ligated with the pHPLT-BPN' partial opt vector that also was digested with the same restriction enzymes. Ligation mixtures were amplified using rolling circle amplification in an Illustra Templiphi kit according to the manufacturer's recommendation (GE Healthcare) to generate multimeric DNA for transformation into *Bacillus subtilis*. For this purpose, 1 μl of the ligation mixture was mixed with 5 μl of the sample buffer, heated to 95° C. for 3 min and cooled on ice. Next, 5 μl of the reaction buffer and 0.2 μl of the enzyme were added to each tube, followed by incubation at 30° C. for 10 hours. Products of the rolling circle amplification were diluted 100 times and used to transform *B. subtilis* cells (ΔaprE, ΔnprE, amyE::xylRPxylAcomK-phleo). An aliquot of the transformation mix was plated on LB plates containing 1.6% skim milk and 10 μg/mL neomycin and incubated overnight at 37° C. Subsequently, the colonies with halos were inoculated in 120 μl of LB media containing 10 μg/mL neomycin.

TABLE 11-6

List of Primers Used to Create RCL4 Libraries

| Library # | Mutated residues in BPN'-v3 | Gene fragment | Common flanking primer names | Mutagenic primer names | SEQ ID NO: |
|---|---|---|---|---|---|
| 1 | 5-7 | 3' | P4976 | P5119 | 245 |
| | | 5' | P4974 | P5120 | 246 |
| 2 | 11-13 | 3' | P4976 | P5121 | 247 |
| | | 5' | P4974 | P5122 | 248 |
| 3 | 20-22 | 3' | P4976 | P5123 | 249 |
| | | 5' | P4974 | P5124 | 250 |
| 4 | 21-23 | 3' | P4976 | P5125 | 251 |
| | | 5' | P4974 | P5126 | 252 |
| 5 | 22-24 | 3' | P4976 | P5127 | 253 |
| | | 5' | P4974 | P5128 | 254 |
| 6 | 23-25 | 3' | P4976 | P5129 | 255 |
| | | 5' | P4974 | P5130 | 256 |
| 7 | 24-26 | 3' | P4976 | P5131 | 257 |
| | | 5' | P4974 | P5132 | 258 |
| 8 | 25-27 | 3' | P4976 | P5133 | 259 |
| | | 5' | P4974 | P5134 | 260 |
| 9 | 26-28 | 3' | P4976 | P5135 | 261 |
| | | 5' | P4974 | P5136 | 262 |
| 10 | 27-29 | 3' | P4976 | P5137 | 263 |
| | | 5' | P4974 | P5138 | 264 |
| 11 | 28-30 | 3' | P4976 | P5139 | 265 |
| | | 5' | P4974 | P5140 | 266 |
| 12 | 29-31 | 3' | P4976 | P5141 | 267 |
| | | 5' | P4974 | P5142 | 268 |
| 13 | 30-32 | 3' | P4976 | P5143 | 269 |
| | | 5' | P4974 | P5144 | 270 |
| 14 | 31-33 | 3' | P4976 | P5145 | 271 |
| | | 5' | P4974 | P5146 | 272 |

TABLE 11-6-continued

List of Primers Used to Create RCL4 Libraries

| Library # | Mutated residues in BPN'-v3 | Gene fragment | Common flanking primer names | Mutagenic primer names | SEQ ID NO: |
|---|---|---|---|---|---|
| 15 | 32-34 | 3' | P4976 | P5147 | 273 |
| | | 5' | P4974 | P5148 | 274 |
| 16 | 33-35 | 3' | P4976 | P5149 | 275 |
| | | 5' | P4974 | P5150 | 276 |
| 17 | 34-36 | 3' | P4976 | P5151 | 277 |
| | | 5' | P4974 | P5152 | 278 |
| 18 | 35-37 | 3' | P4976 | P5153 | 279 |
| | | 5' | P4974 | P5154 | 280 |
| 19 | 36-38 | 3' | P4976 | P5155 | 281 |
| | | 5' | P4974 | P5156 | 282 |
| 20 | 37-39 | 3' | P4976 | P5157 | 283 |
| | | 5' | P4974 | P5158 | 284 |
| 21 | 38-40 | 3' | P4976 | P5159 | 285 |
| | | 5' | P4974 | P5160 | 286 |
| 22 | 41-43 | 3' | P4976 | P5161 | 287 |
| | | 5' | P4974 | P5162 | 288 |
| 23 | 43-45 | 3' | P4976 | P5163 | 289 |
| | | 5' | P4974 | P5164 | 290 |
| 24 | 44-46 | 3' | P4976 | P5165 | 291 |
| | | 5' | P4974 | P5166 | 292 |
| 25 | 51-53 | 3' | P4976 | P5167 | 293 |
| | | 5' | P4974 | P5168 | 294 |
| 26 | 52-54 | 3' | P4976 | P5169 | 295 |
| | | 5' | P4974 | P5170 | 296 |
| 27 | 53-55 | 3' | P4976 | P5171 | 297 |
| | | 5' | P4974 | P5172 | 298 |
| 28 | 54-56 | 3' | P4976 | P5173 | 299 |
| | | 5' | P4974 | P5174 | 300 |
| 29 | 55-57 | 3' | P4976 | P5175 | 301 |
| | | 5' | P4974 | P5176 | 302 |
| 30 | 56-58 | 3' | P4976 | P5177 | 303 |
| | | 5' | P4974 | P5178 | 304 |
| 31 | 57-59 | 3' | P4976 | P5179 | 305 |
| | | 5' | P4974 | P5180 | 306 |
| 32 | 58-60 | 3' | P4976 | P5181 | 307 |
| | | 5' | P4974 | P5182 | 308 |
| 33 | 59-61 | 3' | P4976 | P5183 | 309 |
| | | 5' | P4974 | P5184 | 310 |
| 34 | 60-62 | 3' | P4976 | P5185 | 311 |
| | | 5' | P4974 | P5186 | 312 |
| 35 | 61-63 | 3' | P4976 | P5187 | 313 |
| | | 5' | P4974 | P5188 | 314 |
| 36 | 62-64 | 3' | P4976 | P5189 | 315 |
| | | 5' | P4974 | P5190 | 316 |
| 37 | 67-69 | 3' | P4976 | P5191 | 317 |
| | | 5' | P4974 | P5192 | 318 |
| 38 | 68-70 | 3' | P4976 | P5193 | 319 |
| | | 5' | P4974 | P5194 | 320 |
| 39 | 71-73 | 3' | P4976 | P5195 | 321 |
| | | 5' | P4974 | P5196 | 322 |
| 40 | 74-76 | 3' | P4976 | P5197 | 323 |
| | | 5' | P4974 | P5198 | 324 |
| 41 | 77-79 | 3' | P4976 | P5199 | 325 |
| | | 5' | P4974 | P5200 | 326 |
| 42 | 81-83 | 3' | P4976 | P5201 | 327 |
| | | 5' | P4974 | P5202 | 328 |
| 43 | 83-85 | 3' | P4976 | P5203 | 329 |
| | | 5' | P4974 | P5204 | 330 |
| 44 | 84-86 | 3' | P4976 | P5205 | 331 |
| | | 5' | P4974 | P5206 | 332 |
| 45 | 85-87 | 3' | P4976 | P5207 | 333 |
| | | 5' | P4974 | P5208 | 334 |
| 46 | 86-88 | 3' | P4976 | P5209 | 335 |
| | | 5' | P4974 | P5210 | 336 |
| 47 | 87-89 | 3' | P4976 | P5211 | 337 |
| | | 5' | P4974 | P5212 | 338 |
| 48 | 88-90 | 3' | P4976 | P5213 | 339 |
| | | 5' | P4974 | P5214 | 340 |
| 49 | 89-91 | 3' | P4976 | P5215 | 341 |
| | | 5' | P4974 | P5216 | 342 |
| 50 | 90-92 | 3' | P4976 | P5217 | 343 |
| | | 5' | P4974 | P5218 | 344 |

TABLE 11-6-continued

List of Primers Used to Create RCL4 Libraries

| Library # | Mutated residues in BPN'-v3 | Gene fragment | Common flanking primer names | Mutagenic primer names | SEQ ID NO: |
|---|---|---|---|---|---|
| 51 | 91-93 | 3' | P4976 | P5219 | 345 |
| | | 5' | P4974 | P5220 | 346 |
| 52 | 92-94 | 3' | P4976 | P5221 | 347 |
| | | 5' | P4974 | P5222 | 348 |
| 53 | 93-95 | 3' | P4976 | P5223 | 349 |
| | | 5' | P4974 | P5224 | 350 |
| 54 | 94-96 | 3' | P4976 | P5225 | 351 |
| | | 5' | P4974 | P5226 | 352 |
| 55 | 95-97 | 3' | P4976 | P5227 | 353 |
| | | 5' | P4974 | P5228 | 354 |
| 56 | 96-98 | 3' | P4976 | P5229 | 355 |
| | | 5' | P4974 | P5230 | 356 |
| 57 | 97-99 | 3' | P4976 | P5231 | 357 |
| | | 5' | P4974 | P5232 | 358 |
| 58 | 98-100 | 3' | P4976 | P5233 | 359 |
| | | 5' | P4974 | P5234 | 360 |
| 59 | 99-101 | 3' | P4976 | P5235 | 361 |
| | | 5' | P4974 | P5236 | 362 |
| 60 | 100-102 | 3' | P4976 | P5237 | 363 |
| | | 5' | P4974 | P5238 | 364 |
| 61 | 101-103 | 3' | P4976 | P5239 | 365 |
| | | 5' | P4974 | P5240 | 366 |
| 62 | 102-104 | 3' | P4976 | P5241 | 367 |
| | | 5' | P4974 | P5242 | 368 |
| 63 | 103-105 | 3' | P4976 | P5243 | 369 |
| | | 5' | P4974 | P5244 | 370 |
| 64 | 104-106 | 3' | P4976 | P5245 | 371 |
| | | 5' | P4974 | P5246 | 372 |
| 65 | 105-107 | 3' | P4976 | P5247 | 373 |
| | | 5' | P4974 | P5248 | 374 |
| 66 | 106-108 | 3' | P4976 | P5249 | 375 |
| | | 5' | P4974 | P5250 | 376 |
| 67 | 107-109 | 3' | P4976 | P5251 | 377 |
| | | 5' | P4974 | P5252 | 378 |
| 68 | 108-110 | 3' | P4976 | P5253 | 379 |
| | | 5' | P4974 | P5254 | 380 |
| 69 | 109-111 | 3' | P4976 | P5255 | 381 |
| | | 5' | P4974 | P5256 | 382 |
| 70 | 110-112 | 3' | P4976 | P5257 | 383 |
| | | 5' | P4974 | P5258 | 384 |
| 71 | 111-113 | 3' | P4976 | P5259 | 385 |
| | | 5' | P4974 | P5260 | 386 |
| 72 | 112-114 | 3' | P4976 | P5261 | 387 |
| | | 5' | P4974 | P5262 | 388 |
| 73 | 113-115 | 3' | P4976 | P5263 | 389 |
| | | 5' | P4974 | P5264 | 390 |
| 74 | 114-116 | 3' | P4976 | P5265 | 391 |
| | | 5' | P4974 | P5266 | 392 |
| 75 | 115-117 | 3' | P4976 | P5267 | 393 |
| | | 5' | P4974 | P5268 | 394 |
| 76 | 116-118 | 3' | P4976 | P5269 | 395 |
| | | 5' | P4974 | P5270 | 396 |
| 77 | 117-119 | 3' | P4976 | P5271 | 397 |
| | | 5' | P4974 | P5272 | 398 |
| 78 | 118-120 | 3' | P4976 | P5273 | 399 |
| | | 5' | P4974 | P5274 | 400 |
| 79 | 119-121 | 3' | P4976 | P5275 | 401 |
| | | 5' | P4974 | P5276 | 402 |
| 80 | 120-122 | 3' | P4976 | P5277 | 403 |
| | | 5' | P4974 | P5278 | 404 |
| 81 | 121-123 | 3' | P4976 | P5279 | 405 |
| | | 5' | P4974 | P5280 | 406 |
| 82 | 122-124 | 3' | P4976 | P5281 | 407 |
| | | 5' | P4974 | P5282 | 408 |
| 83 | 123-125 | 3' | P4976 | P5283 | 409 |
| | | 5' | P4974 | P5284 | 410 |
| 84 | 124-126 | 3' | P4976 | P5285 | 411 |
| | | 5' | P4974 | P5286 | 412 |
| 85 | 125-127 | 3' | P4976 | P5287 | 413 |
| | | 5' | P4974 | P5288 | 414 |
| 86 | 126-128 | 3' | P4976 | P5289 | 415 |
| | | 5' | P4974 | P5290 | 416 |

TABLE 11-6-continued

List of Primers Used to Create RCL4 Libraries

| Library # | Mutated residues in BPN'-v3 | Gene fragment | Common flanking primer names | Mutagenic primer names | SEQ ID NO: |
|---|---|---|---|---|---|
| 87 | 129-131 | 3' | P4976 | P5291 | 417 |
| | | 5' | P4974 | P5292 | 418 |
| 88 | 132-134 | 3' | P4976 | P5293 | 419 |
| | | 5' | P4974 | P5294 | 420 |
| 89 | 133-135 | 3' | P4976 | P5295 | 421 |
| | | 5' | P4974 | P5296 | 422 |
| 90 | 134-136 | 3' | P4976 | P5297 | 423 |
| | | 5' | P4974 | P5298 | 424 |
| 91 | 135-137 | 3' | P4976 | P5299 | 425 |
| | | 5' | P4974 | P5300 | 426 |
| 92 | 136-138 | 3' | P4976 | P5301 | 427 |
| | | 5' | P4974 | P5302 | 428 |
| 93 | 137-139 | 3' | P4976 | P5303 | 429 |
| | | 5' | P4974 | P5304 | 430 |
| 94 | 138-140 | 3' | P4976 | P5305 | 431 |
| | | 5' | P4974 | P5306 | 432 |
| 95 | 139-141 | 3' | P4976 | P5307 | 433 |
| | | 5' | P4974 | P5308 | 434 |
| 96 | 140-142 | 3' | P4976 | P5309 | 435 |
| | | 5' | P4974 | P5310 | 436 |
| 97 | 141-143 | 3' | P4976 | P5311 | 437 |
| | | 5' | P4974 | P5312 | 438 |
| 98 | 142-144 | 3' | P4976 | P5313 | 439 |
| | | 5' | P4974 | P5314 | 440 |
| 99 | 143-145 | 3' | P4976 | P5315 | 441 |
| | | 5' | P4974 | P5316 | 442 |
| 100 | 144-146 | 3' | P4976 | P5317 | 443 |
| | | 5' | P4974 | P5318 | 444 |
| 101 | 145-147 | 3' | P4976 | P5319 | 445 |
| | | 5' | P4974 | P5320 | 446 |
| 102 | 146-148 | 3' | P4976 | P5321 | 447 |
| | | 5' | P4974 | P5322 | 448 |
| 103 | 147-149 | 3' | P4976 | P5323 | 449 |
| | | 5' | P4974 | P5324 | 450 |
| 104 | 148-150 | 3' | P4976 | P5325 | 451 |
| | | 5' | P4974 | P5326 | 452 |
| 105 | 149-151 | 3' | P4976 | P5327 | 453 |
| | | 5' | P4974 | P5328 | 454 |
| 106 | 150-152 | 3' | P4976 | P5329 | 455 |
| | | 5' | P4974 | P5330 | 456 |
| 107 | 151-153 | 3' | P4976 | P5331 | 457 |
| | | 5' | P4974 | P5332 | 458 |
| 108 | 158-160 | 3' | P4976 | P5333 | 459 |
| | | 5' | P4974 | P5334 | 460 |
| 109 | 159-161 | 3' | P4976 | P5335 | 461 |
| | | 5' | P4974 | P5336 | 462 |
| 110 | 160-162 | 3' | P4976 | P5337 | 463 |
| | | 5' | P4974 | P5338 | 464 |
| 111 | 163-165 | 3' | P4976 | P5339 | 465 |
| | | 5' | P4974 | P5340 | 466 |
| 112 | 164-166 | 3' | P4976 | P5341 | 467 |
| | | 5' | P4974 | P5342 | 468 |
| 113 | 167-169 | 3' | P4976 | P5343 | 469 |
| | | 5' | P4974 | P5344 | 470 |
| 114 | 168-170 | 3' | P4976 | P5345 | 471 |
| | | 5' | P4974 | P5346 | 472 |
| 115 | 169-171 | 3' | P4976 | P5347 | 473 |
| | | 5' | P4974 | P5348 | 474 |
| 116 | 170-172 | 3' | P4976 | P5349 | 475 |
| | | 5' | P4974 | P5350 | 476 |
| 117 | 171-173 | 3' | P4976 | P5351 | 477 |
| | | 5' | P4974 | P5352 | 478 |
| 118 | 172-174 | 3' | P4976 | P5353 | 479 |
| | | 5' | P4974 | P5354 | 480 |
| 119 | 182-184 | 3' | P4976 | P5355 | 481 |
| | | 5' | P4974 | P5356 | 482 |
| 120 | 183-185 | 3' | P4976 | P5357 | 483 |
| | | 5' | P4974 | P5358 | 484 |
| 121 | 184-186 | 3' | P4976 | P5359 | 485 |
| | | 5' | P4974 | P5360 | 486 |
| 122 | 185-187 | 3' | P4976 | P5361 | 487 |
| | | 5' | P4974 | P5362 | 488 |

TABLE 11-6-continued

List of Primers Used to Create RCL4 Libraries

| Library # | Mutated residues in BPN'-v3 | Gene fragment | Common flanking primer names | Mutagenic primer names | SEQ ID NO: |
|---|---|---|---|---|---|
| 123 | 186-188 | 3' | P4976 | P5363 | 489 |
| | | 5' | P4974 | P5364 | 490 |
| 124 | 192-194 | 3' | P4976 | P5365 | 491 |
| | | 5' | P4974 | P5366 | 492 |
| 125 | 194-196 | 3' | P4976 | P5367 | 493 |
| | | 5' | P4974 | P5368 | 494 |
| 126 | 195-197 | 3' | P4976 | P5369 | 495 |
| | | 5' | P4974 | P5370 | 496 |
| 127 | 196-198 | 3' | P4976 | P5371 | 497 |
| | | 5' | P4974 | P5372 | 498 |
| 128 | 197-199 | 3' | P4976 | P5373 | 499 |
| | | 5' | P4974 | P5374 | 500 |
| 129 | 198-200 | 3' | P4976 | P5375 | 501 |
| | | 5' | P4974 | P5376 | 502 |
| 130 | 203-205 | 3' | P4976 | P5377 | 503 |
| | | 5' | P4974 | P5378 | 504 |
| 131 | 210-212 | 3' | P4976 | P5379 | 505 |
| | | 5' | P4974 | P5380 | 506 |
| 132 | 211-213 | 3' | P4976 | P5381 | 507 |
| | | 5' | P4974 | P5382 | 508 |
| 133 | 216-218 | 3' | P4976 | P5383 | 509 |
| | | 5' | P4974 | P5384 | 510 |
| 134 | 217-219 | 3' | P4976 | P5385 | 511 |
| | | 5' | P4974 | P5386 | 512 |
| 135 | 218-220 | 3' | P4976 | P5387 | 513 |
| | | 5' | P4974 | P5388 | 514 |
| 136 | 219-221 | 3' | P4976 | P5389 | 515 |
| | | 5' | P4974 | P5390 | 516 |
| 137 | 230-232 | 3' | P4976 | P5391 | 517 |
| | | 5' | P4974 | P5392 | 518 |
| 138 | 231-233 | 3' | P4976 | P5393 | 519 |
| | | 5' | P4974 | P5394 | 520 |
| 139 | 232-234 | 3' | P4976 | P5395 | 521 |
| | | 5' | P4974 | P5396 | 522 |
| 140 | 238-240 | 3' | P4976 | P5397 | 523 |
| | | 5' | P4974 | P5398 | 524 |
| 141 | 240-242 | 3' | P4976 | P5399 | 525 |
| | | 5' | P4974 | P5400 | 526 |
| 142 | 246-248 | 3' | P4976 | P5401 | 527 |
| | | 5' | P4974 | P5402 | 528 |
| 143 | 255-257 | 3' | P4976 | P5403 | 529 |
| | | 5' | P4974 | P5404 | 530 |
| 144 | 258-260 | 3' | P4976 | P5405 | 531 |
| | | 5' | P4974 | P5406 | 532 |
| 145 | 265-267 | 3' | P4976 | P5407 | 533 |
| | | 5' | P4974 | P5408 | 534 |

RCL5 Variants

"RCL5" refers to a set of combinatorial variants created by PCR fusion using several BPN' mutants as parent (template) molecules. The mutations introduced in each parent plasmid are shown in Table 11-7 and the mutagenic primers used to create the mutants are indicated in Table 11-8.

TABLE 11-7

List of Parent Plasmids and Mutations Introduced in the RCL5 Variants

| Combinatorial Variant # | Parent Plasmids | Mutations Introduced |
|---|---|---|
| 1 | G97A-G128A-Y217Q-T22N-S24A | N61P-N62S |
| 2 | G97A-G128A-Y217Q-T22N-S24A | T55P |
| 3 | G97A-G128A-Y217Q-T22N-S24A | N61P-S63H |
| 4 | G97A-G128A-Y217Q-T22N-S24A | Q59S-N61P |
| 5 | G97A-G128A-Y217Q-T22N-S24A | L75S-N76Y |
| 6 | G97A-G128A-Y217Q-T22N-S24A | P86S-S87G-A88V |
| 7 | G97A-G128A-Y217Q-T22N-S24A | S87G-A88V-S89A |
| 8 | G97A-G128A-Y217Q-T22N-S24A | S87T-A88L-S89G |
| 9 | G97A-G128A-Y217Q-T22N-S24A | P129Q-S130G-G131S |
| 10 | G97A-G128A-Y217Q-T22N-S24A | V203Y |
| 11 | G97A-G128A-Y217Q-T22N-S24A | G211R-N212S-K213V |
| 12 | G97A-G128A-Y217Q-S24G-N25G | N61P-N62S |
| 13 | G97A-G128A-Y217Q-S24G-N25G | T55P |
| 14 | G97A-G128A-Y217Q-S24G-N25G | N61P-S63H |
| 15 | G97A-G128A-Y217Q-S24G-N25G | Q59S-N61P |
| 16 | G97A-G128A-Y217Q-S24G-N25G | L75S-N76Y |
| 17 | G97A-G128A-Y217Q-S24G-N25G | P86S-S87G-A88V |
| 18 | G97A-G128A-Y217Q-S24G-N25G | S87G-A88V-S89A |
| 19 | G97A-G128A-Y217Q-S24G-N25G | S87T-A88L-S89G |
| 20 | G97A-G128A-Y217Q-S24G-N25G | P129Q-S130G-G131S |
| 21 | G97A-G128A-Y217Q-S24G-N25G | V203Y |
| 22 | G97A-G128A-Y217Q-S24G-N25G | G211R-N212S-K213V |
| 23 | G97A-G128A-Y217Q-S24R | N61P-N62S |
| 24 | G97A-G128A-Y217Q-S24R | T55P |
| 25 | G97A-G128A-Y217Q-S24R | N61P-S63H |
| 26 | G97A-G128A-Y217Q-S24R | Q59S-N61P |
| 27 | G97A-G128A-Y217Q-S24R | L75S-N76Y |
| 28 | G97A-G128A-Y217Q-S24R | P86S-S87G-A88V |
| 29 | G97A-G128A-Y217Q-S24R | S87G-A88V-S89A |
| 30 | G97A-G128A-Y217Q-S24R | S87T-A88L-S89G |
| 31 | G97A-G128A-Y217Q-S24R | P129Q-S130G-G131S |
| 32 | G97A-G128A-Y217Q-S24R | V203Y |
| 33 | G97A-G128A-Y217Q-S24R | G211R-N212S-K213V |
| 34 | G97A-G128A-Y217Q-G23A-S24G-N25G | N61P-N62S |
| 35 | G97A-G128A-Y217Q-G23A-S24G-N25G | T55P |
| 36 | G97A-G128A-Y217Q-G23A-S24G-N25G | N61P-S63H |
| 37 | G97A-G128A-Y217Q-G23A-S24G-N25G | Q59S-N61P |
| 38 | G97A-G128A-Y217Q-G23A-S24G-N25G | L75S-N76Y |
| 39 | G97A-G128A-Y217Q-G23A-S24G-N25G | P86S-S87G-A88V |
| 40 | G97A-G128A-Y217Q-G23A-S24G-N25G | S87G-A88V-S89A |
| 41 | G97A-G128A-Y217Q-G23A-S24G-N25G | S87T-A88L-S89G |
| 42 | G97A-G128A-Y217Q-G23A-S24G-N25G | P129Q-S130G-G131S |
| 43 | G97A-G128A-Y217Q-G23A-S24G-N25G | V203Y |
| 44 | G97A-G128A-Y217Q-G23A-S24G-N25G | G211R-N212S-K213V |
| 45 | G97A-G128A-Y217Q-N61P-N62S | L75S-N76Y |
| 46 | G97A-G128A-Y217Q-N61P-N62S | P86S-S87G-A88V |
| 47 | G97A-G128A-Y217Q-N61P-N62S | S87G-A88V-S89A |
| 48 | G97A-G128A-Y217Q-N61P-N62S | S87T-A88L-S89G |
| 49 | G97A-G128A-Y217Q-N61P-N62S | P129Q-S130G-G131S |
| 50 | G97A-G128A-Y217Q-N61P-N62S | V203Y |
| 51 | G97A-G128A-Y217Q-N61P-N62S | G211R-N212S-K213V |
| 52 | G97A-G128A-Y217Q-T55P | L75S-N76Y |
| 53 | G97A-G128A-Y217Q-T55P | P86S-S87G-A88V |
| 54 | G97A-G128A-Y217Q-T55P | S87G-A88V-S89A |
| 55 | G97A-G128A-Y217Q-T55P | S87T-A88L-S89G |
| 56 | G97A-G128A-Y217Q-T55P | P129Q-S130G-G131S |
| 57 | G97A-G128A-Y217Q-T55P | V203Y |
| 58 | G97A-G128A-Y217Q-T55P | G211R-N212S-K213V |
| 59 | G97A-G128A-Y217Q-N61P-S63H | L75S-N76Y |
| 60 | G97A-G128A-Y217Q-N61P-S63H | P86S-S87G-A88V |
| 61 | G97A-G128A-Y217Q-N61P-S63H | S87G-A88V-S89A |
| 62 | G97A-G128A-Y217Q-N61P-S63H | S87T-A88L-S89G |
| 63 | G97A-G128A-Y217Q-N61P-S63H | P129Q-S130G-G131S |
| 64 | G97A-G128A-Y217Q-N61P-S63H | V203Y |

TABLE 11-7-continued

List of Parent Plasmids and Mutations Introduced in the RCL5 Variants

| Combinatorial Variant # | Parent Plasmids | Mutations Introduced |
|---|---|---|
| 65 | G97A-G128A-Y217Q-N61P-S63H | G211R-N212S-K213V |
| 66 | G97A-G128A-Y217Q-Q59S-N61P | L75S-N76Y |
| 67 | G97A-G128A-Y217Q-Q59S-N61P | P86S-S87G-A88V |
| 68 | G97A-G128A-Y217Q-Q59S-N61P | S87G-A88V-S89A |
| 69 | G97A-G128A-Y217Q-Q59S-N61P | S87T-A88L-S89G |
| 70 | G97A-G128A-Y217Q-Q59S-N61P | P129Q-S130G-G131S |
| 71 | G97A-G128A-Y217Q-Q59S-N61P | V203Y |
| 72 | G97A-G128A-Y217Q-Q59S-N61P | G211R-N212S-K213V |
| 73 | G97A-G128A-Y217Q-L75S-N76Y | P86S-S87G-A88V |
| 74 | G97A-G128A-Y217Q-L75S-N76Y | S87G-A88V-S89A |
| 75 | G97A-G128A-Y217Q-L75S-N76Y | S87T-A88L-S89G |
| 76 | G97A-G128A-Y217Q-L75S-N76Y | P129Q-S130G-G131S |
| 77 | G97A-G128A-Y217Q-L75S-N76Y | V203Y |
| 78 | G97A-G128A-Y217Q-L75S-N76Y | G211R-N212S-K213V |
| 79 | G97A-G128A-Y217Q-P86S-S87G-A88V | P129Q-S130G-G131S |
| 80 | G97A-G128A-Y217Q-P86S-S87G-A88V | V203Y |
| 81 | G97A-G128A-Y217Q-P86S-S87G-A88V | G211R-N212S-K213V |
| 82 | G97A-G128A-Y217Q-S87G-A88V-S89A | P129Q-S130G-G131S |
| 83 | G97A-G128A-Y217Q-S87G-A88V-S89A | V203Y |
| 84 | G97A-G128A-Y217Q-S87G-A88V-S89A | G211R-N212S-K213V |
| 85 | G97A-G128A-Y217Q-S87T-A88L-S89G | P129Q-S130G-G131S |
| 86 | G97A-G128A-Y217Q-S87T-A88L-S89G | V203Y |
| 87 | G97A-G128A-Y217Q-S87T-A88L-S89G | G211R-N212S-K213V |
| 88 | G97A-G128A-Y217Q-P129Q-S130G-G131S | V203Y |
| 89 | G97A-G128A-Y217Q-P129Q-S130G-G131S | G211R-N212S-K213V |
| 90 | G97A-G128A-Y217Q-V203Y | G211R-N212S-K213V |

TABLE 11-8

Primers Used to Create RCL5 Combinatorial Variants

| Mutations Introduced | Gene Fragments | Common 3' & 5' Gene Flanking Primer Names | Primer Name | SEQ ID NO: |
|---|---|---|---|---|
| T22N-S24A | 3' | P4976 | P5432 | 535 |
| | 5' | P4974 | P5433 | 536 |
| S24G-N25G | 3' | P4976 | P5434 | 537 |
| | 5' | P4974 | P5435 | 538 |
| S24R | 3' | P4976 | P5436 | 539 |
| | 5' | P4974 | P5437 | 540 |
| G23A-S24G-N25G | 3' | P4976 | P5438 | 541 |
| | 5' | P4974 | P5439 | 542 |
| N61P-N62S | 3' | P4976 | P5440 | 543 |
| | 5' | P4974 | P5441 | 544 |
| T55P | 3' | P4976 | P5442 | 545 |
| | 5' | P4974 | P5443 | 546 |
| N61P-S63H | 3' | P4976 | P5444 | 547 |
| | 5' | P4974 | P5445 | 548 |
| Q59S-N61P | 3' | P4976 | P5446 | 549 |
| | 5' | P4974 | P5447 | 550 |
| L75S-N76Y | 3' | P4976 | P5448 | 551 |
| | 5' | P4974 | P5449 | 552 |
| P86S-S87G-A88V | 3' | P4976 | P5450 | 553 |
| | 5' | P4974 | P5451 | 554 |
| S87G-A88V-S89A | 3' | P4976 | P5452 | 555 |
| | 5' | P4974 | P5453 | 556 |
| S87T-A88L-S89G | 3' | P4976 | P5454 | 557 |
| | 5' | P4974 | P5455 | 558 |
| P129Q-S130G-G131S | 3' | P4976 | P5456 | 559 |
| | 5' | P4974 | P5457 | 560 |
| V203Y | 3' | P4976 | P5458 | 561 |
| | 5' | P4974 | P5459 | 562 |
| G211R-N212S-K213V | 3' | P4976 | P5460 | 563 |
| | 5' | P4974 | P5461 | 564 |

To create each mutant, two PCR reactions were carried out using either the common 3' gene-flanking primer (P4976, CCTCTCGGTTATGAGTTAGTTC; SEQ ID NO:61) and the mutagenic primer, or the common 5' gene-flanking primer (P4974, GCCTCACATTTGTGCCACCTA; SEQ ID NO:60) and mutagenic primer as shown for each library in Table 11-8. These PCR reactions generated two PCR fragments, one encoding the 5' half of the mutant BPN' gene (5' gene fragment) and the other encoding the 3' half of the mutant BPN' gene (3' gene fragment). Each PCR amplification reaction contained 30 pmol of each primer and 100 ng of the parent molecules listed in Table 11-7. Amplifications were carried out using Vent DNA polymerase (NEB). The PCR reaction (20 μL) was initially heated at 95° C. for 2.5 min followed by 30 cycles of denaturation at 94° C. for 15 sec., annealing at 55° C. for 15 sec. and extension at 72° C. for 40 sec. Following amplification, the 5' and 3' gene fragments were gel-purified by the QIAGEN® gel-band purification kit, mixed (50 ng of each fragment) and amplified by PCR once again using the primers P4973 (SEQ ID NO:62) and P4950 (SEQ ID NO:63) to generate the full-length gene fragment. The PCR conditions were same as described above, except the extension phase, which was carried out at 72° C. for 2 min. The full-length DNA fragment was gel-purified by the QIAGEN® gel-band purification kit, digested by the BamHI and HindIII restriction enzymes and ligated with the pHPLT-BPN' partial opt that also was digested with the same restriction enzymes. Ligation mixtures were amplified using rolling circle amplification by Illustra Templiphi kit according to the manufacturer's instructions (GE Healthcare) to generate multimeric DNA for transformation into *Bacillus subtilis*. For this purpose, 1 μl of the ligation mixture was mixed with 5 μl of the sample buffer, heated to 95° C. for 3 min and cooled on ice. Next, 5 μl of the reaction buffer and 0.2 μl of the enzyme were added to each tube, followed by incubation at 30° C. for 10 hours. Products of the rolling circle amplification were diluted 100 times and used to transform *B. subtilis* cells (ΔaprE, ΔnprE, amyE::xylRPxylAcomK-phleo). An aliquot of the transformation mix was plated on LB plates containing 1.6% skim milk and 10 μg/mL neomycin and incubated overnight at 37° C. Subsequently, the colonies with halos were inoculated in 120 μl of LB media containing 10 μg/mL neomycin.

RCL 6 Combinatorial Libraries

"RCL6" refers to a group of combinatorial libraries created by PCR fusion using several BPN' mutants as parent (template) molecules. A mixture of BPN' mutants were used as templates (parent molecules) in the construction of each of these libraries. The five different mixes of parent molecules used to create these libraries are provided in Table 11-9, and the mutations introduced in each library are listed in Table 11-10.

To create each mutant, two PCR reactions were carried out using either the common 3' gene-flanking primer (P4976, SEQ ID NO:61) and the mutagenic primer, or the common 5' gene-flanking primer (P4974, SEQ ID NO:60) and mutagenic primer as shown for each library in Table 11-10. These PCR reactions generated two PCR fragments, one encoding the 5' half of the mutant BPN' gene (5' gene fragment) and the other encoding the 3' half of the mutant BPN' gene (3' gene fragment). Each PCR amplification reaction contained 30 pmol of each primer and 100 ng of the parent molecules listed in Table 11-9. Amplifications were carried out using Vent DNA polymerase (NEB). The PCR reaction (20 μL) was initially heated at 95° C. for 2.5 min followed by 30 cycles of denaturation at 94° C. for 15 sec., annealing at 55° C. for 15 sec. and extension at 72° C. for 40 sec. Following amplification, the 5' and 3' gene fragments were gel-purified by the QIAGEN® gel-band purification kit, mixed (50 ng of each fragment) and amplified by PCR once again using the primers P4973 (SEQ ID NO:62) and P4950 (SEQ ID NO:63) to generate the full-length gene fragment. The PCR conditions were same as described above, except the extension phase, which was carried out at 72° C. for 2 min. The full-length DNA fragment was gel-purified by the QIAGEN® gel-band purification kit, digested using BamHI and HindIII restriction enzymes and ligated with the pHPLT-BPN' partial opt vector that also was digested with the same restriction enzymes. Ligation mixtures were amplified using rolling circle amplification by Illustra Templiphi kit according to the manufacturer's instructions (GE Healthcare) to generate multimeric DNA for transformation into *Bacillus subtilis*. For this purpose, 1 μl of the ligation mixture was mixed with 5 μl of the sample buffer, heated to 95° C. for 3 min and cooled on ice. Next, 5 μl of the reaction buffer and 0.2 μl of the enzyme were added to each tube, followed by incubation at 30° C. for 10 hours. Products of the rolling circle amplification were diluted 100 times and used to transform *B. subtilis* cells (ΔaprE, ΔnprE, amyE::xylRPxylAcomK-phleo). An aliquot of the transformation mix was plated on LB plates containing 1.6% skim milk and 10 μg/mL neomycin and incubated overnight at 37° C. Subsequently, the colonies with halos were inoculated in 120 μl of LB media containing 10 μg/mL neomycin.

TABLE 11-9

Parent Molecules of BPN' Used to Create RCL6 Libraries
Mixes of Parent Molecules

| Mix 1 | Mix 2 | Mix 3 | Mix 4 | Mix 5 |
|---|---|---|---|---|
| G97A-G128A-Y217Q-S24G-N25G | G97A-G128A-Y217Q-T55P | G97A-G128A-Y217Q-L75S-N76Y | G97A-G128A-Y217Q-P86S-S87G-A88V | G97A-G128A-Y217Q-P129Q-S130G-G131S |
| G97A-G128A-Y217Q-S24R | G97A-G128A-Y217Q-N61P-S63H | | G97A-G128A-Y217Q-S87G-A88V-S89A | |
| G97A-G128A-Y217Q-G23A-S24G-N25G | G97A-G128A-Y217Q-Q59S-N61P | | G97A-G128A-Y217Q-S87T-A88L-S89G | |

TABLE 11-10

Mutations Introduced in the RCL6 Libraries

| Mutations Introduced | Gene Fragment | Common 5' & 3' Gene Flanking Primer Names | Mutagenic Primer Name | SEQ ID NO: |
|---|---|---|---|---|
| V68C, A69G | 3' | P4976 | P5462 | 565 |
| | 5' | P4974 | P5463 | 566 |
| V72I, A73G, delA74, L75S | 3' | P4976 | P5464 | 567 |
| | 5' | P4974 | P5465 | 568 |
| L75H, N76G | 3' | P4976 | P5466 | 569 |
| | 5' | P4974 | P5467 | 570 |
| L75R, N76G, N77S | 3' | P4976 | P5468 | 571 |
| | 5' | P4974 | P5469 | 572 |
| L75G, N76G, N77G | 3' | P4976 | P5470 | 573 |
| | 5' | P4974 | P5471 | 574 |
| A92G | 3' | P4976 | P5472 | 575 |
| | 5' | P4974 | P5473 | 576 |
| delV93, K94S, V95C, L96S | 3' | P4976 | P5474 | 577 |
| | 5' | P4974 | P5475 | 578 |
| V121I_I122S_N123C | 3' | P4976 | P5476 | 579 |
| | 5' | P4974 | P5477 | 580 |
| V121L_N123C | 3' | P4976 | P5478 | 581 |
| | 5' | P4974 | P5479 | 582 |
| I122C_N123S_M124L | 3' | P4976 | P5480 | 583 |
| | 5' | P4974 | P5481 | 584 |
| N123C | 3' | P4976 | P5482 | 585 |
| | 5' | P4974 | P5483 | 586 |
| M124I | 3' | P4976 | P5484 | 587 |
| | 5' | P4974 | P5485 | 588 |
| M124V | 3' | P4976 | P5486 | 589 |
| | 5' | P4974 | P5487 | 590 |
| M124V-L126A | 3' | P4976 | P5488 | 591 |
| | 5' | P4974 | P5489 | 592 |
| L126F, delP129 | 3' | P4976 | P5490 | 593 |
| | 5' | P4974 | P5491 | 594 |
| G127Y | 3' | P4976 | P5492 | 595 |
| | 5' | P4974 | P5493 | 596 |
| G127S_P129D | 3' | P4976 | P5494 | 597 |
| | 5' | P4974 | P5495 | 598 |
| G127N, P129R | 3' | P4976 | P5496 | 599 |
| | 5' | P4974 | P5497 | 600 |
| G128N, insS, P129S | 3' | P4976 | P5498 | 601 |
| | 5' | P4974 | P5499 | 602 |
| G128S_P129V | 3' | P4976 | P5500 | 603 |
| | 5' | P4974 | P5501 | 604 |
| G128S, P129D | 3' | P4976 | P5502 | 605 |
| | 5' | P4974 | P5503 | 606 |
| G128S, P129G | 3' | P4976 | P5504 | 607 |
| | 5' | P4974 | P5505 | 608 |
| H128H, P129Y | 3' | P4976 | P5506 | 609 |
| | 5' | P4974 | P5507 | 610 |
| P129D | 3' | P4976 | P5508 | 611 |
| | 5' | P4974 | P5509 | 612 |

TABLE 11-10-continued

| Mutations Introduced in the RCL6 Libraries | | | | |
|---|---|---|---|---|
| Mutations Introduced | Gene Fragment | Common 5' & 3' Gene Flanking Primer Names | Mutagenic Primer Name | SEQ ID NO: |
| P129E | 3' | P4976 | P5510 | 613 |
| | 5' | P4974 | P5511 | 614 |
| P129V | 3' | P4976 | P5512 | 615 |
| | 5' | P4974 | P5513 | 616 |
| P129G, delS130 | 3' | P4976 | P5514 | 617 |
| | 5' | P4974 | P5515 | 618 |
| P129H, delS130, S132N | 3' | P4976 | P5516 | 619 |
| | 5' | P4974 | P5517 | 620 |
| A134T | 3' | P4976 | P5518 | 621 |
| | 5' | P4974 | P5519 | 622 |
| G97R, insG, A98C | 3' | P4976 | P5520 | 623 |
| | 5' | P4974 | P5521 | 624 |
| A98G, D99G | 3' | P4976 | P5522 | 625 |
| | 5' | P4974 | P5523 | 626 |
| A98G, insR | 3' | P4976 | P5524 | 627 |
| | 5' | P4974 | P5525 | 628 |
| A98D, D99G | 3' | P4976 | P5526 | 629 |
| | 5' | P4974 | P5527 | 630 |
| A98H, D99G, G100D | 3' | P4976 | P5528 | 631 |
| | 5' | P4974 | P5529 | 632 |
| D99R, insN | 3' | P4976 | P5530 | 633 |
| | 5' | P4974 | P5531 | 634 |
| D99V, S101D | 3' | P4976 | P5532 | 635 |
| | 5' | P4974 | P5533 | 636 |
| D99C, insS | 3' | P4976 | P5534 | 637 |
| | 5' | P4974 | P5535 | 638 |
| G100S | 3' | P4976 | P5536 | 639 |
| | 5' | P4974 | P5537 | 640 |
| G100S, S101V | 3' | P4976 | P5538 | 641 |
| | 5' | P4974 | P5539 | 642 |
| G100D | 3' | P4976 | P5540 | 643 |
| | 5' | P4974 | P5541 | 644 |
| G100N | 3' | P4976 | P5542 | 645 |
| | 5' | P4974 | P5543 | 646 |
| S100N, S101L | 3' | P4976 | P5544 | 647 |
| | 5' | P4974 | P5545 | 648 |
| S101G | 3' | P4976 | P5546 | 649 |
| | 5' | P4974 | P5547 | 650 |
| S101D | 3' | P4976 | P5548 | 651 |
| | 5' | P4974 | P5549 | 652 |
| S101V, Q103N | 3' | P4976 | P5550 | 653 |
| | 5' | P4974 | P5551 | 654 |
| S101E | 3' | P4976 | P5552 | 655 |
| | 5' | P4974 | P5553 | 656 |
| A116S, N117G, N118R | 3' | P4976 | P5554 | 657 |
| | 5' | P4974 | P5555 | 658 |
| A116G, N117R | 3' | P4976 | P5556 | 659 |
| | 5' | P4974 | P5557 | 660 |
| A116N, N117S, N118G | 3' | P4976 | P5558 | 661 |
| | 5' | P4974 | P5559 | 662 |
| M222Q | 3' | P4976 | P5560 | 663 |
| | 5' | P4974 | P5561 | 664 |
| S24R | 3' | P4976 | P5562 | 665 |
| | 5' | P4974 | P5563 | 666 |
| N25Y | 3' | P4976 | P5564 | 667 |
| | 5' | P4974 | P5565 | 668 |
| P52D | 3' | P4976 | P5566 | 669 |
| | 5' | P4974 | P5567 | 670 |
| S63T | 3' | P4976 | P5568 | 671 |
| | 5' | P4974 | P5569 | 672 |
| N61E | 3' | P4976 | P5570 | 673 |
| | 5' | P4974 | P5571 | 674 |
| N61P | 3' | P4976 | P5572 | 675 |
| | 5' | P4974 | P5573 | 676 |
| N62Q | 3' | P4976 | P5574 | 677 |
| | 5' | P4974 | P5575 | 678 |
| N62D | 3' | P4976 | P5576 | 679 |
| | 5' | P4974 | P5577 | 680 |
| S63Q | 3' | P4976 | P5578 | 681 |
| | 5' | P4974 | P5579 | 682 |
| V68A | 3' | P4976 | P5580 | 683 |
| | 5' | P4974 | P5581 | 684 |

TABLE 11-10-continued

| Mutations Introduced in the RCL6 Libraries | | | | |
|---|---|---|---|---|
| Mutations Introduced | Gene Fragment | Common 5' & 3' Gene Flanking Primer Names | Mutagenic Primer Name | SEQ ID NO: |
| S87D | 3' | P4976 | P5582 | 685 |
| | 5' | P4974 | P5583 | 686 |
| L96T | 3' | P4976 | P5584 | 687 |
| | 5' | P4974 | P5585 | 688 |
| L126A | 3' | P4976 | P5586 | 689 |
| | 5' | P4974 | P5587 | 690 |
| L126T | 3' | P4976 | P5588 | 691 |
| | 5' | P4974 | P5589 | 692 |
| S125A | 3' | P4976 | P5590 | 693 |
| | 5' | P4974 | P5591 | 694 |
| S130P | 3' | P4976 | P5592 | 695 |
| | 5' | P4974 | P5593 | 696 |
| P129L | 3' | P4976 | P5594 | 697 |
| | 5' | P4974 | P5595 | 698 |
| P129E | 3' | P4976 | P5596 | 699 |
| | 5' | P4974 | P5597 | 700 |
| P129S | 3' | P4976 | P5598 | 701 |
| | 5' | P4974 | P5599 | 702 |
| P40E | 3' | P4976 | P5600 | 703 |
| | 5' | P4974 | P5601 | 704 |
| Y6Q | 3' | P4976 | P5602 | 705 |
| | 5' | P4974 | P5603 | 706 |
| G102A | 3' | P4976 | P5604 | 707 |
| | 5' | P4974 | P5605 | 708 |
| S101N | 3' | P4976 | P5606 | 709 |
| | 5' | P4974 | P5607 | 710 |
| G100E | 3' | P4976 | P5608 | 711 |
| | 5' | P4974 | P5609 | 712 |
| I115V | 3' | P4976 | P5610 | 713 |
| | 5' | P4974 | P5611 | 714 |
| A144K | 3' | P4976 | P5612 | 715 |
| | 5' | P4974 | P5613 | 716 |
| S145D | 3' | P4976 | P5614 | 717 |
| | 5' | P4974 | P5615 | 718 |
| S159K | 3' | P4976 | P5616 | 719 |
| | 5' | P4974 | P5617 | 720 |
| S162K | 3' | P4976 | P5618 | 721 |
| | 5' | P4974 | P5619 | 722 |
| V147P | 3' | P4976 | P5620 | 723 |
| | 5' | P4974 | P5621 | 724 |
| S161P | 3' | P4976 | P5622 | 725 |
| | 5' | P4974 | P5623 | 726 |
| A187D | 3' | P4976 | P5624 | 727 |
| | 5' | P4974 | P5625 | 728 |
| F189D | 3' | P4976 | P5626 | 729 |
| | 5' | P4974 | P5627 | 730 |
| L267V | 3' | P4976 | P5628 | 731 |
| | 5' | P4974 | P5629 | 732 |
| Q206E | 3' | P4976 | P5630 | 733 |
| | 5' | P4974 | P5631 | 734 |
| K213T | 3' | P4976 | P5632 | 735 |
| | 5' | P4974 | P5633 | 736 |
| K213L | 3' | P4976 | P5634 | 737 |
| | 5' | P4974 | P5635 | 738 |
| K265N | 3' | P4976 | P5636 | 739 |
| | 5' | P4974 | P5637 | 740 |
| N240K | 3' | P4976 | P5638 | 741 |
| | 5' | P4974 | P5639 | 742 |
| P239R | 3' | P4976 | P5640 | 743 |
| | 5' | P4974 | P5641 | 744 |
| T242R | 3' | P4976 | P5642 | 745 |
| | 5' | P4974 | P5643 | 746 |
| S89Y | 3' | P4976 | P5644 | 747 |
| | 5' | P4974 | P5645 | 748 |
| P129Q | 3' | P4976 | P5646 | 749 |
| | 5' | P4974 | P5647 | 750 |
| G211T | 3' | P4976 | P5648 | 751 |
| | 5' | P4974 | P5649 | 752 |
| I111V | 3' | P4976 | P5650 | 753 |
| | 5' | P4974 | P5651 | 754 |

RCL 7 Combinatorial Variants

"RCL7" refers to a set of combinatorial variants created by PCR fusion using several BPN' mutants as parent (template) plasmid. The mutations introduced in each parent plasmid are listed in Table 11-11, and the mutagenic primers used to create the mutants are described in Table 11-10.

To create each mutant, two PCR reactions were carried out using either the common 3' gene-flanking primer (P4976, SEQ ID NO:61) and the mutagenic primer, or the common 5' gene-flanking primer (P4974, SEQ ID NO:60) and mutagenic primer as shown for each library in Table 11-10. These PCR reactions generated two PCR fragments, one encoding the 5' half of the mutant BPN' gene (5' gene fragment) and the other encoding the 3' half of the mutant BPN' gene (3' gene fragment). Each PCR amplification reaction contained 30 pmol of each primer and 100 ng of the parent molecules listed in Table 11-11. Amplifications were carried out using Vent DNA polymerase (NEB). The PCR reaction (20 μL) was initially heated at 95° C. for 2.5 min followed by 30 cycles of denaturation at 94° C. for 15 sec., annealing at 55° C. for 15 sec. and extension at 72° C. for 40 sec. Following amplification, the 5' and 3' gene fragments were gel-purified using a QIAGEN® gel-band purification kit, mixed (50 ng of each fragment) and amplified by PCR once again using the primers P4973 (SEQ ID NO:62) and P4950 (SEQ ID NO:63) to generate the full-length gene fragment. The PCR conditions were same as described above, except the extension phase, which was carried out at 72° C. for 2 min. The full-length DNA fragment was gel-purified using a QIAGEN® gel-band purification kit, digested using BamHI and HindIII restriction enzymes, and ligated with the pHPLT-BPN' partial opt that also was digested with the same restriction enzymes. Ligation mixtures were amplified using rolling circle amplification by Illustra Templiphi kit according to the manufacturer's instructions (GE Healthcare) to generate multimeric DNA for transformation into *Bacillus subtilis*. For this purpose, 1 μl of the ligation mixture was mixed with 5 μl of the sample buffer, heated to 95° C. for 3 min and cooled on ice. Next, 5 μl of the reaction buffer and 0.2 μl of the enzyme were added to each tube, followed by incubation at 30° C. for 10 hours. Products of the rolling circle amplification were diluted 100 times and used to transform *B. subtilis* cells (ΔaprE, ΔnprE, amyE::xylRPxylAcomK-phleo). An aliquot of the transformation mix was plated on LB plates containing 1.6% skim milk and 10 μg/mL neomycin and incubated overnight at 37° C. Subsequently, the colonies with halos were inoculated in 120 μl of LB media containing 10 μg/mL neomycin.

TABLE 11-11

List of Parent Plasmids and Introduced Mutations in the RCL7 variants

| Combinatorial Variant # | Parent Plasmid | Mutation(s) Introduced |
|---|---|---|
| 1 | G97A-G128A-Y217Q-T55P | S24R |
| 2 | G97A-G128A-Y217Q-N61E | S24R |
| 3 | G97A-G128A-Y217Q-N61P-S63H | S24R |
| 4 | G97A-G128A-Y217Q-L75S-N76Y | S24R |
| 5 | G97A-G128A-Y217Q-S87T-A88L-S89G | S24R |
| 6 | G97A-G128A-Y217Q-S89Y | S24R |
| 7 | G97A-G128A-Y217Q-I111V | S24R |
| 8 | G97A-G128A-Y217Q-I115V | S24R |
| 9 | G97A-G128A-Y217Q-P129Q-S130G-G131S | S24R |
| 10 | G97A-G128A-Y217Q-P129Q | S24R |
| 11 | G97A-G128A-Y217Q-A134T | S24R |
| 12 | G97A-G128A-Y217Q-A144K | S24R |
| 13 | G97A-G128A-Y217Q-S145D | S24R |
| 14 | G97A-G128A-Y217Q-S159K | S24R |
| 15 | G97A-G128A-Y217Q-S162K | S24R |
| 16 | G97A-G128A-Y217Q-S161P-S78N | S24R |
| 17 | G97A-G128A-Y217Q-V203Y | S24R |
| 18 | G97A-G128A-Y217Q-G211T-S78N | S24R |
| 19 | G97A-G128A-Y217Q-K213T | S24R |
| 20 | G97A-G128A-Y217Q-P239R | S24R |
| 21 | G97A-G128A-Y217Q-N240K | S24R |
| 22 | G97A-G128A-Y217Q-L267V-S78N | S24R |
| 23 | G97A-G128A-Y217Q-A273S-S78N | S24R |
| 24 | G97A-G128A-Y217Q-L75S-N76Y | T55P |
| 25 | G97A-G128A-Y217Q-S87T-A88L-S89G | T55P |
| 26 | G97A-G128A-Y217Q-S89Y | T55P |
| 27 | G97A-G128A-Y217Q-I111V | T55P |
| 28 | G97A-G128A-Y217Q-I115V | T55P |
| 29 | G97A-G128A-Y217Q-P129Q-S130G-G131S | T55P |
| 30 | G97A-G128A-Y217Q-P129Q | T55P |
| 31 | G97A-G128A-Y217Q-A134T | T55P |
| 32 | G97A-G128A-Y217Q-A144K | T55P |
| 33 | G97A-G128A-Y217Q-S145D | T55P |
| 34 | G97A-G128A-Y217Q-S159K | T55P |
| 35 | G97A-G128A-Y217Q-S162K | T55P |
| 36 | G97A-G128A-Y217Q-S161P | T55P |
| 37 | G97A-G128A-Y217Q-V203Y | T55P |
| 38 | G97A-G128A-Y217Q-G211T | T55P |
| 39 | G97A-G128A-Y217Q-K213T | T55P |
| 40 | G97A-G128A-Y217Q-P239R | T55P |
| 41 | G97A-G128A-Y217Q-N240K | T55P |
| 42 | G97A-G128A-Y217Q-L267V | T55P |
| 43 | G97A-G128A-Y217Q-A273S | T55P |
| 44 | G97A-G128A-Y217Q-L75S-N76Y | N61E |
| 45 | G97A-G128A-Y217Q-S87T-A88L-S89G | N61E |
| 46 | G97A-G128A-Y217Q-S89Y | N61E |
| 47 | G97A-G128A-Y217Q-I111V | N61E |
| 48 | G97A-G128A-Y217Q-I115V | N61E |
| 49 | G97A-G128A-Y217Q-P129Q-S130G-G131S | N61E |
| 50 | G97A-G128A-Y217Q-P129Q | N61E |
| 51 | G97A-G128A-Y217Q-A134T | N61E |
| 52 | G97A-G128A-Y217Q-A144K | N61E |
| 53 | G97A-G128A-Y217Q-S145D | N61E |
| 54 | G97A-G128A-Y217Q-S159K | N61E |
| 55 | G97A-G128A-Y217Q-S162K | N61E |
| 56 | G97A-G128A-Y217Q-S161P | N61E |
| 57 | G97A-G128A-Y217Q-V203Y | N61E |
| 58 | G97A-G128A-Y217Q-G211T | N61E |
| 59 | G97A-G128A-Y217Q-K213T | N61E |
| 60 | G97A-G128A-Y217Q-P239R | N61E |
| 61 | G97A-G128A-Y217Q-N240K | N61E |
| 62 | G97A-G128A-Y217Q-L267V | N61E |
| 63 | G97A-G128A-Y217Q-A273S | N61E |
| 64 | G97A-G128A-Y217Q-L75S-N76Y | N61P-S63H |
| 65 | G97A-G128A-Y217Q-S87T-A88L-S89G | N61P-S63H |
| 66 | G97A-G128A-Y217Q-S89Y | N61P-S63H |
| 67 | G97A-G128A-Y217Q-I111V | N61P-S63H |
| 68 | G97A-G128A-Y217Q-I115V | N61P-S63H |
| 69 | G97A-G128A-Y217Q-P129Q-S130G-G131S | N61P-S63H |
| 70 | G97A-G128A-Y217Q-P129Q | N61P-S63H |
| 71 | G97A-G128A-Y217Q-A134T | N61P-S63H |
| 72 | G97A-G128A-Y217Q-A144K | N61P-S63H |
| 73 | G97A-G128A-Y217Q-S145D | N61P-S63H |
| 74 | G97A-G128A-Y217Q-S159K | N61P-S63H |
| 75 | G97A-G128A-Y217Q-S162K | N61P-S63H |
| 76 | G97A-G128A-Y217Q-S161P | N61P-S63H |
| 77 | G97A-G128A-Y217Q-V203Y | N61P-S63H |
| 78 | G97A-G128A-Y217Q-G211T | N61P-S63H |
| 79 | G97A-G128A-Y217Q-K213T | N61P-S63H |
| 80 | G97A-G128A-Y217Q-P239R | N61P-S63H |
| 81 | G97A-G128A-Y217Q-N240K | N61P-S63H |
| 82 | G97A-G128A-Y217Q-L267V | N61P-S63H |
| 83 | G97A-G128A-Y217Q-A273S | N61P-S63H |
| 84 | G97A-G128A-Y217Q-S87T-A88L-S89G | L75S-N76Y |
| 85 | G97A-G128A-Y217Q-S89Y | L75S-N76Y |
| 86 | G97A-G128A-Y217Q-I111V | L75S-N76Y |
| 87 | G97A-G128A-Y217Q-I115V | L75S-N76Y |
| 88 | G97A-G128A-Y217Q-P129Q-S130G-G131S | L75S-N76Y |

TABLE 11-11-continued

List of Parent Plasmids and Introduced Mutations in the RCL7 variants

| Combi-natorial Variant # | Parent Plasmid | Mutation(s) Introduced |
|---|---|---|
| 89 | G97A-G128A-Y217Q-P129Q | L75S-N76Y |
| 90 | G97A-G128A-Y217Q-A134T | L75S-N76Y |
| 91 | G97A-G128A-Y217Q-A144K | L75S-N76Y |
| 92 | G97A-G128A-Y217Q-S145D | L75S-N76Y |
| 93 | G97A-G128A-Y217Q-S159K | L75S-N76Y |
| 94 | G97A-G128A-Y217Q-S162K | L75S-N76Y |
| 95 | G97A-G128A-Y217Q-S161P | L75S-N76Y |
| 96 | G97A-G128A-Y217Q-V203Y | L75S-N76Y |
| 97 | G97A-G128A-Y217Q-G211T | L75S-N76Y |
| 98 | G97A-G128A-Y217Q-K213T | L75S-N76Y |
| 99 | G97A-G128A-Y217Q-P239R | L75S-N76Y |
| 100 | G97A-G128A-Y217Q-N240K | L75S-N76Y |
| 101 | G97A-G128A-Y217Q-L267V | L75S-N76Y |
| 102 | G97A-G128A-Y217Q-A273S | L75S-N76Y |
| 103 | G97A-G128A-Y217Q-I111V | S87T-A88L-S89G |
| 104 | G97A-G128A-Y217Q-I115V | S87T-A88L-S89G |
| 105 | G97A-G128A-Y217Q-P129Q-S130G-G131S | S87T-A88L-S89G |
| 106 | G97A-G128A-Y217Q-P129Q | S87T-A88L-S89G |
| 107 | G97A-G128A-Y217Q-A134T | S87T-A88L-S89G |
| 108 | G97A-G128A-Y217Q-A144K | S87T-A88L-S89G |
| 109 | G97A-G128A-Y217Q-S145D | S87T-A88L-S89G |
| 110 | G97A-G128A-Y217Q-S159K | S87T-A88L-S89G |
| 111 | G97A-G128A-Y217Q-S162K | S87T-A88L-S89G |
| 112 | G97A-G128A-Y217Q-S161P | S87T-A88L-S89G |
| 113 | G97A-G128A-Y217Q-V203Y | S87T-A88L-S89G |
| 114 | G97A-G128A-Y217Q-G211T | S87T-A88L-S89G |
| 115 | G97A-G128A-Y217Q-K213T | S87T-A88L-S89G |
| 116 | G97A-G128A-Y217Q-P239R | S87T-A88L-S89G |
| 117 | G97A-G128A-Y217Q-N240K | S87T-A88L-S89G |
| 118 | G97A-G128A-Y217Q-L267V | S87T-A88L-S89G |
| 119 | G97A-G128A-Y217Q-A273S | S87T-A88L-S89G |
| 120 | G97A-G128A-Y217Q-I111V | S89Y |
| 121 | G97A-G128A-Y217Q-I115V | S89Y |
| 122 | G97A-G128A-Y217Q-P129Q-S130G-G131S | S89Y |
| 123 | G97A-G128A-Y217Q-P129Q | S89Y |
| 124 | G97A-G128A-Y217Q-A134T | S89Y |
| 125 | G97A-G128A-Y217Q-A144K | S89Y |
| 126 | G97A-G128A-Y217Q-S145D | S89Y |
| 127 | G97A-G128A-Y217Q-S159K | S89Y |
| 128 | G97A-G128A-Y217Q-S162K | S89Y |
| 129 | G97A-G128A-Y217Q-S161P | S89Y |
| 130 | G97A-G128A-Y217Q-V203Y | S89Y |
| 131 | G97A-G128A-Y217Q-G211T | S89Y |
| 132 | G97A-G128A-Y217Q-K213T | S89Y |
| 133 | G97A-G128A-Y217Q-P239R | S89Y |
| 134 | G97A-G128A-Y217Q-N240K | S89Y |
| 135 | G97A-G128A-Y217Q-L267V | S89Y |
| 136 | G97A-G128A-Y217Q-A273S | S89Y |
| 137 | G97A-G128A-Y217Q-P129Q-S130G-G131S | I111V |
| 138 | G97A-G128A-Y217Q-P129Q | I111V |
| 139 | G97A-G128A-Y217Q-A134T | I111V |
| 140 | G97A-G128A-Y217Q-A144K | I111V |
| 141 | G97A-G128A-Y217Q-S145D | I111V |
| 142 | G97A-G128A-Y217Q-S159K | I111V |
| 143 | G97A-G128A-Y217Q-S162K | I111V |
| 144 | G97A-G128A-Y217Q-S161P | I111V |
| 145 | G97A-G128A-Y217Q-V203Y | I111V |

TABLE 11-11-continued

List of Parent Plasmids and Introduced Mutations in the RCL7 variants

| Combi-natorial Variant # | Parent Plasmid | Mutation(s) Introduced |
|---|---|---|
| 146 | G97A-G128A-Y217Q-G211T | I111V |
| 147 | G97A-G128A-Y217Q-K213T | I111V |
| 148 | G97A-G128A-Y217Q-P239R | I111V |
| 149 | G97A-G128A-Y217Q-N240K | I111V |
| 150 | G97A-G128A-Y217Q-L267V | I111V |
| 151 | G97A-G128A-Y217Q-A273S | I111V |
| 152 | G97A-G128A-Y217Q-P129Q-S130G-G131S | I115V |
| 153 | G97A-G128A-Y217Q-P129Q | I115V |
| 154 | G97A-G128A-Y217Q-A134T | I115V |
| 155 | G97A-G128A-Y217Q-A144K | I115V |
| 156 | G97A-G128A-Y217Q-S145D | I115V |
| 157 | G97A-G128A-Y217Q-S159K | I115V |
| 158 | G97A-G128A-Y217Q-S162K | I115V |
| 159 | G97A-G128A-Y217Q-S161P | I115V |
| 160 | G97A-G128A-Y217Q-V203Y | I115V |
| 161 | G97A-G128A-Y217Q-G211T | I115V |
| 162 | G97A-G128A-Y217Q-K213T | I115V |
| 163 | G97A-G128A-Y217Q-P239R | I115V |
| 164 | G97A-G128A-Y217Q-N240K | I115V |
| 165 | G97A-G128A-Y217Q-L267V | I115V |
| 166 | G97A-G128A-Y217Q-A273S | I115V |
| 167 | G97A-G128A-Y217Q-A144K | P129Q-S130G-G131S |
| 168 | G97A-G128A-Y217Q-S145D | P129Q-S130G-G131S |
| 169 | G97A-G128A-Y217Q-S159K | P129Q-S130G-G131S |
| 170 | G97A-G128A-Y217Q-S162K | P129Q-S130G-G131S |
| 171 | G97A-G128A-Y217Q-S161P | P129Q-S130G-G131S |
| 172 | G97A-G128A-Y217Q-V203Y | P129Q-S130G-G131S |
| 173 | G97A-G128A-Y217Q-G211T | P129Q-S130G-G131S |
| 174 | G97A-G128A-Y217Q-K213T | P129Q-S130G-G131S |
| 175 | G97A-G128A-Y217Q-P239R | P129Q-S130G-G131S |
| 176 | G97A-G128A-Y217Q-N240K | P129Q-S130G-G131S |
| 177 | G97A-G128A-Y217Q-L267V | P129Q-S130G-G131S |
| 178 | G97A-G128A-Y217Q-A273S | P129Q-S130G-G131S |
| 179 | G97A-G128A-Y217Q-A144K | P129Q |
| 180 | G97A-G128A-Y217Q-S145D | P129Q |
| 181 | G97A-G128A-Y217Q-S159K | P129Q |
| 182 | G97A-G128A-Y217Q-S162K | P129Q |
| 183 | G97A-G128A-Y217Q-S161P | P129Q |
| 184 | G97A-G128A-Y217Q-V203Y | P129Q |
| 185 | G97A-G128A-Y217Q-G211T | P129Q |
| 186 | G97A-G128A-Y217Q-K213T | P129Q |
| 187 | G97A-G128A-Y217Q-P239R | P129Q |
| 188 | G97A-G128A-Y217Q-N240K | P129Q |
| 189 | G97A-G128A-Y217Q-L267V | P129Q |
| 190 | G97A-G128A-Y217Q-A273S | P129Q |
| 191 | G97A-G128A-Y217Q-A144K | A134T |
| 192 | G97A-G128A-Y217Q-S145D | A134T |
| 193 | G97A-G128A-Y217Q-S159K | A134T |
| 194 | G97A-G128A-Y217Q-S162K | A134T |
| 195 | G97A-G128A-Y217Q-S161P | A134T |
| 196 | G97A-G128A-Y217Q-V203Y | A134T |
| 197 | G97A-G128A-Y217Q-G211T | A134T |
| 198 | G97A-G128A-Y217Q-K213T | A134T |
| 199 | G97A-G128A-Y217Q-P239R | A134T |
| 200 | G97A-G128A-Y217Q-N240K | A134T |
| 201 | G97A-G128A-Y217Q-L267V | A134T |
| 202 | G97A-G128A-Y217Q-A273S | A134T |
| 203 | G97A-G128A-Y217Q-S159K | A144K |
| 204 | G97A-G128A-Y217Q-S162K | A144K |
| 205 | G97A-G128A-Y217Q-S161P | A144K |
| 206 | G97A-G128A-Y217Q-V203Y | A144K |
| 207 | G97A-G128A-Y217Q-G211T | A144K |

TABLE 11-11-continued

List of Parent Plasmids and Introduced Mutations in the RCL7 variants

| Combi-natorial Variant # | Parent Plasmid | Mutation(s) Introduced |
|---|---|---|
| 208 | G97A-G128A-Y217Q-K213T | A144K |
| 209 | G97A-G128A-Y217Q-P239R | A144K |
| 210 | G97A-G128A-Y217Q-N240K | A144K |
| 211 | G97A-G128A-Y217Q-L267V | A144K |
| 212 | G97A-G128A-Y217Q-A273S | A144K |
| 213 | G97A-G128A-Y217Q-S159K | S145D |
| 214 | G97A-G128A-Y217Q-S162K | S145D |
| 215 | G97A-G128A-Y217Q-S161P | S145D |
| 216 | G97A-G128A-Y217Q-V203Y | S145D |
| 217 | G97A-G128A-Y217Q-G211T | S145D |
| 218 | G97A-G128A-Y217Q-K213T | S145D |
| 219 | G97A-G128A-Y217Q-P239R | S145D |
| 220 | G97A-G128A-Y217Q-N240K | S145D |
| 221 | G97A-G128A-Y217Q-L267V | S145D |
| 222 | G97A-G128A-Y217Q-A273S | S145D |
| 223 | G97A-G128A-Y217Q-V203Y | S159K |
| 224 | G97A-G128A-Y217Q-G211T | S159K |
| 225 | G97A-G128A-Y217Q-K213T | S159K |
| 226 | G97A-G128A-Y217Q-P239R | S159K |
| 227 | G97A-G128A-Y217Q-N240K | S159K |
| 228 | G97A-G128A-Y217Q-L267V | S159K |
| 229 | G97A-G128A-Y217Q-A273S | S159K |
| 230 | G97A-G128A-Y217Q-V203Y | S162K |
| 231 | G97A-G128A-Y217Q-G211T | S162K |
| 232 | G97A-G128A-Y217Q-K213T | S162K |
| 233 | G97A-G128A-Y217Q-P239R | S162K |
| 234 | G97A-G128A-Y217Q-N240K | S162K |
| 235 | G97A-G128A-Y217Q-L267V | S162K |
| 236 | G97A-G128A-Y217Q-A273S | S162K |
| 237 | G97A-G128A-Y217Q-V203Y | S161P |
| 238 | G97A-G128A-Y217Q-G211T | S161P |
| 239 | G97A-G128A-Y217Q-K213T | S161P |
| 240 | G97A-G128A-Y217Q-239R | S161P |
| 241 | G97A-G128A-Y217Q-N240K | S161P |

TABLE 11-11-continued

List of Parent Plasmids and Introduced Mutations in the RCL7 variants

| Combi-natorial Variant # | Parent Plasmid | Mutation(s) Introduced |
|---|---|---|
| 242 | G97A-G128A-Y217Q-L267V | S161P |
| 243 | G97A-G128A-Y217Q-A273S | S161P |
| 244 | G97A-G128A-Y217Q-G211T | V203Y |
| 245 | G97A-G128A-Y217Q-K213T | V203Y |
| 246 | G97A-G128A-Y217Q-P239R | V203Y |
| 247 | G97A-G128A-Y217Q-N240K | V203Y |
| 248 | G97A-G128A-Y217Q-L267V | V203Y |
| 249 | G97A-G128A-Y217Q-A273S | V203Y |
| 250 | G97A-G128A-Y217Q-P239R | G211T |
| 251 | G97A-G128A-Y217Q-N240K | G211T |
| 252 | G97A-G128A-Y217Q-L267V | G211T |
| 253 | G97A-G128A-Y217Q-A273S | G211T |
| 254 | G97A-G128A-Y217Q-P239R | K213T |
| 255 | G97A-G128A-Y217Q-N240K | K213T |
| 256 | G97A-G128A-Y217Q-L267V | K213T |
| 257 | G97A-G128A-Y217Q-A273S | K213T |
| 258 | G97A-G128A-Y217Q-L267V | P239R |
| 259 | G97A-G128A-Y217Q-A273S | P239R |
| 260 | G97A-G128A-Y217Q-L267V | N240K |
| 261 | G97A-G128A-Y217Q-A273S | N240K |

Example 12

Table of Detergents

The compositions of the detergents used in the assays for Part I Example 12 are shown in Table 12-1. BPN' variant protein samples were added to the detergent compositions as described in Part I Example 1 to assay for the various properties listed.

TABLE 12-1

Composition of Detergents Used in the Assays to Test BPN' Variants

| Ingredient | Composition (wt % of Composition) 1 | 2 | 3 |
|---|---|---|---|
| $C_{12-15}$ Alkylethoxy(1.8)sulphate | 14.7 | 11.6 | |
| $C_{11.8}$ Alkylbenzene sulfonate | 4.3 | 11.6 | 8.3 |
| $C_{16-17}$ Branched alkyl sulphate | 1.7 | 1.29 | |
| $C_{12-14}$ Alkyl-9-ethoxylate | 0.9 | 1.07 | |
| $C_{12}$ dimethylamine oxide | 0.6 | 0.64 | |
| Citric acid | 3.5 | 0.65 | 3 |
| $C_{12-18}$ fatty acid | 1.5 | 2.32 | 3.6 |
| Sodium Borate (Borax) | 2.5 | 2.46 | 1.2 |
| Sodium $C_{12-14}$ alkyl ethoxy 3 sulfate | | | 2.9 |
| $C_{14-15}$ alkyl 7-ethoxylate | | | 4.2 |
| $C_{12-14}$ Alkyl-7-ethoxylate | | | 1.7 |
| Ca formate | 0.09 | 0.09 | |
| A compound having the following general structure: bis(($C_2H_5O$)($C_2H_4O$)$n$)($CH_3$)—$N^+$—$C_xH_{2x}$—$N^+$—($CH_3$)—bis(($C_2H_5O$)($C_2H_4O$)$n$), wherein n = from 20 to 30, and x = from 3 to 8, or sulphated or sulphonated variants thereof | | | 1.2 |
| Random graft co-polymer[1] | | 1.46 | 0.5 |
| Ethoxylated Polyethylenimine[2] | 1.5 | 1.29 | |
| Diethylene triamine pentaacetic acid | 0.34 | 0.64 | |
| Diethylene triamine penta(methylene phosphonic acid) | | | 0.3 |
| Tinopal AMS-GX | | 0.06 | |
| Tinopal CBS-X | 0.2 | 0.17 | |
| Amphiphilic alkoxylated grease cleaning polymer[3] | 1.28 | 1 | 0.4 |
| Ethanol | 2 | 1.58 | 1.6 |
| Propylene Glycol | 3.9 | 3.59 | 1.3 |
| Diethylene glycol | 1.05 | 1.54 | |
| Polyethylene glycol | 0.06 | 0.04 | |

TABLE 12-1-continued

Composition of Detergents Used in the Assays to Test BPN' Variants

| Ingredient | Composition (wt % of Composition) 1 | 2 | 3 |
|---|---|---|---|
| Monoethanolamine | 3.05 | 2.41 | 0.4 |
| NaOH | 2.44 | 1.8 | |
| Sodium Cumene Sulphonate | | | 1 |
| Sodium Formate | | 0.11 | |
| Water, Aesthetics (Dyes, perfumes) and Minors (Enzymes, solvents, structurants) | balance | balance | balance |

[1]"Random graft copolymer" is a polyvinyl acetate grafted polyethylene oxide copolymer having a polyethylene oxide backbone and multiple polyvinyl acetate side chains. The molecular weight of the polyethylene oxide backbone is about 6000 and the weight ratio of the polyethylene oxide to polyvinyl acetate is about 40 to 60 and no more than 1 grafting point per 50 ethylene oxide units.
[2]Polyethylenimine (MW = 600) with 20 ethoxylate groups per —NH.
[3]Amphiphilic alkoxylated grease cleaning polymer is a polyethylenimine (MW = 600) with 24 ethoxylate groups per —NH and 16 propoxylate groups per —NH.

Stain Removal Performance of BPN' Combinatorial Variants

Experiments to evaluate the stain removal performance of BPN' combinatorial variants generated as described in Example 11 were performed using BMI stained microswatches. The assay was performed as described in Example 1 (BMI microswatch assay). Table 12-2 provides Performance Index (PI) values of variants generated from RCL4 library using BMI microswatch assay in Detergent Composition 1 at pH 8 and 16° C. and Detergent Composition 1 at pH 8 and 32° C. and BMI microswatch assay in heat deactivated commercial TIDE® 2× Cold (Procter & Gamble) detergent at 16° C. and pH 8. Heat inactivation of commercial detergent formulas serves to destroy the endogenous enzymatic activity of any protein components while retaining the properties of nonenzymatic components. Heat inactivation of the detergents was performed by placing pre-weighed amounts of liquid detergent (in a glass bottle) in a water bath at 95° C. for 2 hours. The TIDE® 2× Cold detergent was purchased from local supermarket stores. Both unheated and heated detergents were assayed within 5 minutes of dissolving the detergent, in order to accurately determine percentage deactivated. Enzyme activity was tested by AAPF assay. Working solutions were made from the heat inactivated stock. Appropriate amounts of water hardness and buffer were added to the detergent solutions to match the desired conditions (Table 12-2). The solutions were mixed by vortexing or inverting the bottles.

TABLE 12-2

Working Detergent Solutions

| Detergent | Temp (° C.) | Detergent g/L | pH | Buffer | Hardness Gpg |
|---|---|---|---|---|---|
| TIDE ® 2X Cold | 16, 32 | 0.98 | 8 | 5 mM HEPES | 6 |

The sequences of the variants listed in Table 12-3 are relative to BPN'-v3: G97A-G128A-Y217Q. The PI values are calculated relative to BPN'-v3. All mutants in this list have a PI cutoff equal or greater than 0.5 for at least one property tested. "Det. Comp." means Detergent Composition.

TABLE 12-3

Performance Index Values of Variants Generated from RCL4 Library

| Sequence Relative to BPN' | Sequence Relative to BPN'-v3: G97A-G128A-Y217Q | TIDE ® Detergent pH 8, 16° C., BMI PI | Det. Comp. 1, pH 8, 16° C., BMI PI | Det. Comp. 1, pH 8, 32° C., BMI PI |
|---|---|---|---|---|
| S87T-A88L-S89G-G97A-G128A-Y217Q | S87T-A88L-S89G | 1.00 | 1.12 | 0.99 |
| N61P-S63H-G97A-G128A-Y217Q | N61P-S63H | 1.03 | 1.12 | 1.01 |
| S87G-A88V-S89A-G97A-G128A-Y217Q | S87G-A88V-S89A | 1.02 | 1.11 | 0.99 |
| P86S-S87G-A88V-G97A-G128A-Y217Q | P86S-S87G-A88V | 1.00 | 1.10 | 1.00 |
| Q59S-N61P-G97A-G128A-Y217Q | Q59S-N61P | 1.01 | 1.09 | 1.00 |
| S24G-N25G-G97A-G128A-Y217Q | S24G-N25G | 0.99 | 1.09 | 1.02 |
| N61P-N62S-G97A-G128A-Y217Q | N61P-N62S | 0.99 | 1.06 | 0.98 |
| G97A-G128A-P129Q-S130G-G131S-Y217Q | P129Q-S130G-G131S | 0.96 | 1.06 | 0.99 |
| L75S-N76Y-G97A-G128A-Y217Q | L75S-N76Y | 0.99 | 1.06 | 1.00 |
| G97A-G128A-V203Y-Y217Q | V203Y | 0.99 | 1.05 | 1.01 |
| T55P-G97A-G128A-Y217Q | T55P | 0.98 | 1.04 | 0.98 |
| A88V-L90I-G97A-G128A-Y217Q | A88V-L90I | 0.99 | 1.04 | 1.00 |
| G97A-G128A-G211R-N212S-K213V-Y217Q | G211R-N212S-K213V | 0.97 | 1.04 | 0.98 |
| G23A-S24G-N25G-G97A-G128A-Y217Q | G23A-S24G-N25G | 0.98 | 1.04 | 0.98 |
| T22N-S24A-G97A-G128A-Y217Q | T22N-S24A | 0.98 | 1.03 | 0.97 |
| S24R-G97A-G128A-Y217Q | S24R | 0.95 | 1.02 | 0.99 |
| G97A-A98S-G128A-Y217Q | A98S | 0.95 | 1.02 | 0.99 |
| **BPN'-v3: G97A-G128A-Y217Q** | **BPN'-v3** | **1.00** | **1.00** | **1.00** |
| G97A-G128A-T158G-S159G-Y217Q | T158G-S159G | 0.95 | 0.99 | 0.97 |
| Q59E-N61P-G97A-G128A-Y217Q | Q59E-N61P | 0.90 | 0.94 | 0.90 |

TABLE 12-3-continued

Performance Index Values of Variants Generated from RCL4 Library

| Sequence Relative to BPN' | Sequence Relative to BPN'-v3: G97A-G128A-Y217Q | TIDE ® Detergent pH 8, 16° C., BMI PI | Det. Comp. 1, pH 8, 16° C., BMI PI | Det. Comp. 1, pH 8, 32° C., BMI PI |
|---|---|---|---|---|
| G97A-A98E-G128A-Y217Q | A98E | 0.92 | 0.91 | 0.90 |

The invention includes a protease variant having proteolytic activity, the variant comprising an amino acid sequence having at least 60%, 70%, 80%, 85%, 90%, 91%, 92%, 93%, 94%, 95%, 96%, 97%, or 98% or 99% identity to SEQ ID NO:2 or SEQ ID NO:6 and at least one set of amino acid substitutions selected from those in Table 12-3, wherein positions of the variant are numbered by correspondence with positions of the SEQ ID NO:2 sequence. Each such protease variant may be an isolated, recombinant, substantially pure, or non-naturally occurring protease variant. Also included are compositions, including cleaning compositions, comprising at least one such protease variant and methods for cleaning utilizing at least one such protease variant as described in greater detail elsewhere herein.

Table 12-4 provides Performance Index (PI) values of variants generated from RCL 5-7 and FS1-3 using BMI microswatch assay in Detergent Composition 1 (from Table 1-3) at 16° C. and pH 8, BMI microswatch assay in Detergent Composition 2 (from Table 1-3) at 16° C. and pH 8, and stability measured in Detergent Composition 3 (from Table 1-3). PI values for specific activity by AAPF hydrolysis (Specific AAPF PI) were also determined. All assays were performed as described in Example 1. The sequences of the variants listed are relative to BPN'-v3: G97A-G128A-Y217Q. PI values were calculated relative to BPN'-v3. All mutants in this list have a PI cutoff equal or greater than 0.5 for at least one property tested. PI values less than 0.01 were modified to display 0.01 in bold italics.

TABLE 12-4

Performance Index Values of Variants Generated From RCL 5-7 and FS1-3

| Source of Variants | Sequence Relative to BPN' | Sequence Relative to BPN'-v3: G97A-G128A-Y217Q | Det. Comp. 1, pH 8, 16° C., BMI PI | Det. Comp. 2, pH 8, 16° C., BMI PI | Specific AAPF PI | Det. Comp. 3, Stability PI |
|---|---|---|---|---|---|---|
| RCL6 | G97A-G128A-Y217Q-P86S-S87G-A88V-A116N-N117S-N118G | P86S-S87G-A88V-A116N-N117S-N118G | 1.21 | 1.14 | 1.17 | 0.03 |
| FS1 | G97A-G128A-Y217Q-S24G-N25G-N61P-S101N | S24G-N25G-N61P-S101N | 1.05 | 1.12 | 1.96 | 1.00 |
| FS1 | G97A-G128A-Y217Q-S24G-N25G-S53G-T55P-S87T-A88L-S89G-S101N-V203Y | S24G-N25G-S53G-T55P-S87T-A88L-S89G-S101N-V203Y | 1.04 | 1.10 | 1.71 | 0.03 |
| FS1 | G97A-G128A-Y217Q-N61P-S78N-S101N-V203Y | N61P-S78N-S101N-V203Y | 1.03 | 1.10 | 1.73 | 0.33 |
| FS1 | G97A-G128A-Y217Q-T55P-N61P-S78N-S101N-V203Y | T55P-N61P-S78N-S101N-V203Y | 1.06 | 1.10 | 1.97 | 0.39 |
| FS1 | G97A-G128A-Y217Q-S53G-T55P-N61P-S78N-S87T-A88L-S89G-S101N | S53G-T55P-N61P-S78N-S87T-A88L-S89G-S101N | 1.03 | 1.10 | 2.22 | 0.33 |
| RCL7 | G97A-G128A-Y217Q-V203Y-L267V | V203Y-L267V | 1.10 | 1.09 | 1.12 | 0.09 |
| FS1 | G97A-G128A-Y217Q-S24G-N25G-T55P-S101N | S24G-N25G-T55P-S101N | 1.04 | 1.09 | 1.82 | 1.13 |
| RCL7 | G97A-G128A-Y217Q-A134T-L267V | A134T-L267V | 1.13 | 1.08 | 0.93 | 0.66 |
| FS1 | G97A-G128A-Y217Q-S24G-N25G-S53G-T55P-N61P-S78N-S87T-A88L-S89G | S24G-N25G-S53G-T55P-N61P-S78N-S87T-A88L-S89G | 1.01 | 1.08 | 1.10 | 0.29 |

TABLE 12-4-continued

Performance Index Values of Variants Generated From RCL 5-7 and FS1-3

| Source of Variants | Sequence Relative to BPN' | Sequence Relative to BPN'-v3: G97A-G128A-Y217Q | Det. Comp. 1, pH 8, 16° C., BMI PI | Det. Comp. 2, pH 8, 16° C., BMI PI | Specific AAPF PI | Det. Comp. 3, Stability PI |
|---|---|---|---|---|---|---|
| FS1 | G97A-G128A-Y217Q-S24G-N25G-S53G-N61P-S101N-V203Y | S24G-N25G-S53G-N61P-S101N-V203Y | 1.07 | 1.08 | 2.11 | 0.09 |
| RCL6 | G97A-G128A-Y217Q-N25Y-Q59S-N61P | N25Y-Q59S-N61P | 1.07 | 1.08 | 0.85 | 0.66 |
| RCL7 | G97A-G128A-Y217Q-I111V-S161P | I111V-S161P | 1.10 | 1.08 | 0.66 | 0.98 |
| RCL7 | G97A-G128A-Y217Q-I115V-L267V | I115V-L267V | 1.10 | 1.08 | 1.07 | 0.63 |
| FS1 | G97A-G128A-Y217Q-T55P-S78N-S87T-A88L-S89G-S101N-V203Y | T55P-S78N-S87T-A88L-S89G-S101N-V203Y | 0.99 | 1.08 | 1.39 | 0.16 |
| RCL6 | G97A-G128A-Y217Q-N25Y-P129Q-S130G-G131S-A137T | N25Y-P129Q-S130G-G131S-A137T | 1.07 | 1.08 | 0.88 | 0.67 |
| RCL7 | G97A-G128A-Y217Q-N61P-S63H-A128S-P129Q | N61P-S63H-A128S-P129Q | 1.04 | 1.08 | 1.59 | 0.78 |
| FS1 | G97A-G128A-Y217Q-S53G-N61P-S101N-V203Y | S53G-N61P-S101N-V203Y | 1.03 | 1.08 | 1.91 | 0.09 |
| FS1 | G97A-G128A-Y217Q-S24G-N25G-S53G-S78N-S87T-A88L-S89G-S101N | S24G-N25G-S53G-S78N-S87T-A88L-S89G-S101N | 1.08 | 1.07 | 1.44 | 0.33 |
| FS1 | G97A-G128A-Y217Q-N61P-S78N-S87T-A88L-S89G-S101N | N61P-S78N-S87T-A88L-S89G-S101N | 1.07 | 1.07 | 1.80 | 0.31 |
| RCL6 | G97A-G128A-Y217Q-N25Y-N61P-S63H | N25Y-N61P-S63H | 1.06 | 1.07 | 0.74 | 0.60 |
| RCL5 | G97A-G128A-Y217Q-Q59S-N61P-V203Y | Q59S-N61P-V203Y | 0.99 | 1.07 | 0.69 | 0.09 |
| RCL6 | G97A-G128A-Y217Q-V8L-N25Y-P129Q-S130G-G131S | V8L-N25Y-P129Q-S130G-G131S | 1.08 | 1.07 | 1.22 | 0.03 |
| RCL6 | G97A-G128A-Y217Q-P86S-S87G-A88V-P239R | P86S-S87G-A88V-P239R | 1.16 | 1.07 | 1.26 | 0.03 |
| FS1 | G97A-G128A-Y217Q-S24G-N25G-S53G-T55P-N61P-S101N-V203Y | S24G-N25G-S53G-T55P-N61P-S101N-V203Y | 1.02 | 1.07 | 2.07 | 0.11 |
| RCL5 | G97A-G128A-Y217Q-S24G-N25G-P129Q-S130G-G131S | S24G-N25G-P129Q-S130G-G131S | 1.09 | 1.06 | 1.25 | 1.00 |
| FS3 | G97A-G128A-Y217Q-N240K | N240K | 1.04 | 1.06 | 0.90 | 0.94 |
| RCL5 | G97A-G128A-Y217Q-G23A-S24G-N25G- | G23A-S24G-N25G-G211R- | 1.06 | 1.06 | 1.05 | 0.06 |

TABLE 12-4-continued

Performance Index Values of Variants Generated From RCL 5-7 and FS1-3

| Source of Variants | Sequence Relative to BPN' | Sequence Relative to BPN'-v3: G97A-G128A-Y217Q | Det. Comp. 1, pH 8, 16° C., BMI PI | Det. Comp. 2, pH 8, 16° C., BMI PI | Specific AAPF PI | Det. Comp. 3, Stability PI |
|---|---|---|---|---|---|---|
| | G211R-N212S-K213V | N212S-K213V | | | | |
| RCL7 | G97A-G128A-Y217Q-N61P-S63H-S78N-I111V-A134T | N61P-S63H-S78N-I111V-A134T | 1.03 | 1.06 | 0.43 | 1.14 |
| RCL6 | G97A-G128A-Y217Q-S63T-P86S-S87G-A88V | S63T-P86S-S87G-A88V | 1.17 | 1.06 | 1.46 | 0.02 |
| RCL6 | G97A-G128A-Y217Q-G23A-S24G-N25G-A116N-N117S-N118G | G23A-S24G-N25G-A116N-N117S-N118G | 1.08 | 1.06 | 0.91 | 0.21 |
| FS1 | G97A-G128A-Y217Q-S78N-S87T-A88L-S89G-S101N | S78N-S87T-A88L-S89G-S101N | 1.03 | 1.06 | 1.40 | 0.33 |
| RCL6 | G97A-G128A-Y217Q-S24G-N25G-A116N-N117S-N118G | S24G-N25G-A116N-N117S-N118G | 1.06 | 1.06 | 0.74 | 1.05 |
| RCL7 | G97A-G128A-Y217Q-T55P-N240K | T55P-N240K | 1.02 | 1.06 | 0.91 | 0.93 |
| RCL6 | G97A-G128A-Y217Q-T55P-P129V-P194S | T55P-P129V-P194S | 1.07 | 1.06 | 0.85 | 0.86 |
| RCL6 | G97A-G128A-Y217Q-N25Y-S87G-A88V-S89A | N25Y-S87G-A88V-S89A | 1.07 | 1.05 | 1.14 | 0.08 |
| FS1 | G97A-G128A-Y217Q-S24G-N25G-S87T-A88L-S89G-S101N | S24G-N25G-S87T-A88L-S89G-S101N | 1.02 | 1.05 | 1.19 | 0.06 |
| RCL7 | G97A-G128A-Y217Q-P129Q-S130G-G131S-V203Y | P129Q-S130G-G131S-V203Y | 1.04 | 1.05 | 0.94 | 0.05 |
| RCL6 | G97A-G128A-Y217Q-Q59S-N61P-N240K | Q59S-N61P-N240K | 1.05 | 1.05 | 0.80 | 0.84 |
| FS3 | G97A-G128A-Y217Q-S24R-P40E-P129E-S159K-K265R | S24R-P40E-P129E-S159K-K265R | 1.13 | 1.05 | 1.08 | 1.31 |
| RCL7 | G97A-G128A-Y217Q-P52S-T55P-V203Y | P52S-T55P-V203Y | 1.09 | 1.05 | 0.53 | 0.15 |
| RCL6 | G97A-G128A-Y217Q-S24R-P129E | S24R-P129E | 1.11 | 1.05 | 0.88 | 0.59 |
| FS1 | G97A-G128A-Y217Q-S24G-N25G-S53G-N61P-S78N | S24G-N25G-S53G-N61P-S78N | 0.98 | 1.05 | 1.17 | 1.16 |
| FS1 | G97A-G128A-Y217Q-S24G-N25G-T55P-S78N-S101N | S24G-N25G-T55P-S78N-S101N | 1.07 | 1.05 | 1.71 | 1.29 |
| RCL6 | G97A-G128A-Y217Q-P86S-S87G-A88V-A116S-N117G-N118R | P86S-S87G-A88V-A116S-N117G-N118R | 1.10 | 1.05 | 0.76 | 0.05 |
| RCL6 | G97A-G128A-Y217Q-N61P- | N61P-S87T-A88L-S89G | 1.00 | 1.05 | 1.12 | 0.05 |

TABLE 12-4-continued

Performance Index Values of Variants Generated From RCL 5-7 and FS1-3

| Source of Variants | Sequence Relative to BPN' | Sequence Relative to BPN'-v3: G97A-G128A-Y217Q | Det. Comp. 1, pH 8, 16° C., BMI PI | Det. Comp. 2, pH 8, 16° C., BMI PI | Specific AAPF PI | Det. Comp. 3, Stability PI |
|---|---|---|---|---|---|---|
| | S87T-A88L-S89G | | | | | |
| FS1 | G97A-G128A-Y217Q-S24G-N25G-S53G-T55P-S78N-S87T-A88L-S89G | S24G-N25G-S53G-T55P-S78N-S87T-A88L-S89G | 0.96 | 1.05 | 0.96 | 0.29 |
| RCL5 | G97A-G128A-Y217Q-G23A-S24G-N25G-N61P-S63H | G23A-S24G-N25G-N61P-S63H | 1.06 | 1.05 | 0.89 | 0.13 |
| RCL6 | G97A-G128A-Y217Q-S24R-Q59S-N61P | S24R-Q59S-N61P | 1.07 | 1.05 | 0.94 | 0.49 |
| RCL6 | G97A-G128A-Y217Q-N61P-P129Q-S130G-G131S | N61P-P129Q-S130G-G131S | 1.07 | 1.05 | 1.13 | 0.78 |
| FS1 | G97A-G128A-Y217Q-S24G-N25G-S53G-T55P-N61P-S78N-S87T-A88L-S89G-S101N | S24G-N25G-S53G-T55P-N61P-S78N-S87T-A88L-S89G-S101N | 1.05 | 1.04 | 1.98 | 0.32 |
| FS1 | G97A-G128A-Y217Q-S24G-N25G-S53G-T55P-S101N-V203Y | S24G-N25G-S53G-T55P-S101N-V203Y | 1.05 | 1.05 | 1.57 | 0.15 |
| FS1 | G97A-G128A-Y217Q-N61P-S78N-S87T-A88L-S89G-S101N-V203Y | N61P-S78N-S87T-A88L-S89G-S101N-V203Y | 1.02 | 1.04 | 1.60 | 0.12 |
| FS1 | G97A-G128A-Y217Q-S24G-N25G-S53G-T55P-S78N-S101N | S24G-N25G-S53G-T55P-S78N-S101N | 1.03 | 1.04 | 2.01 | 1.27 |
| FS1 | G97A-G128A-Y217Q-S24G-N25G-S53G-S101N-V203Y | S24G-N25G-S53G-S101N-V203Y | 1.01 | 1.04 | 1.77 | 0.07 |
| FS1 | G97A-G128A-Y217Q-S24G-N25G-S78N-S101N-V203Y | S24G-N25G-S78N-S101N-V203Y | 1.09 | 1.04 | 1.54 | 0.28 |
| RCL7 | G97A-G128A-Y217Q-P129Q-S130G-G131S-A133V-L267V | P129Q-S130G-G131S-A133V-L267V | 1.14 | 1.04 | 1.37 | 0.56 |
| FS1 | G97A-G128A-Y217Q-S87T-A88L-S89G-S101N | S87T-A88L-S89G-S101N | 1.05 | 1.04 | 1.44 | 0.07 |
| RCL6 | G97A-G128A-Y217Q-G23A-S24G-N25G-P239R | G23A-S24G-N25G-P239R | 1.07 | 1.04 | 0.92 | 0.16 |
| RCL6 | G97A-G128A-Y217Q-S87G-A88V-S89A-A116N-N117S-N118G | S87G-A88V-S89A-A116N-N117S-N118G | 1.07 | 1.04 | 0.92 | 0.37 |
| RCL6 | G97A-G128A-Y217Q-Q59S-N61P-A116S-N117G-N118R | Q59S-N61P-A116S-N117G-N118R | 1.09 | 1.04 | 0.68 | 0.91 |

TABLE 12-4-continued

| Performance Index Values of Variants Generated From RCL 5-7 and FS1-3 | | | | | | |
|---|---|---|---|---|---|---|
| Source of Variants | Sequence Relative to BPN' | Sequence Relative to BPN'-v3: G97A-G128A-Y217Q | Det. Comp. 1, pH 8, 16° C., BMI PI | Det. Comp. 2, pH 8, 16° C., BMI PI | Specific AAPF PI | Det. Comp. 3, Stability PI |
| RCL5 | G97A-G128A-Y217Q-Q59S-N61P-S87T-A88L-S89G | Q59S-N61P-S87T-A88L-S89G | 1.03 | 1.04 | 0.81 | 0.08 |
| FS1 | G97A-G128A-Y217Q-S24G-N25G-S53G-S87T-A88L-S89G-V203Y | S24G-N25G-S53G-S87T-A88L-S89G-V203Y | 0.96 | 1.04 | 0.73 | 0.04 |
| RCL7 | G97A-G128A-Y217Q-A134T-G211T | A134T-G211T | 1.11 | 1.04 | 0.71 | 0.35 |
| RCL7 | G97A-G128A-Y217Q-T55P-A128S-P129Q | T55P-A128S-P129Q | 1.03 | 1.04 | 2.71 | 1.02 |
| FS1 | G97A-G128A-Y217Q-T55P-S78N-S87T-A88L-S89G-S101N | T55P-S78N-S87T-A88L-S89G-S101N | 1.05 | 1.04 | 1.56 | 0.33 |
| RCL6 | G97A-G128A-Y217Q-P86S-S87G-A88V-T242R | P86S-S87G-A88V-T242R | 1.09 | 1.04 | 0.83 | 0.04 |
| RCL7 | G97A-G128A-Y217Q-S161P-V203Y | S161P-V203Y | 1.04 | 1.04 | 0.81 | 0.09 |
| FS1 | G97A-G128A-Y217Q-S24G-N25G-T55P-N61P-S78N-S101N-V203Y | S24G-N25G-T55P-N61P-S78N-S101N-V203Y | 1.05 | 1.04 | 2.01 | 0.44 |
| RCL7 | G97A-G128A-Y217Q-G211T-L267V | G211T-L267V | 1.08 | 1.03 | 1.16 | 0.30 |
| RCL6 | G97A-G128A-Y217Q-P40E-T55P-N269K | P40E-T55P-N269K | 1.08 | 1.03 | 0.71 | 0.05 |
| RCL6 | G97A-G128A-Y217Q-S24R-A128S-P129G | S24R-A128S-P129G | 1.08 | 1.03 | 1.63 | 0.64 |
| RCL6 | G97A-G128A-Y217Q-S24G-N25G-N61P-N62S-P194L-A232T | S24G-N25G-N61P-N62S-P194L-A232T | 1.15 | 1.03 | 3.06 | 0.35 |
| RCL6 | G97A-G128A-Y217Q-T55P-A116S-N117G-N118R | T55P-A116S-N117G-N118R | 1.07 | 1.03 | 0.83 | 1.06 |
| FS1 | G97A-G128A-Y217Q-S24G-N25G-S53G-S78N-S101N-V203Y | S24G-N25G-S53G-S78N-S101N-V203Y | 1.03 | 1.03 | 1.76 | 0.32 |
| RCL7 | G97A-G128A-Y217Q-P129Q-S130G-G131S-N240K | P129Q-S130G-G131S-N240K | 1.08 | 1.03 | 0.90 | 0.83 |
| FS1 | G97A-G128A-Y217Q-S53G-T55P-N61P-S78N-S87T-A88L-S89G | S53G-T55P-N61P-S78N-S87T-A88L-S89G | 0.93 | 1.03 | 1.00 | 0.33 |
| RCL6 | G97A-G128A-Y217Q-N25Y-P129Q-S130G-G131S | N25Y-P129Q-S130G-G131S | 1.08 | 1.03 | 0.93 | 0.69 |
| RCL6 | G97A-G128A-Y217Q-T55P-I115V | T55P-I115V | 1.06 | 1.03 | 1.07 | 1.07 |

TABLE 12-4-continued

Performance Index Values of Variants Generated From RCL 5-7 and FS1-3

| Source of Variants | Sequence Relative to BPN' | Sequence Relative to BPN'-v3: G97A-G128A-Y217Q | Det. Comp. 1, pH 8, 16° C., BMI PI | Det. Comp. 2, pH 8, 16° C., BMI PI | Specific AAPF PI | Det. Comp. 3, Stability PI |
|---|---|---|---|---|---|---|
| RCL6 | G97A-G128A-Y217Q-N25Y-T55P | N25Y-T55P | 1.05 | 1.03 | 1.00 | 0.80 |
| RCL6 | G97A-G128A-Y217Q-G23A-S24G-N25G-A128S-P129D | G23A-S24G-N25G-A128S-P129D | 0.97 | 1.03 | 1.75 | 0.15 |
| FS1 | G97A-G128A-Y217Q-S53G-S78N-S87T-A88L-S89G-S101N-P129S-V203Y | S53G-S78N-S87T-A88L-S89G-S101N-P129S-V203Y | 1.00 | 1.03 | 1.68 | 0.13 |
| RCL7 | G97A-G128A-Y217Q-T55P-A134T | T55P-A134T | 1.06 | 1.03 | 0.94 | 1.05 |
| RCL7 | G97A-G128A-Y217Q-N61P-S63H-S78N-I111V | N61P-S63H-S78N-I111V | 1.03 | 1.02 | 0.49 | 1.18 |
| FS2 | Y217Q-N61P-A97G-G102A-A128G-P129S | N61P-A97G-G102A-A128G-P129S | 0.98 | 1.02 | NA | NA |
| FS1 | G97A-G128A-Y217Q-S53G-N61P-S101N | S53G-N61P-S101N | 1.02 | 1.02 | 2.08 | 0.88 |
| RCL5 | G97A-G128A-Y217Q-Q59S-N61P-S87G-A88V-S89A | Q59S-N61P-S87G-A88V-S89A | 1.01 | 1.02 | 0.90 | 0.20 |
| FS1 | G97A-G128A-Y217Q-S53G-S87T-A88L-S89G-S101N-V203Y | S53G-S87T-A88L-S89G-S101N-V203Y | 0.96 | 1.02 | 1.11 | 0.04 |
| RCL6 | G97A-G128A-Y217Q-S87T-A88L-S89G-P129S | S87T-A88L-S89G-P129S | 1.06 | 1.02 | 1.21 | 0.10 |
| FS1 | G97A-G128A-Y217Q-S53G-T55P-S78N-S101N-V203Y | S53G-T55P-S78N-S101N-V203Y | 1.03 | 1.02 | 1.70 | 0.48 |
| RCL5 | G97A-G128A-Y217Q-T55P-P129Q-S130G-G131S | T55P-P129Q-S130G-G131S | 1.01 | 1.02 | 1.18 | 0.91 |
| RCL5 | G97A-G128A-Y217Q-Q59S-N61P-P129Q-S130G-G131S | Q59S-N61P-P129Q-S130G-G131S | 0.98 | 1.02 | 0.83 | 0.80 |
| RCL7 | G97A-G128A-Y217Q-A134T-P239R | A134T-P239R | 1.03 | 1.02 | 0.53 | 0.98 |
| RCL5 | G97A-G128A-Y217Q-T55P-V203Y | T55P-V203Y | 1.01 | 1.01 | 1.02 | 0.23 |
| RCL7 | G97A-G128A-Y217Q-T55P-S78N-S89Y | T55P-S78N-S89Y | 1.03 | 1.01 | 1.05 | 1.25 |
| RCL5 | G97A-G128A-Y217Q-T22N-S24A-N61P-S63H | T22N-S24A-N61P-S63H | 1.00 | 1.01 | 0.69 | 0.46 |
| RCL7 | G97A-G128A-Y217Q-S161P-L267V | S161P-L267V | 1.05 | 1.01 | 1.00 | 0.66 |
| RCL6 | G97A-G128A-Y217Q-T55P-L75H-N76G | T55P-L75H-N76G | 1.06 | 1.01 | 0.69 | 0.59 |

TABLE 12-4-continued

Performance Index Values of Variants Generated From RCL 5-7 and FS1-3

| Source of Variants | Sequence Relative to BPN' | Sequence Relative to BPN'-v3: G97A-G128A-Y217Q | Det. Comp. 1, pH 8, 16° C., BMI PI | Det. Comp. 2, pH 8, 16° C., BMI PI | Specific AAPF PI | Det. Comp. 3, Stability PI |
|---|---|---|---|---|---|---|
| RCL7 | G97A-G128A-Y217Q-A134T-S161P | A134T-S161P | 1.07 | 1.01 | 0.73 | 1.00 |
| RCL7 | G97A-G128A-Y217Q-S87T-A88L-S89G-A134T | S87T-A88L-S89G-A134T | 1.08 | 1.01 | 0.66 | 0.13 |
| RCL6 | G97A-G128A-Y217Q-T55P-A116N-N117S-N118G | T55P-A116N-N117S-N118G | 1.06 | 1.01 | 1.06 | 1.11 |
| v12 | G97A-G128S-Y217Q | A128S | 1.02 | 1.01 | 1.65 | 1.00 |
| RCL7 | G97A-G128A-Y217Q-T55P-S78N-I115V | T55P-S78N-I115V | 1.07 | 1.00 | 1.00 | 1.32 |
| RCL6 | G97A-G128A-Y217Q-Y6Q-P129Q-S130G-G131S | Y6Q-P129Q-S130G-G131S | 1.03 | 1.00 | 0.98 | 0.23 |
| RCL7 | G97A-G128A-Y217Q-S24R-P129Q-S130G-G131S | S24R-P129Q-S130G-G131S | 1.06 | 1.00 | 1.11 | 0.61 |
| FS1 | G97A-G128A-Y217Q-S24G-N25G-S53G-S78N-S101N | S24G-N25G-S53G-S78N-S101N | 0.99 | 1.00 | 1.61 | 1.21 |
| RCL6 | G97A-G128A-Y217Q-T55P-P129V | T55P-P129V | 1.07 | 1.00 | 0.70 | 1.00 |
| v3 | G97A-G128A-Y217Q | BPN'-v3 | 1.00 | 1.00 | 1.00 | 1.00 |
| FS2 | G97A-Y217Q-N61P-N62Q-G100N-A128G | N61P-N62Q-G100N-A128G | 0.95 | 1.00 | NA | NA |
| RCL6 | G97A-G128A-Y217Q-T55P-P129Q | T55P-P129Q | 1.10 | 1.00 | 1.77 | 1.15 |
| FS1 | G97A-G128A-Y217Q-S24G-N25G-S53G-T55P-N61P-S78N-S87T-A88L-S89G-S101N-V203Y | S24G-N25G-S53G-T55P-N61P-S78N-S87T-A88L-S89G-S101N-V203Y | 1.05 | 1.00 | 1.84 | 0.12 |
| RCL6 | G97A-G128A-Y217Q-S87T-A88L-S89G-N240K | S87T-A88L-S89G-N240K | 1.04 | 1.00 | 0.83 | 0.10 |
| RCL7 | G97A-G128A-Y217Q-A134T-N240K | A134T-N240K | 1.07 | 0.99 | 0.61 | 0.96 |
| RCL7 | G97A-G128A-Y217Q-S87T-A88L-S89G-P239R | S87T-A88L-S89G-P239R | 1.04 | 0.99 | 0.68 | 0.14 |
| RCL7 | G97A-G128A-Y217Q-P129Q-S130G-G131S-L267V | P129Q-S130G-G131S-L267V | 1.08 | 0.99 | 1.35 | 0.61 |
| RCL7 | G97A-G128A-Y217Q-P129Q-N240K | P129Q-N240K | 1.06 | 0.99 | 1.39 | 1.00 |
| FS1 | G97A-G128A-Y217Q-S78N-S87T-A88L-S89G-V203Y | S78N-S87T-A88L-S89G-V203Y | 0.93 | 0.99 | 0.74 | 0.15 |
| RCL7 | G97A-G128A-Y217Q-I111V-A273S | I111V-A273S | 1.00 | 0.99 | 0.48 | 0.27 |

TABLE 12-4-continued

Performance Index Values of Variants Generated From RCL 5-7 and FS1-3

| Source of Variants | Sequence Relative to BPN' | Sequence Relative to BPN'-v3: G97A-G128A-Y217Q | Det. Comp. 1, pH 8, 16° C., BMI PI | Det. Comp. 2, pH 8, 16° C., BMI PI | Specific AAPF PI | Det. Comp. 3, Stability PI |
|---|---|---|---|---|---|---|
| FS1 | G97A-G128A-Y217Q-S24G-N25G-T55P-S78N-A88V-S101N | S24G-N25G-T55P-S78N-A88V-S101N | 1.03 | 0.99 | 2.17 | 0.71 |
| FS1 | G97A-G128A-Y217Q-S24G-N25G-T55P-S78N | S24G-N25G-T55P-S78N | 0.96 | 0.98 | 1.15 | 1.20 |
| FS1 | G97A-G128A-Y217Q-S24G-N25G-S53G-S78N-S87T-A88L-S101N-V203Y | S24G-N25G-S53G-S78N-S87T-A88L-S101N-V203Y | 1.02 | 0.98 | 1.27 | 0.10 |
| FS1 | G97A-G128A-Y217Q-S24G-N25G-S53G-S78N-S87T-A88L-S89G-V203Y | S24G-N25G-S53G-S78N-S87T-A88L-S89G-V203Y | 0.97 | 0.98 | 0.75 | 0.14 |
| FS1 | G97A-G128A-Y217Q-S24G-N25G-S53G-S78N-S87T-A88L-S89G-S101N-V203Y | S24G-N25G-S53G-S78N-S87T-A88L-S89G-S101N-V203Y | 1.06 | 0.98 | 1.21 | 0.14 |
| RCL5 | G97A-G128A-Y217Q-S87G-A88V-S89A-P129Q-S130G-G131S | S87G-A88V-S89A-P129Q-S130G-G131S | 1.01 | 0.98 | 1.18 | 0.29 |
| RCL7 | G97A-G128A-Y217Q-N61P-S63H-S78N-S161P | N61P-S63H-S78N-S161P | 1.03 | 0.98 | 0.73 | 1.16 |
| FS1 | G97A-G128A-Y217Q-T55P-N61P-S78N-S87T-A88L-S89G-S101N-V203Y | T55P-N61P-S78N-S87T-A88L-S89G-S101N-V203Y | 1.04 | 0.98 | 1.75 | 0.14 |
| RCL7 | G97A-G128A-Y217Q-I111V-P129Q-S130G-G131S | I111V-P129Q-S130G-G131S | 1.00 | 0.98 | 0.52 | 0.97 |
| RCL5 | G97A-G128A-Y217Q-T22N-S24A-T55P | T22N-S24A-T55P | 0.96 | 0.98 | 0.94 | 0.64 |
| RCL7 | G97A-G128A-Y217Q-I115V-N240K | I115V-N240K | 1.04 | 0.98 | 0.66 | 0.90 |
| RCL6 | G97A-G128A-Y217Q-S87G-A88V-S89A-A116N-N117S-N118G-P172H | S87G-A88V-S89A-A116N-N117S-N118G-P172H | 0.98 | 0.98 | 0.66 | 0.40 |
| FS1 | G97A-G128A-Y217Q-S24G-N25G-S78N-S87T-A88L-S89G-S101N | S24G-N25G-S78N-S87T-A88L-S89G-S101N | 1.01 | 0.98 | 1.28 | 0.31 |
| RCL6 | G97A-G128A-Y217Q-S24G-N25G-I115V-A134T | S24G-N25G-I115V-A134T | 1.03 | 0.98 | 0.59 | 1.13 |
| RCL6 | G97A-G128A-Y217Q-T55P-A128S-P129D | T55P-A128S-P129D | 0.97 | 0.97 | 1.39 | 1.00 |

TABLE 12-4-continued

Performance Index Values of Variants Generated From RCL 5-7 and FS1-3

| Source of Variants | Sequence Relative to BPN' | Sequence Relative to BPN'-v3: G97A-G128A-Y217Q | Det. Comp. 1, pH 8, 16° C., BMI PI | Det. Comp. 2, pH 8, 16° C., BMI PI | Specific AAPF PI | Det. Comp. 3, Stability PI |
|---|---|---|---|---|---|---|
| RCL7 | G97A-G128A-Y217Q-I111V-S159K | I111V-S159K | 0.99 | 0.97 | 0.64 | 1.12 |
| RCL7 | G97A-G128A-Y217Q-N240K-A273S | N240K-A273S | 1.03 | 0.96 | 0.64 | 0.19 |
| RCL7 | G97A-G128A-Y217Q-S159K-L267V | S159K-L267V | 1.00 | 0.96 | 1.08 | 0.79 |
| RCL7 | G97A-G128A-Y217Q-I111V-P129Q-G211T | I111V-P129Q-G211T | 1.01 | 0.96 | 0.83 | 0.42 |
| RCL7 | G97A-G128A-Y217Q-I115V-A273S | I115V-A273S | 1.05 | 0.95 | 0.74 | 0.20 |
| RCL6 | G97A-G128A-Y217Q-S89Y | S89Y | 0.99 | 0.95 | 0.70 | 0.88 |
| RCL6 | G97A-G128A-Y217Q-S24R-A116N-N117S-N118G | S24R-A116N-N117S-N118G | 1.08 | 0.95 | 0.91 | 0.60 |
| RCL7 | G97A-G128A-Y217Q-N61E-A144K | N61E-A144K | 1.03 | 0.95 | 0.97 | 1.10 |
| RCL6 | G97A-G128A-Y217Q-P129Q-S130G-G131S-P239R | P129Q-S130G-G131S-P239R | 1.02 | 0.95 | 0.85 | 0.99 |
| RCL7 | G97A-G128A-Y217Q-S87T-A88L-S89G-I115V | S87T-A88L-S89G-I115V | 0.97 | 0.95 | 0.59 | 0.13 |
| RCL6 | G97A-G128A-Y217Q-T55P-A92G | T55P-A92G | 0.96 | 0.94 | 0.56 | 0.91 |
| FS3 | G97A-G128A-Y217Q-S145D-S159K-N240K-Q275E | S145D-S159K-N240K-Q275E | 0.98 | 0.94 | 0.76 | 1.08 |
| RCL7 | G97A-G128A-Y217Q-S89Y-P129Q-S130G-G131S | S89Y-P129Q-S130G-G131S | 1.04 | 0.94 | 0.71 | 0.70 |
| RCL7 | G97A-G128A-Y217Q-P129Q-S130G-G131S-S162K | P129Q-S130G-G131S-S162K | 1.01 | 0.94 | 1.00 | 0.93 |
| RCL7 | G97A-G128A-Y217Q-I111V-A134T | I111V-A134T | 0.98 | 0.94 | 0.37 | 1.06 |
| RCL6 | G97A-G128A-Y217Q-P40E-S53Y-S78Y-P86S-S87G-A88V | P40E-S53Y-S78Y-P86S-S87G-A88V | 0.99 | 0.94 | 0.97 | 0.35 |
| RCL6 | G97A-G128A-Y217Q-S24G-N25G-L75H-N76G | S24G-N25G-L75H-N76G | 0.93 | 0.93 | 0.58 | 0.52 |
| FS2 | G97A-Y217Q-N61P-A128G-P129S-S130P | N61P-A128G-P129S-S130P | 0.85 | 0.93 | 0.65 | 0.92 |
| RCL6 | G97A-G128A-Y217Q-S24R-S145D | S24R-S145D | 0.99 | 0.93 | 0.89 | 0.59 |
| FS3 | G97A-G128A-Y217Q-S24R-S145D-P239R-Q275E | S24R-S145D-P239R-Q275E | 0.92 | 0.92 | 0.63 | 0.68 |
| RCL7 | G97A-G128A-Y217Q-S24R- | S24R-S78N-S182P- | 0.95 | 0.92 | 1.16 | 0.55 |

TABLE 12-4-continued

| Performance Index Values of Variants Generated From RCL 5-7 and FS1-3 | | | | | | |
|---|---|---|---|---|---|---|
| Source of Variants | Sequence Relative to BPN' | Sequence Relative to BPN'-v3: G97A-G128A-Y217Q | Det. Comp. 1, pH 8, 16° C., BMI PI | Det. Comp. 2, pH 8, 16° C., BMI PI | Specific AAPF PI | Det. Comp. 3, Stability PI |
| | S78N-S182P-L267V | L267V | | | | |
| FS1 | G97A-G128A-Y217Q-S53G-N61P-S87T-A88L-S89G-S101N-V203Y | S53G-N61P-S87T-A88L-S89G-S101N-V203Y | 1.04 | 0.92 | 1.67 | 0.02 |
| RCL6 | G97A-G128A-Y217Q-P5S-S87G-A88V-S89A-A116G-N117R | P5S-S87G-A88V-S89A-A116G-N117R | 0.98 | 0.92 | 0.64 | 0.07 |
| FS1 | G97A-G128A-Y217Q-S53G-N61P-S78N-S87T-A88L-S89G-S101N-V203Y | S53G-N61P-S78N-S87T-A88L-S89G-S101N-V203Y | 0.99 | 0.92 | 1.65 | 0.11 |
| RCL6 | G97A-G128A-Y217Q-Q59S-N61P-A116N-N117S-N118G | Q59S-N61P-A116N-N117S-N118G | 0.93 | 0.92 | 0.42 | 1.04 |
| RCL7 | G97A-G128A-Y217Q-P239R-A273S | P239R-A273S | 0.94 | 0.91 | 0.52 | 0.23 |
| FS1 | G97A-G128A-Y217Q-S53G-S78N-S87T-A88L-S89G-S101N-V203Y | S53G-S78N-S87T-A88L-S89G-S101N-V203Y | 0.94 | 0.91 | 1.16 | 0.13 |
| RCL6 | G97A-G128A-Y217Q-S24R-P129V | S24R-P129V | 0.98 | 0.91 | 0.52 | 0.58 |
| RCL7 | G97A-G128A-Y217Q-I111V-P239R | I111V-P239R | 0.97 | 0.91 | 0.38 | 1.08 |
| FS1 | G97A-G128A-Y217Q-S87T-A88L-S89G-S101N-V203Y | S87T-A88L-S89G-S101N-V203Y | 0.90 | 0.91 | 0.79 | 0.05 |
| RCL6 | G97A-G128A-Y217Q-T55P-P129L | T55P-P129L | 0.99 | 0.91 | 0.62 | 0.98 |
| RCL7 | G97A-G128A-Y217Q-S87T-A88L-S89G-I111V | S87T-A88L-S89G-I111V | 0.92 | 0.90 | 0.42 | 0.13 |
| RCL7 | G97A-G128A-Y217Q-S145D-A273S | S145D-A273S | 0.91 | 0.90 | 0.66 | 0.17 |
| RCL6 | G97A-G128A-Y217Q-P129Q-S130G-G131S-T242R | P129Q-S130G-G131S-T242R | 0.94 | 0.90 | 0.51 | 0.89 |
| RCL7 | G97A-G128A-Y217Q-S3F-S87T-A88L-S89G-G211T | S3F-S87T-A88L-S89G-G211T | 0.93 | 0.89 | 0.55 | 0.07 |
| RCL6 | G97A-G128A-Y217Q-S87G-A88V-S89A-S162K | S87G-A88V-S89A-S162K | 0.97 | 0.89 | 1.21 | 0.37 |
| RCL7 | G97A-G128A-Y217Q-S89Y-G211T | S89Y-G211T | 0.89 | 0.88 | 0.53 | 0.41 |
| RCL7 | G97A-G128A-Y217Q-S87T-A88L-S89G-A144K | S87T-A88L-S89G-A144K | 0.93 | 0.88 | 0.74 | 0.12 |
| RCL6 | G97A-G128A-Y217Q-P129Q- | P129Q-S130G- | 0.95 | 0.88 | 1.21 | 0.96 |

TABLE 12-4-continued

Performance Index Values of Variants Generated From RCL 5-7 and FS1-3

| Source of Variants | Sequence Relative to BPN' | Sequence Relative to BPN'-v3: G97A-G128A-Y217Q | Det. Comp. 1, pH 8, 16° C., BMI PI | Det. Comp. 2, pH 8, 16° C., BMI PI | Specific AAPF PI | Det. Comp. 3, Stability PI |
|---|---|---|---|---|---|---|
| | S130G-G131S-S159K | G131S-S159K | | | | |
| RCL6 | G97A-G128A-Y217Q-A116N-N117S-N118G-P129Q-S130G-G131S | A116N-N117S-N118G-P129Q-S130G-G131S | 0.90 | 0.88 | 0.54 | 0.95 |
| RCL6 | G97A-G128A-Y217Q-S24G-N25G-P129V | S24G-N25G-P129V | 0.86 | 0.87 | 0.44 | 1.02 |
| FS1 | G97A-G128A-Y217Q-S24G-N25G-S78N-S87T-A88L-S89G-S101N-V203Y | S24G-N25G-S78N-S87T-A88L-S89G-S101N-V203Y | 0.87 | 0.86 | 0.83 | 0.12 |
| FS2 | G97A-Y217Q-N123G-A128G | N123G-A128G | 0.83 | 0.86 | 1.00 | 0.14 |
| FS2 | G97A-G128A-Y217Q-N61P-N62Q-G100N-G102A-M124I | N61P-N62Q-G100N-G102A-M124I | 0.82 | 0.86 | 5.52 | 0.40 |
| RCL6 | G97A-G128A-Y217Q-S24G-N25G-K141E-T242R | S24G-N25G-K141E-T242R | 0.90 | 0.85 | 0.65 | 1.10 |
| RCL6 | G97A-G128A-Y217Q-S87G-A88V-S89A-A116N-N117S-N118G-A144T | S87G-A88V-S89A-A116N-N117S-N118G-A144T | 0.89 | 0.85 | 0.44 | 0.32 |
| FS1 | G97A-G128A-Y217Q-T55P-N61P-S87T-A88L-S89G-G110C-S130P | T55P-N61P-S87T-A88L-S89G-G110C-S130P | 0.83 | 0.85 | 0.92 | 0.30 |
| RCL6 | G97A-G128A-Y217Q-L75S-N76Y-A116S-N117G-N118R | L75S-N76Y-A116S-N117G-N118R | 0.84 | 0.83 | 0.41 | 0.13 |
| FS3 | G97A-G128A-Y217Q-S145D-S159K-K213L-P239R-N240K | S145D-S159K-K213L-P239R-N240K | 0.74 | 0.81 | 0.38 | 0.65 |
| RCL6 | G97A-G128A-Y217Q-S24R-S87T-A88L-S89G | S24R-S87T-A88L-S89G | 0.86 | 0.80 | 0.53 | 0.08 |
| RCL6 | G97A-G128A-Y217Q-G23A-S24G-N25G-P129V | G23A-S24G-N25G-P129V | 0.88 | 0.79 | 0.53 | 0.20 |
| RCL7 | G97A-G128A-Y217Q-A134T-K213L | A134T-K213L | 0.87 | 0.79 | 0.51 | 0.81 |
| RCL7 | G97A-G128A-Y217Q-S89Y-A273S | S89Y-A273S | 0.81 | 0.79 | 0.48 | 0.19 |
| RCL7 | G97A-G128A-Y217Q-S24R-P239R | S24R-P239R | 0.90 | 0.78 | 0.71 | 0.69 |
| FS2 | G97A-Y217Q-N123G-A128G-P129S | N123G-A128G-P129S | 0.76 | 0.78 | 0.71 | 0.12 |
| RCL7 | G97A-G128A-Y217Q-S89Y-P239R | S89Y-P239R | 0.77 | 0.76 | 0.38 | 0.90 |

TABLE 12-4-continued

Performance Index Values of Variants Generated From RCL 5-7 and FS1-3

| Source of Variants | Sequence Relative to BPN' | Sequence Relative to BPN'-v3: G97A-G128A-Y217Q | Det. Comp. 1, pH 8, 16° C., BMI PI | Det. Comp. 2, pH 8, 16° C., BMI PI | Specific AAPF PI | Det. Comp. 3, Stability PI |
|---|---|---|---|---|---|---|
| RCL6 | G97A-G128A-Y217Q-S24G-N25G-A92G | S24G-N25G-A92G | 0.71 | 0.76 | 0.25 | 0.59 |
| RCL6 | G97A-G128A-Y217Q-N61P-S63H-I115V-A228V | N61P-S63H-I115V-A228V | 0.73 | 0.74 | 0.24 | 0.42 |
| FNA | Y217L | A97G-A128G-Q217L | 0.73 | 0.74 | 1.81 | 1.21 |
| RCL6 | G97A-G128A-Y217Q-L75S-N76Y-P129V | L75S-N76Y-P129V | 0.73 | 0.73 | 0.34 | 0.09 |
| RCL6 | G97A-G128A-Y217Q-S24R-P129L | S24R-P129L | 0.80 | 0.73 | 0.35 | 0.58 |
| RCL6 | G97A-G128A-Y217Q-S87G-A88V-S89A-P129Q-S182Y-S204Y-P239Q | S87G-A88V-S89A-P129Q-S182Y-S204Y-P239Q | 0.69 | 0.73 | 0.90 | 0.36 |
| RCL6 | G97A-G128A-Y217Q-S24R-A92G | S24R-A92G | 0.75 | 0.73 | 0.28 | 0.44 |
| RCL6 | G97A-G128A-Y217Q-S24R-A116S-N117G-N118R | S24R-A116S-N117G-N118R | 0.81 | 0.72 | 0.48 | 0.58 |
| RCL6 | G97A-G128A-Y217Q-G23A-S24G-N25G-A116G-N117R | G23A-S24G-N25G-A116G-N117R | 0.85 | 0.66 | 0.63 | 0.20 |
| RCL6 | G97A-G128A-Y217Q-S24G-N25G-P129L | S24G-N25G-P129L | 0.72 | 0.66 | 0.39 | 1.03 |
| RCL6 | G97A-G128A-Y217Q-S87T-A88L-S89G-S101G | S87T-A88L-S89G-S101G | 0.78 | 0.66 | 0.65 | 0.11 |
| RCL6 | G97A-G128A-Y217Q-G23A-S24G-N25G-P129L | G23A-S24G-N25G-P129L | 0.52 | 0.59 | 0.37 | 0.20 |
| FS1 | G97A-G128A-Y217Q-S53G-N61P-G102A-V203Y | S53G-N61P-G102A-V203Y | 0.55 | 0.58 | 0.29 | 0.16 |
| RCL6 | G97A-G128A-Y217Q-T55P-V147P | T55P-V147P | 0.56 | 0.57 | 0.22 | 1.09 |
| RCL6 | G97A-G128A-Y217Q-Y6Q-L75S-N76Y | Y6Q-L75S-N76Y | 0.55 | 0.52 | 0.24 | 0.17 |
| RCL6 | G97A-G128A-Y217Q-N61P-S63H-V147P | N61P-S63H-V147P | 0.36 | 0.37 | 0.14 | 0.95 |
| RCL6 | G97A-G128A-Y217Q-S24R-V147P | S24R-V147P | 0.16 | 0.22 | 0.08 | 0.85 |
| RCL6 | G97A-G128A-Y217Q-S24G-N25G-V68C-A69G | S24G-N25G-V68C-A69G | 0.21 | 0.18 | 0.06 | 0.71 |
| FS1 | G97A-G128A-Y217Q-S24G-N25G-N61P-L75S-N76Y-S101N-V203Y | S24G-N25G-N61P-L75S-N76Y-S101N-V203Y | 0.19 | 0.18 | 0.08 | 0.38 |

TABLE 12-4-continued

Performance Index Values of Variants Generated From RCL 5-7 and FS1-3

| Source of Variants | Sequence Relative to BPN' | Sequence Relative to BPN'-v3: G97A-G128A-Y217Q | Det. Comp. 1, pH 8, 16° C., BMI PI | Det. Comp. 2, pH 8, 16° C., BMI PI | Specific AAPF PI | Det. Comp. 3, Stability PI |
|---|---|---|---|---|---|---|
| FS1 | G97A-G128A-Y217Q-L75S-N76Y-S78N-S101N-V203Y | L75S-N76Y-S78N-S101N-V203Y | 0.13 | 0.12 | 0.05 | 0.72 |
| FS1 | G97A-G128A-Y217Q-L75S-N76Y-S78N-S87T-A88L-S89G-S101N-S130P | L75S-N76Y-S78N-S87T-A88L-S89G-S101N-S130P | 0.04 | 0.04 | 0.07 | 0.73 |
| FS1 | G97A-G128A-Y217Q-S24G-N25G-S53G-S101N-S130P-V203Y | S24G-N25G-S53G-S101N-S130P-V203Y | 0.06 | 0.04 | 0.06 | 0.33 |
| RCL6 | G97A-G128A-Y217Q-G47E-M50I-L75S-N76Y-S162K | G47E-M50I-L75S-N76Y-S162K | ***0.01*** | 0.03 | 0.02 | 1.21 |
| FS1 | G97A-G128A-Y217Q-S53G-T55P-S87T-A88L-S89G-S101N-S130P-V203Y | S53G-T55P-S87T-A88L-S89G-S101N-S130P-V203Y | ***0.01*** | 0.02 | 0.05 | 0.45 |
| FS1 | G97A-G128A-Y217Q-S24G-N25G-L75S-N76Y-A128T-P129T-S130G-G131Q-S132C-A133G-A134T | S24G-N25G-L75S-N76Y-A128T-P129T-S130G-G131Q-S132C-A133G-A134T | ***0.01*** | ***0.01*** | 0.02 | 1.21 |
| RCL6 | G97A-G128A-Y217Q-P129Q-S130G-G131S-V147P | P129Q-S130G-G131S-V147P | ***0.01*** | ***0.01*** | 0.03 | 1.11 |
| FS1 | G97A-G128A-Y217Q-S53G-T55P-N61P-L75S-N76Y-S87T-A88L-S89G-G102A-S130P-V203Y | S53G-T55P-N61P-L75S-N76Y-S87T-A88L-S89G-G102A-S130P-V203Y | ***0.01*** | ***0.01*** | 0.02 | 1.05 |
| FS1 | G97A-G128A-Y217Q-S53G-T55P-N61P-L75S-N76Y-S101N-S130P-V203Y | S53G-T55P-N61P-L75S-N76Y-S101N-S130P-V203Y | 0.03 | ***0.01*** | 0.02 | 1.03 |

The invention includes a protease variant having proteolytic activity, the variant comprising an amino acid sequence having at least 60%, 70%, 80%, 85%, 90%, 91%, 92%, 93%, 94%, 95%, 96%, 97%, or 98% or 99% identity to SEQ ID NO:2 or SEQ ID NO:6 and at least one set of amino acid substitutions selected from those listed in Table 12-4, wherein positions of the variant are numbered by correspondence with positions of the SEQ ID NO:2 sequence. Each such protease variant may be an isolated, recombinant, substantially pure, or non-naturally occurring protease variant. Also included are compositions, including cleaning compositions, comprising at least one such protease variant and methods for cleaning utilizing at least one such protease variant as described in greater detail elsewhere herein.

Table 12-5 provides the Performance Index (PI) values of BPN' variants (generated as described in "Generation of Variants to Improve BPN' Stability"; see Table 11-3) for stain removal in BMI microswatch assay in Detergent Composition 1 at 16° C. and pH 8 (Det. Comp. 1, pH 8, 16° C., BMI PI) and for stability in LAS/EDTA (LAS/EDTA Stability PI). Assays were performed as described in Example 1 (BMI microswatch assay, LAS/EDTA stability assay). The sequences of the variants are shown relative to both BPN' and FNA. That is, each variant sequence is the BPN' or FNA sequence with the specified variant amino acid substitutions. PI values are shown relative to FNA parent, which is BPN'-Y217L.

TABLE 12-5

| Performance Index of Stability-Improved BPN' Variants | | | |
|---|---|---|---|
| Sequence Relative to FNA: BPN' Y217L | Sequence Relative to BPN' | Det. Comp. 1 pH 8, 16° C., BMI PI | LAS/EDTA Stability PI |
| P40E-S78N-S87D | P40E-S78N-S87D-Y217L | 0.71 | 11.65 |
| P40E | P40E-Y217L | 0.96 | 8.33 |
| T22V-S78N-Q206E-K213N | T22V-S78N-Q206E-K213N-Y217L | 0.75 | 5.95 |
| T22V-S78N-K213N | T22V-S78N-K213N-Y217L | 0.86 | 5.71 |
| S87D | S87D-Y217L | 0.90 | 4.04 |
| S78N | S78N-Y217L | 0.87 | 3.86 |
| K213N | K213N-Y217L | 0.91 | 1.84 |
| Q206E | Q206E-Y217L | 0.86 | 1.76 |
| T22V | T22V-Y217L | 0.97 | 1.46 |
| **FNA** | **Y217L** | **1.00** | **1.00** |

The invention includes a protease variant having proteolytic activity and/or improved stability relative to FNA, the variant comprising an amino acid sequence having at least 60%, 70%, 80%, 85%, 90%, 91%, 92%, 93%, 94%, 95%, 96%, 97%, or 98% or 99% identity to SEQ ID NO:2 or SEQ ID NO:6 and at least one set of amino acid substitutions selected from those listed in Table 12-5, wherein positions of the variant are numbered by correspondence with positions of the SEQ ID NO:2 sequence. Each such protease variant may be an isolated, recombinant, substantially pure, or non-naturally occurring protease variant. Also included are compositions, including cleaning compositions, comprising at least one such protease variant and methods for cleaning utilizing at least one such protease variant as described in greater detail elsewhere herein.

Table 12-6 provides the Performance Index (PI) values of BPN' variants generated from Library Parent: BPN'-v3: G97A-G128A-Y217Q (as described in "Generation of Variants to Improve BPN' Stability"; see Table 11-3) for stain removal in a BMI microswatch assay in Detergent Composition 1 at 16° C. and pH 8 and for stability in LAS/EDTA. Assays were performed as described in Example 1 (BMI microswatch assay and LAS/EDTA stability assay). The Performance Index was calculated relative to BPN'-v3: G97A-G128A-Y217Q. All mutants in this list have a PI cutoff equal or greater than 0.5 for at least one property tested.

TABLE 12-6

| Performance Index of Stability-Improved BPN' Variants | | | |
|---|---|---|---|
| Sequence Relative to BPN'-v3: BPN' G97A-G128A-Y217Q | Sequence Relative to BPN' | Det. Comp. 1 pH 8, 16° C., BMI PI | LAS/EDTA Stability PI |
| S87D-N76D-S78N | S87D-N76D-S78N-G97A-G128A-Y217Q | 0.62 | 2.27 |
| P40E-S78N-S87D | P40E-S78N-S87D-G97A-G128A-Y217Q | 0.21 | 2.18 |
| P40E-S87D | P40E-S87D-G97A-G128A-Y217Q | 0.18 | 2.14 |
| S78N-P40E | S78N-P40E-G97A-G128A-Y217Q | 0.80 | 2.03 |
| S87D-N76D | S87D-N76D-G97A-G128A-Y217Q | 0.55 | 1.89 |
| P40E | P40E-G97A-G128A-Y217Q | 0.84 | 1.79 |
| S78N-S87D | S78N-S87D-G97A-G128A-Y217Q | 0.79 | 1.71 |
| S87D | S87D-G97A-G128A-Y217Q | 0.78 | 1.20 |
| S78N | S78N-G97A-G128A-Y217Q | 0.93 | 1.14 |
| BPN'-v3 | G97A-G128A-Y217Q | 1.00 | 1.00 |

The invention includes a protease variant having proteolytic activity and having improved stability relative to BPN'-v3, the variant comprising an amino acid sequence having at least 60%, 70%, 80%, 85%, 90%, 91%, 92%, 93%, 94%, 95%, 96%, 97%, or 98% or 99% identity to SEQ ID NO:2 or SEQ ID NO:6 and at least one set of amino acid substitutions selected from those listed in Table 12-6, wherein positions of the variant are numbered by correspondence with positions of the SEQ ID NO:2 sequence. Each such protease variant may be an isolated, recombinant, substantially pure, or non-naturally occurring protease variant. Also included are compositions, including cleaning compositions, comprising at least one such protease variant and methods for cleaning utilizing at least one such protease variant as described in greater detail elsewhere herein.

Table 12-7 provides the Performance Index (PI) values of BPN' variants (generated as described in "Generation of BPN' Variants from Five Different Plasmids"; see Table 11-4) for stain removal in a BMI microswatch assay in Detergent Composition 1 at 16° C. and pH 8. Assays were performed as described in Example 1 (BMI microswatch assay). The Performance Index of each variant was calculated relative to BPN'-v3: G97A-G128A-Y217Q. All mutants in this list have a PI cutoff equal or greater than 0.5 for at least one property tested.

TABLE 12-7

| Performance Index of BPN' Variants | | |
|---|---|---|
| Sequence Relative to BPN'-v3 G97A-G128A-Y217Q | Sequence Relative to BPN' | Det. Comp. 1, pH 8, 16° C., BMI PI |
| S101N | G97A-S101N-G128A-Y217Q | 1.12 |
| A137V | G97A-G128A-A137V-Y217Q | 1.12 |
| N61P | N61P-G97A-G128A-Y217Q | 1.11 |
| S130P | G97A-G128A-S130P-Y217Q | 1.09 |
| Q103N | G97A-Q103N-G128A-Y217Q | 1.07 |
| S63T | S63T-G97A-G128A-Y217Q | 1.03 |
| G102A | G97A-G102A-G128A-Y217Q | 1.02 |
| **BPN'-v3** | **BPN'-v3 (G97A-G128A-Y217Q)** | **1.00** |
| N109D-S248R | G97A-N109D-G128A-Y217Q-S248R | 0.96 |
| S87R | S87R-G97A-G128A-Y217Q | 0.95 |
| S188D | G97A-G128A-S188D-Y217Q | 0.95 |
| S87D-S248R | S87D-G97A-G128A-Y217Q-S248R | 0.94 |
| S188D-S248R | G97A-G128A-S188D-S248R-Y217Q | 0.93 |
| S248D | G97A-G128A-S248D-Y217Q | 0.86 |
| N109D-S188D-S248R | G97A-N109D-G128A-S188D-S248R-Y217Q | 0.83 |
| N109D | G97A-N109D-G128A-Y217Q | 0.81 |
| S87R-S248R | S87R-G97A-G128A-Y217Q-S248R | 0.79 |
| N109D-S188R | G97A-N109D-G128A-S188R-Y217Q | 0.77 |
| N76D | N76D-G97A-G128A-Y217Q | 0.75 |
| S87D-N109D-S188D-S248R | S87D-G97A-N109D-G128A-S188D-S248R-Y217Q | 0.58 |
| S87R-N109D-S188D-S248R | S87R-G97A-N109D-G128A-S188D-Y217Q-S248R | 0.55 |
| S87R-S188R-S248R | S87R-G97A-G128A-S188R-Y217Q-S248R | 0.52 |
| A187D | G97A-G128A-A187D-Y217Q | 0.48 |
| N109D-S248D | G97A-N109D-G128A-Y217Q-S248D | 0.47 |
| S87R-N109R-S188R-S248R | S87R-G97A-N109R-G128A-S188R-Y217Q-S248R | 0.39 |
| F189D | G97A-G128A-F189D-Y217Q | 0.31 |
| G100N | G97A-G100N-G128A-Y217Q | 0.28 |
| S87R-N109D-S188D | S87R-G97A-N109D-G128A-S188D-Y217Q | 0.24 |
| S87D-N109D-S188D | S87D-G97A-N109D-G128A-S188D-Y217Q | 0.12 |
| S87R-S188D-S248D | S87R-G97A-G128A-S188D-S248D-Y217Q | 0.09 |
| N62D | N62D-G97A-G128A-Y217Q | 0.09 |

TABLE 12-7-continued

| Performance Index of BPN' Variants | | |
|---|---|---|
| Sequence Relative to BPN'-v3 G97A-G128A-Y217Q | Sequence Relative to BPN' | Det. Comp. 1, pH 8, 16° C., BMI PI |
| S87D-N109D-S188D-S248D | S87D-G97A-N109D-G128A-S188D-Y217Q-S248D | 0.08 |

The invention includes a protease variant having proteolytic activity, the variant comprising an amino acid sequence having at least 60%, 70%, 80%, 85%, 90%, 91%, 92%, 93%, 94%, 95%, 96%, 97%, or 98% or 99% identity to SEQ ID NO:2 or SEQ ID NO:6 and at least one set of amino acid substitutions selected from those listed in Table 12-7, wherein positions of the variant are numbered by correspondence with positions of the SEQ ID NO:2 sequence. Each such protease variant may be an isolated, recombinant, substantially pure, or non-naturally occurring protease variant. Also included are compositions, including cleaning compositions, comprising at least one such protease variant and methods for cleaning utilizing at least one such protease variant as described in greater detail elsewhere herein.

Table 12-8 provides the Performance index (PI) values of BPN' variants (generated as described in "Generation of Combinatorial Libraries and Variants of BPN'-v3+S78N" as described in Example 3) for stain removal using a BMI microswatch assay in Detergent Composition 1 at 16° C. and pH 8. Assays were performed as described in Example 1 (BMI microswatch assay). The Performance Index of each variant was calculated relative to BPN'-S78N-G97A-G128A-Y217Q. PI values less than 0.01 were modified and are indicated as "0.01" in bold italics.

TABLE 12-8

| Performance Index Values of BPN' Variants | | | |
|---|---|---|---|
| Variant | Sequence Relative to BPN' | Sequence Relative to BPN'-v3: G97A-G128A-Y217Q | Det. Comp. 1 pH 8, 16° C., BMI PI |
| v3/S78N/L267V | S78N-G97A-G128A-Y217Q-L267V | S78N-L267V | 1.12 |
| v3/S78N/S161P | S78N-G97A-G128A-Y217Q-S161P | S78N-S161P | 1.05 |
| v3/S78N/I115V | S78N-G97A-G128A-Y217Q-I115V | S78N-I115V | 1.04 |
| v3/S78N/A273S | S78N-G97A-G128A-Y217Q-A273S | S78N-A273S | 1.03 |
| v3/S78N/G211T | S78N-G97A-G128A-Y217Q-G211T | S78N-G211T | 1.00 |
| **V3 + S78N** | **S78N-G97A-G128A-Y217Q** | **S78N** | **1.00** |
| v3/S78N/I111V | S78N-G97A-G128A-Y217Q-I111V | S78N-I111V | 0.98 |
| v3/S78N/V147L | S78N-G97A-G128A-Y217Q-V147L | S78N-V147L | 0.97 |
| v3/S78N/I108V | S78N-G97A-G128A-Y217Q-I108V | S78N-I108V | 0.97 |
| v3/S78N/S89Y | S78N-G97A-G128A-Y217Q-S89Y | S78N-S89Y | 0.94 |
| v3/S78N/A138T | S78N-G97A-G128A-Y217Q-A138T | S78N-A138T | 0.92 |
| v3/S78N/P172V | S78N-G97A-G128A-Y217Q-P172V | S78N-P172V | 0.74 |
| v3/S78N/Q59G | S78N-G97A-G128A-Y217Q-Q59G | S78N-Q59G | 0.64 |

TABLE 12-8-continued

| Performance Index Values of BPN' Variants | | | |
|---|---|---|---|
| Variant | Sequence Relative to BPN' | Sequence Relative to BPN'-v3: G97A-G128A-Y217Q | Det. Comp. 1 pH 8, 16° C., BMI PI |
| GcM96 | G97A-G128A-Y217Q-P129T-V147Q-S159D-S161P-S183T-Q185T-G211A-S224A | P129T-V147Q-S159D-S161P-S183T-Q185T-G211A-S224A | 0.57 |
| GcM91 | G97A-G128A-Y217Q-Q059V-I108V-V147Q-G211A-N252Q | Q059V-I108V-V147Q-G211A-N252Q | 0.55 |
| v3/S78N/Y167A | S78N-G97A-G128A-Y217Q-Y167A | S78N-Y167A | 0.53 |
| v3/S78N/A92G | S78N-G97A-G128A-Y217Q-A92G | S78N-A92G | 0.49 |
| v3/S78N/P129L | S78N-G97A-G128A-Y217Q-P129L | S78N-P129L | 0.48 |
| GcM92 | G97A-G128A-Y217Q-N061A-S087E-M124I-S161P-S224A | N061A-S087E-M124I-S161P-S224A | 0.36 |
| v3/S78N/N62Q | S78N-G97A-G128A-Y217Q-N62Q | S78N-N62Q | 0.27 |
| v3/S78N/V68A | S78N-G97A-G128A-Y217Q-V68A | S78N-V68A | 0.24 |
| GcM94 | G97A-G128A-Y217Q-S063T-S101A-L126V-S183T-T244N | S063T-S101A-L126V-S183T-T244N | 0.12 |
| v3/S78N/M124T | S78N-G97A-G128A-Y217Q-M124T | S78N-M124T | 0.05 |
| GcM95 | G97A-G128A-Y217Q-P040L-S053G-Q059V-N061A-N062Q-S063T-S087E-G100N | P040L-S053G-Q059V-N061A-N062Q-S063T-S087E-G100N | ***0.01*** |
| GcM93 | G97A-G128A-Y217Q-N062Q-G100N-S125A-S159D-N240S | N062Q-G100N-S125A-S159D-N240S | ***0.01*** |
| GcM100 | G97A-G128A-Y217Q-V68A-G102A-G211A-S125A | V68A-G102A-G211A-S125A | ***0.01*** |
| GcM90 | G97A-G128A-Y217Q-S053G-V068A-G102A-P129T-Q185T | S053G-V068A-G102A-P129T-Q185T | ***0.01*** |

The invention includes a protease variant having proteolytic activity, the variant comprising an amino acid sequence having at least 60%, 70%, 80%, 85%, 90%, 91%, 92%, 93%, 94%, 95%, 96%, 97%, or 98% or 99% identity to SEQ ID NO:2 or SEQ ID NO:6 and at least one set of amino acid substitutions selected from those listed in Table 12-8, wherein positions of the variant are numbered by correspondence with positions of the SEQ ID NO:2 sequence. Each such protease variant may be an isolated, recombinant, substantially pure, or non-naturally occurring protease variant. Also included are compositions, including cleaning compositions, comprising at least one such protease variant and methods for cleaning utilizing at least one such protease variant as described in greater detail elsewhere herein.

Table 12-9 provides Performance index (PI) values of BPN' single variants (constructed using PCR fusion as described in PCT App. No. PCT/US09/46156, filed Jun. 3, 2009, which is incorporated by reference herein for such description) for stain removal in a BMI microswatch assay in Detergent Composition 2 at 16° C. and pH 8 and for stability measured in Detergent Composition 3. PI values for specific activity by AAPF hydrolysis (PI specific AAPF) were determined. All assays were performed as described in Example 1. Performance index values were calculated relative to BPN wild type. PI values less than 0.01 are indicated as "0.01" in bold italics. "Det. Comp." means Detergent Composition.

TABLE 12-9

| Performance Index Values for BPN' Single Variants | | | |
|---|---|---|---|
| BPN' Variant | Det. Comp. 2 pH 8, 16° C., BMI PI | PI Specific AAPF | Det. Comp. 3 Stability PI |
| S182E | 1.34 | 1.05 | 0.50 |
| N109I | 1.28 | 1.22 | 0.20 |
| N117H | 1.15 | 0.25 | 0.20 |
| K237D | 1.15 | 0.60 | 0.70 |
| L257Q | 1.14 | 0.94 | 0.80 |
| P225N | 1.13 | 1.02 | 0.70 |
| S105H | 1.11 | 1.07 | ***0.01*** |
| S236I | 1.10 | 0.58 | 0.90 |
| L235H | 1.10 | 0.65 | 0.70 |
| S249E | 1.07 | 0.72 | 0.30 |
| N76E | 1.07 | 0.76 | 0.20 |
| S145N | 1.06 | 1.16 | 1.10 |
| N243D | 1.05 | 1.03 | 0.90 |
| R247N | 1.04 | 1.04 | 0.50 |
| E195N | 1.04 | 1.05 | 0.40 |
| A98K | 1.03 | 0.75 | 0.70 |
| S182N | 0.99 | 1.14 | 0.90 |
| S161H | 0.97 | 1.07 | 0.90 |
| G83H | 0.95 | 0.72 | 0.60 |
| G131D | 0.95 | 1.11 | 1.30 |
| T71C | 0.93 | 1.00 | 1.30 |
| K136Q | 0.93 | 1.02 | 0.80 |
| P40D | 0.93 | 1.20 | 1.20 |
| A187H | 0.91 | 0.95 | 0.60 |
| L250K | 0.90 | 1.02 | 0.40 |
| S9I | 0.87 | 0.20 | ***0.01*** |
| N76M | 0.85 | 0.60 | 0.60 |
| S132D | 0.85 | 0.88 | 0.70 |
| Q19F | 0.83 | 0.47 | 0.30 |
| E112H | 0.83 | 1.02 | ***0.01*** |
| S249P | 0.80 | 1.02 | 0.50 |
| S53D | 0.78 | 0.29 | 0.10 |
| V68E | 0.78 | 0.59 | 1.70 |
| D41I | 0.72 | 1.15 | 0.90 |
| K43H | 0.70 | 0.28 | 0.10 |
| V4H | 0.66 | 0.37 | 0.60 |
| A13Y | 0.64 | 0.48 | ***0.01*** |
| N62P | 0.61 | 0.60 | 1.30 |
| L196E | 0.56 | 0.70 | 0.70 |
| V44D | 0.51 | 0.18 | ***0.01*** |

The invention includes a protease variant having proteolytic activity, the variant comprising an amino acid sequence having at least 60%, 70%, 80%, 85%, 90%, 91%, 92%, 93%, 94%, 95%, 96%, 97%, or 98% or 99% identity to SEQ ID NO:2 or SEQ ID NO:6 and at least one substitution selected from those listed in Table 12-9, wherein positions of the variant are numbered by correspondence with positions of the SEQ ID NO:2 sequence. Each such protease variant may be an isolated, recombinant, substantially pure, or non-naturally occurring protease variant. Also included are compositions, including cleaning compositions, comprising at least one such protease variant and methods for cleaning utilizing at least one such protease variant as described in greater detail elsewhere herein.

Example 13

Hand Dish Liquid Detergent Compositions

In this Example, various hand dish liquid detergent formulations are provided. The following hand dish liquid detergent compositions of the present invention are provided below. In each of these formulations, at least one protease variant provided herein is included at a concentration of from about 0.0001 to about 10 weight percent. In some alternative aspects, other concentrations will find use, as determined by the formulator, based on their needs.

TABLE 13-1

| Light-Duty Liquid Dishwashing Detergent Composition | | | | |
|---|---|---|---|---|
| Composition | 1 | 2 | 3 | 4 |
| Linear Alkylbenzene Sulfonate (1) | — | | — | — |
| Alkyl Ethoxy Sulfate (2) | 18% | 17% | 17% | 18% |
| Paraffin Sulfonate (C15) | — | — | — | — |
| CAP = coco amido propyl Betaine | — | — | 9% | 5% |
| Nonionic (3) | — | — | 1% | — |
| Amine Oxide (4) | 6% | 5.5% | — | 4% |
| Alkylpolyglucoside | | | | 4% |
| Alcohol (5) | — | — | 5% | 7% |
| Pura = polypropyleneglycol | 1% | 0.8% | — | — |
| Citrate | — | — | 0.3% | 0.6% |
| Salt (6) | 1.2% | 1.0% | — | 0.5% |
| SCS = sodium cumene sulfonate | — | — | 0.8% | — |
| glycerol | 15% | 5% | 3% | — |
| Na-lactate | — | — | — | 5% |
| cationic polymer (7) | 0.1% | 0.1% | 0.3% | 0.2% |
| Protease of this invention | 0.0075 | 0.0050 | 0.0025 | 0.030 |
| Glycol distearate from Euperlan ® Cognis | 0.4 | 0 | 0.4 | 0 |
| Hydrogenated Castor Oil Thixcin ® Elementis | 0 | 0.1 | 0 | 0.1 |
| Mica (BASF Mearlin superfine) | 0 | 0.05 | 0 | 0.05 |
| Minors* | Balance to 100% with water | | | |
| pH | 9 | 9 | 6 | 6 |

Optional Minors*: dyes, opacifier, perfumes, preservatives, hydrotropes, processing aids, and/or stabilizers.
(1) Linear Alkylbenzene Sulfonate: LAS: C11.4
(2) Alkyl Ethoxy Sulfate: AExS:
(3) Nonionic: AlkylEthoxylate
(4) Di-methyl coco alkyl amine oxide
(5) Alcohol: Ethanol
(6) Salt: NaCl
(7) cationically modified hydroxyethyl cellulose (Polyquaternium-10 - UCARE LR-400 ex Amerchol).

Example 14

Liquid & Granular Laundry Detergents

This Example provides various formulations for liquid laundry detergents. The following liquid laundry detergent formulations of the present invention are provided below. In each of these formulations, at least one protease variant provided herein is included at a concentration of from about 0.0001 to about 10 weight percent. In some alternative aspects, other concentrations will find use, as determined by the formulator, based on their needs.

| Liquid laundry detergent compositions suitable for front-loading automatic washing machines. | | | | | | | | |
|---|---|---|---|---|---|---|---|---|
| | Composition (wt % of composition) | | | | | | | |
| Ingredient | 1 | 2 | 3 | 4 | 5 | 6 | 7 | 8 |
| Alkylbenzene sulfonic acid | 7 | 11 | 4.5 | 1.2 | 1.5 | 12.5 | 5.2 | 4 |
| Sodium $C_{12-14}$ alkyl ethoxy 3 sulfate | 2.3 | 3.5 | 4.5 | 4.5 | 7 | 18 | 1.8 | 2 |
| $C_{14-15}$ alkyl 8-ethoxylate | 5 | 8 | 2.5 | 2.6 | 4.5 | 4 | 3.7 | 2 |

-continued

| | | | | | | | | |
|---|---|---|---|---|---|---|---|---|
| $C_{12}$ alkyl dimethyl amine oxide | — | — | 0.2 | — | — | — | — | — |
| $C_{12-14}$ alkyl hydroxyethyl dimethyl ammonium chloride | — | — | — | 0.5 | — | — | — | — |
| $C_{12-18}$ Fatty acid | 2.6 | 4 | 4 | 2.6 | 2.8 | 11 | 2.6 | 1.5 |
| Citric acid | 2.6 | 3 | 1.5 | 2 | 2.5 | 3.5 | 2.6 | 2 |
| Cold Water Protease* | 0.05 | 0.03 | 0.04 | 0.03 | 0.04 | 0.03 | 0.03 | 0.02 |
| Amylase (Natalase ®) | 0.1 | 0.2 | 0.15 | — | 0.05 | 0.5 | 0.1 | 0.2 |
| Mannanase (Mannaway ®) | 0.05 | 0.1 | 0.05 | — | — | 0.1 | 0.04 | — |
| Random graft co-polymer[1] | 1 | 0.2 | 1 | 0.4 | 0.5 | 2.7 | 0.3 | 1 |
| A compound having the following general structure: bis($(C_2H_5O)(C_2H_4O)n$)($CH_3$)—$N^+$—$C_xH_{2x}$—$N^+$—($CH_3$)-bis($(C_2H_5O)(C_2H_4O)n$), wherein n = from 20 to 30, and x = from 3 to 8, or sulphated or sulphonated variants thereof | 0.4 | 2 | 0.4 | 0.6 | 1.5 | 1.8 | 0.7 | 0.3 |
| Ethoxylated Polyethylenimine[2] | — | — | — | — | — | 0.5 | — | — |
| Amphiphilic alkoxylated grease cleaning polymer[3] | 0.1 | 0.2 | 0.1 | 0.2 | 0.3 | 0.3 | 0.2 | 0.3 |
| Diethoxylated poly (1,2 propylene terephthalate short block soil release polymer. | — | — | — | — | — | — | 0.3 | — |
| Diethylenetriaminepenta(methylenephosphonic) acid | 0.2 | 0.3 | — | — | 0.2 | — | 0.2 | 0.3 |
| Hydroxyethane diphosphonic acid | — | — | 0.45 | — | — | 1.5 | — | 0.1 |
| FWA | 0.1 | 0.2 | 0.1 | — | — | 0.2 | 0.05 | 0.1 |
| Solvents (1,2 propanediol, ethanol), stabilizers | 3 | 4 | 1.5 | 1.5 | 2 | 4.3 | 2 | 1.5 |
| Hydrogenated castor oil derivative structurant | 0.4 | 0.4 | 0.3 | 0.1 | 0.3 | — | 0.4 | 0.5 |
| Boric acid | 1.5 | 2.5 | | 1.5 | 1.5 | 0.5 | 1.5 | 1.5 |
| Na formate | — | — | — | 1 | — | — | — | — |
| Reversible protease inhibitor[4] | — | — | 0.002 | — | — | — | — | — |
| Perfume | 0.5 | 0.7 | 0.5 | 0.5 | 0.8 | 1.5 | 0.5 | 0.8 |
| Perfume MicroCapsules slurry (30% am) | 0.2 | 0.3 | 0.7 | 0.2 | 0.05 | 0.4 | 0.9 | 0.7 |
| Ethoxylated thiophene Hueing Dye[5] | 0.005 | 0.007 | 0.010 | 0.008 | 0.008 | 0.007 | 0.007 | 0.008 |
| Buffers (sodium hydroxide, Monoethanolamine) | | | | To pH 8.2 | | | | |
| Water and minors (antifoam, aesthetics) | | | | To 100% | | | | |

Liquid laundry detergent compositions suitable for top-loading automatic washing machines.

| | Composition (wt % of composition) | | | | | | | |
|---|---|---|---|---|---|---|---|---|
| Ingredient | 9 | 10 | 11 | 12 | 13 | 14 | 15 | 16 |
| $C_{12-15}$ Alkylethoxy(1.8)sulfate | 20.1 | 15.1 | 20.0 | 15.1 | 13.7 | 16.7 | 10.0 | 9.9 |
| $C_{11.8}$ Alkylbenzene sulfonate | 2.7 | 2.0 | 1.0 | 2.0 | 5.5 | 5.6 | 3.0 | 3.9 |
| $C_{16-17}$ Branched alkyl sulfate | 6.5 | 4.9 | | 4.9 | 3.0 | 9.0 | 2.0 | |
| $C_{12-14}$ Alkyl-9-ethoxylate | 0.8 | 0.8 | 0.8 | 0.8 | 8.0 | 1.5 | 0.3 | 11.5 |
| $C_{12}$ dimethylamine oxide | | | 0.9 | | | | | |
| Citric acid | 3.8 | 3.8 | 3.8 | 3.8 | 3.5 | 3.5 | 2.0 | 2.1 |
| $C_{12-18}$ fatty acid | 2.0 | 1.5 | 2.0 | 1.5 | 4.5 | 2.3 | | 0.9 |
| Cold Water Protease* | 0.1 | 0.2 | 0.1 | 0.1 | 0.1 | 0.1 | 0.1 | 0.1 |
| Amylase (Natalase ®) | 0.7 | 0.3 | 0.6 | 0.3 | 0.6 | 0.4 | | |
| Amylase (Termamyl Ultra ®) | | | | | | | | 1.1 |
| Mannanase (Mannaway ®) | 0.1 | | | | | 0.1 | | |
| Pectate Lyase (Pectawash ®) | 0.1 | | | | | 0.2 | | |
| Borax | 3.0 | 3.0 | | | 2.0 | 3.0 | 3.0 | 3.3 |
| Na & Ca formate | 0.2 | 0.2 | | 0.2 | 0.2 | | 0.7 | |
| A compound having the following general structure: bis($(C_2H_5O)(C_2H_4O)n$)($CH_3$)—$N^+$—$C_xH_{2x}$—$N^+$—($CH_3$)-bis($(C_2H_5O)(C_2H_4O)n$), wherein n = from 20 to 30, and x = from 3 to 8, or sulphated or sulphonated variants thereof | 1.6 | 1.6 | 3.0 | 1.6 | 2.0 | 1.6 | 1.3 | 1.2 |
| Random graft co-polymer[1] | 0.4 | 0.2 | 1.0 | 0.5 | 0.6 | 1.0 | 0.8 | 1.0 |
| Diethylene triamine pentaacetic acid | 0.4 | 0.4 | 0.4 | 0.4 | 0.2 | 0.3 | 0.8 | |
| Tinopal AMS-GX | 0.2 | 0.2 | 0.2 | 0.2 | 0.2 | 0.3 | 0.1 | |
| Tinopal CBS-X | | | | | | 0.1 | | 0.2 |
| Amphiphilic alkoxylated grease cleaning polymer[3] | 1.0 | 1.3 | 1.3 | 1.4 | 1.0 | 1.1 | 1.0 | 1.0 |
| Texcare 240N (Clariant) | | | | 1.0 | | | | |
| Ethanol | 2.6 | 2.6 | 2.6 | 2.6 | 1.8 | 3.0 | 1.3 | |
| Propylene Glycol | 4.6 | 4.6 | 4.6 | 4.6 | 3.0 | 4.0 | 2.5 | |
| Diethylene glycol | 3.0 | 3.0 | 3.0 | 3.0 | 3.0 | 2.7 | 3.6 | |
| Polyethylene glycol | 0.2 | 0.2 | 0.2 | 0.2 | 0.1 | 0.3 | 0.1 | 1.4 |
| Monoethanolamine | 2.7 | 2.7 | 2.7 | 2.7 | 4.7 | 3.3 | 1.7 | 0.4 |
| Triethanolamine | | | | | | | | 0.9 |
| NaOH | to pH 8.3 | to pH 8.3 | to pH 8.3 | to pH 8.3 | to pH 8.3 | to pH 8.3 | to pH 8.3 | to pH 8.5 |
| Suds suppressor | | | | | | | | |
| Dye | 0.01 | 0.01 | 0.01 | | 0.01 | 0.01 | 0.01 | 0.0 |
| Perfume | 0.5 | 0.5 | 0.5 | 0.5 | 0.7 | 0.7 | 0.8 | 0.6 |
| Perfume MicroCapsules slurry (30% am) | 0.2 | 0.5 | 0.2 | 0.3 | 0.1 | 0.3 | 0.9 | 1.0 |
| Ethoxylated thiophene Hueing Dye[5] | 0.003 | 0.002 | 0.002 | 0.005 | 0.002 | 0.004 | 0.004 | 0.003 |
| Water | balance | balance | balance | balance | balance | balance | balance | balance |

-continued

| Granular detergent compositions produced in accordance with the invention suitable for laundering fabrics. | | | | | | |
|---|---|---|---|---|---|---|
| | 17 | 18 | 19 | 20 | 21 | 22 |
| Linear alkylbenzenesulfonate with aliphatic carbon chain length $C_{11}$-$C_{12}$ | 15 | 12 | 20 | 10 | 12 | 13 |
| Other surfactants | 1.6 | 1.2 | 1.9 | 3.2 | 0.5 | 1.2 |
| Phosphate builder(s) | 2 | 3 | 4 | | | |
| Zeolite | | 1 | | 1 | 4 | 1 |
| Silicate | 4 | 5 | 2 | 3 | 3 | 5 |
| Sodium Carbonate | 2 | 5 | 5 | 4 | 0 | 3 |
| Polyacrylate (MW 4500) | 1 | 0.6 | 1 | 1 | 1.5 | 1 |
| Carboxymethyl cellulose (Finnfix BDA ex CPKelco) | 1 | — | 0.3 | — | 1.1 | — |
| Celluclean ® | 0.23 | 0.17 | 0.5 | 0.2 | 0.2 | 0.6 |
| Cold Water Protease* | 0.23 | 0.17 | 0.5 | 0.2 | 0.2 | 0.6 |
| Stainzyme Plus ® | 0.23 | 0.17 | 0.5 | 0.2 | 0.2 | 0.6 |
| Fluorescent Brightener(s) | 0.16 | 0.06 | 0.16 | 0.18 | 0.16 | 0.16 |
| Diethylenetriamine pentaacetic acid or Ethylene diamine tetraacetic acid | 0.6 | | 0.6 | 0.25 | 0.6 | 0.6 |
| $MgSO_4$ | 1 | 1 | 1 | 0.5 | 1 | 1 |
| Bleach(es) and Bleach activator(s) | 6.88 | | 6.12 | 2.09 | 1.17 | 4.66 |
| Ethoxylated thiophene Hueing Dye[5] | 0.002 | 0.001 | 0.003 | 0.003 | — | — |
| Direct Violet 9 ex Ciba Specialty Chemicals | | | | 0.0006 | 0.0004 | 0.0006 |
| Sulfate/Citric Acid/Sodium Bicarbonate/Moisture/perfume | Balance to 100% | | | | | |

[1]Random graft copolymer is a polyvinyl acetate grafted polyethylene oxide copolymer having a polyethylene oxide backbone and multiple polyvinyl acetate side chains. The molecular weight of the polyethylene oxide backbone is about 6000 and the weight ratio of the polyethylene oxide to polyvinyl acetate is about 40 to 60 and no more than 1 grafting point per 50 ethylene oxide units.

[2]Polyethylenimine (MW = 600) with 20 ethoxylate groups per —NH.

[3]Amphiphilic alkoxylated grease cleaning polymer is a polyethylenimine (MW = 600) with 24 ethoxylate groups per —NH and 16 propoxylate groups per —NH

[4]Reversible Protease inhibitor of structure:

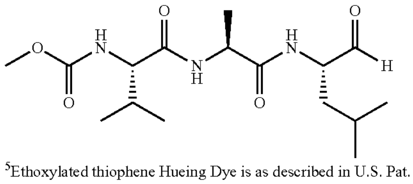

[5]Ethoxylated thiophene Hueing Dye is as described in U.S. Pat. No. 7,208,459 B2.

*Remark: all enzyme levels expressed as % enzyme raw material, except for cold water protease (of this invention) which is expressed as % of active protein added to the product.

Example 15

Unit Dose Compositions

This Example provides various formulations for unit dose laundry detergents. Such unit dose formulations can comprise one or multiple compartments.

The following unit dose laundry detergent formulations of the present invention are provided below.

TABLE 15-1

| Unit Dose Compositions | | | | | |
|---|---|---|---|---|---|
| Ingredients | 1 | 2 | 3 | 4 | 5 |
| Alkylbenzene sulfonic acid C 11-13, 23.5% 2-phenyl isomer | 14.5 | 14.5 | 14.5 | 14.5 | 14.5 |
| $C_{12-14}$ alkyl ethoxy 3 sulfate | 7.5 | 7.5 | 7.5 | 7.5 | 7.5 |
| $C_{12-14}$ alkyl 7-ethoxylate | 13.0 | 13.0 | 13.0 | 13.0 | 13.0 |
| Citric Acid | 0.6 | 0.6 | 0.6 | 0.6 | 0.6 |
| Fatty Acid | 14.8 | 14.8 | 14.8 | 14.8 | 14.8 |
| Enzymes (as % raw material not active) | 1.7 | 1.7 | 1.7 | 1.7 | 1.7 |
| Protease of this invention (as % active) | 0.05 | 0.1 | 0.02 | 0.03 | 0.03 |
| Ethoxylated Polyethylenimine[1] | 4.0 | 4.0 | 4.0 | 4.0 | 4.0 |
| Series 1 GG36 protease (as % active) | 0.02 | 0 | 0.01 | 0.02 | 0.03 |
| Hydroxyethane diphosphonic acid | 1.2 | 1.2 | 1.2 | 1.2 | 1.2 |
| Brightener | 0.3 | 0.3 | 0.3 | 0.3 | 0.3 |
| P-diol | 15.8 | 13.8 | 13.8 | 13.8 | 13.8 |
| Glycerol | 6.1 | 6.1 | 6.1 | 6.1 | 6.1 |
| MEA | 8.0 | 8.0 | 8.0 | 8.0 | 8.0 |
| TIPA | — | — | 2.0 | — | — |
| TEA | — | 2.0 | — | — | — |

TABLE 15-1-continued

| Unit Dose Compositions | | | | | |
|---|---|---|---|---|---|
| Ingredients | 1 | 2 | 3 | 4 | 5 |
| Cumene sulphonate | — | — | — | — | 2.0 |
| cyclohexyl dimethanol | — | — | — | 2.0 | — |
| Water | 10 | 10 | 10 | 10 | 10 |
| Structurant | 0.14 | 0.14 | 0.14 | 0.14 | 0.14 |
| Perfume | 1.9 | 1.9 | 1.9 | 1.9 | 1.9 |
| Buffers (monoethanolamine) | To pH 8.0 | | | | |
| Solvents (1,2 propanediol, ethanol) | To 100% | | | | |

[1]Polyethylenimine (MW = 600) with 20 ethoxylate groups per —NH.

TABLE 15-2

Multiple Compartment Unit Dose Compositions

Multiple compartment unit dose laundry detergent formulations of the present invention are provided below. In these examples the unit dose has three compartments, but similar compositions can be made with two, four or five compartments. The film used to encapsulate the compartments is polyvinyl alcohol.

| Base Composition 1 Ingredients | % |
|---|---|
| Glycerol (min 99) | 5.3 |
| 1,2-propanediol | 10.0 |
| Citric Acid | 0.5 |
| Monoethanolamine | 10.0 |
| Caustic soda | — |
| Dequest 2010 | 1.1 |
| Potassium sulfite | 0.2 |
| Nonionic Marlipal C24EO7 | 20.1 |

TABLE 15-2-continued

Multiple Compartment Unit Dose Compositions
Multiple compartment unit dose laundry detergent formulations of the present invention are provided below. In these examples the unit dose has three compartments, but similar compositions can be made with two, four or five compartments. The film used to encapsulate the compartments is polyvinyl alcohol.

| | |
|---|---|
| HLAS | 24.6 |
| Optical brightener FWA49 | 0.2 |
| C12-15 Fatty acid | 16.4 |
| Polymer Lutensit Z96 | 2.9 |
| Polyethyleneimine ethoxylate PEI600 E20 | 1.1 |
| MgCl2 | 0.2 |
| Solvents (1,2 propanediol, ethanol) | To 100% |

Multi-compartment formulations

| | Composition | | | | | |
|---|---|---|---|---|---|---|
| | 1 | | | 2 | | |
| | Compartment | | | | | |
| | A | B | C | A | B | C |
| Volume of each compartment | 40 ml | 5 ml | 5 ml | 40 ml | 5 ml | 5 ml |
| Active material in Wt. % | | | | | | |
| Perfume | 1.6 | 1.6 | 1.6 | 1.6 | 1.6 | 1.6 |
| Dyes | <0.01 | <0.01 | <0.01 | <0.01 | <0.01 | <0.01 |
| TiO2 | 0.1 | — | — | — | 0.1 | — |
| Sodium Sulfite | 0.4 | 0.4 | 0.4 | 0.3 | 0.3 | 0.3 |
| Acusol 305, Rohm&Haas | 1.2 | | | 2 | — | — |
| Hydrogenated castor oil | 0.14 | 0.14 | 0.14 | 0.14 | 0.14 | 0.14 |
| Base Composition 1 | Add to 100% | Add to 100% | Add to 100% | Add to 100% | Add to 100% | Add to 100% |

Example 16

Cleaning Performance of BPN'-v36 Polypeptide Variants

BPN'-v36 polypeptide variants comprising two amino acid substitutions were constructed by standard PCR fusion using the BPN'-v36 variant as a backbone or parent sequence. For this purpose, two or three partially overlapping fragments were amplified by mutagenic primers prepared such that the primer encoded a desired substitution. PCR amplification reactions were carried out as described in Example 7 of Part I supra. The following BPN'-v36 double mutant variants (i.e., BPN'-v36 with the following two amino acid substitution) were constructed: Q019R-N025D, A001Y-Q275R, V004A-S249N, V004E-S260P, V004A-T55A, Y006F-S249C, Y006D-T55A, V008L-Q275R, Q010R-Q275K, L016Q-Q217H, H017R-T158A, S183D-Q206R, P210S-N212D, S018Y-V203A, S018K-V203I, Y021H-D259G, Y021H-D259R, K027R-N269D, K027R-N269T, S037P-S260F, S037T-S260P, D041E-N077D, D041G-N077E, G166V-S183T, N252S-L257H, V044A-Q206H, V044A-Q206K, V044A-Q206R, N076T-N212D, N076P-N212S, N077D-N252D, N077D-N252T, K141I-S248N, T158I-D259N, T158A-D259P, S161E-Q185H, K237M-H238R, G160A-D259G, G160R-D259V, G215R-D259R, G215D-D259V, N061D-Q206R, N061L-Q206H, S009L-N218S, S161E-S260T, Q019A-N109S, T022S-G166V, Y021H-N252H, P129S-K136R, T022S-T242S, N025K-H238R, N025D-Q185R, S037G-Q275H, K043R-N076S, K043N-Q217R, K043N-S163T, T055A-V147A, N061K-N252K, N062Y-G097D, Y021H-V084E, Y021H-S037E, N062Y-T244A, K027E-Y091F, A074S-P129Q, S249R-Q275R, I079V-Q217H, A098T-T158A, K027R-D120H, Q019R-Q185R, G131S-K265N, A133V-D259N, A144H-T244A, I035V-K043N, G160R-T244A, S161P-T253A, S163T-Q245L, K170R-D259G, S183T-S249R, N184Y-Y262N, V198L-D259G, A200T-H226L, Q206R-S260P, G211V-T244A, Q217R-T244A, L75I-N76D, S260P-Q275L, S260P-Q275R, Y262N-Q275R, V004A-Y006F, H017L-Q019A, N025D-V026A, N118G-V121A, V072F-L075I, S183T-R186K, V203A-Q217R, and S249R-Y262H. The cleaning performance of these variants was tested in a BMI microswatch cleaning assay in Detergent Composition 4 at pH 8 and 16° C. and egg microswatch cleaning assay in Detergent Composition 4 at pH 8 and 16° C. as described in Example 1 of Part I. Results are provided below.

The following BPN' protease variants were determined to have a PI value equal to or greater than 0.9 and equal or less than 1.0 relative to BPN'-v36 in a BMI microswatch cleaning assay in Detergent Composition 4 at pH 8 and 16° C.: BPN'-S024G-S053G-S078N-S101N-G128A-Y217Q amino acid sequence (SEQ ID NO:6) comprising at least one set of amino acid substitutions selected from the group consisting of BPN'-v3, BPN'-v36, S183T-S249R, N61D-Q206R, Y262N-Q275R, K43R-N76S, S183T-S249R, K170R-D259G, Y6F-S249C, Q19A-N109S, H17L-Q19A, Q19R-Q185R, S18Y-V203A, N61D-Q206R, S161E-S260T, S18K-V203I, V4A-T55A, N252S-L257H, S249R-Y262H, N61L-Q206H, N184Y-Y262N, Q19R-N25D, S249R-Y262H, A74S-P129Q, H17L-Q19A, K27R-D120H, V4A-T55A, Y21H-N252H, K27R-N269D, K27R-N269D, A98T-T158A, I79V-Q217H, S9L-N218S, V4A-Y6F, S161P-T253A, V203A-Q217R, T22S-T242S, N76P-N212S, K170R-D259G, S37T-S260P, T55A-V147A, Q19R-Q185R, V4A-Y6F, Q19A-N109S, Y262N-Q275R, G160R-T244A, Q19R-N25D, N25D-Q185R, A98T-T158A, N61L-Q206H, G211V-T244A, S9L-N218S, A144H-T244A, A144H-T244A, S18Y-V203A, Y21H-N252H, A74S-P129Q, A1Y-Q275R, V198L-D259G, T55A-V147A, K141I-S248N, S183T-R186K, S37T-S260P, K27R-D120H, T22S-T242S, S161E-Q185H, P129S-K136R, G211V-T244A, N76P-N212S, K43N-S163T, S37G-Q275H, S161P-T253A, Y6F-S249C, N184Y-Y262N, N252S-L257H, G160R-T244A, S37G-Q275H, P129S-K136R, N62Y-T244A, and S260P-Q275R, wherein amino acid positions of the variant are numbered by correspondence with the sequence of SEQ ID NO:2. Such variants have enhanced proteolytic activity compared to BPN' (SEQ ID NO:2) and a greater PI value than BPN' in this assay. The invention includes a protease variant having enhanced proteolytic activity compared to BPN' (SEQ ID NO:2), a PI value of equal to or greater than 0.9 and equal to or less than 1.0 relative to BPN'-v36 in this assay, the variant comprising an amino acid sequence having at least 60%, 70%, 80%, 85%, 90%, 91%, 92%, 93%, 94%, 95%, 96%, 97%, or 98% or 99% identity to SEQ ID NO:2 or SEQ ID NO:6 and comprising at least one set of amino acid substitutions selected from said group above, wherein amino acid positions of the variant are numbered by correspondence with amino acid positions of the SEQ ID NO:2 sequence. Also included are compositions, including, but not limited to, e.g., cleaning compositions, comprising at least one such variant and methods for cleaning utilizing at least one such protease variant as described in greater detail elsewhere herein.

Also provided is a subtilisin protease variant having enhanced proteolytic activity compared to BPN' in a BMI microswatch cleaning assay in Detergent Composition 4 at pH 8 and 16° C., the variant comprising an amino acid sequence having at least 85%, 90%, 91%, 92%, 93%, 94%, 95%, 96%, 97%, or 98% identity to SEQ ID NO:2, wherein the variant comprises at least one substitution comprising at least one substitution selected from the group of X1Y, X4A, X6F, X9L, X17L, X18K/Y, X19A/R, X21H, X22S, X25D, X27R, X37G/T, X43N/R, X55A, X61D/L, X62Y, X74S, X76P/S, X79V, X98T, X109S, X120H, X129Q/S, X136R, X141I, X144H, X147A, X158A, X160R, X161E/P, X163T, X170R, X183T, X184Y, X185H/R, X186K, X198L, X203A/I, X206H/R, X211V, X212S, X217H/R, X218S, X242S, X244A, X248N, X249C/R, X252H/S, X253A, X257H, X259G, X260P/T, X262H/N, X269D, and X275H/R, and optionally at least one substitution selected from the group of A1Y, V4A, Y6F, S9L, H17L, S18K/Y, Q19A/R, Y21H, T22S, N25D, K27R, S37G/T, K43N/R, T55A, N61D/L, N62Y, A74S, N76P/S, I79V, A98T, N109S, D120H, P129Q/S, K136R, K141I, A144H, V147A, T158A, G160R, S161E/P, S163T, K170R, S183T, N184Y, Q185H/R, R186K, V198L, V203A/I, Q206H/R, G211V, N212S, Q217H/R, N218S, T242S, T244A, S248N, S249C/R, N252H/S, T253A, L257H, D259G, S260P/T, Y262H/N, N269D, and Q275H/R, wherein amino acid positions of the variant are numbered by correspondence with positions of the sequence of SEQ ID NO:2. Such variants have enhanced proteolytic activity compared to the BPN' (SEQ ID NO:2) BPN'-v3, and BPN'-v36 and a PI value greater than that of BPN', BPN'-v3, and BPN'-v36 in this assay. Also included are compositions, including, but not limited to, e.g., cleaning compositions, comprising at least one such variant and methods for cleaning utilizing at least one such protease variant as described in greater detail elsewhere herein.

The following BPN' subtilisin protease variants were determined to have a PI value equal or greater than 0.5 and less than 0.9 relative to BPN'-v36 in a BMI microswatch cleaning assay in Detergent Composition 4 at pH 8 and 16° C.: BPN'-S024G-S053G-S078N-S101N-G128A-Y217Q amino acid sequence (SEQ ID NO:6) comprising at least one set of amino acid substitutions selected from the group consisting of Y21H-D259G, Y21H-D259G, A133V-D259N, I79V-Q217H, S18K-V203I, T158A-D259P, N61K-N252K, K43N-Q217R, T158A-D259P, Q206R-S260P, A133V-D259N, V198L-D259G, N61K-N252K, S161E-S260T, G160A-D259G, K43N-Q217R, A1Y-Q275R, A200T-H226L, Q217R-T244A, S260P-Q275R, Q206R-S260P, T158I-D259N, Q217R-T244A, L75I-N76D, S161E-Q185H, Y21H-S37E, S249R-Q275R, G160A-D259G, T158I-D259N, Y21H-S37E, N76T-N212D, S260P-Q275L, G131S-K265N, V4A-S249N, N25D-Q185R, K43R-N76S, S183D-Q206R, Q10R-Q275K, K43N-S163T, Q10R-Q275K, N25D-V26A, G131S-K265N, S260P-Q275L, K141I-S248N, L16Q-Q217H, S249R-Q275R, K27R-N269T, P210S-N212D, L75I-N76D, S183D-Q206R, N118G-V121A, G215D-D259V, N76T-N212D, V4A-S249N, K27R-N269T, N62Y-G97D, V4E-S260P, G215D-D259V, K27E-Y91F, Y6D-T55A, N77D-N252T, V4E-S260P, Y6D-T55A, N77D-N252T, N25K-H238R, V44A-Q206H, L16Q-Q217H, S37P-S260F, V44A-Q206R, V44A-Q206H, V44A-Q206R, and S37P-S260F, wherein amino acid positions of the variant are numbered by correspondence with the sequence of SEQ ID NO:2. Such variants have proteolytic activity. The invention includes a protease variant having proteolytic activity, having enhanced proteolytic activity greater than BPN', and/or a PI value equal to or greater than 0.5 and less than 0.9 relative to BPN'-v36 in this assay, the variant comprising an amino acid sequence having at least 60%, 70%, 80%, 85%, 90%, 91%, 92%, 93%, 94%, 95%, 96%, 97%, or 98% or 99% identity to SEQ ID NO:2 or SEQ ID NO:6 and comprising at least one set of acid substitutions selected from said group above, wherein amino acid positions of the variant are numbered by correspondence with amino acid positions of the SEQ ID NO:2 sequence. Also included are compositions, including, but not limited to, e.g., cleaning compositions, comprising at least one such variant and methods for cleaning utilizing at least one such protease variant as described in greater detail elsewhere herein.

The following BPN'-v36 variants were determined to have a PI value greater than 1.0, at least 1.1, at least 1.2, at least 1.3, at least 1.4, at least 1.5, at least 1.6, at least 1.7, at least 1.8, at least 1.9, at least 2, from greater than 1.0 to about 10, from greater than 1.0 to about 8, or from greater than 1.0 to about 5 relative to BPN'-v36 in an egg microswatch cleaning assay in Detergent Composition 4 at pH 8 and 16° C.: BPN'-S024G-S053G-S078N-S101N-G128A-Y217Q amino acid sequence (SEQ ID NO:6) comprising at least one set of amino acid substitutions selected from the group consisting of Y21H-D259G, S183T-S249R, N61D-Q206R, Y262N-Q275R, Y021H-D259G, K043R-N076S, S183T-S249R, A133V-D259N, and I079V-Q217H, wherein amino acid positions of the variant are numbered by correspondence with the sequence of SEQ ID NO:2. Such variants have enhanced proteolytic activity compared to the BPN', BPN'-v3, and BPN'-v36, and a greater PI value than BPN', BPN'-v3 and BPN'-v36 in this assay. The invention includes a protease variant having enhanced proteolytic activity compared to BPN' (SEQ ID NO:2), enhanced proteolytic activity compared to BPN', BPN'-v3, and BPN'-v36, a PI value of greater than 1.0 to about 5 relative to BPN'-v3, and/or a PI value of greater than 1.0 to about 5 relative to BPN'-v36 in this assay, the variant comprising an amino acid sequence having at least 60%, 70%, 80%, 85%, 90%, 91%, 92%, 93%, 94%, 95%, 96%, 97%, or 98% or 99% identity to SEQ ID NO:2 or SEQ ID NO:6 and comprising at least one set of amino acid substitutions selected from said group above, wherein amino acid positions of the variant are numbered by correspondence with amino acid positions of the SEQ ID NO:2 sequence. Also included are compositions, including, but not limited to, e.g., cleaning compositions, comprising at least one such variant and methods for cleaning utilizing at least one such protease variant as described in greater detail elsewhere herein.

Also provided is a subtilisin protease variant having enhanced proteolytic activity compared to BPN' in a BMI microswatch cleaning assay in Detergent Composition 4 at pH 8 and 16° C., the variant comprising an amino acid sequence having at least 85%, 90%, 91%, 92%, 93%, 94%, 95%, 96%, 97%, or 98% identity to SEQ ID NO:2, wherein the variant comprises at least one substitution comprising at least one substitution selected from the group of X021H, X043R, X061D, X076S, X079V, X133V, X183T, X206R, X217H, X249R, X259G/N, X262N, and X275R, and optionally at least one substitution selected from the group of Y021H, K043R, N061D, N076S, I079V, A133V, S183T, Q206R, Q217H, S249R, D259G/N, Y262N, and Q275R, wherein amino acid positions of the variant are numbered by correspondence with positions of the sequence of SEQ ID NO:2. Such variants have enhanced proteolytic activity compared to the BPN' (SEQ ID NO:2) BPN'-v3, and BPN'-v36 and a PI value greater than that of BPN', BPN'-v3, and BPN'-v36 in this assay. Also included are compositions, including, but not limited to, e.g., cleaning compositions, comprising at least one such variant and methods for cleaning utilizing at least one such protease variant as described in greater detail elsewhere herein.

The following BPN'-v36 variants were determined to have a PI value equal to or greater than 0.5 and less than or equal to 1.0 relative to BPN'-v36 in an egg microswatch cleaning assay in Detergent Composition 4 at pH 8 and 16° C.: BPN'-

S024G-S053G-S078N-S101N-G128A-Y217Q amino acid sequence (SEQ ID NO:6) comprising at least one set of amino acid substitutions selected from the group consisting of BPN'-v3, BPN'-v36, K170R-D259G, S18K-V203I, Y6F-S249C, Q19A-N109S, H17L-Q19A, Q19R-Q185R, S18Y-V203A, N61D-Q206R, S161E-S260T, S18K-V203I, V4A-T55A, N252S-L257H, S249R-Y262H, N61L-Q206H, N184Y-Y262N, Q19R-N25D, S249R-Y262H, A74S-P129Q, T158A-D259P, H17L-Q19A, K27R-D120H, V4A-T55A, N61K-N252K, Y21H-N252H, K27R-N269D, K43N-Q217R, T158A-D259P, Q206R-S260P, K27R-N269D, A98T-T158A, I79V-Q217H, S9L-N218S, V4A-Y6F, S161P-T253A, V203A-Q217R, T22S-T242S, N76P-N212S, A133V-D259N, K170R-D259G, S37T-S260P, T55A-V147A, V198L-D259G, Q19R-Q185R, V4A-Y6F, Q19A-N109S, Y262N-Q275R, G160R-T244A, Q19R-N25D, N25D-Q185R, N61K-N252K, S161E-S260T, A98T-T158A, N61L-Q206H, G211V-T244A, S9L-N218S, A144H-T244A, A144H-T244A, S18Y-V203A, Y21H-N252H, A74S-P129Q, G160A-D259G, K43N-Q217R, A1Y-Q275R, A1Y-Q275R, A200T-H226L, Q217R-T244A, S260P-Q275R, V198L-D259G, T55A-V147A, Q206R-S260P, K141I-S248N, S183T-R186K, T158I-D259N, S37T-S260P, K27R-D120H, T22S-T242S, Q217R-T244A, S161E-Q185H, P129S-K136R, G211V-T244A, N76P-N212S, L75I-N76D, S161E-Q185H, Y21H-S37E, S249R-Q275R, G160A-D259G, K43N-S163T, T158I-D259N, Y21H-S37E, S37G-Q275H, S161P-T253A, N76T-N212D, S260P-Q275L, Y6F-S249C, N184Y-Y262N, G131S-K265N, V4A-S249N, N25D-Q185R, N252S-L257H, K43R-N76S, S183D-Q206R, G160R-T244A, Q10R-Q275K, S37G-Q275H, K43N-S163T, Q10R-Q275K, N25D-V26A, P129S-K136R, G131S-K265N, S260P-Q275L, K141I-S248N, T22S-G166V, N62Y-T244A, L16Q-Q217H, S249R-Q275R, S260P-Q275R, K27R-N269T, P210S-N212D, L75I-N76D, S183D-Q206R, N118G-V121A, G215D-D259V, N76T-N212D, V4A-S249N, K27R-N269T, G166V-S183T, N62Y-G97D, V4E-S260P, G215D-D259V, K27E-Y91F, Y21H-D259R, Y6D-T55A, N77D-N252T, V4E-S260P, Y6D-T55A, N77D-N252T, Y21H-D259R, N25K-H238R, N77D-N252D, V44A-Q206H, L16Q-Q217H, V72F-L75I, S37P-S260F, V72F-L75I, N77D-N252D, V44A-Q206R, S163T-Q245L, V44A-Q206H, V44A-Q206R, S37P-S260F, G215R-D259R, V44A-Q206K, and V44A-Q206K, wherein amino acid positions of the variant are numbered by correspondence with the sequence of SEQ ID NO:2. Such variants have proteolytic activity. The invention includes a protease variant having proteolytic activity and/or a PI value equal to or greater than 0.5 and equal to or less than 1.0 relative to BPN'-v36 in this assay, the variant comprising an amino acid sequence having at least 60%, 70%, 80%, 85%, 90%, 91%, 92%, 93%, 94%, 95%, 96%, 97%, or 98% or 99% identity to SEQ ID NO:2 or SEQ ID NO:6 and comprising at least one set of acid substitutions selected from said group above, wherein amino acid positions of the variant are numbered by correspondence with amino acid positions of the SEQ ID NO:2 sequence. Also included are compositions, including, but not limited to, e.g., cleaning compositions, comprising at least one such variant and methods for cleaning utilizing at least one such protease variant as described in greater detail elsewhere herein.

Example 17

Cleaning Performance of Additional BPN'-v36 Polypeptide Variants

The following BPN'-v36 variants were synthesized at DNA2.0 (Menlo Park, Calif.) using the pHPLT-BPN'-v36 plasmid containing the BPN' expression cassette served as template DNA (parent plasmid) for cloning: N109G-A128S-S224A, N109G-A128S-S224A-N243V, A88T-N109G-A116T-A128S-S224A-N243V, N61G-N109G-A128S-S224A, N61G-N109G-A128S-S224A-N243V, N61G-A88T-N109G-A116T-A128S-S224A-N243V, N109Q-A128S-S224A, N109Q-A128S-S224A-N243V, A88T-N109Q-A116T-A128S-S224A-N243V, N109S-A128S-S224A, N109S-A128S-S224A-N243V, A88T-N109S-A116T-A128S-S224A-N243V, N109M-A128S-S224A, N109M-A128S-S224A-N243V, A88T-N109M-A116T-A128S-S224A-N243V, N109G-A114S-A128S, N109G-A114S-A128S-N243V, A88T-N109G-A114S-A116T-A128S-N243V, N109G-A114S-A128S-S224A, N109G-A114S-A128S-S224A-N243V, N109G-A128S-S183V, N109G-A128S-S183L, N109G-A128S-S183L-S224A, N109G-A114S-A128S-S183L-S224A, A88T-N109G-A114S-A116T-A128S-S183L-S224A-N243V, N76D-N109G-A128S-S224A, N101Q-N109Q-A128S-S224A-N243V, N101Q-N109Q-A128S-P129S-S130T-S224A-N243V, N109G-A128S-P129S-S130T-S224A-N243V, S33T-A128S-N218S, S33T-N109G-A128S-N218S-N243V, S33T-N61G-N109G-A128S-N218S-N243V, S33T-N109G-A128S-G169A-N218S-N243V, S33T-S63G-N109G-A128S-N218S-N243V, S33T-N76D-N109G-A128S-N218S-N243V, S33T-S63G-N109G-A128S-G169A-N218S-N243V, I31L-S33T-S 63G-N109G-A128S-G169A-N218S-N243V, S33T-N61G-S63G-N109G-A128S-N218S-N243V, S33T-N61G-A88T-N109G-A116T-A128S-N218S-N243V, S33T-N61G-S63G-N109G-A128S-G131H-G169A-N218S-N243V, S33T-N61P-S63G-N109G-A128S-G131H-G169A-N218S-N243V, S33T-N109G-A128S-N218S-S224A-N243V, S63G-N109Q-A128S-S224A-N243V, S63G-N109Q-A128S-G131H-S224A-N243V, N61P-S63G-N109Q-A128S-S224A-N243V, N61P-S63G-N109Q-A128S-G131H-S224A-N243V, A1G-N61P-S63G-N109Q-A128S-G131H-S224A-N243V, I31L-N61P-S63G-N109Q-A128S-G131H-S224A-N243V, N61P-S63G-N109Q-A128S-G131H-S224A-N243V-S249Q, S33T-T55P-N61P-S63G-N109Q-A128S-G131H-S224A-N243V, S33T-T55P-N61P-S63G-A88T-N109G-A116T-A128S-G131H-S224A-N243V, S33T-T55P-N61P-S63G-A88T-N109G-A116T-A128S-G131H-S224A-N243V-S249Q, A1G-I31L-S33T-T55P-N61P-S63G-A88T-N109G-A116T-A128S-G131H-S224A-N243V-S249Q, N61P-S63G-N109Q-A128S-G131H-G169A-S224A-N243V-S249Q, and A1G-I31L-S33T-T55P-N61P-S63G-A88T-N109G-A116T-A128S-G131H-G169A-S224A-N243V-S249Q.

The variants were grown for protein expression as described in Example 11 of Part I. These variants were tested for their performance in the BMI microswatch cleaning assay in Detergent Composition 4 at pH 8 and 16° C., the egg microswatch cleaning assay in Detergent Composition 4 at pH 8 and 16° C., and the AAPF assay as described in Example 1 of Part I. Results are provided below.

The following BPN'-v36 variants were determined to have a PI value greater than 1.0, at least 1.1, at least 1.2, at least 1.3, at least 1.4, at least 1.5, at least 1.6, at least 1.7, at least 1.8, at least 1.9, at least 2, from greater than 1.0 to about 10, from greater than 1.0 to about 8, or from greater than 1.0 to about 5 relative to BPN'-v36 in a BMI microswatch cleaning assay in Detergent Composition 4 at pH 8 and 16° C.: BPN'-S024G-S053G-S078N-S101N-G128A-Y217Q amino acid sequence (SEQ ID NO:6) comprising at least one set of amino acid substitutions selected from the group consisting of N61P-S63G-N109Q-A128S-S224A-N243V, A88T-N109G-A114S-A116T-A128S-N243V, A88T-N109G-A114S-

A116T-A128S-S183L-S224A-N243V, N109G-A128S-S183V, N109G-A128S-N243V-K256R, N109M-A128S-S224A, A88T-N109S-A116T-A128S-S224A-N243V, N109Q-A128S-S224A-N243V, A88T-N109M-A116T-A128S-S224A-N243V, N109S-A128S-S224A-N243V, A88T-N109G-A116T-N243V, N101Q-N109Q-A128S-S224A-N243V, N109G-A116T-N243V-K256R, N109G-A128S-P129S-S130T-S224A-N243V, and A88T-N109Q-A116T-A128S-S224A-N243V, wherein amino acid positions of the variant are numbered by correspondence with the sequence of SEQ ID NO:2. Such variants have enhanced proteolytic activity compared to the BPN', BPN'-v3, and BPN'-v36, and a greater PI value than BPN', BPN'-v3 and BPN'-v36 in this assay. The invention includes a protease variant having enhanced proteolytic activity compared to BPN' (SEQ ID NO:2), enhanced proteolytic activity compared to BPN', BPN'-v3, and BPN'-v36, a PI value of greater than 1.0 to about 5 relative to BPN'-v3, and/or a PI value of greater than 1.0 to about 5 relative to BPN'-v36 in this assay, the variant comprising an amino acid sequence having at least 60%, 70%, 80%, 85%, 90%, 91%, 92%, 93%, 94%, 95%, 96%, 97%, or 98% or 99% identity to SEQ ID NO:2 or SEQ ID NO:6 and comprising at least one set of amino acid substitutions selected from said group above, wherein amino acid positions of the variant are numbered by correspondence with amino acid positions of the SEQ ID NO:2 sequence. Also included are compositions, including, but not limited to, e.g., cleaning compositions, comprising at least one such variant and methods for cleaning utilizing at least one such protease variant as described in greater detail elsewhere herein.

Also provided is a subtilisin protease variant having enhanced proteolytic activity compared to BPN'-v36 and/or a PI value of equal to or greater than 1.0 compared to BPN'-v36 in a BMI microswatch cleaning assay in Detergent Composition 4 at pH 8 and 16° C., the variant comprising an amino acid sequence having at least 85%, 90%, 91%, 92%, 93%, 94%, 95%, 96%, 97%, or 98% identity to SEQ ID NO:2, wherein the variant comprises at least one substitution comprising at least one substitution selected from the group of X61G/P/S, X63G, X88T, X101Q, X109G/M/Q/S, X114S, X116T, X128S, X129S, X130T, X158S, X183L/V, X224A, X243V, X248A, and X256R, and optionally at least one substitution selected from the group of N61G/P/S, S63G, A88T, N101Q, N109G/M/Q/S, A114S, A116T, A128S, P129S, S130T, T158S, S183L/V, S224A, N243V, S248A, and K256R, wherein amino acid positions of the variant are numbered by correspondence with positions of the sequence of SEQ ID NO:2. Such variants have enhanced proteolytic activity compared to the BPN' (SEQ ID NO:2) BPN'-v3, and BPN'-v36 and a PI value greater than that of BPN', BPN'-v3, and BPN'-v36 in this assay. Also included are compositions, including, but not limited to, e.g., cleaning compositions, comprising at least one such variant and methods for cleaning utilizing at least one such protease variant as described in greater detail elsewhere herein.

The following BPN'-v36 variants were determined to have a PI value equal to or greater than 0.9 and equal to or less than 1.0 relative to BPN'-v36 in a BMI microswatch cleaning assay in Detergent Composition 4 at pH 8 and 16° C.: BPN'-S024G-S053G-S078N-S101N-G128A-Y217Q amino acid sequence (SEQ ID NO:6) comprising at least one set of amino acid substitutions selected from the group consisting of G24S-G53S-N78S-G97A-N101S-A128S, G24S-G53S-N78S-G97A-N101S, BPN'-v36, S33T-T55P-N61P-S63G-A88T-N109G-A116T-A128S-G131H-S224A-N243V, S33T-N61G-S63G-N109G-A128S-N218S-N243V, S33T-S63G-N109G-A128S-N218S-N243V, S33T-T55P-N61P-S63G-N109Q-A128S-G131H-S224A-N243V, N61P-S63G-N109Q-A128S-G131H-G169A-S224A-N243V-S249Q, S33T-N61G-A88T-N109G-A116T-A128S-N218S-N243V, S33T-N109G-A128S-N218S-N243V, S33T-N76D-N109G-A128S-N218S-N243V, S33T-N76D-N109G-A128S-N218S-N243V-S248N-K256R, S33T-N61G-N109G-A128S-N218S-N243V, S33T-A128S-N218S, A1G-N61P-S63G-N109Q-A128S-G131H-S224A-N243V, N61P-S63G-N109Q-A128S-G131H-S224A-N243V-S249Q, N61P-S63G-N109Q-A128S-G131H-S224A-N243V, S63G-N109Q-A128S-G131H-S224A-N243V, N109G-A114S-A128S, N109G-A114S-A128S-S183L-S224A, N109G-A114S-A128S-S224A, N109G-A114S-A128S-S224A-N243V, A88T-N109G-A116T-A128S-S224A-N243V, N61G-A88T-N109G-A116T-A128S-S224A-N243V, N109G-A114S-A128S-N243V, N109G-A128S-S224A-N243V, N109G-A128S-S224A, N109G-A128S-S183L-S224A, N61G-N109G-A128S-S224A, N109G-A128S-S183L, S33T-N76D, N109S-A128S-S224A, N101Q-N109Q-A128S-P129S-S130T-S224A-N243V, S63G-N109Q-A128S-S224A-N243V, N109M-A128S-S224A-N243V, S63G-N109G, N109G-K256R, S63G-N76D, S33T-N109G-A128S-G169A-N218S-N243V, and S33T-N109G-A128S-N218S-S224A-N243V, wherein amino acid positions of the variant are numbered by correspondence with the sequence of SEQ ID NO:2. Such variants have proteolytic activity. The invention includes a protease variant having proteolytic activity, enhanced proteolytic activity compared to BPN', and/or a PI value equal to or greater than 0.9 and less or equal to 1.0 relative to BPN'-v36 in this assay, the variant comprising an amino acid sequence having at least 60%, 70%, 80%, 85%, 90%, 91%, 92%, 93%, 94%, 95%, 96%, 97%, or 98% or 99% identity to SEQ ID NO:2 or SEQ ID NO:6 and comprising at least one set of acid substitutions selected from said group above, wherein amino acid positions of the variant are numbered by correspondence with amino acid positions of the SEQ ID NO:2 sequence. Also included are compositions, including, but not limited to, e.g., cleaning compositions, comprising at least one such variant and methods for cleaning utilizing at least one such protease variant as described in greater detail elsewhere herein.

The following BPN'-v36 variants were determined to have a PI value equal to or greater than 0.5 and less than 0.9 relative to BPN'-v36 in a BMI microswatch cleaning assay in Detergent Composition 4 at pH 8 and 16° C.: BPN'-S024G-S053G-S078N-S101N-G128A-Y217Q amino acid sequence (SEQ ID NO:6) comprising at least one set of amino acid substitutions selected from the group consisting of I31L-S33T-S63G-N109G-A128S-G169A-N218S-N243V, A10-I31L-S33T-T55P-N61P-S63G-A88T-N109G-A116T-A128S-G131H-G169A-S224A-N243V-S249Q, S33T-N61G-S63G-N109G-A128S-G131H-G169A-N218S-N243V, S33T-S63G-N109G-A128S-G169A-N218S-N243V, S33T-T55P-N61P-S63G-A88T-N109G-A116T-A128S-G131H-S224A-N243V-S249Q, S33T-N76D-A128S-N218S, N76D-N109G-A128S-S224A, and S33T-N61P-S63G-N109G-A128S-G131H-G169A-N218S-N243V, wherein amino acid positions of the variant are numbered by correspondence with the sequence of SEQ ID NO:2. Such variants have proteolytic activity. The invention includes a protease variant having proteolytic activity and/or a PI value equal to or greater than 0.5 and less than 0.9 relative to BPN'-v36 in this assay, the variant comprising an amino acid sequence having at least 60%, 70%, 80%, 85%, 90%, 91%, 92%, 93%, 94%, 95%, 96%, 97%, or 98% or 99% identity to SEQ ID NO:2 or SEQ ID NO:6 and comprising at least one set of acid substitutions selected from said group above, wherein amino acid positions of the variant are numbered by correspondence with amino acid positions of the SEQ ID NO:2 sequence. Also included are compositions, including, but not limited to, e.g., cleaning compositions, comprising at least one such variant and methods for cleaning utilizing at least one such protease variant as described in greater detail elsewhere herein.

The following BPN'-v36 variants were determined to have a PI value greater than 1.0, at least 1.1, at least 1.2, at least 1.3, at least 1.4, at least 1.5, at least 1.6, at least 1.7, at least 1.8, at least 1.9, at least 2, from greater than 1.0 to about 10, from greater than 1.0 to about 8, or from greater than 1.0 to about 5 relative to BPN'-v36 in an egg microswatch cleaning assay in Detergent Composition 4 at pH 8 and 16° C.: BPN'-S024G-S053G-S078N-S101N-G128A-Y217Q amino acid sequence (SEQ ID NO:6) comprising at least one set of amino acid substitutions selected from the group consisting of S33T-T55P-N61P-S63G-A88T-N109G-A116T-A128S-G131H-S224A-N243V, S33T-N61G-S63G-N109G-A128S-N218S-N243V, S33T-S63G-N109G-A128S-N218S-N243V, N61P-S63G-N109Q-A128S-G131H-G169A-S224A-N243V-S249Q, S33T-N61G-A88T-N109G-A116T-A128S-N218S-N243V, S33T-N109G-A128S-N218S-N243V, S33T-A128S-N218S, A1G-N61P-S63G-N109Q-A128S-G131H-S224A-N243V, N61P-S63G-N109Q-A128S-G131H-S224A-N243V-S249Q, S63G-N109Q-A128S-G131H-S224A-N243V, N61P-S63G-N109Q-A128S-S224A-N243V, A88T-N109G-A114S-A116T-A128S-N243V, A88T-N109G-A114S-A116T-A128S-S183L-S224A-N243V, N109G-A114S-A128S, N109G-A114S-A128S-S183L-S224A, N109G-A114S-A128S-S224A, N109G-A114S-A128S-S224A-N243V, A88T-N109G-A116T-A128S-S224A-N243V, N61G-A88T-N109G-A116T-A128S-S224A-N243V, N109G-A128S-S183V, N109G-A114S-A128S-N243V, N109G-A128S-N243V-S248A, N109G-A128S-S224A-N243V, N109G-A128S-N243V-K256R, N109G-A128S-S224A, N109G-A128S-S183L-S224A, N61G-N109G-A128S-S224A, N109M-A128S-S224A, A88T-N109S-A116T-A128S-S224A-N243V, N109M-A128S-S224A-N243V, S63G-A128S, A88T-N109G-A116T-N243V, N101Q-N109Q-A128S-S224A-N243V, N109G-A116T-N243V-K256R, N109G-A116T, S63G-N109G, A88T-N109G, N109G-K256R, N61G-N109G-N243V, S33T-N109G-A128S-G169A-N218S-N243V, S33T-N109G-A128S-N218S-S224A-N243V, N109G-A128S-P129S-S130T-S224A-N243V, and A88T-N109Q-A116T-A128S-S224A-N243V, wherein amino acid positions of the variant are numbered by correspondence with the sequence of SEQ ID NO:2. Such variants have enhanced proteolytic activity compared to the BPN', BPN'-v3, and BPN'-v36, and a greater PI value than BPN', BPN'-v3 and BPN'-v36 in this assay. The invention includes a protease variant having enhanced proteolytic activity compared to BPN'(SEQ ID NO:2), enhanced proteolytic activity compared to BPN', BPN'-v3, and BPN'-v36, a PI value of greater than 1.0 to about 5 relative to BPN'-v3, and/or a PI value of greater than 1.0 to about 5 relative to BPN'-v36 in this assay, the variant comprising an amino acid sequence having at least 60%, 70%, 80%, 85%, 90%, 91%, 92%, 93%, 94%, 95%, 96%, 97%, or 98% or 99% identity to SEQ ID NO:2 or SEQ ID NO:6 and comprising at least one set of amino acid substitutions selected from said group above, wherein amino acid positions of the variant are numbered by correspondence with amino acid positions of the SEQ ID NO:2 sequence. Also included are compositions, including, but not limited to, e.g., cleaning compositions, comprising at least one such variant and methods for cleaning utilizing at least one such protease variant as described in greater detail elsewhere herein.

Also provided is a subtilisin protease variant having enhanced proteolytic activity compared to BPN'-v36 and/or a PI value of greater than 1.0 compared to BPN'-v36 in an egg microswatch cleaning assay in Detergent Composition 4 at pH 8 and 16° C., the variant comprising an amino acid sequence having at least 85%, 90%, 91%, 92%, 93%, 94%, 95%, 96%, 97%, or 98% identity to SEQ ID NO:2, wherein the variant comprises at least one substitution comprising at least one substitution selected from the group of X1G, X33T, X55P, X61G/P/S, X63G, X76D, X88T, X101Q, X109G/M/Q/S, X114S, X116T, X128S, X129S, X130T, X131H, X158S, X169A, X183L/V, X218S, X224A, X243V, X248A/N, X249Q, X256R, and optionally at least one substitution selected from the group of A1G, S33T, T55P, N61G/P/S, S63G, N76D, A88T, N101Q, N109G/M/Q/S, A114S, A116T, A128S, P129S, S130T, G131H, T158S, G169A, S183L/V, N218S, S224A, N243V, S248A/N, S249Q, K256R, wherein amino acid positions of the variant are numbered by correspondence with positions of the sequence of SEQ ID NO:2. Such variants have enhanced proteolytic activity compared to the BPN' (SEQ ID NO:2) BPN'-v3, and BPN'-v36 and a PI value greater than that of BPN', BPN'-v3, and BPN'-v36 in this assay. Also included are compositions, including, but not limited to, e.g., cleaning compositions, comprising at least one such variant and methods for cleaning utilizing at least one such protease variant as described in greater detail elsewhere herein.

The following BPN'-v36 variant was determined to have a PI value equal to or greater than 0.5 and equal to or less than 1.0 relative to BPN'-v36 in an egg BMI microswatch cleaning assay in Detergent Composition 4 at pH 8 and 16° C.: BPN'-S024G-S053G-S078N-S101N-G128A-Y217Q amino acid sequence (SEQ ID NO:6) comprising amino acid substitutions selected from the group consisting of substitutions S33T-N76D-A128S-N218S, N76D-N109G-A128S-S224A, and S063G-N76D, wherein amino acid positions of the variant are numbered by correspondence with the sequence of SEQ ID NO:2. Such variants have proteolytic activity. The invention includes a protease variant having proteolytic activity and/or a PI value equal to or greater than 0.5 and equal to or less than 1.0 relative to BPN'-v36 in this assay, the variant comprising an amino acid sequence having at least 60%, 70%, 80%, 85%, 90%, 91%, 92%, 93%, 94%, 95%, 96%, 97%, or 98% or 99% identity to SEQ ID NO:2 or SEQ ID NO:6 and comprising amino acid substitutions selected from the group consisting of S33T-N76D-A128S-N218S, N76D-N109G-A128S-S224A, and S063G-N076D, wherein amino acid positions of the variant are numbered by correspondence with amino acid positions of the SEQ ID NO:2 sequence. Also included are compositions, including, but not limited to, e.g., cleaning compositions, comprising at least one such variant and methods for cleaning utilizing at least one such protease variant as described in greater detail elsewhere herein.

The following BPN'-v36 variants were determined to have a PI value greater than 1.0, at least 1.1, at least 1.2, at least 1.3, at least 1.4, at least 1.5, at least 1.6, at least 1.7, at least 1.8, at least 1.9, at least 2, from greater than 1.0 to about 10, from greater than 1.0 to about 8, or from greater than 1.0 to about 5 relative to BPN'-v36 in an AAPF proteolytic assay: BPN'-S024G-S053G-S078N-S101N-G128A-Y217Q amino acid sequence (SEQ ID NO:6) comprising at least one set of amino acid substitutions selected from the group consisting of G24S-G53S-N78S-G97A-N101S-A128S, I31L-S33T-S63G-N109G-A128S-G169A-N218S-N243V, A1G-I31L-S33T-T55P-N61P-S63G-A88T-N109G-A116T-A128S-G131H-G169A-S224A-N243V-S249Q, S33T-N61G-S63G-

N109G-A128S-G131H-G169A-N218S-N243V, S33T-S63G-N109G-A128S-G169A-N218S-N243V, S33T-T55P-N61P-S63G-A88T-N109G-A116T-A128S-G131H-S224A-N243V, S33T-T55P-N61P-S63G-A88T-N109G-A116T-A128S-G131H-S224A-N243V-S249Q, S33T-N61G-S63G-N109G-A128S-N218S-N243V, S33T-S63G-N109G-A128S-N218S-N243V, S33T-T55P-N61P-S63G-N109Q-A128S-G131H-S224A-N243V, N61P-S63G-N109Q-A128S-G131H-G169A-S224A-N243V-S249Q, S33T-N61G-A88T-N109G-A116T-A128S-N218S-N243V, S33T-N109G-A128S-N218S-N243V, S33T-N76D-N109G-A128S-N218S-N243V, S33T-N76D-N109G-A128S-N218S-N243V-S248N-K256R, S33T-N61G-N109G-A128S-N218S-N243V, S33T-N76D-A128S-N218S, S33T-A128S-N218S, A1G-N61P-S63G-N109Q-A128S-G131H-S224A-N243V, N61P-S63G-N109Q-A128S-G131H-S224A-N243V-S249Q, N61P-S63G-N109Q-A128S-G131H-S224A-N243V, S63G-N109Q-A128S-G131H-S224A-N243V, N61P-S63G-N109Q-A128S-S224A-N243V, A88T-N109G-A114S-A116T-A128S-N243V, A88T-N109G-A114S-A116T-A128S-S183L-S224A-N243V, N109G-A114S-A128S, N109G-A114S-A128S-S183L-S224A, N109G-A114S-A128S-S224A, N109G-A114S-A128S-S224A-N243V, A88T-N109G-A116T-A128S-S224A-N243V, N61G-A88T-N109G-A116T-A128S-S224A-N243V, N109G-A128S-S183V, N109G-A114S-A128S-N243V, N109G-A128S-N243V-S248A, N109G-A128S-S224A-N243V, N109G-A128S-N243V-K256R, N109G-A128S-S224A, N109G-A128S-S183L-S224A, N61G-N109G-A128S-S224A, N76D-N109G-A128S-S224A, N109M-A128S-S224A, N109G-A128S-S183L, S33T-N76D, A88T-N109S-A116T-A128S-S224A-N243V, N109Q-A128S-S224A-N243V, N109S-A128S-S224A, A88T-N109M-A116T-A128S-S224A-N243V, N101Q-N109Q-A128S-P129S-S130T-S224A-N243V, S63G-N109Q-A128S-S224A-N243V, N109M-A128S-S224A-N243V, S63G-A128S, N109S-A128S-S224A-N243V, A88T-N109G-A116T-N243V, N61S-N109G-N243V, N101Q-N109Q-A128S-S224A-N243V, N109G-A116T-N243V-K256R, A88T-N109G-A116T-T158S-N243V-K256R, N109G-A116T, S63G-N109G, A88T-N109G, N109G-K256R, N61G-N109G-N243V, S33T-N61P-S63G-N109G-A128S-G131H-G169A-N218S-N243V, S33T-N109G-A128S-G169A-N218S-N243V, S33T-N109G-A128S-N218S-S224A-N243V, N109G-A128S-P129S-S130T-S224A-N243V, and A88T-N109Q-A116T-A128S-S224A-N243V, wherein amino acid positions of the variant are numbered by correspondence with the sequence of SEQ ID NO:2. Such variants have enhanced proteolytic activity compared to the BPN', BPN'-v3, and BPN'-v36, and a greater PI value than BPN', BPN'-v3 and BPN'-v36 in this assay. The invention includes a protease variant having enhanced proteolytic activity compared to BPN' (SEQ ID NO:2), enhanced proteolytic activity compared to BPN', BPN'-v3, and BPN'-v36, a PI value of greater than 1.0 to about 5 relative to BPN'-v3, and/or a PI value of greater than 1.0 to about 5 relative to BPN'-v36 in this assay, the variant comprising an amino acid sequence having at least 60%, 70%, 80%, 85%, 90%, 91%, 92%, 93%, 94%, 95%, 96%, 97%, or 98% or 99% identity to SEQ ID NO:2 or SEQ ID NO:6 and comprising at least one set of amino acid substitutions selected from said group above, wherein amino acid positions of the variant are numbered by correspondence with amino acid positions of the SEQ ID NO:2 sequence. Also included are compositions, including, but not limited to, e.g., cleaning compositions, comprising at least one such variant and methods for cleaning utilizing at least one such protease variant as described in greater detail elsewhere herein.

Also provided is a subtilisin protease variant having enhanced proteolytic activity compared to BPN'-v36 and/or a PI value of greater than 1.0 compared to BPN'-v36 in An AAPF proteolytic assay, the variant comprising an amino acid sequence having at least 85%, 90%, 91%, 92%, 93%, 94%, 95%, 96%, 97%, or 98% identity to SEQ ID NO:2, wherein the variant comprises at least one substitution comprising at least one substitution selected from the group of X1G, X31L, X33T, X55P, X61G/P/S, X63G, X76D, X88T, X101Q, X109G/M/Q/S, X114S, X116T, X128S, X129S, X130T, X131H, X158S, X169A, X183L/V, X218S, X224A, X243V, X248A/N, X249Q, and X256R, and optionally at least one substitution selected from the group of A1G, I31L, S33T, T55P, N61G/P/S, S63G, N76D, A88T, N101Q, N109G/M/Q/S, A114S, A116T, A128S, P129S, S130T, G131H, T158S, G169A, S183L/V, N218S, S224A, N243V, S248A/N, S249Q, and K256R, wherein amino acid positions of the variant are numbered by correspondence with positions of the sequence of SEQ ID NO:2. Such variants have enhanced proteolytic activity compared to the BPN' (SEQ ID NO:2) BPN'-v3, and BPN'-v36 and a PI value greater than that of BPN', BPN'-v3, and BPN'-v36 in this assay. Also included are compositions, including, but not limited to, e.g., cleaning compositions, comprising at least one such variant and methods for cleaning utilizing at least one such protease variant as described in greater detail elsewhere herein.

The following BPN'-v36 variant was determined to have a PI value equal to or greater than 0.5 and equal to or less than 1.0 relative to BPN'-v36 in an AAPF proteolytic assay: BPN'-S024G-S053G-S078N-S101N-G128A-Y217Q amino acid sequence (SEQ ID NO:6) comprising amino acid substitutions G24S-G53S-N78S-G97A-N101S or S063G-N76D, wherein amino acid positions of the variant are numbered by correspondence with the sequence of SEQ ID NO:2. Such variants have proteolytic activity. The invention includes a protease variant having proteolytic activity and/or a PI value equal to or greater than 0.5 and equal to or less than 1.0 relative to BPN'-v36 in this assay, the variant comprising an amino acid sequence having at least 60%, 70%, 80%, 85%, 90%, 91%, 92%, 93%, 94%, 95%, 96%, 97%, or 98% or 99% identity to SEQ ID NO:2 or SEQ ID NO:6 and comprising substitutions G24S-G53S-N78S-G97A-N101S or S063G-N76D, wherein amino acid positions of the variant are numbered by correspondence with amino acid positions of the SEQ ID NO:2 sequence. Also included are compositions, including, but not limited to, e.g., cleaning compositions, comprising at least one such variant and methods for cleaning utilizing at least one such protease variant as described in greater detail elsewhere herein.

Example 18

Cleaning Performance of Polypeptide BPN'-v36 Polypeptides Variants from Combinatorial Libraries Based on BPN'-v36 Polypeptide Two separate combinatorial libraries (AJ1 and AJ2) were synthesized by DNA2.0 (Menlo Park, Calif.) and were delivered as individual ligation reactions. The pHPLT-BPN'-v36 plasmid (FIG. 4) containing the BPN' expression cassette served as template DNA (parent plasmid) for library construction. A list of the possible amino acid positions and substitutions for each library is shown in Table 23-1. The ligation reactions for each library were used to transform *B. subtilis*, and the library variants were grown up for protein expression as described in Example 11 The variants were tested for performance in the BMI microswatch cleaning assay in Detergent Composition 4 (from Table 1-3) at pH 8 and 16° C. as described in Example 1.

TABLE 18-1

| Possible Substitutions for Combinatorial Libraries AJ1 and AJ2 | | | |
|---|---|---|---|
| AJ1 | | AJ2 | |
| Position | Possible Substitutions | Position | Possible Substitutions |
| S33 | G, S | E54 | E, Q |
| D60 | D, G | D99 | D, N |
| N62 | N, L, S | D120 | D, N |
| S63 | S, R, L, N, G | D140 | D, N |
| S125 | S, A | E156 | E, Q |
| Q217 | Q, R, E, L, G | D197 | D, N |
| M222 | M, L, S | K12 | K, T |
| | | K27 | K, S |
| | | K43 | K, T |
| | | K141 | K, Y |
| | | K213 | K, Q |
| | | K237 | K, A |
| | | K256 | K, Q |

The following BPN'-v36 variants were determined to have a PI value equal to or greater than 0.5 and less or equal to 1.0 relative to BPN'-v36 in the BMI microswatch cleaning assay in Detergent Composition 4 at pH 8 and 16° C.: BPN'-S024G-S053G-S078N-S101N-G128A-Y217Q amino acid sequence (SEQ ID NO:6) comprising at least one set of amino acid substitutions selected from the group consisting of BPN'v36, BPN'v3 (G024S-G053S-N078S-G097A-N101S), BPN'v3 (G024S-G053S-N078S-G097A-N101S, BPN' v12 (G024S-G053S-N078S-G097A-N101S-A128S), N062L, N062L-S063G, N062S, N062S-S063G-Q217L, N062S-S063L-Q217L, N062S-S063N, N062S-S063R, Q217E, S063G, S063G-Q217L, S063G-Q217L-M222S, S063L-Q217L, S063N, S063N-Q217L, D099N-K141Y-K213Q, D099N-K141Y-K256Q, K043T, K043T-K141Y-E156Q, N062L-Q217E, N062L-Q217L, N062L-S063G-Q217E, N062L-S063L, N062L-S063N-Q217L, N062S-Q217L, N062S-S063G, N062S-S063L, N062S-S063N-Q217L, N062S-S063R-Q217E, Q217L, S063G-Q217E, S063N-Q217E, S063R, S063R-Q217E, S063R-Q217L,), D099N-K141Y-K213Q, D099N-K141Y-K256Q, K043T, K043T-K141Y-E156Q, N062L-Q217E, N062L-Q217L, N062L-S063G-Q217E, N062L-S063L, N062S-Q217L, N062S-S063G, N062S-S063L, N062S-S063N-Q217L, Q217L, S063G-Q217E, S063N-Q217E, S063R, S063R-Q217E, and S063R-Q217L, wherein amino acid positions of the variant are numbered by correspondence with the sequence of SEQ ID NO:2. Such variants have proteolytic activity. The invention includes a protease variant having proteolytic activity and/or a PI value equal to or greater than 0.5 and equal to or less than 1.0 relative to BPN'-v36 in this assay, the variant comprising an amino acid sequence having at least 60%, 70%, 80%, 85%, 90%, 91%, 92%, 93%, 94%, 95%, 96%, 97%, or 98% or 99% identity to SEQ ID NO:2 or SEQ ID NO:6 and comprising at least one set of acid substitutions selected from said group above, wherein amino acid positions of the variant are numbered by correspondence with amino acid positions of the SEQ ID NO:2 sequence. Also included are compositions, including, but not limited to, e.g., cleaning compositions, comprising at least one such variant and methods for cleaning utilizing at least one such protease variant as described in greater detail elsewhere herein.

The following BPN'-v36 variants were determined to have a PI value equal to or greater than 0.5 and less than 0.9 relative to BPN'-v36 in the BMI microswatch cleaning assay in Detergent Composition 4 at pH 8 and 16° C.: BPN'-S024G-S053G-S078N-S101N-G128A-Y217Q amino acid sequence (SEQ ID NO:6) comprising at least one set of amino acid substitutions selected from the group consisting of D099N, K141Y-E156Q, N062L-S063L-Q217L, N062L-S063N, N062L-S063N-Q217E, N062L-S063R, N062L-S063R-Q217L, N062S-Q217E, N062S-S063G-Q217E, N062S-S063G-Q217R, N062S-S063N-Q217R, S063G-S125A, D060G-Q217L, D120N-K141Y-K213Q, K043T-D099N-D120N-K141Y, K043T-D099N-K141Y-K256Q, K043T-K237A, N062L-S063G-Q217R, N062L-S063G-S125A, N062L-S063L-Q217E, N062L-S063N-S125A-Q217L, N062S-Q217R, N062S-S063L-Q217E, N062S-S063R-Q217L, S063G-M222S, S063G-Q217R, D120N-E156Q-K256Q, K141Y-D197N, N062L-Q217R, N062L-S063G-Q217L-M222S, N062L-S063L-Q217R, N062L-S063N-Q217R, N062S-Q217G, N062S-S063G-Q217G, N062S-S063G-Q217L-M222L, N062S-S063G-S125A-Q217L, N062S-S063N-Q217E, Q217G, S033G-N062S-S063G, S063G-Q217G, S063G-Q217L-M222L, S063G-S125A-Q217R, S063L-Q217R, S063N-M222S, S063N-Q217R, S063N-S125A-Q217L, S063R-Q217R, S063R-S125A-Q217L, D099N-E156Q-K256Q, E156Q, K012T-D099N-K213Q, K012T-K256Q, K043T-D099N-K141Y-K213Q, K043T-E156Q, K141Y-K213Q, N062L-Q217G, N062L-Q217L-M222L, N062L-Q217L-M222S, N062L-S063G-M222S, N062L-S063G-Q217L-M222L, N062L-S063G-Q217R-M222S, N062L-S063N-Q217L-M222S, N062L-S063N-S125A, N062L-S063R-S125A, N062L-S125A, N062S-S063G-M222S, N062S-S063G-Q217G-M222S, N062S-S063G-S125A, N062S-S063N-Q217L-M222L, N062S-S063N-S125A-Q217L, N062S-S063R-Q217G, N062S-S063R-Q217L-M222S, Q217G-M222S, Q217L-M222S, Q217R, S033G-S063G-Q217R, S063G-Q217E-M222S, S063G-S125A-Q217G, S063L-Q217E, S063N-Q217G, S063N-Q217G-M222S, S063N-Q217L-M222S, S063R-Q217L-M222S, and S063R-S125A, wherein amino acid positions of the variant are numbered by correspondence with the sequence of SEQ ID NO:2. Such variants have proteolytic activity. The invention includes a protease variant having proteolytic activity and/or a PI value equal to or greater than 0.5 and less than 0.9 relative to BPN'-v36 in this assay, the variant comprising an amino acid sequence having at least 60%, 70%, 80%, 85%, 90%, 91%, 92%, 93%, 94%, 95%, 96%, 97%, or 98% or 99% identity to SEQ ID NO:2 or SEQ ID NO:6 and comprising at least one set of acid substitutions selected from said group above, wherein amino acid positions of the variant are numbered by correspondence with amino acid positions of the SEQ ID NO:2 sequence. Also included are compositions, including, but not limited to, e.g., cleaning compositions, comprising at least one such variant and methods for cleaning utilizing at least one such protease variant as described in greater detail elsewhere herein.

PART II

Methods for Making GG36 Cold Water Protease Variants

A variety of methods are known in the art that are suitable for generating modified polynucleotides of the invention that encode GG36 cold water protease variants, including, but not limited to, for example, site-saturation mutagenesis, scanning mutagenesis, insertional mutagenesis, deletion mutagenesis, random mutagenesis, site-directed mutagenesis, and directed-evolution, as well as various other recombinatorial approaches. Non-limiting exemplary methods of making the Series I GG36 cold water protease variants are provided in the section above entitled "Vectors, Cells, and Methods for Making Protease Variant Polypeptides of the Invention."

Example 19

For testing of enzyme activity in heat-inactivated detergents, working solutions of detergents are made from the heat inactivated stocks. Appropriate amounts of water hardness (e.g., 6 gpg or 12 gpg) and buffer are added to the detergent solutions to match the desired conditions. The solutions are mixed by vortexing or inverting the bottles. The following Table provides information regarding some of the commercially-available detergents and test conditions used herein. In some experiments, additional and/or other commercially available detergents find use in the following Examples.

TABLE 19-1

Laundry and Dish Washing Conditions

| Region | Form | Dose | Detergent* | Buffer | Gpg | pH | T (° C.) |
|---|---|---|---|---|---|---|---|
| Laundry (Heavy Duty Liquid and Granular) | | | | | | | |
| NA | HDL | 0.78 g/l | P&G TIDE ® 2X | 5 mM HEPES | 6 | 8.0 | 20 |
| WE | HDL | 5.0 g/L | Henkel PERSIL ™ | 5 mM HEPES | 12 | 8.2 | 40 |
| WE | HDG | 8.0 g/L | P&G ARIEL ® | 2 mM $Na_2CO_3$ | 12 | 10.5 | 40 |
| JPN | HDG | 0.7 g/L | P&G TIDE ® | 2 mM $Na_2CO_3$ | 6 | 10.0 | 20 |
| NA | HDG | 1.0 g/L | P&G TIDE ® | 2 mM $Na_2CO_3$ | 6 | 10.0 | 20 |
| Automatic Dish Washing | | | | | | | |
| WE | ADW | 3.0 g/L | RB CALGONIT ™ | 2 mM $Na_2CO_3$ | 21 | 10.0 | 40 |
| NA | ADW | 3.0 g/L | P&G CASCADE ® | 2 mM $Na_2CO_3$ | 9 | 10.0 | 40 |

In some additional Examples, the following solutions find use:

TABLE 19-2

Working Detergent Solutions

| Detergent | Temp (C.) | Detergent g/L | pH | Buffer | Gpg |
|---|---|---|---|---|---|
| TIDE ® 2X Cold | 16 | 0.98 | 8 | 5 mM HEPES | 6 |
| TIDE ® 2X Cold | 32 | 0.98 | 8 | 5 mM HEPES | 6 |
| TIDE ® 2X Cold | 16 | 0.98 | 7 | 5 mM MOPS | 6 |

Table 19-3 provides granular laundry detergent compositions produced in accordance with the invention suitable for laundering fabrics.

TABLE 19-3

Granular Laundry Detergent Compositions and Their Components

| Component | Detergent Compositions 1 | 2 | 3 | 4 | 5 | 6 |
|---|---|---|---|---|---|---|
| Linear alkylbenzenesulfonate with aliphatic carbon chain length $C_{11}$-$C_{12}$ | 15 | 12 | 20 | 10 | 12 | 13 |
| Other surfactants | 1.6 | 1.2 | 1.9 | 3.2 | 0.5 | 1.2 |
| Phosphate builder(s) | 2 | 3 | 4 | | | |
| Zeolite | | 1 | | 1 | 4 | 1 |
| Silicate | 4 | 5 | 2 | 3 | 3 | 5 |
| Sodium Carbonate | 2 | 5 | 5 | 4 | 0 | 3 |
| Polyacrylate (MW 4500) | 1 | 0.6 | 1 | 1 | 1.5 | 1 |
| Carboxymethyl cellulose (Finnfix BDA ex CPKelco) | 1 | — | 0.3 | — | 1.1 | — |
| Celluclean ® (15.6 mg/g) | 0.23 | 0.17 | 0.5 | 0.2 | 0.2 | 0.6 |
| Cold Water Protease variant* | 0.23 | 0.17 | 0.05 | 0.2 | 0.03 | 0.1 |
| Stainzyme Plus ® (14 mg/g) | 0.23 | 0.17 | 0.5 | 0.2 | 0.2 | 0.6 |
| Mannaway 4.0T (4 mg/g) | 0.1 | | | 0.1 | | 0.1 |
| Lipex 100T (18.6 mg/g) | 0.2 | | 0.1 | | 0.3 | |
| Fluorescent Brightener(s) | 0.16 | 0.06 | 0.16 | 0.18 | 0.16 | 0.16 |
| Diethylenetriamine pentaacetic acid or Ethylene diamine tetraacetic acid | 0.6 | | 0.6 | 0.25 | 0.6 | 0.6 |
| $MgSO_4$ | 1 | 1 | 1 | 0.5 | 1 | 1 |
| Bleach(es) and Bleach activator(s) | 6.88 | | 6.12 | 2.09 | 1.17 | 4.66 |
| Ethoxylated thiophene Hueing Dye[5] | 0.002 | 0.001 | 0.003 | 0.003 | — | — |
| Direct Violet 9 ex Ciba Specialty Chemicals | | | | 0.0006 | 0.0004 | 0.0006 |
| Sulfate/Citric Acid/Sodium Bicarbonate/ Moisture/ perfume | Balance to 100% | | | | | |

In Table 19-3, all enzyme levels expressed as % enzyme raw material, except for cold water protease variant (of this invention) which is expressed as % of active protein added to the product. Table 19-4 provides granular laundry detergent compositions suitable for top-loading automatic washing machines (detergent compositions 7-9) and front loading washing machines (detergent compositions 10-11). The GG36 protease variant tested and/or BPN' variant and/or cold water protease variant of the present invention is added separately to these formulations.

TABLE 19-4

Granular Laundry Detergent Compositions and Their Components

| Component | Detergent Composition 7 | 8 | 9 | 10 | 11 |
|---|---|---|---|---|---|
| Surfactants | | | | | |
| $C_{16-17}$ Branched alkyl sulfate | 3.55 | 15.8 | | | |
| $C_{12-14}$ alkyl sulphate | | | 1.5 | | |
| Sodium linear alkylbenzenesulfonate with aliphatic chain length $C_{11}$-$C_{12}$ | 9.6 | | 10.6 | 7.5 | 9 |
| Sodium $C_{14/15}$ alcohol ethoxy-3-sulfate | 1.15 | | | 2.88 | |
| Sodium $C_{14/15}$ alkyl sulphate | 2.37 | | | | |
| $C_{14/15}$ alcohol ethoxylate with average 7 moles of ethoxylation | | | | 1.17 | 1 |
| mono-$C_{8-10}$ alkyl mono-hydroxyethyl di-methyl quaternary ammonium chloride | | | | | 0.45 |
| Di methyl hydroxyl ethyl lauryl ammonium chloride | | | 0.18 | | |
| Zeolite A | 13.9 | 4.7 | 0.01 | 2.9 | 1.8 |
| Sodium Silicate 1.6.ratio | 4 | 0.2 | | 4 | 4 |
| Sodium Silicate 2.35.ratio | | | 8 | | |
| Citric Acid | | | | 2.5 | 1.4 |
| Sodium tripolyphosphate | | | 5 | | |
| Sodium Carbonate | 24.1 | 30 | 16.9 | 24.4 | 21 |
| Nonanoyloxybenzenesuplhonate | 5.78 | 2.81 | 0.96 | | |
| Oxaziridinium-based bleach booster | | | | 0.03 | 0.017 |
| Tetrasodium S,S-ethylenediaminedisuccinate | | | | 0.2 | |
| Diethylenetriamine penta (methylene phosphonic acid), heptasodium salt | 0.61 | | | | 0.33 |
| Hydroxyethane dimethylene phosphonic acid | | | | 0.29 | 0.45 |
| Ethylene diamine tetraacetate | | | 0.27 | | |
| MgSO4 | | | 0.47 | 0.5994 | 0.782 |
| Sodium Percarbonate | 7 | 4.4 | | 15.9 | 19.1 |
| Tetra Acetyl Ethylene Diamine | | | | 3.3 | 4.6 |
| Sodium Perborate Monohydrate | | | 1.2 | | |
| Carboxymethyl cellulose (e.g., Finnfix BDA ex CPKelco) | 0.1 | | 0.17 | 1.69 | 0.23 |
| Sodium Acrylic acid/maleic acid co-polymer (70/30) | 0.0236 | 3.8 | | 2 | 2.5 |
| Sodium polyacrylate (Sokalan PA30 CL) | 4 | | 0.84 | | |
| Terephthalate polymer | | | | 0.23 | |
| Polyethylene glycol/vinyl acetate random graft co polymer | | | 0.89 | 0.89 | 0.91 |
| Photobleach-zinc phthalocyanine tetrasulfonate | | | 0.005 | 0.001 | 0.002 |
| C.I. Fluorescent Brightener 260 | 0.11 | 0.15 | 0.04 | 0.23 | 0.15 |
| C.I. Fluorescent Brightener 351 (Tinopal ® CBS) | | | 0.1 | | |
| Suds suppressor granule | | 0.25 | | 0.07 | 0.04 |
| Hydrophobically modified carboxy methyl cellulose (Finnifix ® SH-1) | | | 0.019 | 0.028 | |
| Bentonite | | | 8.35 | | |
| Miscellaneous (Dyes, perfumes, process aids, moisture and sodium sulphate) | Balance | Balance | Balance | Balance | Balance |

In Table 19-4, surfactant ingredients can be obtained from any suitable supplier, including but not limited to BASF (e.g., LUTENSOL®), Shell Chemicals, Stepan, Huntsman, and Clariant (e.g., PRAEPAGEN®). Zeolite can be obtained from sources such as Industrial Zeolite. Citric acid and sodium citrate can be obtained from sources such as Jungbunzlauer. Sodium percarbonate, sodium carbonate, sodium bicarbonate and sodium sesquicarbonate can be obtained from sources such as Solvay. Acrylate/maleate copolymers can be obtained from sources such as BASF. Carboxymethylcellulose and hydrophobically modified carboxymethyl cellulose can be obtained from sources such as CPKelco. C.I. Fluorescent Brightener 260 can be obtained from 3V Sigma (e.g., OPTIBLANC®, OPTIBLANC® 2M/G, OPTIBLANC® 2MG/LT Extra, or OPTIBLANC® Ecobright. Tetrasodium S,S-ethylenediamine disuccinate can be obtained from sources such as Innospec. Terephthalate co-polymer can be obtained from Clariant (e.g., REPELOTEX SF 2). In addition, 1-Hydroxyethane-1,1-diphosphonic acid can be obtained from Thermphos. Oxaziridinium-based bleach booster has the following structure, where R1=2-butyloctyl, and was produced according to US 2006/0089284A1.

The enzymes NATALASE®, TERMAMYL®, STAINZYME PLUS®, CELLUCLEAN® and MANNAWAY® can be obtained from Novozymes. Zinc phthalocyanine tetrasulfonate can be obtained from Ciba Specialty Chemicals (e.g., TINOLUX® BMC). Suds suppressor granule can be obtained from Dow Corning. In these detergent compositions, random graft copolymer is a polyvinyl acetate grafted polyethylene oxide copolymer having a polyethylene oxide backbone and multiple polyvinyl acetate side chains. The molecular weight of the polyethylene oxide backbone is about 6000 and the weight ratio of the polyethylene oxide to polyvinyl acetate is about 40 to 60 and no more than 1 grafting point per 50 ethylene oxide units.

Assays and Test Methods

This Example describes the various assays used and provides further details of Test Methods 4-6.

TCA Assay for Protein Content Determination in 96-Well Microtiter Plates

For GG36 and GG36 variants, this assay was started using filtered *B. subtilis* culture supernatants from microtiter plates grown 2-3 days at 37° C. with shaking at 250 rpm and humidified aeration. A fresh 96-well flat bottom microtiter plate (MTP; Costar 9017 medium binding clear polystyrene plate) was used for the assay. First, 100 μL/well of 0.25N HCl was placed in each well. Then, 20-25 μL of filtered culture supernatant were added and the solution was mixed on a table top mixer (e.g., Lab line Instruments, Titer plate shaker, model 4825) for 5-10 seconds. The light scattering/absorbance at 405 nm was then determined, in order to provide the "blank" reading. For the "test" reading, 100 μL/well of 30% (w/v) trichloroacetic acid (TCA) was added to each well containing the mixture of HCl and culture supernatant, and the plate was incubated for 10 minutes at room temperature. After briefly mixing the solution on a table top mixer for no more than 2-3 sec, the light scattering/absorbance at 405 nm was determined. The turbidity/light scatter increase in the samples correlates to the total amount of precipitable protein in the culture supernatant. The calculations were performed by subtracting the "blank" reading (obtained after addition of HCl only, no TCA) from the "test" reading (obtained after addition of TCA, as described above) to provide a relative measure of the protein content in the samples. If desired, a standard curve can be created by calibrating the TCA readings with AAPF assays of clones with known conversion factors. However, the TCA results are linear with respect to protein concentration from 50 to 500 parts per million (ppm) of protein (where 1 ppm corresponds to 1 mg/L) and can thus be plotted directly against enzyme performance for the purpose of choosing variants with desired performance.

AAPF Protease Assay in 96-Well Microtiter Plates

In order to determine the protease activity of the serine protease variants, the hydrolysis of N-succinyl-L-alanyl-L-alanyl-L-prolyl-L-phenyl-p-nitroanilide (suc-AAPF-pNA) was measured. The reagent solutions used were: 100 mM Tris/HCl, pH 8.6, containing 0.005% TWEEN®-80 (Tris dilution buffer); 100 mM Tris buffer, pH 8.6, containing 1 mM $CaCl_2$ and 0.005% TWEEN®-80 (Tris/Ca buffer); and 160 mM suc-AAPF-pNA in DMSO (suc-AAPF-pNA stock solution) (Sigma: S-7388). To prepare a suc-AAPF-pNA working solution, 1 ml suc-AAPF-pNA stock solution was added to 100 ml Tris/Ca buffer and mixed well for at least 10 seconds. The assay was performed by adding 10 μl of diluted protease solution to each well of a 96-well MTP, immediately followed by the addition of 190 μl of 1 mg/ml suc-AAPF-pNA working solution. The solutions were mixed for 5 sec, and the absorbance change in kinetic mode (25 readings in 5 minutes) was read at 405 nm in an MTP reader, at 25° C. The protease activity was expressed as AU (activity=$\Delta OD \cdot min^{-1} ml^{-1}$).

Eglin C Inhibition Assay

As described herein, serine protease concentration and specific activity was determined by titration with an inhibitor called eglin c. Eglin c from the leech *Hirudo medicinalis* is a tight-binding protein inhibitor of subtilisins and ASP protease (Heinz et al., Biochemistry, 31: 8755-66 [1992]), and can therefore be used to measure protease enzyme concentration, which in turn permits specific activity to be calculated. The gene for eglin c was synthesized and expressed in *E. coli* by standard methods. Its properties and inhibitory potency were the same as eglin c purchased from Sigma.

(i) Concentration Determination of an Eglin C Stock Solution

A sample of *Bacillus lentus* subtilisin of known specific activity was diluted in 100 mM Tris buffer, pH 8.6, containing 1 mM $CaCl_2$ and 0.005% TWEEN®-80 (Tris/Ca buffer), to a concentration appropriate for AAPF protease assay described above. Several dilutions of the eglin c stock solution were also made in the Tris/Ca buffer. An aliquot of each diluted eglin c solution was mixed with an equal volume of the diluted *Bacillus lentus* subtilisin solution. An aliquot of the Tris/Ca buffer only, without eglin c, was also mixed with an equal volume of the diluted *Bacillus lentus* subtilisin solution, in order to measure uninhibited subtilisin activity in the absence of eglin c. The mixed solutions were incubated at room temperature for 15-30 minutes and the protease activity of each sample was then measured by AAPF assay described above. Using the known specific activity of *Bacillus lentus* subtilisin, the concentration of active protease in each sample was determined. The concentration of eglin c in each sample was then calculated based on the decrease of the observed protease activity as compared to the uninhibited subtilisin sample that was mixed with Tris/Ca buffer only (without eglin c). Thus, using the known dilutions and volumes of the eglin c solutions, the concentration of eglin c in the stock solution was determined.

(ii) Concentration and Specific Activity Determination of Subtilisin Variants

Samples of subtilisin variants were diluted in 100 mM Tris buffer, pH 8.6, containing 1 mM $CaCl_2$ and 0.005% TWEEN®-80 (Tris/Ca buffer). Several dilutions of the eglin c stock solution of known concentration were also made in the Tris/Ca buffer. An aliquot of each diluted eglin c solution was mixed with an equal volume of a subtilisin variant solution. The mixed solutions were incubated at room temperature for 15-30 minutes and the protease activity of each sample was then measured by AAPF assay. Using the observed decrease of the protease activity upon addition of each eglin c sample and the known concentration of the eglin c, the concentration of the eglin c necessary for the complete inhibition of each subtilisin enzyme variant was calculated. This concentration is equivalent to the enzyme concentration in the sample. An aliquot of the Tris/Ca buffer only, without eglin c, was also mixed with each subtilisin variant sample and the protease activity in the absence of eglin c was measured by AAPF assay. The specific activity of the subtilisin variants was then calculated using the enzyme concentrations as determined above.

BMI Microswatch Assay of Test Methods 4-6

Blood milk and ink (BMI) stained microswatches (EMPA116) of 5.5 millimeter circular diameter were obtained from CFT. In one method, the EMPA116 BMI fabric is pre-rinsed in water prior to cutting them into a 96 well microtiter plate (Corning 3641), one microswatch per well. In the second method the EMPA 116 cloth is cut directly into a 96 well microtiter plate (Corning 3641) where the swatches are then rinsed with two water washes. The rinses are carried out by adding 200 µl of Milli Q water to each well/swatch and mixing them on a table top mixer (Lab line instruments, Titer plate shaker, model 4825) for 15 minutes at a setting of 7. The wash liquor is removed and 200 µl of water is added again to the swatch for another 15 minute rinse. The wash water is removed and the swatches are then air dried in the microtiter plate.

Detergent compositions 7-11 (Table 19-4) were diluted in Milli-Q (deionized) water to final working concentrations described in Table 19-1. These detergents were buffered with 2 mM sodium carbonate, pH 10.3. Additionally, a water hardness composition (3:1 Ca:Mg.—$CaCl_2$:$MgCl_2$.$6H_2O$) was added to each detergent solution to the final concentration described in Table 19-5. The detergent solutions were mixed at room temperature for 0.5 to 2 hours, centrifuged in 50 mL polypropylene conical tubes at 3000×g for 5-10 minutes and were kept at room temperature for the 32° C. assays or pre-equilibrated in an ice-water bath for the 16° C. assays. Then, 190 µl of the desired detergent solution was added to each well of the MTP containing BMI microswatches. To this mixture, 5-15 µl of the diluted enzyme master dilution solution were added, making the approximate concentration of enzyme in the reaction 0.25-2 µg/ml. The enzyme master dilution solution was prepared from the filtered culture supernatants (see TCA assay described above) at ~2.5-20 µg/mL. The MTP was sealed with tape and placed in the iEMS incubator/shaker (Thermo/Labsystems) pre-set at 16° C. in a refrigerator for 30 minutes or at 32° C. on the benchtop for 30 minutes, with agitation at 1400 rpm. Following incubation under the appropriate conditions, 120-125 µl of the solution from each well was transferred into a fresh MTP (Corning 9017). The new MTP containing 125 µl of solution/well was read at 600 nm (with 5 sec mixing mode in the plate reader) using the MTP SpectraMax reader. Blank controls containing a microswatch and detergent without any enzyme were also included. The absorbance value obtained was corrected for the blank value (substrate without enzyme), providing a measure of hydrolytic activity. For each sample (variant) the performance index was calculated. The performance index compares the performance of the variant (measured value) and the standard enzyme (theoretical value) at the same protein concentration. In addition, the theoretical values can be calculated, using the parameters of a performance dose response curve of the standard protease. A performance index (PI) that is greater than 1 (PI>1) identifies a better variant as compared to the standard (e.g., wild-type), while a PI of 1 (PI=1) identifies a variant that performs the same as the standard, and a PI that is less than 1 (PI<1) identifies a variant that performs worse than the standard. Thus, the PI identifies winners, as well as variants that are less desirable for use under certain circumstances.

TABLE 19-5

Final Detergent, Water Hardness, and Buffer Concentrations Used for BMI Microswatch Assays

| Detergent Composition | Final Detergent Concentration (g/L) | Final Water Hardness* (gpg) | Final Sodium Carbonate Buffer Concentration (mM) |
|---|---|---|---|
| 7 | 0.808 | 6 | 2 |
| 8 | 1 | 3 | 2 |
| 9 | 2.3 | 12 | 2 |
| 10 | 5.9 | 12 | 2 |
| 11 | 8.3 | 12 | 2 |

LAS/EDTA Stability Assay

The stability of protease variants in the presence of a representative anionic surfactant (LAS=linear alkylbene sulfonate, sodium dodecylbenzenesulfonate-DOBS) and di-sodium EDTA is measured after incubation under defined conditions and the residual activity is determined using the AAPF assay described above. The reagents used were dodecyllbenzene sulfonate, sodium salt (DOBS; Sigma No. D-2525), TWEEN®-80 (Sigma No. P-8074), di-sodium EDTA (Siegfried Handel No. 164599-02), HEPES (Sigma No. H-7523), unstressed buffer: 50 mM HEPES (11.9 g/l)+0.005% TWEEN®-80, pH 8.0, Stress buffer: 50 mM HEPES (11.9 g/l), 0.1% (w/v) DOBS (1 g/l), 10 mM EDTA (3.36 g/l), pH 8.0, reference protease and protease variant culture supernatants, containing 200-400 mg/ml protein. The equipment used is V- or U-bottom MTP as dilution plates (Greiner 651101 and 650161 respectively), F-bottom MTP (Corning 9017) for unstress and LAS/EDTA buffer as well as for suc-AAPF-pNA plates, Biomek FX (Beckman Coulter), Spectramax Plus 384 MTP Reader (Molecular Devices), and iEMS Incubator/Shaker (Thermo/Labsystems).

The iEMS incubator/shaker (Thermo/Labsystems) is set at 29° C. Culture supernatants were diluted into plates containing unstress buffer to a concentration of ~25 ppm (master dilution plate). For the assay, 20 µl of sample from the master dilution plate is added to plates containing 180 µl unstress buffer to give a final incubation concentration of 2.5 ppm. The contents were mixed and kept at room temperature and the AAPF assay is performed on this plate. In addition, 20 µl of sample from the master dilution plate is also added to plates containing 180 µl stress buffer (50 mM HEPES (11.9 g/l), 0.1% (w/v) DOBS (1 g/l), 10 mM EDTA (3.36 g/l), pH 8.0). The solutions were mixed and immediately placed in 29° C. iEMS shaker for 30 min at 400 rpm. Following 30 minutes of incubation, the AAPF assay is performed on the stress plate. The stability of the samples is determined by calculating the ratio of the residual and initial AAPF activity as follows: Residual Activity (%)=[mOD·min-1 stressed]*100/[mOD·min-1 unstressed].

The final detergent, water hardness and buffer concentrations are determined based on the assay system to be used (e.g., North American, Japanese, Western European, or Central European conditions). In some aspects, the stain removal performance of the protease variants is determined in commercially available detergents. Heat inactivation of commercial detergent formulas serves to destroy the enzymatic activity of any protein components while retaining the properties of non-enzymatic components. Thus, this method is suitable for preparing commercially purchased detergents for use in testing the enzyme variants of the present invention.

Baked Egg Microtiter Assay

For this assay, 96-well baked egg yolk substrate plates are prepared from chicken egg yolks. Chicken egg yolks are separated from the whites, released from the membrane sac, and diluted 20% (vol/weight) with Milli-Q water. The diluted yolk is stirred for 15 min at room temperature using a magnetic stirrer. Five μL are carefully pipetted into the center of each well of a 96-well V-bottom plate (Costar #3894) using an 8-channel pipette. The plates are baked at 90° C. for 1 hour and cooled at room temperature. The baked egg yolk substrate plates are stored at room temperature and used within one week of preparation. Automatic dish detergents are prepared as described herein and pre-heated to 50° C. A 190 μL aliquot of detergent is added to each well of the 96-well plate using an 8-channel pipette. Ten μL of diluted enzyme is added to each well using a 96-channel pipetting device. The plate is carefully sealed with an adhesive foil sealer and incubated at 50° C. with shaking for 30 min. 120 μL of the reaction mixture is transferred to a new 96-well flat-bottom plate, and the absorbance/light scattering is determined at 405 nm. The absorbance/light scattering at 405 nm is proportional to egg yolk removal.

Performance Index

The performance index compares the performance of the variant (measured value) and the standard enzyme (theoretical value) at the same protein concentration. In addition, the theoretical values can be calculated, using the parameters of a performance dose response curve of the standard protease. Various terms set forth below are used to describe the variant: non-deleterious variants have a PI>0.05; deleterious variants have a PI=0.05; combinable variants are those for which the variant has performance index values greater than or equal to 0.2 for at least one property, and >0.05 for all properties. Combinable variants are those that can be combined to deliver proteins with appropriate performance indices for one or more desired properties. These data find use in engineering any subtilisin/subtilase. Even if the subtilase to be engineered has an amino acid different from that of subtilisin GG36 at particular positions, these data find use in finding substitutions that will alter the desired properties by identifying the best choices for substitutions, including substitutions to the GG36 wild type amino acid.

Example 20

Generation of GG36 Single Mutants Using Site Evaluation Libraries (SELs)

The construction of GG36 SELs described in this example was performed by GENEART using their proprietary methods and technology platform for gene optimization, gene synthesis, library generation and analysis (WO 2004/059556A3, European Patent Nos. 0 200 362 and 0 201 184; and U.S. Pat. Nos. 4,683,195, 4,683,202 and 6,472,184). The GG36 SELs were produced at positions pre-selected by the inventors using the pHPLT-GG36 *B. subtilis* expression plasmid (see FIG. 6). This *B. subtilis* expression plasmid contains the GG36 expression cassette shown below, the *B. licheniformis* LAT promoter (Plat), and additional elements from pUB110 (McKenzie et al., Plasmid, 15:93-103, 1986) including a replicase gene (reppUB), a neomycin/kanamycin resistance gene (neo) and a bleomycin resistance marker (bleo) (FIG. 4 in U.S. Pat. No. 6,566,112). The pHPLT-GG36 plasmid map is provided at FIG. 6. The GG36 expression cassette sequence is provided below.

The DNA sequence of GG36 (the signal sequence is shown in lower case letters, propeptide in lower case, underlined text, and GG36 mature sequence in uppercase letters) is provided below:

(SEQ ID NO: 756)

```
Gtgagaagcaaaaaattgtggatcgtcgcgtcgaccgcactactcatttc
tgttgctttcagttcatcgatcgcatcggctgctgaagaagcaaaagaaa
aatatttaattggctttaatgagcaggaagctgtcagtgagtttgtagaa
caagtagaggcaaatgacgaggtcgccattctctctgaggaagaggaagt
cgaaattgaattgcttcatgaatttgaaacgattcctgttttatccgttg
agttaagcccagaagatgtggacgcgcttgagctcgatccagcgatttct
tatattgaagaggatgcagaagtaacgacaatgGCGCAATCAGTGCCATG
GGGAATTAGCCGTGTGCAAGCCCCAGCTGCCCATAACCGTGGATTGACAG
GTTCTGGTGTAAAAGTTGCTGTCCTCGATACAGGTATTTCCACTCATCCA
GACTTAAATATTCGTGGTGGCGCTAGCTTTGTACCAGGGGAACCATCCAC
TCAAGATGGGAATGGGCATGGCACGCATGTGGCCGGGACGATTGCTGCTT
TAAACAATTCGATTGGCGTTCTTGGCGTAGCGCCGAGCGCGGAACTATAC
GCTGTTAAAGTATTAGGGGCGAGCGGTTCAGGTTCGGTCAGCTCGATTGC
CCAAGGATTGGAATGGGCAGGGAACAATGGCATGCACGTTGCTAATTTGA
GTTTAGGAAGCCCTTCGCCAAGTGCCACACTTGAGCAAGCTGTTAATAGC
GCGACTTCTAGAGGCGTTCTTGTTGTAGCGGCATCTGGAAATTCAGGTGC
AGGCTCAATCAGCTATCCGGCCCGTTATGCGAACGCAATGGCAGTCGGAG
CTACTGACCAAAACAACAACCGCGCCAGCTTTTCACAGTATGGCGCAGGG
CTTGACATTGTCGCACCAGGTGTAAACGTGCAGAGCACATACCCAGGTTC
AACGTATGCCAGCTTAAACGGTACATCGATGGCTACTCCTCATGTTGCAG
GTGCAGCAGCCCTTGTTAAACAAAAGAACCCATCTTGGTCCAATGTACAA
ATCCGCAATCATCTAAAGAATACGGCAACGAGCTTAGGAAGCACGAACTT
GTATGGAAGCGGACTTGTCAATGCAGAAGCTGCAACTCGTTAA
```

The protein sequence of GG36 (the signal sequence is shown in lower case letters, propeptide in lower case, underlined text, and GG36 mature protease sequence in uppercase letters) is provided below:

(SEQ ID NO: 757)

```
vrskklwivastallisvafsssiasaaeeakekyligfneqeavsefv
eqveandevailseeeveiellhefetipvlsvelspedvdaleldpa
isyieedaevttmAQSVPWGISRVQAPAAHNRGLTGSGVKVAVLDTGIS
THPDLNIRGGASFVPGEPSTQDGNGHGTHVAGTIAALNNSIGVLGVAPS
AELYAVKVLGASGSGSVSSIAQGLEWAGNNGMHVANLSLGSPSPSATLE
QAVNSATSRGVLVVAASGNSGAGSISYPARYANAMAVGATDQNNNRASF
SQYGAGLDIVAPGVNVQSTYPGSTYASLNGTSMATPHVAGAAALVKQKN
PSWSNVQIRNHLKNTATSLGSTNLYGSGLVNAEAATR.
```

The method of mutagenesis was based on the codon-specific mutation approach in which all possible amino acid substitutions are simultaneously created at a specific codon of interest using forward and reverse mutagenesis primers that contain a degenerate codon, NNS ((A, C, T or G), (A, C, T or G), (C or G)) at the site of interest. To construct each of the GG36 SELs, three PCR reactions were performed: two mutagenesis reactions (primary PCR1 and PCR2) to introduce the mutated codon of interest in the mature GG36 DNA sequence using the NNS forward and reverse mutagenesis primers (25-45 nucleotides long), and a third reaction to fuse the two mutagenesis PCR products together to construct the pHPLT-GG36 expression vector having the desired mutated codons in the mature GG36 sequence.

The primer sequences used in this Example are provided below:

TABLE 20-1

| Primers | |
|---|---|
| Sequence | Primer Name |
| CGCGCTT**GAGCTC**GATCCAGCGATTTC (SEQ ID NO: 758) | SacI-Fw |
| GTCTCC**AAGCTT**TAACGAGTTGCAG (SEQ ID NO: 759) | HindIII-Rv |
| GCAATTC**AGATCT**TCCTTCAGGTTATGACC (SEQ ID NO: 760) | pHPLT-BglII-Fw |
| GCATCGA**AGATCT**GATTGCTTAACTGCTTC (SEQ ID NO: 761) | pHPLT-BglII-Rv |

The Phusion High-Fidelity DNA Polymerase (Finnzymes catalog no. F-530L) was used for all PCRs, and the reactions were executed according to manufacturer's protocols that were supplied with the polymerase. In particular, for primary PCR 1, 1 μL (10 μM) of each of the pHPLT-BglII-Fw primer and a NNS reverse mutagenesis primer were used, and for primary PCR 2, 1 μL (10 μM) of the pHPLT-BglII-Rv primer and a NNS forward mutagenesis primer were used. Each reaction also included 1 μL of the pHPLT-GG36 plasmid template DNA (0.1-1 ng/μL). An MJ Research PTC-200 Peltier thermal cycler was used for the PCRs. The reactions yielded two fragments of approximately 2 to 3 kb having approximately 30 nucleotide overlap surrounding the GG36 codon of interest. The fragments obtained were fused in a third PCR similar to the ones described above using 1 μL of primary PCR 1 reaction mix, 1 μL of primary PCR 2 reaction mix and 1 μL (10 μM) of each of the forward and reverse SacI-Fw and HindIII-Rv primers. The amplified linear 859 bp fragment encoding the GG36 variant gene was purified (using QIAGEN® Qiaquick PCR purification kit) and digested with the SacI and HindIII restriction enzymes to create cohesive ends on both sides of the fusion fragment. About 50 ng of plasmid pHPLT-GG36 was also purified after digestion with SacI and HindIII, resulting in a 3.9 kb vector backbone fragment. The digested vector fragment was ligated with 50 ng of the digested 859 bp fragment encoding the variant enzyme using the T4 DNA ligase (Invitrogen) following the manufacturer's protocol for cloning of cohesive ends. Subsequently, the ligation mixture was used to transform *B. subtilis* cells (ΔaprE, ΔnprE, oppA, ΔspoIIE, degUHy32, ΔamyE::[xylR, pxylA-comK]) as described (WO 2002/014490).

To express the variant proteins for further biochemical analyses, the *B. subtilis* strains carrying the GG36 variant plasmids were inoculated into microtiter plates containing 150 μl Luria broth medium supplemented with 10 μg/ml neomycin. Plates were grown overnight at 37° C. with 300 rpm shaking and 80% humidity using Enzyscreen lids for microtiter plates (Enzyscreen). Ten microliters from the overnight culture plate were used to inoculate a new microliter plate containing 190 μl of MBD medium (a MOPS based defined medium) with 10 ug/ml neomycin. MBD medium was prepared essentially as known in the art (see Neidhardt et al., J. Bacteriol. 119:736-747 [1974]), except that $NH_4Cl$, $FeSO_4$, and $CaCl_2$ were omitted from the base medium, 3 mM $K_2HPO_4$ was used, and the base medium was supplemented with 60 mM urea, and 100 ml of a solution made of 210 g/L glucose, and 350 g/L maltodextrin. The micronutrients were made up as a 100× stock solution containing in one liter, 400 mg $FeSO_4.7H_2O$, 100 mg $MnSO_4.H_2O$, 100 mg $ZnSO_4.7H_2O$, 50 mg $CuCl_2.2H_2O$, 100 mg $CoCl_2.6H_2O$, 100 mg $NaMoO_4.2H_2O$, 100 mg $Na_2B_4O_7.10H_2O$, 10 ml of 1M $CaCl_2$, and 10 ml of 0.5 M sodium citrate. The MBD medium containing microtiter plates were grown for 68 hours at 37° C., 300 rpm, and 80% humidity using Enzyscreen lids (Enzyscreen) for determining protein expression. The next day, cultures were filtered through a micro-filter plate (0.22 μm; Millipore) and the resulting filtrate was used for biochemical analysis. The TCA and BMI microswatch assays for the detergent compositions 7-11 were carried out as described in Example 19. Performance indices were also calculated as described under the BMI assay of Test Methods 4-6 as described in detail in Example 19, and they are shown in Table 20-2 relative to GG36. In the following Tables, the detergent compositions ("Det.") correspond to those shown in Table 19-4, above. Also, as indicated, the amino acid position is listed according to BPN' numbering.

TABLE 20-2

Single Variants of GG36 with Performance Indices of at Least 0.2 Relative to GG36 in Either TCA or BMI Microswatch Cleaning at 16° C. in Detergents 7-11.

| GG36 Amino Acid Position (BPN' Numbering) | WT Residue | Mutant Residue |
|---|---|---|
| 1 | A | R |
| 2 | Q | A |
| 2 | Q | R |
| 2 | Q | S |
| 2 | Q | M |
| 2 | Q | W |
| 3 | S | R |
| 4 | V | R |
| 4 | V | S |
| 4 | V | C |
| 8 | I | A |
| 9 | S | W |
| 9 | S | F |
| 9 | S | A |
| 10 | R | A |
| 10 | R | M |
| 10 | R | S |
| 10 | R | H |
| 12 | Q | F |
| 12 | Q | R |
| 14 | P | F |
| 14 | P | K |
| 14 | P | Q |
| 15 | A | R |
| 15 | A | F |
| 16 | A | S |
| 17 | H | R |
| 17 | H | F |
| 17 | H | M |
| 18 | N | R |
| 18 | N | K |
| 20 | G | R |
| 20 | G | K |
| 20 | G | F |
| 22 | T | R |
| 22 | T | Q |
| 22 | T | L |
| 22 | T | V |
| 22 | T | W |
| 22 | T | Y |
| 22 | T | A |

TABLE 20-2-continued

Single Variants of GG36 with Performance Indices of at Least 0.2 Relative to GG36 in Either TCA or BMI Microswatch Cleaning at 16° C. in Detergents 7-11.

| GG36 Amino Acid Position (BPN' Numbering) | WT Residue | Mutant Residue |
|---|---|---|
| 23 | G | A |
| 23 | G | S |
| 23 | G | F |
| 24 | S | R |
| 24 | S | W |
| 24 | S | H |
| 24 | S | L |
| 24 | S | Q |
| 24 | S | F |
| 25 | G | R |
| 25 | G | F |
| 25 | G | V |
| 26 | V | F |
| 27 | K | R |
| 27 | K | L |
| 27 | K | V |
| 27 | K | F |
| 28 | V | A |
| 28 | V | E |
| 28 | V | N |
| 29 | A | T |
| 30 | V | E |
| 31 | L | F |
| 33 | T | S |
| 33 | T | G |
| 33 | T | D |
| 34 | G | P |
| 35 | I | M |
| 36 | S | T |
| 36 | S | F |
| 36 | S | R |
| 38 | T | R |
| 38 | T | F |
| 38 | T | L |
| 40 | P | H |
| 40 | P | W |
| 40 | P | R |
| 40 | P | N |
| 40 | P | T |
| 40 | P | L |
| 42 | L | I |
| 43 | N | R |
| 43 | N | A |
| 43 | N | S |
| 43 | N | W |
| 43 | N | F |
| 43 | N | I |
| 43 | N | D |
| 43 | N | M |
| 45 | R | T |
| 46 | G | R |
| 48 | A | R |
| 50 | F | C |
| 51 | V | W |
| 51 | V | F |
| 51 | V | H |
| 52 | P | F |
| 52 | P | N |
| 52 | P | E |
| 55 | P | Y |
| 57 | T | R |
| 59 | Q | A |
| 59 | Q | F |
| 59 | Q | R |
| 60 | D | P |
| 60 | D | A |
| 60 | D | Q |
| 62 | N | Q |
| 62 | N | E |
| 63 | G | S |
| 63 | G | A |
| 63 | G | M |
| 63 | G | V |
| 63 | G | T |
| 63 | G | H |
| 63 | G | Q |
| 63 | G | I |
| 63 | G | D |
| 63 | G | E |
| 63 | G | P |
| 64 | H | F |
| 64 | H | T |
| 68 | V | A |
| 68 | V | C |
| 69 | A | N |
| 69 | A | T |
| 69 | A | W |
| 69 | A | P |
| 71 | T | G |
| 72 | I | C |
| 74 | A | C |
| 75 | L | R |
| 75 | L | A |
| 75 | L | E |
| 75 | L | F |
| 78 | S | R |
| 78 | S | I |
| 78 | S | N |
| 79 | I | Q |
| 79 | I | W |
| 81 | V | R |
| 82 | L | R |
| 82 | L | T |
| 82 | L | M |
| 82 | L | F |
| 82 | L | V |
| 85 | A | M |
| 86 | P | W |
| 86 | P | I |
| 86 | P | L |
| 89 | E | P |
| 89 | E | W |
| 89 | E | T |
| 89 | E | I |
| 89 | E | H |
| 89 | E | V |
| 89 | E | F |
| 89 | E | L |
| 89 | E | W |
| 89 | E | G |
| 91 | Y | F |
| 91 | Y | N |
| 92 | A | F |
| 94 | K | N |
| 99 | S | F |
| 99 | S | T |
| 99 | S | M |
| 99 | S | G |
| 99 | S | P |
| 100 | G | I |
| 100 | G | S |
| 100 | G | N |
| 100 | G | Q |
| 101 | S | N |
| 101 | S | G |
| 101 | S | T |
| 101 | S | A |
| 101 | S | D |
| 101 | S | F |
| 101 | S | D |
| 101 | S | E |
| 101 | S | P |

TABLE 20-2-continued

Single Variants of GG36 with Performance Indices of at Least 0.2 Relative to GG36 in Either TCA or BMI Microswatch Cleaning at 16° C. in Detergents 7-11.

| GG36 Amino Acid Position (BPN' Numbering) | WT Residue | Mutant Residue |
|---|---|---|
| 102 | G | A |
| 102 | G | N |
| 102 | G | T |
| 102 | G | E |
| 102 | G | H |
| 103 | S | N |
| 103 | S | G |
| 103 | S | D |
| 104 | V | L |
| 104 | V | I |
| 104 | V | E |
| 104 | V | D |
| 105 | S | T |
| 105 | S | Q |
| 105 | S | E |
| 106 | S | V |
| 106 | S | G |
| 106 | S | T |
| 106 | S | A |
| 106 | S | E |
| 106 | S | D |
| 106 | S | F |
| 107 | I | F |
| 107 | I | M |
| 108 | A | I |
| 108 | A | G |
| 109 | Q | M |
| 111 | L | V |
| 111 | L | I |
| 112 | E | V |
| 112 | E | L |
| 112 | E | Q |
| 114 | A | G |
| 115 | G | R |
| 115 | G | K |
| 116 | N | L |
| 116 | N | A |
| 116 | N | K |
| 117 | N | F |
| 118 | G | I |
| 118 | G | R |
| 119 | M | C |
| 120 | H | A |
| 120 | H | F |
| 120 | H | R |
| 121 | V | E |
| 121 | V | F |
| 123 | N | G |
| 123 | N | E |
| 124 | L | S |
| 128 | S | N |
| 128 | S | M |
| 128 | S | H |
| 128 | S | Q |
| 128 | S | I |
| 128 | S | F |
| 128 | S | L |
| 128 | S | D |
| 129 | P | E |
| 132 | S | A |
| 132 | S | E |
| 138 | A | G |
| 144 | S | R |
| 147 | V | L |
| 148 | L | I |
| 158 | A | E |
| 159 | G | C |
| 159 | G | E |
| 160 | S | D |
| 166 | S | E |
| 166 | S | D |
| 167 | Y | W |
| 175 | M | V |
| 177 | V | C |
| 181 | D | A |
| 182 | Q | R |
| 183 | N | D |
| 183 | N | R |
| 183 | N | I |
| 183 | N | F |
| 183 | N | M |
| 185 | N | I |
| 185 | N | E |
| 185 | N | V |
| 186 | R | H |
| 186 | R | K |
| 188 | S | R |
| 188 | S | E |
| 188 | S | D |
| 192 | Y | W |
| 192 | Y | H |
| 194 | A | V |
| 194 | A | F |
| 194 | A | E |
| 197 | D | F |
| 198 | I | L |
| 198 | I | F |
| 203 | V | E |
| 203 | V | C |
| 208 | T | S |
| 209 | Y | N |
| 209 | Y | S |
| 209 | Y | F |
| 209 | Y | T |
| 209 | Y | H |
| 209 | Y | L |
| 209 | Y | G |
| 209 | Y | E |
| 210 | P | V |
| 210 | P | R |
| 210 | P | L |
| 211 | G | R |
| 211 | G | Q |
| 212 | S | I |
| 212 | S | F |
| 212 | S | M |
| 213 | T | A |
| 214 | Y | F |
| 215 | A | F |
| 215 | A | N |
| 215 | A | H |
| 215 | A | E |
| 215 | A | D |
| 216 | S | F |
| 216 | S | A |
| 217 | L | E |
| 217 | L | N |
| 217 | L | D |
| 218 | N | P |
| 218 | N | E |
| 218 | N | D |
| 224 | T | A |
| 224 | T | G |
| 227 | V | I |
| 230 | A | E |
| 231 | A | I |
| 231 | A | C |
| 233 | L | C |
| 234 | V | F |
| 235 | K | F |
| 236 | Q | N |
| 236 | Q | F |

TABLE 20-2-continued

Single Variants of GG36 with Performance Indices of at Least 0.2 Relative to GG36 in Either TCA or BMI Microswatch Cleaning at 16° C. in Detergents 7-11.

| GG36 Amino Acid Position (BPN' Numbering) | WT Residue | Mutant Residue |
|---|---|---|
| 238 | N | R |
| 238 | N | K |
| 238 | N | L |
| 239 | P | R |
| 239 | P | S |
| 239 | P | R |
| 239 | P | H |
| 239 | P | N |
| 239 | P | K |
| 239 | P | T |
| 239 | P | F |
| 239 | P | G |
| 240 | S | R |
| 241 | W | R |
| 242 | S | R |
| 242 | S | L |
| 243 | N | R |
| 243 | N | F |
| 244 | V | R |
| 246 | I | S |
| 248 | N | I |
| 248 | N | V |
| 248 | N | R |
| 249 | H | R |
| 249 | H | T |
| 250 | L | I |
| 251 | K | R |
| 251 | K | S |
| 252 | N | R |
| 252 | N | F |
| 252 | N | H |
| 252 | N | I |
| 253 | T | R |
| 253 | T | F |
| 253 | T | I |
| 254 | A | C |
| 256 | S | N |
| 258 | G | R |
| 260 | T | V |
| 260 | T | I |
| 262 | L | H |
| 262 | L | D |
| 263 | Y | F |
| 265 | S | F |
| 267 | L | N |
| 267 | L | M |
| 267 | L | V |
| 269 | N | R |
| 269 | N | I |
| 270 | A | C |
| 271 | E | T |
| 271 | E | V |
| 271 | E | L |
| 271 | E | H |
| 271 | E | F |
| 271 | E | P |
| 271 | E | A |
| 271 | E | M |
| 271 | E | I |
| 272 | A | F |
| 272 | A | R |
| 273 | A | I |
| 273 | A | F |
| 274 | T | G |

TABLE 20-3

| GG36 Single Variants with Performance Indices of at Least 1.5 Relative to GG36 BMI Microswatch Cleaning at 32° C. in Detergent 7. GG36 Variant |
|---|
| N62E |
| A158E |
| G159E |

TABLE 20-4

| GG36 Single Variants with Performance Indices of at least 1.2 Relative to GG36 BMI Microswatch Cleaning at 32° C. in Detergent 10. GG36 Variant |
|---|
| A1R |
| S78R |
| V244R |
| N269R |
| E271L |

Example 21

Construction and Cleaning Performance of the NHJ1 and WCE1 Sets of GG36 Variants The NHJ1 and WCE1 set of GG36 variants described herein were constructed at DNA 2.0, Inc., using the pHPLT-GG36 *B. subtilis* expression plasmid described above (FIG. 6). The variants were expressed in *B. subtilis* cells (genotype: ΔaprE, ΔnprE, amyE::xylRPxylAcomK-phleo) as described in Example 20, and were further characterized using the TCA assay for protein content determination, LAS/EDTA stability assay, and BMI microswatch cleaning assay as described in Example 19. These results are shown in Tables 21-1 and 21-2. In the following Tables, the detergent compositions ("Det.") correspond to those shown in Table 19-4, above. Also, as indicated, the amino acid position is listed according to BPN' numbering.

TABLE 21-1

NHJ1 Variants with Performance Indices of at least 0.25 Relative to GG36 in Any One of TCA, LAS/EDTA Stability, or BMI Microswatch Cleaning at 16° C. in Detergents 7, 8 or 9.
GG36 Variant (BPN' numbering)

| | | |
|---|---|---|
| N062E-A158E | S101A-H249R | A016S-S101A |
| S103G-A158E | S188D-H249R | E089P-S101A |
| S128N-A158E | V104L-H249R | N062E-S103G |
| A016S-A158E | Y209E-H249R | T022A-S103G |
| V104L-A158E | T022A-H249R | A016S-S103G |
| E089P-A158E | S128N-H249R | S101A-S103G |
| L111V-A158E | S103G-H249R | E089P-S103G |
| T022A-A158E | E089P-H249R | N062E-S128N |
| S101A-A158E | T022A-L111V | A016S-S128N |
| L148I-A158E | S101A-L111V | T022A-S128N |
| P129E-A158E | A016S-L111V | S101A-S128N |
| T022A-E089P | V104L-L111V | V104L-S128N |
| A016S-E089P | N062E-L111V | E089P-S128N |
| N062E-E089P | S103G-L111V | S103G-S128N |
| N062E-E271F | E089P-L111V | L111V-S128N |
| A158E-E271F | A016S-L148I | L111V-S188D |
| R186H-E271F | N062E-L148I | N062E-S188D |
| P129E-E271F | T022A-L148I | A016S-S188D |
| L111V-E271F | P129E-L148I | L148I-S188D |
| Y209E-E271F | V104L-L148I | T022A-S188D |
| A016S-E271F | S103G-L148I | S128N-S188D |
| S188D-E271F | S128N-L148I | S101A-S188D |
| T022A-E271F | S101A-L148I | V104L-S188D |
| G159E-E271F | E089P-L148I | E089P-S188D |
| V104L-E271F | L111V-L148I | P129E-S188D |

TABLE 21-1-continued

NHJ1 Variants with Performance Indices of at least 0.25 Relative to GG36 in Any One of TCA, LAS/EDTA Stability, or BMI Microswatch Cleaning at 16° C. in Detergents 7, 8 or 9.
GG36 Variant (BPN' numbering)

| | | |
|---|---|---|
| S101A-E271F | A016S-N062E | G159E-S188D |
| E089P-E271F | T022A-N062E | R186H-S188D |
| S128N-E271F | N062E-P129E | S103G-S188D |
| S103G-E271F | T022A-P129E | A158E-S188D |
| L148I-E271F | S128N-P129E | A016S-T022A |
| H249R-E271F | A016S-P129E | A016S-V104L |
| N062E-G159E | S101A-P129E | T022A-V104L |
| A016S-G159E | V104L-P129E | S101A-V104L |
| S128N-G159E | E089P-P129E | N062E-V104L |
| L148I-G159E | S103G-P129E | S103G-V104L |
| L111V-G159E | L111V-P129E | E089P-V104L |
| E089P-G159E | N062E-R186H | G159E-Y209E |
| T022A-G159E | S128N-R186H | L111V-Y209E |
| P129E-G159E | S101A-R186H | S101A-Y209E |
| S103G-G159E | T022A-R186H | A016S-Y209E |
| V104L-G159E | A016S-R186H | S128N-Y209E |
| A158E-G159E | A158E-R186H | L148I-Y209E |
| S101A-G159E | E089P-R186H | P129E-Y209E |
| A158E-H249R | P129E-R186H | N062E-Y209E |
| L111V-H249R | G159E-R186H | T022A-Y209E |
| P129E-H249R | S103G-R186H | S103G-Y209E |
| N062E-H249R | V104L-R186H | A158E-Y209E |
| A016S-H249R | L111V-R186H | S188D-Y209E |
| R186H-H249R | L148I-R186H | V104L-Y209E |
| L148I-H249R | N062E-S101A | E089P-Y209E |
| G159E-H249R | T022A-S101A | R186H-Y209E |

TABLE 21-2

WCE1 Variants with Performance Indices of at least 0.2 Relative to GG36 in Any One of TCA, LAS/EDTA Stability, or BMI Microswatch Cleaning at 16° C. in Detergents 10 or 11.
GG36 Variant (BPN' Numbering)

| | | |
|---|---|---|
| N018R-W241R | G115R-S212F | A001R-L082R |
| G020R-W241R | G020R-S212F | S078R-L082R |
| S024R-W241R | S009A-S212F | G020R-L082R |
| S009A-W241R | N043R-S212F | T022R-L082R |
| G020R-W241R | S078R-S212F | V004R-L082R |
| V004R-W241R | L082R-S212F | N043R-L082R |
| N043R-W241R | S009A-S078R | N043R-H249R |
| S078R-W241R | G020R-S078R | G020R-H249R |
| T022R-W241R | S024R-S078R | V004R-H249R |
| G115R-W241R | T022R-S078R | N018R-H249R |
| A001R-W241R | N018R-S078R | S009A-H249R |
| S212F-W241R | V004R-S078R | S212F-H249R |
| L082R-W241R | A001R-S078R | T022R-H249R |
| N018R-V244R | N043R-S078R | S024R-H249R |
| S024R-V244R | T022R-S024R | G115R-H249R |
| S078R-V244R | G020R-S024R | A001R-H249R |
| G020R-V244R | N018R-S024R | L082R-H249R |
| S212F-V244R | A001R-S024R | S242R-H249R |
| S009A-V244R | V004R-S024R | W241R-H249R |
| L082R-V244R | S009A-S024R | V244R-H249R |
| A001R-V244R | V004R-S009A | S078R-H249R |
| N043R-V244R | A001R-S009A | N018R-G115R |
| T022R-V244R | S242R-N269R | G020R-G115R |
| V004R-V244R | S024R-N269R | T022R-G115R |
| G115R-V244R | G020R-N269R | S078R-G115R |
| W241R-V244R | T022R-N269R | S009A-G115R |
| S242R-V244R | H249R-N269R | V004R-G115R |
| A001R-V004R | S212F-N269R | A001R-G115R |
| S009A-T022R | N043R-N269R | L082R-G115R |
| N018R-T022R | V244R-N269R | N043R-G115R |
| G020R-T022R | A001R-N269R | S024R-G115R |
| V004R-T022R | N018R-N269R | S009A-G020R |
| A001R-T022R | S078R-N269R | N018R-G020R |
| S024R-S242R | S009A-N269R | V004R-G020R |
| N018R-S242R | G115R-N269R | A001R-G020R |
| V004R-S242R | W241R-N269R | S009A-E271L |
| G020R-S242R | V004R-N269R | G020R-E271L |
| S212F-S242R | L082R-N269R | S024R-E271L |

TABLE 21-2-continued

WCE1 Variants with Performance Indices of at least 0.2 Relative to GG36 in Any One of TCA, LAS/EDTA Stability, or BMI Microswatch Cleaning at 16° C. in Detergents 10 or 11.
GG36 Variant (BPN' Numbering)

| | | |
|---|---|---|
| L082R-S242R | N018R-N043R | V244R-E271L |
| S078R-S242R | G020R-N043R | W241R-E271L |
| A001R-S242R | V004R-N043R | N043R-E271L |
| S009A-S242R | T022R-N043R | T022R-E271L |
| T022R-S242R | S009A-N043R | H249R-E271L |
| G115R-S242R | A001R-N043R | S212F-E271L |
| N043R-S242R | S024R-N043R | G115R-E271L |
| W241R-S242R | S009A-N018R | S242R-E271L |
| N018R-S212F | V004R-N018R | S078R-E271L |
| T022R-S212F | A001R-N018R | V004R-E271L |
| V004R-S212F | S024R-L082R | N269R-E271L |
| S024R-S212F | S009A-L082R | A001R-E271L |
| A001R-S212F | N018R-L082R | N018R-E271L |
| | | L082R-E271L |

Example 22

Construction and Cleaning Performance of NHJ4 Set of GG36 Variants

The NHJ4 set of GG36 variants described in Table 22-1 below were constructed using the pHPLT-GG36 *B. subtilis* expression plasmid (FIG. 6) using PCR fusion or the QUIKCHANGE® Multi Site-directed mutagenesis kit ("QCMS kit"; Stratagene) as described below.

a) Construction of NHJ4 Variants by QUIKCHANGE® Multi Site-Directed Mutagenesis

Variants created using the QUIKCHANGE® Multi Site-Directed Mutagenesis are shown in Table 22-1. The parent plasmid pHPLT-GG36 (template DNA) was methylated using two micrograms of DNA and Dam methylase (NEB), according to the manufacturer's instructions. Site-directed mutants were made by a QuikChange® Multi Site-Directed Mutagenesis Kit ("QCMS kit"; Stratagene) following the manufacturer's protocol. The following mutations were introduced in the parent plasmid S101A-S103G-V104L, G159E, T22A, Y209E, E271F, S101A, S103G, L111V, S128N, N62E, and S188D, For efficient transformation of *B. subtilis*, DNA from the QCMS reaction mixtures was amplified by rolling circle amplification (RCA) using the Illustra Templiphi kit (GE Healthcare) and the reaction was performed according to the manufacturer's protocol. One microliter of ten-fold diluted amplified DNA was used to transform 50 μL of competent *B. subtilis* cells (genotype: ΔaprE, ΔnprE, amyE::xylRPxylAcomK-phleo). The transformation mixture was shaken at 37° C. for 1 hour. Ten microliter aliquots of the transformation mixture were plated on skim milk (1.6%) Luria agar plates supplemented with 10 μg/ml of neomycin (Teknova). Subsequently, the colonies with halos were inoculated in 120 μl of LB media containing 10 μg/mL neomycin for plasmid DNA extraction (QIAprep Spin Miniprep kit, Qiagen). The extracted plasmids were sequenced to confirm the presence of the desired mutations.

b) Construction of NHJ4 Variants by Extension PCR

Ten combinatorial mutants of GG36 were created by extension PCR. The list of mutations introduced in the GG36 gene contained in the pHPLT plasmid were T22A, N62E, S103G, S103G-L111V, S101G-S103A-V104I, S101A-S103G-V104L, S101A, S128N, G159D, G159E, Y209E, and L111V. To create each mutant, PCR fragments containing the desired mutations were amplified using mutagenic primers as well as forward and reverse primers to amplify the entire GG36 variant. Each PCR amplification reaction contained 30 pmol of each mutagenic primer and 100 ng of the DNA template, pHPLT-GG36 plasmid. Amplifications were carried out using Vent DNA polymerase (NEB). The PCR reaction (20 µL) was initially heated at 95° C. for 2.5 min followed by 30 cycles of denaturation at 94° C. for 15 sec., annealing at 55° C. for 15 sec. and extension at 72° C. for 1 min. Following amplification, 2 to 4 PCR fragments for each variant were gel-purified, using a QIAGEN® gel-band purification kit and mixed (50 ng of each fragment). These mixtures served as DNA templates for the extension PCR to generate the full-length gene fragments. The PCR conditions were same as described above, except the extension phase, which was carried out at 72° C. for 2 min. The full-length DNA fragment was gel-purified using a QIAGEN® gel-band purification kit, digested with the BamHI and HindIII restriction enzymes and ligated with the pHPLT-GG36, which was digested with the same restriction enzymes. One microliter of the ligation mixtures was amplified using rolling circle amplification by Illustra Templiphi kit according to the manufacturer's instructions (GE Healthcare) to generate multimeric DNA for transformation into *Bacillus subtilis*. Products of the rolling circle amplification were diluted 100-times and used to transform *B. subtilis* cells (genotype: ΔaprE, ΔnprE, amyE::xylRPxylA-comK-phleo). An aliquot of the transformation mix was plated on LB plates containing 1.6% skim milk and 10 µg/mL neomycin and incubated overnight at 37° C. Subsequently, the colonies with halos were inoculated in 120 µl of Luria broth medium containing 10 µg/mL neomycin for plasmid DNA extraction (QIAprep Spin Miniprep kit, Qiagen). The extracted plasmids were sequenced to confirm the presence of the desired mutations. Variants created by the extension PCR are shown in Table 22-1.

To express the NHJ4 set of variant proteins for further biochemical analyses, the *B. subtilis* strains carrying the variant plasmids were inoculated into microliter plates containing 150 µl Luria broth medium supplemented with 10 µg/ml neomycin. The cultures were grown up for protein expression as described in Example 20, and they were filtered through a micro-filter plate (0.22 µm; Millipore) also as described in Example 20. The resulting filtrate was used for biochemical analysis. The eglin c inhibition assay for protein content determination and BMI microswatch assays tested in various detergents were carried out as described in Example 19. Performance indices are also calculated as described under the BMI assay description of Test Methods 4-6 further detailed in Example 19. Table 22-1 provides information regarding these multiple mutation variants and the results obtained for them. The PI values are relative to GG36. In the following Tables, the detergent compositions ("Det.") correspond to those shown in Table 19-4, above. Also, as indicated, the amino acid position is listed according to BPN' numbering.

TABLE 22-1

NHJ4 Multiple Mutation Variants with BMI Cleaning Performance Indices of at Least 0.2 Relative to GG36 in Detergents 7, 8 or 9 at 16° C.

| Variant Name | Created by | Mutations, (BPN' Numbering) GG36 |
|---|---|---|
| NHJ4-1 | Extension PCR | S101G S103A V104I |
| NHJ4-10 | Extension PCR | T22A S101A Y209E |
| NHJ4-11 | Extension PCR | S103G L111V G159E |
| NHJ4-12 | Extension PCR | T22A S103G G159E |
| NHJ4-13 | QCMS | T22A L111V G159E |
| NHJ4-14 | QCMS | T22A S128N E271F Y209E |
| NHJ4-15 | QCMS | T22A S103G L111V |
| NHJ4-16 | QCMS | N62E L111V S128N |
| NHJ4-17 | QCMS | T22A L111V S128N |
| NHJ4-18 | Extension PCR | T22A N62E L111V |
| NHJ4-19 | QCMS | S101A S103G V104L S188D |
| NHJ4-2 | Extension PCR | S101G S103A V104I G159D |
| NHJ4-20 | Extension PCR | S101A S103G V104L S128N |
| NHJ4-24 | QCMS | T22A S101A G159E |
| NHJ4-3 | Extension PCR | S101A S103G V104L |
| NHJ4-4 | Extension PCR | S101A S103G V104L G159E |
| NHJ4-5 | Extension PCR | T22A S101A S103G V104L |
| NHJ4-6 | QCMS | S101A S103G V104L Y209E |
| NHJ4-7 | QCMS | T22A Y209E E271F |
| NHJ4-8 | QCMS | T22A S101A E271F |
| NHJ4-9 | QCMS | S101A Y209E E271F |

Example 23

Construction and Cleaning Performance of NHJ3 Set of GG36 Variants

Figure 7:
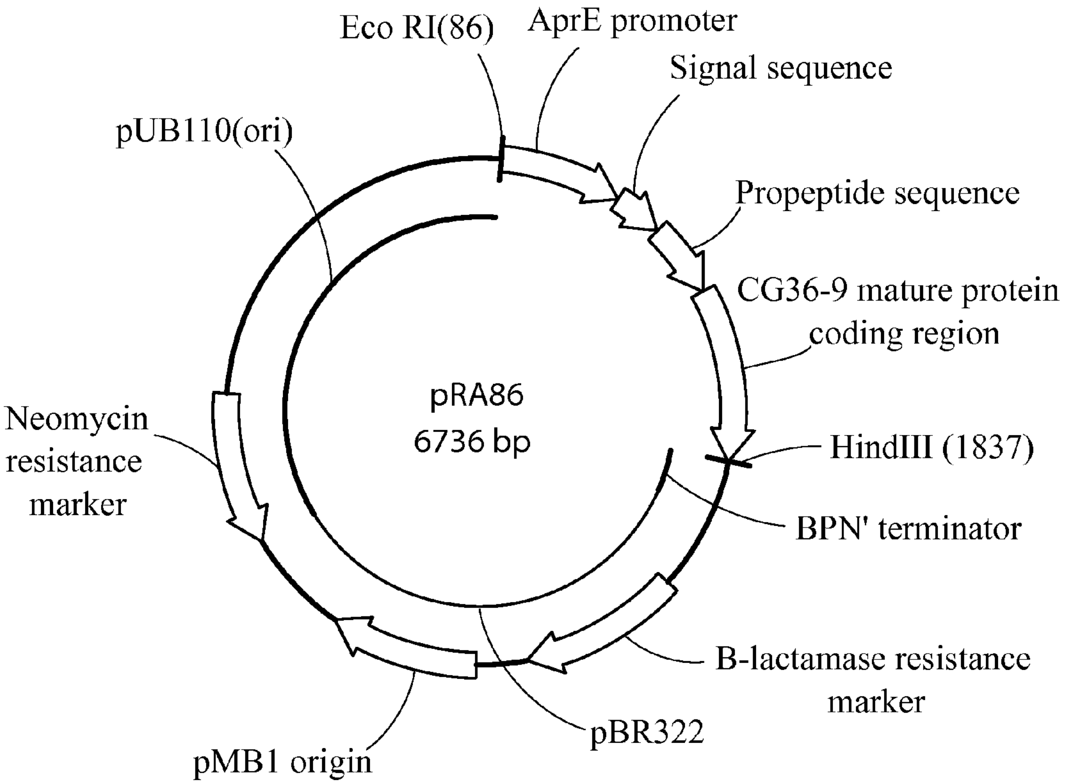
FIG. 7 provides a map of pRA68.

The NHJ3 set of variants described herein are based on a variant of GG36 (referred to as GG36-9) containing the following mutations: S101G, S103A, V104I, G159D, A232V, Q236H, Q245R, N248D, and N252K (BPN' numbering). These variants were created using the QUIKCHANGE® Lightning Site-Directed Mutagenesis Kit (QCLDS kit; Stratagene), with the pRA68 plasmid (see FIG. 7) as the DNA template. Plasmid pRA68 was derived from the pBN3 vector (see Babe et al., Biotech. Appl. Biochem. 27:117-124 [1998]).

The DNA sequence of GG36-9 variant (the signal sequence is shown in lower case letters, propeptide in lower case, underlined text, and GG36-9 mature sequence in upper-case letters) is provided below:

```
                                      (SEQ ID NO: 762)
Gtgagaagcaaaaaattgtggatcgtcgcgtcgaccgcactactcatttc

tgttgcttttagttcatcgatcgcatcggctgctgaagaagcaaaagaaa

aatatttaattggctttaatgagcaggaagctgtcagtgagtttgtagaa

caagtagaggcaaatgacgaggtcgccattctctctgaggaagaggaagt

cgaaattgaattgcttcatgaatttgaaacgattcctgttttatccgttg

agttaagcccagaagatgtggacgcgcttgaactcgatccagcgatttct

tatattgaagaggatgcagaagtaacgacaatgGCGCAATCAGTGCCATG

GGGAATTAGCCGTGTGCAAGCCCCGGCTGCCCATAACCGTGGATTGACAG

GTTCTGGTGTAAAAGTTGCTGTCCTCGATACAGGTATTTCCACTCATCCA

GACTTAAATATTCGTGGTGGCGCTAGCTTTGTACCAGGGGAACCATCCAC

TCAAGATGGGAATGGGCATGGCACGCATGTGGCCGGGACGATTGCTGCTC

TAAACAATTCGATTGGCGTACTTGGCGTAGCGCCGAGCGCGGAACTATAC

GCTGTTAAAGTATTAGGGGCGAGCGGTGGGGGCGCCATCAGCTCGATTGC

CCAAGGATTGGAATGGGCAGGGAACAATGGCATGCACGTTGCTAATTTGA

GTTTAGGAAGCCCTTCGCCAAGTGCCACACTTGAGCAAGCTGTTAATAGC
```

-continued

GCGACTTCTAGGGGCGTTCTTGTTGTAGCGGCATCTGGAAATTCGGGTGC

AGACTCAATCAGCTATCCGGCCCGTTATGCGAACGCAATGGCAGTCGGAG

CTACTGACCAAAACAACAACCGCGCCAGCTTTTCACAGTATGGCGCAGGG

CTTGACATCGTCGCACCAGGTGTAAACGTGCAGAGCACATACCCAGGTTC

AACGTATGCCAGCTTAAACGGTACATCGATGGCTACTCCTCATGTTGCAG

GTGCAGCAGTCCTTGTTAAACATAAGAACCCATCTTGGTCCAATGTACGA

ATCCGCGATCATCTAAAGAAAACGGCAACGAGCTTAGGAAGCACGAACTT

GTATGGAAGCGGACTTGTCAATGCCGAAGCTGCAACTCGTTAA

The protein sequence of the GG36-9 variant (the signal sequence is shown in lower case letters, propeptide in lower case, underlined text, and GG36-9 mature protease sequence in uppercase letters) is provided below:_

(SEQ ID NO: 763)

vrskklwivastallisvafsssiasa<u>aeeakekyligfneqeavsefv</u>

<u>eqveandevailseeeeveiellhefetipvlsvelspedvdaleldpa</u>

<u>isyieedaevttm</u>AQSVPWGISRVQAPAAHNRGLTGSGVKVAVLDTGIS

THPDLNIRGGASFVPGEPSTQDGNGHGTHVAGTIAALNNSIGVLGVAPS

AELYAVKVLGASGGGAISSIAQGLEWAGNNGMHVANLSLGSPSPSATLE

QAVNSATSRGVLVVAASGNSGADSISYPARYANAMAVGATDQNNNRASF

SQYGAGLDIVAPGVNVQSTYPGSTYASLNGTSMATPHVAGAAVLVKHKN

PSWSNVRIRDHLKKTATSLGSTNLYGSGLVNAEAATR

To create the NHJ3 variants using the QCLSD kit, mutagenic primers were designed for each of the variants according to the manufacturer's protocol. The mutagenesis reaction for each variant consisted of 0.5 µl of 10× Buffer, 0.5 µL of pRA68 plasmid DNA (168 ng/µL), 0.5 µl forward mutagenic primer (25 µM), 0.5 µl reverse mutagenesis primer (25 µM), 1 µl dNTPs (supplied in the QCLSD kit), 1.5 µl Quik solution (supplied in the QCLMS kit), 1 µl Enzyme blend (supplied in the QCLSD kit), and 40 µl of distilled, deionized water to make up a 50 µL reaction volume as per the manufacturer's instructions. The cycling program was 1 cycle at 95° C. for 2 minutes, 18 cycles of 95° C. for 20 seconds, 60° C. for 10 seconds and 68° C. for 3 minutes, 22 seconds, and a final cycle of 68° C. for 5 minutes. Next, 1 µL of DpnI restriction enzyme supplied in the kit was used to digest the plasmid DNA in the reaction, and then 2 µL of the reaction was used to transform TOP 10 *E. coli* competent cells (Invitrogen). The *E. coli* transformants were selected on Luria broth medium plates containing 50 µg/mL(ppm) carbenicillin after overnight growth at 37° C. Plasmid DNA was extracted from 4-8 *E. coli* colonies grown in LA medium containing 50 µg/mL(ppm) carbenicillin using the QIAprep spin miniprep kit (Qiagen). The plasmids were sequenced to confirm the presence of the desired mutations. The variant plasmids were then transformed into *B. subtilis* cells as described in Example 20. The *B. subtilis* variant strains were grown up as described in Example 20 for further biochemical analysis, such as protein content determination using the eglin c inhibition assay (Example 19) and a BMI microswatch cleaning assay (Test Methods 4-6, Example 19). The results are provided below in Tables 23-1 and 23-2. The PIs are relative to GG36. In the following Tables, the detergent compositions ("Det.") correspond to those shown in Table 19-4, above. Also, as indicated, the amino acid position is listed according to BPN' numbering.

TABLE 23-1

NHJ3 Multiple Mutation Variants with BMI Cleaning Performance Indices of at Least 1.1 Relative to GG36 in Detergents 7, 8, or 9 at 16° C.

| Variant | Variant Sequence Relative to GG36 (Using BPN' Numbering) GG36 |
|---|---|
| NHJ3-1 | S103A-V104I-G159D-A232V-Q236H-Q245R-N248D-N252K |
| NHJ3-2 | S101G-V104I-G159D-A232V-Q236H-Q245R-N248D-N252K |
| NHJ3-3 | S101G-S103A-G159D-A232V-Q236H-Q245R-N248D-N252K |
| NHJ3-4 | S101G-S103A-V104L-A232V-Q236H-Q245R-N248D-N252K |
| NHJ3-5 | S101G-S103A-V104L-G159D-Q236H-Q245R-N248D-N252K |
| NHJ3-6 | S101G-S103A-V104L-G159D-A232V-Q245R-N248D-N252K |
| NHJ3-7 | S101G-S103A-V104L-G159D-A232V-Q236H-N248D-N252K |
| NHJ3-8 | S101G-S103A-V104L-G159D-A232V-Q236H-Q245R-N252K |
| NHJ3-9 | S101G-S103A-V104L-G159D-A232V-Q236H-Q245R-N248D |

TABLE 23-2

NHJ3 Multiple Mutation Variants with BMI Cleaning Performance Indices of at Least 0.3 Relative to GG36 in Detergents 10 or 11 at 16° C.

| Variant | Variant Sequence Relative to GG36 (Using BPN' Numbering) GG36 |
|---|---|
| NHJ3-1 | S103A-V104I-G159D-A232V-Q236H-Q245R-N248D-N252K |
| NHJ3-2 | S101G-V104I-G159D-A232V-Q236H-Q245R-N248D-N252K |
| NHJ3-3 | S101G-S103A-G159D-A232V-Q236H-Q245R-N248D-N252K |
| NHJ3-4 | S101G-S103A-V104L-A232V-Q236H-Q245R-N248D-N252K |
| NHJ3-5 | S101G-S103A-V104L-G159D-Q236H-Q245R-N248D-N252K |
| NHJ3-6 | S101G-S103A-V104L-G159D-A232V-Q245R-N248D-N252K |
| NHJ3-7 | S101G-S103A-V104L-G159D-A232V-Q236H-N248D-N252K |
| NHJ3-8 | S101G-S103A-V104L-G159D-A232V-Q236H-Q245R-N252K |
| NHJ3-9 | S101G-S103A-V104L-G159D-A232V-Q236H-Q245R-N248D |

Example 24

Construction and Cleaning Performance of NHJ5 Set of GG36 Variants

Figure 8:
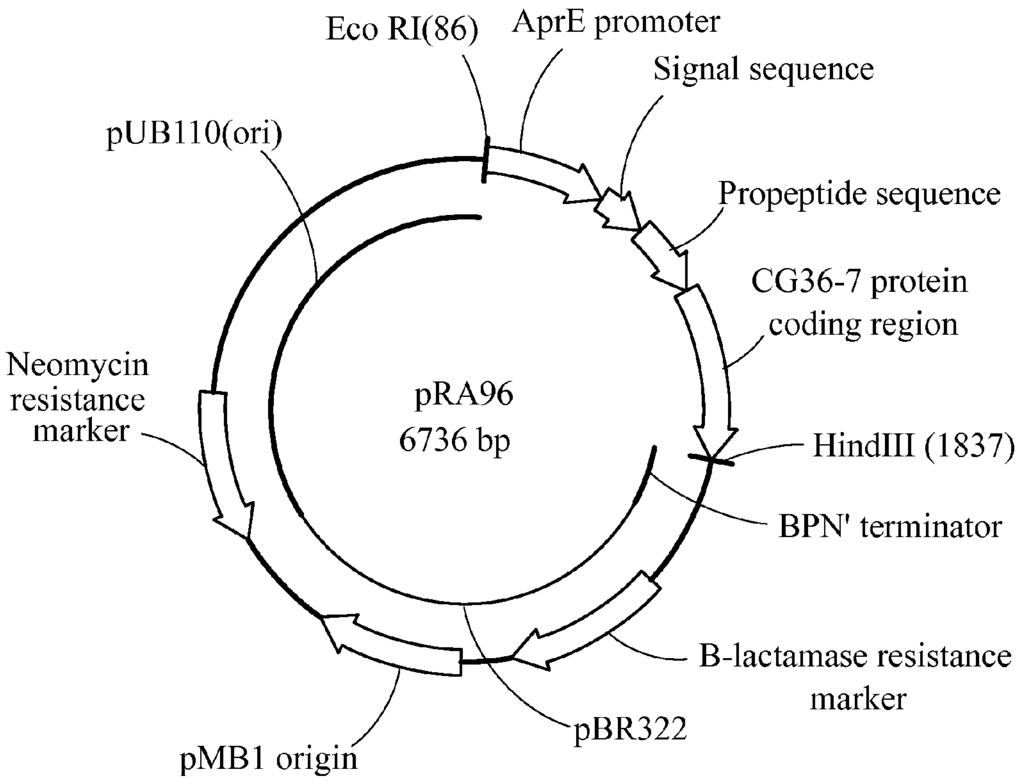
FIG. 8 provides a map of pRA96.

The NHJ5 set of variants described herein are based on a variant of GG36 (referred to as GG36-7) containing the following mutations: S101G, S103A, V104I, G159D, A232V, Q245R, N248D, and (BPN' numbering). These variants were created using the QUIKCHANGE®Lightning Multi Site-Directed Mutagenesis Kit ("QCLMS kit") with the pRA96 plasmid as the DNA template (see FIG. 8). The mutations incorporated included: H243R(H249R), E265F (E271F), D157E (D159E), A156E (A158E), A156E-D157G (A158E-D159E), T22A, N60E (N62E), N232R(N238R), D242R (D248R), T247R (T253R), S24R, N74D (N76D) {GG36 Numbering and BPN' Numbering Shown in Parentheses.

The variants were generated using the methods described in Example 23. The *B. subtilis* variant strains were grown up as described in Example 20 for further biochemical analysis, such as protein content determination using the eglin c inhibition assay (Example 19) and the BMI microswatch cleaning assay (Example 19). The results are provided below in Table 24-1. The PI values are relative to GG36. In the following Tables, the detergent compositions ("Det.") correspond to those shown in Table 19-4, above. Also, as indicated, the amino acid position is listed according to BPN' numbering.

The DNA sequence of GG36-7 variant (the signal sequence is shown in lower case letters, propeptide in lower case, underlined text, and GG36-7 mature protease sequence in uppercase letters) is provided below:_

(SEQ ID NO: 764)

gtgagaagcaaaaaattgtggatcgtcgcgtcgaccgcactactcattt
ctgttgcttttagttcatcgatcgcatcggctgctgaagaagcaaaaga
aaaatatttaattggctttaatgagcaggaagctgtcagtgagtttgta
gaacaagtagaggcaaatgacgaggtcgccattctctctgaggaagagg
aagtcgaaattgaattgcttcatgaatttgaaacgattcctgttttatc
cgttgagttaagcccagaagatgtggacgcgcttgaactcgatccagcg
atttcttatattgaagaggatgcagaagtaacgacaatgGCGCAATCAG
TGCCATGGGGAATTAGCCGTGTGCAAGCCCCGGCTGCCCATAACCGTGG
ATTGACAGGTTCTGGTGTAAAAGTTGCTGTCCTCGATACAGGTATTTCC
ACTCATCCAGACTTAAATATTCGTGGTGGCGCTAGCTTTGTACCAGGGG
AACCATCCACTCAAGATGGGAATGGGCATGGCACGCATGTGGCCGGGAC
GATTGCTGCTCTAAACAATTCGATTGGCGTACTTGGCGTAGCGCCGAGC
GCGGAACTATACGCTGTTAAAGTATTAGGGGCGAGCGGTGGGGGCGCCA
TCAGCTCGATTGCCCAAGGATTGGAATGGGCAGGGAACAATGGCATGCA
CGTTGCTAATTTGAGTTTAGGAAGCCCTTCGCCAAGTGCCACACTTGAG
CAAGCTGTTAATAGCGCGACTTCTAGGGGCGTTCTTGTTGTAGCGGCAT
CTGGAAATTCGGGTGCAGACTCAATCAGCTATCCGGCCCGTTATGCGAA
CGCAATGGCAGTCGGAGCTACTGACCAAAACAACAACCGCGCCAGCTTT
TCACAGTATGGCGCAGGGCTTGACATCGTCGCACCAGGTGTAAACGTGC
AGAGCACATACCCAGGTTCAACGTATGCCAGCTTAAACGGTACATCGAT
GGCTACTCCTCATGTTGCAGGTGCAGCAGTCCTTGTTAAACAAAAGAAC
CCATCTTGGTCCAATGTACGAATCCGCGATCATCTAAAGAATACGGCAA
CGAGCTTAGGAAGCACGAACTTGTATGGAAGCGGACTTGTCAATGCCGA
AGCTGCAACTCGT The protein sequence of GG36-7 variant (signal sequence is shown in lower case letters, propeptide in lower case, underlined text, and GG36-7 mature protease sequence in uppercase letters) is provided below:_

(SEQ ID NO: 765)

vrskklwivastallisvafsssiasaaeeakekyligfneqeavsefv
eqveandevailseeeeveiellhefetipvlsvelspedvdaleldpa
isyieedaevttmAQSVPWGISRVQAPAAHNRGLTGSGVKVAVLDTGIS
THPDLNIRGGASFVPGEPSTQDGNGHGTHVAGTIAALNNSIGVLGVAPS
AELYAVKVLGASGGGAISSIAQGLEWAGNNGMHVANLSLGSPSPSATLE
QAVNSATSRGVLVVAASGNSGADSISYPARYANAMAVGATDQNNNRASF
SQYGAGLDIVAPGVNVQSTYPGSTYASLNGTSMATPHVAGAAVLVKQKN
PSWSNVRIRDHLKNTATSLGSTNLYGSGLVNAEAATR

TABLE 24-1

NHJ5 Multiple Mutation Variants with BMI Cleaning Performance Indices of at Least 0.6 Relative to GG36 in Detergents 7-11 at 16° C.

| Variant | Variant Sequence Relative to GG36 (BPN' Numbering) GG36 |
|---|---|
| GG36-7 | S101G-S103A-V104I-G159D-A232V-Q245R-N248D |
| NHJ5-1 | S101G-S103A-V104I-G159D-A232V-Q245R-N248D-E271F |
| NHJ5-2 | S101G-S103A-V104I-G159D-A232V-Q245R-N248D-N238R |
| NHJ5-3 | S101G-S103A-V104I-G159D-A232V-Q245R-N248D-N248R |
| NHJ5-4 | S101G-S103A-V104I-G159D-A232V-Q245R-N248D-T253R |
| NHJ5-5 | S101G-S103A-V104I-G159D-A232V-Q245R-N248D-S24R |
| NHJ5-6 | S101G-S103A-V104I-G159D-A232V-Q245R-N248D-N76D |
| NHJ5-7 | S101G-S103A-V104I-G159E-A232V-Q245R-N248D-H249R |
| NHJ5-8 | S101G-S103A-V104I-G159E-A232V-Q245R-N248D-E271F |
| NHJ5-9 | S101G-S103A-V104I-A158E-A232V-Q245R-N248D-H249R |
| NHJ5-10 | S101G-S103A-V104I-A158E-A232V-Q245R-N248D-E271F |
| NHJ5-11 | T22A-S101G-S103A-V104I-G159D-A232V-Q245R-N248D-H249R |
| NHJ5-12 | T22A-S101G-S103A-V104I-G159D-A232V-Q245R-N248D-E271F |
| NHJ5-13 | N62E-S101G-S103A-V104I-G159D-A232V-Q245R-N248D-H249R |
| NHJ5-14 | N62E-S101G-S103A-V104I-G159D-A232V-Q245R-N248D-E271F |

Example 25

Construction of NHJ2 Combinatorial Library

This Example describes the construction of a GG36 combinatorial library involving one or more of the following mutations: A16S, T22A, S101A, S103G, V104L, L111V, S128N, and L148I (BPN' numbering). The pHPLT-GG36 *B. subtilis* expression plasmid was provided to DNA 2.0 Inc. for the generation of NHJ2 combinatorial library. A ligation reaction of the constructed NHJ2 library was provided by DNA 2.0, Inc. for transformation in the *B. subtilis* strain (genotype: ΔaprE, ΔnprE, amyE::xylRPxylAcomK-phleo). The variants generated containing one or several of the mutations described herein are tested for cold water cleaning applications using methods and detergent compositions described herein.

Example 26

Construction of Additional Libraries and GG36 Variants

Additional libraries and variants are constructed using the following set of mutations: AIR, A230E, E271L, G115R, G20R, H249R, K235F, K27V/F/L, L75E, L82R, N18R, N269R, N43D, N43R, N76D, R45T, S212F, S242R, S24R, S78R, S9A, T22R, V121E, V244R, V28E, V30E, V4R, W241R (BPN' numbering). The variants generated containing one or more of these mutations are tested for cold water cleaning applications using methods and detergent compositions described herein.

Additional sets of GG36 variants are constructed and tested for cold water cleaning applications using methods and detergent compositions described herein include: G20R-N43R-H249R, G20R-T22R-N43R, G20R-N43R-S242R, G20R-N43R-E271L, G20R-N43R-V244R, G20R-S24R-N43R-S242R, S9A-T22R-S78R-S212F-W241R, S9A-G20R-N43R-S212F, S9A-N43R-S212F, G20R-N43R-S212F, G20R-T22R-N43R-S212F, S24R-S78R-S212F, S9A-N43R-S78R, S9A-N43R-S78R-S242R, S9A-G20R-N43R-S78R, G20R-S24R-N43R-S78R-S242R, T22R-S24R-S78R-

S212F, S9A-G20R-N43R-S78R-S242R, G20R-N43R-S78R-H249R, G20R-N43R-S78R, S9A-S78R-S212F, S9A-T22R-N43R-S78R, S9A-G20R-S24R-N43R, S9A-T22R-S78R-S212F, V4R-S9A-T22R-S78R-S212F, G20R-S24R-N43R, A1R-S9A-N43R, G20R-S24R-N43R-G115R, S9A-S24R-N43R, G20R-T22R-S24R-N43R, A1R-S24R-N43R, S9A-G20R-S24R-N43R-S242R, S9A-G20R-T22R-S78R-S212F, S9A-S24R-N43R-V244R, S9A-S24R-N43R-S242R, V4R-S9A-T22R-S24R-S212F and T22R-S24R-N43R (BPN' numbering).

Example 27

Construction and Cleaning Performance of the GG36 Library WCE2

The WCE2 combinatorial library was generated by DNA 2.0, Inc. using the pHPLT-GG36 *B. subtilis* expression plasmid. A ligation reaction of the constructed WCE2 library was provided by DNA 2.0, Inc. for transformation in the *B. subtilis* strain (genotype: ΔaprE, ΔnprE, amyE::xylRPxylAcomK-phleo). The set of mutations used to generate the WCE2 library are A230E, G20R, H249R, N18R, N43R/D, N76D, R45T, S242R, and S24R (BPN' numbering). The variants generated containing one or more of these mutations are tested for cold water cleaning applications using methods and detergent compositions described herein.

Example 28

Construction and Cleaning Performance of the WCE3 Set of GG36 Variants

This Example describes the WCE3 set of mutants based on the GG36 variants, GG36-7 (Example 23) and GG36-9 (Example 22). These variants are: S101G-S103A-V104I-A232V-Q245R-N248D, S101G-S103A-V104I-G159D-A232V-Q245R, S101G-S103A-V104I-G159R-A232V-Q245R-N248D, S101G-S103A-V104I-G159D-A232V-Q245R-N248R, S101G-S103A-V104I-A232V-Q245R, S101G-S103A-V104I-A232V-Q245R-N248R, S101G-S103A-V104I-G159R-A232V-Q245R-N248R, and S101G, S103A, V104I, A232V, Q236H, Q245R, and N252K. They were created using the QuikChange® Lightning Multi Site-Directed Mutagenesis Kit (QCLMS kit; Stratagene) with the pRA96 plasmid as the DNA template described in Example 23. The variants generated will be tested for cold water cleaning applications using methods and detergent compositions described in this application.

Example 29

Construction of Additional Libraries and Variants of GG36

Figure 6:
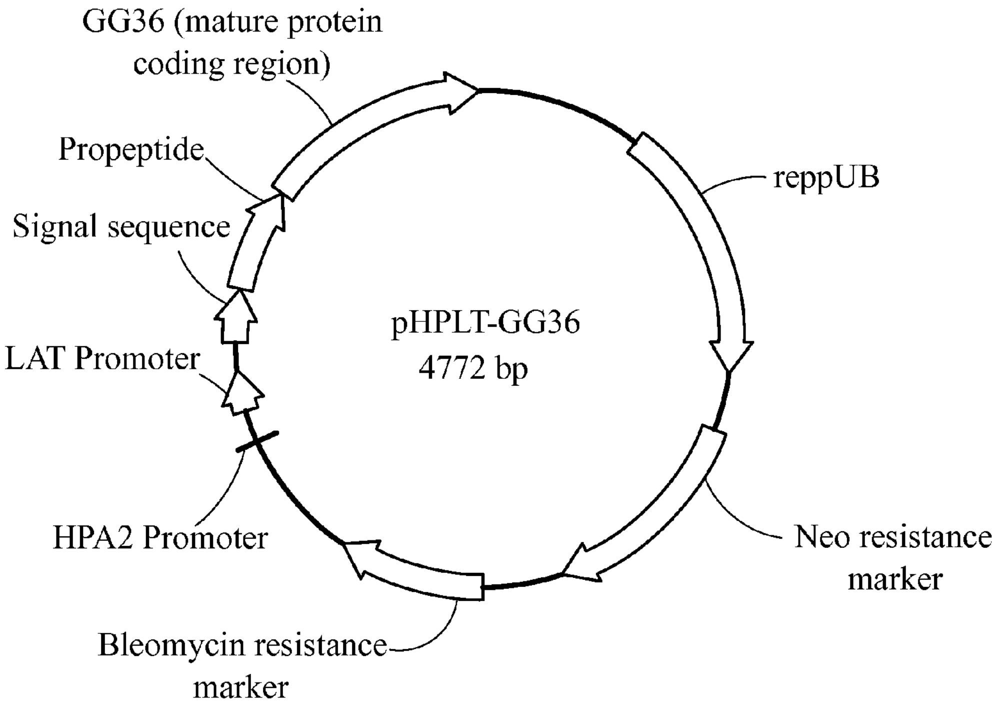
FIG. 6 provides map of pHPLT-GG36.

This Example describes the construction of GG36 variants and libraries using one or more of the following mutations: A16S, T22A, S24R, N62E, N76D, E89P, S101A/G, S103G/A, V104L/I, L111V, S128N, P129E, A232V, L148I, A158E, G159D/E, S166D, R186H, S188D, Y209E, Q236H, N238R, Q245R, N248D/R, H249R, N252K/R, T253R, E271F (BPN' numbering) using a *B. subtilis* expression plasmid (e.g., pHPLT-GG36; FIG. 6). The variants generated containing one or more of these mutations are tested for cold water cleaning applications using methods and detergent compositions described herein.

Example 30

Construction of Additional Libraries and Variants of GG36

This Example describes the construction of GG36 variants and libraries in *B. subtilis* using one or more of the following mutations (BPN' numbering): A1R, Q2S, Q2M, Q2A, Q2R, Q2W, S3R, V4R, V4S, V4C, 18A, S9A, S9F, S9W, R10S, R10A, R10H, R10M, Q12F, Q12R, P14K, P14F, P14Q, A15R, A15F, A16S, H17R, H17M, H17F, N18R, N18K, G20F, G20K, G20R, T22A, T22R, T22Y, T22V, T22Q, T22L, T22W, G23A, G23S, G23F, S24R, S24F, S24W, S24Q, S24H, S24L, G25V, G25F, G25R, V26F, K27L, K27F, K27R, K27V, V28A, V28N, V28E, A29T, V30E, L31F, T33S, T33G, T33D, G34P, 135M, S36T, S36F, S36R, T38L, T38F, T38R, P40N, P40L, P40T, P40W, P40H, P40R, L42I, N43A, N43F, N43I, N43S, N43R, N43M, N43W, N43D, R45T, G46R, A48R, F50C, V51W, V51F, V51H, P52F, P52E, P52N, P55Y, T57R, Q59A, Q59F, Q59R, D60P, D60Q, D60A, N62E, N62Q, G63V, G63M, G63T, G63I, G63A, G63S, G63H, G63Q, G63D, G63E, G63P, H64F, H64T, V68A, V68C, A69N, A69T, A69P, A69W, T71G, 172C, A74C, L75A, L75F, L75E, L75R, N76D, S78R, S78N, S78I, 179W, 179Q, V81R, L82F, L82T, L82V, L82R, L82M, A85M, P86W, P86L, P86I, E89P, E89T, E89G, E89H, E89L, E89V, E89W, E89F, E89I, Y91N, Y91F, A92F, K94N, S99F, S99T, S99P, S99G, S99M, G100S, G100N, G100Q, G100I, S101A, S101N, S101G, S101T, S101D, S101E, S101P, S101F, G102A, G102T, G102N, G102H, G102E, S103G, S103N, S103D, S103A, V104L, V104I, V104E, V104D, S105T, S105E, S105Q, S106G, S106T, S106E, S106D, S106A, S106V, S106F, I107M, I107F, A108I, A108G, Q109M, L111V, L111I, E112V, E112L, E112Q, A114G, G115K, G115R, N116K, N116A, N116L, N117F, G118R, G118I, M119C, H120A, H120F, H120R, V121F, V121E, N123G, N123E, L124S, S128D, S128F, S128L, S128N, S128H, S128M, S128I, S128Q, P129E, S132A, S132E, A138G, S144R, V147L, L148I, A158E, G159D, G159E, G159C, S160D, S166D, S166E, Y167W, M175V, V177C, D181A, Q182R, N183I, N183D, N183M, N183F, N183R, N185E, N185V, N185I, R186H, R186K, S188E, S188D, S188R, Y192H, Y192W, A194E, A194V, A194F, D197F, I198L, I198F, V203E, V203C, T208S, Y209S, Y209N, Y209F, Y209T, Y209E, Y209H, Y209G, Y209L, P210R, P210V, P210L, G211Q, G211R, S212I, S212M, S212F, T213A, Y214F, A215N, A215D, A215E, A215H, A215F, S216F, S216A, L217E, L217N, L217D, N218D, N218P, N218E, T224A, T224G, V227I, A230E, A231I, A231C, A232V, L233C, V234F, K235F, Q236F, Q236N, Q236H, N238R, N238K, N238L, P239K, P239G, P239R, P239H, P239T, P239N, P239S, P239F, S240R, W241R, S242L, S242R, N243F, N243R, V244R, Q245R, I246S, N248D, N248V, N248I, N248R, H249R, H249T, L250I, K251R, K251S, N252I, N252F, N252R, N252K, N252H, T253I, T253R, T253F, A254C, S256N, G258R, T260V, T260I, L262D, L262H, Y263F, S265F, L267V, L267N, L267M, N269I, N269R, A270C, E271I, E271V, E271H, E271M, E271L, E271P, E271A, E271F, E271T, A272F, A272F, A272R, A273F, A273I, and T274G. The variants generated containing one or more of these mutations are tested for cold water cleaning applications using methods and detergent compositions described herein.

Example 31

Cleaning Performance Assay on BMI Swatch at 60F (Test Method 2)

The stain removal performance of the protease variants was determined in commercially available detergents (unless otherwise stated). Heat inactivation of commercial detergent formulas serves to destroy the enzymatic activity of any protein components while retaining the properties of non-enzymatic components. Thus this method was suitable for preparing commercially purchased detergents for use in testing the enzyme variants of the present invention.

Microswatches:

Microswatches of ¼" circular diameter were ordered and delivered by CFT (Vlaardingen, The Netherlands). Single microswatches or two microswatches were placed vertically in each well of a 96-well MTP to expose the whole surface area (i.e., not flat on the bottom of the well).

BMI Microswatch Assay

Microswatches containing blood milk and ink (BMI) of 0.25 inch circular diameter were obtained from CFT. Before cutting of the swatches, the fabric (EMPA 116) was washed with water. One microswatch was vertically placed in each well of a 96-well microtiter plate (hereinafter referred to as MTP) in order to expose the whole surface area (i.e., not flat on the bottom of the well). The desired detergent solution was prepared as described herein. After equilibrating the Thermomixer at 25° C., 190 μl of detergent solution was added to each well of the MTP, containing microswatches. To this mixture, 10 μl of the diluted enzyme solution was added so that the final enzyme concentration was 1 μg/ml (determined from TCA assay). The MTP was sealed with tape and placed in the incubator for 30 minutes, with agitation at 1400 rpm. Following incubation under the appropriate conditions, 100 μl of the solution from each well was transferred into a fresh MTP. The new MTP containing 100 μl of solution/well was read at 405 nm using a MTP SpectraMax reader. Blank controls, as well as a control containing two microswatches and detergent but no enzyme were also included.

"Pre-Washed" Swatch

This type of microswatch was pre-washed in deionised water for 20 minutes at ambient temperature. After the pre-washing step, the swatches were put on top of paper towels to dry. The air-dried swatches were then punched using a ¼" circular die on an expulsion press. Finally two microswatches were put into each well of a 96-well MTP vertically to expose the whole surface area (i.e. not flat on the bottom of the well).

Detergents

For North American (NA) and Western European (WE) heavy duty liquid laundry (HDL) detergents, heat inactivation was performed by placing pre-weighed liquid detergent (in a glass bottle) in a water bath at 95° C. for 2 hours. All detergents were purchased from local supermarket stores. Both un-heated and heated detergents were assayed within 5 minutes of dissolving the detergent to accurately determine percentage deactivated. Enzyme activity was tested by the AAPF assay.

For testing of enzyme activity in heat-inactivated detergents, working solutions of detergents were made from the heat inactivated stocks. Appropriate amounts of water hardness (for instance 6 gpg for NA HDL and 12 gpg for WE HDL) and buffer were added to the detergent solutions to match the desired conditions as specified in Table 31-1 below. The solutions were mixed by vortexing or inverting the bottles.

TABLE 31-1

Laundry and Dish Washing Conditions

| Region | Form | Dose | Detergent* | Buffer | gpg | pH | T (° C.) |
|---|---|---|---|---|---|---|---|
| Laundry (heavy duty liquid and granular) | | | | | | | |
| NA | HDL | 0.78 g/l | P&G TIDE ® 2X | 5 mM HEPES | 6 | 8.0 | 20 |
| WE | HDL | 5.0 g/L | Henkel Persil | 5 mM HEPES | 12 | 8.2 | 40 |
| JPN | HDG | 0.7 g/L | P&G TIDE ® | 2 mM $Na_2CO_3$ | 6 | 10.0 | 20 |

*Abbreviations: Procter & Gamble (P&G);

Enzymes and Equipment

Samples of reference serine proteases variants thereof were obtained from filtered culture broth of cultures grown in MTP plates. The equipment used was a Biomek FX Robot (Beckman Coulter), a SpectraMAX MTP Reader (type 340; Molecular Devices), an iEMS incubator/shaker (Thermo/Labsystems); F-bottom MTPs (Costar type 9017 used for reading reaction plates after incubation); and V-bottom MTPs (Greiner 651101 used for pre-dilution of supernatant). In this assay, the proteases hydrolyze the substrate and liberate pigment and insoluble particles from the substrate. Thus the rate of turbidity is a measure of enzyme activity.

The stain removal performance of reference serine proteases and variants therefrom on microswatches was determined on a MTP scale in commercially available heat-inactivated detergent. The reagents used were: 5 mM HEPES, pH 8.0 or 5 mM MOPS, pH 7 buffer, 3:1 Ca:Mg for medium water hardness. ($CaCl_2$: $MgCl_2.6H_2O$); 15000 grains per gallon (gpg) stock diluted to 6 gpg, 2 BMI (blood/milk/ink) swatches per plate: EMPA-116 BMI cotton swatches processed by CFT: pre-rinsed and punched 2 swatches per well, and heat inactivated TIDE® 2× Cold off-the-shelf detergent in which lack of protease activity was confirmed.

TABLE 31-2

Working Detergent Solutions

| Detergent | Temp (C.) | Detergent g/L | pH | Buffer | gpg | Protease |
|---|---|---|---|---|---|---|
| TIDE ® 2X Cold | 16 | 0.98 | 8 | 5 mM HEPES | 6 | BPN' |
| TIDE ® 2X Cold | 32 | 0.98 | 8 | 5 mM HEPES | 6 | BPN' |
| TIDE ® 2X Cold | 16 | 0.98 | 7 | 5 mM MOPS | 6 | BPN' |

The incubator was set at the desired temperature (16° C. or 32° C.). 10 μL samples from the master dilution plate of ~10 ppm enzyme was added to BMI 2-swatch plates with 190 μL working detergent solutions listed above. The volume was adjusted to give final concentration of 0.5 ppm for variants in the assay plates. The plates were immediately transferred to iEMS incubators and incubated for 30 minutes with 1400 rpm shaking at given temperature. Following incubation, 100 μL of supernatant was transferred into a new 96-well plate and the absorbance was measured in MTP Reader at 405 nm and/or 600 nm. Control wells, containing 1 or 2 microswatches and detergent without the addition of protease samples were also included in the test. The measurement at 405 nm provides a higher value and tracks pigment removal, while the measurement at 600 nm tracks turbidity and cleaning.

Calculation of the Stain Removal Activity for all Microswatch Assay Methods:

The absorbance value obtained was corrected for the blank value (substrate without enzyme), providing a measure of hydrolytic activity. For each sample (variant) the performance index was calculated. The performance index compares the performance of the variant (actual value) and the standard enzyme (theoretical value) at the same protein concentration. In addition, the theoretical values can be calculated, using the parameters of the Langmuir equation of the standard enzyme.

Performance Index

The performance index compares the performance of the variant (actual value) and the standard or reference protease (theoretical value) at the same protein concentration. In addition, the theoretical values can be calculated, using the parameters of the binding curve (i.e., Langmuir equation) of the standard protease. A performance index (PI) that is greater than 1 (PI>1) identifies a better variant as compared to the standard (e.g., wild-type), while a PI of 1 (PI=1) identifies a variant that performs the same as the standard, and a PI that is less than 1 (PI<1) identifies a variant that performs worse than the standard. Thus, the PI identifies winners, as well as variants that are less desirable for use under certain circumstances.

TCA Assay for Protein Content Determination in 96-Well Microtiter Plates

For BPN' (e.g., reference protease) and BPN' variants, this assay was started using filtered culture supernatant from microtiter plates grown 3-4 days at 33° C. with shaking at 230 rpm and humidified aeration. A fresh 96-well flat bottom microtiter plate (MTP) was used for the assay. First, 100 μL/well of 0.25N HCl was placed in each well. Then, 50 μL of filtered culture broth was added. The light scattering/absorbance at 405 nm (use 5 sec mixing mode in the plate reader) was then determined, in order to provide the "blank" reading. For the test, 100 μL/well of 15% (w/v) trichloroacetic acid (TCA) was placed in the plates and incubated between 5 and 30 min at room temperature. The light scattering/absorbance at 405 nm (use 5 sec mixing mode in the plate reader) was then determined.

The equipment used was a Biomek FX Robot (Beckman Coulter) and a SpectraMAX (type 340; Molecular Devices) MTP Reader; the MTP's were from Costar (type 9017). The equipment used was a Biomek FX Robot (Beckman Coulter) and a SpectraMAX type 340 (Molecular Devices) MTP Reader; and the MTPs were type 9017 (Costar).

The calculations were performed by subtracting the blank (no TCA) from the test reading with TCA to provide a relative measure of the protein content in the samples. If desired, a standard curve can be created by calibrating the TCA readings with AAPF assays of clones with known conversion factors. However, the TCA results are linear with respect to protein concentration from 50 micrograms to 500 micrograms protein per ml (ppm) and can thus be plotted directly against enzyme performance for the purpose of choosing good-performing variants. The turbidity/light scatter increase in the samples correlates to the total amount of precipitable protein in the culture supernatant.

AAPF Protease Assay in 96-Well Microtiter Plates

In order to determine the protease activity of the proteases and variants thereof of the present invention, the hydrolysis of N-succinyl-L-alanyl-L-alanyl-L-prolyl-L-phenyl-p-nitroanilide (suc-AAPF-pNA) was measured. The reagent solutions used were: 100 mM Tris/HCl, pH 8.6, containing 0.005% TWEEN®-80 (Tris dilution buffer); 100 mM Tris buffer, pH 8.6, containing 10 mM $CaCl_2$ and 0.005% TWEEN®-80 (Tris/Ca buffer); and 160 mM suc-AAPF-pNA in DMSO (suc-AAPF-pNA stock solution) (Sigma: S-7388). To prepare a suc-AAPF-pNA working solution, 1 ml suc-AAPF-pNA stock solution was added to 100 ml Tris/Ca buffer and mixed well for at least 10 seconds. The assay was performed by adding 10 μl of diluted protease solution to each well, immediately followed by the addition of 190 μl 1 mg/ml suc-AAPF-pNA working solution. The solutions were mixed for 5 sec., and the absorbance change in kinetic mode (20 readings in 5 minutes) was read at 410 nm in an MTP reader, at 25° C. The protease activity was expressed as AU (activity=$\Delta OD \cdot min^{-1} ml^{-1}$).

Stability Assay

The stability of protease variants was determined in the presence of 40% concentrated solution of detergent composition 3 shown in Table 1-3 diluted in water. The reagents used were the detergent composition 3 shown in Table 1-3 diluted to 50% in Milli-Q water, 10 mM MES 0.01% Tween 80 pH 5.8 master dilution buffer, AAPF reagents: see protocol AAPF assay. The equipment used was F-bottom MTP (Corning 9017) for dilution of diluted enzyme into detergent as well as for suc-AAPF-pNA plates, Biomek FX (Beckman Coulter), Spectramax Plus 384 MTP Reader (Molecular Devices), iEMS Incubator/Shaker (1 mm amplitude) (Thermo Electron Corporation), sealing tape: Nunc (236366), Circulating Reservoir (Beckman Fx).

The detergent composition 3 shown in Table 1-3 was initially diluted to 50% in water. This detergent was kept at room temperature and cycled through the circulating reservoir. The iEMS incubators/shakers (Thermo/Labsystems) were pre-set at 43°. Culture supernatants were diluted into plates containing master dilution buffer to a concentration of ~20 ppm (master dilution plate). 40 μl of sample from the master dilution plate was added to plates containing 160 μl 50% detergent composition 3 shown in Table 1-3 to give a final incubation concentration of 4 ppm. The contents were mixed and kept at room temperature and triplicate AAPF assays were performed immediately on these plates and recorded as unstressed reads. The AAPF assay was modified such that 20 μL of sample from the step above was added to 190 μL of suc-AAPF-pNA working solution. The plates were immediately covered with sealing tape and placed in 43° C. iEMS shakers for 30 min at 650 rpm. Following 30 minutes of incubation, triplicate AAPF assays were performed on these stress plates and recorded as stressed reads. The stability of the samples was determined by calculating the ratio of the residual and initial AAPF activity as follows: Residual Activity (%)=[mOD·min-1 stressed]*100/[mOD·min-1 unstressed].

LAS/EDTA Stability Assay

The stability of protease variants in the presence of a representative anionic surfactant (LAS=linear alkylbene sulfonate, sodium dodecylbenzenesulfonate-DOBS) and di-sodium EDTA was measured after incubation under defined conditions and the residual activity was determined using the AAPF assay. The reagents used were dodecyllbenzene sulfonate, sodium salt (DOBS, Sigma No. D-2525), TWEEN®-80 (Sigma No. P-8074), di-sodium EDTA (Siegfried Handel No. 164599-02), HEPES (Sigma No. H-7523), unstress buffer: 50 mM HEPES (11.9 g/l)+0.005% TWEEN®-80, pH 8.0, Stress buffer: 50 mM HEPES (11.9 g/l), 0.1% (w/v) DOBS (1 g/l), 10 mM EDTA (3.36 g/l), pH 8.0, reference protease and protease variant culture supernatants, containing 200-400 μg/ml protein. The equipment used was V- or U-bottom MTP as dilution plates (Greiner 651101 and 650161 respectively), F-bottom MTP (Corning 9017) for unstress and LAS/EDTA buffer as well as for suc-AAPFpNA plates, Biomek FX (Beckman Coulter), Spectramax Plus 384 MTP Reader (Molecular Devices), iEMS Incubator/Shaker (1 mm amplitude) (Thermo Electron Corporation), sealing tape: Nunc (236366).

The iEMS incubator/shaker (Thermo/Labsystems) was set at 29° C. Culture supernatants were diluted into plates containing unstress buffer to a concentration of ~25 ppm (master dilution plate). 20 µl of sample from the master dilution plate was added to plates containing 180 µl unstress buffer to give a final incubation concentration of 2.5 ppm. The contents were mixed and kept at room temperature and a AAPF assay was performed on this plate. 20 µl of sample from the master dilution plate was also added to plates containing 180 µl stress buffer (50 mM HEPES (11.9 g/l), 0.1% (w/v) DOBS (1 g/l), 10 mM EDTA (3.36 g/l), pH 8.0). The solutions were mixed and immediately placed in 29° C. iEMS shaker for 30 min at 400 rpm. Following 30 minutes of incubation, a AAPF assay was performed on the stress plate. The stability of the samples was determined by calculating the ratio of the residual and initial AAPF activity as follows: Residual Activity (%)=[mOD·min-1 stressed]*100/[mOD·min-1 unstressed].

Performance Data of BPN' Variants

The below tables exemplify the performance of the Series 1 BPN' cold water protease variants described in this patent as assayed by Test Method 2.

TABLE 31-3

| Performance of Single Mutation Proteases | |
|---|---|
| Library Parent: | BPN' Wild type (Enzyme of SEQ ID NO: 2) |
| PI reference: | calculated relative to BPN' WT for the BMI pH 8 16° C. assay. |
| Detergents: | Commercial heat deactivated Tide 2X Cold |

Description:

In this Example, results of experiments conducted to determine protein expression, stain removal activity, LAS stability, and AAPF activity (tests of properties of interest) of BPN' and BPN'-variants are described. BPN' single variants were constructed using PCR fusion as described in USPA 2009/46156, filed Jun. 3, 2009, herein incorporated by reference. The results were obtained using the methods described in Test Method 2. As described throughout, functionality of the BPN' variants was quantified as a performance index (PI), which is the ratio of performance of a variant to a parent protein. Table 32-1 provides Performance index values (PI) of subtilisin BPN' variants. Performance indices less than or equal to 0.1 were fixed to 0.1 and indicated in bold italics in the table. Also, for the stability measure, if the Performance index of activity in the stability assays was less than or equal to 0.1, the associated stability performance index was fixed to 0.1.

TABLE 31-3

Performance Index Values for BPN' Variants

| Position | BPN' variant | TCA PI | PI BMI pH 8 16 C. | PI BMI pH 7 16 C. | PI BMI pH 8 32 C. | LAS-EDTA PI | specific AAPF PI |
|---|---|---|---|---|---|---|---|
| 2 | Q002W | 0.2 | 3.8 | 6.9 | 2.4 | ***0.1*** | 0.5 |
| 5 | P005K | 0.2 | 4.5 | 2.6 | 0.7 | 0.6 | 0.1 |
| 5 | P005L | 0.2 | 1.5 | 1.4 | 1.5 | ***0.1*** | 0.5 |
| 5 | P005Y | 0.2 | 3.3 | 3.3 | 2.2 | ***0.1*** | 0.4 |
| 7 | G007T | 0.2 | 3.0 | 2.4 | 3.0 | 0.1 | 0.2 |
| 8 | V008G | 0.3 | 1.4 | 0.5 | 1.4 | ***0.1*** | 0.4 |
| 8 | V008K | 0.2 | 3.1 | 3.0 | 3.1 | 0.2 | 0.5 |
| 8 | V008P | 0.2 | 2.7 | 3.0 | 2.9 | ***0.1*** | 0.6 |
| 11 | I011G | 0.2 | 2.2 | 2.2 | 1.6 | 0.4 | 0.3 |

TABLE 31-3-continued

Performance Index Values for BPN' Variants

| Position | BPN' variant | TCA PI | PI BMI pH 8 16 C. | PI BMI pH 7 16 C. | PI BMI pH 8 32 C. | LAS-EDTA PI | specific AAPF PI |
|---|---|---|---|---|---|---|---|
| 11 | I011H | 0.2 | 36.5 | 114.2 | 1.9 | 0.8 | 0.4 |
| 11 | I011S | 0.3 | 1.3 | 1.7 | 1.3 | 0.3 | 1.0 |
| 12 | K012L | 0.2 | 3.1 | 4.6 | 2.0 | 0.6 | 0.3 |
| 13 | A013M | 0.2 | 1.4 | ***0.1*** | 0.8 | ***0.1*** | ***0.1*** |
| 16 | L016W | 0.2 | 3.4 | 6.2 | 3.2 | 0.1 | 0.4 |
| 23 | G023S | 0.2 | 10.8 | 4.1 | 2.6 | 1.1 | 0.1 |
| 26 | V026H | 0.5 | 1.5 | 0.9 | 1.2 | 1.1 | 0.9 |
| 26 | V026W | 0.3 | 2.3 | 1.2 | 2.1 | 1.1 | 1.0 |
| 26 | V026Y | 0.3 | 1.3 | 1.3 | 1.5 | 1.0 | 1.0 |
| 27 | K027P | 0.2 | 1.3 | 3.4 | 2.1 | 1.1 | 0.5 |
| 28 | V028Q | 0.2 | 2.8 | 2.0 | 1.4 | 1.6 | 0.3 |
| 28 | V028S | 0.2 | 5.7 | 5.2 | 3.4 | 1.1 | 0.4 |
| 28 | V028T | 0.6 | 1.3 | 1.2 | 1.1 | 1.0 | 1.2 |
| 29 | A029C | 0.8 | 1.3 | 1.2 | 1.1 | 0.9 | 0.8 |
| 29 | A029D | 0.2 | 3.0 | 2.7 | 2.3 | 0.9 | 0.4 |
| 29 | A029S | 0.5 | 1.6 | 1.1 | 1.2 | 1.1 | 1.0 |
| 29 | A029T | 0.2 | 2.0 | 1.6 | 1.6 | 1.1 | 0.5 |
| 29 | A029V | 0.4 | 1.9 | 1.5 | 1.6 | 1.0 | 0.8 |
| 30 | V030D | 0.2 | 2.3 | 2.3 | 2.0 | 0.9 | 0.2 |
| 30 | V030E | 0.2 | 30.2 | 33.3 | 4.3 | 0.8 | 0.2 |
| 30 | V030G | 0.2 | 7.6 | 3.7 | 1.4 | ***0.1*** | ***0.1*** |
| 30 | V030T | 0.3 | 1.4 | 1.3 | 1.4 | 0.9 | 0.4 |
| 31 | I031E | 0.2 | 2.6 | 2.0 | 2.4 | 1.1 | 1.1 |
| 31 | I031G | 0.2 | 5.4 | 3.7 | 2.4 | 1.1 | 0.4 |
| 31 | I031H | 0.3 | 2.0 | 1.6 | 1.8 | 1.3 | 1.2 |
| 31 | I031K | 0.3 | 1.8 | 1.3 | 1.4 | 1.2 | 1.0 |
| 31 | I031N | 0.2 | 2.3 | 2.0 | 2.0 | 1.3 | 0.7 |
| 31 | I031Q | 0.2 | 5.4 | 3.5 | 3.1 | 1.1 | 0.6 |
| 31 | I031S | 0.2 | 3.7 | 2.8 | 2.9 | 1.1 | 0.9 |
| 31 | I031Y | 0.2 | 4.1 | 3.0 | 3.1 | 0.9 | 0.9 |
| 33 | S033F | 0.5 | 1.4 | 0.6 | 1.0 | ***0.1*** | ***0.1*** |
| 33 | S033H | 0.5 | 1.7 | 0.8 | 1.2 | ***0.1*** | ***0.1*** |
| 36 | D036L | 0.3 | 1.9 | 1.3 | 1.4 | ***0.1*** | 0.7 |
| 37 | S037P | 0.5 | 1.5 | 0.9 | 1.1 | 0.4 | 0.7 |
| 41 | D041A | 0.2 | 2.5 | ***0.1*** | 0.8 | 0.1 | 0.2 |
| 41 | D041C | 0.3 | 1.7 | 0.3 | 1.1 | ***0.1*** | 0.5 |
| 41 | D041M | 0.2 | 10.4 | ***0.1*** | 0.6 | ***0.1*** | ***0.1*** |
| 41 | D041N | 0.3 | 2.1 | 1.3 | 1.4 | ***0.1*** | 0.5 |
| 41 | D041S | 0.2 | 3.1 | 1.5 | 1.2 | 0.5 | 0.3 |
| 42 | L042S | 0.2 | 32.8 | ***0.1*** | 0.4 | ***0.1*** | ***0.1*** |
| 42 | L042Y | 0.2 | 3.6 | 4.4 | 1.9 | ***0.1*** | 0.4 |
| 44 | V044H | 0.2 | 1.6 | 2.6 | 1.6 | 0.5 | 0.4 |
| 44 | V044Q | 0.2 | 1.5 | 2.9 | 1.5 | 0.6 | 0.3 |
| 44 | V044T | 0.3 | 1.3 | 1.9 | 1.3 | 0.7 | 1.3 |
| 46 | G046F | 0.4 | 1.4 | 1.0 | 1.0 | 1.0 | 0.9 |
| 46 | G046L | 0.3 | 1.6 | 1.4 | 1.4 | 0.8 | 0.8 |
| 46 | G046M | 0.4 | 1.3 | 0.8 | 1.1 | 0.9 | 1.0 |
| 46 | G046V | 0.2 | 4.9 | 3.3 | 2.1 | 0.8 | 0.7 |
| 47 | G047T | 0.2 | 4.5 | 4.8 | 2.3 | 0.5 | 0.1 |
| 47 | G047W | 0.2 | 2.6 | 2.4 | 2.2 | 0.5 | 0.2 |
| 49 | S049I | 0.2 | 2.2 | 2.5 | 2.1 | 0.5 | 0.1 |
| 49 | S049V | 0.2 | 1.6 | 1.4 | 2.1 | 0.4 | 0.3 |
| 50 | M050D | 0.2 | 6.4 | 0.9 | 0.9 | 1.0 | 0.2 |
| 50 | M050I | 0.3 | 1.6 | 0.9 | 1.1 | 0.9 | 0.6 |
| 50 | M050R | 0.3 | 1.4 | 0.7 | 1.1 | 1.0 | 0.8 |
| 51 | V051A | 0.4 | 1.4 | 1.3 | 1.2 | 0.9 | 0.4 |
| 51 | V051G | 0.2 | 3.4 | 4.3 | 1.4 | ***0.1*** | ***0.1*** |
| 51 | V051S | 0.3 | 1.8 | 2.0 | 1.4 | 0.9 | 0.4 |
| 52 | P052C | 0.3 | 1.4 | 1.6 | 0.9 | 1.0 | 0.4 |
| 52 | P052I | 0.5 | 1.3 | 1.5 | 1.1 | 0.8 | 0.6 |
| 52 | P052L | 0.5 | 1.3 | 1.2 | 1.3 | 0.8 | 0.6 |
| 52 | P052M | 0.4 | 1.4 | 1.3 | 1.1 | 0.7 | 0.5 |
| 52 | P052V | 0.3 | 1.8 | 1.6 | 1.0 | 1.0 | 0.5 |
| 52 | P052W | 0.4 | 1.5 | 1.3 | 1.4 | 1.0 | 0.8 |
| 52 | P052Y | 0.4 | 1.6 | 1.4 | 1.3 | 1.0 | 0.6 |
| 54 | E054R | 0.2 | 1.5 | 1.8 | 1.7 | 0.6 | 0.6 |
| 56 | N056G | 0.3 | 1.6 | 1.1 | 1.2 | 0.4 | 0.5 |
| 56 | N056I | 0.2 | 1.7 | 1.3 | 1.4 | 0.6 | 0.5 |
| 56 | N056K | 0.2 | 2.1 | 1.5 | 1.9 | 0.5 | 0.4 |
| 56 | N056M | 0.3 | 1.5 | 1.2 | 1.2 | 0.5 | 0.4 |
| 56 | N056Q | 0.3 | 1.7 | 1.3 | 1.2 | 0.8 | 0.4 |
| 56 | N056R | 0.2 | 4.9 | 4.0 | 2.2 | 0.5 | 0.3 |
| 56 | N056V | 0.3 | 1.4 | 1.3 | 1.0 | 0.5 | 0.5 |
| 56 | N056Y | 0.3 | 1.3 | 1.3 | 1.3 | 0.7 | 0.4 |

TABLE 31-3-continued

Performance Index Values for BPN' Variants

| Position | BPN' variant | TCA PI | PI BMI pH 8 16 C. | PI BMI pH 7 16 C. | PI BMI pH 8 32 C. | LAS-EDTA PI | specific AAPF PI |
|---|---|---|---|---|---|---|---|
| 57 | P057I | 0.3 | 2.2 | 2.0 | 1.6 | 0.4 | 0.3 |
| 57 | P057K | 0.2 | 1.5 | 1.8 | 1.1 | 0.3 | 0.3 |
| 57 | P057L | 0.2 | 2.6 | 2.0 | 1.5 | 0.4 | 0.3 |
| 57 | P057R | 0.2 | 2.3 | 3.1 | 1.5 | 0.4 | 0.4 |
| 57 | P057T | 0.3 | 2.5 | 2.0 | 2.3 | 0.5 | 0.6 |
| 57 | P057V | 0.2 | 3.6 | 6.0 | 3.5 | 0.3 | 0.5 |
| 58 | F058T | 0.4 | 1.4 | 1.8 | 1.2 | 0.7 | 1.0 |
| 59 | Q059P | 0.3 | 1.9 | 2.0 | 1.5 | 0.8 | 0.4 |
| 59 | Q059W | 0.2 | 1.4 | 1.6 | 1.2 | 1.0 | 0.5 |
| 61 | N061P | 1.4 | 1.5 | 1.0 | 0.8 | 1.0 | 1.4 |
| 62 | N062D | 1.5 | 1.4 | 1.2 | 0.9 | 1.1 | 0.7 |
| 62 | N062M | 1.8 | 1.3 | 1.1 | 1.1 | 1.1 | 0.6 |
| 62 | N062Q | 1.5 | 1.3 | 1.2 | 1.1 | 1.2 | 0.6 |
| 63 | S063C | 1.6 | 1.3 | 1.0 | 0.7 | 1.3 | 0.8 |
| 63 | S063Q | 1.6 | 1.4 | 0.8 | 1.1 | 1.0 | 1.0 |
| 63 | S063T | 1.0 | 1.3 | 1.0 | 1.0 | 1.0 | 0.9 |
| 65 | G065Q | 0.2 | 1.7 | 2.1 | 2.3 | 1.2 | 0.7 |
| 68 | V068A | 1.0 | 1.8 | 1.1 | 1.3 | 1.0 | 0.1 |
| 68 | V068G | 0.5 | 1.8 | 1.3 | 1.4 | ***0.1*** | ***0.1*** |
| 68 | V068M | 1.2 | 1.3 | 0.9 | 1.2 | ***0.1*** | ***0.1*** |
| 68 | V068S | 1.3 | 1.7 | 1.3 | 1.1 | ***0.1*** | ***0.1*** |
| 69 | A069C | 0.4 | 1.7 | 0.9 | 1.2 | 0.7 | 0.5 |
| 69 | A069D | 0.3 | 2.0 | ***0.1*** | ***0.1*** | ***0.1*** | ***0.1*** |
| 69 | A069F | 0.2 | 13.7 | 1.3 | 0.5 | ***0.1*** | ***0.1*** |
| 69 | A069H | 0.2 | 39.0 | 2.2 | 0.7 | 0.7 | 0.1 |
| 69 | A069M | 0.2 | 7.2 | 0.7 | 0.6 | 0.5 | 0.1 |
| 69 | A069N | 0.2 | 2.5 | 0.1 | ***0.1*** | ***0.1*** | ***0.1*** |
| 69 | A069P | 0.3 | 1.8 | ***0.1*** | ***0.1*** | ***0.1*** | ***0.1*** |
| 69 | A069Q | 0.2 | 5.2 | 0.1 | ***0.1*** | ***0.1*** | ***0.1*** |
| 69 | A069R | 0.4 | 2.0 | ***0.1*** | ***0.1*** | ***0.1*** | ***0.1*** |
| 69 | A069T | 0.5 | 1.6 | 1.0 | 1.0 | 1.0 | 0.7 |
| 71 | T071D | 0.2 | 41.1 | 34.6 | 1.5 | 0.2 | 0.1 |
| 71 | T071E | 0.3 | 2.2 | 1.9 | 1.0 | 0.1 | 0.3 |
| 71 | T071G | 0.2 | 3.3 | 1.6 | 1.9 | ***0.1*** | 0.4 |
| 71 | T071K | 0.2 | 37.0 | 45.5 | 2.2 | 0.1 | 0.2 |
| 71 | T071M | 0.3 | 1.3 | 1.2 | 1.1 | ***0.1*** | 0.4 |
| 72 | V072D | 0.2 | 2.5 | 1.7 | 1.9 | 0.7 | 0.2 |
| 72 | V072G | 0.4 | 1.5 | 1.1 | 1.4 | 0.8 | 0.7 |
| 72 | V072K | 0.2 | 2.8 | 2.1 | 2.8 | 1.7 | 0.3 |
| 72 | V072Q | 0.3 | 1.6 | 1.5 | 1.7 | 0.6 | 0.6 |
| 72 | V072S | 0.4 | 1.4 | 1.4 | 1.3 | 0.8 | 0.9 |
| 72 | V072T | 0.6 | 1.4 | 1.0 | 1.1 | 0.9 | 1.0 |
| 73 | A073E | 0.5 | 1.6 | 1.2 | 1.1 | 0.2 | 0.8 |
| 73 | A073I | 0.2 | 22.5 | 15.7 | 6.1 | 0.1 | 0.3 |
| 73 | A073K | 0.2 | 3.5 | 2.5 | 2.6 | 0.1 | 0.3 |
| 73 | A073M | 0.2 | 1.7 | 1.4 | 1.5 | 0.3 | 0.4 |
| 73 | A073Q | 0.6 | 1.3 | 1.3 | 1.1 | 0.5 | 0.9 |
| 73 | A073S | 1.0 | 1.4 | 0.9 | 1.0 | 0.8 | 1.1 |
| 73 | A073V | 0.4 | 1.4 | 1.2 | 1.5 | 0.1 | 0.8 |
| 74 | A074E | 0.3 | 4.3 | ***0.1*** | ***0.1*** | ***0.1*** | ***0.1*** |
| 74 | A074F | 0.3 | 2.6 | ***0.1*** | ***0.1*** | ***0.1*** | ***0.1*** |
| 74 | A074H | 0.3 | 3.2 | ***0.1*** | ***0.1*** | ***0.1*** | ***0.1*** |
| 74 | A074I | 0.3 | 2.1 | ***0.1*** | ***0.1*** | ***0.1*** | ***0.1*** |
| 74 | A074L | 0.3 | 2.2 | ***0.1*** | ***0.1*** | ***0.1*** | ***0.1*** |
| 74 | A074M | 0.2 | 5.3 | ***0.1*** | ***0.1*** | ***0.1*** | ***0.1*** |
| 74 | A074Q | 0.3 | 2.9 | 0.1 | ***0.1*** | ***0.1*** | ***0.1*** |
| 74 | A074R | 0.3 | 1.9 | ***0.1*** | ***0.1*** | ***0.1*** | ***0.1*** |
| 74 | A074V | 0.3 | 3.6 | 0.1 | ***0.1*** | ***0.1*** | ***0.1*** |
| 74 | A074W | 0.3 | 2.5 | ***0.1*** | ***0.1*** | ***0.1*** | ***0.1*** |
| 74 | A074Y | 0.3 | 2.8 | 0.1 | ***0.1*** | ***0.1*** | ***0.1*** |
| 75 | L075A | 1.1 | 1.4 | 1.0 | 1.0 | ***0.1*** | 1.0 |
| 76 | N076A | 1.1 | 1.7 | 0.8 | 1.0 | ***0.1*** | 1.0 |
| 77 | N077G | 0.2 | 1.5 | 0.8 | 1.0 | ***0.1*** | 0.1 |
| 77 | N077L | 0.2 | 2.2 | 0.2 | 0.8 | 0.1 | 0.1 |
| 77 | N077P | 0.2 | 2.2 | ***0.1*** | 0.6 | 0.3 | 0.1 |
| 77 | N077Q | 0.2 | 2.1 | 0.8 | 1.2 | ***0.1*** | 0.4 |
| 77 | N077R | 0.2 | 2.5 | 0.1 | 0.9 | 0.1 | 0.2 |
| 77 | N077S | 0.3 | 1.7 | 1.3 | 1.2 | ***0.1*** | 0.8 |
| 77 | N077T | 0.2 | 4.2 | 1.3 | 1.5 | ***0.1*** | 0.3 |
| 78 | S078W | 1.0 | 1.3 | 0.7 | 1.0 | 0.3 | 1.1 |
| 80 | G080H | 0.2 | 11.3 | 32.2 | 3.1 | ***0.1*** | 0.3 |
| 81 | V081D | 0.2 | 1.4 | 0.8 | 0.6 | 0.1 | 0.1 |
| 81 | V081F | 0.9 | 1.3 | 0.9 | 1.1 | ***0.1*** | 0.8 |
| 81 | V081H | 0.7 | 1.5 | 1.0 | 1.0 | ***0.1*** | 0.7 |
| 81 | V081N | 0.4 | 1.3 | 0.9 | 1.2 | ***0.1*** | 0.7 |
| 81 | V081Q | 0.6 | 1.3 | 0.8 | 1.1 | ***0.1*** | 0.9 |
| 81 | V081R | 0.2 | 2.0 | 1.5 | 1.8 | ***0.1*** | 0.6 |
| 81 | V081W | 0.6 | 1.4 | 0.8 | 1.2 | ***0.1*** | 0.8 |
| 82 | L082G | 0.2 | 2.2 | 1.7 | 1.5 | 0.1 | 0.4 |
| 82 | L082N | 0.3 | 1.8 | 1.5 | 1.7 | ***0.1*** | 0.6 |
| 82 | L082W | 0.2 | 10.3 | 8.5 | 4.2 | 0.7 | 0.4 |
| 85 | A085I | 0.2 | 1.7 | 0.7 | 0.7 | ***0.1*** | ***0.1*** |
| 85 | A085T | 0.4 | 1.4 | 1.1 | 0.9 | 0.6 | 1.0 |
| 85 | A085V | 0.2 | 2.5 | 2.5 | 2.3 | 0.7 | 0.5 |
| 86 | P086A | 0.5 | 1.3 | 1.1 | 1.3 | 0.7 | 1.1 |
| 86 | P086G | 0.4 | 1.4 | 0.9 | 1.3 | 0.1 | 0.8 |
| 86 | P086M | 0.3 | 2.0 | 1.8 | 1.8 | 0.1 | 1.0 |
| 86 | P086Q | 0.3 | 1.5 | 1.6 | 2.0 | 0.1 | 0.9 |
| 86 | P086R | 0.2 | 3.5 | 3.8 | 2.7 | 0.7 | 0.7 |
| 86 | P086T | 0.3 | 1.7 | 1.8 | 1.9 | 0.2 | 1.1 |
| 86 | P086W | 0.4 | 1.4 | 1.5 | 1.3 | 0.4 | 1.4 |
| 86 | P086Y | 0.4 | 1.5 | 1.2 | 1.7 | 0.9 | 1.4 |
| 87 | S087F | 0.9 | 1.4 | 0.9 | 1.1 | 0.5 | 1.0 |
| 87 | S087I | 0.6 | 1.4 | 0.8 | 1.0 | 0.4 | 0.9 |
| 87 | S087L | 1.1 | 1.3 | 1.0 | 1.1 | 0.8 | 1.0 |
| 87 | S087M | 1.0 | 1.3 | 1.0 | 1.1 | 0.7 | 1.0 |
| 87 | S087Q | 0.8 | 1.3 | 0.9 | 1.0 | 0.8 | 0.9 |
| 87 | S087V | 0.9 | 1.3 | 1.0 | 1.2 | 0.9 | 1.2 |
| 87 | S087W | 0.9 | 1.4 | 1.0 | 1.3 | 0.5 | 1.1 |
| 88 | A088D | 0.3 | 1.4 | 1.6 | 1.3 | 0.7 | 0.7 |
| 88 | A088E | 0.2 | 11.4 | 17.5 | 1.7 | 0.6 | 0.2 |
| 88 | A088K | 0.2 | 2.4 | 3.0 | 1.7 | 0.8 | 0.7 |
| 88 | A088P | 0.2 | 2.2 | 3.4 | 2.0 | 0.9 | 0.6 |
| 88 | A088Q | 0.2 | 1.9 | 2.0 | 1.2 | 0.5 | 0.5 |
| 89 | S089D | 1.2 | 1.4 | 1.0 | 1.1 | 0.8 | 1.0 |
| 89 | S089Q | 0.2 | 108.1 | 37.2 | 0.2 | ***0.1*** | ***0.1*** |
| 89 | S089V | 0.7 | 1.3 | 1.3 | 1.2 | 0.7 | 1.3 |
| 90 | L090D | 0.2 | 2.4 | 2.1 | 2.2 | 0.6 | 0.5 |
| 90 | L090E | 0.2 | 1.6 | 1.4 | 1.5 | 1.0 | 0.5 |
| 90 | L090F | 0.3 | 1.6 | 0.8 | 1.4 | 0.3 | 0.3 |
| 90 | L090H | 0.2 | 2.0 | 2.2 | 2.3 | 1.0 | 0.9 |
| 90 | L090P | 0.3 | 1.6 | 1.7 | 1.6 | 0.9 | 0.9 |
| 90 | L090S | 0.2 | 1.6 | 1.9 | 1.6 | 0.7 | 0.9 |
| 90 | L090T | 0.2 | 3.9 | 3.3 | 2.5 | 0.8 | 1.0 |
| 91 | Y091L | 0.2 | 1.6 | 2.8 | 1.7 | 1.0 | 0.5 |
| 91 | Y091Q | 0.2 | 7.6 | 26.9 | 2.0 | 1.2 | 0.3 |
| 91 | Y091T | 0.2 | 3.7 | 8.1 | 2.7 | 0.9 | 0.6 |
| 92 | A092C | 0.3 | 2.6 | 2.0 | 1.7 | 0.6 | 0.3 |
| 92 | A092I | 0.3 | 1.7 | 1.5 | 1.6 | 0.7 | 0.3 |
| 92 | A092M | 0.2 | 2.5 | 2.6 | 2.9 | 0.6 | 0.2 |
| 92 | A092N | 0.2 | 6.4 | 7.3 | 5.5 | 0.7 | 0.2 |
| 92 | A092P | 0.3 | 1.6 | 2.3 | 2.1 | 0.9 | 0.5 |
| 92 | A092V | 0.3 | 1.4 | 1.3 | 1.7 | 0.6 | 0.5 |
| 93 | V093D | 0.2 | 2.4 | 3.4 | 2.0 | 1.1 | 0.7 |
| 93 | V093F | 0.2 | 1.3 | 2.2 | 1.5 | 1.0 | 0.6 |
| 93 | V093L | 0.6 | 1.4 | 1.1 | 1.0 | 0.8 | 1.0 |
| 93 | V093T | 0.3 | 1.5 | 1.7 | 1.4 | 1.1 | 1.0 |
| 94 | K094C | 0.2 | 1.3 | 1.4 | 1.1 | 1.0 | 0.2 |
| 94 | K094R | 0.4 | 1.4 | 1.5 | 1.3 | 0.8 | 0.4 |
| 94 | K094S | 0.2 | 4.2 | 3.8 | 2.5 | 1.0 | 0.2 |
| 95 | V095I | 0.4 | 2.4 | 1.2 | 1.3 | ***0.1*** | ***0.1*** |
| 96 | L096F | 0.5 | 2.0 | 0.8 | 1.4 | 0.9 | 0.6 |
| 96 | L096H | 0.2 | 1.9 | 0.2 | 0.4 | ***0.1*** | ***0.1*** |
| 96 | L096I | 0.8 | 1.6 | 0.9 | 1.0 | 1.2 | 0.4 |
| 96 | L096M | 0.9 | 1.5 | 1.1 | 1.2 | 0.9 | 0.5 |
| 96 | L096N | 0.2 | 6.1 | 0.9 | 0.7 | ***0.1*** | ***0.1*** |
| 96 | L096Q | 0.2 | 31.7 | 6.8 | 3.9 | ***0.1*** | ***0.1*** |
| 96 | L096S | 0.2 | 3.8 | 1.0 | 1.5 | ***0.1*** | ***0.1*** |
| 96 | L096T | 0.4 | 2.3 | 1.3 | 1.4 | ***0.1*** | ***0.1*** |
| 96 | L096V | 1.0 | 1.4 | 0.9 | 1.3 | 1.1 | 0.1 |
| 96 | L096W | 0.2 | 5.0 | 1.6 | 2.2 | 1.0 | 0.3 |
| 96 | L096Y | 0.3 | 2.0 | 0.7 | 1.2 | ***0.1*** | ***0.1*** |
| 97 | G097A | 0.9 | 1.6 | 1.0 | 1.3 | 1.0 | 0.8 |
| 97 | G097C | 1.0 | 1.7 | 1.1 | 1.1 | 1.0 | 0.5 |
| 97 | G097D | 1.6 | 1.4 | 0.8 | 1.2 | 1.0 | 0.8 |
| 97 | G097E | 1.1 | 1.4 | 0.8 | 1.1 | 1.1 | 0.7 |
| 97 | G097F | 0.3 | 1.9 | 1.0 | 1.4 | 0.9 | 0.3 |
| 97 | G097L | 0.8 | 1.4 | 1.1 | 1.2 | 1.1 | 0.7 |

TABLE 31-3-continued

Performance Index Values for BPN' Variants

| Position | BPN' variant | TCA PI | PI BMI pH 8 16 C. | PI BMI pH 7 16 C. | PI BMI pH 8 32 C. | LAS-EDTA PI | specific AAPF PI |
|---|---|---|---|---|---|---|---|
| 97 | G097M | 0.8 | 1.3 | 1.0 | 1.2 | 1.1 | 0.9 |
| 97 | G097P | 0.4 | 2.4 | 1.6 | 1.3 | 1.1 | 0.7 |
| 97 | G097Q | 1.0 | 1.4 | 0.8 | 1.0 | 1.2 | 1.0 |
| 97 | G097S | 1.0 | 1.5 | 1.1 | 1.1 | 0.9 | 1.0 |
| 97 | G097V | 0.5 | 1.6 | 1.1 | 1.2 | 1.0 | 1.0 |
| 97 | G097W | 0.2 | 3.0 | 1.5 | 1.5 | 1.0 | 0.3 |
| 97 | G097Y | 0.4 | 1.4 | 0.9 | 1.0 | 0.9 | 0.3 |
| 99 | D099C | 0.7 | 1.5 | 0.8 | 1.1 | 1.1 | 0.6 |
| 99 | D099E | 1.0 | 1.4 | 0.8 | 1.0 | 1.0 | 0.8 |
| 99 | D099I | 0.4 | 1.6 | 0.6 | 1.1 | 1.0 | 0.6 |
| 99 | D099M | 0.6 | 1.4 | 0.7 | 1.2 | 0.9 | 0.7 |
| 99 | D099P | 0.4 | 2.0 | 0.9 | 1.2 | 1.0 | 0.4 |
| 99 | D099V | 0.4 | 1.7 | 0.8 | 1.1 | 0.9 | 0.6 |
| 99 | D099Y | 0.5 | 1.4 | 0.6 | 1.1 | 0.9 | 0.6 |
| 100 | G100D | 0.8 | 1.4 | 1.4 | 1.1 | 0.9 | 0.3 |
| 100 | G100E | 0.5 | 1.7 | 1.5 | 1.3 | 1.0 | 0.3 |
| 100 | G100H | 0.6 | 1.4 | 1.2 | 1.1 | 0.9 | 0.3 |
| 100 | G100I | 0.3 | 1.8 | 1.6 | 1.2 | ***0.1*** | ***0.1*** |
| 100 | G100K | 0.7 | 1.5 | 1.0 | 1.2 | 0.9 | 0.3 |
| 100 | G100M | 1.1 | 1.4 | 1.2 | 1.2 | 0.8 | 0.2 |
| 100 | G100Q | 0.7 | 1.6 | 1.2 | 1.4 | 1.0 | 0.4 |
| 100 | G100T | 0.3 | 2.2 | 1.6 | 1.5 | 1.0 | 0.2 |
| 100 | G100V | 0.3 | 2.0 | 1.6 | 1.4 | 1.0 | 0.1 |
| 100 | G100Y | 0.5 | 1.6 | 1.3 | 1.1 | 1.0 | 0.2 |
| 101 | S101A | 1.3 | 1.4 | 1.0 | 1.1 | 1.1 | 1.1 |
| 101 | S101E | 1.4 | 1.5 | 1.2 | 1.1 | 1.1 | 0.7 |
| 101 | S101G | 0.4 | 1.3 | 0.5 | 0.7 | 1.1 | 0.2 |
| 101 | S101N | 1.2 | 1.5 | 1.0 | 1.1 | 1.1 | 1.0 |
| 101 | S101P | 0.3 | 3.6 | 1.4 | 1.8 | 1.1 | 0.3 |
| 101 | S101Q | 0.6 | 1.6 | 0.8 | 1.1 | 1.0 | 1.2 |
| 101 | S101T | 0.9 | 1.3 | 0.7 | 1.2 | 1.0 | 1.1 |
| 101 | S101V | 0.9 | 1.4 | 0.7 | 1.2 | 0.9 | 1.2 |
| 102 | G102A | 1.1 | 1.5 | 1.3 | 1.2 | 1.0 | 0.3 |
| 102 | G102S | 0.8 | 1.6 | 1.1 | 1.0 | 1.1 | 0.1 |
| 103 | Q103E | 1.2 | 1.4 | 1.2 | 1.1 | 1.0 | 0.6 |
| 103 | Q103G | 0.4 | 1.5 | 1.1 | 1.3 | 1.1 | 0.4 |
| 103 | Q103H | 0.9 | 1.4 | 0.9 | 0.9 | 0.9 | 0.7 |
| 103 | Q103K | 0.2 | 2.6 | 1.4 | 1.3 | 1.0 | 0.5 |
| 103 | Q103N | 1.4 | 1.4 | 1.2 | 0.9 | 1.0 | 0.7 |
| 104 | Y104L | 0.2 | 1.5 | 1.5 | 1.2 | ***0.1*** | ***0.1*** |
| 104 | Y104M | 0.3 | 1.5 | 1.5 | 1.3 | 1.2 | 0.1 |
| 104 | Y104N | 0.5 | 1.4 | 1.8 | 1.0 | 1.1 | 0.1 |
| 104 | Y104T | 0.4 | 1.3 | 1.7 | 1.4 | 2.0 | 0.1 |
| 104 | Y104V | 0.3 | 1.7 | 1.2 | 1.4 | ***0.1*** | ***0.1*** |
| 105 | S105D | 0.4 | 1.3 | 1.0 | 1.2 | 1.1 | 0.9 |
| 105 | S105I | 0.2 | 1.6 | 1.1 | 0.7 | 1.0 | 0.3 |
| 105 | S105R | 0.2 | 3.0 | 3.4 | 1.0 | 1.2 | 0.2 |
| 105 | S105V | 0.2 | 2.8 | 3.1 | 2.8 | 1.0 | 0.8 |
| 106 | W106A | 0.4 | 1.4 | 1.2 | 1.1 | 0.9 | 0.4 |
| 106 | W106C | 0.4 | 1.4 | 1.1 | 1.0 | 0.9 | 0.2 |
| 106 | W106E | 0.4 | 1.7 | 1.3 | 1.2 | 1.1 | 0.4 |
| 106 | W106F | 0.8 | 1.3 | 0.8 | 1.3 | 1.0 | 0.4 |
| 106 | W106G | 0.2 | 1.4 | 1.3 | 1.2 | 0.9 | 0.1 |
| 106 | W106I | 0.3 | 1.5 | 1.1 | 1.3 | 1.1 | 0.4 |
| 106 | W106L | 0.3 | 1.6 | 1.1 | 1.4 | 1.1 | 0.3 |
| 106 | W106M | 0.4 | 1.4 | 1.1 | 1.1 | 0.9 | 0.3 |
| 106 | W106S | 0.4 | 1.4 | 0.9 | 1.2 | 2.0 | 0.2 |
| 106 | W106T | 0.4 | 1.4 | 1.2 | 1.3 | 0.9 | 0.3 |
| 106 | W106V | 0.3 | 1.5 | 1.2 | 1.2 | 0.9 | 0.5 |
| 107 | I107R | 0.2 | 2.3 | 2.3 | 1.9 | 1.2 | 0.1 |
| 107 | I107S | 0.5 | 1.4 | 0.9 | 1.2 | 1.0 | 0.1 |
| 107 | I107T | 0.7 | 1.4 | 2.3 | 0.9 | 1.0 | 0.1 |
| 108 | I108S | 0.2 | 2.4 | 8.6 | 1.3 | 0.9 | 0.1 |
| 108 | I108T | 0.3 | 1.8 | 1.7 | 1.5 | 0.9 | 0.8 |
| 110 | G110S | 0.3 | 2.2 | 1.4 | 1.7 | 0.9 | 0.5 |
| 110 | G110T | 0.2 | 4.6 | 4.0 | 2.8 | 0.9 | 0.5 |
| 111 | I111A | 0.2 | 3.8 | 2.4 | 1.9 | 0.9 | 0.3 |
| 111 | I111C | 0.4 | 1.9 | 1.5 | 1.5 | 0.9 | 0.9 |
| 111 | I111F | 0.5 | 1.7 | 1.1 | 1.2 | ***0.1*** | ***0.1*** |
| 111 | I111L | 1.0 | 1.3 | 1.0 | 1.1 | 1.0 | 0.7 |
| 111 | I111M | 0.8 | 1.4 | 1.0 | 1.0 | 1.1 | 0.7 |
| 111 | I111T | 0.3 | 3.1 | 1.6 | 1.7 | 1.0 | 0.9 |
| 111 | I111V | 0.7 | 1.6 | 1.0 | 1.3 | 1.0 | 0.8 |
| 112 | E112I | 0.2 | 7.2 | 2.7 | 2.7 | 1.1 | 0.6 |
| 112 | E112L | 0.2 | 19.7 | 11.6 | 3.8 | 1.1 | 0.6 |
| 112 | E112T | 0.3 | 2.9 | 2.1 | 2.0 | 1.0 | 0.9 |
| 113 | W113H | 0.2 | 1.5 | 1.7 | 1.5 | 1.1 | 0.6 |
| 114 | A114I | 0.2 | 3.4 | 2.6 | 2.5 | 0.9 | 0.4 |
| 114 | A114V | 0.3 | 1.6 | 2.2 | 1.6 | 0.9 | 1.0 |
| 115 | I115A | 0.4 | 1.6 | 1.0 | 1.1 | 0.9 | 0.8 |
| 115 | I115E | 0.3 | 2.3 | 1.7 | 1.6 | 0.9 | 0.7 |
| 115 | I115F | 0.3 | 2.0 | 1.2 | 1.4 | 0.9 | 0.6 |
| 115 | I115H | 0.2 | 4.9 | 2.5 | 2.4 | 0.9 | 0.5 |
| 115 | I115M | 0.9 | 1.5 | 1.0 | 1.1 | 1.0 | 0.9 |
| 115 | I115N | 0.2 | 8.3 | 8.4 | 2.6 | 1.0 | 0.4 |
| 115 | I115P | 0.2 | 1.8 | 0.1 | 0.2 | ***0.1*** | ***0.1*** |
| 115 | I115Q | 0.6 | 1.3 | 0.8 | 1.2 | 1.0 | 1.0 |
| 115 | I115R | 0.4 | 1.4 | 1.0 | 1.2 | 1.0 | 0.9 |
| 115 | I115S | 0.2 | 4.2 | 2.4 | 2.2 | 0.9 | 0.7 |
| 115 | I115T | 0.6 | 1.5 | 0.9 | 1.1 | 0.9 | 0.9 |
| 115 | I115V | 0.8 | 1.4 | 1.0 | 1.3 | 0.9 | 1.6 |
| 115 | I115Y | 0.2 | 4.8 | 4.1 | 2.5 | 0.9 | 0.8 |
| 117 | N117K | 0.2 | 1.9 | 1.9 | 1.8 | 1.0 | 0.9 |
| 117 | N117V | 0.2 | 5.4 | 4.1 | 2.1 | 1.0 | 0.5 |
| 117 | N117W | 0.3 | 2.1 | 1.8 | 1.6 | 1.0 | 1.1 |
| 118 | N118I | 0.2 | 4.9 | 5.9 | 2.0 | 1.1 | 0.6 |
| 118 | N118L | 0.2 | 1.5 | 1.9 | 1.3 | 1.0 | 1.1 |
| 118 | N118V | 0.2 | 1.4 | 1.9 | 1.5 | 1.0 | 1.0 |
| 119 | M119F | 0.3 | 1.6 | 1.9 | 1.6 | 1.3 | 0.8 |
| 119 | M119N | 0.2 | 2.0 | 2.6 | 1.8 | 1.1 | 0.8 |
| 120 | D120Y | 0.2 | 1.3 | 1.7 | 1.3 | 1.0 | 0.7 |
| 122 | I122R | 0.2 | 2.8 | ***0.1*** | ***0.1*** | ***0.1*** | ***0.1*** |
| 122 | I122S | 0.2 | 6.5 | 6.1 | 2.6 | 1.9 | 0.4 |
| 122 | I122T | 0.3 | 1.8 | 1.8 | 1.1 | 1.4 | 0.9 |
| 123 | N123A | 0.8 | 1.7 | 1.4 | 1.1 | ***0.1*** | ***0.1*** |
| 123 | N123C | 1.0 | 1.5 | 1.4 | 1.4 | 0.5 | 0.1 |
| 123 | N123G | 0.5 | 1.8 | 1.6 | 1.3 | 0.4 | 0.1 |
| 123 | N123S | 0.9 | 1.3 | 1.2 | 1.1 | 0.2 | 0.1 |
| 124 | M124A | 0.6 | 1.4 | 1.0 | 1.0 | 1.0 | 0.7 |
| 124 | M124H | 0.2 | 1.4 | 0.3 | 0.3 | ***0.1*** | ***0.1*** |
| 124 | M124N | 0.2 | 3.0 | 0.8 | 0.8 | ***0.1*** | ***0.1*** |
| 124 | M124Q | 0.2 | 5.2 | 2.6 | 1.4 | ***0.1*** | ***0.1*** |
| 124 | M124S | 0.3 | 2.8 | 1.4 | 1.5 | 0.9 | 0.1 |
| 124 | M124T | 0.5 | 1.8 | 1.3 | 1.4 | 0.9 | 0.2 |
| 124 | M124V | 1.1 | 1.4 | 1.2 | 1.1 | 0.9 | 0.3 |
| 125 | S125A | 0.9 | 1.9 | 1.4 | 1.2 | 1.1 | 0.1 |
| 126 | L126A | 0.9 | 1.6 | 1.1 | 1.2 | ***0.1*** | ***0.1*** |
| 126 | L126Q | 0.3 | 3.1 | 0.9 | 1.1 | ***0.1*** | ***0.1*** |
| 126 | L126S | 0.7 | 1.6 | 0.9 | 0.9 | ***0.1*** | ***0.1*** |
| 126 | L126T | 0.5 | 2.4 | 1.5 | 1.4 | ***0.1*** | ***0.1*** |
| 126 | L126Y | 0.6 | 1.5 | 1.1 | 1.3 | ***0.1*** | ***0.1*** |
| 128 | G128E | 0.3 | 1.6 | 1.2 | 1.5 | ***0.1*** | ***0.1*** |
| 128 | G128N | 0.6 | 1.6 | 1.6 | 1.3 | ***0.1*** | ***0.1*** |
| 128 | G128T | 0.3 | 2.2 | 2.4 | 1.6 | ***0.1*** | ***0.1*** |
| 129 | P129V | 0.7 | 1.4 | 1.3 | 1.1 | 0.8 | 0.8 |
| 130 | S130P | 0.6 | 1.3 | 1.3 | 1.0 | 0.7 | 0.1 |
| 132 | S132I | 0.3 | 1.6 | 1.8 | 1.3 | 0.8 | 0.6 |
| 132 | S132N | 0.9 | 1.4 | 1.4 | 1.2 | 1.0 | 0.9 |
| 132 | S132P | 0.2 | 9.4 | 11.7 | 2.5 | 1.0 | 0.2 |
| 132 | S132Q | 0.3 | 1.4 | 1.3 | 1.2 | 0.7 | 0.9 |
| 132 | S132V | 0.2 | 3.3 | 2.4 | 2.1 | 0.8 | 0.6 |
| 134 | A134I | 0.3 | 1.6 | 1.2 | 1.3 | 0.9 | 0.9 |
| 134 | A134L | 0.2 | 1.9 | 2.4 | 1.8 | 1.1 | 0.6 |
| 134 | A134M | 0.2 | 1.4 | 1.2 | 1.3 | 1.1 | 0.5 |
| 135 | L135I | 0.3 | 1.4 | 1.0 | 1.1 | 0.7 | 0.2 |
| 135 | L135T | 0.2 | 3.4 | 2.3 | 2.1 | 0.6 | 0.1 |
| 135 | L135V | 0.3 | 2.1 | 1.1 | 1.3 | 0.6 | 0.2 |
| 135 | L135W | 0.3 | 2.1 | 2.0 | 1.5 | 0.8 | 0.2 |
| 135 | L135Y | 0.3 | 1.9 | 2.0 | 1.7 | ***0.1*** | ***0.1*** |
| 136 | K136D | 0.2 | 1.6 | 1.5 | 0.9 | 0.4 | 0.5 |
| 136 | K136F | 0.3 | 1.4 | 1.6 | 1.2 | 0.6 | 0.8 |
| 136 | K136I | 0.2 | 2.2 | 2.5 | 1.4 | 0.4 | 0.5 |
| 136 | K136V | 0.2 | 2.2 | 2.4 | 2.0 | 0.5 | 0.8 |
| 136 | K136Y | 0.3 | 1.8 | 1.4 | 1.2 | 0.4 | 0.9 |
| 137 | A137P | 0.2 | 3.9 | 3.4 | 1.8 | 0.2 | 0.1 |
| 138 | A138D | 0.2 | 1.5 | 4.6 | 2.3 | 0.3 | 0.2 |
| 138 | A138E | 0.4 | 1.4 | 1.0 | 1.1 | 0.9 | 0.8 |
| 138 | A138F | 0.2 | 2.6 | 2.7 | 2.0 | 0.8 | 0.3 |

TABLE 31-3-continued

| Performance Index Values for BPN' Variants | | | | | | | |
|---|---|---|---|---|---|---|---|
| Position | BPN' variant | TCA PI | PI BMI pH 8 16 C. | PI BMI pH 7 16 C. | PI BMI pH 8 32 C. | LAS-EDTA PI | specific AAPF PI |
| 138 | A138H | 0.2 | 2.0 | 2.2 | 1.8 | 0.7 | 0.5 |
| 138 | A138Q | 0.2 | 11.9 | 16.2 | 5.0 | 0.9 | 0.8 |
| 138 | A138Y | 0.2 | 6.0 | 9.1 | 3.3 | 0.6 | 0.5 |
| 142 | A142G | 0.5 | 1.3 | 1.2 | 1.0 | 1.0 | 1.2 |
| 142 | A142I | 0.3 | 1.6 | 1.4 | 1.5 | 0.6 | 0.8 |
| 142 | A142T | 0.3 | 1.3 | 1.6 | 1.5 | 0.8 | 1.1 |
| 142 | A142V | 0.4 | 1.5 | 1.2 | 1.2 | 0.8 | 1.1 |
| 143 | V143W | 0.7 | 1.4 | 0.8 | 1.0 | 0.9 | 0.9 |
| 144 | A144P | 0.2 | 1.8 | 2.6 | 1.2 | 0.4 | 0.3 |
| 146 | G146L | 0.2 | 2.2 | 3.8 | 1.9 | 1.1 | 0.6 |
| 146 | G146T | 0.3 | 1.5 | 1.8 | 1.6 | 0.7 | 1.1 |
| 146 | G146Y | 0.2 | 1.7 | 2.2 | 1.6 | 0.9 | 0.9 |
| 147 | V147D | 0.2 | 2.3 | 3.1 | 2.1 | 1.2 | 0.5 |
| 147 | V147P | 0.3 | 1.7 | 2.1 | 1.5 | 0.8 | 1.1 |
| 147 | V147W | 0.3 | 2.0 | 2.2 | 1.3 | 0.9 | 0.9 |
| 147 | V147Y | 0.3 | 2.3 | 2.3 | 1.5 | 0.9 | 0.8 |
| 148 | V148N | 0.4 | 1.4 | 1.4 | 1.1 | 0.8 | 1.1 |
| 148 | V148Y | 0.2 | 1.6 | 1.5 | 1.6 | 0.6 | 0.4 |
| 149 | V149E | 0.2 | 2.7 | 3.7 | 2.5 | 1.0 | 0.4 |
| 151 | A151T | 0.5 | 1.4 | 1.2 | 1.2 | 0.6 | 0.6 |
| 153 | A153T | 0.2 | 4.4 | 4.3 | 3.0 | ***0.1*** | 0.3 |
| 153 | A153V | 0.3 | 1.3 | 1.2 | 1.4 | 0.3 | 0.9 |
| 159 | S159K | 1.2 | 1.4 | 0.9 | 1.0 | 1.0 | 1.1 |
| 164 | T164W | 0.2 | 1.6 | 2.3 | 1.7 | 0.1 | 0.2 |
| 165 | V165T | 0.2 | 1.5 | 2.0 | 1.9 | 0.1 | 0.2 |
| 167 | Y167A | 0.7 | 1.4 | 1.1 | 1.3 | 0.7 | 0.6 |
| 167 | Y167D | 0.3 | 1.4 | 1.6 | 1.3 | 0.1 | 0.1 |
| 167 | Y167E | 0.4 | 1.5 | 1.7 | 1.3 | 0.5 | 0.1 |
| 167 | Y167M | 0.2 | 1.7 | 1.3 | 1.4 | 0.4 | 0.2 |
| 167 | Y167P | 0.3 | 1.8 | 1.9 | 1.6 | ***0.1*** | ***0.1*** |
| 167 | Y167S | 0.3 | 1.4 | 1.3 | 1.3 | 0.2 | 0.3 |
| 167 | Y167T | 0.3 | 1.5 | 1.3 | 1.4 | 0.3 | 0.4 |
| 168 | P168L | 0.2 | 2.0 | 0.9 | 0.3 | ***0.1*** | ***0.1*** |
| 168 | P168T | 0.2 | 3.0 | 0.3 | ***0.1*** | ***0.1*** | ***0.1*** |
| 169 | G169C | 0.2 | 3.0 | 2.2 | 2.4 | 1.0 | 0.5 |
| 170 | K170E | 0.2 | 2.9 | 0.1 | 1.2 | ***0.1*** | ***0.1*** |
| 170 | K170N | 0.3 | 1.6 | 1.4 | 1.2 | 0.5 | 0.6 |
| 170 | K170P | 0.2 | 2.5 | 2.6 | 1.6 | 0.9 | 0.7 |
| 170 | K170Q | 0.5 | 1.3 | 1.2 | 1.1 | 0.8 | 0.6 |
| 170 | K170S | 0.5 | 1.3 | 1.1 | 0.9 | 0.9 | 0.8 |
| 170 | K170T | 0.3 | 1.5 | 1.5 | 1.1 | 0.5 | 0.5 |
| 170 | K170Y | 0.4 | 1.4 | 1.2 | 1.0 | 0.9 | 0.7 |
| 171 | Y171C | 0.2 | 12.3 | 8.6 | 1.8 | 0.8 | 0.1 |
| 171 | Y171D | 0.2 | 4.6 | 3.5 | 1.1 | ***0.1*** | ***0.1*** |
| 171 | Y171L | 0.2 | 4.1 | 3.4 | 2.4 | 0.3 | 0.3 |
| 171 | Y171N | 0.2 | 2.2 | ***0.1*** | 0.5 | ***0.1*** | ***0.1*** |
| 171 | Y171W | 0.5 | 1.4 | 1.0 | 1.0 | 0.6 | 0.4 |
| 172 | P172E | 0.8 | 1.3 | 1.2 | 1.0 | 1.2 | 1.0 |
| 172 | P172G | 0.3 | 1.4 | 1.2 | 1.2 | 1.0 | 0.9 |
| 172 | P172I | 0.5 | 1.4 | 1.1 | 1.1 | 0.9 | 1.1 |
| 172 | P172L | 0.5 | 1.5 | 1.1 | 1.1 | 1.0 | 1.0 |
| 172 | P172V | 0.5 | 1.4 | 1.2 | 1.2 | 0.8 | 1.2 |
| 172 | P172Y | 0.3 | 1.7 | 1.3 | 1.4 | 0.8 | 0.9 |
| 173 | S173H | 0.5 | 1.4 | 0.9 | 1.2 | 0.8 | 0.9 |
| 173 | S173W | 0.3 | 1.9 | 1.3 | 1.5 | 0.6 | 0.9 |
| 173 | S173Y | 0.4 | 1.7 | 1.0 | 1.4 | 0.7 | 0.9 |
| 174 | V174A | 0.5 | 1.4 | 1.2 | 1.1 | 0.8 | 1.0 |
| 174 | V174I | 0.4 | 1.5 | 0.9 | 1.1 | 0.6 | 0.6 |
| 174 | V174L | 0.2 | 93.0 | 66.8 | 4.2 | 0.5 | 0.3 |
| 174 | V174S | 0.4 | 1.4 | 1.0 | 1.2 | 0.9 | 0.8 |
| 175 | I175A | 0.2 | 6.1 | 9.3 | 1.8 | 0.4 | 0.3 |
| 175 | I175F | 0.3 | 1.7 | 1.2 | 1.3 | 0.6 | 0.8 |
| 175 | I175R | 0.2 | 1.5 | ***0.1*** | 0.1 | ***0.1*** | ***0.1*** |
| 175 | I175T | 0.3 | 2.0 | 1.6 | 1.4 | 0.5 | 0.9 |
| 175 | I175V | 0.3 | 2.0 | 1.3 | 1.4 | 0.9 | 1.1 |
| 176 | A176V | 0.2 | 1.5 | ***0.1*** | 0.6 | ***0.1*** | ***0.1*** |
| 177 | V177W | 0.2 | 3.8 | 5.4 | 4.5 | 0.2 | 0.5 |
| 180 | V180F | 0.2 | 1.7 | ***0.1*** | 1.5 | ***0.1*** | ***0.1*** |
| 180 | V180H | 0.2 | 2.3 | 2.9 | 1.9 | 0.1 | 0.1 |
| 180 | V180Q | 0.2 | 4.6 | 4.6 | 2.1 | ***0.1*** | 0.3 |
| 182 | S182W | 0.3 | 1.5 | 1.4 | 1.4 | 0.3 | 1.0 |
| 184 | N184A | 0.3 | 1.4 | 1.9 | 1.4 | 0.7 | 0.7 |
| 184 | N184L | 1.0 | 1.4 | 0.9 | 1.1 | 0.7 | 0.9 |
| 184 | N184V | 0.7 | 1.3 | 1.1 | 1.0 | 0.3 | 1.0 |

TABLE 31-3-continued

| Performance Index Values for BPN' Variants | | | | | | | |
|---|---|---|---|---|---|---|---|
| Position | BPN' variant | TCA PI | PI BMI pH 8 16 C. | PI BMI pH 7 16 C. | PI BMI pH 8 32 C. | LAS-EDTA PI | specific AAPF PI |
| 185 | Q185D | 0.3 | 2.0 | 1.7 | 1.4 | 0.6 | 0.6 |
| 185 | Q185E | 0.8 | 1.4 | 1.1 | 0.9 | 1.2 | 1.0 |
| 185 | Q185I | 0.9 | 1.5 | 1.0 | 1.0 | 0.9 | 1.2 |
| 185 | Q185S | 0.8 | 1.4 | 1.0 | 1.1 | 0.8 | 1.1 |
| 185 | Q185T | 0.8 | 1.4 | 1.3 | 1.1 | 1.0 | 1.2 |
| 186 | R186C | 0.4 | 1.9 | 1.6 | 1.1 | 0.6 | 0.5 |
| 186 | R186D | 0.2 | 11.1 | 16.4 | 0.2 | ***0.1*** | ***0.1*** |
| 186 | R186E | 0.2 | 23.1 | 23.9 | 1.8 | 0.1 | 0.1 |
| 186 | R186F | 0.3 | 1.3 | 1.4 | 0.9 | 0.2 | 0.3 |
| 186 | R186G | 0.3 | 2.2 | 1.9 | 1.2 | 0.2 | 0.6 |
| 186 | R186I | 0.4 | 1.3 | 2.1 | 1.3 | 0.9 | 0.8 |
| 186 | R186L | 0.5 | 1.6 | 1.4 | 1.2 | 0.9 | 0.9 |
| 186 | R186N | 0.3 | 2.5 | 3.7 | 1.5 | 0.3 | 0.4 |
| 186 | R186P | 0.2 | 3.0 | 2.3 | 1.0 | 0.1 | 0.2 |
| 186 | R186Q | 0.4 | 1.5 | 2.1 | 1.3 | 0.8 | 0.9 |
| 186 | R186S | 0.3 | 2.4 | 1.9 | 1.4 | 0.3 | 0.4 |
| 186 | R186T | 0.2 | 8.6 | 7.0 | 2.7 | 0.4 | 0.4 |
| 186 | R186V | 0.4 | 2.0 | 2.0 | 1.4 | 0.9 | 0.8 |
| 186 | R186W | 0.6 | 1.5 | 1.7 | 1.1 | 1.1 | 1.0 |
| 186 | R186Y | 0.4 | 1.5 | 2.0 | 1.4 | 0.8 | 0.7 |
| 187 | A187D | 0.9 | 1.5 | 1.0 | 1.0 | 0.4 | 0.2 |
| 187 | A187E | 0.7 | 1.4 | 1.5 | 1.0 | 0.2 | 0.3 |
| 187 | A187Q | 0.5 | 1.3 | 1.2 | 0.9 | ***0.1*** | 0.4 |
| 190 | S190G | 0.3 | 1.5 | 2.2 | 1.3 | 0.1 | 0.6 |
| 190 | S190N | 0.2 | 1.6 | 2.0 | 1.1 | 0.1 | 0.1 |
| 192 | Y192D | 0.2 | 1.9 | 2.2 | 1.2 | 0.1 | 0.1 |
| 192 | Y192E | 0.4 | 1.4 | 1.6 | 1.1 | ***0.1*** | 0.2 |
| 192 | Y192L | 0.2 | 1.9 | 1.9 | 1.5 | ***0.1*** | 0.2 |
| 192 | Y192Q | 0.4 | 2.1 | 1.3 | 1.2 | 0.2 | 0.6 |
| 193 | G193H | 0.2 | 2.7 | ***0.1*** | ***0.1*** | ***0.1*** | ***0.1*** |
| 193 | G193Q | 0.2 | 2.4 | ***0.1*** | 0.1 | ***0.1*** | ***0.1*** |
| 193 | G193T | 0.2 | 4.8 | 0.5 | 0.1 | ***0.1*** | ***0.1*** |
| 193 | G193V | 0.2 | 2.3 | 1.2 | ***0.1*** | ***0.1*** | ***0.1*** |
| 194 | P194E | 0.7 | 1.5 | 1.1 | 1.0 | 1.0 | 1.3 |
| 194 | P194I | 0.5 | 1.6 | 1.1 | 1.2 | 0.9 | 1.1 |
| 194 | P194L | 0.6 | 1.6 | 0.9 | 1.3 | 0.9 | 1.1 |
| 194 | P194M | 0.6 | 1.4 | 1.1 | 1.1 | 0.8 | 1.5 |
| 194 | P194N | 0.5 | 1.8 | 1.0 | 1.2 | 0.1 | 1.7 |
| 194 | P194T | 0.6 | 1.3 | 1.4 | 1.1 | 0.9 | 1.2 |
| 194 | P194V | 0.5 | 1.7 | 1.1 | 1.2 | 0.8 | 1.4 |
| 195 | E195C | 0.3 | 1.4 | 0.9 | 0.6 | 0.4 | 0.2 |
| 195 | E195K | 0.2 | 3.7 | 2.6 | 2.2 | 0.3 | 0.5 |
| 195 | E195W | 0.2 | 4.3 | 1.3 | 1.3 | 0.1 | 0.1 |
| 196 | L196I | 0.4 | 1.7 | 1.2 | 1.2 | 0.8 | 1.0 |
| 196 | L196M | 0.4 | 1.5 | 1.0 | 1.1 | 0.2 | 0.7 |
| 196 | L196T | 0.2 | 3.9 | 2.9 | 2.7 | 1.0 | 0.7 |
| 196 | L196V | 0.3 | 2.0 | 1.3 | 1.5 | 0.7 | 0.8 |
| 197 | D197I | 0.2 | 3.1 | 4.1 | 2.6 | ***0.1*** | 0.3 |
| 197 | D197M | 0.2 | 1.5 | 0.7 | 1.1 | 0.1 | 0.1 |
| 199 | M199F | 0.2 | 28.7 | 28.8 | 2.6 | 0.1 | 0.2 |
| 199 | M199Q | 0.2 | 2.1 | 1.7 | 1.7 | 0.8 | 0.6 |
| 200 | A200C | 0.7 | 1.3 | 0.9 | 1.2 | 0.6 | 1.2 |
| 200 | A200H | 0.2 | 5.0 | ***0.1*** | 0.2 | ***0.1*** | ***0.1*** |
| 200 | A200N | 0.5 | 1.3 | 1.2 | 1.2 | 0.7 | 1.3 |
| 200 | A200T | 0.4 | 1.7 | 1.0 | 1.4 | 0.2 | 0.7 |
| 200 | A200V | 0.2 | 5.1 | 2.3 | 2.5 | ***0.1*** | 0.4 |
| 200 | A200Y | 0.2 | 2.6 | ***0.1*** | 0.1 | ***0.1*** | ***0.1*** |
| 201 | P201L | 0.3 | 1.7 | 1.7 | 2.1 | ***0.1*** | 0.6 |
| 201 | P201T | 0.2 | 4.0 | 4.1 | 3.5 | ***0.1*** | 0.9 |
| 201 | P201V | 0.2 | 8.3 | 11.8 | 6.0 | ***0.1*** | 0.7 |
| 203 | V203G | 0.2 | 8.7 | 7.7 | 4.9 | 0.1 | 0.3 |
| 205 | I205L | 0.3 | 1.4 | 1.0 | 0.9 | ***0.1*** | 0.5 |
| 205 | I205T | 0.8 | 1.6 | 1.2 | 1.1 | 0.8 | 1.3 |
| 208 | T208C | 0.8 | 1.5 | 1.1 | 1.2 | 0.8 | 1.1 |
| 208 | T208L | 0.9 | 1.4 | 1.1 | 1.1 | ***0.1*** | 1.2 |
| 208 | T208M | 0.2 | 5.7 | 6.0 | 1.8 | 0.4 | 0.4 |
| 208 | T208P | 0.4 | 1.7 | 1.1 | 1.2 | ***0.1*** | 0.7 |
| 208 | T208V | 0.6 | 1.3 | 1.4 | 1.2 | ***0.1*** | 0.9 |
| 209 | L209C | 0.8 | 1.4 | 1.0 | 1.1 | 0.9 | 1.5 |
| 209 | L209W | 0.8 | 1.4 | 1.0 | 1.1 | 0.3 | 1.3 |
| 210 | P210C | 0.4 | 1.5 | 0.9 | 1.0 | 0.2 | 0.8 |
| 210 | P210D | 0.3 | 1.4 | 0.8 | 1.2 | 0.1 | 0.3 |
| 210 | P210E | 0.4 | 1.7 | 1.1 | 1.3 | 0.4 | 0.7 |
| 210 | P210F | 0.2 | 10.3 | 3.5 | 2.0 | 0.1 | 0.1 |

TABLE 31-3-continued

| Performance Index Values for BPN' Variants | | | | | | | |
|---|---|---|---|---|---|---|---|
| Position | BPN' variant | TCA PI | PI BMI pH 8 16 C. | PI BMI pH 7 16 C. | PI BMI pH 8 32 C. | LAS-EDTA PI | specific AAPF PI |
| 210 | P210G | 0.3 | 1.8 | 1.0 | 1.3 | ***0.1*** | 0.6 |
| 210 | P210Q | 0.3 | 3.0 | 2.3 | 2.0 | ***0.1*** | 0.8 |
| 210 | P210R | 0.2 | 3.3 | 2.8 | 2.4 | ***0.1*** | 0.5 |
| 210 | P210S | 0.6 | 1.4 | 1.1 | 1.2 | 0.4 | 1.3 |
| 210 | P210V | 0.5 | 1.4 | 1.2 | 1.1 | 0.2 | 0.8 |
| 211 | G211A | 0.9 | 1.5 | 1.1 | 1.0 | 1.0 | 0.9 |
| 211 | G211D | 1.0 | 1.5 | 1.2 | 1.0 | 1.4 | 1.0 |
| 211 | G211E | 0.9 | 1.3 | 1.1 | 1.1 | 1.3 | 0.9 |
| 211 | G211P | 0.9 | 1.3 | 1.7 | 1.0 | 0.6 | 1.0 |
| 211 | G211T | 0.8 | 1.4 | 1.4 | 1.2 | 0.7 | 1.1 |
| 211 | G211V | 0.8 | 1.3 | 1.2 | 0.9 | 0.5 | 0.9 |
| 211 | G211W | 0.8 | 1.3 | 1.1 | 1.2 | 0.2 | 1.0 |
| 212 | N212E | 1.0 | 1.4 | 1.1 | 0.9 | 1.2 | 0.8 |
| 212 | N212T | 0.2 | 6.1 | 4.4 | 3.0 | 0.6 | 1.3 |
| 213 | K213Q | 1.0 | 1.4 | 1.0 | 1.0 | 1.5 | 1.0 |
| 213 | K213T | 0.9 | 1.4 | 1.2 | 0.9 | 1.5 | 0.9 |
| 214 | Y214A | 0.2 | 2.4 | 1.6 | 0.7 | 0.2 | 0.1 |
| 214 | Y214D | 0.2 | 3.2 | 3.2 | 1.7 | 0.2 | 0.1 |
| 214 | Y214N | 0.2 | 1.7 | 1.6 | 1.3 | 0.7 | 0.2 |
| 214 | Y214P | 0.2 | 2.1 | 2.3 | 1.4 | ***0.1*** | 0.7 |
| 214 | Y214S | 0.2 | 2.2 | 1.1 | 1.5 | 0.2 | 0.1 |
| 215 | G215D | 0.9 | 1.3 | 1.1 | 1.1 | 1.0 | 0.7 |
| 215 | G215Q | 0.8 | 1.4 | 1.0 | 1.0 | 0.1 | 0.7 |
| 215 | G215V | 0.4 | 1.5 | 0.9 | 1.2 | 0.1 | 0.5 |
| 216 | A216E | 1.2 | 1.4 | 0.9 | 1.0 | 1.4 | 0.8 |
| 217 | Y217E | 1.0 | 1.4 | 1.0 | 1.2 | 1.3 | 0.5 |
| 217 | Y217L | 1.0 | 1.3 | 1.0 | 1.1 | 1.4 | 3.5 |
| 217 | Y217M | 0.9 | 1.3 | 1.2 | 1.1 | 1.5 | 1.8 |
| 218 | N218P | 0.3 | 1.6 | 0.8 | 1.2 | 0.2 | 0.6 |
| 223 | A223W | 0.2 | 1.5 | 0.8 | 0.2 | ***0.1*** | ***0.1*** |
| 224 | S224D | 0.2 | 1.6 | 0.6 | 0.3 | ***0.1*** | ***0.1*** |
| 224 | S224N | 0.4 | 1.8 | 1.6 | 1.3 | 0.6 | 0.2 |
| 224 | S224Q | 0.3 | 2.0 | 0.1 | 0.2 | ***0.1*** | ***0.1*** |
| 226 | H226E | 0.2 | 1.5 | 1.9 | 1.2 | ***0.1*** | 0.5 |
| 226 | H226T | 0.4 | 1.4 | 1.4 | 1.2 | ***0.1*** | 0.9 |
| 227 | V227G | 0.3 | 1.6 | 1.4 | 1.1 | 0.9 | 0.7 |
| 227 | V227L | 0.5 | 1.4 | 1.3 | 1.0 | 0.4 | 0.9 |
| 227 | V227S | 0.2 | 14.7 | 19.5 | 4.2 | 0.5 | 0.5 |
| 230 | A230H | 0.2 | 10.4 | 16.2 | 3.8 | 0.1 | 0.4 |
| 230 | A230N | 0.2 | 1.8 | 2.2 | 1.7 | 0.6 | 0.6 |
| 231 | A231W | 0.2 | 4.4 | 5.9 | 4.4 | 0.3 | 0.2 |
| 231 | A231Y | 0.3 | 1.5 | 2.1 | 1.6 | 0.2 | 0.4 |
| 232 | A232N | 0.2 | 1.6 | 2.2 | 1.5 | 1.1 | 0.4 |
| 234 | I234W | 0.2 | 4.8 | 6.8 | 2.4 | 0.1 | 0.2 |
| 235 | L235N | 0.3 | 1.3 | 1.5 | 1.2 | 1.2 | 0.7 |
| 236 | S236W | 0.2 | 2.1 | 3.4 | 2.3 | 0.8 | 0.5 |
| 238 | H238A | 0.3 | 1.3 | 1.4 | 1.1 | 1.1 | 0.5 |
| 238 | H238G | 0.2 | 5.2 | 6.0 | 2.4 | 1.0 | 0.4 |
| 238 | H238I | 0.2 | 7.7 | 7.0 | 3.6 | 1.1 | 0.5 |
| 239 | P239H | 0.9 | 1.4 | 1.0 | 1.1 | 1.1 | 1.1 |
| 239 | P239S | 0.9 | 1.3 | 1.0 | 1.0 | 1.1 | 1.3 |
| 241 | W241G | 0.3 | 1.4 | 1.1 | 0.9 | 1.0 | 0.6 |
| 241 | W241Q | 0.7 | 1.4 | 1.0 | 1.1 | 1.1 | 1.1 |
| 247 | R247H | 0.3 | 1.3 | 1.5 | 1.3 | 0.3 | 0.7 |
| 247 | R247L | 0.3 | 1.7 | 1.5 | 1.3 | 0.1 | 0.6 |
| 247 | R247W | 0.3 | 1.4 | 1.4 | 1.0 | 0.3 | 0.7 |
| 247 | R247Y | 0.3 | 1.5 | 2.2 | 1.5 | 0.2 | 0.9 |
| 250 | L250E | 0.2 | 2.6 | ***0.1*** | 0.1 | ***0.1*** | ***0.1*** |
| 250 | L250T | 0.3 | 1.5 | 2.3 | 1.7 | 0.8 | 0.8 |
| 252 | N252Q | 1.4 | 1.3 | 1.1 | 1.1 | 1.1 | 1.0 |
| 253 | T253Y | 0.2 | 3.5 | 2.0 | 1.6 | 0.2 | 0.1 |
| 254 | T254D | 0.3 | 2.3 | 1.8 | 1.7 | ***0.1*** | 0.5 |
| 254 | T254Q | 0.2 | 32.6 | 41.1 | 3.7 | ***0.1*** | 0.5 |
| 254 | T254R | 0.2 | 7.7 | 3.7 | 1.6 | ***0.1*** | 0.6 |
| 255 | T255L | 1.0 | 1.5 | 1.0 | 1.0 | ***0.1*** | 1.0 |
| 255 | T255P | 0.2 | 1.6 | 1.0 | 1.4 | ***0.1*** | 0.4 |
| 256 | K256G | 0.7 | 1.3 | 0.9 | 1.0 | ***0.1*** | 1.0 |
| 256 | K256R | 1.1 | 1.4 | 1.0 | 1.1 | ***0.1*** | 0.9 |
| 258 | G258P | 0.3 | 1.4 | 1.6 | 1.6 | ***0.1*** | 0.7 |
| 263 | Y263D | 0.3 | 1.6 | 1.4 | 1.2 | ***0.1*** | 0.7 |
| 263 | Y263K | 0.2 | 2.4 | 2.8 | 1.9 | 0.1 | 0.3 |
| 263 | Y263R | 0.2 | 8.0 | 4.1 | 1.7 | 0.1 | 0.3 |
| 265 | K265P | 0.3 | 1.6 | 1.9 | 1.6 | 1.0 | 0.8 |
| 268 | I268S | 0.3 | 1.4 | 1.3 | 1.6 | ***0.1*** | 0.8 |

TABLE 31-3-continued

| Performance Index Values for BPN' Variants | | | | | | | |
|---|---|---|---|---|---|---|---|
| Position | BPN' variant | TCA PI | PI BMI pH 8 16 C. | PI BMI pH 7 16 C. | PI BMI pH 8 32 C. | LAS-EDTA PI | specific AAPF PI |
| 268 | I268T | 0.3 | 1.9 | 2.0 | 1.8 | 0.8 | 0.4 |
| 268 | I268W | 0.2 | 2.8 | 2.4 | 0.2 | ***0.1*** | ***0.1*** |
| 270 | V270F | 0.2 | 2.4 | 2.9 | 1.1 | 0.2 | 0.1 |
| 273 | A273K | 0.2 | 1.6 | 1.6 | 1.9 | ***0.1*** | 0.6 |
| 273 | A273P | 0.3 | 1.5 | 1.7 | 1.8 | ***0.1*** | 0.7 |
| 273 | A273R | 0.2 | 1.4 | 1.2 | 2.0 | ***0.1*** | 0.6 |
| 273 | A273V | 0.5 | 1.4 | 1.2 | 1.2 | 0.3 | 0.8 |
| 273 | A273W | 0.3 | 2.1 | 2.0 | 1.5 | ***0.1*** | 0.8 |
| 274 | A274W | 0.4 | 1.3 | 0.7 | 1.1 | 0.5 | 0.7 |

TABLE 31-4

| | |
|---|---|
| Parent: | FNA (SEQ ID NO: 2 with Y217L mutation) |
| Measure: | PI versus FNA for BMI pH 8 16 C. assay |
| Detergent: | As indicated in table 31-1 (NA Detergent was Commercial heat deactivated Tide 2X; WE detergent was commercial heat deactivated Western European Henkel Persil liquid laundry and Japan laundry was heat deactivated Japanese Tide laundry powder detergent). |

Figure 9:
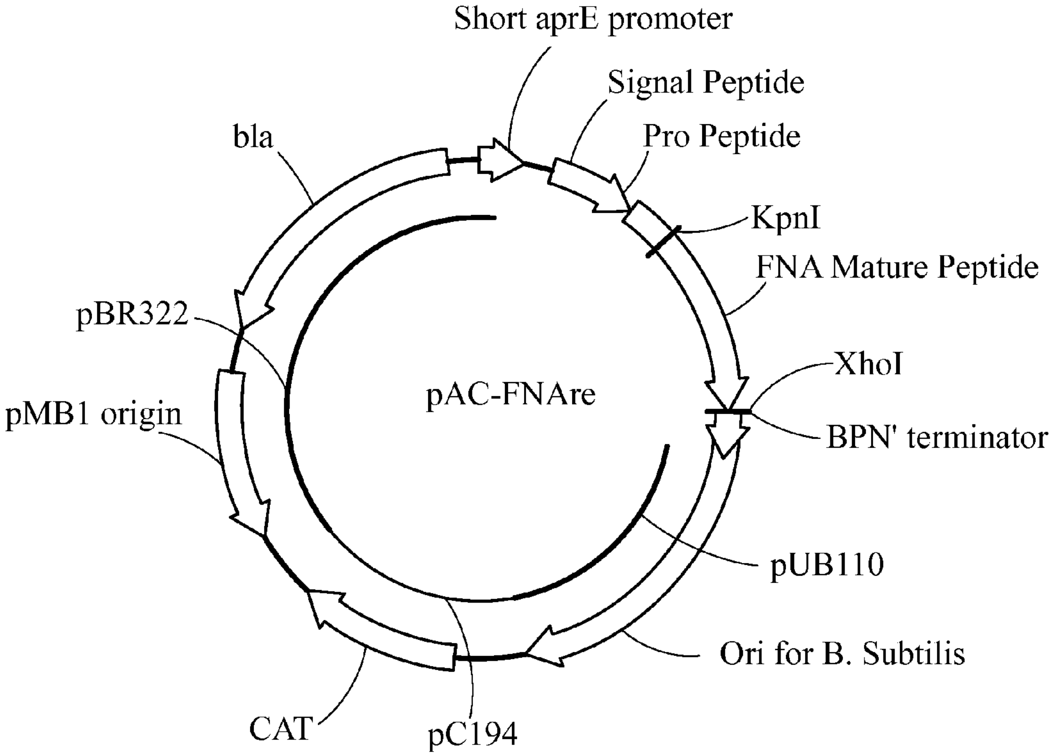
FIG. 9 provides a map of pAC-FNAre.

Generation of Combinatorial Variants of BPN'-Y217L Involving Charged Residue Substitutions The pAC-FNAre plasmid in FIG. 9 containing the BPN'-Y217L gene was sent to DNA 2.0 Inc. (Menlo Park, Calif.) for the generation of combinatorial variants containing substitutions involving charge changes. They were also provided with the *Bacillus subtilis* strain (genotype: ΔaprE, ΔnprE, ΔspoIIE, amyE::xylRPxylAcomK-phleo) for transformations. The subtilisin BPN'-Y217L combinatorial charge variants were designed by identifying four well-distributed, surface-exposed, uncharged polar amino-acid residues outside the active site. These residues are Ser-87, Asn-109, Ser-188, and Ser-248. The variants were supplied as glycerol stocks from DNA 2.0. *B. subtilis* transformants containing BPN' variant proteins were replicated with a steel 96-well replicator from glycerol stocks into 96-well culture plates (BD, 353075) containing 200 μl of LB media+25 μg/ml chloramphenicol, grown overnight at 37° C., 220 rpm in a humidified enclosure. 200 μl from the overnight culture was used to inoculate 2000 μl MBD defined media+25 μg/ml chloramphenicol in 5 ml plastic shake tubes. MBD (a MOPS based defined medium) was made essentially as known in the art (See, Neidhardt et al., J. Bacteriol., 119: 736-747 [1974]), except that $NH_4Cl$, $FeSO_4$, and $CaCl_2$ were omitted from the base medium, 3 mM $K_2HPO_4$ was used, and the base medium was supplemented with 60 mM urea, 75 g/L glucose, and 1% soytone. The micronutrients were made up as a 100x stock solution containing in one liter, 400 mg $FeSO_47H_2O$, 100 mg $MnSO_4.H_2O$, 100 mg $ZnSO_47H_2O$, 50 mg $CuCl_22H_2O$, 100 mg $CoCl_26H_2O$, 100 mg $NaMoO_42H_2O$, 100 mg $Na_2B_4O_710H_2O$, 10 ml of 1M $CaCl_2$, and 10 ml of 0.5 M sodium citrate. Shake tubes were incubated at 37° C., 220 rpm, for 60 hours. Following 60 hours, culture broth was spun down in a centrifuge at greater than 8000×RCF. The supernatant solution was decanted into 15 ml polypropylene conical tubes for storage. No further purification or concentration was performed. Supernatant stocks were formulated to 40% propylene glycol for long-term stability.

Description

This example describes the testing of BPN'-Y217L variants in BMI microswatch assays in detergents representing various market geographies (e.g., differing pH, T, and/or water hardness), in laundry applications, as described in Test Method 2.

TABLE 31-4

Performance of combinatorial variants of BPN'-Y217L involving charged residue substitutions

| Variants | Net Charge | Laundry PI NA | PI WE Laundry | Laundry PI JPN |
|---|---|---|---|---|
| N109D-Y217L-S248R | 0 | 1.2 | 1.9 | 1.6 |
| N109D-S188R-Y217L | 0 | 1.3 | 1.5 | 1.3 |
| S87D-Y217L-S248R | 0 | 1.2 | 1.5 | 1.5 |
| S87R-N109D-Y217L-S248R | 1 | 1.2 | 1.5 | 2.3 |
| S87R-N109D-S188D-Y217L-S248R | 0 | 1.2 | 1.5 | 1.0 |

TABLE 31-5

Wash Performance of selected Double Mutant Proteases

| | |
|---|---|
| Parent: | BPN' wild type (SEQ ID NO: 2) |
| Measure: | PI at least 1.3 for BMI assay pH 8 16 C. versus wild type (SEQ ID NO: 2) |
| Detergent: | Commercial heat deactivated Tide 2X Cold |

Description

The BPN' double mutants shown in Table 31-5 below were produced by DNA 2.0 (Menlo Park, Calif.), using BPN' as the parent gene contained in the expression plasmid pHPLT-BPN' partial opt. Plasmid pHPLT-BPN' partial opt was also created by DNA 2.0 (Menlo Park, Calif.) using a codon optimized gene encoding the BPN' protease and the pHPLT-BPN' plasmid described above (also see FIG. 3).

The DNA sequence of the pHPLT-BPN' expression cassette (aprE-BPN' hybrid leader, BPN' pro and BPN' mature DNA sequence from *B. amyloliquefaciens*) provided below, encodes the BPN' precursor protein:

GTGAGAAGCAAAAAATTGTGGATCAGTTTGCTGTTTGCTTTAGCGTTAA

TCTTTACGATGGCGTTCGGCAGCACATCCTCTGCCCAGGCGGCAGGGAA

ATCAAACGGGGAAAAGAAATATATTGTCGGGTTTAAACAGACAATGAGC

ACGATGAGCGCCGCTAAGAAGAAAGATGTCATTTCTGAAAAAGGCGGGA

AAGTGCAAAAGCAATTCAAATATGTAGACGCAGCTTCAGCTACATTAAA

CGAAAAAGCTGTAAAAGAATTGAAAAAAGACCCGAGCGTCGCTTACGTT

GAAGAAGATCACGTAGCACATGCGTACGCGCAGTCCGTGCCTTACGGCG

TATCACAAATTAAAGCCCCTGCTCTGCACTCTCAAGGCTACACTGGATC

AAATGTTAAAGTAGCGGTTATCGACAGCGGTATCGACTCGAGCCATCCA

GATCTTAAAGTCGCTGGAGGGGCTTCTATGGTGCCGTCCGAAACAAACC

CGTTTCAAGATAACAATTCTCATGGCACACACGTCGCAGGAACGGTTGC

GGCGTTAAACAATTCTATTGGCGTGCTTGGTGTAGCCCCGTCTGCTTCG

CTCTACGCCGTTAAAGTTCTTGGCGCAGACGGATCAGGCCAATACTCAT

GGATTATCAACGGCATCGAATGGGCCATCGCGAATAACATGGATGTAAT

CAACATGAGCCTGGGAGGACCAAGCGGCAGTGCGGCACTTAAAGCAGCA

GTTGATAAAGCTGTTGCATCTGGTGTCGTCGTAGTAGCGGCAGCTGGGA

-continued

ATGAGGGAACATCCGGATCATCGAGTACCGTCGGTTATCCAGGCAAGTA

CCCTTCAGTGATTGCAGTGGGCGCTGTAGACTCTTCAAATCAACGTGCC

TCTTTTTCCTCCGTGGGACCGGAGCTGGATGTCATGGCCCCTGGCGTTT

CTATTCAATCGACGCTTCCAGGGAACAAGTATGGTGCGTATAACGGGAC

TTCCATGGCCTCGCCGCATGTAGCTGGGGCGGCCGCATTGATTCTTTCT

AAGCACCCGAACTGGACAAACACTCAAGTCCGCAGCAGTTTAGAAAACA

CCACTACAAAACTTGGTGATTCTTTCTACTATGGAAAAGGGCTGATCAA

CGTACAGGCGGCAGCTCAG

In the above sequence, bold indicates the DNA that encodes the mature protease, standard font indicates the leader sequence (aprE-BPN' hybrid leader), and the underlined indicates the pro sequences (BPN'). The amino acid sequence of the mature BPN' protease is SEQ ID NO:2. The plasmid map The BPN' variant proteins were also produced as described earlier. Protein concentration of culture supernatants was determined by TCA precipitation as described in TCA assay of Test Method 2. The stain removal performance of the variants was tested in laundry applications on EMPA 116 swatches (BMI stain, CFT) at pH 8/16° C., pH 7/16° C. and pH 8/32° C. using methods described in Test Method 2 assay methods, with the following modifications. The test detergent used was heat inactivated TIDE® 2× Cold detergent (Procter & Gamble). Heat inactivation of commercial detergent formulas serves to destroy the endogenous enzymatic activity of any protein components while retaining the properties of nonenzymatic components. Heat inactivation of the detergents was performed by placing pre-weighed amounts of liquid detergent (in a glass bottle) in a water bath at 95° C. for 2 hours. The detergent was purchased from local supermarket stores. Both unheated and heated detergents were assayed within 5 minutes of dissolving the detergent, in order to accurately determine percentage deactivated. Functionality of BPN' variants was quantified as a performance index (PI) (i.e., the ratio of performance of a variant relative to parent BPN'). Results are shown in Table 31-5—in this Table, "ND" indicates "not determined." Data are shown for variants having a PI of at least 1.3 for BMI pH8 16C cleaning assay.

TABLE 31-5

PI Values of BPN' Variants Tested for Expression (TCA) and Stain Removal Performance (BMI pH 8/16° C., BMI pH 7/16° C., and BMI pH 8/32° C.)

| Variant | TCA | BMI pH 8/16° C. | BMI pH 7/16° C. | BMI pH 8/32° C. |
|---|---|---|---|---|
| G128A-Y217Q | 1.2 | 1.4 | 1.1 | 1.2 |
| I111V-M124V | 0.9 | 1.3 | ND | ND |
| M124V-Y217Q | 1.5 | 1.4 | 1.1 | 1.2 |
| N62Q-G97A | 1.5 | 1.3 | 1.2 | 1.2 |
| S89Y-M124V | 1.1 | 1.3 | ND | ND |
| V68A-A92G | 0.8 | 1.4 | ND | ND |
| V68A-G97A | 2.1 | 1.3 | ND | ND |
| V68A-I111V | 2.1 | 1.3 | ND | ND |
| V68A-S89Y | 1.7 | 1.4 | ND | ND |
| V68A-V227T | 1.0 | 1.4 | ND | ND |
| V68A-Y217Q | 2.3 | 1.3 | ND | ND |
| W106F-Y217Q | 0.9 | 1.4 | ND | ND |

TABLE 31-6

| Wash Performance of Selected Series 1 BPN' Cold Water Proteases | |
|---|---|
| Parent: | BPN' wild type (SEQ ID NO: 2) |
| Measure: | PI at least 1.3 for BMI assay pH 8 16 C. versus wild type (SEQ ID NO: 2) |
| Detergent: | Commercial heat deactivated Tide 2X Cold |

Description

BPN' multiple mutation libraries (or combinatorial libraries) were produced by Geneart or DNA 2.0, using BPN' as the parent protein. Protein concentration of culture supernatants was determined by TCA precipitation as described in Test Method 2. The stain removal performance of the variants was tested in laundry applications on EMPA 116 swatches (BMI stain, CFT) at pH 8/16° C., pH 7/16° C. and pH 8/32° C. using methods described in Test Method 2, with the following modifications. The test detergent used was heat inactivated TIDE® 2× Cold detergent (Procter & Gamble), prepared as described in Test Method 2. Heat inactivation of commercial detergent formulas serves to destroy the endogenous enzymatic activity of any protein components while retaining the properties of non-enzymatic components. Heat inactivation of the detergents was performed by placing pre-weighed amounts of liquid detergent (in a glass bottle) in a water bath at 95° C. for 2 hours. The detergent was purchased from local supermarket stores. Both unheated and heated detergents were assayed within 5 minutes of dissolving the detergent, in order to accurately determine percentage deactivated. Enzyme activity was tested by AAPF assay. Functionality of BPN' variants was quantified as a performance index (PI) (i.e., the ratio of performance of a variant relative to parent BPN'). Results are shown in Table 31-6. Performance indices less than or equal to 0.1 were fixed to 0.1 and indicated in bold italics in the table. For every variant with a TCA protein performance index less than or equal to 0.1, all values were fixed at 0.1.

TABLE 31-6

PI Values of BPN' Variants Tested for Expression (TCA) and Stain Removal Performance (BMI pH 8/16° C., BMI pH 7/16° C., and BMI pH 8/32° C.)

| Variant | TCA | BMI pH 8/16° C. | BMI pH 7/16° C. | BMI pH 8/32° C. |
|---|---|---|---|---|
| G97A-G128A-Y217Q | 1.3 | 1.4 | 1.2 | 1.2 |
| G97A-L126A-Y217Q | 1.1 | 1.3 | 1.2 | 1.2 |
| G97A-M124V-L126A-Y217Q | 1.8 | 1.4 | 1.2 | 1.2 |
| G97A-N123G-Y217Q | 0.6 | 1.4 | 1.2 | 1.1 |
| L96T-G97A-Y217Q | 0.5 | 1.3 | 1.1 | 1.1 |
| M124V-L126A-Y217Q | 1.7 | 1.4 | 1.2 | 1.2 |
| N62Q-G128A-Y217Q | 0.7 | 1.3 | 1.2 | 1.1 |
| N62Q-G97A-Y217Q | 1.7 | 1.4 | 1.2 | 1.3 |

TABLE 31-7

| Wash Performance of Selected Series 1 BPN' Cold Water Protease Variants | |
|---|---|
| Parent: | FNA (SEQ ID NO: 2 with Y217L mutation) |
| Measure: | PI versus FNA for BMI pH 8 16 C. assay |
| Detergent: | Commercial heat deactivated Tide 2X Cold |

Description

Saturation libraries at positions 97-128-217 in BPN' (parent) were produced by DNA 2.0. Protein concentration of culture supernatants was determined by TCA precipitation as described in Test Method 2. The stain removal performance of the variants was tested in laundry applications on EMPA 116 swatches (BMI stain, CFT) at pH8/16° C. using methods described in Test Method 2. Functionality of BPN' variants was quantified as a performance index (PI) (i.e., the ratio of performance of a variant relative to FNA). Results are shown in Table 31-7.

TABLE 31-7

PI Values of BPN' Variants Tested for Protein Determination (TCA) and Stain Removal Performance (BMI pH 8/16° C.)

| Variants | TCA | BMI pH 8 16° C. |
|---|---|---|
| G97N-G128A-Y217M | 1.1 | 1.4 |
| G97G-G128S-Y217E | 1.5 | 1.4 |
| G97A-G128A-Y217Q | 1.3 | 1.4 |
| G97M-G128S-Y217E | 1.2 | 1.4 |
| G97A-G128S-Y217Q | 1.9 | 1.3 |
| G97D-G128S-Y217Q | 1.6 | 1.3 |
| G97M-G128G-Y217M | 1.6 | 1.3 |
| G97G-G128S-Y217Q | 1.6 | 1.3 |
| G97S-G128S-Y217Q | 1.5 | 1.3 |
| G97G-G128A-Y217Q | 1.3 | 1.3 |
| G97S-G128A-Y217E | 1.0 | 1.3 |
| G97A-G128S-Y217L | 2.2 | 1.3 |
| G97A-G128A-Y217N | 1.2 | 1.3 |
| G97Q-G128S-Y217L | 1.9 | 1.3 |
| G97A-G128A-Y217M | 1.5 | 1.3 |
| G97A-G128A-Y217S | 1.4 | 1.3 |
| G97D-G128A-Y217Q | 1.1 | 1.3 |
| G97M-G128S-Y217Q | 1.0 | 1.3 |
| G97Q-G128G-Y217D-S87Y | 1.5 | 1.3 |
| G97S-G128A-Y217N | 1.1 | 1.3 |
| G97A-G128S-Y217T | 1.6 | 1.3 |
| G97D-G128S-Y217E | 1.0 | 1.3 |
| G97D-G128A-Y217L | 1.4 | 1.3 |
| G97G-G128S-Y217E-S78P-A272T | 1.0 | 1.3 |
| G97T-G128S-Y217D | 1.1 | 1.3 |
| G97D-G128A-Y217I | 1.0 | 1.3 |
| G97Q-G128S-Y217Q | 1.6 | 1.3 |
| G97G-G128A-Y217D | 1.1 | 1.3 |
| G97Q-G128A-Y217N | 1.1 | 1.3 |
| G97S-G128A-Y217M | 1.4 | 1.3 |
| G97S-G128S-Y217N | 1.6 | 1.3 |
| G97S-G128S-Y217M | 1.5 | 1.3 |
| G97E-G128S-Y217M | 1.6 | 1.2 |
| G97S-G128P-Y217Q | 1.0 | 1.2 |
| G97T-G128S-Y217Q | 1.1 | 1.2 |
| G97D-G128S-Y217Q-A73T | 1.2 | 1.2 |
| G97E-G128S-Y217N | 1.2 | 1.2 |
| G97G-G128A-Y217I | 1.5 | 1.2 |
| G97Q-G128A-Y217D | 1.1 | 1.2 |
| G97Q-G128S-Y217M | 2.0 | 1.2 |
| G97R-G128T-Y217Q-S162P | 0.7 | 1.2 |
| G97S-G128S-Y217D | 1.5 | 1.2 |
| G97T-G128P-Y217I | 1.3 | 1.2 |
| G97Q-G128G-Y217E | 1.6 | 1.2 |
| G97C-G128G-Y217N | 1.3 | 1.2 |
| G97D-G128S-Y217H | 1.5 | 1.2 |
| G97M-G128S-Y217L | 1.0 | 1.2 |
| G97M-G128S-Y217N | 1.0 | 1.2 |
| G97S-G128S-Y217E | 0.6 | 1.2 |
| G97M-G128S-Y217I | 1.1 | 1.2 |
| G97A-G128P-Y217A | 0.8 | 1.2 |
| G97R-G128S-Y217D | 1.0 | 1.2 |

TABLE 31-8

| Wash Performance of Selected Series 1 BPN' Cold Water Protease Variants | |
|---|---|
| Parent: | BPN' v3 (SEQ ID NO: 4) |
| Measure: | PI versus above parent using BMI pH 8 16° C. assay |
| Detergent: | Commercial heat deactivated Tide 2X Cold |

Description

Additional BPN' multiple mutation libraries were produced by Geneart or Gene Oracle, using BPN': G97A-G128A-Y217Q protein as the parent molecule. Results of experiments conducted to determine stain removal activity (microswatch assay to determine stain removal performance in laundry applications using EMPA 116 swatches (BMI stain, CFT Vlaardingen) (BMI pH8, BMI pH7, BMI 32° C.), protein determination by TCA precipitation, and LAS/EDTA stability (tests of properties of interest) of BPN' variants are shown in table 31-8. The results were obtained using the methods described in Test Method 2, with the following modifications for the stain removal performance assay. The test detergent used was heat inactivated TIDE® 2× Cold detergent (Procter & Gamble, Cincinnati, Ohio, USA). Heat inactivation of commercial detergent formulas serves to destroy the endogenous enzymatic activity of any protein components while retaining the properties of non-enzymatic components. Heat inactivation of the detergents was performed by placing pre-weighed amounts of liquid detergent (in a glass bottle) in a water bath at 95° C. for 2 hours. The detergent was purchased from local supermarket stores. Both unheated and heated detergents were assayed within 5 minutes of dissolving the detergent to accurately determine percentage deactivated. Enzyme activity was tested by AAPF assay. As described throughout herein, functionality of BPN' variants was quantified as a performance index (PI), which is the ratio of performance of a variant to parent protein BPN': G97A-G128A-Y217Q (i.e. enzyme of SEQ ID NO:4).

TABLE 31-8

Stain removal performance of multiple mutation variants of BPN'

| Variant | BMI pH 8 16 C. | BMI pH 7 16 C. | BMI pH 8 32° C. | TCA |
|---|---|---|---|---|
| G97A-G128A-Y217Q-S145D | 1.1 | 1.0 | 1.2 | 1.0 |
| G97A-G128A-Y217Q-P239R | 1.0 | 1.0 | 1.1 | 0.7 |
| G97A-G128A-Y217Q-N61E-P129E-S162K-K213L-N240K | 1.0 | 0.9 | 1.1 | 1.0 |
| G97A-G128A-Y217Q-N61E | 1.0 | 1.0 | 1.1 | 1.3 |
| G97A-G128A-Y217Q-P40E-A144K-K213L | 1.0 | 0.9 | 0.9 | 0.8 |
| G97A-G128A-Y217Q-P129E | 1.0 | 1.0 | 1.0 | 1.0 |
| G97A-G128A-Y217Q-N61E-P129E-S159K | 1.0 | 1.0 | 1.1 | 1.2 |
| G97A-G128A-Y217Q-K213L | 1.0 | 1.0 | 1.0 | 1.1 |
| G97A-G128A-Y217Q-S87D | 1.0 | 1.0 | 1.0 | 0.8 |
| G97A-G128A-Y217Q-Q206E | 1.0 | 1.0 | 1.0 | 1.0 |
| G97A-G128A-Y217Q-S24R-P40E-S145D-S159K-K213L | 1.0 | 1.0 | 1.0 | 0.9 |
| G97A-G128A-Y217Q-K265N | 1.0 | 1.0 | 1.0 | 0.9 |
| G97A-G128A-Y217Q-S24R | 1.0 | 0.9 | 1.0 | 1.0 |
| G97A-G128A-Y217Q-P40E | 1.0 | 1.0 | 1.0 | 0.8 |
| G97A-G128A-Y217Q-Q275E | 1.0 | 1.0 | 1.0 | 1.0 |
| G97A-G128A-Y217Q-P129E-S145D-N240K | 1.0 | 1.0 | 1.0 | 0.8 |
| G97A-G128A-Y217Q-A144K | 1.0 | 0.9 | 1.0 | 0.9 |
| G97A-G128A-Y217Q-S159K | 0.9 | 0.9 | 1.0 | 1.0 |
| G97A-G128A-Y217Q-S162K | 0.9 | 0.9 | 1.0 | 1.0 |
| G97A-G128A-Y217Q-N240K | 0.9 | 0.9 | 1.0 | 0.7 |

TABLE 31-9

Wash Performance of Selected Series 1 BPN' Cold Water Protease Variants

| | |
|---|---|
| Parent: | BPN' v3 (G97A-G128A-Y217Q) |
| Measure: | PI relative to BPN' v3 (G97A-G128A-Y217Q) in BMI pH 8 16 C. assay |
| Detergent: | Commercial heat deactivated Tide 2X Cold |

Description

Additional BPN' multiple mutation libraries were produced by Geneart or Gene Oracle, using BPN': G97A-G128A-Y217Q protein as the parent molecule. Results of experiments conducted to determine stain removal activity (microswatch assay to determine stain removal performance in laundry applications using EMPA 116 swatches (BMI stain, CFT Vlaardingen) (BMI pH8, BMI pH7, BMI 32° C.), protein determination by TCA precipitation, and LAS/EDTA stability (tests of properties of interest) of BPN' variants are shown in table 31-9. The results were obtained using the methods described in Test method 2, with the following modifications for the stain removal performance assay. The test detergent used was heat inactivated TIDE® 2× Cold detergent (Procter & Gamble, Cincinnati, Ohio, USA). Heat inactivation of commercial detergent formulas serves to destroy the endogenous enzymatic activity of any protein components while retaining the properties of non-enzymatic components. Heat inactivation of the detergents was performed by placing pre-weighed amounts of liquid detergent (in a glass bottle) in a water bath at 95° C. for 2 hours. The detergent was purchased from local supermarket stores. Both unheated and heated detergents were assayed within 5 minutes of dissolving the detergent to accurately determine percentage deactivated. Enzyme activity was tested by AAPF assay. As described throughout herein, functionality of BPN' variants was quantified as a performance index (PI), which is the ratio of performance of a variant to parent protein BPN': G97A-G128A-Y217Q (i.e. enzyme of SEQ ID NO:4).

TABLE 31-9

Stain removal performance of multiple mutation variants of BPN'

| Mutations | BMI pH 8 | BMI pH 7 | TCA | LAS/ EDTA |
|---|---|---|---|---|
| G97A-G128A-Y217Q-S53G | 1.1 | 1.0 | 1.2 | 1.0 |
| G97A-G128A-Y217Q-S78N | 1.0 | 1.0 | 1.0 | 1.5 |
| G97A-G128A-Y217Q-S53G-S78N | 1.0 | 1.0 | 1.1 | 1.4 |
| G97A-G128A-Y217Q-S53G-I111V | 1.0 | 1.0 | 0.8 | 1.2 |
| G97A-G128A-Y217Q-S53G-N117S | 0.9 | 1.0 | 0.8 | 1.3 |
| G97A-G128A-Y217Q-S53G-S132N | 0.9 | 0.9 | 0.7 | 1.0 |
| G97A-G128A-Y217Q-Y104N-S132N | 1.0 | 1.1 | 0.7 | 1.3 |
| G97A-G128A-Y217Q-S53G-S78N-I111V | 1.0 | 1.0 | 0.9 | 1.7 |
| G97A-G128A-Y217Q-S53G-S78N-N117S | 0.9 | 0.9 | 0.7 | 1.6 |
| G97A-G128A-Y217Q-S53G-S78N-S132N | 1.0 | 0.9 | 0.8 | 1.5 |
| G97A-G128A-Y217Q-S53G-Y104N-S132N | 0.9 | 1.0 | 1.2 | 1.1 |
| G97A-G128A-Y217Q-S78N-Y104N-S132N | 1.0 | 1.0 | 0.8 | N/D |

TABLE 31-10

| | |
|---|---|
| Parent | FNA (BPN' Y217L) |
| Measure | PI relative to FNA (BPN' Y217L) for BMI pH 8 16° C. assay |
| Detergent: | Commercial heat-deactivated Tide 2X |

Targeted ISD (Insertion Substitution Deletion) Library Construction

Figure 10:
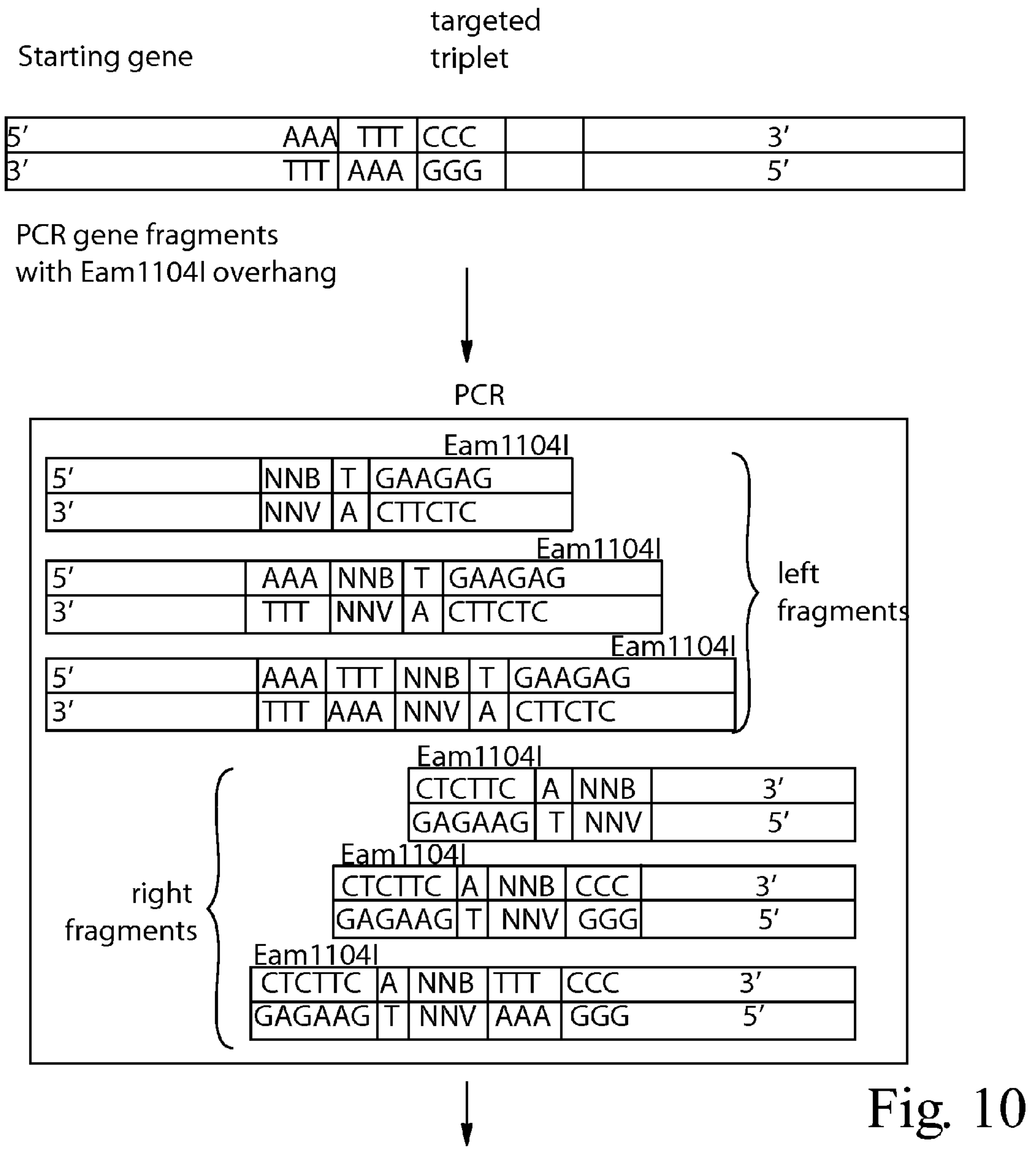
FIG. 10 is a schematic representation of method or targeted ISD library construction.
Figure 10:
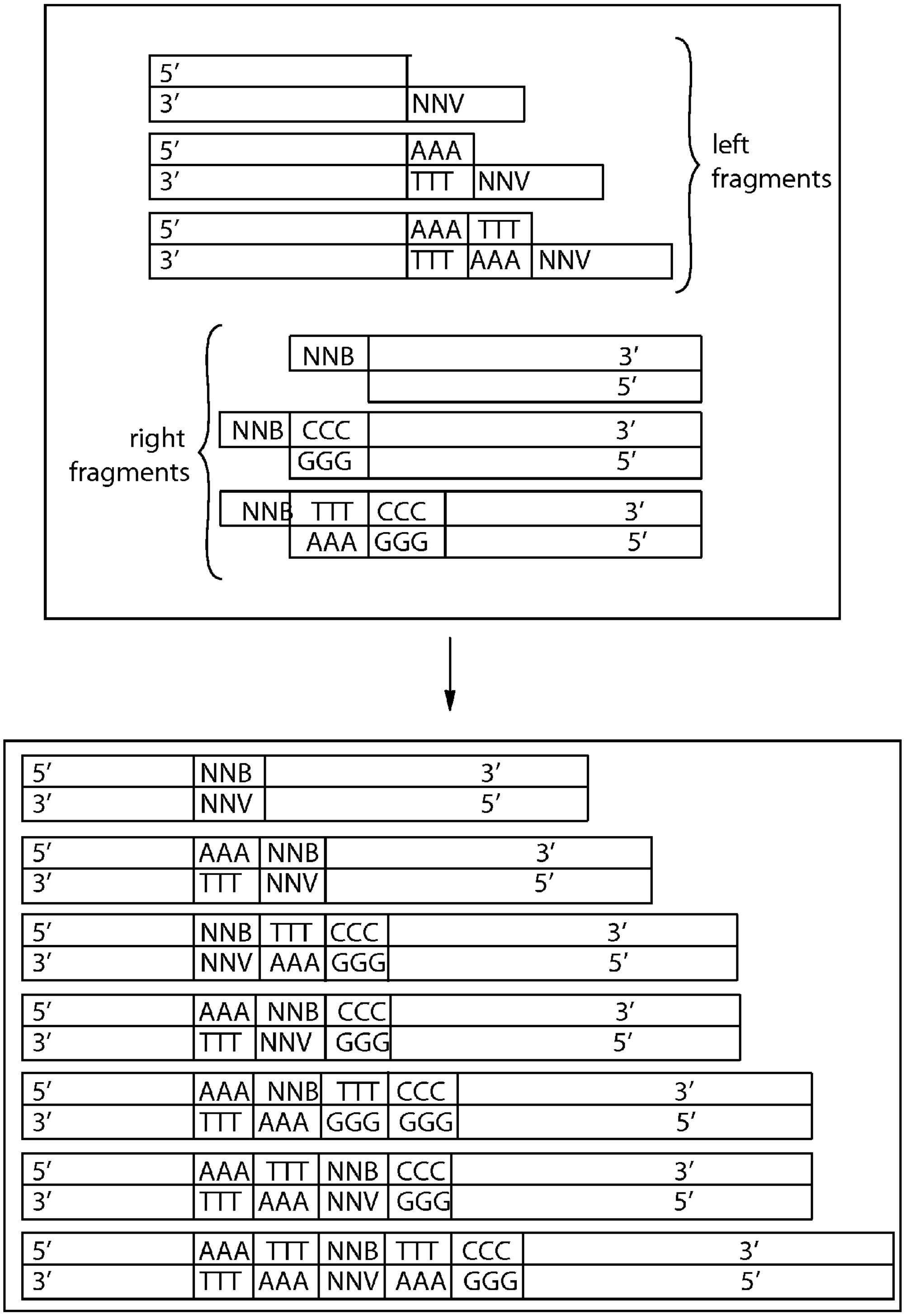

A PCR-based method was used to create a library of modified *B. amyloliquefaciens* subtilisin BPN'-Y217L (commercially available as PURAFECT® PRIME subtilisin) polynucleotides containing in-frame insertions, deletions and/or substitutions in two regions of BPN'-Y217L (positions 63-77 and 92-132 of the mature region) as shown in FIG. 10. This method is basically identical to the described in Pisarchik et al., Prot. Eng. Des. Select., 20:257-265 [2007] with several minor variations. First, we used EamI restriction enzyme to generate sticky ends in our PCR fragments instead of KasI.

We also introduced degenerate codon (NDT) right next to the sticky end. Finally, we placed primers much more densely with every following primer being moved only 3 bp downstream until the end of the targeted region was reached.

Two sets of oligonucleotides that evenly cover the targeted regions of the BPN'-Y217L gene of a full-length protein of 392 amino acids, in both forward and reverse direction were used to amplify the 5' and 3' segments of the portion of the BPN'-Y217L gene. The coding region of the BPN'-Y217L mature protease contains the KpnI and XhoI restriction sites for cloning purposes:

*gaattcatctcaaaaaaatgggtctactaaaatattattccatctatt*

*ataataaattcacagaatagtcttttaagtaagtctactctgaattt*

*ttttaaaaggagagggtaaagagtgagaagcaaaaaatt*gtgagaagca aaaaattgtggatcagtttgctgtttgctttagcgttaatctttacgat ggcgttcggcagcacatccagcgcgcaggctgcagggaaatcaaacggg gaaaagaaatatattgtcgggtttaaacagacaatgagcacgatgagcg ccgctaagaagaaagacgtcatttctgaaaaaggcgggaaagtgcaaaa gcaattcaaatatgtagacgcagctagcgctacattaaacgaaaaagct gtaaaagaattgaaaaaagacccgagcgtcgcttacgttgaagaagatc acgtagcacacgcgtacgcgcagtccgtgccatatggcgtatcacaaat taaagcccctgctctgcactctcaaggctacaccggttcaaatgttaaa gtagcggttatcgacagcggtatcgattcttctcatccagatcttaaag tagcaggcggagccagcatggttccttctgaaacaaatcctttccaaga caacaactctcacggaacacacgttgctggtaccgttgcggctcttaat aactcaatcggtgtattaggcgttgcgccaagcgcatcactttacgctg taaaagttctcggcgccgacggttccggccaatacagctggatcattaa cggaatcgagtgggcgatcgcaaacaatatggacgttattaacatgagc ctcggcggaccgtccggttctgctgctttaaaagcggcagttgataaag ccgttgcatccggcgtcgtagtcgttgcggcagccggcaacgaaggcac ttccggcagctcaagcacagtgggctaccctggtaaataccettctgtc attgcagtaggcgctgtcgacagcagcaaccaaagagcatctttctcaa gcgtaggacctgagctcgatgtcatggcacctggcgtatctatccaaag cacgcttcctggaaacaaatacggcgcgttgaacggtacatcaatggca tctccgcacgttgccggagccgcggctttgattctttctaagcacccga actggacaaacactcaagtccgcagctctctagaaaacaccactacaaa acttggtgattctttctactatggaaaagggctgatcaatgtacaggcg gcagctcagtaa_aactcgagataaaaaaccggccttggccccgccggtt_

_ttttat_

The amino acid sequence of the BPN'-Y217L precursor protein is provided below. In this sequence, bold indicates the mature BPN'-Y217L protease:

mrskklwisllfalaliftmafgstssaqaagksngekkyivgfkqtms tmsaakkkdvisekggkvqkqfkyvdaasatlnekavkelkkdpsvayv -continued eedhvahayaqsvpygvsqikapalhsqgytgsnvkvavidsgidsshp dlkvaggasmvpsetnpfqdnnshgthvagtvaalnnsigvlgvapsas lyavkvlgadgsgqyswiingiewaiannmdvinmslggpsgsaalkaa vdkavasgvvvvaaagnegtsgssstvgypgkypsviavgavdssnqra sfssvgpeldvmapgvsiqstlpgnkygalngtsmasphvagaaalils khpnwtntqvrsslenttklgdsfyygkglinvqaaaq.

The amino acid sequence of the mature BPN'-Y217L protease was used as the basis for making the variant libraries described herein:

aqsvpygvsqikapalhsqgytgsnvkvavidsgidsshpdlkvaggas mvpsetnpfqdnnshgthvagtvaalnnsigvlgvapsaslyavkvlga dgsgqyswiingiewaiannmdvinmslggpsgsaalkaavdkavasgv vvvaaagnegtsgssstvgypgkypsviavgavdssnqrasfssvgpel dvmapgvsiqstlpgnkygalngtsmasphvagaaalilskhpnwtntq vrsslenttklgdsfyygkglinvqaaaq

Figure 11:
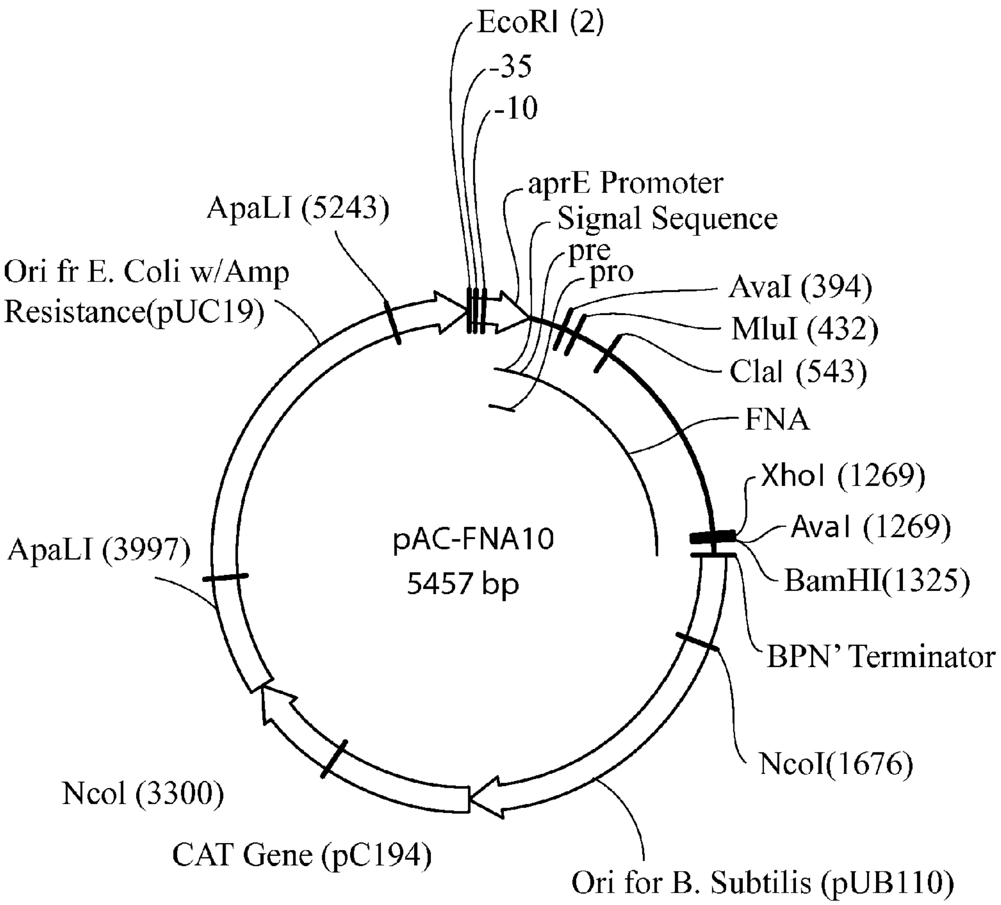
FIG. 11 provides a map of pAC-FNA10.
Figure 12:
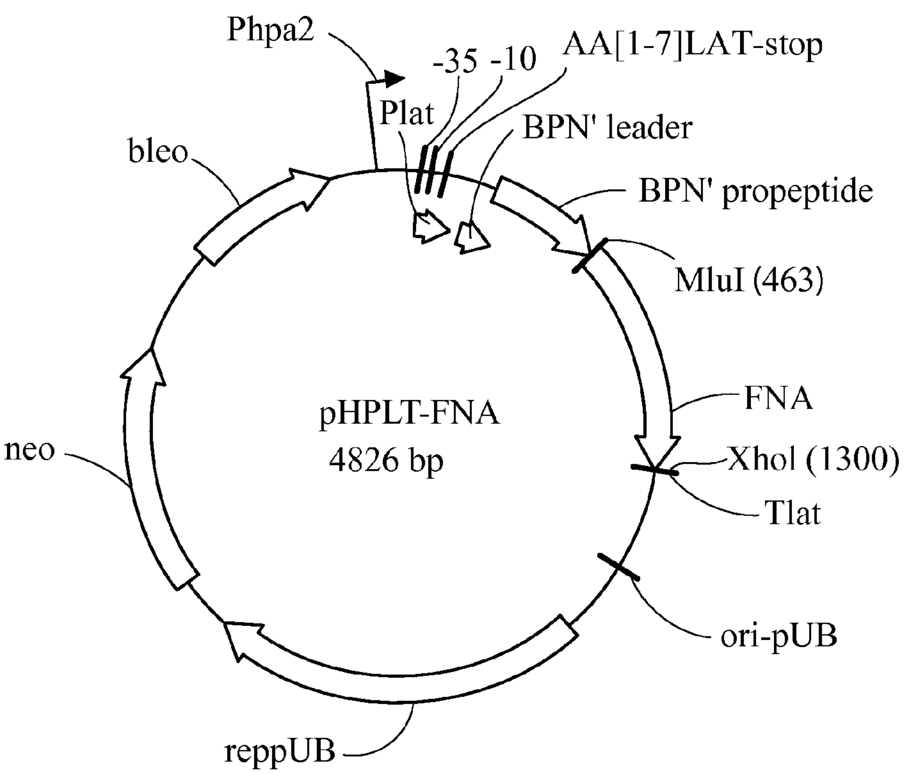
FIG. 12 provides a map of pHPLT-FNA

Each amplification reaction contained 30 pmol of each oligonucleotide and 100 ng of pAC-FNA10 template DNA (see FIG. 11). Amplifications were carried out using Vent DNA polymerase (New England Biolabs). The PCR mix (20 ul) was initially heated at 95° C. for 2.5 min followed by 30 cycles of denaturation at 94° C. for 15 s, annealing at 55° C. for 15 s and extension at 72° C. for 40 s. Following amplification, left and right fragments generated by the PCR reactions were purified by the Qiagen gel-band purification kit (Valencia, Calif.) and mixed (about 200 ng of each fragment). Every mix contained three left fragments targeting three adjacent codons and three right fragments targeting same codons. These mixes were digested with EamI 104I, ligated with T4 DNA ligase and amplified by flanking primers (P4299 CGTTGAAGAAGATCACGTAGCA, and P3246 TTTATTTTATAAACTCATTCCCTGAT) to generate the full-length gene fragment. The PCR conditions were same as described above, except the extension phase, which was carried out at 72° C. for 2 min. The resulting fragments were purified by the Qiagen gel-band purification kit (Valencia, Calif.), digested with MluI and XhoI, and cloned into the MluI/XhoI sites in the *Bacillus subtilis* expression plasmid pHPLT-FNA (see FIG. 12).

The BPN'-Y217L expression cassette from the pHPLT vector (Plat promoter-pre-pro-BPN'-Y217L-terminator) used has the polynucleotide sequence shown below.

GCTTTTCTTTTGGAAGAAAATATAGGGAAAATGGTACTTGTTAAAAATT

CGGAATATTTATACAATATCATATGTTTCACATTGAAAGGGGAGGAAAA

TCGTGAAACAACAAAAACGGCTTTAGTCTAGCAAAAGGAGAGGGTAAAG

AGTGAGAAGCAAAAAATTGTGGATCAGTTTGCTGTTTGCTTTAGCGTTA

ATCTTTACGATGGCGTTCGGCAGCACATCCTCTGCCCAGGCGGCAGGGA

AATCAAACGGGGAAAAGAAATATATTGTCGGGTTTAAACAGACAATGAG

CACGATGAGCGCCGCTAAGAAGAAAGATGTCATTTCTGAAAAAGGCGGG

AAAGTGCAAAAGCAATTCAAATATGTAGACGCAGCTTCAGCTACATTAA

-continued

```
ACGAAAAAGCTGTAAAAGAATTGAAAAAAGACCCGAGCGTCGCTTACGT

TGAAGAAGATCACGTAGCACACGCGTACGCGCAGTCCGTGCCTTACGGC

GTATCACAAATTAAAGCCCCTGCTCTGCACTCTCAAGGCTACACTGGAT

CAAATGTTAAAGTAGCGGTTATCGACAGCGGTATCGATTCTTCTCATCC

TGATTTAAAGGTAGCAGGCGGAGCCAGCATGGTTCCTTCTGAAACAAAT

CCTTTCCAAGACAACAACTCTCACGGAACTCACGTTGCCGGCACAGTTG

CGGCTCTTAATAACTCAATCGGTGTATTAGGCGTTGCGCCAAGCGCATC

ACTTTACGCTGTAAAAGTTCTCGGTGCTGACGGTTCCGGCCAATACAGC

TGGATCATTAACGGAATCGAGTGGGCGATCGCAAACAATATGGACGTTA

TTAACATGAGCCTCGGCGGACCTTCTGGTTCTGCTGCTTTAAAAGCGGC

AGTTGATAAAGCCGTTGCATCCGGCGTCGTAGTCGTTGCGGCAGCCGGT

AACGAAGGCACTTCCGGCAGCTCAAGCACAGTGGGCTACCCTGGTAAAT

ACCCTTCTGTCATTGCAGTAGGCGCTGTTGACAGCAGCAACCAAAGAGC

ATCTTTCTCAAGCGTAGGACCTGAGCTTGATGTCATGGCACCTGGCGTA

TCTATCCAAAGCACGCTTCCTGGAAACAAATACGGCGCGTTGAACGGTA

CATCAATGGCATCTCCGCACGTTGCCGGAGCGGCTGCTTTGATTCTTTC

TAAGCACCCGAACTGGACAAACACTCAAGTCCGCAGCAGTTTAGAAAAC

ACCACTACAAAACTTGGTGATTCTTTCTACTATGGAAAAGGGCTGATCA

ACGTACAGGCGGCAGCTCAGTAAACTCGAGAGAGGACGGATTTCCTGAA

GGAAATCCGTTTTTTTATTTTAAGCTTG
```

Ligation mixtures were amplified using rolling circle amplification by Illustra Templiphi kit according to the manufacturer's recommendation (GE Healthcare, Piscataway, N.J.) to generate multimeric DNA for transformation into *Bacillus subtilis*. For this purpose, 1 μl of the ligation mixture was mixed with 5 μl of the sample buffer, heated to 95° C. for 3 min and cooled on ice. Next, 5 μl of the reaction buffer and 0.2 μl of the enzyme were added to each tube, followed by incubation at 30° C. for 10 hours. Products of the rolling circle amplification were diluted 100 times and used to transform *B. subtilis* cells (ΔaprE, ΔnprE, amyE::xylRPxylAcomK-phleo). An aliquot of the transformation mix was plated on LB plates containing 1.6% skim milk and 10 μg/mL neomycin and incubated overnight at 37° C. Subsequently, colonies with halos were inoculated in 120 μl of LB media containing 10 μg/mL neomycin, covered with Enzyscreen lids and incubated overnight at 37° C. and 70% humidity with vigorous shaking (250 rpm). Next morning overnight cultures were frozen and screened later in the BMI assays as described in Test Method 2.

Description

Results of experiments conducted to determine stain removal activity (microswatch assay to determine stain removal performance in laundry applications using EMPA 116 swatches (BMI stain, CFT) at pH 8/16° C. and protein determination by TCA precipitation (tests of properties of interest) of BPN'-Y217L variants are shown in Table 31-10. The results were obtained using the methods described in Test Method 2 with the following modifications for the stain removal performance assay. The test detergent used was heat inactivated Tide 2× detergent (Procter & Gamble). Heat inactivation of commercial detergent formulas serves to destroy the endogenous enzymatic activity of any protein components while retaining the properties of nonenzymatic components. Heat inactivation of the detergents was performed by placing pre-weighed amounts of liquid detergent (in a glass bottle) in a water bath at 95° C. for 2 hours. The detergent was purchased from local supermarket stores. Both unheated and heated detergents were assayed within 5 minutes of dissolving the detergent to accurately determine percentage deactivated. Enzyme activity was tested by AAPF assay. As described throughout functionality of BPN'-Y217L variants was quantified as a performance index ("Pi" or "PI"), which is the ratio of performance of a variant to parent protein BPN'-Y217L.

Data are shown for variants with a PI of at least 1.1 relative to FNA in BMI assays at 16 C.

TABLE 31-10

Mutations and Performance Index for TCA protein and BMI Activity for BPN' Variants

| Mutations | TCA PI | PI on BMI at pH 8 16° C. |
|---|---|---|
| Y217L-V068C-A069G | 0.4 | 1.2 |
| Y217L-I079F-A098G | 1.2 | 1.2 |
| Y217L-P086T-S101D-Q103S-V147I | 0.4 | 1.3 |
| Y217L-A088T-P129S-G146D | 0.7 | 1.2 |
| Y217L-V093I-G128D-P129R | 0.6 | 1.2 |
| Y217L-Z096.01D-A098R | 0.7 | 1.2 |
| Y217L-Z096.01H-A098G | 0.3 | 1.2 |
| Y217L-G097S-Z097.01S-A098G-A273T | 0.4 | 1.2 |
| Y217L-A098S-D099G-G100D | 0.3 | 1.3 |
| Y217L-Z098.01N | 0.5 | 1.3 |
| Y217L-D099G-Z099.01N | 0.3 | 1.2 |
| Y217L-D099G-Z099.01S | 0.2 | 1.2 |
| Y217L-D099V-S101D | 0.5 | 1.2 |
| Y217L-Z099.01S | 0.5 | 1.2 |
| Y217L-G100D | 0.5 | 1.2 |
| Y217L-S101D-Q103H | 0.9 | 1.2 |
| Y217L-S101G-A151V | 0.4 | 1.2 |
| Y217L-S101H-G102S | 0.7 | 1.2 |
| Y217L-S101H-Q103D | 1.0 | 1.2 |
| Y217L-G102R-Q103C-Y104C-V192I | 0.3 | 1.3 |
| Y217L-Q103D | 1.0 | 1.2 |
| Y217L-V121I-I122S-N123C | 0.6 | 1.4 |
| Y217L-V121L-N123C | 1.0 | 1.2 |
| Y217L-I122S-N123S | 0.6 | 1.3 |
| Y217L-M124I | 1.7 | 1.2 |
| Y217L-M124V | 1.1 | 1.2 |
| Y217L-L126F-P129Z-S182N | 1.5 | 1.2 |
| Y217L-L126Y | 1.0 | 1.3 |
| Y217L-G127S-P129D | 0.7 | 1.3 |
| Y217L-Z127.01N-G128S-P129S | 0.6 | 1.2 |
| Y217L-G128H-P129Y | 0.4 | 1.2 |
| Y217L-G128S-P129D | 0.9 | 1.4 |
| Y217L-G128S-P129D-S248R | 0.9 | 1.3 |
| Y217L-G128S-P129G | 1.1 | 1.4 |
| Y217L-P129G-G131Z | 0.6 | 1.2 |
| Y217L-P129G-S130H-S132Z | 0.4 | 1.2 |
| Y217L-P129H-G131Z | 0.6 | 1.2 |
| Y217L-P129L | 1.0 | 1.2 |
| Y217L-P129S-S130H-S132Z | 0.5 | 1.2 |
| Y217L-P129Z | 0.6 | 1.2 |
| Y217L-P129Z-S130G | 0.5 | 1.3 |
| Y217L-P129Z-S130G-G131H-S132H | 1.1 | 1.2 |
| Y217L-P129Z-S130H | 0.6 | 1.2 |
| Y217L-S130V-G131D-S132I | 1.0 | 1.2 |

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm".

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A composition comprising an isolated protein comprising a protease variant wherein (i) the protease variant has at least 95% identity to SEQ ID NO: 6, (ii) the protease variant comprises, compared to the parent protease of SEQ ID NO: 2, the substitutions S024G+S053G+S078N+S101N+G128A+Y217Q, and (iii) the protease variant has suc-AAPF-pNA proteolytic activity.

2. The composition according to claim 1, wherein said protease variant has a total net charge of −1, 0 or +1 relative to the parent protease of SEQ ID NO: 2.

3. The composition of claim 1, said composition comprising an adjunct ingredient selected from the group consisting of: a surfactant, a builder, a chelating agent, a dye transfer inhibiting agent, a dispersant, one or more additional enzymes, an enzyme stabilizer, a catalytic material, a bleach activator, a hydrogen peroxide, a source of hydrogen peroxide, a preformed peracid, a polymeric dispersing agent, a clay soil removal/anti-redeposition agent, a brightener, a suds suppressor, a dye, a perfume, a perfume delivery system, a structure elasticizing agent, a fabric softener, a carrier, a hydrotrope, a processing aid, a solvent, a pigment and mixtures thereof.

4. The composition according to claim 1, said composition comprising a second non-immunoequivalent protease that is a subtilisin (EC 3.4.21.62) protease.

5. The composition of claim 1, said composition comprising an additional enzyme selected from the group consisting of hemicellulases, peroxidases, proteases, cellulases, cellobiose dehydrogenases, xyloglucanases, xylanases, lipases, phospholipases, esterases, cutinases, pectinases, mannanases, pectate lyases, keratinases, reductases, oxidases, phenoloxidases, lipoxygenases, ligninases, pullulanases, tannases, pentosanases, lichenases glucanases, arabinosidases, hyaluronidase, chondroitinase, laccase, amylases, and mixtures thereof.

6. The composition of claim 1, wherein said composition is a detergent composition.

* * * * *